US010808246B2

(12) United States Patent
Manoharan et al.

(10) Patent No.: US 10,808,246 B2
(45) Date of Patent: Oct. 20, 2020

(54) OLIGONUCLEOTIDE-LIGAND CONJUGATES AND PROCESS FOR THEIR PREPARATION

(71) Applicant: ALNYLAM PHARMACEUTICALS, INC., Cambridge, MA (US)

(72) Inventors: Muthiah Manoharan, Cambridge, MA (US); Jayaprakash K. Nair, Cambridge, MA (US); Pachamuthu Kandasamy, Cambridge, MA (US); Shigeo Matsuda, Cambridge, MA (US); Alexander V. Kelin, Cambridge, MA (US); Muthusamy Jayaraman, Cambridge, MA (US); Kallanthottathil G. Rajeev, Cambridge, MA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 510 days.

(21) Appl. No.: 14/901,945

(22) PCT Filed: Jul. 11, 2014

(86) PCT No.: PCT/US2014/046425
§ 371 (c)(1),
(2) Date: Dec. 29, 2015

(87) PCT Pub. No.: WO2015/006740
PCT Pub. Date: Jan. 15, 2015

(65) Prior Publication Data
US 2016/0376585 A1 Dec. 29, 2016

Related U.S. Application Data
(60) Provisional application No. 61/845,279, filed on Jul. 11, 2013.

(51) Int. Cl.
*C12N 15/113* (2010.01)
*C07H 21/00* (2006.01)
(Continued)

(52) U.S. Cl.
CPC .......... *C12N 15/113* (2013.01); *A61K 47/549* (2017.08); *C07H 21/00* (2013.01);
(Continued)

(58) Field of Classification Search
CPC .................. A61K 47/48092; C07H 21/00; C12N 15/111; C12N 15/113; C12N 2310/14;
(Continued)

(56) References Cited

U.S. PATENT DOCUMENTS 5,574,142 A * 11/1996 Meyer, Jr. ........ A61K 47/48092
530/300
6,525,031 B2 * 2/2003 Manoharan ............ C12N 15/87
435/6.16
(Continued)

FOREIGN PATENT DOCUMENTS

WO WO-2007091269 A2 8/2007
WO WO-2009073809 A2 6/2009
(Continued)

OTHER PUBLICATIONS (S) International Prelminary Report on Patentability ((PCT/ISA/237), dated Jan. 12, 2016, PCT/US2014/046425 (PCT equivalent of U.S. Appl. No. 14/0901,945), filed Dec. 29, 2015; copy supplied by applicant.*

(Continued)

*Primary Examiner* — Lawrence E Crane
(74) *Attorney, Agent, or Firm* — Blank Rome LLP

(57) ABSTRACT

The present invention relates to ligand conjugates of iRNA agents (such as siRNA) of the formula (Continued)

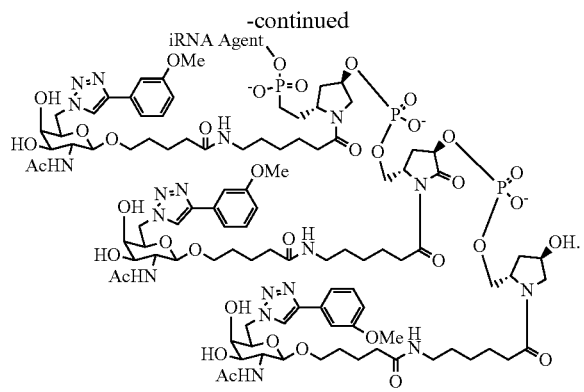

-continued

9 Claims, 14 Drawing Sheets

(51) Int. Cl.
C12N 15/11 (2006.01)
A61K 47/54 (2017.01)
(52) U.S. Cl.
CPC ........ *C12N 15/111* (2013.01); *C12N 2310/14* (2013.01); *C12N 2310/351* (2013.01); *C12N 2320/30* (2013.01); *C12N 2320/32* (2013.01); *C12N 2330/30* (2013.01)
(58) Field of Classification Search
CPC .......... C12N 2310/351; C12N 2320/30; C12N 2320/32; C12N 2330/30
See application file for complete search history.

(56) References Cited

U.S. PATENT DOCUMENTS

| 8,106,022 | B2* | 1/2012 | Manoharan | C07H 21/02 514/25 |
| 8,362,229 | B2* | 1/2013 | Aygun | C12N 15/111 536/23.1 |
| 8,501,930 | B2* | 8/2013 | Rozema | A61K 47/48261 530/300 |
| 8,575,123 | B2* | 11/2013 | Manoharan | A61K 47/48092 424/93.1 |
| 9,107,957 | B2* | 8/2015 | Rozema | A61K 47/48261 |
| 9,198,972 | B2* | 12/2015 | Manoharan | A61K 47/48092 |
| 9,526,796 | B2* | 12/2016 | Rozema | A61K 47/48261 |
| 9,566,340 | B2* | 2/2017 | Manoharan | A61K 47/48092 |
| 2011/0123520 | A1 | 5/2011 | Manoharan et al. | |

FOREIGN PATENT DOCUMENTS

| WO | WO-2011100131 A2 | 8/2011 |
| WO | WO-2012083185 A2 | 6/2012 |
| WO | WO-2013075035 A1 | 5/2013 |
| WO | WO-2013166121 A1 | 11/2013 |

OTHER PUBLICATIONS

Mamidyala, et al., Glycomimetic Ligands for the Human Asialogylcoprotein Receptor, J. Am. Chem. Soc., 134(4), 1978-1981, 2012.
Sehgal A., "RNai-Mediated Inhibition of Natural Anticoagulants for Treatment of Hemophilia" Jul. 3, 2012, retrieved from internet: URL:http://www.alnylam.com/capella/wp-content/uploads/2012/07/ALNY-WFH-AT3poster-July2012.pdf.
Fiona L. Lin et al., "Carb-85: Novel saccaride-peptide hybrid copolymers as siRNA delivery agents", American Chemical Society, Abstracts of Papers (At the National Meeting) vol. 234, Aug. 1, 2007-Aug. 23, 2007, pp. Carb-85.
Fiona L. Lin et al., "Poly 152-Synthesis and evaluation of novel sacchride-peptide hybrid copolymers as siRNA delivery agents" Abstracts of Papers American Chemical Society, 236, Aug. 2008, pp. 152-Poly, & 236th National Meeting of the American Chemical Society; Philadelphia, PA, Aug. 17-21, 2008.
International Search Report issued in PCT/US2014/046425 dated Mar. 17, 2015.
Prakash T.K et al., "Targeted delivery of antisense oligonucleotides to hepatocytes using triantennary N-acetyl galactosamine improves potency 10-fold in mice" Nucleic Acids Research, 42(3) Jul. 3, 2014, pp. 8796-8807.
Hangeland J.J. et al., "Cell Type specific and ligand specific enhancement of cellular uptake of oligodeoxynucleoside methylphosphonates covalently linked with a neoglycopeptide, YEE9ah-GalNac)3", Bioconjugate Chemistry, 6(6), Nov. 1, 1995, pp. 695-701.
Manoharan Muthiah, Oligonucleotide conjugates as potential antisense drugs with improved uptake, biodistribution, targeted delivery, and mechanisms of action'< Antisense & Nucleic Acid Drug Development, 12(2), Apr. 1, 2012, pp. 103-128.
Hangeland J. et al., "Tissue distribution and metabolism of the A32PU-labeled oligodeoxynucleoside methylphosphonate-neoglycopeptide conjugate, ayee (AH-GALNAC)3U-SMCC-AET-PUMPT7, in the mouse" Antisense & Nucleic Acid Drug Development, 7(3), Jan. 1, 1997, pp. 141-149.
Sabine M.W. Van Rosenberg et al., ":A targeted peptide nucleic acid to down-regulate mouse microsomal triglyceride transfer protein expression in hepatocytes" Bioconjugate Chemistry, 14(6), Nov. 1, 2003, pp. 1077-1082.
Biessen E. A.L. et al., "Design of a targeted peptide nucleic acid prodrug to inhibit hepatic human microsomal triglyceride transfer protein expression in hepatocytes" Bioconjugates Chemistry, 13, Jan. 1, 2002, pp. 295-302.

* cited by examiner

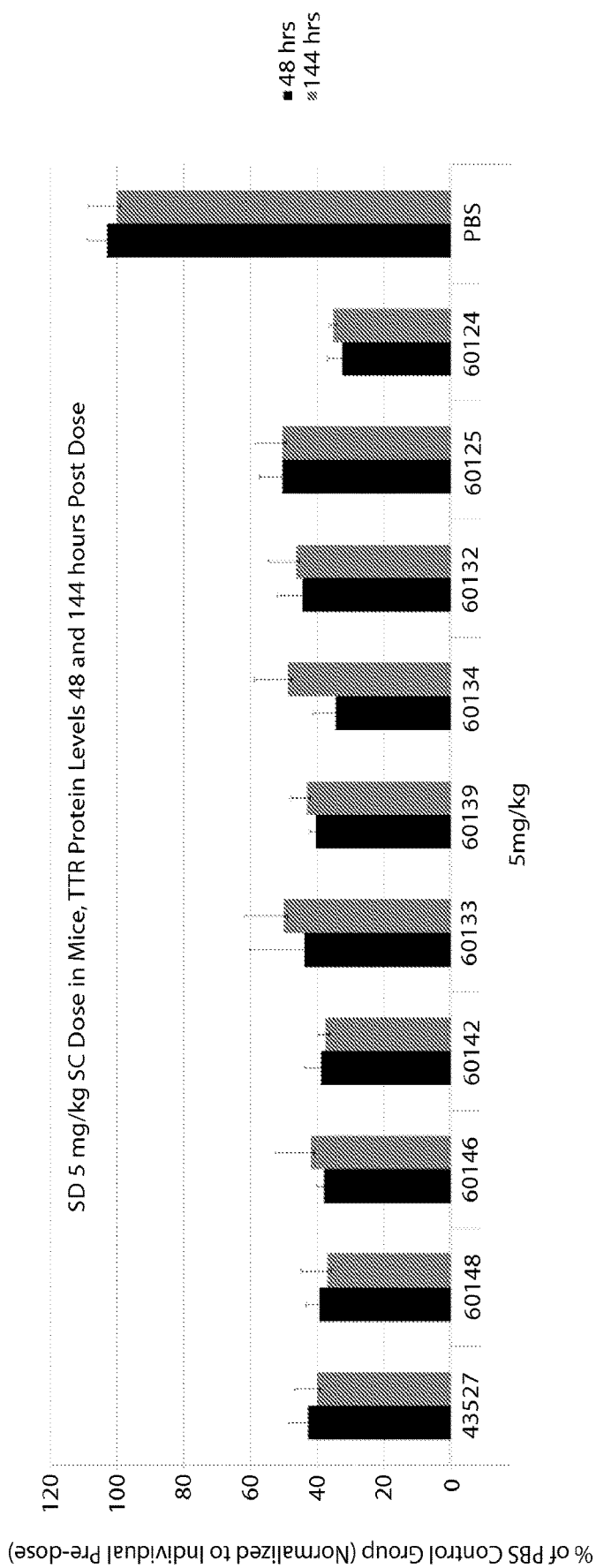
Figure 1. In vivo TTR gene silencing by ligand-conjugated TTR siRNA

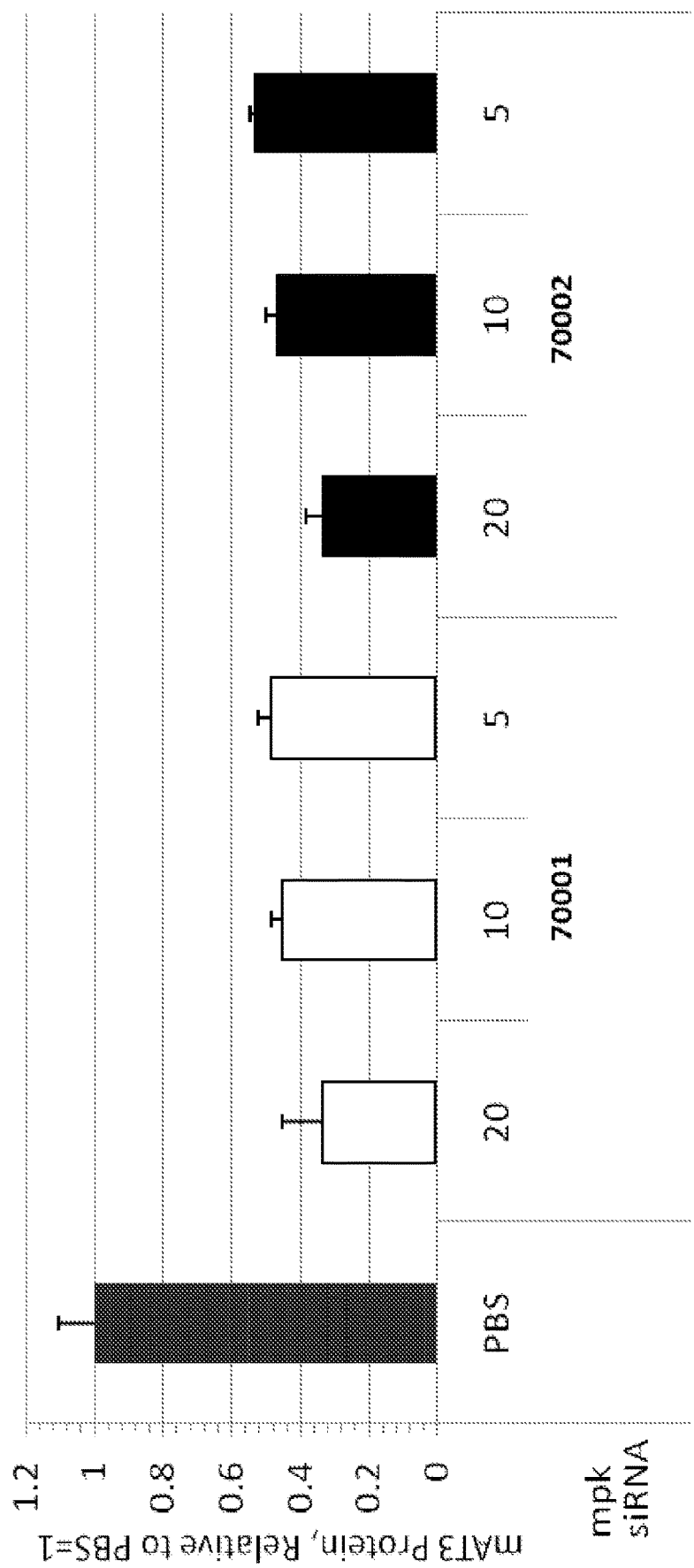
Figure 2. *In vivo* gene silencing by AT3 siRNA-ligand conjugate.

OLIGONUCLEOTIDE-LIGAND CONJUGATES AND PROCESS FOR THEIR PREPARATION

RELATED APPLICATIONS

This application claims the benefit of U.S. Provisional Application No. 61/845,279, filed Jul. 11, 2013, which is hereby incorporated by reference in its entirety.

FIELD OF THE INVENTION

The present invention relates to ligand conjugates of oligonucleotides (e.g., iRNA agents) and methods for their preparation. The ligands are derived primarily from monosaccharides. These conjugates are useful for the in vivo delivery of oligonucleotides.

BACKGROUND OF THE INVENTION

Efficient delivery to cells in vivo requires specific targeting and substantial protection from the extracellular environment, particularly serum proteins. One method of achieving specific targeting is to conjugate a targeting moiety to the iRNA agent. The targeting moiety helps in targeting the iRNA agent to the required target site. One way a targeting moiety can improve delivery is by receptor mediated endocytotic activity. This mechanism of uptake involves the movement of iRNA agent bound to membrane receptors into the interior of an area that is enveloped by the membrane via invagination of the membrane structure or by fusion of the delivery system with the cell membrane. This process is initiated via activation of a cell-surface or membrane receptor following binding of a specific ligand to the receptor. Many receptor-mediated endocytotic systems are known and have been studied, including those that recognize sugars such as galactose, mannose, mannose-6-phosphate, peptides and proteins such as transferrin, asialoglycoprotein, vitamin B12, insulin and epidermal growth factor (EGF). The Asialoglycoprotein receptor (ASGP-R) is a high capacity receptor, which is highly abundant on hepatocytes. The ASGP-R shows a 50-fold higher affinity for N-Acetyl-D-Galactosylamine (GalNAc) than D-Gal. Previous work has shown that multivalency is required to achieve nM affinity, while spacing among sugars is also crucial.

Recently, certain carbohydrate conjugates have been shown to be a valuable delivery alternatively to liposomes for siRNA delivery.

SUMMARY OF THE INVENTION

The present invention relates to ligand conjugates of oligonucleotides or other biologically active agents which have one or more advantageous properties, such as improved delivery of the oligonucleotide or other biologically active agents, lower manufacturing costs or fewer manufacturing issues, or better chemical stability. These conjugates provide effective delivery of oligonucleotides and other biologically active agents.

In one embodiment, the present invention relates to a ligand (e.g., carbohydrate) conjugate of an oligonucleotide (e.g., an iRNA agent) or other biologically active agent of the formula I:

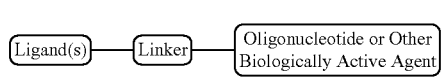

Formula I wherein
the Oligonucleotide is an oligonucleotide, such as an siRNA, microRNA, antimiR, antagomir, microRNA mimic, decoy, immune stimulatory, G-quadruplex, splice altering, ssRNA, antisense, aptamer, stem-loop RNA or DNA or one of the two strands of any double stranded RNA or DNA or double stranded shortemer RNA or DNA (e.g, siRNA);

the Biologically Active Agent is any biologically active agent;

the Linker is a linking group between the Ligand(s) and the Oligonucleotide or other biologically active agent, where the Linker may be selected from the linking groups in Table 1 or 1A; and the Ligand(s) are sugar-derived, where (i) the Ligand(s) may be attached to the same or different atoms in the Linker, (ii) the conjugate contains from 1 to 12 Ligands (preferably 1 to 5 or 1 to 3 Ligands), and (iii) the Ligand(s) may be selected from
(a) the Ligands in Table 2 or 2A,
(b) —$R^2$—$(R^3)_k$, where
$R^2$ is absent (in which case k=1) or a spacer (also referred to as a ligand backbone) having two or more sites of attachment for the $R^3$ groups,
$R^3$ is a targeting monomer selected from Table 3, and k is 1 to 6 (preferably 1 to 5 or 1 to 3), each $R^3$ may be attached to the same or different atoms in $R^2$; and
(c) the Ligands in Table 4 or 4A.

The conjugate includes at least one Linker from Table 1 or 1A or from the examples, one Ligand from Table 2, 2A, 4, or 4A, or one targeting monomer from Table 3 or 3A. For example, the nucleoside linkers described in the examples can be used as the Linker. In one embodiment, the conjugate includes (i) at least one Linker from Table 1 or 1A or from the examples, (ii) one Ligand from Table 2, 2A, 4, or 4A, and (iii) one targeting monomer from Table 3 or 3A.

$R^2$ can be an amino acid-, polypeptide- (e.g., a dipeptide or tripeptide), heteroaryl- (e.g., a triazole), or sugar-containing group. In one preferred embodiment, each $R^3$ group is attached via an amide, ether, or amino group to $R^2$. In one embodiment, $R^3$ is attached via an amide group. Each entry in Tables 2, 2A, 4, and 4A shows a spacer bound to at least one targeting monomer. The spacers are bound to the targeting monomers either through a heteroatom (which is at a terminus of the spacer), such as a nitrogen atom, or at the anomeric carbon to the sugar group of a targeting monomer (as shown below). The heteroatom attachment point in the structures shown in Tables 2, 2A, 4, and 4A is the first nitrogen atom when walking along the chain from the sugar group (left side of the ligand) to the remainder of the ligand (right side). The spacers for two ligands in Table 2A are shown in the table below (the arrows indicate the points of attachment for the targeting monomers $R^3$, and the right side of the spacer is attached to the Linker). Suitable spacers are also shown in Table 5 below.

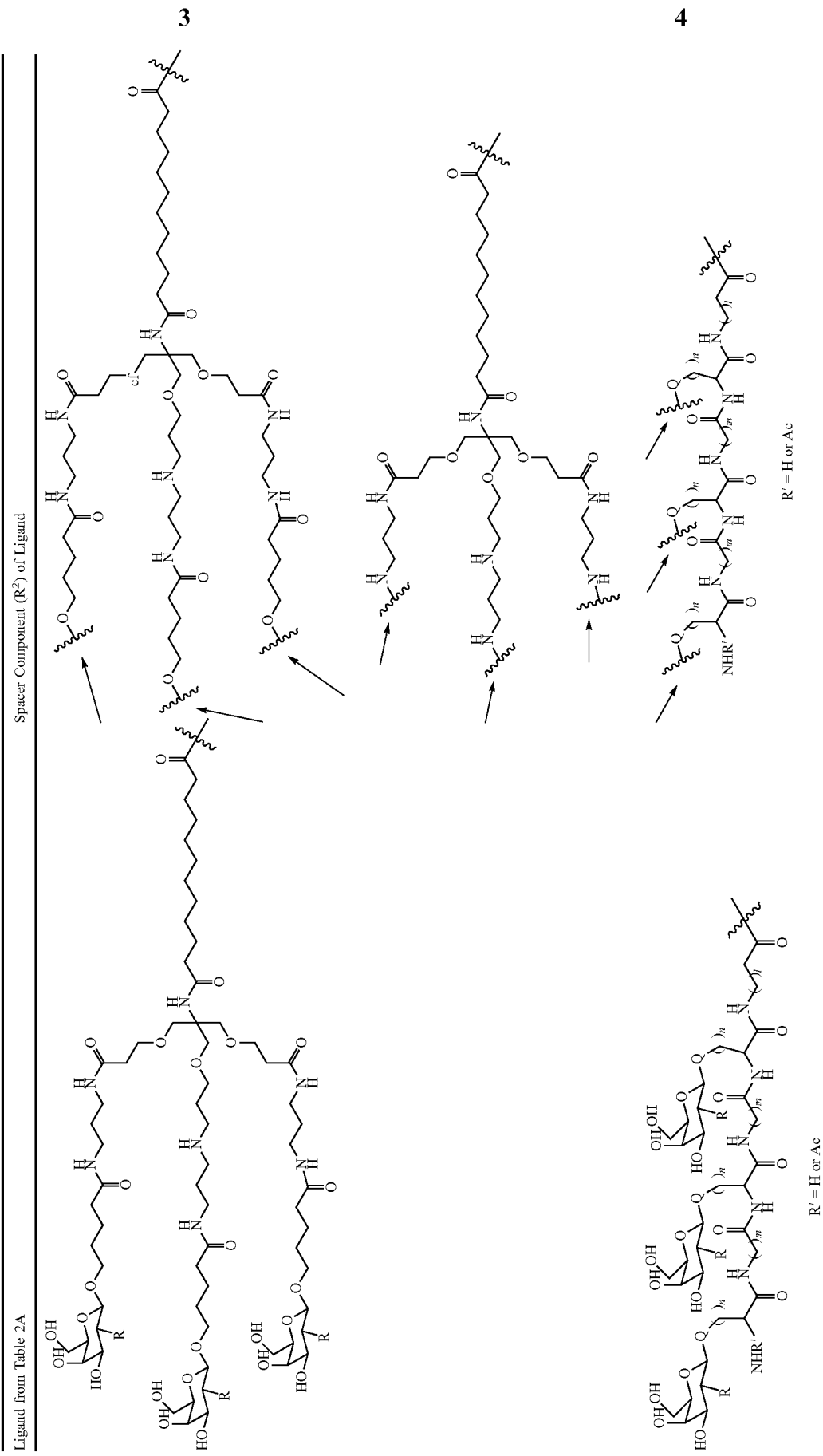

The Oligonucleotide is preferably attached to the Linker through (i) the 3' or 5'-terminal of the oligonucleotide, (ii) one or more sugar moieties of the nucleoside present in the oligonucleotide independent of position, or (iii) one or more base moieties of the nucleoside present independent of position.

In one embodiment, the Ligand is conjugated to one of the two strands of a double stranded siRNA via a Linker.

In one embodiment, the Ligand(s) target the asialoglycoprotein receptor (ASGPR). In another embodiment, the Ligand(s) target the liver, such as the parenchymal cells of the liver. The Ligand(s) may be an unmodified or modified monosaccharide, disaccharide, trisaccharide, tetrasaccharide, or higher polysaccharide.

The oligonucleotide can be attached to the Linker via a cleavable group (e.g., phosphate, phosphorothiate, or amide) or a non-cleavable group (e.g., ether, carbamate, or C—C (e.g., a bond between two carbon atoms or —CH$_2$—CH$_2$—)). As described herein, the cleavable or non-cleavable group is within the Oligonucleotide of Formula I.

In one embodiment, the -Linker-Ligand is not L96 (shown in the examples).

In the formulas of the conjugates described herein (such as Formula (I)), the oligonucleotide or other biologically active agent can be replaced by a component of a lipid nanoparticle (LNP) (such as a PEG-lipid or cationic lipid) or a polymer. The conjugated LNP component or conjugated polymer may be useful as delivery agents for facilitating delivery of a biologically active agent to a target site.

TABLE 1

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

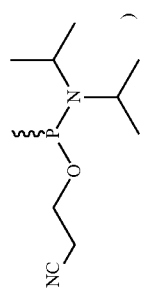

(e.g., 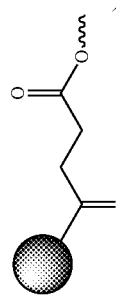)

compatible with solid phase oligonucleotide synthesis and deprotection or attached to a solid support (e.g., 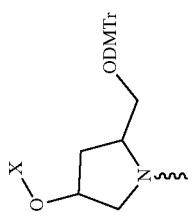)

the enables solid phase oligonucleotide synthesis.

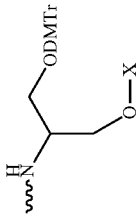
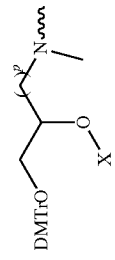
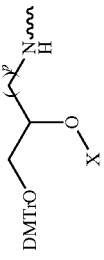

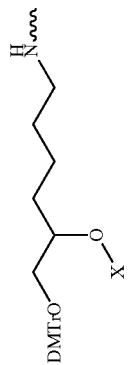

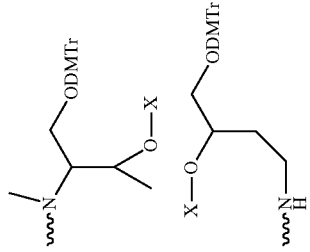

TABLE 1-continued

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

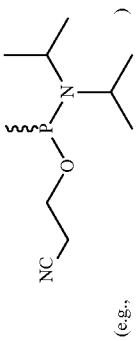

(e.g., a reactive phosphoramidite)

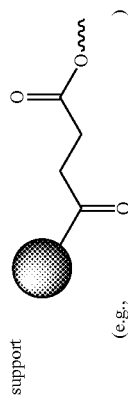

(e.g., compatible with solid phase oligonucleotide synthesis and deprotection or attached to a solid support the enables solid phase oligonucleotide synthesis.)

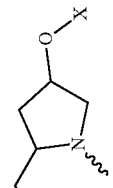

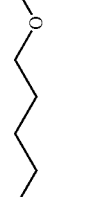

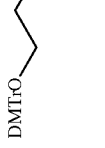

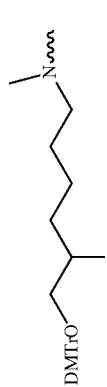

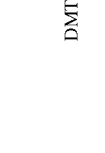

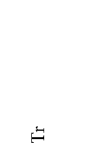

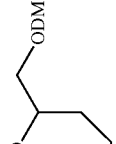

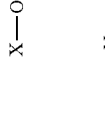

TABLE 1-continued

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

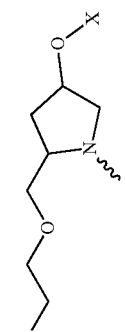

(e.g.,  a reactive phosphoramidite)

(e.g., 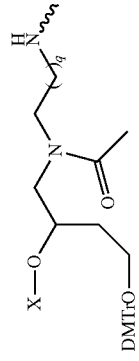 compatible with solid phase oligonucleotide synthesis and deprotection or attached to a solid support)

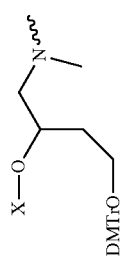

(e.g., the enables solid phase oligonucleotide synthesis.)

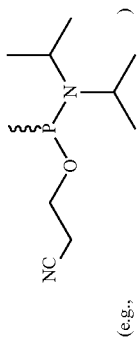

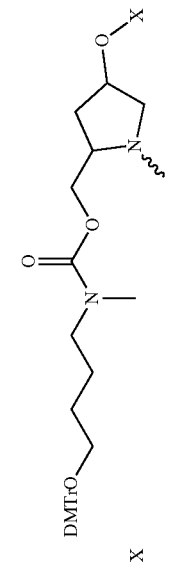

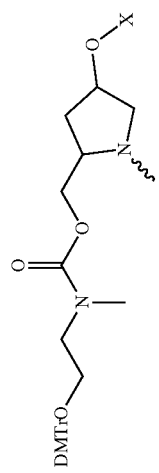

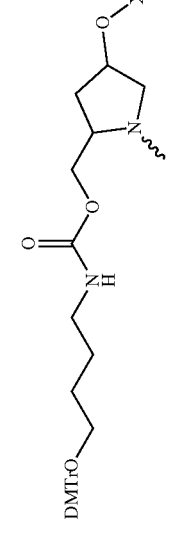

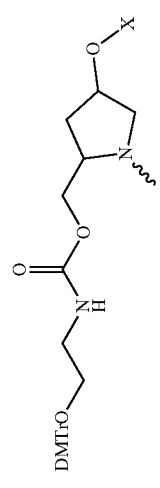

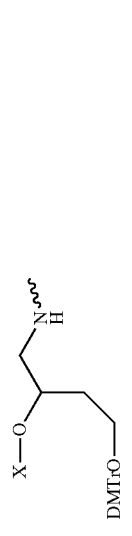

TABLE 1-continued

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

(e.g., a reactive phosphoramidite)

(e.g., compatible with solid phase oligonucleotide synthesis and deprotection or attached to a solid support the enables solid phase oligonucleotide synthesis.)

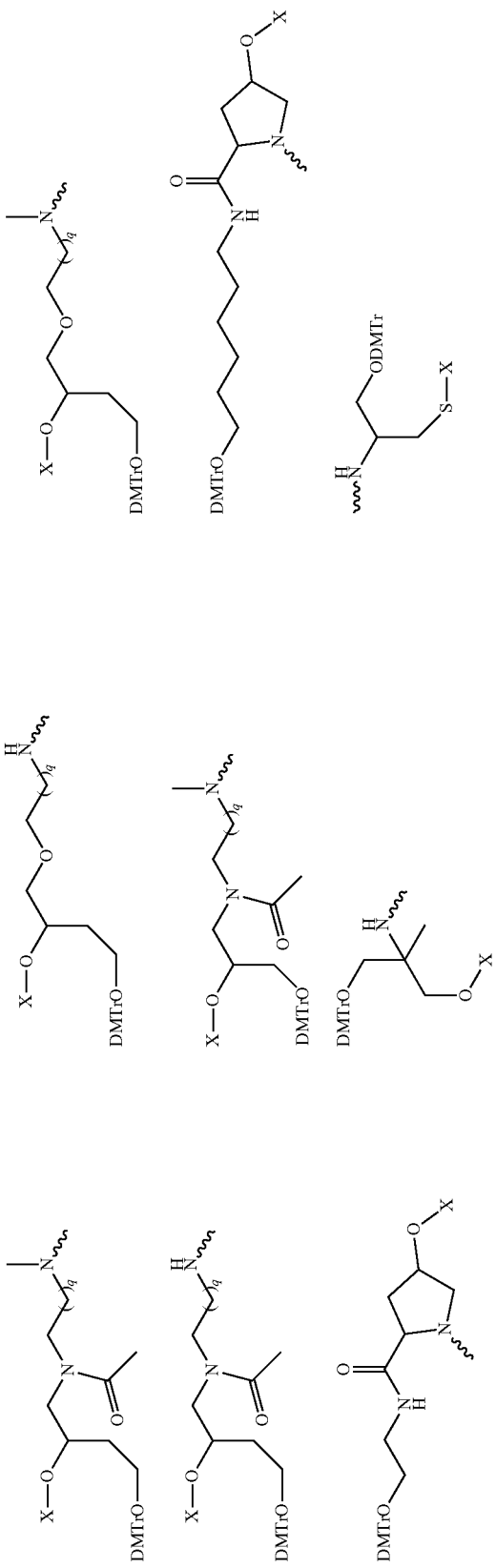

TABLE 1-continued

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

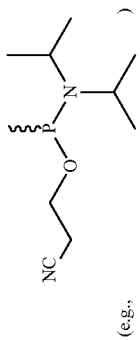

(e.g., a reactive phosphoramidite)

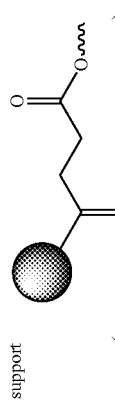

(e.g., support compatible with solid phase oligonucleotide synthesis and deprotection or attached to a solid support the enables solid phase oligonucleotide synthesis.)

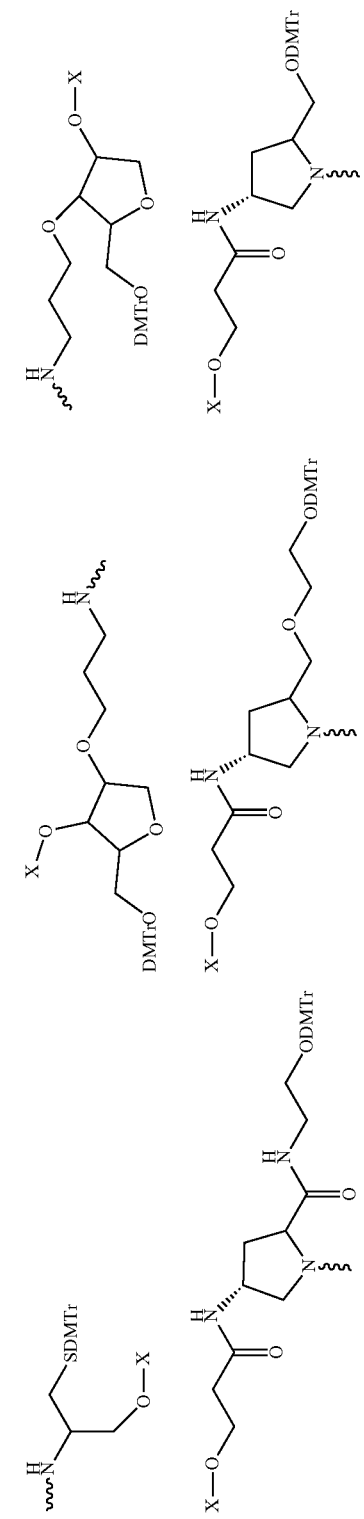

TABLE 1-continued

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite

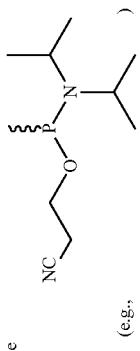
(e.g., a reactive phosphoramidite)

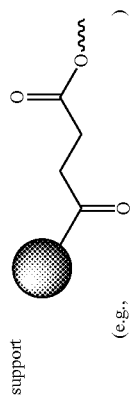
(e.g., support compatible with solid phase oligonucleotide synthesis and deprotection or attached to a solid support that enables solid phase oligonucleotide synthesis.)

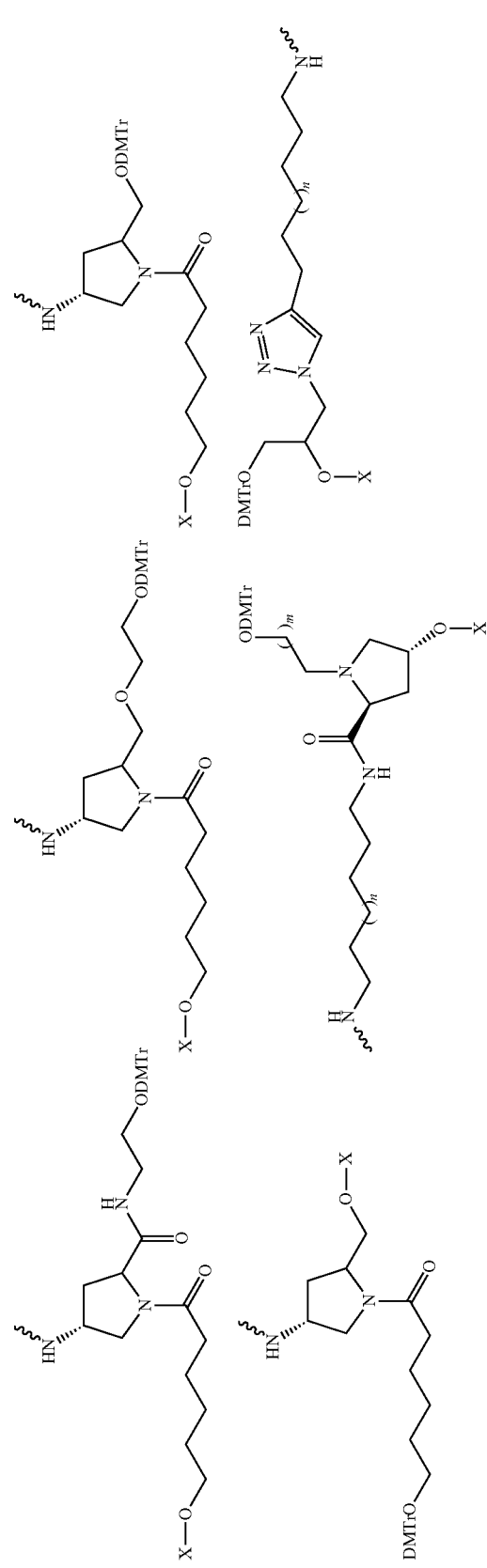

TABLE 1-continued

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

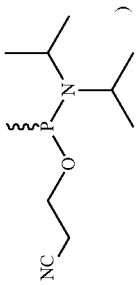

(e.g., )

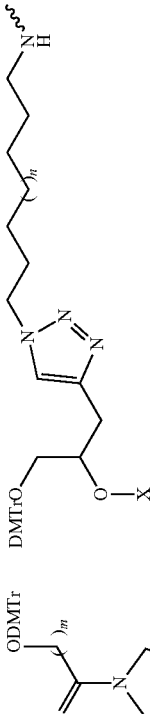

(e.g., 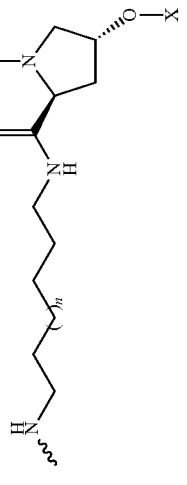 support compatible with solid phase oligonucleotide synthesis and deprotection or attached to a solid the enables solid phase oligonucleotide synthesis.

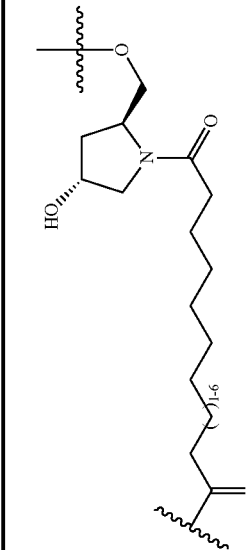

The top right squiggly line is the point of attachment to the oligonucleotide or other biologically active agent. The bottom left squiggly link is the point of attachment for the Ligand.

TABLE 1-continued

Linker Groups[a,b]

The Linkers below are shown with the protecting group DMTr. When conjugated, the DMTr group is removed and the adjacent oxygen atom is the site of attachment of the Linker to the oligonucleotide (e.g., to a cleavable group of the oligonucleotide). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

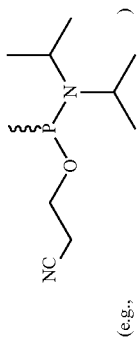

(e.g., 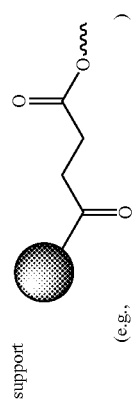

compatible with solid phase oligonucleotide synthesis and deprotection or attached to a solid support (e.g., the enables solid phase oligonucleotide synthesis.

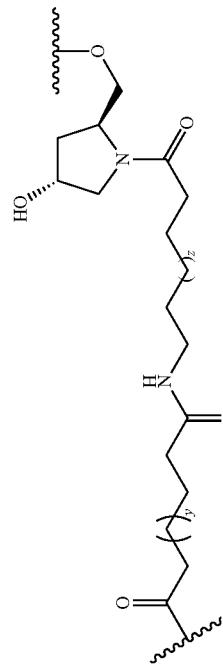

where y is 1-120 and z is 1-20

When conjugated, the DMTr group is removed and the adjacent oxygen is the site of attachment of the Linker to the oligonucleotide (e.g., via a cleavable group such as a phosphate or phosphorothioate) or other biologically active agent

[a] indicates the site of attachment of the Ligand.
[b] Each structure represents chirally pure or racemic isomers when one or more asymmetric centers are present.

TABLE 1A

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite (e.g., 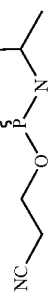 )

compatible with solid phase oligonucleotide synthesis and deprotection or ttached to a solid support (e.g., 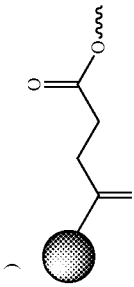 )

that enables solid phase oligonucleotide synthesis. The phrase "oligonucleotide/nucleotide" is meant to refer to a single nucleotide or an oligonucleotide.

 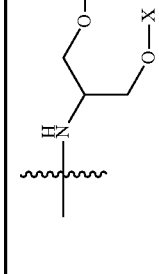

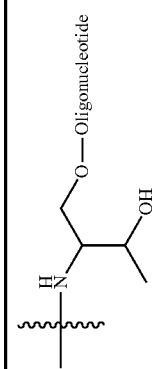 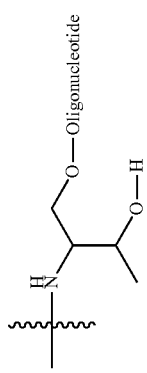

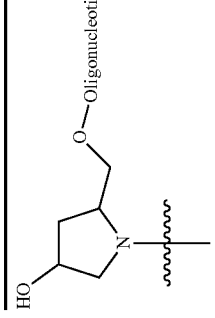 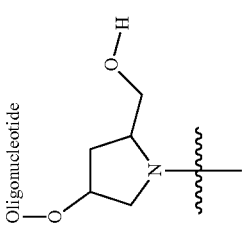

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

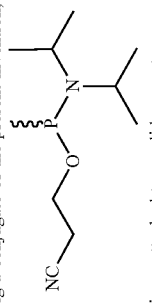

(e.g.,

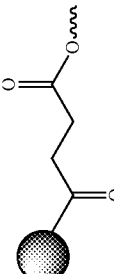

compatible with solid phase oligonucleotide synthesis and deprotection or ttached to a solid support (e.g.,

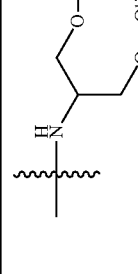

that enables solid phase oligonucleotide synthesis. The phrase "oligonucleotide/nucleotide" is meant to refer to a single nucleotide or an oligonucleotide.

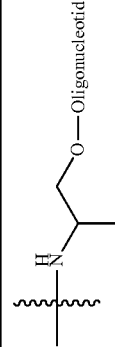
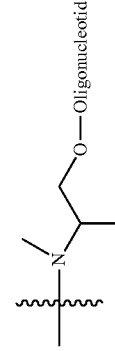
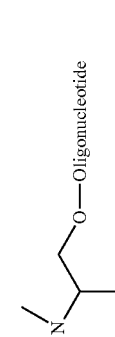
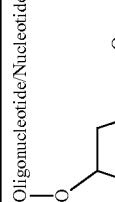
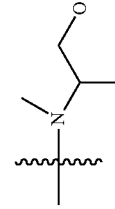

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite (e.g., 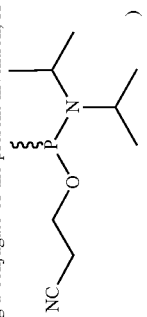)

compatible with solid phase oligonucleotide synthesis and deprotection or ttached to a solid support (e.g., 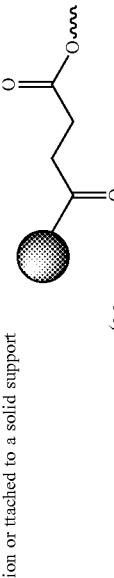)

that enables solid phase oligonucleotide synthesis. The phrase "oligonucleotide/nucleotide" is meant to refer to a single nucleotide or an oligonucleotide.

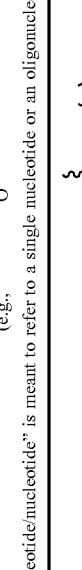
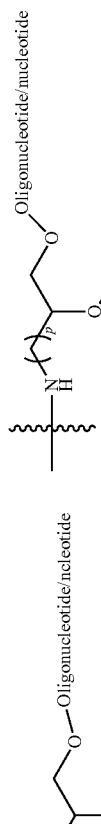

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite (e.g., 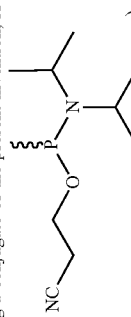)

compatible with solid phase oligonucleotide synthesis and deprotection or ttached to a solid support (e.g., 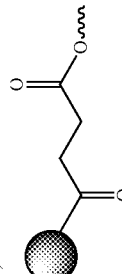)

that enables solid phase oligonucleotide synthesis. The phrase "oligonucleotide/nucleotide" is meant to refer to a single nucleotide or an oligonucleotide.

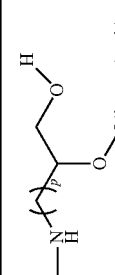

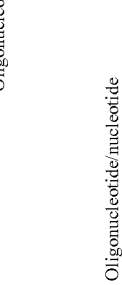

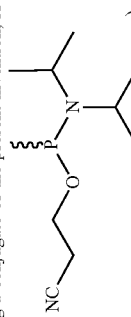

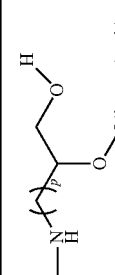

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite (e.g., 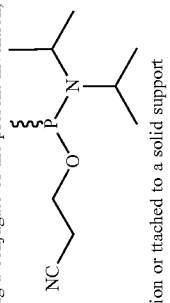)

compatible with solid phase oligonucleotide synthesis and deprotection or ttached to a solid support (e.g., 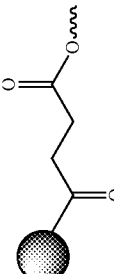)

that enables solid phase oligonucleotide synthesis. The phrase "oligonucleotide/nucleotide" is meant to refer to a single nucleotide or an oligonucleotide.

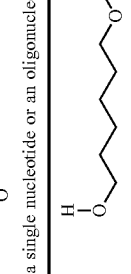

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite

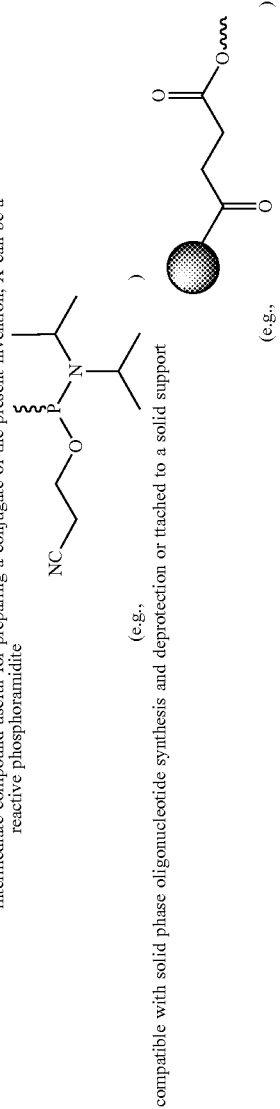

(e.g., compatible with solid phase oligonucleotide synthesis and deprotection or ttached to a solid support

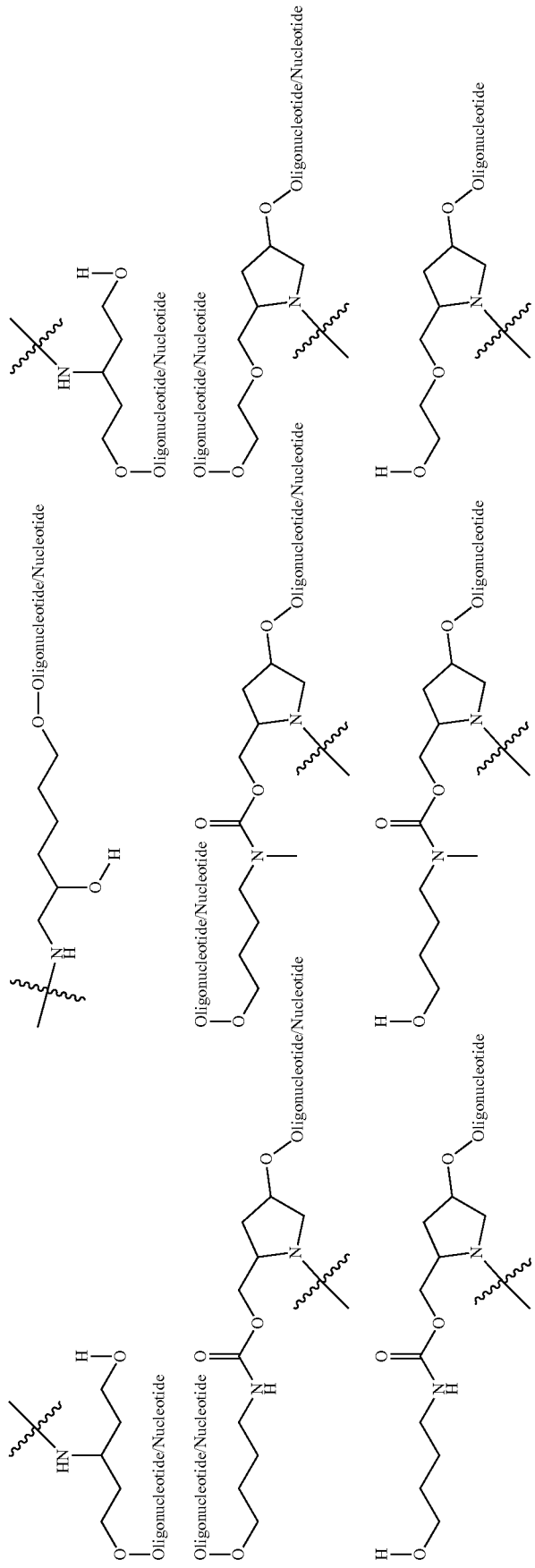

that enables solid phase oligonucleotide synthesis. The phrase "oligonucleotide/nucleotide" is meant to refer to a single nucleotide or an oligonucleotide.

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite (e.g., 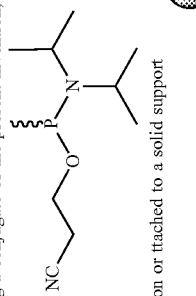)

compatible with solid phase oligonucleotide synthesis and deprotection or ttached to a solid support (e.g., 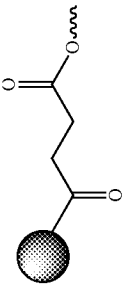)

that enables solid phase oligonucleotide synthesis. The phrase "oligonucleotide/nucleotide" is meant to refer to a single nucleotide or an oligonucleotide.

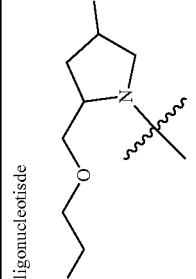

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite (e.g., [structure]) compatible with solid phase oligonucleotide synthesis and deprotection or ttached to a solid support (e.g., [structure]) that enables solid phase oligonucleotide synthesis. The phrase "oligonucleotide/nucleotide" is meant to refer to a single nucleotide or an oligonucleotide.

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

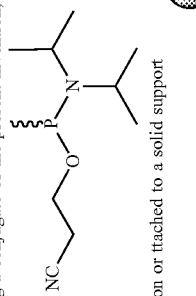

(e.g.,

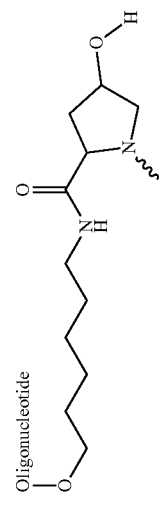

) compatible with solid phase oligonucleotide synthesis and deprotection or ttached to a solid support (e.g.,

) that enables solid phase oligonucleotide synthesis. The phrase "oligonucleotide/nucleotide" is meant to refer to a single nucleotide or an oligonucleotide.

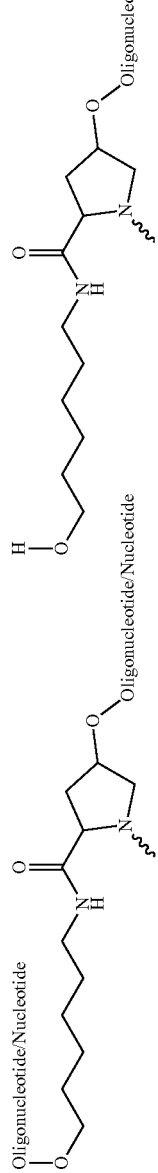
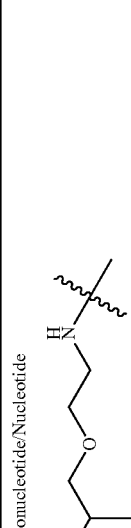
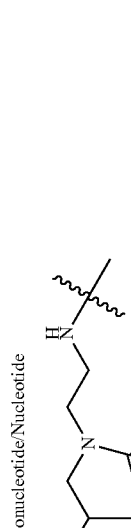
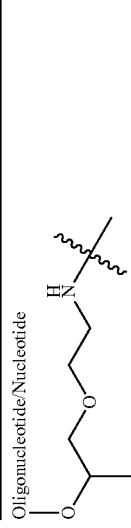
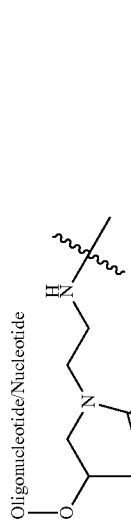

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite

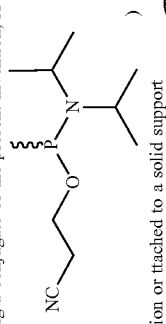

(e.g., compatible with solid phase oligonucleotide synthesis and deprotection or ttached to a solid support

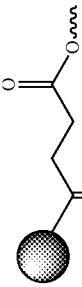

(e.g., 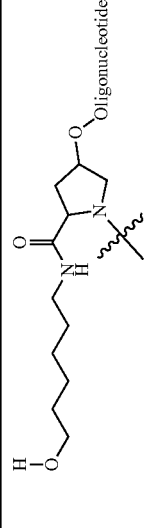 ) that enables solid phase oligonucleotide synthesis. The phrase "oligonucleotide/nucleotide" is meant to refer to a single nucleotide or an oligonucleotide.

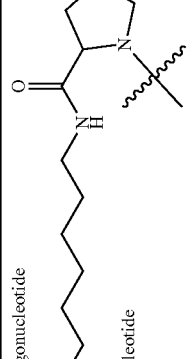
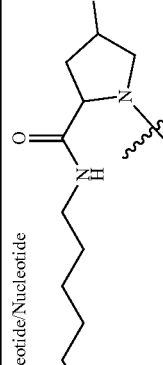
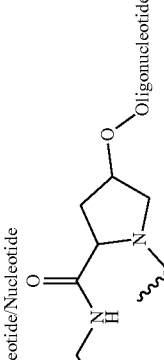
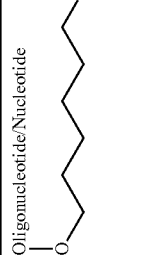
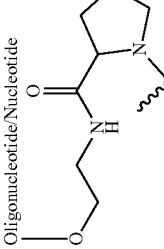

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

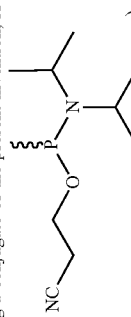

(e.g., compatible with solid phase oligonucleotide synthesis and deprotection or ttached to a solid support

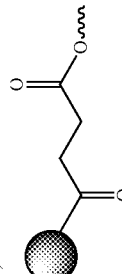

(e.g., that enables solid phase oligonucleotide synthesis. The phrase "oligonucleotide/nucleotide" is meant to refer to a single nucleotide or an oligonucleotide.

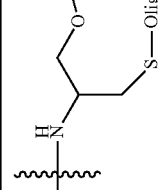
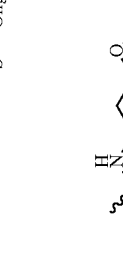
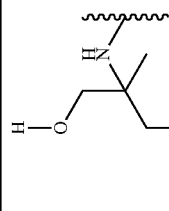
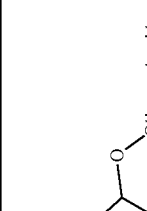
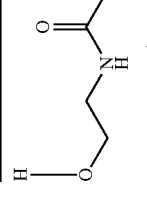
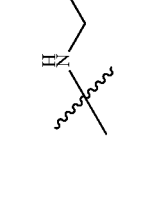
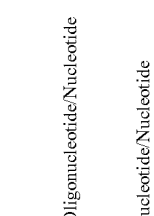
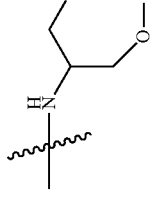
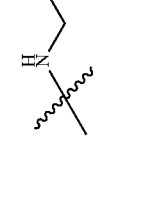
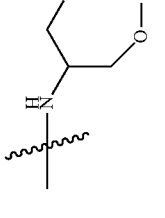

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite (e.g.,

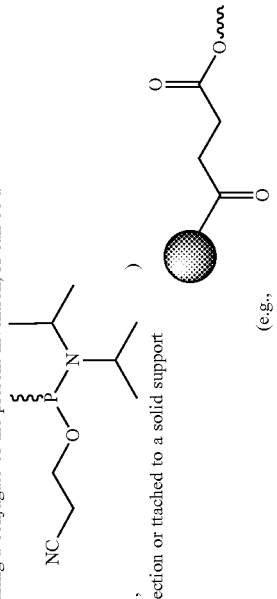

) compatible with solid phase oligonucleotide synthesis and deprotection or ttached to a solid support (e.g.,

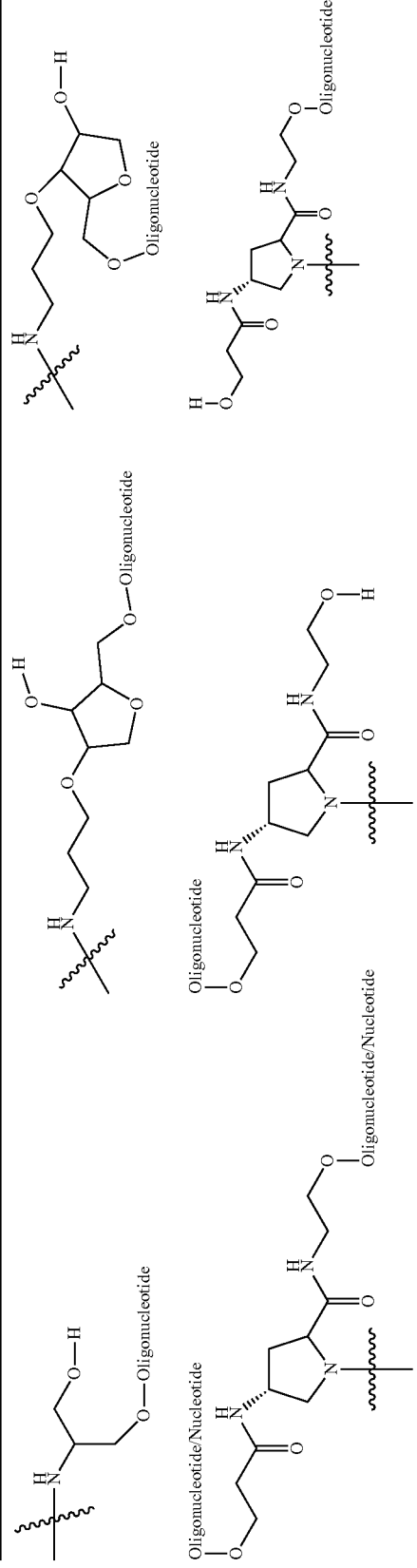

) that enables solid phase oligonucleotide synthesis. The phrase "oligonucleotide/nucleotide" is meant to refer to a single nucleotide or an oligonucleotide.

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

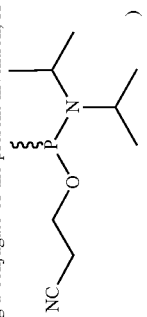

(e.g., compatible with solid phase oligonucleotide synthesis and deprotection or attached to a solid support

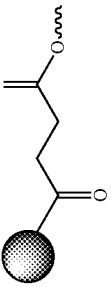

(e.g., that enables solid phase oligonucleotide synthesis. The phrase "oligonucleotide/nucleotide" is meant to refer to a single nucleotide or an oligonucleotide.

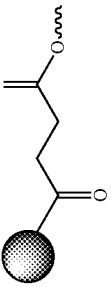
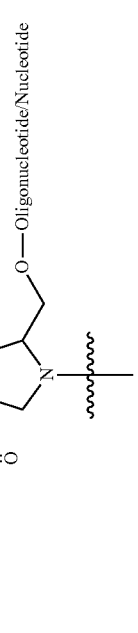
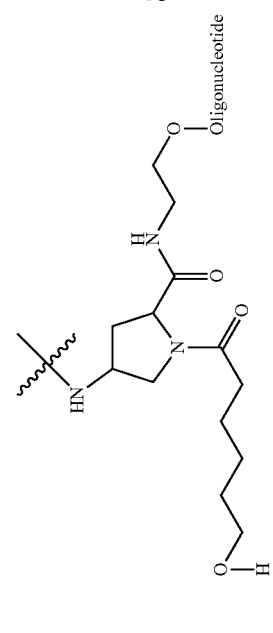
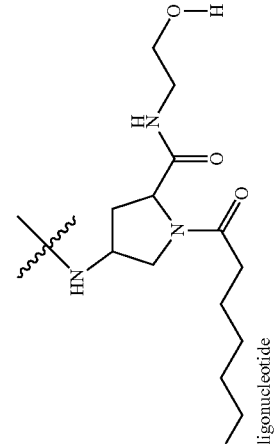
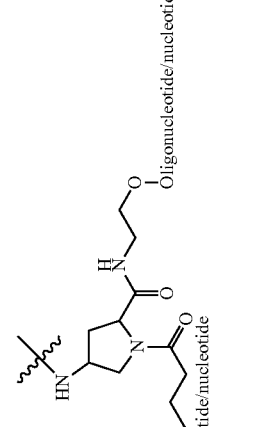
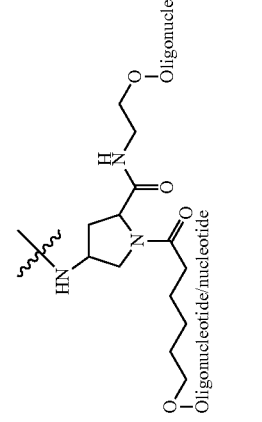

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite (e.g., 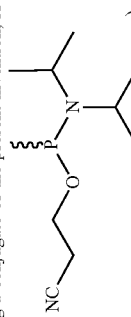)

compatible with solid phase oligonucleotide synthesis and deprotection or ttached to a solid support (e.g., 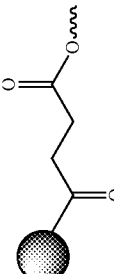)

that enables solid phase oligonucleotide synthesis. The phrase "oligonucleotide/nucleotide" is meant to refer to a single nucleotide or an oligonucleotide.

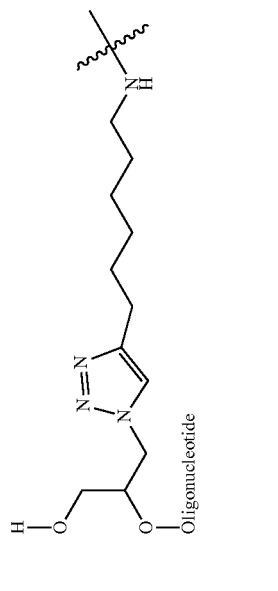
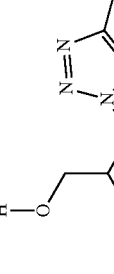
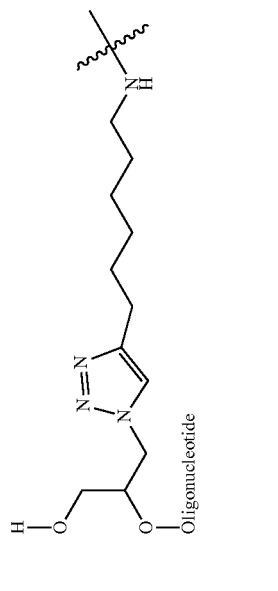
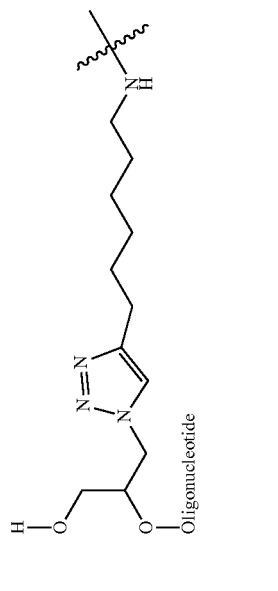
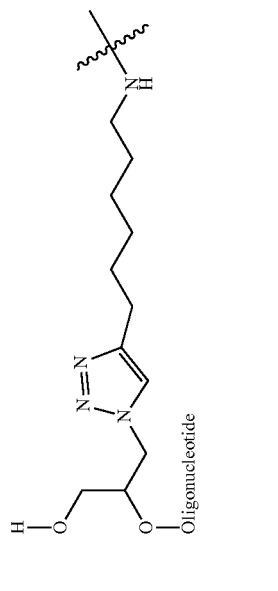
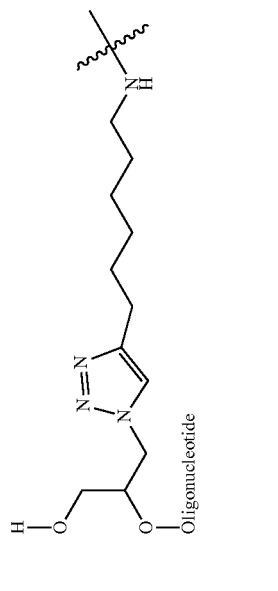
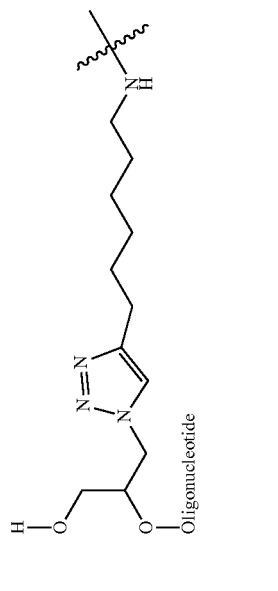
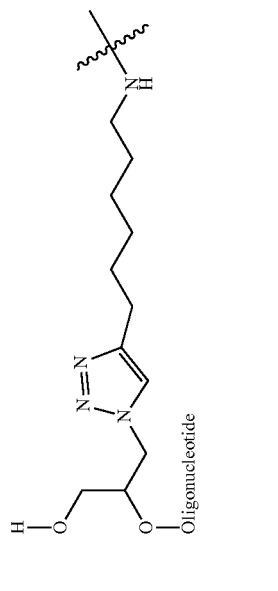

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH₂. When the Linker group is incorporated into an intermediate compound useful for preparing a conjugate of the present invention, X can be a reactive phosphoramidite

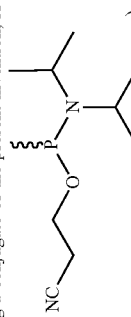

(e.g., compatible with solid phase oligonucleotide synthesis and deprotection or ttached to a solid support

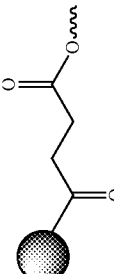

(e.g., that enables solid phase oligonucleotide synthesis. The phrase "oligonucleotide/nucleotide" is meant to refer to a single nucleotide or an oligonucleotide.

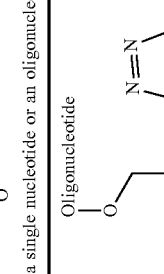

TABLE 1A-continued

Linker Groups

The Linkers below in Table 1A are shown with one or more oligonucleotides attached to them. It will be understood to those skilled in the art that the Linker is the chemical moiety without the oligonucleotide(s). The squiggly line is the point of attachment for the Ligand. X can be hydrogen, a leaving group, —OH, or —NH$_2$. When the Linker group is incorporated into an intermediate compound useful for preparing a conjugate of the present invention, X can be a reactive phosphoramidite

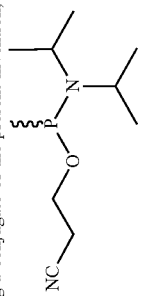

(e.g., compatible with solid phase oligonucleotide synthesis and deprotection or ttached to a solid support

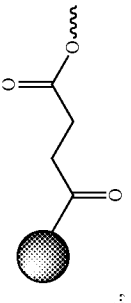

(e.g.,

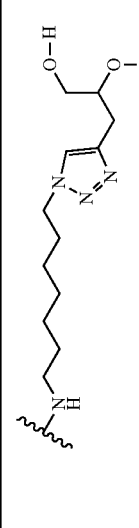

)

that enables solid phase oligonucleotide synthesis. The phrase "oligonucleotide/nucleotide" is meant to refer to a single nucleotide or an oligonucleotide.

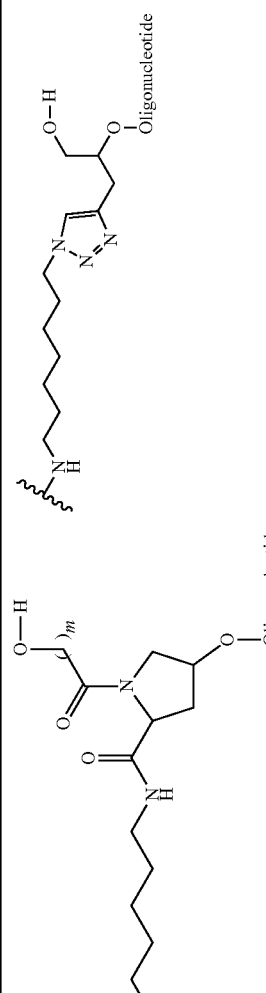

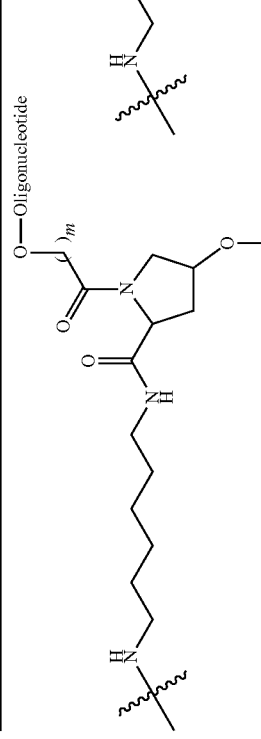

∿∿∿ indicates site of attachment of the ligand;

Each structure represents chirally pure or racemic isomers when one or more asymmetric centers present. The linkage between oligonucleotide/nucleotide and the conjugate moiety is phosphate phorphosphorothioate.
m and p are independently 1-8 (e.g., 1-4).

TABLE 2

Ligands[a,b,d]

TABLE 2-continued
Ligands[a,b,d]
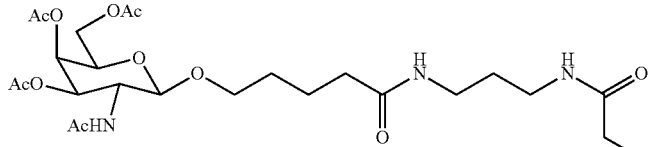
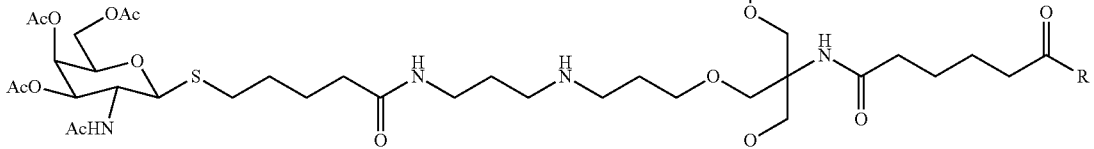
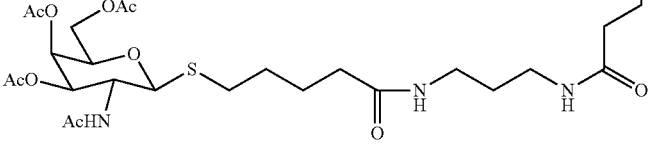

TABLE 2-continued
Ligands[a,b,d]
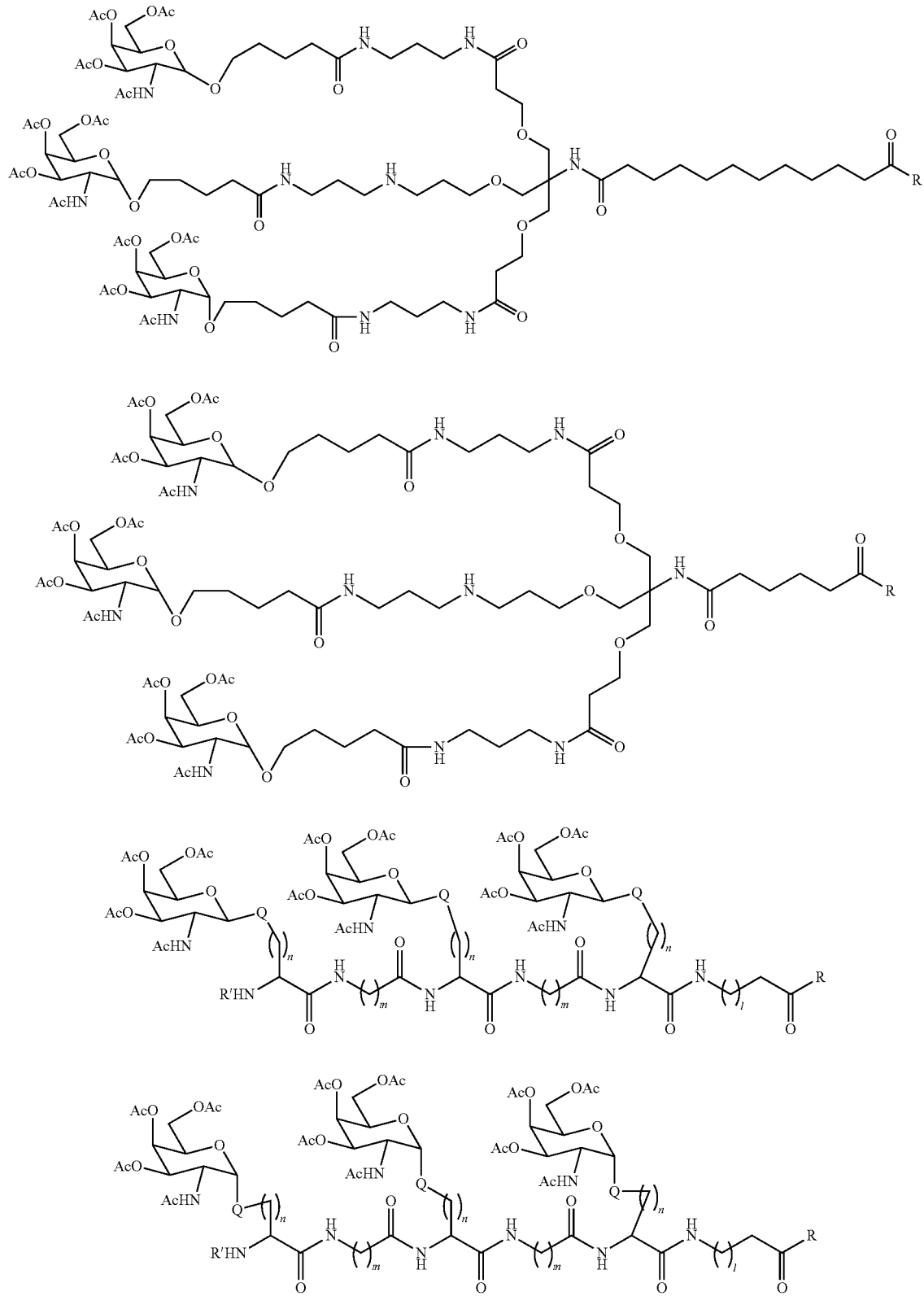

TABLE 2-continued
Ligands[a,b,d]
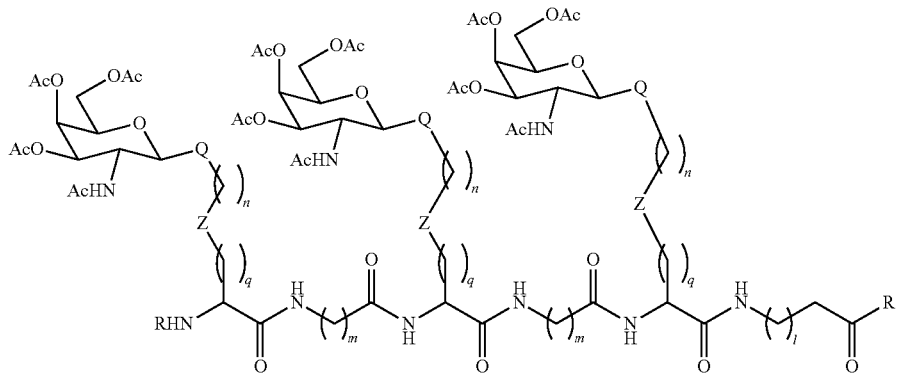
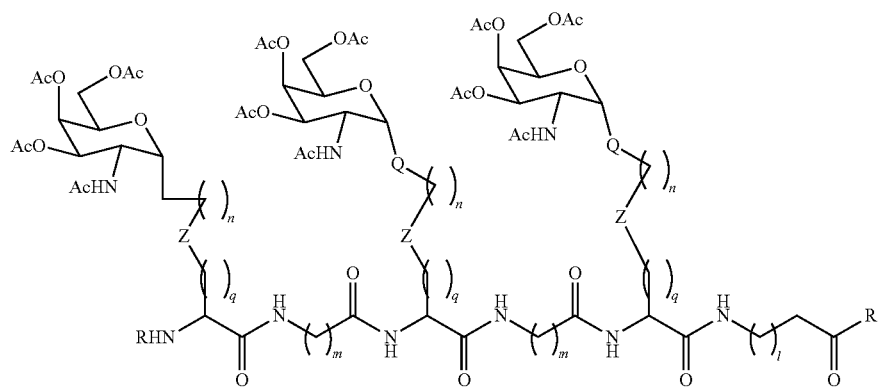
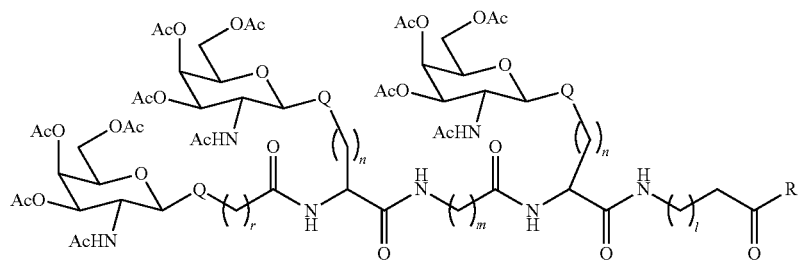
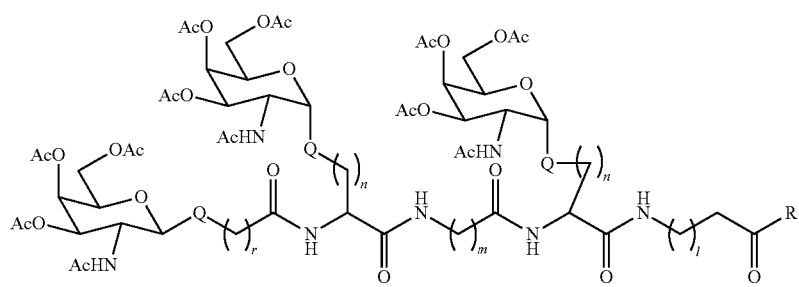

TABLE 2-continued
Ligands[a,b,d]
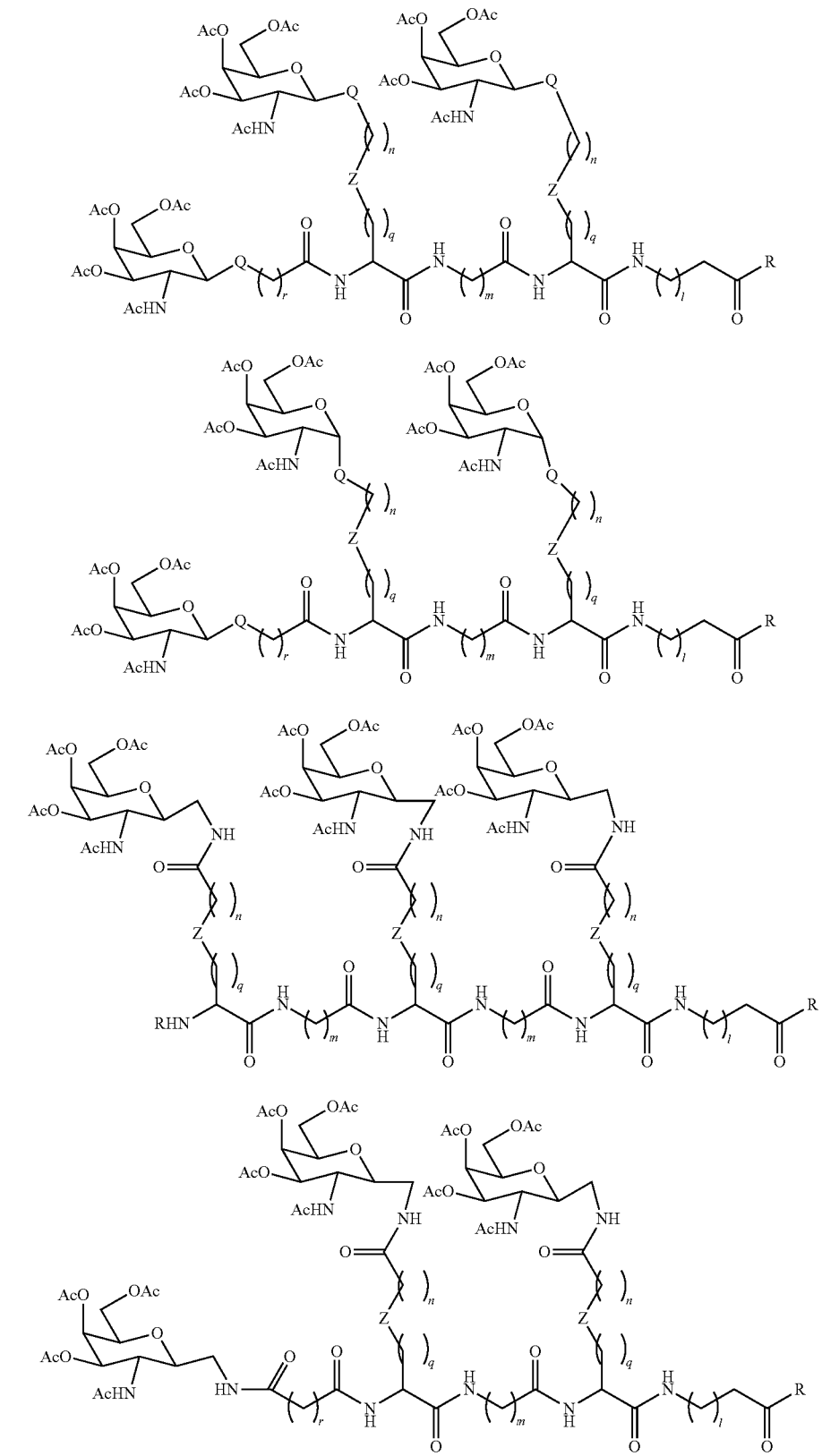

TABLE 2-continued

Ligands[a,b,d]

TABLE 2-continued

Ligands[a,b,d]

TABLE 2-continued
Ligands[a,b,d]
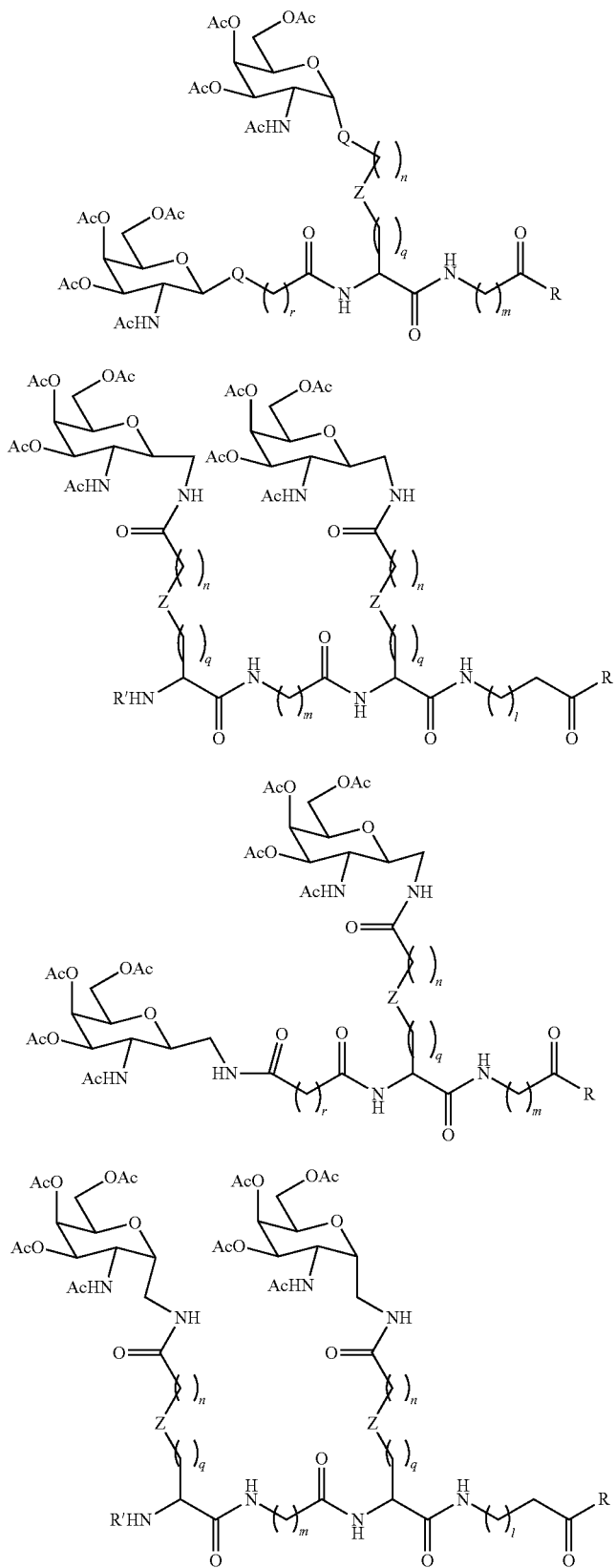

TABLE 2-continued
Ligands[a,b,d]
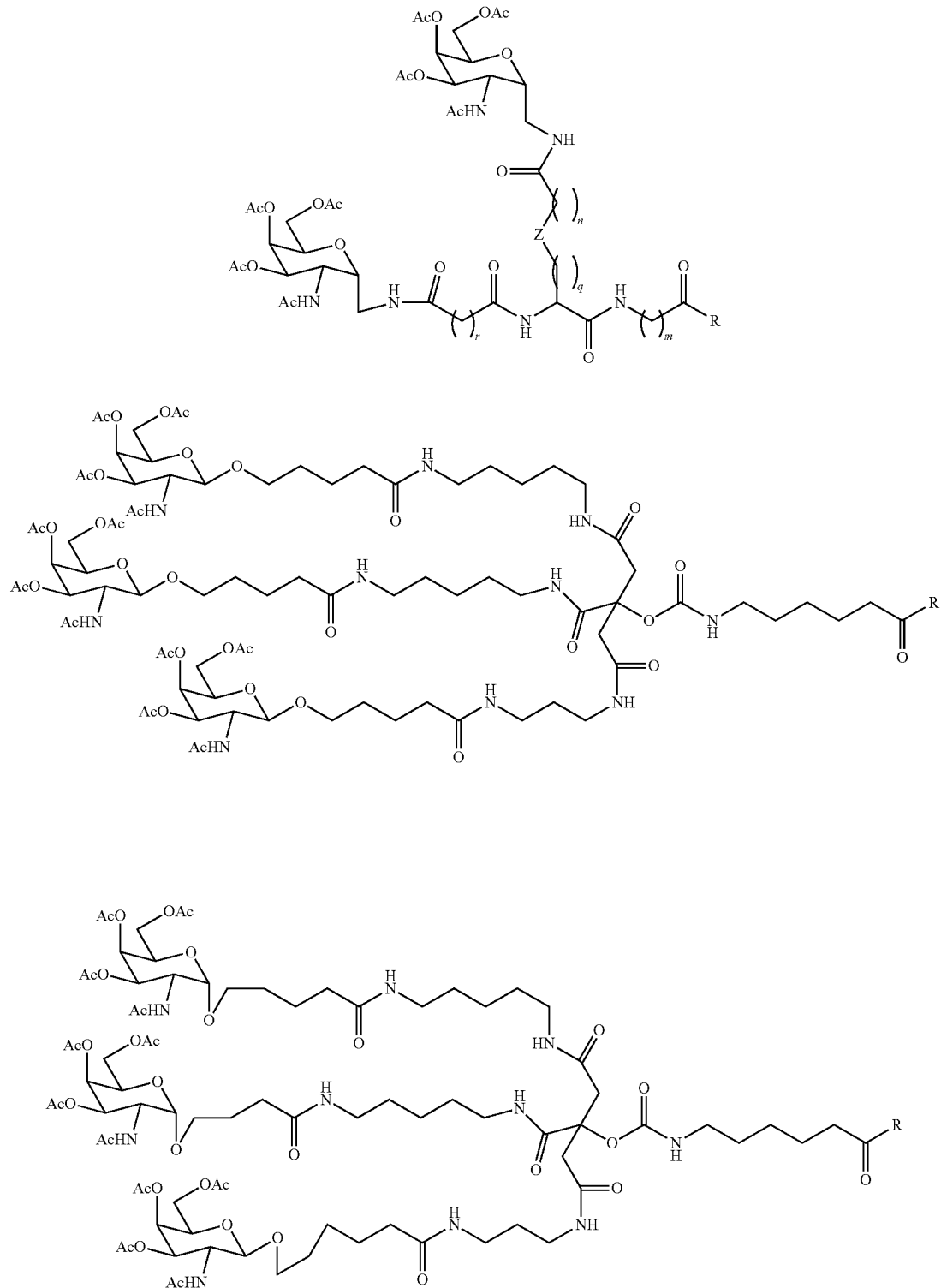

TABLE 2-continued
Ligands[a,b,d]
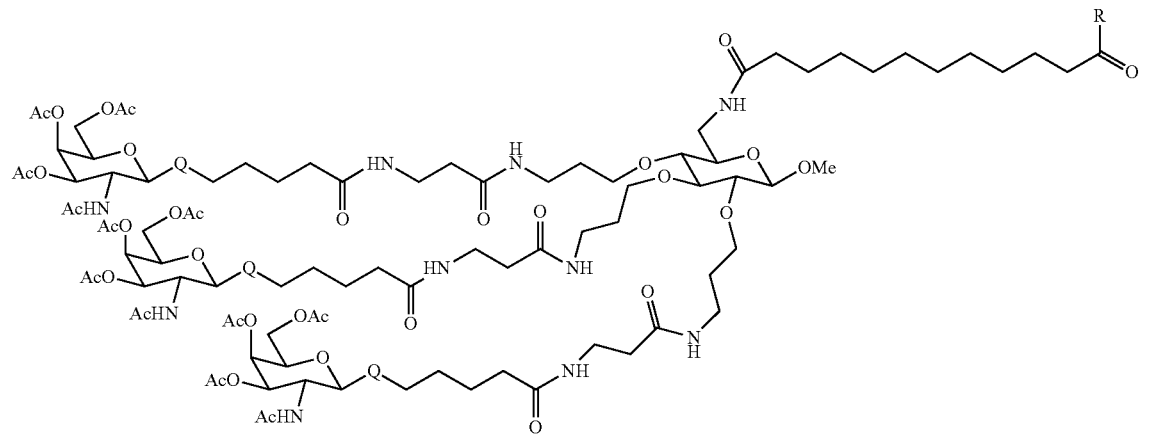
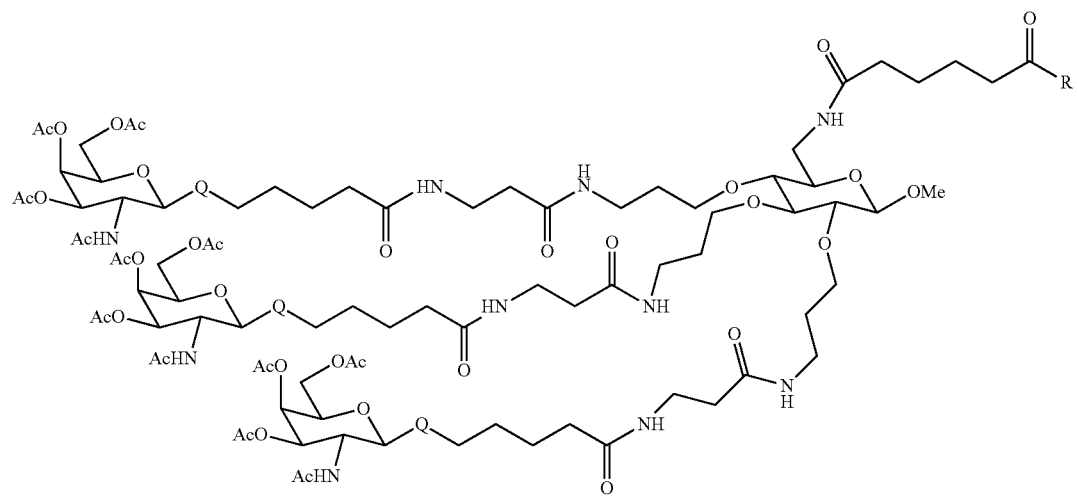
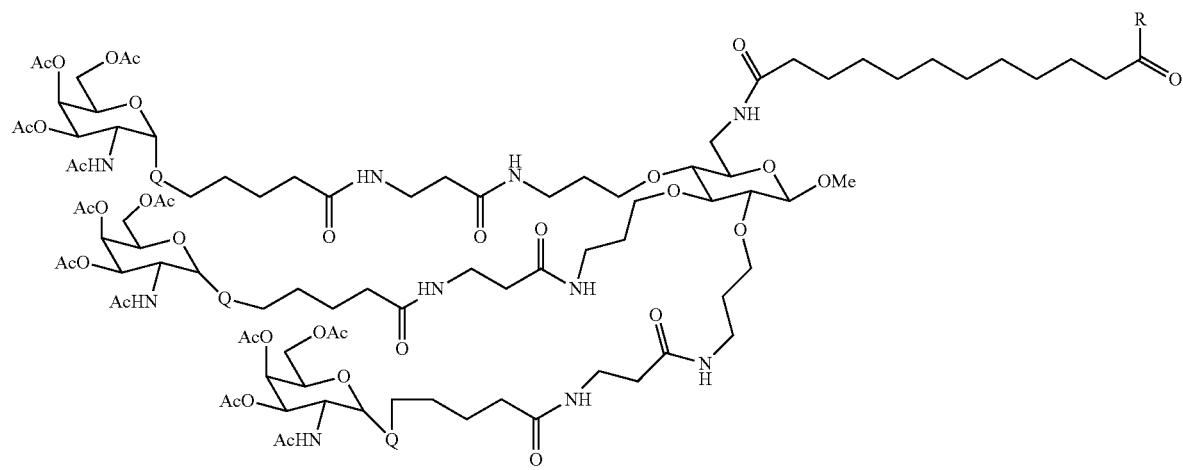

TABLE 2-continued
Ligands[a,b,d]
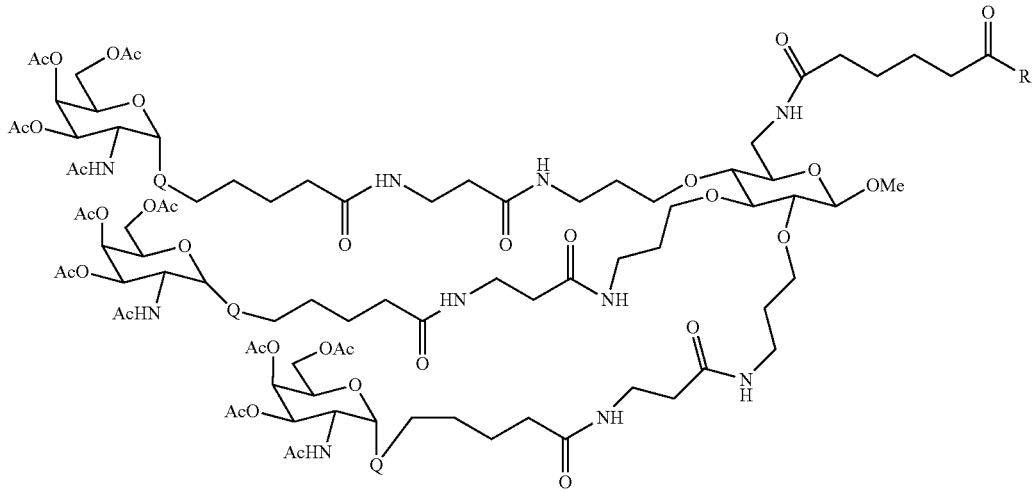
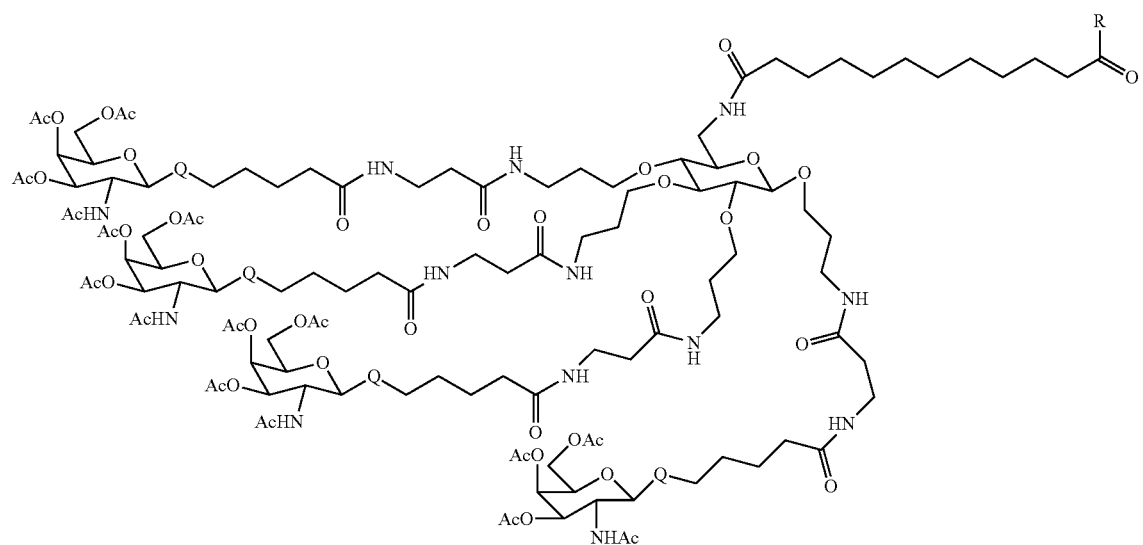

TABLE 2-continued
Ligands[a,b,d]
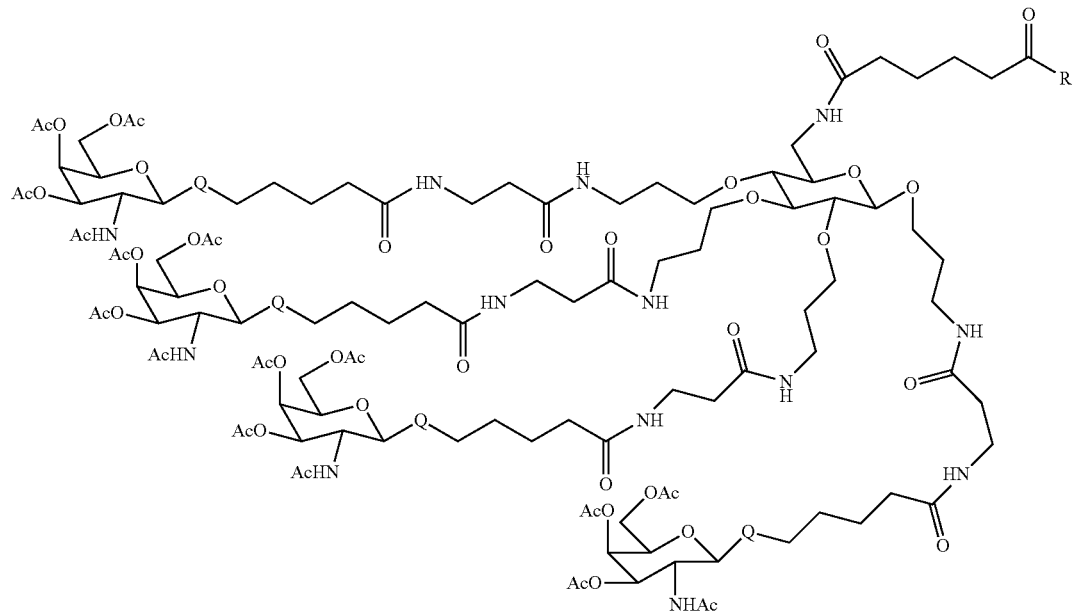
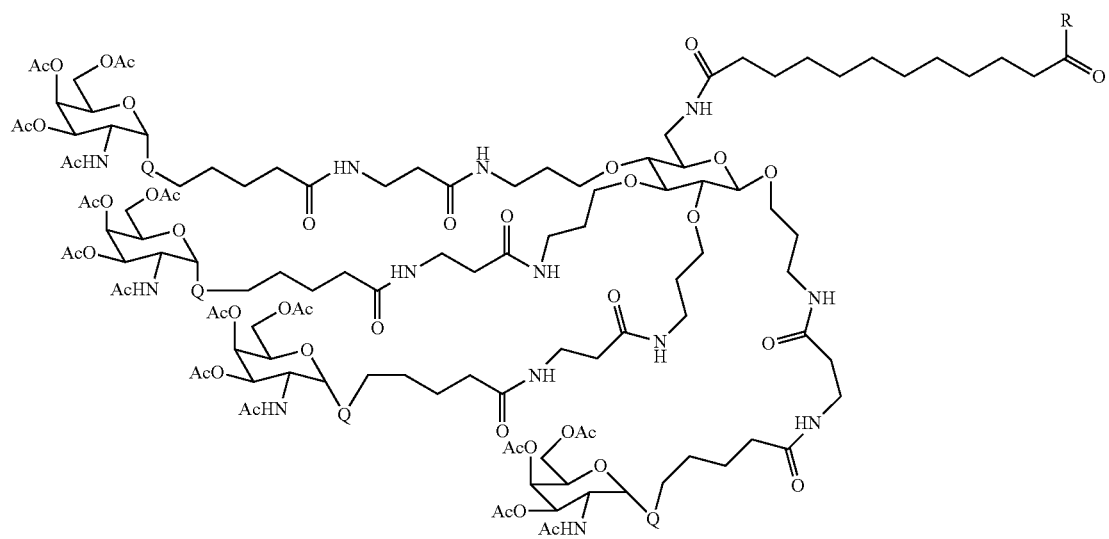

TABLE 2-continued
Ligands[a,b,d]
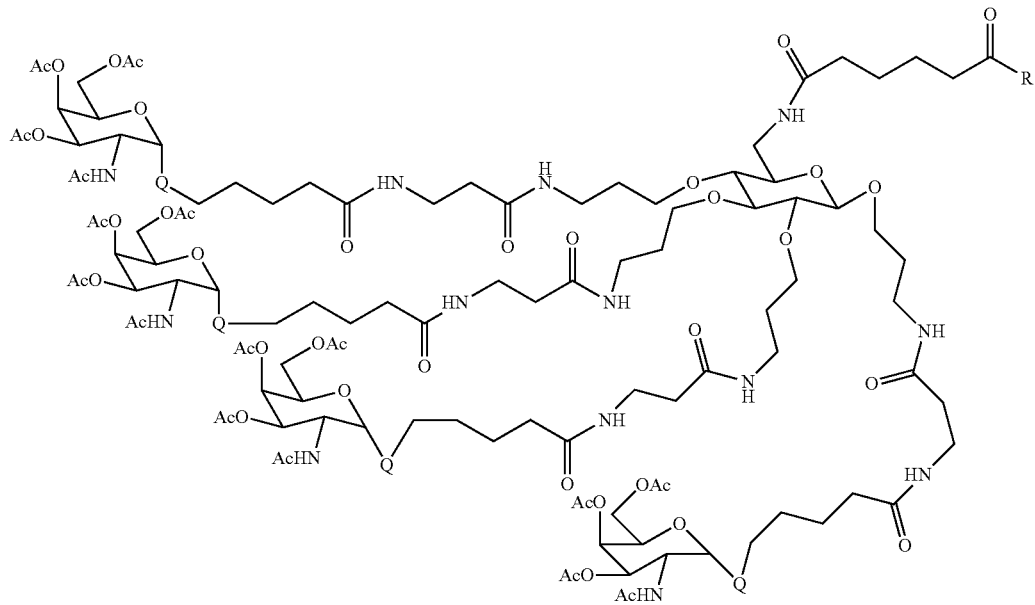
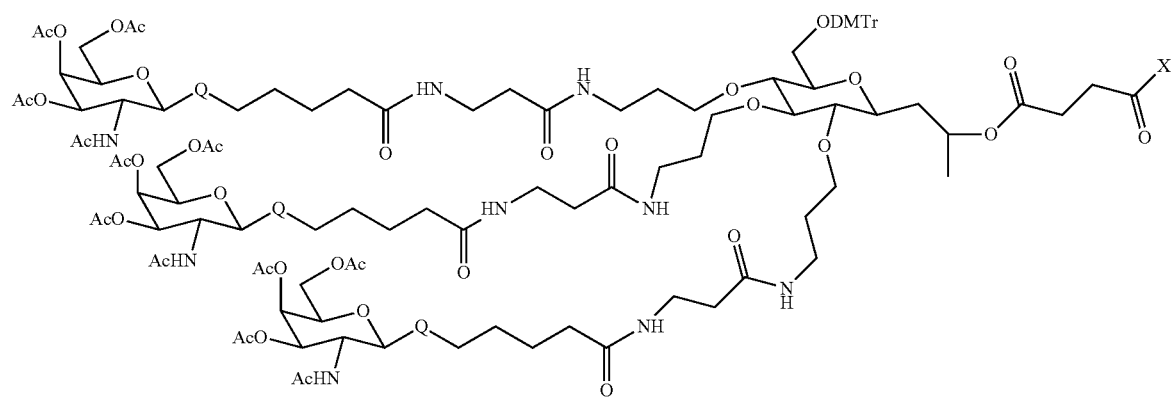
where X is the point of attachemnt to the Linker
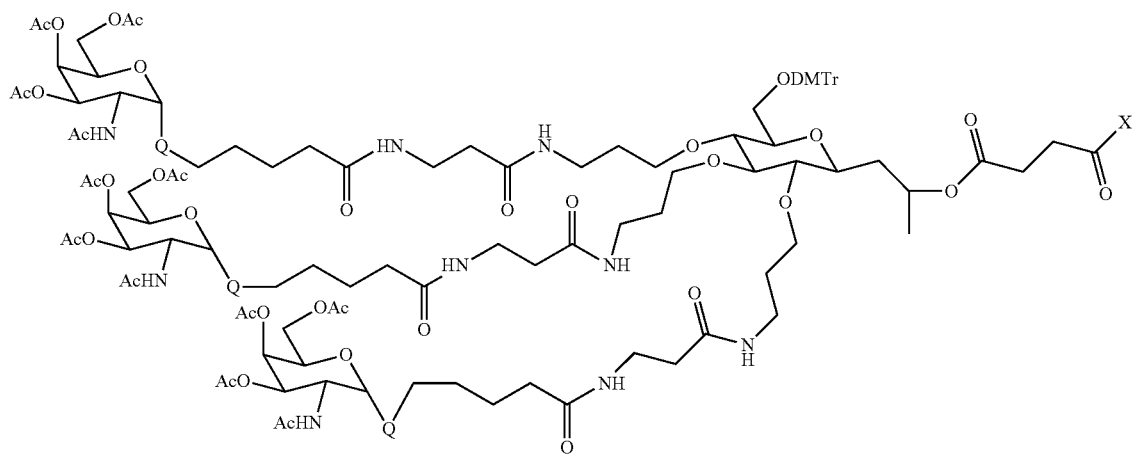
Where X is the point of attachemnt to the Linker TABLE 2-continued
Ligands[a,b,d]
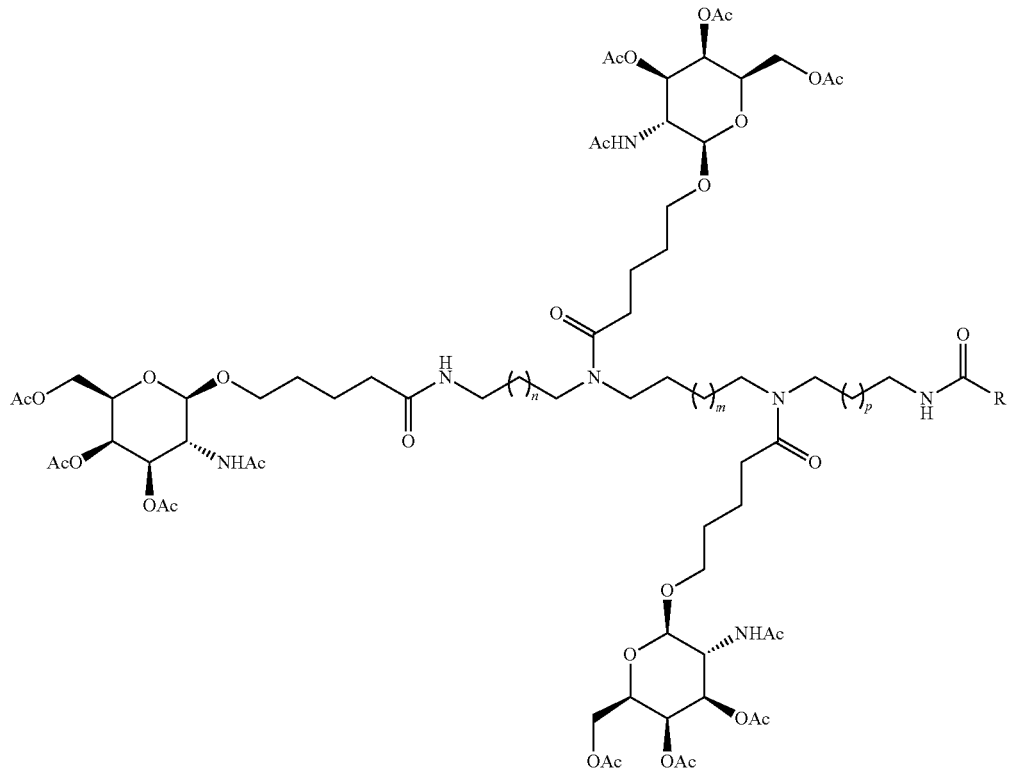
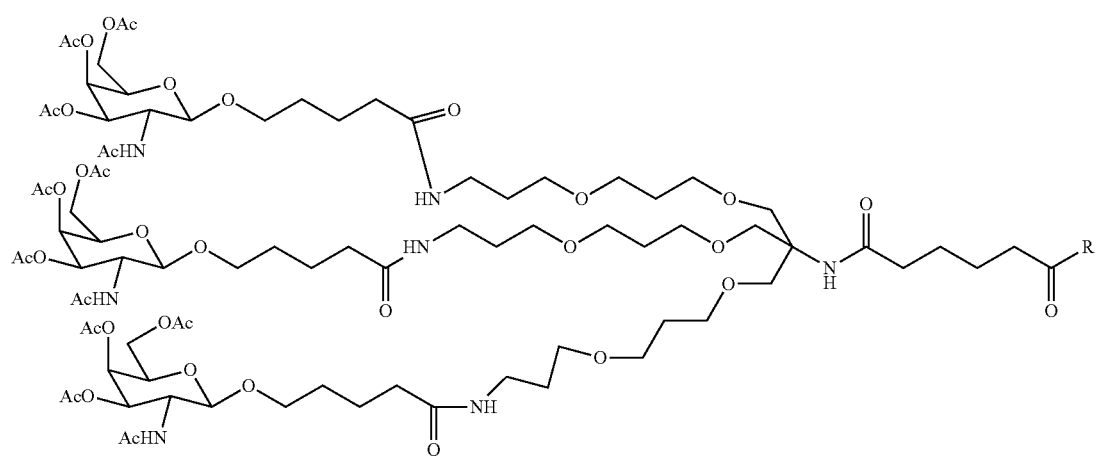

TABLE 2-continued
Ligands[a,b,d]
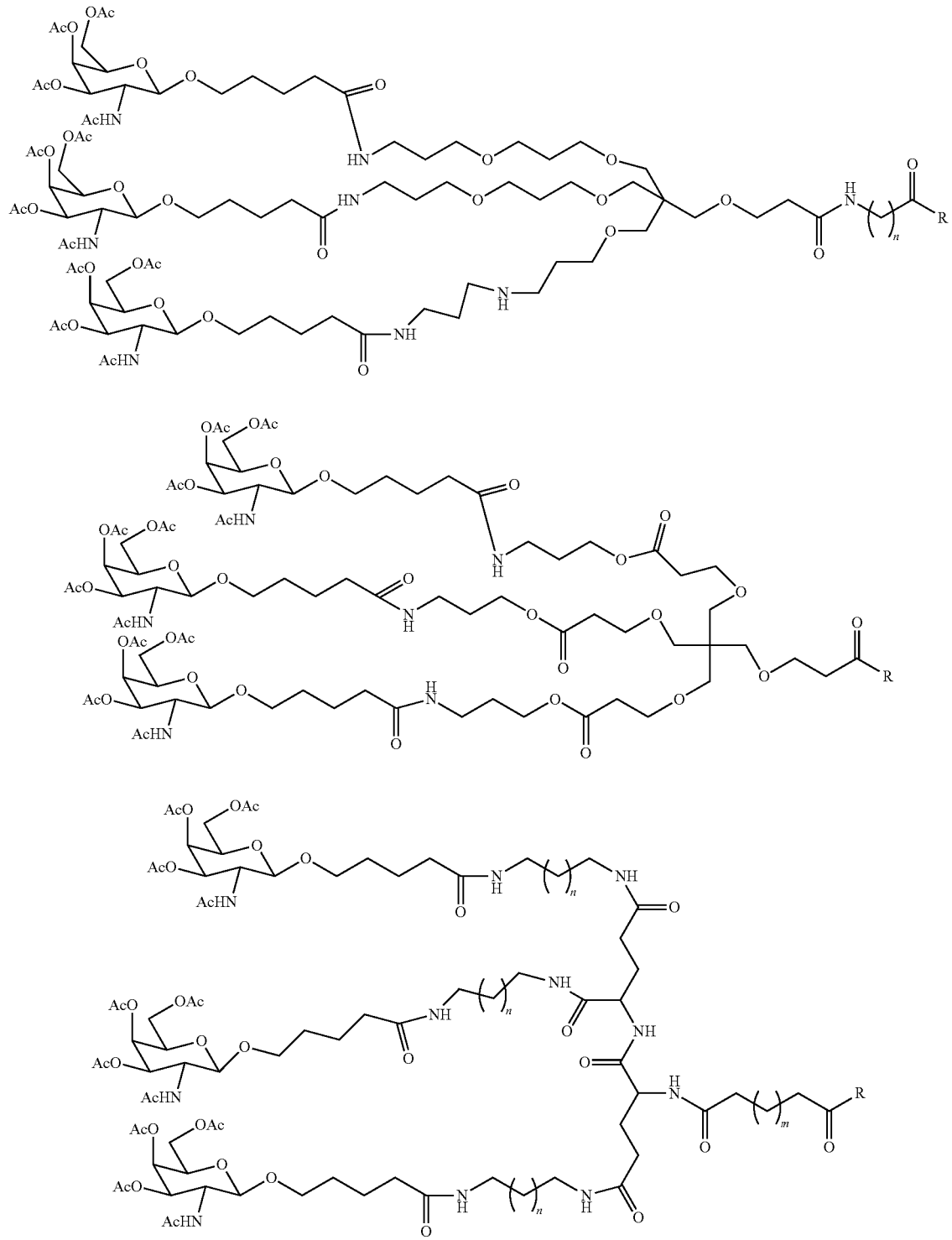

TABLE 2-continued
Ligands[a,b,d]
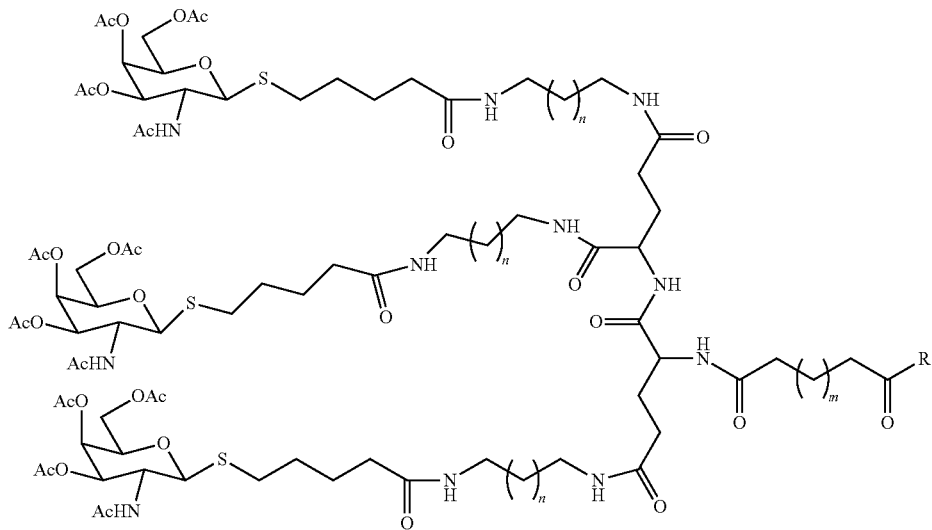
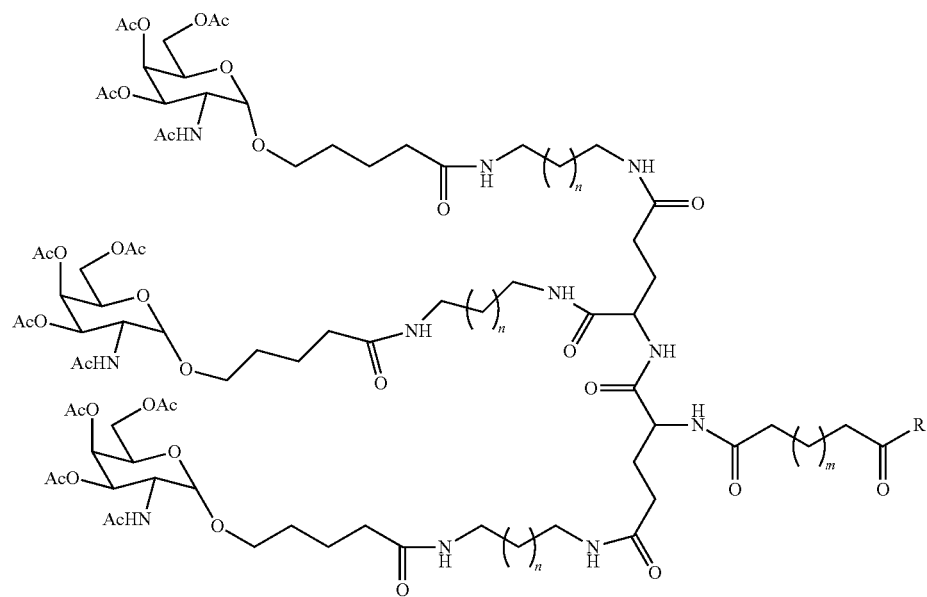

TABLE 2-continued

Ligands[a,b,d]

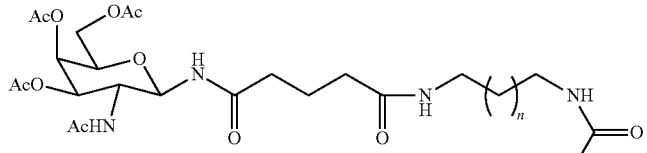

[a] Q = O, S, CH$_2$;

Z = —CONH—, —NHCO—, —OC(O)NH—, or —NHC(O)O—;

R is the point of attachment to a Linker;

R' = Ac, COCF$_3$ or any amine protecting group compatible with oligonucleotide (RNA/DNA) synthesis and deprotection conditions.

[b] each of the variables l, m, n, p, q, and r independently ranges from about 0 to about 10.

[d] Each structure represents chirally pure or racemic isomers when one or more asymmetric centers are present.

TABLE 2A

Ligands[a,b,c,d]

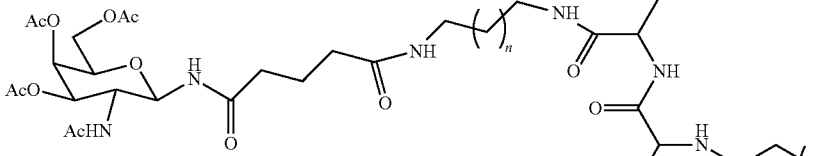

TABLE 2A-continued
Ligands[a,b,c,d]
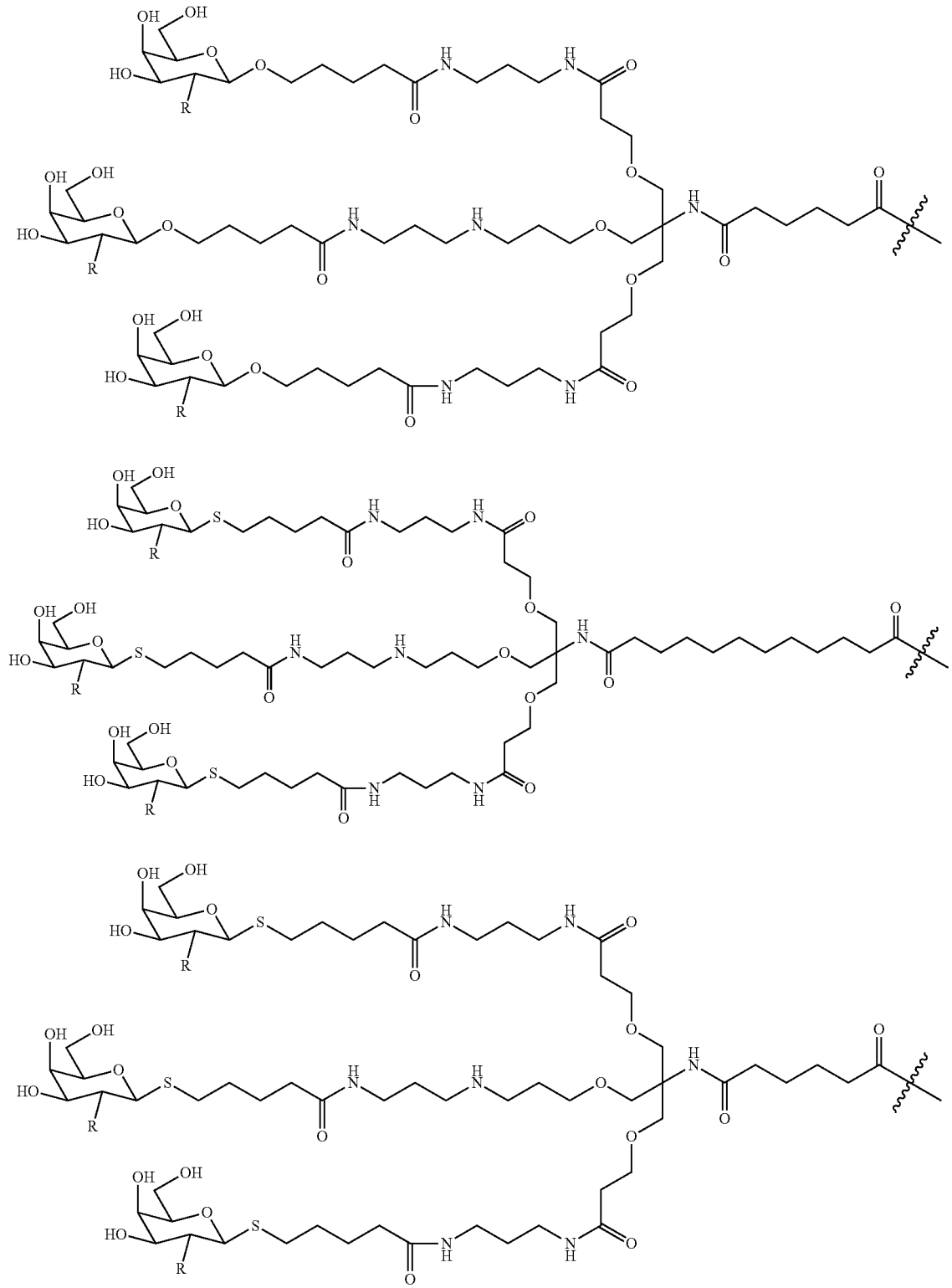

TABLE 2A-continued
Ligands[a,b,c,d]
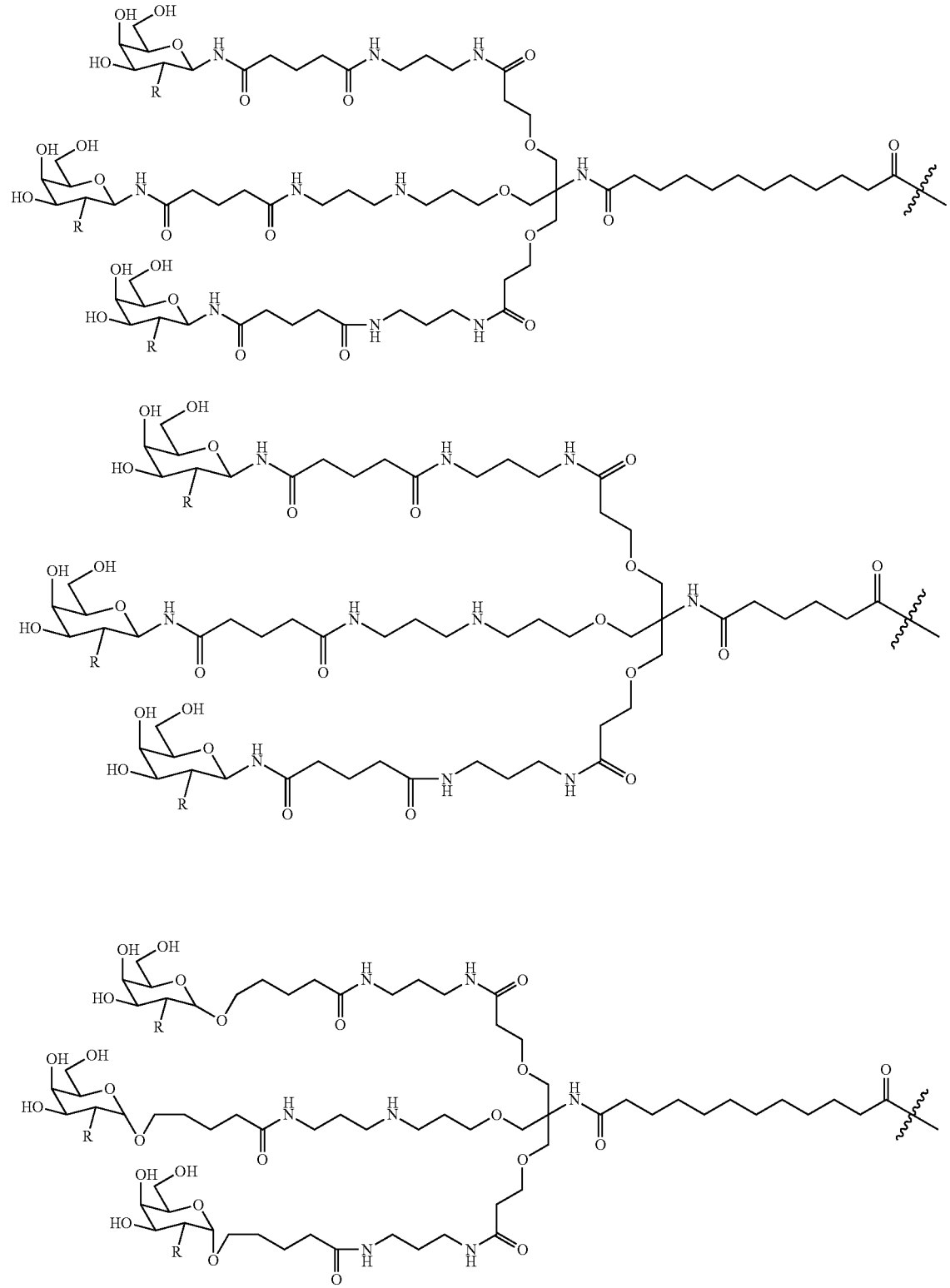

TABLE 2A-continued
Ligands[a,b,c,d]
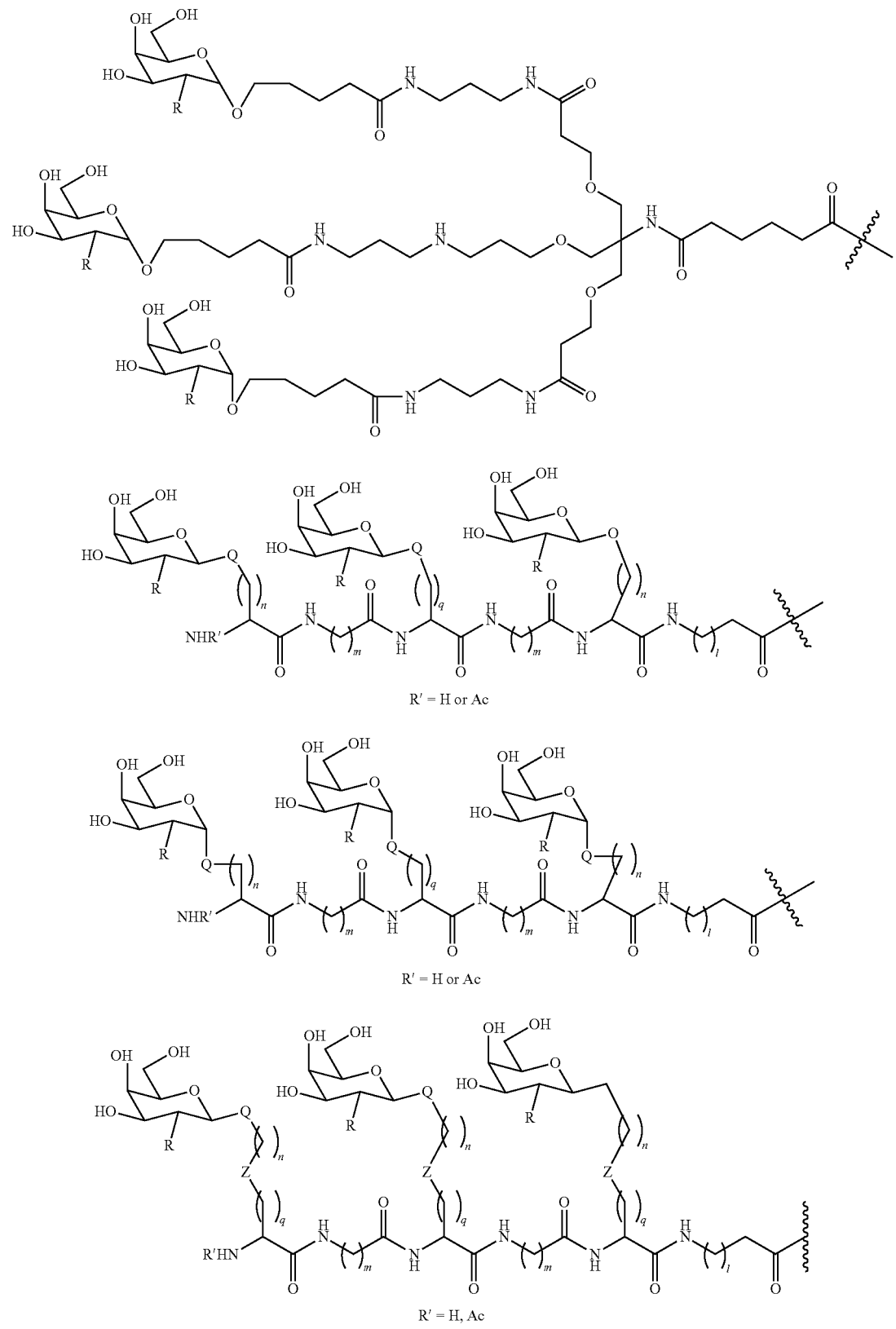

TABLE 2A-continued
Ligands[a,b,c,d]
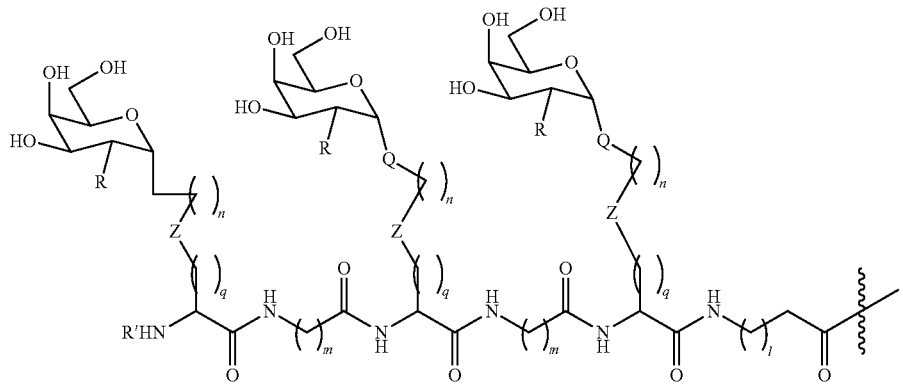
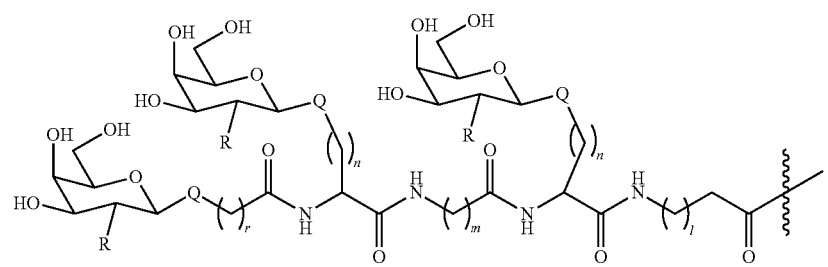
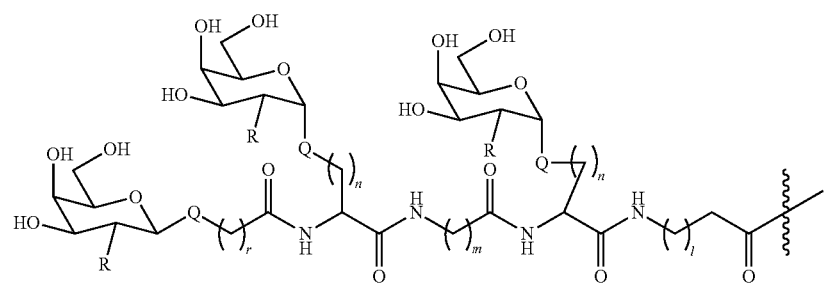
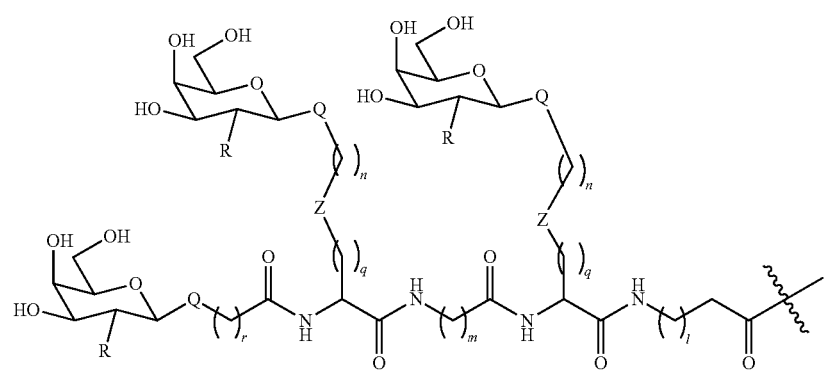

TABLE 2A-continued
Ligands[a,b,c,d]
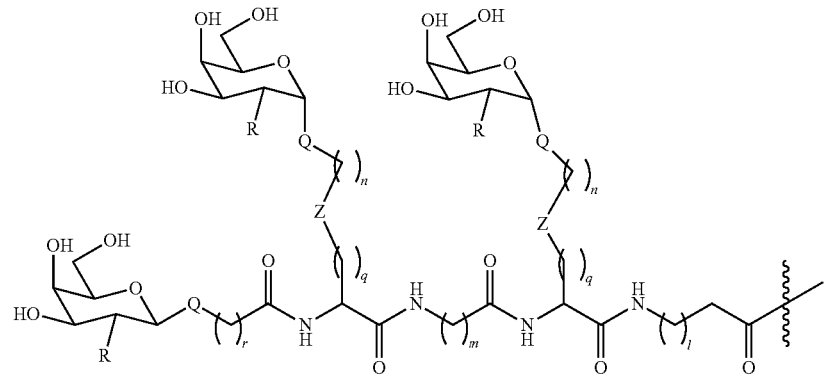
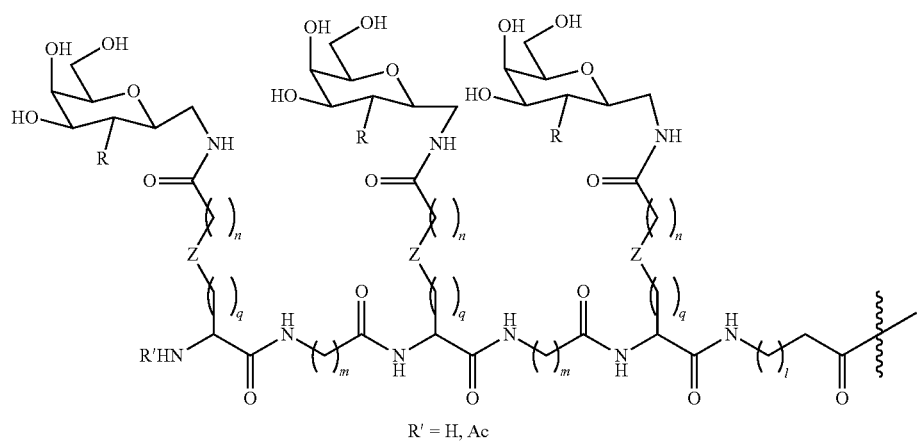
R' = H, Ac
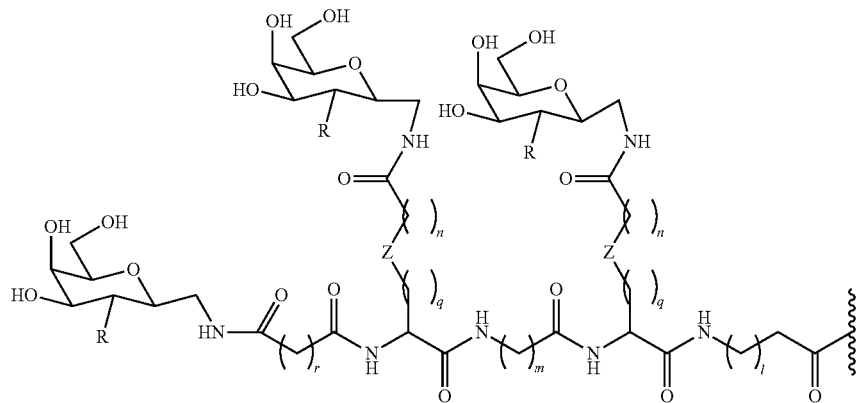

TABLE 2A-continued
Ligands[a,b,c,d]
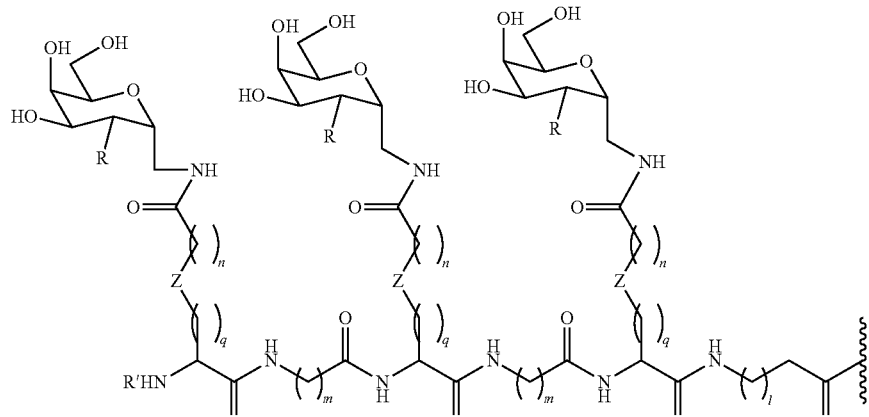
R' = H, Ac
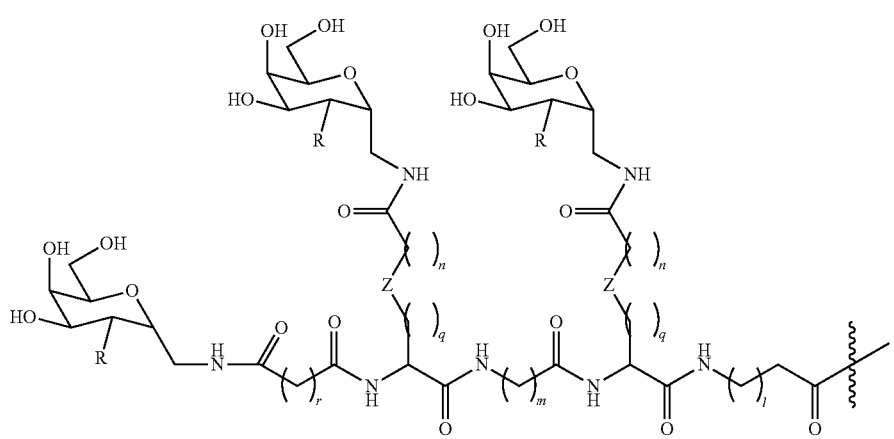
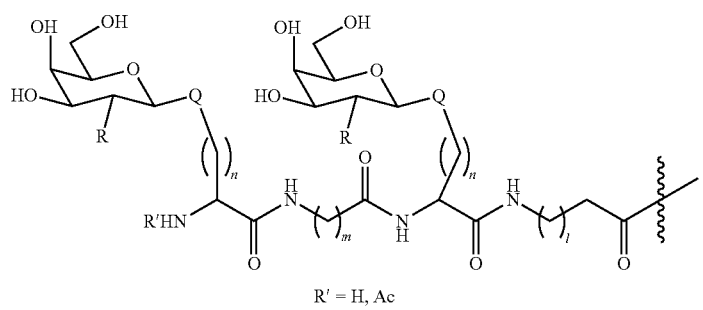
R' = H, Ac
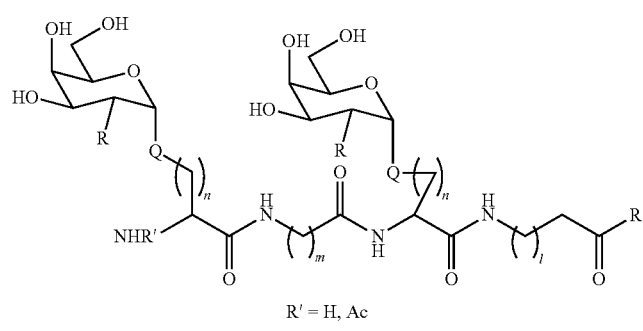
R' = H, Ac TABLE 2A-continued
Ligands[a,b,c,d]
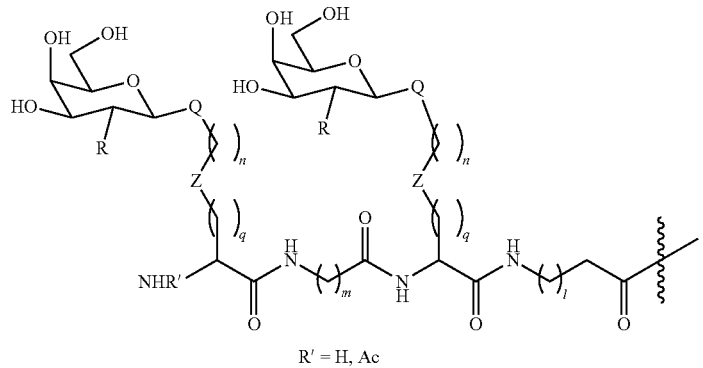
R' = H, Ac
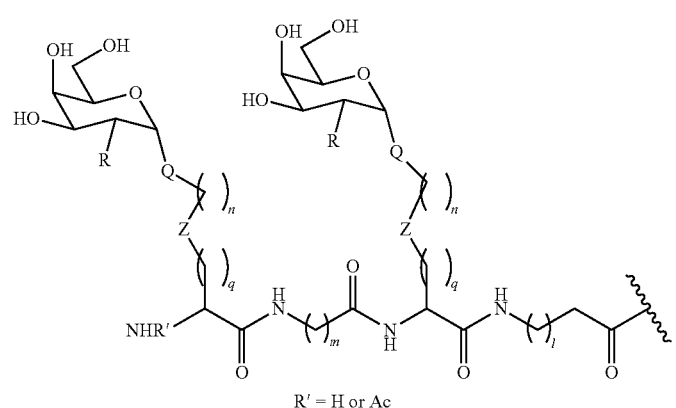
R' = H or Ac
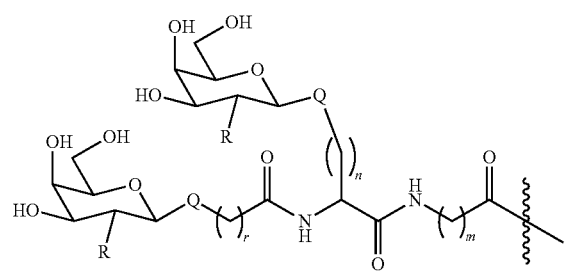
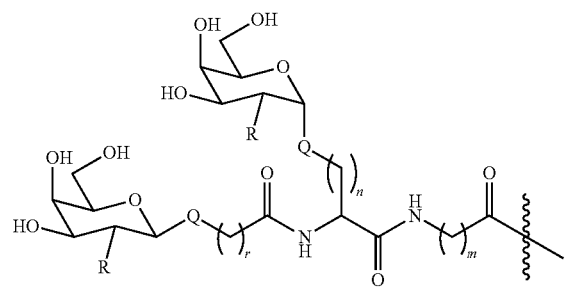

TABLE 2A-continued
Ligands[a,b,c,d]
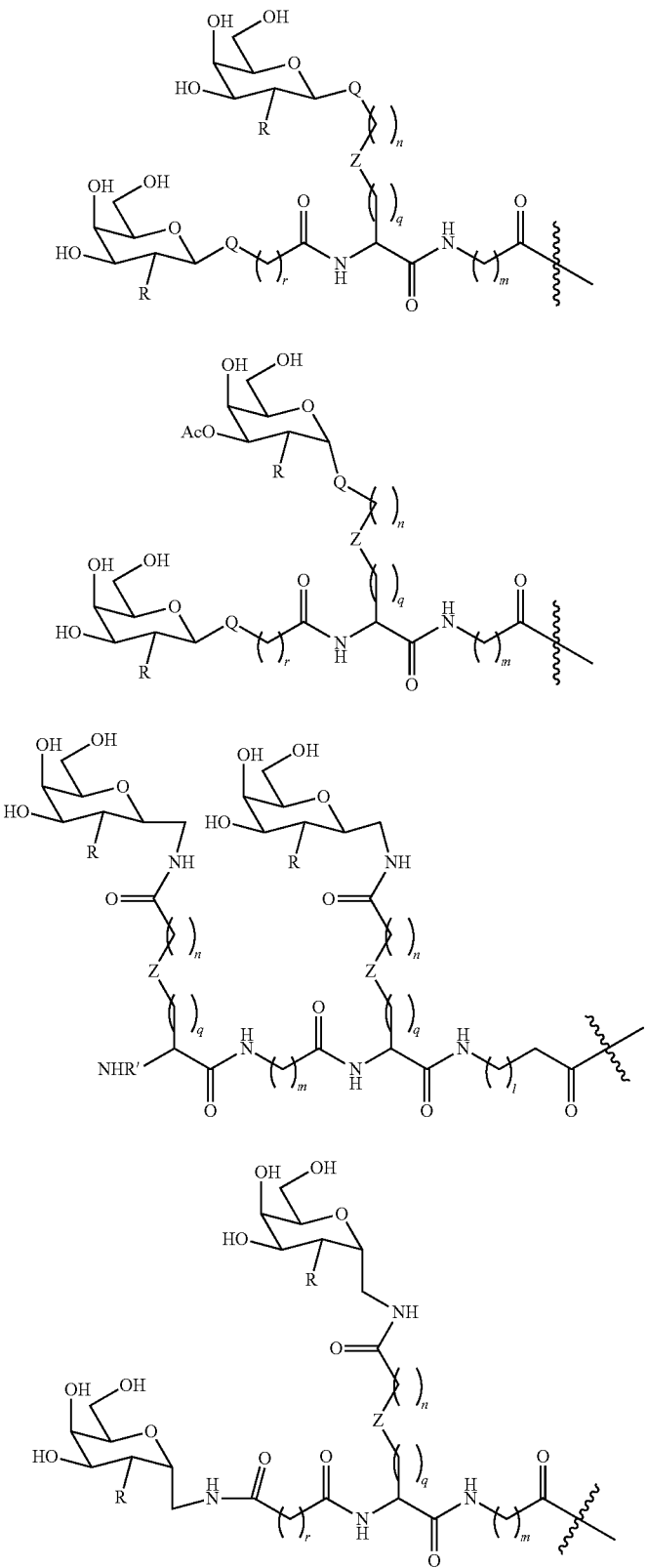

TABLE 2A-continued
Ligands[a,b,c,d]
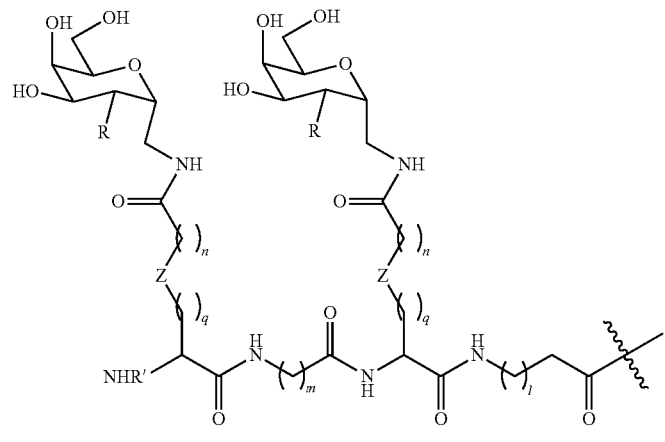
R' = H or Ac
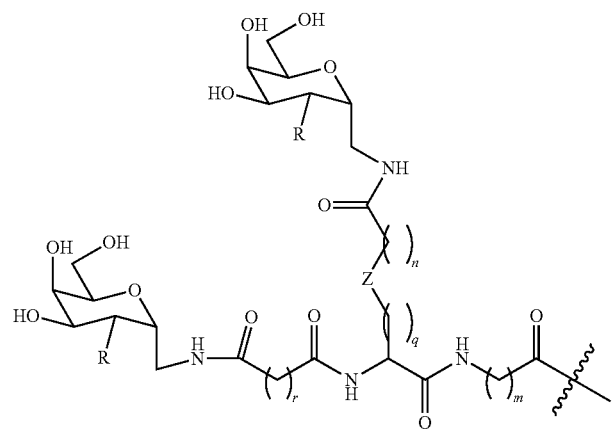
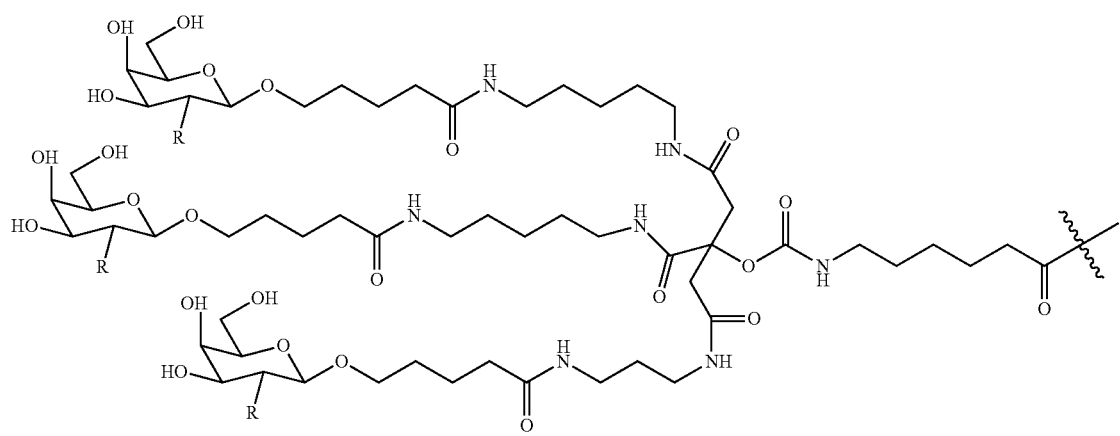

TABLE 2A-continued
Ligands[a,b,c,d]
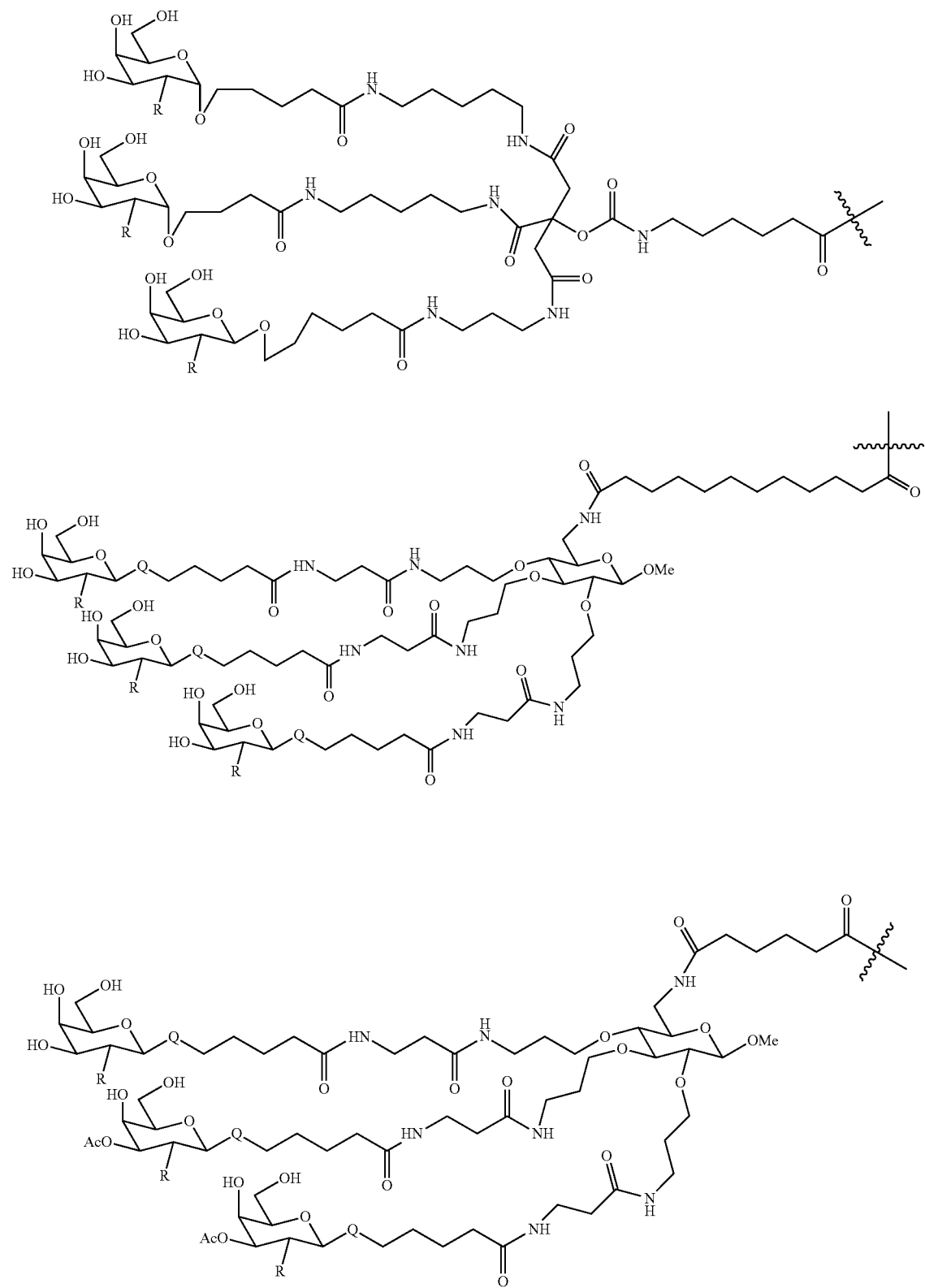

TABLE 2A-continued
Ligands[a,b,c,d]
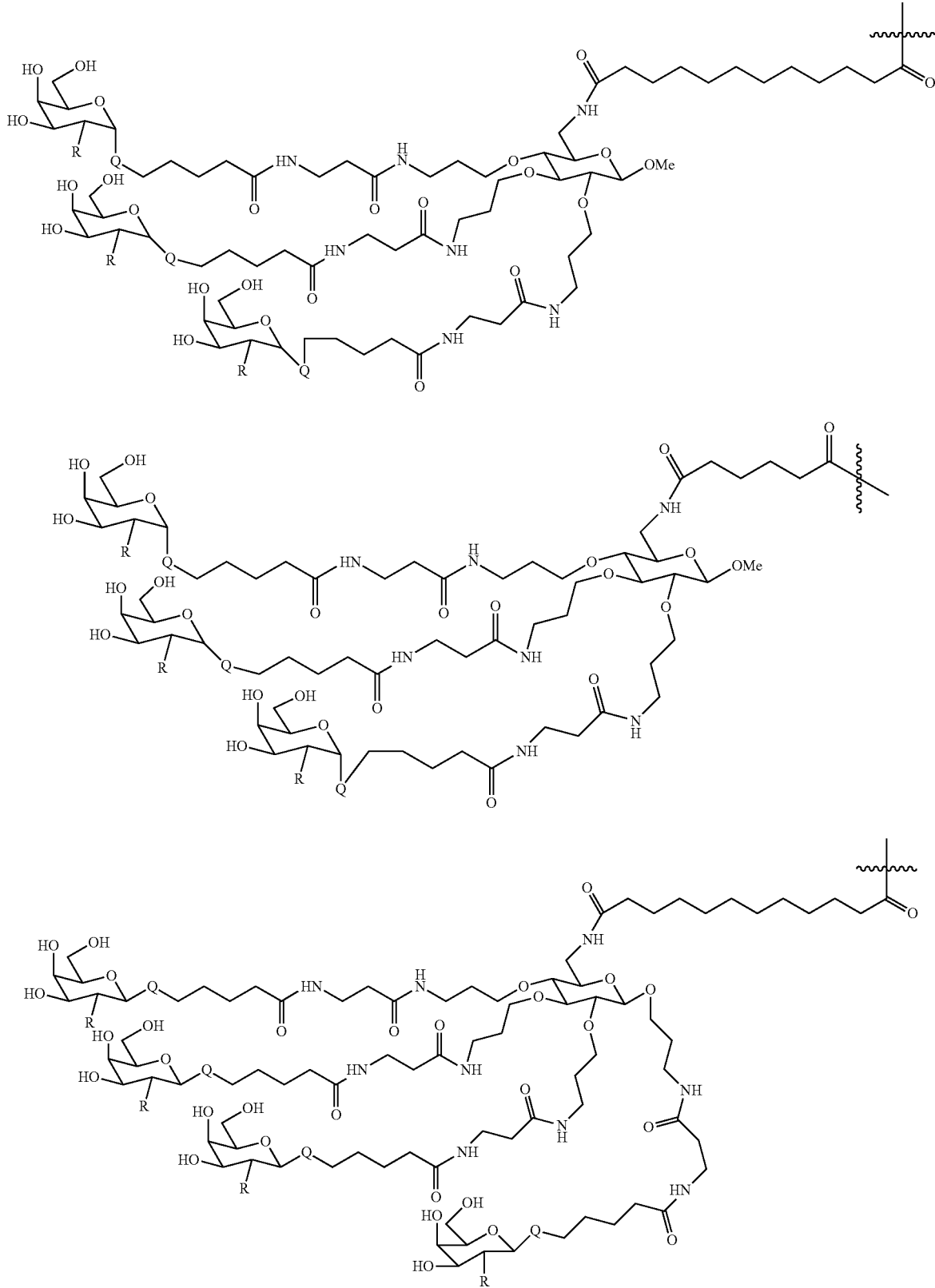

111
TABLE 2A-continued
Ligands[a,b,c,d]
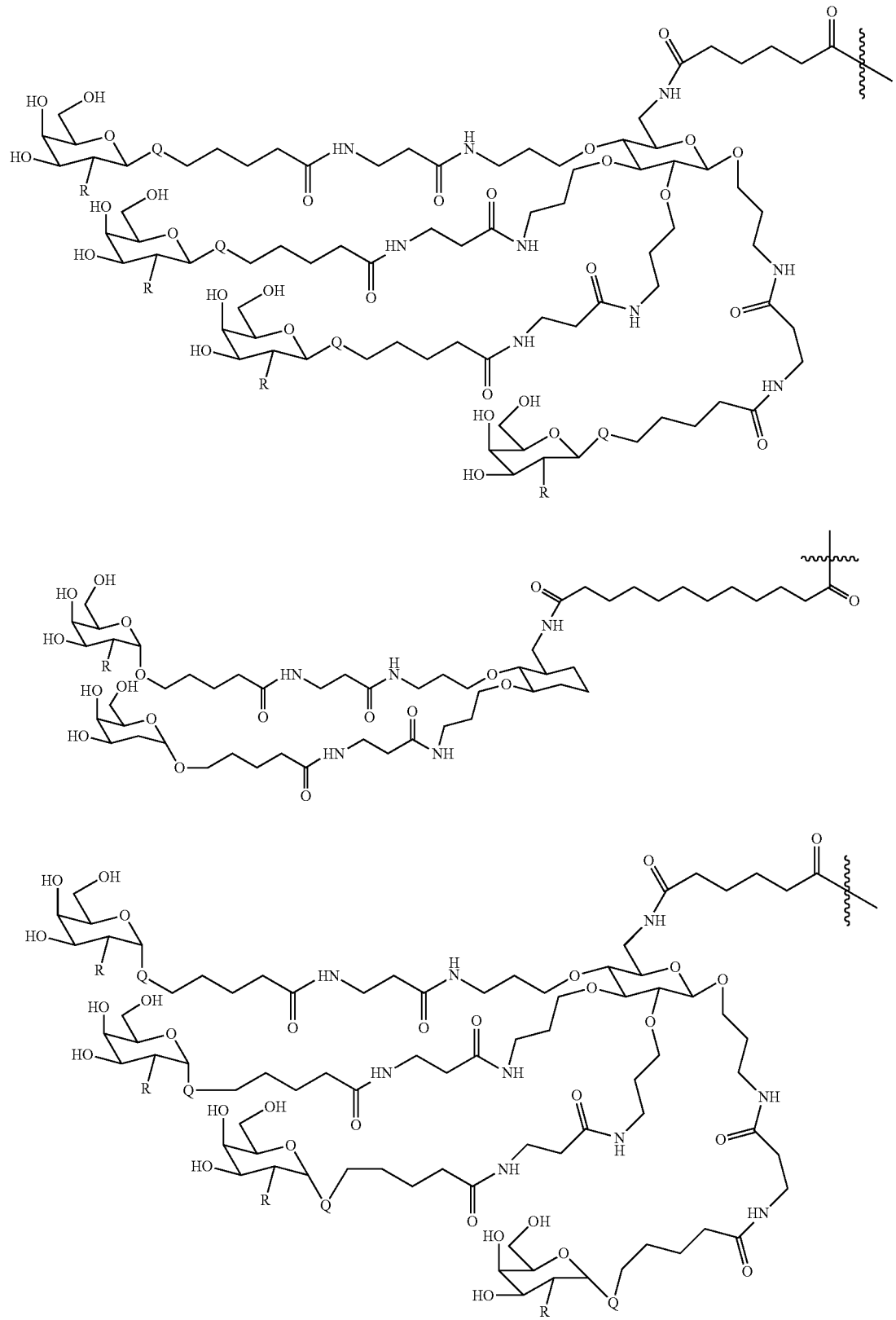

TABLE 2A-continued
Ligands[a,b,c,d]
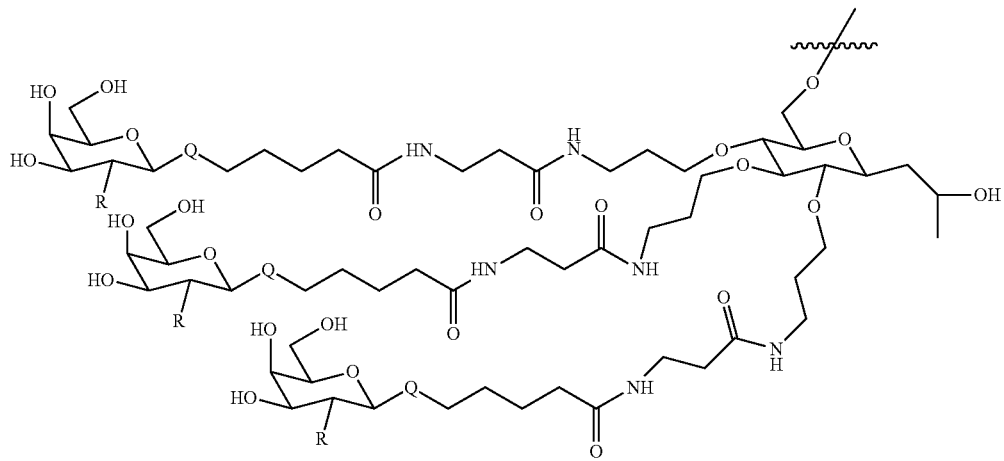
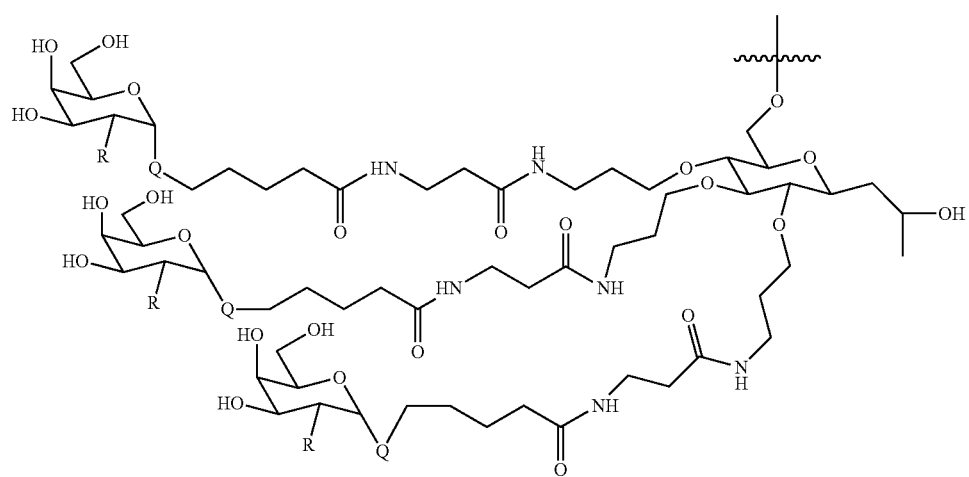

TABLE 2A-continued
Ligands[a,b,c,d]
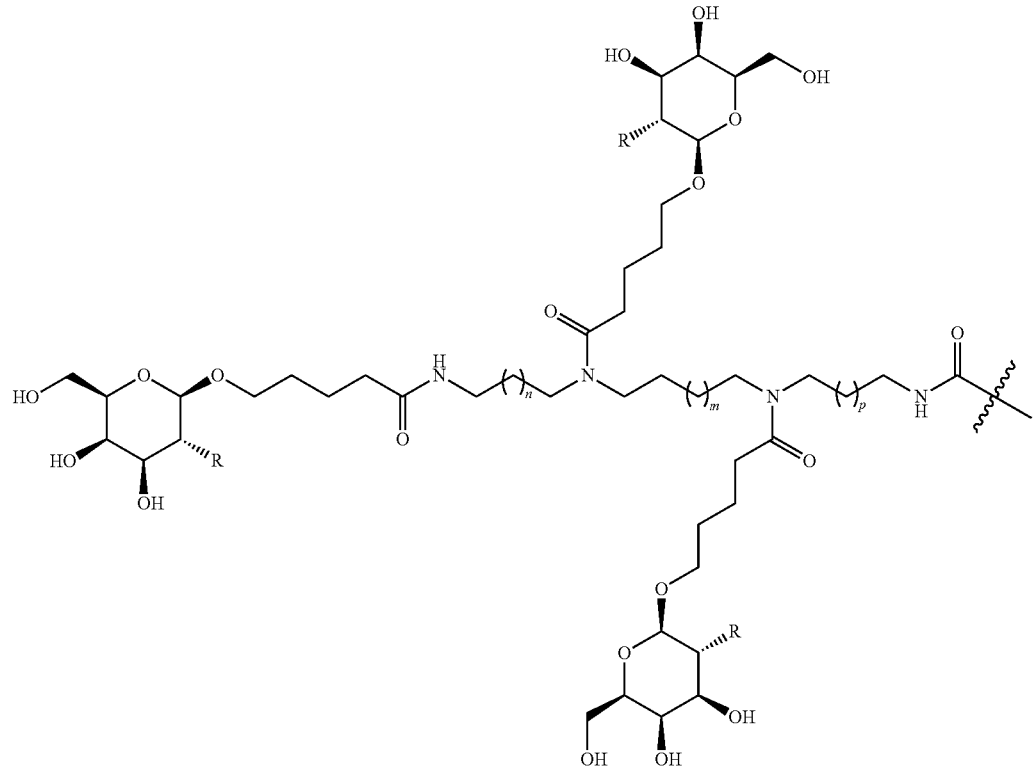
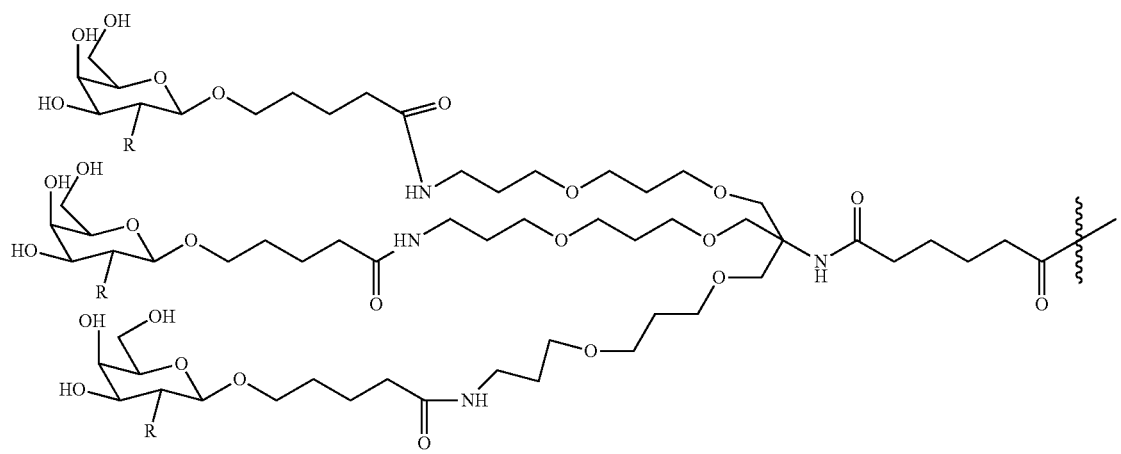

TABLE 2A-continued
Ligands[a,b,c,d]
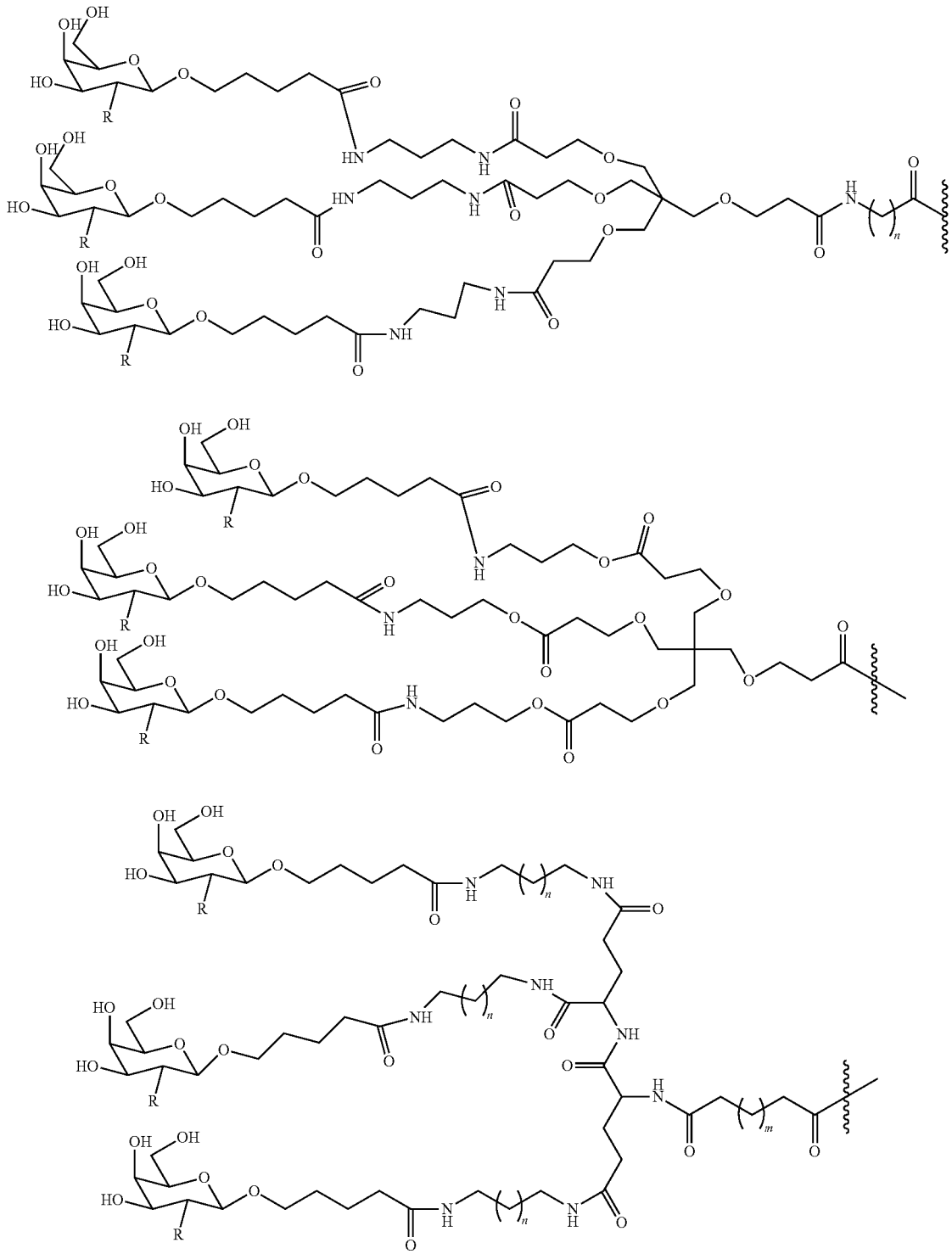

119 120
TABLE 2A-continued
Ligands[a,b,c,d]
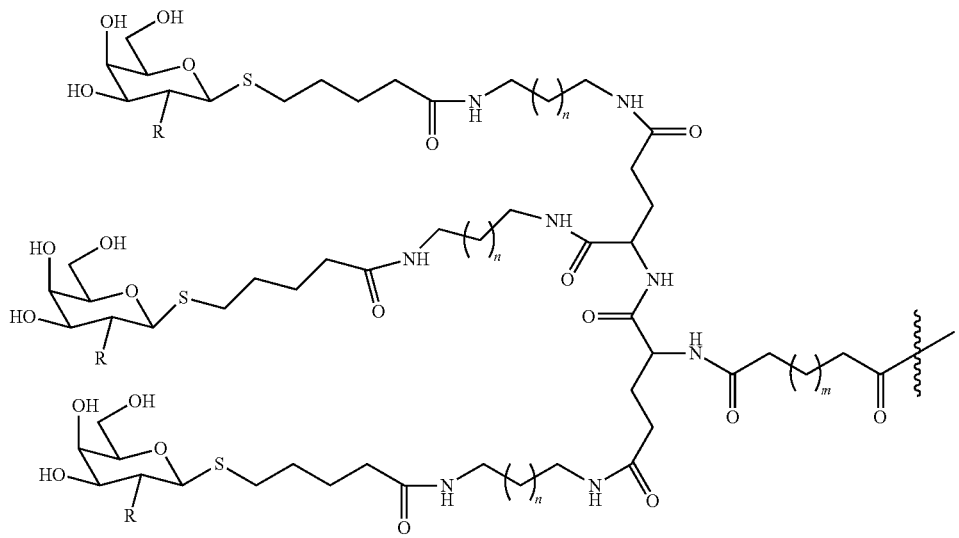
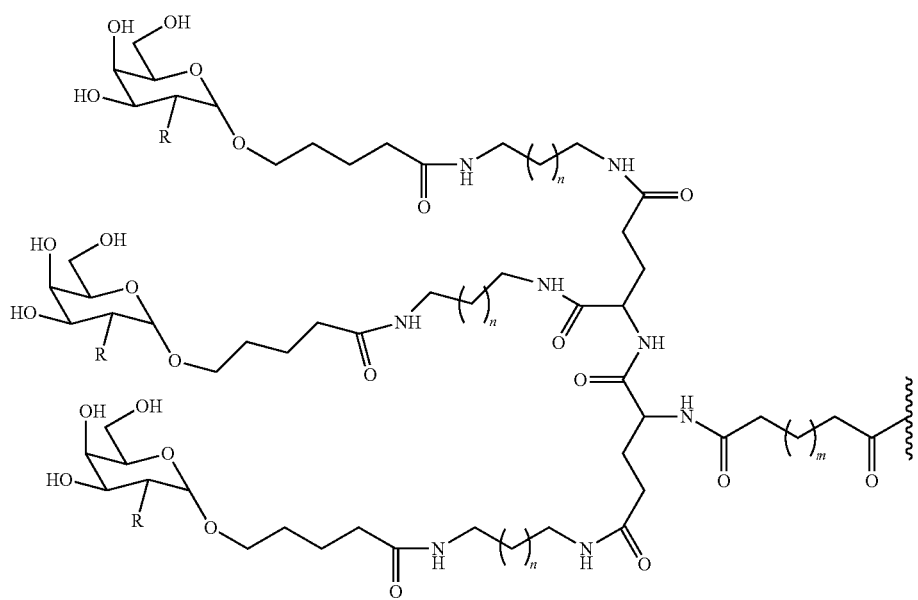

TABLE 2A-continued

Ligands[a,b,c,d]

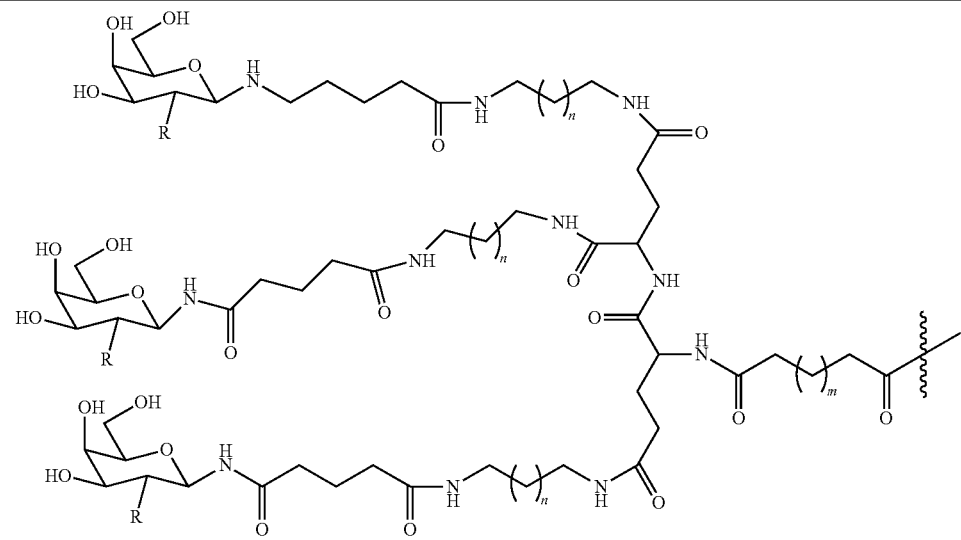

[a] Q is O, S, or CH$_2$; and Z is —CONH—, —NHCO—, —OC(O)NH—, or —NHC(O)O—.
[b] each of the variables l, m, n, p, q, and r independently ranges from about 0 to about 10.
[c] ⁓ indicates site of attachment of the Ligand to the Linker.
[d] Each structure represents chirally pure or racemic isomers when one or more asymmetric centers are present.
The variable R, unless otherwise specified, is OH or NHAc.

TABLE 3[a]

Targeting Monomers (R[3])

TABLE 3ª-continued

Targeting Monomers (R³)

TABLE 3$^a$-continued

Targeting Monomers (R$^3$)

TABLE 3[a]-continued
Targeting Monomers (R[3])
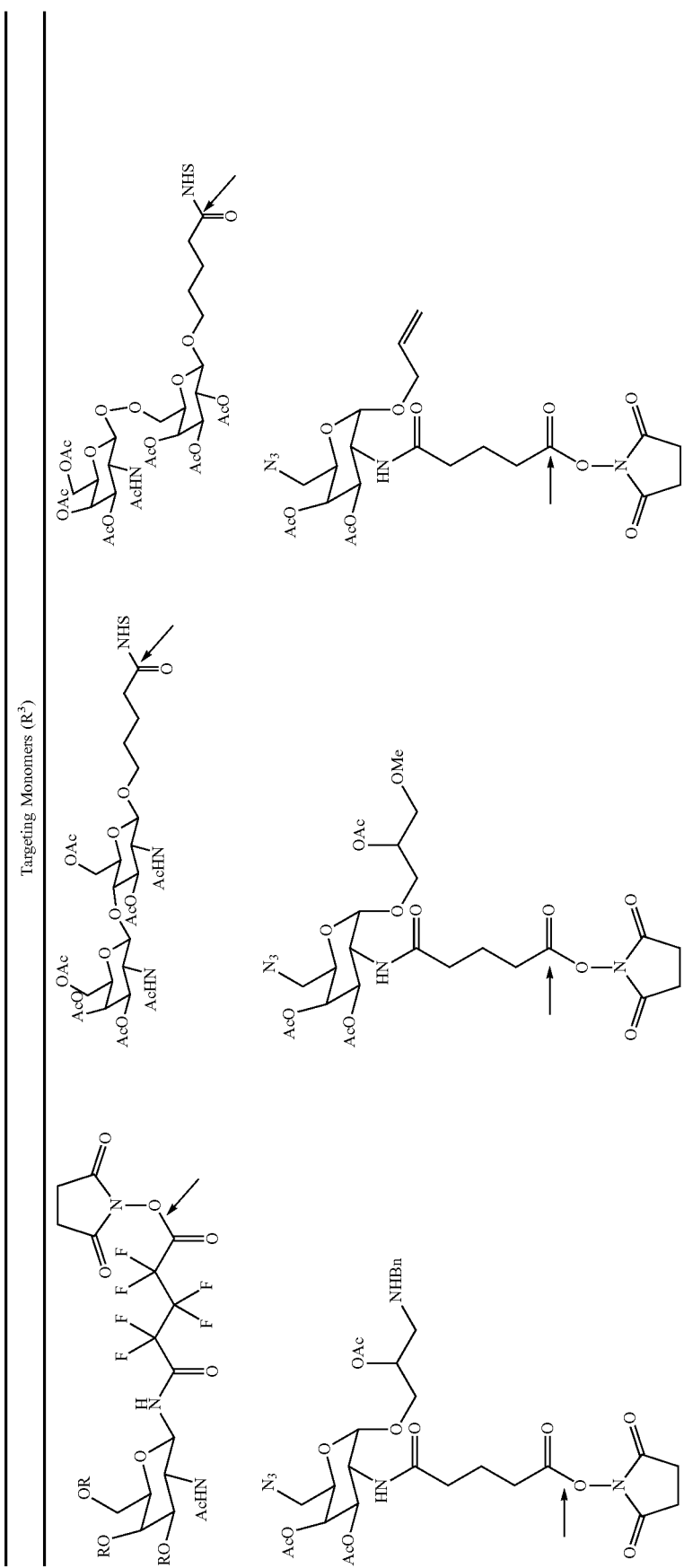

TABLE 3<sup>a</sup>-continued
Targeting Monomers (R³)
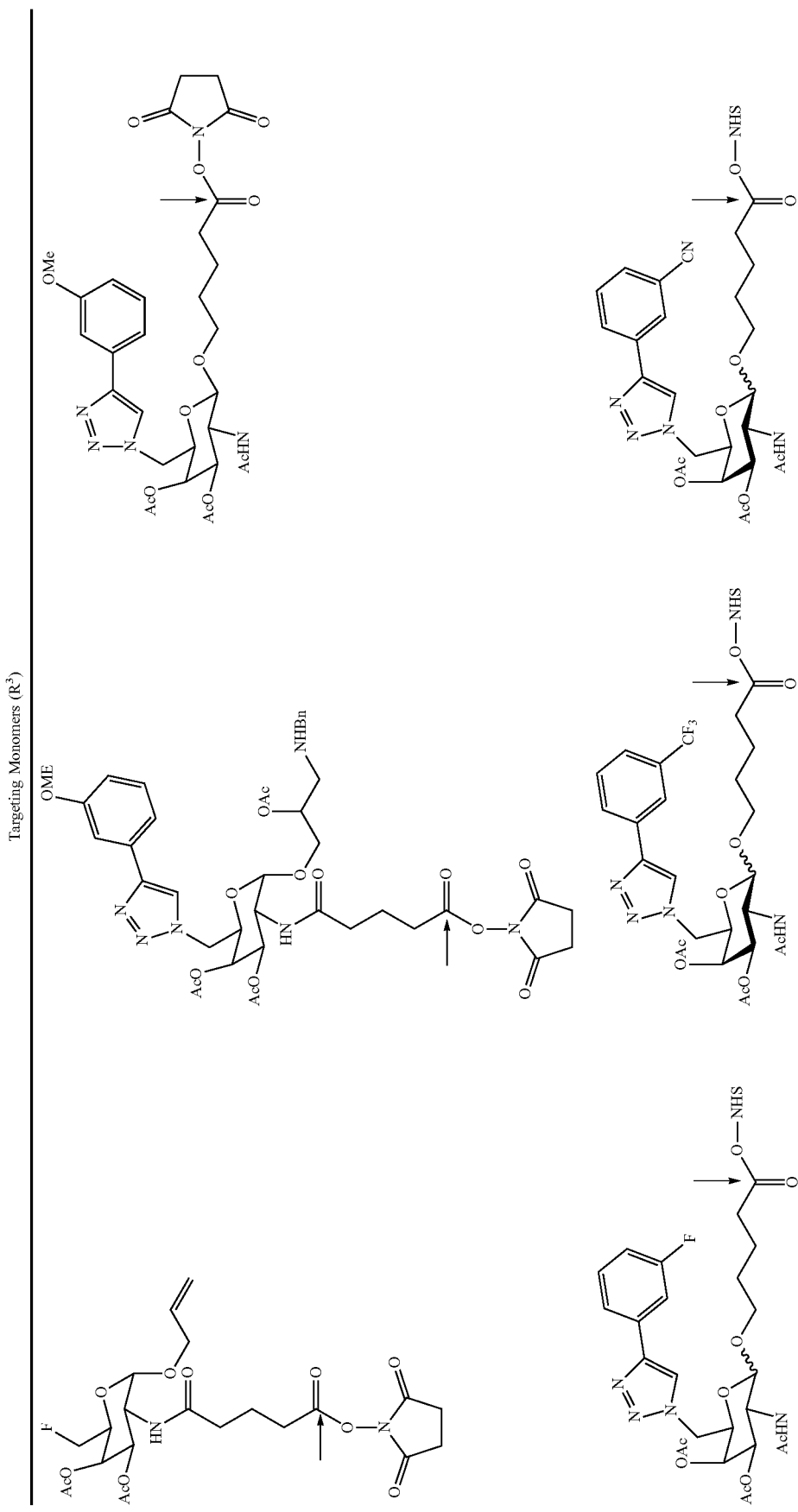

TABLE 3[a]-continued
Targeting Monomers (R[3])
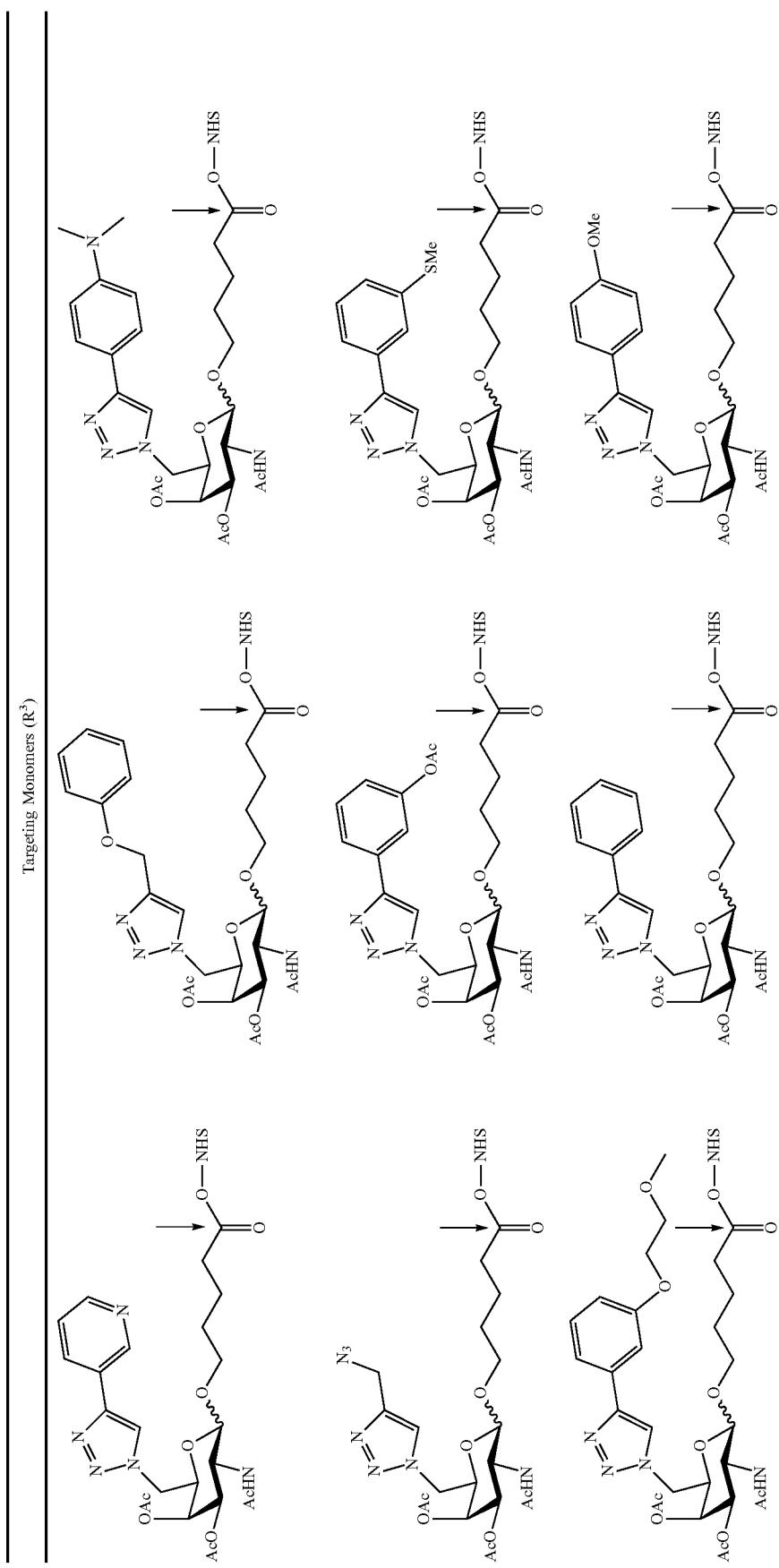

TABLE 3[a]-continued
Targeting Monomers (R[3])
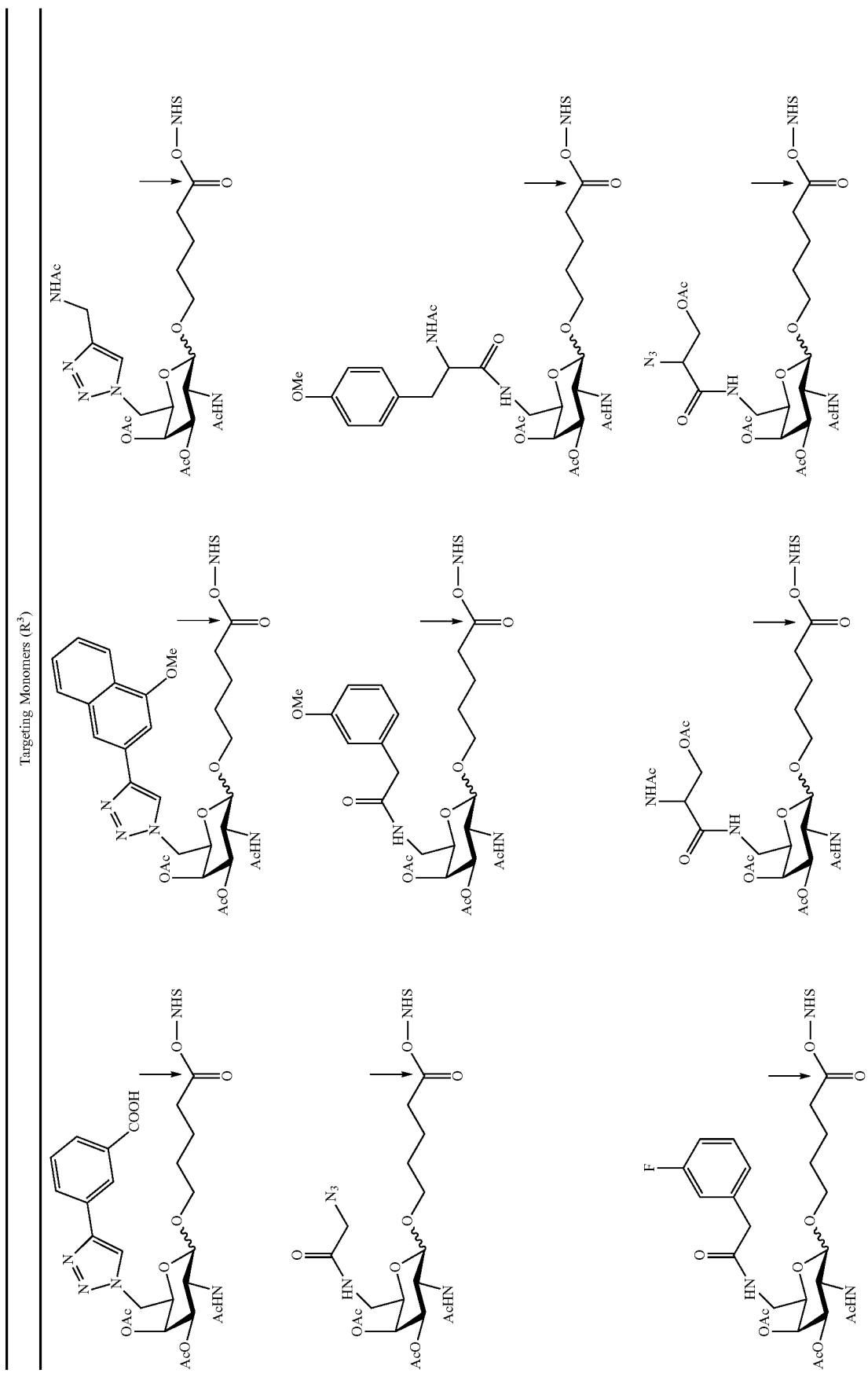

TABLE 3[a]-continued
Targeting Monomers (R[3])
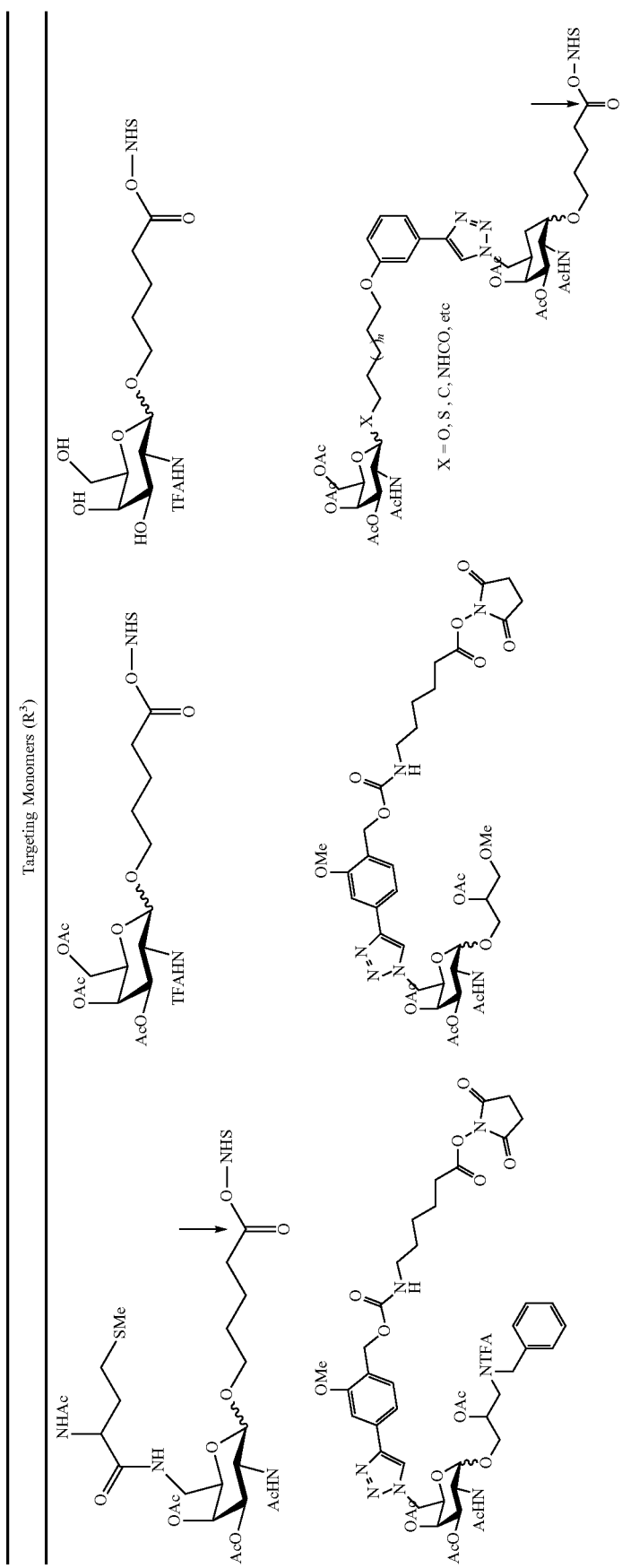

TABLE 3ᵃ-continued
Targeting Monomers (R³)
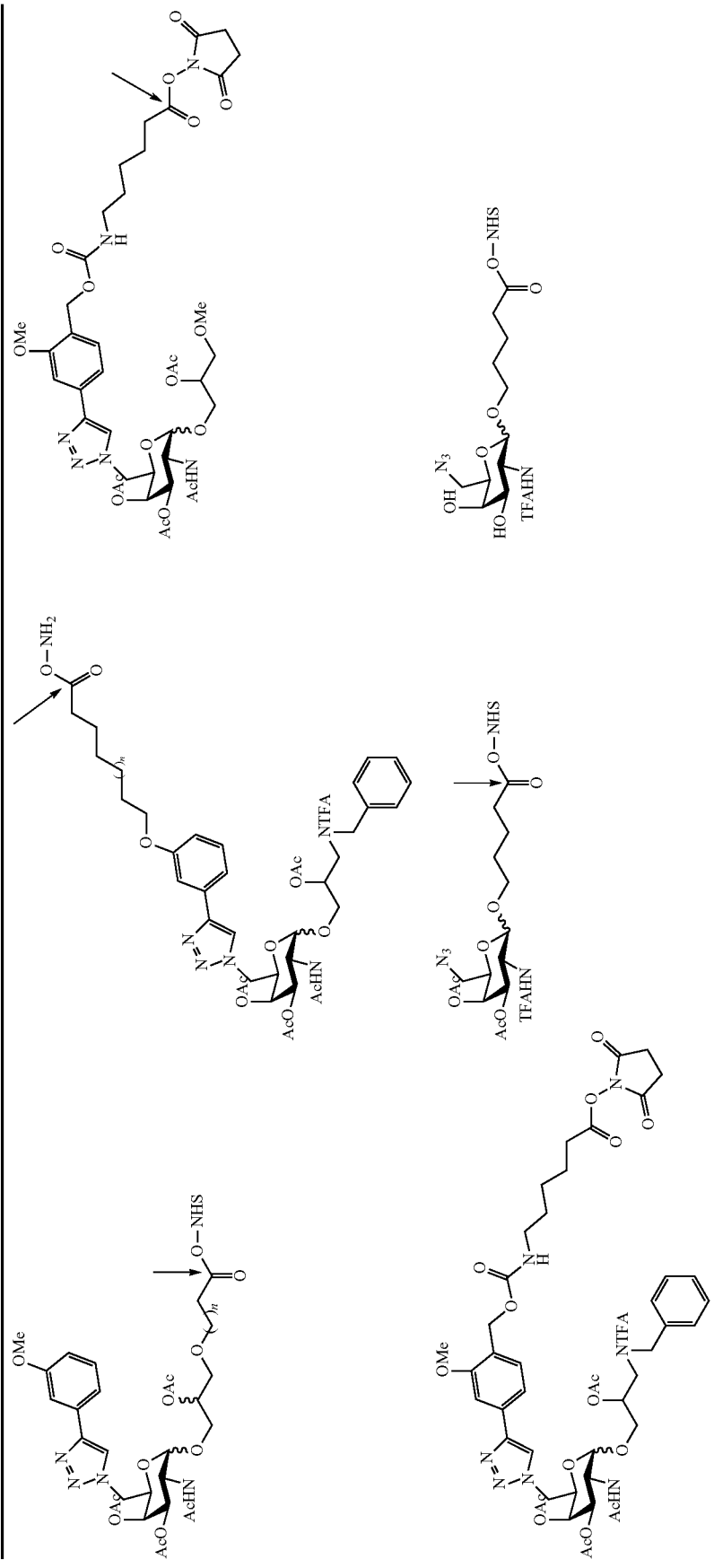

TABLE 3ᵃ-continued
Targeting Monomers (R³)
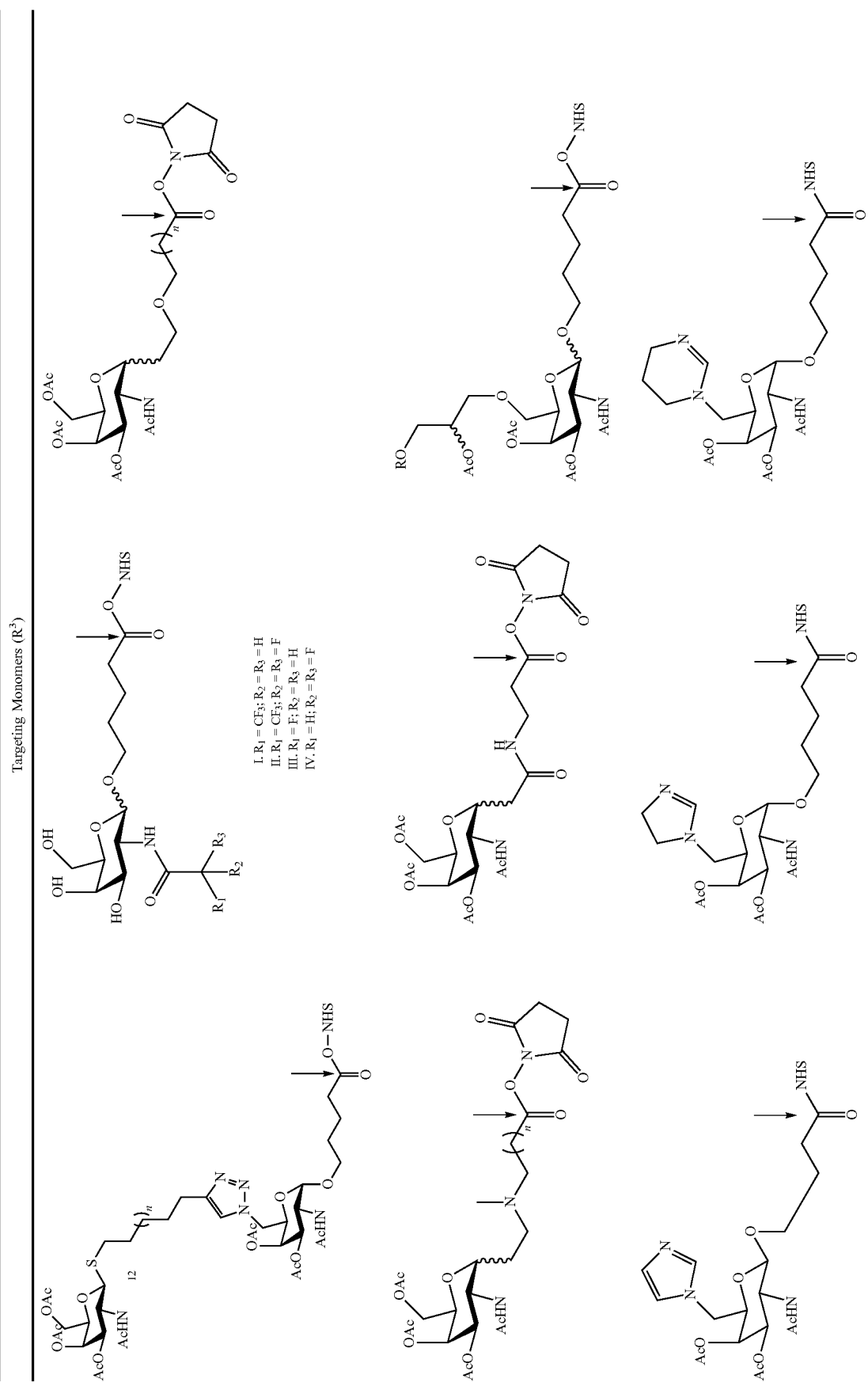

TABLE 3[a]-continued

Targeting Monomers (R[3])

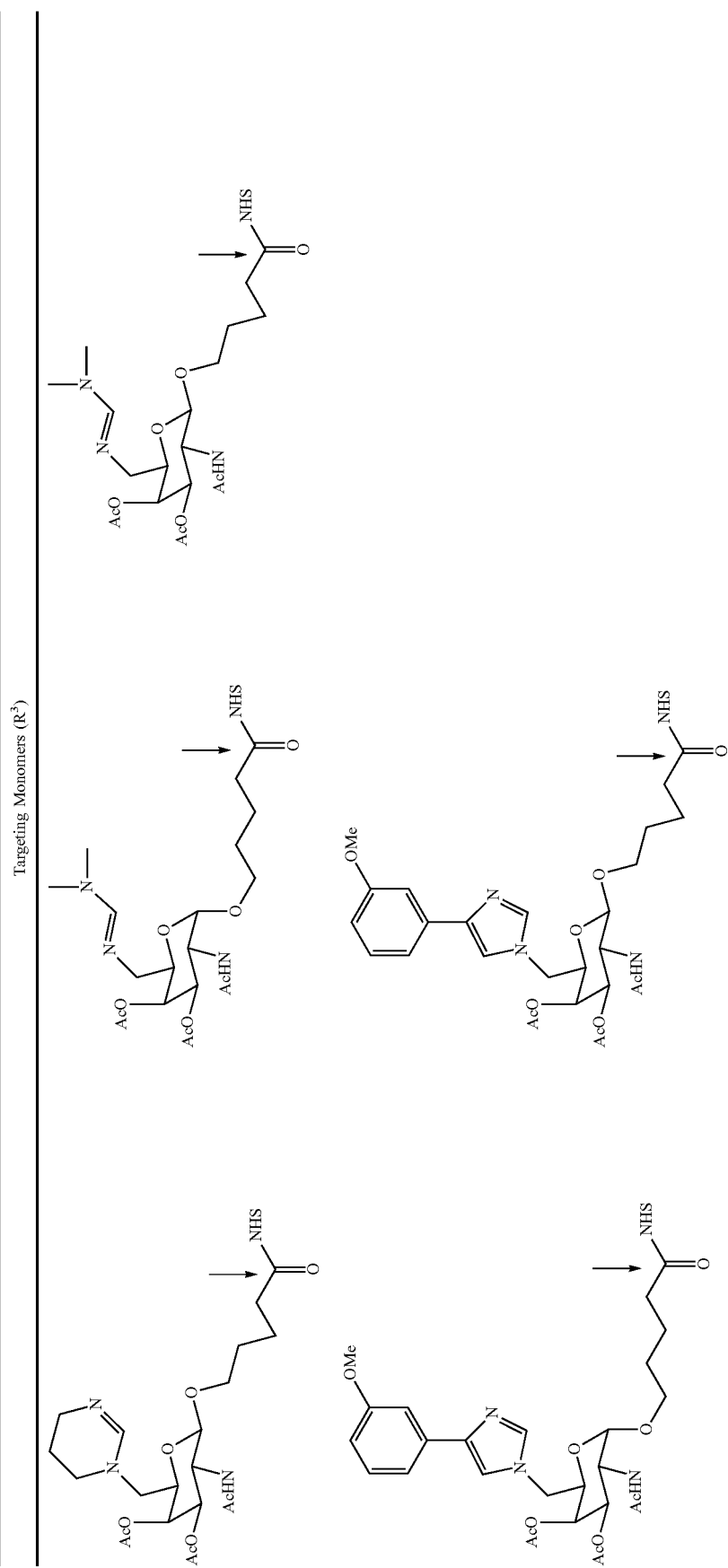

[a]These groups are functional monomers to conjugate to amino linked oligonucleotides. Each structure represents chirally pure or racemic isomers when one or more asymmetric centers are present.
→ indicate site of conjugation.
The variable X, unless otherwise specified, is O, S, C, or NHCO.
The variable n, unless otherwise specified, is 1-8 (e.g., 1-4).

TABLE 3A
Targeting Monomers (R³)
Table 1. ASGPR Ligand Mimics[a]
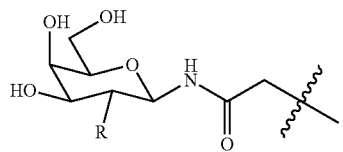
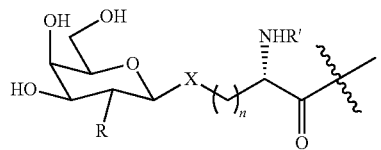
X = O and S
R' = H, Ac
n = 0, 1, 4
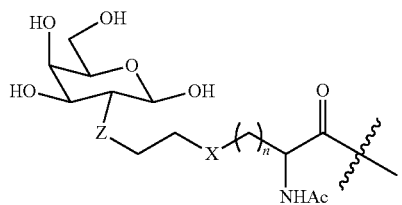
R = NH, NHAc or O
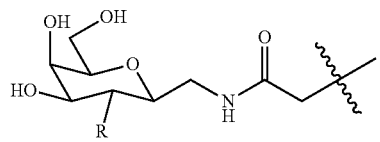
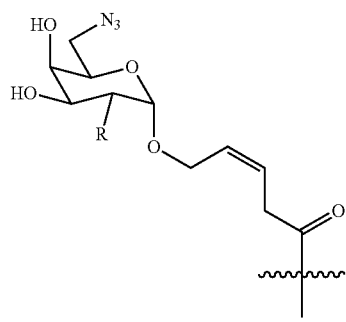
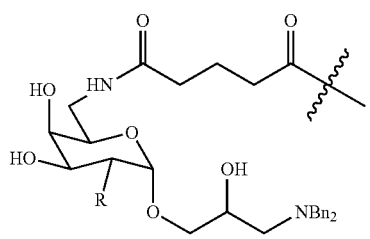
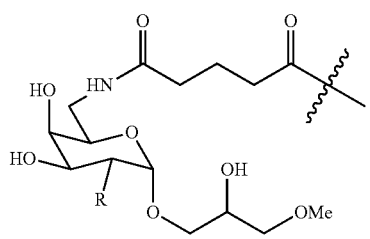

TABLE 3A-continued
Targeting Monomers (R³)
Table 1. ASGPR Ligand Mimics[a]
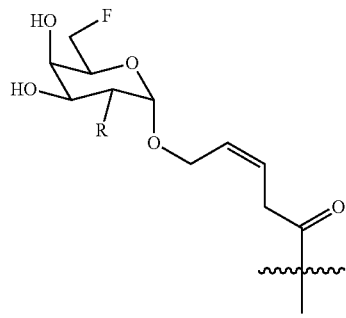
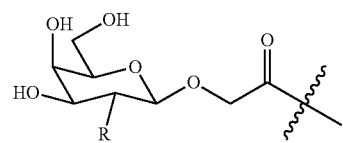
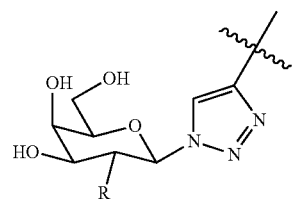
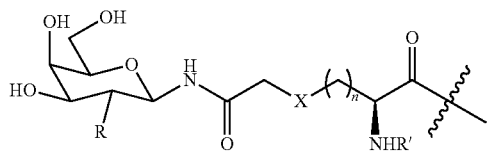
X = CH₂, O, S—S, NH
R = H or Ac
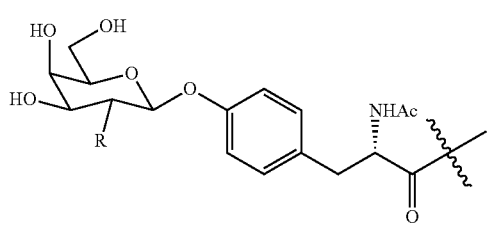
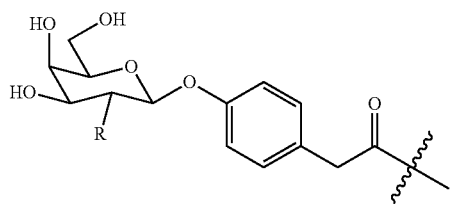
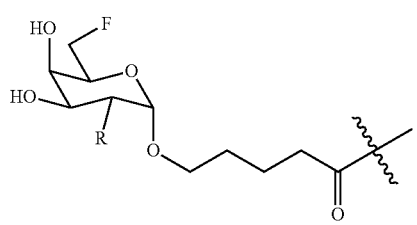

TABLE 3A-continued
Targeting Monomers (R³)
Table 1. ASGPR Ligand Mimics[a]
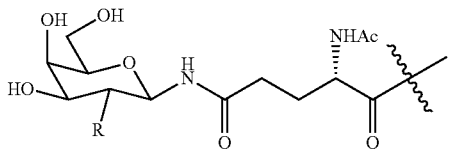
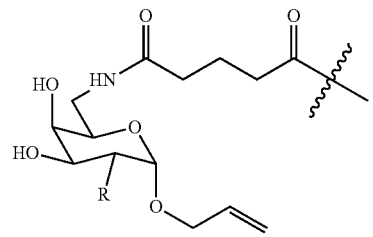
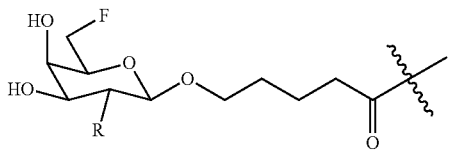
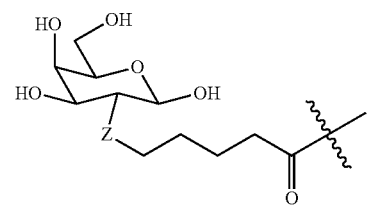
Z = NH, NAc or O
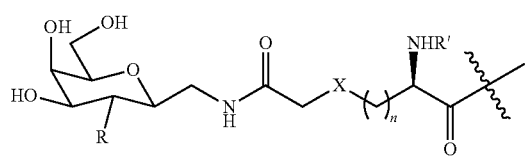
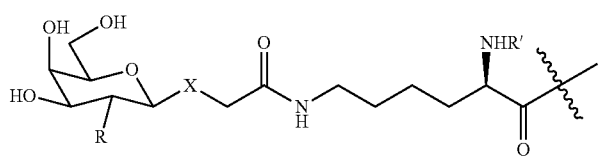
X = O, S
R' = H or Ac
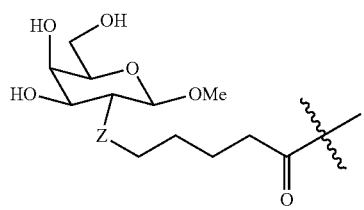
Z = NH, NHAc or S TABLE 3A-continued
Targeting Monomers (R³)
Table 1. ASGPR Ligand Mimics[a]
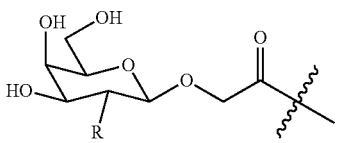
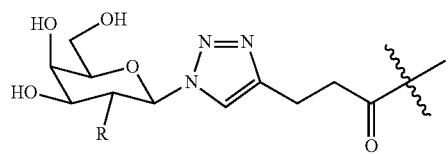
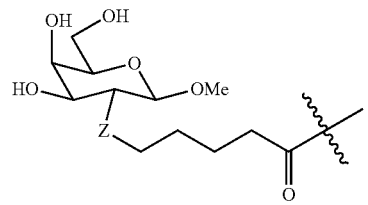
Z = NH, NHAc or O
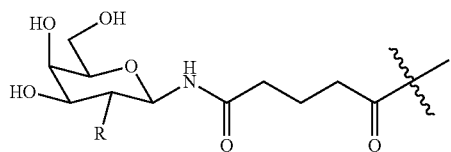
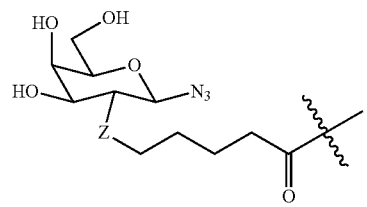
Z = NH, NAc or O
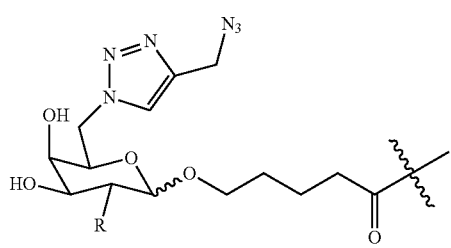
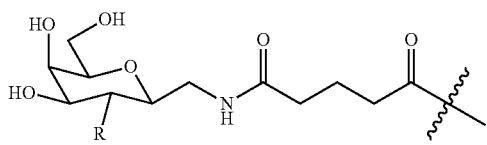

TABLE 3A-continued
Targeting Monomers (R³)
Table 1. ASGPR Ligand Mimics[a]
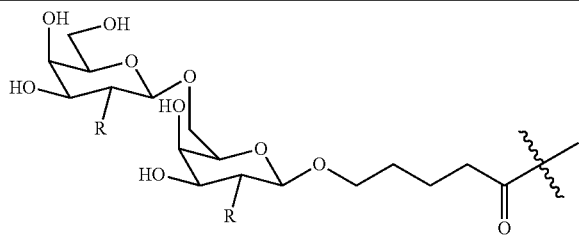
R' = OH or NHAc
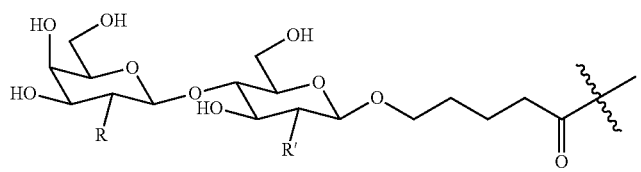
R' = OH or NHAc
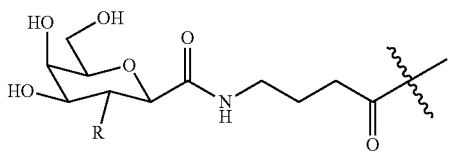
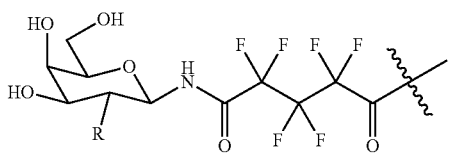
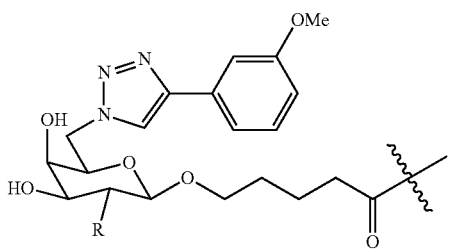
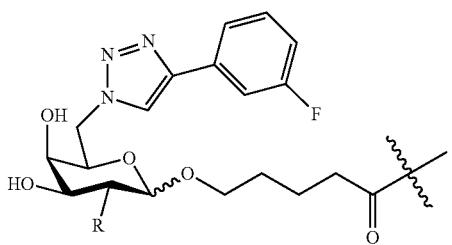
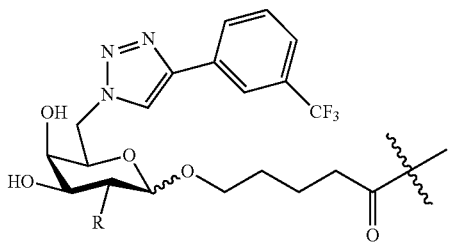

TABLE 3A-continued
Targeting Monomers (R³)
Table 1. ASGPR Ligand Mimics[a]
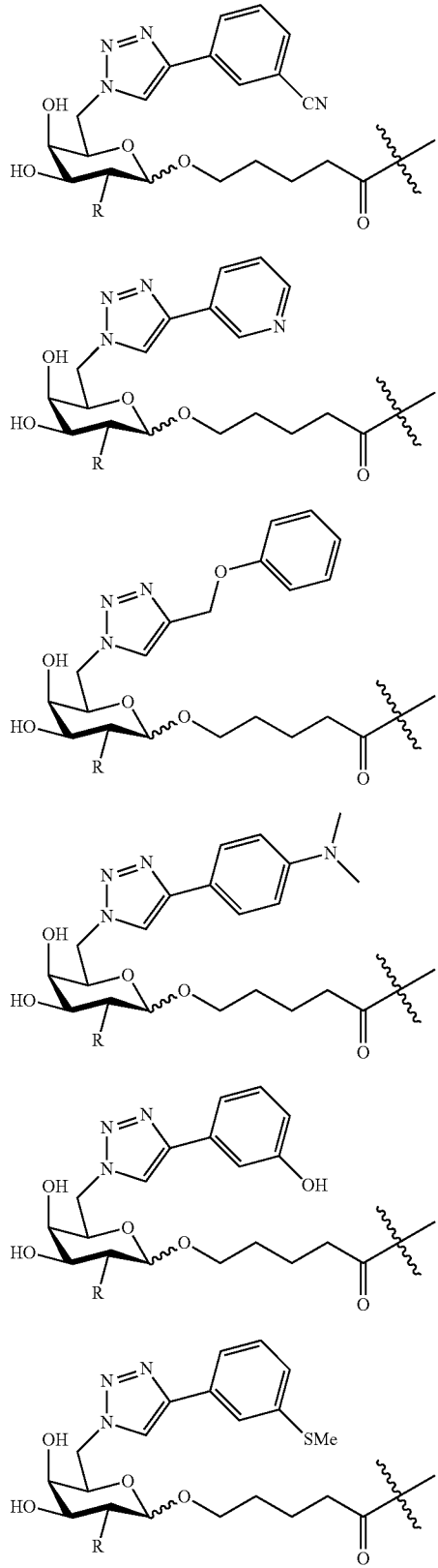

TABLE 3A-continued
Targeting Monomers (R³)
Table 1. ASGPR Ligand Mimics[a]
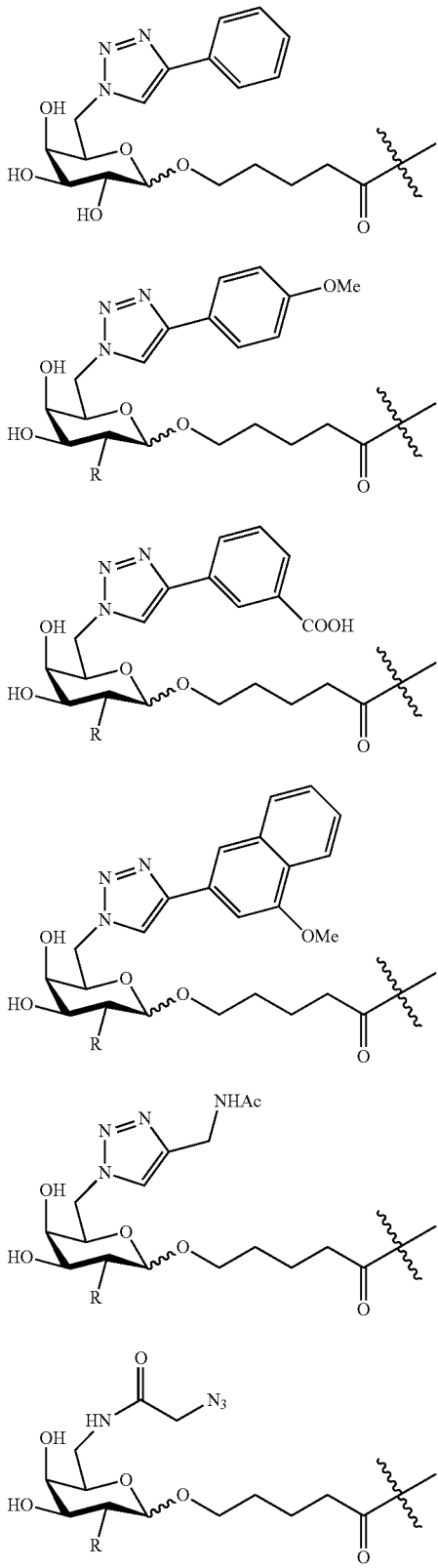

TABLE 3A-continued
Targeting Monomers (R³)
Table 1. ASGPR Ligand Mimics[a]
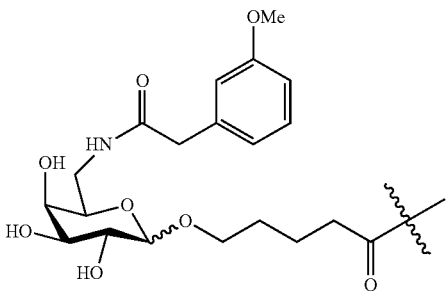
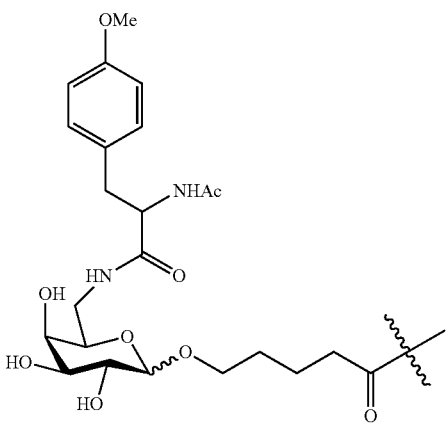
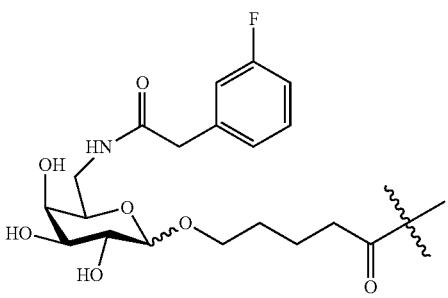
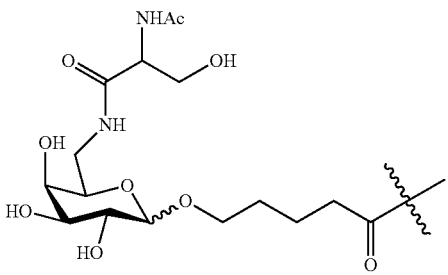
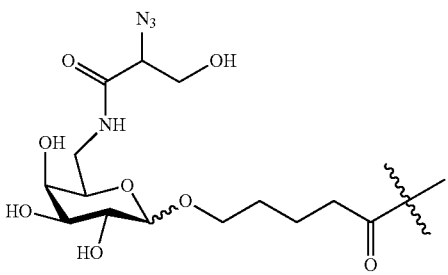

161 162
TABLE 3A-continued
Targeting Monomers (R³)
Table 1. ASGPR Ligand Mimics[a]
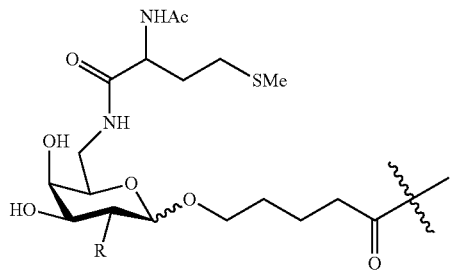
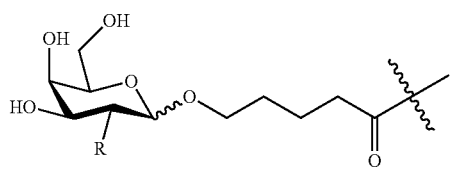
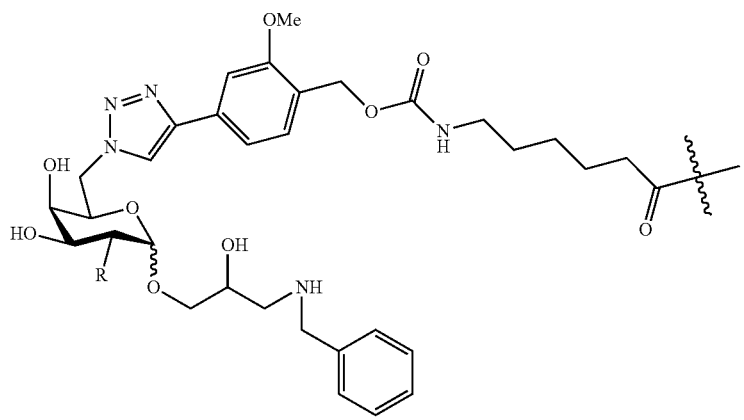
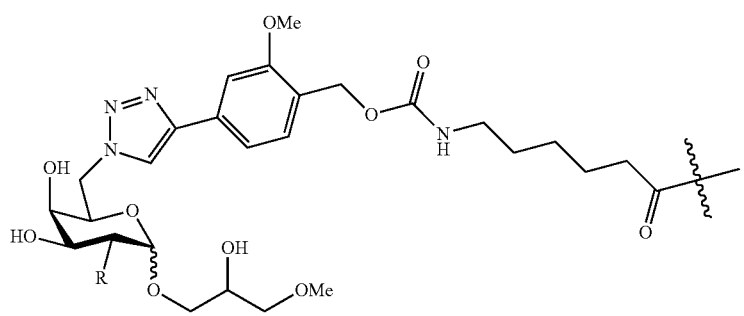

TABLE 3A-continued
Targeting Monomers (R³)
Table 1. ASGPR Ligand Mimics[a]
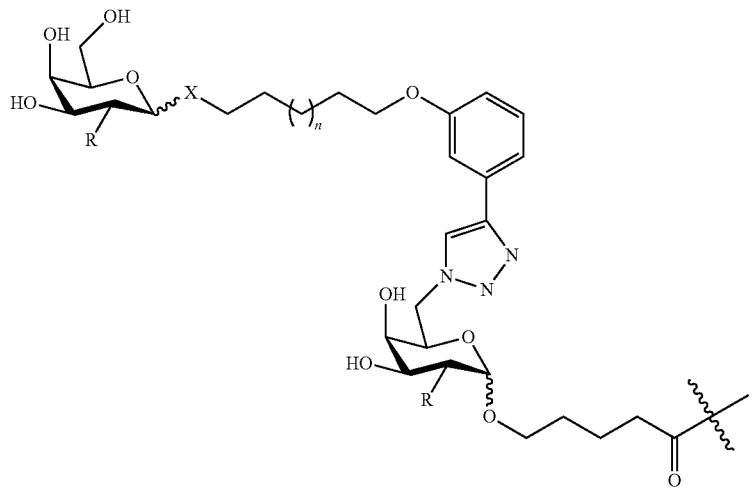
X = O, S, C, NHCO, etc
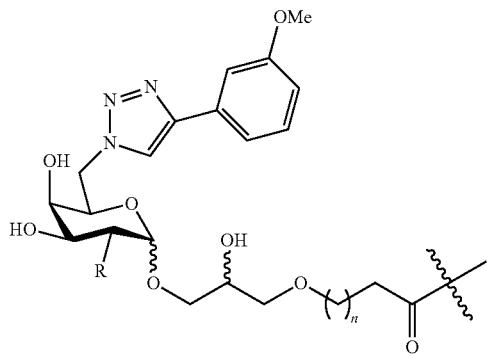
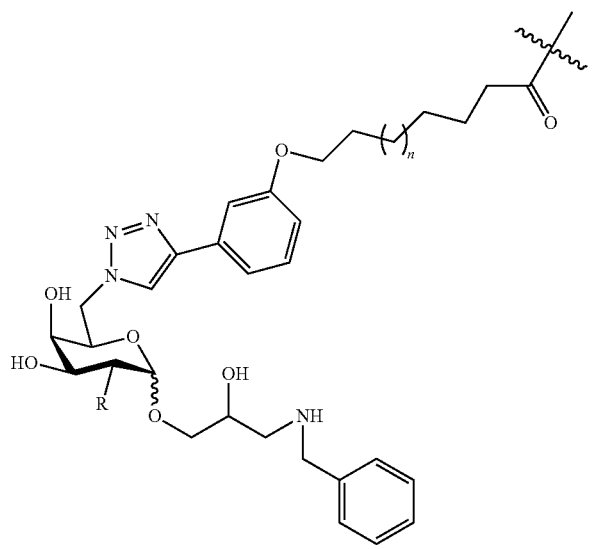

TABLE 3A-continued
Targeting Monomers (R³)
Table 1. ASGPR Ligand Mimics[a]
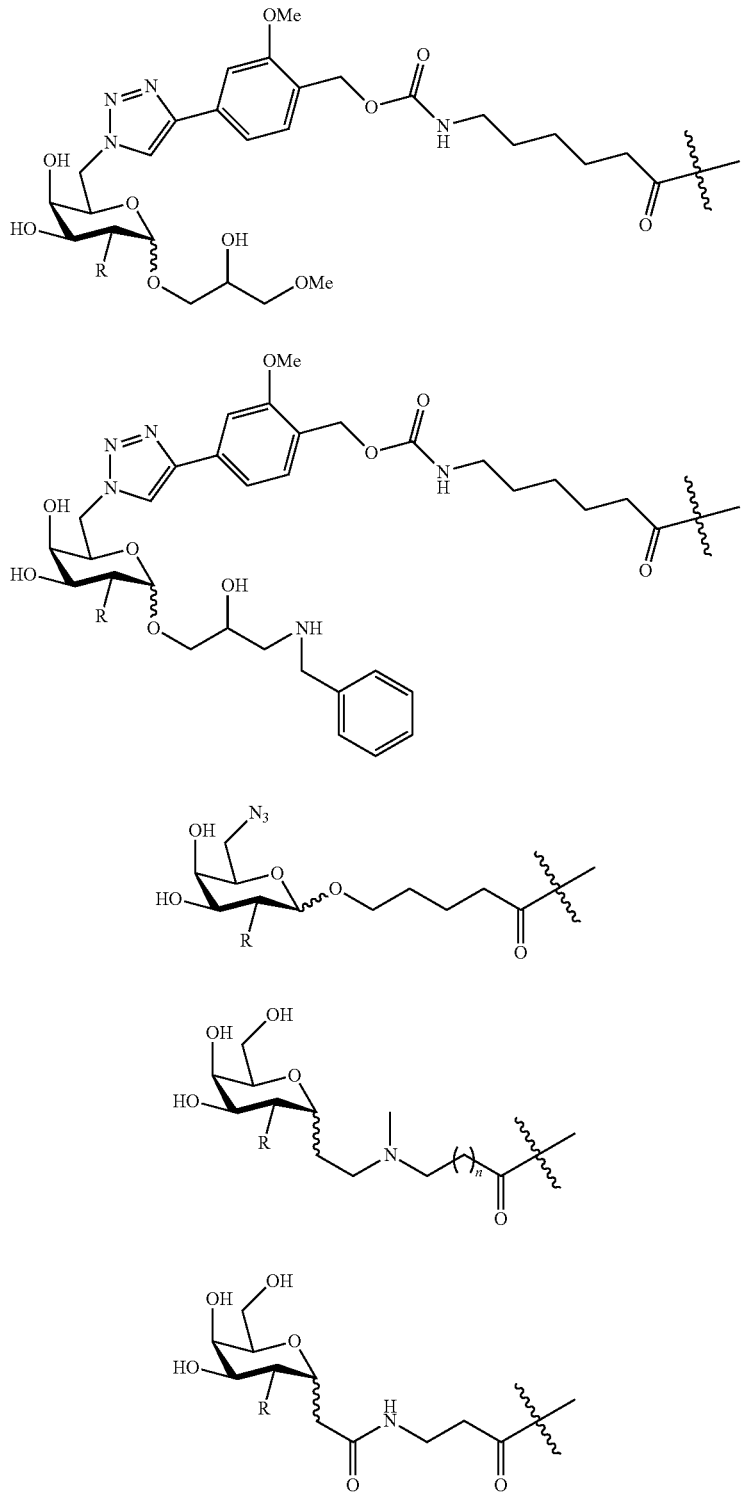

TABLE 3A-continued
Targeting Monomers (R³)
Table 1. ASGPR Ligand Mimics[a]
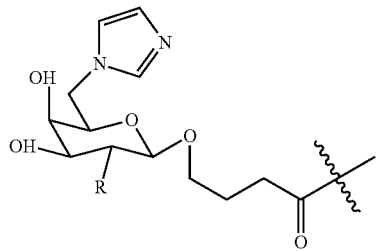
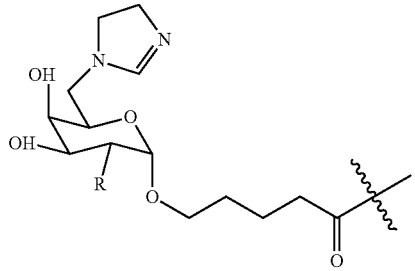
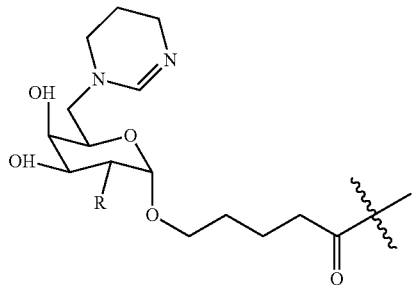
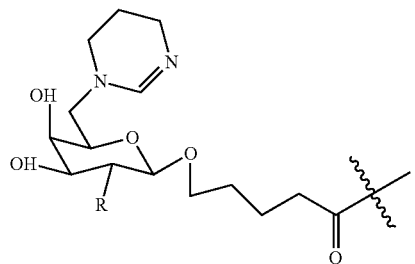
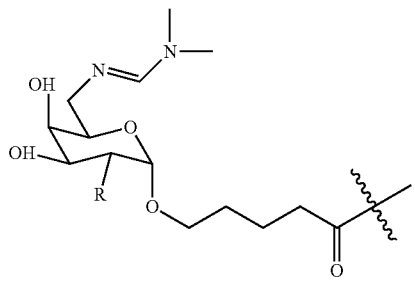

TABLE 3A-continued
Targeting Monomers (R³)
Table 1. ASGPR Ligand Mimics[a]
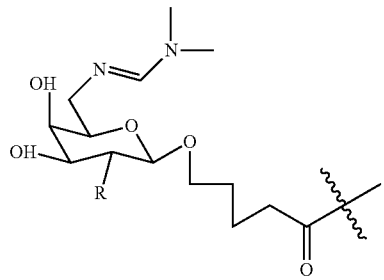
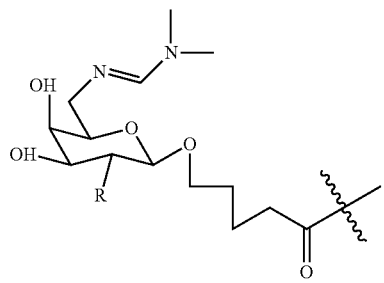
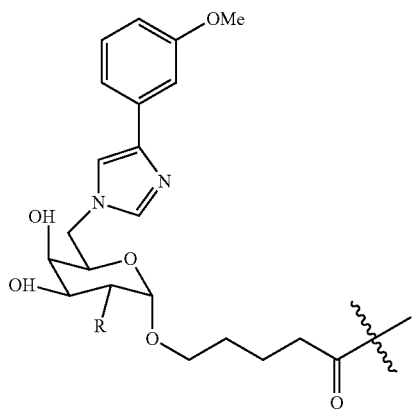
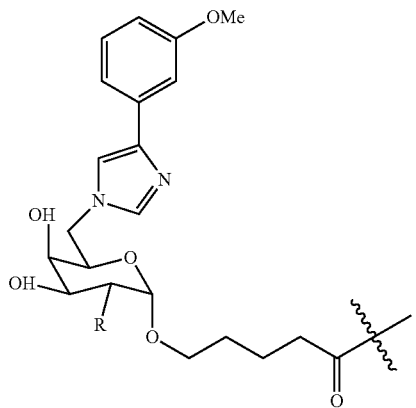

TABLE 3A-continued
Targeting Monomers (R³)
Table 1. ASGPR Ligand Mimics[a]
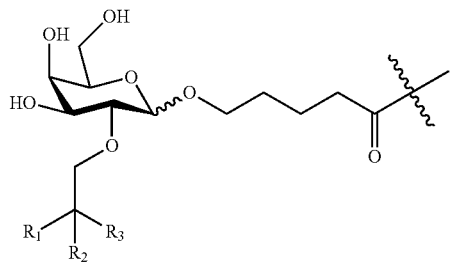
I. R₁ = CF₃; R₂ = R₃ = H
II. R₁ = CF₃; R₂ = R₃ = F
III. R₁ = F; R₂ = R₃ = H
IV. R₁ = H; R₂ = R₃ = F
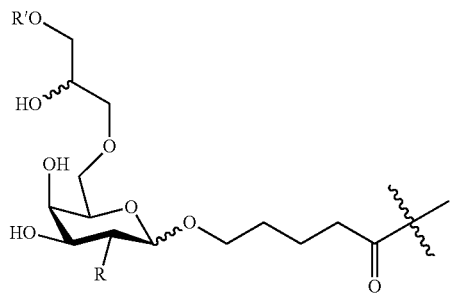
R' = Me or H
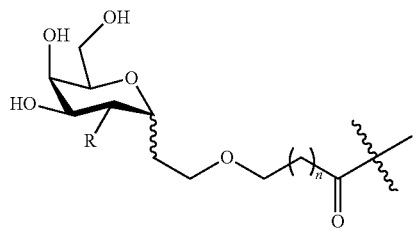
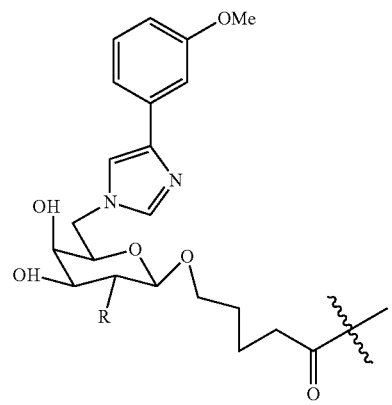

TABLE 3A-continued
Targeting Monomers (R³)
Table 1. ASGPR Ligand Mimics[a]
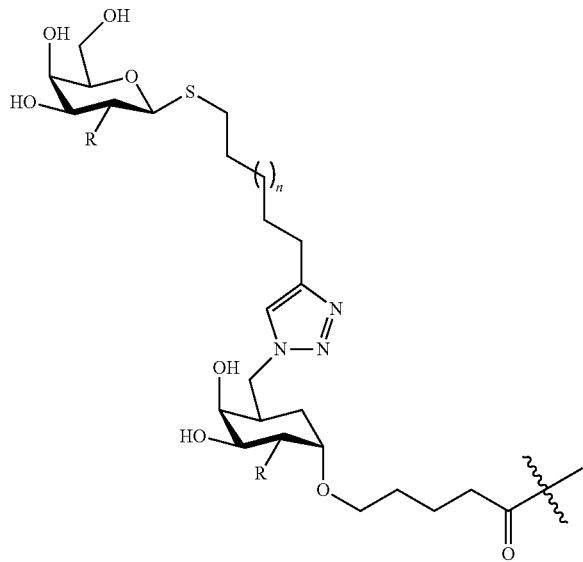
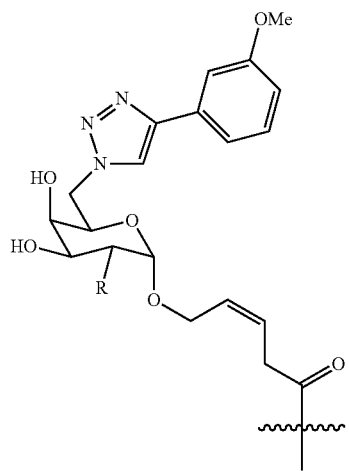
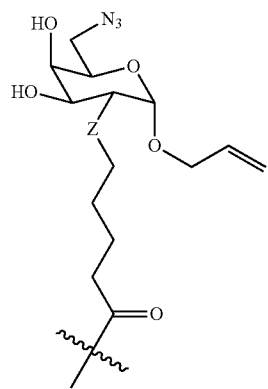
Z = NH, NAc or O TABLE 3A-continued
Targeting Monomers (R³)
Table 1. ASGPR Ligand Mimics[a]
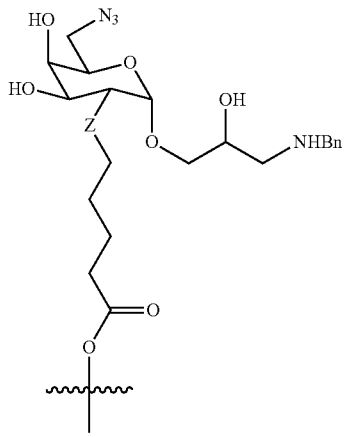
Z = NH, NAc or O
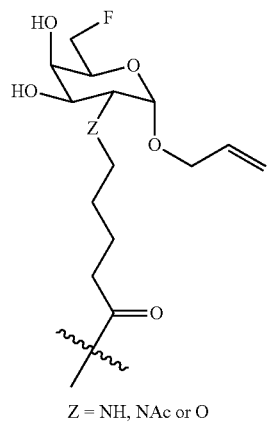
Z = NH, NAc or O
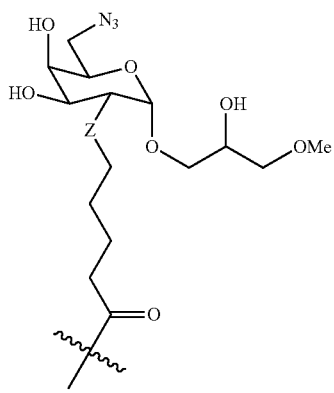
Z = NH, NAc or O TABLE 3A-continued Targeting Monomers ($R^3$)
Table 1. ASGPR Ligand Mimics[a]

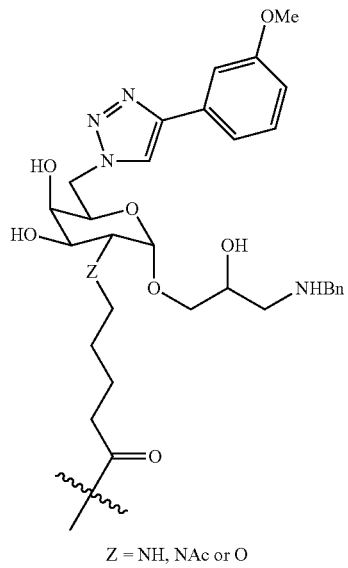

Z = NH, NAc or O

The variable R, unless otherwise specified, is OH or NHAc.
The variable n, unless otherwise specified, is 1-8 (for example, 1-4).
The variable R', unless otherwise specified, is H or Ac.
The variable X, unless otherwise specified, is O, S, C, or NHCO.
The variable Z, unless otherwise specified, is NH, NHAc, S, or O.

Ligands

The ligands can also be selected from the two generic formula below

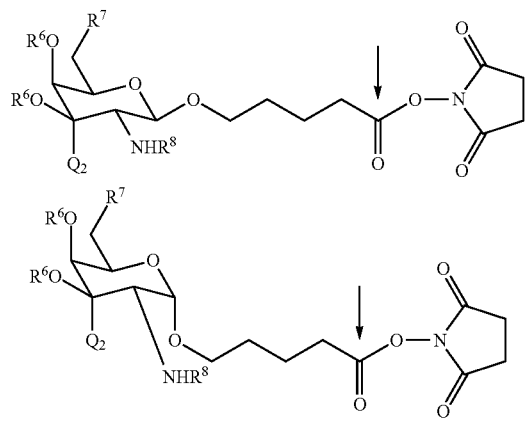

where the arrow indicates the point of attachment to the oligonucleotide conjugate (i.e., the ligand is attached through its carbonyl group). Intermediates useful for introducing the ligand include the compounds shown above. In the formulas above, the variables have the definitions provided below.

$R^6$ is H or Ac;

$R^7$ is —OH or —NHR$^9$;

$R^8$ is Ac or $R^9$; where at least one of $R^7$ and $R^8$ is a nitrogen containing moiety;

$R^9$ is

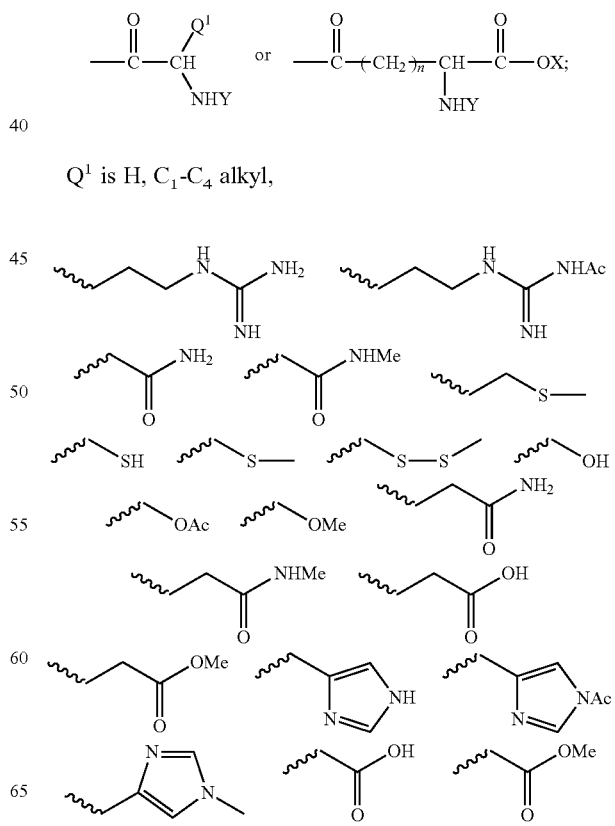

$Q^1$ is H, $C_1$-$C_4$ alkyl,

179
-continued
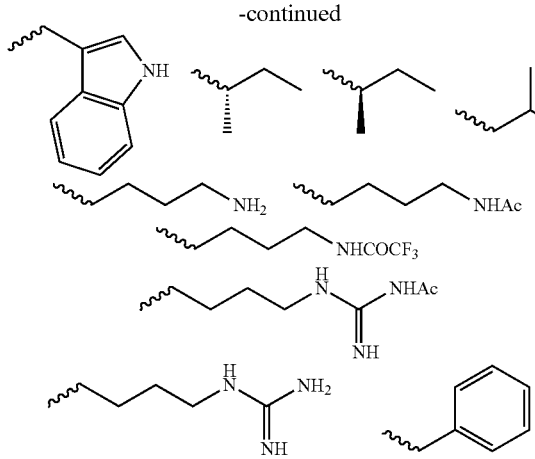
180
-continued
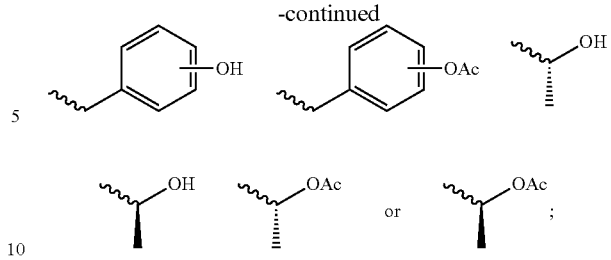
$Q^2$ is H or $C_1$-$C_4$ alkyl;
X is H or Me;
Y is H, Ac, or $COCF_3$; and
n is 1 to 8 (e.g., 1 to 4).
The ligands may have the formulas shown in Table 4 or 4A below.
TABLE 4[b]
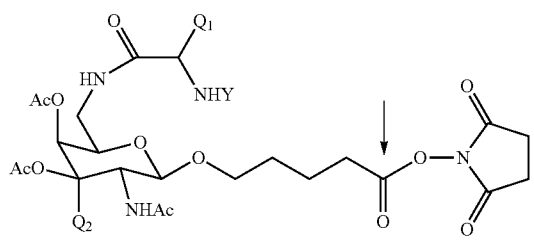
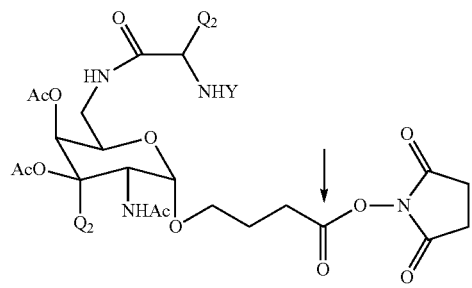
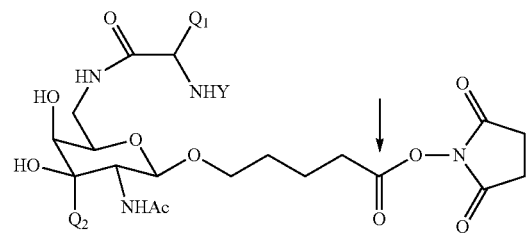
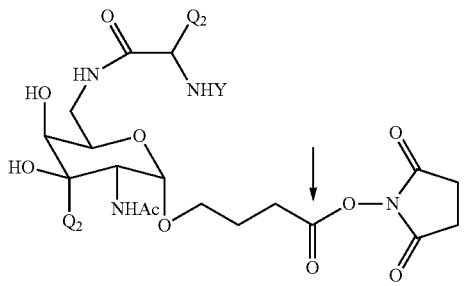

TABLE 4[b]-continued
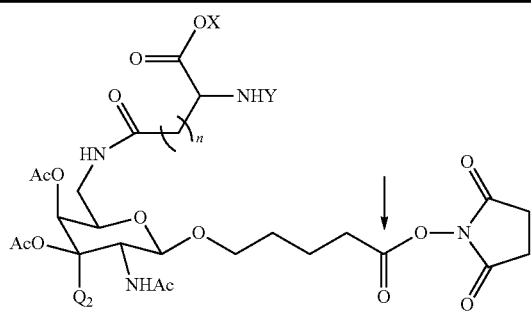
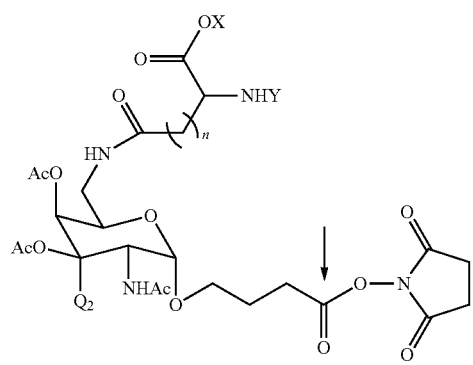
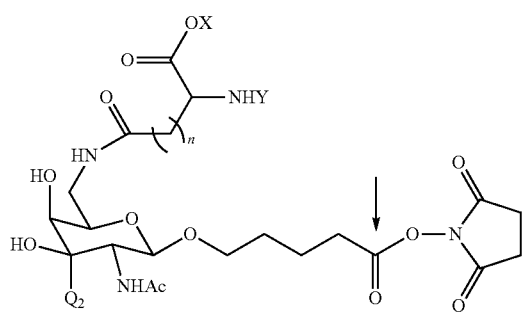
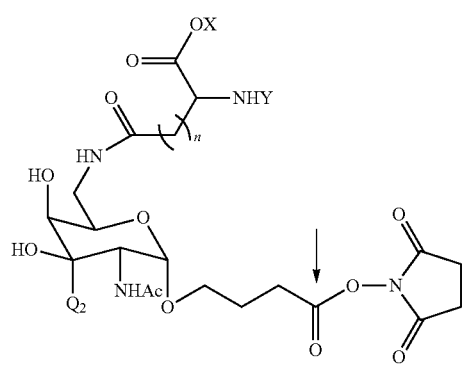
X =  H, Me
Y =  H, Ac, COCF$_3$
Q1 =  H, CH$_3$, Et, $n$Pr, isoPr, $n$Bu, isoBu
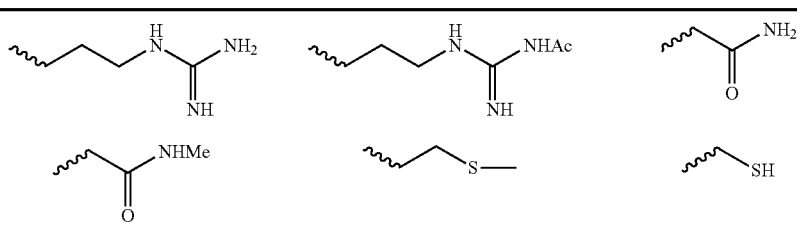

TABLE 4[b]-continued
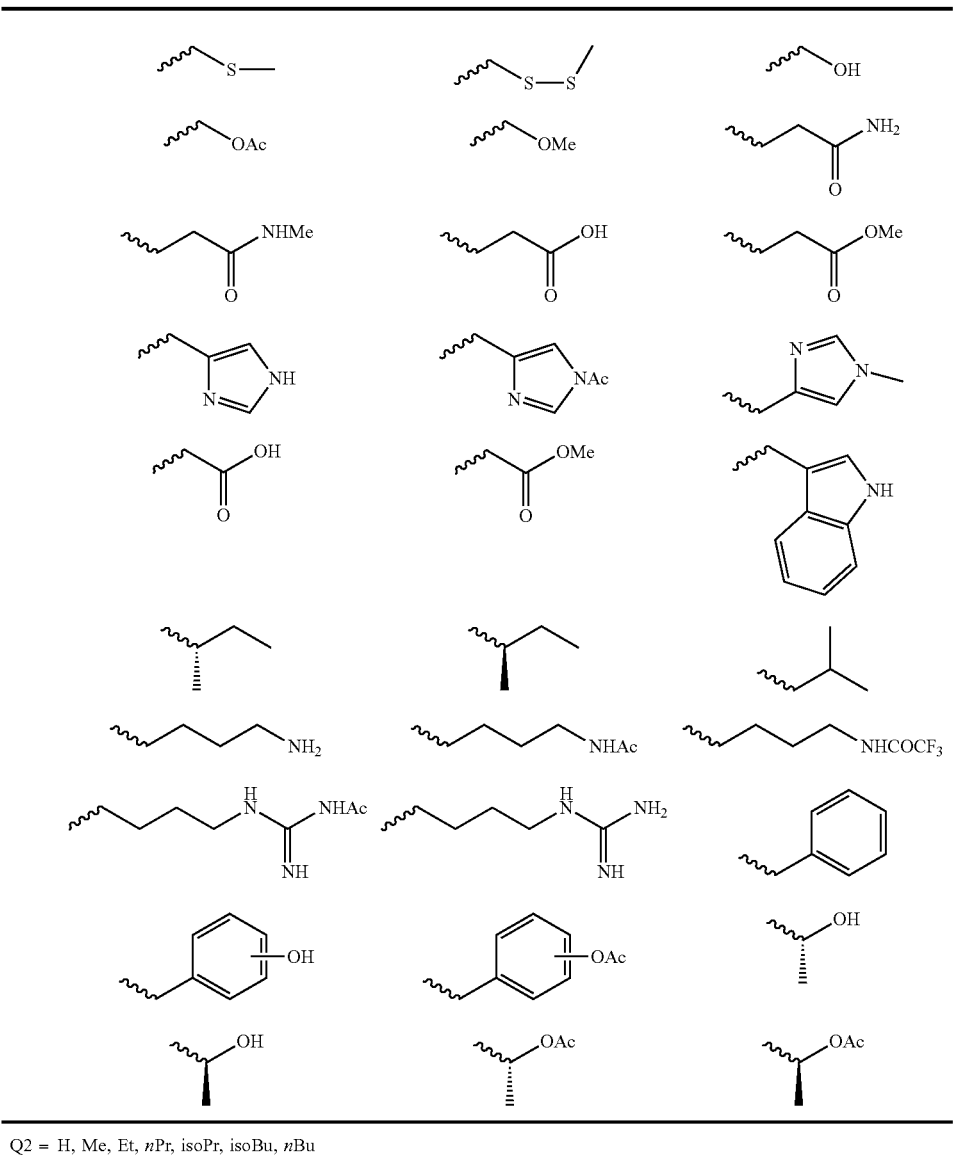
Q2 = H, Me, Et, nPr, isoPr, isoBu, nBu
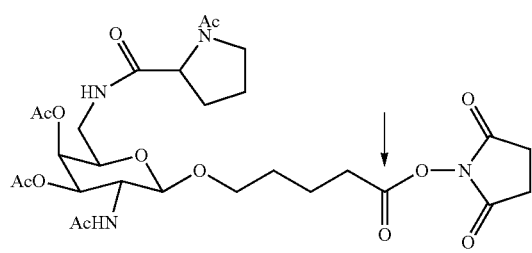
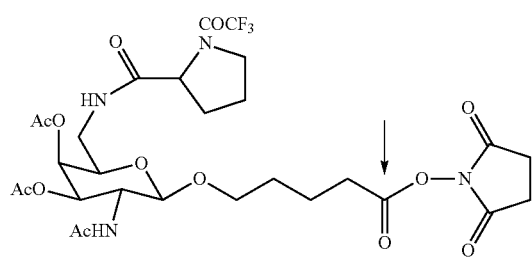

TABLE 4[b]-continued
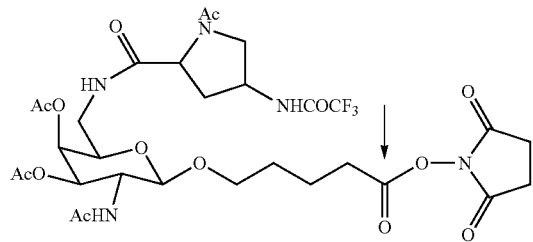
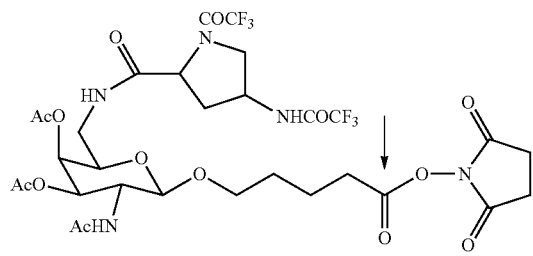
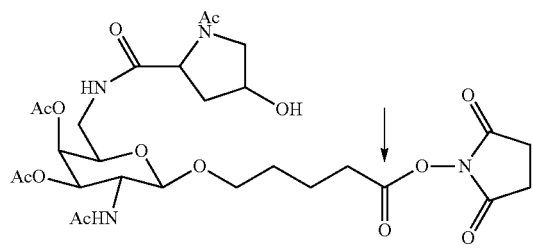
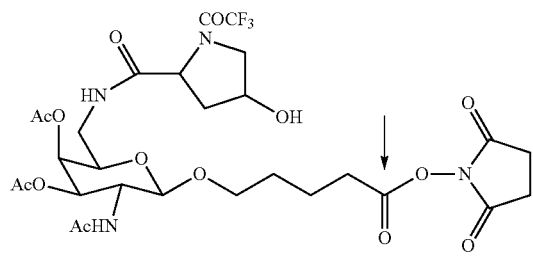
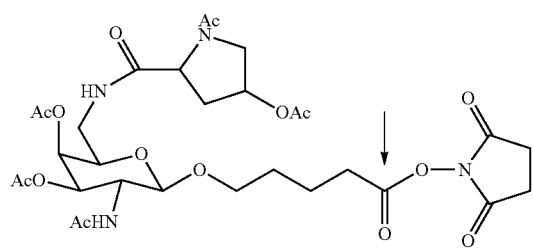
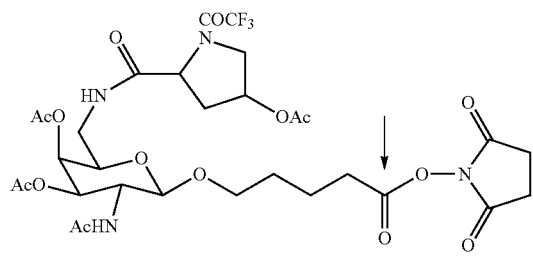

TABLE 4[b]-continued
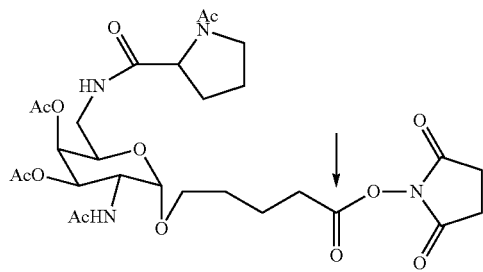
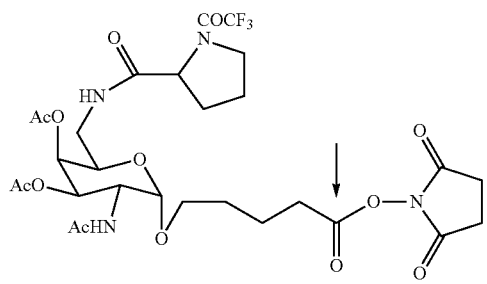
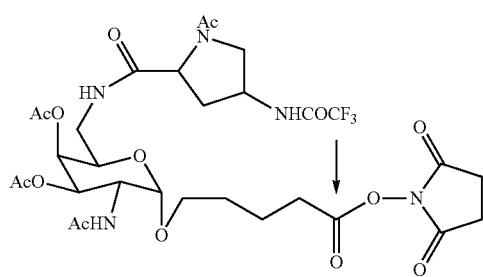
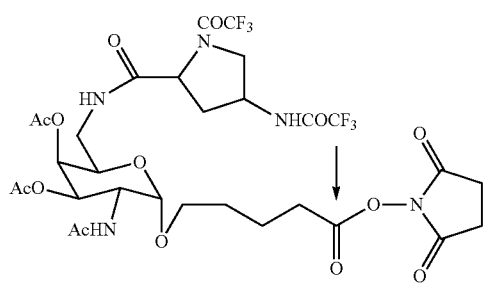
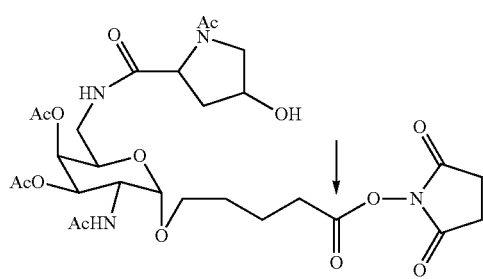

TABLE 4[b]-continued
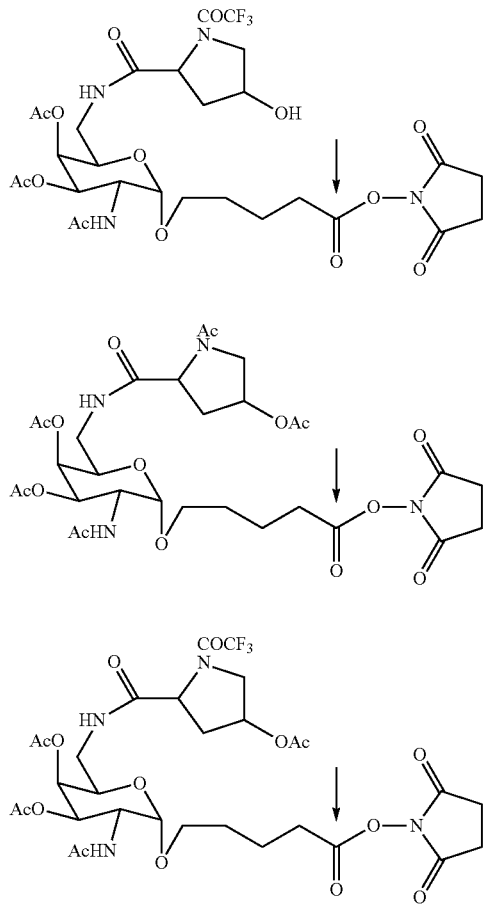
$n$ is 1 to 8, e.g., 1 to 4
[b] Each structure represents chirally pure or racemic isomers when one or more asymmetric centers are present.
The arrow indicates the point of attachment to the Linker.
TABLE 4A[b]
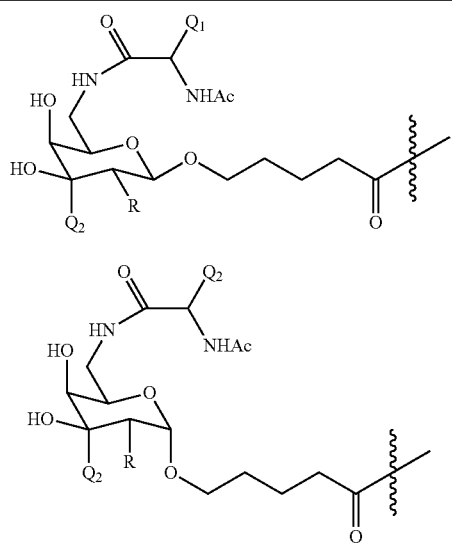

TABLE 4A[b]-continued
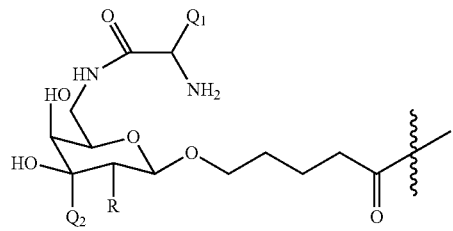
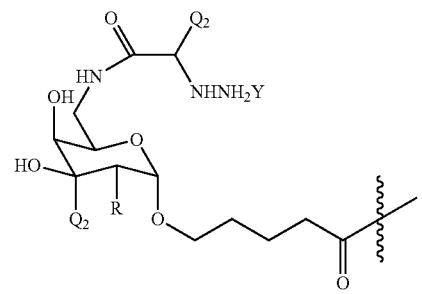
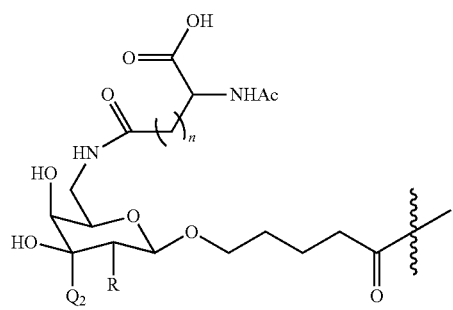
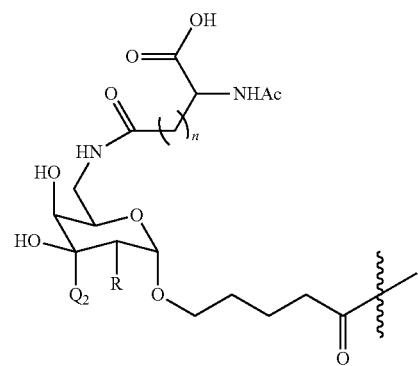
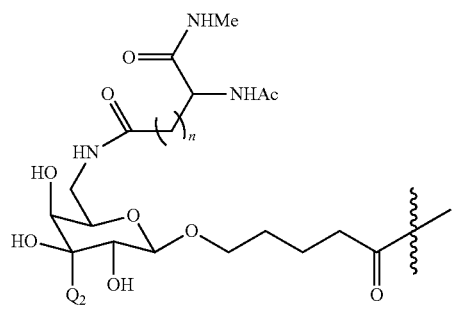

TABLE 4A[b]-continued
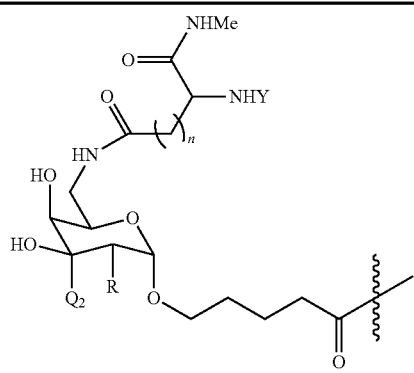
X = H, Me
Y = H, Ac, COCF₃
Q1 = H, CH₃, Et, nPr, isoPr, nBu, isoBu
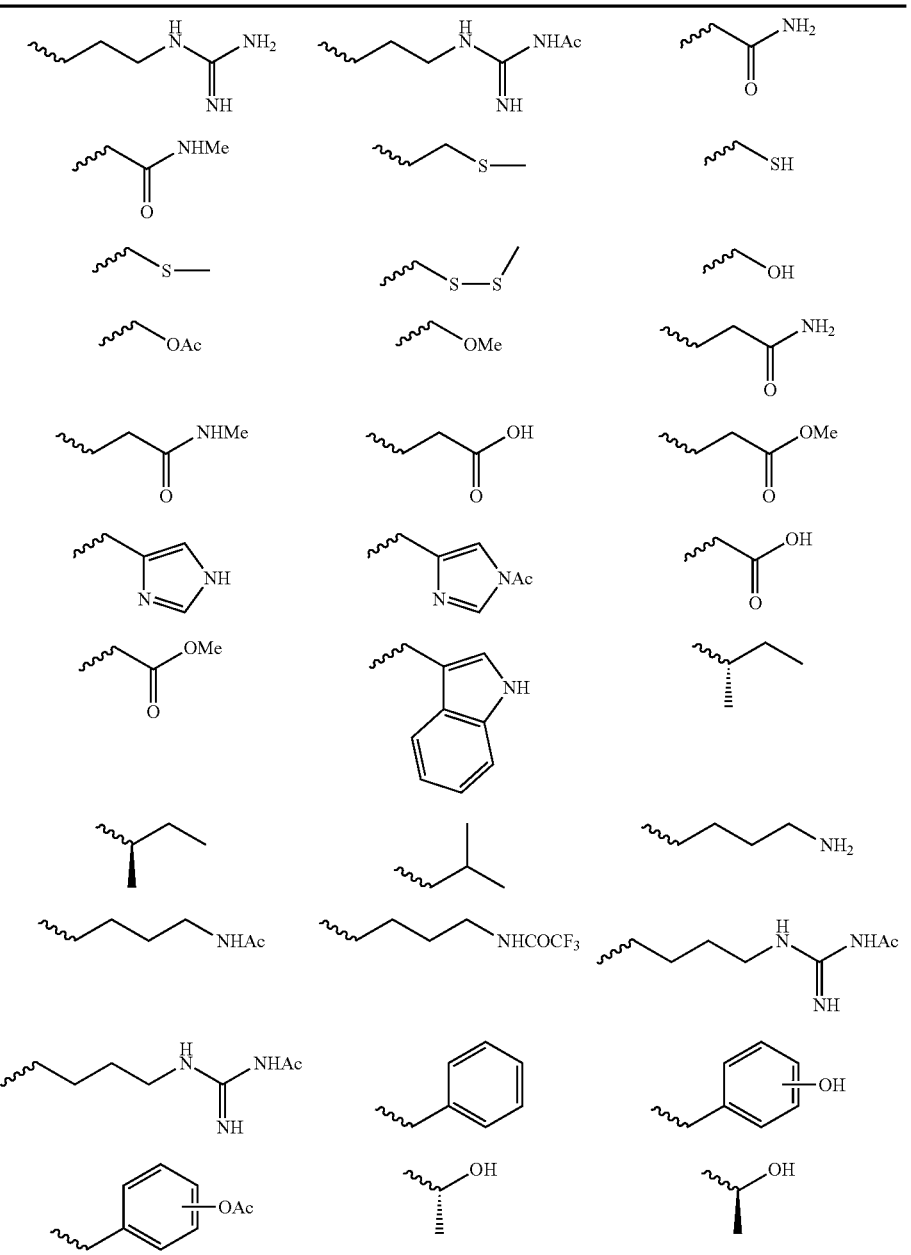

TABLE 4A[b]-continued
| 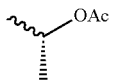 | 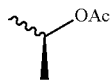 |
| Q2 | H, Me, Et, nPr, isoPr, isoBu, nBu |
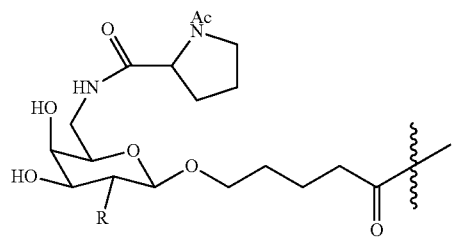
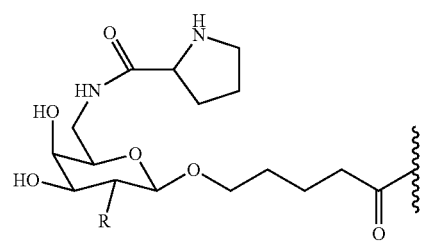
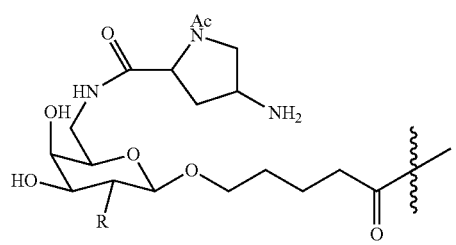
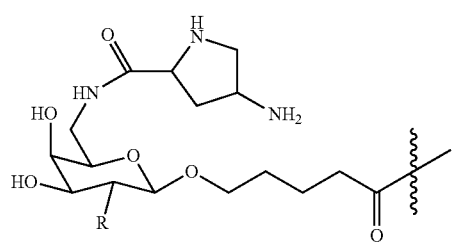
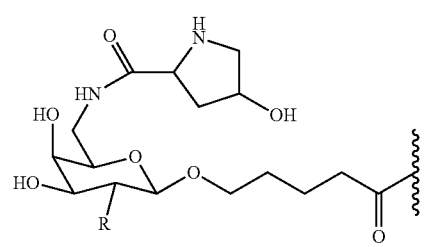
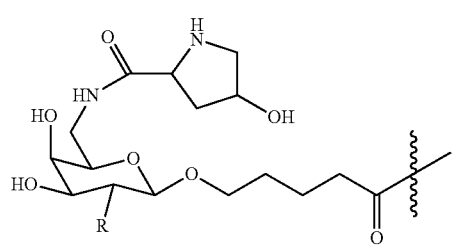

TABLE 4A[b]-continued
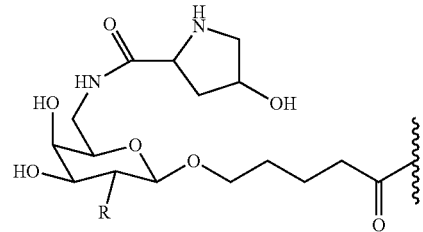
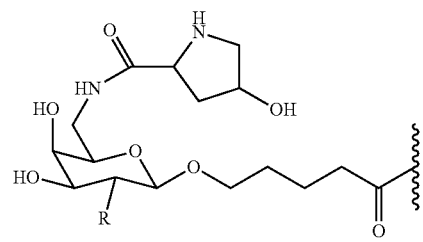
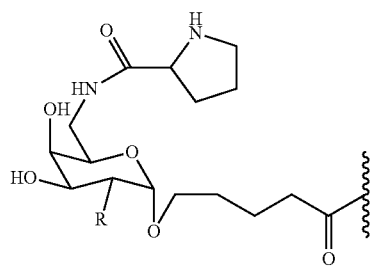
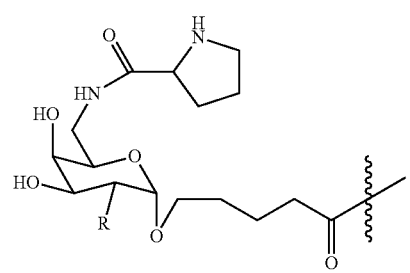
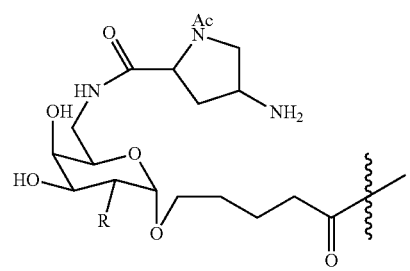

TABLE 4A[b]-continued
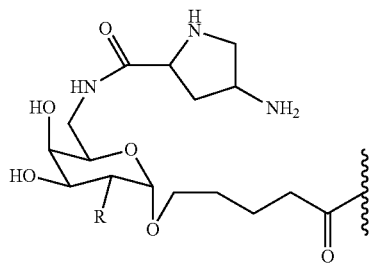
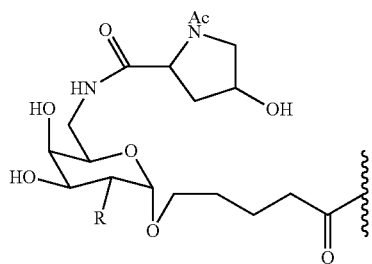
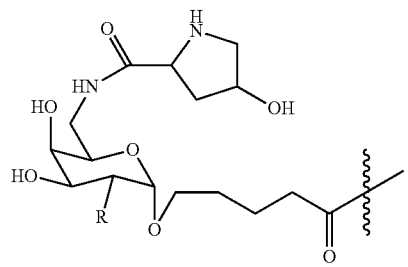
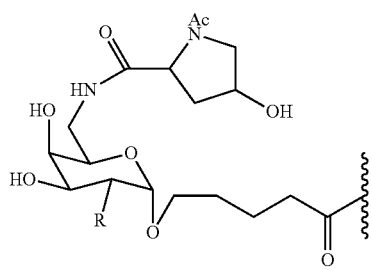
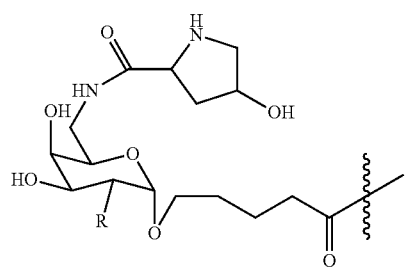
$n$ is 1 to 8, e.g., 1 to 4
[b] Each structure represents chirally pure or racemic isomers when one or more asymmetric centers present
R = OH or NHAc in all occurrence
The squiggly linke indicates the point of attachment to the Linker.

TABLE 5
Spacers (R²)
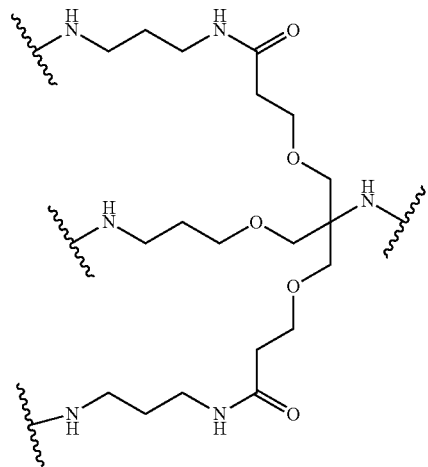 [SMILES: *NCCCNC(=O)CCOCC(COCCCN*)(COCCC(=O)NCCCN*)N*]
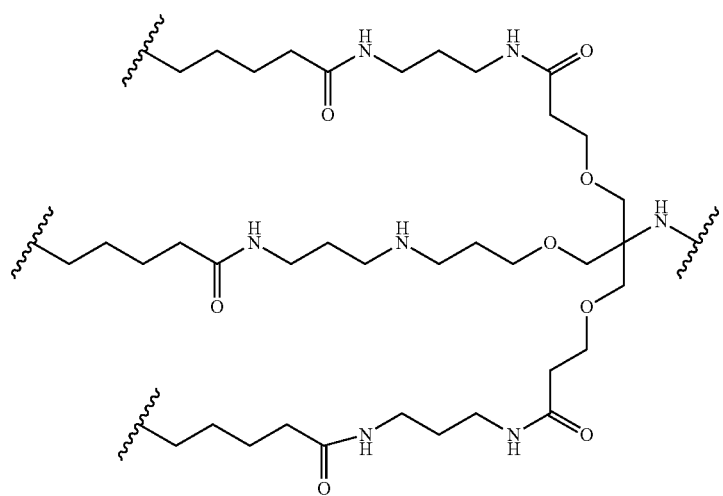 [SMILES: *CCCCC(=O)NCCCNCCCOCC(COCCC(=O)NCCCNC(=O)CCCC*)(COCCC(=O)NCCCNC(=O)CCCC*)N*]
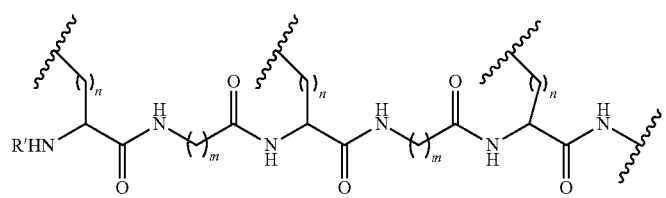
R' = H or Ac
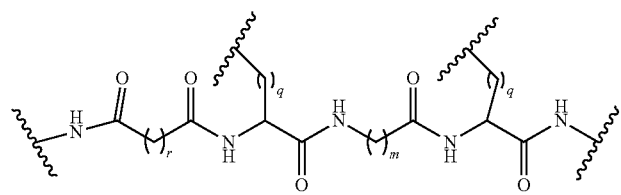

TABLE 5-continued
Spacers ($R^2$)
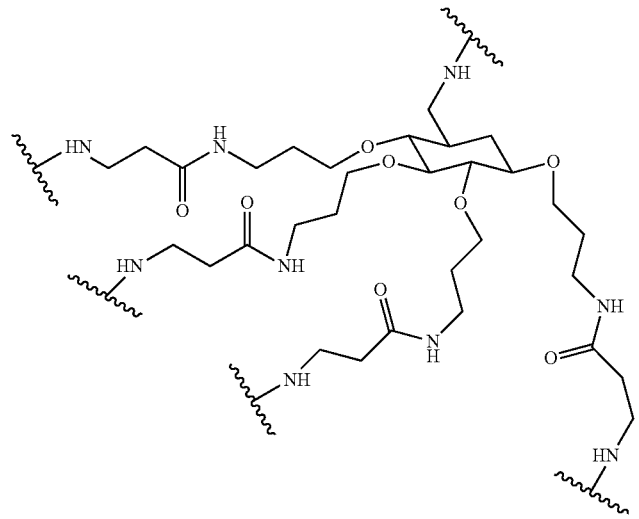
(the Linker attached through the NH group at
the 6-position of the sugar shown above.)
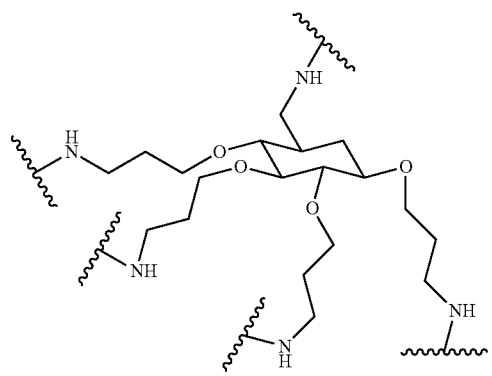
(the Linker attached through the NH group at
the 6-position of the sugar shown above.)
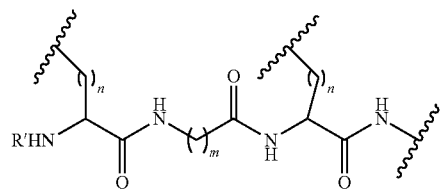
R' = H, Ac
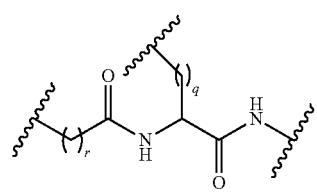

TABLE 5-continued

Spacers (R²)

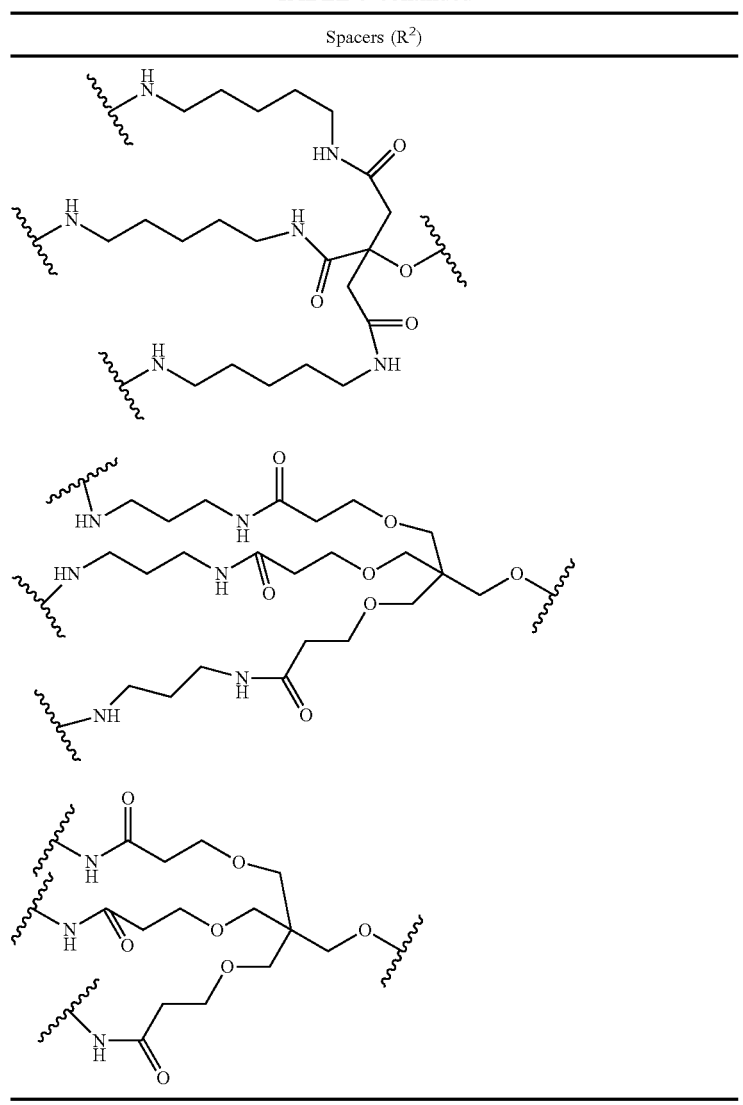

All the squiggly lines (except for the right most squiggly lines) are the points of attachment for the targeting monomers R³. The right most squiggly line is the point of attachment of the Linker. Each of the variables m, n, q, and r independently ranges from about 0 to about 10.

In tables 2, 2A, 3, 3A, 4, and 4A and other formulas which include one or more —OAc substituents on the sugar moiety, the compounds of the present invention include the identical compounds containing —OH substituents at the one or more —OAc positions shown. In general, the acetyl (Ac) group acts as protecting group for the hydroxyl moiety. Accordingly, it will be understood by those skilled in the art that the corresponding hydroxy compounds are within the scope of the present invention and are intended to be used in the final conjugates with an oligonucleotide or other biologically active agent.

In addition, the compounds of the present invention also include those in which any —NHAc substituent on the sugar moiety is replaced with a hydroxy group (e.g., where the —NHAc group at the 2-position of the sugar moiety is replaced with a 2-OH group). In one embodiment, in addition to the replacement of the —NHAc group(s) with hydroxy group(s), any —OAc substituents on the sugar moiety are also replaced with hydroxy group(s).

In one embodiment, the Ligand(s) are selected from:

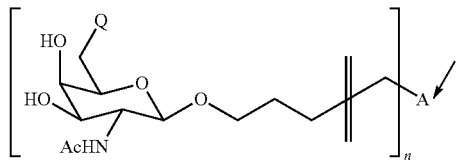

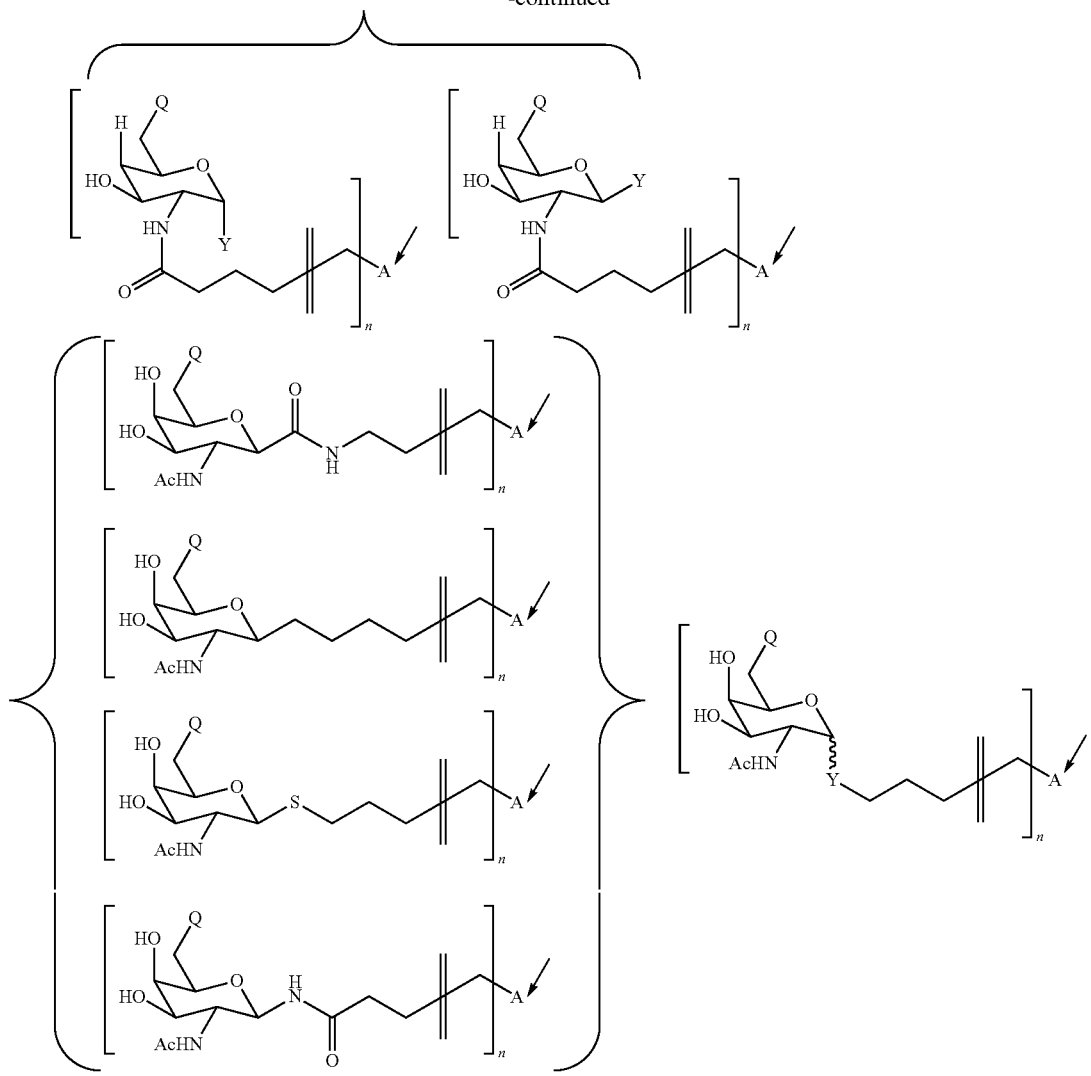

where

A is the attachment point to the Linker, and can represent a bond or a chemical linkage group (e.g., an amide, carbamate, urea, —C—N— (e.g., —CH$_2$—NH— or —C(R$^a$)(R$^b$)—N(R$^c$)— where R$^a$, R$^b$, and R$^c$ are independent selected from hydrogen, alkyl, and aryl), C=NH, ether, thioether, triazole, oxime, or hydrazine) which is attached to the Linker;

Y is any functional group (e.g., when used as a divalent group, it can be —CONH—, —NHCO—, or S, or, e.g., when used as a monovalent group, it can be —OH, —SH, or halogen), —CH$_2$—, protecting group, or chemically inactive cap;

Q is OH, or any modification to the C6 position of the sugar described herein; and n is 1 to 6.

In yet another embodiment, the sugar moiety in any of the aforementioned ligands or targeting monomers (such as in Tables 2, 2A, 3, 3A, 4, and 4A) may be replaced with the sugar moiety of formula III below

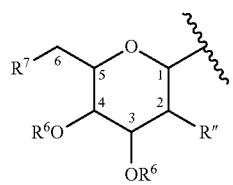

Formula III wherein each occurrence of R$^6$ is independently as defined above (e.g., H or Ac);

R$^7$ and R″ are independently selected from —Z—R$^{10}$, unsubstituted and substituted heteroaryl (e.g., a triazole or imidazole), —N$_3$, —CN, and substituted and unsubstituted acetylene;

each occurrence of Z is independently O, NH, or S;

each occurrence of R$^{10}$ is independently H, unsubstituted or substituted alkyl, unsubstituted acyl (e.g., —COCH$_3$), substituted acyl (e.g., —COCF$_3$), —OC(O)OR$^{11}$, —NHC(O)OR$^{11}$, —NHC(O)NHR$^{11}$, or an amino acid; and each occurrence of R$^{11}$ is independently H or unsubstituted or substituted alkyl, with the proviso that $R^7$ is not —OH or —OAc when (i) $R^6$ is H or (ii) R" is OH or NHAc.

Yet another embodiment is an intermediate compound of the formula

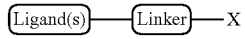

where

Ligand(s) and Linker are as defined above, and

X is

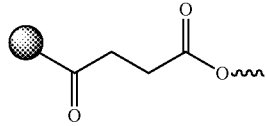

(where the sphere represents a solid support),

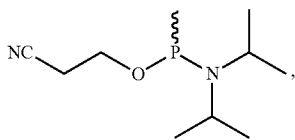

a leaving group, H, —OH, or —NH$_2$.

These intermediates are useful for preparing the olignucleotide-ligand conjugates of the present invention.

Yet another embodiment is an intermediate compound of the formula IIIA

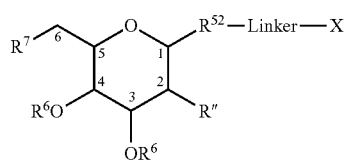

Formula IIIA wherein $R^{52}$ is a bivalent chemical group of 1 to 12 atoms in length;

Linker is defined as above;

each occurrence of $R^6$ is independently as defined above (e.g., H or Ac);

$R^7$ and R" are independently selected from —Z—$R^{10}$, unsubstituted and substituted heteroaryl (e.g., a triazole or imidazole), —N$_3$, —CN, and substituted and unsubstituted acetylene;

each occurrence of Z is independently O, NH, or S;

each occurrence of $R^{10}$ is independently H, unsubstituted or substituted alkyl, unsubstituted acyl (e.g., —COCH$_3$), substituted acyl (e.g., —COCF$_3$), —OC(O)O$R^{11}$, —NHC(O)O$R^{11}$, —NHC(O)NH$R^{11}$, or an amino acid;

each occurrence of $R^{11}$ is independently H or unsubstituted or substituted alkyl; and X is

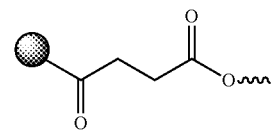

(where the sphere represents a solid support),

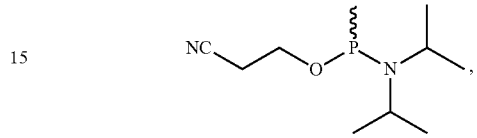

a leaving group, H, —OH, or —NH$_2$, with the proviso that $R^7$ is not —OH or —OAc when (i) $R^6$ is H or (ii) R" is OH or NHAc.

In one preferred embodiment, the substitutions at the 3- and 4-positions of the sugar group in formula III or IIIA are equatorial and axial, respectively.

In one embodiment, the sugar in formula III or IIIA is in an alpha configuration. In another embodiment, the sugar is in a beta configuration.

The present invention also includes compounds of formula IIIA where X is replaced by an oligonucleotide or other biologically active agent as described herein.

The same linkage or a combination of linkages described herein can be used for attaching two or more ligand/linker moieties to the oligonucleotide or other biologically active agent. For example, in one embodiment, the invention relates to a conjugate of an oligonucleotide (e.g., an iRNA agent) or other biologically active agent of the formula IV

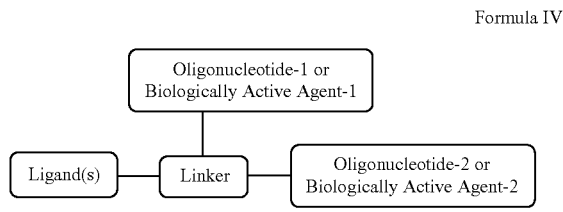

Formula IV wherein the Ligand(s) and Linker are as defined above;

Oligonucleotide-1 and Oligonucleotide-2 have the same definition as Oligonucleotide above;

Biologically Active Agent-1 and Biologically Active Agent-2 have the same definition as Biologically Active Agent above; and each Ligand may be the same or different and each Oligonucleotide may be the same or different.

In formula IV, the Linker connects two segments of the oligonucleotide (oligonucleotide 1 and 2) via two linkages. Each segment of the oligonucleotide represents at least one nucleoside moiety.

Yet another embodiment is a conjugate of an oligonucleotide (e.g., an iRNA agent) or other biologically active agent of the formula V:

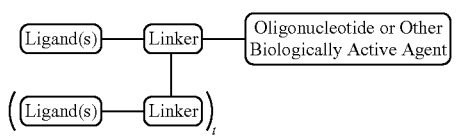

Formula V wherein
each Oligonucleotide (or Biologically Active Agent) and Ligand are independently as defined herein;
each Linker can independently be any those described herein (e.g., in Table 1 or 1A) or can have the formula

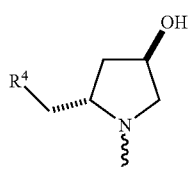

where $R^4$ is the site of attachment to the oligonucleotide (for example, via a cleavable group in the oligonucleotide), and the hydroxy group on the hydroxyproline is the site of attachment for an additional -Linker-Ligand group; and
t ranges from 1 to 6 (e.g., 1, 2, 3, 4, 5, or 6).
In one preferred embodiment, t is 2.
In one preferred embodiment, the oligonucleotides in the conjugates described herein are attached to the Linker via a phosphate, phosphorothioate, or a combination thereof.
In one embodiment, the conjugate is an oligonucleotide conjugate having the formula:

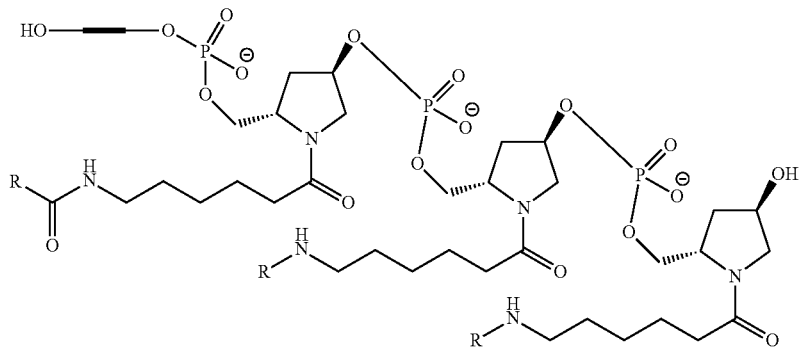

wherein each R is independently a Ligand (such as those described herein). In one preferred embodiment, the Ligands R are the same.

The present invention also relates to a ligand conjugate of an oligonucleotide where at least one nucleoside is conjugated to a carbohydrate-containing Ligand either (i) through the nucleobase of the nucleoside or (ii) at the 2'-position of the nucleoside.

One embodiment is a carbohydrate conjugate of an oligonucleotide, wherein at least one nucleoside in the oligonucleotide is conjugated to a carbohydrate-containing Ligand (e.g., a sugar-containing Ligand) via a nitrogen atom in the nucleobase of the nucleoside. Any Ligand described herein may be used. In one embodiment, the nucleoside in the conjugate is of the formula VI:

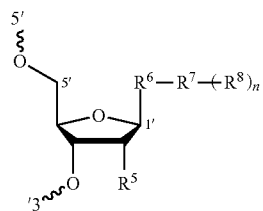

Formula VI where
the 5' and 3' ends of the nucleoside in Formula VI are each attached to another nucleoside of the oligonucleotide or to a terminus;
$R^6$ is a nucleobase (e.g., uracil, cytosine, adenosine, or guanine) and optionally has a nitrogen-containing moiety bound to the nucleobase;
$R^7$ is a Linker, where $R^7$ is bound to a nitrogen atom (e.g., an amino group) in $R^6$;
each $R^8$ is independently a Ligand. Each $R^8$ may be attached to the same or different atoms in the Linker $R^7$. The ligand $R^8$ can be, for example, —$R^2$—$R^3$ or the ligands in Tables 2, 2A, 4, and 4A In one embodiment, $R^6$ is uracil substituted at its 5-position with an amide group —C(O)NH—, where $R^7$ is bound to $R^6$ through the nitrogen atom of the amide group.

In another embodiment, $R^6$ is cytosine substituted at its 5-position with an amide group —C(O)NH—, where $R^7$ is bound to $R^6$ through the nitrogen atom of the amide group.

Another embodiment is a carbohydrate conjugate of an oligonucleotide, wherein at least one nucleoside in the oligonucleotide is conjugated to a Ligand (e.g., sugar-containing Ligand) at its 2'-position. Any Ligand described herein may be used. In one embodiment, the nucleoside in the conjugate is of the formula VII:

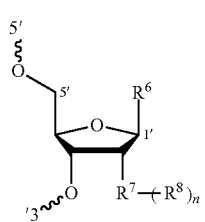

Formula VII where
the 5' and 3' ends of the nucleoside in Formula VII are each attached to another nucleoside of the oligonucleotide or to a terminus;

$R^6$ is a nucleobase;

$R^7$ is a Linker;

each $R^8$ is independently a Ligand. Each $R^8$ may be attached to the same or different atoms in the Linker $R^7$. In one preferred embodiment, the oligonucleotide is attached to the Linker via a phosphate, phosphorothioate, or a combination thereof. For example, the oligonucleotide may be attached to a Linker at the 3'-end via a phosphate and/or a phosphorothioate at the 5'-end, or vice versa.

The ligand moiety (e.g., a carbohydrate moiety) facilitates delivery of the oligonucleotide to the target site. One way a ligand moiety can improve delivery is by receptor mediated endocytotic activity. Without being bound by any particular theory, it is believed that this mechanism of uptake involves the movement of the oligonucleotide bound to membrane receptors into the interior of an area that is enveloped by the membrane via invagination of the membrane structure or by fusion of the delivery system with the cell membrane. This process is initiated via activation of a cell-surface or membrane receptor following binding of a specific ligand to the receptor. Receptor-mediated endocytotic systems include those that recognize sugars such as galactose. The ligand moiety therefore may include one or more monosaccharides, disaccharides, trisaccharides, tetrasaccharides, oligosaccharides, or polysaccharides, such as those described above. In one preferred embodiment, the ligand moiety may be a moiety which is recognized by a human asialoglycoprotein receptor (ASGPR), such as human asialoglycoprotein receptor 2 (ASGPR2). Such a carbohydrate moiety may, for instance, comprise a sugar (e.g., galactose or N-acetyl-D-galactosylamine).

Yet another embodiment is an oligonucleotide in which two or more nucleotides each have a -Linker-Ligand moiety. The -Linker-Ligand moieties in the oligonucleotide may be the same or different. In one embodiment, the first, third, and fifth nucleotides from the 5' terminus are each conjugated to a -Linker-Ligand moiety. In another embodiment, the first, third, and fifth nucleotides from the 3' terminus are each conjugated to a -Linker-Ligand moiety. In yet another embodiment, the first, third, and fifth nucleotides from the 3' and 5' ends of the oligonucleotide are each conjugated to a -Linker-Ligand moiety.

Yet another embodiment is a method of formulating a therapeutic RNA by preparing a conjugate of an iRNA agent of the present invention, where a strand of the iRNA agent comprises the therapeutic RNA.

Yet another embodiment is a method of delivering a therapeutic RNA to a patient in need thereof by administering to the patient a conjugate of an iRNA agent of the present invention, where the a strand of the iRNA agent comprises the therapeutic RNA. Preferred routes of administration include the subcutaneous and intravenous routes.

DESCRIPTION OF THE DRAWINGS

FIG. 1 is a bar graph showing transthyretin (TTR) protein levels 48 and 144 hours after administration of TTR siRNA conjugates in mice relative to control mice according to the procedure in Example 33.

FIG. 2 is a bar graph showing antithrombin 3 (AT3) protein levels following administration of AT3 siRNA conjugates in mice relative to control mice according to the procedure in Example 34.

DETAILED DESCRIPTION OF THE INVENTION

Definitions

Figure 3A:
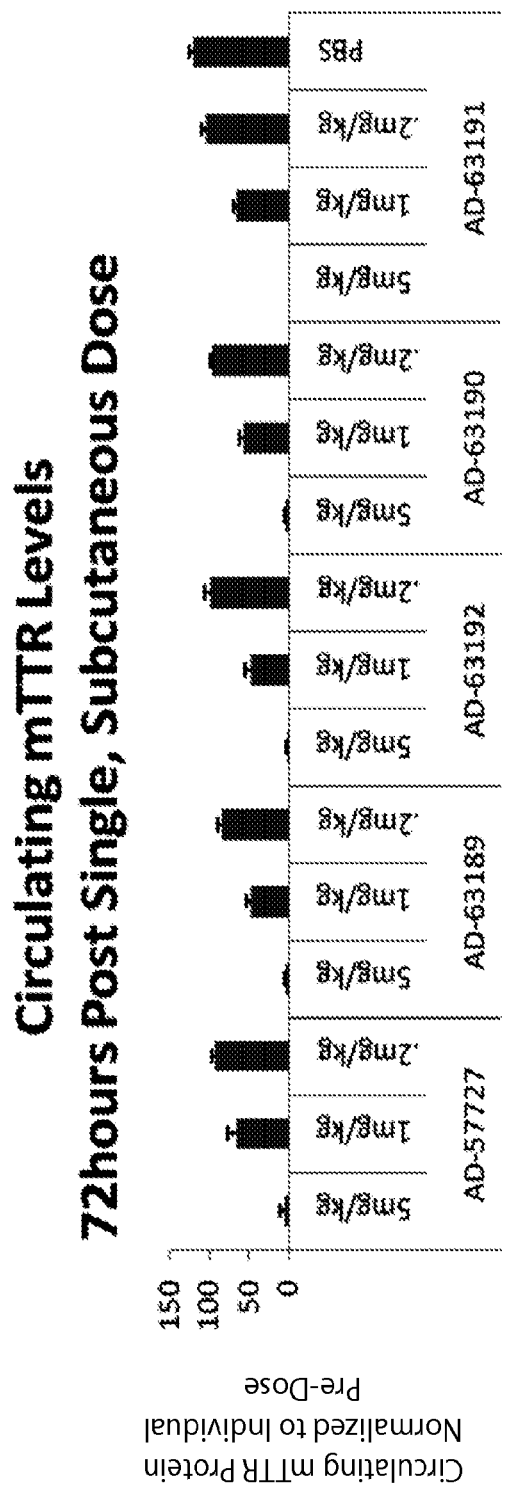
FIGS. 3A and 3B are bar graphs showing mTTR protein levels 72 hours (FIG. 3A) and 144 hours (FIG. 3B) following a single subcutaneous dose of conjugates 57727, 63189, 63192, 63190 and 63191 to mice according to the procedure in Example 62.

The term "oligonucleotide" refers to a chemically modified or unmodified nucleic acid molecule (RNA or DNA) having a length of less than about 100 nucleotides (for example, less than about 50 nucleotides. The nucleic acid can, for example, be (i) single stranded DNA or RNA, (ii) double stranded DNA or RNA, including double stranded DNA or RNA having a hairpin loop, or (iii) DNA/RNA hybrids. Non-limiting examples of double stranded RNA include siRNA (small interfering RNA). Single stranded nucleic acids include, e.g., antisense oligonucleotides, ribozymes, microRNA, and triplex forming oligonucleotides. In one embodiment, the oligonucleotide has a length ranging from about 5 to about 50 nucleotides (such as from about 10 to about 50 nucleotides). In another embodiment, the oligonucleotide has a length ranging from about 6 to about 30 nucleotides, such as from about 15 to about 30 nucleotides. In yet another embodiment, the oligonucleotide has a length ranging from about 18 to about 23 nucleotides.

The term "GalNAc" refers to N-acetyl-galactosamine.

The term "solid support," as used herein denotes in particular any particle, bead, or surface upon which synthesis of an oligonucleotide occurs. Solid supports which can be used in the different embodiments of the processes described herein can be selected for example from inorganic supports and organic supports. Inorganic supports are preferably selected from silica gel and controlled pore glass (CPG). Organic supports are preferably selected from highly cross-linked polystyrene, Tentagel (grafted copolymers consisting of a low crosslinked polystyrene matrix on which polyethylene glycol (PEG or POE) is grafted), polyvinylacetate (PVA), Poros—a copolymer of polystyrene/divinyl benzene, aminopolyethyleneglycol and cellulose. Preferred solid supports amenable to this invention include those that are hydrophobic. Preferred embodiments of the invention utilize polystyrene based solid supports. Many other solid supports are commercially available and amenable to the present invention.

The term "hydroxy protecting group," as used herein, refers to a labile chemical moiety which protects a hydroxyl group against undesired reactions during synthetic procedure(s). After the synthetic procedure(s), the hydroxy protecting group may be selectively removed. Hydroxy protecting groups as known in the art are described generally in T. H. Greene and P. G. M. Wuts, *Protective Groups in Organic Synthesis*, 3rd edition, John Wiley & Sons, New York (1999). Examples of hydroxyl protecting groups include, but are not limited to, benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, and triisopropylsilyl. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which protects an amino group against undesired reactions during synthetic procedures. After the synthetic procedure(s), the amino protecting group as described herein may be selectively removed. Amino protecting groups as known in the are described generally in T. H. Greene and P. G. M. Wuts, *Protective Groups in Organic Synthesis*, 3rd edition, John Wiley & Sons, New York (1999). Examples of amino protecting groups include, but are not limited to, acetyl, t-butoxycarbonyl, 9-fluorenylmethoxycarbonyl, and benzyloxycarbonyl.

The term "carboxylic acid protecting group" refers to carboxylic acid protecting groups employed to block or protect the carboxylic acid functionality while reactions involving other functional sites of the compound are carried out. Such carboxy protecting groups may be noted for their ease of cleavage by hydrolytic or by hydrogenolytic methods to the corresponding carboxylic acid. Examples of carboxylic acid ester protecting groups include, but are not limited to, methyl, tert-butyl, benzyl, 4-methoxybenzyl, C2-C6 alkanoyloxymethyl, 2-iodoethyl, 4-nitrobenzyl, diphenylmethyl (benzhydryl), phenacyl, 4-halophenacyl, dimethylallyl, 2,2,2-trichloroethyl, tri(C1-C3 alkyl)silyl, succinimidomethyl and like ester forming moieties. In addition to ester protection of carboxy groups, such groups can also be protected as the mixed anhydride, such as that formed with acetyl chloride, propionyl chloride, isobutyryl chloride and other acid chlorides in the presence of a tertiary amine base. Other known carboxy protecting groups such as those described by E. Haslam in *Protective Groups in Organic Chemistry*, supra, Chapter 5, are suitable. The ester forming protecting groups are preferred.

In the foregoing definitions hydroxy and carboxy protecting groups are not exhaustively defined. The function of such groups is to protect the reactive functional groups during the preparative steps and then to be removed at some later point in time without disrupting the remainder of the molecule. Many protecting groups are known in the art, and the use of other protecting groups not specifically referred to hereinabove are equally applicable.

Suitable peptide coupling reagents include, but are not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino)phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). EDC, HOAT, BOP-Cl and PyBrOP are preferred peptide coupling reagents. The amount of peptide coupling reagent is in the range of about 1.0 to about 10.0 equivalents. Optional reagents that may be used in the amide bond-forming reaction include DMAP (4-dimethylaminopyridine) or active ester reagents, such as HOBT (1-hydroxybenzotriazole), HOAT (hydroxyazabenzotriazole), HOSu (hydroxysuccinimide), HONB (endo-N-hydroxy-5-norbornene-2,3-dicarboxamide), in amounts ranging from about 1.0 to about 10.0 equivalents.

The term "halo" refers to any radical of fluorine, chlorine, bromine or iodine.

The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally interrupted with N, O, or S. For example, $C_1$-$C_{10}$ indicates that the group may have from 1 to 10 (inclusive) carbon atoms in it. The term "alkylene" refers to a divalent alkyl (i.e., —R—).

The term "alkoxy" refers to an —O-alkyl radical.

The term "alkylenedioxo" refers to a divalent species of the structure —O—R—O—, in which R represents an alkylene.

The term "aminoalkyl" refers to an alkyl substituted with an amino group.

The term "mercapto" refers to an —SH radical.

The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl and naphthyl.

The terms "arylalkyl" and "aralkyl" refers to an alkyl substituted with an aryl.

The term "arylalkoxy" refers to an alkoxy substituted with an aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively), and 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, and thiazolyl.

The terms "heteroarylalkyl" and "heteroaralkyl" refer to an alkyl substituted with a heteroaryl.

The term "heteroarylalkoxy" refers to an alkoxy substituted with a heteroaryl.

The term "heterocyclyl" refers to a non-aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, where the heteroatoms are selected from O, N, or S (e.g., carbon atoms and 1-3, 1-6, or 1-9 heteroatoms of N, O, or S if monocyclic, bicyclic, or tricyclic, respectively), and 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, and tetrahydrofuranyl.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by one or more substituents.

The term "DMTr" refers to 4,4'-dimethoxytrityl, unless otherwise specified.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

The term "monosaccharide" embraces radicals of allose, altrose, arabinose, cladinose, erythrose, erythrulose, fructose, D-fucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose and xylulose. The monosaccharide can be in D- or L-configuration. The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or C═O replaced by C═S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, preferably galactosamine, glucosamine, mannosamine, fucosamine, quinovosamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide" and "polysaccharide" embrace radicals of abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructooligosaccharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, β-maltose, maltriose, mannan-oligosaccharide, manninotriose, melezitose, melibiose, muramic acid, mycarose, mycinose, neuraminic acid, nigerose, nojirimycin, noviose, oleandrose, panose, paratose, planteose, primeverose, raffinose, rhodinose, rutinose, sarmentose, sedoheptulose, sedoheptulosan, solatriose, sophorose, stachyose, streptose, sucrose, α,α-trehalose, trehalosamine, turanose, tyvelose, xylobiose, umbelliferose and the like. Further, it is understood that the "disaccharide", "trisaccharide" and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

Oligonucleotide

The oligonucleotide can be an siRNA, microRNA, anti-microRNA, microRNA mimics, antimiR, antagomir, dsRNA, ssRNA, aptamer, immune stimulatory, decoy oligonucleotides, splice altering oligonucleotides, triplex forming oligonucleotides, G-quadruplexes or antisense. In one embodiment, the oligonucleotide is an iRNA agent.

In some embodiments, the oligonucleotide of the invention comprises one or more monomers that are UNA (unlocked nucleic acid) nucleotides. UNA refers to an unlocked acyclic nucleic acid, wherein at least one of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see Fluiter et al., *Mol. Biosyst.*, 2009, 10, 1039, which is hereby incorporated by reference).

The term "iRNA agent" refers to an RNA agent (or can be cleaved into an RNA agent) which can down regulate the expression of a target gene (e.g., a siRNA), preferably an endogenous or pathogen target RNA. While not wishing to be bound by theory, an iRNA agent may act by one or more of a number of mechanisms, including post-transcriptional cleavage of a target mRNA (referred to in the art as RNAi), or pre-transcriptional or pre-translational mechanisms. An iRNA agent can include a single strand or can include more than one strands, e.g., it can be a double stranded iRNA agent. If the iRNA agent is a single strand it can include a 5' modification which includes one or more phosphate groups or one or more analogs of a phosphate group. In one preferred embodiment, the iRNA agent is double stranded.

The iRNA agent typically includes a region of sufficient homology to the target gene, and is of sufficient length in terms of nucleotides, such that the iRNA agent, or a fragment thereof, can mediate down regulation of the target gene. The iRNA agent is or includes a region which is at least partially, and in some embodiments fully, complementary to the target RNA. It is not necessary that there be perfect complementarity between the iRNA agent and the target, but the correspondence is preferably sufficient to enable the iRNA agent, or a cleavage product thereof, to direct sequence specific silencing, e.g., by RNAi cleavage of the target RNA, e.g., mRNA.

The nucleotides in the iRNA agent may be modified (e.g., one or more nucleotides may include a 2'-F or 2'-OCH$_3$ group), or be nucleotide surrogates. The single stranded regions of an iRNA agent may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis. Modifications can also include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. In some embodiments, the different strands will include different modifications.

In some embodiments, it is preferred that the strands be chosen such that the iRNA agent includes a single strand or unpaired region at one or both ends of the molecule. A double stranded iRNA agent preferably has its strands paired with an overhang, e.g., one or two 5' or 3' overhangs (preferably at least a 3' overhang of 2-3 nucleotides). Preferred iRNA agents will have single-stranded overhangs, preferably 3' overhangs, of 1 or preferably 2 or 3 nucleotides in length at each end. The overhangs can be the result of one strand being longer than the other, or the result of two strands of the same length being staggered.

Preferred lengths for the duplexed regions between the strands of the iRNA agent are between 6 and 30 nucleotides in length. The preferred duplexed regions are between 15 and 30, most preferably 18, 19, 20, 21, 22, and 23 nucleotides in length. Other preferred duplexed regions are between 6 and 20 nucleotides, most preferably 6, 7, 8, 9, 10, 11 and 12 nucleotides in length.

The oligonucleotide may be that described in U.S. Patent Publication Nos. 2009/0239814, 2012/0136042, 2013/0158824, or 2009/0247608, each of which is hereby incorporated by reference.

A "single strand siRNA compound" as used herein, is an siRNA compound which is made up of a single molecule. It may include a duplexed region, formed by intra-strand pairing, e.g., it may be, or include, a hairpin or pan-handle structure. Single strand siRNA compounds may be antisense with regard to the target molecule A single strand siRNA compound may be sufficiently long that it can enter the RISC and participate in RISC mediated cleavage of a target mRNA. A single strand siRNA compound is at least 14, and in other embodiments at least 15, 20, 25, 29, 35, 40, or 50 nucleotides in length. In certain embodiments, it is less than 200, 100, or 60 nucleotides in length.

Hairpin siRNA compounds will have a duplex region equal to or at least 17, 18, 19, 29, 21, 22, 23, 24, or 25 nucleotide pairs. The duplex region will may be equal to or less than 200, 100, or 50, in length. In certain embodiments, ranges for the duplex region are 15-30, 17 to 23, 19 to 23, and 19 to 21 nucleotides pairs in length. The hairpin may have a single strand overhang or terminal unpaired region. In certain embodiments, the overhangs are 2-3 nucleotides in length. In some embodiments, the overhang is at the sense side of the hairpin and in some embodiments on the antisense side of the hairpin.

A "double stranded siRNA compound" as used herein, is an siRNA compound which includes more than one, and in some cases two, strands in which interchain hybridization can form a region of duplex structure.

The antisense strand of a double stranded siRNA compound may be equal to or at least, 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length. As used herein, term "antisense strand" means the strand of an siRNA compound that is sufficiently complementary to a target molecule, e.g. a target RNA.

The sense strand of a double stranded siRNA compound may be equal to or at least 14, 15, 16 17, 18, 19, 25, 29, 40, or 60 nucleotides in length. It may be equal to or less than 200, 100, or 50, nucleotides in length. Ranges may be 17 to 25, 19 to 23, and 19 to 21 nucleotides in length.

The double strand portion of a double stranded siRNA compound may be equal to or at least, 14, 15, 16 17, 18, 19, 20, 21, 22, 23, 24, 25, 29, 40, or 60 nucleotide pairs in length. It may be equal to or less than 200, 100, or 50, nucleotides pairs in length. Ranges may be 15-30, 17 to 23, 19 to 23, and 19 to 21 nucleotides pairs in length.

In many embodiments, the siRNA compound is sufficiently large that it can be cleaved by an endogenous molecule, e.g., by Dicer, to produce smaller siRNA compounds, e.g., siRNAs agents The sense and antisense strands may be chosen such that the double-stranded siRNA compound includes a single strand or unpaired region at one or both ends of the molecule. Thus, a double-stranded siRNA compound may contain sense and antisense strands, paired to contain an overhang, e.g., one or two 5' or 3' overhangs, or a 3' overhang of 1-3 nucleotides. The overhangs can be the result of one strand being longer than the other, or the result of two strands of the same length being staggered. Some embodiments will have at least one 3' overhang. In one embodiment, both ends of an siRNA molecule will have a 3' overhang. In some embodiments, the overhang is 2 nucleotides.

In certain embodiments, the length for the duplexed region is between 15 and 30, or 18, 19, 20, 21, 22, and 23 nucleotides in length, e.g., in the ssiRNA compound range discussed above. ssiRNA compounds can resemble in length and structure the natural Dicer processed products from long dsiRNAs. Embodiments in which the two strands of the ssiRNA compound are linked, e.g., covalently linked are also included. Hairpin, or other single strand structures which provide the required double stranded region, and a 3' overhang are also contemplated.

The siRNA compounds described herein, including double-stranded siRNA compounds and single-stranded siRNA compounds can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an ssiRNA compound of 21 to 23 nucleotides.

In one embodiment, an siRNA compound is "sufficiently complementary" to a target RNA, e.g., a target mRNA, such that the siRNA compound silences production of protein encoded by the target mRNA. In another embodiment, the siRNA compound is "exactly complementary" to a target RNA, e.g., the target RNA and the siRNA compound anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in certain embodiments, the siRNA compound specifically discriminates a single-nucleotide difference. In this case, the siRNA compound only mediates RNAi if exact complementary is found in the region (e.g., within 7 nucleotides of) the single-nucleotide difference.

MicroRNAs

Micro RNAs (miRNAs) are a highly conserved class of small RNA molecules that are transcribed from DNA in the genomes of plants and animals, but are not translated into protein. Processed miRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "miRBase: microRNA sequences, targets and gene nomenclature" Griffiths-Jones S, Grocock R J, van Dongen S, Bateman A, Enright A J. NAR, 2006, 34, Database Issue, D140-D144; "The microRNA Registry" Griffiths-Jones S. NAR, 2004, 32, Database Issue, D109-D111; and also at http://microrna.sanger.ac.uk/sequences/.

Antisense Oligonucleotides

In one embodiment, a nucleic acid is an antisense oligonucleotide directed to a target polynucleotide. The term "antisense oligonucleotide" or simply "antisense" is meant to include oligonucleotides that are complementary to a targeted polynucleotide sequence. Antisense oligonucleotides are single strands of DNA or RNA that are complementary to a chosen sequence, e.g. a target gene mRNA. Antisense oligonucleotides are thought to inhibit gene expression by binding to a complementary mRNA. Binding to the target mRNA can lead to inhibition of gene expression either by preventing translation of complementary mRNA strands by binding to it, or by leading to degradation of the target mRNA. Antisense DNA can be used to target a specific, complementary (coding or non-coding) RNA. If binding takes places this DNA/RNA hybrid can be degraded by the enzyme RNase H. In particular embodiments, antisense oligonucleotides contain from about 10 to about 50 nucleotides, more preferably about 15 to about 30 nucleotides. The term also encompasses antisense oligonucleotides that may not be exactly complementary to the desired target gene. Thus, instances where non-target specific-activities are found with antisense, or where an antisense sequence containing one or more mismatches with the target sequence is the most preferred for a particular use, are contemplated.

Antisense oligonucleotides have been demonstrated to be effective and targeted inhibitors of protein synthesis, and, consequently, can be used to specifically inhibit protein synthesis by a targeted gene. The efficacy of antisense oligonucleotides for inhibiting protein synthesis is well established. For example, the synthesis of polygalacturonase and the muscarine type 2 acetylcholine receptor are inhibited by antisense oligonucleotides directed to their respective mRNA sequences (U.S. Pat. Nos. 5,739,119 and 5,759,829 each of which is incorporated by reference). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun. 10; 240(4858):1544-6; Vasanthakumar and Ahmed, Cancer Commun. 1989; 1(4):225-32; Peris et al., Brain Res Mol Brain Res. 1998 Jun. 15; 57(2):310-20; U.S. Pat. Nos. 5,801,154; 5,789,573; 5,718,709 and 5,610,288, each of which is incorporated by reference). Furthermore, antisense constructs have also been described that inhibit and can be used to treat a variety of abnormal cellular proliferations, e.g. cancer (U.S. Pat. Nos. 5,747,470; 5,591,317 and 5,783,683, each of which is incorporated by reference).

Methods of producing antisense oligonucleotides are known in the art and can be readily adapted to produce an antisense oligonucleotide that targets any polynucleotide sequence. Selection of antisense oligonucleotide sequences specific for a given target sequence is based upon analysis of the chosen target sequence and determination of secondary structure, $T_m$, binding energy, and relative stability. Antisense oligonucleotides may be selected based upon their relative inability to form dimers, hairpins, or other secondary structures that would reduce or prohibit specific binding to the target mRNA in a host cell. Highly preferred target regions of the mRNA include those regions at or near the AUG translation initiation codon and those sequences that are substantially complementary to 5' regions of the mRNA. These secondary structure analyses and target site selection considerations can be performed, for example, using v.4 of the OLIGO primer analysis software (Molecular Biology Insights) and/or the BLASTN 2.0.5 algorithm software (Altschul et al., Nucleic Acids Res. 1997, 25(17):3389-402).

Antagomirs

Antagomirs are RNA-like oligonucleotides that harbor various modifications for RNAse protection and pharmacologic properties, such as enhanced tissue and cellular uptake. They differ from normal RNA by, for example, complete 2'-O-methylation of sugar, phosphorothioate backbone and, for example, a cholesterol-moiety at 3'-end. Antagomirs may be used to efficiently silence endogenous miRNAs by forming duplexes comprising the antagomir and endogenous miRNA, thereby preventing miRNA-induced gene silencing. An example of antagomir-mediated miRNA silencing is the silencing of miR-122, described in Krutzfeldt et al, Nature, 2005, 438: 685-689, which is expressly incorporated by reference herein in its entirety. Antagomir RNAs may be synthesized using standard solid phase oligonucleotide synthesis protocols. See U.S. Patent Application Publication Nos. 2007/0123482 and 2007/0213292 (each of which is incorporated herein by reference).

An antagomir can include ligand-conjugated monomer subunits and monomers for oligonucleotide synthesis. Exemplary monomers are described in U.S. Patent Application Publication No. 2005/0107325, which is incorporated by reference in its entirety. An antagomir can have a ZXY structure, such as is described in WO 2004/080406, which is incorporated by reference in its entirety. An antagomir can be complexed with an amphipathic moiety. Exemplary amphipathic moieties for use with oligonucleotide agents are described in WO 2004/080406, which is incorporated by reference in its entirety.

Aptamers

Aptamers are nucleic acid or peptide molecules that bind to a particular molecule of interest with high affinity and specificity (Tuerk and Gold, Science 249:505 (1990); Ellington and Szostak, Nature 346:818 (1990), each of which is incorporated by reference in its entirety). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9 (1999), and Hermann and Patel, Science 287:820-5 (2000), each of which is incorporated by reference in its entirety. Aptamers may be RNA or DNA based, and may include a riboswitch. A riboswitch is a part of an mRNA molecule that can directly bind a small target molecule, and whose binding of the target affects the gene's activity. Thus, an mRNA that contains a riboswitch is directly involved in regulating its own activity, depending on the presence or absence of its target molecule. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer may be prepared by any known method, including synthetic, recombinant, and purification methods, and may be used alone or in combination with other aptamers specific for the same target. Further, as described more fully herein, the term "aptamer" specifically includes "secondary aptamers" containing a consensus sequence derived from comparing two or more known aptamers to a given target.

Ribozymes

According to another embodiment, nucleic acid-lipid particles are associated with ribozymes. Ribozymes are RNA molecules complexes having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). For example, a large number of ribozymes accelerate phosphoester transfer reactions with a high degree of specificity, often cleaving only one of several phosphoesters in an oligonucleotide substrate (Cech et al., Cell. 1981 December; 27(3 Pt 2):487-96; Michel and Westhof, J Mol Biol. 1990 Dec. 5; 216(3):585-610; Reinhold-Hurek and Shub, Nature. 1992 May 14; 357(6374):173-6). This specificity has been attributed to the requirement that the substrate bind via specific base-pairing interactions to the internal guide sequence ("IGS") of the ribozyme prior to chemical reaction.

At least six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nucleic acid molecule may be formed in a hammerhead, hairpin, a hepatitis δ virus, group I intron or RNaseP RNA (in association with an RNA guide sequence) or Neurospora VS RNA motif, for example. Specific examples of hammerhead motifs are described by Rossi et al. Nucleic Acids Res. 1992 Sep. 11; 20(17):4559-65. Examples of hairpin motifs are described by Hampel et al. (Eur. Pat. Appl. Publ. No. EP 0360257), Hampel and Tritz, Biochemistry 1989 Jun. 13; 28(12):4929-33; Hampel et al., Nucleic Acids Res. 1990 Jan. 25; 18(2):299-304 and U.S. Pat. No. 5,631,359. An example of the hepatitis δ virus motif is described by Perrotta and Been, Biochemistry. 1992 Dec. 1; 31(47):11843-52; an example of the RNaseP motif is described by Guerrier-Takada et al., Cell. 1983 December; 35(3 Pt 2):849-57; Neurospora VS RNA ribozyme motif is described by Collins (Saville and Collins, Cell. 1990 May 18; 61(4):685-96; Saville and Collins, Proc Natl Acad Sci USA. 1991 Oct. 1; 88(19):8826-30; Collins and Olive, Biochemistry. 1993 Mar. 23; 32(11):2795-9); and an example of the Group I intron is described in U.S. Pat. No. 4,987,071. Important characteristics of enzymatic nucleic acid molecules used are that they have a specific substrate binding site which is complementary to one or more of the target gene DNA or RNA regions, and that they have nucleotide sequences within or surrounding that substrate binding site which impart an RNA cleaving activity to the molecule. Thus the ribozyme constructs need not be limited to specific motifs mentioned herein.

Methods of producing a ribozyme targeted to any polynucleotide sequence are known in the art. Ribozymes may be designed as described in Int. Pat. Appl. Publ. Nos. WO 93/23569 and WO 94/02595, each specifically incorporated herein by reference, and synthesized to be tested in vitro and in vivo, as described therein.

Ribozyme activity can be optimized by altering the length of the ribozyme binding arms or chemically synthesizing ribozymes with modifications that prevent their degradation by serum ribonucleases (see e.g., Int. Pat. Appl. Publ. Nos. WO 92/07065, WO 93/15187, and WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Immunostimulatory Oligonucleotides

Nucleic acids associated with lipid particles may be immunostimulatory, including immunostimulatory oligonucleotides (ISS; single- or double-stranded) capable of inducing an immune response when administered to a subject, which may be a mammal or other patient. ISS include, e.g., certain palindromes leading to hairpin secondary structures (see Yamamoto S., et al. (1992) J. Immunol. 148: 4072-4076, which is incorporated by reference in its entirety), or CpG motifs, as well as other known ISS features (such as multi-G domains, see WO 96/11266, which is incorporated by reference in its entirety).

The immune response may be an innate or an adaptive immune response. The immune system is divided into a more innate immune system, and acquired adaptive immune system of vertebrates, the latter of which is further divided into humoral cellular components. In particular embodiments, the immune response may be mucosal.

In particular embodiments, an immunostimulatory nucleic acid is only immunostimulatory when administered in combination with a lipid particle, and is not immunostimulatory when administered in its "free form." Such an oligonucleotide is considered to be immunostimulatory.

Immunostimulatory nucleic acids are considered to be non-sequence specific when it is not required that they specifically bind to and reduce the expression of a target polynucleotide in order to provoke an immune response. Thus, certain immunostimulatory nucleic acids may comprise a sequence corresponding to a region of a naturally occurring gene or mRNA, but they may still be considered non-sequence specific immunostimulatory nucleic acids.

In one embodiment, the immunostimulatory nucleic acid or oligonucleotide comprises at least one CpG dinucleotide. The oligonucleotide or CpG dinucleotide may be unmethylated or methylated. In another embodiment, the immunostimulatory nucleic acid comprises at least one CpG dinucleotide having a methylated cytosine. In one embodiment, the nucleic acid comprises a single CpG dinucleotide, wherein the cytosine in said CpG dinucleotide is methylated. In an alternative embodiment, the nucleic acid comprises at least two CpG dinucleotides, wherein at least one cytosine in the CpG dinucleotides is methylated. In a further embodiment, each cytosine in the CpG dinucleotides present in the sequence is methylated. In another embodiment, the nucleic acid comprises a plurality of CpG dinucleotides, wherein at least one of said CpG dinucleotides comprises a methylated cytosine.

Linker

The Linker can be any suitable group for coupling the oligonucleotide to the Ligand(s). Other examples of Linkers are described in International Publication No. WO 2009/082607 and U.S. Patent Publication Nos. 2009/0239814, 2012/0136042, 2013/0158824, or 2009/0247608, each of which is hereby incorporated by reference.

Attachment Point of Oligonucleotide to Linker

The oligonucleotide can be attached to the Linker via any suitable group for coupling the two. The group can be cleavable or non-cleavable. Examples of Linkers and suitable coupling groups are described herein. Other examples of coupling groups are described in International Publication No. WO 2009/082607 and U.S. Patent Publication Nos. 2009/0239814, 2012/0136042, 2013/0158824, or 2009/0247608, each of which is hereby incorporated by reference. Suitable coupling groups include, for example, $NR^8$, C(O), C(O)NH, SO, $SO_2$, $SO_2NH$ or a chain of atoms, such as, but not limited to, alkyl, alkenyl, alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkynyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, each of which may be substituted or unsubstituted, and which one or more methylenes can be interrupted or terminated by O, S, S(O), $SO_2$, $N(R^8)$, C(O), substituted or unsubstituted aryl, substituted or unsubstituted heteroaryl, or substituted or unsubstituted heterocyclic, where $R^8$ is hydrogen, acyl, aliphatic or substituted aliphatic.

A cleavable group is one which is sufficiently stable outside the cell, but which upon entry into a target cell is cleaved to release the two parts the group is holding together. In a preferred embodiment, the cleavable group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable group by reduction; esterases; endosomes or agents that can create an acidic environment, e.g., those that result in a pH of five or lower; enzymes that can hydrolyze or degrade an acid cleavable group by acting as a general acid, peptidases (which can be substrate specific), and phosphatases.

A cleavable group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable group that is cleaved at a preferred pH, thereby releasing the cationic lipid from the ligand inside the cell, or into the desired compartment of the cell.

A conjugate can include a cleavable group that is cleavable by a particular enzyme. The type of cleavable group incorporated into a conjugate can depend on the cell to be targeted. For example, liver targeting ligands can be linked to the cationic lipids through a chemical moiety that includes an ester group. Liver cells are rich in esterases, and therefore the group will be cleaved more efficiently in liver cells than in cell types that are not esterase-rich. Other cell-types rich in esterases include cells of the lung, renal cortex, and testis.

Coupling groups that contain peptide bonds can be used when targeting cell types rich in peptidases, such as liver cells and synoviocytes.

In general, the suitability of a candidate cleavable group can be evaluated by testing the ability of a degradative agent (or condition) to cleave the candidate group. It will also be desirable to also test the candidate cleavable group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

i. Redox Cleavable Groups

One class of cleavable groups are redox cleavable groups that are cleaved upon reduction or oxidation. An example of reductively cleavable group is a disulphide linking group (—S—S—). To determine if a candidate cleavable group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Groups

Phosphate-based cleavable groups are cleaved by agents that degrade or hydrolyze the phosphate group. An example of an agent that cleaves phosphate groups in cells are enzymes such as phosphatases in cells. Examples of phosphate-based linking groups are —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—s—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—. A preferred embodiment is —O—P(O)(OH)—O—. These candidates can be evaluated using methods analogous to those described above.

iii. Acid Cleavable Groups

Acid cleavable groups are linking groups that are cleaved under acidic conditions. In preferred embodiments acid cleavable groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Groups

Ester-based cleavable groups are cleaved by enzymes such as esterases and amidases in cells. Examples of ester-based cleavable groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

Peptide-based cleavable groups are cleaved by enzymes such as peptidases and proteases in cells. Peptide-based cleavable groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The Ligands

The Ligand can be any ligand described herein.

Other suitable ligands are described in U.S. Patent Publication Nos. 2009/0239814, 2012/0136042, 2013/0158824, or 2009/0247608, each of which is hereby incorporated by reference.

Formulations

The conjugates described herein can be formulated for administration to a subject. For ease of exposition the formulations, compositions and methods in this section are discussed largely with regard to conjugates of unmodified iRNA agents. It will understood, however, that these formulations, compositions and methods can be practiced with conjugates of other oligonucleotides, e.g., modified iRNA agents, and such practice is within the invention.

A formulated iRNA conjugate can assume a variety of states. In some examples, the conjugate is at least partially crystalline, uniformly crystalline, and/or anhydrous (e.g., less than 80, 50, 30, 20, or 10% water). In another example, the iRNA conjugate is in an aqueous phase, e.g., in a solution that includes water.

The aqueous phase or the crystalline conjugates can, e.g., be incorporated into a delivery vehicle, e.g., a liposome (particularly for the aqueous phase) or a particle (e.g., a microparticle as can be appropriate for a crystalline composition). Generally, the iRNA conjugate is formulated in a manner that is compatible with the intended method of administration. The iRNA conjugate can be incorporated into a nucleic acid lipid nanoparticle. In one embodiment, each nanoparticle includes the conjugate, a cationic lipid (e.g., a cationic lipid having a p$K_a$ ranging from about 4 to about 11, such as from about 5 to about 7), a non-cationic lipid (such as a neutral lipid), an aggregation reducing agents (such as polyethylene glycol (PEG) or PEG-modified lipid), and optionally a sterol (e.g., cholesterol).

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An iRNA conjugate can be formulated in combination with another agent, e.g., another therapeutic agent or an agent that stabilizes an iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA composition includes at least one second therapeutic agent (e.g., an agent other than an RNA or a DNA). For example, an iRNA composition for the treatment of a viral disease, e.g., HIV, might include a known antiviral agent (e.g., a protease inhibitor or reverse transcriptase inhibitor). In another example, an iRNA composition for the treatment of a cancer might further comprise a chemotherapeutic agent.

The iRNA conjugate may be formulated with a drug that affects (for example, increases) the uptake of the iRNA agent into a cell. The drug can be administered before, after, or at the same time that the iRNA agent is administered. The drug can also be covalently linked to the iRNA agent. The drug can be, for example, a lipopolysaccharide, an activator of p38 MAP kinase, or an activator of NF-κB. The drug can have a transient effect on the cell.

In one embodiment, the drug used increases the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The drug can also increase the uptake of the iRNA conjugate into the cell, for example, by activating an inflammatory response. Exemplary drug's that would have such an effect include tumor necrosis factor alpha (TNF-α), interleukin-1 beta, or gamma interferon.

The invention is further illustrated by the following examples, which should not be construed as further limiting. The contents of all references, pending patent applications and published patents, cited throughout this application are hereby expressly incorporated by reference.

EXAMPLES

Abbreviations: TBAHS is Tetrabutylammonium hydrogen sulfate; DCM is dichloromethane; NHS is N-hydroxysuccinamide; DIEA is N,N-diisopropylethylamine; EDC is 1-Ethyl-3-(3-dimethylaminopropyl)carbodiimide.

Example 1: Synthesis of Triantennary GalNAc Monomers with Acyclic Linker-1

The triantennary GalNAc moieties 211a-d are synthesized as shown in Scheme 1 below.

Scheme 1

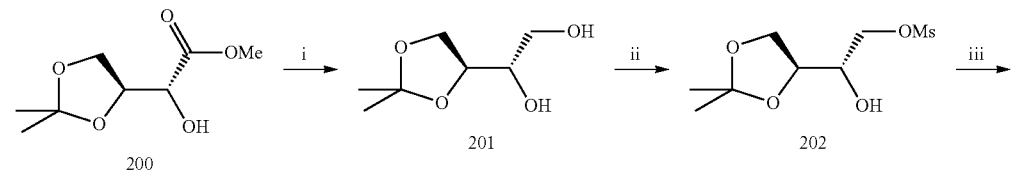

200     201     202

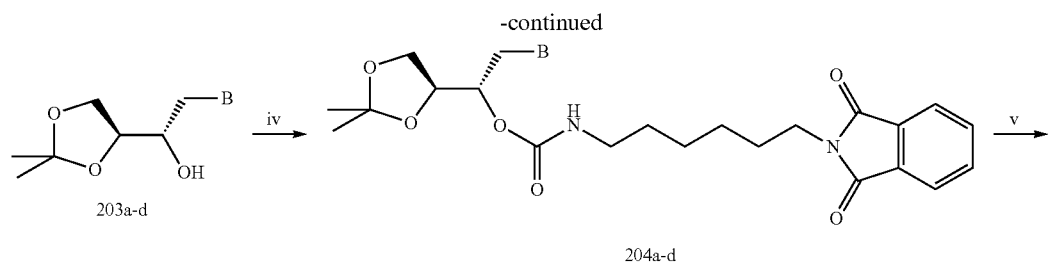
204a-d
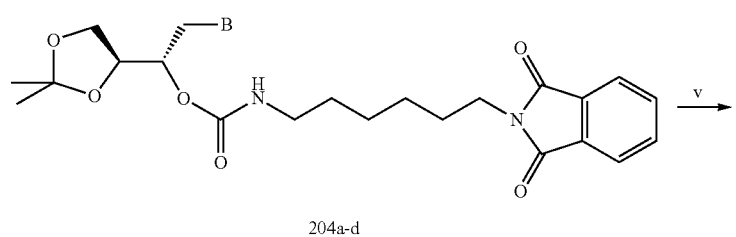
204a-d
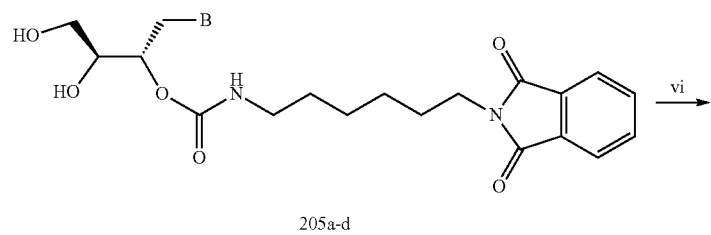
205a-d
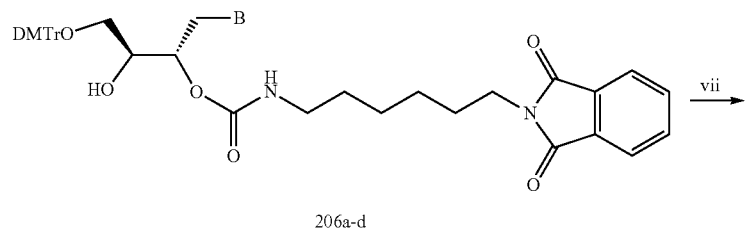
206a-d
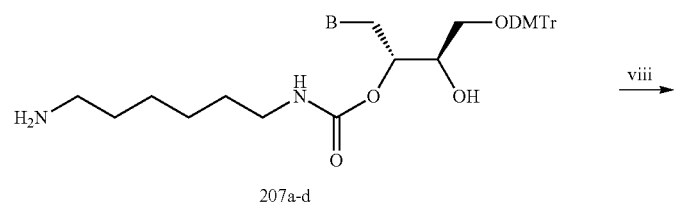
207a-d

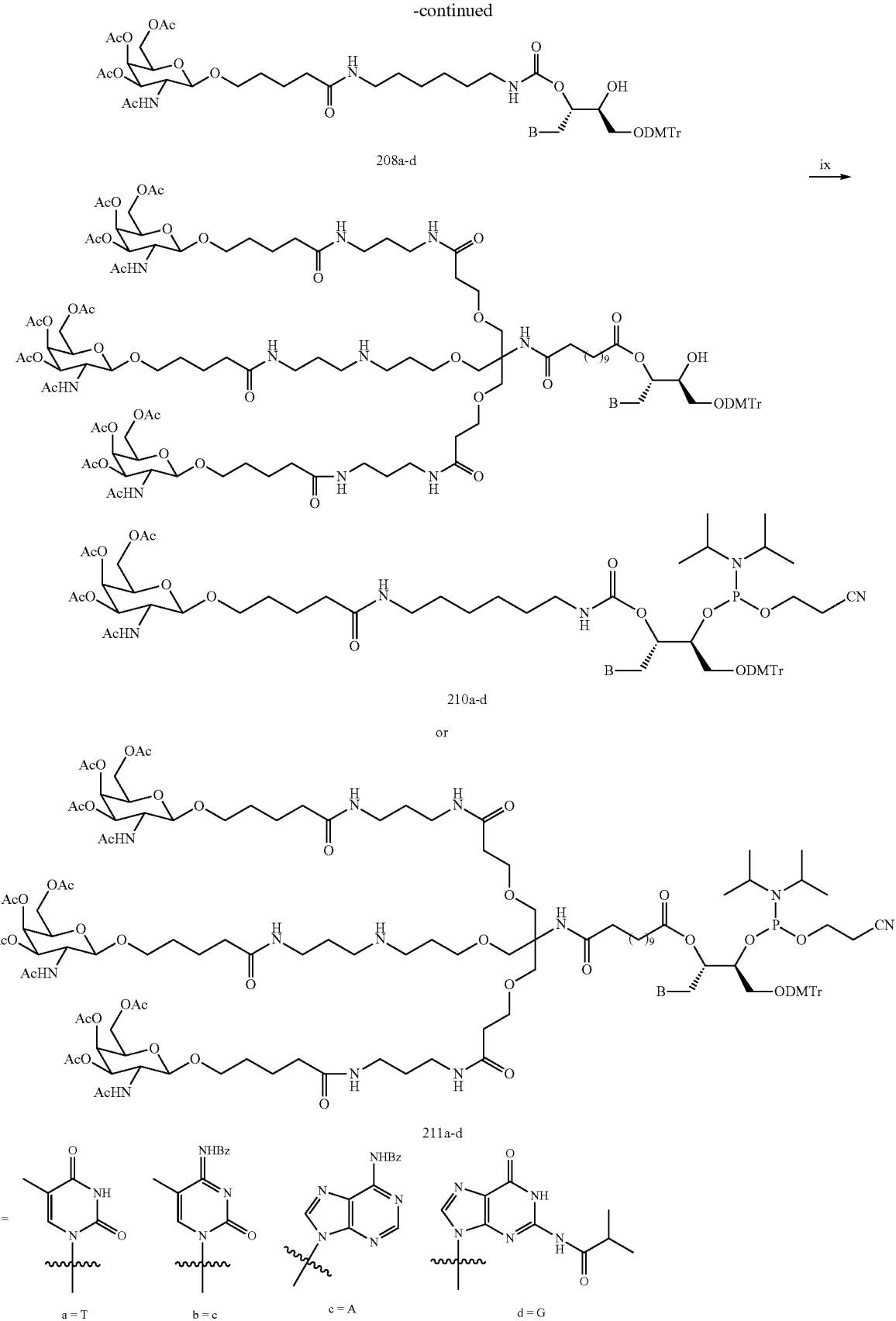

i) NaBH$_4$, MeOH; ii) CH$_2$Cl$_2$, MsCl, NEt$_3$; iii) T or N4-Bz-C or N6-A or N2-iBu-G, CsCO$_3$, NaI, DMF, 110° C., 20-60 min; iv) a) DSC, NEt$_3$, b) N6-Phth-hexanediamine, CH$_2$Cl$_2$; v) AcOH; vi) DMTrCl, py; vii) MeNH$_2$; viii) R1 or R2, EDCI, DIPEA, CH$_2$Cl$_2$; ix) 2-cyanoethyl-N, N-diisopropylchlorophosphoramidite, DIPEA, CH$_2$Cl$_2$ i. Synthesis of (S)-1-((S)-2,2-dimethyl-1,3-dioxolan-4-yl)ethane-1,2-diol 201

To a stirred solution of the commercially available (R)-methyl 2-((S)-2,2-dimethyl-1,3-dioxolan-4-yl)-2-hydroxyacetate 200 (1.9 g) in methanol (60 mL), solid sodium borohydride (0.4 g) is added at 0-5° C. and after the addition the reaction mixture is warmed to room temperature and stirred for 20 min. The reaction mixture is diluted with saturated ammonium chloride and extracted with dichloromethane. The organic layer is dried over Na$_2$SO$_4$ and concentrated to isolate the crude product (1.6 g) which is used as such in the next step without further purification.

ii. Synthesis of (S)-2-((S)-2,2-dimethyl-1,3-dioxolan-4-yl)-2-hydroxyethyl methanesulfonate 202

To a solution of the alcohol 201 (1.6 g) in dichloromethane (60 mL) triethylamine (1.5 mL) is added and the mixture cooled with stirring. To this stirred solution methanesulfonyl chloride (1.3 g) in dichloromethane (30 mL) is added drop wise and the mixture is stirred at room temperature for two hours after which the reaction mixture is washed with satd. NaHCO$_3$ solution (100 mL) followed by brine (100 mL) and the organic layer after drying over anhyd. Na$_2$SO$_4$ is concentrated. The thus obtained crude product on purification using silica gel provided the pure product.

iii. General Procedure for the Synthesis of 203a-d

In a general procedure the nucleo base (2 eq.) is dissolved in anhydrous DMF (100 mL) at 110° C. and to this stirred solution solid CsCO$_3$ (2 g) and sodium iodide (2 g) is added and the mixture stirred vigorously. To this stirred solution a solution of the mesylate 202 (1 eq.) in anhydrous DMF (10 mL) is added dropwise. The reaction mixture after stirring at 110° C. for an additional 30 min. is concentrated under reduced pressure. The residue is dissolved in ethyl acetate and the organic layer is washed with satd. NaHCO$_3$ (100 mL), brine (100 mL) and dried (anhyd. Na$_2$SO$_4$). The concentration of the organic layer provided the crude product which is purified by flash column chromatography to isolate the pure product 203a-d.

iv. Synthesis of 204a-d

The alcohol 203a-d is initially treated with disuccinimidylcarbonate (DSC) in the presence of triethylamine to afford the succinimidylester which on treatment with monophthalimidoprotected hexanediamine in the presence of pyridine provide the amine substituted products 204a-d after column purification.

v. Synthesis of 205a-d

The acetonide protection in 204a-d is removed by treating with acetic acid under reported conditions to afford 205a-d which is used in the next step as such.

vi. Synthesis of 206a-d

Treatment of the diol 205a-d with DMTrCl in pyridine would provide the mono DMT protected alcohol 206a-d.

vii. Synthesis of 207a-d

The phthalimido protected amines 206a-d are treated with a solution of methylamine in methanol (20×) at room temperature overnight. The concentration of the reaction mixture followed by column purification provides the deprotected amines 207a-d.

viii. Synthesis of 208a-d

Coupling of the monoantennary GalNAc containing carboxylic acid with the amines 207a-d using EDC and Hunig's base would lead to the ligand conjugated monomers 208a-d.

ix. Synthesis of 209a-d

Using a similar coupling procedure coupling of the triantennary GalNAc containing carboxylic acid with the amines 207a-d would lead to the trianetannary GalNAc conjugated monomers 209a-d x. Synthesis of 210a-d and 211a-d

Phosphitylation of the alcohols 208a-d and 209a-d using 2-cyanoethyl-N, N-diisopropylchlorophosphoramidite in the presence of Hunig's base in CH$_2$Cl$_2$ provided the corresponding amidites 210a-d and 211a-d after flash column purification.

Example 2: Synthesis of Triantennary GalNAc Monomers with Acyclic Linker-2

The triantennary GalNAc moieties 219 are synthesized as shown in Scheme 2 below.

Scheme 2

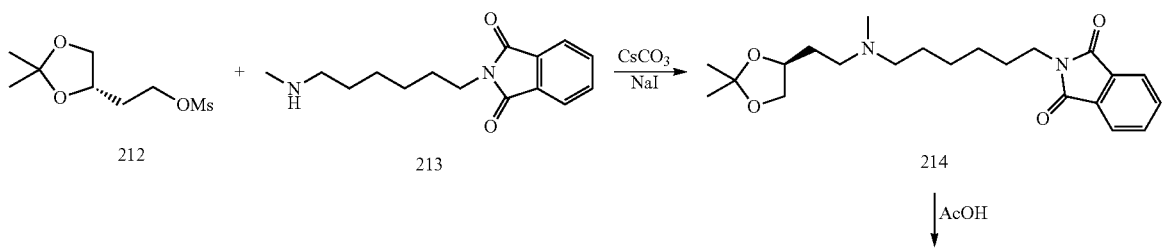

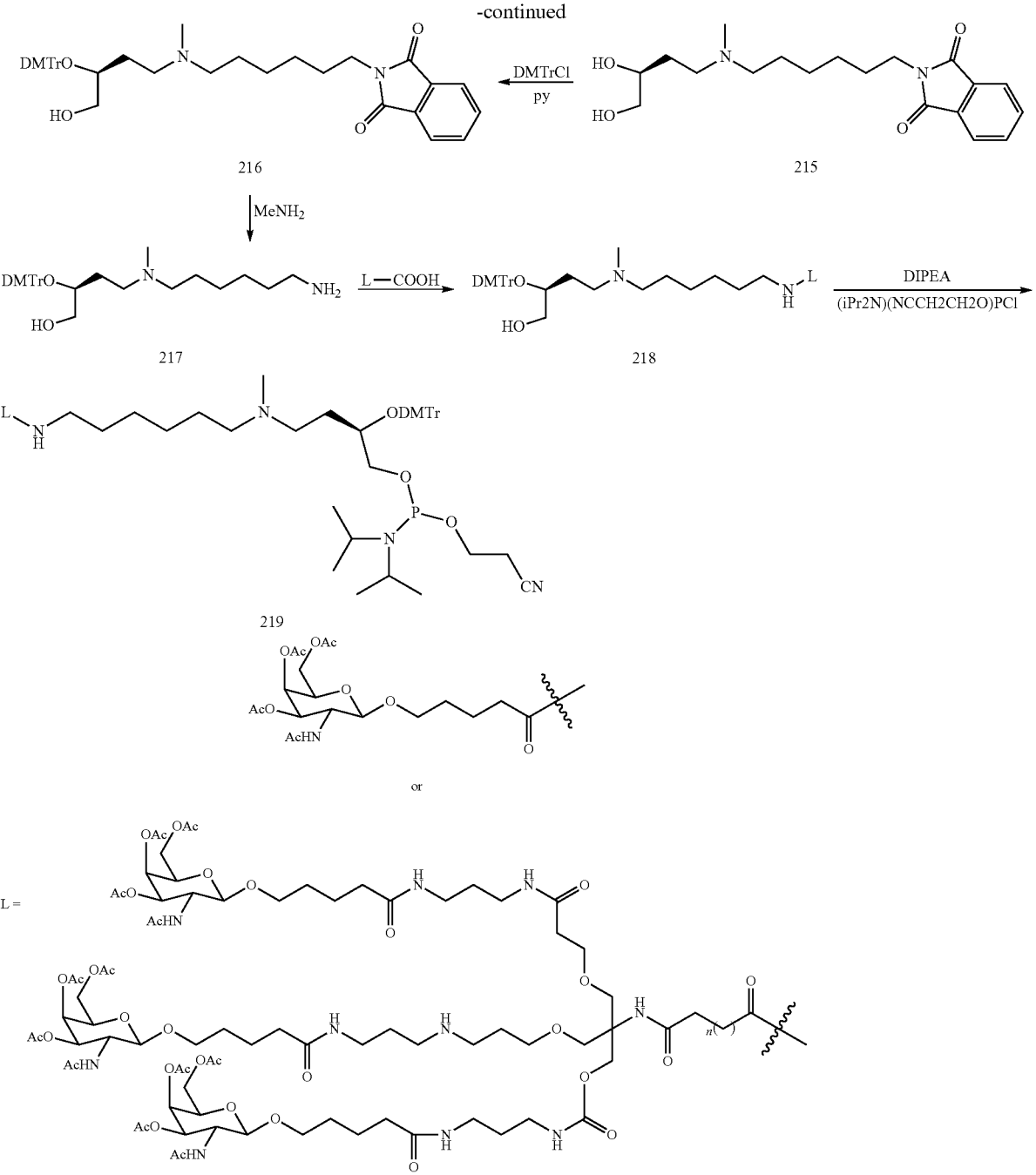
Example 3: Synthesis of Triantennary GalNAc Monomers with Acyclic Linker-3
The triantennary GalNAc moiety 215 is synthesized as shown in Scheme 3 below.
Scheme 3
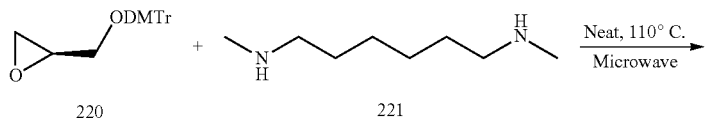

-continued

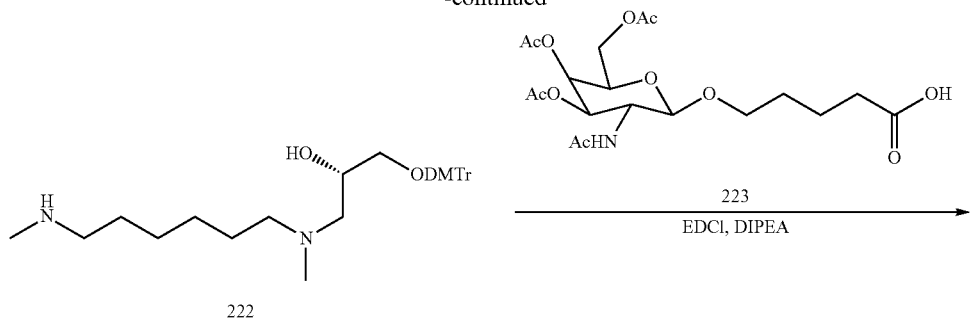

222
223
EDCl, DIPEA

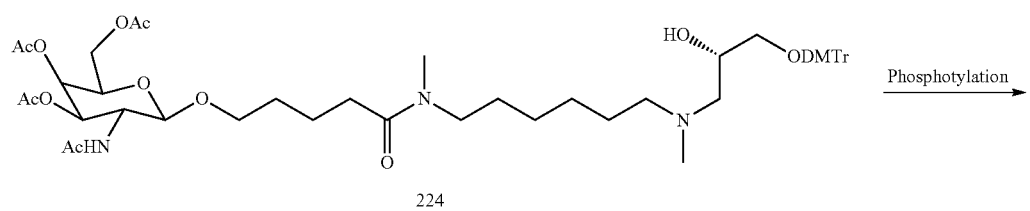

224

Phosphotylation

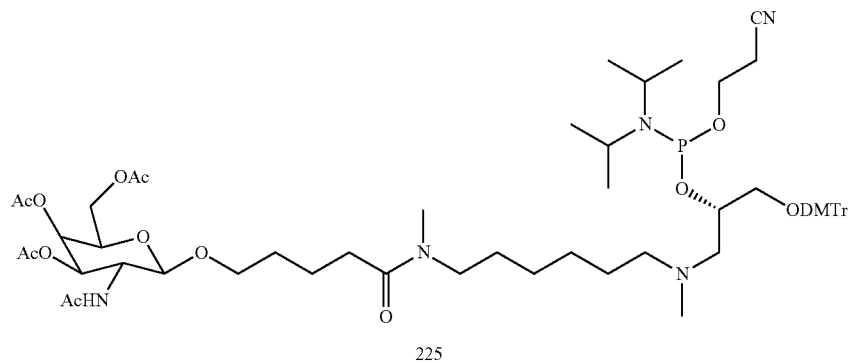

225 i. Synthesis of 222

The commercially available (R)-glycidol was converted to the ODMTr protected epoxide 220 as reported in the literature. Treatment of the epoxide 220 (1.12 g, 3 mmol) with the 1,6-dimethylaminohexane 221 (6 mmol, 2 eq.) at 110° C. under microwave irradiation for 30 min provided the epoxide opened product 222 in 90% yield.

ii. Synthesis of 224

The coupling of the amine 222 with the carboxylic acid 223 provided the coupled product 224 in good yields.

iii. Synthesis of 225

Phosphitylation of the alcohols 224 using 2-cyanoethyl-N,N-diisopropylchlorophosphoramidite in the presence of Hunig's base in $CH_2Cl_2$ provided the corresponding amidite 225 after flash column purification.

Example 4: General Structure for Tri-Antennary α-Anomer-Conjugate Building Block The tri-antennary α-anomers having the formula below are prepared.

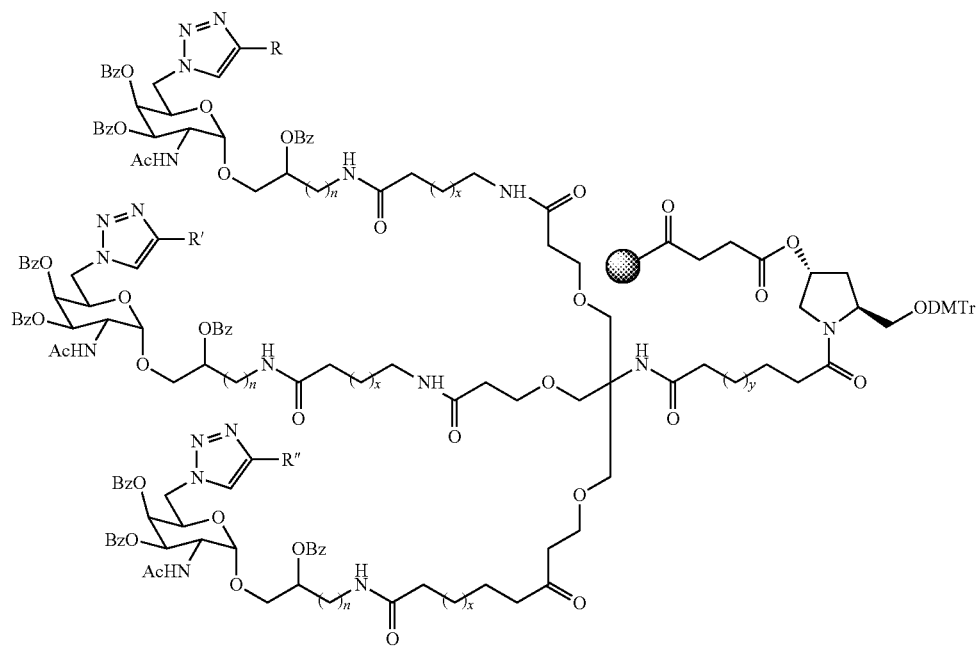

R = Aryl, aliphatic, heteroaromatic, sugar (e.g. galactose, galNAc) n = 1-10
R' = Aryl, aliphatic, heteroaromatic, sugar (e.g. galactose, galNAc) x = 1-10
R" = Aryl, aliphatic, heteroaromatic, sugar (e.g. galactose, galNAc) y = 1-20

For example, R, R', and R" may be independently, $C_6$-$C_{10}$ aryl, $C_6$-$C_{10}$ heteroaromatic, $C_1$-$C_{20}$ alkyl, or a sugar (e.g., galactose or GalNAc).

The tri-antennary α-anomers having the formula below are also prepared.

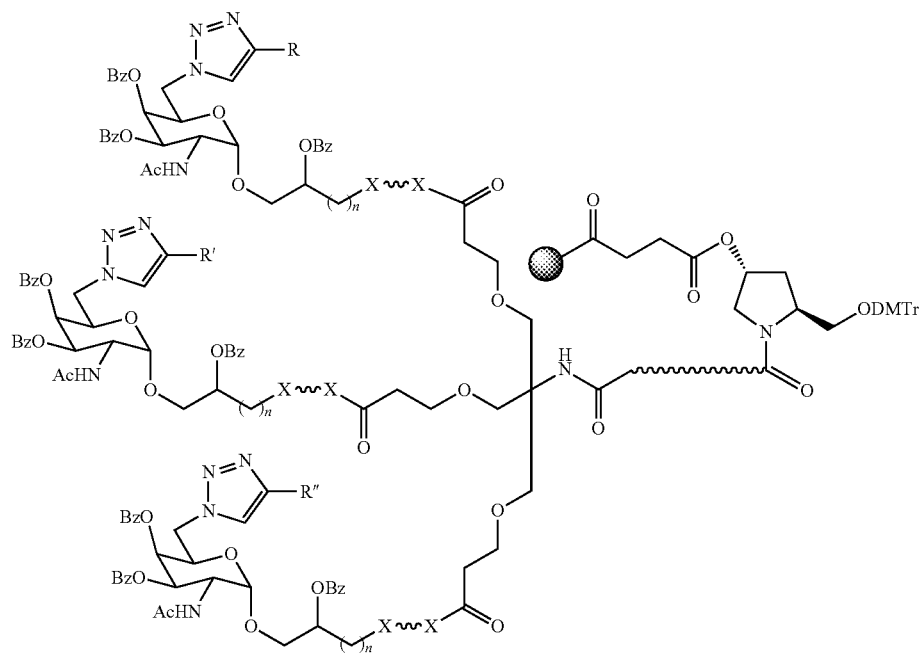

R = Aryl, aliphatic, heteroaromatic, sugar (e.g. galactose, galNAc)
R' = Aryl, aliphatic, heteroaromatic, sugar (e.g. galactose, galNAc)
R" = Aryl, aliphatic, heteroaromatic, sugar (e.g. galactose, galNAc)
n = 1-10
X = NH, NMe, Amide, Carbamate, Urea, Ether
∿∿∿ = Alkyl, PEG For example, R, R', and R" may be independently, $C_6$-$C_{10}$ aryl, $C_6$-$C_{10}$ heteroaromatic, $C_5$-$C_{20}$ alkyl, or a sugar (e.g., galactose or GalNAc).

Example 5: General Structure of Tri-Antennary-β-Anomer-Conjugate Building Block

The tri-antennary β-anomers having the formula below are prepared.

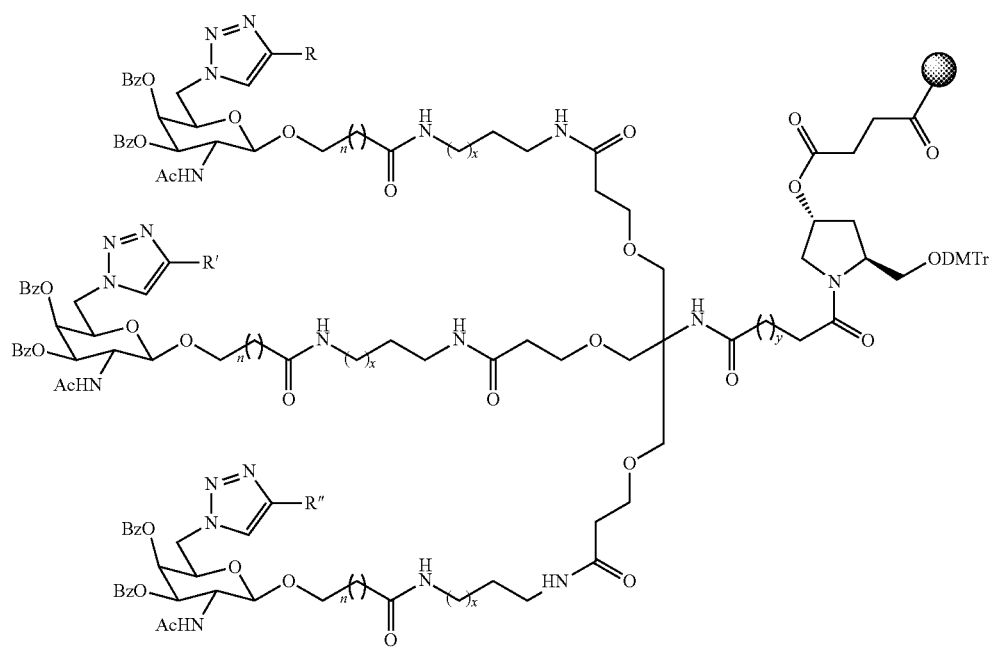

R = Aryl, aliphatic, heteroaromatic, sugar (e.g. galactose, galNAc) n = 1-10
R' = Aryl, aliphatic, heteroaromatic, sugar (e.g. galactose, galNAc) x = 1-10
R" = Aryl, aliphatic, heteroaromatic, sugar (e.g. galactose, galNAc) y = 0-20

For example, R, R', and R" may be independently, $C_6$-$C_{10}$ aryl, $C_6$-$C_{10}$ heteroaromatic, $C_1$-$C_{20}$ alkyl, or a sugar (e.g., galactose or GalNAc).

Example 6: General Structure of Bi-Antennary α-Anomer-Conjugate Building Block

The bi-antennary α-anomers having the formula below are prepared.

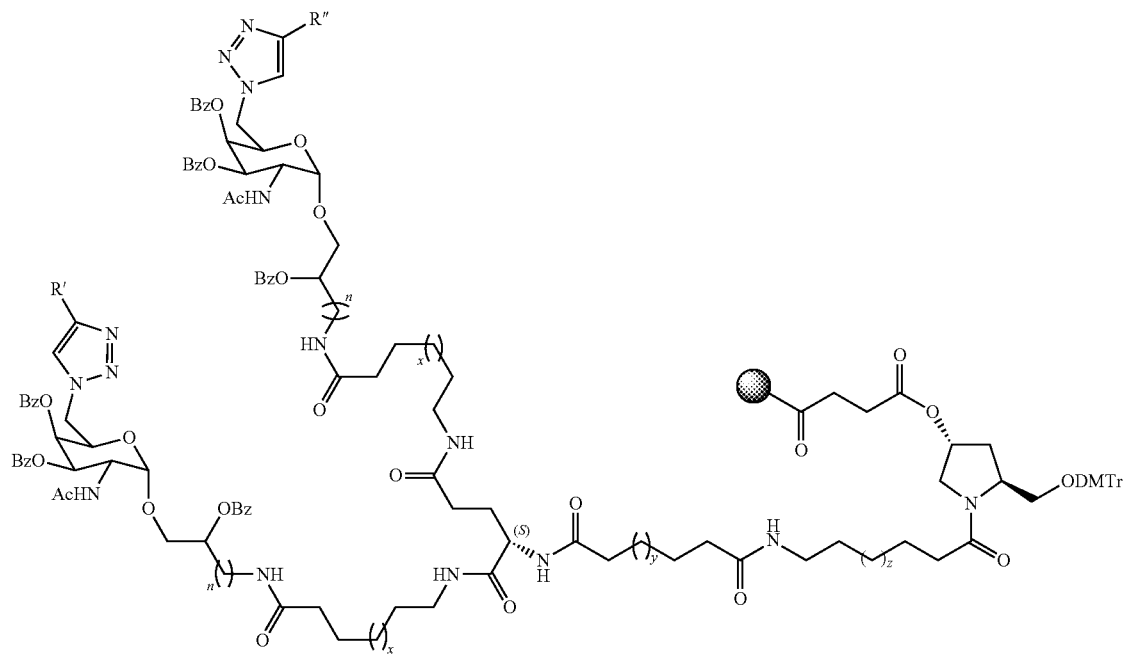

R″ = Aryl, aliphatic, heteroaromatic, sugar (e.g. galactose, galNAc)
R′ = Aryl, aliphatic, heteroaromatic, sugar (e.g. galactose, galNAc)
n = 1-10
x = 1-10
y = 1-20
z = 1-20

For example, R, R′, and R″ may be independently, $C_6$-$C_{10}$ aryl, $C_6$-$C_{10}$ heteroaromatic, $C_1$-$C_{20}$ alkyl, or a sugar (e.g., galactose or GalNAc).

Example 7: Synthesis Mono-, Bi- and Tri-Conjugate Building Blocks

The mono-, bi- and tri-conjugate building blocks may be prepared from azide intermediates as shown below.

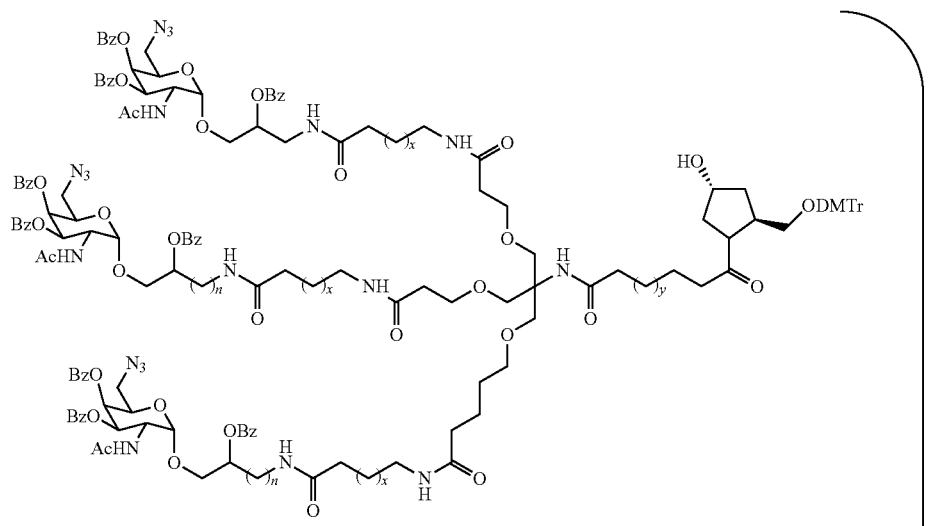

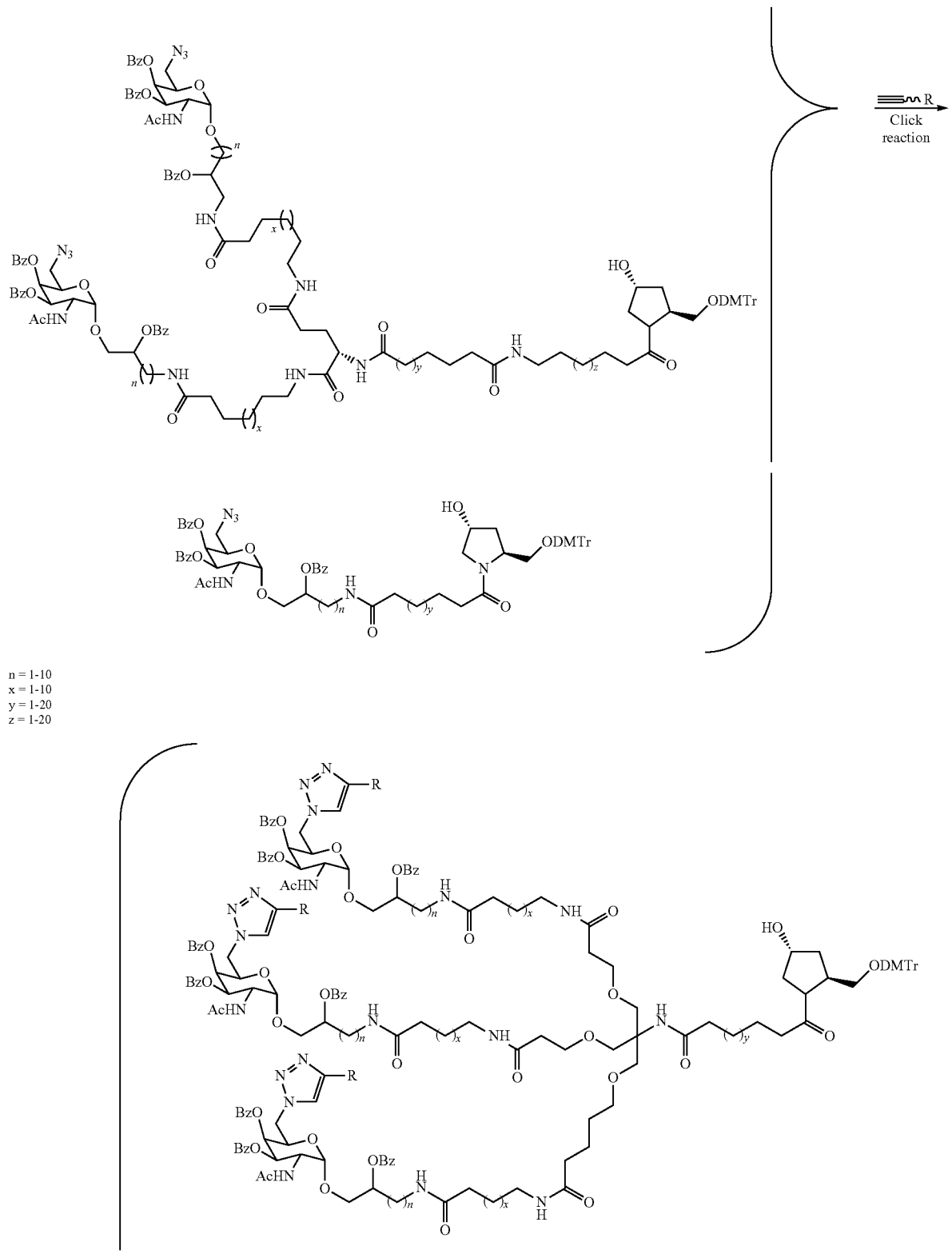
n = 1-10
x = 1-10
y = 1-20
z = 1-20

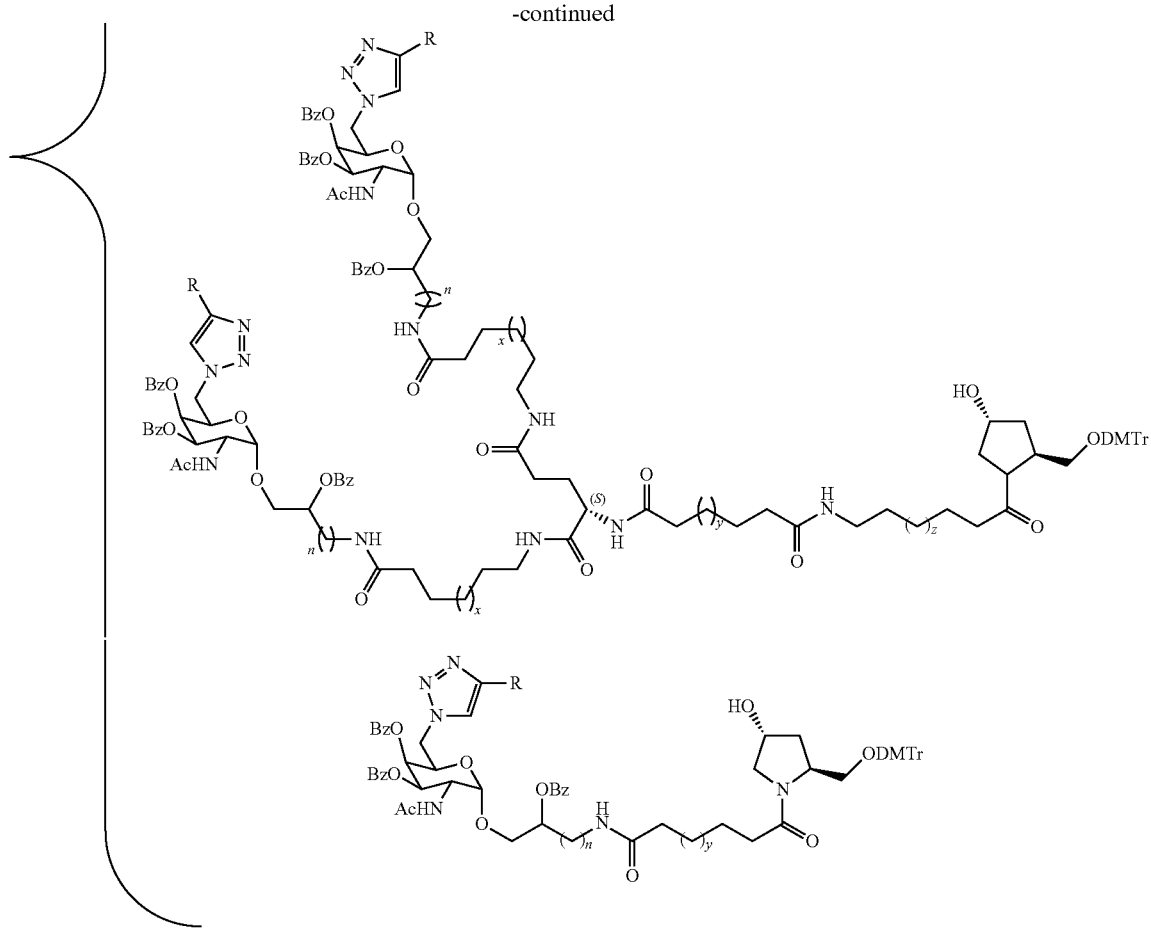
R = Aryl, aliphatic, heteroaromatic, sugar (eg. Galactose, GalNAc), amino acids
n = 1-10
x = 1-10
y = 1-20
z = 1-20
Example 8: Synthesis of Intermediates of ASGPR Ligand (Schemes 4-8)
Intermediates useful for preparing ASGPR ligands may be synthesized as shown in Schemes 4-8 below.
Scheme 4
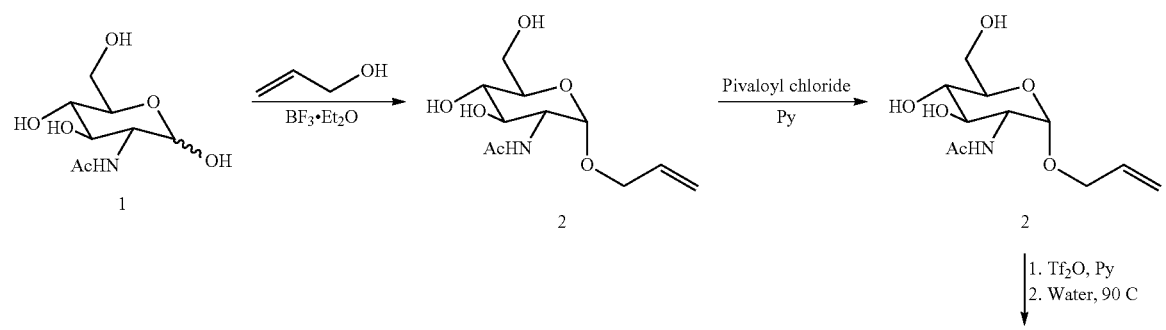

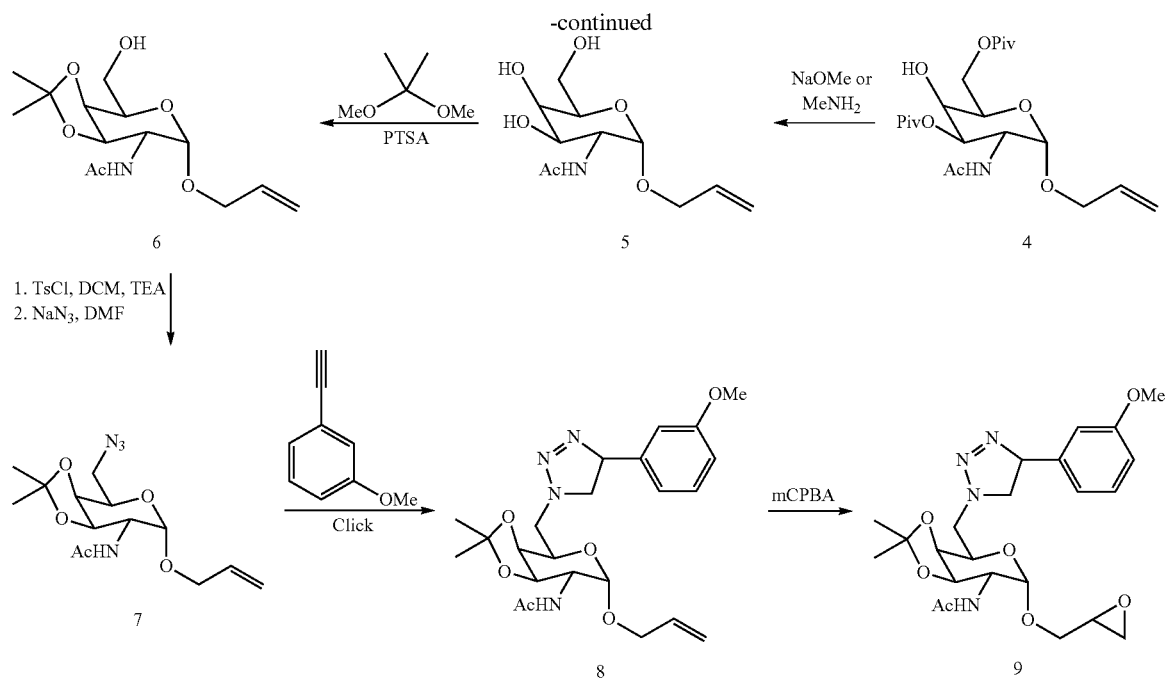

Synthesis of compound 9: N-Acetyl glucosamine (50 g, 226 mmol) are taken in allyl alcohol and is heated at 90° C. for 24 hr. The reaction mixture is cooled to room temperature and the ally alcohol is removed by distillation. The residue is dissolved in pyridine and reacted with pivaloyl chloride to obtain the compound 3. The pivaloyl ester is reacted with triflic anhydride in pyridine for 2 hrs and the mixture is quenched by adding water. The mixture is heated at 90° C. for 24 h to obtain the product 4. The ester groups are removed by treatment with sodium methoxide and compound 5 isolated. The hydroxyl groups are protected by dimethoxy propane to obtain the product 6. It is then reacted with tosyl chloride and sodium azide in DMF to obtain the compound 7. Compound 7 is subjected to Click cycloaddition and epoxidation with MCPBA to generate the compound 9.

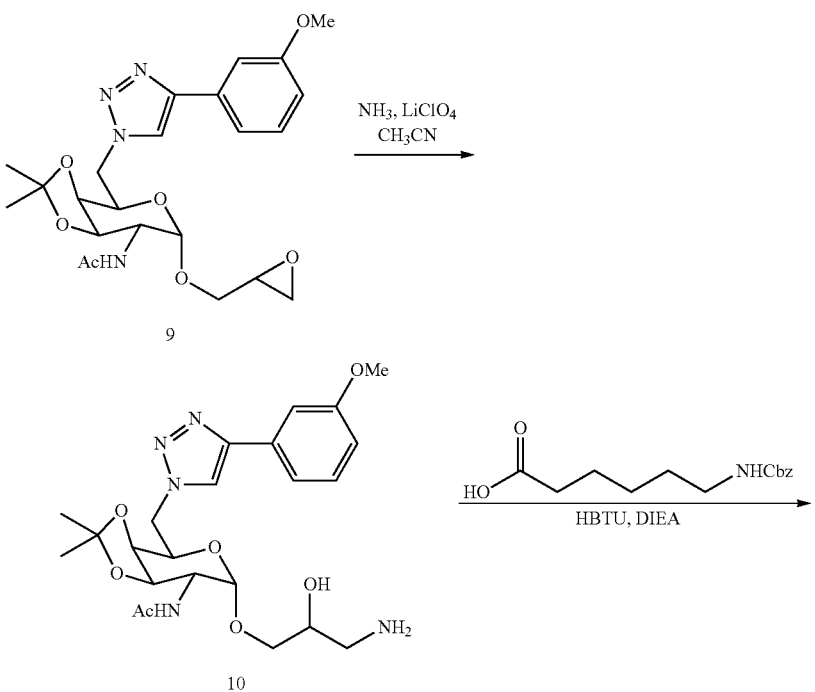

-continued

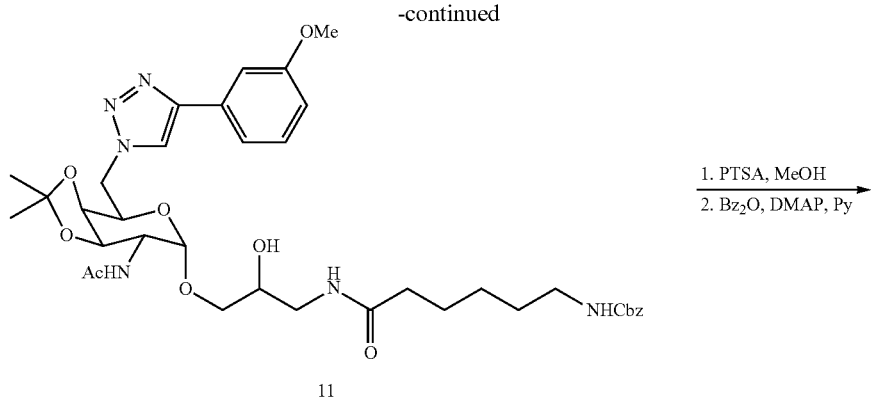

11

1. PTSA, MeOH
2. Bz₂O, DMAP, Py

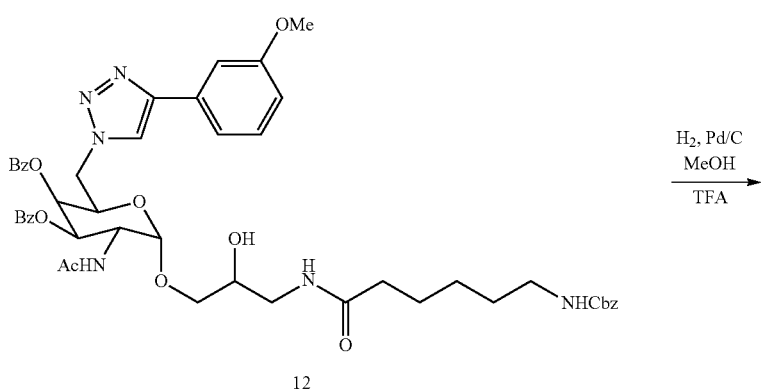

12

H₂, Pd/C
MeOH
TFA

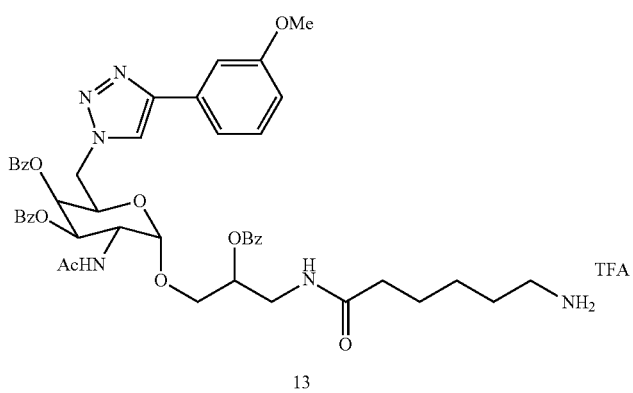

13

Synthesis of compound 13: The epoxide 13 is reacted with ammonia in the presence of LiClO₄ to generate the amino alcohol 10. This is coupled with N-Cbz amino hexanoic acid under peptide coupling conditions to obtain the compound 11. Removal of acetonide protection and benzoylation of the hydroxyl groups generate the compound 12. Hydrogenation of compound 12 using Pd/C in MeOH generates the amine 13 as a TFA salt.

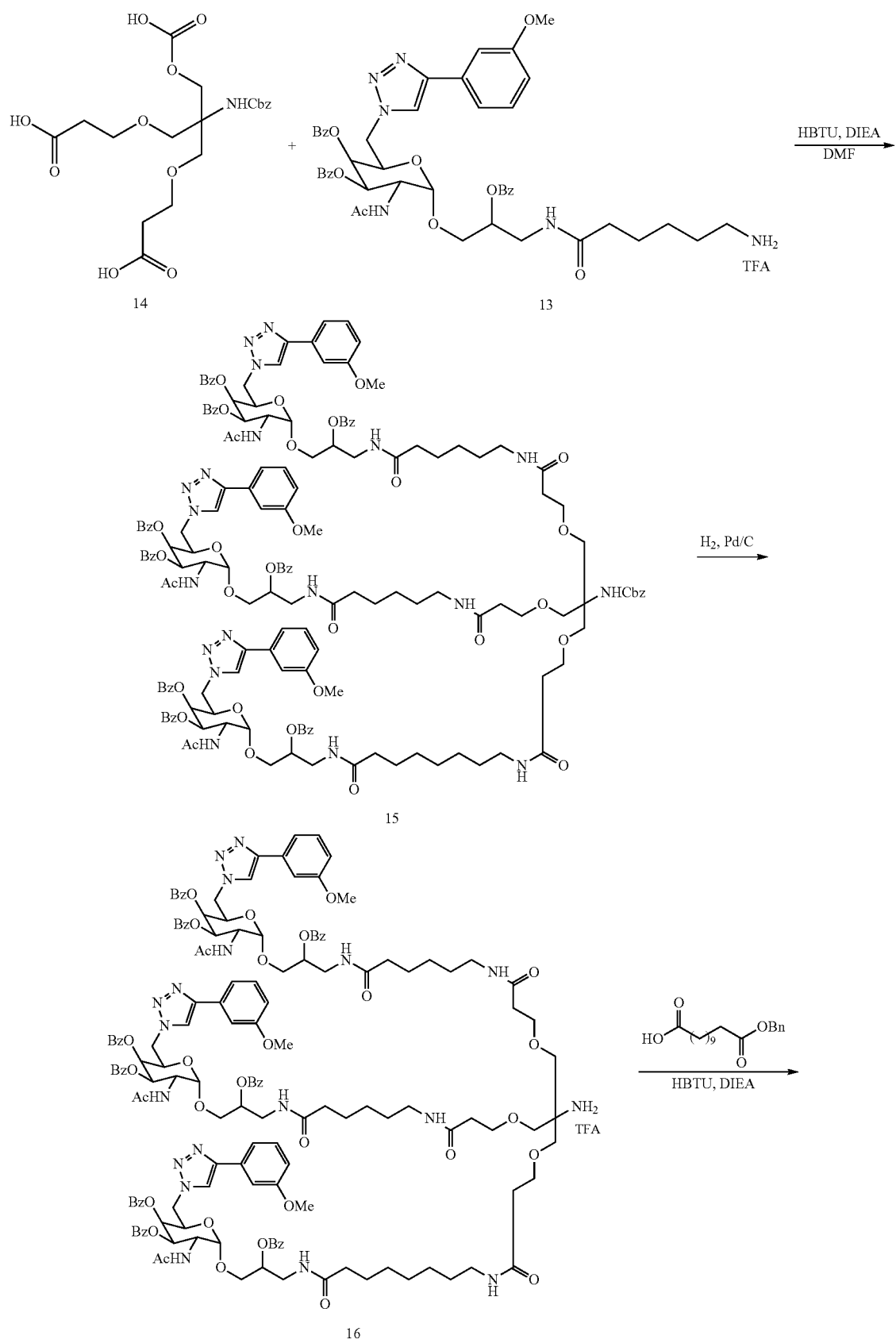
Scheme 6

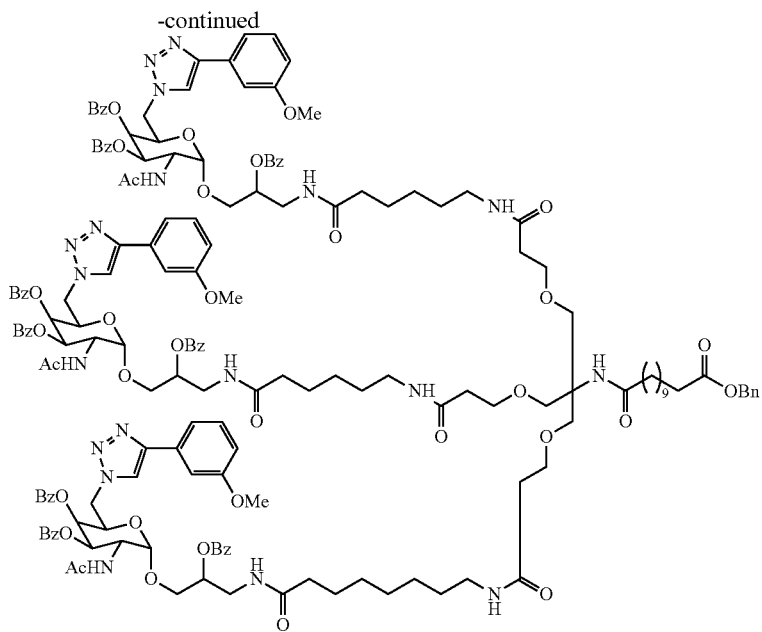
17
Synthesis of compound 17: Under peptide coupling conditions, the amine 13 is reacted with tricarboxylic acid 14 to generate the compound 15. Hydrogenation yields the compound 16, which is then reacted with monobenzyl dodecane dioic acid to provide the protected tri-antennary intermediate 17.
Scheme 7
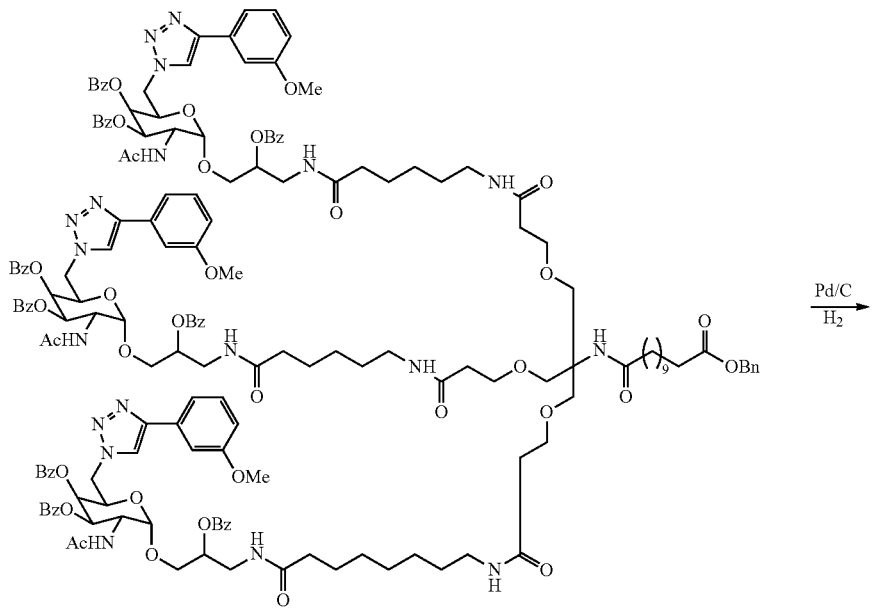
17

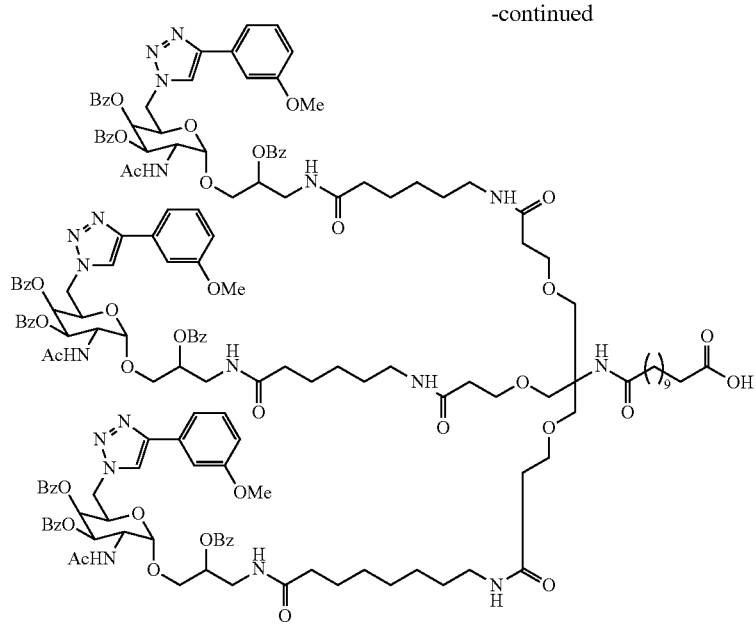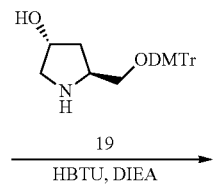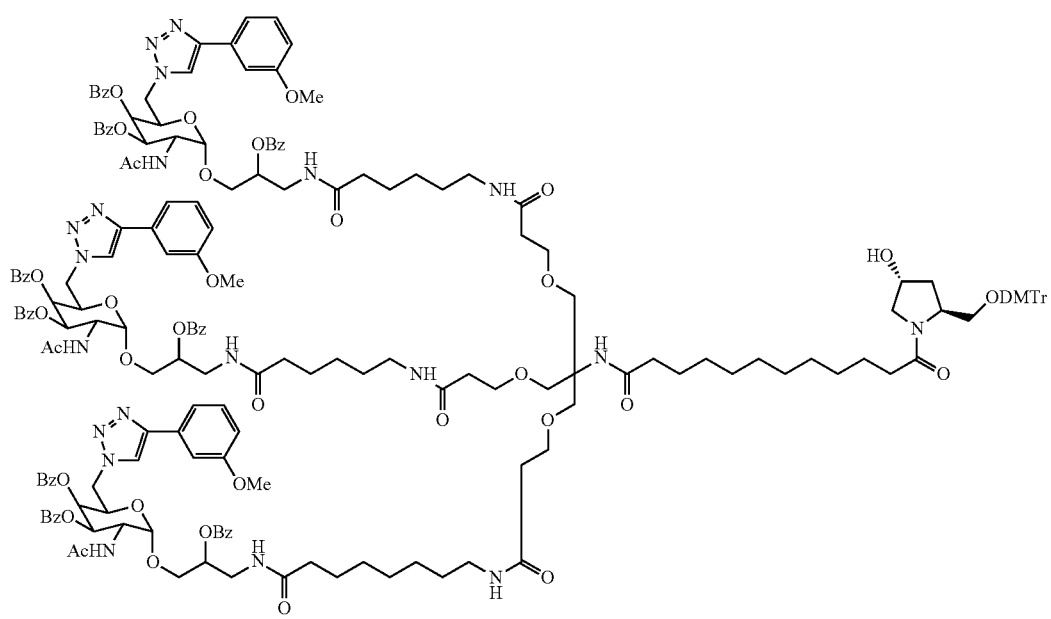
Synthesis of hydroxy proline intermediate 20: Compound 17 is hydrogenated under balloon pressure to obtain the carboxylic acid 18, which is then reacted with amine 19 to generate compound 20 under peptide coupling conditions.

Scheme 8
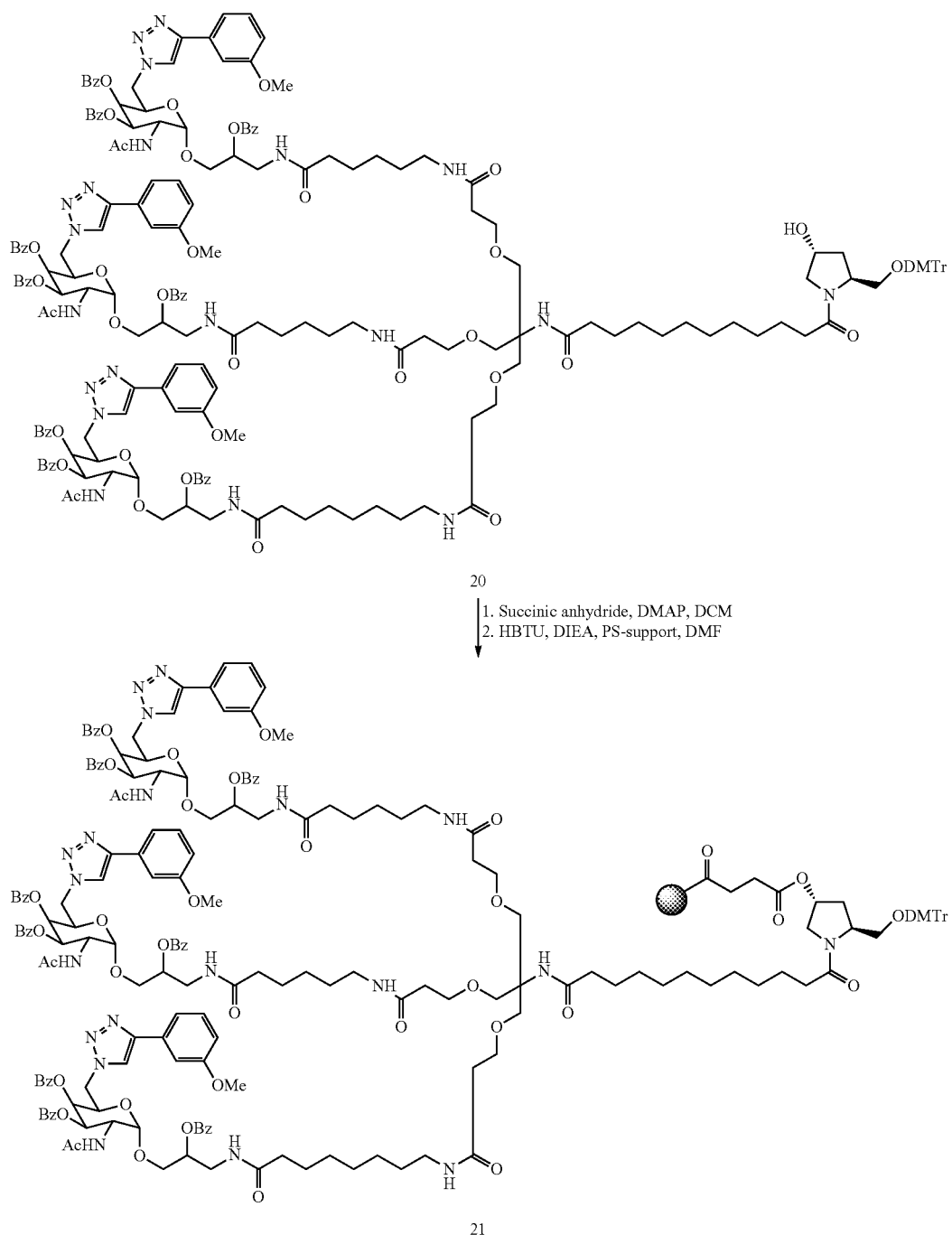
Synthesis of solid support 21: The hydroxy proline 20 is treated with succinic anhydride and DMAP to generate a succinate derivative. This succinate derivative is loaded onto a solid support using peptide coupling conditions to obtain the support 21.

Example 9: Synthesis of Tri-Antennary β-Anomer-Conjugate Building Block (Schemes 9-10)

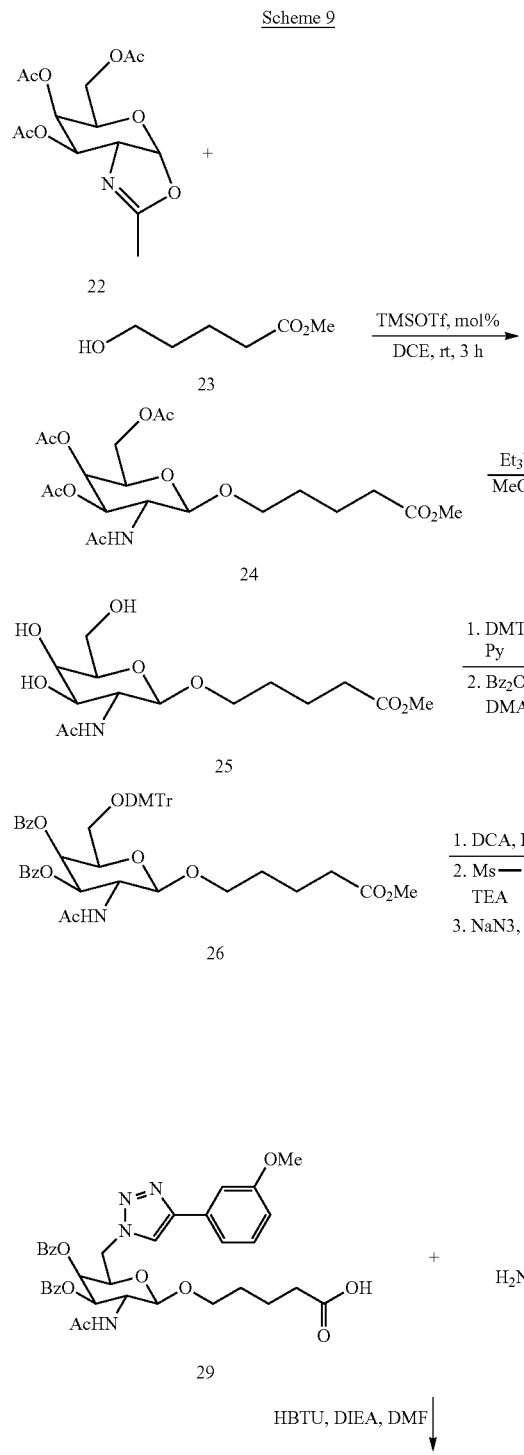

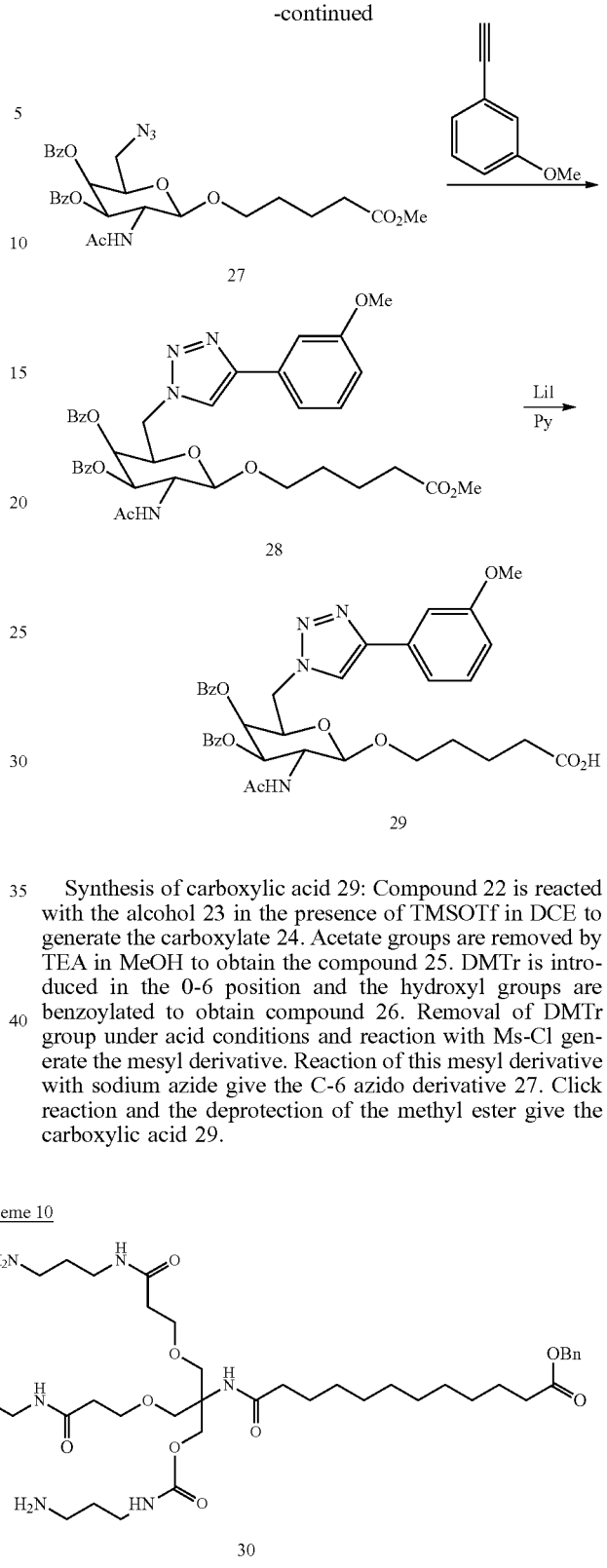

Synthesis of carboxylic acid 29: Compound 22 is reacted with the alcohol 23 in the presence of TMSOTf in DCE to generate the carboxylate 24. Acetate groups are removed by TEA in MeOH to obtain the compound 25. DMTr is introduced in the 0-6 position and the hydroxyl groups are benzoylated to obtain compound 26. Removal of DMTr group under acid conditions and reaction with Ms-Cl generate the mesyl derivative. Reaction of this mesyl derivative with sodium azide give the C-6 azido derivative 27. Click reaction and the deprotection of the methyl ester give the carboxylic acid 29.

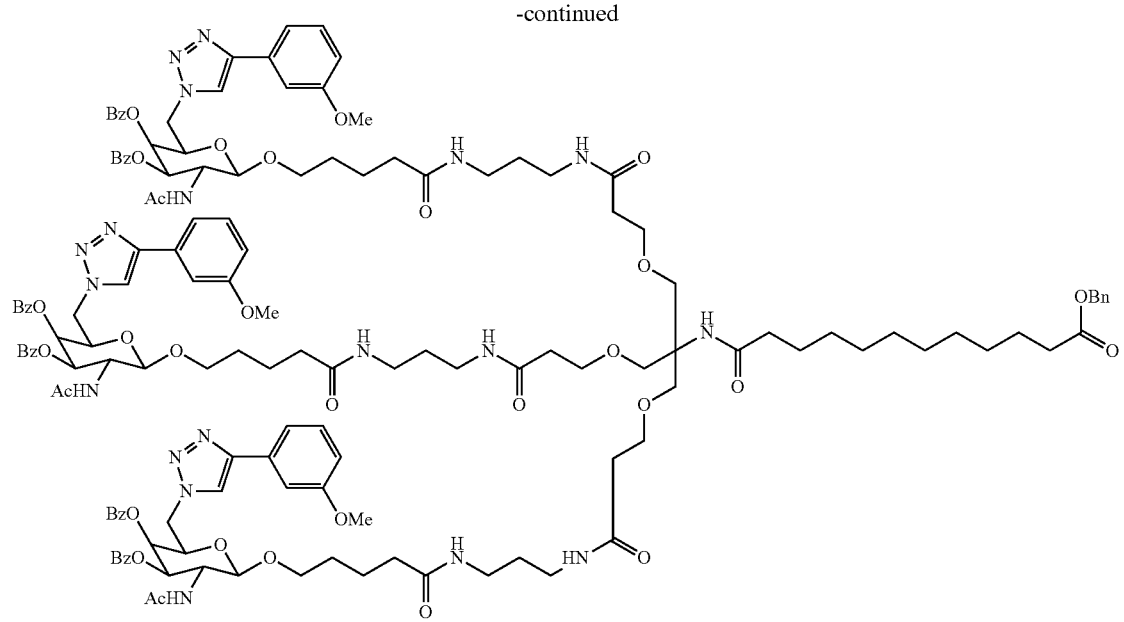
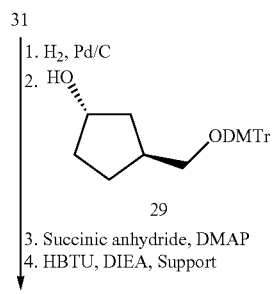
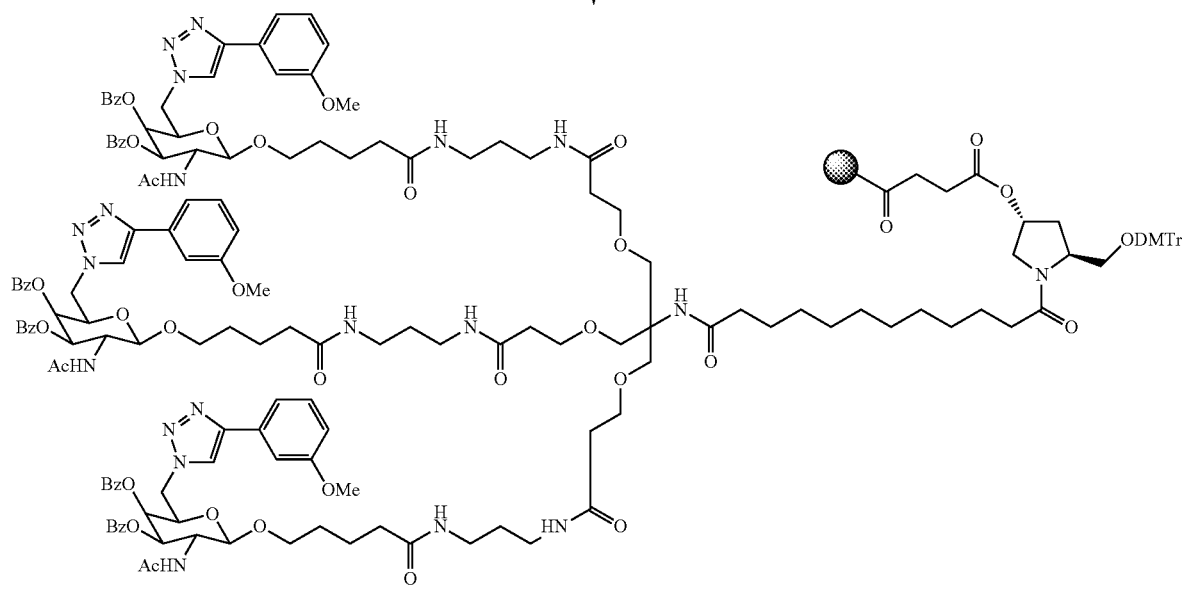
Synthesis of solid support 32: The carboxylic acid 29 is reacted with Tri-antennary amine under peptide coupling conditions generate the tri-antennary derivative 31. This is hydrogenated and the carboxylic acid is reacted with hydroxy proline. This intermediate is reacted with succinic anhydride and the succinate is loaded on to the solid support to get compound 32.

Example 10: Synthesis of Bi-Antennary α-Anomer-Conjugate Building Block (Schemes 11-14)
Scheme 11
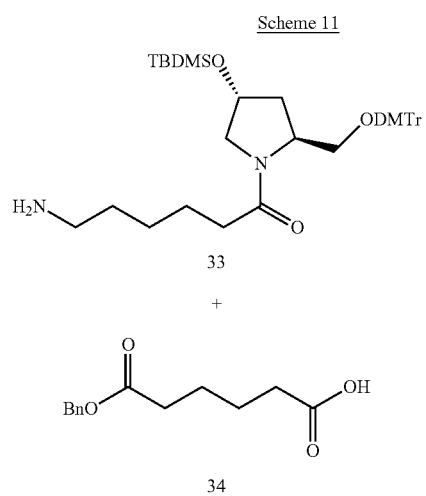
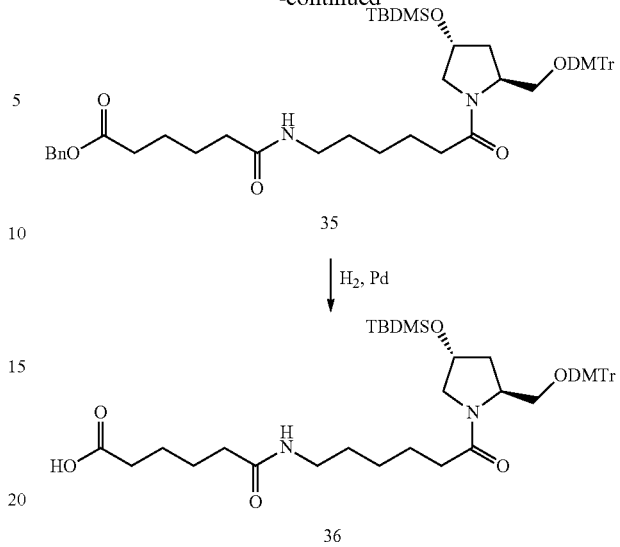
Synthesis of carboxylic acid 36: Hydroxy proline derivative 33 is reacted with monobenzyl hexane dioic acid using HBTU/DIEA to generate the carboxylate 35, which is further hydrogenated to yield the carboxylic acid 36.

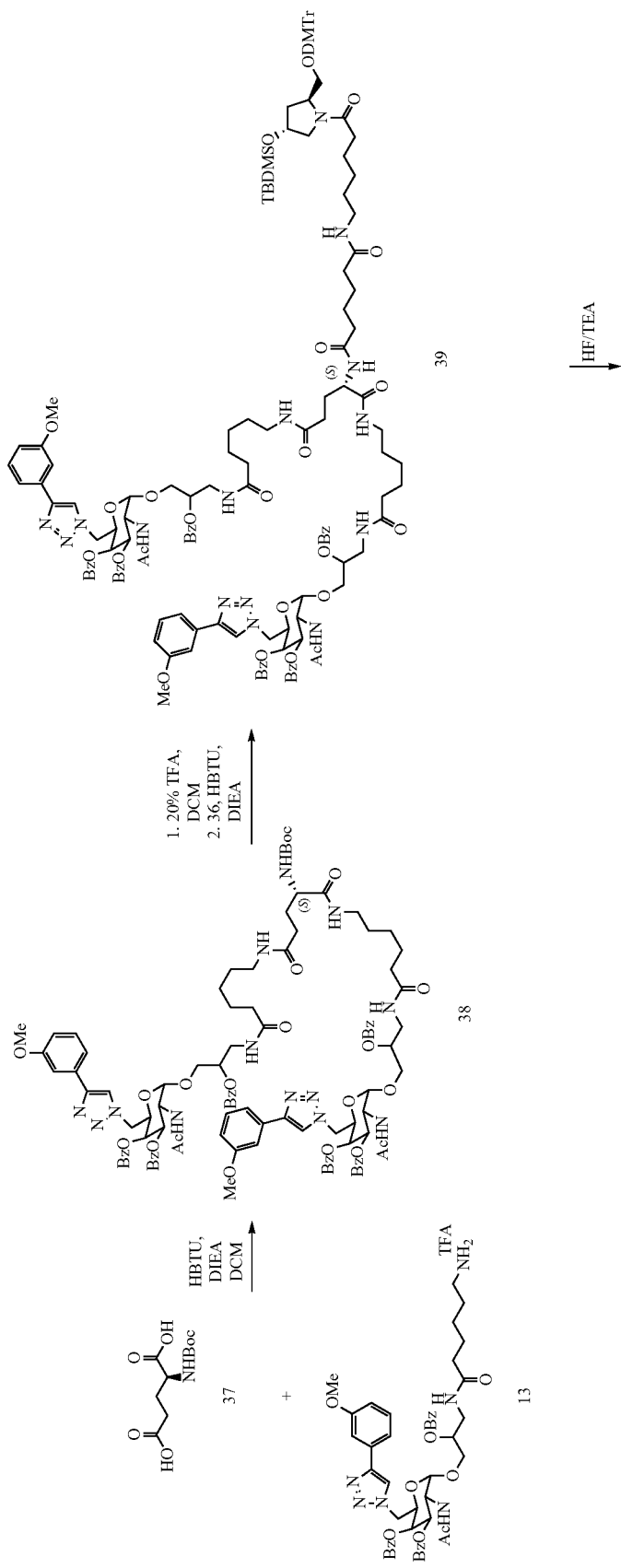

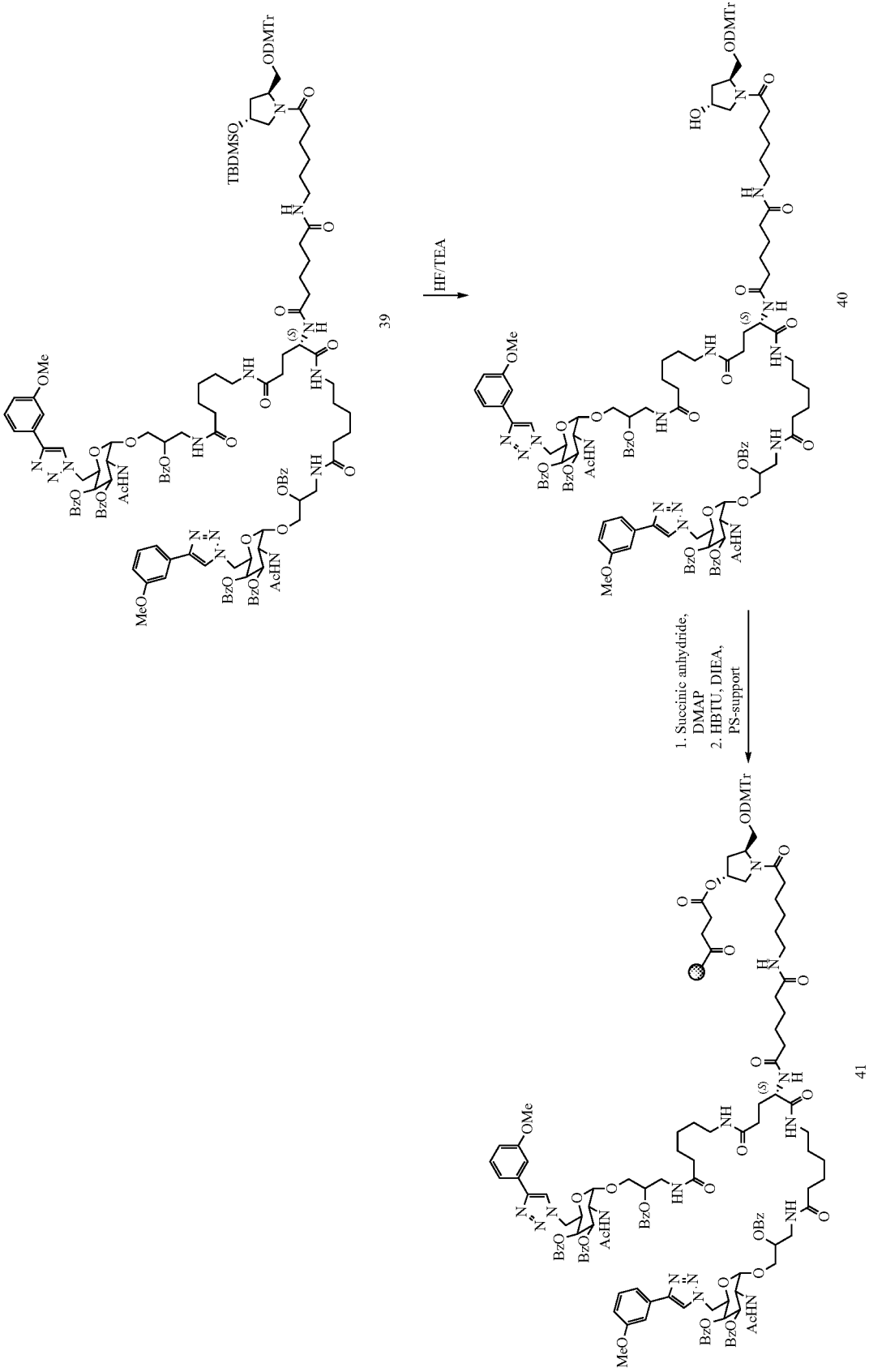

Synthesis of Bi-antennary solid support 41: N-Boc glutamic acid is reacted with the amine 13 using HBTU/DIEA give compound 38. Deprotection of the Boc protecting group and reaction of the carboxylic acid 36 with this amine yield the hydroxy proline derivative 39. Removal of TBDMS and reaction of succinic anhydride with this hydroxyl group generate the succinate derivative. This is loaded onto the solid support to give the bi-antennary solid support 41.

Similarly, compound 54 can be prepared as shown in Schemes 13 and 14 below.

Scheme 13

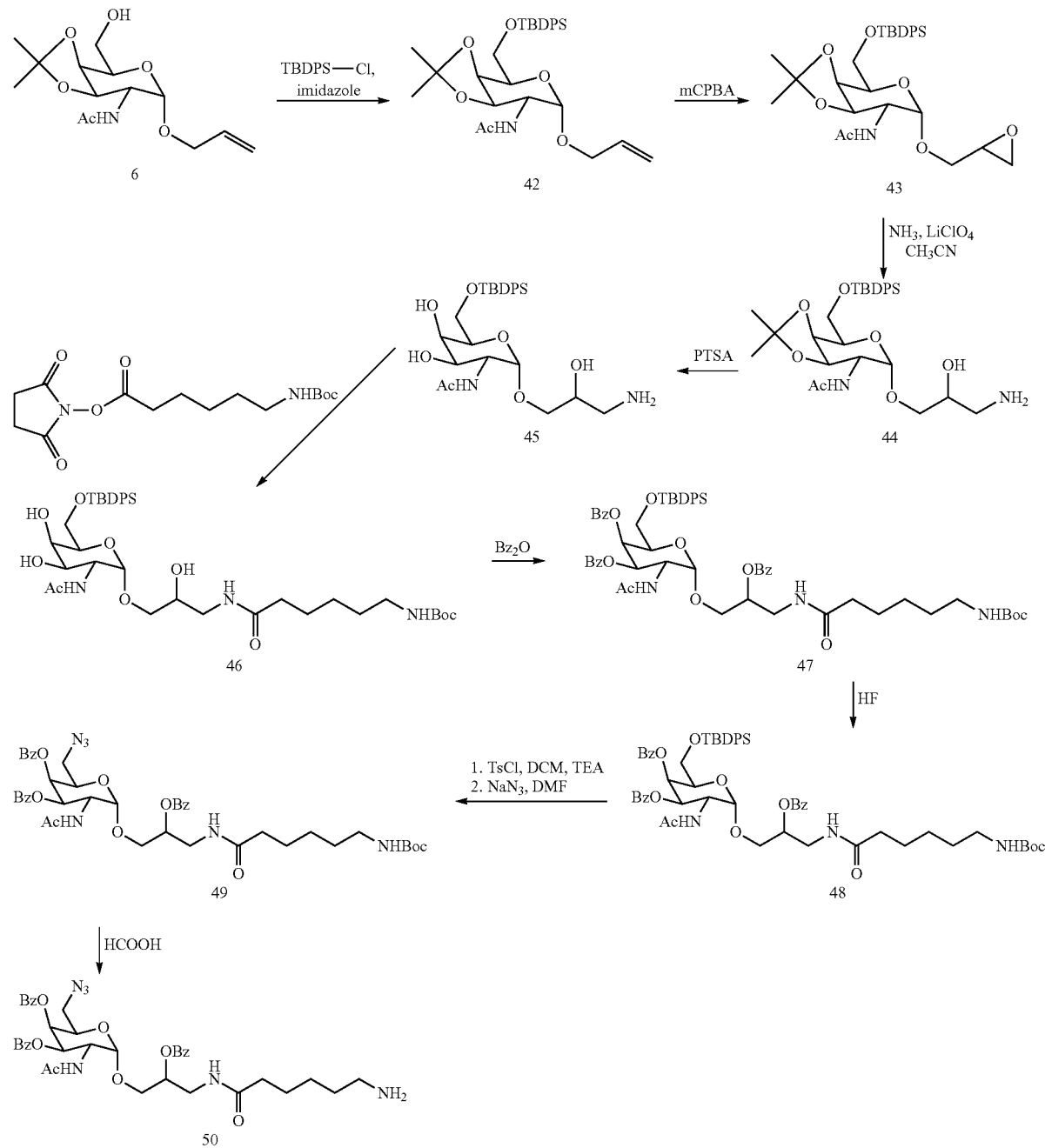

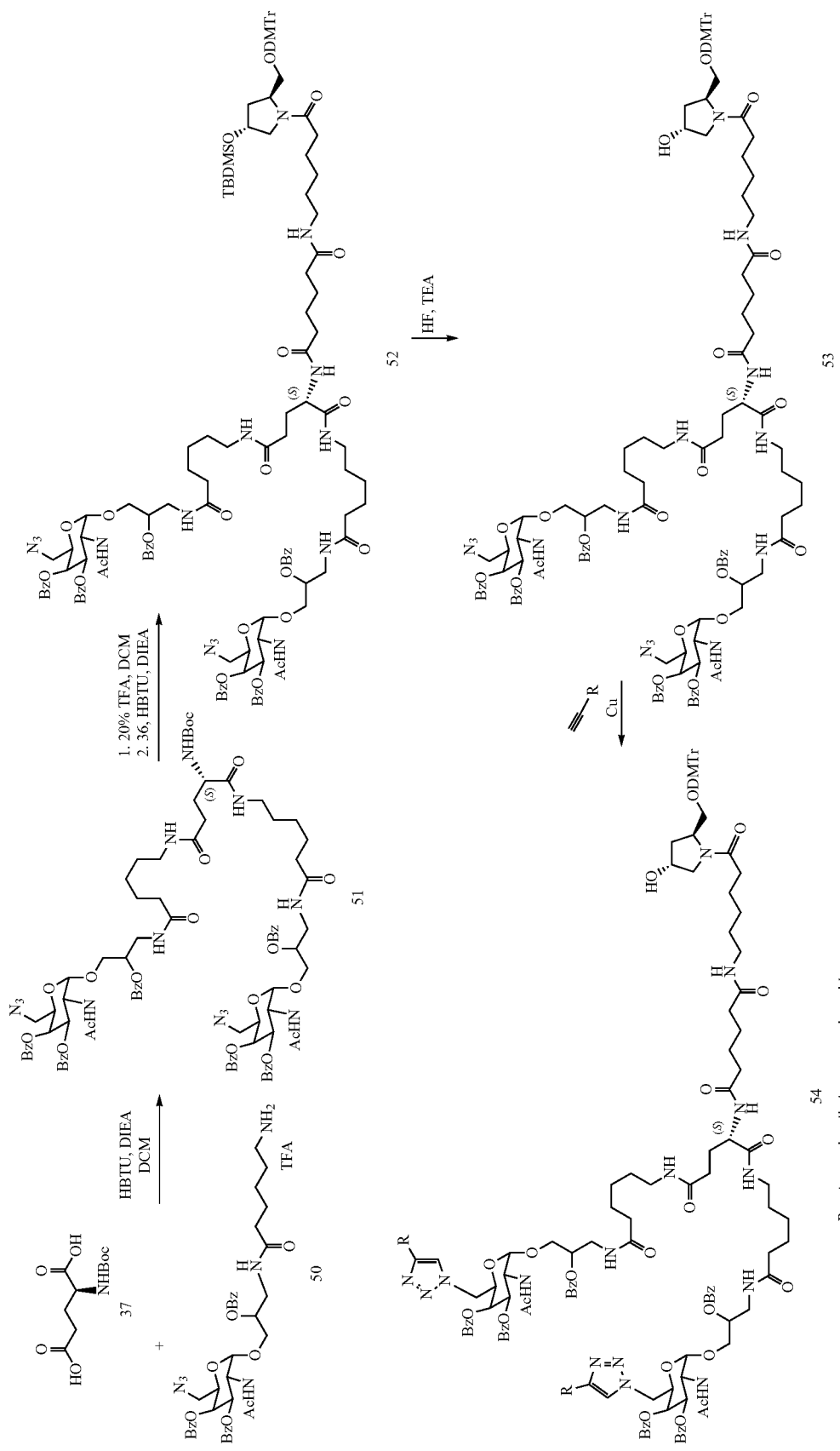

Example 11: Synthesis of Triantennary α-Anomeric Building Block

The triantennary α-anomeric building block 55 can be prepared by scheme 15 below.

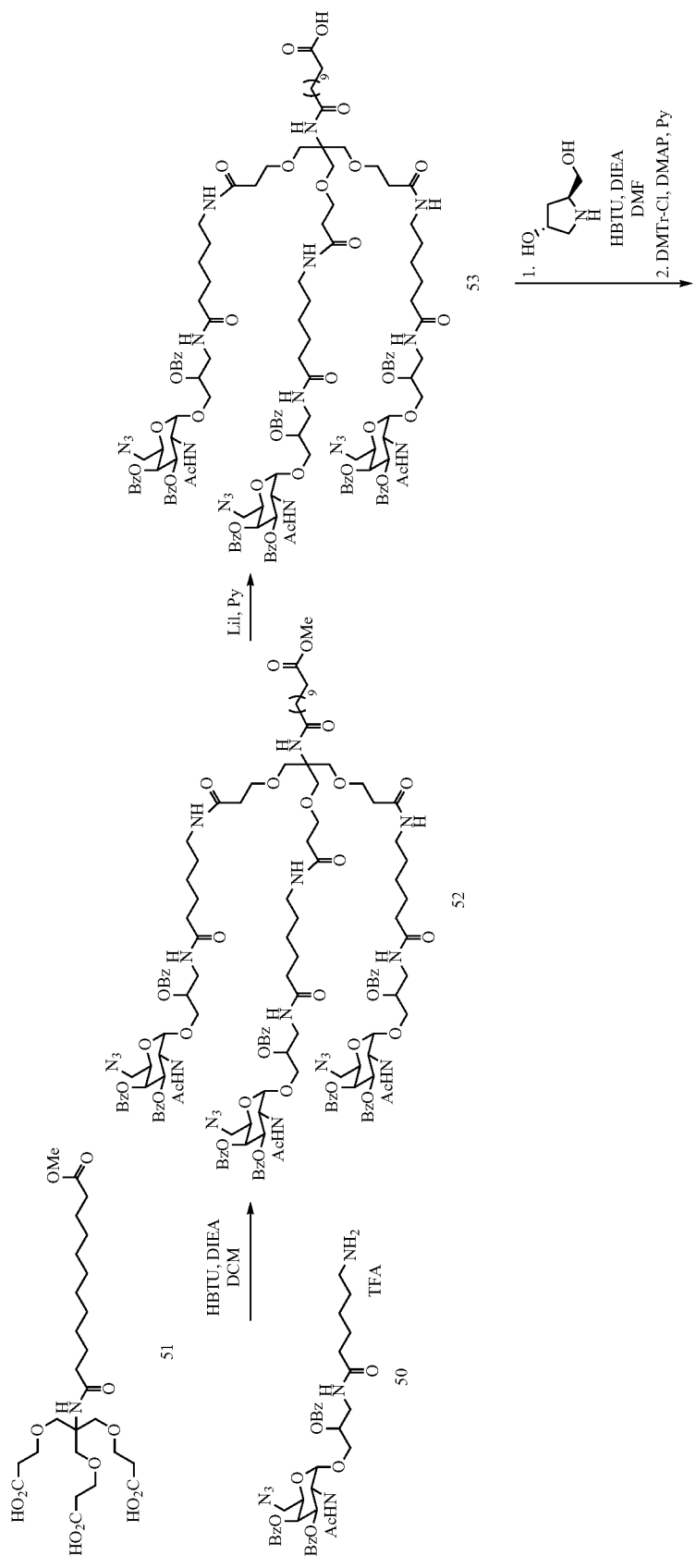
Scheme 15

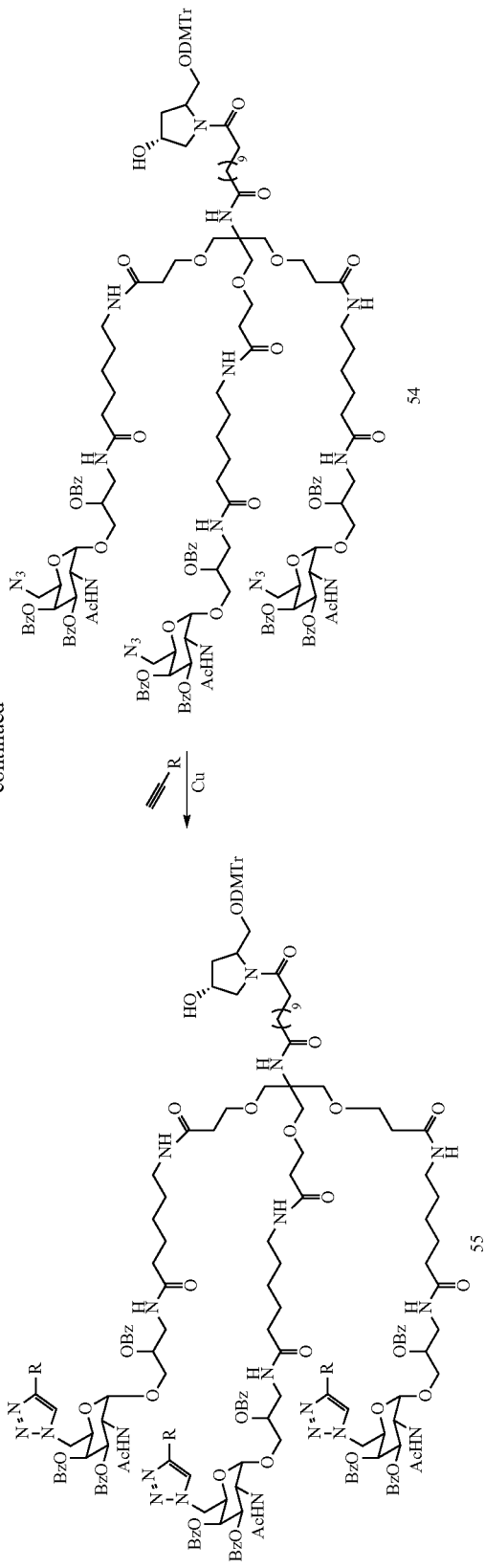

Example 12: Synthesis of Tri-Antennary α-Anomer siRNA Conjugate

Using the conjugate building block 32 described earlier (see scheme 10), RNA is synthesized with the ligand attached to 3'-end of the sense strand according to known procedures. This is annealed with an antisense strand. The product is shown below.

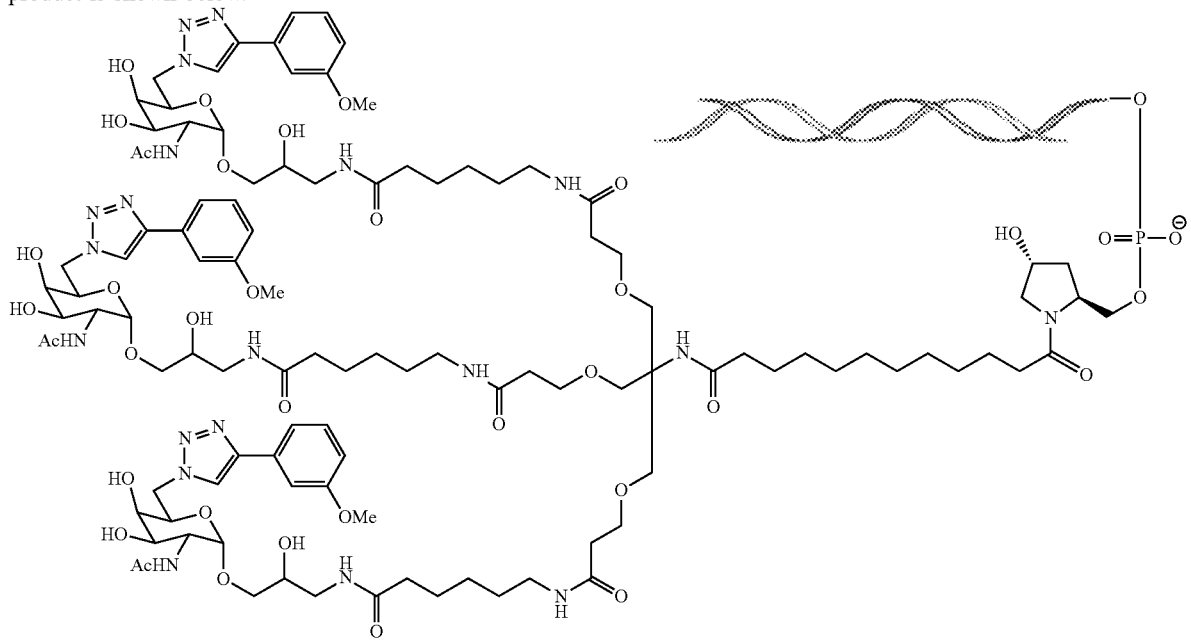

Example 13: Synthesis of Tri-Antennary β-Anomer siRNA Conjugate

Using the conjugate building block 32 described earlier (see scheme 10), RNA is synthesized with the ligand attached to 3'-end of the sense strand according to known procedures. This is annealed with an antisense strand. The product is shown below.

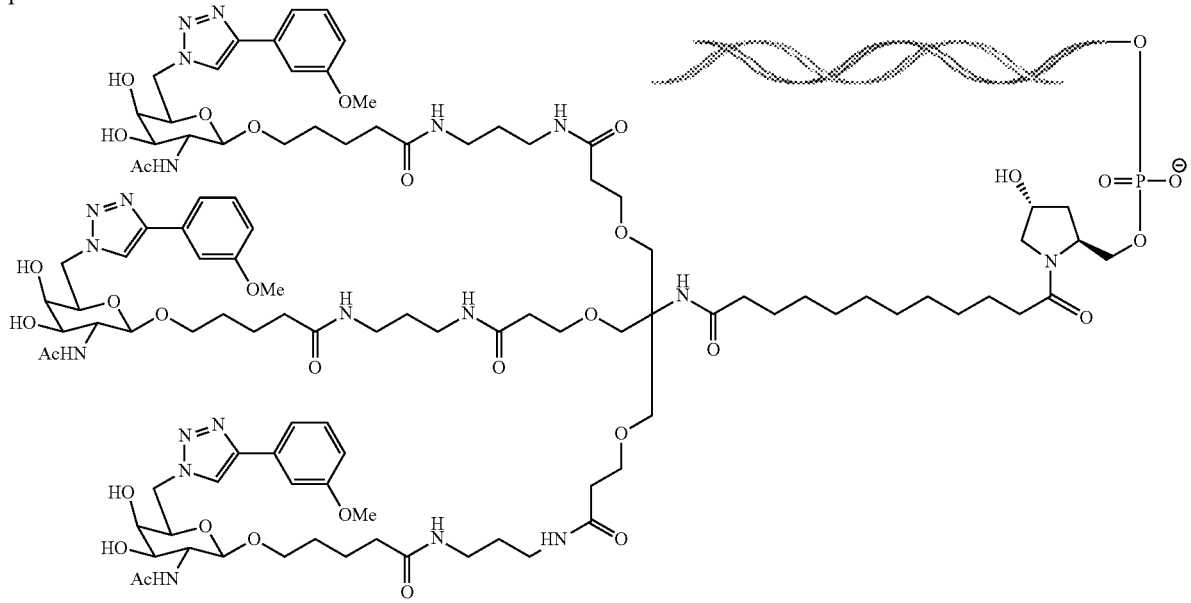

Example 14: Synthesis of Bi-Antennary α-Anomer siRNA Conjugate

Using the conjugate building block 41 described earlier (see scheme 12), RNA is synthesized with the ligand attached to 3'-end of the sense strand according to known procedures. This is annealed with an antisense strand.

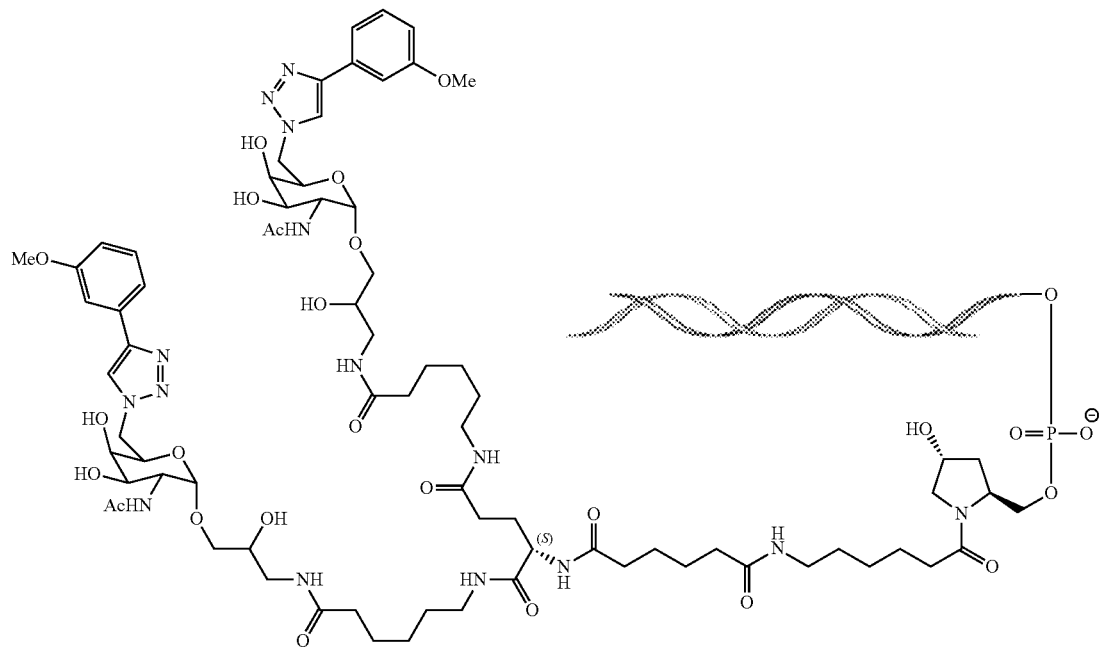

Example 15: Synthesis of Mono-GalNAc Building Blocks for Oligonucleotide Conjugation The Mono-GalNAc building blocks 104 and 105 are prepared as shown in Scheme 16.

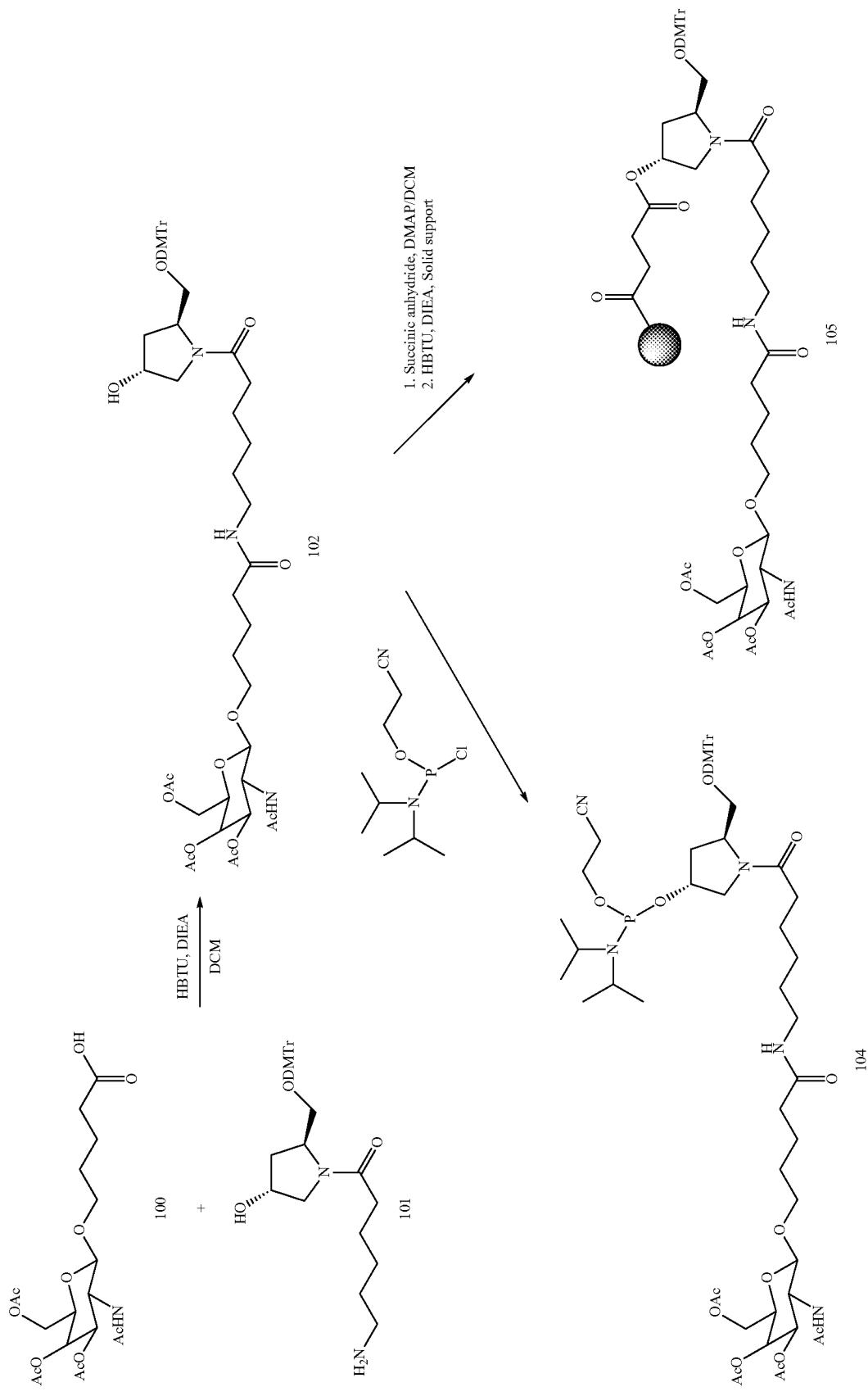
Scheme 16

Synthesis of 102: GalNAc acid 100 (8.39 g, 18.71 mmol) and hydroxy proline amine (10.00 g, 18.77 mmol) were taken together in dichloromethane. HBTU (10.68 g, 28.12 mmol) and DIEA (9.80 mL, 3 eq.) were added and stirred the mixture for 2 hrs at ambient temperature. The product was TLC checked and the reaction mixture was transferred to a separatory funnel and washed with water and brine. The organic layer was dried over sodium sulfate and the solvent was removed. The crude product was purified by silica gel chromatography using dichloromethane and MeOH as solvents to get the compound 102 as a pale yellow fluffy solid (11.77 g, 63%). $^1$H NMR (400 MHz, DMSO) δ 7.80 (d, J=9.2 Hz, 1H), 7.69 (t, J=5.6 Hz, 1H), 7.39-7.09 (m, 9H), 6.86 (ddd, J=9.0, 5.4, 2.1 Hz, 4H), 5.20 (d, J=3.4 Hz, 1H), 5.03-4.83 (m, 2H), 4.47 (d, J=8.5 Hz, 1H), 4.41-4.07 (m, 2H), 4.04-3.95 (m, 3H), 3.86 (dt, J=11.2, 8.9 Hz, 1H), 3.79-3.68 (m, 6H), 3.68-3.36 (m, 3H), 3.21-2.88 (m, 5H), 2.26-2.14 (m, 2H), 2.09 (s, 3H), 2.02 (t, J=6.7 Hz, 2H), 1.98 (s, 3H), 1.87 (d, J=7.5 Hz, 3H), 1.76 (s, 3H), 1.53-1.29 (m, 7H).

Synthesis of 104: Hydroxy proline derivative 102 (6.00 g, 6.24 mmol) was dissolved in dichloromethane (100 mL). DIEA (2.20 mL, 3 eq) and chloroamidite reagent were added. the reaction mixture was stirred for 30 minutes and TLC checked. It was transferred to a separatory funnel and washed with water and sodium bicarbonate solution. The organic layer was dried over sodium sulfate and the crude product was purified by silica gel chromatography using dichloromethane and MeOH as eluent to get the compound as a white fluffy solid. $^1$H NMR (400 MHz, DMSO) δ 7.80 (d, J=9.2 Hz, 1H), 7.68 (s, 1H), 7.42-7.06 (m, 8H), 7.01-6.73 (m, 4H), 5.20 (d, J=3.3 Hz, 1H), 4.96 (dd, J=11.2, 3.3 Hz, 1H), 4.63 (d, J=4.7 Hz, 1H), 4.47 (d, J=8.5 Hz, 1H), 4.15 (s, 1H), 4.01 (s, 3H), 3.86 (d, J=11.0 Hz, 1H), 3.70 (d, J=16.5 Hz, 9H), 3.45 (ddd, J=37.0, 23.3, 16.4 Hz, 6H), 2.99 (dd, J=12.3, 6.4 Hz, 3H), 2.74 (dd, J=9.2, 5.8 Hz, 2H), 2.21 (s, 2H), 2.09 (s, 3H), 2.05-1.95 (m, 5H), 1.88 (s, 3H), 1.76 (s, 3H), 1.52-1.16 (m, 11H), 1.16-1.02 (m, 11H). $^{31}$P NMR δ=151.78, 151.61, 151.50, 151.30.

Synthesis of 105: Compound 102 (2.10 g, 2.18 mmol) was dissolved in DCM (20 mL). To this mixture succinic anhydride (0.441 g, 4.36 mmol) and DMAP (0.532 g, eq) followed by TEA (1 ML) were added. The reaction mixture was stirred overnight at room temperature. Its TLC was checked and the reaction mixture was washed with water and brine. The organic layer was dried over sodium sulfate and the crude product filtered through a small pad of silica gel. The solvent was removed and this material was used for the next reaction. The succinate from the above reaction was dissolved in anhydrous acetonitrile. HBTU (1.59 g, 4.20 mmols) and DIEA (1.10 ml) were added and the mixture was swirled for 5 minutes. A polystyrene solid support was added to the reaction mixture and the mixture was shaken overnight at ambient temperature. the solid support was filtered, washed and capped using acetic anhydride/Py mixture. The solid support was again washed with dichloromethane, MeOH/DCM and ether (27.10 g, 55 umol/g).

Example 16: Synthesis of Mono Antennary Alpha Anomer siRNA

Using the conjugate building blocks 104 and 105 described earlier (see scheme 16), RNA is synthesized with the ligands attached to 3'-end of the sense strand according to known procedures. This is annealed with an antisense strand. The product is shown below.

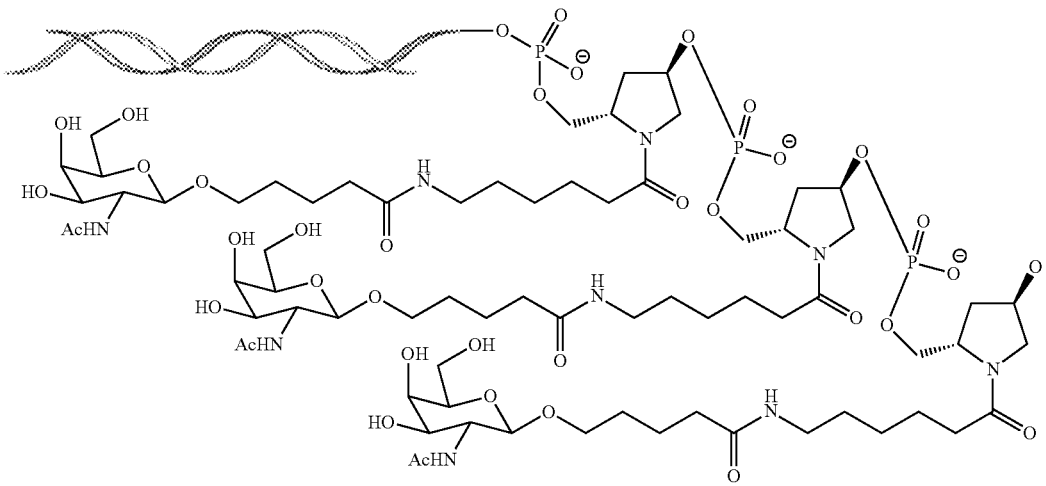 [SMILES: COP(=O)([O-])OC[C@@H]1C[C@@H](OP(=O)([O-])OC[C@@H]2C[C@@H](OP(=O)([O-])OC[C@@H]3C[C@@H](O)CN3C(=O)CCCCCNC(=O)CCCCOC3OC(CO)C(O)C(O)C3NC(C)=O)CN2C(=O)CCCCCNC(=O)CCCCOC2OC(CO)C(O)C(O)C2NC(C)=O)CN1C(=O)CCCCCNC(=O)CCCCOC1OC(CO)C(O)C(O)C1NC(C)=O]

Example 17: Synthesis of Trifluoroacetamide Derivative for Post-Synthetic Conjugation The intermediate compound 8 is prepared as shown in Scheme 17 below.

Scheme 17
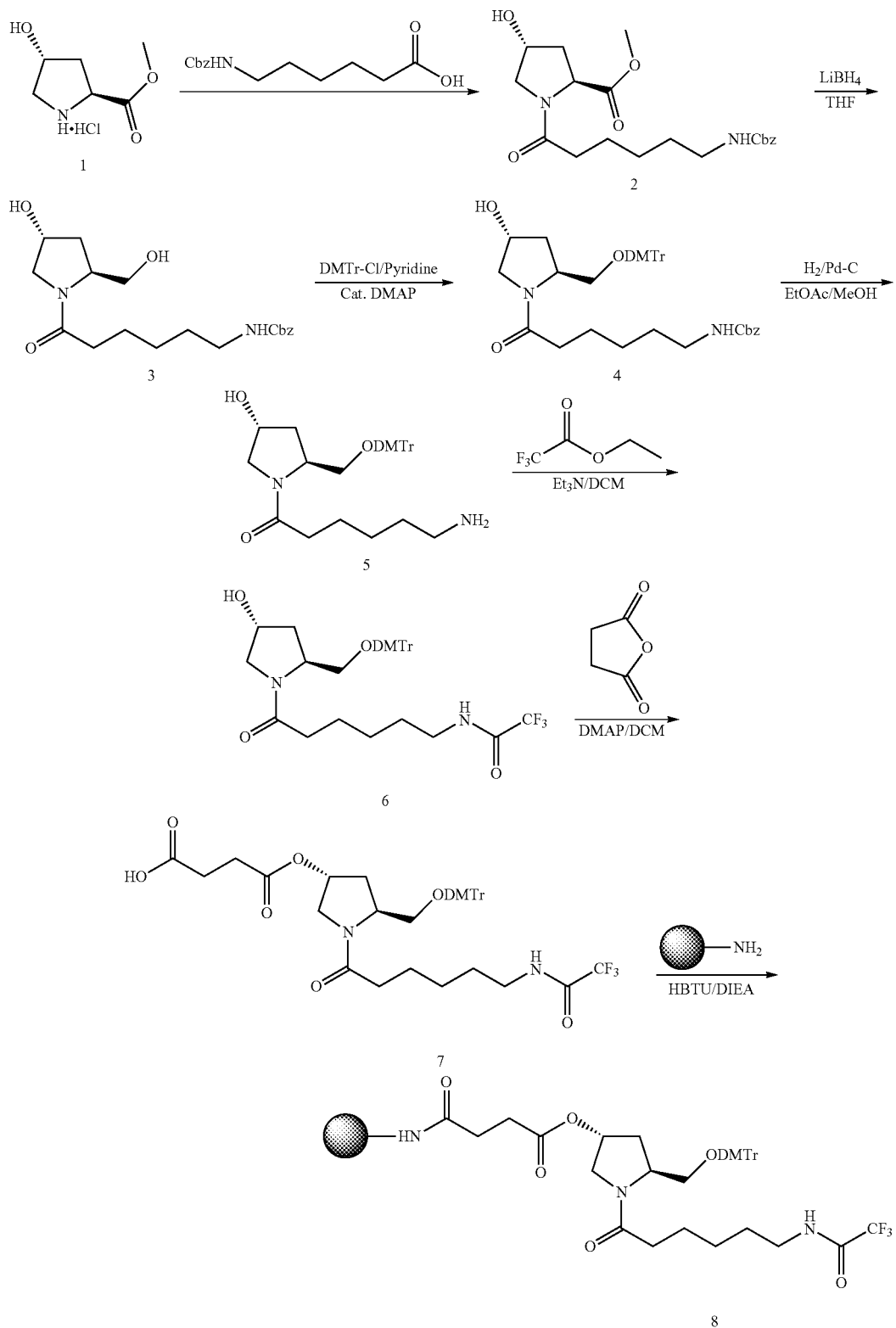
Synthesis of Compound 2: Z-aminocaproic acid (22.2 g, 82.50 mmols) was dissolved in DMF (250 mL) and cooled to 0° C. To the solution were added diisopropyl ethyl amine (44.4 mL, 275 mmols), HBTU (40.4 g, 106.7 mmols), and HOBT (30.0 g, 220 mmols). After stirring under argon for 20 minutes at 0° C., 4-hydroxy-1-proline methyl ester hydrochloride (20.0 g, 110 mmols) was added and the stirring was continued under argon at room temperature overnight. The reaction mixture was evaporated to dryness. To the residue ethyl acetate (250 mL) was added. The organic layer was washed with water, saturated sodium bicarbonate, water again, and saturated sodium chloride. The organic layer was dried over sodium sulfate, filtered and evaporated to dryness. Crude Compound 2 (Rf=0.5 in 10% MeOH/DCM, 24.30 g) was obtained. Compound 2 was purified by column chromatography first by eluting with 2% methanol/dichloromethane to remove impurities followed by 5% methanol/dichloromethane gave 21.36 g (65%). $^1$H NMR (400 MHz, DMSO-$d_6$): Observed rotamers due to amide bond at the ring. δ 7.35 (m, 5H), 5.15 (d, OH, $D_2O$ exchangeable), 4.99 (s, 2H), 4.27 (m, 1H), 3.97 (m, 1H), 3.58 (s, 1H) 3.20-3.47 (m, 5H), 2.94-3.02 (m, 2H), 2.10-2.32 (m, 2H), 1.74-2.01 (m, 2H), 1.35-1.4 (m, 4H), 1.22-1.28 (m, 4H).

Synthesis of Compound 3: Compound 2 (21.36 g, 54.43 mmols) was dissolved in THF (200 mL). The reaction mixture was stirred under argon for 20 minutes at 0° C. Then lithium borohydride (1.19 g, 54.43 mmols) was added to the solution over 20 minutes at 0° C., and the stirring was continued under argon at room temperature overnight. The reaction mixture was cooled to 0° C. The excess lithium borohydride was quenched with 5M NaOH (30 mL). After stirring for 30 minutes the reaction mixture was evaporated to dryness. To the residue dichloromethane (200 mL) was added. The organic layer was washed with water and saturated sodium chloride. The organic layer was dried over sodium sulfate, filtered and evaporated to dryness. Crude Compound 3 (Rf=0.4 in 10% MeOH/DCM, 35.88 g) was obtained. Compound 3 was purified by column chromatography by eluting with 3% methanol/dichloromethane to remove impurities followed by 5% methanol/dichloromethane to obtain 9.21 g (49%). $^1$H NMR (400 MHz, DMSO-$d_6$): Observed rotamers due to amide bond at the ring. δ 7.35 (m, 5H), 4.99 (s, H), 4.91 (d, OH, $D_2O$ exchangeable), 4.77 (t, OH, $D_2O$ exchangeable), 4.27 (m, 1H), 3.97 (m, 1H), 3.20-3.47 (m, 5H), 2.94-3.02 (m, 2H), 2.10-2.32 (m, 2H), 1.74-2.01 (m, 2H), 1.35-1.4 (m, 4H), 1.22-1.28 (m, 4H). $^{13}$C NMR (100 m MHz, DMSO-$d_6$): δ 171.4, 171.1 (minor due to rotamer), 156.1, 137.3, 128.9, 128.3, 128.2, 127.7, 125.3, 68.2, 67.4, 65.1, 63.4, 62.0, 57.6, 55.1, 54.9, 53.3, 40.1, 39.9, 39.7, 39.5, 39.3, 39.1, 38.9, 37.4, 36.1, 34.2, 32.6, 29.3, 26.1, 26.0, 24.6, 24.1, 21.0.

Synthesis of Compound 4: Compound 3 (9.21 g, 25.27 mmols) was co-evaporated with anhydrous pyridine (80 mL) twice. Then the compound was placed under hard vacuum overnight to dry. Compound 3 was taken from the hard vacuum and dissolved in anhydrous pyridine (200 mL). To this solution a catalytic amount of dimethylamino pyridine (0.35 g, 2.53 mmols) was added. The reaction mixture stirred under argon for 30 minutes at 0° C. Then DMT-Cl (9.0 g, 26.53 mmols) was added to the solution at 0° C. The mixture stirred under vacuum followed by argon, and stirring was continued under argon at room temperature overnight. The excess DMT-Cl was quenched with the addition of methanol (15 mL). The reaction mixture was evaporated to dryness, and to the residue dichloromethane (200 mL) was added. The organic layer was washed with water, saturated sodium bicarbonate, water again, and saturated sodium chloride. The organic layer was dried over sodium sulfate, filtered and evaporated to dryness. Crude Compound 4 (Rf=0.6 in 100% EtOAc, 14.02 g) was obtained. Compound 4 was purified by column chromatography by first eluting with 50% ethyl acetate (1% TEA) in hexanes to remove impurities followed by 100% ethyl acetate (1% TEA) to give 12.36 g (73.4%) as a white foamy solid. $^1$H NMR (400 MHz, DMSO-$d_6$): δ 7.17-7.33 (m, 14H), 4.99 (s, 2H), 4.91 (d, OH, $D_2O$ exchangeable), 4.37 (m, 1H), 4.01 (m, 1H), 3.72 (s, 6H) 3.56 (m, 1H) 3.29 (m, 1H), 3.14 (m, 1H), 2.93-3.02 (m, 4H), 2.18 (m, 2H) 1.74-2.01 (m, 2H), 1.37-1.41 (m, 6H).

Synthesis of Compound 5: Compound 4 (12.36 g, 18.54 mmols) was dissolved in 10% methanol/ethyl acetate (300 mL) and purged with argon. To the reaction mixture was added 10% palladium by wt. on active carbon wet Degussa type (1.3 g). The flask was re-purged with argon. The flask was purged with hydrogen twice, then hydrogen was bubbled through the reaction mixture for 10 seconds. The reaction mixture continued to stir under hydrogen at room temperature overnight. The reaction mixture was decanted onto a sintered funnel packed with celite and washed twice with methanol. The organic layer was evaporated to dryness affording compound 5 (Rf=0.05 10% MeOH/DCM, 9.16 g, 93%) as a white solid, which required no further purification. 1H NMR (400 MHz, DMSO-$d_6$): δ 7.15-7.31 (m, 9H), 6.86 (m, 4H) 4.99 (s, 1H), 4.37 (m, 1H), 4.01 (m, 2H), 3.72 (s, 6H) 3.56 (m, 1H) 3.29 (m, 1H), 3.14 (m, 1H), 2.93-3.02 (m, 2H), 2.45 (m, 2H), 2.18 (m, 2H) 1.74-2.01 (m, 2H), 1.37-1.41 (m, 3H) 1.13-1.38 (m, 4H).

Synthesis of Compound 6: Compound 5 (9.16 g, 17.2 mmols) was dissolved in dichloromethane (200 mL). The reaction mixture stirred under argon for 10 minutes at 10° C. To the reaction mixture, triethyl amine (4.80 mL, 34.4 mmols) was added dropwise as the mixture continued to stir under argon for 20 minutes at 10° C. To the reaction mixture ethyl trifluoro acetate (3.05 mL, 25.8 mmols) was added dropwise as the mixture continued to stir under argon for 10 minutes at 10° C. The reaction mixture continued to stir under argon at room temperature overnight. The reaction mixture was washed with water and saturated sodium chloride. The organic layer was dried over sodium sulfate, filtered and evaporated to dryness. Crude Compound 6 (Rf=0.6 10% MeOH/DCM, 10.89 g) was obtained. Upon column purification by eluting with 5% methanol/dichloromethane (1% TEA), Compound 6 (8.76 g, 81%) was obtained as a yellow foamy solid. $^1$H NMR (400 MHz, DMSO-$d_6$): δ 7.56-7.09 (m, 9H), 7.01-6.52 (m, 4H), 5.34-5.04 (m, 1H), 4.99-4.78 (m, 1H), 4.48-4.25 (m, 2H), 3.83-3.67 (m, 6H), 3.60-3.50 (m, 1H), 3.49-3.18 (m, 2H), 3.16-2.91 (m, 2H), 2.89-2.56 (m, 2H), 2.54-2.32 (m, 2H), 2.32-1.69 (m, 3H), 1.59-1.03 (m, 4H). $^{19}$F NMR (400 MHz, DMSO-$d_6$): −77.14 (s, 3F).

Synthesis of compound 7: Compound 6 (8.76 g, 13.93 mmols), dimethylamino pyridine (5.10 g, 41.79 mmols), and triethyl amine (3.90 mL, 27.86 mmols) were dissolved in dichloromethane (300 mL). The reaction mixture was stirred under argon for 10 minutes. Then succinic anhydride (2.80 g, 27.86 mmols) was added and the mixture continued stirring under argon at room temperature overnight. The reaction mixture was washed with a solution of slightly saturated sodium chloride twice. The organic layer was dried over sodium sulfate, filtered and evaporated to dryness. Compound 7 (Rf=0.9 10% MeOH/DCM, 10.87 g, 94%) was obtained as a white solid, which required no further purification.

Synthesis of Compound 8: Compound 7 (2.00 g, 2.41 mmols) was dissolved in acetonitrile (100 mL). To the solution, diisopropyl ethyl amine (1.68 mL, 9.64 mmols) and HBTU (1.83 g, 4.82 mmols) were added. The reaction mixture was shaken for 10 minutes. CPG (27 g) was added to the flask and the mixture continued to shake overnight. The CPG compound and reaction mixture were decanted over a sintered funnel. The reaction mixture was washed with 1% triethyl amine/dichloromethane, followed by two washes of 10% methanol/dichloromethane, another wash of 1% triethyl amine/dichlormethane, and anhydrous diethyl ether. The CPG compound was suction dried for 1 hour, then recovered from the funnel and placed under hard vacuum for 2 hours. CPG compound (5.0 mg) was sent for de-blocking. To the remaining CPG compound was added 25% acetic anhydride/pyridine (100 mL) and the mixture was shaken overnight. The CPG compound and reaction mixture were placed over a sintered funnel and washed in the same manner as before. The CPG compound was suction dried for 1 hour, removed from the funnel and placed under hard vacuum for 2 hours. The CPG compound (7.1 mg) was sent for de-blocking. Spectrophotometer: Before capping 0.9892 Abs (502.0 nm) 65 micromol/g, After capping 1.4403 (502.0 nm) 67 micromol/g.

Synthesis of Compound 9: Compound 6 (8.89 g, 14.14 mmols) and diisopropyl ethyl amine (4.93 mL, 28.28 mmols) were dissolved in anhydrous dichloromethane (60 mL). The reaction mixture was stirred under argon for 5 minutes. Then N,N-diisopropylamino cyanoethyl phosphoramidic chloride (5.63 mL, 16.26 mmols) was added to the reaction mixture. The reaction mixture continued stirring under argon at room temperature for 30 minutes. Completion of the reaction was observed by TLC. The reaction mixture was diluted with dichloromethane (100 mL). The organic layer was washed with water, saturated sodium bicarbonate, water again, and saturated sodium chloride. The organic layer was dried over sodium sulfate, filtered and evaporated to dryness affording crude Compound 9 (Rf=0.44 5% MeOH/DCM, 11.02 g). Upon column purification by eluting with 3% methanol/dichloromethane (1% TEA), Compound 9 (6.31 g, 54%) was obtained as a yellow solid. $^1$H NMR (400 MHz, DMSO-$d_6$) δ 9.37 (s, 1H), 7.63 (d 1H), 7.42-6.98 (m, 8H), 6.92-6.77 (m, 4H), 4.25-3.90 (m, 2H), 3.78-3.64 (m, 7H), 3.48 (d, 3H), 3.29 (d, 1H), 3.23-2.92 (m, 4H), 2.86 (d, 1H), 2.73 (t, 1H), 2.58 (t, 1H), 2.53-2.47 (m, 4H), 2.33-1.87 (m, 4H), 1.55-0.97 (m, 12H). $^{31}$P (400 MHz, DMSO-$d_6$): 151.68 (d, 1P).

Example 18: Synthesis of Carbamate Linker for Post-Synthetic Conjugation

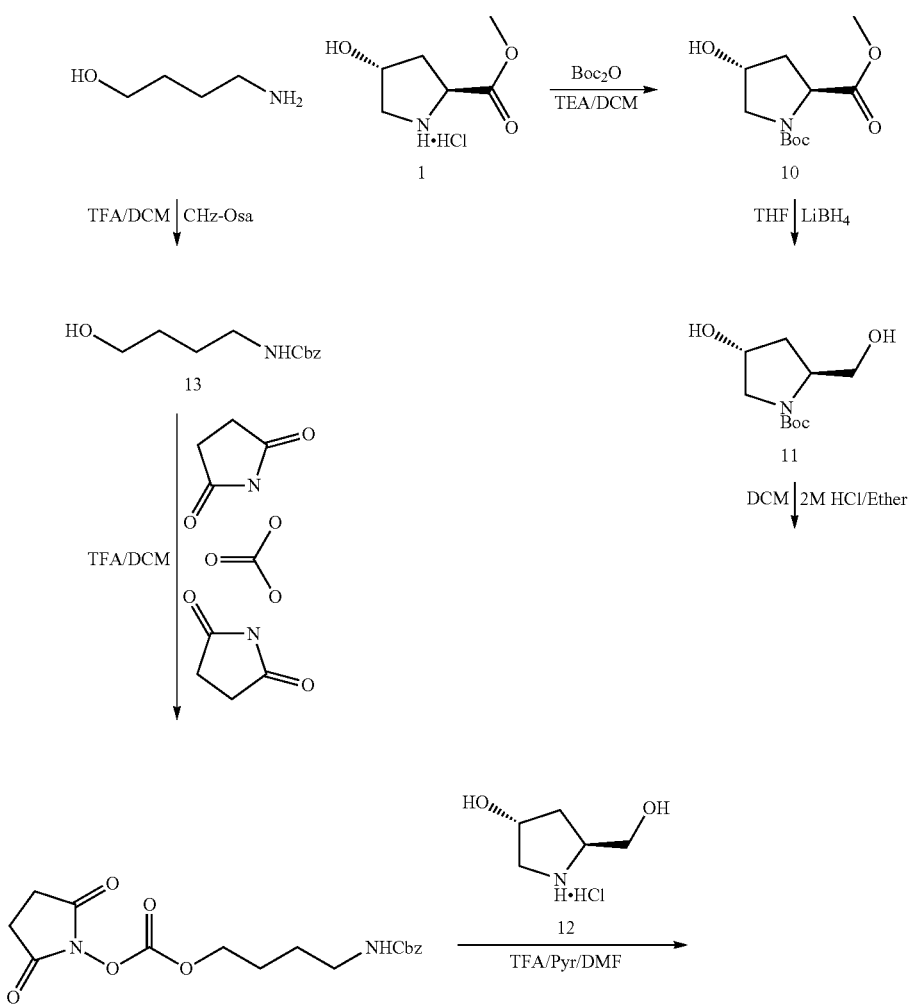

Scheme 18

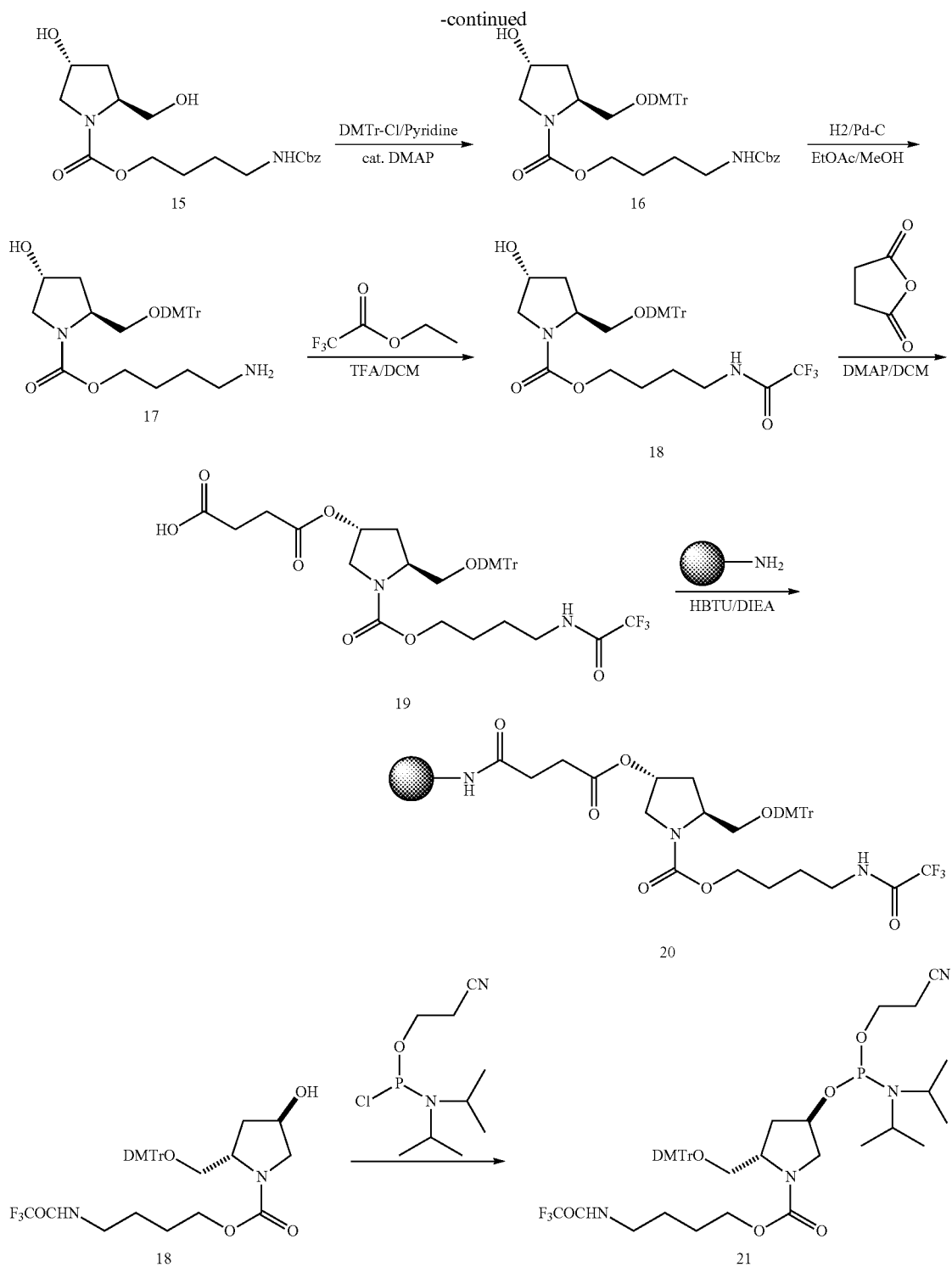

4-Z-aminobutanol 13: 4-aminobutan-1-ol (26 mL, 280 mmols) and Cbz-OSuccinate (104.7 g, 420 mmols) were dissolved in dichloromethane (200 mL). The reaction mixture was stirred under argon for 20 minutes at 10° C. Then triethyl amine (78 mL, 560 mmols) was added to the solution while the reaction mixture continued stirring under argon at 10° C. The reaction mixture continued stirring under argon at room temperature overnight. The reaction mixture was washed with water, saturated sodium bicarbonate, water again, and saturated sodium chloride. The organic layer was dried over sodium sulfate, filtered and evaporated to dryness affording crude Compound 2 (Rf=0.5 10% MeOH/DCM, 71.97 g) as a white solid. This was used in the next step without further purification.

DSC activated 4-Z-aminobutanol 14: Crude Compound 13 (6.0 g) and DSC (10.33 g 40.31 mmols) were dissolved in dichloromethane (100 mL). The reaction mixture stirred under argon for 30 minutes at 0° C. Triethyl amine (7.88 mL, 53.74 mmols) was added dropwise as the mixture stirred under argon for 5 minutes at 0° C. The reaction mixture continued to stir under argon at room temperature overnight. The reaction mixture was diluted in dichloromethane (100 mL). The organic layer was washed with water, water again, and saturated sodium chloride. The organic layer was dried over sodium sulfate, filtered and evaporated to dryness affording crude Compound 14 (Rf=0.85 10% MeOH/DCM, 11.14 g) as a light brown solid. This was used in the next step without further purification.

Compound 17: Compound 16 (5.00 g, 7.48 mmols) was dissolved in 10% methanol/ethyl acetate (100 mL) and purged with argon. To the reaction mixture was added 10% palladium by wt. on active carbon wet Degussa type (0.5 g). The flask was re-purged with argon. The flask was purged with hydrogen twice, then hydrogen was bubbled through the reaction mixture for 10 seconds. The reaction mixture continued to stir under hydrogen at room temperature overnight. The reaction mixture was decanted onto a sintered funnel packed with Celite and washed twice with methanol. The organic layer was evaporated to dryness affording Compound 17 (Rf=0.03 5% MeOH/DCM, 3.4 g, 87%) as a white solid, which required no further purification. $^1$H NMR (400 MHz, DMSO-$d_6$) δ 7.41-7.14 (m, 9H), 6.99-6.72 (m, 4H), 4.96 (d, 1H), 4.30 (s, 1H), 4.04-3.58 (m, 6H), 3.46-3.25 (m, 1H), 3.21-2.81 (m, 3H), 2.52-2.46 (m, 2H), 1.97 (d, 3H), 1.63-1.42 (m, 4H).

Compound 18: Compound 17 (3.2 g, 5.98 mmols) was dissolved in dichloromethane (80 mL). The reaction mixture stirred under argon for 10 minutes at 10° C. To the reaction mixture, triethyl amine (1.67 mL, 11.96 mmols) was added dropwise as the mixture continued to stir under argon for 20 minutes at 10° C. To the reaction mixture, ethyl trifluoro acetate (1.06 mL, 8.97 mmols) was added dropwise as the mixture continued to stir under argon for 10 minutes at 10° C. The reaction mixture continued to stir under argon at room temperature overnight. The reaction mixture was washed with water, saturated sodium bicarbonate, water again, and saturated sodium chloride. The organic layer was dried over sodium sulfate, filtered and evaporated to dryness. Compound 18 (Rf=0.45 5% MeOH/DCM, 3.33 g, 88%) was obtained as a yellow foamy solid, which required no further purification. $^1$H NMR (400 MHz, DMSO-$d_6$) δ 7.46-7.03 (m, 9H), 6.86 (d, 4H), 4.93 (s, 1H), 4.29 (s, 1H), 4.11-3.63 (m, 2H), 3.53-2.79 (m, 5H), 2.53 (d, 2H), 2.30 (d, 2H), 1.99 (d, 3H), 1.76 (s, 1H), 1.36 (t, 4H). $^{19}$F NMR (400 MHz, DMSO-$d_6$): −77.11 (s, 3F).

Compound 19: Compound 18 (2.0 g, 3.17 mmols), dimethylamino pyridine (1.16 g, 3.48 mmols), and triethyl amine (0.88 mL, 6.34 mmols) were dissolved in dichloromethane (50 mL). The reaction mixture was stirred under argon for 10 minutes. Then succinic anhydride (0.63 g, 6.34 mmols) was added and the mixture continued stirring under argon at room temperature overnight. The reaction mixture was washed with a solution of slightly saturated sodium chloride twice. The organic layer was dried over sodium sulfate, filtered and evaporated to dryness. Crude Compound 19 (Rf=0.9 10% MeOH/DCM, 3.23 g) was obtained. Upon column purification by eluting with 5% methanol/dichloromethane (1% TEA), Compound 12 (2.58 g, 98%) was obtained as a white solid. $^1$H NMR (400 MHz, DMSO-$d_6$): δ 9.43 (d, 1H), 7.45-7.04 (m, 9H), 7.02-6.71 (m, 4H), 5.51-4.91 (m, 2H), 4.16-2.95 (m, 9H), 2.67 (q, 4H), 2.58-2.36 (m, 6H), 2.31-2.02 (m, 2H), 1.33 (d, 4H).

Compound 20: Compound 19 (2.03 g, 2.40 mmols) was dissolved in acetonitrile (100 mL). To the solution, diisopropyl ethyl amine (1.67 mL, 9.64 mmols) and HBTU (1.82 g, 4.82 mmols) were added. The reaction mixture was shaken for 10 minutes. CPG (27 g) was added to the flask and the mixture continued to shake overnight. The CPG compound and reaction mixture were decanted over sintered funnel. The reaction mixture was washed with 1% triethyl amine/dichloromethane, followed by two washes of 10% methanol/dichloromethane, another wash of 1% triethyl amine/dichlormethane, and anhydrous diethyl ether. The CPG compound was suction dried for 1 hour, then recovered from the funnel and placed under hard vacuum for 2 hours. The CPG compound (6.7 mg) was sent for de-blocking. To the remaining CPG compound was added 25% acetic anhydride/pyridine (150 mL) and the mixture was shaken overnight. The CPG compound and reaction mixture were placed over a sintered funnel and washed in the same manner as before. The CPG compound was suction dried for 1 hour, removed from the funnel and placed under hard vacuum for 2 hours. The CPG compound (6.9 mg) was sent for de-blocking. Spectrophotometer: Before capping 1.8396 Abs (502.0 nm) 90.3 micromol/g, After capping 1.8798 Abs (502.0 nm) 89.6 micromol/g.

Compound 21: Compound 18 (4.26 g, 6.75 mmols) and diisopropyl ethyl amine (2.35 mL, 13.5 mmols) were dissolved in anhydrous dichloromethane (40 mL). The reaction mixture stirred under argon for 5 minutes. Then N,N-diisopropylamino cyanoethyl phosphoramidic chloride (1.73 mL, 7.76 mmols) was added to the reaction mixture. The reaction mixture continued stirring under argon at room temperature for 30 minutes. Completion of the reaction was observed by TLC. The reaction mixture was diluted with dichloromethane (100 mL). The organic layer was washed with water, saturated sodium bicarbonate, water again, and saturated sodium chloride. The organic layer was dried over sodium sulfate, filtered and evaporated to dryness affording crude Compound 14 (Rf=0.44 5% MeOH/DCM, 11.02 g). Upon column purification by eluting with 3% methanol/dichloromethane (1% TEA), Compound 14 (6.31 g, 54%) was obtained as a yellow solid. $^1$H NMR (400 MHz, DMSO-$d_6$) δ 7.41-6.99 (m, 8H), 6.85 (d, 4H), 4.10-3.62 (m, 2H), 3.59-3.24 (m, 7H), 3.13 (d, 3H), 2.75-2.68 (m, 1H), 2.59-2.45 (m, 4H), 2.10 (d, 1H), 1.37 (t, 1H), 1.25-1.00 (m, 10H).

Example 19: GalNAc Conjugation on Pyrimidines, Purines, and Abasic Sites (Schemes 19-33)

Using palladium coupling chemistry, GalNAc ligands and cationic molecules can be introduced at the C-5 position of pyrimidine nucleosides with various substituents at the 2'-position. As shown in schemes below (Scheme 19-Scheme 27), the nucleoside building blocks can be synthesized accordingly. In Schemes 28 and 29, designed purine nucleoside analogs containing GalNAc ligands are shown. In Scheme 30, GalNAc ligands are introduced at the C-1' position. Using Click chemistry, as shown in scheme 31 and 32, GalNAc can be introduced at an abasic site. Scheme 33 shows convertible nucleoside approaches to introduce GalNAc ligands at the C-2 position on a purine ring.

Scheme 19. Synthesis of uridine analogs with cationic functional groups at C-5 positions
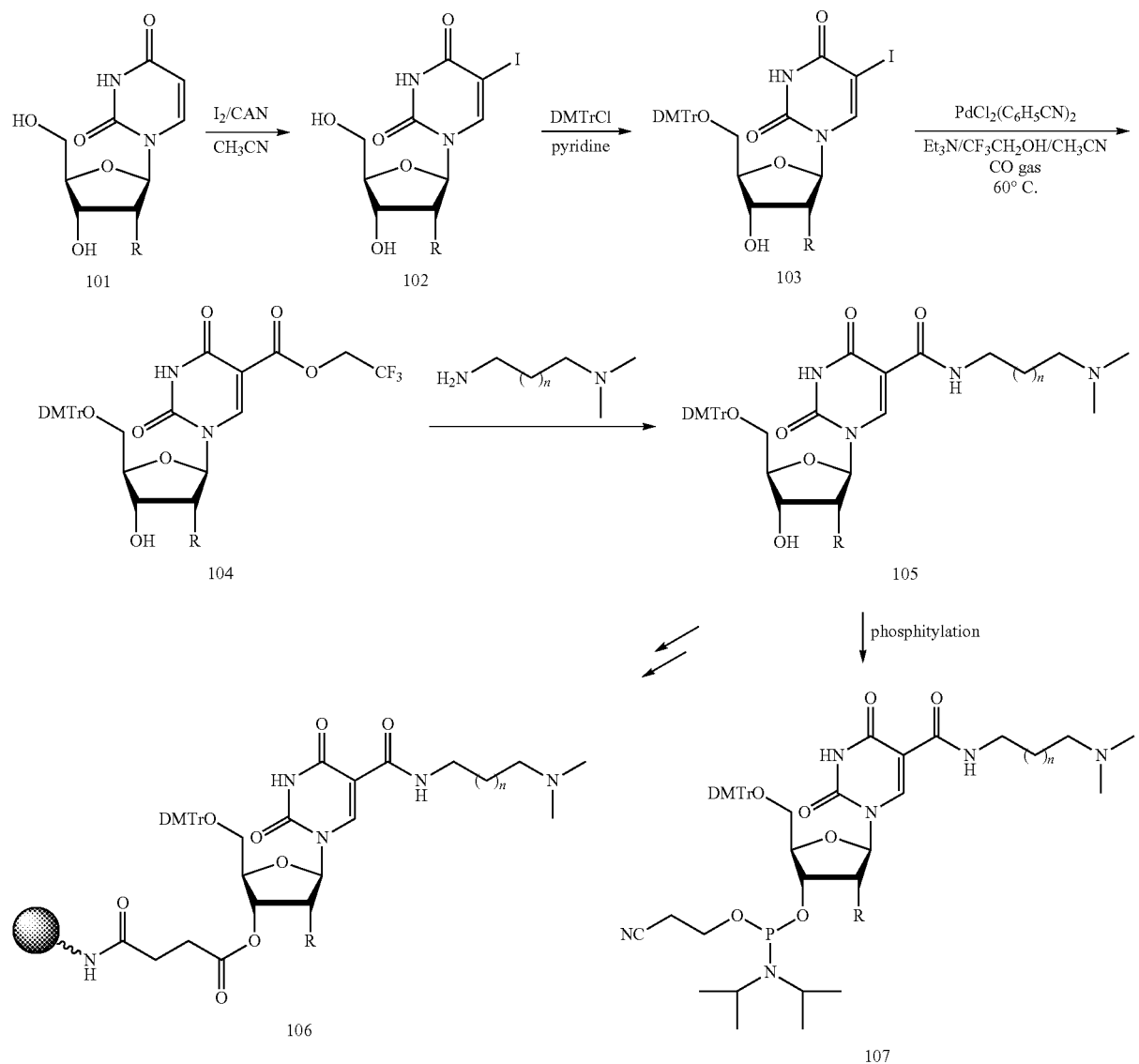
n = 1-9
Scheme 20. Synthesis of uridine analogs with GalNAc ligand at C-5 position
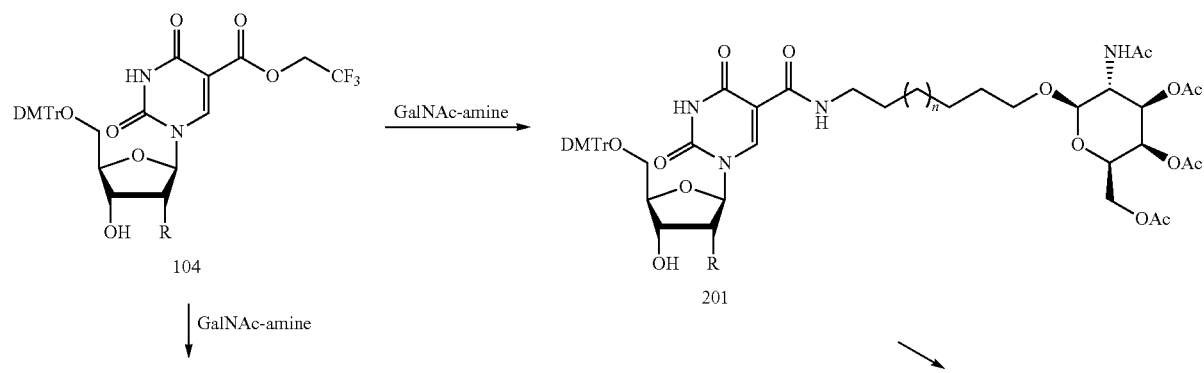

303 304
-continued
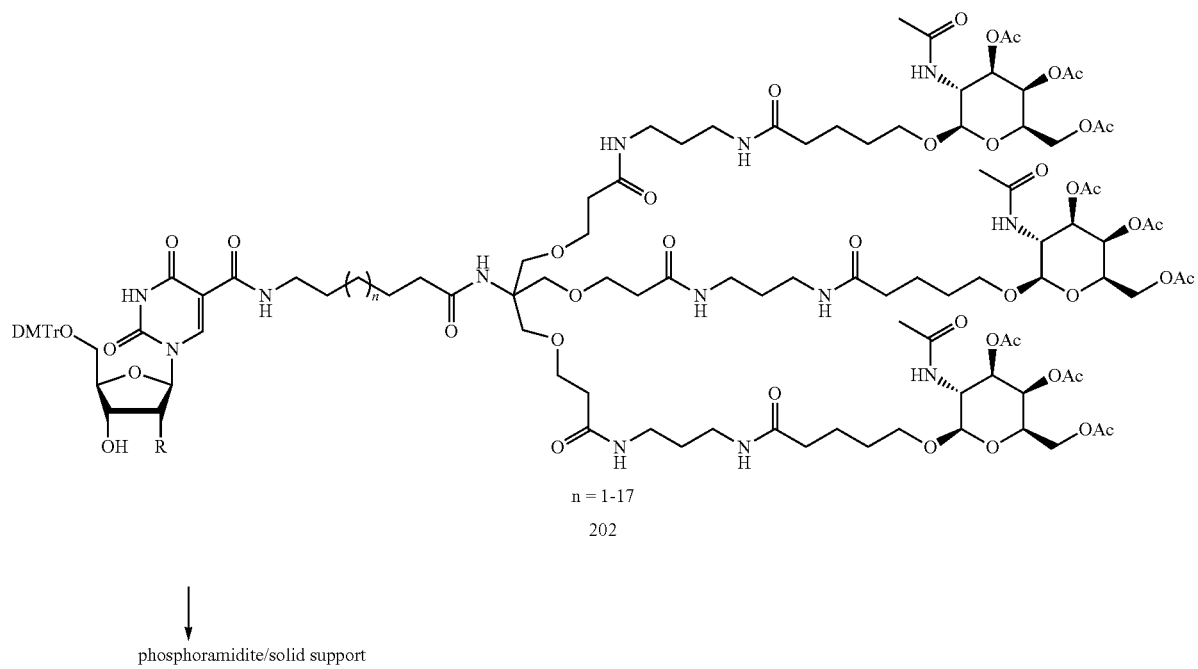
n = 1-17
202
↓ phosphoramidite/solid support
R = H, OH, OTBS, OMe, F, OCH₂CH₂OCH₃, etc.
Scheme 21. Synthesis of cytidine analogs with cationic functional groups at C-5 position
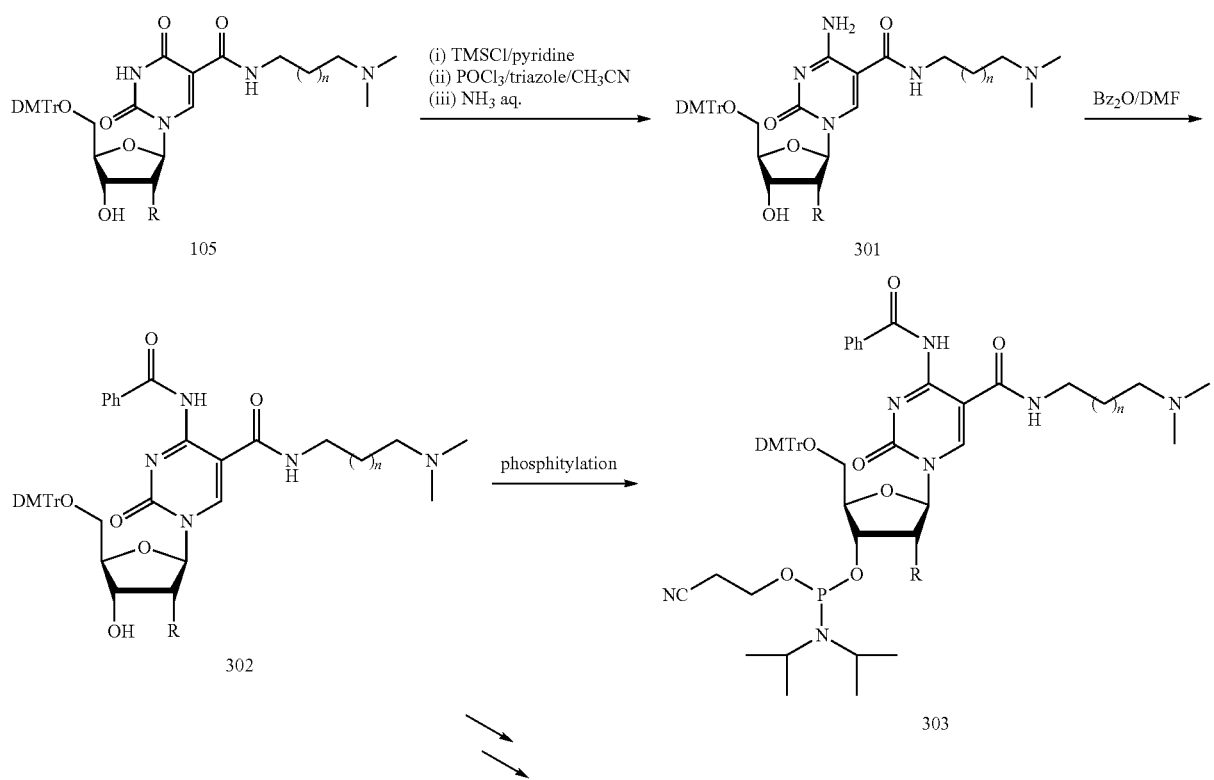

305
306
-continued
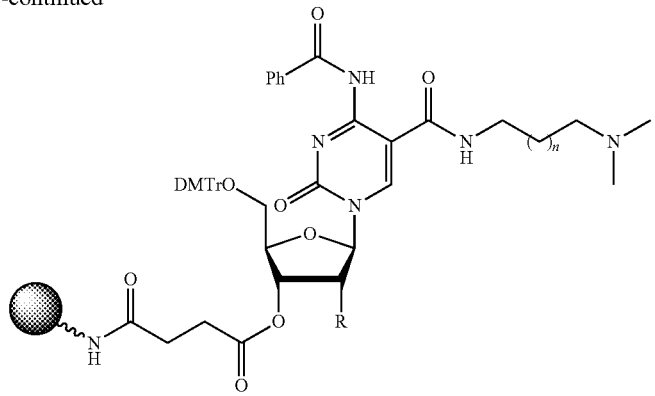
304
n = 1-9  R = H, OH, OTBS, OMe, F, OCH$_2$CH$_2$OCH$_3$, etc.
Scheme 22. Alternate route for synthesis of cytidine analogs with cationic functional groups at C-5 position
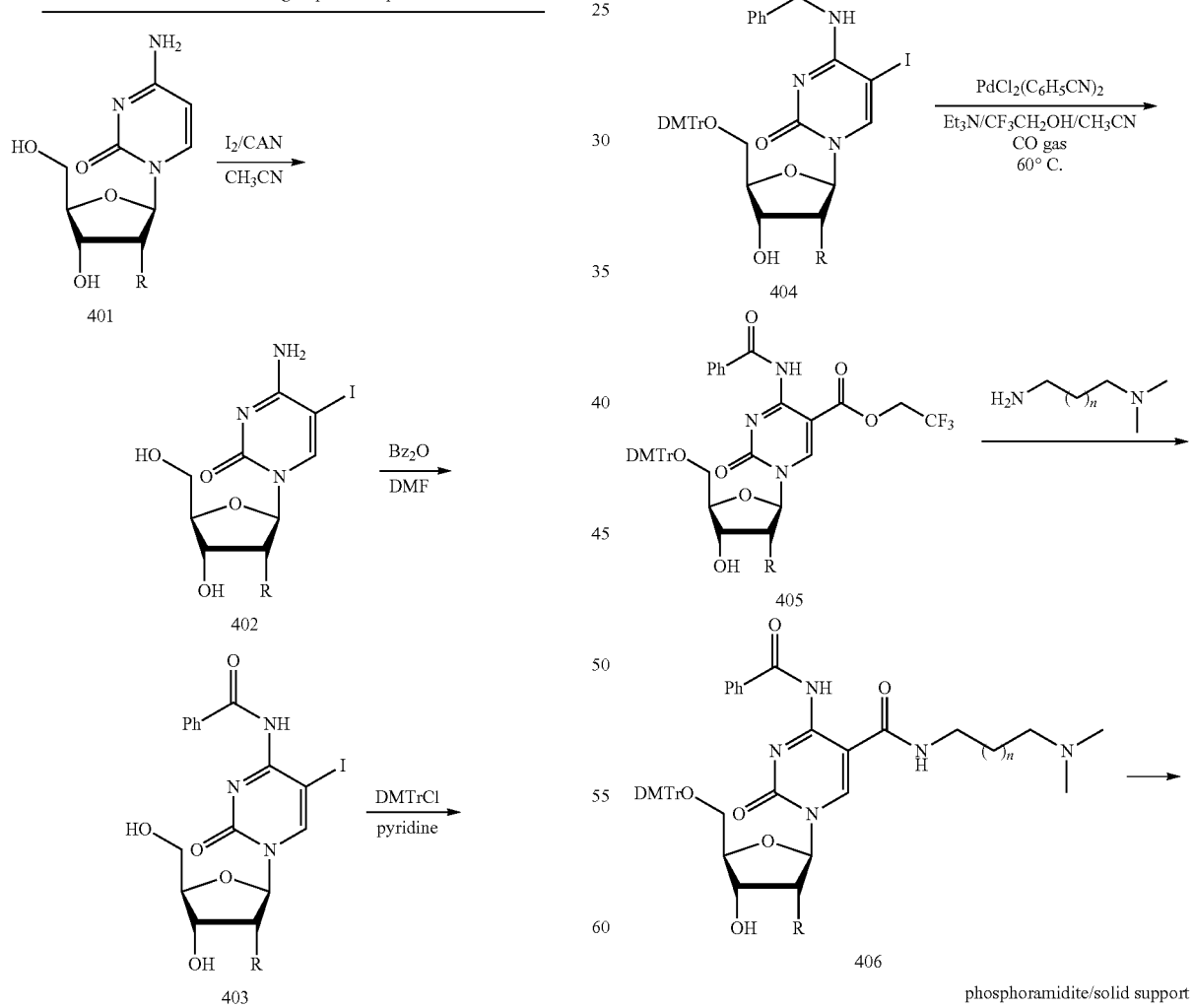
n = 1-9  R = H, OH, OTBS, OMe, F, OCH$_2$CH$_2$OCH$_3$, etc.

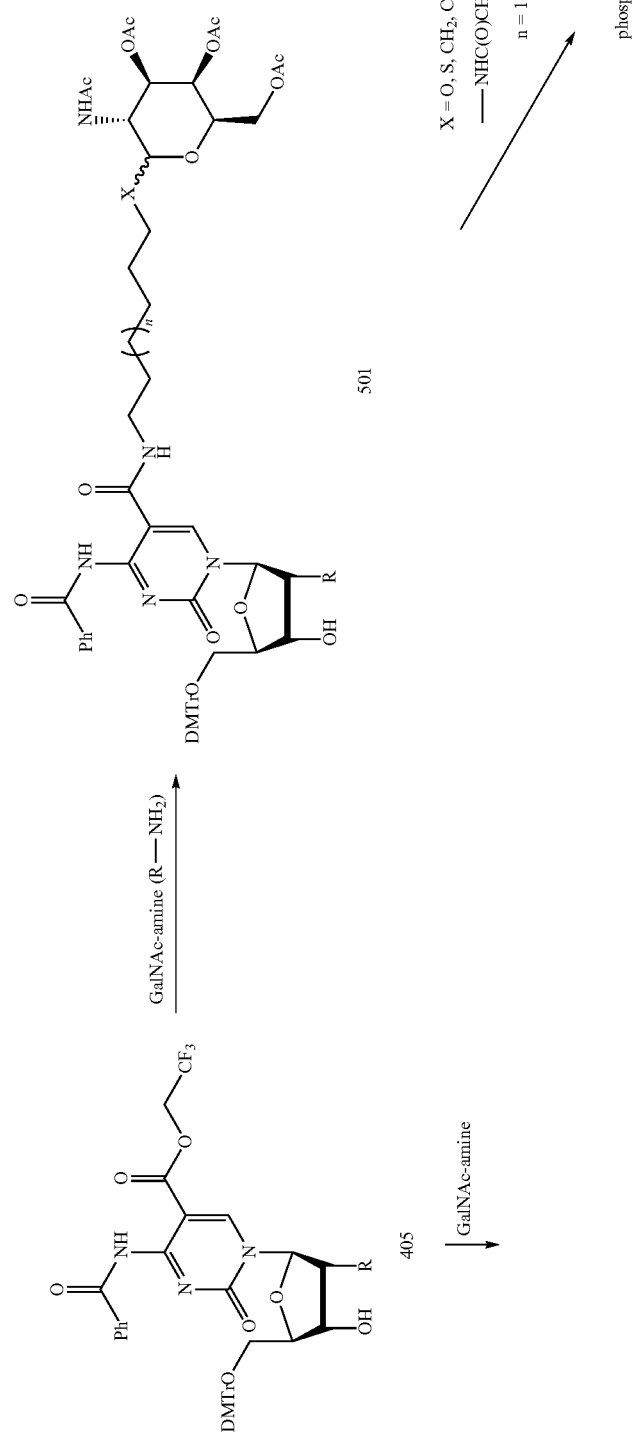

-continued
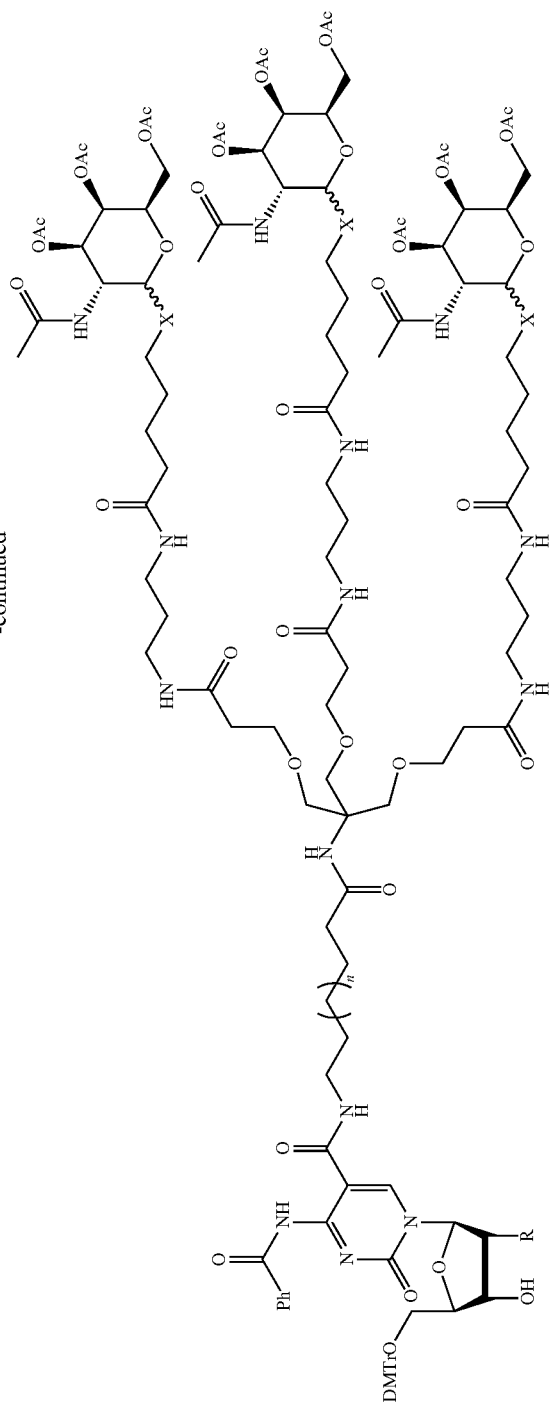
R = H, OH, OTBS, OMe, F, OCH₂CH₂OCH₃, etc.
n = 1-17
502
phosphoramidite/solid support →

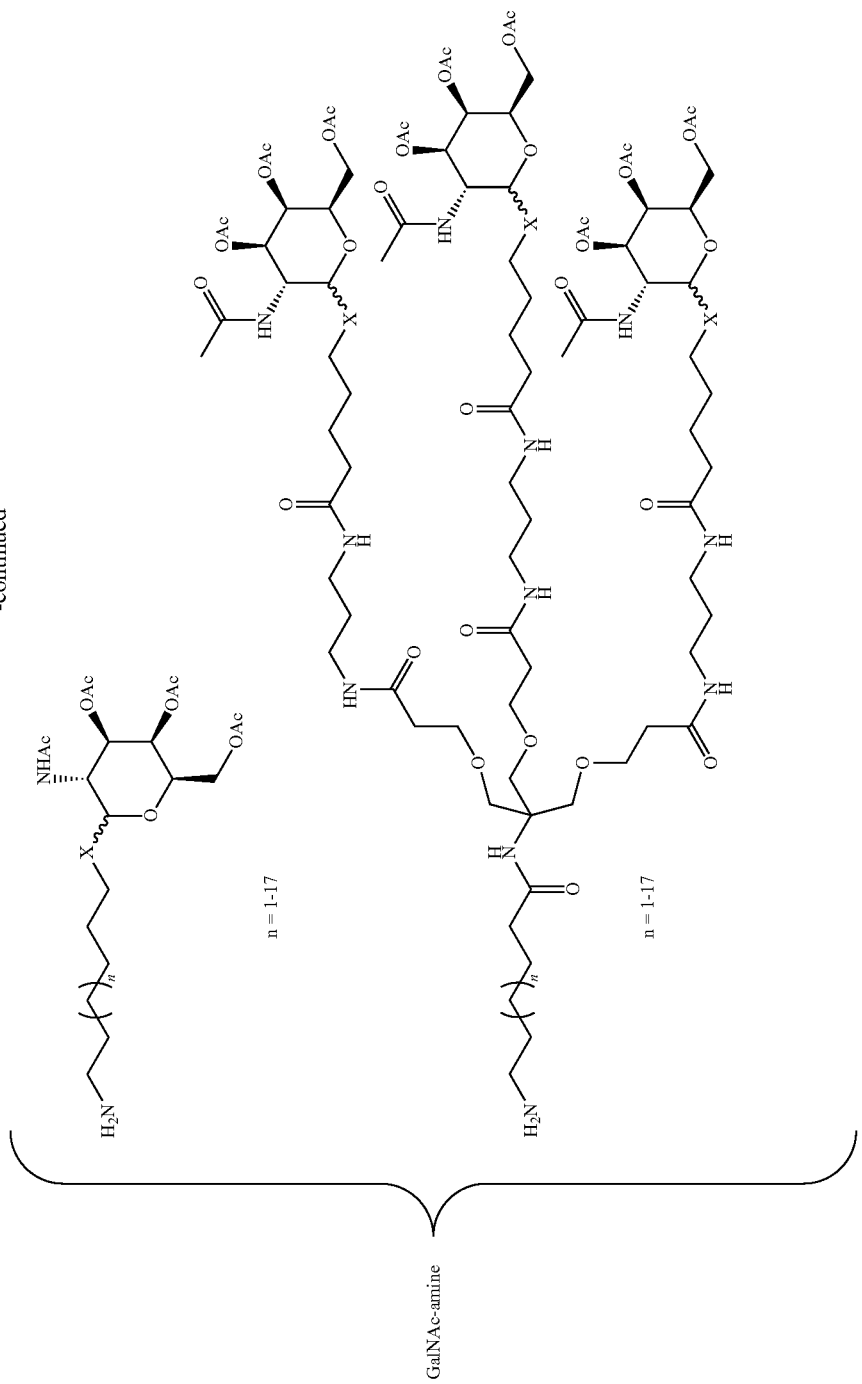

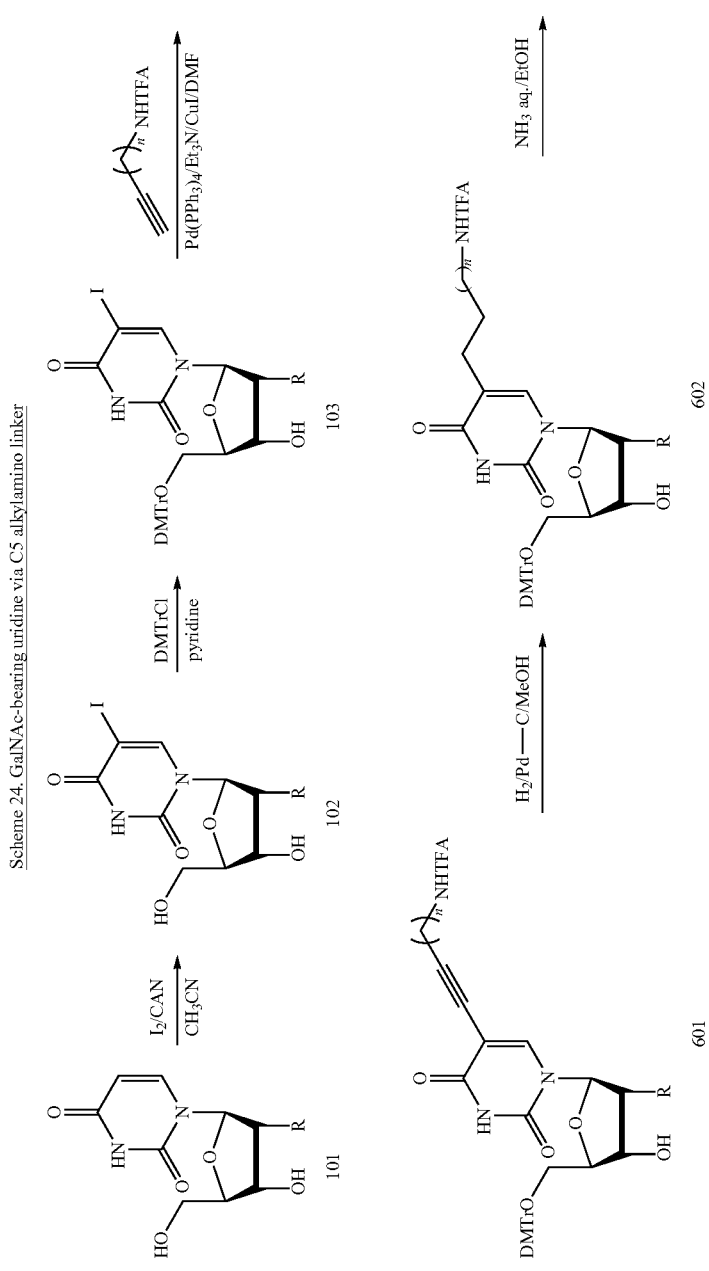

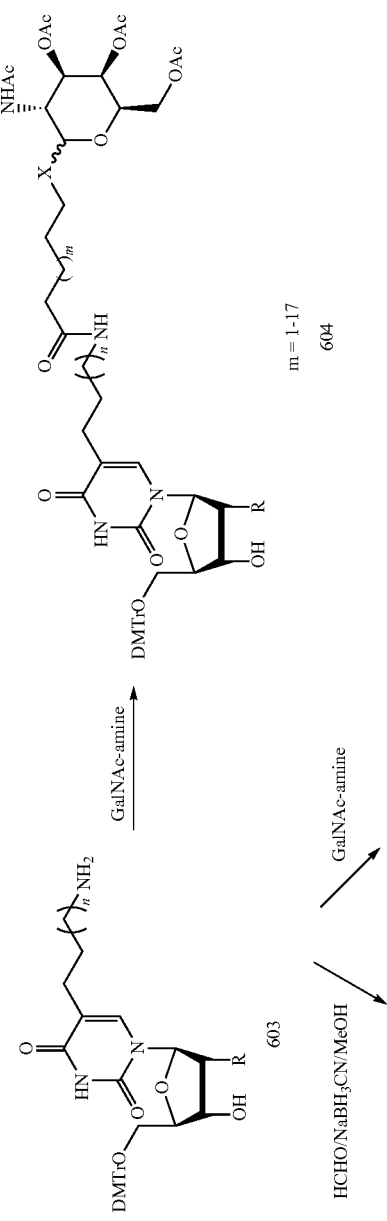
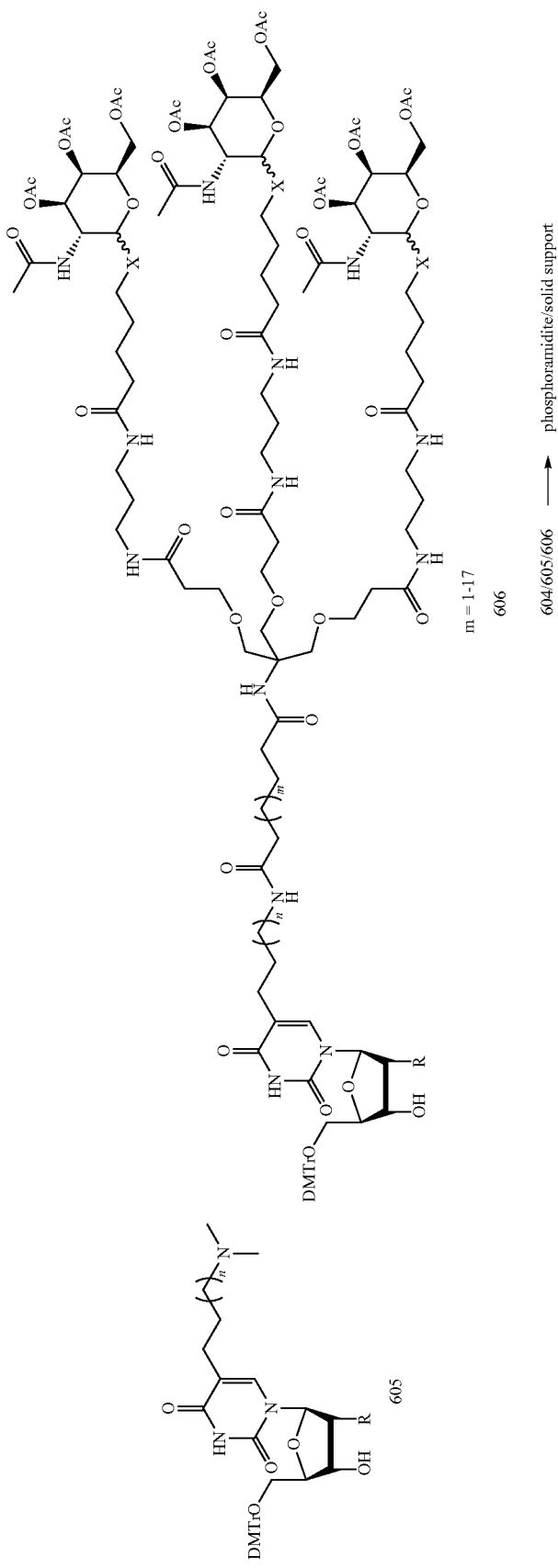

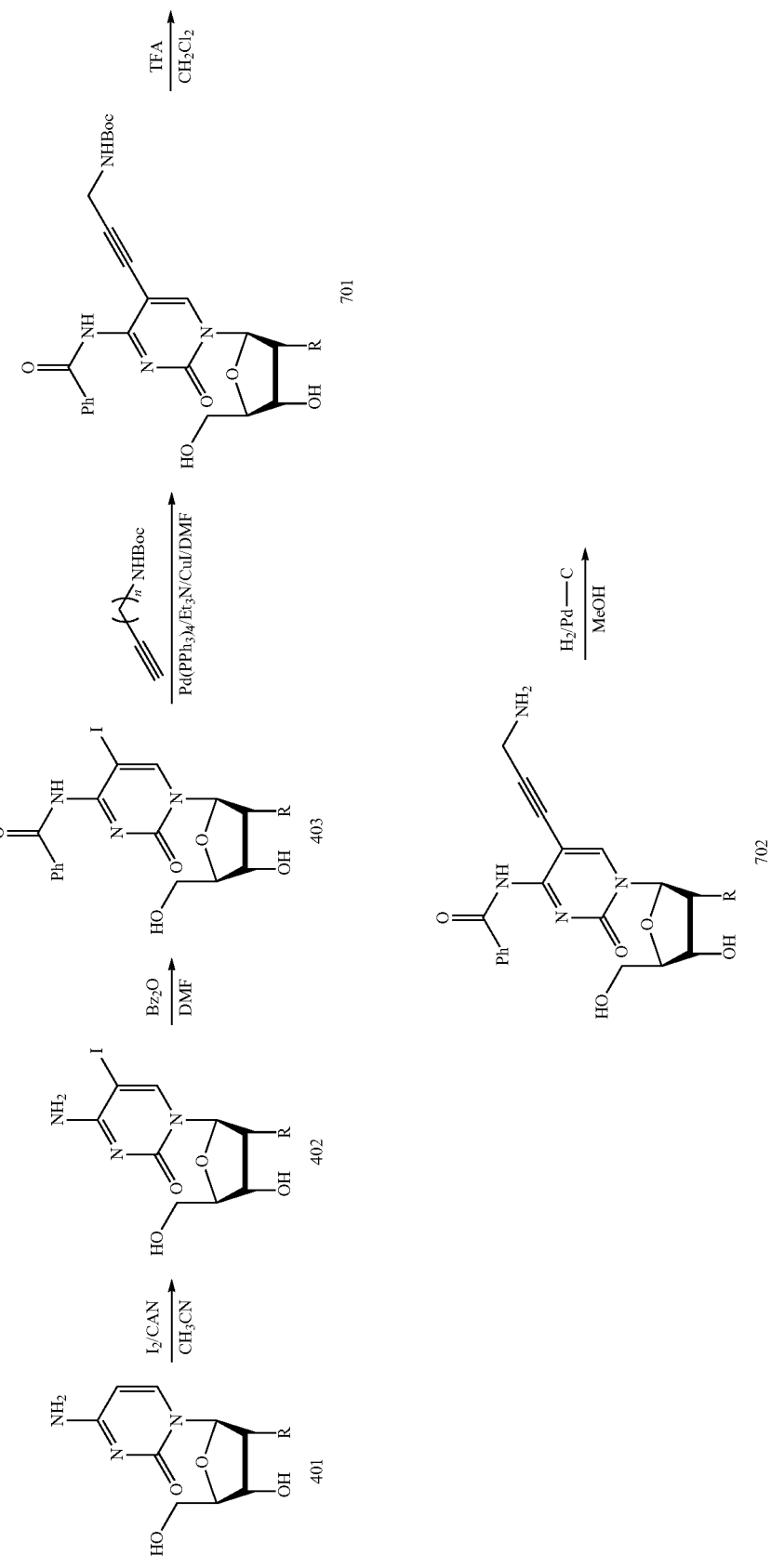

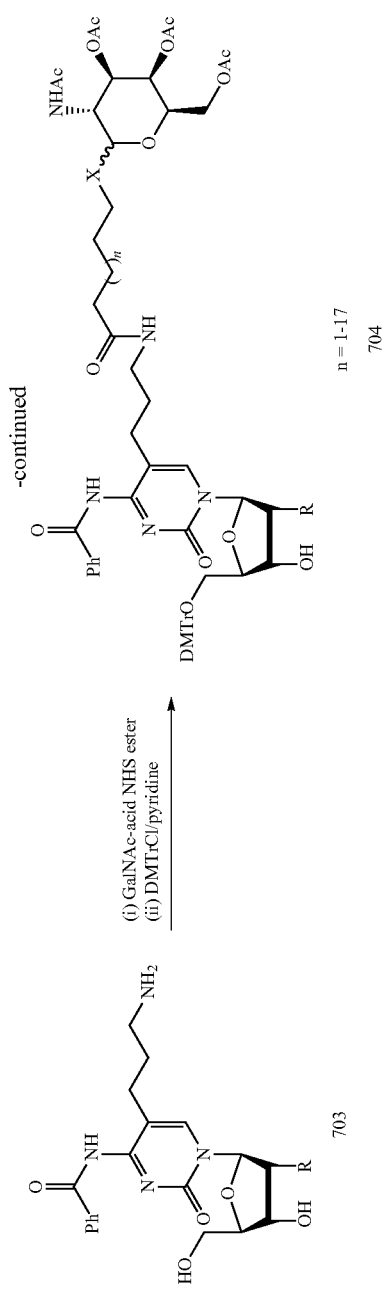
704/705/706 → phosphoramidite/solid support
R = H, OH, OTBS, OMe, F, OCH₂CH₂OCH₃, etc. X = O, S, CH₂, NHCO, CONH, NHCOO, etc.

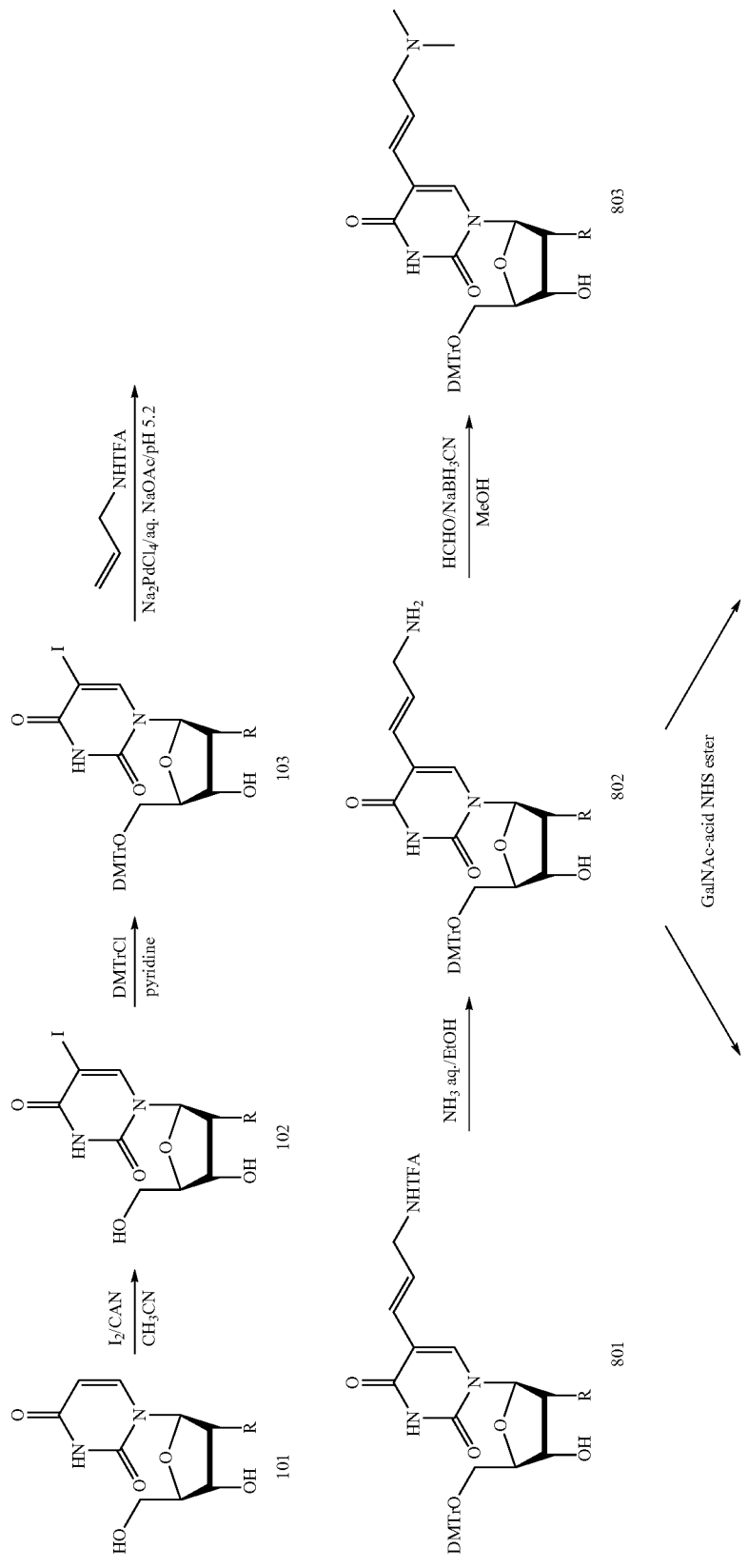

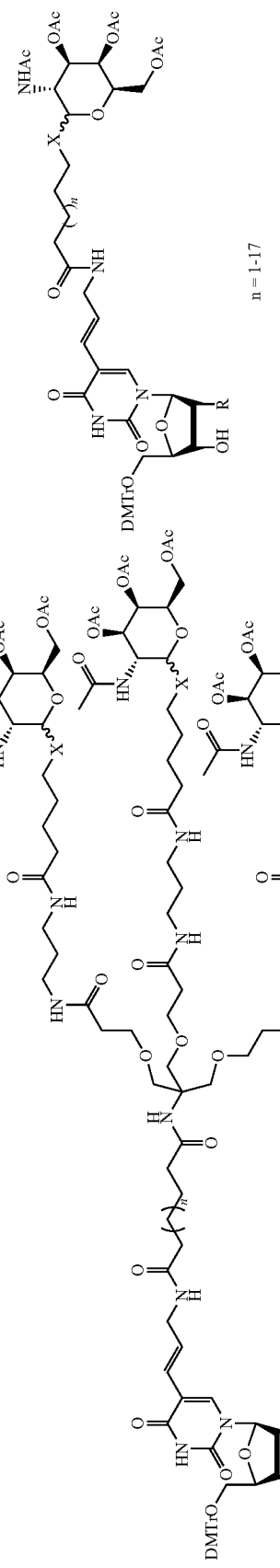

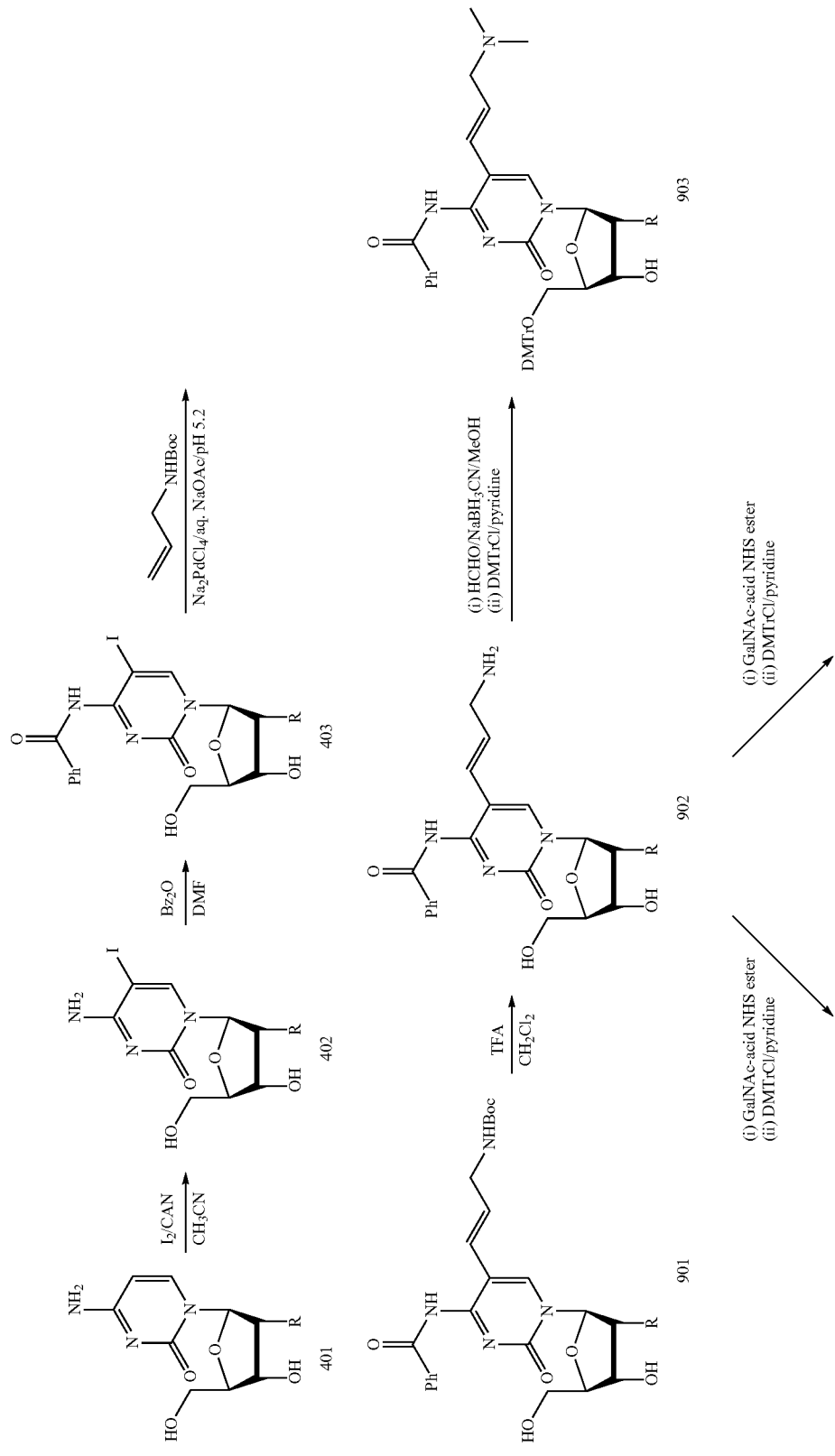

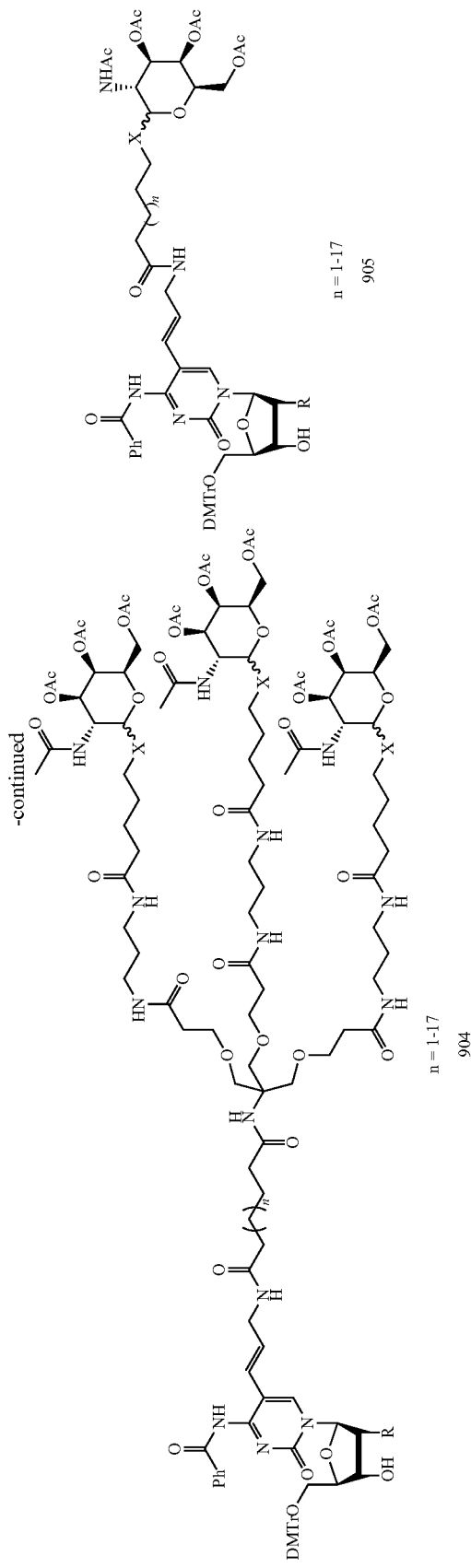

Scheme 28. Adenosine analogs bearings GalNAc targeting lignads
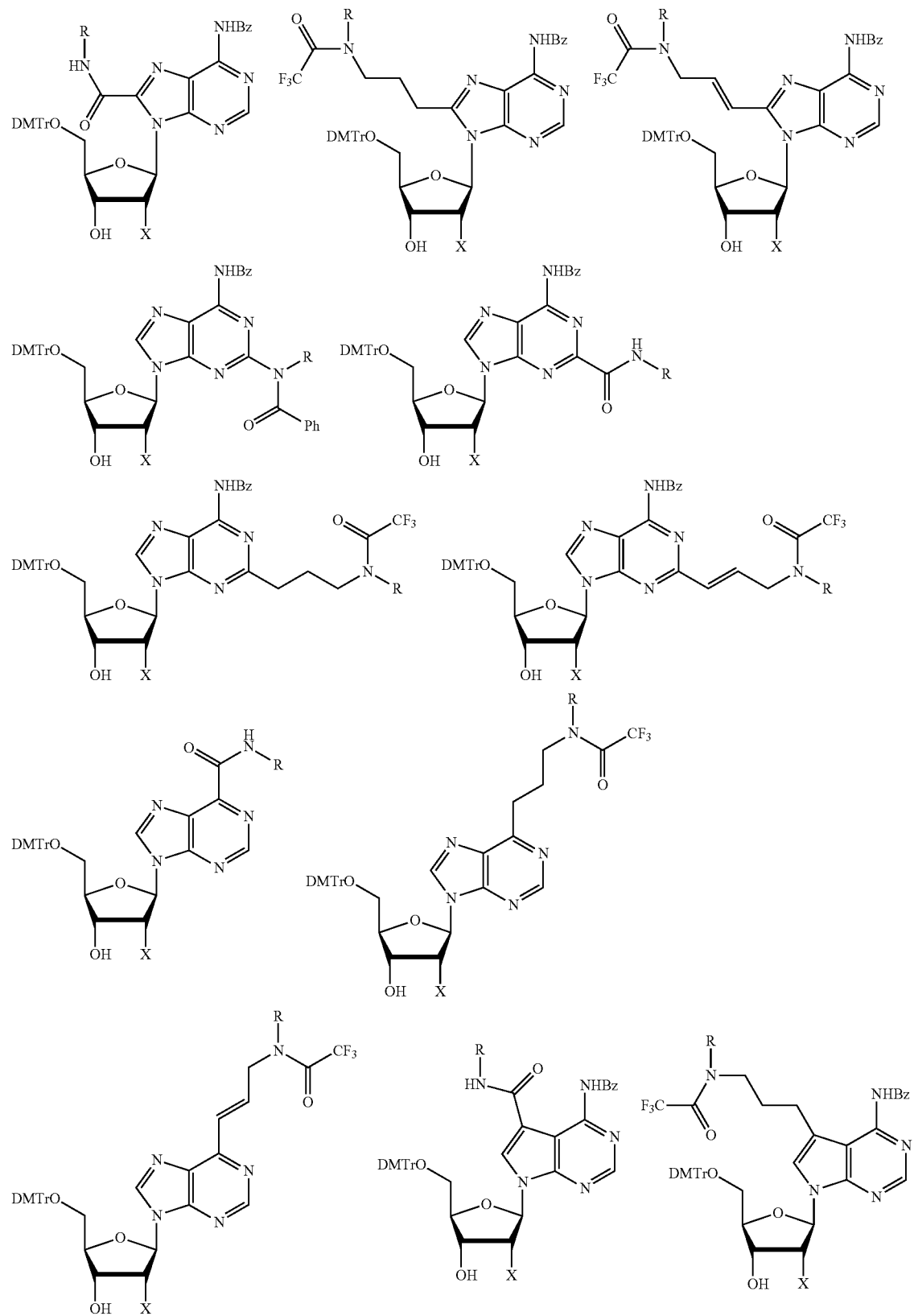

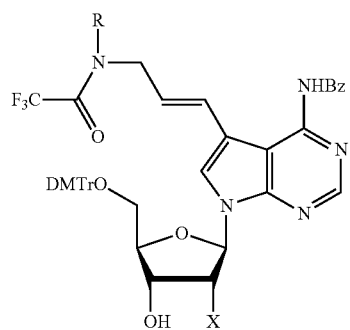
X = H, OH, OTBS, OMe, F, OCH₂CH₂OCH₃, etc.
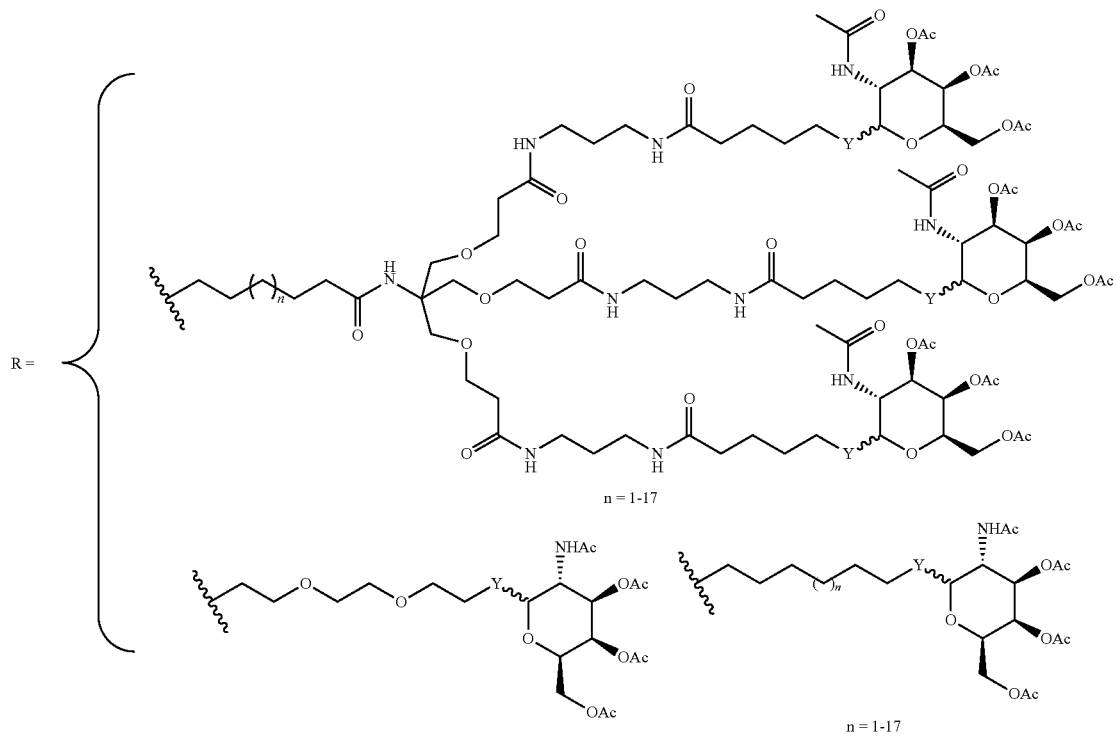
n = 1-17
n = 1-17
Y = O, S, CH₂, NHCO, CONH, NHCOO, etc.
Scheme 29. Guanosine analogs bearing GalNAc targeting lignads
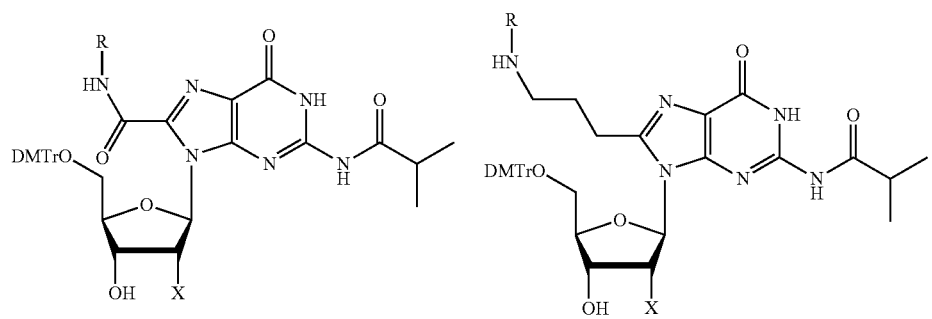

-continued
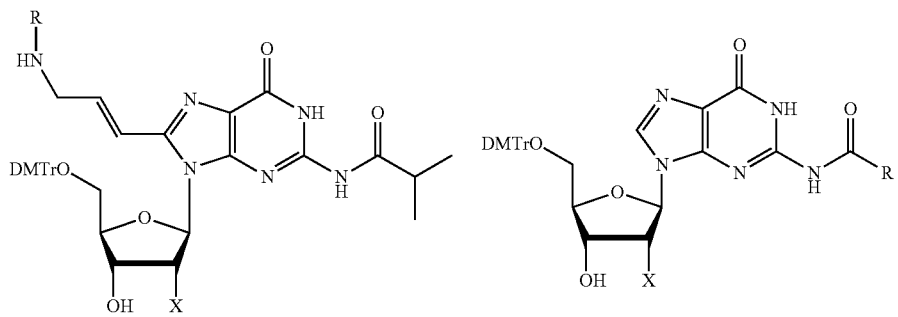
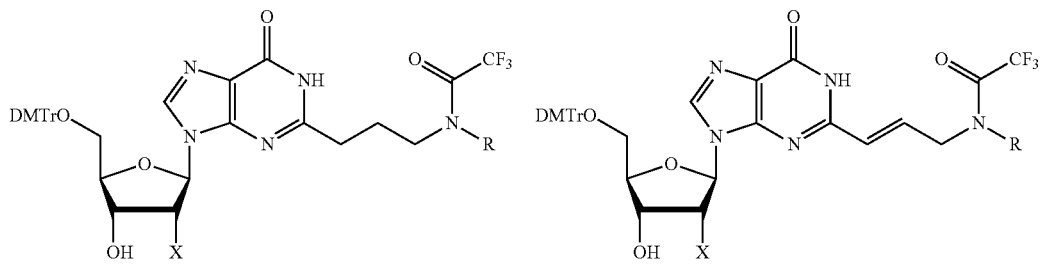
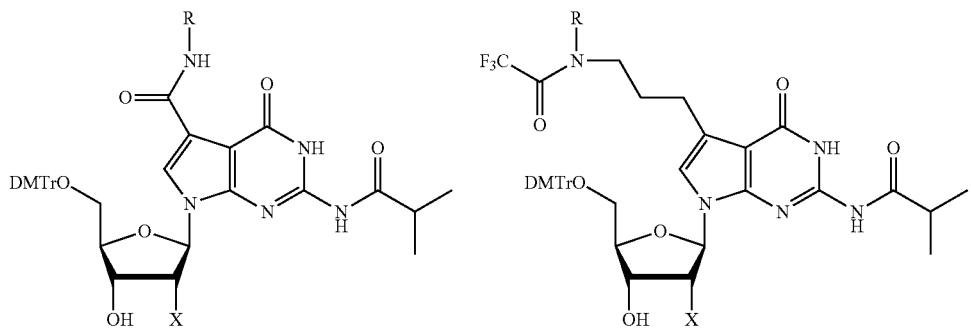
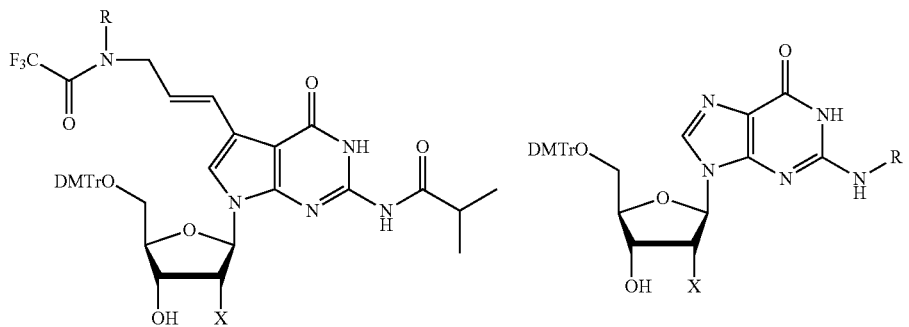

-continued
X = H, OH, OTBS, OMe, F, OCH₂CH₂OCH₃, etc.
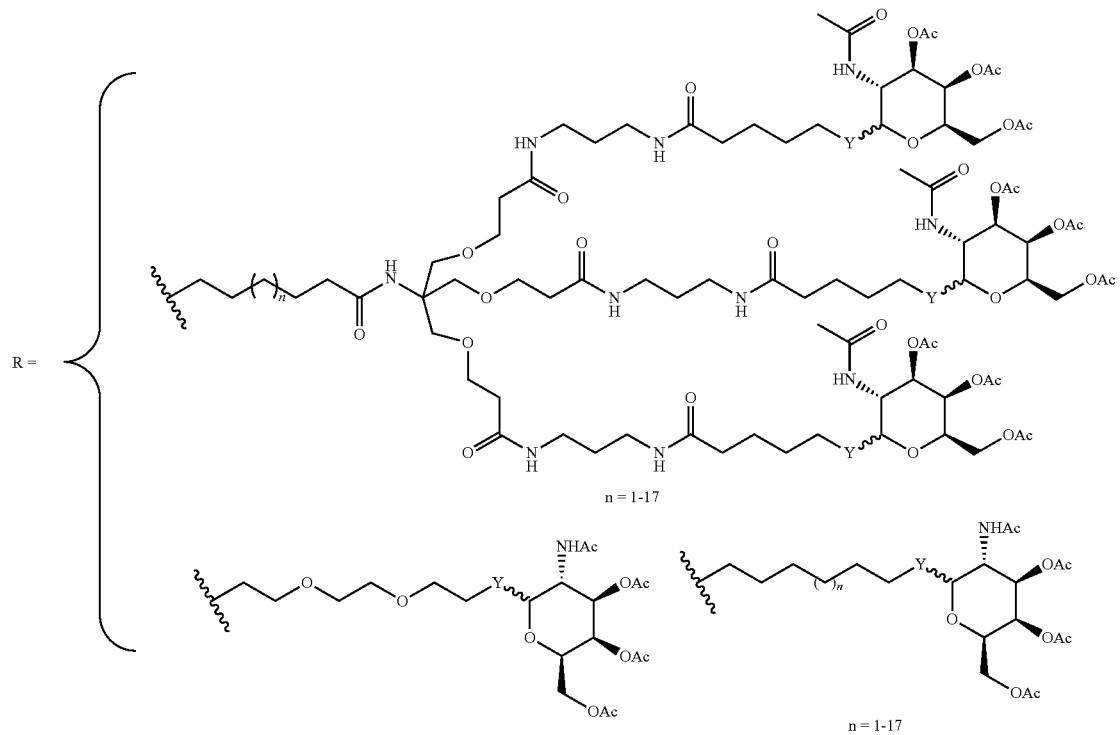
n = 1-17
Y = O, S, CH₂, NHCO, CONH, NHCOO, etc.

Scheme 30. Synthesis of GalNAc ligand at abasic site
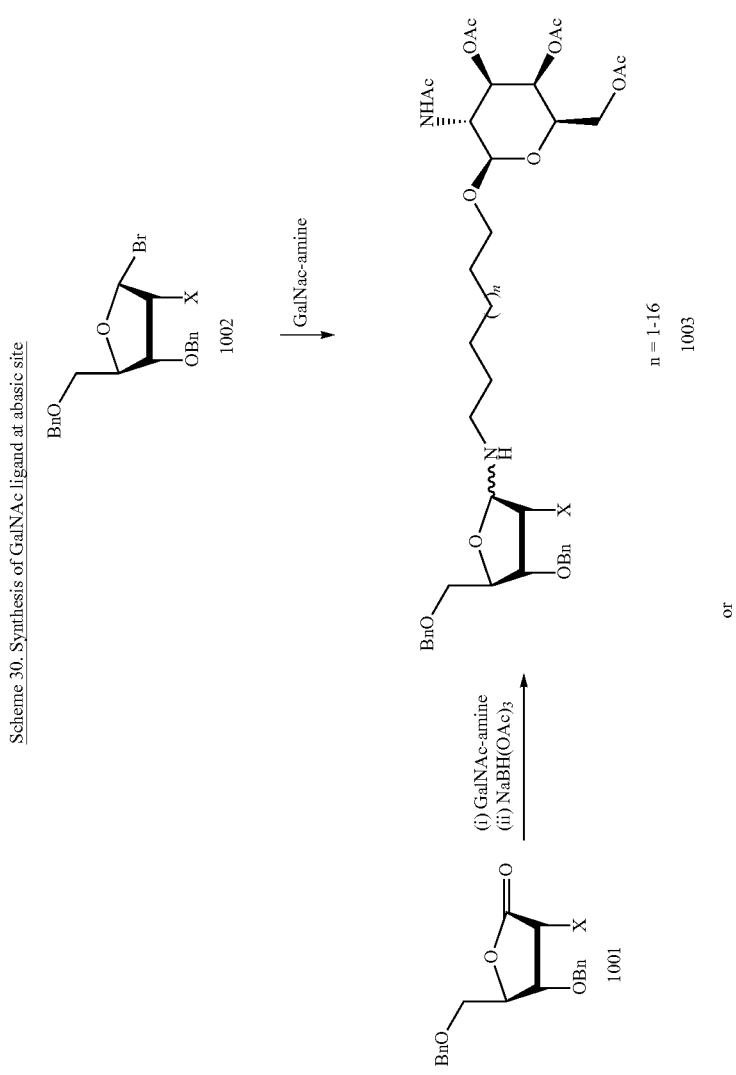

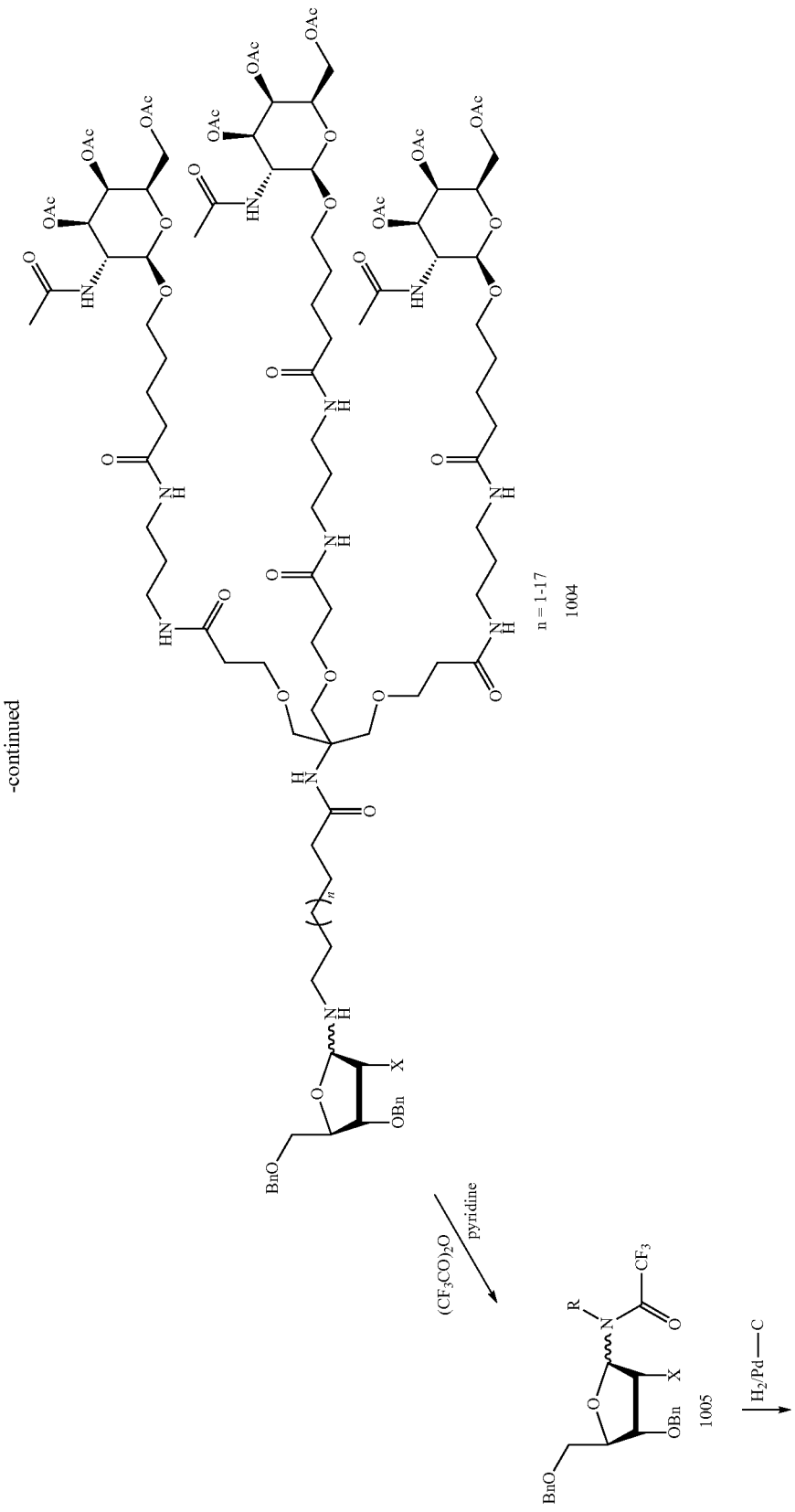

-continued
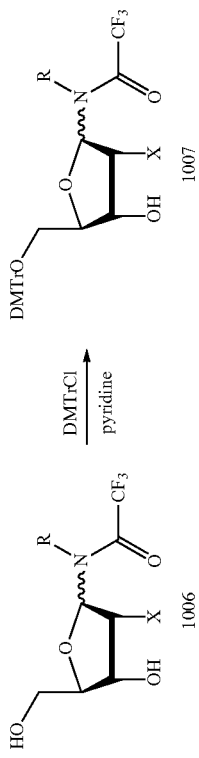
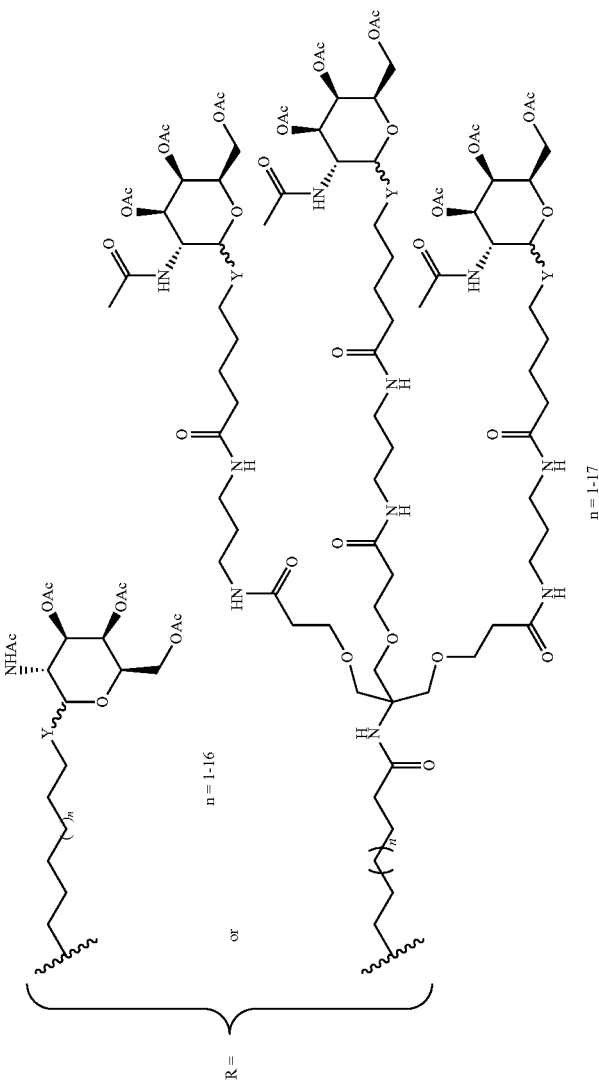
X = H, OH, OTBS, OMe, F, OCH$_2$CH$_2$OCH$_3$, etc. Y = O, S, CH$_2$, NHCO, CONH, NHCOO, etc.

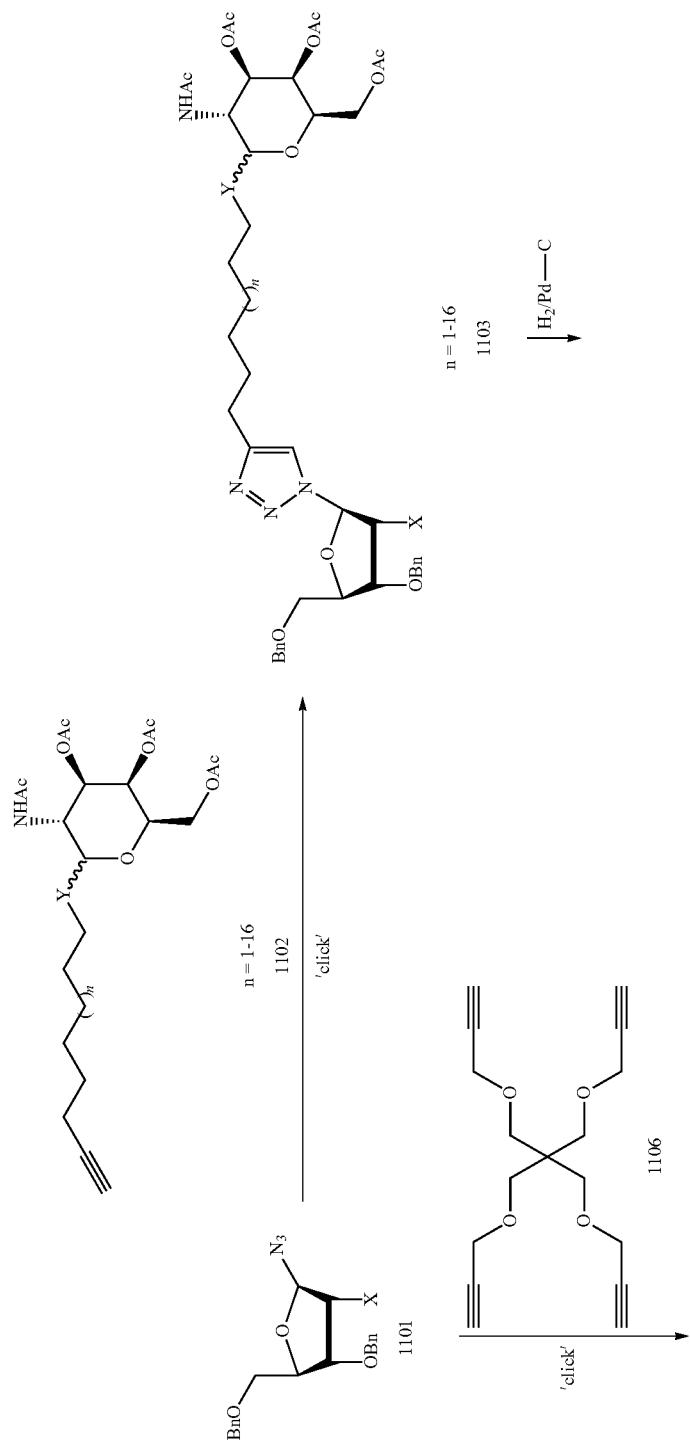
Scheme 31. Synthesis of GalNAc ligand at abasic site by click reaction -continued
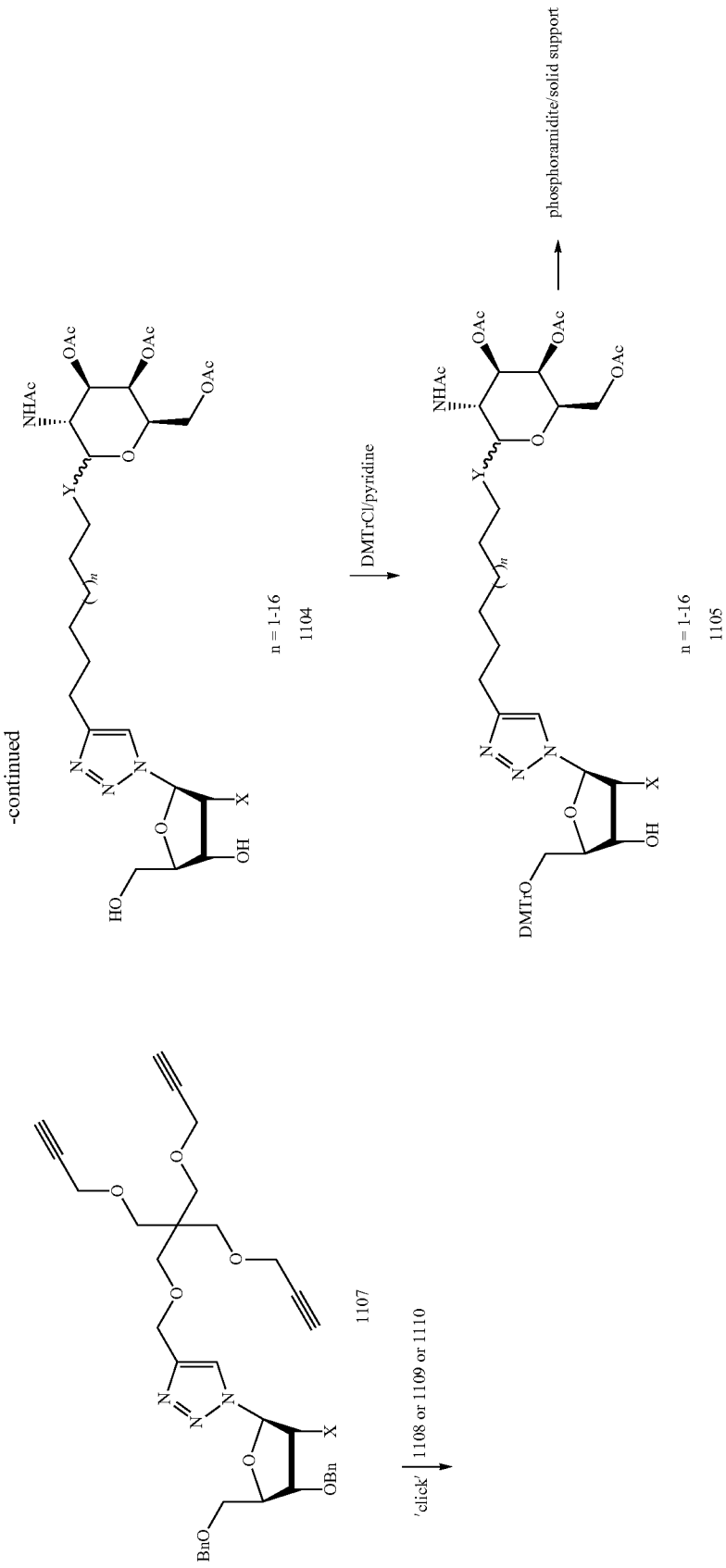

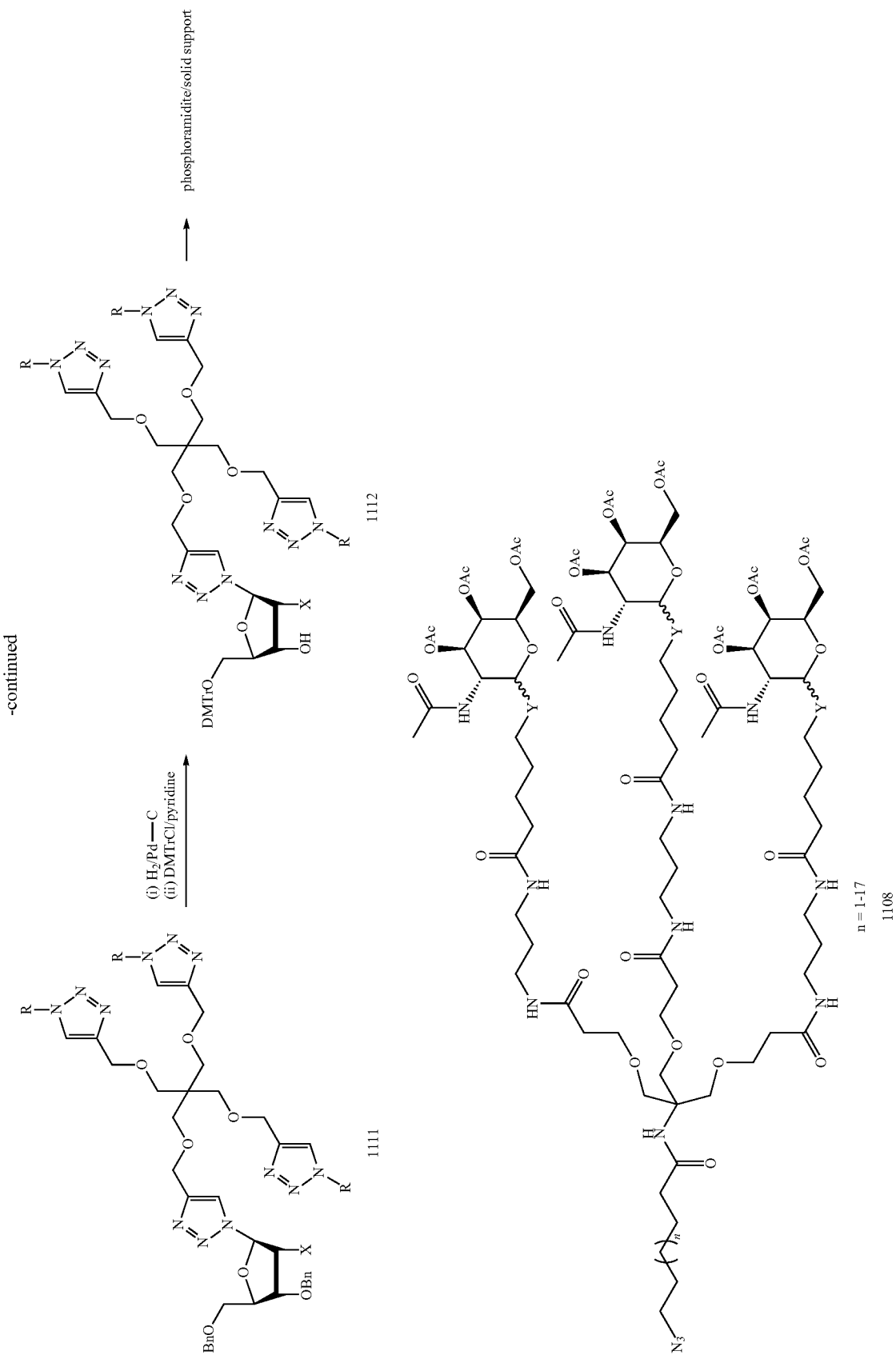

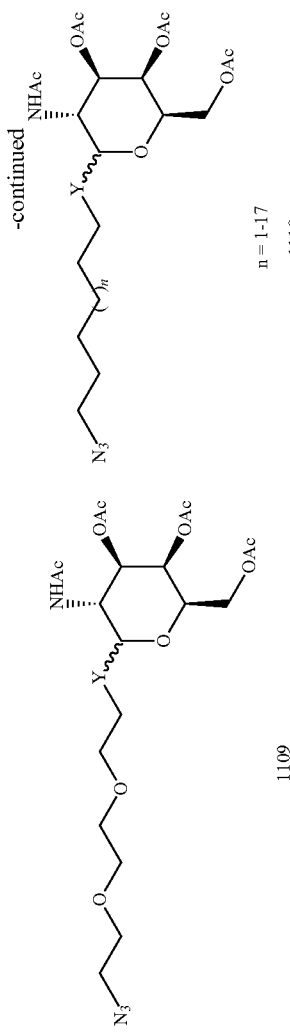

Scheme 32. Synthesis of GalNAc ligand at abasic site by click reaction-2
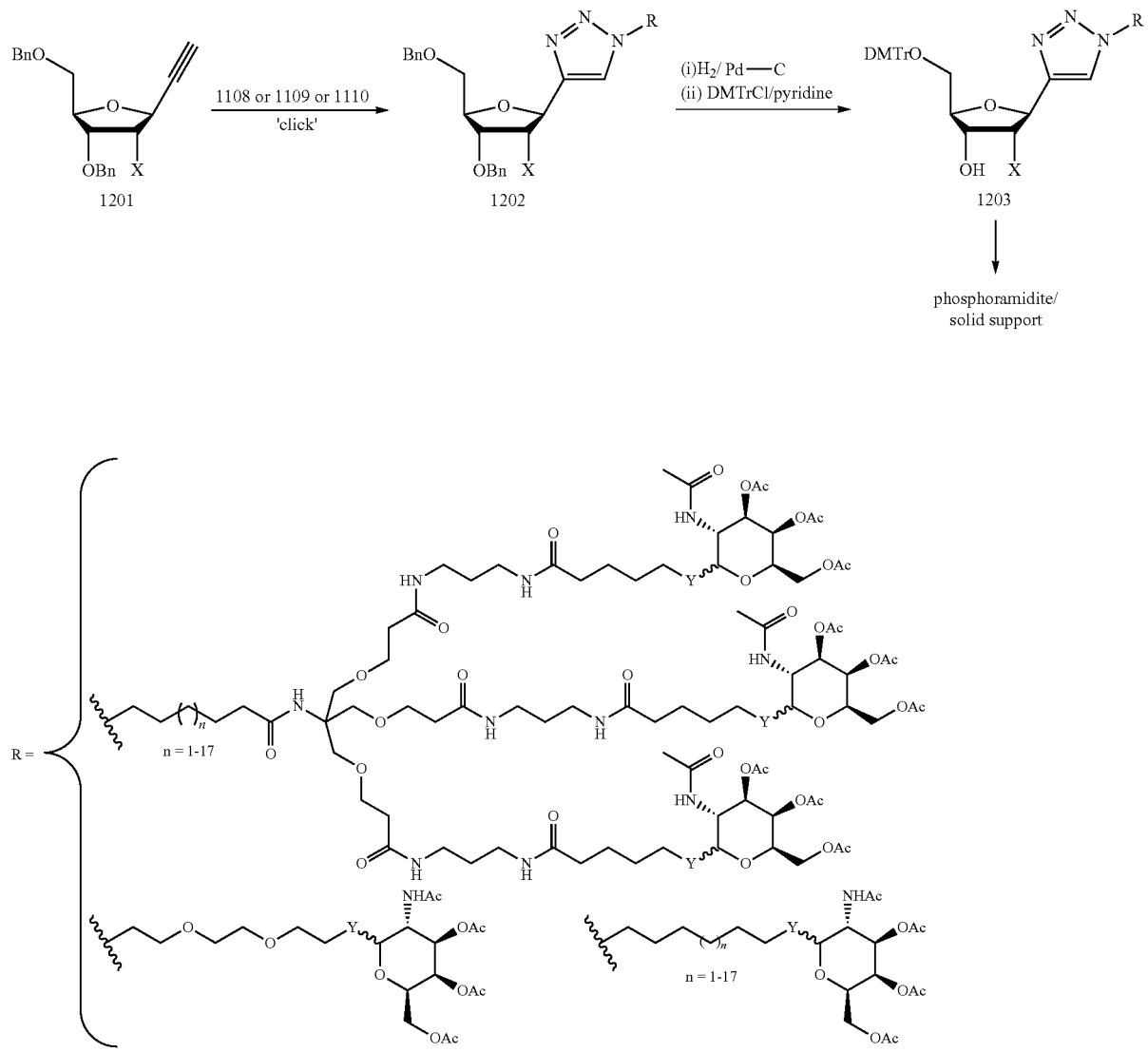
X = H, OH, OTBS, OMe, F, OCH$_2$CH$_2$OCH$_3$, etc.
Y = O, S, CH$_2$, NHCO, CONH, NHCOO, etc.
Scheme 33. Incorporation of GalNAc-amine to C-2 position on purine
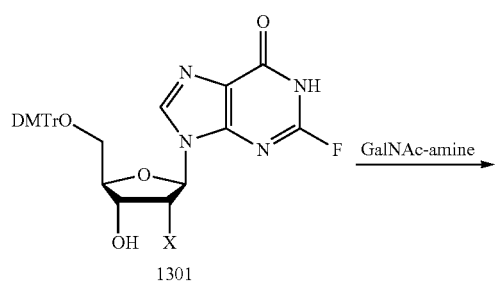

-continued
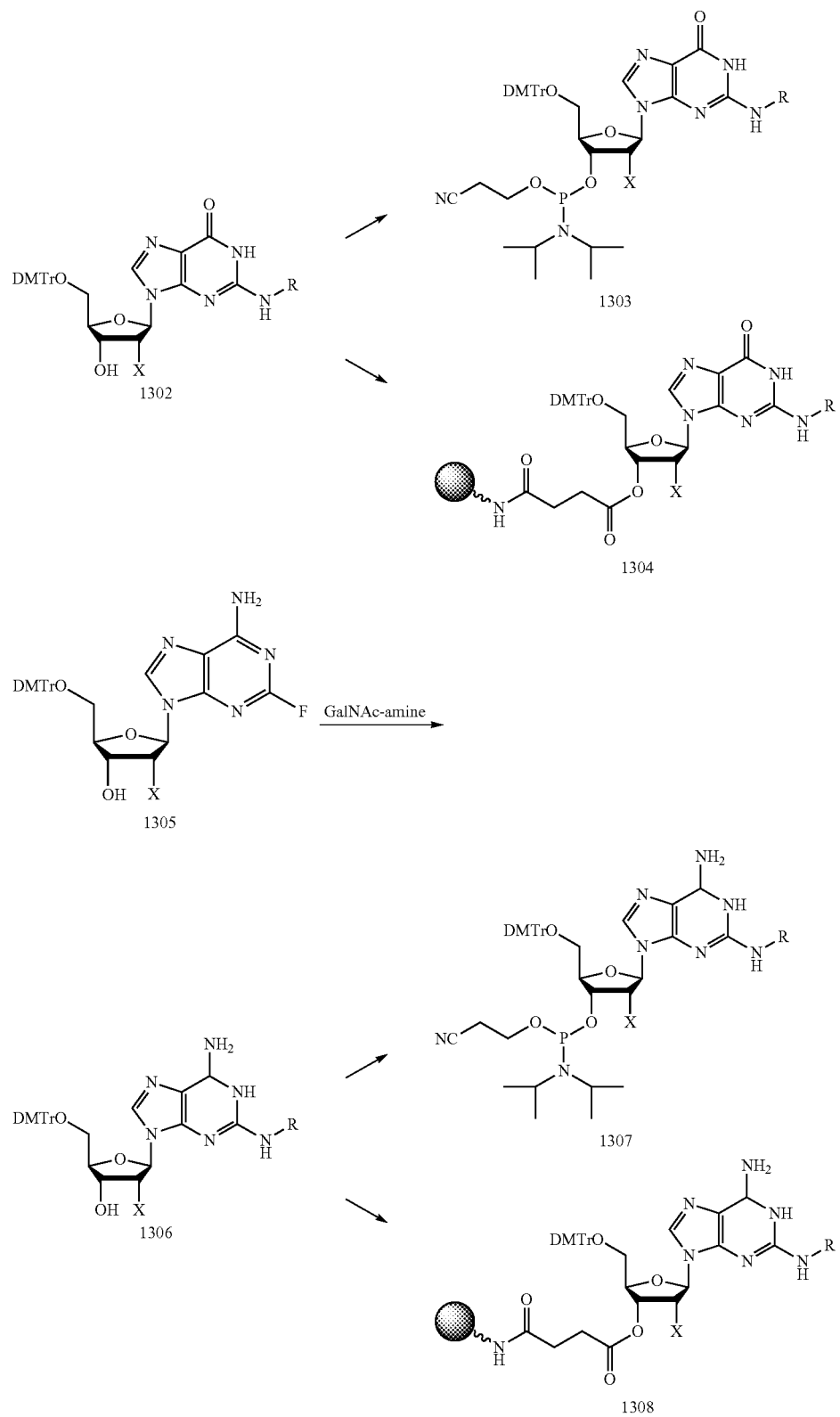

Post-synthetic modification

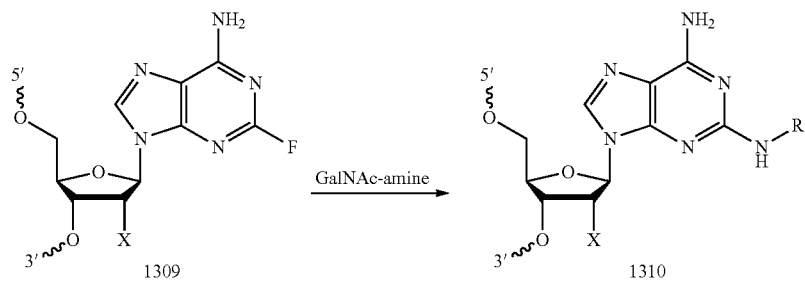

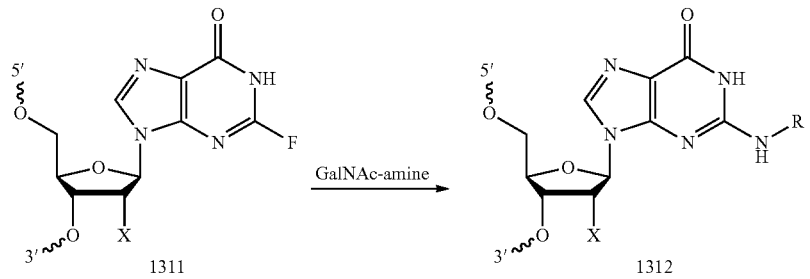

X = H, OH, OTBS, OMe, F, OCH₂CH₂OCH₃, etc.
R² = H, Bz
Y = O, S, CH₂, NHCO, CONH, NHCOO, etc.

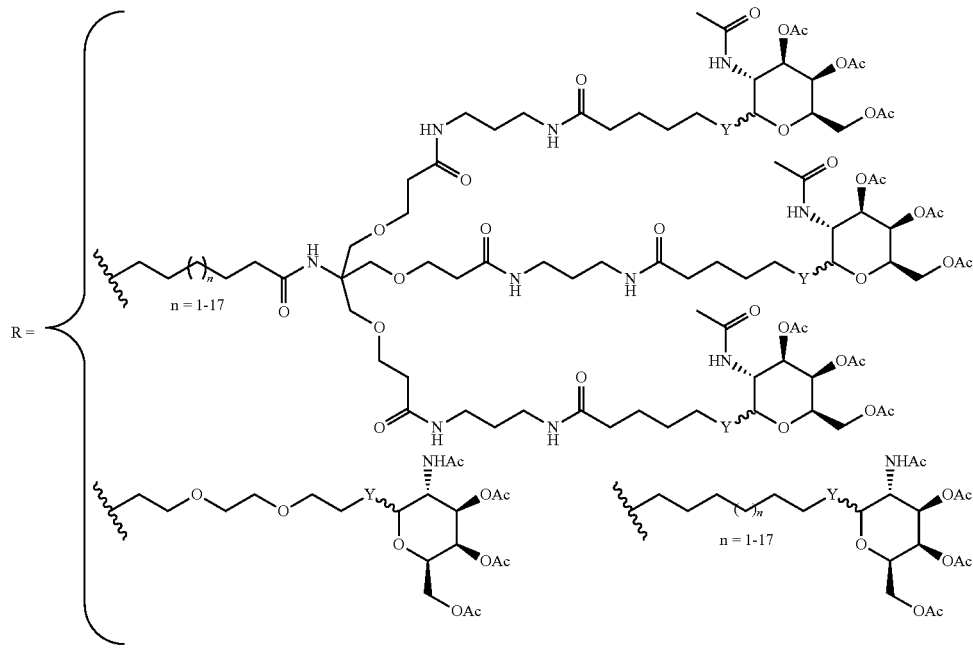

i. Synthesis of Compound 103 (R=F)

To a solution of 102 (R=F; 11.2 g, 30.1 mmol; Antiviral Chemistry & Chemotherapy, 2010, 21, 15-31) in pyridine (70 mL), was added DMTrCl (11.2 g, 32.1 mmol). The reaction mixture was stirred at room temperature for 14 hours and then evaporated. The residue was extracted with CH₂Cl₂ and saturated NaHCO₃ aq. and dried over anhydrous Na₂SO₄. The crude was purified by silica gel column chromatography (5% MeOH in CH₂Cl₂, R$_f$=0.23) to give compound 103 (17.8 g, 26.4 mmol, 88%). ¹H NMR (DMSO-d₆, 400 MHz): δ 11.81 (s, 1H), 8.07 (s, 1H), 7.46-7.14 (m, 10H), 6.88 (dd, J=8.9, 1.8 Hz, 4H), 5.83 (d, J=20.5 Hz, 1H), 5.60 (d, J=7.0 Hz, 1H), 5.16 (dd, J=53.4, 4.8 Hz, 1H), 4.43-4.20 (m, 1H), 4.08-3.90 (m, 1H), 3.74 (s, 7H), 3.23 (d, J=2.7 Hz, 2H). ¹³C NMR (100 MHz, DMSO-d₆): δ 160.68, 158.09, 158.07, 149.89, 145.13, 144.72, 136.12, 135.46, 135.37, 129.71, 127.93, 127.67, 126.70, 123.90, 85.61, 81.30, 69.75, 62.47, 55.06, 55.03.

ii. Synthesis of Compound 104 (R=F)

To a solution of compound 103 (R=F; 6.40 g, 9.49 mmol) in CH₃CN (75 mL) were added PdCl₂ (PhCN)₂ (73 mg, 0.190 mmol), Et₃N (2.65 mL, 19.0 mmol) and CF₃CH₂OH (6.91 mL, 94.9 mmol). The mixture was stirred at 60° C. under CO gas atmosphere. After evaporation, the residue was extracted with CH₂Cl₂ and saturated aqueous NaHCO$_3$. The organic layer was separate and dried over anhydrous Na$_2$SO$_4$. The filtrate was concentrated and the resulting crude material was purified by silica gel column chromatography (0-5% MeOH in CH$_2$Cl$_2$) to give 104 (4.30 g, 6.37 mmol, 67%, R$_f$=0.32 developed by 5% MeOH in CH$_2$Cl$_2$). $^1$H NMR (400 MHz, DMSO-d$_6$): δ 11.78 (s, 1H), 8.52 (s, 1H), 7.41 (d, J=7.4 Hz, 2H), 7.34-7.16 (m, 8H), 6.93-6.80 (m, 4H), 5.90 (d, J=20.1 Hz, 1H), 5.63 (d, J=7.1 Hz, 1H), 5.26 (d, J=4.4 Hz, 1H), 5.12 (d, J=4.5 Hz, 1H), 4.50-4.17 (m, 3H), 4.07 (dd, J=7.3, 5.0 Hz, 1H), 3.73 (d, J=1.2 Hz, 7H), 3.31-3.17 (m, 2H). $^{13}$C NMR (100 MHz, DMSO-d$_6$): δ 160.70, 158.96, 158.08, 158.06, 149.18, 148.89, 144.76, 135.47, 135.33, 129.70, 129.66, 127.80, 127.61, 126.66, 124.62, 121.86, 102.57, 94.10, 92.27, 90.68, 90.32, 85.56, 81.36, 68.11, 67.95, 62.36, 59.26, 58.91, 54.98. $^{19}$F NMR (376 MHz, DMSO-d$_6$): δ −74.94, −74.96, −74.99, −201.81, −201.86, −201.87, −201.93, −201.95, −202.01, −202.07. Molecular weight for C$_{33}$H$_{30}$F$_4$N$_2$NaO$_9$ (M+Na)$^+$ Calc. 697.1785, Found 697.2.

iii. Synthesis of Compound 105 (R=F)

Compound 104 (R=F; 4.15 g, 6.15 mmol) was treated with 3-(dimethylamino)-1-propylamine (25 mL) at room temperature overnight. The reaction mixture was extracted with CH$_2$Cl$_2$ and saturated aqueous NaHCO$_3$ and the organic layer was dried over anhydrous Na$_2$SO$_4$ to give crude 105. Molecular weight for C$_{36}$H$_{42}$FN$_4$O$_8$(M+H)$^+$ Calc. 677.2987, Found 677.1.

Example 20. GalNAc Conjugation on Ribose Ring (Schemes 34-44)

A synthetic approach to conjugate GalNAc and its derivatives to the ribose rings in nucleosides is shown below. Tin-modified nucleosides can be coupled with alkyl bromides to generate 2'- and 3'-coupled products. Each of the resulting primary amines or activated esters as well as terminal alkenes can be coupled with GalNAc ligands using appropriate reaction conditions. These building blocks are incorporated into oligonucleotides using standard phosphoramidite chemistry. GalNAc ligands can also be conjugated with oligonucleotides by post-synthetic approaches.

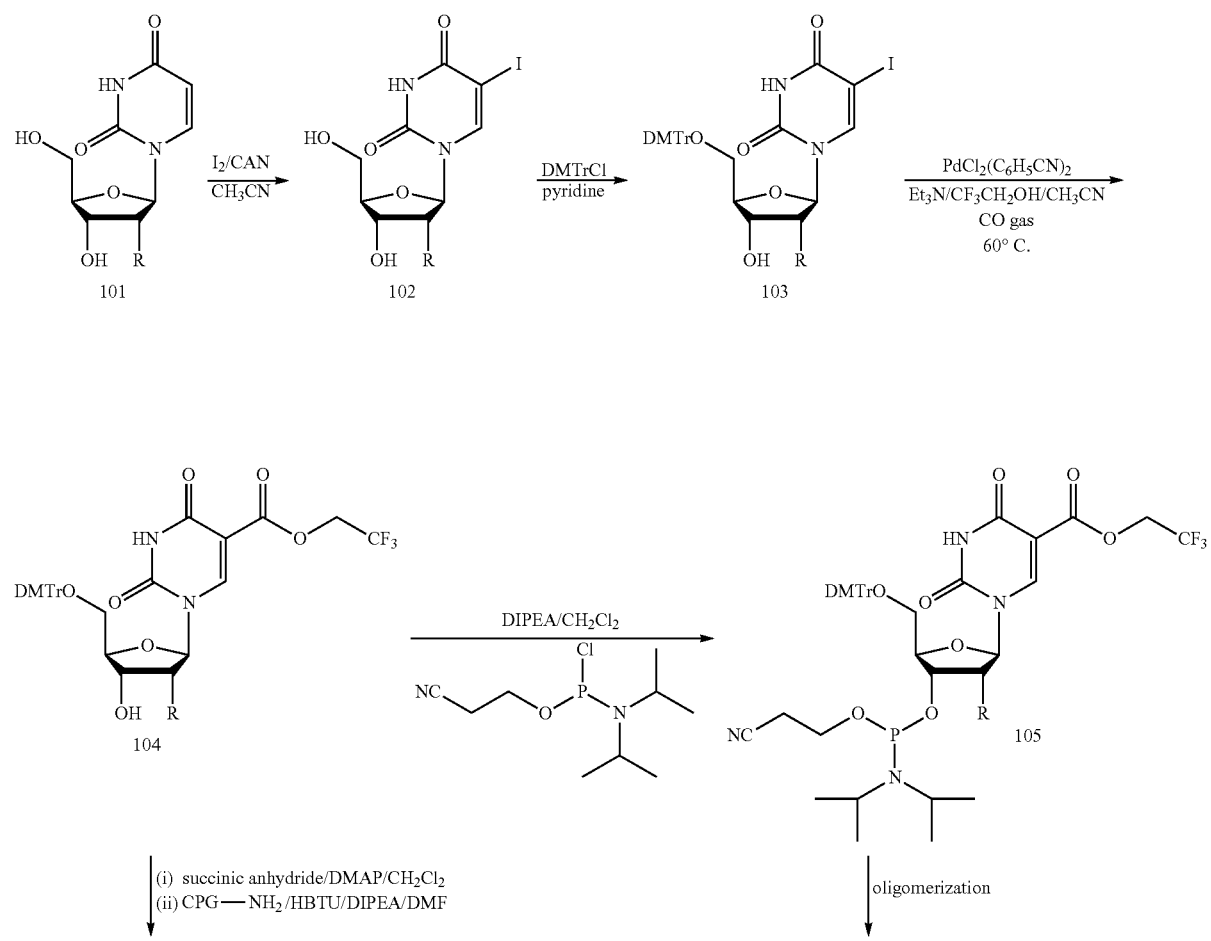

Scheme 34. Synthesis of uridine analogs for post-synthetic conjugation

359 360
-continued
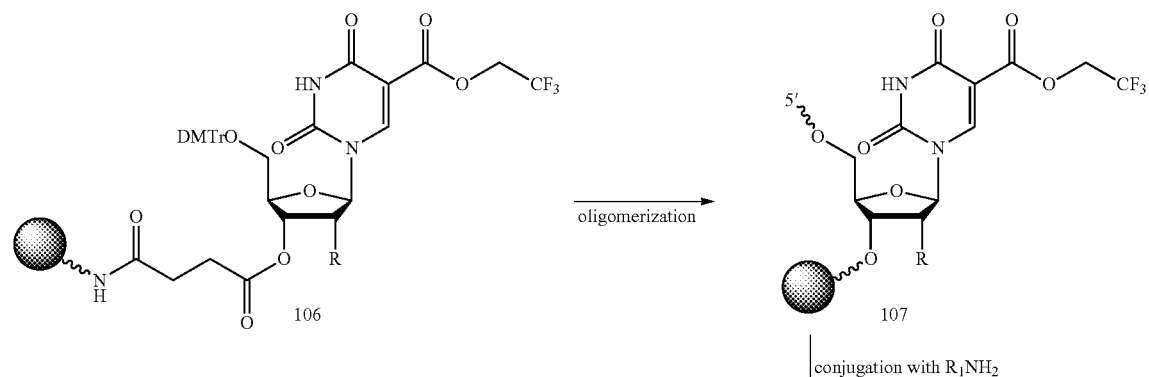
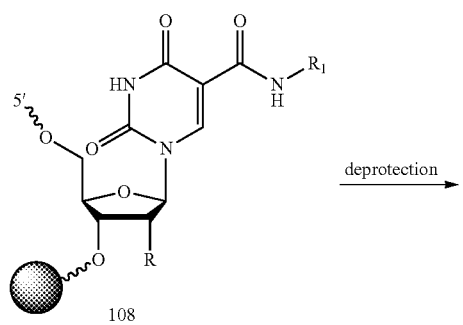
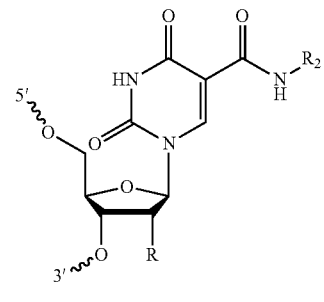
R= H, OH, OTBS, OMe, F, OCH$_2$CH$_2$OCH$_3$, etc.

-continued
R₁ = 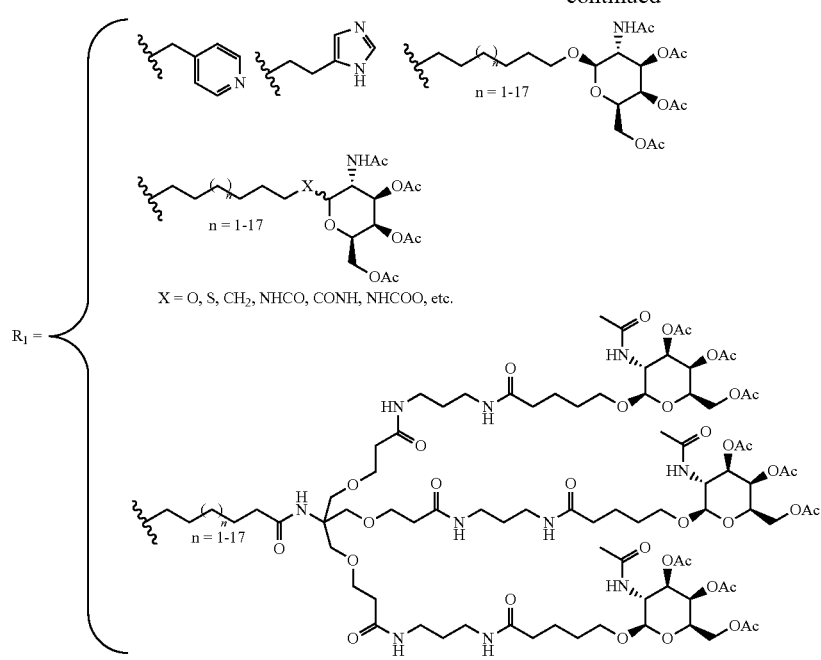
R₂ = 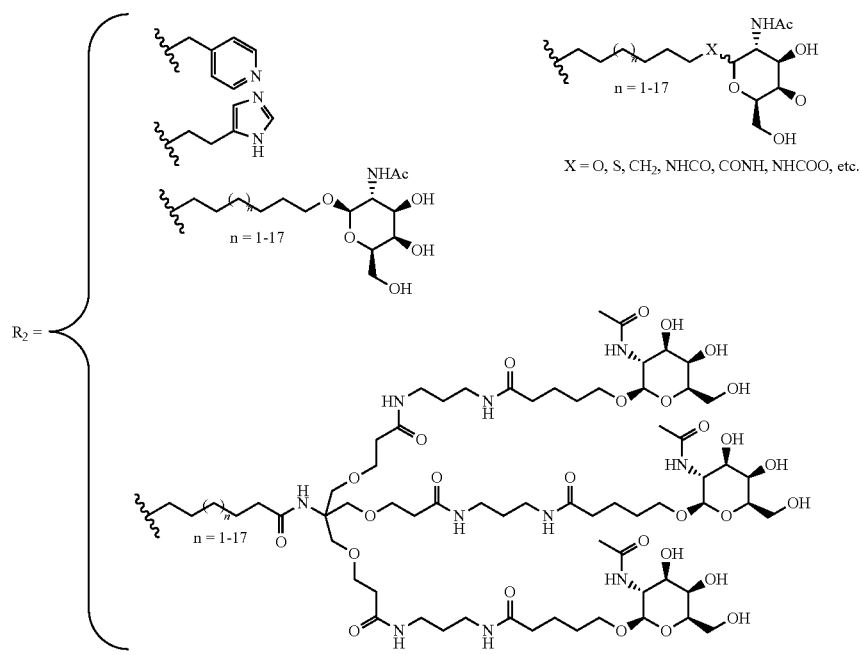

Scheme 35. Synthesis of uridine analogs with GalNAc ligand at C-5 position
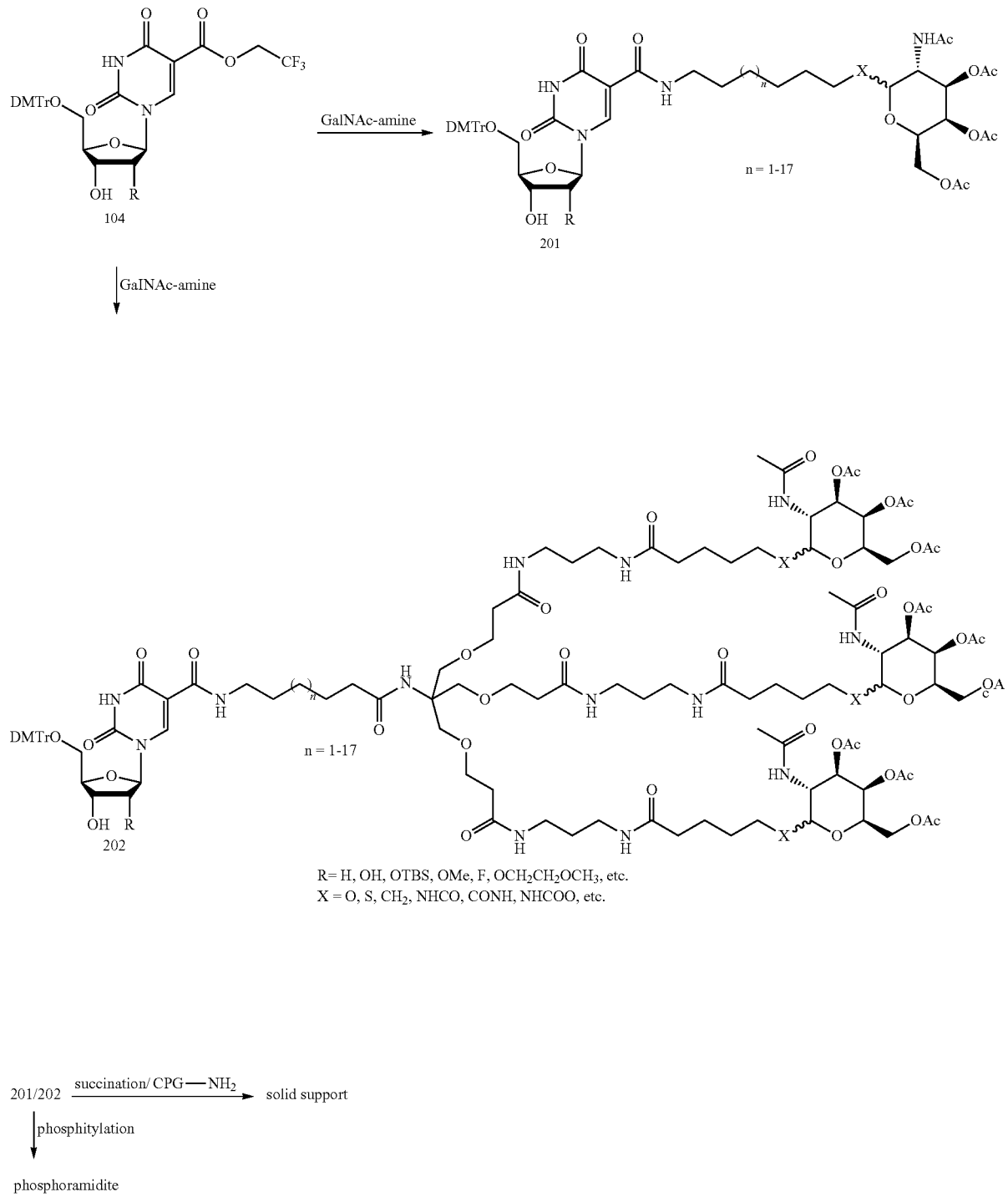
R = H, OH, OTBS, OMe, F, OCH$_2$CH$_2$OCH$_3$, etc.
X = O, S, CH$_2$, NHCO, CONH, NHCOO, etc.
201/202 $\xrightarrow{\text{succination/CPG-NH}_2}$ solid support
↓ phosphitylation
phosphoramidite -continued
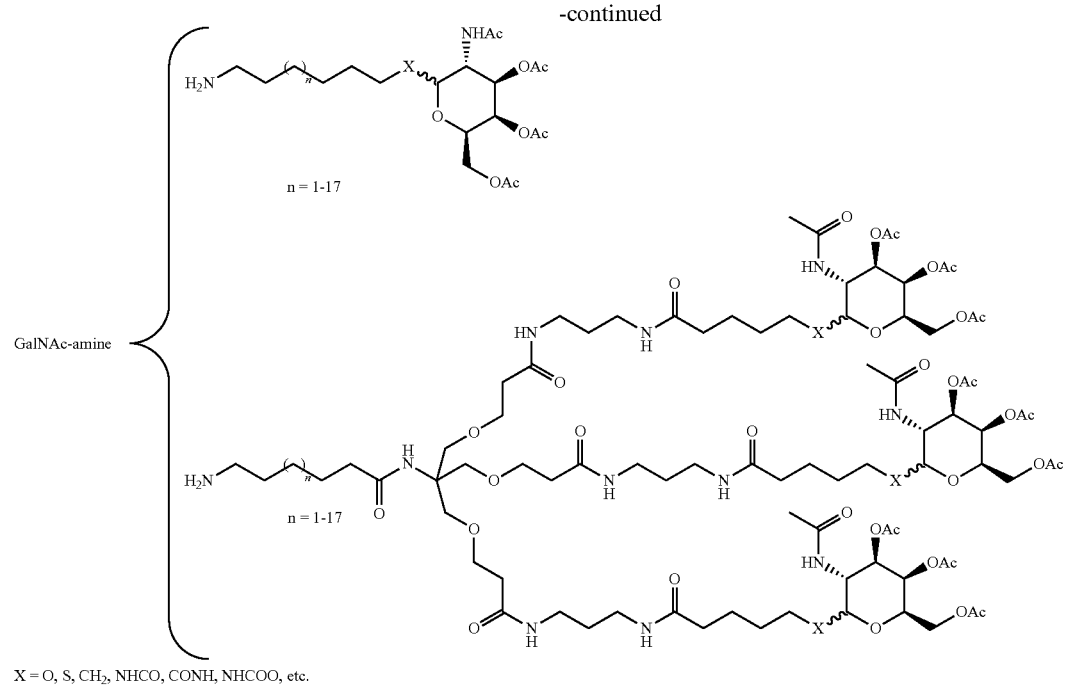
X = O, S, CH$_2$, NHCO, CONH, NHCOO, etc.

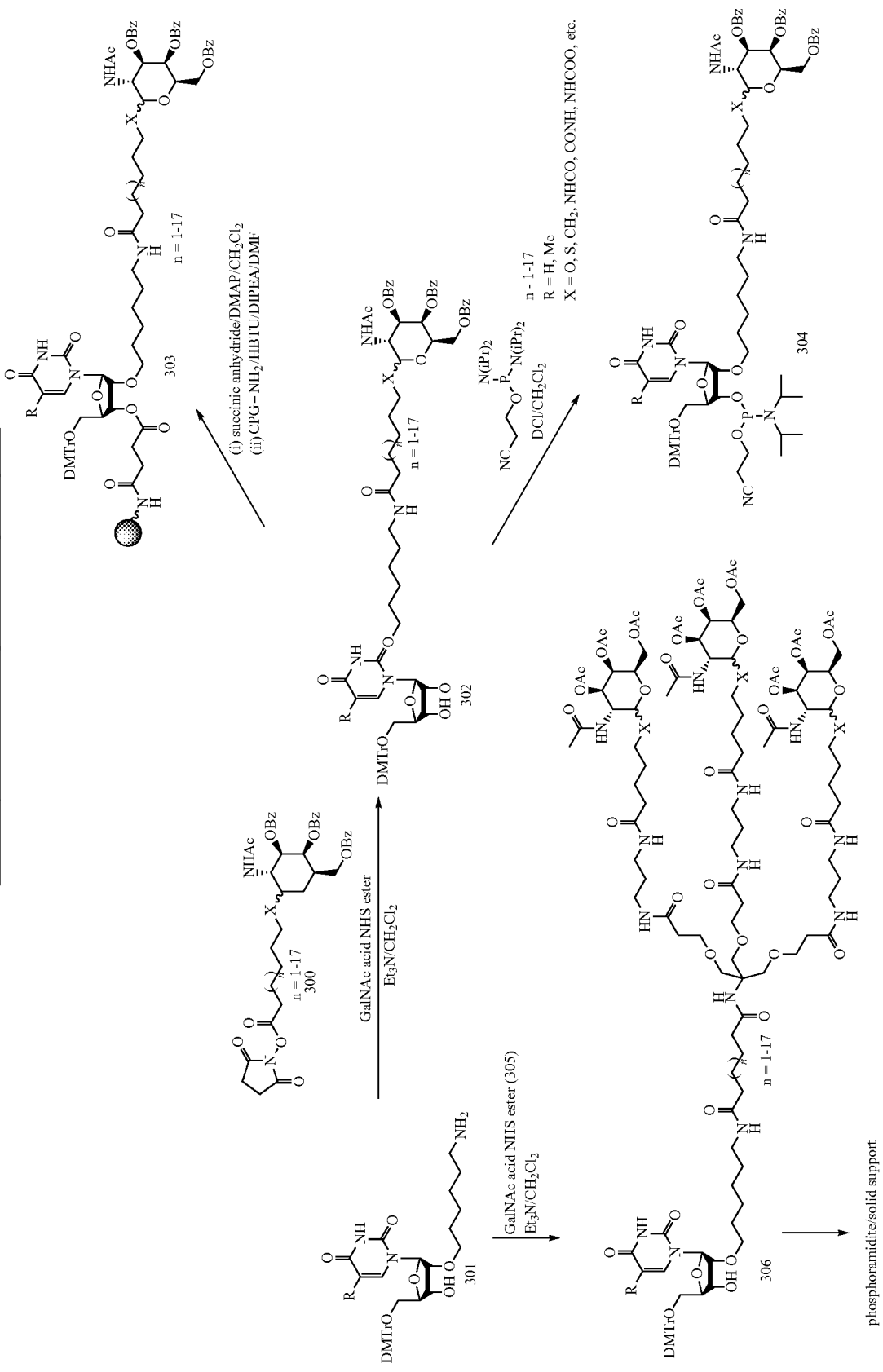

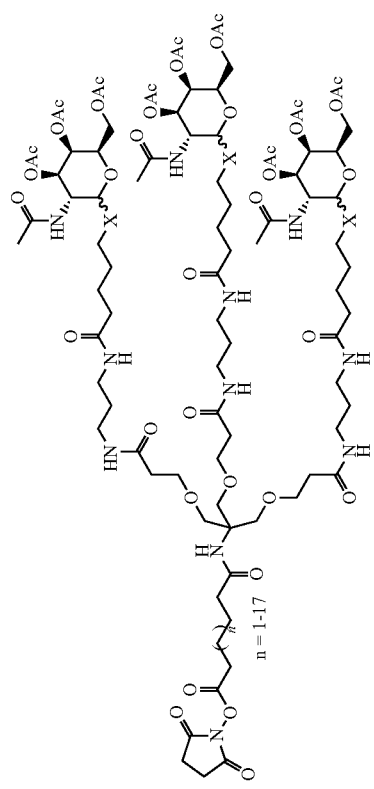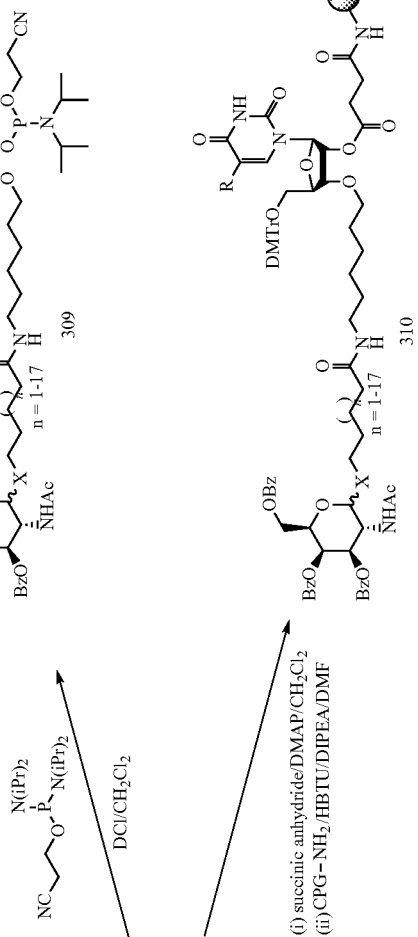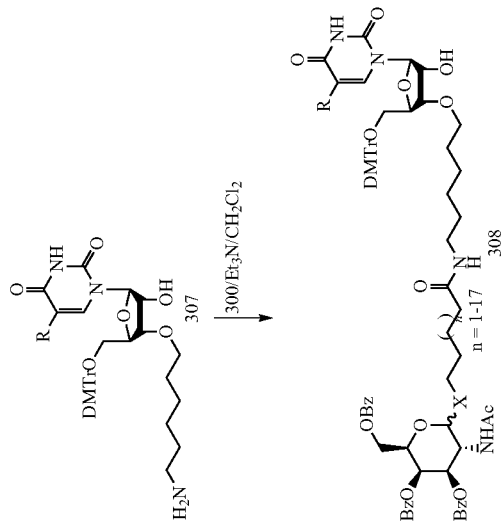

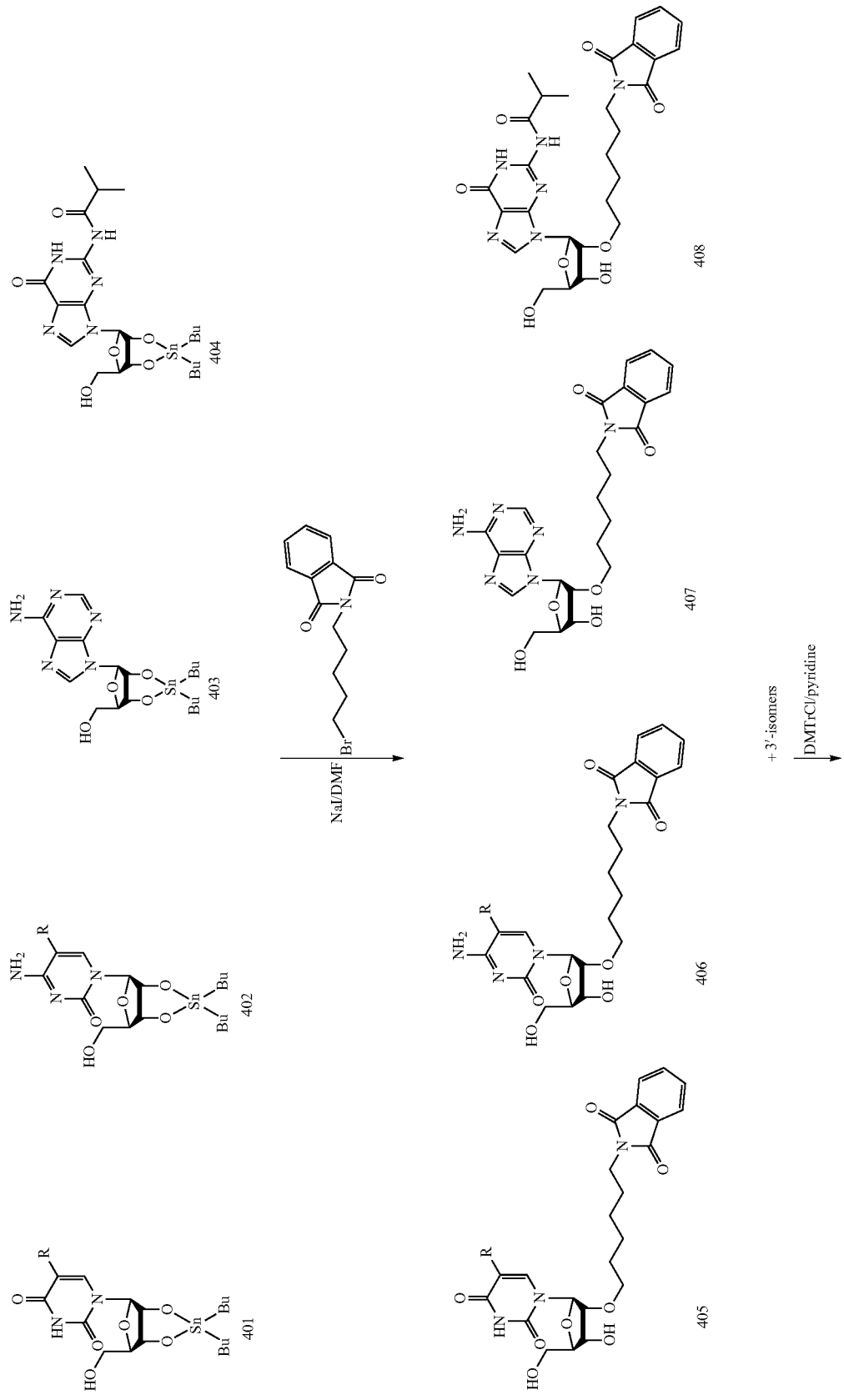

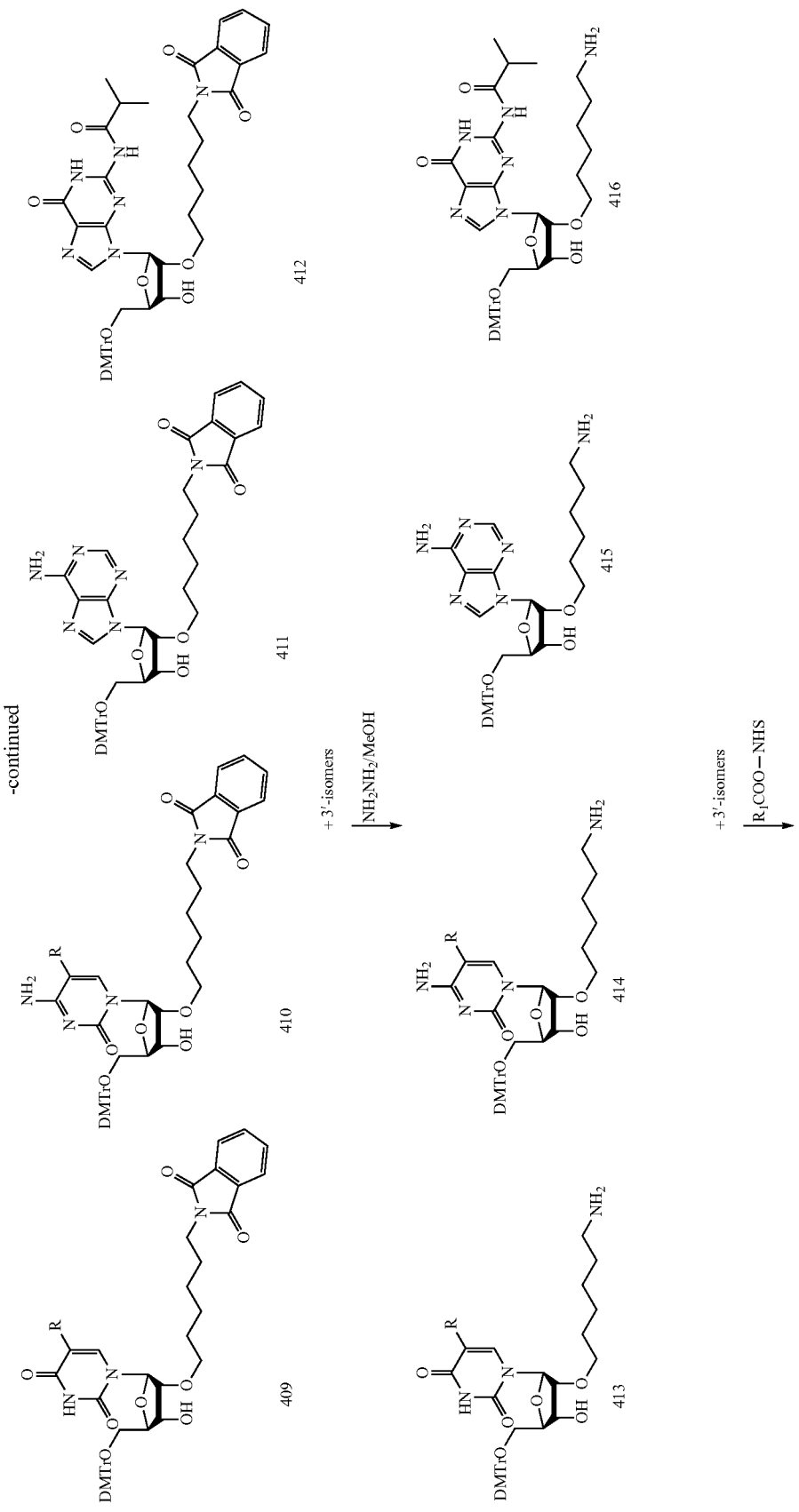

-continued
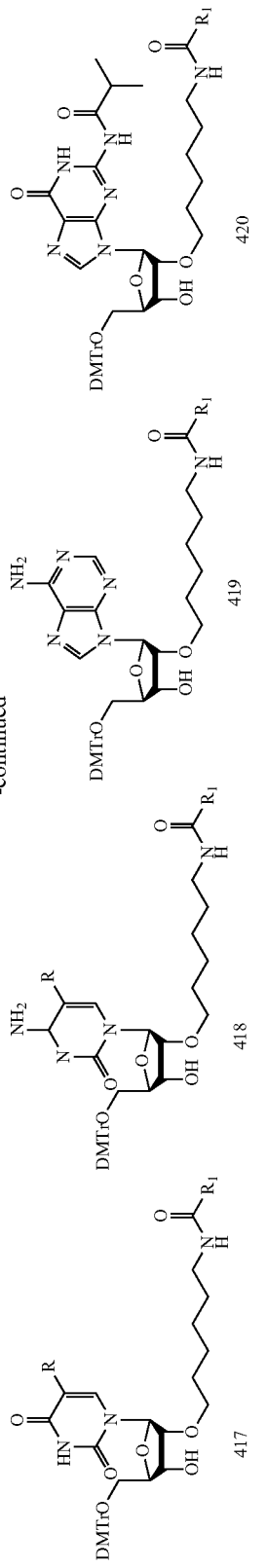
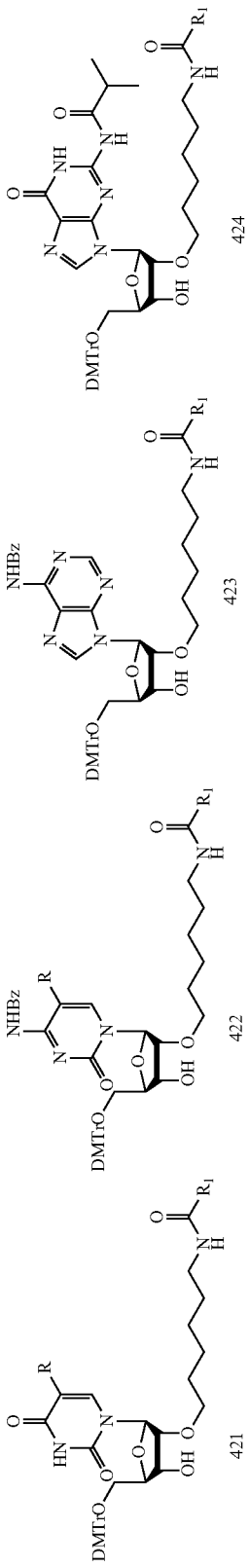
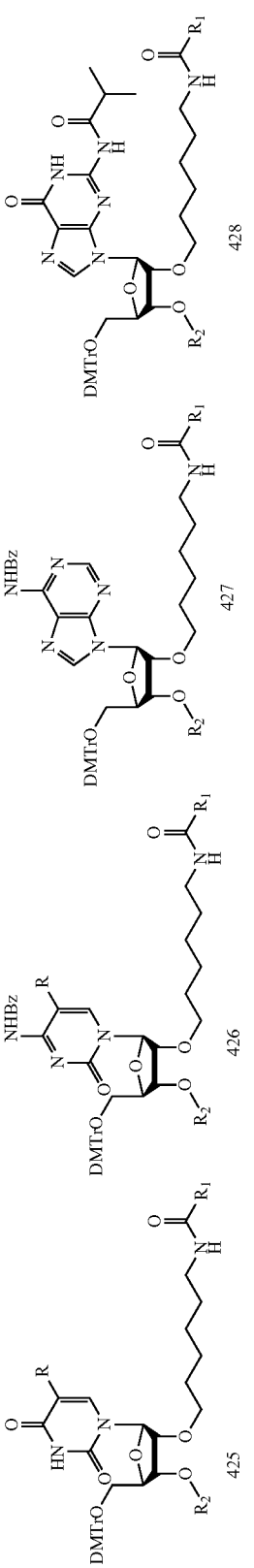

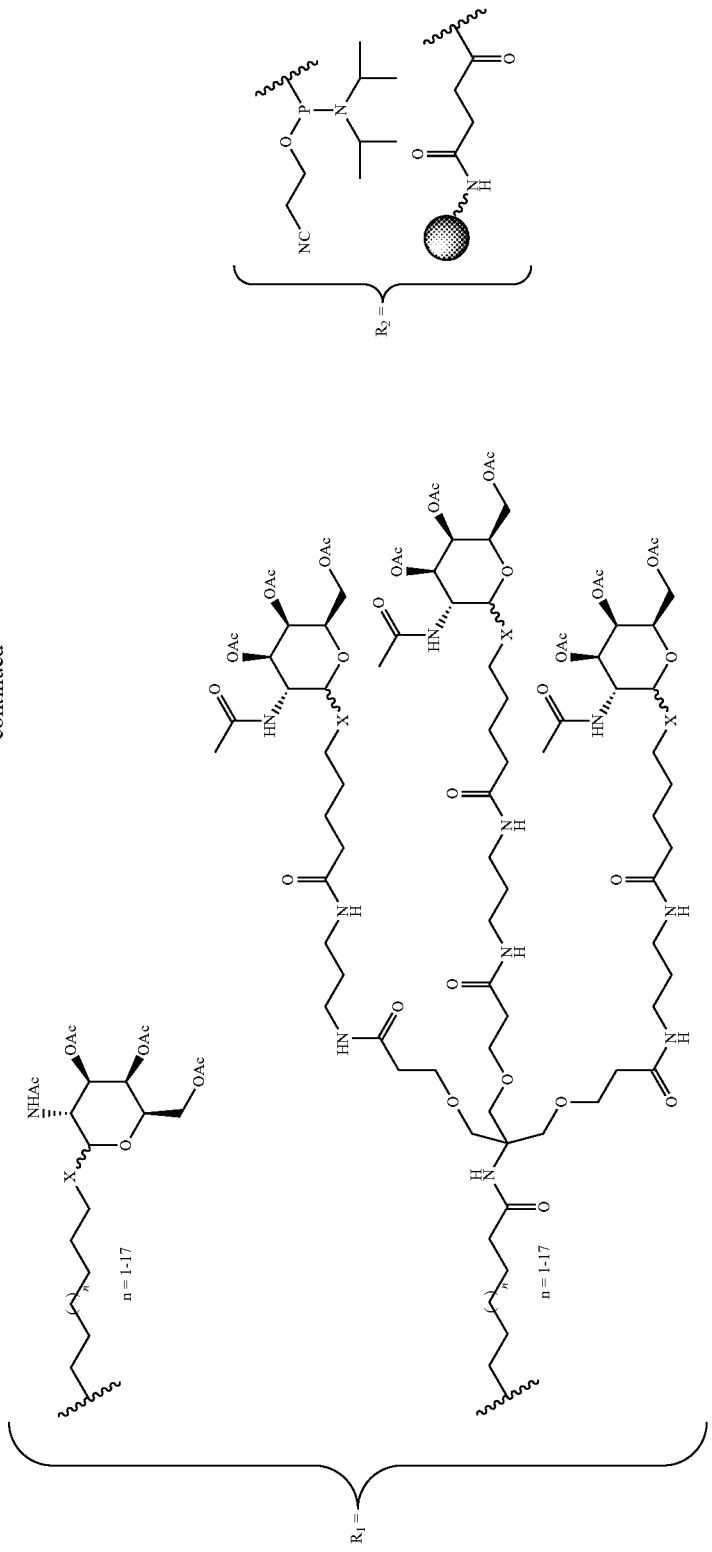

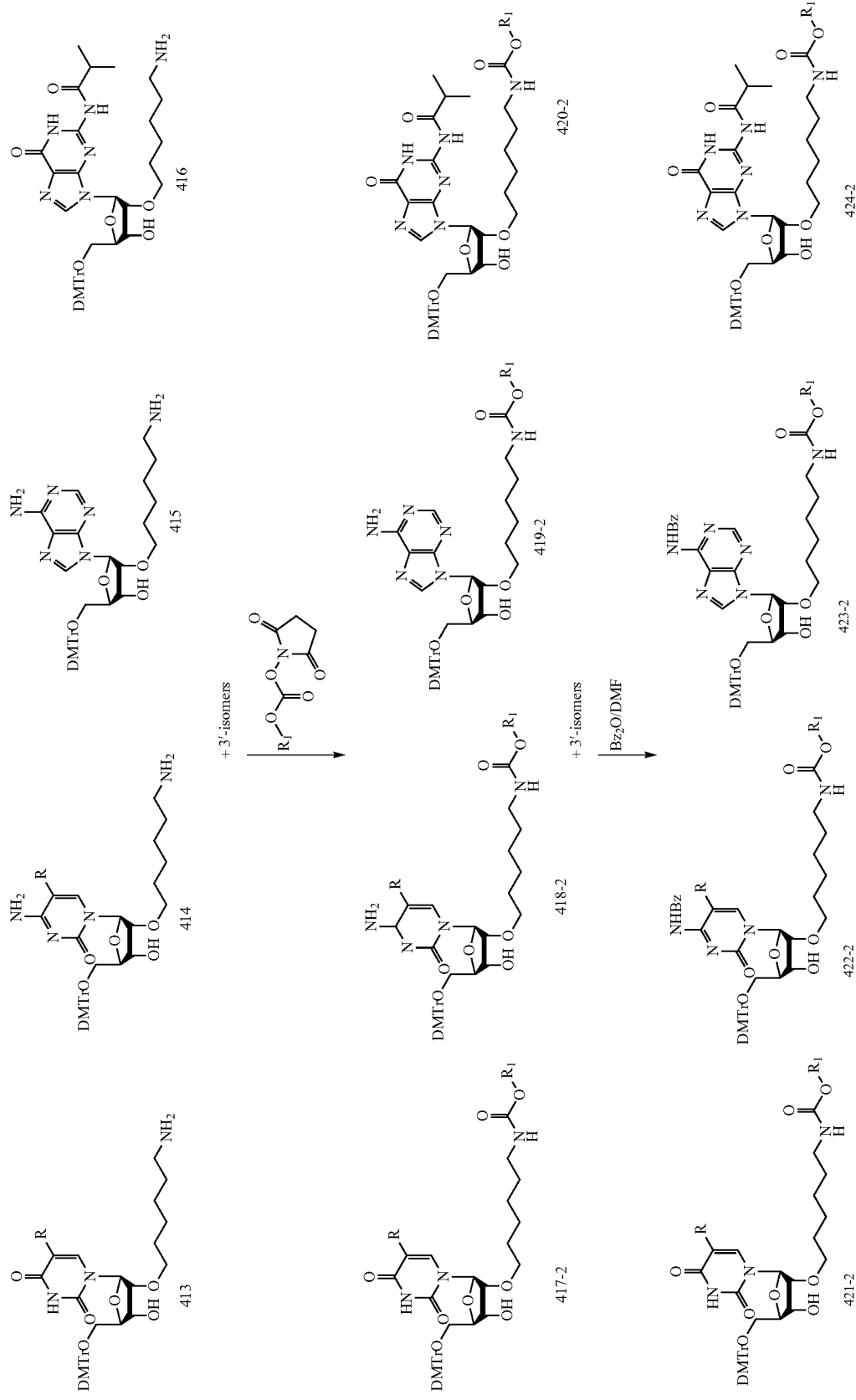
Scheme 38. Synthesis of nucleoside building blocks for GalNAc conjugation at 2' position via carbamate linkage -continued
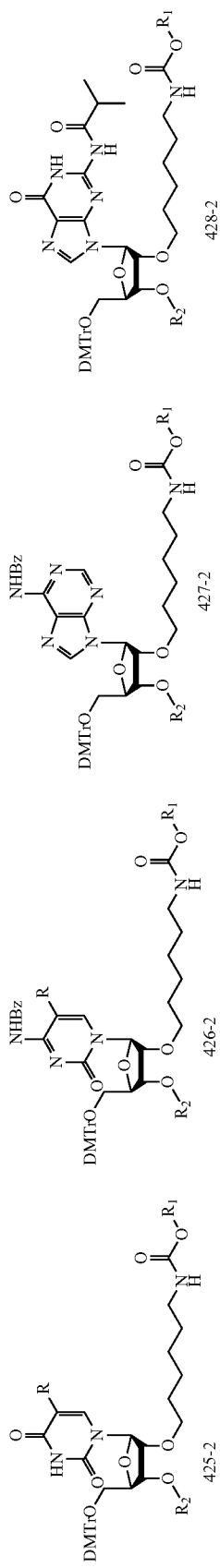
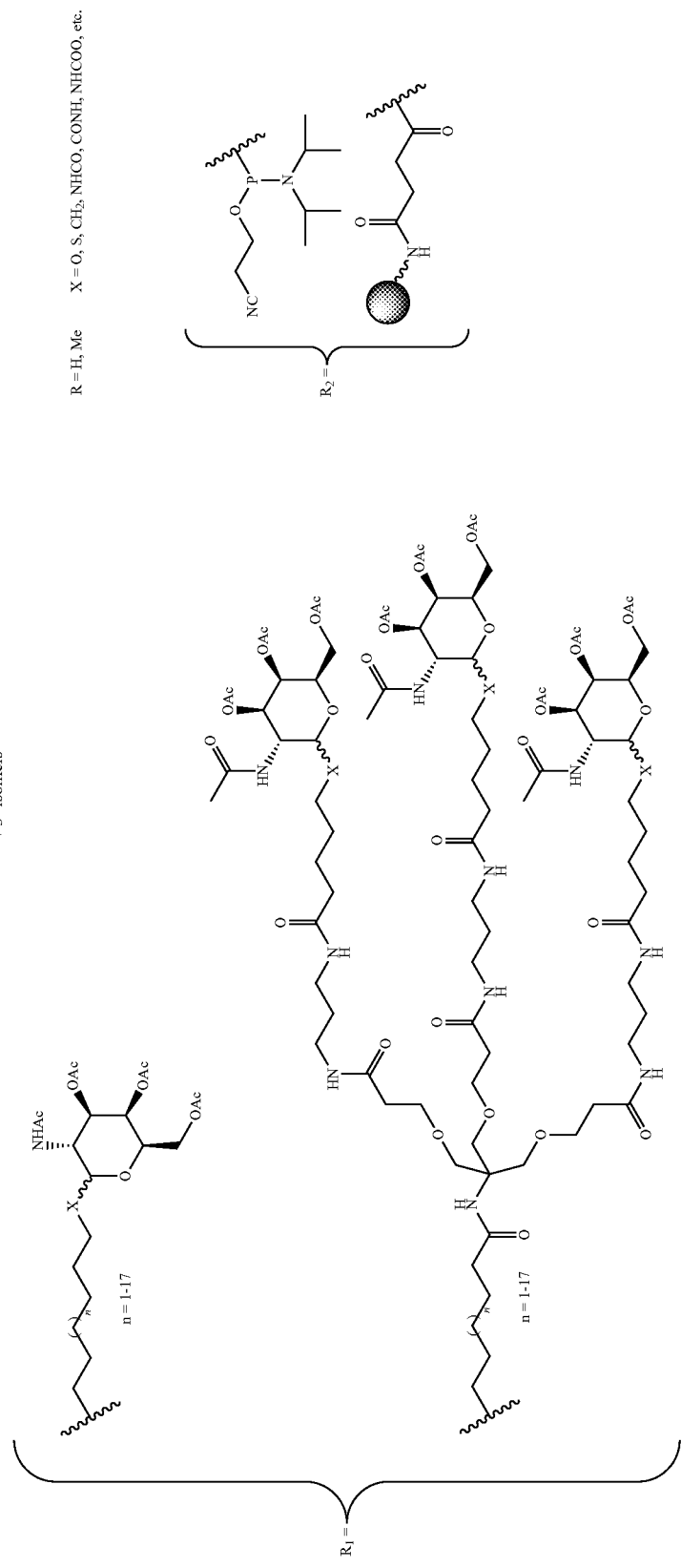

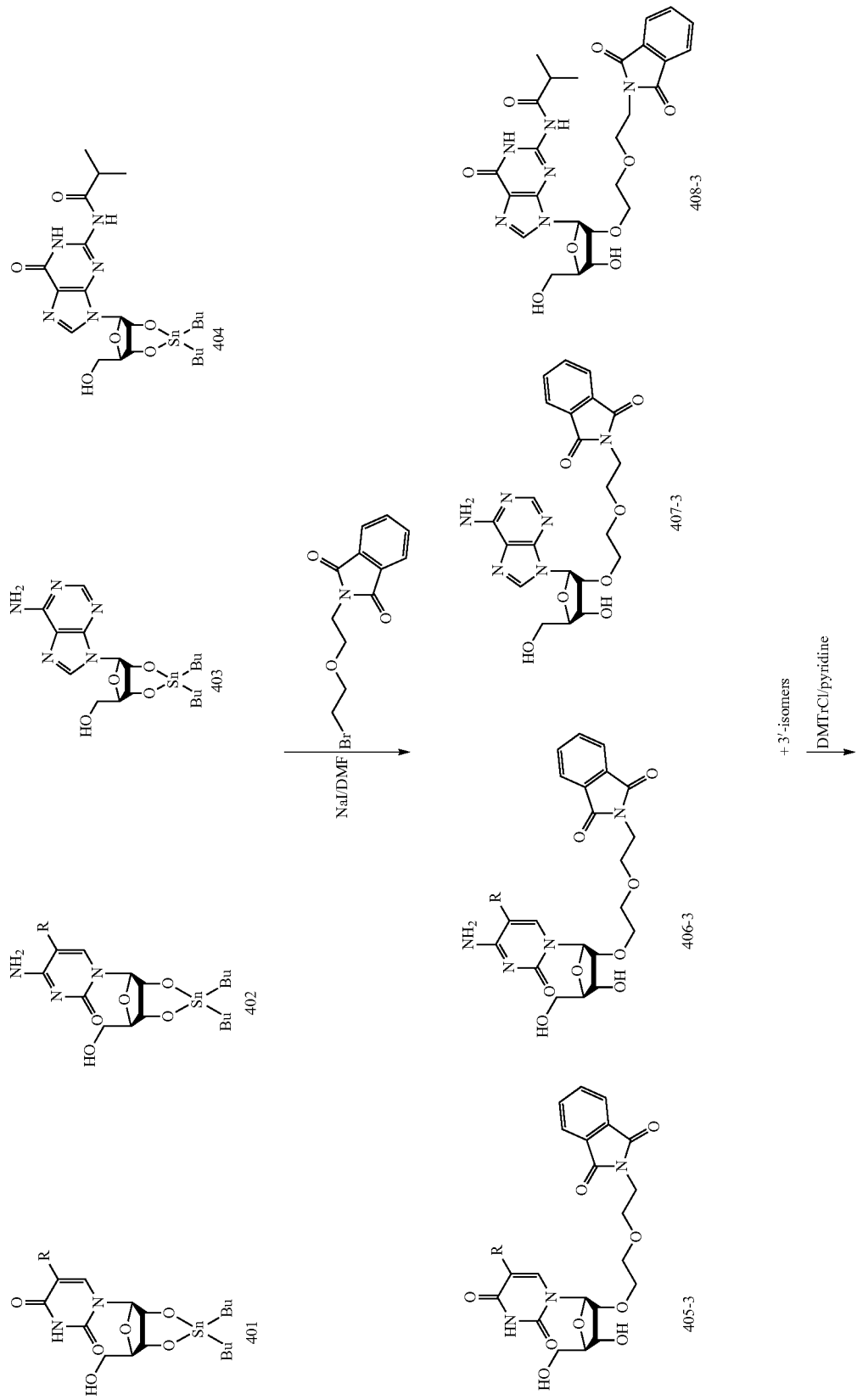

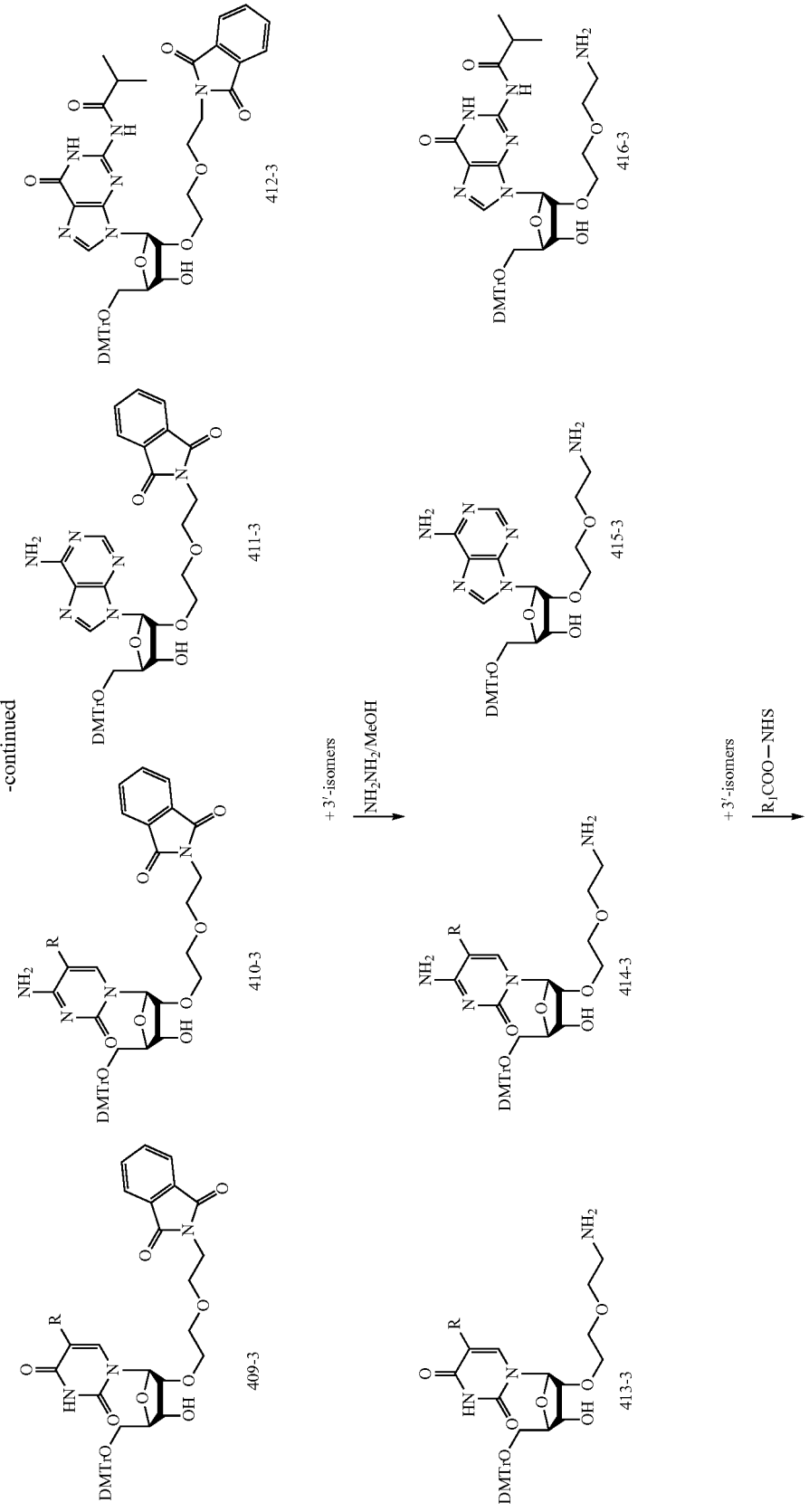

-continued
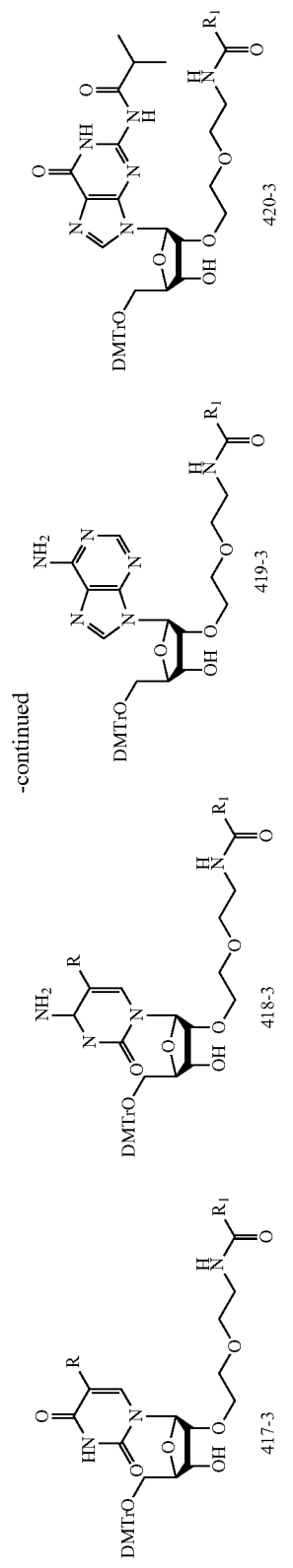
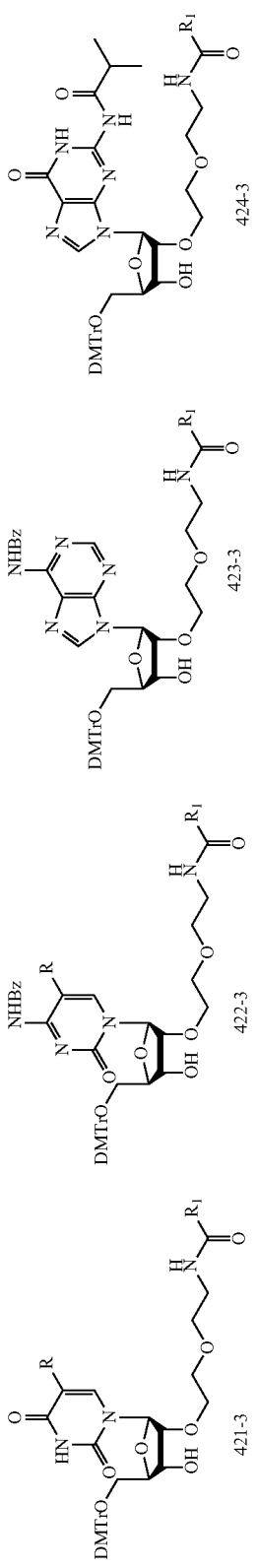

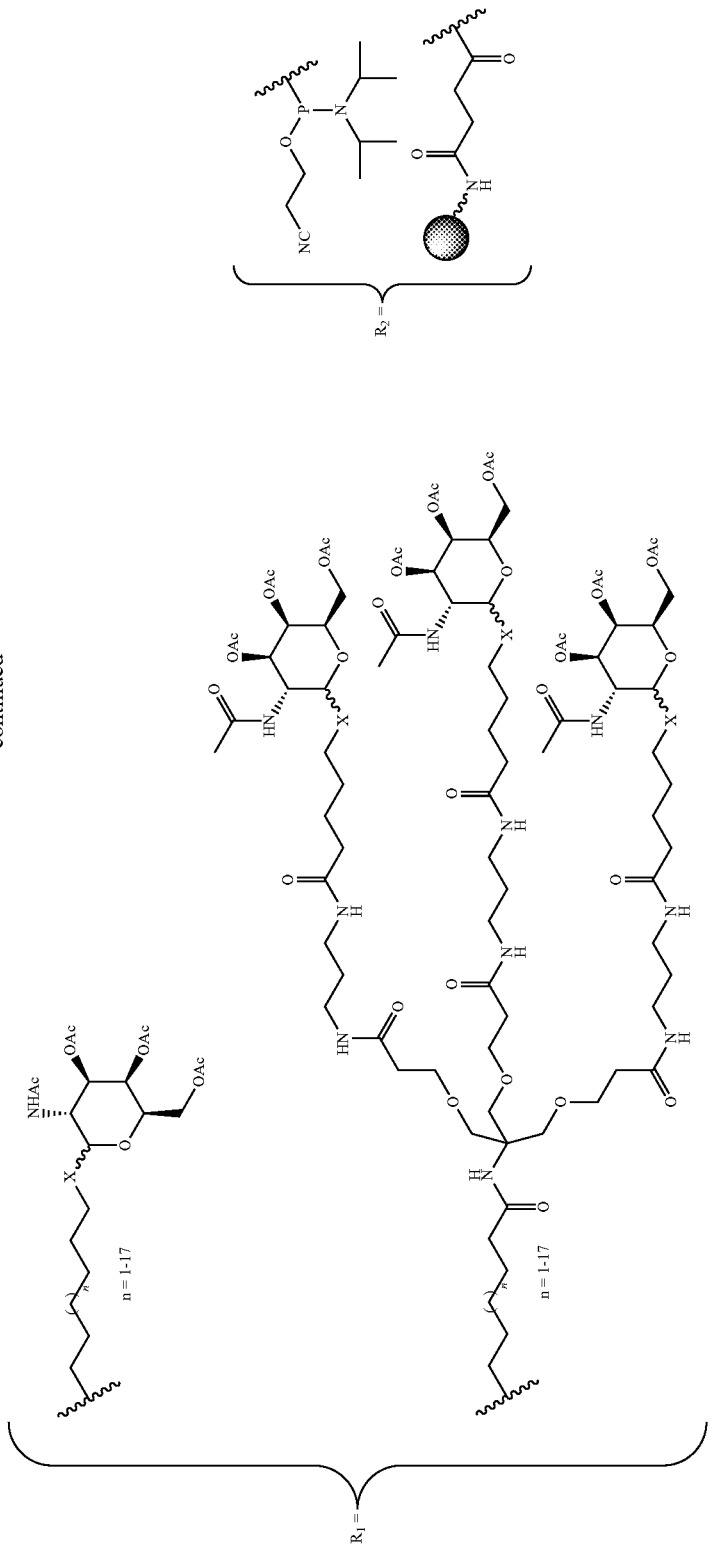

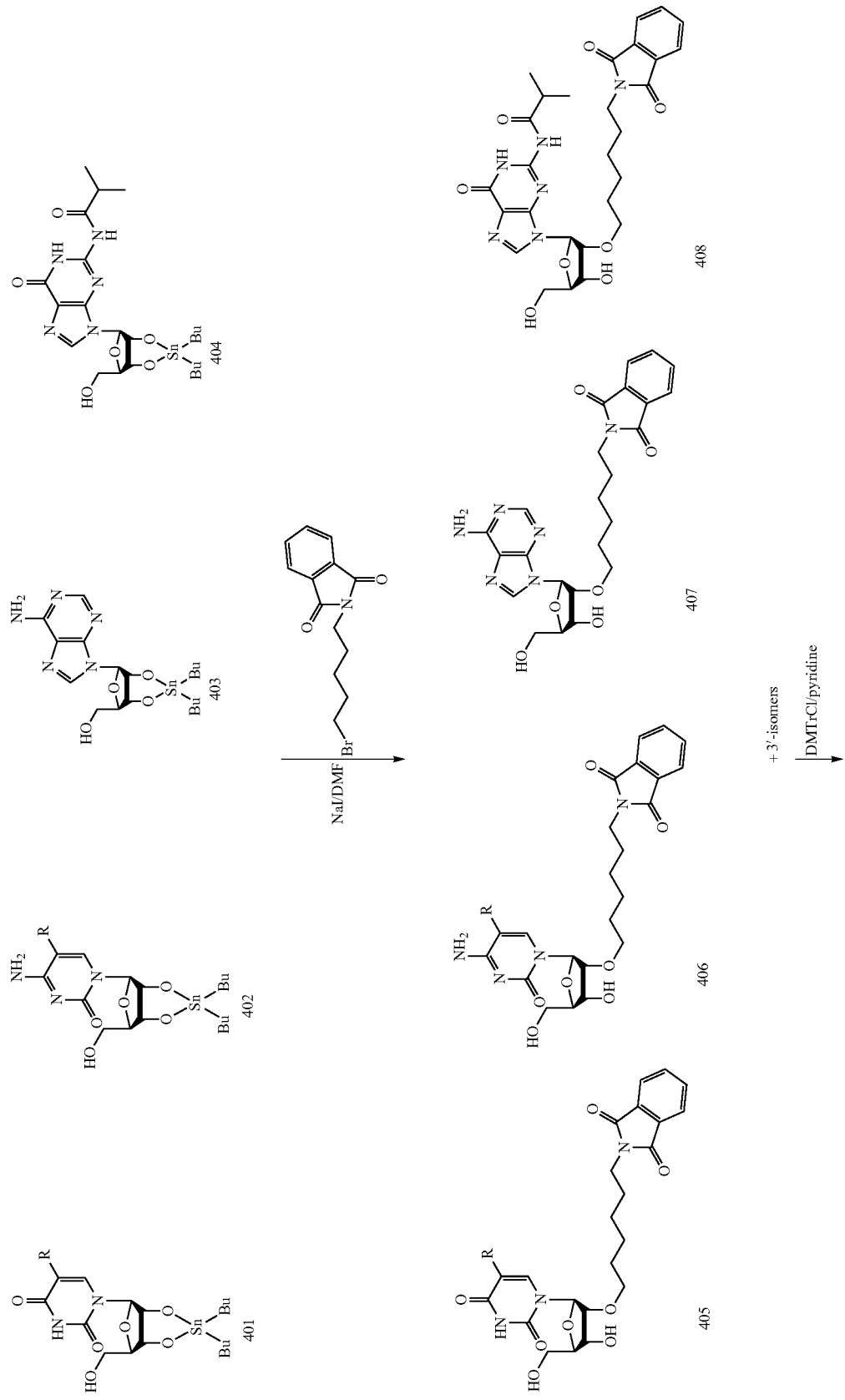

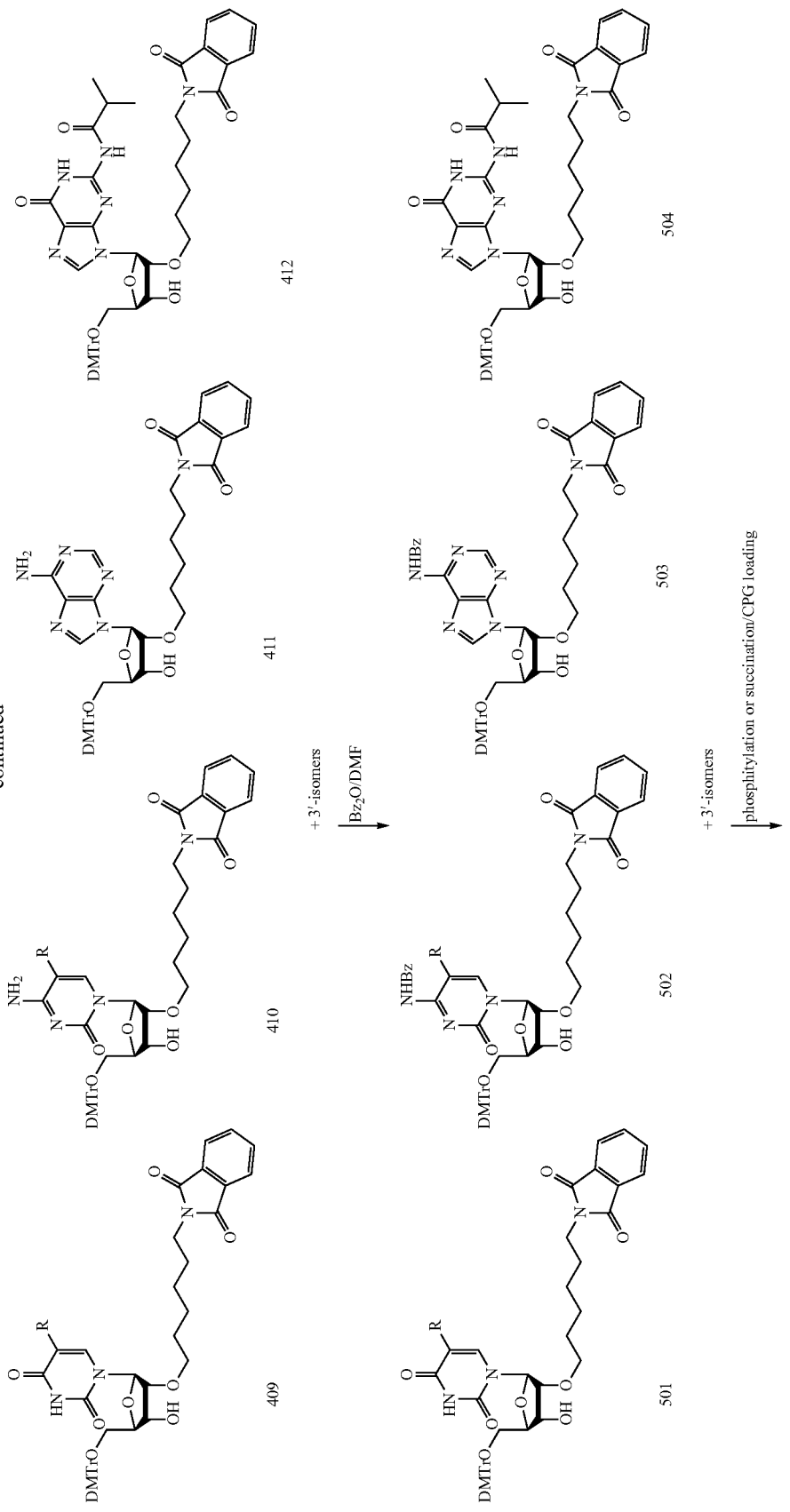

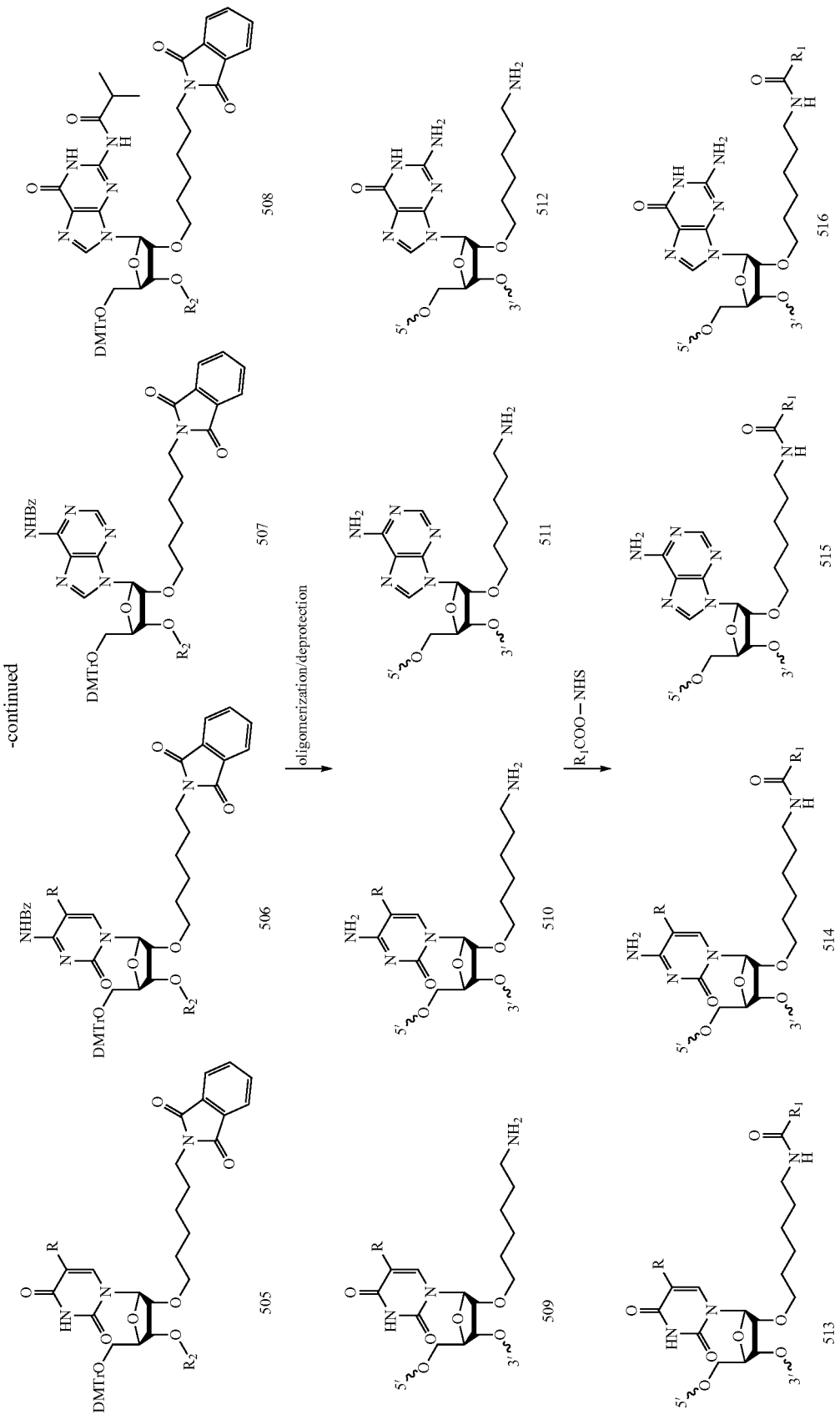

-continued
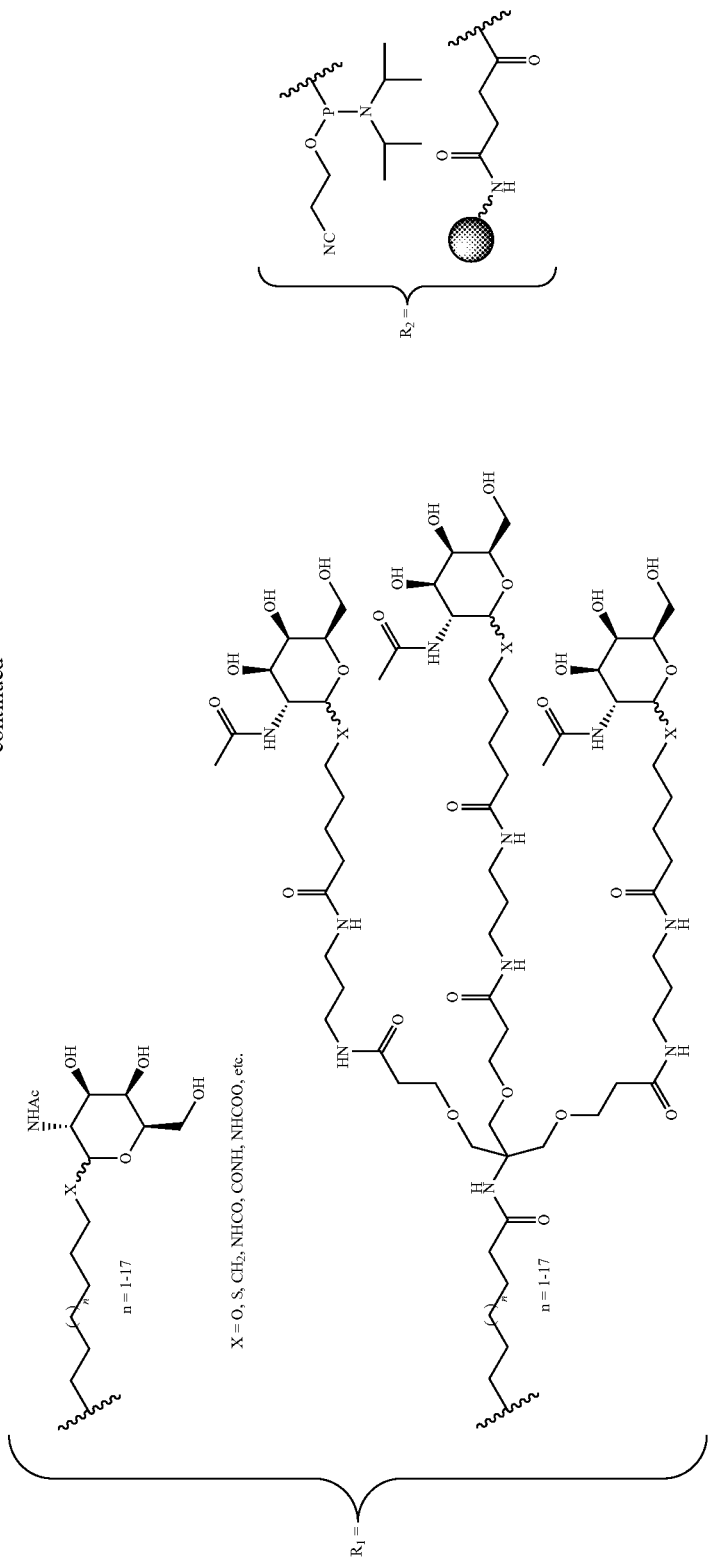

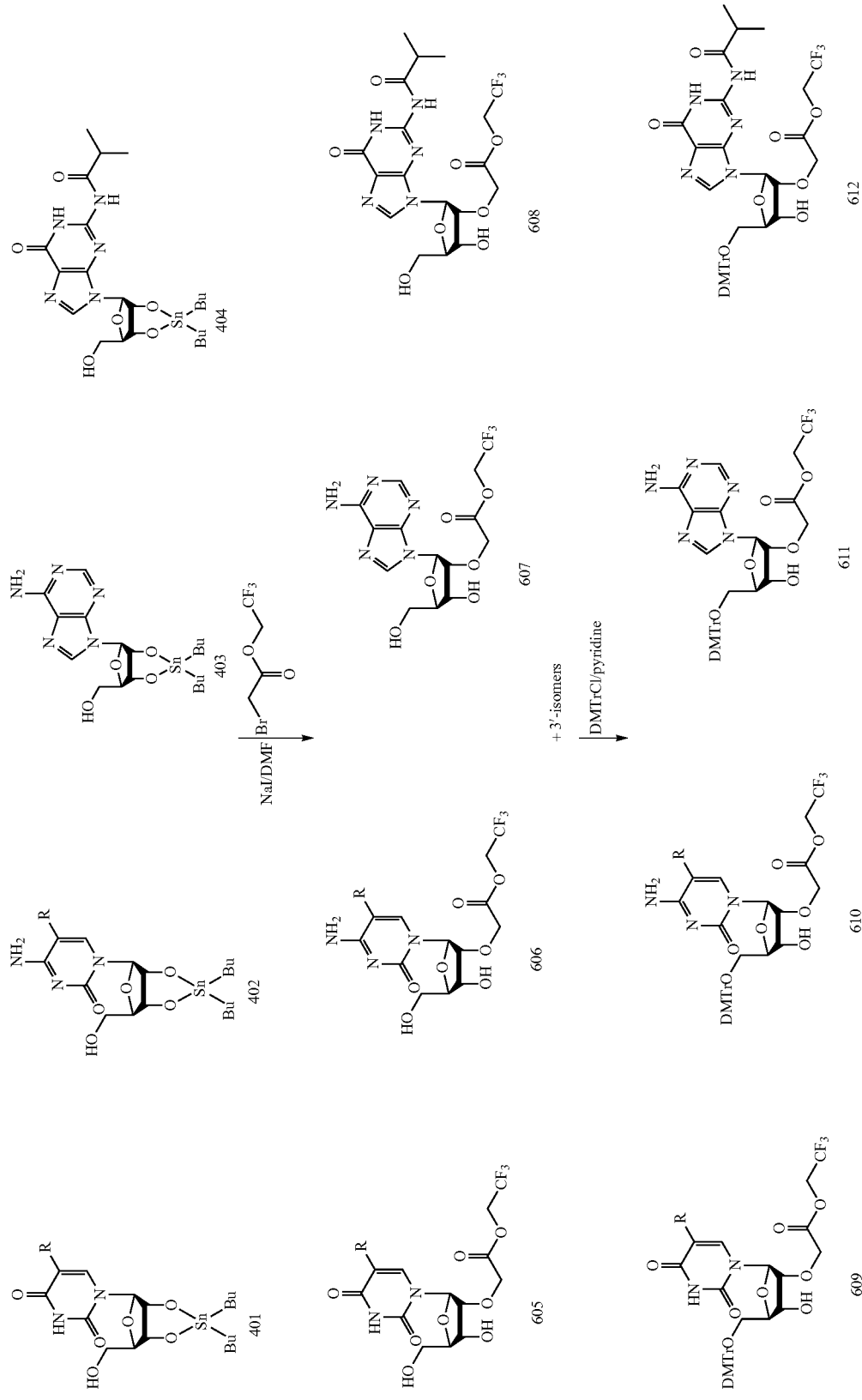
Scheme 41. Synthesis of nucleoside building blocks for GalNac conjugation

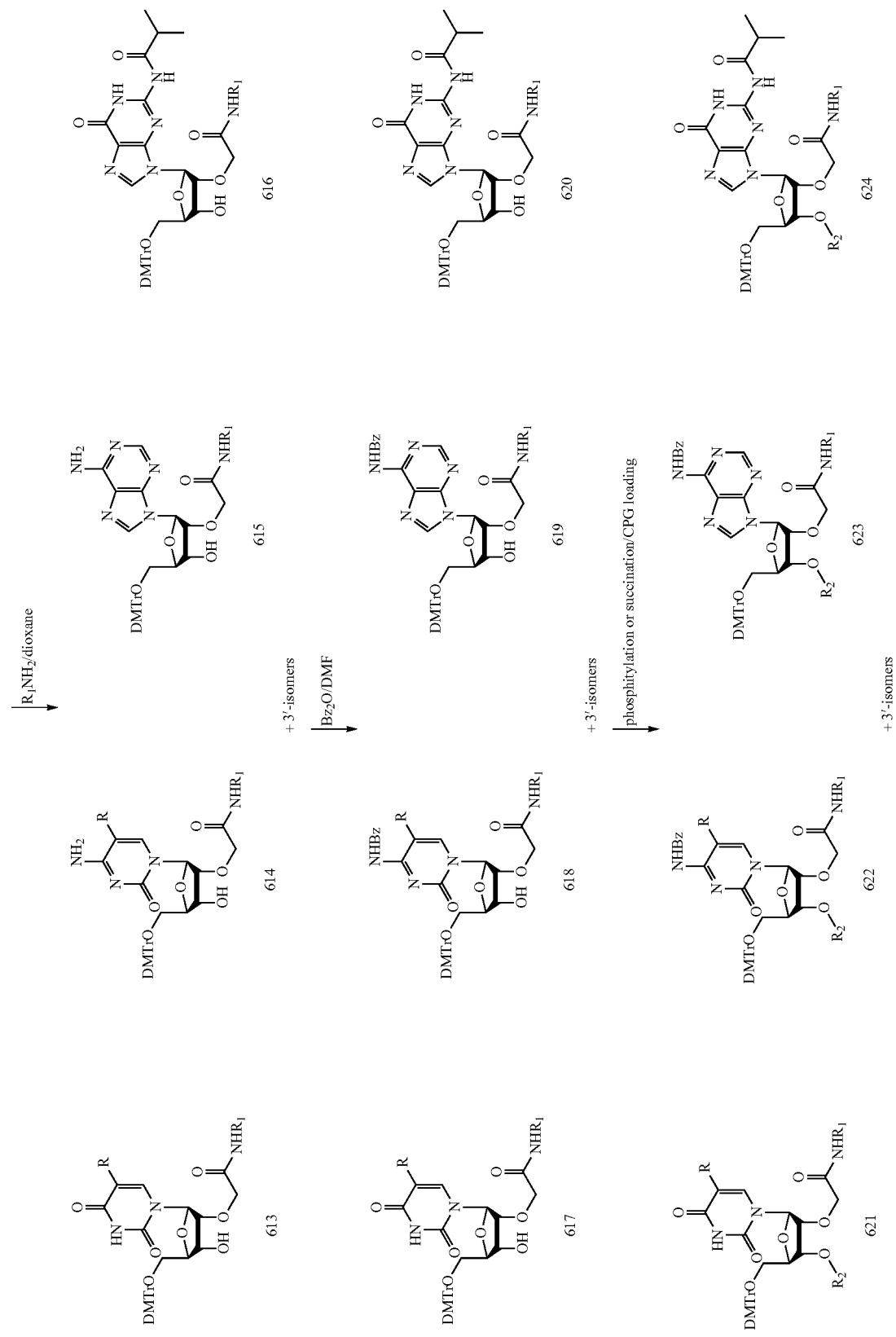

-continued
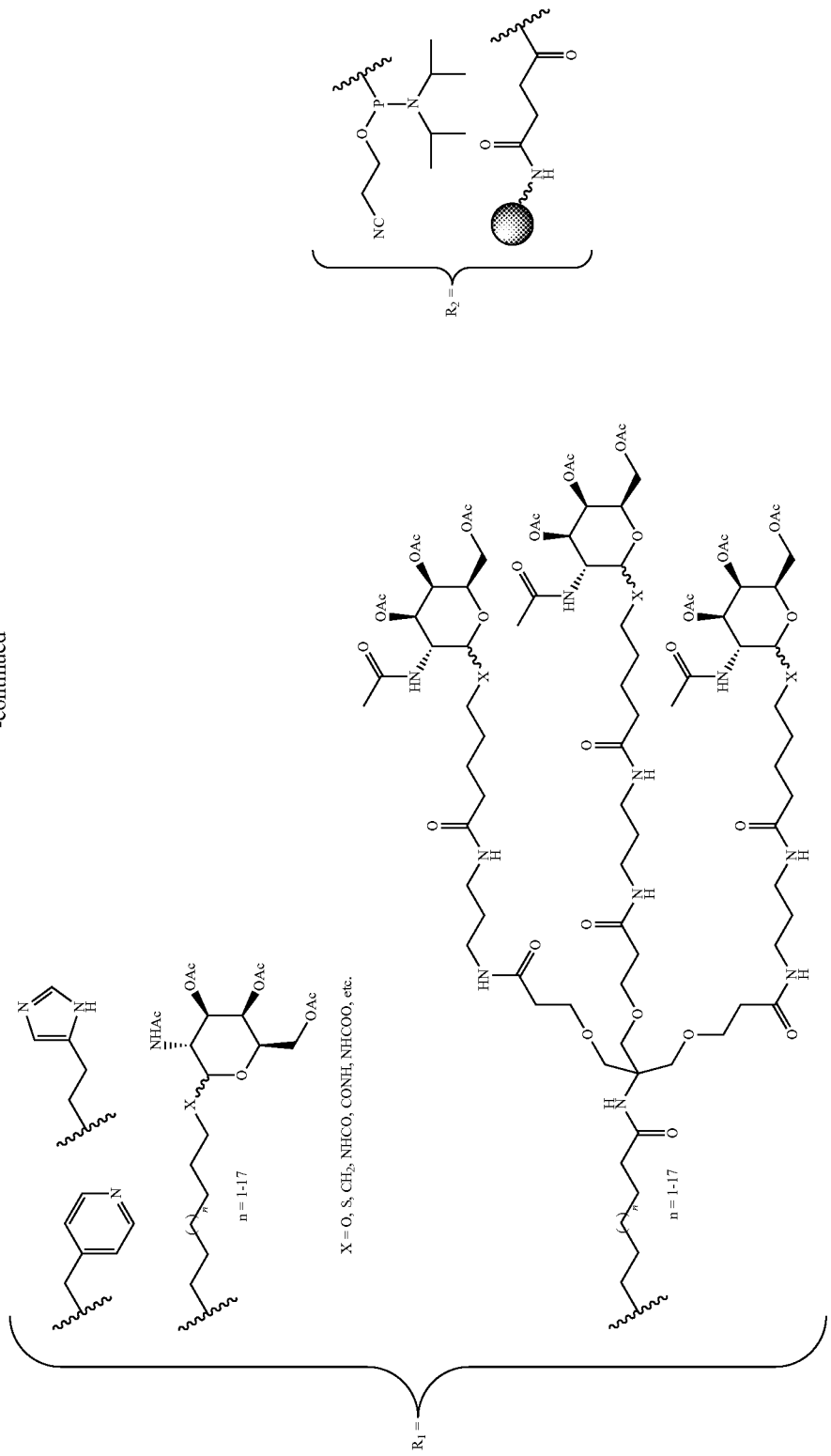

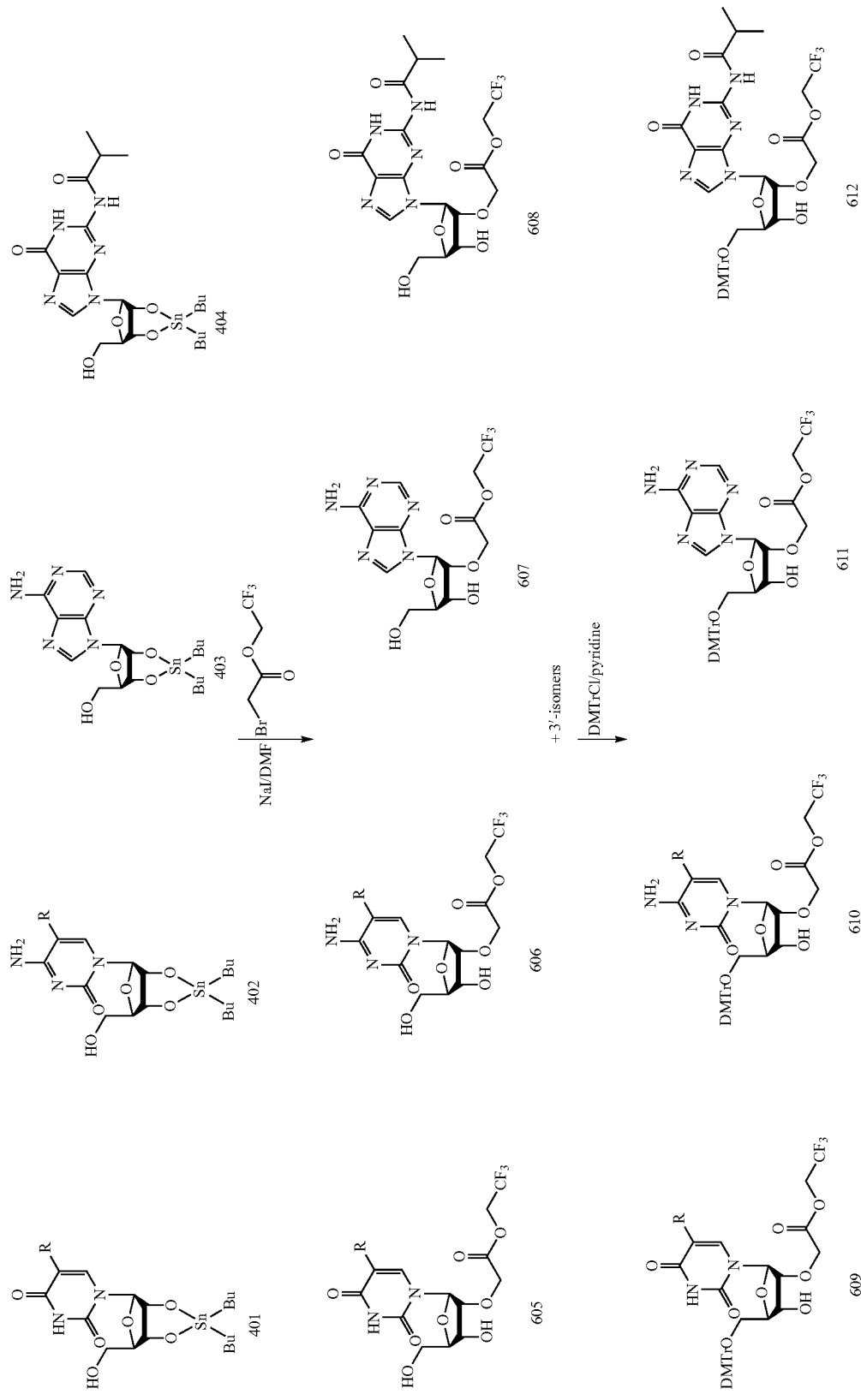

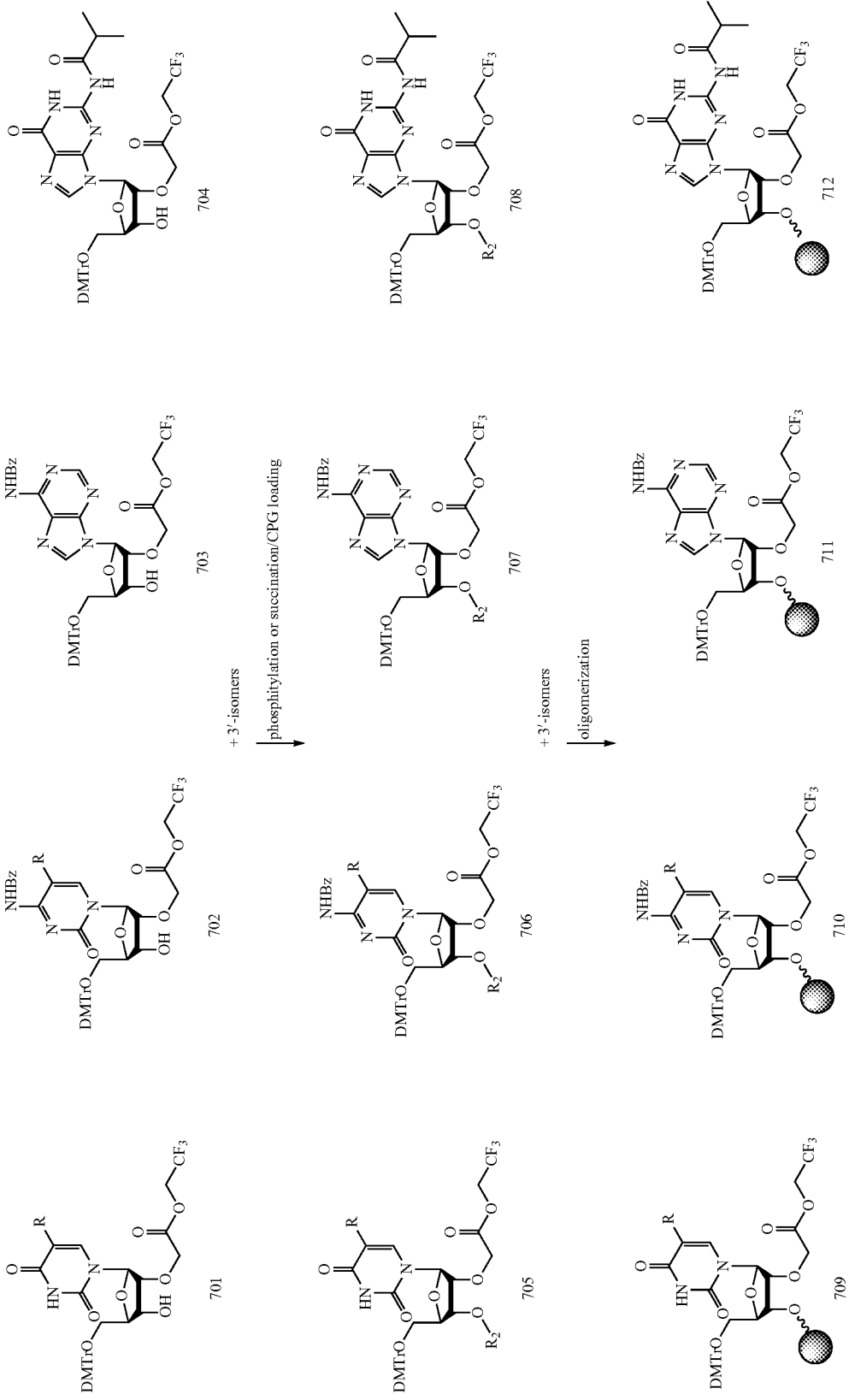

-continued
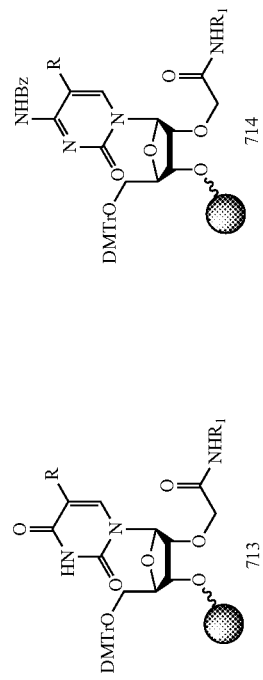
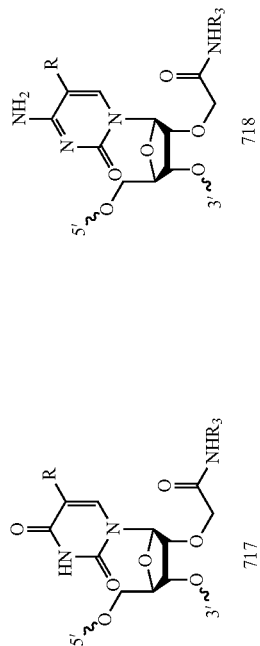
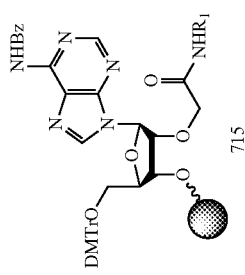
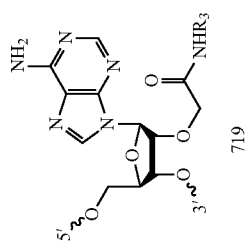
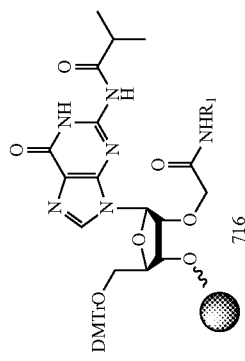
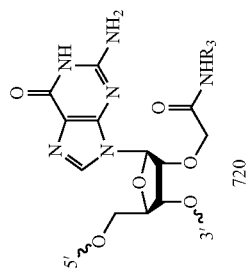
$R_1$—$NH_2$ → + 3'-isomers → deprotection + 3'-isomers

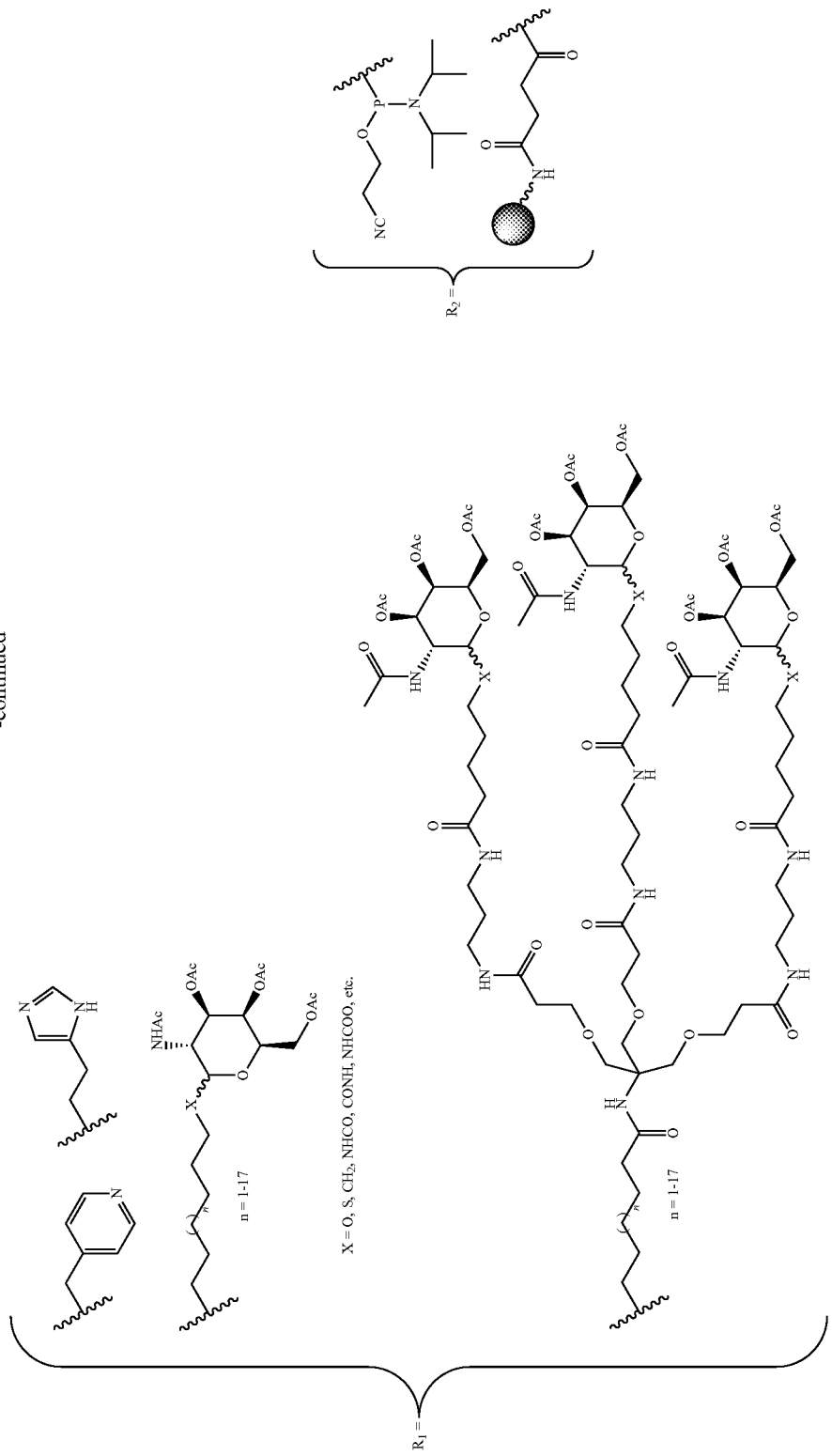

-continued
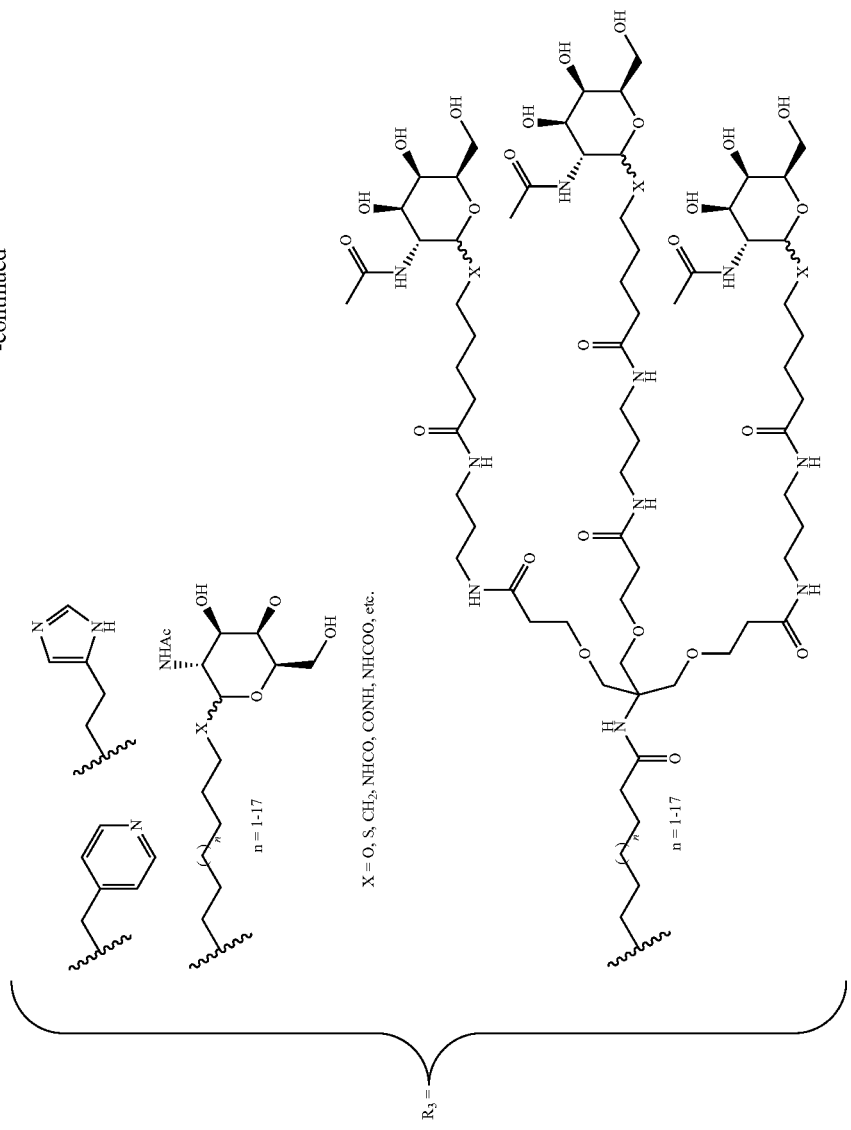

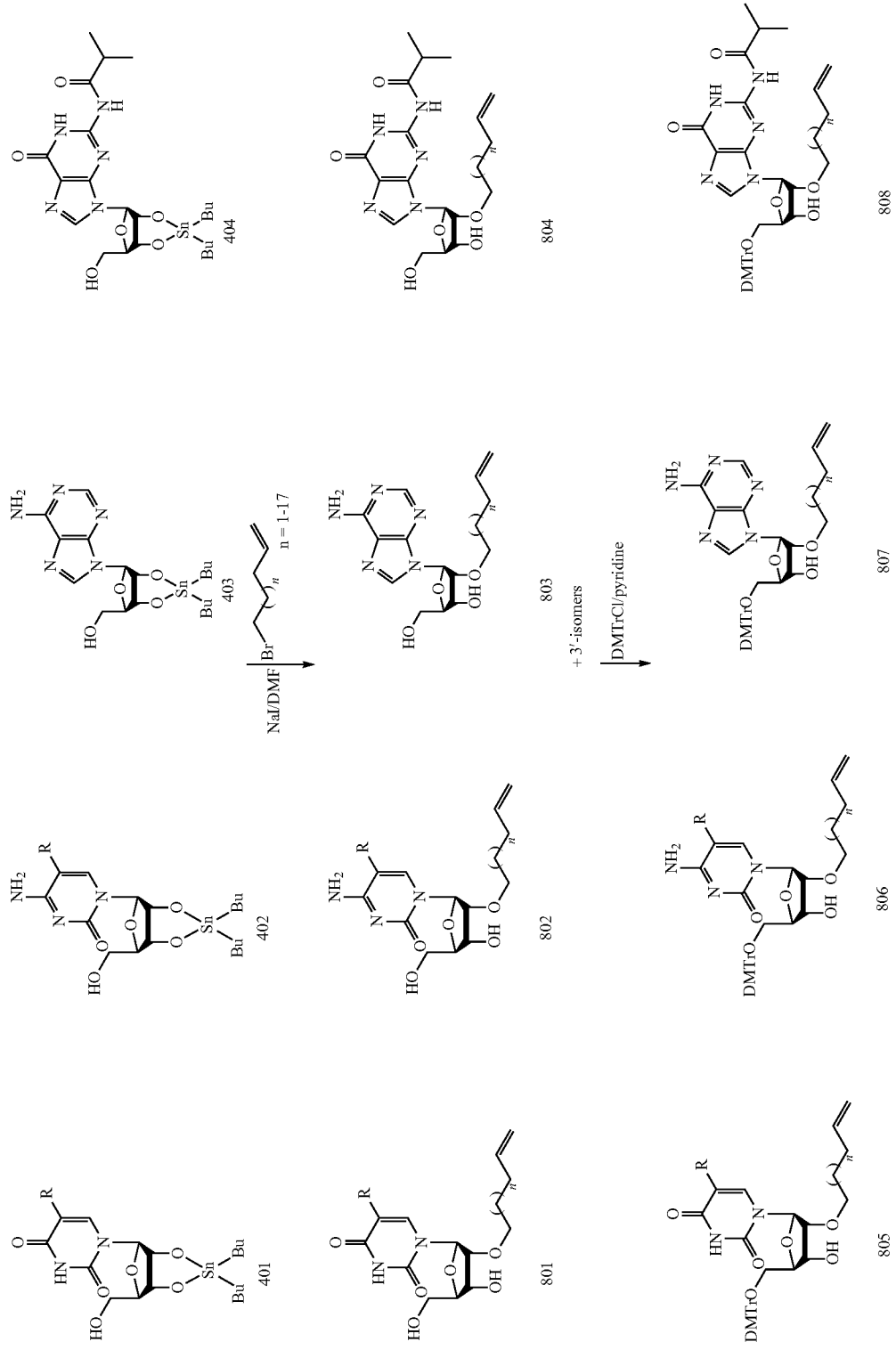

417
418
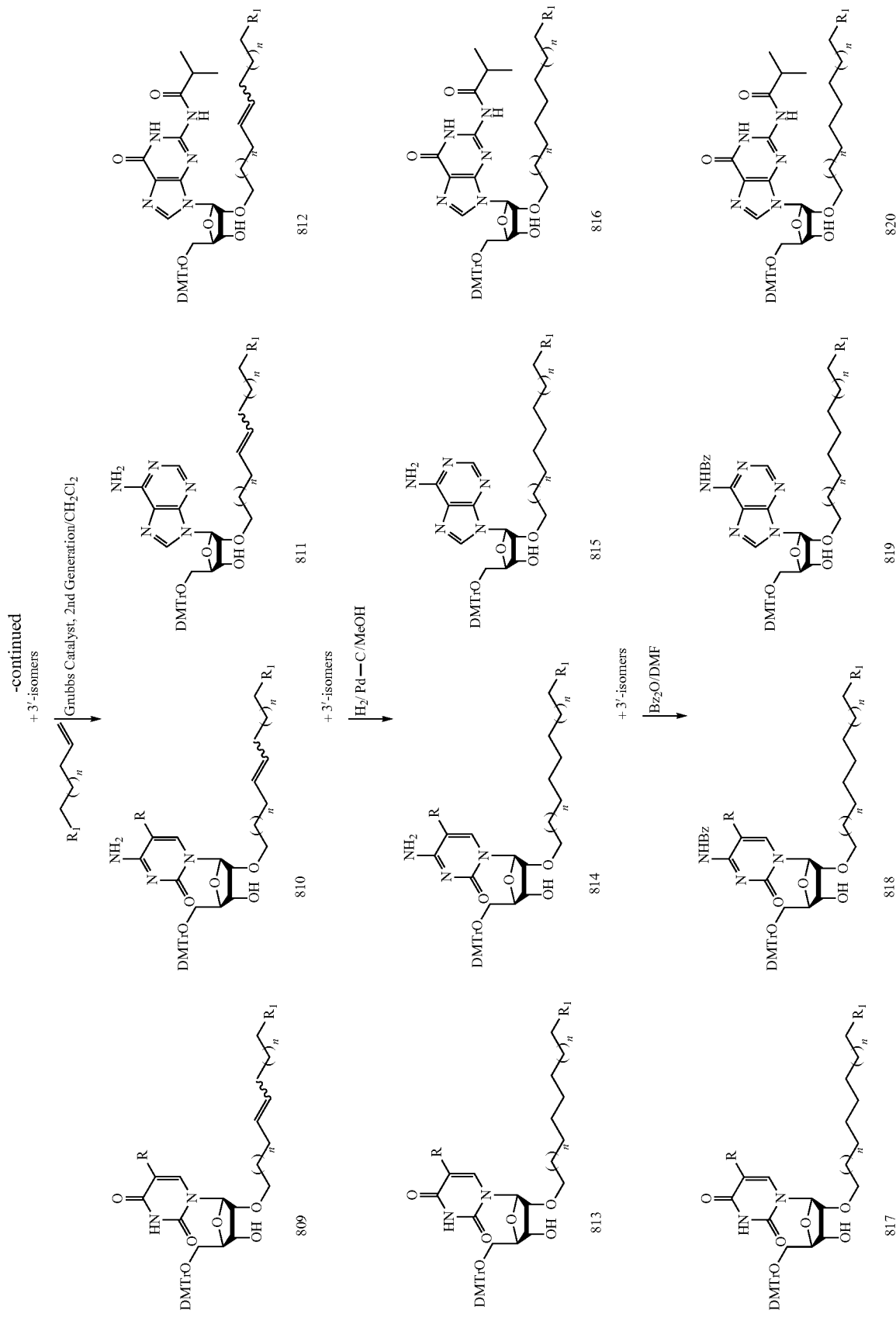

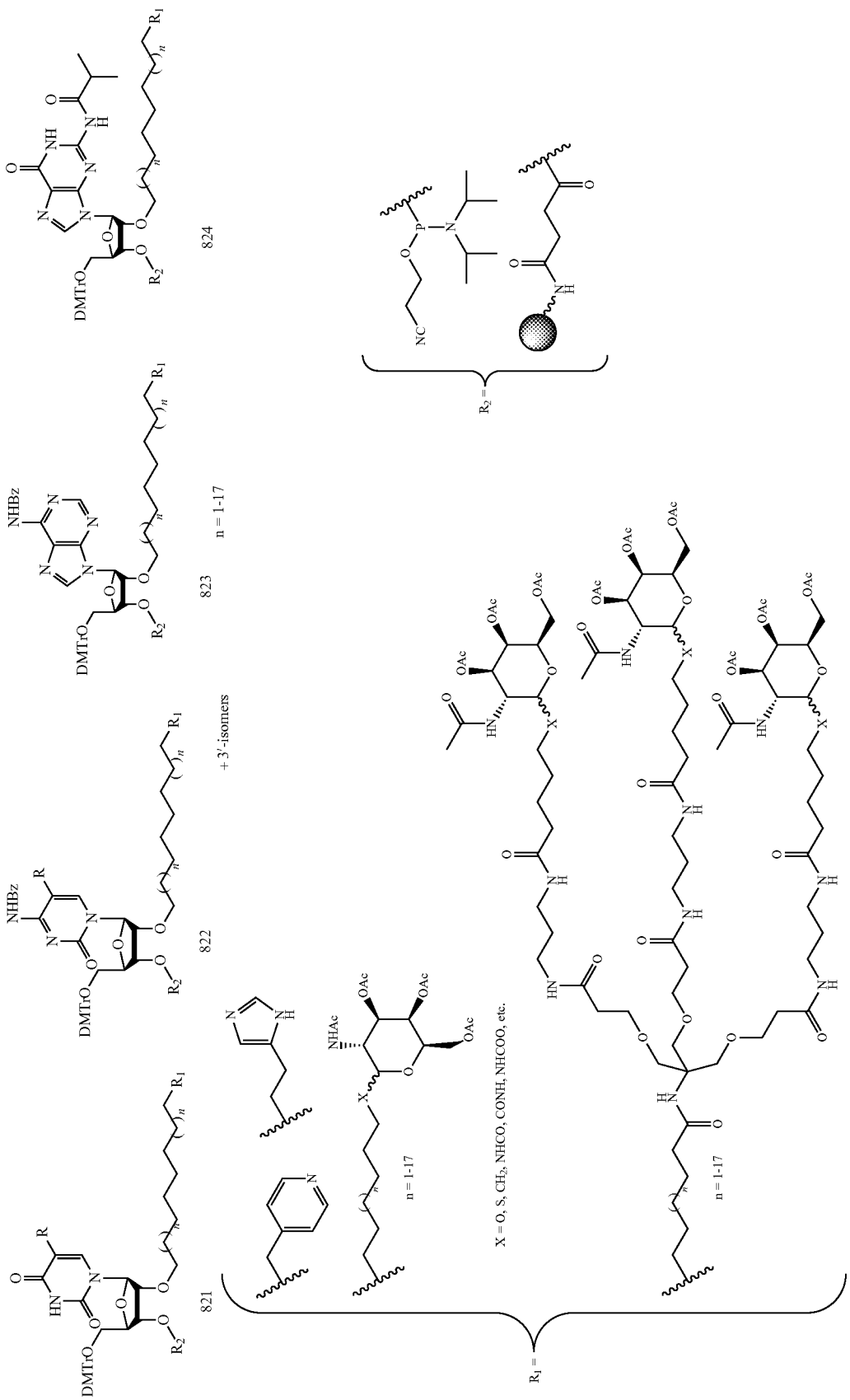

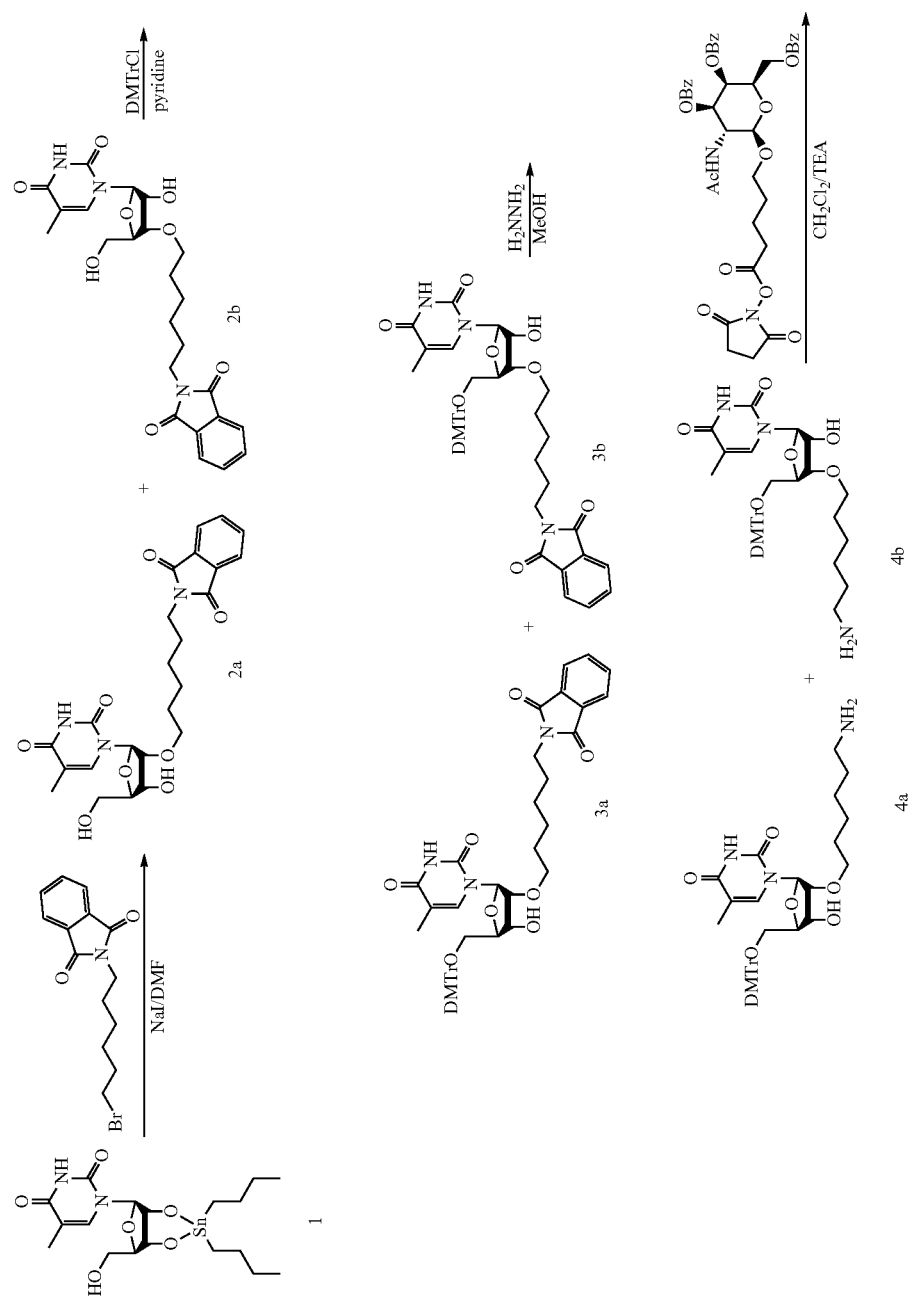

-continued
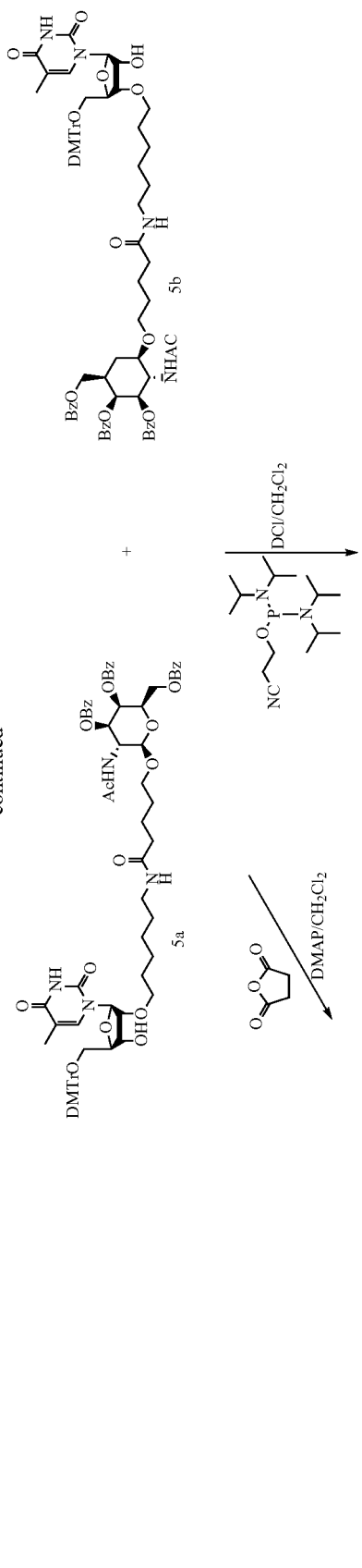
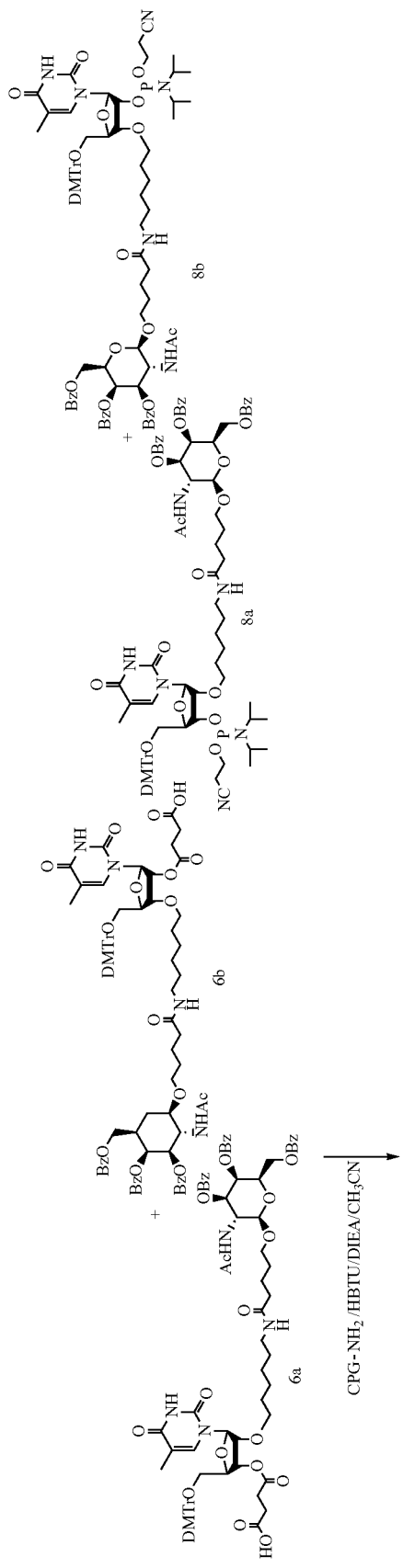
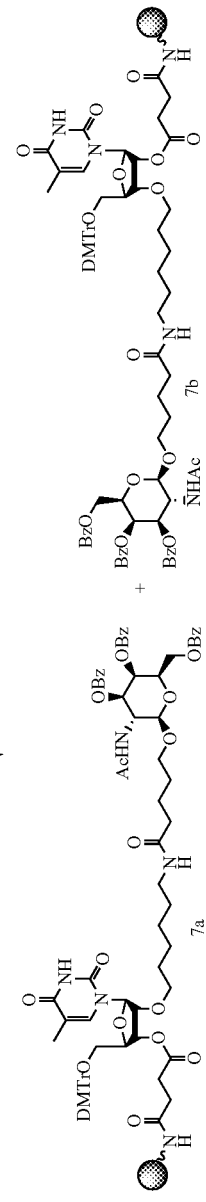

2'- and 3'-O-phthalimidohexyl-5-methyluridine (2a, 2b)

A solution of 2',3'-O-dibutylstannylene-5-methyluridine (28 g, 57.24 mmol) obtained as reported (J Org. Chem., 1974, 24-30), 6-bromohexyl phthalimide (35.5 g, 114.48 mmol) and NaI (1.72 g, 11.45 mmol) in DMF (105 mL) was heated at 100° C. in a microwave for 3.5 hours. After removing DMF, the residue was purified by silica gel column chromatography ($R_f$=0.26 in 5% MeOH in $CH_2Cl_2$) to obtain 2'- and 3'-isomers of the O-phthalmidohexyl-5-methyuridine as an inseparable mixture (10.1 g, 20.7 mmol, 36%). MS m/z 488.0 $(M+H)^+$, 510.2 $(M+Na)^+$, 486.2 $(M-H)$. $^1H$ NMR (400 MHz, DMSO-$d_6$): δ 11.29 (s, 1H), 7.88-7.79 (m, 4H), 7.78-7.70 (m, 1H), 5.81 (d, J=5.3 Hz, 1H), 5.72 (d, J=5.6 Hz, 1H), 5.25 (d, J=6.2 Hz, 1H), 5.12 (t, J=5.0 Hz, 1H), 5.00 (d, J=5.9 Hz, 1H), 4.14 (dd, J=11.3, 5.6 Hz, 1H), 4.07 (dd, J=10.1, 5.0 Hz, 1H), 3.89-3.79 (m, 2H), 3.76-3.72 (m, 1H), 3.63 (ddd, J=11.1, 8.8, 5.4 Hz, 1H), 3.59-3.47 (m, 4H), 3.41 (dt, J=11.6, 6.6 Hz, 1H), 3.28 (s, 1H), 1.75 (d, J=3.7 Hz, 3H), 1.64-1.41 (m, 5H), 1.27 (d, J=14.2 Hz, 5H). $^{13}C$ NMR (100 MHz, DMSO-$d_6$): δ 167.99, 167.97, 163.78, 163.73, 150.79, 150.57, 136.22, 136.07, 134.40, 131.60, 131.56, 123.02, 109.38, 109.26, 87.73, 85.89, 85.07, 82.71, 80.82, 77.49, 72.43, 69.69, 69.51, 68.38, 60.86, 60.61, 54.92, 37.39, 37.35, 29.23, 28.96, 27.93, 27.76, 26.15, 26.07, 25.76, 25.39, 25.16, 24.96, 21.27, 12.26.

5'-O-Dimethoxytrityl-2'-O-phthalimidohexyl-5-methyluridine (3a)

The mixture of 2a and 2b (10.11 g, 20.73 mmol) was co-evaporated with pyridine (50 mL) then dissolved in pyridine (80 mL) and cooled to 0° C. in an ice bath. To this mixture, dimethoxytrityl chloride (7.73 g, 22.80 mmol) was added and reaction stirred at 0° C. for 2 hours then at room temperature for 1 hour. An additional 0.4 eq of dimethoxytrityl chloride was added and reaction stirred overnight. Reaction quenched with MeOH (5 mL) then evaporated in vacuo. The reaction mixture was diluted with DCM and washed with brine twice. The organic layer was dried with $Na_2SO_4$ and evaporated in vacuo, then purified via silica gel column chromatography to yield 4.48 g of 3a (27.4%, 5.67 mmol; $R_f$=0.35 in 60% EtOAc in hexane). MS m/z 812.3 $(M+Na)^+$, 788.3 $(M-H)$. $^1H$ NMR (400 MHz, DMSO-$d_6$): δ 11.35 (s, 1H), 7.87-7.77 (m, 4H), 7.48 (d, J=0.8 Hz, 1H), 7.38 (d, J=7.4 Hz, 2H), 7.30 (t, J=7.6 Hz, 2H), 7.23 (dd, J=12.1, 8.1 Hz, 5H), 6.89 (d, J=8.0 Hz, 4H), 5.11 (d, J=6.3 Hz, 1H), 4.18 (dd, J=11.1, 5.4 Hz, 1H), 3.99 (ddd, J=12.0, 11.2, 5.9 Hz, 3H), 3.72 (s, 6H), 3.62-3.46 (m, 4H), 3.21 (ddd, J=12.9, 10.7, 3.3 Hz, 2H), 1.98 (d, J=1.8 Hz, 1H), 1.60-1.44 (m, 5H), 1.38 (s, 3H), 1.35-1.19 (m, 5H), 1.16 (t, J=7.1 Hz, 1H), 0.87 (dd, J=10.1, 4.7 Hz, 1H). $^{13}C$ NMR (100 MHz, DMSO-$d_6$): δ 170.33, 167.92, 163.61, 158.19, 158.16, 150.41, 144.67, 135.45, 135.32, 135.11, 134.33, 131.58, 129.74, 127.93, 127.65, 126.84, 122.97, 113.27, 109.60, 86.46, 85.91, 83.09, 80.53, 69.63, 68.76, 63.48, 63.19, 59.75, 55.06, 37.31, 30.16, 28.89, 27.92, 26.07, 24.95, 20.76, 20.72, 18.60, 14.08, 13.55, 11.66.

5'-O-Dimethoxytrityl-3'-O-phthalimidohexyl-5-methyluridine (3b)

The 3'-isomer (3b) was isolated by column chromatography (3.36 g, 20.5%, 4.26 mmol; $R_f$=0.18 in 60% EtOAc in hexane). MS m/z 812.0 $(M+Na)^+$, 788.3 $(M-H)$. $^1H$ NMR (400 MHz, DMSO-$d_6$): δ 11.34 (s, 1H), 7.88-7.76 (m, 4H), 7.50 (s, 1H), 7.36 (d, J=7.5 Hz, 2H), 7.33-7.15 (m, 7H), 6.87 (d, J=7.8 Hz, 4H), 5.75-5.69 (m, 1H), 5.37 (d, J=6.0 Hz, 1H), 4.27 (dd, J=10.5, 5.1 Hz, 1H), 4.05-3.94 (m, 2H), 3.91 (t, J=5.2 Hz, 1H), 3.71 (s, 6H), 3.56 (ddd, J=22.7, 11.8, 6.7 Hz, 3H), 3.21 (ddd, J=24.1, 10.8, 3.3 Hz, 2H), 1.98 (t, J=4.5 Hz, 1H), 1.60-1.37 (m, 7H), 1.34-1.13 (m, 5H), 0.94-0.83 (m, 1H). $^{13}C$ NMR (100 MHz, DMSO-$d_6$): δ 170.41, 167.93, 163.69, 158.17, 158.16, 150.57, 144.63, 135.73, 135.30, 135.17, 134.35, 131.58, 129.71, 127.91, 127.63, 126.82, 122.97, 113.24, 109.37, 88.69, 85.91, 80.60, 77.27, 72.18, 69.67, 63.49, 62.95, 59.76, 55.03, 54.90, 37.33, 30.17, 29.09, 27.88, 26.08, 25.08, 20.76, 20.72, 18.87, 18.61, 14.09, 13.55, 11.74.

5'-O-Dimethoxytrityl-2'-O-aminohexyl-5-methyluridine (4a)

3a (15.0 g, 18.99 mmol) was dissolved in 190 mL MeOH. Hydrazine (3.04 g, 94.52 mmol) was added to heterogeneous mixture and heated to reflux (66° C.) for 3.5 hours. The mixture was cooled to room temperature and evaporated in vacuo to yield a white powder. The product was dissolved in DCM and washed with ammonium hydroxide and saturated NaCl solution twice. The DCM layer was dried with $MgSO_4$ and evaporated in vacuo to yield 11.8 g. The crude material was used for next step. ($R_f$=0.02 in 5% MeOH in DCM). MS m/z 660.2 $(M+H)^+$, 682.1 $(M+Na)^+$, 658.1 $(M-H)^+$. $^1H$ NMR (400 MHz, DMSO-$d_6$): δ 7.48 (s, 1H), 7.38 (d, J=7.5 Hz, 2H), 7.30 (t, J=7.5 Hz, 2H), 7.24 (d, J=8.9 Hz, 5H), 6.89 (d, J=8.4 Hz, 4H), 5.84 (d, J=5.0 Hz, 1H), 5.74 (s, 1H), 4.19 (t, J=5.0 Hz, 1H), 3.97 (t, J=4.9 Hz, 2H), 3.72 (s, 6H), 3.63-3.45 (m, 3H), 3.27-3.15 (m, 3H), 1.48 (d, J=6.4 Hz, 2H), 1.38 (s, 3H), 1.34-1.18 (m, 6H).

5'-O-Dimethoxytrityl-2'-O-aminohexyl-C5-GalNAc (O-Bz)-5-methyluridine (5a)

Crude 4a (6.00 g) was dissolved in DCM (250 mL) and triethylamine (3.8 mL, 27.30 mmol) and stirred for 10 minutes. GalNAc-C5-NHS ester (7.31 g, 10.0 mmol) was added and the reaction mixture was stirred for 2 hours. The reaction mixture was diluted with DCM and washed with brine then the organic layer was dried with $Na_2SO_4$ and evaporated in vacuo. The crude was purified via column chromatography ($R_f$=0.36 in 5% MeOH in DCM) to yield 5a (9.56 g, 7.49 mmol, 83%). MS m/z 1298.3 $(M+Na)^+$. $^1H$ NMR (400 MHz, DMSO-$d_6$): δ 11.36 (s, 1H), 7.99-7.86 (m, 5H), 7.73-7.52 (m, 8H), 7.48 (t, J=7.7 Hz, 3H), 7.41-7.34 (m, 4H), 7.30 (t, J=7.6 Hz, 2H), 7.23 (dd, J=11.1, 8.1 Hz, 4H), 6.88 (d, J=8.1 Hz, 4H), 5.83 (d, J=4.8 Hz, 1H), 5.74 (d, J=3.9 Hz, 1H), 5.35 (dd, J=11.1, 3.3 Hz, 1H), 5.11 (d, J=6.3 Hz, 1H), 4.72 (d, J=8.5 Hz, 1H), 4.50-4.39 (m, 2H), 4.38-4.14 (m, 4H), 3.95 (t, J=4.8 Hz, 2H), 3.82-3.68 (m, 7H), 3.63-3.43 (m, 4H), 3.28-3.15 (m, 3H), 2.98 (dd, J=12.9, 6.5 Hz, 2H), 2.03 (s, 2H), 1.69 (s, 3H), 1.49 (s, 6H), 1.40-1.15 (m, 9H). $^{13}C$ NMR (100 MHz, DMSO-$d_6$): δ 171.73, 169.40, 165.20, 165.16, 164.86, 163.62, 158.18, 158.15, 150.41, 144.64, 135.31, 135.10, 133.50, 129.73, 129.16, 129.00, 128.70, 128.59, 127.91, 127.64, 126.82, 113.26, 109.59, 100.89, 85.91, 83.09, 80.60, 71.86, 69.97, 69.74, 68.77, 67.92, 63.19, 62.03, 55.04, 49.74, 35.03, 29.17, 29.04, 28.59, 26.25, 25.12, 22.69, 21.85, 11.66.

5'-O-Dimethoxytrityl-2'-O-aminohexyl-C5-GalNAc (O-Bz)-3'-O-succinate-5-methyluridine (6a)

5a (2.00 g, 1.57 mmol) was dissolved in DCM (50 mL). DMAP (574 mg, 4.70 mmol) and succinic anhydride (313 mg, 3.14 mmol) were added and reaction mixture stirred for 17 hours at room temperature. Product was purified via silica gel column chromatography (Φ=4.2 cm×15 cm) treated with 2% TEA in DCM. Product was eluted with 0-5% MeOH and 2-5% TEA in DCM and co-evaporated with acetonitrile in vacuo to yield 2.11 g (91%, 1.43 mmol) of 6a as a TEA salt ($R_f$=0.41 in 5% MeOH/5% TEA in DCM). MS m/z 1397.4 (M+Na)$^+$, 1373.4 (M−H)$^−$. $^1$H NMR (400 MHz, DMSO-$d_6$): δ 11.44 (s, 1H), 8.11 (d, J=9.0 Hz, 1H), 7.90 (dd, J=10.2, 4.1 Hz, 4H), 7.75 (s, 1H), 7.72-7.52 (m, 7H), 7.51-7.44 (m, 3H), 7.34 (ddd, J=24.0, 13.7, 7.9 Hz, 6H), 7.22 (d, J=8.7 Hz, 5H), 6.89 (d, J=7.9 Hz, 4H), 5.83 (d, J=6.1 Hz, 1H), 5.73 (d, J=3.4 Hz, 1H), 5.36 (dd, J=11.1, 3.3 Hz, 1H), 5.26-5.22 (m, 1H), 4.75 (d, J=8.5 Hz, 1H), 4.47-4.40 (m, 2H), 4.37-4.22 (m, 3H), 4.12 (d, J=3.5 Hz, 1H), 3.83-3.69 (m, 6H), 3.53-3.19 (m, 15H), 2.97 (d, J=7.8 Hz, 2H), 2.04 (s, 2H), 1.68 (s, 2H), 1.56-1.11 (m, 15H). $^{13}$C NMR (100 MHz, DMSO-$d_6$): δ 173.40, 171.76, 171.63, 169.39, 165.20, 165.15, 164.86, 163.50, 158.22, 150.50, 144.48, 135.12, 134.95, 133.48, 129.70, 129.16, 129.03, 128.70, 128.58, 127.95, 127.61, 113.30, 110.16, 100.91, 86.13, 69.97, 67.91, 62.04, 55.04, 49.73, 45.48, 40.12, 39.92, 39.71, 39.50, 39.29, 39.08, 38.87, 38.33, 34.98, 29.13, 28.93, 26.19, 25.08, 22.68, 21.82, 11.69, 10.48.

5'-O-Dimethoxytrityl-2'-O-aminohexyl-C5-GalNAc(O-Bz)-3'-O-CPG-5-methyluridine (7a)

To a solution of 6a (2.01 g, 1.36 mmol) in acetonitrile (100 mL) was added HBTU (1.03 g, 2.72 mmol), DIEA (528 mg, 4.08 mmol) and CPG (16.0 g, 130 μmol/g, 540 A) and the mixture was shaken for 24 hours. CPG was filtered out and washed with DCM, 20% MeOH in DCM, then ether. Then CPG was treated with acetic anhydride (25 mL) in pyridine (75 mL) and TEA (1 mL) for 1 hour. CPG was filtered out and washed with the same solvents above. Loading was measured twice with a spectrophotometer and average loading calculated (73.1 μmol/g).

5'-O-Dimethoxytrityl-2'-O-aminohexyl-C5-GalNAc(O-Bz)-3'-O—(N,N-diisopropyl)-β-cyanoethylphosphoramidite-5-methyluridine (8a)

5a (2.90 g, 2.27 mmol) was co-evaporated with anhydrous acetonitrile twice then put under a strict argon atmosphere. 5a was dissolved in anhydrous DCM (35 mL) and cooled to 0° C. 2-cyanoethyl-N,N,N',N'-tetraisopropylphosphordiamidite (1.37 g, 4.55 mmol) was added to stirring mixture followed by DCI (268 mg, 2.27 mmol). Mixture stirred at 0° C. for 20 minutes then room temperature for 17 hours. Reaction mixture was diluted with DCM, then washed with brine, and dried with $Na_2SO_4$ to give a pale yellow foam. The crude was purified via silica gel column chromatography (Φ=4.2 cm×19 cm; $R_f$=0.39 in EtOAc) to yield 3.20 g of 8a (95%, 2.17 mmol). MS m/z 1498.3 (M+Na)$^+$. $^1$H NMR (400 MHz, DMSO-$d_6$): δ 11.39 (s, 1H), 8.06-7.84 (m, 5H), 7.78-7.16 (m, 21H), 6.93-6.82 (m, 4H), 5.82 (d, J=4.3 Hz, 1H), 5.74 (s, 1H), 5.35 (dd, J=11.1, 3.1 Hz, 1H), 4.73 (d, J=8.5 Hz, 1H), 4.50-4.20 (m, 5H), 4.10 (dd, J=12.8, 7.7 Hz, 2H), 3.74 (t, J=11.5 Hz, 7H), 3.66-3.44 (m, 6H), 3.29-3.18 (m, 2H), 2.98 (d, J=5.3 Hz, 2H), 2.76 (t, J=5.8 Hz, 1H), 2.57 (dd, J=10.0, 5.3 Hz, 2H), 2.49 (d, J=1.5 Hz, 5H), 2.04 (s, 2H), 1.70 (s, 3H), 1.59-1.03 (m, 29H), 0.99-0.81 (m, 4H). $^{13}$C NMR (125 MHz, DMSO-$d_6$) δ 171.60, 169.26, 165.07, 165.03, 164.73, 163.48, 158.10, 158.07, 150.24, 150.22, 144.39, 144.34, 135.32, 135.08, 134.99, 134.97, 134.87, 134.80, 133.64, 133.37, 133.34, 129.65, 129.07, 129.03, 128.90, 128.88, 128.87, 128.83, 128.56, 128.45, 127.75, 127.56, 127.50, 126.74, 118.72, 118.57, 113.08, 109.63, 109.54, 100.76, 87.02, 86.62, 85.92, 85.90, 82.13, 79.89, 71.72, 69.84, 68.61, 67.78, 62.57, 62.23, 61.89, 58.43, 57.81, 57.65, 54.91, 49.60, 46.05, 45.53, 42.42, 34.88, 29.02, 28.97, 28.45, 26.17, 25.04, 24.19, 24.13, 24.03, 22.55, 21.71, 11.50. $^{31}$P NMR (162 MHz, DMSO-$d_6$) δ 154.01, 153.65.

5'-O-Dimethoxytrityl-3'-O-aminohexyl-5-methyluridine (4b)

3b (3.64 g, 4.61 mmol) was dissolved in MeOH. Hydrazine (738 mg, 23.04 mmol) was added and reaction mixture refluxed for 5.5 hours. The same procedures were followed as described for 4a to yield 2.93 g of crude 4b. ($R_f$=0.02 in 5% MeOH in DCM). MS m/z 660.2 (M+H)$^+$, 682.1 (M+Na)$^+$, 658.1 (M−H)$^−$. $^1$H NMR (400 MHz, DMSO-$d_6$) δ 7.50 (s, 1H), 7.43-7.16 (m, 9H), 6.88 (d, J=8.7 Hz, 4H), 5.73 (d, J=4.6 Hz, 1H), 4.29 (t, J=4.8 Hz, 1H), 4.02-3.89 (m, 3H), 3.46-3.15 (m, 5H), 2.24-2.16 (m, 1H), 2.05 (s, 1H), 1.58-1.10 (m, 13H). $^{13}$C NMR (100 MHz, DMSO-$d_6$): δ 163.73, 158.04, 158.02, 150.58, 144.49, 135.54, 135.18, 135.06, 129.56, 127.78, 127.50, 126.69, 113.11, 109.23, 88.49, 85.78, 80.47, 77.20, 72.02, 69.62, 62.84, 54.91, 41.44, 33.12, 29.17, 26.24, 26.11, 25.31, 11.62.

5'-O-Dimethoxytrityl-3'-O-aminohexyl-C5-GalNAc(O-Bz)-5-methyluridine (5b)

To a solution of 4b (2.85 g, 4.32 mmol) in DCM (45 mL) and TEA (1.8 mL) was added GalNAc-NHS ester (3.47 g, 4.75 mmol). Reaction stirred for 2 hours before additional 0.2 eq of GalNAc-NHS ester was added then stirred an additional 1 hour. The same procedures were followed as described for 5a to yield 3.62 g of 5b (2.84 mmol, 66%). ($R_f$=0.24 in 5% MeOH in DCM). MS m/z 1297.4 (M+Na)$^+$. $^1$H NMR (400 MHz, DMSO-$d_6$): δ 11.35 (s, 1H), 8.02-7.87 (m, 5H), 7.74-7.44 (m, 11H), 7.41-7.34 (m, 4H), 7.33-7.19 (m, 7H), 6.88 (d, J=8.8 Hz, 4H), 5.74 (dd, J=5.9, 4.1 Hz, 2H), 5.41-5.33 (m, 2H), 4.73 (d, J=8.5 Hz, 1H), 4.44 (t, J=7.9 Hz, 2H), 4.31 (ddd, J=16.9, 12.6, 7.9 Hz, 3H), 4.03-3.95 (m, 1H), 3.91 (t, J=5.1 Hz, 1H), 3.83-3.75 (m, 1H), 3.72 (s, 6H), 3.63-3.45 (m, 2H), 3.22 (dd, J=7.8, 2.9 Hz, 2H), 2.99 (d, J=6.2 Hz, 2H), 2.87 (s, 1H), 2.72 (s, 1H), 2.04 (t, J=6.4 Hz, 2H), 1.69 (s, 3H), 1.55-1.14 (m, 14H). $^{13}$C NMR (125 MHz, DMSO-$d_6$): δ 171.74, 169.40, 165.20, 165.16, 164.86, 163.65, 162.27, 158.16, 150.57, 144.58, 135.70, 135.32, 135.17, 133.74, 133.45, 129.68, 129.15, 129.01, 128.94, 128.67, 128.57, 127.89, 127.63, 126.81, 113.23, 109.37, 100.89, 88.58, 85.91, 80.64, 77.36, 72.17, 71.84, 69.98, 69.73, 68.74, 67.92, 62.98, 62.03, 55.02, 54.85, 49.75, 40.33, 40.05, 39.77, 39.49, 39.21, 38.94, 38.66, 38.34, 35.74, 35.02, 30.74, 29.23, 29.12, 28.58, 26.26, 25.21, 22.66, 21.84, 11.68.

5'-O-Dimethoxytrityl-3'-O-aminohexyl-C5-GalNAc(O-Bz)-2'-O-succinate-5-methyluridine (6b)

To a solution of 5b (1.10 g, 0.86 mmol) in DCM (20 mL) was added DMAP (315 mg, 2.58 mmol) and succinic anhydride (172 mg, 1.73 mmol). Reaction mixture was stirred for 23 hours then purified in similar manner to 6a and co-evaporated with acetonitrile in vacuo to yield 1.03 g of 6b (81%, 0.70 mmol). ($R_f$=0.18 in 5% MeOH in DCM). MS m/z 1397.4 (M+Na)$^+$, 1373.4 (M−H)$^−$. $^1$H NMR (400 MHz, DMSO-$d_6$): δ 8.09 (d, J=9.3 Hz, 1H), 7.91 (t, J=6.9 Hz, 4H), 7.76 (t, J=5.4 Hz, 1H), 7.69 (dd, J=11.3, 7.5 Hz, 3H), 7.65-7.51 (m, 5H), 7.47 (t, J=7.7 Hz, 2H), 7.41-7.33 (m, 4H), 7.32-7.16 (m, 7H), 6.87 (d, J=8.7 Hz, 4H), 5.85 (d, J=3.9 Hz, 1H), 5.74 (d, J=3.2 Hz, 1H), 5.48-5.41 (m, 1H), 5.36 (dd, J=11.1, 3.2 Hz, 1H), 5.29 (s, 1H), 4.75 (d, J=8.5 Hz, 1H), 4.49-4.39 (m, 2H), 4.38-4.19 (m, 4H), 3.28 (ddd, J=37.9, 12.7, 5.4 Hz, 11H), 3.08-2.90 (m, 3H), 2.69 (q, J=7.2 Hz, 5H), 2.60-2.52 (m, 2H), 2.05 (d, J=3.5 Hz, 2H), 1.76 (s, 1H), 1.69 (s, 3H), 1.56-0.94 (m, 28H). $^{13}$C NMR (100 MHz, DMSO-d$_6$): δ 173.63, 173.44, 172.79, 171.92, 171.52, 169.54, 165.29, 165.24, 164.94, 163.78, 158.23, 150.33, 144.57, 136.18, 135.27, 135.18, 133.84, 133.58, 129.77, 129.24, 129.05, 128.76, 128.65, 127.96, 127.70, 126.90, 113.29, 109.73, 100.98, 85.97, 80.75, 73.31, 71.96, 70.48, 62.40, 55.10, 52.06, 51.36, 45.45, 35.04, 33.35, 29.20, 29.09, 28.95, 28.77, 22.70, 21.89, 11.81, 10.05, 7.26, 7.17.

5'-O-Dimethoxytrityl-3'-O-aminohexyl-C5-GalNAc (O-Bz)-2'-O-CPG-5-methyluridine (7b)

To a solution of 6b (970 mg, 0.66 mmol) in acetonitrile (50 mL) was added HBTU (497 mg, 1.31 mmol), DIEA (339 mg, 1.97 mmol) and CPG (8.20 g, 130 µmol/g, 540 A) and the mixture was shaken for 21 hours. CPG was filtered, washed, capped and measured in the same manner as 7a to yield CPG 7b with an average loading of 56.1 µmol/g.

5'-O-Dimethoxytrityl-3'-O-aminohexyl-C5-GalNAc (O-Bz)-2'-O-(cyanoethyl N,N-diisopropyl)-phosphoramidite-5-methyluridine (8b)

5b (1.98 g, 1.55 mmol) was treated in the same manner described for 8a and silica gel column chromatography gave 1.89 g (83%, 1.28 mmol) of 8b. (R$_f$=0.43 in 100% EtOAc). MS m/z 1497.4 (M+Na)$^+$, 1474.3 (M−H)$^−$. $^1$H NMR (400 MHz, DMSO-d$_6$): δ 11.38 (s, 1H), 8.00-7.87 (m, 5H), 7.75-7.18 (m, 22H), 6.88 (dd, J=8.9, 2.7 Hz, 4H), 5.88 (dd, J=9.2, 5.1 Hz, 1H), 5.75 (d, J=3.2 Hz, 1H), 5.36 (dd, J=11.1, 3.2 Hz, 1H), 4.73 (d, J=8.5 Hz, 1H), 4.61-4.50 (m, 1H), 4.49-4.40 (m, 2H), 4.38-4.23 (m, 2H), 4.01 (ddd, J=19.3, 11.6, 4.8 Hz, 3H), 3.85-3.47 (m, 14H), 2.98 (s, 2H), 2.71 (ddd, J=11.6, 8.9, 3.9 Hz, 2H), 2.10-1.95 (m, 4H), 1.69 (s, 3H), 1.57-0.99 (m, 31H), 0.94-0.83 (m, 2H). $^{13}$C NMR (125 MHz, DMSO-d$_6$): δ 171.72, 169.37, 165.18, 165.14, 164.85, 163.58, 163.50, 158.18, 158.16, 150.48, 150.43, 144.52, 135.15, 134.98, 133.74, 133.48, 133.44, 129.66, 129.14, 129.01, 128.99, 128.98, 128.93, 128.67, 128.56, 127.91, 127.88, 127.57, 126.84, 118.81, 118.71, 113.25, 113.21, 109.72, 109.68, 100.86, 86.17, 86.02, 71.82, 69.95, 69.86, 68.72, 67.88, 63.45, 62.00, 55.00, 49.72, 39.80, 39.63, 39.46, 39.30, 39.13, 38.96, 38.33, 35.00, 30.12, 30.03, 29.26, 29.14, 29.11, 28.56, 26.29, 25.27, 25.25, 24.28, 24.22, 24.08, 24.02, 22.65, 21.84, 20.67, 19.80, 19.75, 19.67, 19.62, 18.56, 14.04, 13.50, 11.68, 11.55. $^{31}$P NMR (162 MHz, DMSO-d$_6$) δ 155.08, 154.60.

Example 21. Synthesis of S- and C-Linked GalNAc Derivatives and Building Blocks (Schemes 45-51)

Scheme 45
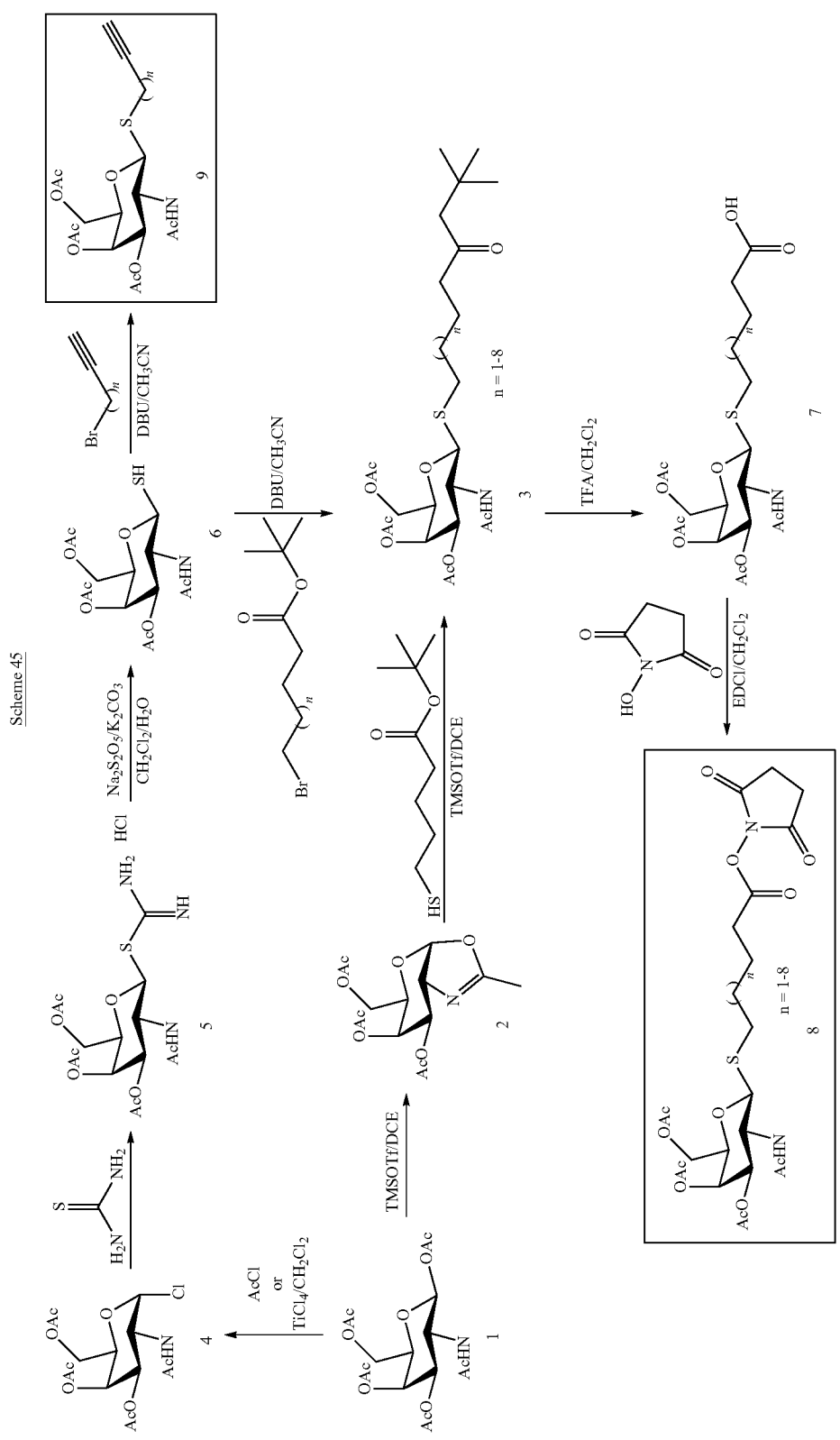

Scheme 46
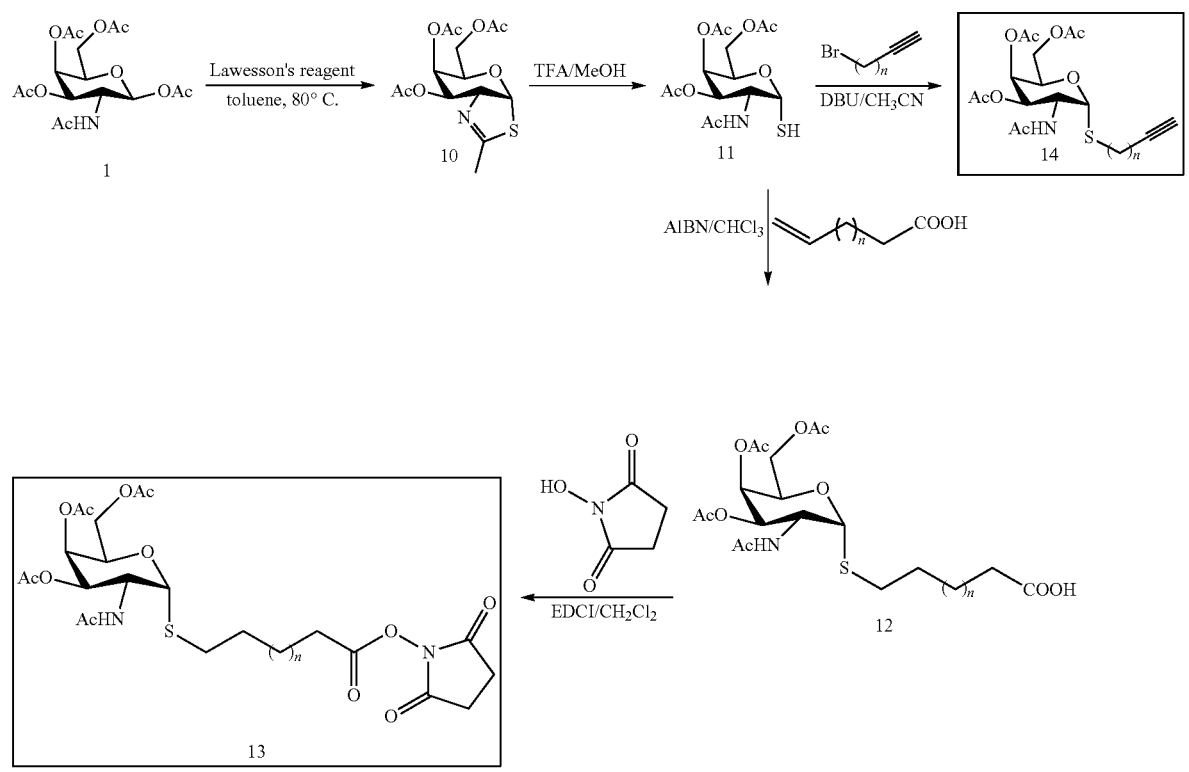
Scheme 47
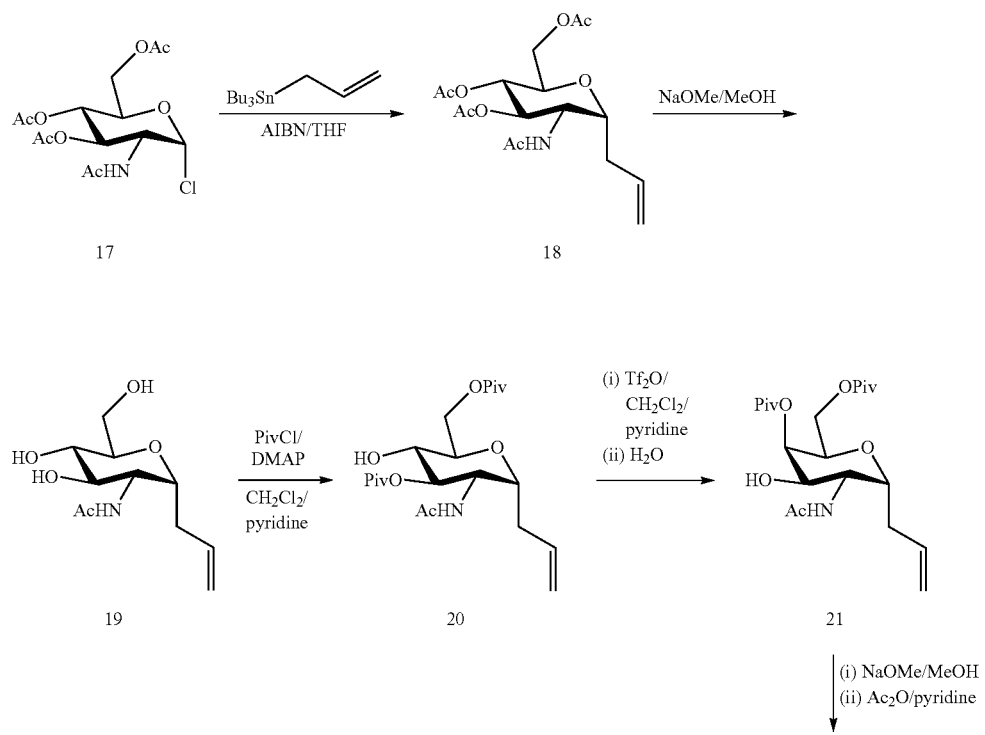

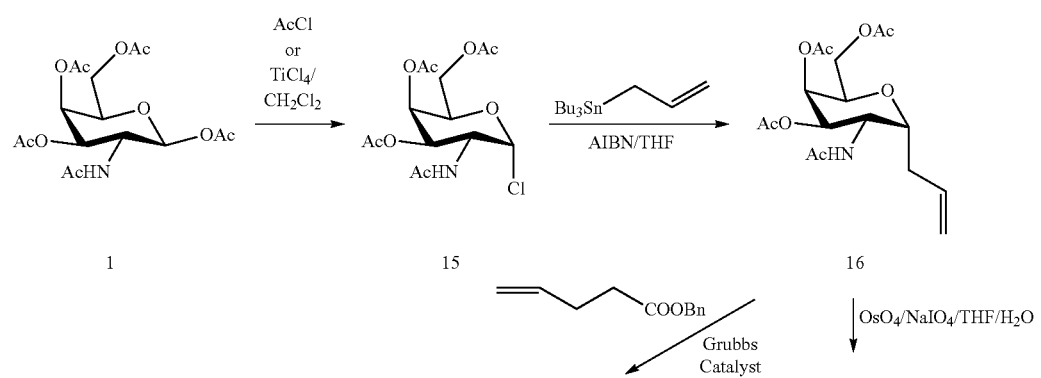
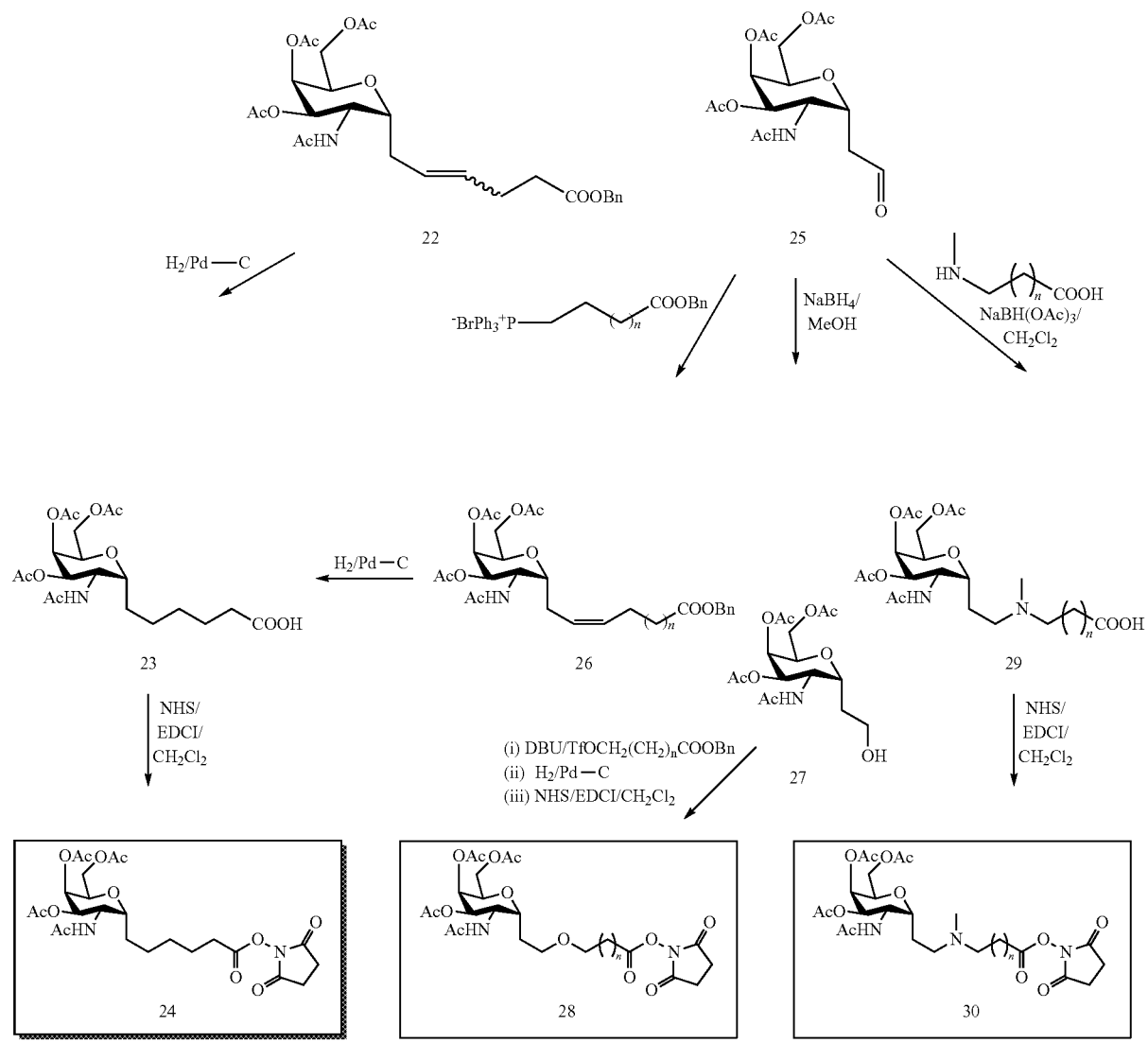

Scheme 48
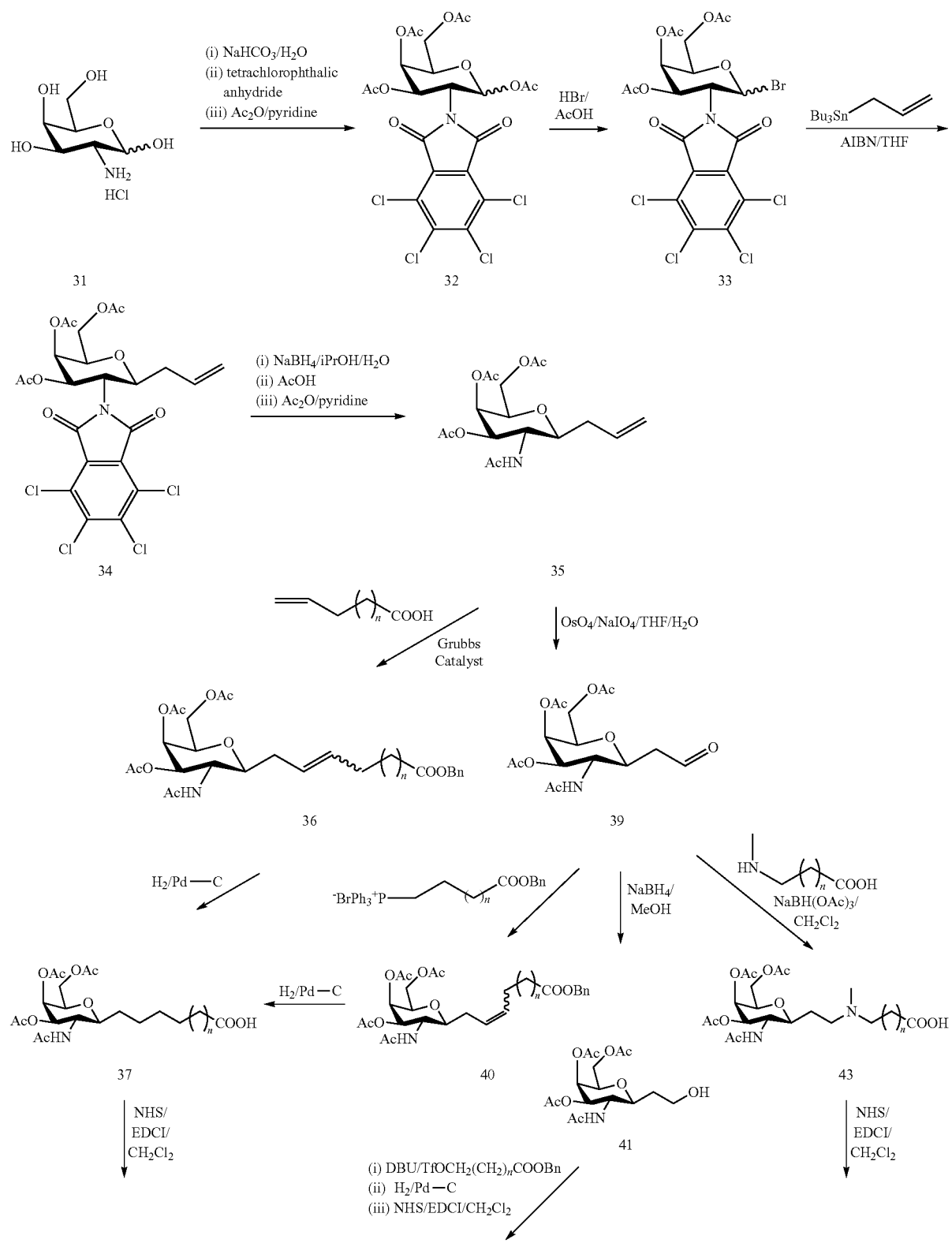

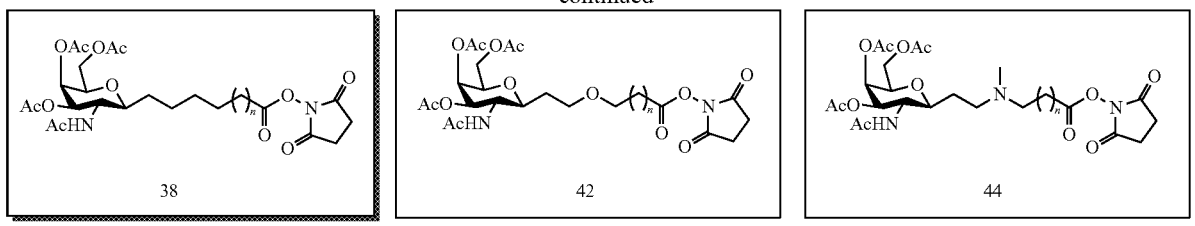
Scheme 49
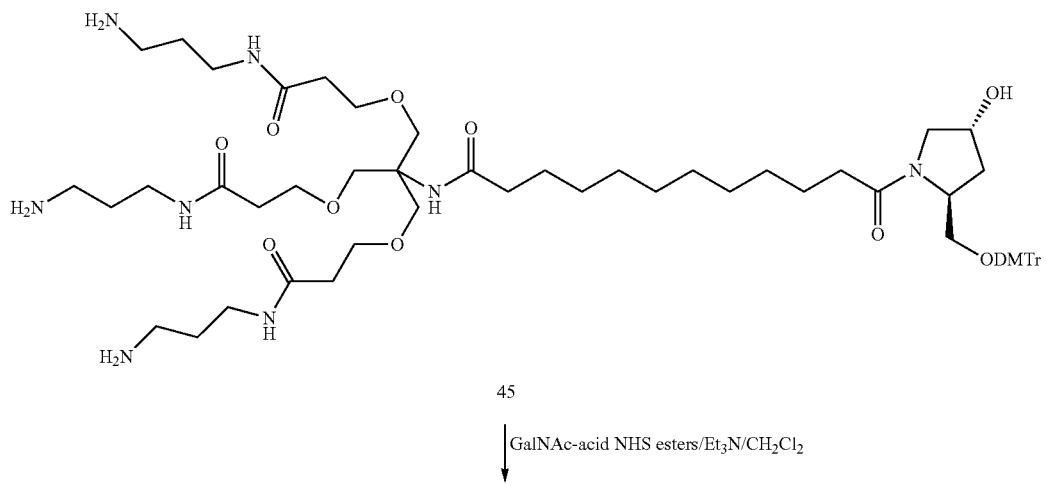
| GalNAc-acid NHS esters/Et₃N/CH₂Cl₂
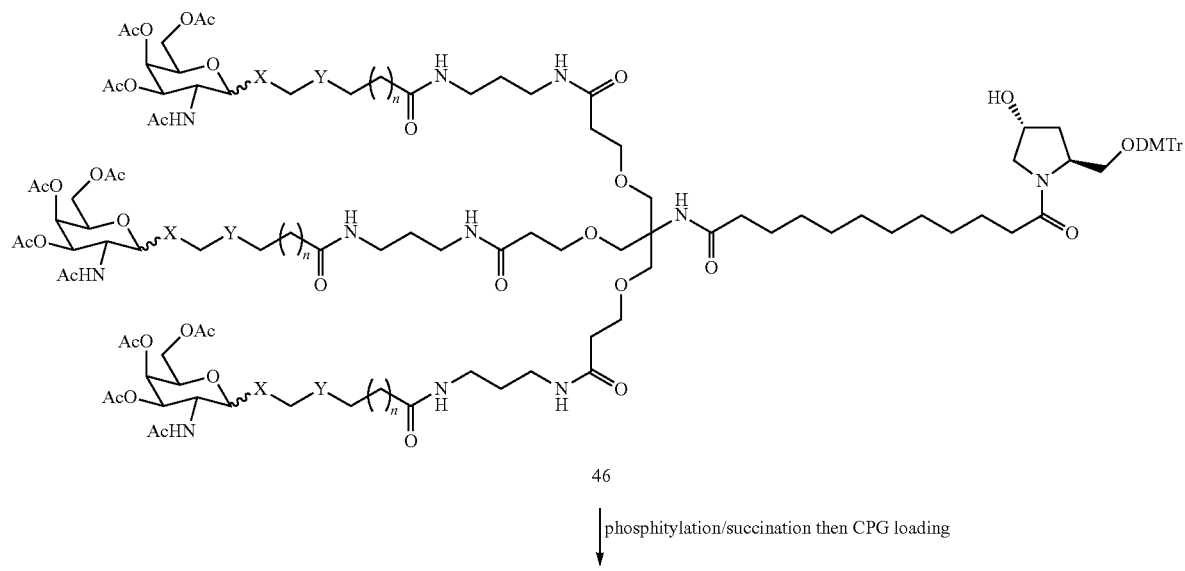
| phosphitylation/succination then CPG loading -continued
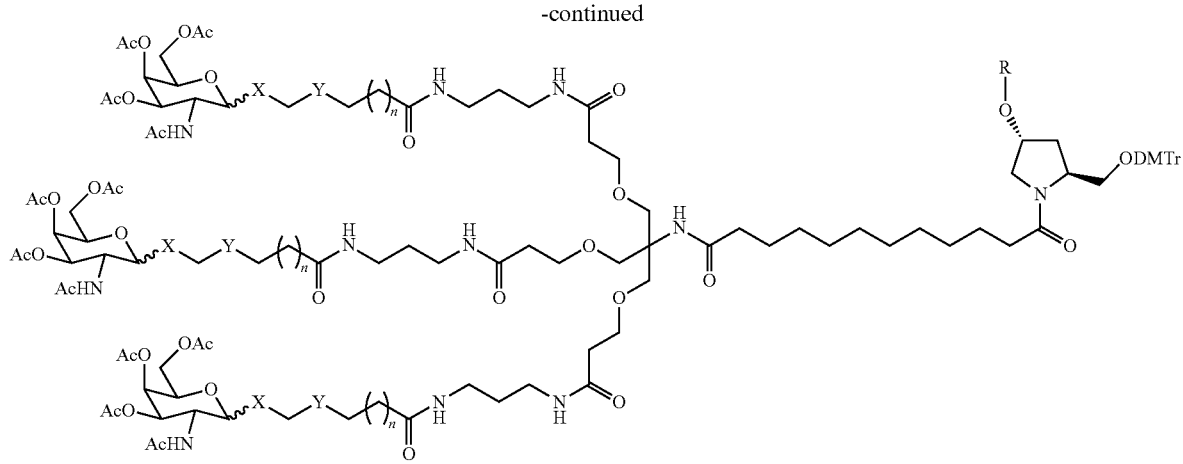
47
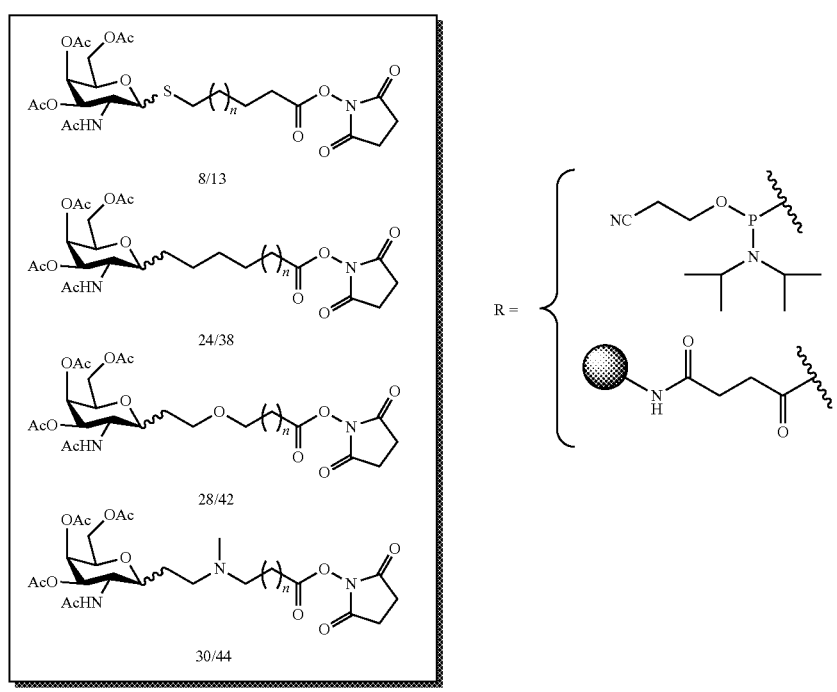
GalNAc-acid NHS esters
Scheme 50
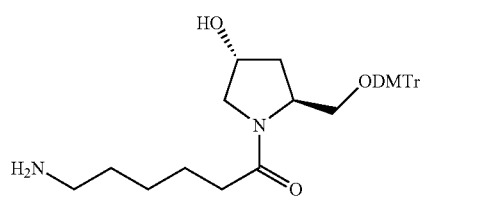
48
GalNAc-acid NHS esters/Et₃N/CH₂Cl₂

-continued
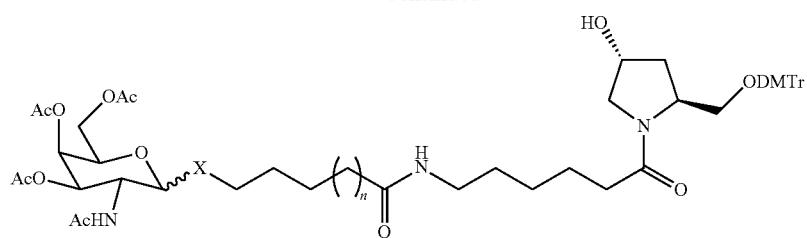
49
↓ phosphitylation/succination then CPG loading
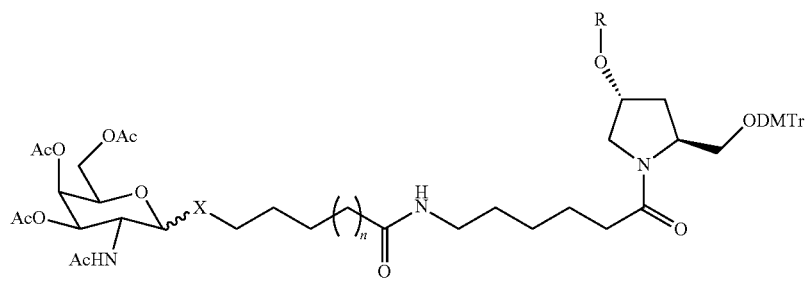
50
X = O, S, NHCO, CH₂, CH₂CH₂O, CH₂CH₂N(Me), CH₂CH₂NH
n = 1-6
GalNAc-acid NHS esters
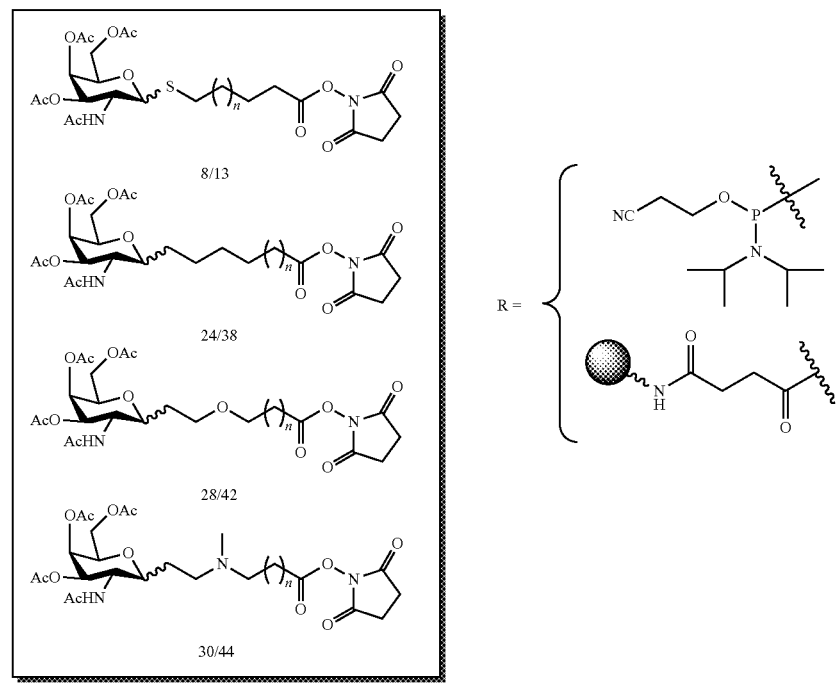

Scheme 51
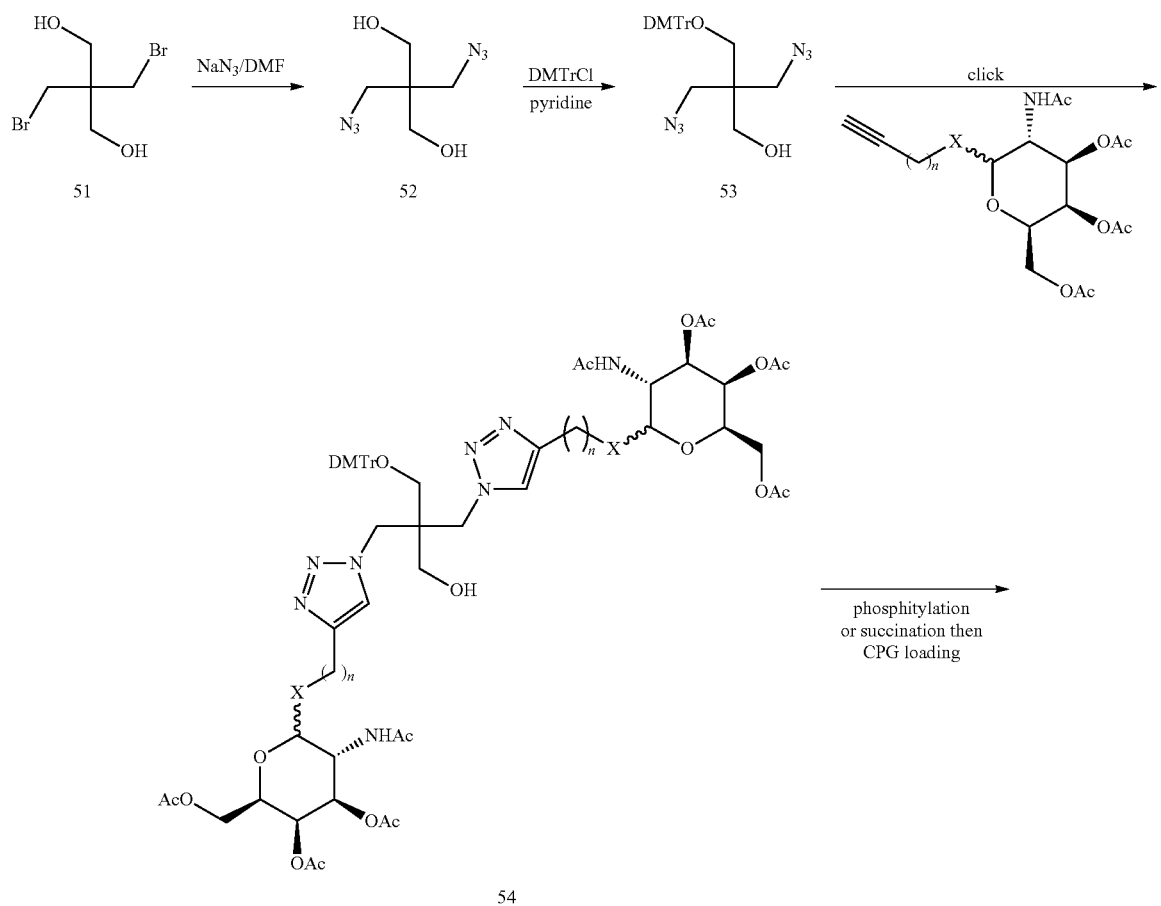

X = O, S, CH$_2$, NHCO, CONH, NHCOO, etc.
n = 1-8

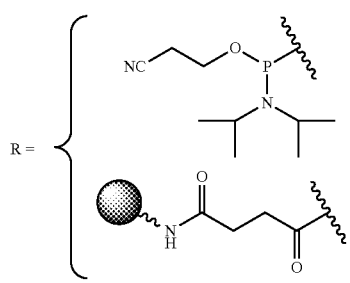

Syntheses of Compounds (Schemes 45-51)

Compound 1 (15.6 g, 40.1 mmol) was treated with TMSOTf (7.98 mL, 44.1 mmol) in DCE to give compound 2. Molecular weight for C$_{14}$H$_{20}$NO$_8$ (M+H)$^+$ Calc. 330.12, Found 330.0.

Synthesis of Compound 3:

Compound 2 (1.65 g, 5 mmol) and tert-butyl 5-mercaptopentanoate (1.0 g, 5.25 mmol) in DCE were treated with TMSOTf (0.181 mL, 1.0 mmol) overnight. Aqueous work-up and silica gel column purification gave compound 3 (380 mg, 0.731 mmol, 15%). Molecular weight for C$_{23}$H$_{37}$NNaO$_{10}$S (M+H)$^+$ Calc 542.20, Found 542.1.

Synthesis of Compound 7:

To a solution of compound 3 (380 mg, 0.731 mmol) in CH$_2$Cl$_2$ (4 mL) was added TFA (1 mL) at 0° C. The mixture was stirred at 0° C. for 2 h then at room temperature for 3 h. The solvent was evaporated and the residue was co-evaporated with toluene to give crude compound 7. This material was used for next step without purification. Molecular weight for C$_{19}$H$_{30}$NO$_{10}$S (M+H)$^+$ Calc 464.1590, Found 464.1.

Synthesis of Compound 8:

Compound 7 from the previous step (~0.731 mmol) was treated with N-hydroxysuccinimide (168 mg, 1.46 mmol) in the presence of EDCI (280 mg, 1.46 mmol) and DIEA (0.764 mL, 4.38 mmol) in CH$_2$Cl$_2$ (5 mL) for 14 h. Aqueous work-up then column chromatography gave compound 8 (284 mg, 0.507 mmol, 69% over 2 steps). Molecular weight for C$_{23}$H$_{33}$N$_2$O$_{12}$S (M+H)$^+$ Calc. 561.1754, Found 561.1.

S-alkylation of compound 6 with alkyne bromide gives compound 9. In a similar way, compound 14 is prepared from compound 11 (J. Org. Chem., 2002, 67, 2995-2999). The acid 12 is prepared according to the reported procedure.

Synthesis of Compound 13:

Compound 12 (2.40 g, 5.18 mmol) was treated with N-hydroxysuccinimide (716 mg, 6.22 mmol) in the presence of EDCI (1.19 g, 6.22 mmol) and DIEA (2.70 mL, 15.5 mmol) in CH$_2$Cl$_2$ (30 mL) for 14 h. Aqueous work-up then column chromatography gave compound 13 (1.83 g, 3.26 mmol, 63%). Molecular weight for C$_{23}$H$_{33}$N$_2$O$_{12}$S (M+H)$^+$ Calc. 561.1754, Found 561.2.

Compound 16 was prepared using reported procedures (J. Org. Chem., 2006, 71, 3619-3622; Carbohydrate Research, 1998, 309, 319-330).

Synthesis of Compound 22:

Compound 16 (1.94 g, 5.22 mmol), benzyl 4-pentenoate (2.99 g, 15.7 mmol) and Grubbs Catalyst, 2nd Generation (433 mg, 0.522 mmol) in CH$_2$Cl$_2$ (20 mL) were heated at 40° C. for 40 h. The solvent was removed and the residue was purified by silica gel column chromatography to give compound 22 (1.87 g, 3.50 mmol, 67%). Molecular weight for C$_{27}$H$_{36}$NO$_{10}$ (M+H)$^+$ Calc. 534.2339, Found 534.2.

Synthesis of Compound 23:

To a solution of compound 22 (1.85 g, 3.47 mmol) in EtOAc (30 mL) was added palladium on carbon (Aldrich: 330108-50G, 10 wt. %, Degussa type E101 NE/W: 185 mg). The reaction mixture was stirred under H$_2$ atmosphere for 14 h. After filtration through Celite, the filtrate was removed in vacuo. The residue was purified by silica gel column chromatography to give compound 23 (903 mg, 2.03 mmol, 59%). Molecular weight for C$_{20}$H$_{32}$NO$_{10}$ (M+H)$^+$ Calc. 446.2026, Found 446.1.

Synthesis of Compound 24:

Compound 23 (326 mg, 0.732 mmol) was treated with N-hydroxysuccinimide (127 mg, 1.10 mmol) in the presence of EDCI (211 mg, 1.10 mmol) and DIEA (0.383 mL, 2.20 mmol) in CH$_2$Cl$_2$ (5 mL) for 14 h. Aqueous work-up then column chromatography gave compound 24 (300 mg, 0.553 mmol, 76%). Molecular weight for C$_{24}$H$_{35}$N$_2$O$_{12}$ (M+H)$^+$ Calc. 543.2190, Found 543.2.

Oxidative cleavage of 16 gives aldehyde 25. It is reduced to an alcohol and subjected to O-alkylation with a benzyl-protected triflate followed by deprotection and esterification to give 28. Reductive amination of 25 gives acid 29 and is followed by esterification to give 30.

Compound 35 can be synthesized in a similar way reported in the literature (J. Org. Chem., 1996, 61, 6442-6445). As described above for Scheme 48, compounds 38, 42, and 44 are prepared.

Activated esters 8, 13, 24, 38, 28, 42, 30, 44 are coupled with triamine- (45) or monoamine- (48) containing hydroxyprolinol to give 46 and 49, respectively. These compounds are converted to their corresponding phosphoramidites or loaded onto solid supports.

DMTr-protected di-azide 53 is coupled with alkyne-containing GalNAc derivatives using Click chemistry to give compound 54. It is converted to its corresponding phosphoramidite or loaded onto solid support to yield 55.

Example 22. Synthesis of C2-Derivatized Galactosamine Analogs for ASGPR Binding (Schemes 52-53)

C2-derivatized galactosamine analogs may be prepared as shown in Schemes 52 and 53 below.

Scheme 52

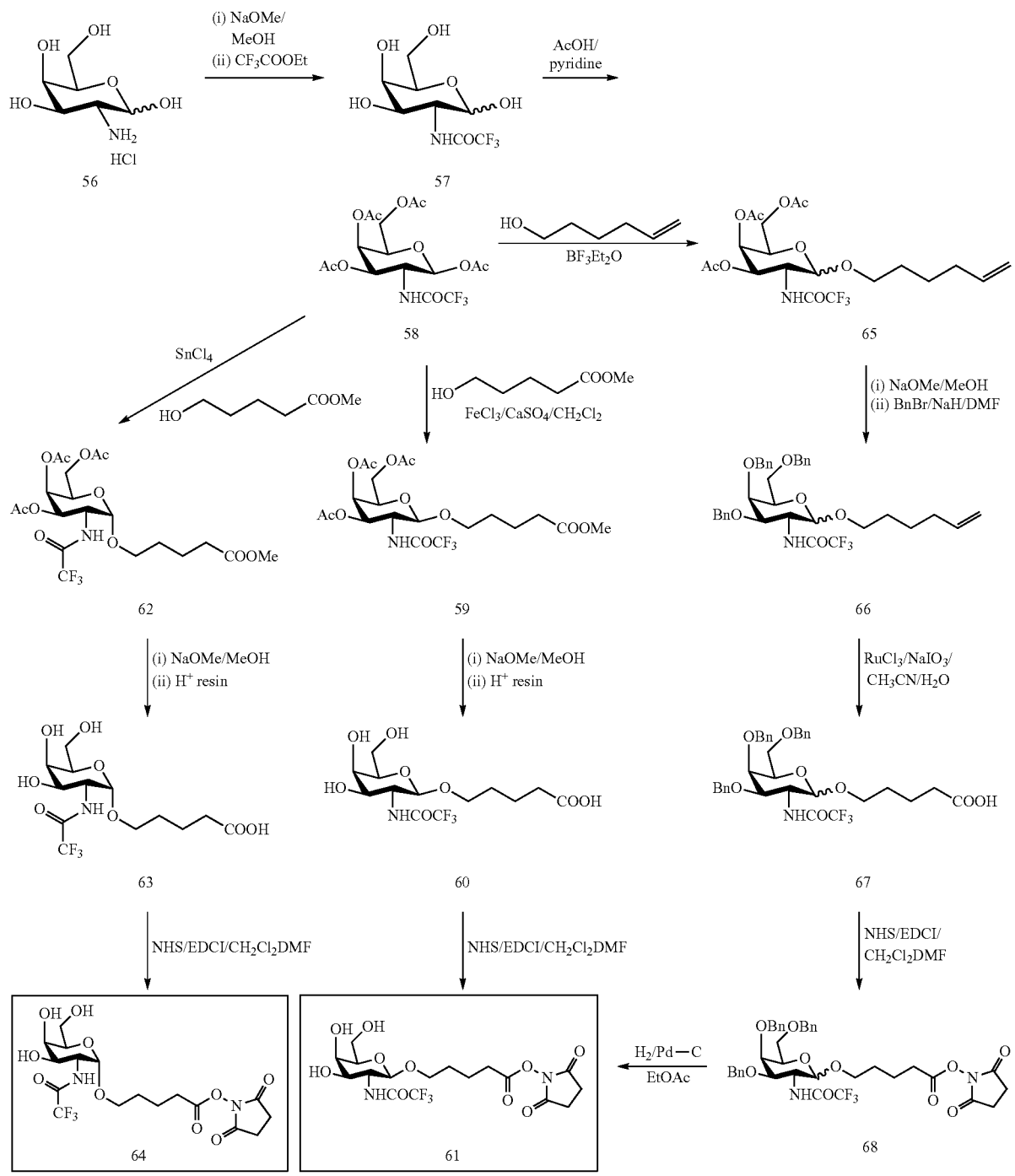

Compound 58 is prepared in a similar way to reported procedures (see, e.g., WO96/39411). O-alkylation followed by selective cleavage of acetyl groups gives compound 60 and 63. The NHS esters 61 and 64 are prepared by a standard esterification. Acetyl groups of 65 are removed selectively and the resulting hydroxyl groups are protected by benzyl groups to give 66. Oxidative cleavage of terminal alkene gives 67. Esterification followed by hydrogenation gives 61/64.

Scheme 53
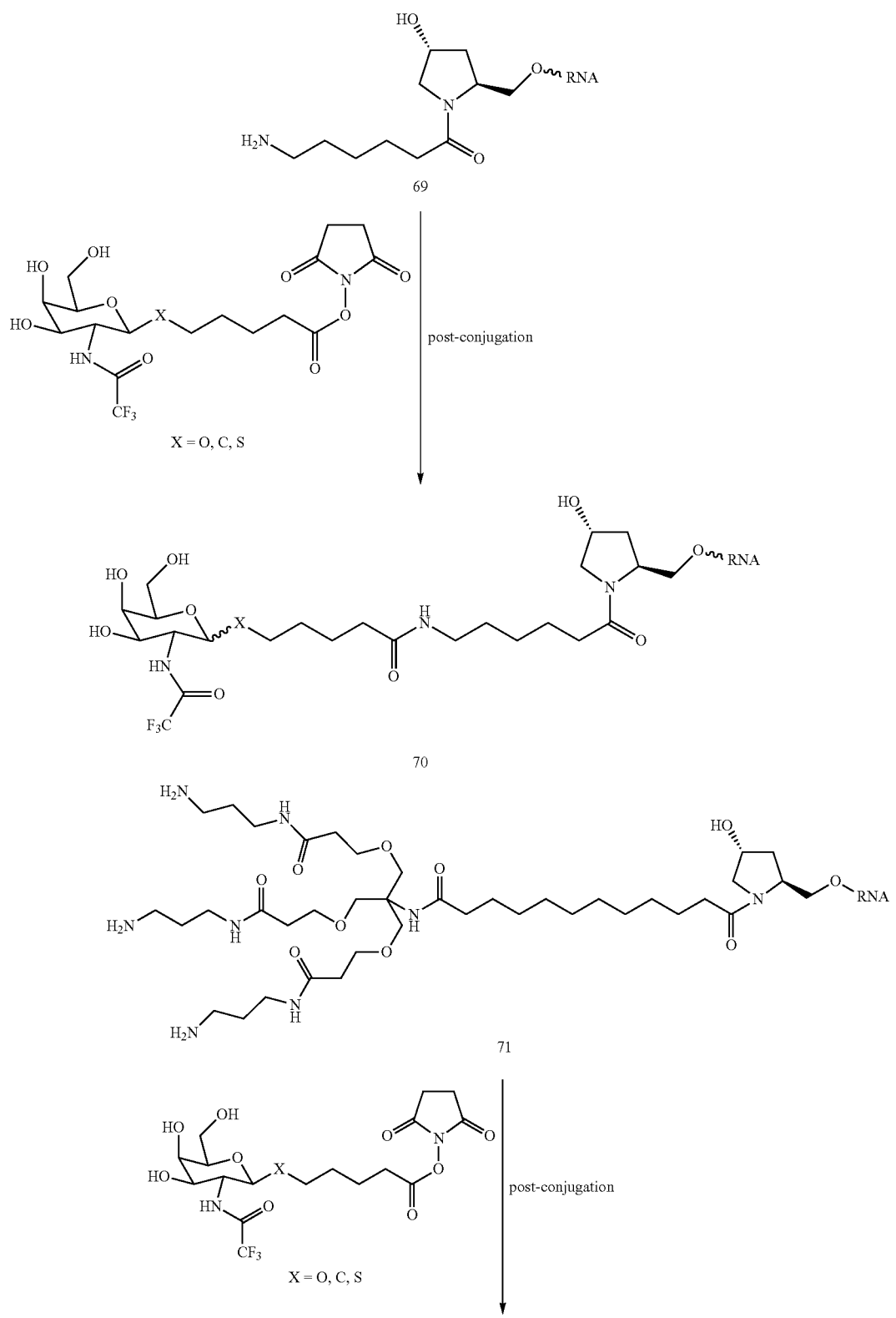

453

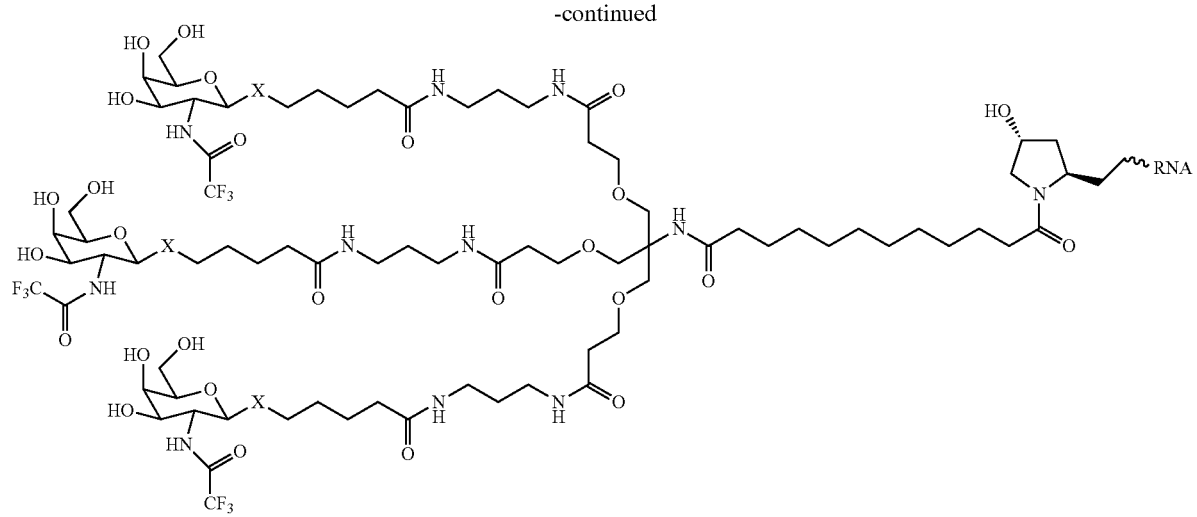

72

X = O, C, S

Trifluoromethyl acetamide- (TFA-) protected galactosamine (GalN-TFA) NHS esters are coupled with amine-containing oligonucleotides (69/71) to generate Gal-TFA containing oligonucleotides (70/72) in a post-synthetic approach.

Example 23. Synthesis of ASGPR Ligand Mimics Containing Pseudouridine Scaffold (Schemes 55-56)

Psuedouridine ligands may be prepared as shown in Schemes 55 and 56.

Scheme 55

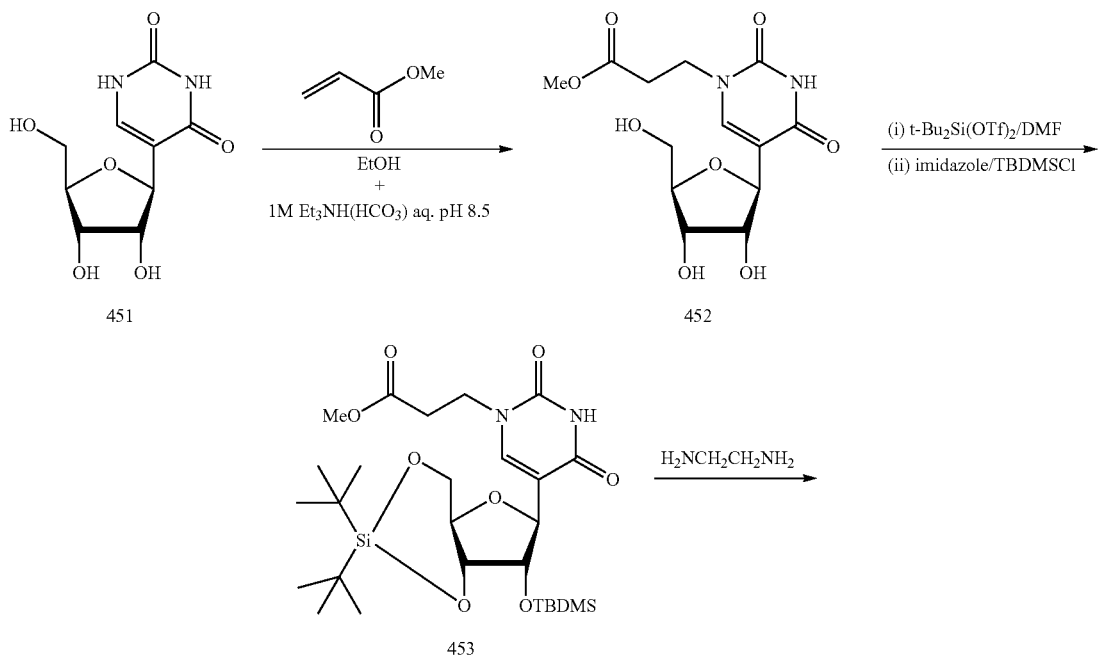

455
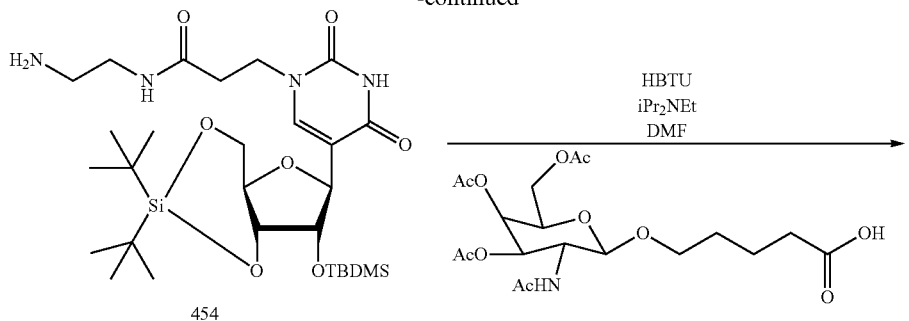
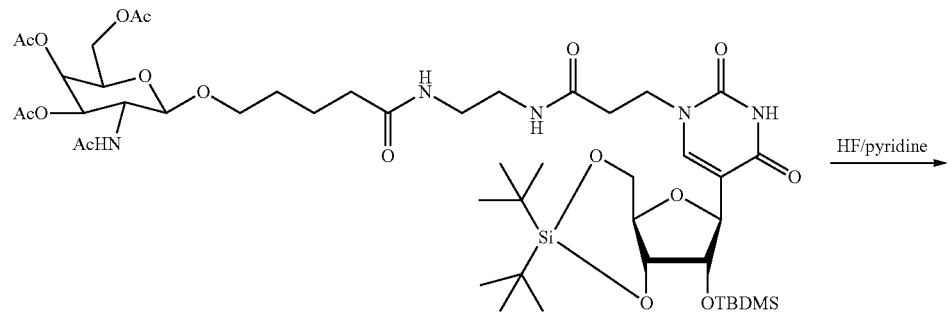
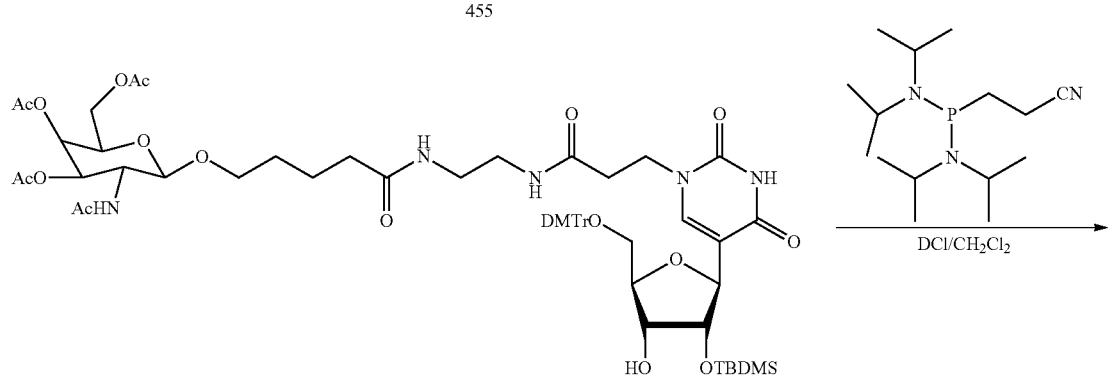
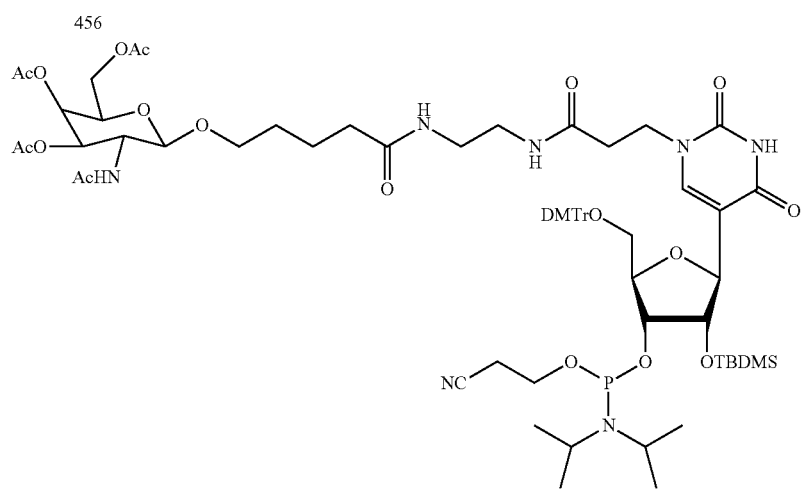
Compound 452:
To a solution of pseudouridine 451 (20 g, 81.9 mmol) in 1M triethylammoniumbicarbonate buffer (pH 8.5, 780 mL) and EtOH (940 mL), methyl acrylate (235 mL, 2.6 μmol) was added dropwise. The reaction mixture was stirred for 16 hours. After removal of the solvent, the crude material was purified by silica gel column chromatography (10% MeOH in $CH_2Cl_2$, $R_f$=0.23) to give compound 452 (26.6 g, 80.5 mmol, 98%). H NMR (MeOH-d$_4$, 400 MHz): δ 7.77 (d, J=0.8 Hz, 1H), 4.58 (d, J=4.8 Hz, 1H), 4.15 (t, J=5.2 Hz, 1H), 4.05 (t, J=5.0 Hz, 1H), 3.98-4.02 (m, 2H), 3.91-3.94 (m, D H), 3.80 (dd, J=12.0 Hz, 3.3 Hz, 1H), 3.67 (s, 3H), 3.66 (dd, J=12.0 Hz, 3.3 Hz, 1H), 2.73-2.77 (m, 2H). $^{13}$C NMR (CDCl$_3$, 100 MHz): δ 173.1, 165.4, 152.5, 145.8, 112.9, 85.6, 81.5, 75.6, 72.6, 63.3, 52.5, 46.2, 33.7. MW for C$_{13}$H$_{19}$N$_2$O$_8$ (M+H)$^+$ Calc. 330.11, Found 331.0.

Compound 453:

To a solution of compound 452 (11.67 g, 35.3 mmmmol) in DMF (65 mL), di-tert-butylsily bis(trifluoromethanesulfonate) (15.46 m, 42.4 mmol) was added dropwise under stirring at 0° C. The reaction mixture was kept stirring at 0° C. for 30 min and treated with imidazole (12.0 g, 176.5 mmol). The mixture was stirred at 0° C. for 10 min and then at room temperature for 30 min. TBDMSCl (7.98 g, 53.0 mmol) was added and the reaction mixture was heated at 75° C. for 6 hours. The reaction mixture was extracted with Et$_2$O and saturated NaHCO$_3$ aq., dried over anhydrous Na$_2$SO$_4$, and concentrated. The residue was purified by silica gel column chromatography (hexane:EtOAc=1:1, R$_f$=0.50) to give compound 453 (15.0 g, 25.6 mmol, 73%). $^1$H NMR (DMSO-d$_6$, 400 MHz): δ 11.39 (s, 1H), 7.54 (s, 1H), 4.55 (s, 1H), 4.34-4.38 (m, 1H), 4.18 (d, J=4.4 Hz, 1H), 3.86-4.00 (m, 5H), 3.58 (s, 3H), 2.67 (t, J=6.6 Hz, 2H), 1.02 (s, 9H), 0.99 (s, 9H), 0.89 (s, 9H), 0.13 (s, 3H), 0.087 (s, 3H). MW for C$_{27}$H$_{49}$N$_2$O$_8$Si$_2$ (M+H)$^+$ Calc. 585.30, Found 585.2.

Compound 454:

Compound 453 (1.24 g, 2.12 mmol) was treated with ethylenediamine (10 mL) at room temperature for 2 hours. Ethylenediamine was removed by evaporation and the residue was dried in vacuo. The crude was extracted with CH$_2$Cl$_2$ and saturated NaHCO$_3$ aq., dried over anhydrous Na$_2$SO$_4$, and concentrated to give 454 as a white solid (1.16 g, 1.89 mmol, 89%). $^1$H NMR (MeOD-d$_4$, 400 MHz): δ 7.49 (s, 1H), 4.63 (s, 1H), 4.39-4.41 (m, 1H), 4.29 (d, J=3.6 Hz, 1H), 4.00-4.04 (m, 5H), 3.18-3.26 (m, 2H), 2.69 (t, J=6.2 Hz, 2H), 2.56-2.61 (m, 2H), 1.07 (s, 9H), 1.04 (s, 9H), 0.94 (s, 9H), 0.17 (s, 3H), 0.13 (s, 3H). MW for C$_{28}$H$_{53}$N$_4$O$_7$Si$_2$ (M+H)$^+$ Calc. 613.35, Found 613.2.

Compound 455:

To a solution of GalNAc acid (930 mg, 2.08 mmol) in DMF (10 mL), HBTU (789 mg, 2.08 mmol) and iPr2NEt (1.65 mL, 9.45 mmol) were added. After 10 min, compound 454 in DMF (15 mL) was added to the solution and stirred overnight. The reaction mixture was extracted with Et$_2$O and saturated NaHCO$_3$ aq. and dried over anhydrous Na$_2$SO$_4$. After evaporation, the crude was purified by silica gel column chromatography (10% MeOH in CH$_2$Cl$_2$, R$_f$=0.43) to give compound 455 (1.83 g, 1.76 mmol, 93%). $^1$H NMR (DMSO-d$_6$, 400 MHz): δ 11.36 (s, 1H), 7.98 (s, 1H), 7.82 (d, J=9.2 Hz, 1H), 7.77, (s, 1H), 7.51 (s, 1H), 5.21 (d, J=3.6 Hz, 1H), 4.96 (dd, J=11.4 Hz, 3.4 Hz, 1H), 4.53 (s, 1H), 4.48 (d, J=8.4 Hz, 1H), 4.33-4.36 (m, 1H), 4.18 (d, J=4.4 Hz, 1H), 3.85-4.02 (m, 9H), 3.67-3.73 (m, 1H), 3.37-3.43 (m, 1H), 3.04 (s, 4H), 2.39-2.44 (m, 2H), 2.10 (s, 3H), 2.02-2.05 (m, 2H), 1.99 (s, 3H), 1.89 (s, 3H), 1.77 (s, 3H), 1.46-1.49 (m, 4H), 1.01 (s, 9H), 0.99 (s, 9H), 0.89 (s, 9H), 0.12 (s, 3H), 0.080 (s, 3H). $^{13}$C NMR (DMSO-d$_6$, 100 MHz): δ 172.0, 169.8, 169.7, 169.5, 169.2, 162.3, 150.3, 143.4, 110.6, 100.8, 83.4, 76.2, 74.7, 73.1, 70.3, 69.7, 68.5, 67.5, 66.6, 61.3, 54.9, 54.8, 49.3, 44.6, 38.3, 38.0, 34.9, 33.9, 28.5, 27.3, 26.7, 25.7, 25.6, 22.6, 22.0, 21.6, 20.4, 20.3, 19.8, 17.8, −4.5, −5.1. MW for C$_{47}$H$_{79}$N$_5$NaO$_{17}$Si$_2$ (M+Na)$^+$ Calc. 1064.49, Found 1064.2.

Compound 456:

Hydrogen fluoride-pyridine (~70% HF, 0.165 mL, 6.34 mmol) was diluted in pyridine (2 mL) under cooling. The resulting solution was added to a solution of compound 455 in CH$_2$Cl$_2$ at 0° C. and the mixture was stirred at 0° C. for 2 hours. The reaction solution was diluted in CH$_2$Cl$_2$, washed with saturated NaHCO$_3$ aq., and dried over anhydrous Na$_2$SO$_4$. After evaporation, the crude was dried in vacuo to give a white foam. To a solution of this material in pyridine (15 mL), DMTrCl (596 mg, 1.76 mmol) was added. The reaction mixture was stirred at room temperature for 4 hours and then evaporated. The residue was extracted with CH$_2$Cl$_2$ and saturated NaHCO$_3$ aq. and dried over anhydrous Na$_2$SO$_4$. The crude was purified by silica gel column chromatography (10% MeOH in CH$_2$Cl$_2$, R$_f$=0.57) to give compound 456 (1.65 g, 1.37 mmol, 78%). $^1$H NMR (DMSO-d$_6$, 400 MHz): δ 11.33 (s, 1H), 7.92 (s, 1H), 7.81 (d, J=9.6 Hz, 1H), 7.75, (s, 1H), 7.42-7.44 (m, 3H), 7.19-7.32 (m, 7H), 6.87-6.90 (m, 4H), 5.21 (d, J=3.2 Hz, 1H), 4.96 (dd, J=11.4 Hz, 3.4 Hz, 1H), 4.63 (d, J=6.4 Hz, 1H), 4.53 (d, J=2.4 Hz, 1H), 4.48 (d, J=8.4 Hz, 1H), 4.02-4.07 (m, 4H), 3.81-3.91 (m, 3H), 3.73 (s, 6H), 3.68-3.70 (m, 2H), 3.53-3.63 (m, 1H), 3.23-3.40 (m, 2H), 3.02-3.14 (m, 5H), 2.32-2.35 (m, 2H), 2.10 (s, 3H), 2.00-2.04 (m, 2H), 1.99 (s, 3H), 1.89 (s, 3H), 1.76 (s, 3H), 1.44-1.47 (m, 4H), 0.87 (s, 9H), 0.064 (s, 3H), 0.041 (s, 3H). MW for C$_{60}$H$_{81}$N$_5$NaO$_{19}$Si (M+Na)$^+$ Calc. 1226.52, Found 1226.4.

Compound 457:

To a solution of compound 456 (1.86 g, 1.54 mmol) in CH$_2$Cl$_2$ (20 mL), 2-cyanoethyl N,N,N',N'-tetraisopropylphosphordiamidite (1.47 mL, 4.63 mmol) and 4,5-dicyanoimidazole (182 mg, 1.54 mmol) were added at 0° C. The reaction mixture was stirred at room temperature for 20 hours under argon atmosphere. The reaction mixture was diluted with CH$_2$Cl$_2$ (300 mL) and washed with saturated NaHCO$_3$ (100 mL). The organic layer was separate and dried over anhydrous Na$_2$SO$_4$. The filtrate was concentrated and the resulting crude material was purified by silica gel column chromatography (EtOAc then 0-3% MeOH in CH$_2$Cl$_2$) to give 457 (1.80 g, 1.28 mmol, 83%, R$_f$=0.43 developed by 10% MeOH in CH$_2$Cl$_2$). $^1$H NMR (400 MHz, DMSO-d$_6$): δ 11.34 (s, 0.5H), 11.33 (s, 0.5H), 7.91 (s, 1H), 7.81 (d, J=9.2, 1H), 7.75 (s, 1H), 7.56 (s, 0.5H), 7.52 (s, 0.5H), 7.43 (t, J=8.2, 2H), 7.19-7.32 (m, 7H), 6.85-6.90 (m, 4H), 5.21 (s, 0.5H), 5.21 (s, 0.5H), 4.96 (dd, J=11.2, 3.4, 1H), 4.47-4.51 (m, 2H), 4.36-4.41 (m, 1H), 4.02-4.07 (m, 5H), 3.83-3.90 (m, 1H), 3.73 (s, 3H), 3.72 (s, 3H), 3.69-3.71 (m, 3H), 3.31-3.60 (m, xx H), 3.04-3.26 (m, 6H), 2.69-2.73 (m, 1H), 2.35 (t, J=6.3, 2H), 2.10 (s, 3H), 2.03 (m, 2H), 1.99 (s, 3H), 1.89 (s, 3H), 1.77 (s, 3H), 1.45-1.48 (m, 4H), 0.91-1.08 (m, 12H), 0.85 (s, 9H), 0.063 (s, 1.5H), 0.046 (s, 1.5H), 0.035 (3H). $^{31}$P NMR (DMSO-d$_6$, 162 MHz) δ 147.92, 147.70. MW for C$_{69}$H$_{98}$N$_7$NaO$_{20}$PSi (M+Na)$^+$ Calc. 1426.63, Found 1426.5.

Scheme 56
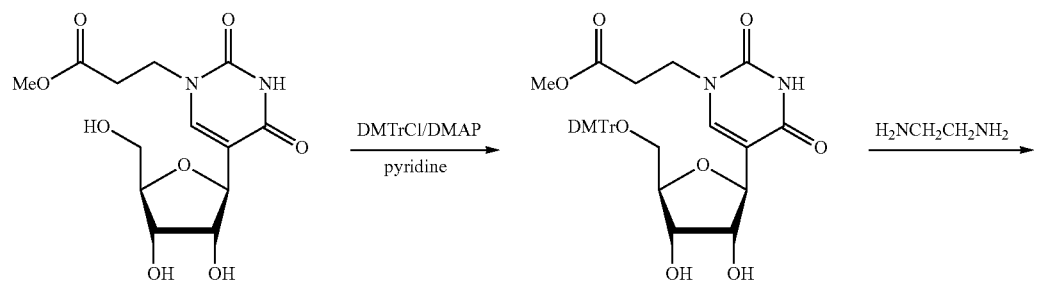
452 458
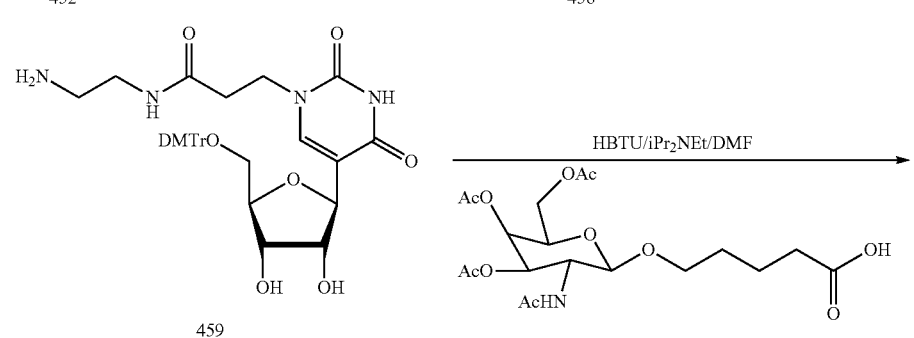
459
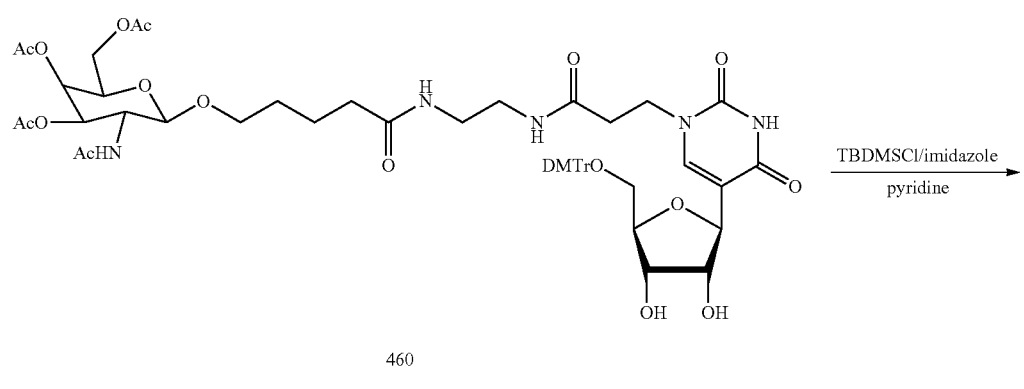
460
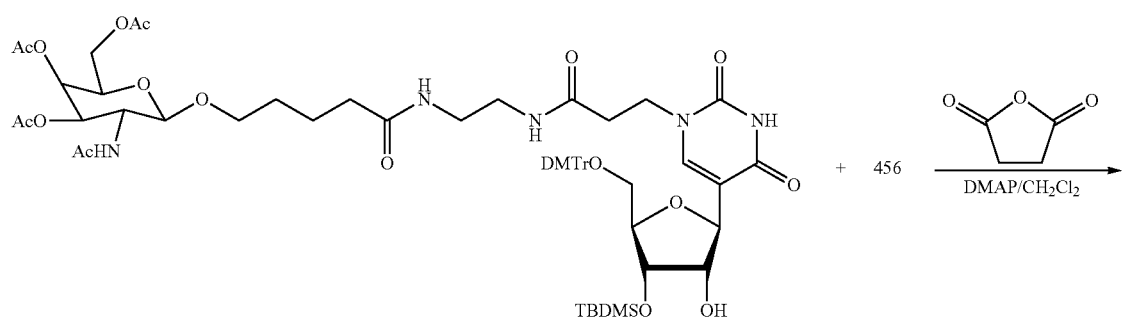
461

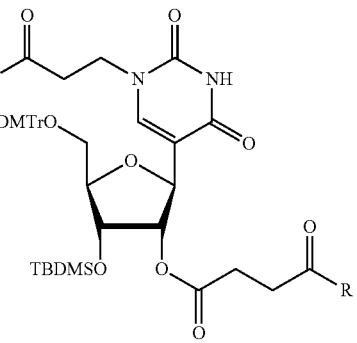

HBTU/iPrNEt/DMF/
polystyrene support

462: R = OH
463: R = NH-polystyrene support

Compound 458:

To a solution of 452 (21.5 g, 65.1 mmol) in pyridine (400 mL), DMAP (1.59 g, 13.0 mmol) and DMTrCl (22.1 g, 65.1 mmol) were added. The reaction mixture was stirred at room temperature for 6 hours and then evaporated. The residue was extracted with EtOAc and saturated $NaHCO_3$ aq., dried over anhydrous $Na_2SO_4$, and purified by silica gel column chromatography (5% MeOH in $CH_2Cl_2$, $R_f$=0.30) to give 458 (36.2 g, 57.2 mmol, 88%). $^1$H NMR (DMSO-$d_6$, 400 MHz): δ 11.37 (s, 1H), 7.48 (s, 1H), 7.36 (d, J=8.0 Hz, 2H), 7.27-7.32 (m, 6H), 7.20-7.23 (m, 1H), 6.87-6.90 (m, 4H), 5.06 (d, J=4.8 Hz, 1H), 4.80 (d, J=6.4 Hz, 1H), 4.54 (d, J=2.8 Hz, 1H), 3.84-3.93 (m, 1H), 3.73 (s, 6H), 3.56-3.69 (m, 2H), 3.53 (s, 3H), 3.15-3.17 (m, 2H), 2.58 (t, J=6.6 Hz, 2H). $^{13}$C NMR (MeOH-$d_4$, 100 MHz): δ 172.7, 165.5, 160.2, 152.7, 146.4, 144.5, 137.4, 137.3, 131.5, 131.4, 129.6, 128.9, 128.0, 114.2, 114.0, 87.5, 83.0, 81.1, 76.2, 72.4, 64.7, 55.8, 52.4, 46.2, 33.5. MW for $C_{34}H_{36}N_2NaO_{10}$ (M+Na)$^+$ Calc. 655.23, Found 655.2.

Compound 459:

Compound 458 (13.9 g, 22.0 mmol) was treated with ethylenediamine (75 mL) at room temperature for 18 hours. Ethylenediamine was removed by evaporation and co-evaporated with toluene. The residue was extracted with $CH_2Cl_2$/MeOH (180 mL/20 mL) and $H_2O$ (50 mL) and the organic layer was dried over anhydrous $Na_2SO_4$, and then concentrated. The crude was crystallized with hexane and $CH_2Cl_2$ to give 459 as a pale yellow solid (11.7 g, 17.7 mmol, 80%). $^1$H NMR (MeOD-$d_4$, 400 MHz): δ 7.57 (s, 1H), 7.21-7.48 (m, 9H), 6.86-6.88 (m, 4H), 4.71 (d, J=3.2 Hz, 1H), 4.02-4.17 (m, 3H), 3.79-3.82 (m, 1H), 3.78 (s, 6H), 3.31-3.36 (m, 3H), 3.15 (t, J=6.2 Hz, 2H), 2.63 (t, J=6.0 Hz, 2H), 2.41 (t, J=6.2 Hz, 2H). MW for $C_{35}H_{40}N_4NaO_9$ (M+H)$^+$ Calc. 683.27, Found 683.2.

Compound 460:

To a solution of GalNAc acid (5.60 g, 12.5 mmol) in DMF (50 mL), HBTU (4.70 g, 12.4 mmol) and iPr2NEt (10.3 mL, 59.3 mmol) were added. After 10 min, compound 459 in DMF (50 mL) was added to the solution and stirred overnight. The reaction mixture was extracted with EtOAc and $H_2O$ and dried over anhydrous $Na_2SO_4$. After evaporation, the crude was purified by silica gel column chromatography (10% MeOH in $CH_2Cl_2$, $R_f$=0.50) to give compound 460 (6.85 g, 6.28 mmol, 59%). $^1$H NMR (DMSO-$d_6$, 400 MHz): δ 11.33 (s, 1H), 7.93 (s, 1H), 7.81 (d, J=9.2 Hz, 1H), 7.75, (s, 1H), 7.41-7.44 (m, 3H), 7.27-7.31 (m, 6H), 7.18-7.22 (m, 1H), 6.87-6.89 (m, 4H), 5.21 (d, J=3.2 Hz, 1H), 5.03 (d, J=4.8 Hz, 1H), 4.96 (dd, J=11.2 Hz, 3.6 Hz, 1H), 4.78 (d, J=6.4 Hz, 1H), 4.51 (d, J=2.8 Hz, 1H), 4.48 (d, J=8.4 Hz, 1H), 4.02 (m, 3H), 3.82-3.92 (m, 4H), 3.73 (s, 6H), 3.54-3.70 (m, 3H), 3.36-3.42 (m, 1H), 3.02-3.21 (m, 6H), 2.35 (t, J=6.6 Hz, 2H), 2.09 (s, 3H), 2.02 (t, J=7.0 Hz, 2H), 1.99 (s, 3H), 1.88 (s, 3H), 1.76 (s, 3H), 1.43-1.49 (m, 4H). $^{13}$C NMR (DMSO-$d_6$, 100 MHz): δ 172.0, 169.9, 169.8, 169.5, 169.4, 169.2, 162.6, 157.9, 150.3, 144.9, 143.2, 135.7, 135.6, 129.7, 127.7, 126.5, 113.0, 111.3, 100.9, 85.2, 80.7, 79.8, 73.5, 70.8, 70.4, 69.7, 68.5, 66.6, 64.1, 61.3, 54.9, 54.8, 49.3, 48.5, 44.8, 38.3, 38.1, 34.9, 33.9, 28.5, 22.7, 21.6, 20.4, 20.3. MW for $C_{54}H_{67}N_5NaO_{19}$ (M+Na)$^+$ Calc. 1112.43, Found 1112.2.

Compound 461:

To a solution of compound 460 (1.55 g, 1.42 mmol) in pyridine (10 mL), TBDMSCl (214 mg, 1.42 mmol) and imidazole (290 mg, 4.26 mmol) were added. The reaction mixture was stirred overnight. After evaporation, the residue was extracted with $CH_2Cl_2$ and saturated $NaHCO_3$ aq. and dried over anhydrous $Na_2SO_4$. The crude material was purified by silica gel column chromatography (5% MeOH in $CH_2Cl_2$, $R_f$=0.15) to give compound 461 (550 mg, 0.457 mmol, 32%) and its 2'-O-TBDMS isomer 456 (390 mg, 0.324 mmol, 23%). $^1$H NMR (DMSO-$d_6$, 400 MHz): δ 11.32 (s, 1H), 7.94 (s, 1H), 7.82 (d, J=9.2 Hz, 1H), 7.75, (s, 1H), 7.54 (s, 1H), 7.40-7.41 (m, 2H), 7.21-7.32 (m, 7H), 6.87-6.89 (m, 4H), 5.21 (d, J=3.2 Hz, 1H), 4.96 (dd, J=11.2 Hz, 3.6 Hz, 1H), 4.73 (d, J=4.8 Hz, 1H), 4.47-4.49 (m, 2H), 3.95-4.02 (m, 5H), 3.83-3.88 (m, 2H), 3.72 (s, 6H), 3.68-3.71 (m, 3H), 3.38-3.41 (m, 1H), 3.03-3.19 (m, 6H), 2.39 (t, J=6.6 Hz, 2H), 2.10 (s, 3H), 2.02 (t, J=7.0 Hz, 2H), 1.99 (s, 3H), 1.89 (s, 3H), 1.77 (s, 3H), 1.45-1.50 (m, 4H), 0.74 (s, 9H), −0.034, (s, 3H), −0.11 (s, 3H). MW for $C_{60}H_{81}N_5NaO_{19}Si$ (M+Na)$^+$ Calc. 1226.52, Found 1227.4.

Compound 462:

To a solution of compound 461 (2.28 g, 1.89 mmol) in $CH_2Cl_2$ (60 mL), DMAP (693 mg, 5.67 mmol) and succinic anhydride (378 mg, 3.78 mmol) were added. The reaction mixture was stirred overnight at room temperature. Silica gel column chromatography (10% MeOH/10% $Et_3N$ in $CH_2Cl_2$, $R_f$=0.44) of the crude mixture without aqueous work-up gave the compound 462 as the corresponding triethylammonium salt (2.50 g, 1.78 mmol, 94%). $^1$H NMR (DMSO-$d_6$, 400 MHz): δ 8.42 (s, 1H), 8.18 (s, 1H), 8.05 (d, J=9.2 Hz, 1H), 7.71 (s, 1H), 7.48-7.50 (m, 2H), 7.29-7.40

(m, 7H), 6.95-6.97 (m, 4H), 5.28-5.30 (m, 2H), 5.07 (dd, J=11.2 Hz, 3.6 Hz, 1H), 4.70 (d, J=4.0 Hz, 1H), 4.60 (d, J=8.4 Hz, 1H), 4.37 (t, J=5.8 Hz, 1H), 4.09-4.13 (m, 3H), 3.91-3.97 (m, 2H), 3.81 (s, 6H), 3.78-3.85 (m, 3H), 3.42-3.49 (m, 2H), 3.27-3.30 (m, 1H), 3.10-3.16 (m, 5H), 2.43-2.53 (m, 5H), 2.18 (s, 3H), 2.12 (t, J=7.2 Hz, 2H), 2.07 (s, 3H), 1.97 (s, 3H), 1.85 (s, 3H), 1.52-1.57 (m, 4H), 0.79 (s, 9H), 0.00 (s, 3H), −0.075 (s, 3H). $^{13}$C NMR (DMSO-d$_6$, 100 MHz): δ 173.8, 172.2, 172.1, 171.5, 169.9, 169.6, 169.5, 169.3, 162.5, 158.1, 150.4, 144.7, 144.6, 135.5, 135.4, 129.7, 127.7, 126.6, 113.1, 109.5, 100.9, 85.6, 81.6, 77.5, 74.2, 71.0, 70.5, 69.8, 68.5, 66.7, 63.6, 61.4, 52.0, 49.3, 38.4, 38.2, 34.9, 34.0, 30.0, 29.5, 28.5, 25.8, 25.5, 25.4, 22.7, 21.6, 21.4, 20.5, 20.4, 17.5, 14.7, 7.1, −5.1, −5.4. MW for $C_{64}H_{84}N_5O_{22}Si$ (M−H)$^-$ Calc. 1302.54, Found 1302.4.

Compound 463:

To a solution of compound 462 (98 mg, 0.07 mmol) in DMF (10 mL), HBTU (30 mg, 0.077 mmol), iPr2NEt (0.061 mL, 0.35 mmol), and aminomethyl polystyrene support (ARTVISION, considered as 70 μmol/g, 1.10 g, 0.077 mmol) were successively added. The mixture was shaken for 24 hours, then filtered, washed with CH$_2$Cl$_2$, and dried in vacuo. The residual amino groups were capped by shaking for 1 hour with pyridine (15 mL), acetic anhydride (5 mL), and triethylamine (1 mL). After filtering, washing with CH$_2$Cl$_2$ (100 mL), then 50% MeOH/CH$_2$Cl$_2$ (100 mL), and drying in vacuo gave compound 463 (1.12 g). Loading: 47 μmol/g.

Example 24. Synthesis of ASGPR Ligand Mimics Containing N-Glycosidic Linkage (Schemes 57-63)

ASGPR ligands containing N-glycosidic linkages can be prepared as shown in Schemes 57-63.

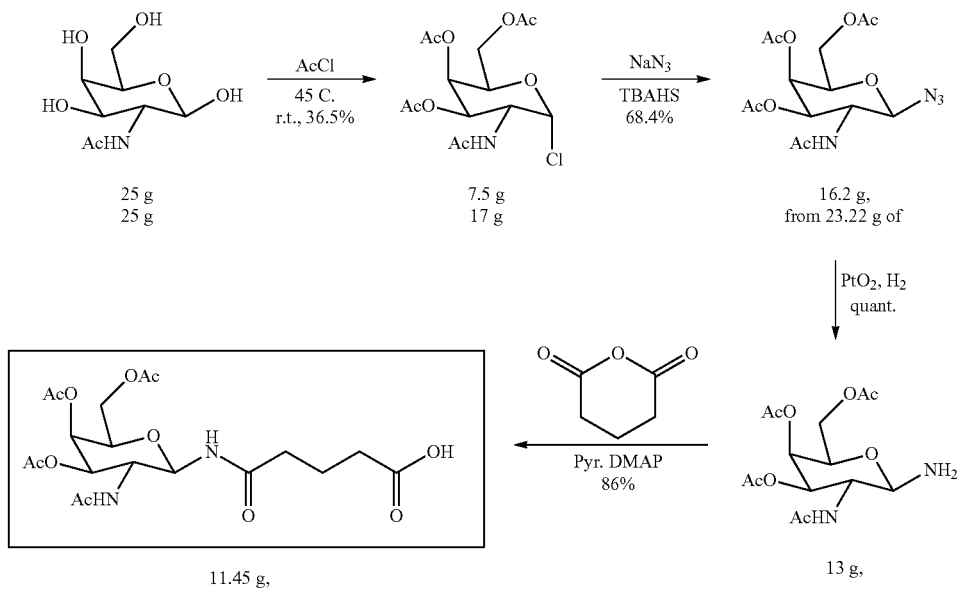

Scheme 57

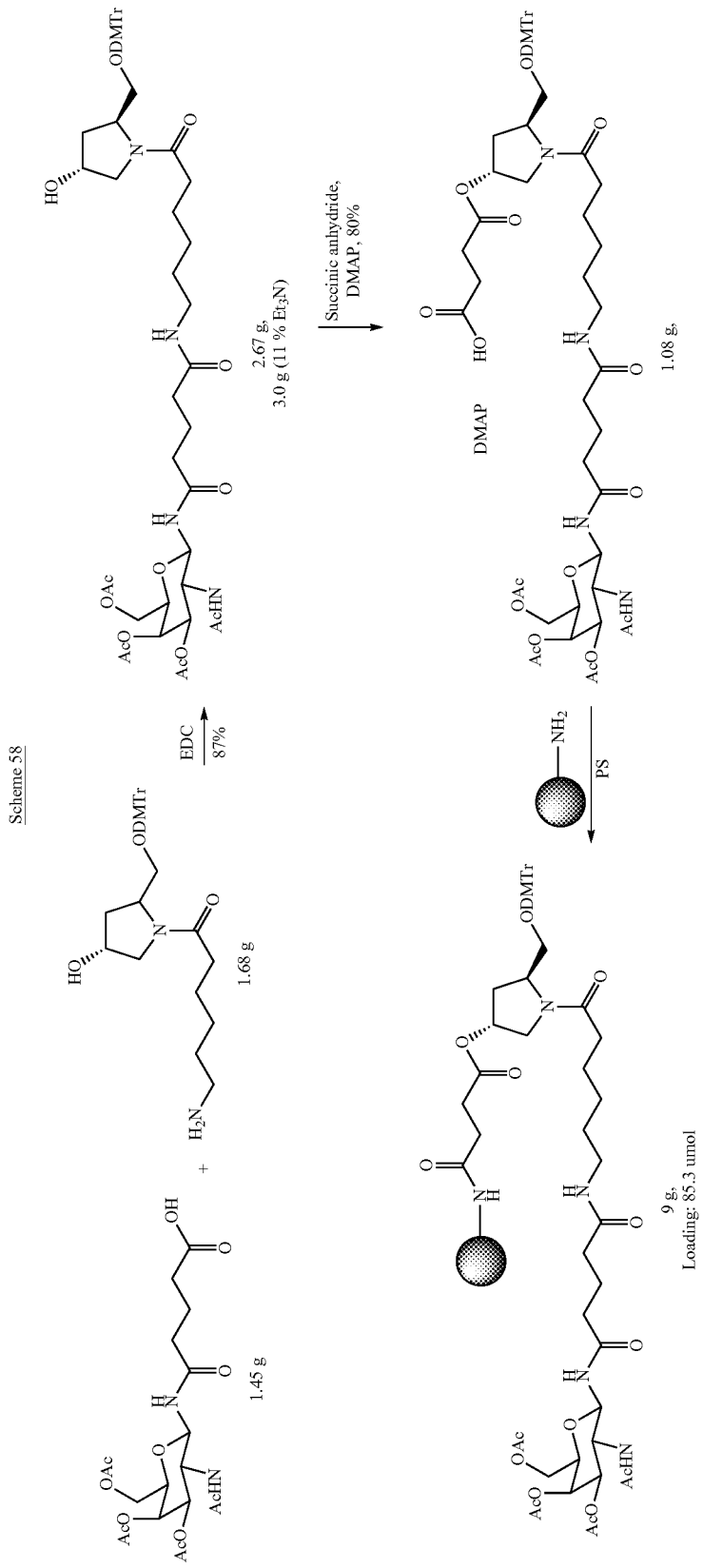
Scheme 58

Scheme 59
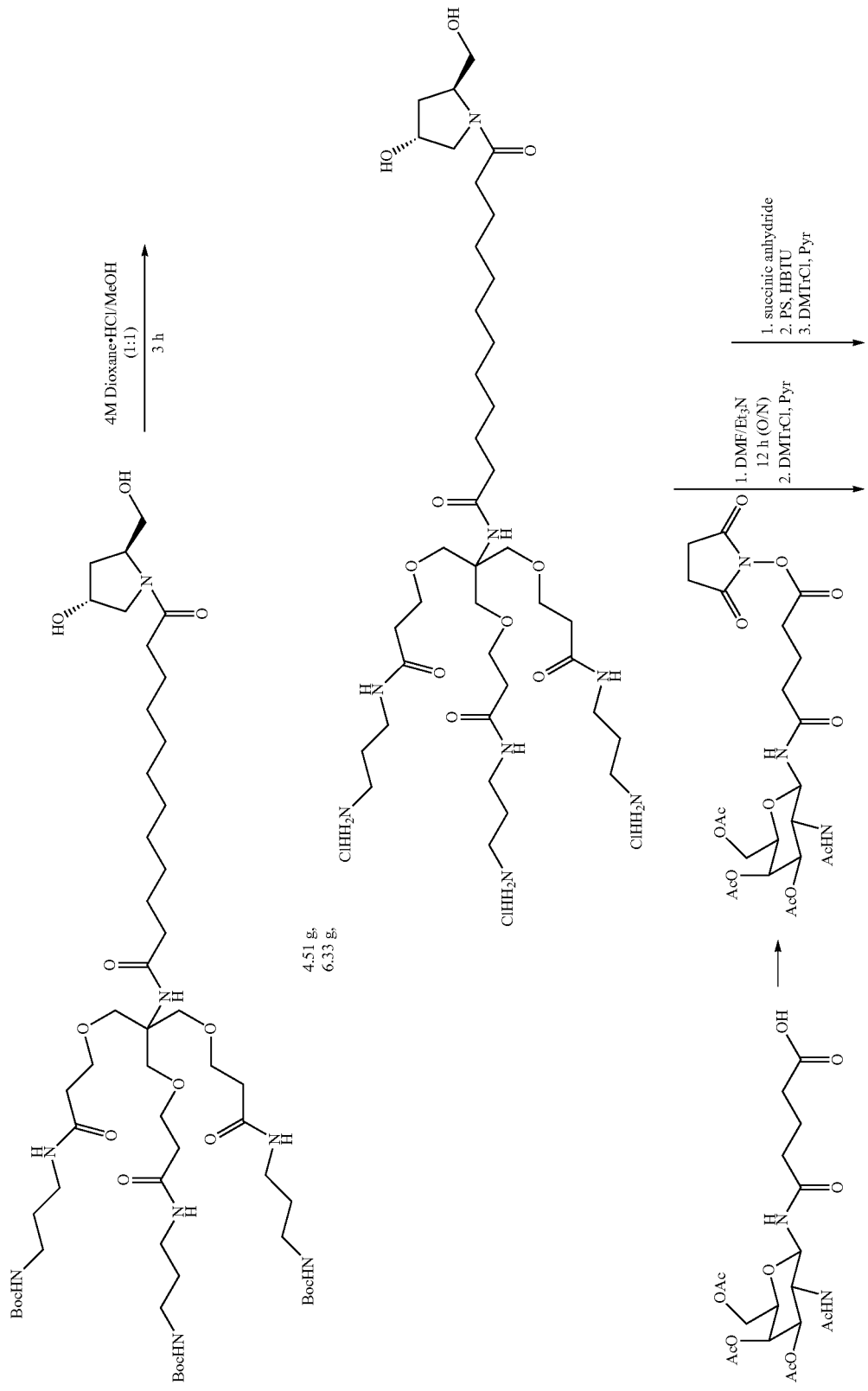

-continued
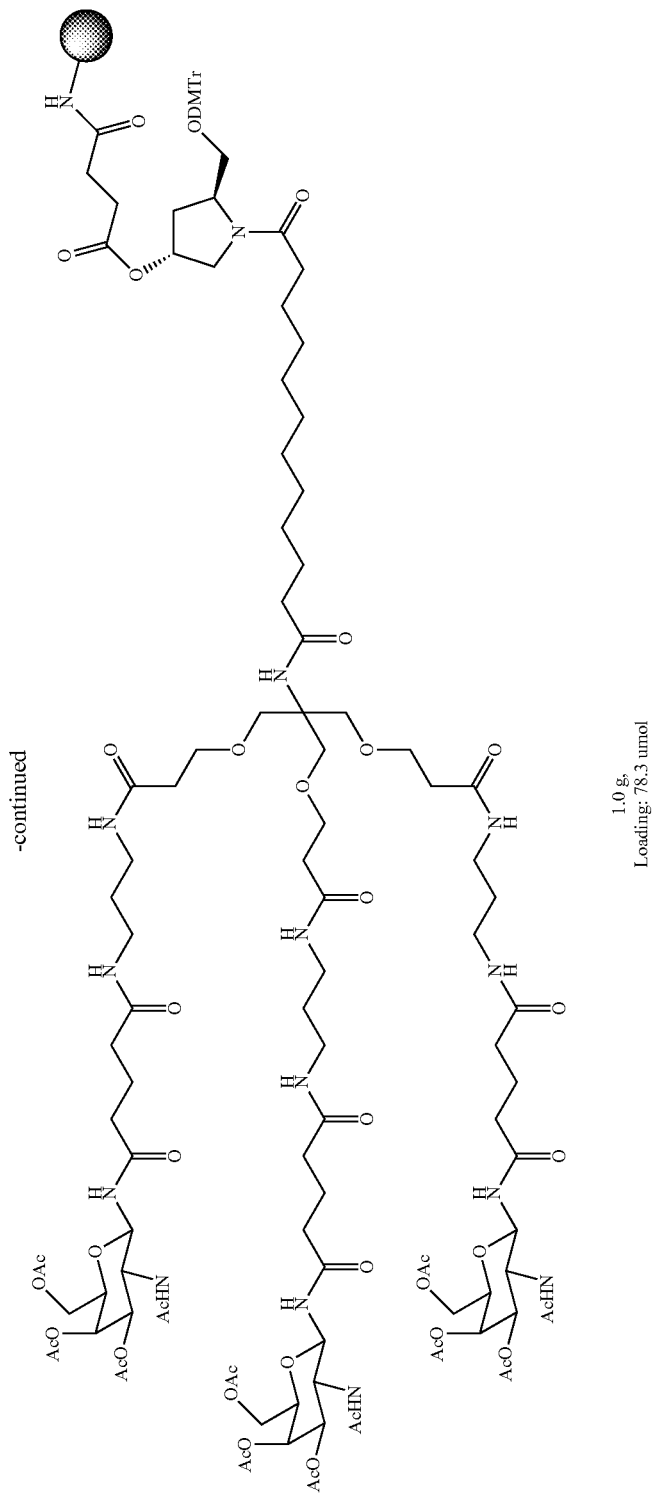
1.0 g,
Loading: 78.3 umol

Scheme 60
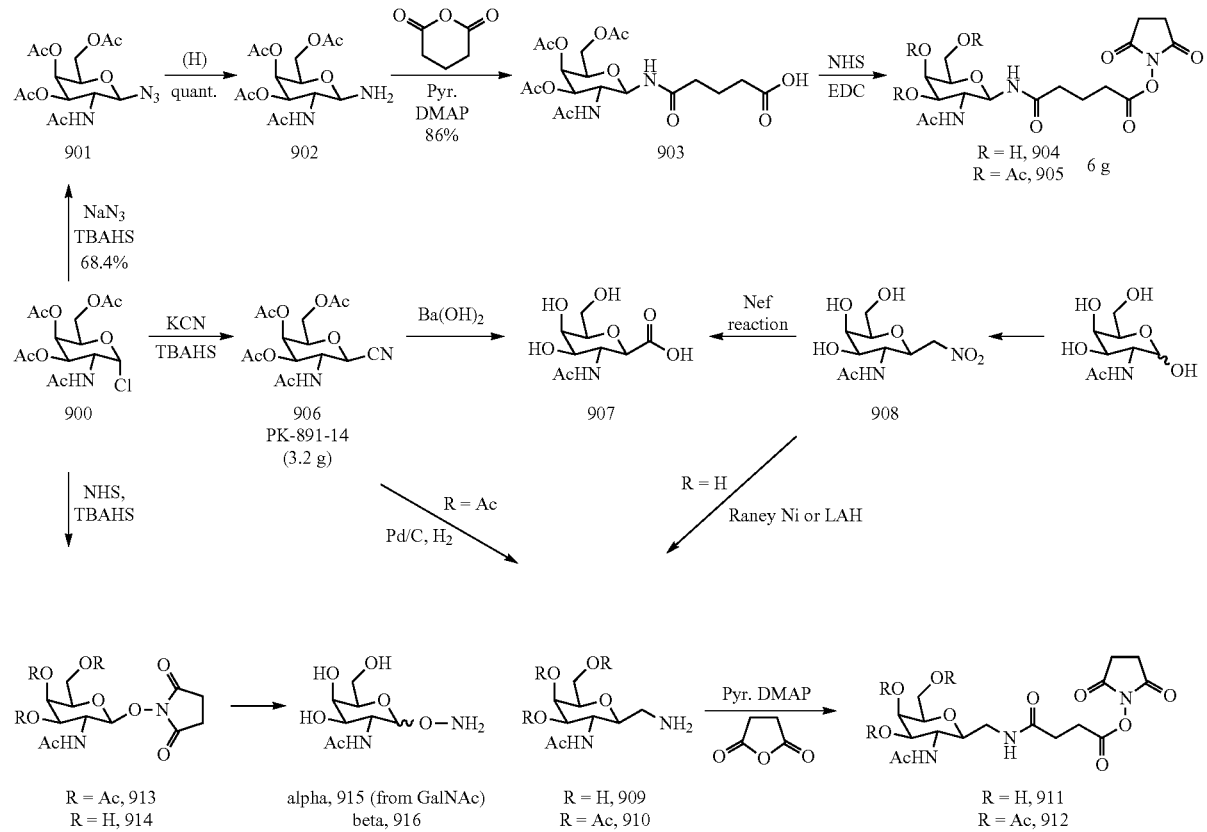
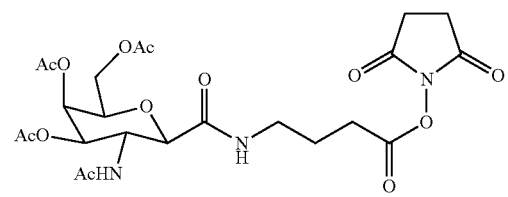
Scheme 61
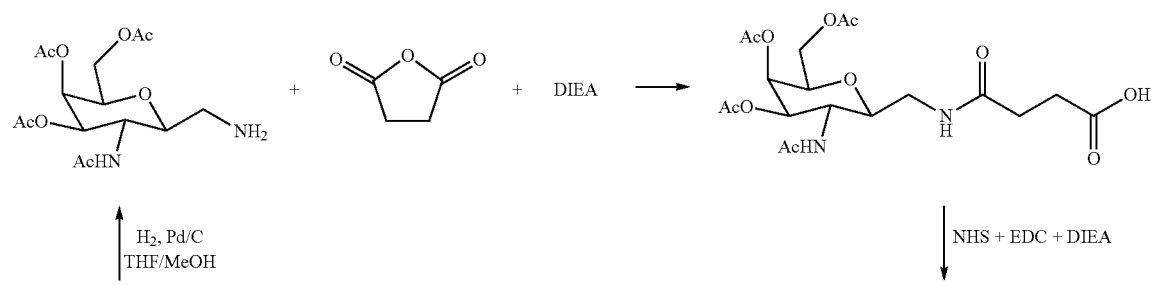

473                                              474
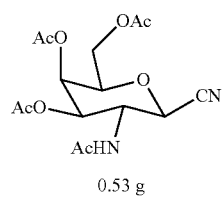
0.53 g
-continued
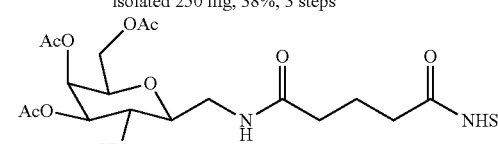
not observed
| H₂, Pd/C
| THF/MeOH
▼
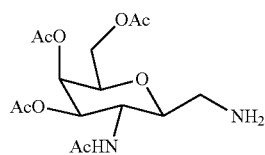
+ 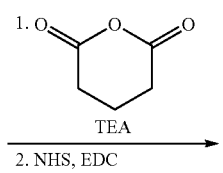 + Pyr. →<br>DCC, NHS
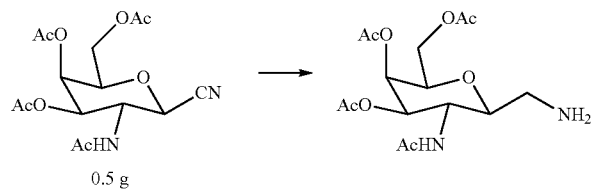
isolated 250 mg, 38%, 3 steps
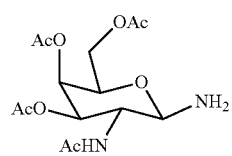
0.5 g
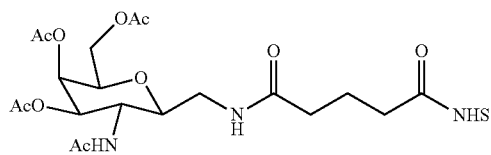
300 mg (need to be purified)
Scheme 62
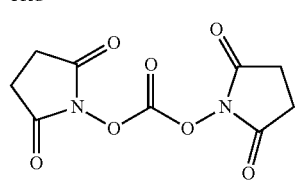
3g
TRC
-continued
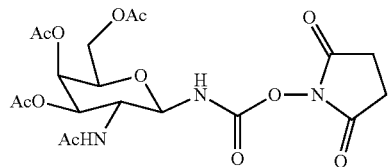
3.8 g, 95%

Scheme 63
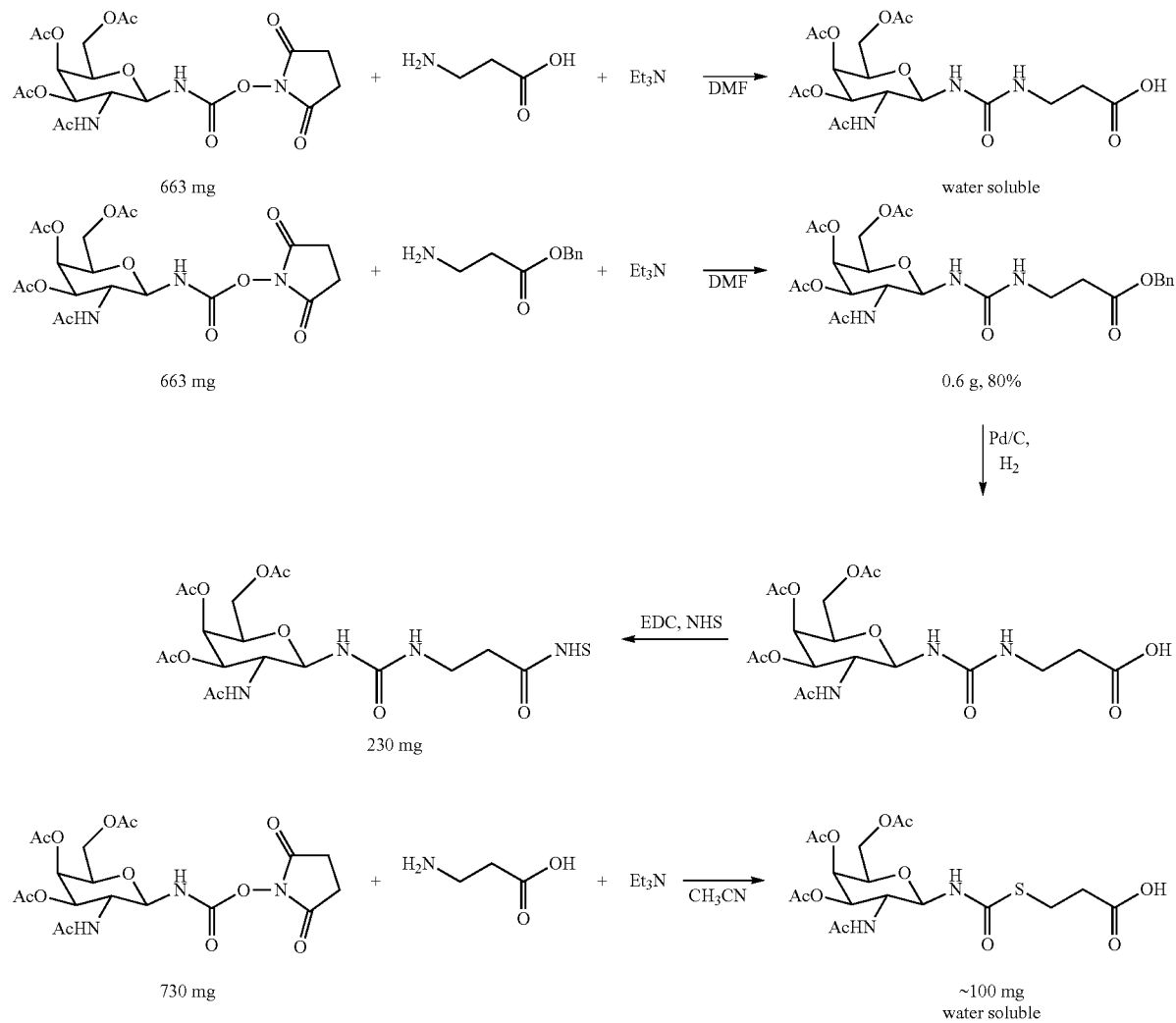
Example 25. ASGPR Ligand Mimics (Schemes 64-73)
The ASGPR ligands below can be prepared as shown in Schemes 64-73.
Scheme 64
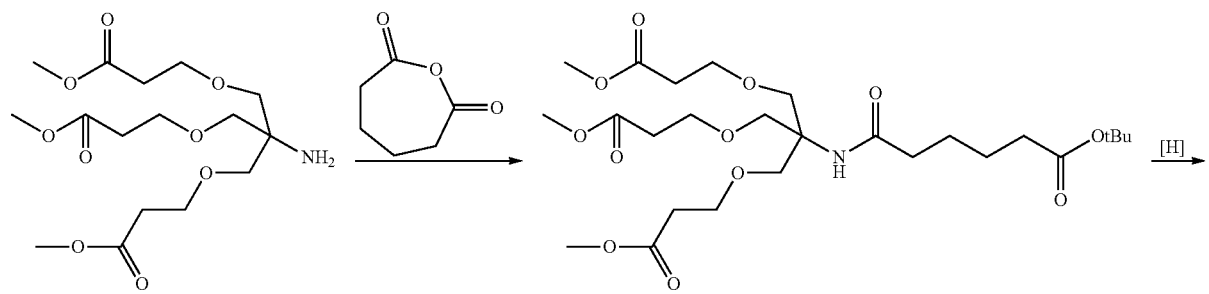

477 478
-continued
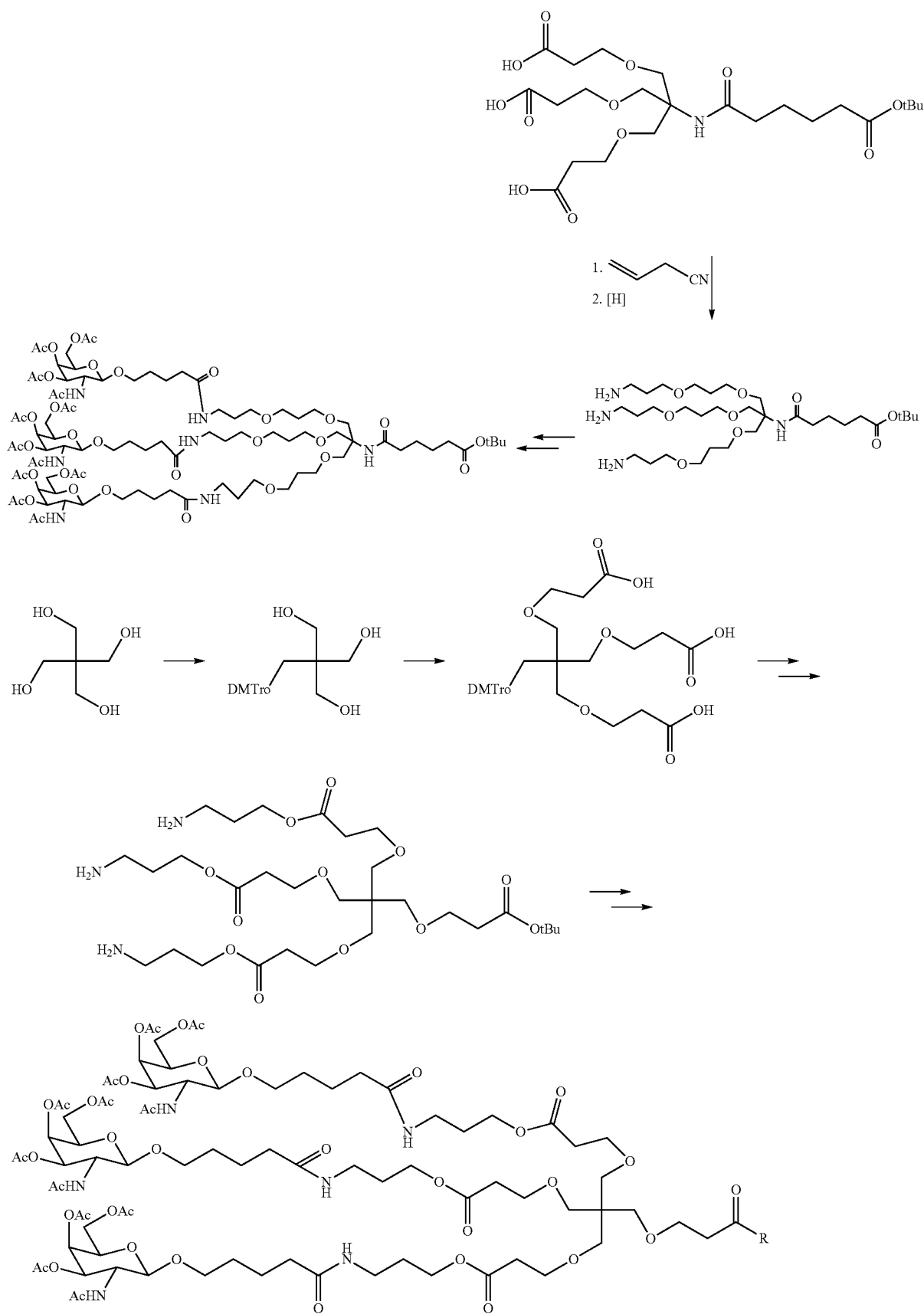

479 480
-continued
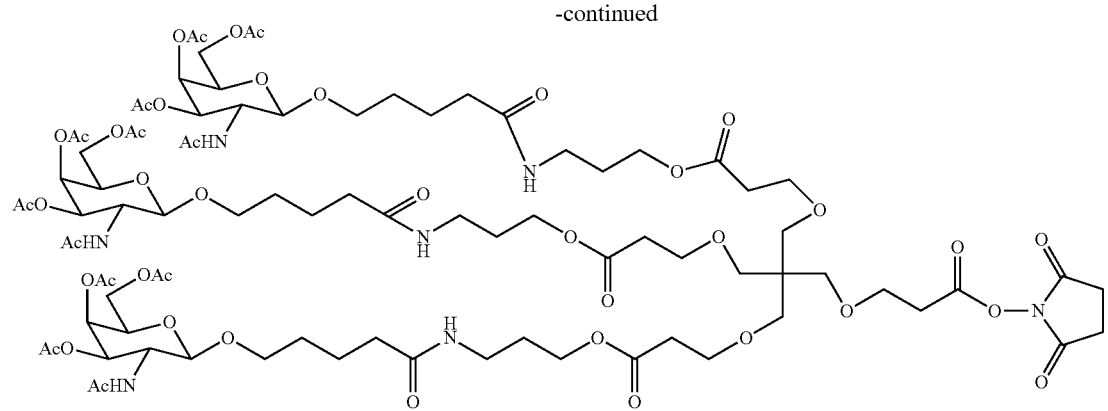
Scheme 65
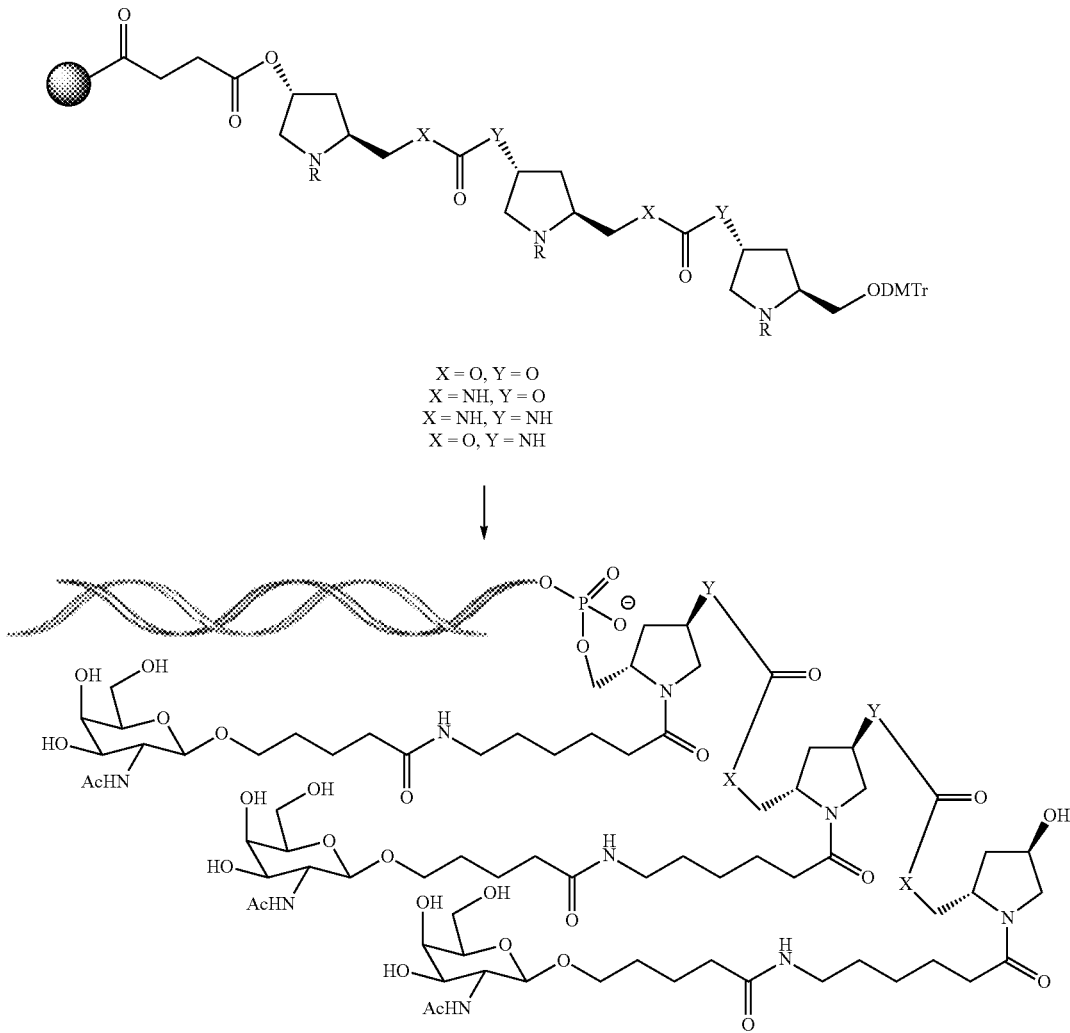
X = O, Y = O
X = NH, Y = O
X = NH, Y = NH
X = O, Y = NH Scheme 66
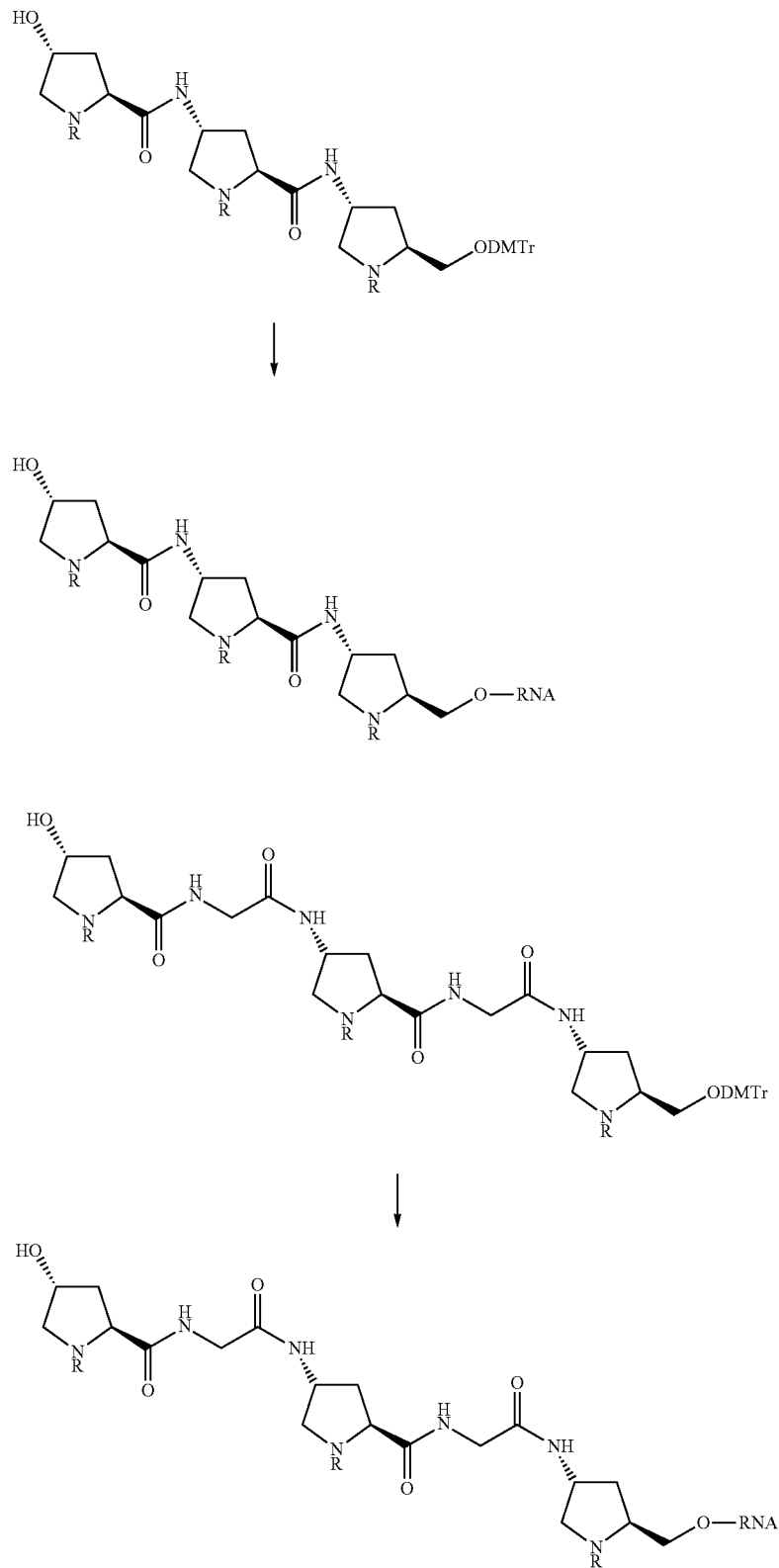

Scheme 67
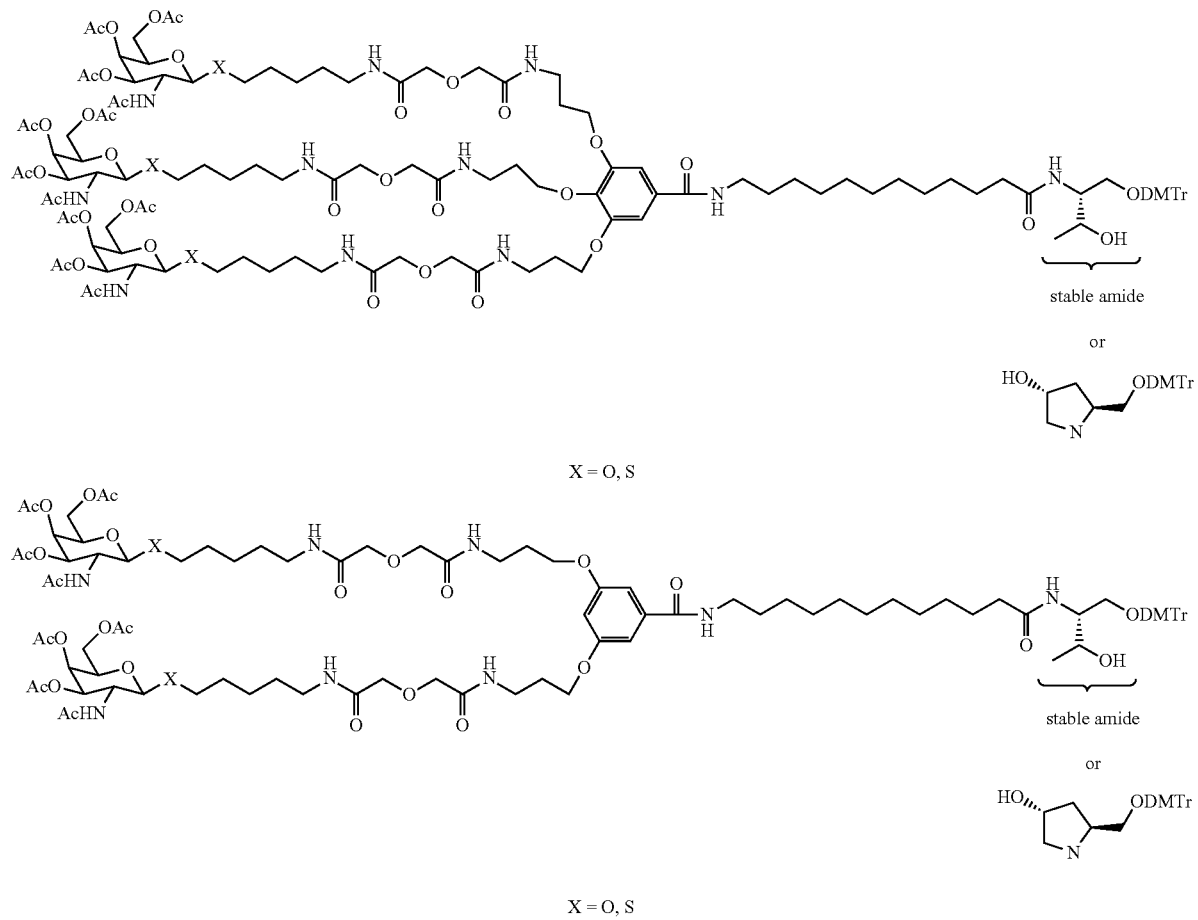
X = O, S
X = O, S
Scheme 68
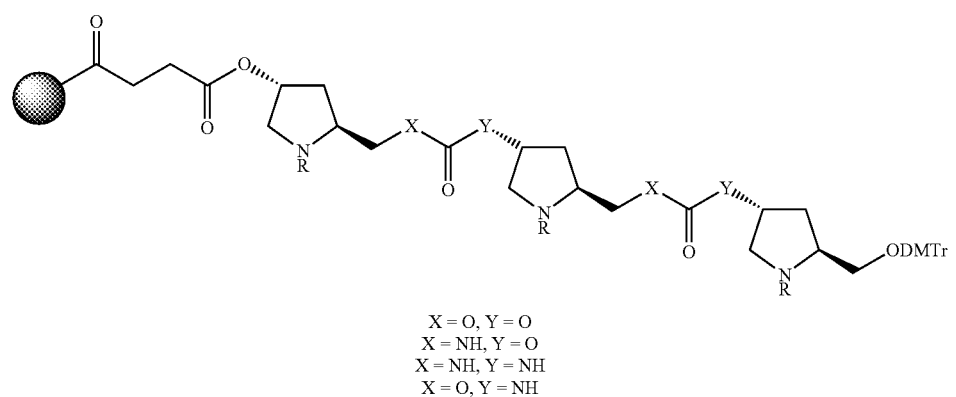
X = O, Y = O
X = NH, Y = O
X = NH, Y = NH
X = O, Y = NH 485
486
-continued
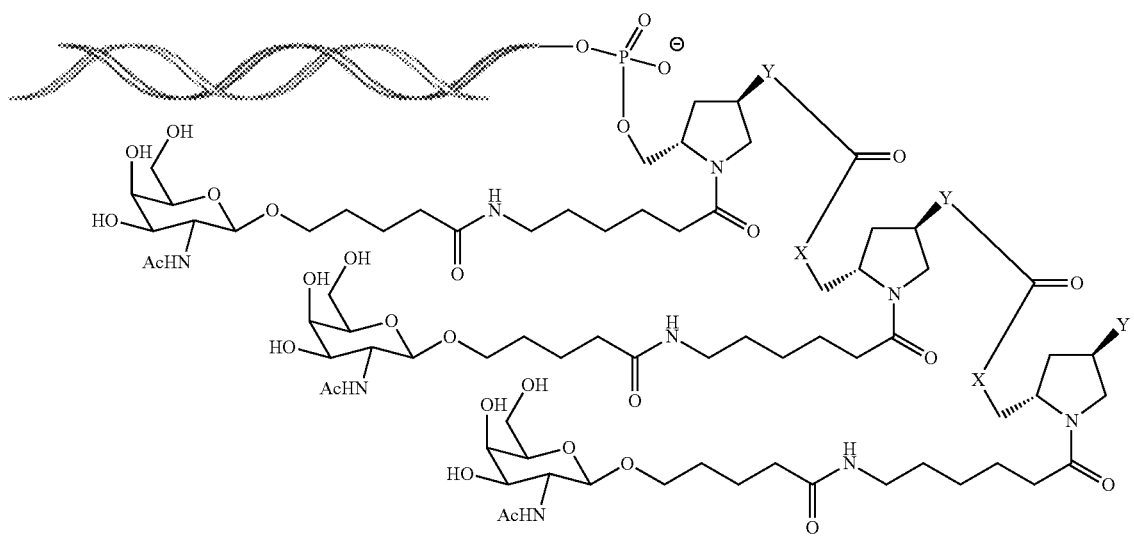
Scheme 69
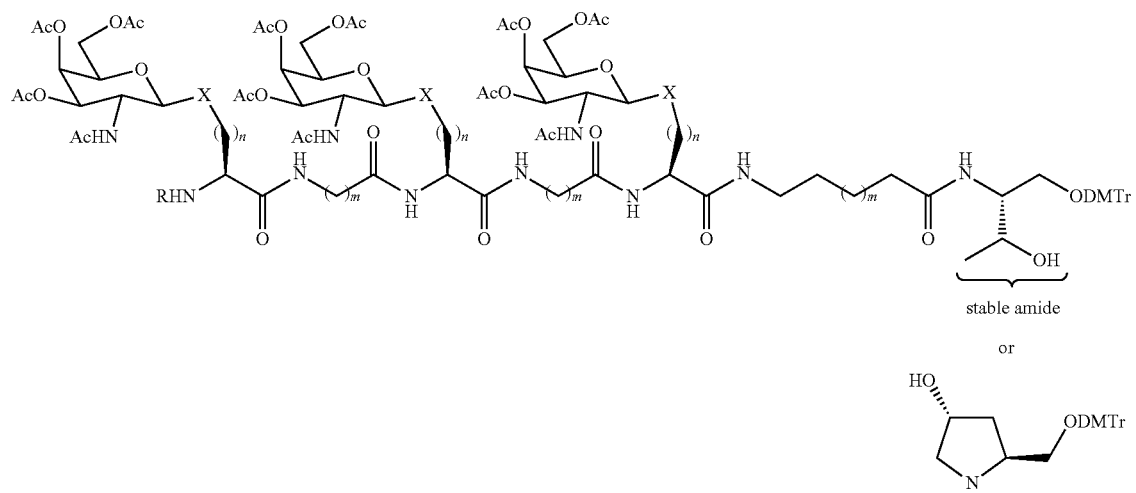
R = Ac, TFA, H
n = 1, 2
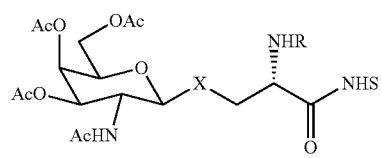
X = O and S
R = TFA, Ac
n = 0, 1, 4

487
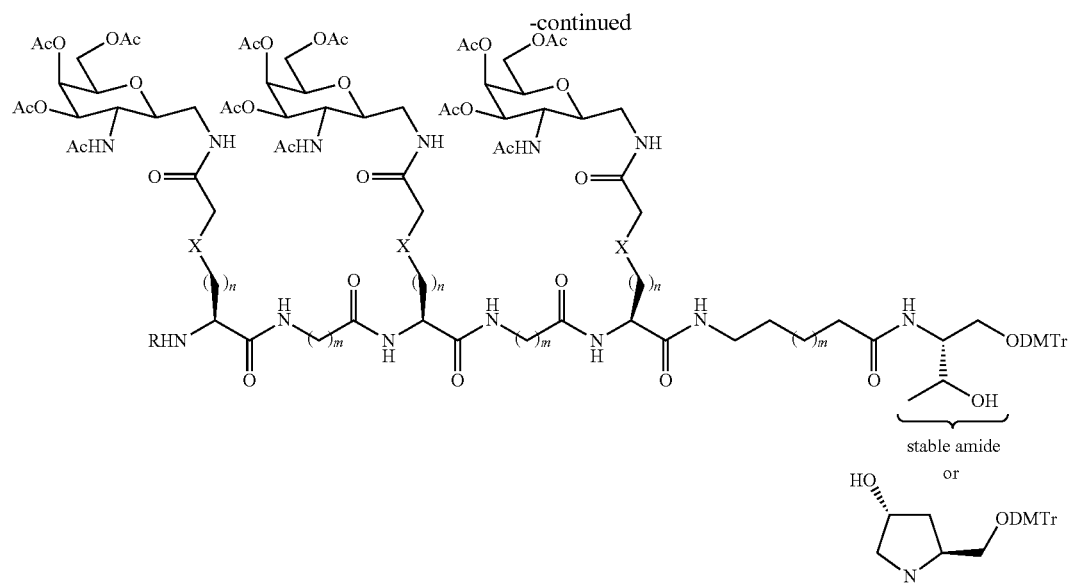
-continued
R = Ac, TFA, H
n = 1, 2
488
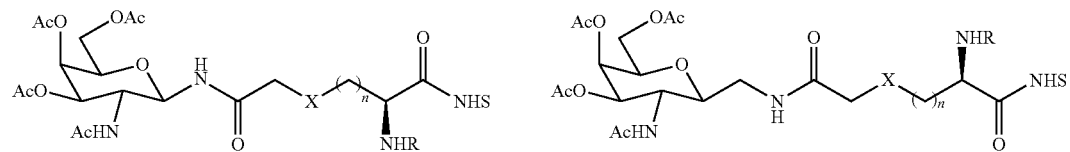
Scheme 70
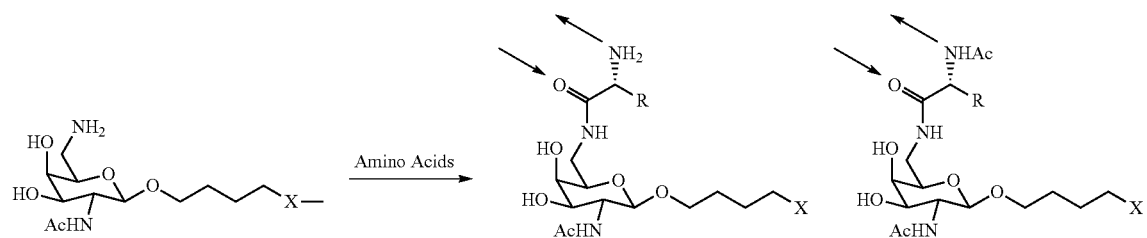

489 | 490
Scheme 71
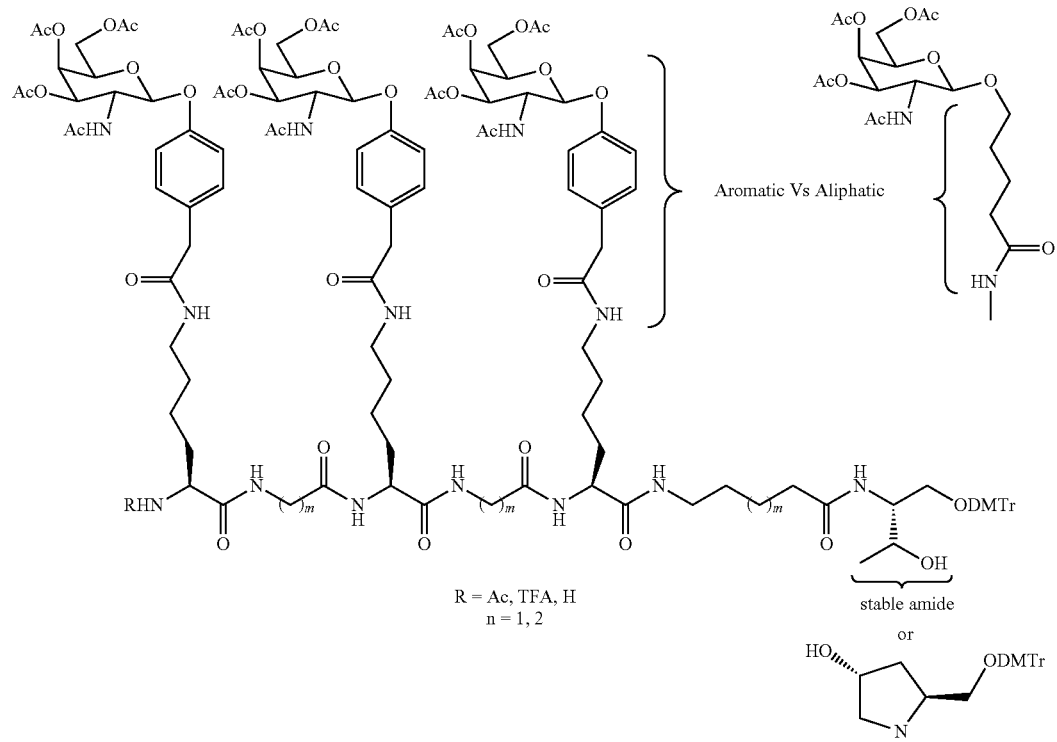
Scheme 72
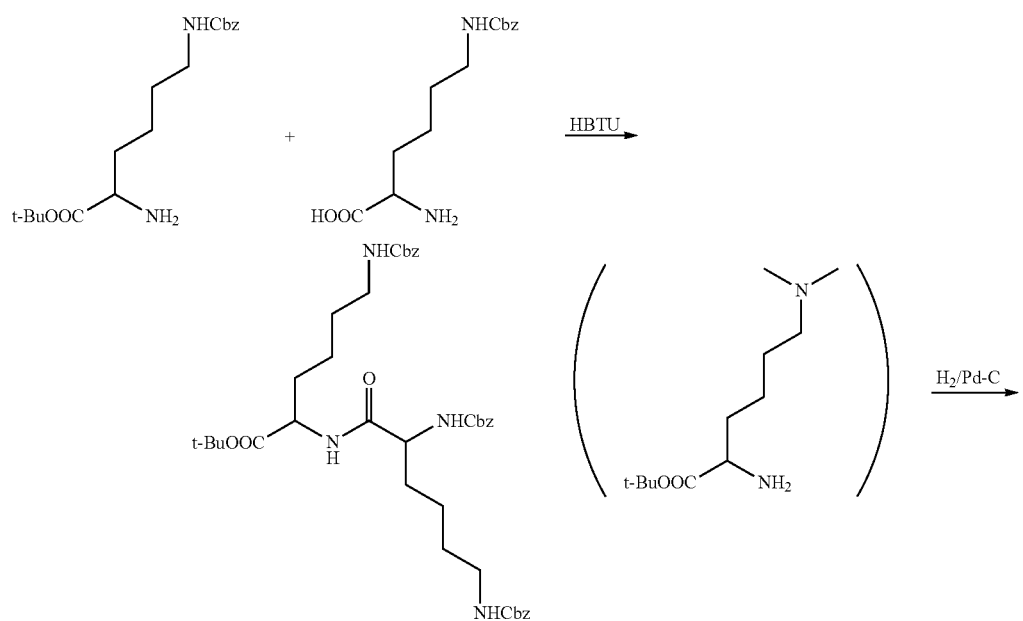

491
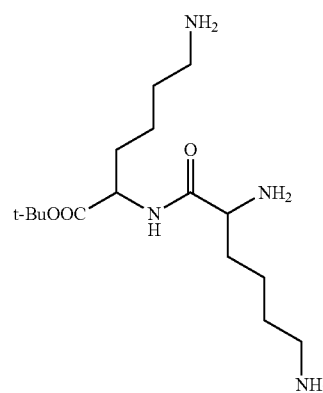
492
-continued
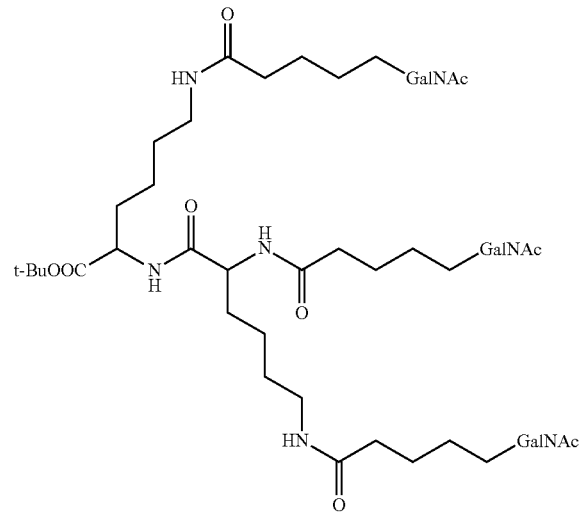
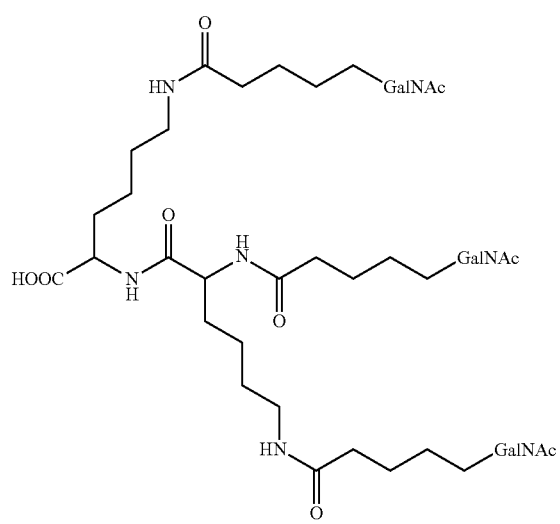
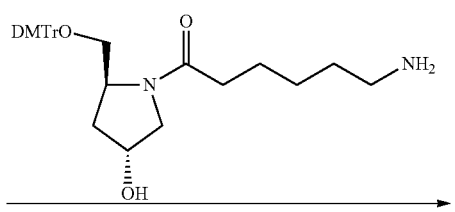
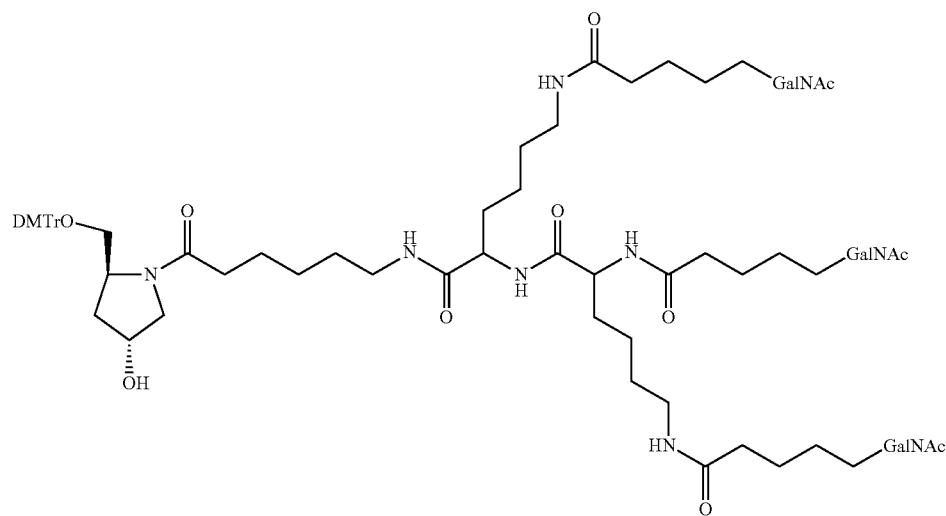

493 494
Scheme 73
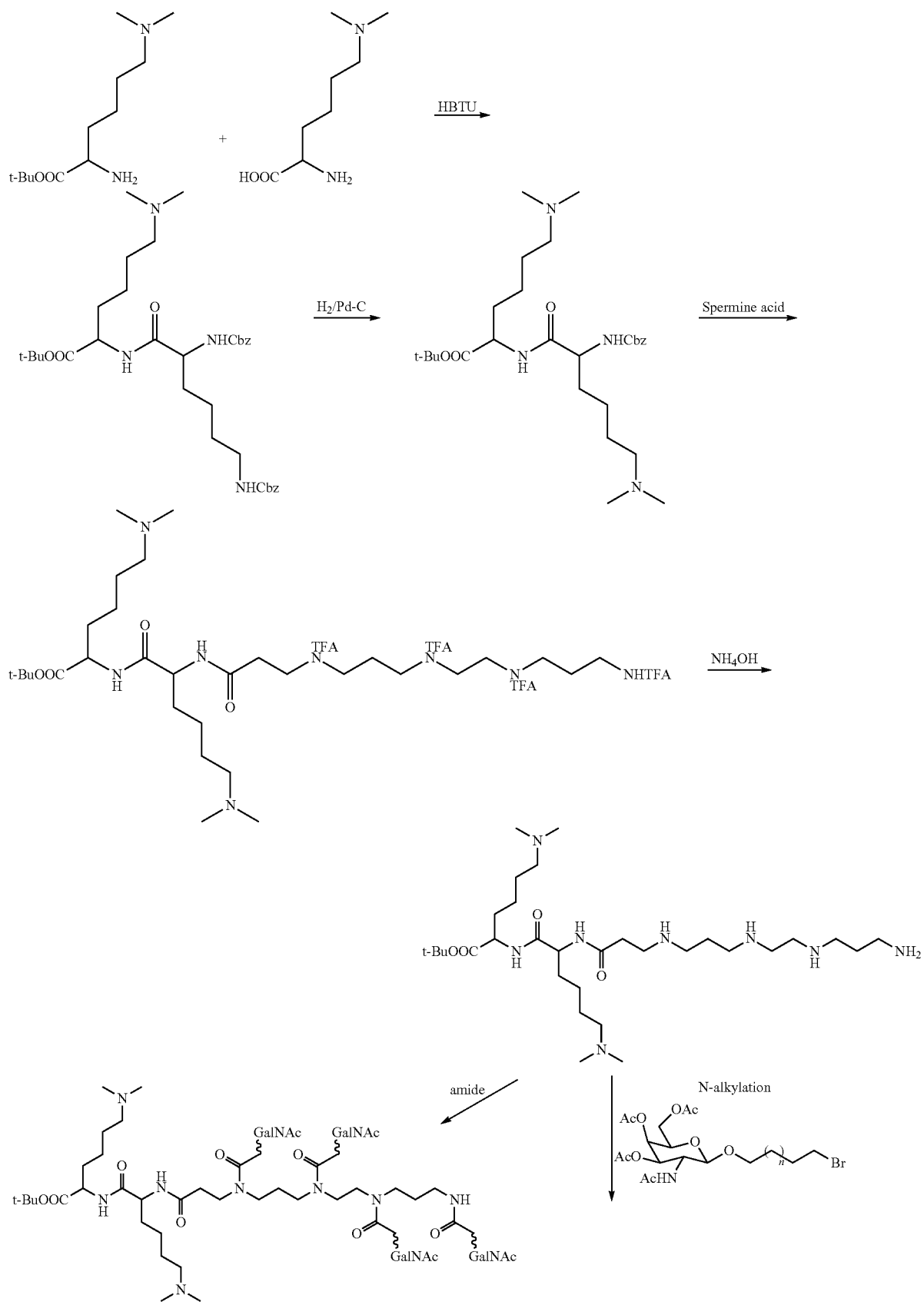

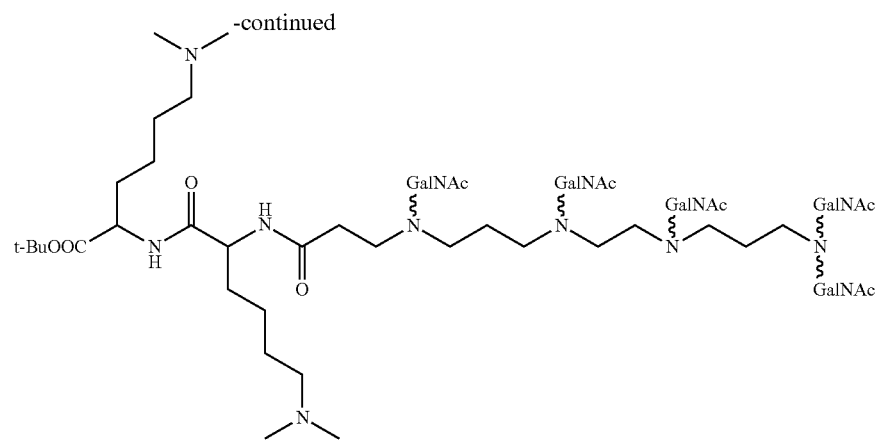
Example 26. Amino Linkers for Conjugation of Ligand to Oligonucleotides (Schemes 74-76)
Amino linkers for conjugating ligands to oligonucleotides can be prepared by Schemes 74-76 below.
Scheme 74
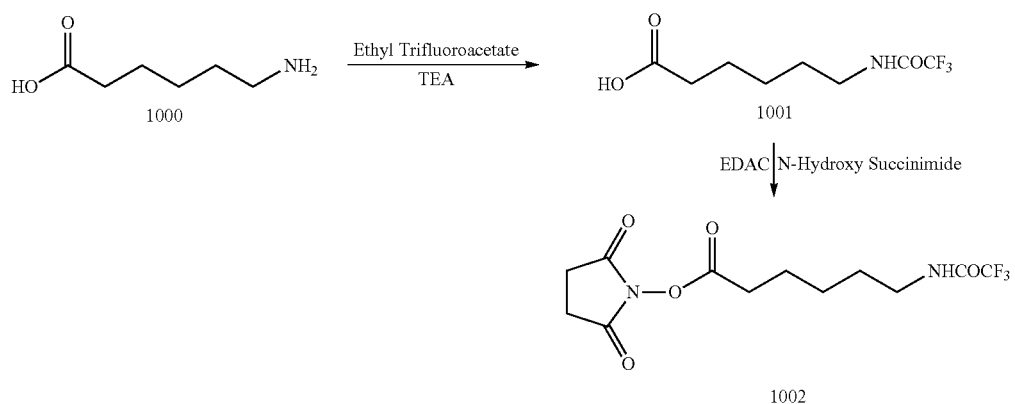
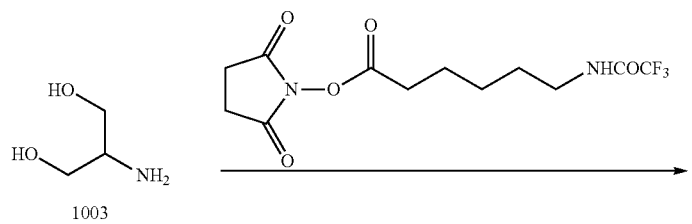
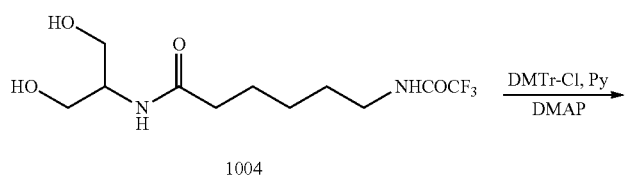

US 10,808,246 B2
497
-continued
498
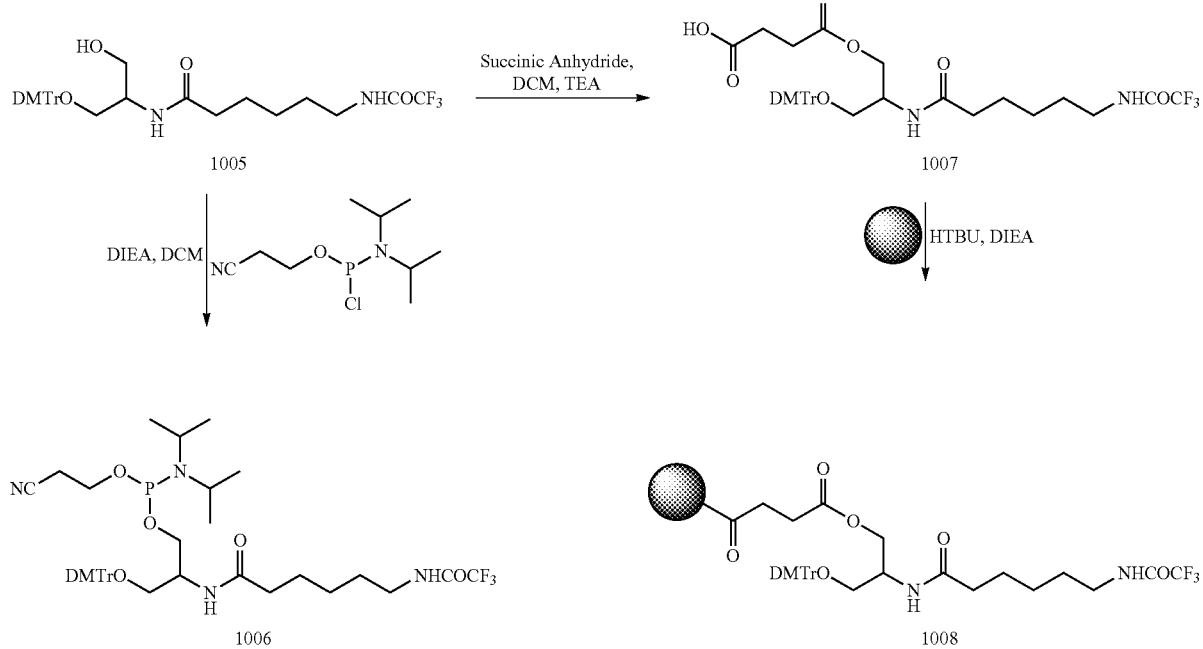
Scheme 75
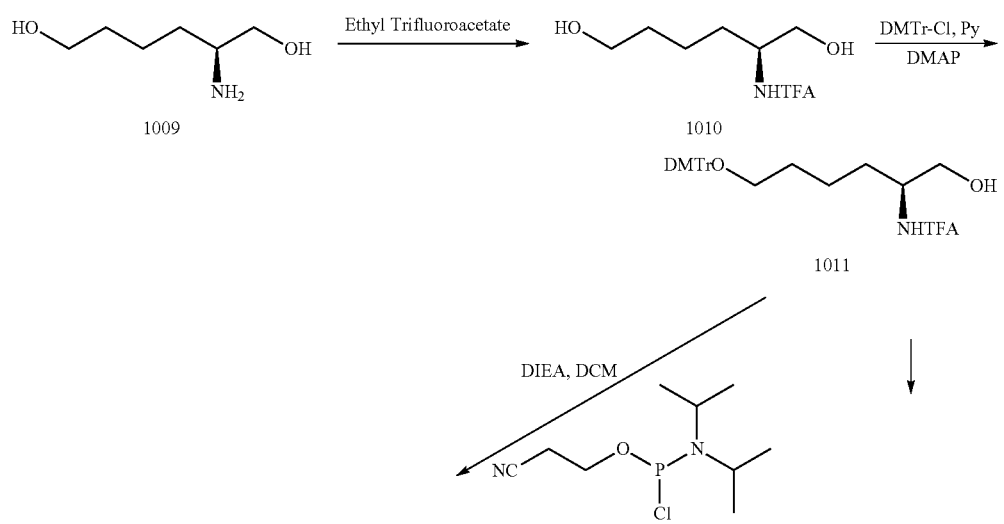

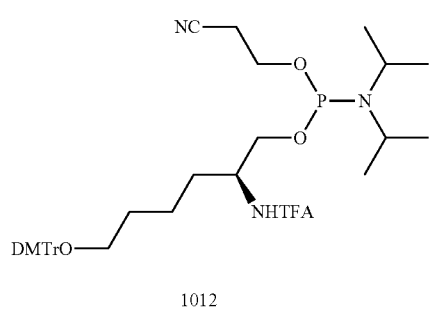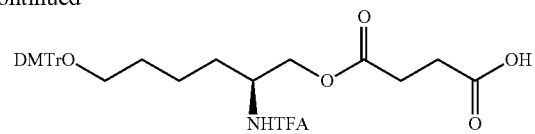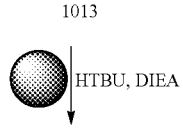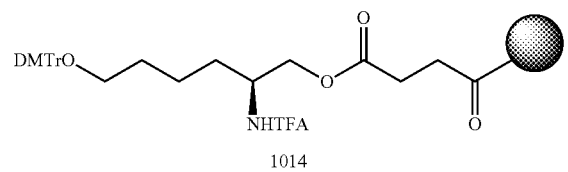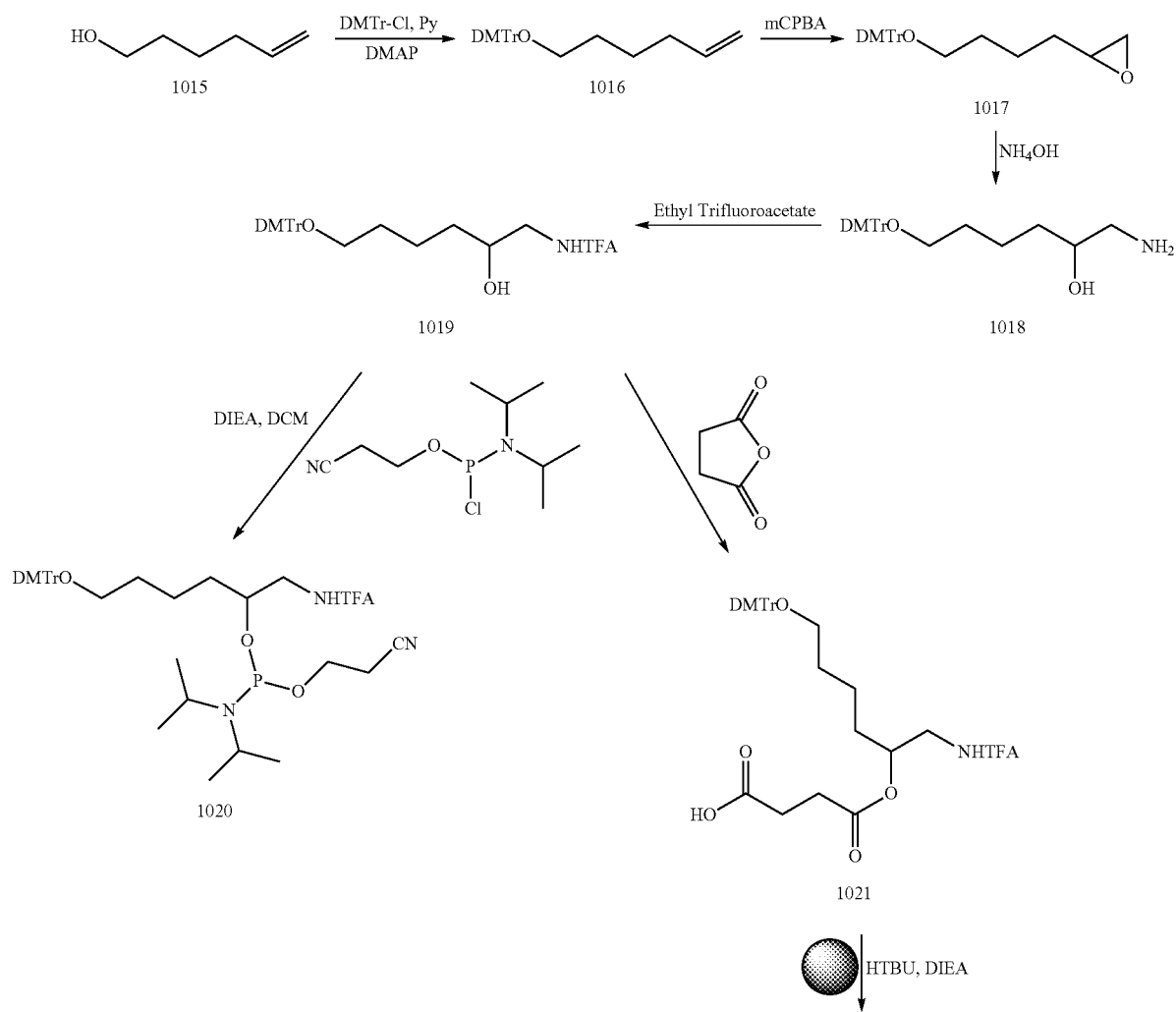

-continued
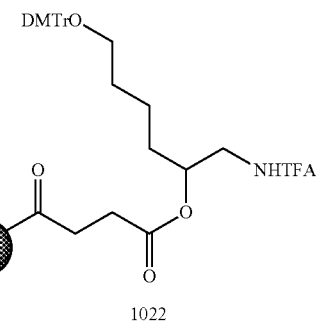
1022
Example 27. ASGPR Ligand Mimics—Carbohydrate Scaffold
The ASGPR ligand below can be prepared as shown in Scheme 77.
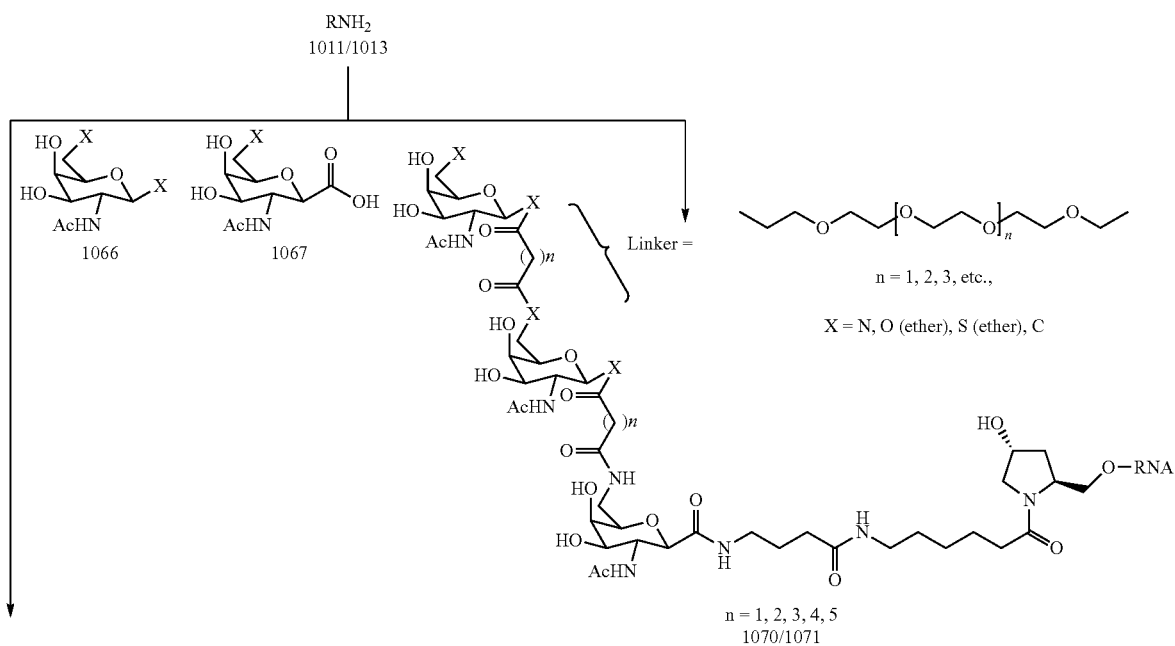

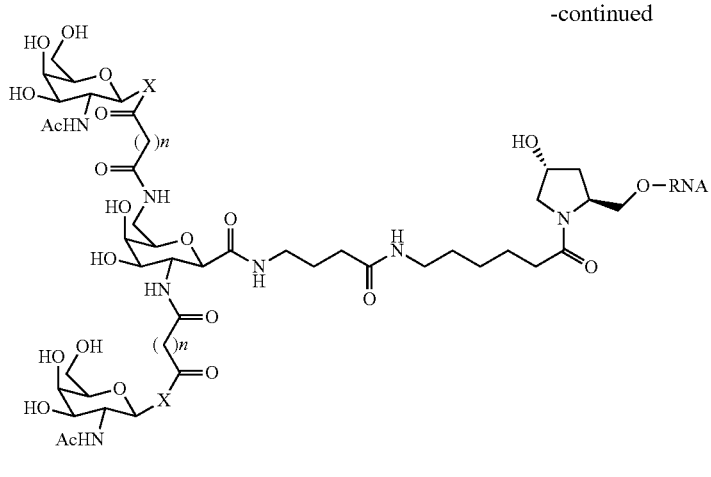
n = 1, 2, 3, 4, 5
1068/1069
Example 28. Conjugation of GalNAc Ligand to C2 of Purine Base
GalNAc ligands can be prepared to the C2 position of a purine base as shown in Scheme 78 below.
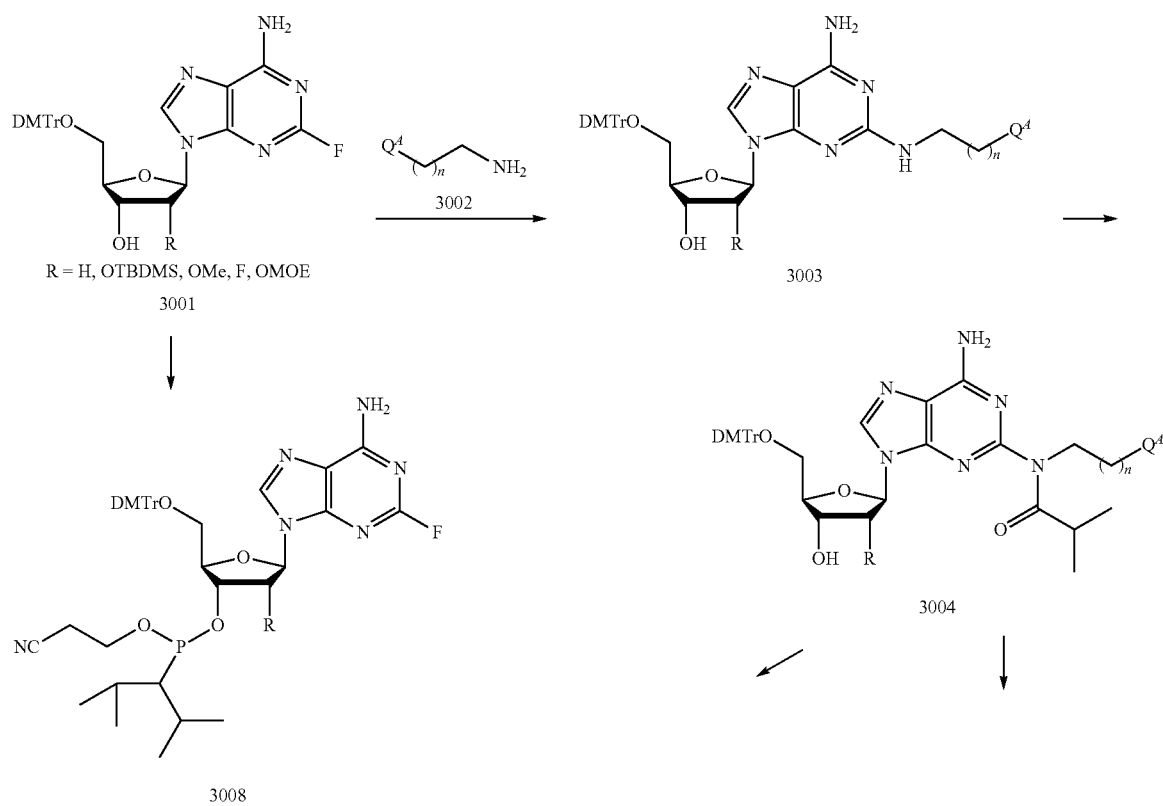

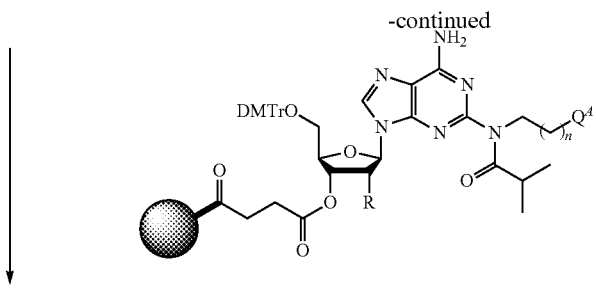

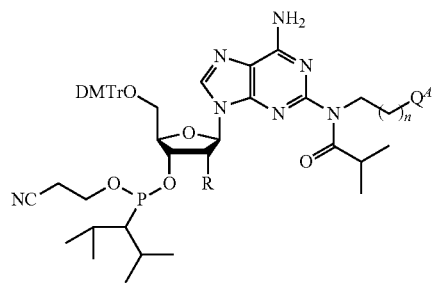

3006

3005

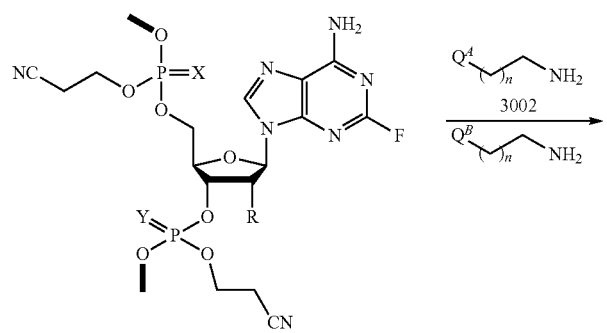

3009
X, Y = O or S

3007
X, Y = O or S
R = H, OH, OMe, F, OMOE n = 1-10
$Q^A$ = Functional group protected/masked ligand moiety
$Q^B$ = Functional group unprotected/unmasked ligand moiety $Q^A$ and $Q^B$ are any of the ASGPR ligands described herein.

Example 29 siRNA-Ligand Conjugates

RNA Synthesis and Duplex Annealing
1. Oligonucleotide Synthesis

All oligonucleotides were synthesized on an AKTAoligopilot synthesizer or an ABI 394 synthsizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis unless otherwise specified. The 2'-F phosphoramidites, 5'-O-dimethoxytrityl-N4-acetyl-2'-fluoro-cytidine-3'-O—N,N'-diisopropyl-2-cyanoethyl-phosphoramidite and 5'-O-dimethoxytrityl-2'-fluoro-uridine-3'-O—N,N'-diisopropyl-2-cyanoethyl-phosphoramidite were purchased from (Promega). All phosphoramidites were used at a concentration of 0.2M in acetonitrile (CH₃CN) except for guanosine which was used at 0.2M concentration in 10% THF/ANC (v/v). Coupling/recycling time of 16 minutes was used. The activator was 5-ethyl thiotetrazole (0.75M, American International Chemicals), for the PO-oxidation Iodine/Water/Pyridine was used and the PS-oxidation PADS (2%) in 2,6-lutidine/ACN (1:1 v/v) was used.

Ligand conjugated strands were synthesized using a solid support containing the corresponding ligand. For example, the introduction of a carbohydrate moiety/ligand (for e.g., GalNAc) at the 3'-end of a sequence was achieved by starting the synthesis with the corresponding carbohydrate solid support. Similarly a cholesterol moiety at the 3'-end was introduced by starting the synthesis on the cholesterol support. In general, the ligand moiety was tethered to trans-4-hydroxyprolinol via a tether of choice as described in the previous examples to obtain a hydroxyprolinol-ligand moiety. The hydroxyprolinol-ligand moiety was then coupled to a solid support via a succinate linker or was converted to phosphoramidite via standard phosphitylation conditions to obtain the desired carbohydrate conjugate building blocks. Fluorophore labeled siRNAs were synthesized from the corresponding phosphoramidite or solid support, purchased from Biosearch Technologies. The oleyl lithocholic (GalNAc)₃ polymer support made in house at a loading of 38.6 μmol/gram. The Mannose (Man)₃ polymer support was also made in house at a loading of 42.0 μmol/gram.

Conjugation of the ligand of choice at the desired position, for example at the 5'-end of the sequence, was achieved by coupling of the corresponding phosphoramidite to the growing chain under standard phosphoramidite coupling conditions unless otherwise specified. An extended 15 minute coupling of 0.1M solution of phosphoramidite in anhydrous $CH_3CN$ in the presence of 5-(ethylthio)-1H-tetrazole activator to a solid bound oligonucleotide. Oxidation of the internucleotide phosphite to the phosphate was carried out using standard iodine-water as reported in (1) Beaucage, S. L. (2008) Solid-phase synthesis of siRNA oligonucleotides. Curr. Opin. Drug Discov. Devel., 11, 203-216; (2) Mueller, S., Wolf, J. and Ivanov, S. A. (2004) Current Strategies for the Synthesis of RNA. Curr. Org. Synth., 1, 293-307 and (3) Xia, J., Noronha, A., Toudjarska, I., Li, F., Akinc, A., Braich, R., Frank-Kamenetsky, M., Rajeev, K. G., Egli, M. and Manoharan, M. (2006) Gene Silencing Activity of siRNAs with a Ribo-difluorotoluyl Nucleotide. ACS Chem. Biol., 1, 176-183 or by treatment with tert-butyl hydroperoxide/acetonitrile/water (10:87:3) with a 10 minute oxidation wait time conjugated oligonucleotide. Phosphorothioate was introduced by the oxidation of phosphite to phosphorothioate by using a sulfur transfer reagent such as DDTT (purchased from AM Chemicals), PADS and or Beaucage reagent. The cholesterol phosphoramidite was synthesized in house, and used at a concentration of 0.1 M in dichloromethane. Coupling time for the cholesterol phosphoramidite was 16 minutes.

2. Deprotection-I (Nucleobase Deprotection)

After completion of synthesis, the support was transferred to a 100 ml glass bottle (VWR). The oligonucleotide was cleaved from the support with simultaneous deprotection of base and phosphate groups with 80 mL of a mixture of ethanolic ammonia [ammonia: ethanol (3:1)] for 6.5 h at 55° C. The bottle was cooled briefly on ice and then the ethanolic ammonia mixture was filtered into a new 250 ml bottle. The CPG was washed with 2×40 mL portions of ethanol/water (1:1 v/v). The volume of the mixture was then reduced to ~30 ml by roto-vap. The mixture was then frozen on dry ice and dried under vacuum on a speed vac.

3. Deprotection-II (Removal of 2' TBDMS Group)

The dried residue was resuspended in 26 ml of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction was then quenched with 50 ml of 20 mM sodium acetate and pH adjusted to 6.5, and stored in freezer until purification.

4. Analysis

The oligonucleotides were analyzed by high-performance liquid chromatography (HPLC) prior to purification and selection of buffer and column depends on nature of the sequence and or conjugated ligand.

5. HPLC Purification

The ligand conjugated oligonucleotides were purified by reverse phase preparative HPLC. The unconjugated oligonucleotides were purified by anion-exchange HPLC on a TSK gel column packed in house. The buffers were 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides were pooled, desalted, and lyophilized. Approximately 0.15 OD of desalted oligonucleotides were diluted in water to 150 μl and then pipetted in special vials for CGE and LC/MS analysis. Compounds were finally analyzed by LC-ESMS and CGE.

6. RNAi Agent Preparation

For the preparation of RNAi agent, equimolar amounts of sense and antisense strand were heated in 1×PBS at 95° C. for 5 minutes and slowly cooled to room temperature. The integrity of the duplex was confirmed by HPLC analysis. Table 1 below reflects the synthesized RNAi agents.

Example 30: Synthesis of siRNA-Ligand Conjugates Using Post-Synthetic Methods

The single stranded oligonucleotides containing desired amino linkers were synthesized using the corresponding amino linker monomers compatible with solid phase oligonucleotide synthesis and deprotection conditions as described in Example 30 (Schemes 79). After deprotection the amino linked oligonucleotides were reacted with NHS esters of the ligand shown in the Table below the Scheme 79 followed by treatment with ammonia and HPLC purification. Each purified ligand-conjugated single stranded oligonucleotide was annealed with equimolar mixture of complementary strand yielded the siRNAs shown in Table 5. The (1+1+1) design shown in Scheme 79 and in Table 5 was obtained by coupling of amino linker phosphoramidite to the amino linker solid support successively (two synthesis cycle) followed by successive coupling of nucleoside phosphoramidite monomers as described in Example 29.

Post Synthetic Conjugation of Ligand to Oligonucleotides

Scheme 79

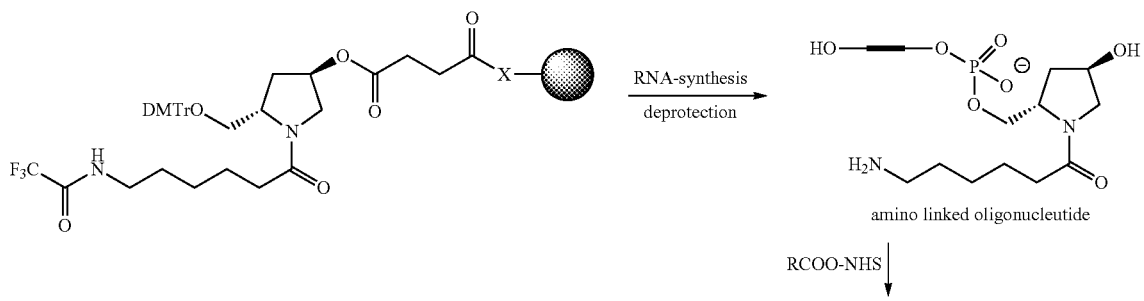

amino linked oligonucleutide

-continued
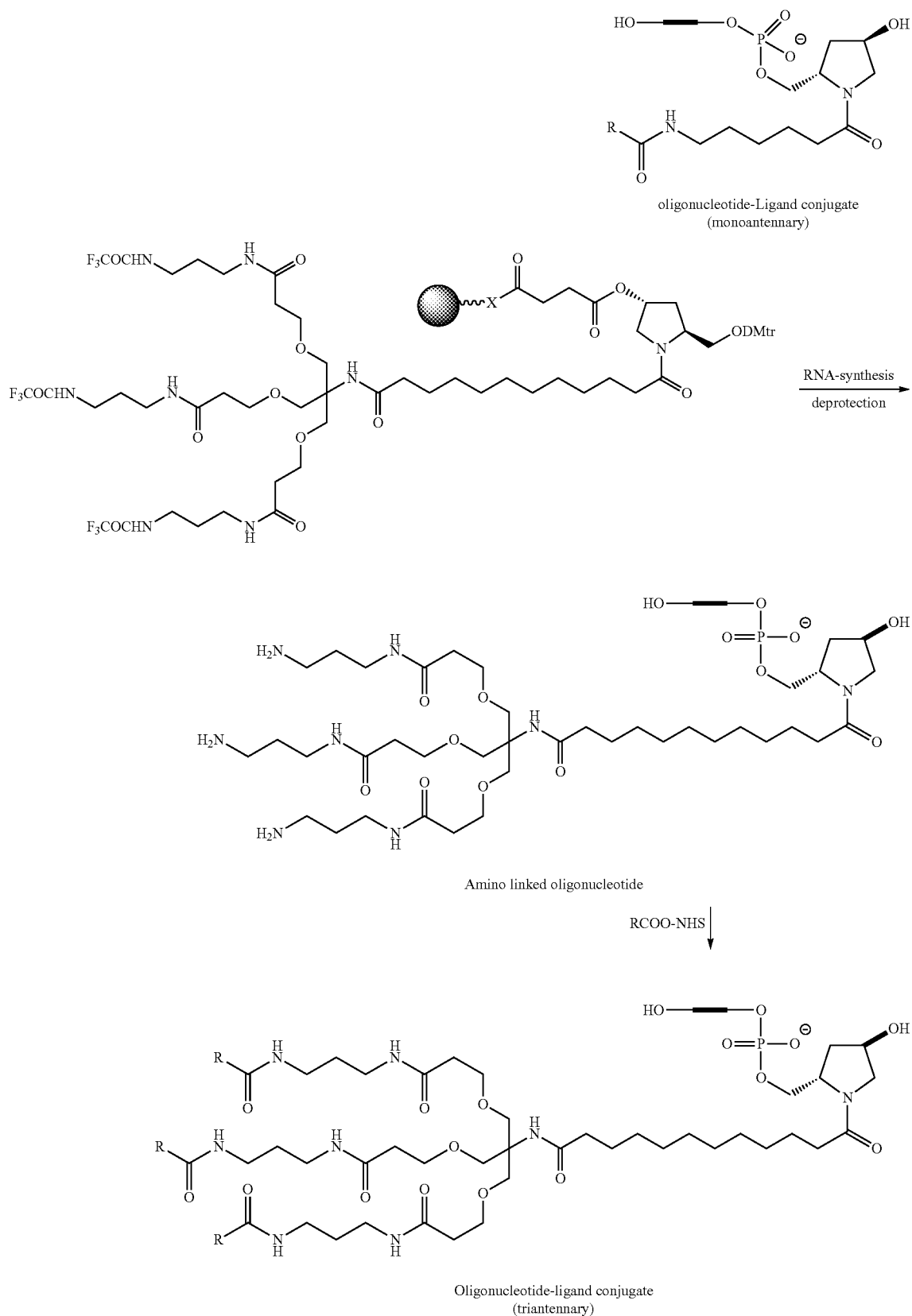

511
512
-continued
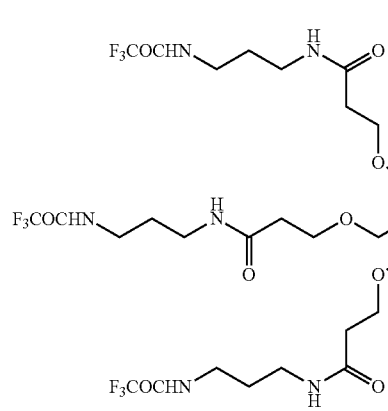
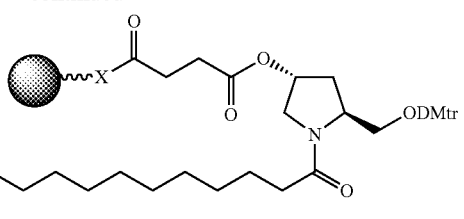
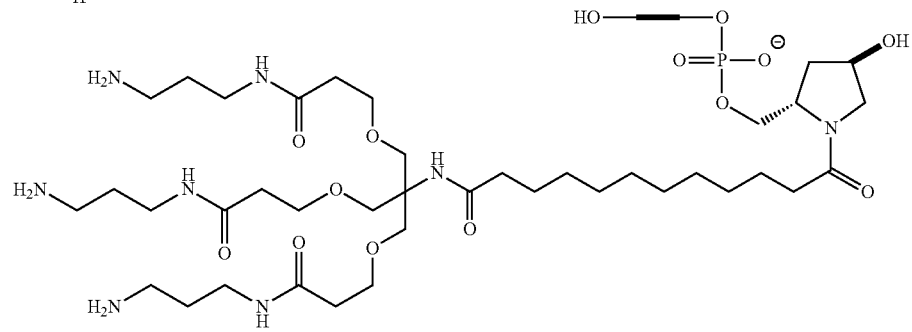
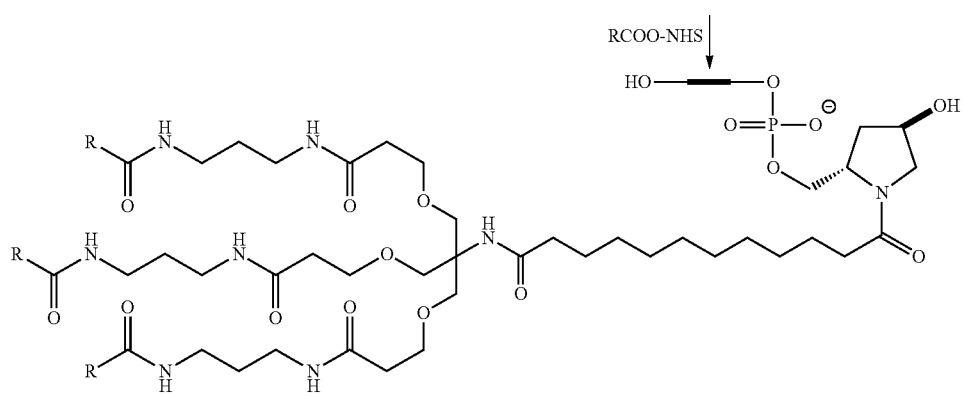
Oligonucleotide-ligand conjugate
(triantennary)
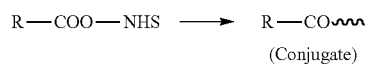
(Conjugate)
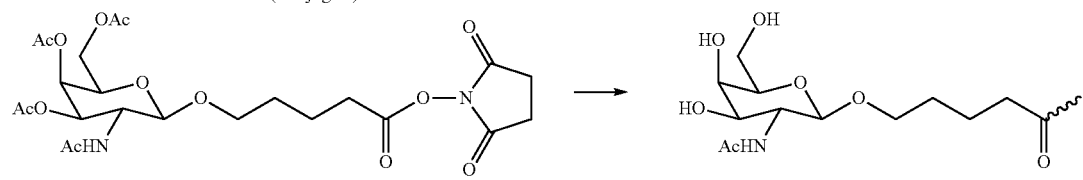
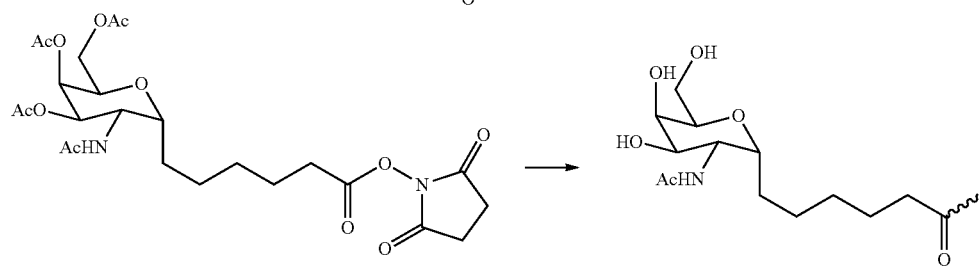

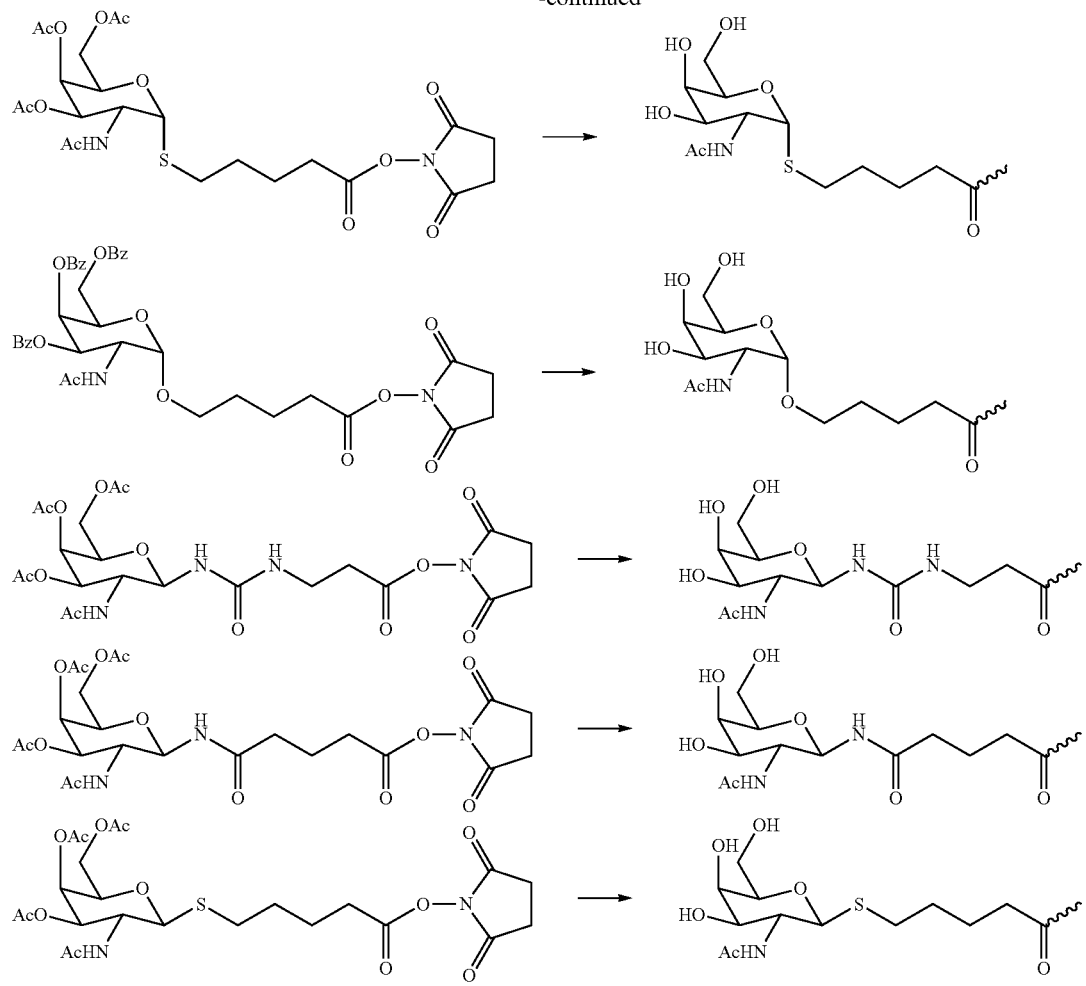

The TTR siRNA in each conjugate was the same. Similarly, the AT3 siRNA in each conjugate was the same. The following ligands were attached to the 3' end of the sense strand of each siRNA. The left side of the ligand description indicates the site of attachment to the 3' terminus of the sense strand.

TABLE 1

| siRNA-Ligand conjugates | | |
|---|---|---|
| Conjugate | Target | Sequence 5'-3' |
| 43527 | TTR | L96 |
| 60148 | TTR | L193L193L193 |
| 60146 | TTR | s(T3gs)(T3gs)(T3g) |
| 60142 | TTR | s(Tgs)(Tgs)(Tg) |
| 60133 | TTR | L199L199L199 |
| 60139 | TTR | L204L204L204 |
| 60134 | TTR | L200L200L200 |
| 60132 | TTR | L198L198L198 |
| 60125 | TTR | L207L207L207 |
| 60124 | TTR | L203L203L203 |
| 60122 | TTR | L203 |
| 60123 | TTR | L206 |
| 60135 | TTR | L207 |
| 60136 | TTR | L208 |
| 60129 | TTR | L198 |
| 60126 | TTR | L197 |
| 60131 | TTR | L200 |
| 60127 | TTR | L202 |
| 60130 | TTR | L199 |
| 60128 | TTR | L201 |
| 60137 | TTR | L204 |

TABLE 1-continued

| | siRNA-Ligand conjugates | |
|---|---|---|
| Conjugate | Target | Sequence 5'-3' |
| 60138 | TTR | L205 |
| 60140 | TTR | (Tg)(Tg)(Tg) |
| 60144 | TTR | (T3g)(T3g)(T3g) |
| 60141 | TTR | (Tg) |
| 60143 | TTR | s(Tg) |
| 60145 | TTR | (T3g) |
| 60147 | TTR | s(T3g) |
| 58036 | TTR | L194L194L194 |
| 58037 | TTR | L195L195L195 |
| 58038 | TTR | L194 is on the 3th, 4th, and 5th nucleotide from the 3' end |
| 58039 | TTR | L195 is on the 3th, 4th, and 5th nucleotide from the 3' end |
| 58138 | TTR | L193L193L193 |
| | | (but different modified antisense strand) |
| 55727 | TTR | L96 on different siRNA |
| | | AfaCfaGfuGfuUfCfUfuGfcUfcUfaUfaAfL96 |
| 70001 | AT3 | L96 |
| 70002 | AT3 | L193L193L193 |

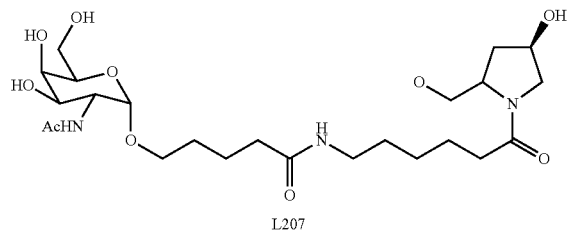 [SMILES: CC(=O)NC1C(OCCCCC(=O)NCCCCCC(=O)N2C[C@H](O)CC2CO)OC(CO)C(O)C1O]
L207

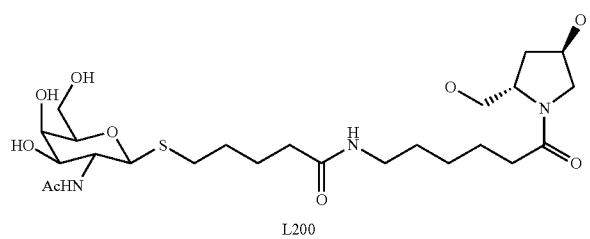 [SMILES: CC(=O)NC1C(SCCCCC(=O)NCCCCCC(=O)N2C[C@H](O)C[C@H]2CO)OC(CO)C(O)C1O]
L200

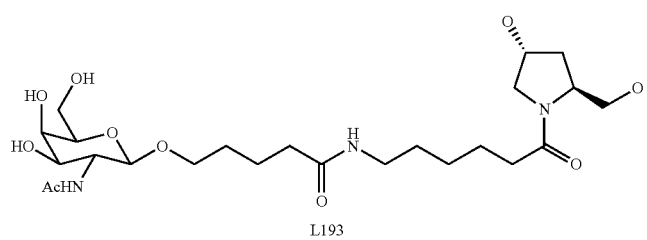 [SMILES: CC(=O)NC1C(OCCCCC(=O)NCCCCCC(=O)N2C[C@H](O)C[C@H]2CO)OC(CO)C(O)C1O]
L193

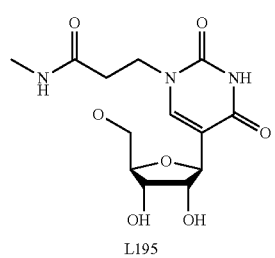
L195

TABLE 1-continued siRNA-Ligand conjugates

| Conjugate | Target | Sequence 5'-3' |
| --- | --- | --- |

L197

L201

L96

Example 31 In Vitro Screening of RNAi Agents

Cell Culture and Transfections

Human Hep3B cells or rat H.II.4.E cells (ATCC, Manassas, Va.) were grown to near confluence at 37° C. in an atmosphere of 5% CO2 in RPMI (ATCC) supplemented with 10% FBS, streptomycin, and glutamine (ATCC) before being released from the plate by trypsinization. Transfection was carried out by adding 14.8 µl of Opti-MEM plus 0.2 µl of Lipofectamine RNAiMax per well (Invitrogen, Carlsbad Calif. cat #13778-150) to 5 µl of siRNA duplexes per well into a 96-well plate and incubated at room temperature for 15 minutes. 80 µl of complete growth media without antibiotic containing ~2×104 Hep3B cells were then added to the siRNA mixture. Cells were incubated for either 24 or 120 hours prior to RNA purification. Single dose experiments were performed at 10 nM and 0.1 nM final duplex concentration and dose response experiments were done using 8, 4 fold serial dilutions with a maximum dose of 10 nM final duplex concentration.

Total RNA Isolation Using DYNABEADS mRNA Isolation Kit (Invitrogen, Part #: 610-12)

Cells were harvested and lysed in 150 µl of Lysis/Binding Buffer then mixed for 5 minutes at 850 rpm using an Eppendorf Thermomixer (the mixing speed was the same throughout the process). Ten microliters of magnetic beads and 80 µl Lysis/Binding Buffer mixture were added to a round bottom plate and mixed for 1 minute. Magnetic beads were captured using magnetic stand and the supernatant was removed without disturbing the beads. After removing the supernatant, the lysed cells were added to the remaining beads and mixed for 5 minutes. After removing the supernatant, magnetic beads were washed 2 times with 150 µl Wash Buffer A and mixed for 1 minute. Beads were capture again and supernatant removed. Beads were then washed with 150 µl Wash Buffer B, captured and supernatant was removed. Beads were next washed with 150 µl Elution Buffer, captured and supernatant removed. Beads were allowed to dry for 2 minutes. After drying, 50 µl of Elution Buffer was added and mixed for 5 minutes at 70° C. Beads were captured on magnet for 5 minutes. 40 µl of supernatant was removed and added to another 96 well plate.

cDNA Synthesis Using ABI High Capacity cDNA Reverse Transcription Kit (Applied Biosystems, Foster City, Calif., Cat #4368813)

A master mix of 1 µl 10× Buffer, 0.4 µl 25× dNTPs, 1 µl Random primers, 0.5 µl Reverse Transcriptase, 0.5 µl RNase inhibitor and 1.6 µl of $H_2O$ per reaction were added into 5 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR

2 µl of cDNA were added to a master mix containing 0.5 µl GAPDH TaqMan Probe (Applied Biosystems Cat #4326317E (human) Cat #4308313 (rodent)), 0.5 µl TTR TaqMan probe (Applied Biosystems cat # HS00174914_ml (human) cat # Rn00562124_ml (rat)) and 5 µl Lightcycler 480 probe master mix (Roche Cat #04887301001) per well in a 384 well plate (Roche cat #04887301001). Real time PCR was done in a Roche LC 480 Real Time PCR machine (Roche). Each duplex was tested in at least two independent transfections and each transfection was assayed in duplicate, unless otherwise noted.

To calculate relative fold change, real time data were analyzed using the $\Delta\Delta Ct$ method and normalized to assays performed with cells transfected with 10 nM AD-1955, or mock transfected cells. $IC_{50}$s were calculated using a 4 parameter fit model using XLFit and normalized to cells transfected with non-target specific control or naïve cells over the same dose range, or to its own lowest dose. $IC_{50}$s were calculated for each individual transfection as well as in combination, where a single $IC_{50}$ was fit to the data from both transfections.

Example 32: In Vitro Silencing Activity of Chemically Modified RNAi Agents that Target TTR The following experiments demonstrated the beneficial effects of chemical modifications, including the introduction of triplet repeat motifs, together with a $GalNAc_3$ ligand, on the silencing activity of RNAi agents that target TTR.

Protocol for Assessment of $IC_{50}$ in Hep3B Cells

The $IC_{50}$ for each modified siRNA was determined in Hep3B cells by standard reverse transfection using Lipofectamine RNAiMAX. In brief, reverse transfection was carried out by adding 5 µL of Opti-MEM to 5 µL of siRNA duplex per well into a 96-well plate along with 10 µL of Opti-MEM plus 0.5 µL of Lipofectamine RNAiMax per well (Invitrogen, Carlsbad Calif. cat #13778-150) and incubating at room temperature for 15-20 minutes. Following incubation, 100 µL of complete growth media without antibiotic containing 12,000-15,000 Hep3B cells was then added to each well. Cells were incubated for 24 hours at 37° C. in an atmosphere of 5% CO2 prior to lysis and analysis of TTR and GAPDH mRNA by bDNA (Quantigene). Seven different siRNA concentrations ranging from 10 nM to 0.6 pM were assessed for $IC_{50}$ determination and TTR/GAPDH for siRNA transfected cells was normalized to cells transfected with 10 nM Luc siRNA.

Protocol for Assessment of Free-Uptake $IC_{50}$

Free uptake silencing in primary cynomolgus or mouse hepatocytes was assessed following incubation with TTR siRNA for 4 hours or 24 hours. Silencing was measured at 24 hours from the initial exposure.

Example 33: TTR mRNA Silencing and TTR Protein Suppression in Mice

To assess the efficacy of the RNAi agents, these agents were administered to mice. The RNAi agents or PBS control were administered to mice in a single subcutaneous dose of 5 mg/kg or 1 mg/kg. After approximately 48 hours, mice were anesthetized with 200 µl of ketamine, and then exsanguinated by severing the right caudal artery. Whole blood was isolated and plasma was isolated and stored at −80C until assaying. Liver tissue was collected, flash-frozen and stored at −80C until processing.

Efficacy of treatment was evaluated by (i) measurement of TTR mRNA in liver at 48 and 144 hours post-dose, and (ii) measurement of TTR protein in plasma at prebleed and at 48/144 hours post-dose. TTR liver mRNA levels were assayed utilizing the Branched DNA assays-QuantiGene 2.0 (Panomics cat #: QS0011). Briefly, mouse liver samples were ground and tissue lysates were prepared. Liver lysis mixture (a mixture of 1 volume of lysis mixture, 2 volume of nuclease-free water and 10 ul of Proteinase-K/ml for a final concentration of 20 mg/ml) was incubated at 65° C. for 35 minutes. 20 µl of Working Probe Set (TTR probe for gene target and GAPDH for endogenous control) and 80 ul of tissue-lysate were then added into the Capture Plate. Capture Plates were incubated at 55° C.±1° C. (aprx. 16-20 hrs). The next day, the Capture Plates were washed 3 times with 1× Wash Buffer (nuclease-free water, Buffer Component 1 and Wash Buffer Component 2), then dried by centrifuging for 1 minute at 240 g. 100 µl of pre-Amplifier Working Reagent was added into the Capture Plate, which was sealed with aluminum foil and incubated for 1 hour at 55° C.±1° C. Following 1 hour incubation, the wash step was repeated, then 100 µl of Amplifier Working Reagent was added. After 1 hour, the wash and dry steps were repeated, and 100 µl of Label Probe was added. Capture plates were incubated 50° C.±1° C. for 1 hour. The plate was then washed with 1× Wash Buffer, dried and 100 µl Substrate was added into the Capture Plate. Capture Plates were read using the SpectraMax Luminometer following a 5 to 15 minute incubation. bDNA data were analyzed by subtracting the average background from each triplicate sample, averaging the resultant triplicate GAPDH (control probe) and TTR (experimental probe) values, and then computing the ratio: (experimental probe-background)/(control probe-background).

Plasma TTR levels were assayed utilizing the commercially available kit according to manufacturer's guidelines. Briefly, mouse plasma was diluted 1:10,000 in 1× mix diluents and added to pre-coated plates along with kit standards, and incubated for 2 hours at room temperature followed by 5× washes with kit wash buffer. Fifty microliters of biotinylated prealbumin antibody was added to each well and incubated for 1 hr at room temperature, followed by 5× washes with wash buffer. Fifty microliters of streptavidin-peroxidase conjugate was added to each well and plates were incubated for 30 minutes at room temperature followed by washing as previously described. The reaction was developed by the addition of 50 µl/well of chromogen substrate and incubation for 10 minutes at room temperature with stopping of reaction by the addition of 50 µl/well of stop solution. Absorbance at 450 nm was read on a Versamax microplate reader (Molecular Devices, Sunnyvale, Calif.) and data were analyzed utilizing the Softmax 4.6 software package (Molecular Devices).

The results of representative siRNA-conjugate efficacy is shown in FIG. 1. Most of anomeric linkage modified ligands showed similar TTR protein suppression at 5 mg/kg dose.

Example 34: AT3 mRNA Silencing In Vitro and In Vivo

The AT3 in vivo gene silencing in mice was determined by single subcutaneous administration of the AT3 siRNA-ligand conjugate by following a similar protocols described in Examples 33 for the TTR gene silencing in vivo. The in vitro gene silencing was evaluated by following similar protocols described in Examples 31 and 32.

The siRNA conjugate 54944 and 56881 were subcutaneously administered to C57/BL6 mice at three different single dose levels: 5, 10 and 25 mg/kg and AT3 protein level relative to PBS control was measured 72 hour post dose. The results are shown in FIG. 2. Conjugates 54944 and 56881 are referred to above and in FIG. 2 as 70001 and 70002, respectively.

Example 35: Synthesis of Mono-GalNAc Building Blocks for Oligonucleotide Conjugation The mono-GalNAc building block shown can be prepared as shown in Scheme 80.

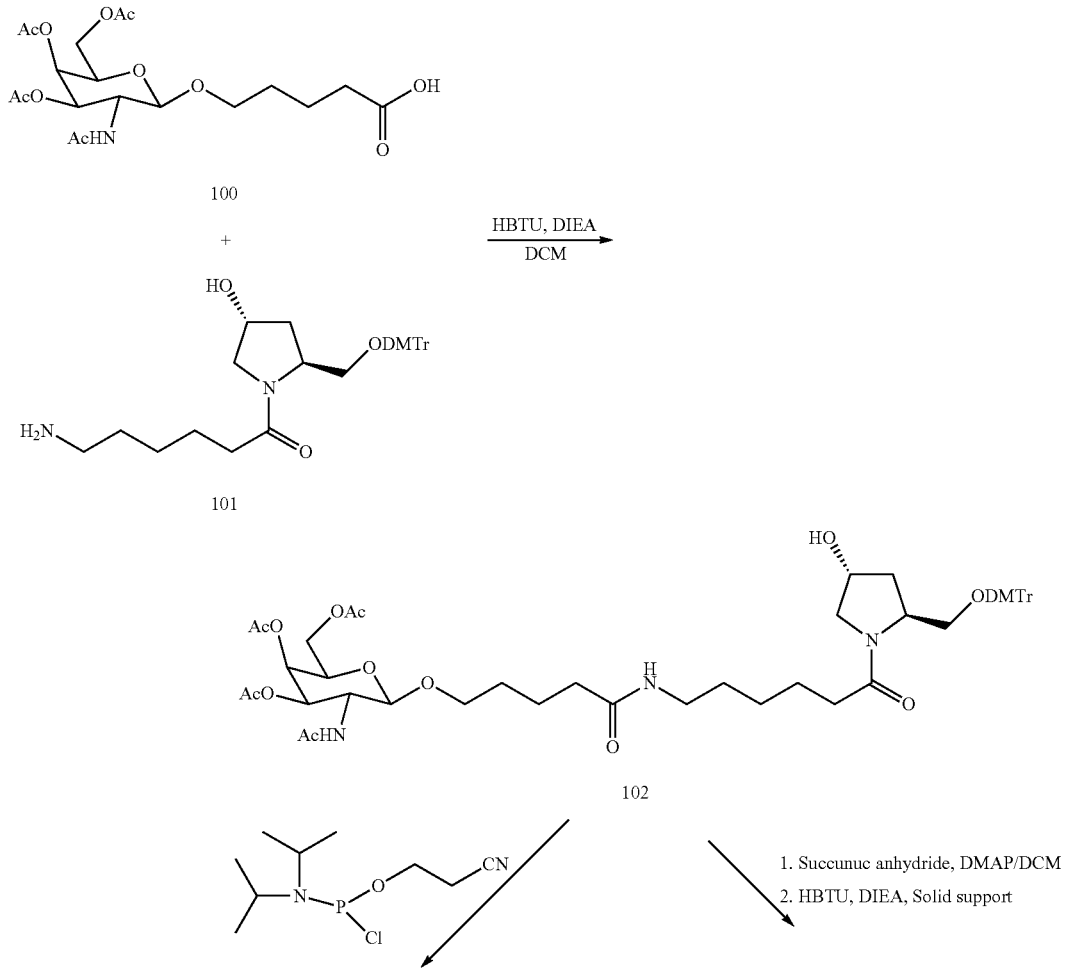

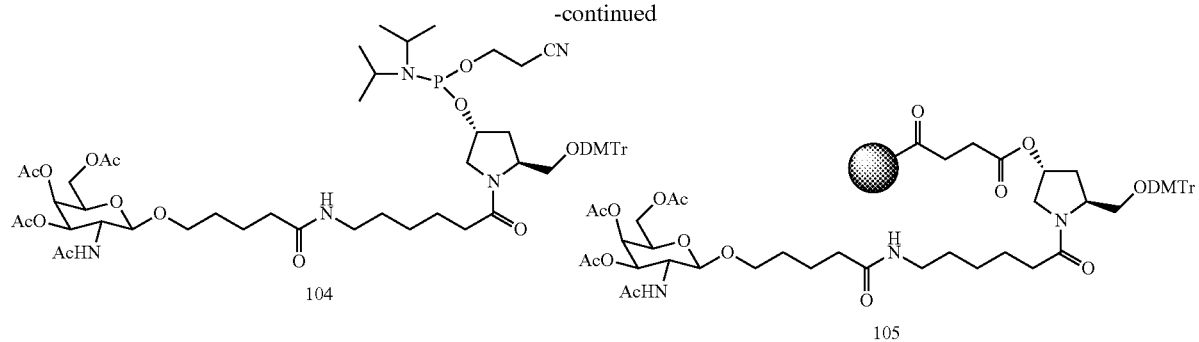

Synthesis of 102: GalNAc acid 100 (8.39 g, 18.71 mmol) and hydroxy proline amine (10.00 g, 18.77 mmol) were taken together in dichloromethane. HBTU (10.68 g, 28.12 mmol) and DIEA (9.80 mL, 3 eq.) were added and stirred the mixture for 2 hrs at ambient temperature. The TLC was checked and the reaction mixture was transferred to a separatory funnel and washed with water and brine. The organic layer was dried over sodium sulfate and the solvent removed. Crude product was purified by silica gel chromatography using dichloromethane and MeOH as solvents to get the compound 102 as a pale yellow fluffy solid (11.77 g, 63%). $^1$H NMR (400 MHz, DMSO) δ 7.80 (d, J=9.2 Hz, 1H), 7.69 (t, J=5.6 Hz, 1H), 7.39-7.09 (m, 9H), 6.86 (ddd, J=9.0, 5.4, 2.1 Hz, 4H), 5.20 (d, J=3.4 Hz, 1H), 5.03-4.83 (m, 2H), 4.47 (d, J=8.5 Hz, 1H), 4.41-4.07 (m, 2H), 4.04-3.95 (m, 3H), 3.86 (dt, J=11.2, 8.9 Hz, 1H), 3.79-3.68 (m, 6H), 3.68-3.36 (m, 3H), 3.21-2.88 (m, 5H), 2.26-2.14 (m, 2H), 2.09 (s, 3H), 2.02 (t, J=6.7 Hz, 2H), 1.98 (s, 3H), 1.87 (d, J=7.5 Hz, 3H), 1.76 (s, 3H), 1.53-1.29 (m, 7H).

Synthesis of 104: Hydroxy proline derivative 102 (6.00 g, 6.24 mmol) was dissolved in dichloromethane (100 mL). To that DIEA (2.20 mL, 3 eq) and chloroamidite reagent were added. The reaction mixture was stirred for 30 minutes and checked by TLC. It was transferred to a separatory funnel and washed with water and sodium bicarbonate solution. The organic layer was dried over sodium sulfate and the crude product was purified by silica gel chromatography using dichloromethane and MeOH as eluent to get the compound as a white fluffy solid. $^1$H NMR (400 MHz, DMSO) δ 7.80 (d, J=9.2 Hz, 1H), 7.68 (s, 1H), 7.42-7.06 (m, 8H), 7.01-6.73 (m, 4H), 5.20 (d, J=3.3 Hz, 1H), 4.96 (dd, J=11.2, 3.3 Hz, 1H), 4.63 (d, J=4.7 Hz, 1H), 4.47 (d, J=8.5 Hz, 1H), 4.15 (s, 1H), 4.01 (s, 3H), 3.86 (d, J=11.0 Hz, 1H), 3.70 (d, J=16.5 Hz, 9H), 3.45 (ddd, J=37.0, 23.3, 16.4 Hz, 6H), 2.99 (dd, J=12.3, 6.4 Hz, 3H), 2.74 (dd, J=9.2, 5.8 Hz, 2H), 2.21 (s, 2H), 2.09 (s, 3H), 2.05-1.95 (m, 5H), 1.88 (s, 3H), 1.76 (s, 3H), 1.52-1.16 (m, 11H), 1.16-1.02 (m, 11H). $^{31}$P NMR δ=151.78, 151.61, 151.50, 151.30.

Synthesis of 105: Compound 102 (2.10 g, 2.18 mmol) was dissolved in DCM (20 mL). To this mixture, succinic anhydride (0.441 g, 4.36 mmol) and DMAP (0.532 g, eq) followed by TEA (1 ml) were added. The reaction mixture was stirred overnight at room temperature. The TLC of the reaction mixture was checked and the reaction mixture was washed with water and brine. The organic layer was dried over sodium sulfate and the crude product filtered through a small pad of silica gel. Solvent was removed and this material was used for the next reaction. The succinate from the above reaction was dissolved in anhydrous acetonitrile. HBTU (1.59 g, 4.20 mmols) and DIEA (1.10 ml) were added and the mixture was swirled for 5 minutes. A polystyrene solid support was added to the reaction mixture and the mixture was shaken overnight at ambient temperature. The solid support was filtered, and washed and capped using acetic anhydride/Py mixture. The solid support was again washed with dichloromethane, MeOH/DCM and ether (27.10 g, 55 umol/g).

Example 36: Synthesis of Mono-GalNAc NHS Esters for Oligonucleotide Conjugation

Mono-GalNAc NHS esters useful for oligonucleotide conjugation can be prepared as shown in Schemes 81-86 below.

Scheme 81

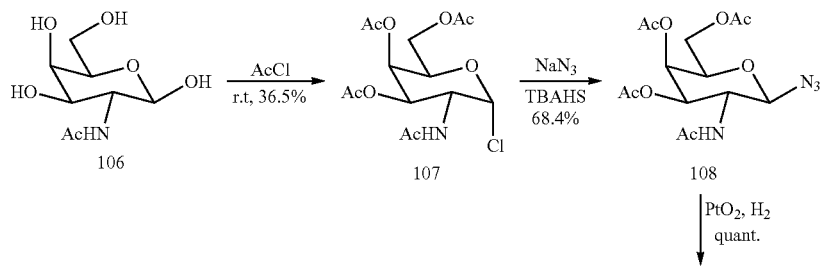

525
-continued
526
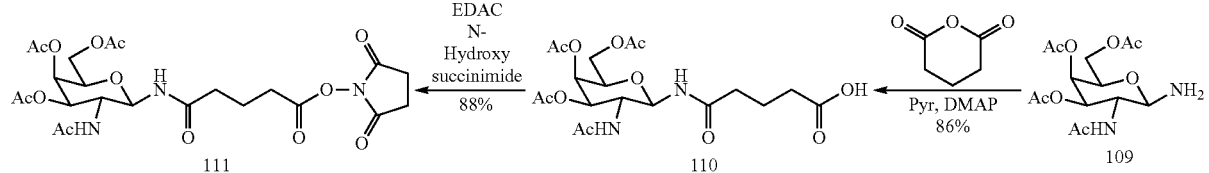

Scheme 82
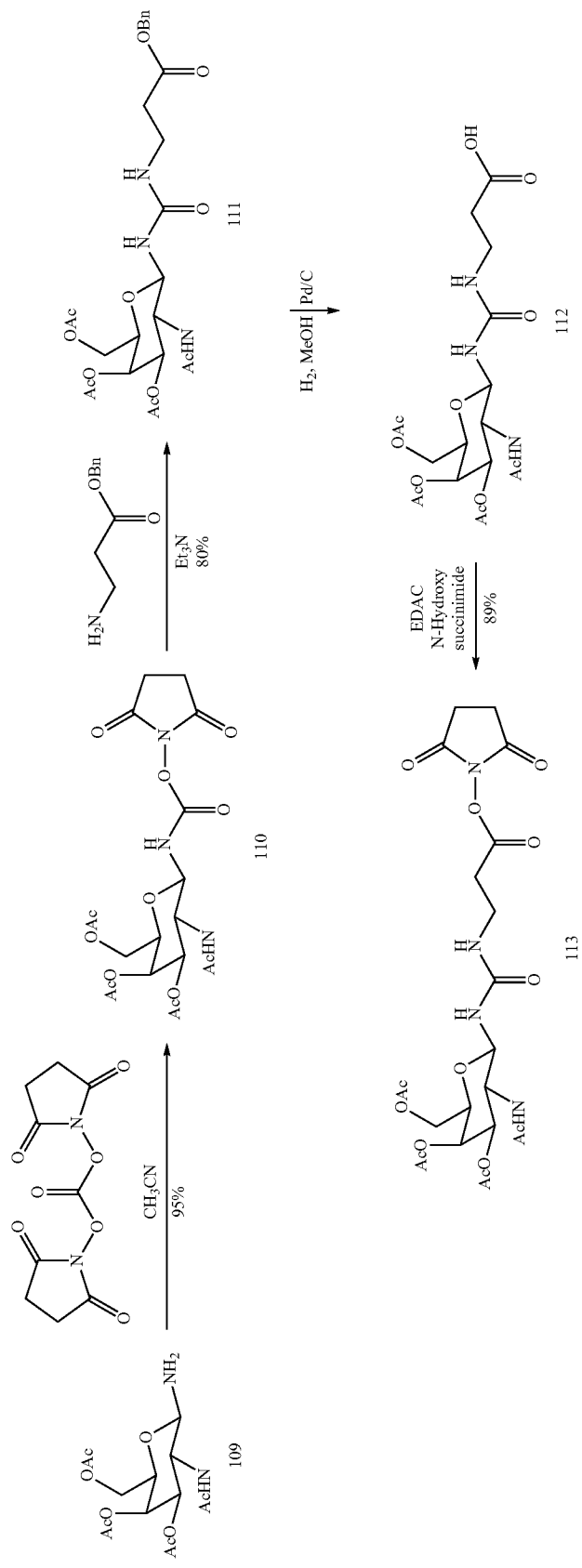

Scheme 83
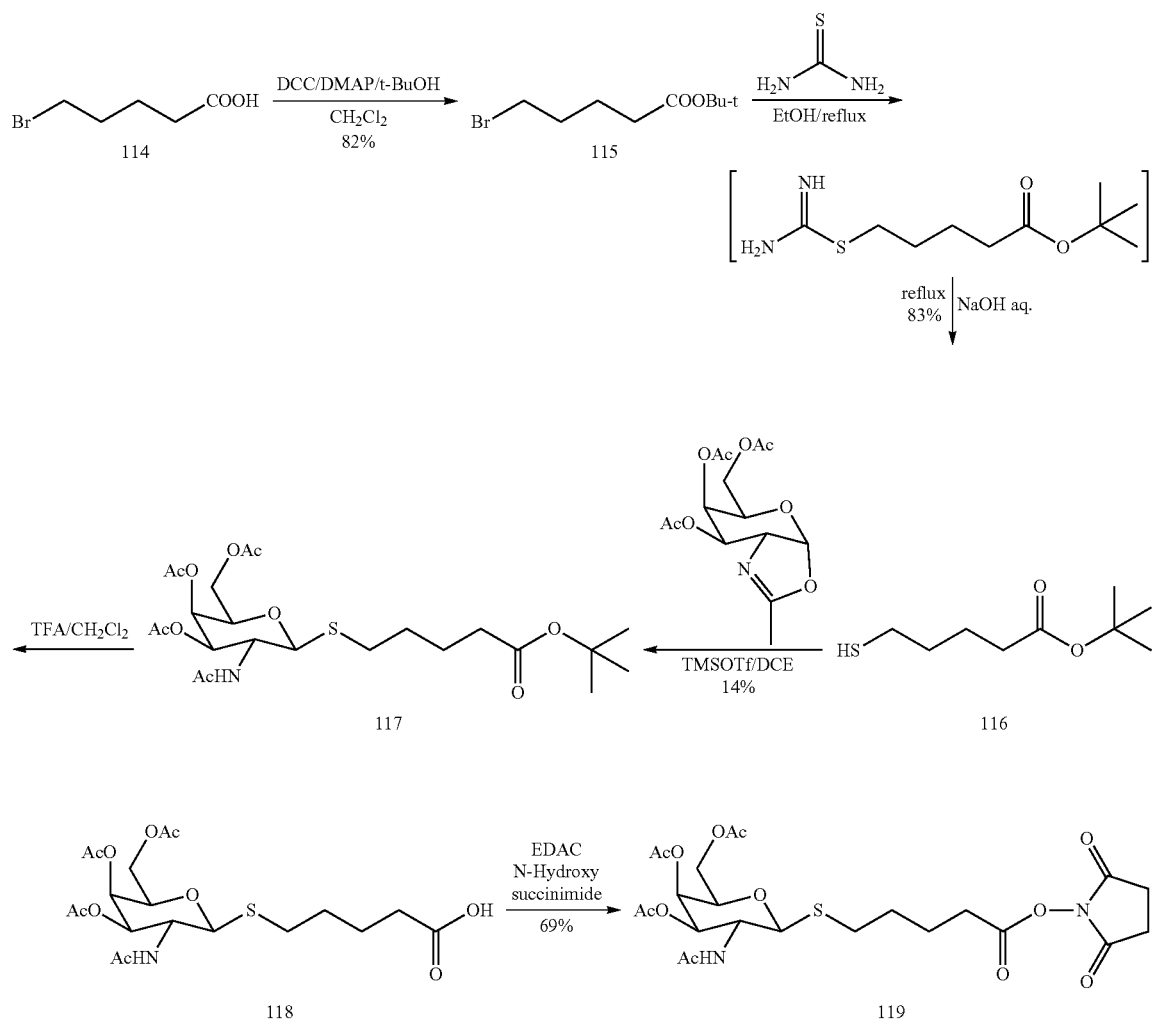
Scheme 84
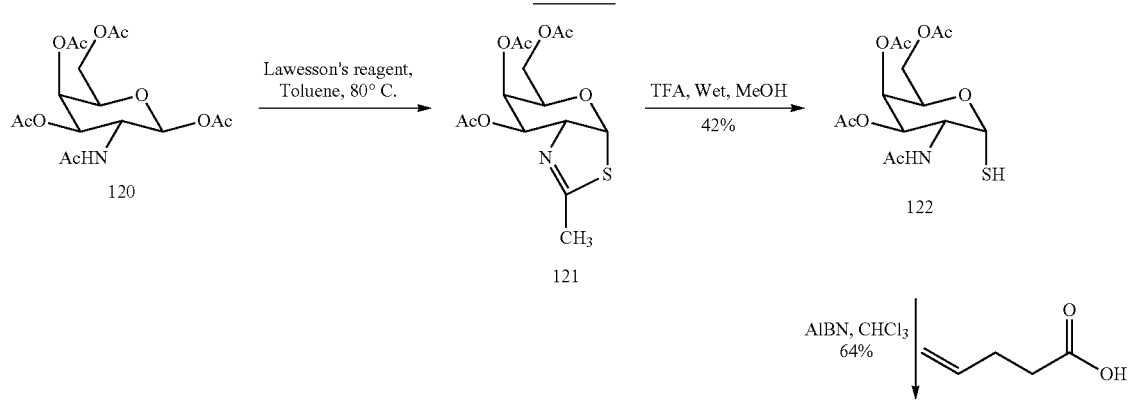

531                                                                                      532
-continued
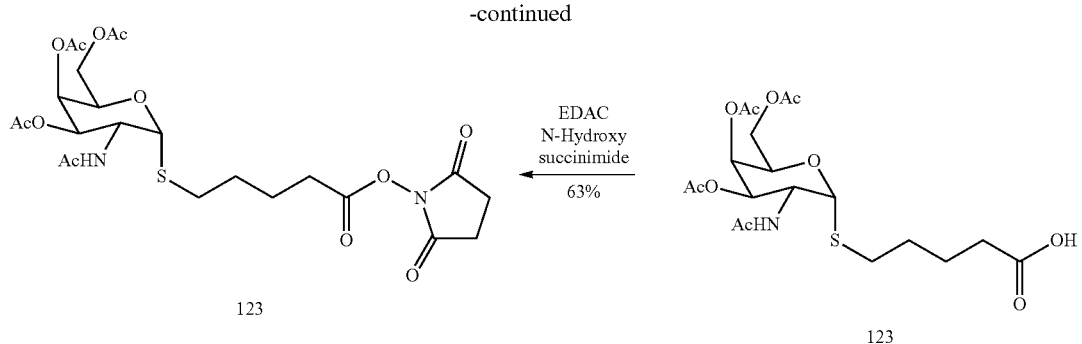
123                                                                                      123
Scheme 85
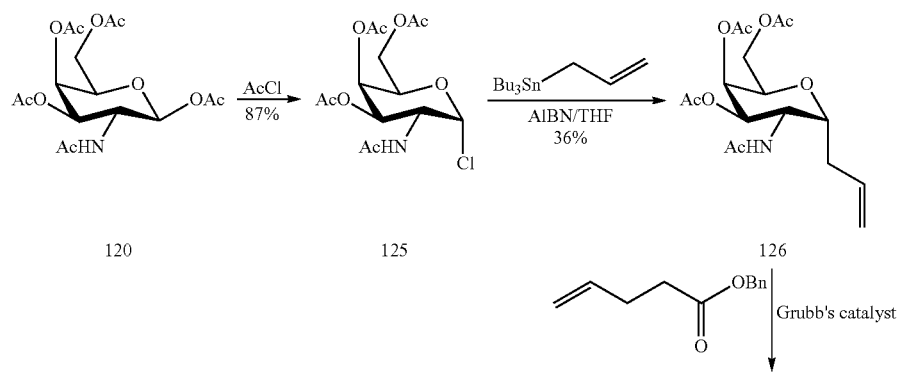
120                         125                         126
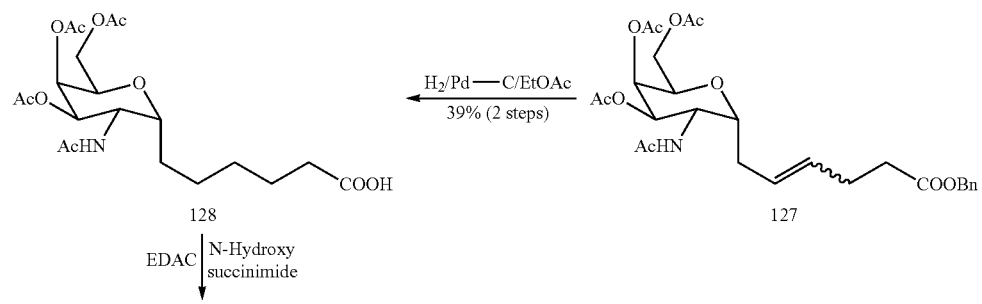
128                                                     127
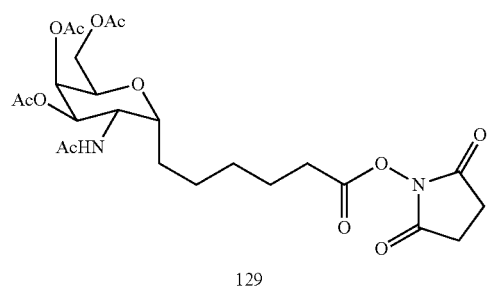
129

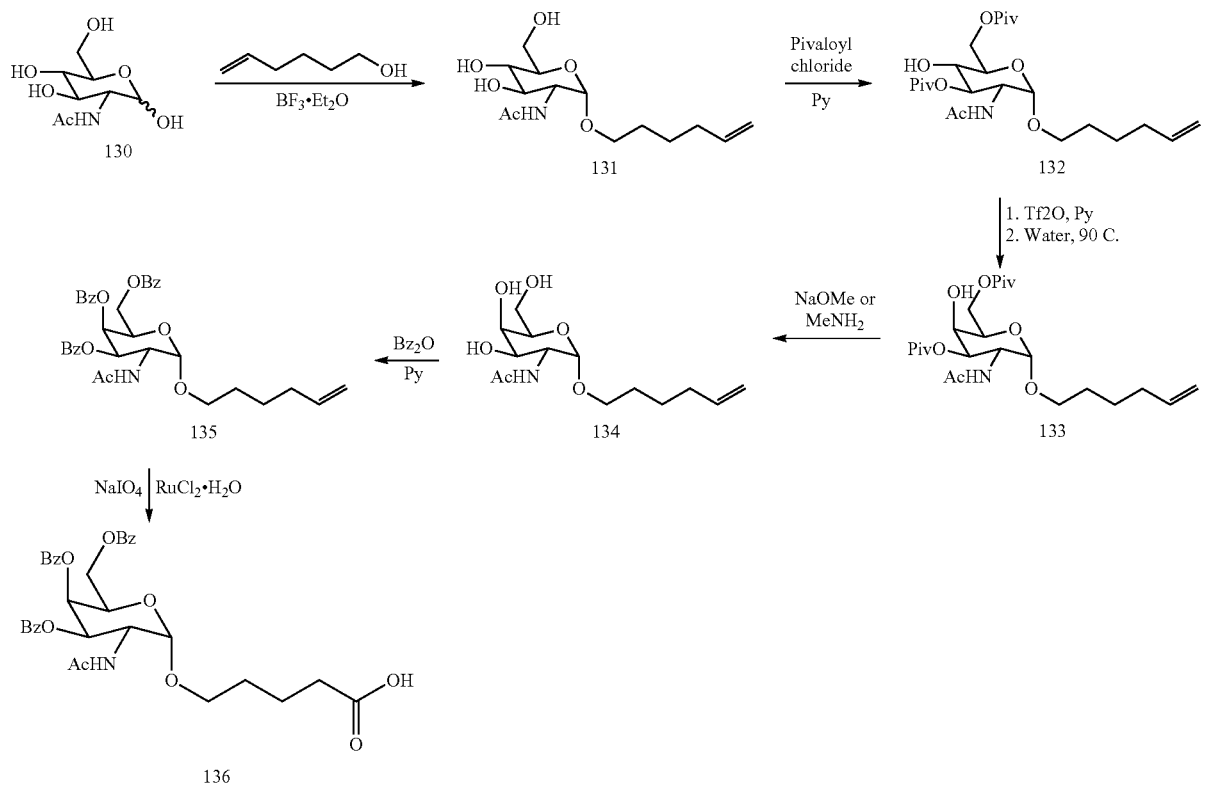
Example 37: Synthesis of Amide- and Carbamate-Linked Building Blocks for Oligonucleotide Conjugation
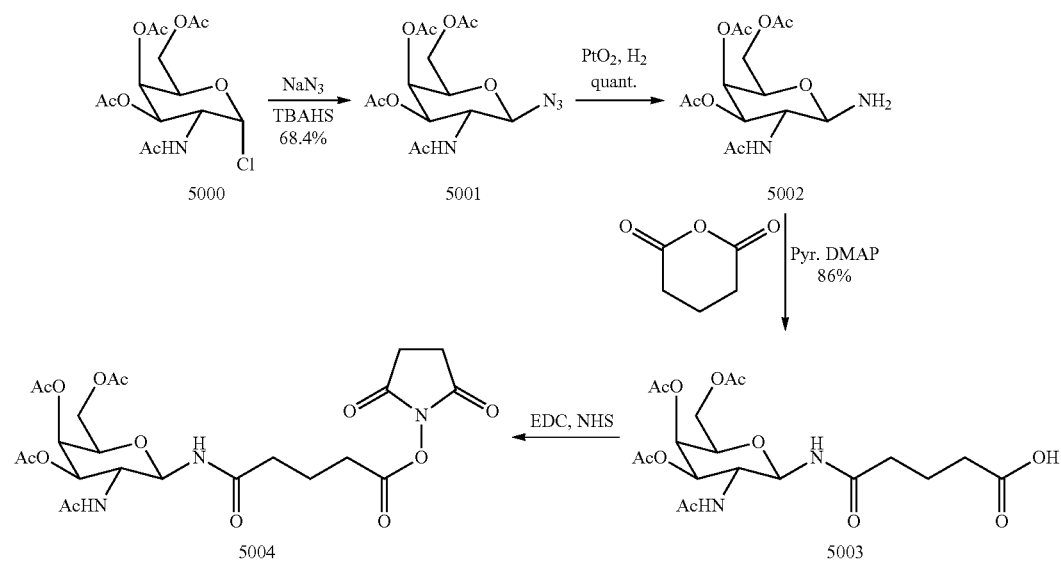

Synthesis of Compound 5001:

To a stirred solution of compound 5000 (23.22 g, 63.6 mmol) in DCM was added NaN$_3$ (12.4 g, 190.8 mmol) and TBAHS (21.6 g, 63.6 mmol) followed by the addition of 150 mL of a saturated NaHCO$_3$ solution. The resulting mixture was stirred for 14 hours. The reaction mixture was then extracted with ethyl acetate (3×250 ml), washed with water, brine and dried over anhydrous Na$_2$SO$_4$. Concentration of the solvent gave the crude material. This material was dissolved in ethyl acetate (150 mL) followed by the addition of 150 mL of hexane, which resulted in precipitation of the product as a white solid. The solid was dried under reduced pressure to afford compound 5001 (16.2 g, 68.4%). LCMS for compound 5001: Calculated: 372.33 (M$^+$), Found: 407.1 (M$^-$+Cl$^-$).

Synthesis of compound 5002:

To a stirred solution of compound 5001 (13.2 g, 35.5 mmol) in THF (600 mL) was added PtO$_2$ (0.6 g) and the reaction mixture was stirred under hydrogen atmosphere at room temperature for 14 hours. The catalyst was removed by filtration. Concentration of the solvent afforded compound 5002 (13.0 g).

Synthesis of Compound 5003:

To a stirred solution of compound 5002 (10.0 g, 28.89 mmol) and glutaric anhydride (3.29 g, 28.89 mmol) in DCM (100 mL) were added pyridine (4.6 g) and DMAP (0.176 g). The reaction mixture was stirred for 14 hours. The resulting mixture was concentrated, then subjected to a filter column to afford compound 5003 (11.45 g, 86%). LCMS for compound 5003: Calculated: 460.43 (M$^+$), Found: 459.3 (M$^-$−1), 495.0 (M$^-$+Cl$^-$).

Synthesis of Compound 5004:

To a stirred solution of compound 5003 (7.6 g, 16.51 mmol), NHS (2.09 g, 18.16 mmol) and EDC (3.8 g, 19.8 mmol) in DCM (100 mL) was added DIEA (7.16 mL, 41.27 mmol) dropwise. The resulting mixture was stirred for 14 hours. 100 mL of water was then added, and the product was extracted with DCM (2×50 mL), washed with citric acid (20%), saturated NaHCO$_3$, brine, then dried over anhydrous Na$_2$SO$_4$. Concentration of the solvent afforded compound 5004 (6 g, 65%). LCMS for compound 5004: Calculated: 557.5 (M$^+$), Found: 558.0 (M$^+$+1).

Synthesis of Compound 5005:

To a stirred solution of compound 5002 (3.0 g, 8.66 mmol) in acetonitrile (50 mL) was added DSC (2.22 g, 8.66 mmol) and the resulting mixture was stirred overnight (14 hours) at room temperature. The solvent was concentrated, then the product was extracted with ethyl acetate (3×50 mL), washed with water, 10% citric acid, brine and dried over anhydrous Na$_2$SO$_4$. Concentration of the solvent afford compound 5005 (3.8 g, 95%). LCMS Calculated for C$_{19}$H$_{25}$N$_3$O$_{12}$: 487.41 (M$^+$), Found: 488.1 (M$^+$+1), 510.1 (M$^+$+Na$^+$).

Synthesis of Compound 5006:

To a stirred solution of compound 5005 (0.663 g, 1.36 mmol) in DCM (15 mL) were added amine (0.526 g, 1.5 mmol) and triethylamine (0.4 mL). The solvent was concentrated, then the product was extracted with ethyl acetate (3×50 mL), washed with water, 10% citric acid, brine and dried over anhydrous Na$_2$SO$_4$. Concentration of the solvent afforded compound 5006 (0.7 g, 93%). LCMS Calculated for C$_{25}$H$_{33}$N$_3$O$_{11}$ 551.54 (M$^+$), Found: 552.2 (M$^+$+1), 574.2 (M$^+$+Na$^+$).

Synthesis of Compound 5007:

To a stirred solution of compound 5005 (0.7 g, 1.26 mmol) in EtOH (15 mL) was added Pd/C (0.1 g) and the resulting mixture was stirred under a hydrogen atmosphere overnight (14 h). The catalysts was removed by filtration over celite, and the mixture was washed with EtOH (950 mL) and concentrated to afford the product which was used for the next step without purification. To a stirred solution of the above acid in DCM (20 mL) were added EDC (488 mg, 2.56 mmol), NHS (730 mg, 6.35 mmol) and DIEA (0.88 mL, 5.07 mmol). The reaction mixture was stirred overnight. Concentration of the reaction mixture followed by column chromatography afforded compound 5007 (250 mg, 35%). LCMS Calculated for C$_{22}$H$_{30}$N$_4$O$_{13}$: 558.49 (M$^+$), Found: 559.2 (M$^+$+1), 581.1 (M$^+$+Na$^+$).

Scheme 88

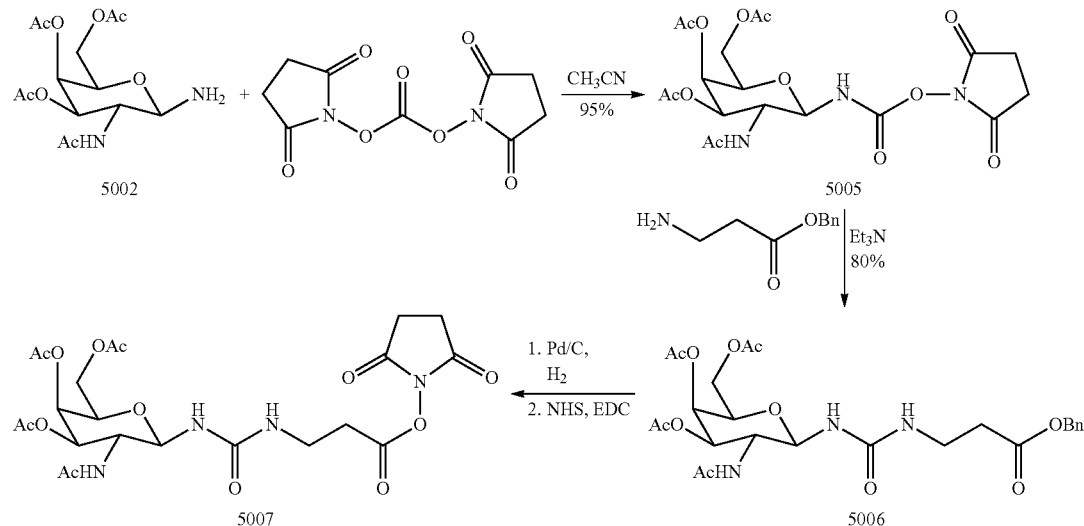

Example 38: Synthesis of S- and C-Linked GalNAc Derivatives and the Building Blocks Scheme 89

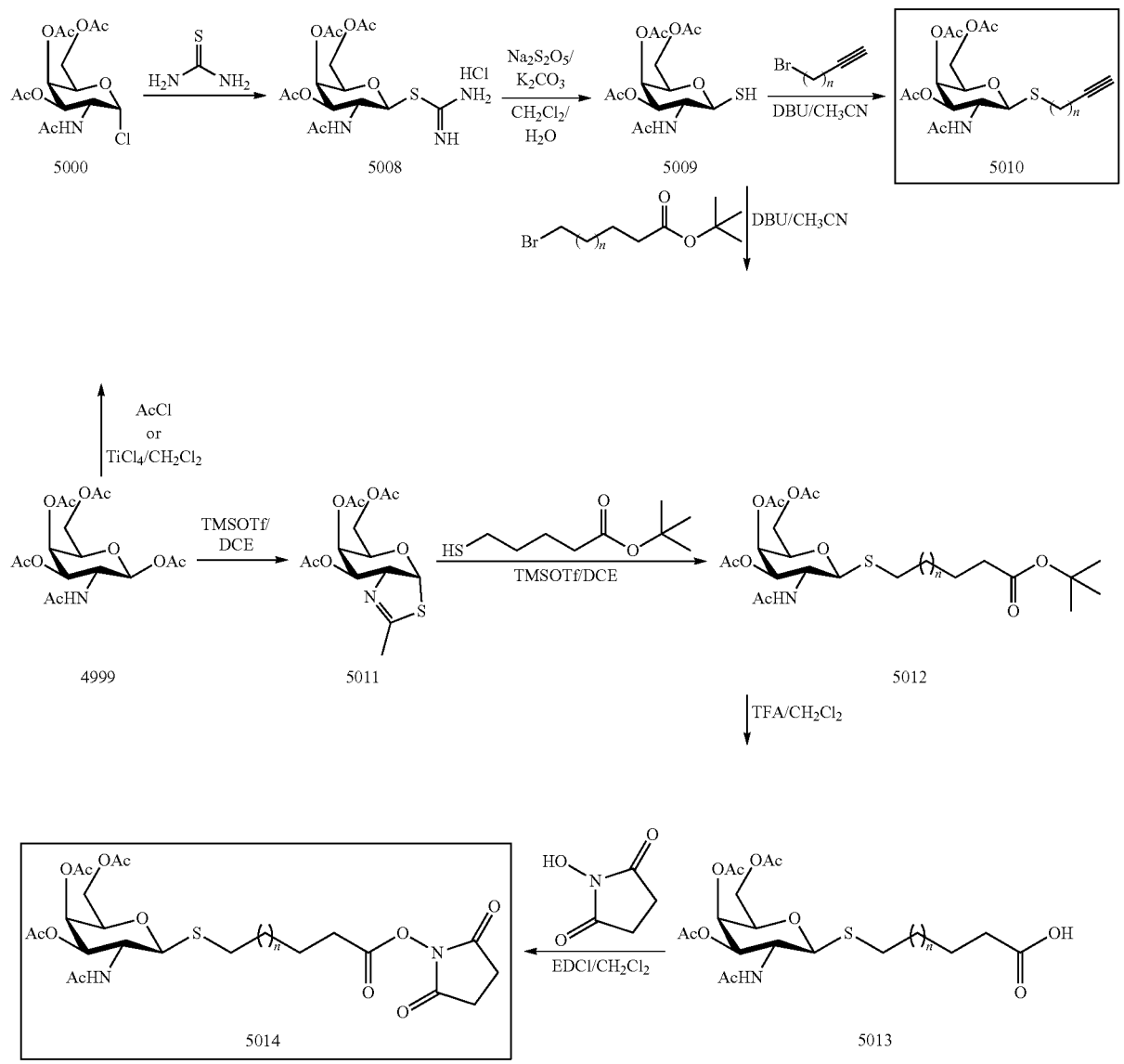

Synthesis of Compound 5012:

Compound 4999 (15.6 g, 40.1 mmol) was treated with TMSOTf (7.98 mL, 44.1 mmol) in DCE to afford compound 5011. Molecular weight for $C_{14}H_{20}NO_8$ (M+H)$^+$ Calc. 330.12, Found 330.0. Compound 5011 (1.65 g, 5 mmol) and tert-butyl 5-mercaptopentanoate (1.0 g, 5.25 mmol) in DCE were treated with TMSOTf (0.181 mL, 1.0 mmol) overnight. Aqueous work-up and silica gel column purification afforded compound 5012 (380 mg, 0.731 mmol, 15%). Molecular weight for $C_{23}H_{37}NNaO_{10}S$ (M+H)$^+$ Calc 542.20, Found 542.1.

Synthesis of Compound 5013:

To a solution of compound 5012 (380 mg, 0.731 mmol) in $CH_2Cl_2$ (4 mL) was added TFA (1 mL) at 0° C. The mixture was stirred at 0° C. for 2 hours then at room temperature for 3 hours. The solvent was evaporated and the residue was co-evaporated with toluene to afford crude compound 5013. This material was used for next step without purification. Molecular weight for $C_{19}H_{30}NO_{10}S$ (M+H)$^+$ Calc 464.1590, Found 464.1.

Synthesis of Compound 5014:

Compound 5013 from the previous step (~0.731 mmol) was treated with N-hydroxy succinimide (168 mg, 1.46 mmol) in the presence of EDCI (280 mg, 1.46 mmol) and DIEA (0.764 mL, 4.38 mmol) in $CH_2Cl_2$ (5 mL) for 14 hours. Aqueous work-up then column chromatography afforded compound 5014 (284 mg, 0.507 mmol, 69% over 2 steps). Molecular weight for $C_{23}H_{33}N_2O_{12}S$ (M+H)$^+$ Calc. 561.1754, Found 561.1.

S-alkylation of compound 5009 with alkyne bromide affords compound 5010.

Scheme 90

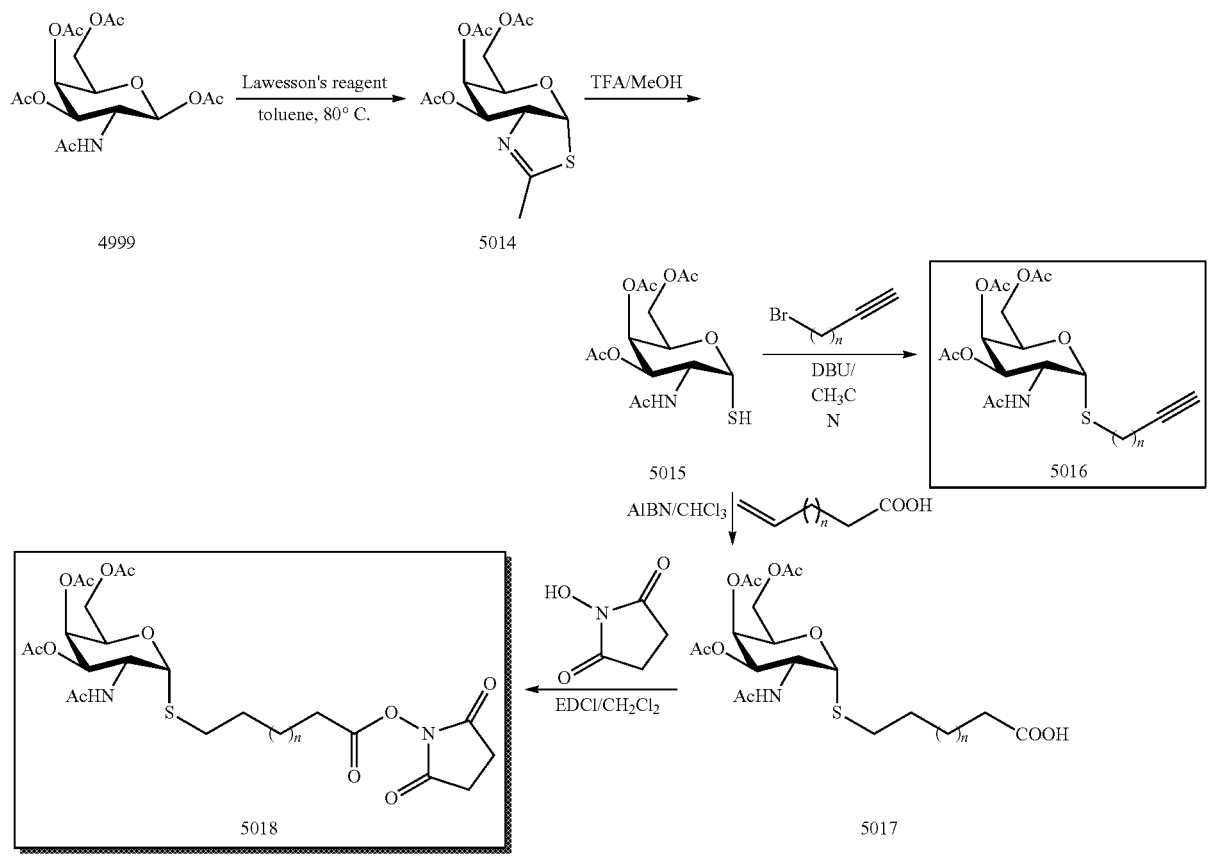

Compound 5016 is prepared from compound 5015 (see, *J. Org. Chem.*, 67, 2995-2999, 2002). The acid 5017 is prepared according to the reported procedure.

Synthesis of Compound 5018:

Compound 5017 (2.40 g, 5.18 mmol) was treated with N-hydroxysuccinimide (716 mg, 6.22 mmol) in the presence of EDCI (1.19 g, 6.22 mmol) and DIEA (2.70 mL, 15.5 mmol) in $CH_2Cl_2$ (30 mL) for 14 h. Aqueous work-up followed by column chromatography afforded compound 5018 (1.83 g, 3.26 mmol, 63%). Molecular weight for $C_{23}H_{33}N_2O_{12}S$ $(M+H)^+$ Calc. 561.1754, Found 561.2.

Scheme 91

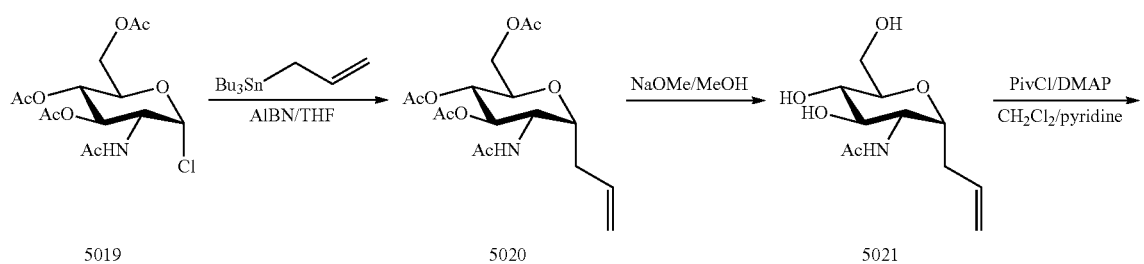

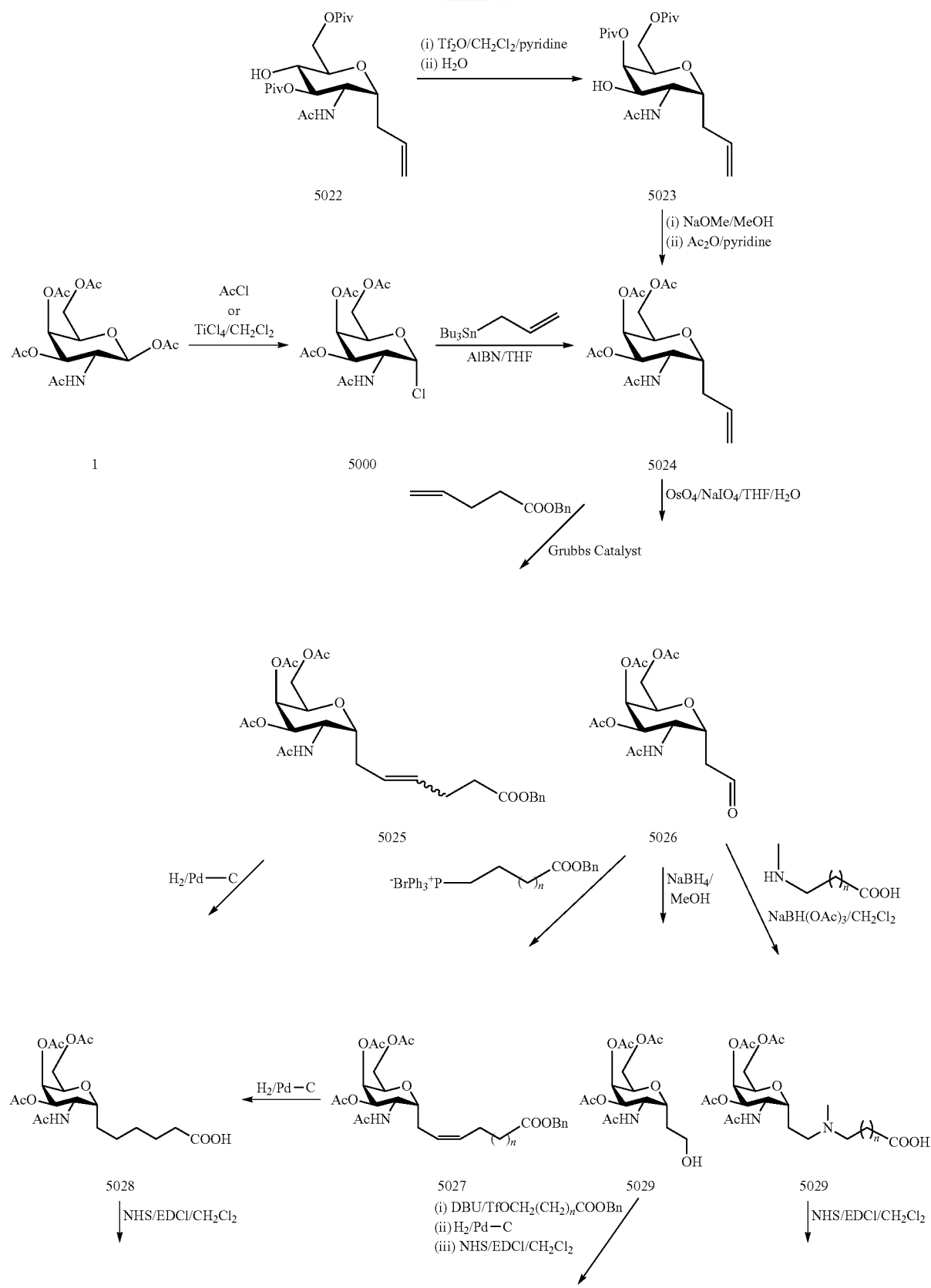

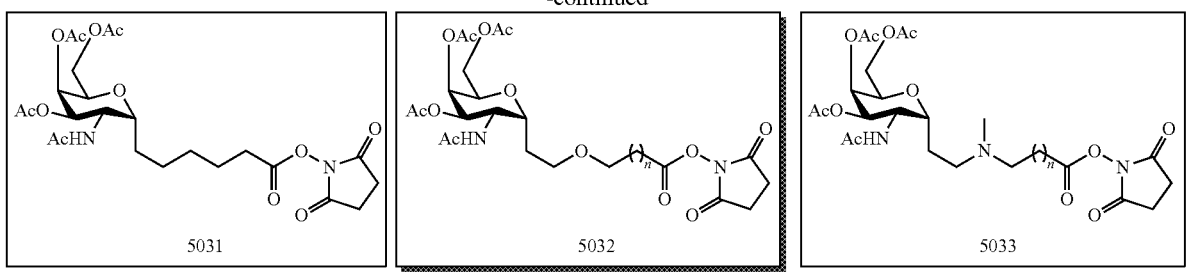

Compound 5024 was prepared using reported procedures (see, *J. Org. Chem.*, 71, 3619-362, 2006 and *Carbohydrate Research*, 309, 319-330, 1998).

Synthesis of Compound 5025:

Compound 5024 (1.94 g, 5.22 mmol), benzyl 4-pentenoate (2.99 g, 15.7 mmol) and Grubbs Catalyst, 2nd Generation (433 mg, 0.522 mmol) in $CH_2Cl_2$ (20 mL) were heated at 40° C. for 40 hours. The solvent was removed and the residue was purified by silica gel column chromatography to afford compound 5025 (1.87 g, 3.50 mmol, 67%). Molecular weight for $C_{27}H_{36}NO_{10}$ $(M+H)^+$ Calc. 534.2339, Found 534.2.

Synthesis of Compound 5028:

To a solution of compound 5025 (1.85 g, 3.47 mmol) in EtOAc (30 mL) was added palladium on carbon (Aldrich: 330108-50G, 10 wt. %, Degussa type E101 NE/W: 185 mg). The reaction mixture was stirred under an atmosphere of hydrogen for 14 hours. After filtration through Celite, the filtrate was removed in vacuo. The residue was purified by silica gel column chromatography to afford compound 5028 (903 mg, 2.03 mmol, 59%). Molecular weight for $C_{20}H_{32}NO_{10}$ $(M+H)^+$ Calc. 446.2026, Found 446.1.

Synthesis of Compound 5031:

Compound 5028 (326 mg, 0.732 mmol) was treated with N-hydroxysuccinimide (127 mg, 1.10 mmol) in the presence of EDCI (211 mg, 1.10 mmol) and DIEA (0.383 mL, 2.20 mmol) in $CH_2Cl_2$ (5 mL) for 14 hours. Aqueous work-up followed by column chromatography afforded compound 5031 (300 mg, 0.553 mmol, 76%). Molecular weight for $C_{24}H_{35}N_2O_{12}$ $(M+H)^+$ Calc. 543.2190, Found 543.2.

Oxidative cleavage of compound 5024 affords aldehyde 5026. It is reduced to alcohol and then O-alkylation with benzyl-protected triflate followed by deprotection and esterification affords compound 5032. Reductive amination of compound 5026 affords acid compound 5030 which is esterified to afford compound 5033.

Scheme 92

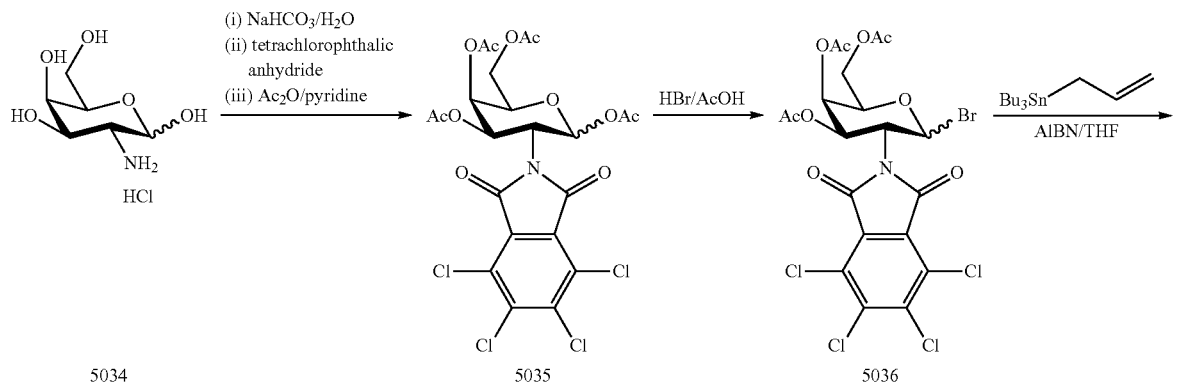

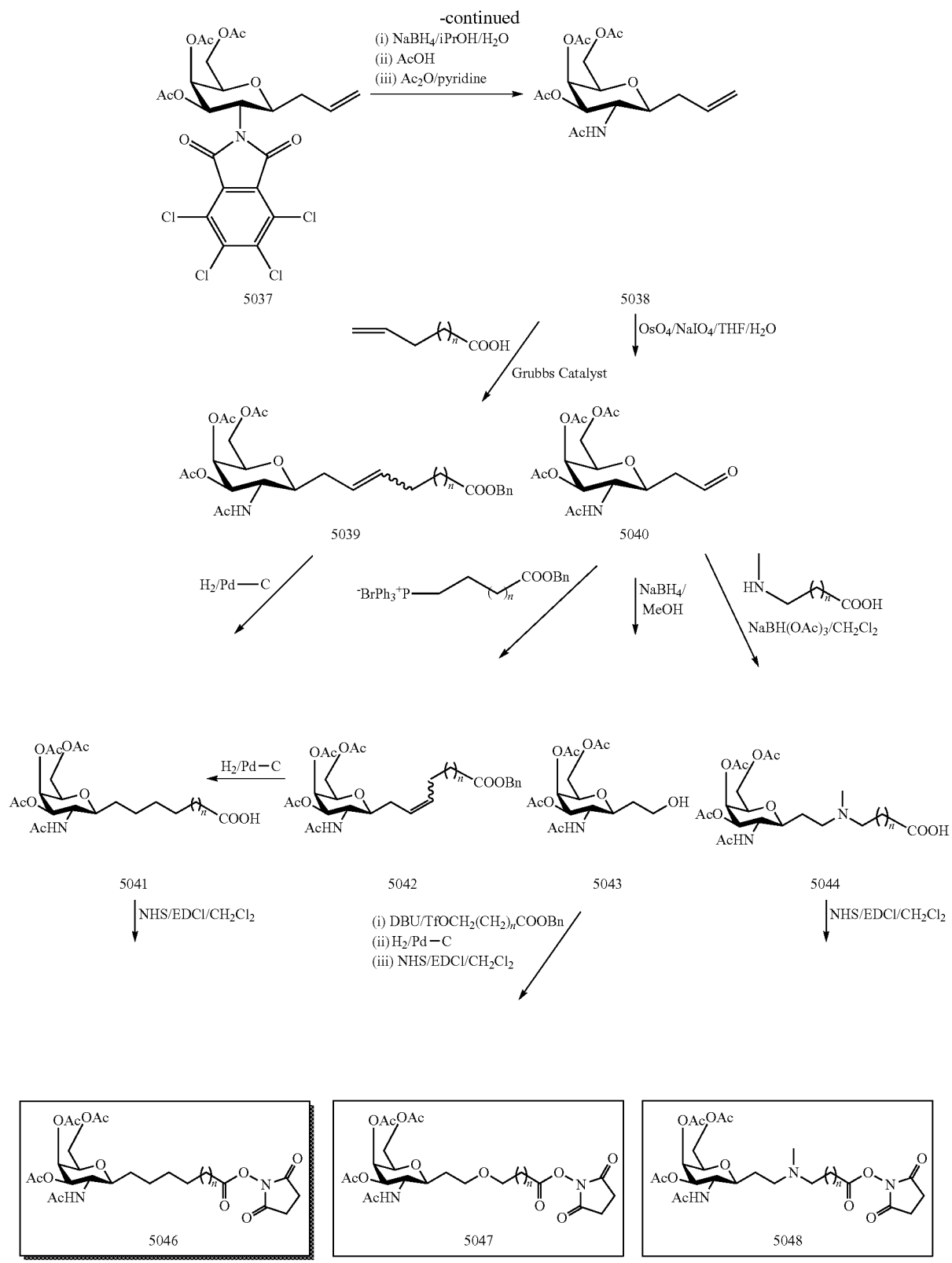
Compound 5048 was prepared in a similar manner to that reported in the literature (see, *J. Org. Chem.*, 61, 6442-6445, 1996). Compounds 5046, 5047, and 5048 are prepared in an analogous manner to that shown in Scheme 91.

Example 39

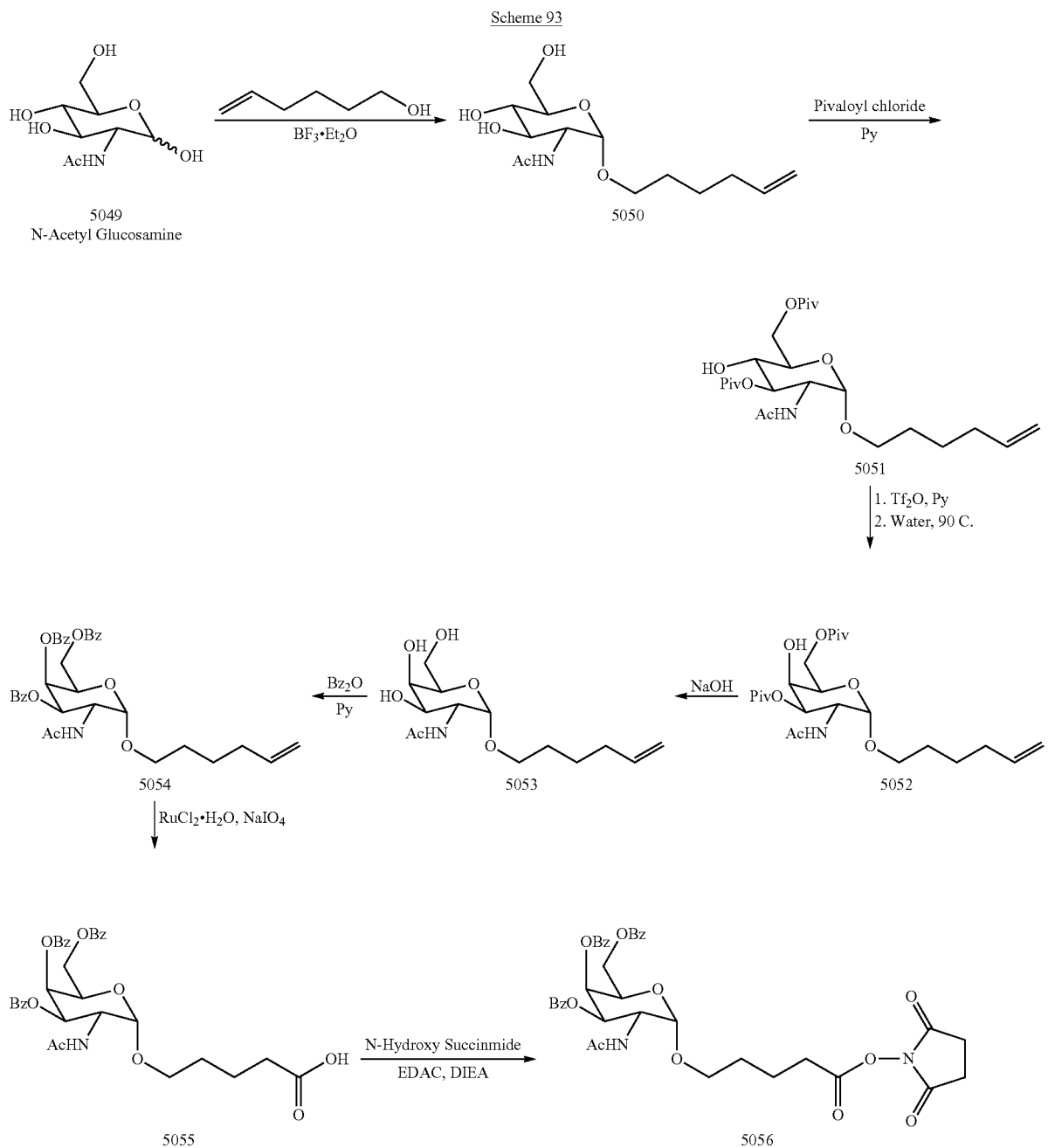

Synthesis of Compound 5050:

N-Acetyl glucosamine (10 g) was refluxed with hexenol (excess) in the presence of $BF_3 \cdot Et_2O$ to afford compound 5050.

Synthesis of Compound 5052:

Compound 5050 was treated with pivolyl chloride as reported in the literature. This pivolyl ester was treated with triflic anhydride followed under reflux with water to afford compound 5052.

Synthesis of Compound 5055:

Compound 5052 was first treated with sodium hydroxide to remove pivolyl ester, then the resulting trihydroxyl derivate was treated with benzoic anhydride to afford compound 5054. The double bond was later oxidized to afford the carboxylic acid 5055.

Synthesis of Compound 5056:

Compound 5055 (502 mg, 0.732 mmol) was treated with N-hydroxysuccinimide (127 mg, 1.10 mmol) in the presence of EDCI (211 mg, 1.10 mmol) and DIEA (0.383 mL, 2.20 mmol) in $CH_2Cl_2$ (5 mL) for 14 hours. Aqueous work-up followed by column chromatography afforded compound 5056 (400 mg, 0.553 mmol, 76%). Molecular weight for $C_{38}H_{38}N_2O_{13}$ $(M+H)^+$ Calc. 730.24, Found 730.25.

Example 40: Synthesis of New GalNAc Conjugates Using Post-Synthetic Methods
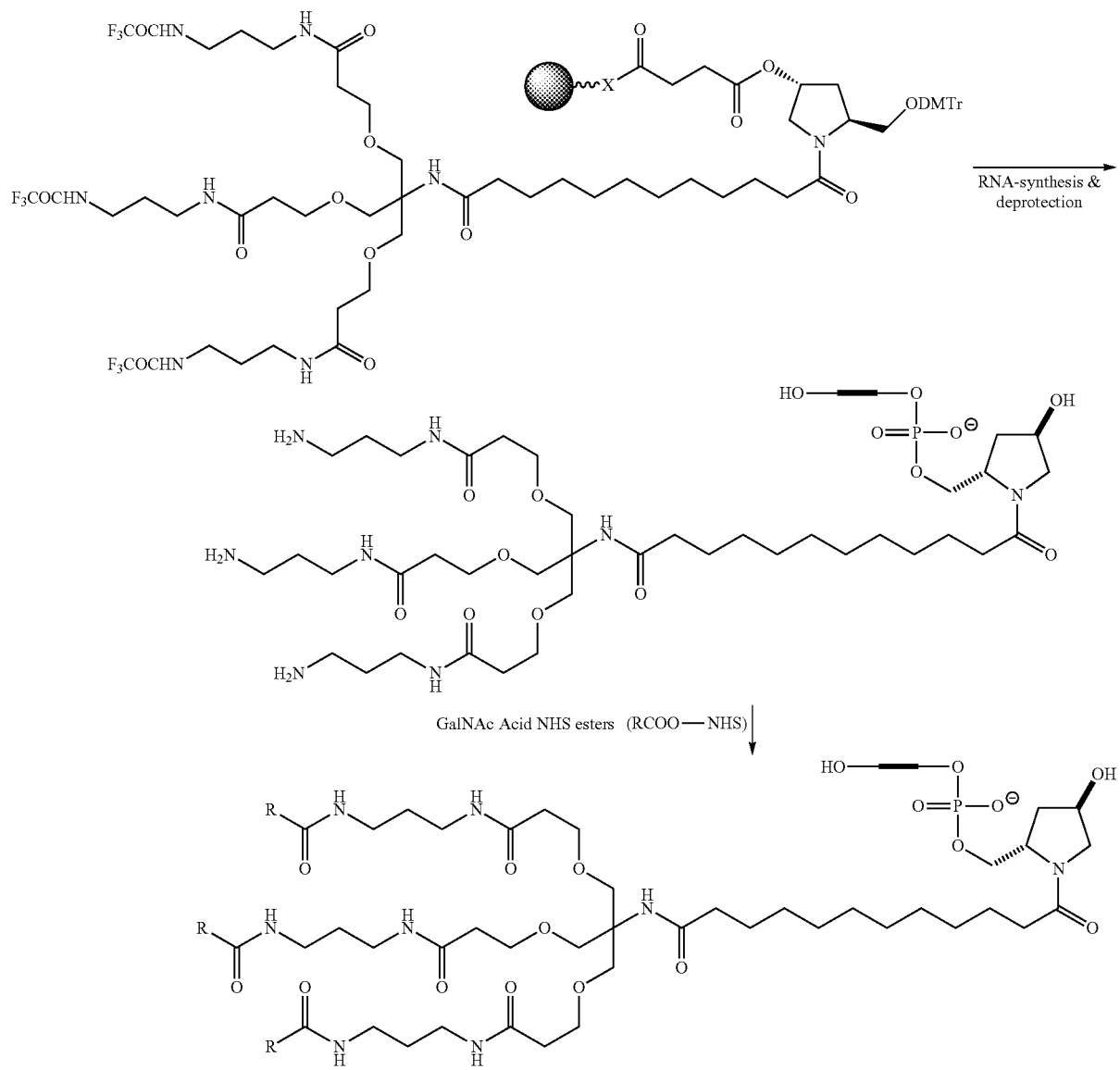
Scheme 94
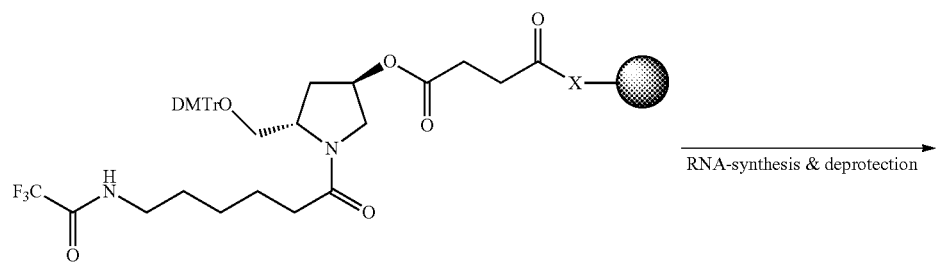
Scheme 95

-continued
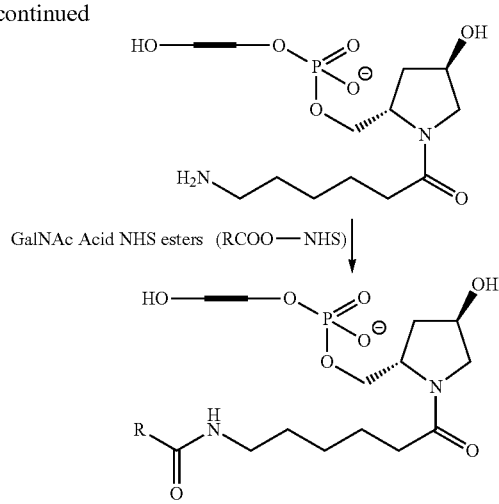
GalNAc Acid NHS esters (RCOO—NHS)
Scheme 96
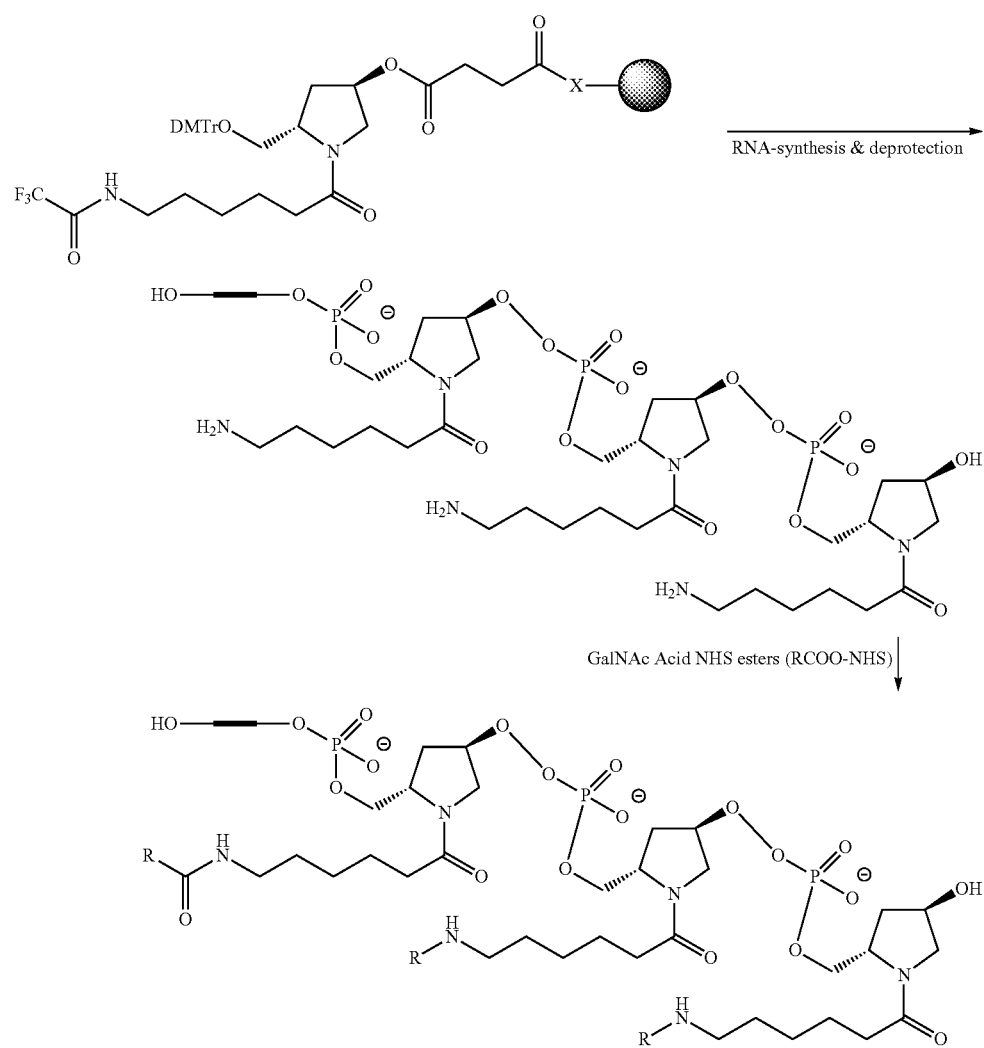
RNA-synthesis & deprotection
GalNAc Acid NHS esters (RCOO-NHS)

The GalNAc groups in the table below were conjugated to an siRNA by the procedures described in Schemes 94, 95 or 96, above.
| GalNAc NHS Esters (RCOO-NHS) | R |
|---|---|
| 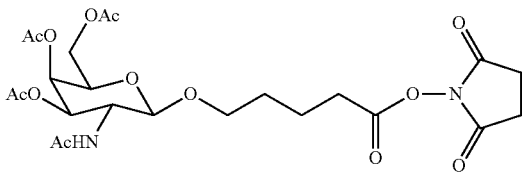 [SMILES: CC(=O)NC1C(OCCCCC(=O)ON2C(=O)CCC2=O)OC(COC(C)=O)C(OC(C)=O)C1OC(C)=O] | 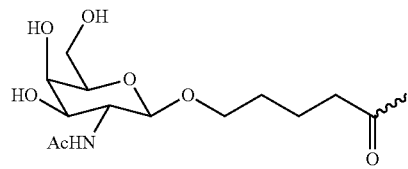 |
| 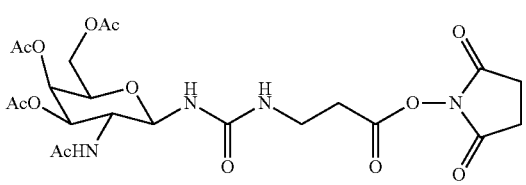 [SMILES: CC(=O)NC1C(NC(=O)NCCC(=O)ON2C(=O)CCC2=O)OC(COC(C)=O)C(OC(C)=O)C1OC(C)=O] | 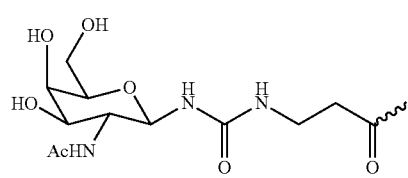 |
| 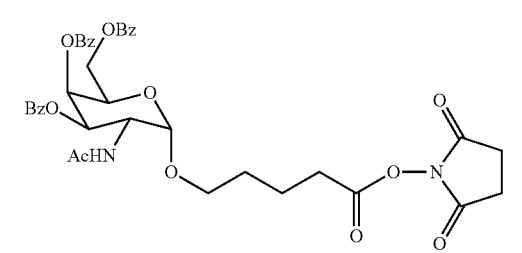 | 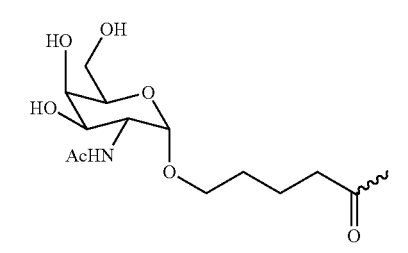 |
| 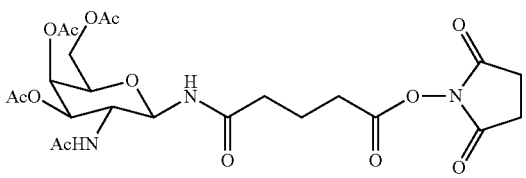 [SMILES: CC(=O)NC1C(NC(=O)CCCC(=O)ON2C(=O)CCC2=O)OC(COC(C)=O)C(OC(C)=O)C1OC(C)=O] | 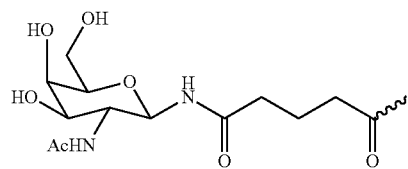 |
| 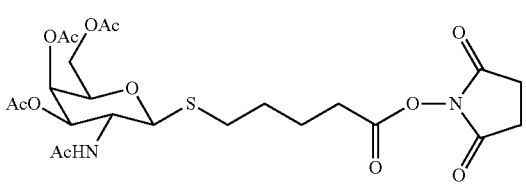 [SMILES: CC(=O)NC1C(SCCCCC(=O)ON2C(=O)CCC2=O)OC(COC(C)=O)C(OC(C)=O)C1OC(C)=O] | 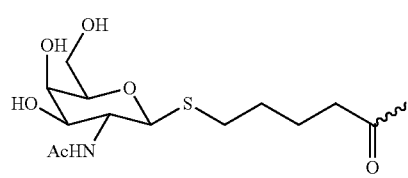 |
| 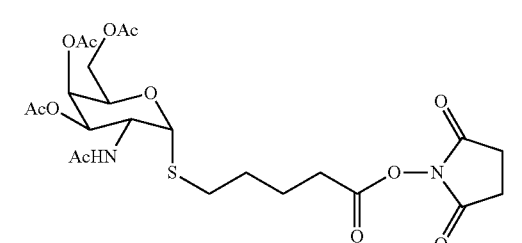 | 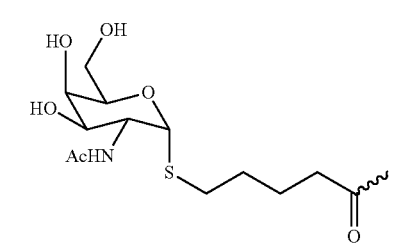 |
| 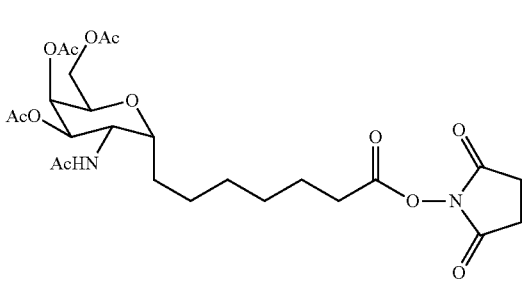 [SMILES: CC(=O)NC1C(CCCCCCC(=O)ON2C(=O)CCC2=O)OC(COC(C)=O)C(OC(C)=O)C1OC(C)=O] | 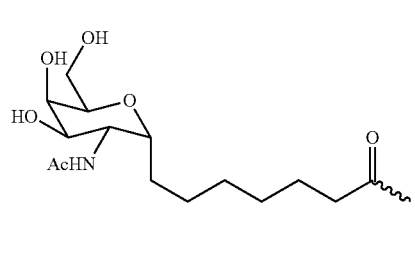 |

Example 41: siRNA-Ligand Conjugates siRNA-Ligand conjugates were prepared. The siRNA in each conjugate was the same and targeted to TTR. The following ligands were attached to the 3' end of the sense strand of each siRNA. The left side of the ligand description indicates the site of attachment to the 3' terminus of the sense strand.

TTR siRNA Ligand Conjugates

| siRNA Conjugate | Ligand (attached to 3' terminus of sense strand) |
|---|---|
| 43527 | L96 |
| 60148 | Q150Q150L193 |
| 60146 | (T3gs)(T3gs)(T3g) |
| 60142 | (Tgs)(Tgs)(Tg) |
| 60133 | Q155Q155L199 |
| 60139 | Q160Q160L204 |
| 60134 | Q156Q156L200 |
| 60132 | Q154Q154L198 |
| 60125 | Q161Q161L207 |
| 60124 | Q159Q159L203 |
| 60122 | L203 |
| 60123 | L206 |
| 60135 | L207 |
| 60136 | L208 |
| 60129 | L198 |
| 60126 | L197 |
| 60131 | L200 |
| 60127 | L202 |
| 60130 | L199 |
| 60128 | L201 |
| 60137 | L204 |
| 60138 | L205 |
| 60140 | (Tg)(Tg)(Tg) |
| 60144 | (T3g)(T3g)(T3g) |
| 60141 | (Tg) |
| 60143 | s(Tg) |
| 60145 | (T3g) |
| 60147 | s(T3g) |

The siRNA-Ligand conjugates 43527, 60148, 60146, 60142, 60133, 60139, 60134, 60132 and/or 60125 are tested in mice as described in Example 33. The results are provided in FIG. 1.

Example 42: siRNA-Ligand Conjugates siRNA-Ligand conjugates were prepared. The siRNA in each conjugate was targeted to TTR. The following ligands were attached to the sense strand of the siRNA at the positions indicated.

| siRNA | Ligand (5'-3') |
|---|---|
| 56718 | -(Uyg)(Ayg)(Ayg) |
| 56719 | -(Cyg)(Uyg)(Ayg)-<br>(These are the 4th, 5th and 6th nucleotides from the 3' end of the siRNA) |
| 56720 | -(Gyg)(Cyg)(Uyg)-<br>(These are the 7th, 8th and 9th nucleotides from the 3' end of the siRNA) |
| 56721 | -(Cyg)(Uyg)(Uyg)-<br>(These are the 10th, 11th and 12th nucleotides from the 3' end of the siRNA) |
| 56722 | -(Gyg)(Uyg)(Uyg)-<br>(These are the 7th, 8th and 9th nucleotides from the 5' end of the siRNA) |
| 56723 | -(Ayg)(Gyg)(Uyg)-<br>(These are the 4th, 5th and 6th nucleotides from the 5' end of the siRNA) |
| 56724 | (Ayg)(Ayg)(Cyg)-<br>(These are at the 5' end of the siRNA) |
| 56725 | (Ayg)<br>This ligand is at each of the 5' and 3' ends of the siRNA<br>(Uyg)<br>This ligand is the 10th nucleotide from the 3' end of the siRNA |
| 56726 | (Ayg)<br>This ligand is at each of the 5' and 3' ends of the siRNA<br>(Uyg)<br>This ligand is the 11th nucleotide from the 3' end of the siRNA |
| 56727 | (Ayg)<br>This ligand is at the 3' end and is also the 4th nucleotide from the end<br>(Uyg)<br>This ligand is the 7th nucleotide from the 3' end |
| 56729 | (Uyg)(Uyg)(Tyg)<br>(These ligands are at the 3' end of the siRNA) |
| 55727 | L96<br>(This ligand is at the 3' end of the siRNA) |

The Chemical Structures for Uyg, Ayg, Gyg and Cyg are Given in the Table of Chemical Groups Provided at the End of the Experimental Section.

FIGS. 4-7 show the binding affinities of the siRNA-ligand conjugates 56718-56727, 56729 and 55727.

Example 43: siRNA-Ligand Conjugates

The siRNA-Ligand conjugates in the table below were prepared. The siRNA in each conjugate was the same and targeted to AT3. The following ligands were attached to the sense strand of each siRNA as indicated.

AT3 siRNA Sequence 5'-3'

| siRNA | Sequence 5'-3' |
|---|---|
| 56874 | Q151L96 (at the 3' end of the siRNA) |
| 56875 | Q151Q151L96 (at the 3' end of the siRNA) |
| 56876 | Q151 (at the 5' end of the siRNA)<br>L96 (at the 3' end of the siRNA) |
| 56877 | Q151 (at the 5' end of the siRNA) |
| 56878 | Q150L96 (at the 3' end of the siRNA) |
| 56879 | Q150Q150L96 (at the 3' end of the siRNA) |
| 56880 | Q150Q150Q150L96 (at the 3' end of the siRNA) |
| 56881 | Q150Q150L193 (at the 3' end of the siRNA) |
| 56882 | L193 (at the 3' end of the siRNA) |
| 54944 | L96 (at the 3' end of the siRNA) |

Example 44

The siRNA-Ligand conjugates in the table were prepared. The siRNA in each conjugate was the same and targeted to AT3. The ligands were attached to the sense strand at the positions indicated in the table.

Figure 8:
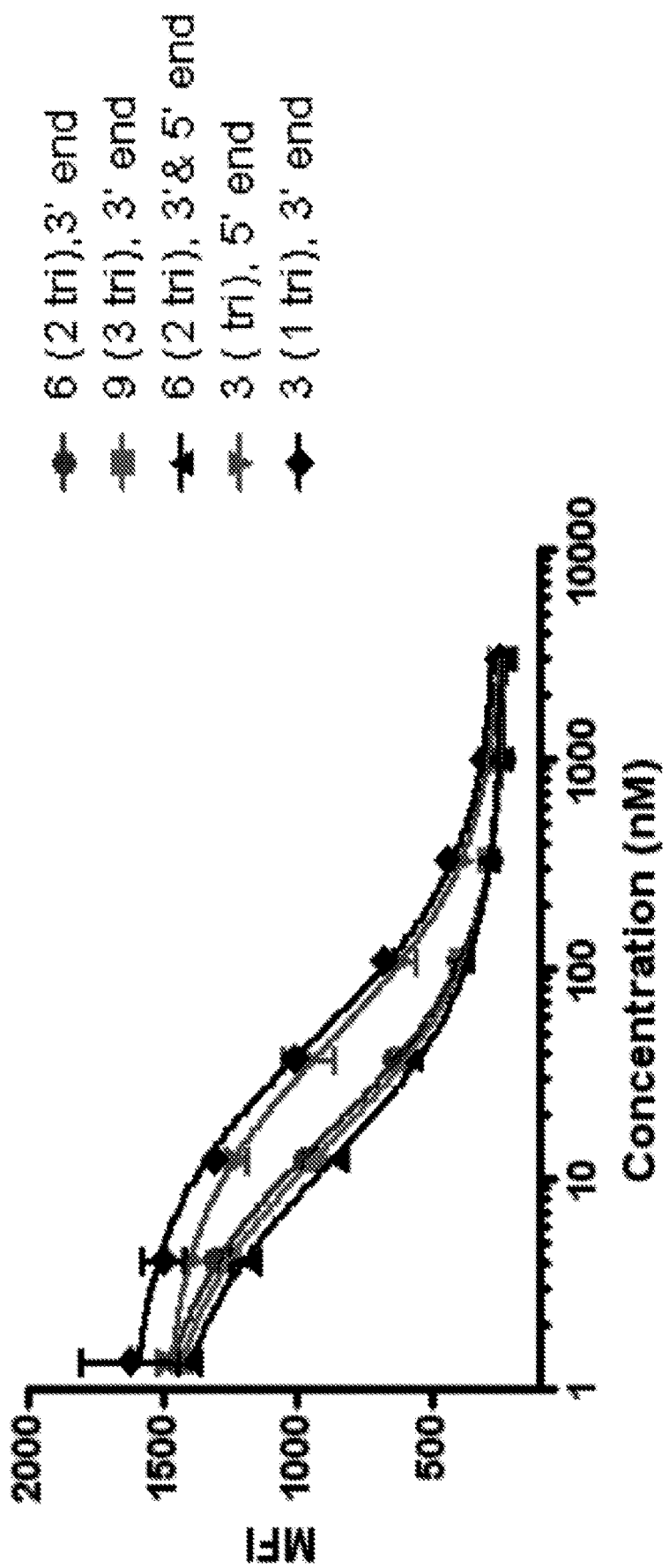
FIGS. 8 and 9 are graphs the median fluorescence intensity (MFI) at various concentrations for the TTR siRNA conjugates 56876, 66875, 56874, 66878, 56880, 56879, 54944, 56877, 56881 and/or 56882 in Example 44.
Figure 9:
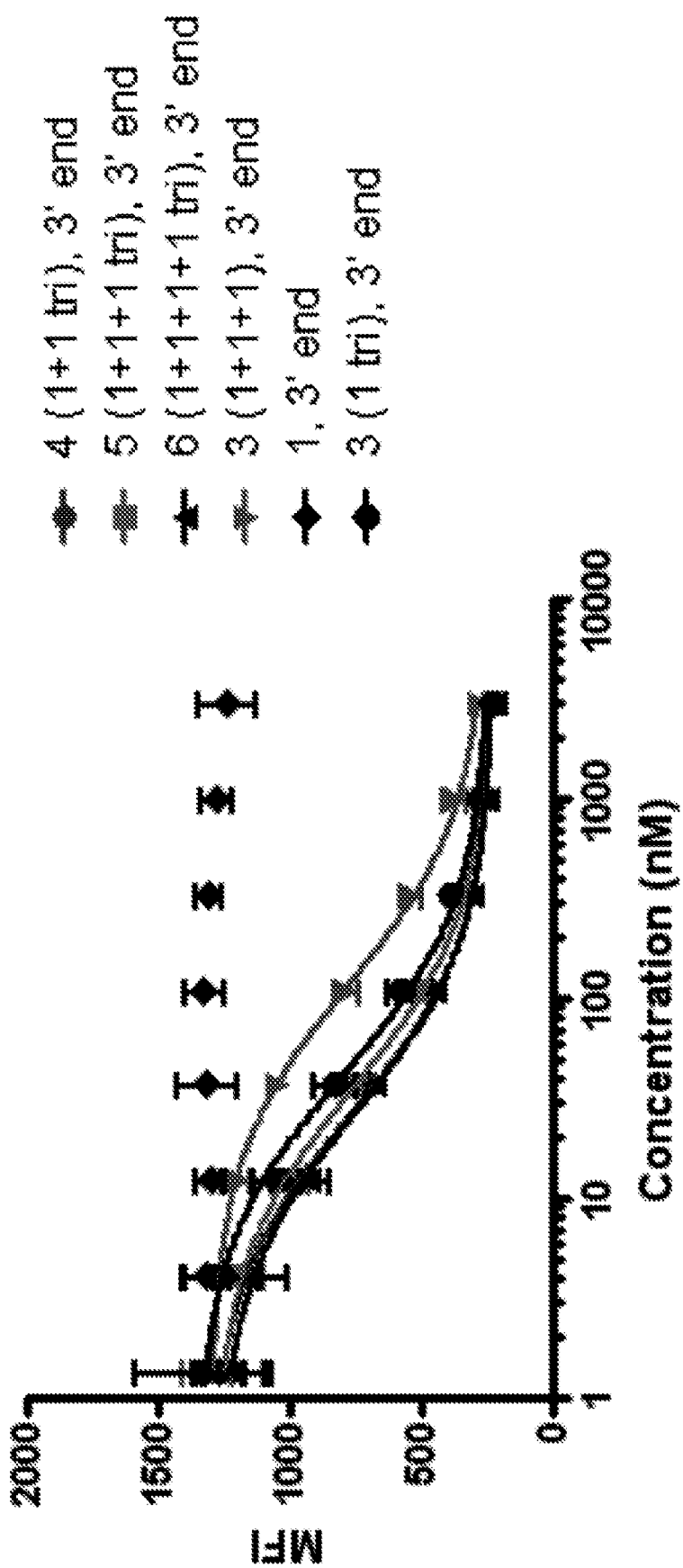

FIGS. 8 and 9 show the binding affinities of the SiRNA-ligand conjugates 56876, 66875, 56874, 66878, 56880, 56879, 54944, 56877, 56881 and/or 56882. The Ki values for these conjugates are reported below.

| Duplex | Sense Sequence (5' to 3') | # GalNac/position | Ki (nM) |
| --- | --- | --- | --- |
| 56876 | Q151 (at the 5' end of the siRNA) L96 (at the 3' end of the siRNA) | 6 (2 tri), 3' & 5' end | 5.168 |
| 56875 | Q151Q151L96 (at the 3' end of the siRNA) | 9 (3 tri), 3' end | 6.372 |
| 56874 | Q151L96 (at the 3' end of the siRNA) | 6 (2 tri), 3' end | 7.174 |
| 56878 | Q150L96 (at the 3' end of the siRNA) | 4 (1 + 1 tri), 3' end | 11.72 |
| 56880 | Q150Q150Q150L96 (at the 3' end of the siRNA) | 6 (1 + 1 + 1 + 1 tri), 3' end | 11.93 |
| 56879 | Q150Q150L96 (at the 3' end of the siRNA) | 5 (1 + 1 + 1 tri), 3' end | 15.66 |
| 54944 | L96 (at the 3' end of the siRNA) | 3 (1 tri), 3' end | 19.085 |
| 56877 | Q151 (at the 5' end of the siRNA) | 3 (tri), 5' end | 20.39 |
| 56881 | Q150Q150L193 (at the 3' end of the siRNA) | 3 (1 + 1 + 1), 3' end | 51.34 |
| 56882 | L193 (at the 3' end of the siRNA) | 1,3' end | N/A |

Example 45: siRNA's with Different GalNAc Ligands (Triantennary Derivatives)

siRNA-Ligand conjugates were prepared. The siRNA in each conjugate was the same and targeted to TTR. The following ligands were attached to the 3' end of the sense strand of each siRNA. The left side of the ligand description indicates the site of attachment to the 3' terminus of the sense strand.

TTR siRNA Ligand Conjugates

| siRNA Conjugate | Ligand (attached to 3' terminus of sense strand) |
| --- | --- |
| 60123 | L206 -- Urea, Trianternnary(3) |
| 60136 | L208 -- Alpha, Trianternnary(3) |
| 60126 | L197 -- Amide, Trianternnary(3) |
| 60127 | L202 -- Beta-Thio, Trianternnary(3) |
| 60128 | L201 -- Alpha-Thio, Trianternnary(3) |
| 60138 | L205 -- Alpha, C-glycoside, Trianternnary(3) |
| 43527 | L96 -- , Trianternnary (Control) |

Figure 10:
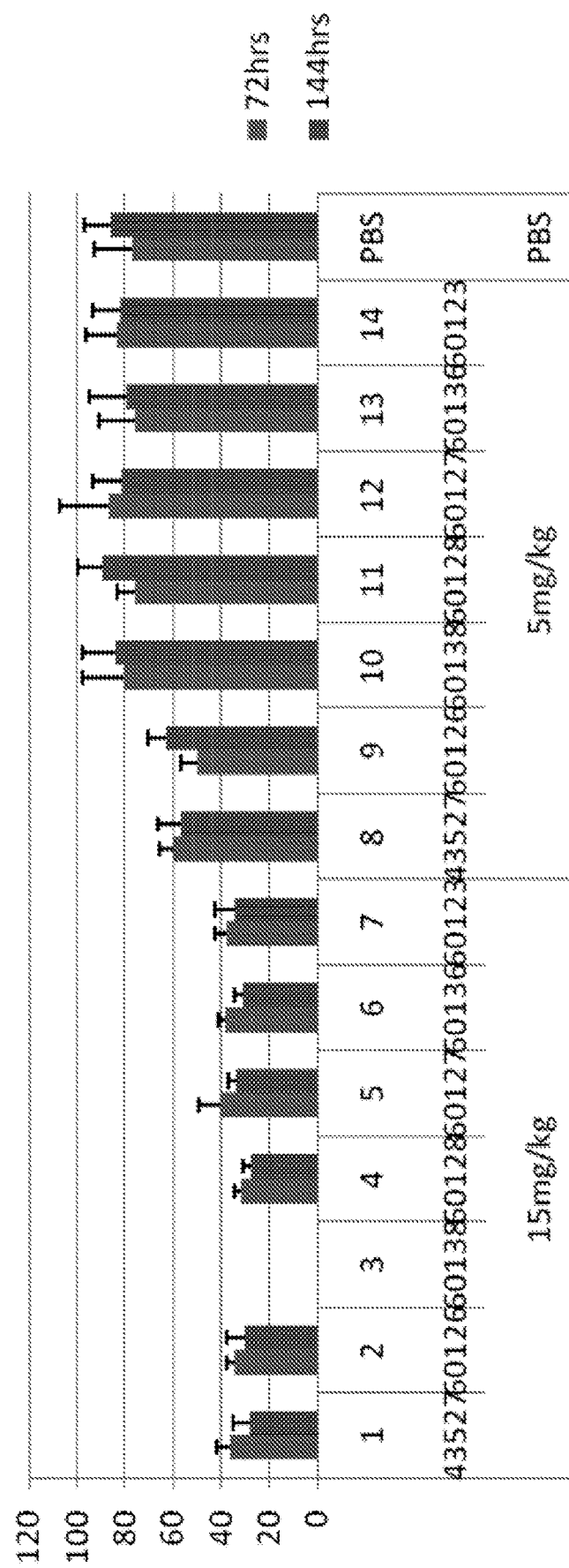
FIG. 10 is a bar graph showing TTR protein levels 48 and 144 hours after administration of TTR siRNA conjugates 43527, 60126, 60138, 60128, 60127, 60316, and 60123 (at 15 mg/kg and 5 mg/kg doses) in mice relative to control mice as described in Example 45.

FIG. 10 shows the in vivo efficacy of the triantennary GalNAc ligands 43527, 60126, 60138, 60128, 60127, 60316, and 60123 (at 15 mg/kg and 5 mg/kg doses) after 72 and 144 hours.

Example 46: siRNA's with Different GalNAc Ligands (Triantennary Derivatives (1+1+1))

siRNA-Ligand conjugates were prepared. The siRNA in each conjugate was the same and targeted to TTR. The following ligands were attached to the 3' end of the sense strand of each siRNA. The left side of the ligand description indicates the site of attachment to the 3' terminus of the sense strand.

TTR siRNA Ligand Conjugates

Figure 11:
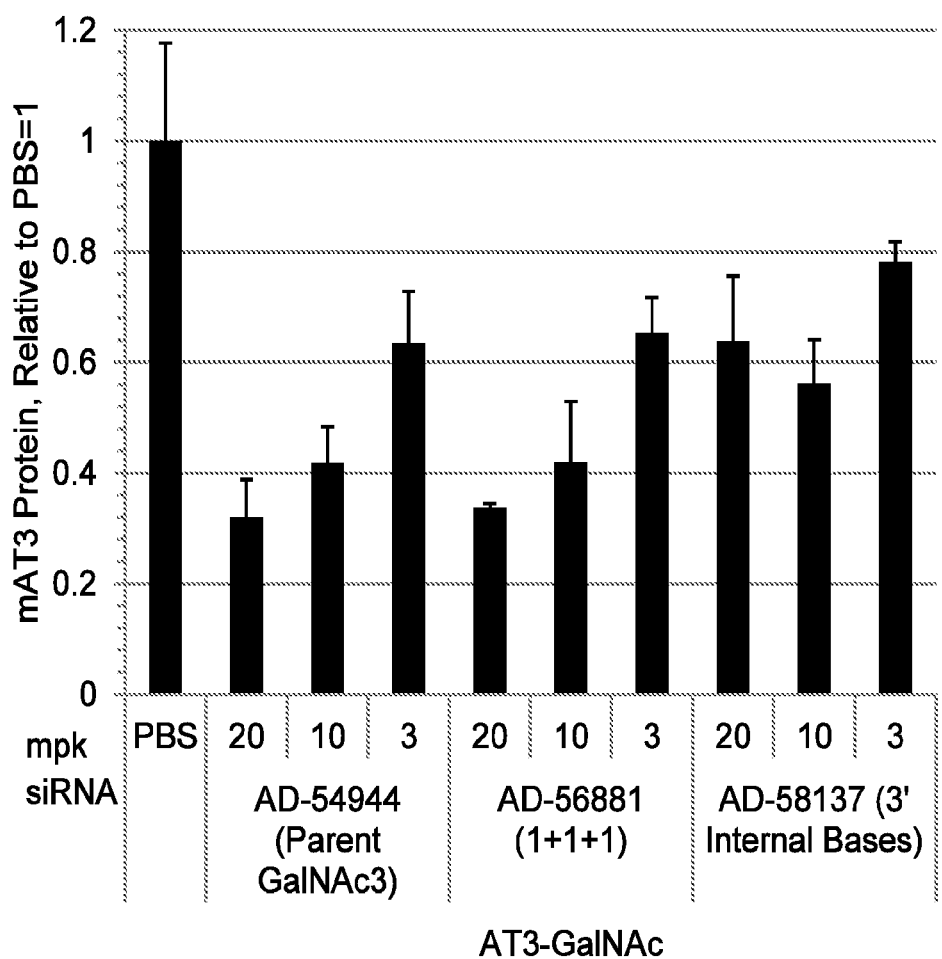
FIG. 11 is a bar graph showing AT3 protein levels following administration of AT3 siRNA conjugates 54944, 56881 and 58137 in mice relative to control mice as described in Example 46.

| siRNA Conjugate | Ligand (attached to 3' terminus of sense strand) |
| --- | --- |
| 60124 | Q159Q159L203 -- Urea, 1 + 1 + 1 |
| 60125 | Q161Q161L207 -- Alpha, 1 + 1 + 1 |
| 60132 | Q154Q154L198 -- Amide, 1 + 1 + 1 |
| 60134 | Q156Q156L200 -- Beta-Thio, 1 + 1 + 1 |
| 60133 | Q155Q155L199 -- Alpha-Thio, 1 + 1 + 1 |
| 60139 | Q160Q160L204 -- Alpha, C-glycoside, 1 + 1 + 1 |
| 60148 | Q150Q150L193 -- Beta, 1 + 1 + 1 | siRNA conjugates directed to AT3, two of which are described in Examples 30 and 34, were prepared and tested. The structure of 58137 is provided below. Each conjugate had the same AT3 siRNA sequence. FIG. 11 shows the in vivo efficacy of triantennary GalNAc ligands 54944, 56881 and 58137 [(1+1+1) design].

Figure 12:
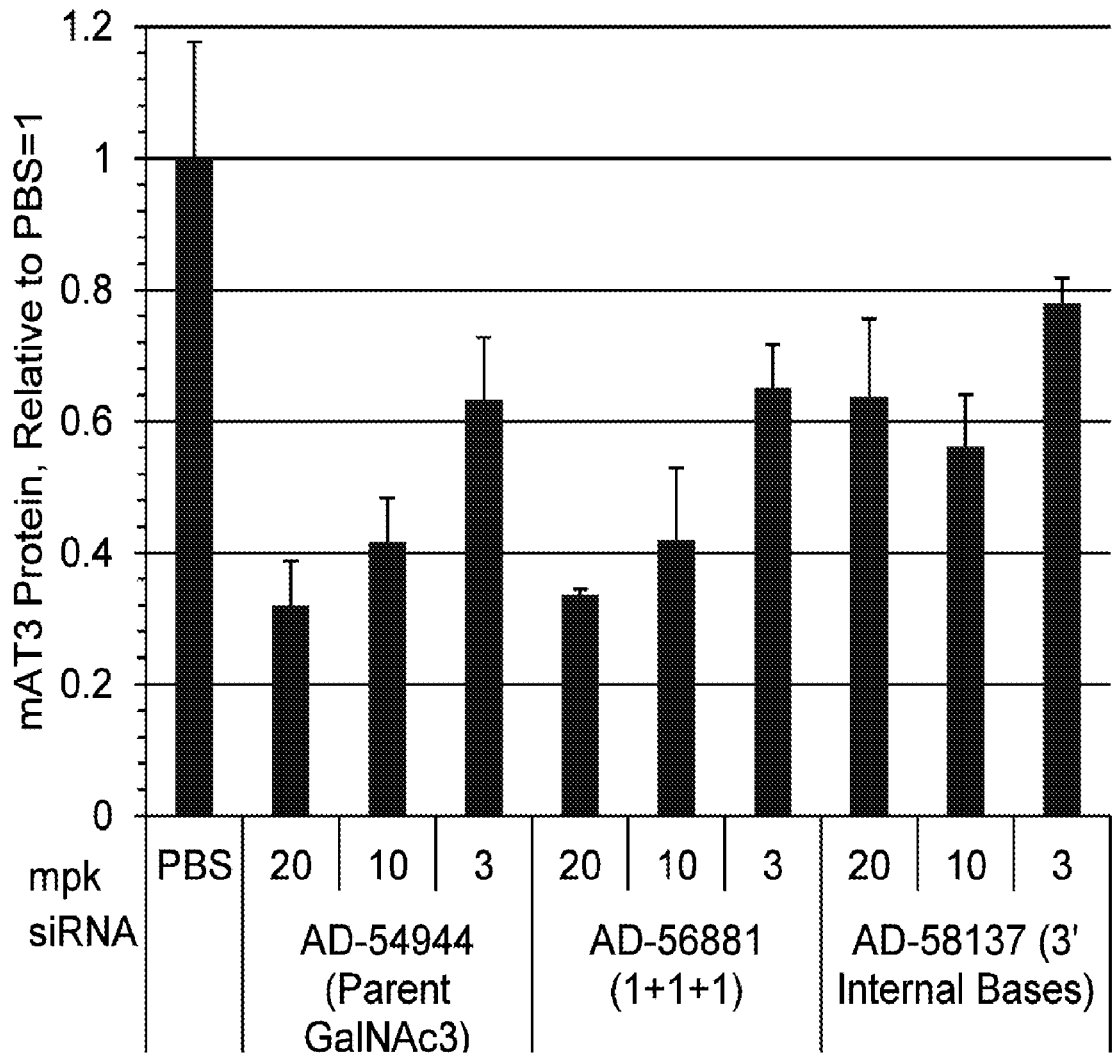
FIG. 12 is a bar graph showing mTTR protein levels following administration of mTTR siRNA conjugates 55727, 58138 and 58139 in mice relative to control mice as described in Example 46.

| siRNA Conjugate | Ligand (attached to 3' terminus of sense strand) |
| --- | --- |
| 54944 | L96 |
| 56881 | Q150Q150L193 |
| 58137 | (Uyg)(Uyg)(Uyg) | siRNA conjugates directed to TTR were prepared and tested. Each conjugate had the same TTR siRNA sequence. The following ligands were attached to the 3' end of the sense strand of each siRNA. The left side of the ligand description indicates the site of attachment to the 3' terminus of the sense strand. FIG. 12 shows the in vivo efficacy of triantennary GalNAc ligands 55727, 58138 and 58139 [(1+1+1) design]. The ligand designs for duplexes 55727, 58138 and 58139 are provided below.

| siRNA Conjugate | Ligand (attached to 3' terminus of sense strand) |
| --- | --- |
| 55727 | L96 |
| 58138 | Q150Q150L193 |
| 58139 | (Uyg)(Uyg)(Uyg) |

Example 47
Scheme 97
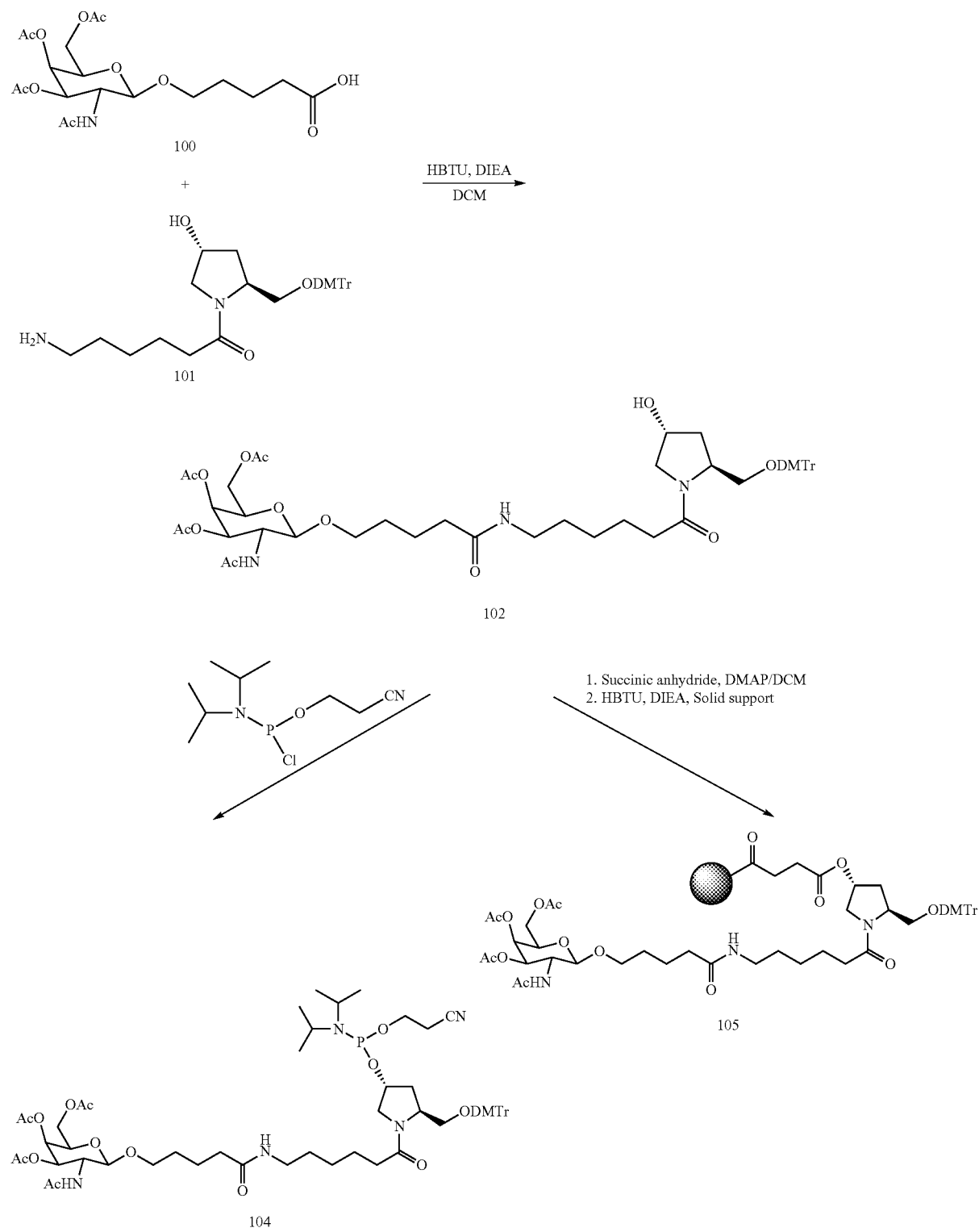

Synthesis of Compound 102:

GalNAc acid 100 (8.39 g, 18.71 mmol) and hydroxy proline amine (10.00 g, 18.77 mmol) were taken together in dichloromethane. HBTU (10.68 g, 28.12 mmol) and DIEA (9.80 mL, 3 eq.) were added and the mixture was stirred for 2 hours at ambient temperature. The product was checked by thin layer chromatography and the reaction mixture was transferred to a separatory funnel and washed with water and brine. The organic layer was dried over sodium sulfate and the solvent was removed. The crude product was purified by silica gel chromatography using dichloromethane and MeOH as solvents to afford compound 102 as a pale yellow fluffy solid (11.77 g, 63%). $^1$H NMR (400 MHz, DMSO-$d_6$): δ 7.80 (d, J=9.2 Hz, 1H), 7.69 (t, J=5.6 Hz, 1H), 7.39-7.09 (m, 9H), 6.86 (ddd, J=9.0, 5.4, 2.1 Hz, 4H), 5.20 (d, J=3.4 Hz, 1H), 5.03-4.83 (m, 2H), 4.47 (d, J=8.5 Hz, 1H), 4.41-4.07 (m, 2H), 4.04-3.95 (m, 3H), 3.86 (dt, J=11.2, 8.9 Hz, 1H), 3.79-3.68 (m, 6H), 3.68-3.36 (m, 3H), 3.21-2.88 (m, 5H), 2.26-2.14 (m, 2H), 2.09 (s, 3H), 2.02 (t, J=6.7 Hz, 2H), 1.98 (s, 3H), 1.87 (d, J=7.5 Hz, 3H), 1.76 (s, 3H), 1.53-1.29 (m, 7H).

Synthesis of Compound 104:

Hydroxy proline derivative 102 (6.00 g, 6.24 mmol) was dissolved in dichloromethane (100 mL). DIEA (2.20 mL, 3 eq) and 2-cyanoethyl diisopropylchlorophosphoramidite were added. The reaction mixture was stirred for 30 minutes and checked by thin layer chromatography. The mixture was transferred to a separatory funnel and washed with water and sodium bicarbonate solution. The organic layer was dried over sodium sulfate and the crude product was purified by silica gel chromatography using dichloromethane and MeOH as eluent to afford the compound as a white fluffy solid. $^1$H NMR (400 MHz, DMSO-$d_6$): δ 7.80 (d, J=9.2 Hz, 1H), 7.68 (s, 1H), 7.42-7.06 (m, 8H), 7.01-6.73 (m, 4H), 5.20 (d, J=3.3 Hz, 1H), 4.96 (dd, J=11.2, 3.3 Hz, 1H), 4.63 (d, J=4.7 Hz, 1H), 4.47 (d, J=8.5 Hz, 1H), 4.15 (s, 1H), 4.01 (s, 3H), 3.86 (d, J=11.0 Hz, 1H), 3.70 (d, J=16.5 Hz, 9H), 3.45 (ddd, J=37.0, 23.3, 16.4 Hz, 6H), 2.99 (dd, J=12.3, 6.4 Hz, 3H), 2.74 (dd, J=9.2, 5.8 Hz, 2H), 2.21 (s, 2H), 2.09 (s, 3H), 2.05-1.95 (m, 5H), 1.88 (s, 3H), 1.76 (s, 3H), 1.52-1.16 (m, 11H), 1.16-1.02 (m, 11H). $^{31}$P NMR: δ 151.78, 151.61, 151.50, 151.30.

Synthesis of Compound 105

Compound 102 (2.10 g, 2.18 mmol) was dissolved in DCM (20 mL). To this mixture succinic anhydride (0.441 g, 4.36 mmol) and DMAP (0.532 g, eq) followed by TEA (1 ML) were added. The reaction mixture was stirred overnight at room temperature. The reaction was checked by thin layer chromatography, then the reaction mixture was washed with water and brine. The organic layer was dried over sodium sulfate and the crude product filtered through a small pad of silica gel. The solvent was removed and this material was used for the next reaction. The succinate from the above reaction was dissolved in anhydrous acetonitrile. HBTU (1.59 g, 4.20 mmols) and DIEA (1.10 ml) were added and the mixture was swirled for 5 minutes. A polystyrene solid support was added to the reaction mixture and the mixture was shaken overnight at ambient temperature. The solid support was filtered, washed and capped using acetic anhydride/pyridine mixture. The solid support was again washed with dichloromethane, MeOH/DCM and ether (27.10 g, 55 µmol/g).

Example 48: Synthesis of Amino Linkers for Post-Synthetic Conjugation

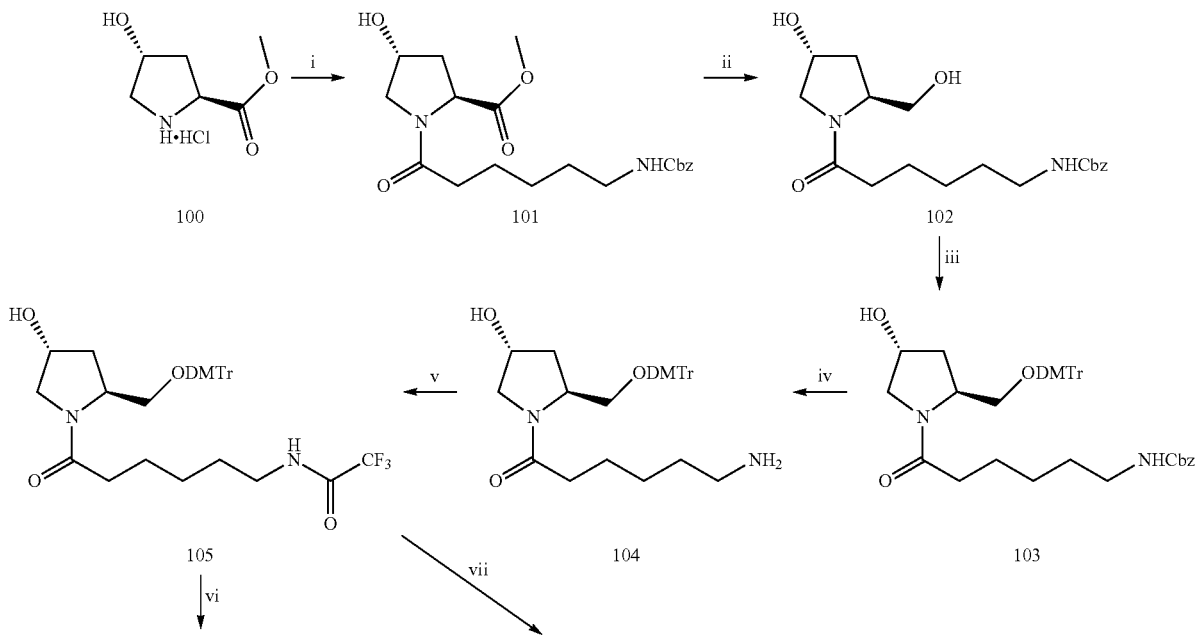

Scheme 98

-continued

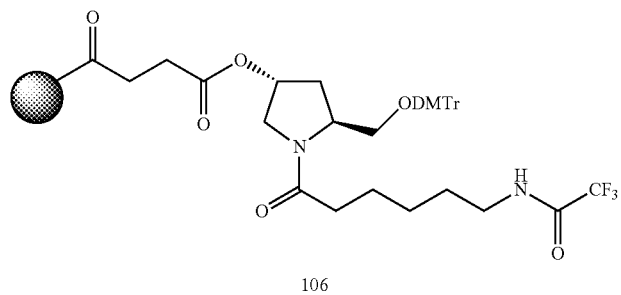

106

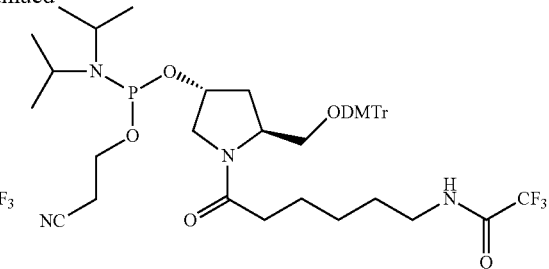

107 i) NCbz amino hexanoic acid, HBTU, DIEA/DMF (65%); ii) LiBH4, THF(49%); iii) DMTr—Cl, DMAP/Py;
iv) Pd/C, H₂, EtOAC/MeOH (93%); v) Ethyl trifluoroacetate, TEA/DCM (81%); vi) a. Succinic anhydride,
DMAP, TEA, DCM; b. HBTU, DIEA, CPG, MeCN (66 µmol/g); vi) 2-cyanoethyl diisopropylchlorophosphoramidite,
DIEA/DCM (54%).

Compound 101A:

Z-Aminocaproic acid (22.2 g, 82.50 mmol) was dissolved in DMF (250 mL) and cooled to 0° C. To the solution were added diisopropyl ethyl amine (44.4 mL, 275 mmols), HBTU (40.4 g, 106.7 mmol), and HOBT (30.0 g, 220 mmol). After stirring under argon for 20 minutes at 0° C., 4-Hydroxy-L-proline methyl ester hydrochloride (20.0 g, 110 mmol) was added and the stirring was continued under argon at room temperature overnight. The reaction mixture was evaporated to dryness. To the residue ethyl acetate (250 mL) was added. The organic layer was washed with water, saturated sodium bicarbonate, water again, and saturated sodium chloride. The organic layer was dried over sodium sulfate, filtered and evaporated to dryness. Crude compound 101A (Rf=0.5 in 10% MeOH/DCM, 24.30 g) was obtained. Compound 101A was purified by column chromatography first by eluting with 2% methanol/dichloromethane to remove impurities followed by 5% methanol/dichloromethane to afford 21.36 g (65%) of product. 1H NMR (400 MHz, DMSO-$d_6$): δ 7.35 (m, 5H), 5.15 (d, OH, D₂O exchangeable), 4.99 (s, 2H), 4.27 (m, 1H), 3.97 (m, 1H), 3.58 (s, 1H) 3.20-3.47 (m, 5H), 2.94-3.02 (m, 2H), 2.10-2.32 (m, 2H), 1.74-2.01 (m, 2H), 1.35-1.4 (m, 4H), 1.22-1.28 (m, 4H)

Compound 102A:

Compound 101A (21.36 g, 54.43 mmol) was dissolved in THF (200 mL). The reaction mixture stirred under argon for 20 minutes at 0° C. Then lithium borohydride (1.19 g, 54.43 mmol) was added to the solution over 20 minutes at 0° C., and the stirring was continued under argon at room temperature overnight. The reaction mixture was cooled to 0° C. The excess lithium borohydride was quenched with 5M NaOH (30 mL). After stirring for 30 minutes the reaction mixture was evaporated to dryness. To the residue dichloromethane (200 mL) was added. The organic layer was washed with water and saturated sodium chloride. The organic layer was dried over sodium sulfate, filtered and evaporated to dryness. Crude compound 102A (Rf=0.4 in 10% MeOH/DCM, 35.88 g) was obtained. Compound 102A was purified by column chromatography by eluting with 3% methanol/dichloromethane to remove impurities followed by 5% methanol/dichloromethane to afford 9.21 g (49%) of product. ¹H NMR (400 MHz, DMSO-$d_6$): δ 7.35 (m, 5H), 4.99 (s, 2H), 4.91 (d, OH, D₂O exchangeable), 4.77 (t, OH, D₂O exchangeable), 4.27 (m, 1H), 3.97 (m, 1H), 3.20-3.47 (m, 5H), 2.94-3.02 (m, 2H), 2.10-2.32 (m, 2H), 1.74-2.01 (m, 2H), 1.35-1.4 (m, 4H), 1.22-1.28 (m, 4H).

Compound 103A:

Compound 102A (9.21 g, 25.27 mmols) was co-evaporated with anhydrous pyridine (80 mL) twice. Then the compound was placed under hard vacuum overnight to dry. Compound 102A was taken from hard vacuum and dissolved in anhydrous pyridine (200 mL). To this solution a catalytic amount of dimethylamino pyridine (0.35 g, 2.53 mmol) was added. The reaction mixture stirred under argon for 30 minutes at 0° C. Then DMT-Cl (9.0 g, 26.53 mmols) was added to the solution at 0° C. The mixture was stirred under vacuum followed by argon, and stirring was continued under argon at room temperature overnight. The excess DMT-Cl was quenched by the addition of methanol (15 mL). The reaction mixture was evaporated to dryness, and to the residue dichloromethane (200 mL) was added. The organic layer was washed with water, saturated sodium bicarbonate, water again, and saturated sodium chloride. The organic layer was dried over sodium sulfate, filtered and evaporated to dryness. Crude compound 103A (Rf=0.6 in 100% EtOAc, 14.02 g) was obtained. Compound 103A was purified by column chromatography by first eluting with 50% ethyl acetate (1% TEA) in hexanes to remove impurities followed by 100% ethyl acetate (1% TEA) to afford 12.36 g (73.4%) of the product as a white foamy solid. ¹H NMR (400 MHz, DMSO-$d_6$): δ 7.17-7.33 (m, 14H), 4.99 (s, 2H), 4.91 (d, OH, D₂O exchangeable), 4.37 (m, 1H), 4.01 (m, 1H), 3.72 (s, 6H) 3.56 (m, 1H) 3.29 (m, 1H), 3.14 (m, 1H), 2.93-3.02 (m, 4H), 2.18 (m, 2H) 1.74-2.01 (m, 2H), 1.37-1.41 (m, 6H).

Compound 104A:

Compound 103A (12.36 g, 18.54 mmol) was dissolved in 10% methanol/ethyl acetate (300 mL) and purged with argon. To the reaction mixture was added 10% palladium by wt. on active carbon wet Degussa type (1.3 g). The flask was re-purged with argon. The flask was purged with hydrogen twice, and then hydrogen was bubbled through the reaction mixture for 10 seconds. The reaction mixture continued to stir under hydrogen at room temperature overnight. The reaction mixture was decanted onto a sintered funnel packed with celite and washed twice with methanol. The organic layer was evaporated to dryness affording compound 104A (eluent 10% MeOH in DCM, 9.16 g, 93%) as a white solid, which required no further purification. ¹H NMR (400 MHz, DMSO-$d_6$): δ 7.15-7.31 (m, 9H), 6.86 (m, 4H) 4.99 (s, 1H), 4.37 (m, 1H), 4.01 (m, 2H), 3.72 (s, 6H) 3.56 (m, 1H) 3.29 (m, 1H), 3.14 (m, 1H), 2.93-3.02 (m, 2H), 2.45 (m, 2H), 2.18 (m, 2H) 1.74-2.01 (m, 2H), 1.37-1.41 (m, 3H) 1.13-1.38 (m, 4H). MS: 533.4 (+H), 555.3 (+Na).

Compound 105A:

Compound 104A (9.16 g, 17.2 mmol) was dissolved in dichloromethane (200 mL). The reaction mixture stirred under argon for 10 minutes at 10° C. To the reaction mixture triethylamine (4.80 mL, 34.4 mmol) was added drop wise as the mixture continued to stir under argon for 20 minutes at 10° C. To the reaction mixture ethyl trifluoroacetate (3.05 mL, 25.8 mmol) was added drop wise as the mixture continued to stir under argon for 10 minutes at 10° C. The reaction mixture continued to stir under argon at room temperature overnight. The reaction mixture was washed with water and saturated sodium chloride. The organic layer was dried over sodium sulfate, filtered and evaporated to dryness. Crude Compound 105A (Rf=0.6 10% MeOH in DCM, 10.89 g) was obtained. Upon column purification by eluting with 5% methanol/dichloromethane (1% TEA) Compound 105A (8.76 g, 81%) was obtained as a yellow foamy solid. $^1$H NMR (400 MHz, DMSO-d$_6$): δ 7.56-7.09 (m, 9H), 7.01-6.52 (m, 4H), 5.34-5.04 (m, 1H), 4.99-4.78 (m, 1H), 4.48-4.25 (m, 2H), 3.83-3.67 (m, 6H), 3.60-3.50 (m, 1H), 3.49-3.18 (m, 2H), 3.16-2.91 (m, 2H), 2.89-2.56 (m, 2H), 2.54-2.32 (m, 2H), 2.32-1.69 (m, 3H), 1.59-1.03 (m, 4H). $^{19}$F NMR (DMSO-d$_6$): −77.14 (s, 3F). MS: 627.3 (−H), 663.3 (+Cl).

Compound 106A:

Compound 105A (8.76 g, 13.93 mmol), DMAP (5.10 g, 41.79 mmol), and triethylamine (3.90 mL, 27.86 mmol) were dissolved in dichloromethane (300 mL). The reaction mixture was stirred under argon for 10 minutes. Then, succinic anhydride (2.80 g, 27.86 mmol) was added and the mixture continued stirring under argon at room temperature overnight. The reaction mixture was washed with saturated sodium chloride solution twice. The organic layer was dried over sodium sulfate, filtered and evaporated to dryness. Compound 106A (Rf=0.9 10% MeOH in DCM, 10.87 g, 94%) was obtained as a white solid, which required no further purification. MS: 727.2 (−H), 763.2 (+Cl). The succinate thus obtained (2.00 g, 2.41 mmol) was dissolved in acetonitrile (100 mL). To the solution diisopropylethylamine (1.68 mL, 9.64 mmol) and HBTU (1.83 g, 4.82 mmols) were added. The reaction mixture was shaken for 10 minutes. Long chain amino alkyl controlled pore glass support (CPG) (27 g) was added to the flask and the mixture continued to shake overnight. The CPG compound and reaction mixture were decanted over a sintered funnel. The reaction mixture was washed with 1% triethylamine/dichloromethane, followed by two washes of 10% methanol in dichloromethane, another wash of 1% triethylamine in dichloromethane, and anhydrous diethyl ether. The CPG compound was suction dried for 1 hour, then recovered from the funnel and placed under hard vacuum for 2 hours. The CPG was capped with 25% acetic anhydride in pyridine (100 mL) and the mixture shook for 4 hrs. The washing procedure repeated as above and dried the compound under vacuum to obtain the CPG 106A (28 g, 67 μmol/g).

Compound 107A:

Compound 105A (8.89 g, 14.14 mmol) and diisopropylethylamine (4.93 mL, 28.28 mmol) were dissolved in anhydrous dichloromethane (60 mL). The reaction mixture was stirred under argon for 5 minutes. Then 2-cyanoethyl diisopropylchlorophosphoramidite (5.63 mL, 16.26 mmol) was added to the reaction mixture. The reaction mixture continued stirring under argon at room temperature for 30 minutes. The reaction mixture was diluted with dichloromethane (100 mL). The organic layer was washed with water, saturated sodium bicarbonate, water again, and saturated sodium chloride. The organic layer was dried over sodium sulfate, filtered and evaporated to dryness affording crude Compound 107A (Rf=0.44 5% MeOH in DCM, 11.02 g). Upon column purification by eluting with 3% methanol in DCM (1% TEA). Compound 107A (6.31 g, 54%) was obtained as a yellow solid. $^1$H NMR (400 MHz, DMSO-d$_6$): δ 9.37 (s, 1H), 7.63 (d 1H), 7.42-6.98 (m, 8H), 6.92-6.77 (m, 4H), 4.25-3.90 (m, 2H), 3.78-3.64 (m, 7H), 3.48 (d, 3H), 3.29 (d, 1H), 3.23-2.92 (m, 4H), 2.86 (d, 1H), 2.73 (t, 1H), 2.58 (t, 1H), 2.53-2.47 (m, 4H), 2.33-1.87 (m, 4H), 1.55-0.97 (m, 12H). $^{31}$P (DMSO-d$_6$): 151.68 (d, 1P).

Scheme 99

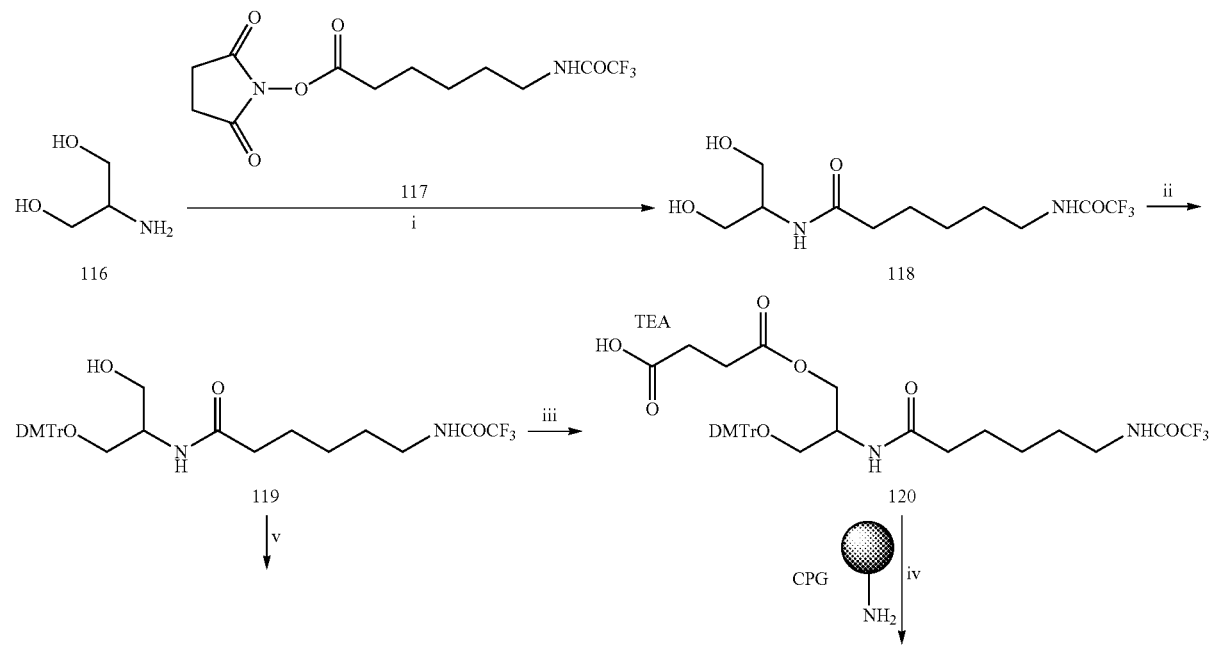

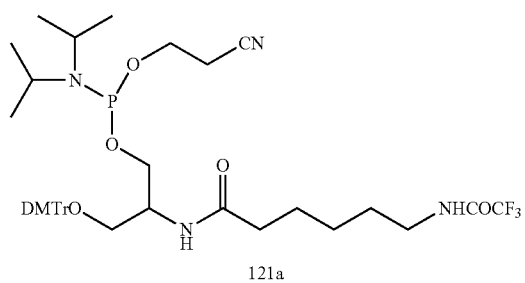 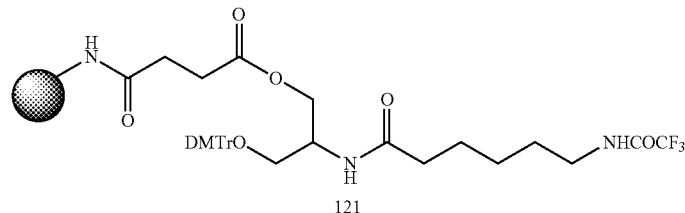

i) DMF, TEA (78%); ii) DMTr—Cl, DMAP/Py; iii) Succinic anhydride, DMAP, TEA, DCM; iv) HBTU, DIEA, CPG, MeCN, (14 g, 77 µmol/g) v) 2-cyanoethyl diisopropylchlorophosphoramidite, DIEA/DCM (74%).

Compound 118:

Serinol 116 (2.05 g, 22.5 mmol) and compound 117 (8.03 g, 24.75 mmol) were dissolved in DMF (120 mL) under argon. Triethylamine (5.0 mL, 67.5 mmol) was added to the reaction mixture, which was stirred at room temperature overnight. The reaction mixture was evaporated to dryness and the residue was dissolved in ethyl acetate (120 mL). It was then washed with water (30 mL) and saturated sodium chloride (2×50 mL). The organic layer was dried over sodium sulfate, filtered and evaporated to dryness. The crude compound (5.33 g, Rf=0.21 15% MeOH in DCM,) was purified silica gel column chromatography using 10% methanol in dichloromethane as eluent to afford compound 118 (4.98 g, 78%) as a white foam. m/z: 324.13 (+Na). 1H NMR (400 MHz, DMSO-$d_6$): δ 9.39 (s, 2 NH, $D_2O$ exchangeable), 3.34-3.06 (m, 7H), 3.06-2.91 (m, 2 OH, $D_2O$ exchangeable), 2.30-2.00 (m, 2H), 1.97-0.86 (m, 6H). $^{13}C$ NMR (101 MHz, $CD_3CN$): δ 172.18 (s), 156.41 (s), 117.50 (s), 60.30 (s), 52.85 (s), 38.88 (s), 35.35 (s), 28.11 (s), 25.90 (s), 25.29 (s).

Compound 119:

Compound 118 (3.70 g, 12.3 mmol) was co-evaporated with anhydrous pyridine (30 mL) twice, then dried under high vacuum overnight. It was then dissolved in anhydrous pyridine (90 mL). To this solution a catalytic amount of DMAP (0.15 g, 1.23 mmol) was added and stirred the mixture under Argon for 30 minutes at 0° C. DMTr-Cl (4.38 g, 12.9 mmol) was added to the solution at 0° C. and continued the stirring at room temperature for 2 hours. The volatiles were then removed under vacuum. The residue was dissolved in dichloromethane (150 mL) and washed with water (2×100 mL) followed by saturated sodium chloride (100 mL). The organic layer was dried over sodium sulfate, filtered and evaporated to dryness. The crude compound (6.83 g, Rf=0.44 in 5% MeOH in DCM) was purified by silica gel column chromatography by first eluting with dichloromethane (with 1% TEA) followed by 3% methanol in dichloromethane (with 1% TEA) to obtain compound 119 (2.32 g, 23%) as a white foam. m/z: 601.2 (−1), 637.2 (+Cl). $^1H$ NMR (400 MHz, DMSO-$d_6$): δ 9.38 (s, 2 NH, $D_2O$ exchangeable), 7.31-7.13 (m, 7H), 6.86 (d, J=8.9 Hz, 6H), 4.60 (t, J=5.2 Hz, 1H), 3.72 (s, 6H), 3.54-3.23 (m, 6H), 2.95 (ddd, J=36.9, 8.8, 5.8 Hz, 1 OH, $D_2O$ exchangeable), 2.08 (t, J=7.4 Hz, 2H), 1.47 (tt, J=14.6, 7.4 Hz, 2H), 1.34-1.12 (m, 4H). $^{13}C$ NMR (101 MHz, $CD_3CN$): δ 172.83 (s), 158.97 (s), 157.28 (s), 156.93 (s), 146.13 (s), 136.82 (s), 136.52 (s), 130.70 (s), 128.68 (d, J=4.0 Hz), 127.49 (s), 118.41 (s), 115.54 (s), 114.02 (s), 86.08 (s), 63.66 (s), 61.84 (s), 55.93 (s), 51.77 (s), 46.68 (s), 40.99 (d, J=21.0 Hz), 40.72 (s), 40.68 (s), 40.47 (s), 40.26 (s), 40.05 (s), 39.84 (s), 36.31 (s), 29.04 (s), 26.85 (s), 25.95 (s).

Compound 120:

Compound 119 (1.0 g, 1.7 mmol), DMAP (620 mg, 5.1 mmol), and triethylamine (0.5 mL, 3.4 mmol) were dissolved in dichloromethane (15 mL). The reaction mixture was stirred under argon for 5 minutes. Then, succinic anhydride (340 mg, 3.4 mmol) was added and continued stirring under argon at room temperature overnight. The reaction mixture was diluted in dichloromethane (100 mL) washed with saturated sodium chloride (2×25 mL). The organic layer was dried over sodium sulfate, filtered and evaporated to dryness. The crude compound (Rf=0.3 50% EtOAc in Hex) 1.01 g (98%) was obtained as a white solid, which was used for the next reaction without further purification. MS: 702.3 (−H), 737.5 (+Cl). $^1H$ NMR (400 MHz, DMSO-$d_6$): δ 9.42 (t, J=5.2 Hz, 2 NH, $D_2O$ exchangeable), 7.87 (s, 1 OH, $D_2O$ exchangeable), 7.47-7.15 (m, 7H), 6.99-6.74 (m, 6H), 4.32-3.94 (m, 3H), 3.90-3.42 (m, 8H), 3.31-2.72 (m, 6H), 2.57-2.29 (m, 2H), 1.30-0.87 (m, 6H).

Compound 121:

The succinate 120 (1.0 g, 1.4 mmol) was dissolved in acetonitrile (60 mL). To this solution diisopropylethylamine (1.15 mL, 5.6 mmol) and HBTU (1.26 g, 2.8 mmol) were added. The reaction mixture was swirled until all contents were dissolved. CPG (14 g) was added to the flask and the mixture shook overnight. The CPG was filtered and washed consecutively with dichloromethane, 10% methanol in dichloromethane, dichloromethane and anhydrous diethyl ether. The CPG was suction dried for 1 hour, then recovered from the funnel and placed under hard vacuum for 2 hours. The loaded CPG was capped with 25% acetic anhydride/pyridine (100 mL) for three hours. The CPG was filtered and the same washing procedure described earlier was repeated. The CPG was suction dried for 1 hour and dried under high vacuum overnight to afford compound 120 (14 g, 77 µmol/g).

Scheme 100

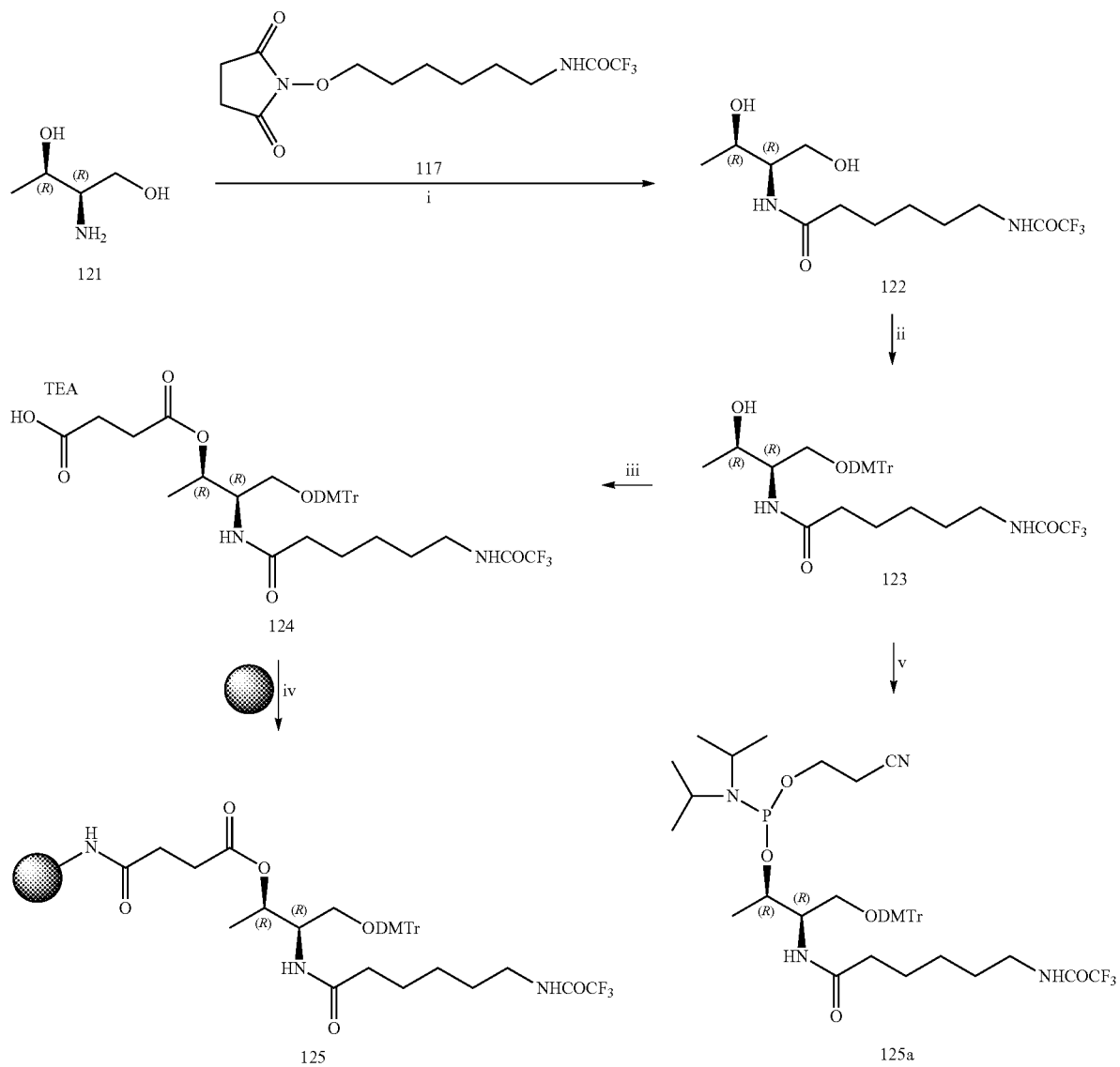

i) DMF, TEA (87%); ii) DMTr—Cl, DMAP/Py (11%); iii) Succinic anhydride, DMAP, TEA, DCM; iv) HBTU, DIPEA, CPG, MeCN (10 g, 71 μmol/g) v) 2-cyanoethyl diisopropylchlorophosphoramidite, DIEA/DCM (64%).

Compound 122:

L-Threoninol (3.54 g, 33.7 mmol) and compound 117 (12.0 g, 37.1 mmol) were dissolved in DMF (90 mL) under argon. Triethylamine (14.0 mL, 101.1 mmol) was added to the reaction mixture, which stirred at room temperature overnight. The reaction mixture was evaporated to dryness and the residue dissolved in ethyl acetate (120 mL). It was then washed with water (50 mL) and saturated sodium chloride (2×50 mL). The organic layer was dried over sodium sulfate, filtered and evaporated to dryness. The crude compound (3.60 g, Rf=0.43 50% EtOAc in Hexane) was purified silica gel column chromatography using 50% ethyl acetate in hexane followed by 100% ethyl acetate as eluent to afford compound 122 (3.20 g, 87%) as a yellow foam. m/z: 315.1 (+H). $^1$H NMR (400 MHz, DMSO-d$_6$): δ 8.76 (t, 2 NH, D$_2$O exchangeable) 3.93-3.21 (m, 1H), 3.21-3.01 (m, 2 OH, D$_2$O exchangeable), 3.05-2.83 (m, 3H), 2.75-2.51 (m, 1H), 2.55-2.37 (m, 1H), 2.20-1.98 (m, 2H), 1.70-1.39 (m, 7H), 1.28-1.06 (m, 3H). $^{13}$C NMR (101 MHz, DMSO-d$_6$): δ 176.1 (s), 156.3 (s), 158.33 (s), 65.36 (s), 64.20 (s), 60.51, 38.88 (s), 36.34 (s), 27.98 (s), 25.79 (s), 25.70-24.33 (m), 20.05 (s).

Compound 123:

Compound 122 (3.00 g, 9.60 mmol) was co-evaporated with anhydrous pyridine (15 mL) twice and dried under high vacuum overnight. It was then dissolved in anhydrous pyridine (90 mL). To this solution a catalytic amount of DMAP (0.12 g, 0.96 mmol) was added and the mixture was stirred under argon for 30 minutes at 0° C. DMTr-Cl (3.39 g, 10.08 mmol) was added to the solution at 0° C. and stirring was continued at room temperature for 2 hours. The volatiles were then removed under vacuum. The residue was dissolved in dichloromethane (150 mL) and washed with water (2×100 mL) followed by saturated sodium chloride (100 mL). The organic layer was dried over sodium sulfate, filtered and evaporated to dryness. The crude compound (7.02 g, Rf=0.6 in 25% EtOAc in Hexane) was purified by silica gel column chromatography by first eluting with 5% ethyl acetate in hexane (with 1% TEA) followed by 15% ethyl acetate in hexane (with 1% TEA) to obtain compound 123 (700 mg, 11%) as a white foam. m/z: 615.2 (−1), 651.2 (+Cl). $^1$H NMR (400 MHz, DMSO-$d_6$): δ 8.76 (t, 2 NH, $D_2O$ exchangeable) 7.87-6.93 (m, 7H), 6.93-6.63 (m, 6H), 4.19-3.63 (m, 10H), 3.61 (m, 1 OH, $D_2O$ exchangeable), 2.74-1.98 (m, 4H), 1.71-1.10 (m, 6H), 1.08-0.76 (m, 3H). $^{13}$C NMR (101 MHz, DMSO-$d_6$): δ 172.12 (d, J=9.4 Hz), 157.88 (d, J=15.4 Hz), 145.13 (s), 140.22 (s), 135.86 (d, J=6.4 Hz), 131.07-130.03 (m), 130.03-129.28 (m), 128.90 (s), 127.66 (d, J=7.1 Hz), 127.38 (s), 126.45 (d, J=9.7 Hz), 112.89 (d, J=30.1 Hz), 85.08 (s), 65.00 (s), 63.22 (d, J=48.5 Hz), 54.97 (s), 53.72 (s), 45.56 (s), 40.02 (d, J=21.0 Hz), 39.85-39.80 (m), 39.71 (s), 39.50 (s), 39.29 (s), 39.08 (s), 38.88 (s), 35.24 (s), 28.02 (s), 25.86 (s), 25.13 (d, J=13.6 Hz), 21.15 (s), 20.20 (s), 10.35 (s).

Compound 124:

Compound 123 (600 mg, 1.0 mmol), DMAP (420 mg, 3.0 mmol), and triethylamine (0.4 mL, 2.0 mmol) were dissolved in dichloromethane (15 mL). The reaction mixture was stirred under argon for 5 minutes. Then succinic anhydride (230 mg, 2.0 mmol) was added and stirring was continued under argon at room temperature overnight. The reaction mixture was diluted in dichloromethane (50 mL) washed with saturated sodium chloride (2×25 mL). The organic layer was dried over sodium sulfate, filtered and evaporated to dryness. Compound 124 (Rf=0.6 25% EtOAc in hexane) 760 mg (99%) was obtained as a grey foam, which was used for the next reaction without further purification. MS: 715.3 (−H).

Compound 125:

Compound 124 (760 mg, 1.0 mmol) was dissolved in acetonitrile (60 mL). To this solution diisopropylethylamine (0.74 mL, 4.0 mmol) and HBTU (800 mg, 2.0 mmol) were added. The reaction mixture was swirled until all contents were dissolved. CPG (10 g) was added to the flask and the mixture was shaken overnight. The CPG was filtered and washed consecutively with dichloromethane, 10% methanol in dichloromethane, dichloromethane and anhydrous diethyl ether. The CPG was suction dried for 1 hour, then recovered from the funnel and placed under hard vacuum for 2 hours. The loaded CPG was capped with 25% acetic anhydride in pyridine (100 mL) for three hours. The CPG was filtered and the same washing procedure described earlier was repeated. The CPG was suction dried for 1 hour and dried under high vacuum overnight to afford compound 125 (10.2 g, 71 μmol/g).

Scheme 101

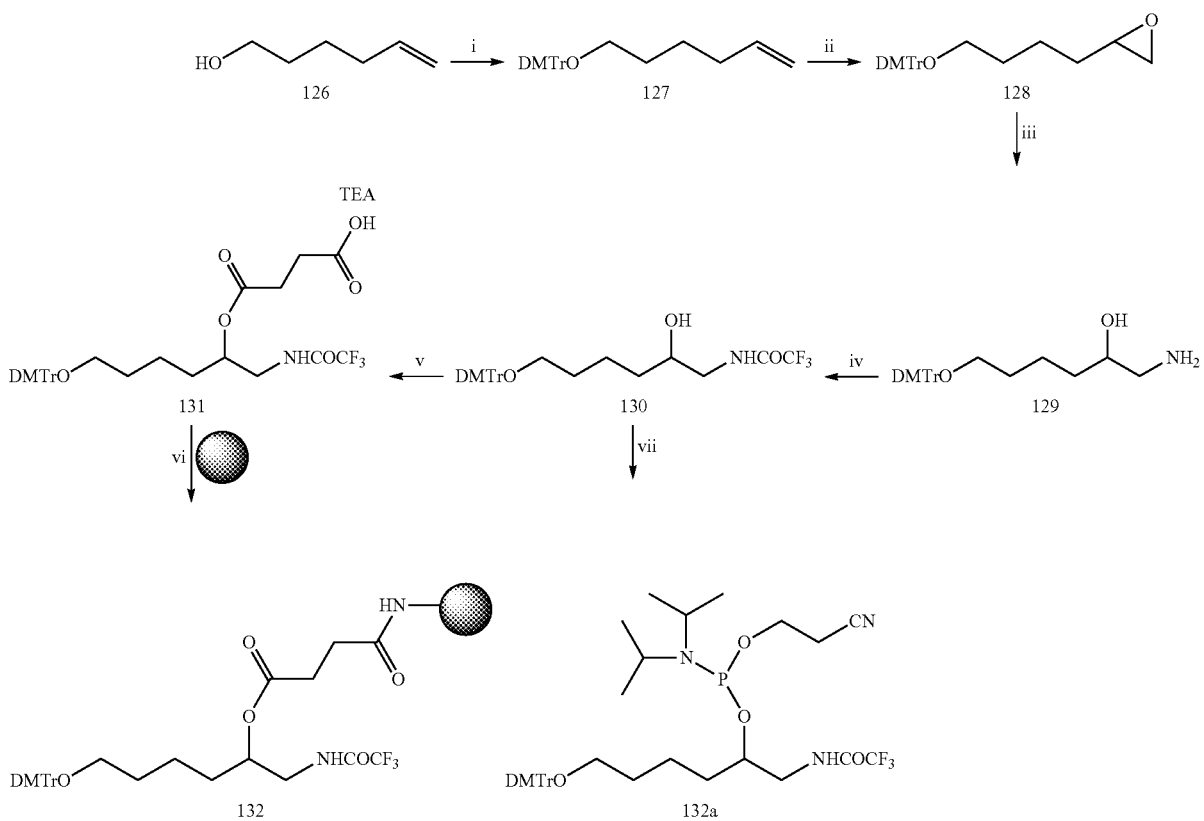

i) DMTr—Cl, DMAP/Py (95%); ii) mCPBA, NaHCO₃, DCM (97.3%) iii) Ammonium hydroxide, EtOH; iv) Ethyl trifluoroacetate, TEA; DCM v) Succinic anydride, DMAP, TEA, DCM; vi) HBTU, DIEA, CPG, MeCN (27 g, 83 μmol/g) vii) 2-cyanoethyl diisopropylchlorophosphoramidite, DIEA/DCM (80%).

Compound 127:

5-Hexenol (6.0 mL, 50.5 mmol) was dissolved in dichloromethane (120 mL). To this solution triethylamine (14 mL, 151.5 mmol) was added. The reaction mixture stirred under argon for 30 minutes at 0° C. Then DMTr-Cl (18 g, 53.0 mmol) was added to the solution at 0° C. The mixture stirred under vacuum followed by argon, and stirring was continued under argon at room temperature for 4 hours. The reaction mixture was washed with water twice followed by saturated sodium chloride. The organic layer was dried over sodium sulfate, filtered and evaporated to dryness to afford compound 127 (Rf=0.85 in 25% EtOAc in Hexane) (18.9 g, 95%) as a yellow oil. $^1$H NMR (400 MHz, DMSO-$d_6$): δ 7.42-7.03 (m, 7H), 7.01-6.74 (m, 6H), 5.85-5.63 (m, 1H), 5.05-4.77 (m, 2H), 3.93-3.47 (m, 6H), 2.93 (dd, J=21.1, 14.7 Hz, 2H), 2.49 (dd, J=3.5, 1.7 Hz, 2H), 1.66-1.47 (m, 4H).

Compound 128:

Compound 127 (5.0 g, 12.5 mmol) and sodium bicarbonate (4.2 g, 25 mmol) were mixed in dichloromethane (250 mL). The reaction mixture was stirred for 5 minutes at room temperature. Then meta-chloroperbenzoic acid (16 g, 31.25 mmol) was added and the mixture continued stirring at room temperature overnight. The reaction mixture was quenched by the addition of sodium bisulfite (500 mg) and allowed to stir at room temperature for 30 minutes. The reaction mixture was washed with water, saturated bicarbonate solution, water, and saturated sodium chloride. The organic layer was dried over sodium sulfate, filtered and evaporated to dryness, to afford compound 128 (Rf=0.25 5% EtOAc in hexane) (5.06 g, 97.3%) as a yellow solid, which required no further purification. $^1$H NMR (400 MHz, DMSO-$d_6$): δ 7.48-7.08 (m, 7H), 6.88 (t, J=5.9 Hz, 6H), 3.74 (d, J=19.4 Hz, 3H), 3.32 (s, 6H), 3.04-2.77 (m, 1H), 2.65-2.35 (m, 2H), 1.69-1.09 (m, 6H).

Compound 129:

Compound 128 (5.0 g, 9.56 mmol) was dissolved in ethanol (15 mL). 30% Ammonium hydroxide in water (3 mL) was added to the reaction mixture, which was stirred at 85° C. in an oil bath in a pressure vessel overnight. The reaction mixture was evaporated to dryness and then co-evaporated with toluene (10 mL) twice. The compound was then co-evaporated with dichloromethane (50 mL) affording crude compound 129 (Rf=0.1 25% EtOAc in hexane, 5.48 g) as a brown oil, which was used without purification.

Compound 130:

Compound 129 (5.48 g, crude) was dissolved in dichloromethane (100 mL). The reaction mixture stirred under argon for 10 minutes at 10° C. To the reaction mixture triethylamine (4.0 mL, 19.1 mmol) was added dropwise as the mixture continued to stir under argon for 20 minutes at 10° C. To the reaction mixture ethyl trifluoroacetate (5.0 mL, 28.7 mmol) was added drop wise at 10° C. The reaction mixture continued to stir under argon at room temperature overnight. The reaction mixture was then washed with water twice followed by saturated sodium chloride. The organic layer was dried over sodium sulfate, filtered and evaporated to dryness affording crude compound 130 (Rf=0.43 50% EtOAc/Hex, 6.12 g). Purification of Compound 130 by silica gel column chromatography by first eluting with 5% ethyl acetate in hexane (1% TEA) to remove impurities followed by 10% ethyl acetate in hexane (1% TEA) to elute product from further impurities afforded 1.51 g (30% from compound 129) as a white foam. $^1$H NMR (400 MHz, DMSO-$d_6$): δ 7.69-7.12 (m, 7H, 1 NH, $D_2O$ exchangeable), 7.10-6.70 (m, 6H), 4.12-3.48 (m, 9H, 1 OH, $D_2O$ exchangeable), 3.29 (dd, J=19.7, 12.9 Hz, 2H), 2 1.57-1.17 (m, 6H). $^{13}$C NMR (101 MHz, DMSO-$d_6$): δ 157.97 (s), 156.56 (s), 156.20 (s), 145.27 (s), 136.08 (s), 129.58 (s), 127.69 (d, J=7.7 Hz), 126.51 (s), 117.45 (s), 114.58 (s), 113.09 (s), 85.15 (s), 67.93 (s), 62.78 (s), 54.96 (s), 45.67 (s), 40.13 (s), 39.92 (s), 39.71 (s), 39.50 (s), 39.30 (s), 39.09 (s), 38.88 (s), 34.28 (s), 29.51 (s), 21.92 (s).

Compound 131:

Compound 130 (1.49 g, 2.8 mmol), DMAP (1.02 g, 8.4 mmol), and triethylamine (0.8 mL, 5.6 mmol) were dissolved in dichloromethane (30 mL). The reaction mixture was stirred under argon for 5 minutes. Then succinic anhydride (600 mg, 5.6 mmol) was added and the mixture continued stirring under argon at room temperature overnight. The reaction mixture was diluted in dichloromethane (100 mL) then washed with two 50 mL portions of slightly saturated sodium chloride. The organic layer was dried over sodium sulfate, filtered and evaporated to dryness. Compound 131 (Rf=0.24 25% EtOAc in hexane) (1.77 g, 99%) was obtained as a white foam, which required no further purification.

Compound 132:

Compound 131 (1.77 g, 2.8 mmol) was dissolved in acetonitrile (120 mL). To the solution diisopropylethylamine (1.95 mL, 11.2 mmol) and HBTU (2.13, 5.6 mmol) were added. The reaction mixture was swirled until all contents were dissolved. CPG (26 g) was added to the flask and the mixture was shaken overnight. The reaction mixture were decanted over a sintered funnel and was washed with 1% triethylamine/dichloromethane, followed by two washes of 10% methanol in dichloromethane, another wash of 1% triethylamine in dichloromethane, and anhydrous diethyl ether. The CPG was suction dried for 1 hour, then recovered from the funnel and placed under hard vacuum for 2 hours, then it was capped with 25% acetic anhydride in pyridine (200 mL) and the mixture was shaken for three hours. The reaction mixture was then placed over a sintered funnel and washed in the same manner as before. The CPG was suction dried for 1 hour, removed from the funnel and placed under hard vacuum overnight. (27 g, 83 μmol/g).

Scheme 102

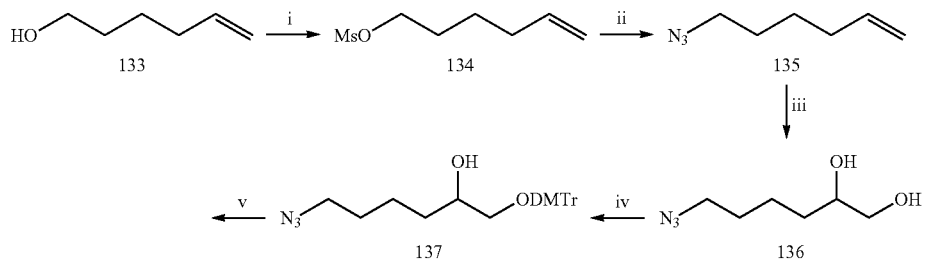

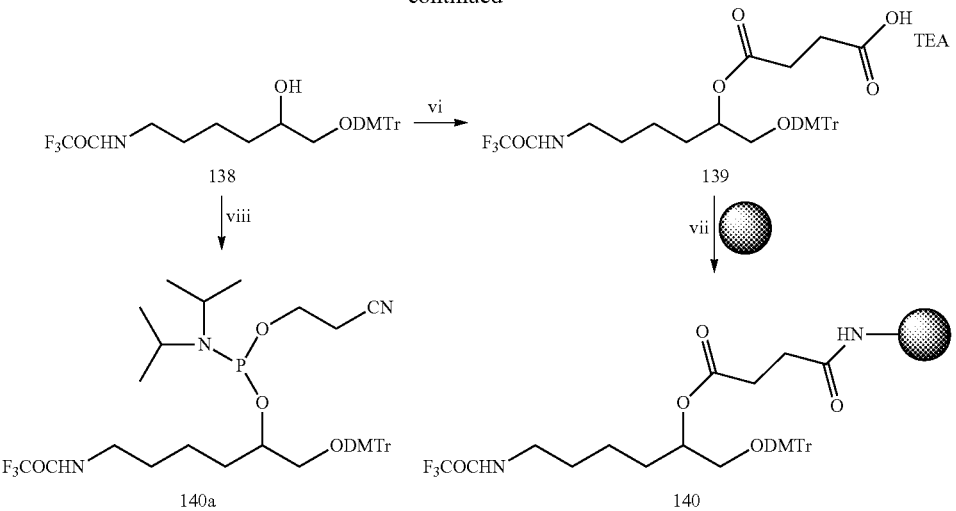

i) MsCl, TEA, DCM; ii) NaN₃, DMF; iii) OsO₄, NMO, Acetone/Water; iv) DMTr—Cl, DMAP/Py; v) a. PPh₃, Water/THF b. Ethyl trifluoroacetate, TEA, DCM; vii) Succinic anydride, DMAP, TEA, DCM; vi) HBTU, DIEA, CPG, MeCN (12 g, 77 µmol/g) vii) 2-cyanoethyl diisopropylchlorophosphoramidite, DIEA/DCM (76%).

Compound 134:

5-Hexenol (6.0 mL, 50.5 mmol) and sodium azide (17 g, 252.5 mmol) were dissolved in DMF (120 mL). To this solution triethylamine (14 mL, 151.5 mmol) was added. The reaction mixture stirred under argon for 10 minutes. Then methanesulfonyl chloride (4.25 mL, 50.5 mmol) was added to the solution dropwise over 20 minutes. Stirring was continued under argon at room temperature for 2 days. The reaction mixture was decanted into iced water, which was then washed with 5×50 mL portions of diethyl ether. The organic layer was dried over sodium sulfate, filtered and evaporated to dryness, to afford crude compound 134 (Rf=0.67 in 5% MeOH/DCM, 6.0 g). Purification of compound 134 by column chromatography by first eluting with dichloromethane to remove impurities followed by 2% methanol/dichloromethane afforded 4.6 g (72%) of a clear liquid. $^1$H NMR (400 MHz, DMSO-d₆): δ 5.78 (ddt, J=16.9, 10.2, 6.6 Hz, 1H), 5.16-4.74 (m, 2H), 2.68-2.14 (m, 2H), 1.64-1.27 (m, 4H), 1.24-0.92 (m, 2H)

Compound 135:

Compound 134 (4.5 g, 25.5 mmol) was taken in DMF (100 mL) in a pressure bottle. To this mixture NaN₃ (10 g) was added and the mixture was heated at 80° C. overnight. Solids were then removed by filtration. Volatiles were removed under vacuum and the residue was extracted with ethyl acetate and washed with water and brine. The organic layer was dried over sodium sulfate and the solvent was removed to afford compound afford 134134 as pale yellow liquid (3.6 g, 82%). m/z: 132.1 (—N₂).

Compound 136:

Compound 135 (2.0 g, 16 mmol) and N-methylmorpholine-N-oxide (2.25 g, 19.2 mmols) were dissolved in 10% water in acetone (60 mL). The reaction was stirred for 5 minutes at room temperature. Then osmium tetroxide in 10% water in acetone (1.3 mL, 0.16 mmol) was added and the mixture continued stirring at room temperature overnight. The reaction mixture was decanted over Celite and washed with two 50 mL portions of scetone. The reaction mixture was evaporated to dryness then dissolved in 100 mL of ethyl acetate. The organic layer was washed with a 50 mL portion of 1N HCl. The organic layer was dried over sodium sulfate, filtered and evaporated to dryness, to afford Compound 136 1.70 g (67%) as a tan liquid, which required no further purification.

Compound 137:

Compound 136 (1.5 g, 9.40 mmols) was co-evaporated with anhydrous pyridine (10 mL) twice. Then the compound was placed under high vacuum overnight to dry. The compound was then taken from high vacuum and dissolved in anhydrous pyridine (60 mL). To this solution a catalytic amount of DMAP (0.11 g, 0.94 mmol) was added. The reaction mixture was stirred under argon for 30 minutes at 0° C. Then DMT-Cl (3.35 g, 10.06 mmol) was added to the solution at 0° C. The mixture stirred under vacuum followed by argon, and stirring was continued under argon at room temperature for 1.5 hours. The reaction mixture was evaporated to dryness, and to the residue dichloromethane (100 mL) was added. The organic layer was washed with water twice followed by saturated brine. The organic layer was dried over sodium sulfate, filtered and evaporated to dryness, affording crude compound 137 (Rf=0.8 1:1 EtOAc/Hexane, 5.3.3 g) as an orange oil, which was used without purification.

Compound 138:

Compound 137 (3.3 g, crude) and triphenylphosphine (1.7 g, 6.48 mmol) were dissolved tetrahydrofuran. The reaction mixture was stirred for 5 minutes at room temperature. Then water (1 mL) was added and the mixture continued stirring at room temperature overnight. When completion of the reaction was observed by TLC, the reaction mixture was evaporated to dryness, then co-evaporated with toluene. The reaction mixture was dissolved in dichloromethane (60 mL). The reaction mixture stirred under argon for 10 minutes at 10° C. To the reaction mixture triethylamine (1.5 mL, 10.75 mmol) was added dropwise as the mixture continued to stir under argon for 20 minutes at 10° C. To the reaction mixture ethyl trifluoroacetate (6.5 mL, 54.0 mmols) was added dropwise as the mixture continued to stir under argon for 10 minutes at 10° C. The reaction mixture continued to stir under argon at room temperature overnight. The reaction mixture was washed with water, saturated bicarbonate solution, water, and saturated sodium chloride. The organic layer was dried over sodium sulfate, filtered and evaporated to dryness affording crude compound 138 (Rf=0.5 50% EtOAc/Hex, 3.40 g). Purification of the compound by column chromatography by first eluting with 5% ethyl acetate in hexane to remove impurities followed by 15% ethyl acetate in hexane afforded 2.1 g (42% from Compound 136) as a yellow oil. $^1$H NMR (400 MHz, DMSO-$d_6$): δ 9.36 (s, 1 NH, $D_2O$ exchangeable), 7.47-7.14 (m, 7H), 6.87 (d, J=8.8 Hz, 6H), 3.86-3.48 (m, 7H), 3.33 (s, 1 OH, $D_2O$ exchangeable), 3.13 (dd, J=12.1, 6.4 Hz, 4H), 1.54-1.06 (m, 6H). $^{19}$F NMR (376 MHz, DMSO-$d_6$): δ-82.54 (s). $^{13}$C NMR (101 MHz, DMSO-$d_6$): δ 161.42 (s), 159.73 (s), 159.37 (s), 148.65 (s), 139.41 (d, J=6.7 Hz), 136.65 (s), 135.74-135.30 (m), 134.92 (d, J=9.8 Hz), 133.16 (s), 132.18 (d, J=11.8 Hz), 131.18 (d, J=6.0 Hz), 129.96 (s), 116.51 (s), 88.50 (s), 72.39 (s), 71.10 (s), 63.20 (s), 58.43 (s), 43.58 (s), 43.37 (s), 43.16 (s), 42.95 (s), 42.80-42.53 (m), 42.33 (s), 36.88 (s), 31.79 (s), 25.67 (s), 17.51 (s).

Compound 139:

Compound 138 (1.0 g, 1.9 mmols), DMAP (700 mg, 5.7 mmols), and triethylamine (0.55 mL, 3.8 mmols) were dissolved in dichloromethane (20 mL). The reaction mixture was stirred under argon for 5 minutes. Then succinic anhydride (380 mg, 3.8 mmol) was added and the mixture continued stirring under argon at room temperature overnight. The reaction mixture was diluted in dichloromethane (50 mL) then washed with two 25 mL portions of slightly saturated sodium chloride. The organic layer was dried over sodium sulfate, filtered and evaporated to dryness. Compound 139 (eluent 1:1 EtOAc/Hexane) 1.18 g (99%) was obtained as a pink oil, which required no further purification.

Compound 140:

Compound 139 (1.18 g, 1.9 mmols) was dissolved in acetonitrile (60 mL). To the solution diisopropylethylamine (1.3 mL, 7.6 mmol) and HBTU (1.43 g, 3.8 mmol) were added. The reaction mixture was swirled until all the contents were dissolved. CPG (12 g) was added to the flask and the mixture was shaken overnight. The CPG compound and reaction mixture were decanted over a sintered funnel. The reaction mixture was washed with 1% triethylamine in dichloromethane, followed by two washes of 10% methanol/dichloromethane, another wash of 1% triethylamine in dichloromethane, and anhydrous diethyl ether. The CPG was suction dried for 1 hour, then recovered from the funnel and placed under high vacuum for 2 hours. The CPG was capped with 25% acetic anhydride/pyridine (100 mL) and the mixture was shaken for three hours. The reaction mixture were placed over a sintered funnel and washed in the same manner as before. The CPG 140 thus obtained was suction dried for 1 hour, removed from the funnel and placed under high vacuum overnight (12 g, 77 μmol/g).

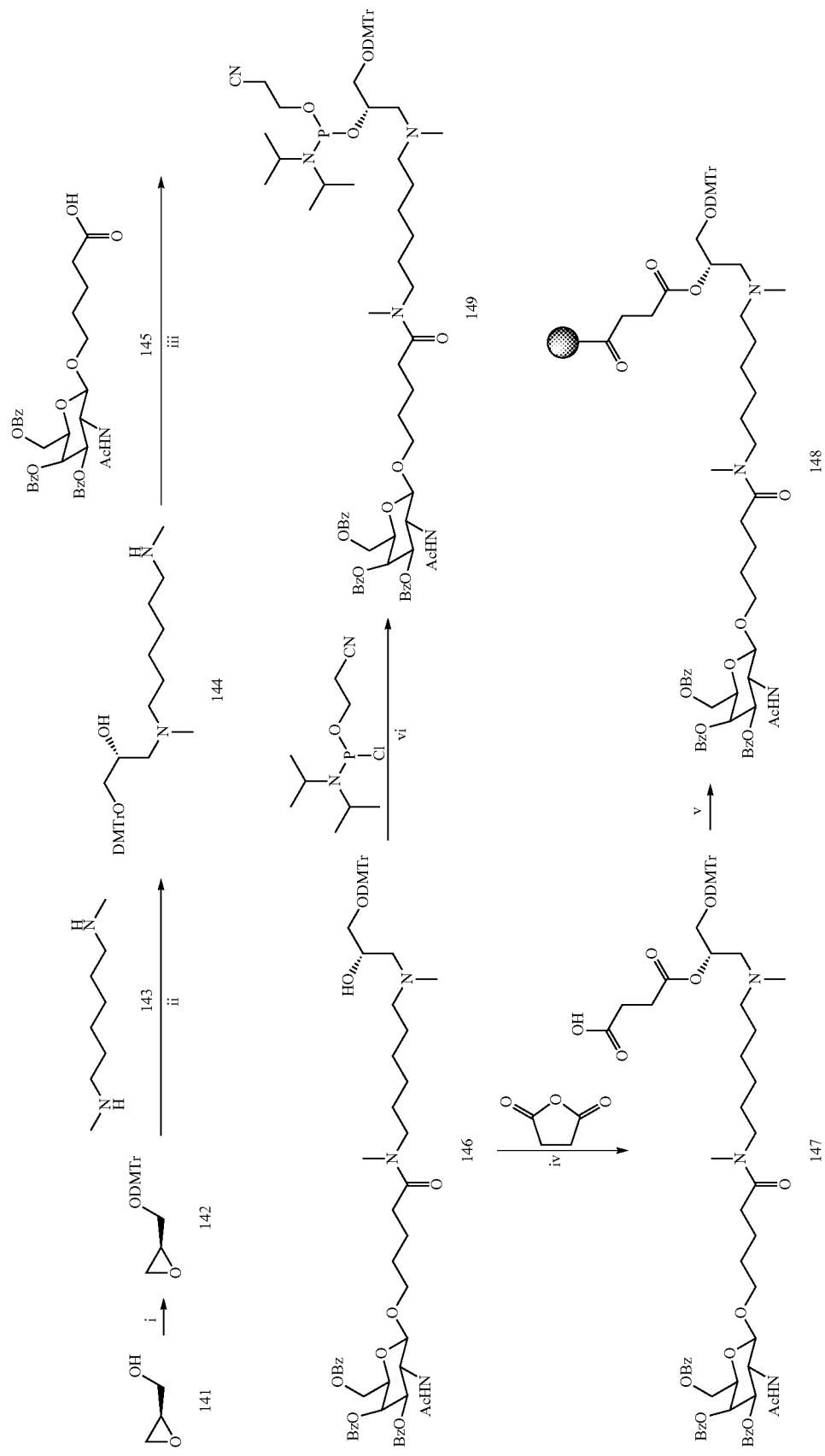

Compound 142:

To a stirred solution of (R)-glycidol (2.3 g, 31 mmol) in DCM was added triethylamine (5 mL, 36.5 mmol) followed by the addition of a 1 M solution of DMTrCl (10.66 g, 31.5 mmol) in DCM at room temperature. The reaction was left to stir until there was no starting material as shown by TLC. A few drops of MeOH was added to hydrolyze any unreacted DMTrCl and the mixture was stirred for 10 minutes. The product was washed with $H_2O$, brine, and dried over $Na_2SO_4$. The product was purified by column chromatography using a gradient of Hexane/EtOAc (9:1) to afford 6 g (52%) of the pure product 142. $^1$H NMR (400 MHz, DMSO-$d_6$): δ 7.38 (d, J=7.6 Hz, 2H), 7.31 (t, J=7.6 Hz, 2H), 7.27-7.12 (m, 5H), 6.87 (d, J=6.1 Hz), 4H), 3.72 (s, 6H), 3.24 (dd, J=10.9, 2.4 Hz, 1H), 3.15-3.08 (m, 1H), 2.86 (dd, J=10.9, 6.0 Hz, 1H), 2.70 (t, J=4.6 Hz, 1H), 2.54 (m, 1H). $^{13}$C NMR (101 MHz, DMSO-$d_6$): δ 158.07, 144.75, 135.48, 135.45, 129.60, 127.85, 127.59, 126.69, 113.46, 113.21, 85.46, 64.52, 55.01, 50.37, 43.59.

Compound 144:

To a stirred solution of N1,N6-dimethylhexane-1,6-diamine 143 (4.225 g, 29 mmol) and $K_2CO_3$ (0.15 g, 1 mmol) dissolved in DMF and heated to 90° C. was added drop-wise compound 142 (5.06 g, 13.5 mmol). The reaction mixture was stirred overnight until no compound 142 remained. The reaction was quenched with ice, extracted with DCM, dried over $Na_2SO_4$, and purified by column chromatography using a gradient of DCM (2.5% $NEt_3$) MeOH (30%) to afford 7.8 g (63%) of pure compound 144. $^1$H NMR (500 MHz, DMSO-$d_6$): δ 7.40 (d, J=7.6 Hz, 2H), 7.35-7.14 (m, 7H), 6.88 (d, J=8.5 Hz, 4H), 4.12 (s, 1H), 3.80-3.64 (s, 6H), 3.37 (m, 2H), 3.11-2.89 (m, 5H), 2.85 (dt, J=15.1, 7.6 Hz, 1H), 2.82-2.76 (m, 2H), 2.69 (s, 3H), 2.48-2.38 (s, 3H), 1.61 (m, 4H), 1.28 (m, 4H). $^{13}$C NMR (DMSO-$d_6$): δ 158.03, 144.82, 135.54, 135.48, 129.72, 127.79, 127.69, 126.63, 113.15, 85.41, 65.77, 64.74, 58.49, 55.03, 54.92, 52.02, 47.83, 45.17, 40.00, 39.92, 39.83, 39.76, 39.66, 39.50, 39.33, 39.16, 39.00, 32.11, 25.50, 25.40, 24.99, 23.29, 8.37, 7.23.

Compound 146:

(OBz) GalNAc Acid 145 (6.95 g, 13.3 mmol), HOBt (3.59 g, 26.6 mmol), HBTU (5.04 g, 13.3 mmol), and DIPEA (5 mL, 28.5 mmol) were stirred in anhydrous DMF (80 mL) for 15 minutes. To this solution was added Compound 144. The mixture was stirred for 45 minutes until no starting material remained. The product was dissolved in ethyl acetate (100 ml) and the organic layer was washed with $H_2O$, saturated $NaHCO_3$, brine, dried over $Na_2SO_4$ then purified by column chromatography using a gradient of EtOAc (1% $NEt_3$): MeOH (15%) to afford 5.35 g (36%) of pure Compound 146. 1H NMR (400 MHz, DMSO-$d_6$): δ 8.08-7.85 (m, 4H), 7.82-7.11 (m, 20H), 6.86 (d, J=8.8 Hz, 4H), 5.76 (d, J=3.3 Hz, 1H), 5.36 (dt, J=26.7, 13.3 Hz, 1H), 4.75 (d, J=8.5 Hz, 1H), 4.61-4.40 (m, 3H), 4.32 (ddd, J=25.2, 16.9, 9.1 Hz, 2H), 3.88-3.60 (m, 1H), 3.71 (s, 6H), 3.63-3.45 (m, 1H), 3.18 (dd, J=14.6, 7.4 Hz, 2H), 3.03-2.81 (m, 4H), 2.74 (s, 3H), 2.42-2.29 (m, 1H), 2.31-2.12 (m, 5H), 2.07 (s, 3H), 1.69 (s, 3H), 1.60-0.99 (m, 12H). $^{13}$C NMR (DMSO-$d_6$): δ 171.45, 171.37, 170.36, 170.29, 169.32, 165.19, 165.14, 164.86, 157.91, 145.23, 145.22, 136.01, 135.98, 133.75, 133.49, 133.45, 129.70, 129.57, 129.20, 129.15, 129.02, 128.99, 128.95, 128.68, 128.57, 127.78, 127.62, 126.45, 113.10, 112.98, 100.85, 85.01, 71.88, 69.98, 68.80, 68.73, 67.94, 67.72, 66.39, 63.45, 62.08, 60.72, 59.72, 57.68, 57.64, 54.96, 54.88, 49.72, 48.89, 46.60, 42.83, 40.09, 40.00, 39.92, 39.83, 39.76, 39.67, 39.59, 39.50, 39.33, 39.17, 39.00, 34.67, 32.69, 32.17, 31.51, 30.14, 28.65, 28.54, 27.90, 26.76, 26.74, 26.48, 26.22, 26.06, 22.67, 21.41, 21.11, 20.73, 20.69, 18.58, 14.06, 13.52.

Compound 147:

To a stirred solution of Compound 146 (1.136 g, 1 mmol) and DIPEA (1 mL, 6 mmol) in DCM was added succinic anhydride (220 mg, 2.2 mmol). The reaction was stirred overnight until no starting material remained. The product was washed with $H_2O$, then brine, and dried over $Na_2SO_4$ to afford 850 mg (69%) of Compound 147. $^1$H NMR (500 MHz, DMSO-$d_6$): δ 8.11 (dd, J=15.3, 9.3 Hz, 1H), 7.98-7.84 (m, 4H), 7.73-7.16 (m, 19H), 6.87 (d, J=8.7 Hz, 4H), 5.74 (d, J=3.1 Hz, 1H), 5.36 (dd, J=11.1, 2.6 Hz, 1H), 5.01 (s, 1H), 4.76 (dd, J=8.5, 2.6 Hz, 1H), 4.45 (m, 2H), 4.37-4.23 (m, 2H), 3.71 (s, 6H), 3.54 (dd, J=13.7, 10.4 Hz, 1H), 3.21-3.02 (m, 4H), 3.02-2.93 (m, 4H), 2.87 (s, 2H), 2.73 (s, 1H), 2.55-2.30 (m, 8H), 2.30-2.12 (m, 5H), 2.07 (s, 3H), 1.68 (s, 3H), 1.58-1.07 (m, 8H). $^{13}$C NMR (126 MHz, DMSO-$d_6$): δ 173.83, 172.03, 171.45, 171.38, 169.31, 165.19, 165.13, 164.85, 158.01, 144.84, 135.54, 133.74, 133.45, 129.57, 129.19, 129.14, 129.02, 128.99, 128.94, 128.67, 128.56, 127.75, 127.59, 126.59, 113.10, 100.84, 85.14, 71.92, 70.73, 69.97, 68.72, 67.93, 63.16, 62.09, 57.39, 57.33, 56.90, 54.97, 49.69, 48.89, 47.86, 46.59, 42.65, 40.00, 39.92, 39.83, 39.76, 39.67, 39.59, 39.50, 39.33, 39.16, 39.00, 38.23, 34.68, 32.72, 32.68, 32.15, 31.49, 30.09, 29.89, 29.84, 28.62, 28.53, 27.89, 26.72, 26.34, 26.16, 26.01, 22.66, 21.40, 21.09, 20.46, 16.64

Compound 148:

Compound 147 (0.85 g, 0.64 mmol), CPG (5 g, 0.67 mmol), HBTU (0.485 g, 1.3 mmol), and DIPEA (0.4 mL, 2 mmol) were dissolved in acetonitrile and shaken for 2 hours. The product was filtered, washed with DCM, a solution of DCM: MeOH (9:1), and then dried. The solid was then shaken with a solution of pyridine:acetic anhydride (35%) for 3 hours for capping. The product was filtered, washed with DCM, DCM:MeOH (9:1), hexanes, DCM, and then dried under vacuum to afford 5.2 g (70.4 μmol/g loading) of Compound 148.

Compound 149:

Compound 146 (2.3 g, 2.025 mmol) was azeotroped in pyridine 3× to ensure removal of all moisture, and from this point forward, kept under argon. All solvents used were degassed with argon. To a stirred solution of Compound 4 and DIPEA (1.3 mL, 7.2 mmol) in pyridine at 0° C. was added 2-cyanoethyl diisopropylchlorophosphoramidite (1 g, 4.2 mmol). The mixture was stirred until TLC indicated elimination of all starting materials. The reaction mixture was concentrated, dissolved in a solution of EtOAc:$NEt_3$ (1%):DCM (20%), and run through a quick filtration column of silica gel using EtOAc:$NEt_3$ (3%):DCM (25%) in order to filter off any salts. The filtrate was concentrated, dissolved again in EtOAc, and heptane was added until the product oiled out. The supernatant layer was decanted and the product was concentrated. The product was again dissolved in EtOAc and added drop-wise to a solution of 0° C. heptanes until it precipitated. The heptanes were decanted and the solid was dried to afford 2.2 g (79%) of Compound 149. $^{31}$P NMR (162 MHz, $CD_3CN$) δ 148.03, 147.94. 1H NMR (400 MHz, $CD_3CN$): δ 8.00-7.95 (m, 4H), 7.80-7.76 (m, 2H), 7.69-7.42 (m, 10H), 7.38-7.18 (m, 10H), 6.89-6.66 (m, 5H), 5.83 (d, J=3.0 Hz, 1H), 5.45-5.37 (m, 1H), 4.80 (d, J=8.6 Hz, 1H), 4.51 (ddd, J=10.7, 6.4, 2.3 Hz, 1H), 4.41-4.31 (m, 3H), 3.77-3.75 (m, 5H), 3.31-3.07 (m, 4H), 2.93-2.34 (m, 8H), 2.32-2.18 (m, 5H), 2.14 (m, 4H), 1.94 (dt, J=4.9, 2.5 Hz, 3H), 1.77-1.73 (m, 3H), 1.64-1.56 (m, 4H), 1.36-1.10 (m, 16H), 1.09 (d, J=6.8 Hz, 2H), 0.99 (d, J=6.2 Hz, 1H). $^{13}$C NMR (101 MHz, $CD_3CN$): δ 173.16, 171.09, 166.76, 166.71, 166.43, 159.80, 159.75, 146.11, 137.19, 136.98, 136.93, 134.74, 134.45, 134.36, 131.12, 131.06, 130.87, 130.59, 130.56, 130.50, 130.46, 130.38, 129.94, 129.66, 129.59, 129.16, 129.07, 128.97, 128.90, 128.84, 128.78, 127.96, 127.90, 118.73, 118.37, 114.19, 114.14, 114.06, 114.01, 101.98, 87.45, 87.15, 73.13, 71.75, 70.13, 69.21, 63.22, 59.00, 56.00, 55.98, 51.70, 50.42, 48.02, 46.06, 43.01, 42.79, 35.70, 33.56, 32.93, 32.69, 29.84, 29.75, 29.19, 28.25, 28.09, 27.96, 27.87, 27.50, 27.36, 25.12, 23.48, 23.31, 23.18, 22.55, 22.28, 20.94, 20.89, 20.66, 14.47, 2.21, 2.02, 1.81, 1.61, 1.40, 1.19, 0.99, 0.89, 0.78.

Example 49

Scheme 104

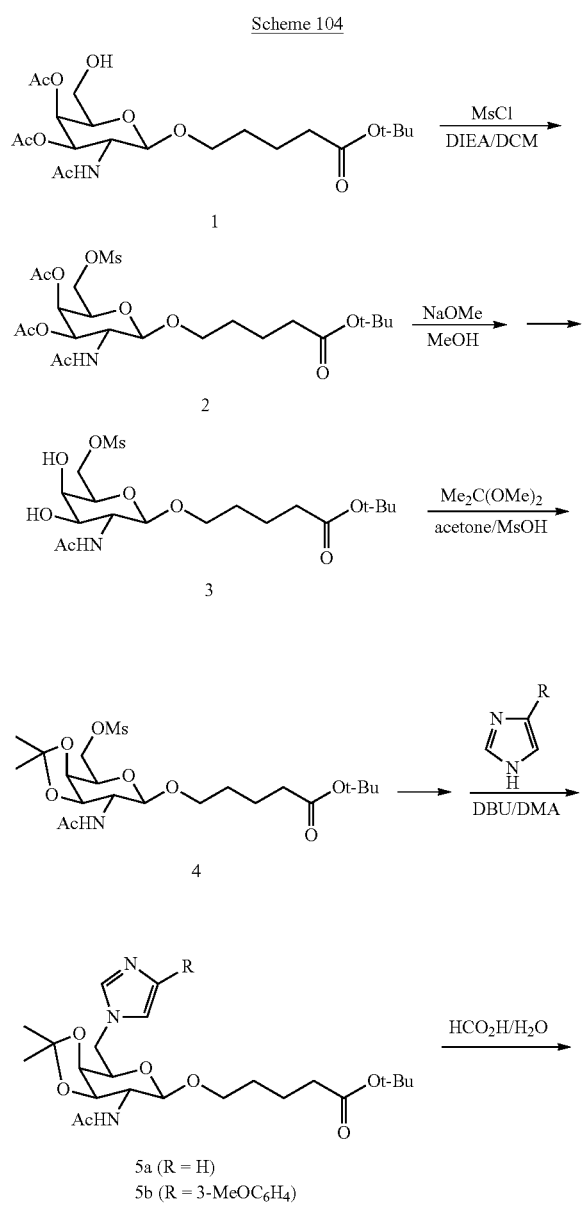

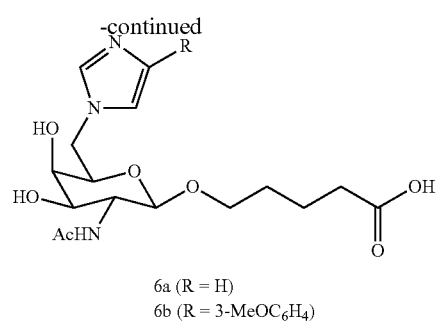

6a (R = H)
6b (R = 3-MeOC$_6$H$_4$)

3,4-Di-acetyl-6-mesyl GalNAc Ester 2

To a solution of 6-hydroxy derivative 1 (2.00 g, 4.3 mmol) in anhydrous DCM (20 mL) were added consecutively DIEA (1.2 mL, 6.5 mmol), and mesyl chloride (0.5 mL, 6.5 mmol) under Ar atmosphere. The mixture was stirred at room temperature overnight, then quenched by addition of 5% aq. NaCl (60 mL). The organic phase was separated, dried over anhydrous sodium sulfate and evaporated under reduced pressure. The residue was co-evaporated once with anhydrous ACN, and the remaining foamy amorphous solid was dried under high vacuum overnight to afford 2.38 g (quantitative) of crude compound 2 that was used in the next step without further purification. MS (in AcOEt): (+) mode: 484 (M−t-Bu); (−) mode: 598 (M+AcOH). $^1$H$^1$ NMR (400 MHz), DMSO-d$_6$, J (Hz): 1.38 (s, 9H); 1.47 (m, 4H); 1.76 (s, 3H); 1.88 (s, 3H); 2.10 (s, 3H); 2.16 (t, 2H, J=7.1); 3.18 (s, 3H); 3.41 (m, 1H); 3.71 (m, 1H); 3.87 (q, 1H, J=8.9); 4.10 (m, 1H); 4.19 (m, 2H); 4.50 (d, 1H, J=8.5); 4.96 (dd, 1H, J$_1$=3.4, J$_2$=11.2); 5.25 (d, 1H, J=2.8); 1.80 (d, 1H, J=9.2).

Unprotected 6-mesyl GalNAc Ester 3

To a cold (0° C.) solution of 3,4-diacetyl derivative 2 (1.29 g, 2.2 mmol) in anhydrous MeOH (10 mL) was added a 25 wt. % solution of MeONa in MeOH (0.05 mL, 0.22 mmol) under an argon atmosphere. The mixture was stirred at 0° C. for 2.5 h, quenched by addition of triethylamine hydrochloride (34 mg, 0.25 mmol), and evaporated in vacuum to afford 1.20 g (quantitative) of crude compound 3 that was used in the next step without further purification. MS (in MeOH): (+) mode: 400 (M−t-Bu); (−) mode: 490 (M+Cl). H$^1$ NMR (400 MHz), DMSO-d$_6$, J (Hz): 1.37 (s, 9H); 1.46 (m, 4H); 1.78 (s, 3H); 2.16 (t, 2H, J=7.5); 3.17 (s, 3H); 3.36 (m, 1H); 3.46 (m, 1H); 3.67 (m, 4H); 4.28 (m, 3H); 4.72 (d, 1H, J=6.2); 4.85 (d, 1H, J=4.0); 7.63 (d, 1H, J=9.0).

3,4-Isopropyliden-6-mesyl GalNAc Ester 4

The residue from the previous step containing crude compound 3 (1.20 g, 2.2 mmol) was dissolved in a mixture of 2,2-dimethoxypropane (10 mL) and acetone (2 mL), followed by addition of methanesulfonic acid (2 drops). The mixture was stirred at room temperature for 2.5 hours, neutralized by addition of triethylamine (4 drops), and partitioned between ethyl acetate and saturated sodium bicarbonate. The organic phase was separated, washed with saturated NaCl, dried over anhydrous sodium sulfate, evaporated in vacuum, the residue was co-evaporated with anhydrous ACN, and dried under high vacuum to afford 1.10 g (quantitative) of crude compound 4 that was used in the next step without further purification. MS (in AcOEt): (+) mode:

496 (M), 440 (M-t-Bu); (−) mode: 530 (M+Cl), 554 (M+AcOH); H¹ NMR (400 MHz), DMSO-d$_6$, J (Hz): 1.23 (s, 3H); 1.38 (s, 9H); 1.40 (s, 3H); 1.46 (m, 4H); 1.79 (s, 3H); 2.16 (t, 2H, J=7.0); 3.21 (s, 3H); 3.67 (m, 1H), 3.55 (m, 1H); 3.68 (m, 1H); 4.14 (m, 3H); 4.27 (dd, 1H, J$_1$=8.4, J$_2$=10.7); 4.36 (d, 1H, J=8.7); 4.42 (dd, 1H, J$_1$=3.3, J$_2$=10.9); 7.86 (d, 1H, J=9.0).

6-(1-Imidazolyl) Ester 5a

A solution of mesylate compound 4 (200 mg, 0.4 mmol), imidazole (136 mg, 2 mmol), and DBU (0.075 mL, 0.5 mmol) in anhydrous DMA (3 mL) was heated at 140° C. under and argon atmosphere for 23 hours. The mixture was cooled to room temperature, diluted with a 1:1 mixture of saturated ammonium chloride and water (40 mL), and extracted with AcOEt. The organic phase was separated, washed twice with saturated brine, dried over anhydrous sodium sulfate, evaporated and the residue was chromatographed over a column of silica gel with gradient of MeOH in AcOEt (0-50%) to afford 74 mg (40%) of compound 5a. MS (in AcOEt): (+) mode: 468 (M); (−) mode: 502 (M+Cl), 526 (M+AcOH). ¹H NMR (400 MHz), ACN-d$_3$, J (Hz): 1.29 (s, 3H); 1.41 (s, 9H); 1.48 (s, 3H); 1.50 (m, 4H); 1.85 (s, 3H); 2.16 (t, 2H, J=7.0); 3.31 (dt, 1H, J$_1$=6.2, J$_2$=10.0); 3.64 (m, 2H); 3.99 (m, 1H); 4.03 (dd, 1H, J$_1$=2.0, J$_2$=5.1); 4.20 (m, 3H); 4.30 (d, 1H, J=8.8); 6.67 (d, 1H, J=9.2); 6.92 (s split, 1H); 7.08 (s split, 1H); 7.52 (s split, 1H).

6-(3-[3-Methoxyphenyl]-imidazolyl-1) Ester 5b

A solution of mesylate compound 4 (300 mg, 0.6 mmol), 2-(3-methoxyphenyl)imidazole (520 mg, 3 mmol), and DBU (0.14 mL, 0.9 mmol) in anhydrous DMA (4 mL) was heated at 140° C. under an argon atmosphere for 76 hours. The mixture was cooled to room temperature, diluted with a 1:1 mixture of saturated ammonium chloride and water (40 mL), and extracted with AcOEt. The organic phase was separated, washed consecutively with 5% aq. NaCl, saturated NaCl, dried over anhydrous sodium sulfate, evaporated. The residue was chromatographed over a column of silica gel with gradient of MeOH in AcOEt (0-30%) to afford 63 mg (18%) of compound 5b. MS (in AcOEt): (+) mode: 574 (M); (−) mode: 608 (M+Cl), 532 (M+AcOH). ¹H NMR (400 MHz), ACN-d$_3$, J (Hz): 1.31 (s, 3H); 1.40 (s, 9H); 1.47 (m, 4H); 1.50 (s, 3H); 1.85 (s, 3H); 2.13 (t, 2H, J=7.1); 3.33 (m, 1H); 3.65 (m, 2H); 3.80 (s, 3H); 4.03 (m, 1H); 4.08 (dd, 1H, J$_1$=2.1, J$_2$=5.2); 4.20 (m, 3H); 4.32 (d, 1H, J=8.8); 6.48 (d, 1H, J=9.2); 6.77 (ddd, 1H, J$_1$=1.2, J$_2$=2.5, J$_3$=8.1); 7.52 (t, 1H, J=8.2); 7.33 (m, 2H); 7.48 (d, 1H, J=1.3); 7.56 (d, 1H, J=1.3).

Deprotected Imidazolyl Derivatives 6a and 6b:

Protected derivative 5a or 5b (0.11 mmol) was dissolved in 98% formic acid (2 mL), and water (0.05 mL) was added. The solution was allowed to stay at room temperature overnight, the formic acid was evaporated in vacuum, and the residue was co-evaporated twice with 1:1 mixture of ethanol and toluene (6 mL). The residue was dissolved in methanol (3 mL), triethylamine (0.15 mL) was added and the solution was stirred at 65° C. for 4 hours. Methanol was removed in vacuum, and the residue was co-evaporated 3 times with 3 mL of pyridine to afford 49 and 73 mg of crude compounds 6a and 6b respectively. The products were further purified by crystallization from acetonitrile-methanol mixtures. 6a: MS (in MeOH): (+) mode: 472 (MH⁺); (−) mode: 370 (M−H⁺). ¹H NMR (400 MHz), DMSO-d$_6$, J (Hz): 1.44 (m, 4H); 1.78 (s, 3H); 2.17 (t, 2H, J=7.0); 3.26 (m, 1H); 3.43 (dd, 1H, J$_1$=3.0, J$_2$=10.6); 3.51 (d, 1H, J=2.8); 3.57 (m, 2H); 3.70 (q, 1H, J=10.4); 4.11 (m, 2H); 4.18 (d, 1H, J=8.4); 6.86 (s, 1H); 7.14 (s, 1H); 7.59 (m, 2H); 12.0 (s broad, COOH). 6b: MS (in MeOH): (+) mode: 478 (MH⁺); (−) mode: 476 (M−H+). H¹ NMR (400 MHz), DMSO-d$_6$, J (Hz): 1.44 (m, 4H); 1.78 (s, 3H); 2.16 (t, 2H, J=7.0); 3.28 (m, 1H); 3.45 (m, 1H); 3.55 (s broad, 1H); 3.62 (m, 2H); 3.71 (m, 1H); 3.76 (s, 3H); 4.15 (m, 2H); 4.22 (d, 1H, J=8.4); 4.71 (s broad, 1H, OH); 4.92 (s broad, 1H, OH); 6.73 (ddd, 1H, J$_1$=1.4, J$_2$=2.5, J$_3$=8.0); 7.23 (t, 1H, J=8.0); 7.28 (m, 2H); 7.63 (m, 3H); 12.0 (s broad, COOH).

Example 50

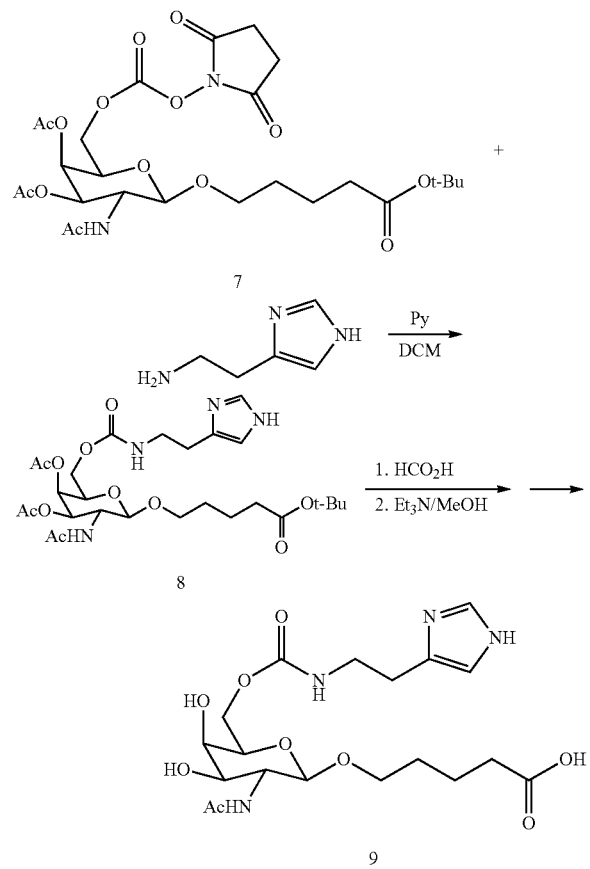

Scheme 105

Histamine Derivative 8:

A suspension of NHS ester compound 7 (200 mg, 0.33 mmol) and histamine base (52 mg, 0.47 mmol) in anhydrous DCM (3 mL) and pyridine (0.05 mL) was stirred at room temperature for 5 days. The reaction was quenched by addition of saturated aqueous sodium bicarbonate and the product was extracted with ethyl acetate. The organic phase was separated, washed with saturated brine, and dried over anhydrous sodium sulfate. The product compound 8 was isolated by column chromatography on silica gel using a gradient of MeOH in DCM (0-30%). Yield: 64 mg, 32%. MS (in MeOH): (+) mode: 599 (M); (−) mode: 633 (M+Cl). ¹H NMR (400 MHz), ACN-d$_3$, J (Hz): 1.41 (s, 9H); 1.54 (m, 4H); 1.83 (s, 3H); 1.91 (s, 3H); 2.09 (s, 3H); 2.18 (t, 2H, J=7.0); 2.69 (t, 2H, J=6.5); 3.29 (m, 2H); 3.47 (m, 1H); 3.78

(m, 1H); 3.87 (t, 1H, J=6.3); 3.94 (q, 1H, J=11.0); 4.04 (m, 2H); 4.51 (d, 1H, J=8.5); 5.00 (dd, 1H, J$_1$=3.2, J$_2$=11.2); 5.26 (d, 1H, J=2.9); 5.91 (s broad, 1H); 6.40 (d, 1H, J=9.4); 6.81 (s broad, 1H); 7.49 (s broad, 1H).

Deprotected Histamine Derivative 9:

A solution of protected histamine derivative 8 (63 mg, 0.11 mmol) in 98% formic acid (2 mL) was maintained at room temperature overnight, then diluted with toluene (10 mL) and evaporated in vacuum. The residue was co-evaporated once with a MeOH-ACN mixture and once with a MeOH-pyridine mixture. The product was dried in high vacuum, dissolved in methanol (3 mL) and triethylamine (0.3 mL) was added. The mixture was stirred at 65° C. overnight, filtered, evaporated, and the residue was co-evaporated 3 times with pyridine (3 mL), one time with ACN (5 mL), and dried under high vacuum to afford 50 mg (quant) of compound 9 as a highly hygroscopic white solid. MS (in MeOH): (−) mode: 457 (M−H). $^1$H NMR (400 MHz), DMSO-d$_6$, J (Hz): 1.46 (m, 4H); 1.78 (s, 3H); 2.18 (t, 2H, J=7.3); 2.61 (t, 2H, J=7.6); 3.18 (q, 2H, J=6.9); 3.34 (m, 2H); 3.44 (dd, 1H, J$_1$=3.0, J$_2$=10.6); 3.51 (t, 1H, J=5.8); 3.60 (d, 1H, J=2.4); 3.68 (m, 2H); 4.04 (d, 2H, J=5.8); 4.23 (d, 1H, J=8.4); 4.67 (s broad, 2H); 6.77 (s, 1H); 7.23 (t, 1H, J=5.5); 7.52 (s, 1H); 7.60 (d, 1H, J=9.0); 12.01 (s broad, 2H).

Example 51

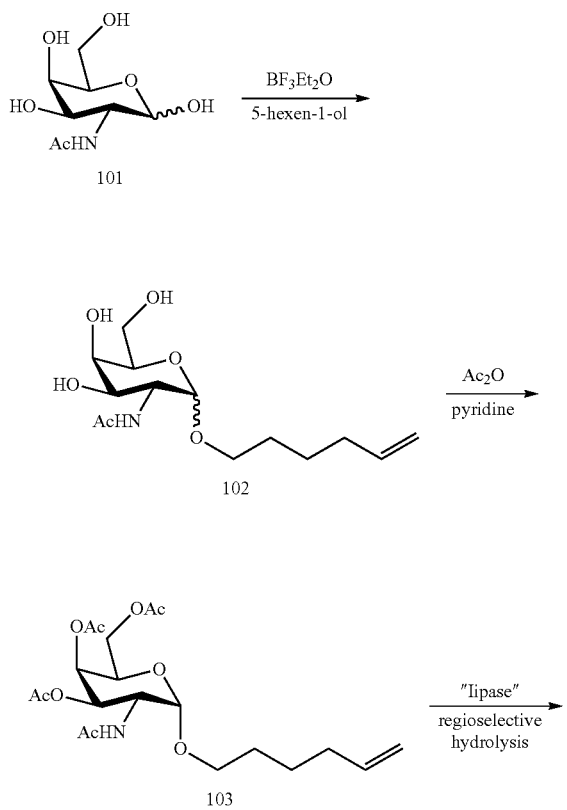

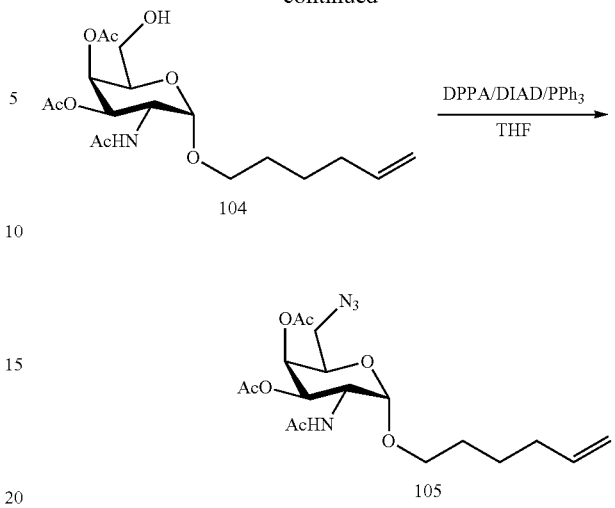

Synthesis of Compound 102:

Compound 101 (5 g, 22.6 mmol) was heated at 100° C. with 5-hexen-1-ol (80 mL) and boron trifluoride diethyl etherate (0.5 mL) for 16 hours. Trituration with Et$_2$O afforded compound 102 (4.0 g, 13.2 mmol, 58%). Molecular weight for C$_{14}$H$_{26}$NO$_6$ (M+H)$^+$ Calc. 304.1760, Found 304.2.

Synthesis of Compound 103:

Compound 102 (1.48 g, 4.88 mmol) was treated in pyridine (30 mL) and Ac$_2$O (10 mL). Aqueous work-up and silica gel column purification afforded compound 103 (1.48 g, 3.45 mmol, 70%). Molecular weight for C$_{20}$H$_{32}$NO$_9$ (M+H)$^+$ Calc 430.2077, Found 430.2.

Synthesis of Compound 104:

Compound 103 (1.37 g, 3.19 mmol) was treated with lipase from *Candida rugosa* (3.43 g) in dioxane (13.7 mL) and potassium hydrogen phthalate buffer (54.8 mL, pH=4) for 64 hours. Aqueous work-up and silica gel column purification afforded compound 104 (680 mg, 1.76 mmol, 55%). $^1$H NMR (400 MHz, CDCl$_3$) δ 5.85-5.75 (m, 1H), 5.59 (d, J=9.7 Hz, 1H), 5.33-5.32 (m, 1H), 5.21 (dd, J=11.3 Hz, 3.2 Hz, 1H), 5.06-4.96 (m, 2H), 4.86 (d, J=3.7 Hz, 1H), 4.63-4.57 (m, 1H), 4.01 (td, J=6.5 Hz, 1.2 Hz, 1H), 3.73-3.62 (m, 2H), 3.51-3.39 (m, 2H), 2.19 (s, 3H), 2.12-2.06 (m, 2H), 2.02 (s, 3H), 1.96 (s, 3H), 1.66-1.59 (m, 2H), 1.49-1.41 (m, 2H).

Synthesis of Compound 105:

Compound 104 (747 mg, 1.74 mmol) was treated with triphenylphosphine (913 mg, 3.48 mmol), diisopropyl azodicarboxylate (0.674 mL, 3.48 mL) and diphenyl phosphoryl azide (0.752 mL, 3.48 mL) in THF (17 mL) for 18 hours. Aqueous work-up and silica gel column purification gave compound 105 (752 mg, quantitative). $^1$H NMR (400 MHz, CDCl$_3$) δ 5.85-5.75 (m, 1H), 5.56 (d, J=9.7 Hz, 1H), 5.30 (d, J=2.7 Hz, 1H), 5.15 (dd, J=11.3, 3.3 Hz, 1H), 5.05-4.97 (m, 2H), 4.88 (d, J=3.7 Hz, 1H), 4.60-4.54 (m, 1H), 4.06 (dd, J=8.8, 3.6 Hz, 1H), 3.77-3.71 (m, 1H), 3.49-3.40 (m, 2H), 3.13 (dd, J=12.8, 4.1 Hz, 1H), 2.17 (s, 3H), 2.12-2.07 (m, 2H), 1.99 (s, 3H), 1.96 (s, 3H), 1.65-1.60 (m, 2H), 1.50-1.44 (m, 2H).

Example 52
Scheme 107
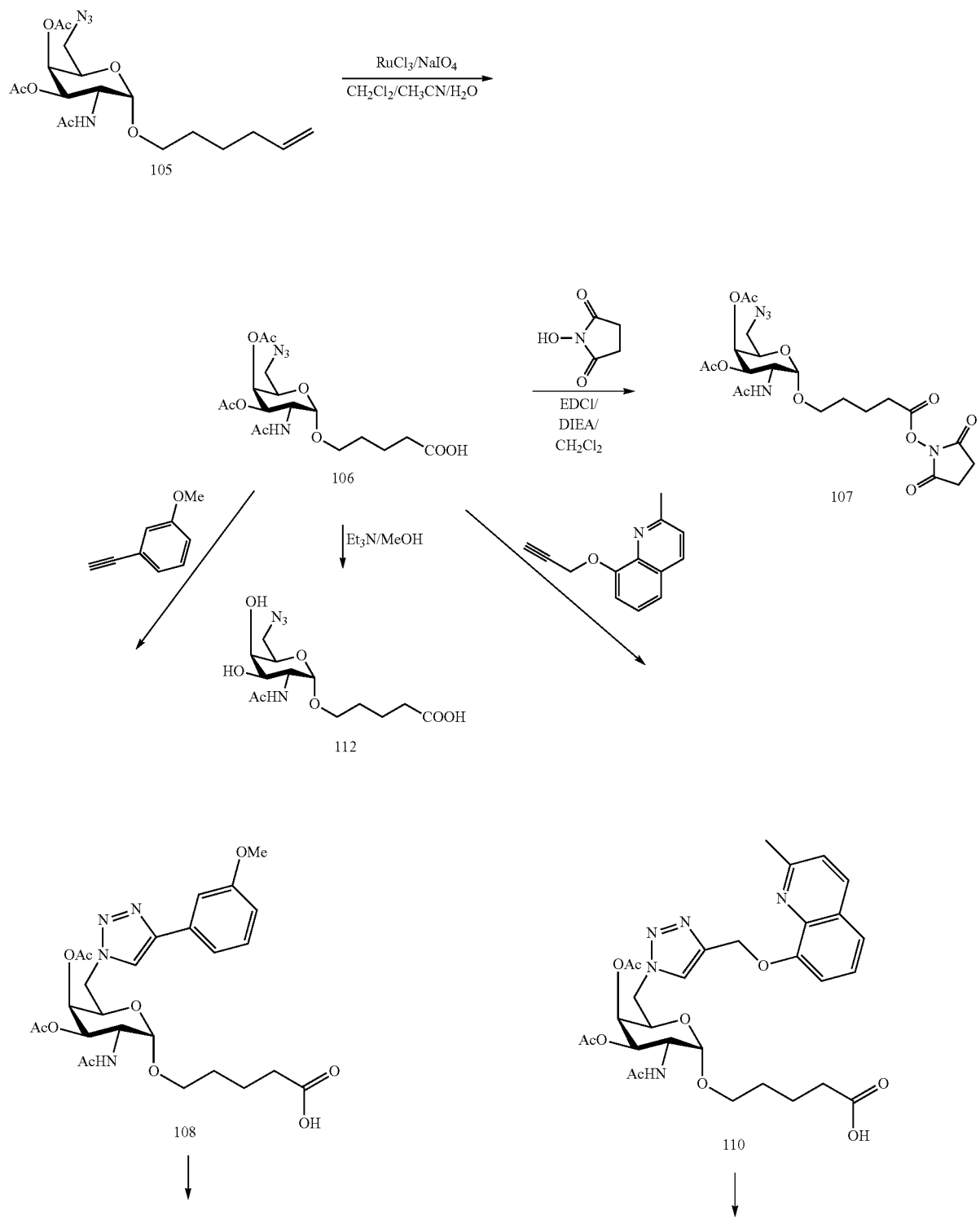

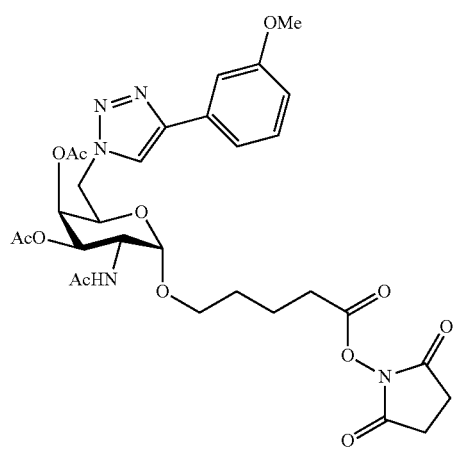

109

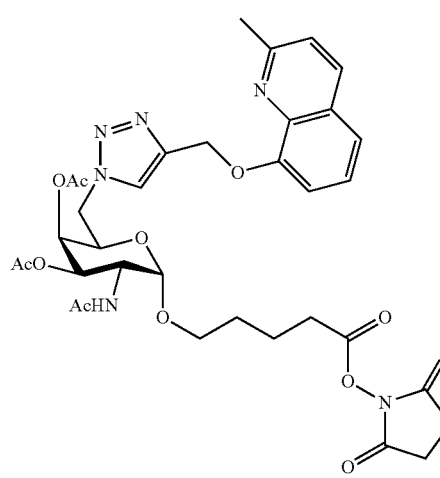

111

Synthesis of Compound 106:

Compound 105 (730 mg, 1.77 mmol) was treated with ruthenium (III) chloride hydrate (18 mg, 0.089 mmol) and sodium periodate (1.89 g, 8.85 mL) in $CH_2Cl_2$ (5 mL) and $CH_3CN$ (5 mL) and $H_2O$ (7 mL) for 18 hours. Aqueous work-up and silica gel column purification afforded compound 106 (677 mg, 1.57 mmol, 89%). Molecular weight for $C_{17}H_{27}N_4O_9$ $(M+H)^+$ Calc 431.1778, Found 431.1.

Synthesis of Compound 107:

Compound 106 (200 mg, 0.465 mmol) was treated with N-hydroxysuccinimide (80 mg, 0.698 mmol), N-(3-Dimethylaminopropyl)-N'-ethylcarbodiimide hydrochloride (134 mg, 0.698 mmol) and DIEA (0.244 mL, 1.40 mmol) in $CH_2Cl_2$ (3 mL) for 18 hours. Aqueous work-up and silica gel column purification afforded compound 107 (183 mg, 0.347 mmol, 75%). Molecular weight for $C_{21}H_{30}N_5O_{11}$ $(M+H)^+$ Calc 528.1942, Found 528.1.

Synthesis of Compound 108:

To a solution of compound 106 (227 mg, 0.527 mmol) and 3-ethynylanisole (0.080 mL, 0.632 mmol) in MeOH (2 mL) were added a solution of THPTA (11 mg, 0.0264 mmol) and $CuSO_4.5H_2O$ (1.3 mg, 0.00527 mmol) in $H_2O$ (0.1 mL) and a solution of sodium ascorbate (10 mg, 0.0527 mmol) in $H_2O$ (0.1 mL). The reaction mixture was stirred at room temperature for 18 hours. Aqueous work-up and silica gel column purification afforded compound 108 (264 mg, 0.469 mmol, 89%). Molecular weight for $C_{26}H_{35}N_4O_{10}$ $(M+H)^+$ Calc 563.2353, Found 563.2.

Synthesis of Compound 109:

Compound 108 (233 mg, 0.414 mmol) was treated with N-hydroxysuccinimide (72 mg, 0.621 mmol), N-(3-Dimethylaminopropyl)-N'-ethylcarbodiimide hydrochloride (119 mg, 0.621 mmol) and DIEA (0.216 mL, 1.24 mmol) in $CH_2Cl_2$ (4 mL) for 18 hours. Aqueous work-up and silica gel column purification afforded compound 109 (100 mg, 0.152 mmol, 37%). Molecular weight for $C_{30}H_{38}N_5O_{12}$ $(M+H)^+$ Calc 660.2517, Found 660.2.

Synthesis of Compound 110:

To a solution of compound 106 (223 mg, 0.518 mmol) and 2-methyl-8-(prop-2-yn-1-yloxy)quinoline (123 mg, 0.622 mmol) in MeOH (2 mL) were added a solution of THPTA (11.2 mg, 0.0259 mmol) and $CuSO_4.5H_2O$ (1.3 mg, 0.00518 mmol) in $H_2O$ (0.1 mL) and a solution of sodium ascorbate (10.3 mg, 0.0518 mmol) in $H_2O$ (0.1 mL). The reaction mixture was stirred at room temperature for 18 hours. Aqueous work-up and silica gel column purification afforded compound 110 (320 mg, 0.510 mmol, 98%). Molecular weight for $C_{30}H_{38}N_5O_{10}$ $(M+H)^+$ Calc 628.2619, Found 628.2.

Synthesis of Compound 111:

Compound 110 (307 mg, 0.489 mmol) was treated with N-hydroxysuccinimide (85 mg, 0.734 mmol), N-(3-Dimethylaminopropyl)-N'-ethylcarbodiimide hydrochloride (141 mg, 0.734 mmol) and DIEA (0.256 mL, 1.47 mmol) in $CH_2Cl_2$ (4 mL) for 18 hours. Aqueous work-up and silica gel column purification afforded compound 111 (155 mg, 0.207 mmol, 42%). Molecular weight for $C_{34}H_{41}N_6O_{12}$ $(M+H)^+$ Calc 725.2782, Found 725.1.

Synthesis of Compound 112:

Compound 106 (240 mg, 0.558 mmol) was treated in MeOH (9 mL) and $Et_3N$ (1 mL) for 5 days to afford compound 112 (250 mg, 0.558 mmol, quantitative). Molecular weight for $C_{13}H_{23}N_4O_7$ $(M+H)^+$ Calc 347.1567, Found 347.1.

Example 53

Scheme 108

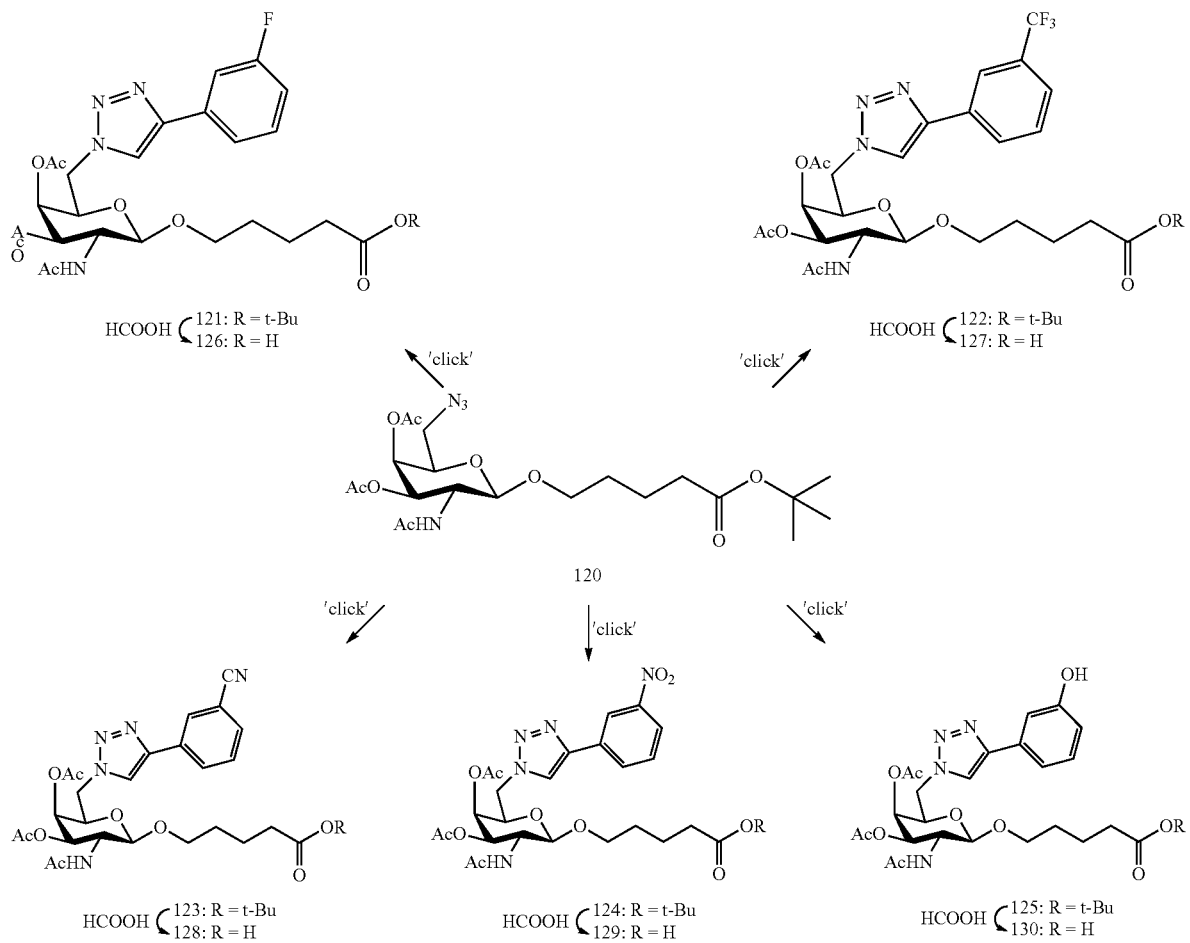

Synthesis of Compound 121:

Using compound 120 in place of compound 106, a procedure analogous to that described for compound 108 was followed to afford compound 121 (300 mg, 0.495 mmol, 80%). Molecular weight for $C_{29}H_{40}FN_4O_9(M+H)^+$ Calc 607.2779, Found 607.1.

Synthesis of Compound 122:

Using compound 120 in place of compound 106, a procedure analogous to that described for compound 108 was followed to afford compound 122 (417 mg, 0.635 mmol, 90%). Molecular weight for $C_{30}H_{40}F_3N_4O_9(M+H)^+$ Calc 657.2747, Found 657.2.

Synthesis of Compound 123:

Using compound 120 in place of compound 106, a procedure analogous to that described for compound 108 was followed to afford compound 123 (343 mg, 0.559 mmol, 80%). Molecular weight for $C_{30}H_{40}N_5O_9$ $(M+H)^+$ Calc 614.2826, Found 614.2.

Synthesis of Compound 124:

Using compound 120 in place of compound 106, a procedure analogous to that described for compound 108 was followed to afford compound 124 (340 mg, 0.537 mmol, 79%). Molecular weight for $C_{29}H_{40}N_5O_{11}$ $(M+H)^+$ Calc 634.2724, Found 634.0.

Synthesis of Compound 125:

Using compound 120 in place of compound 106, a procedure analogous to that described for compound 108 was followed to afford compound 125 (323 mg, 0.54 mmol, 83%). Molecular weight for $C_{29}H_{41}N_4O_{10}$ $(M+H)^+$ Calc 605.2823, Found 605.2.

Synthesis of Compound 126:

Compound 121 (290 mg, 0.478 mmol) was treated with formic acid (10 mL) for 18 hours. After removing the solvent, silica gel column purification afforded compound 126 (241 mg, 0.438 mmol, 92%). Molecular weight for $C_{25}H_{32}FN_4O_9$ $(M+H)^+$ Calc 551.2153, Found 551.0.

Synthesis of Compound 127:

Compound 122 (407 mg, 0.620 mmol) was treated with formic acid (10 mL) for 18 hours. After removing the solvent, silica gel column purification afforded compound 127 (318 mg, 0.530 mmol, 85%). Molecular weight for $C_{26}H_{32}F_3N_4O_9$ $(M+H)^+$ Calc 601.2121, Found 601.0.

Synthesis of Compound 128:

Compound 123 (333 mg, 0.543 mmol) was treated with formic acid (10 mL) for 18 hours. After removing the solvent, silica gel column purification afforded compound 128 (281 mg, 0.504 mmol, 93%). Molecular weight for $C_{26}H_{32}N_5O_9$ $(M+H)^+$ Calc 558.2200, Found 558.2.

Synthesis of Compound 129:
Compound 124 (330 mg, 0.521 mmol) was treated with formic acid (10 mL) for 18 hours. After removing the solvent, silica gel column purification afforded compound 129 (277 mg, 0.480 mmol, 92%). Molecular weight for $C_{25}H_{32}N_5O_{11}$ (M+H)$^+$ Calc 578.2098, Found 578.0.

Synthesis of Compound 130:
Compound 125 (313 mg, 0.518 mmol) was treated with formic acid (10 mL) for 18 h. After removing the solvent, silica gel column purification afforded compound 130 (253 mg, 0.461 mmol, 89%). Molecular weight for $C_{25}H_{33}N_4O_{10}$ (M+H)$^+$ Calc 549.2197, Found 549.0.

Example 54

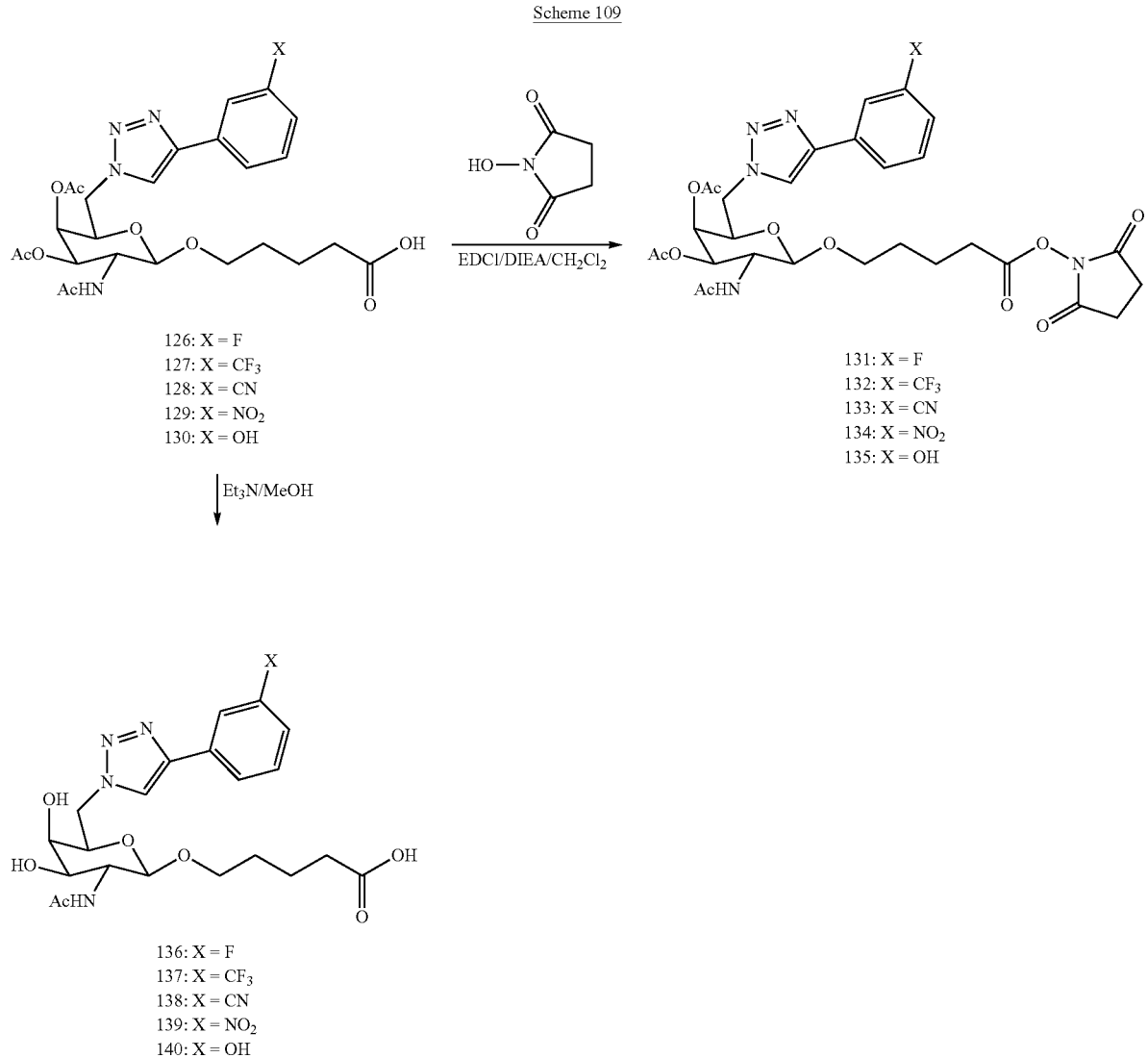

Scheme 109

126: X = F
127: X = CF$_3$
128: X = CN
129: X = NO$_2$
130: X = OH

131: X = F
132: X = CF$_3$
133: X = CN
134: X = NO$_2$
135: X = OH

136: X = F
137: X = CF$_3$
138: X = CN
139: X = NO$_2$
140: X = OH

The NHS ester compounds 131, 132, 133, 134 and 135 are prepared by a standard esterification process with N-hydroxysuccinimide using compounds 126, 127, 128, 129 and 130, respectively. Fully deprotected GalNAc derivatives 136, 137, 138, 139 and 140 are prepared from compounds 126, 127, 128, 129 and 130 by treatment with Et$_3$N/MeOH.

Example 55

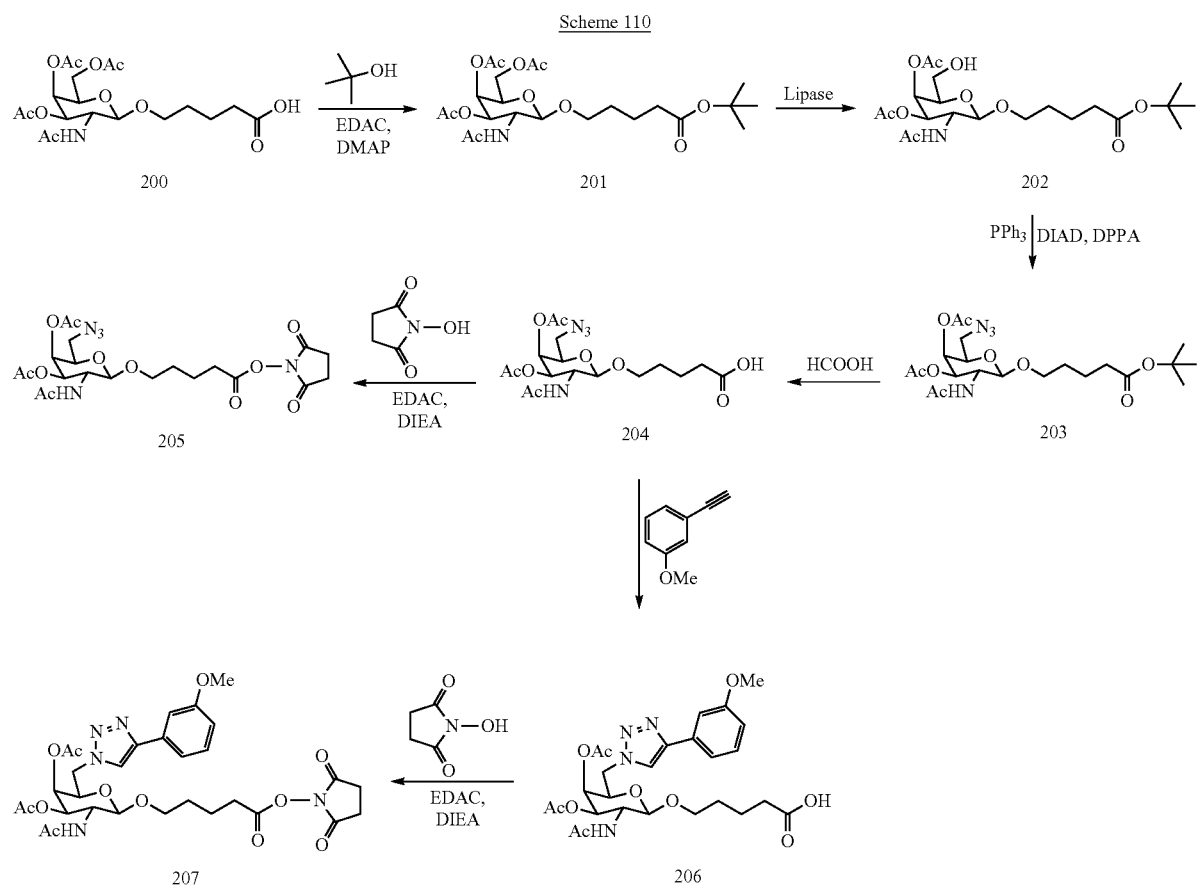

Scheme 110

Synthesis of 201:

Compound 200 (20 g, 44.74 mmol) was stirred in dichloromethane (150 mL). EDAC (12.8 g, 65 mmol), DMAP (2 g, catalytic), and t-butanol (20 mL) were then added. The mixture was stirred for two days at room temperature. The solvents were then removed in vacuo. The residue was extracted with dichloromethane (3×100 mL) and dried over sodium sulfate. The crude product was purified by silica gel chromatography using ethyl acetate and hexane to afford compound 201 (15 g, 68%). Molecular weight for $C_{23}H_{37}NO_{11}$ Calc. 503.24, Found 526.23 (M+Na).

Synthesis of Compound 202:

Using a procedure similar to that described for the synthesis of compound 104, 10 g of compound 201 was converted to compound 202 (7.6 g, 78%). Molecular weight for $C_{21}H_{35}NO_{10}$ Calc. 461.23, Found 484.25 (M+Na).

Synthesis of Compound 203:

Using a procedure similar to that described for the synthesis of compound 105, compound 203 was synthesized (5.2 g, 64%). Molecular weight for $C_{21}H_{34}N_4O_9$ Calc. 486.23, Found 509.24 (M+Na).

Synthesis of Compound 204:

Compound 203 (6.34 g, 13.03 mmol) was stirred in formic acid (20 ml) overnight. Solvent was removed and the residue dissolved in dichloromethane and washed with water and brine. The crude product was purified by silica gel chromatography using ethyl acetate/hexane to afford compound 204. (4.6 g, 82%). Molecular weight for $C_{17}H_{26}N_4O_9$ Calc. 430.17, Found 453.18 (M+Na).

Synthesis of Compound 205:

Compound 204 (0.50 g, 1.16 mmol) was dissolved in dichloromethane (50 mL). N-hydroxy succinimide (0.200 g, 1.5 eq), EDAC and DIEA were then added and the resulting mixture was stirred overnight. The mixture was then washed with water and brine. The solvent was removed and the residue was purified by filtration chromatography using ethyl acetate/hexane to afford compound 205.

Synthesis of Compound 206:

Compound 204 (1.00 g, 2.32 mmol) was stirred in a mixture of methanol/water (2:1). 1-ethynyl-3-methoxybenzene (204A) (0.367 g, 2.7 mmol), $CuSO_4.x\ H_2O$ (0.050 g, catalytic amount) and sodium ascorbate (0.25 g, 1 mmol)) were then added and the mixture was stirred overnight. The solvent was removed and the residue was dissolved in dichloromethane, then washed with water, brine and dried over sodium sulfate. The crude product was purified by silica gel chromatography to afford Compound 206. Molecular weight for $C_{26}H_{34}N_4O_{10}$ Calc. 562.23, Found 585.22 (M+Na).

Synthesis of Compound 207:

Compound 207 was prepared using a procedure similar to that described for the synthesis of compound 205 (320 mg, 95%).

Example 56

Scheme 111

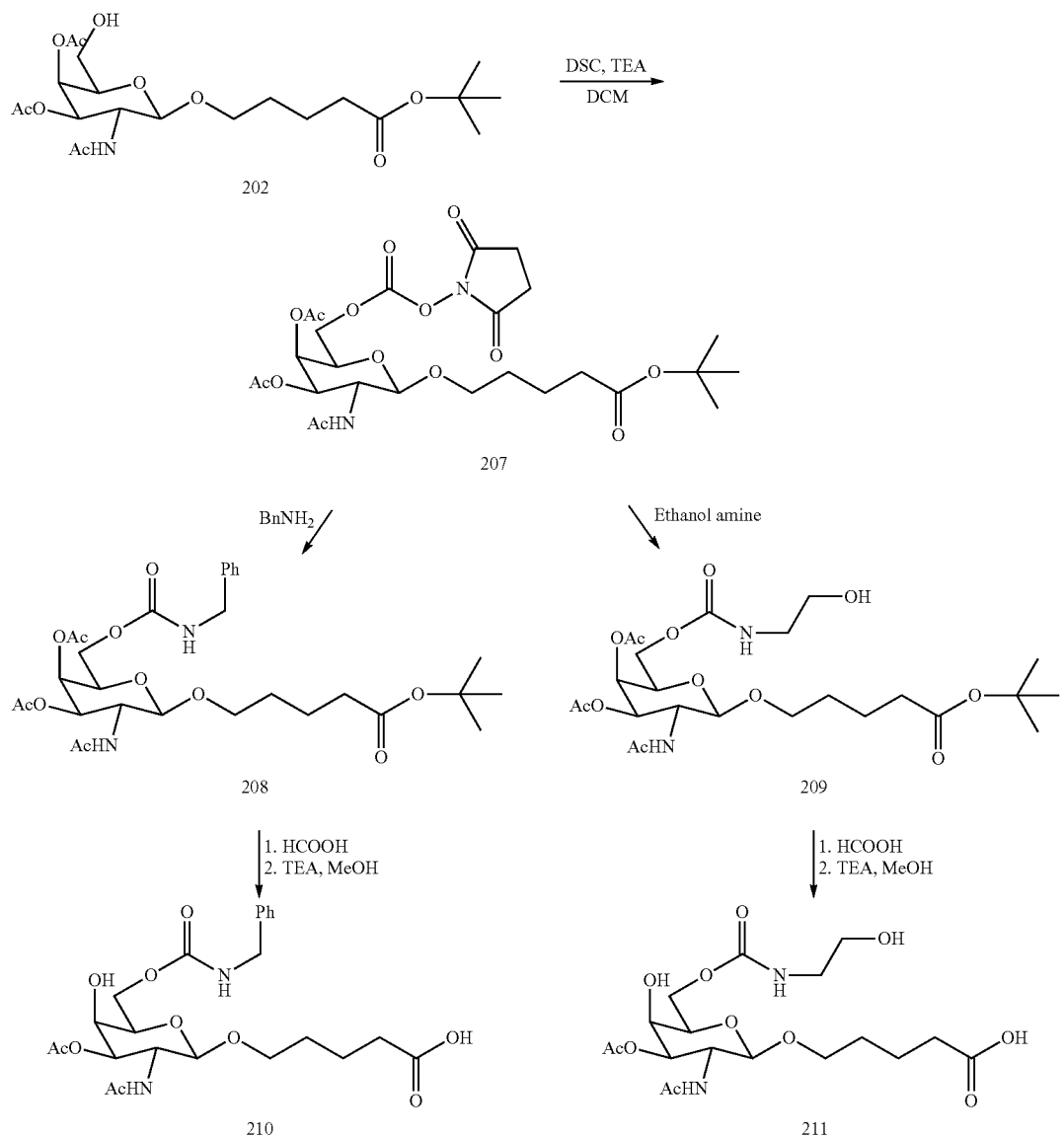

Synthesis of Compound 207:

Compound 202 (2.8 g, 6.07 mmol) was dissolved in dichloromethane (100 mL) and the mixture was cooled in an ice-water bath. To this mixture DSC (1.3 g, 1.5 eq) and TEA (0.7 mL) were added and the solution was stirred overnight. The reaction mixture was then diluted with dichloromethane and transferred to a separatory funnel. The mixture was washed with water and brine, then dried over sodium sulfate. Solvents were removed in vacuo and the residue was dried under vacuum overnight. The resulting product was used for the next reaction stage without any further purification.

Synthesis of Compound 208:

The DSC derivative compound 207 (0.5 g, 0.83 mmol) was stirred in dichloromethane (20 mL). Benzyl amine (0.100 g, 1 mmol) and pyridine (5 mL) were added and the mixture was stirred overnight. Solvents were then removed in vacuo. The residue was dissolved in dichloromethane and washed with water and brine. The crude product was purified by silica gel chromatography using dichloromethane/methanol to afford compound 208 (0.300 g, 65%). Molecular weight for $C_{29}H_{42}N_2O_{11}$ Calc. 594.28, Found 595.29 (M+).

Synthesis of Compound 209:

The DSC derivative compound 207 (0.5 g, 0.83 mmol) was stirred in dichloromethane (20 mL). Ethanol amine (0.07 g, 1 mmol) and pyridine (5 mL) were then added and the mixture was stirred overnight. Solvents were then removed in vacuo. The residue was dissolved in dichloromethane and washed with water and brine. The crude product was purified by silica gel chromatography using dichloromethane/methanol to afford compound 209 (0.25 g, 42%). Molecular weight for $C_{24}H_{40}N_2O_{12}$ Calc. 548.26, Found 549.27 (M+H).

Synthesis of Compound 210:

Compound 208 (250 mg, 0.42 mmol) was dissolved in formic acid (20 mL) and the solution was stirred overnight. Solvents were then removed under reduced pressure. The crude compound was dissolved in dichloromethane and washed with water and brine. Solvents were removed in vacuo and the residue was purified by silica gel chromatography using dichloromethane/methanol to afford compound 210 (200 mg, 87%). This compound was then dissolved in methanol and TEA (2 mL) was added. After stirring overnight at room temperature, solvents were removed in vacuo and the residue was co-evaporated with pyridine two times. The product was further dissolved in water then lyophilized to afford compound 210 as white powder. Molecular weight for $C_{21}H_{30}N_2O_9$ Calc. 454.20, Found 477.21 (M+Na).

Synthesis of Compound 211:

Compound 211 was prepared from compound 209 using a method similar to that used for the preparation of compound 210. Molecular weight for $C_{16}H_{28}N_2O_{10}$ Calc. 408.17, Found 431.20 (M+Na).

Example 57

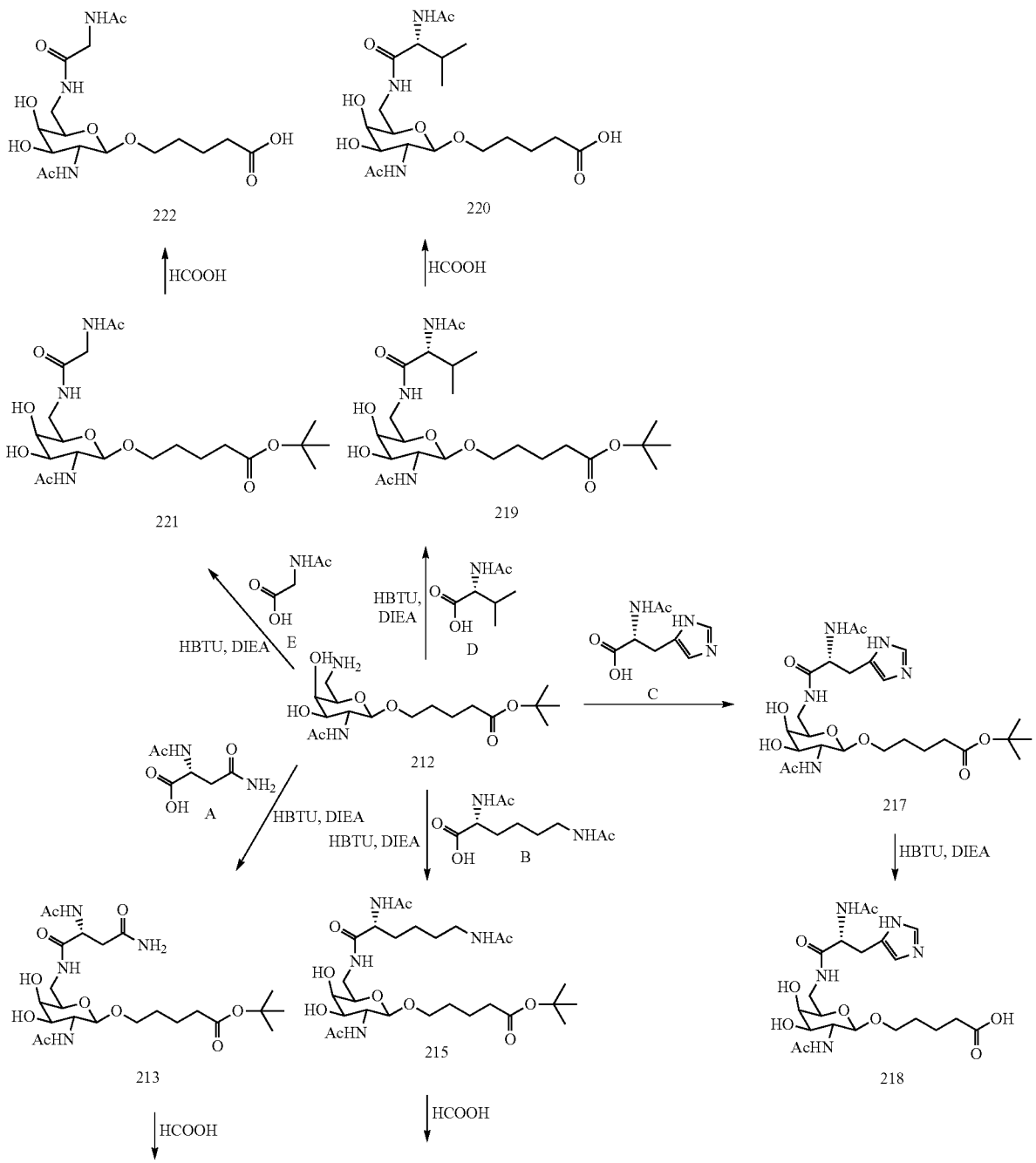

Scheme 112

-continued

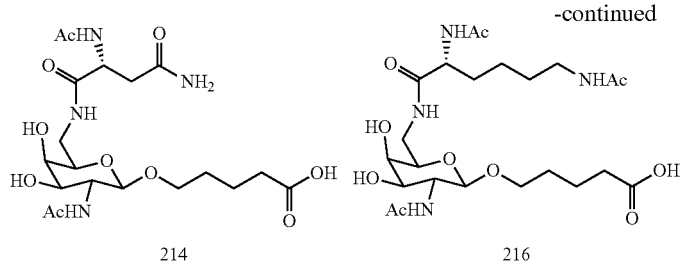

Synthesis of Compound 213:

Glutamate derivative A (0.174 g, 1 mmol) was dissolved in DMF (10 mL). HBTU (0.390 g, 1.05 mmol) and DIEA were added and the mixture was stirred for few minutes at room temperature. Amino derivative compound 212 (0.400 g, 1 mmol) in DMF was added to this solution and stirring was continued overnight. Solvents were then removed under reduced pressure. The crude compound was purified by silica gel chromatography using dichloromethane/methanol to afford compound 213 (0.350 g, 57%). Molecular weight for $C_{23}H_{40}N_4O_{10}$ Calc. 532.27, Found 555.28 (M+Na).

Synthesis of Compound 214:

Compound 213 (300 mg, 0.56 mmol) was dissolved in formic acid and the mixture was stirred overnight at room temperature. The solvent was removed in vacuo and the residue co-evaporated with toluene two times. This residue was dissolved in water and lyophilized to afford compound 214 (200 mg, 74%) as a white powder. Molecular weight for $C_{19}H_{32}N_4O_{10}$ Calc. 476.21, Found 477.20 (M+H).

Synthesis of Compound 215:

Compound 215 was prepared using a similar procedure from compound B (140 mg). Molecular weight for $C_{27}H_{48}N_4O_{10}$ Calc. 588.34, Found 611.33 (M+Na).

Synthesis of Compound 216:

Compound 216 was prepared from compound 215 using a similar procedure used for preparing compound 214 (0.125 g, 35%) Molecular weight for $C_{23}H_{40}N_4O_{10}$ Calc. 532.27, Found 555.25 (M+Na).

Synthesis of Compound 217:

Compound 216 was prepared from compound C and amino derivative 212 (0.250 mg, 65%) Molecular weight for $C_{25}H_{41}N_5O_9$ Calc. 555.29, Found 556.31 (M+H).

Synthesis of Compound 218:

Compound 218 was prepared from compound 217 using a similar procedure used for preparing compound 214 (0.140 mg, 45%) Molecular weight for $C_{21}H_{33}N_5O_9$ Calc. 499.23, Found 500.25 (M+H).

Synthesis of Compound 219:

Compound 219 was prepared from compound D and amino derivative 212 using a similar procedure used for preparing compound 213 (0.525 g, 43%). Molecular weight for $C_{24}H_{43}N_3O_9$ Calc. 517.30, Found 518.28 (M+H).

Synthesis of Compound 220:

Compound 220 was prepared from compound 219 using a similar procedure used for preparing compound 214 (95 mg, 26%). Molecular weight for $C_{20}H_{35}N_3O_9$ Calc. 461.24, Found 462.26 (M+H).

Synthesis of Compound 221:

Compound 221 was prepared from compound from compound E and amino derivative compound 212. (0.320 g, 65%) Molecular weight for $C_{21}H_{37}N_3O_9$ Calc. 475.25, Found 476.23 (M+H).

Synthesis of Compound 222:

Compound 222 was prepared from compound 221 using a similar procedure used for preparing compound 214 (85 mg, 56%) Molecular weight for $C_{17}H_{29}N_3O_9$ Calc. 419.19, Found 420.20 (M+Na).

Example 58

Scheme 113

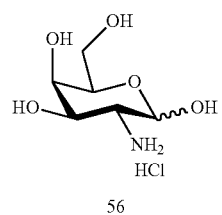

56

(i) NaOMe/MeOH
(ii) CF$_3$COOEt

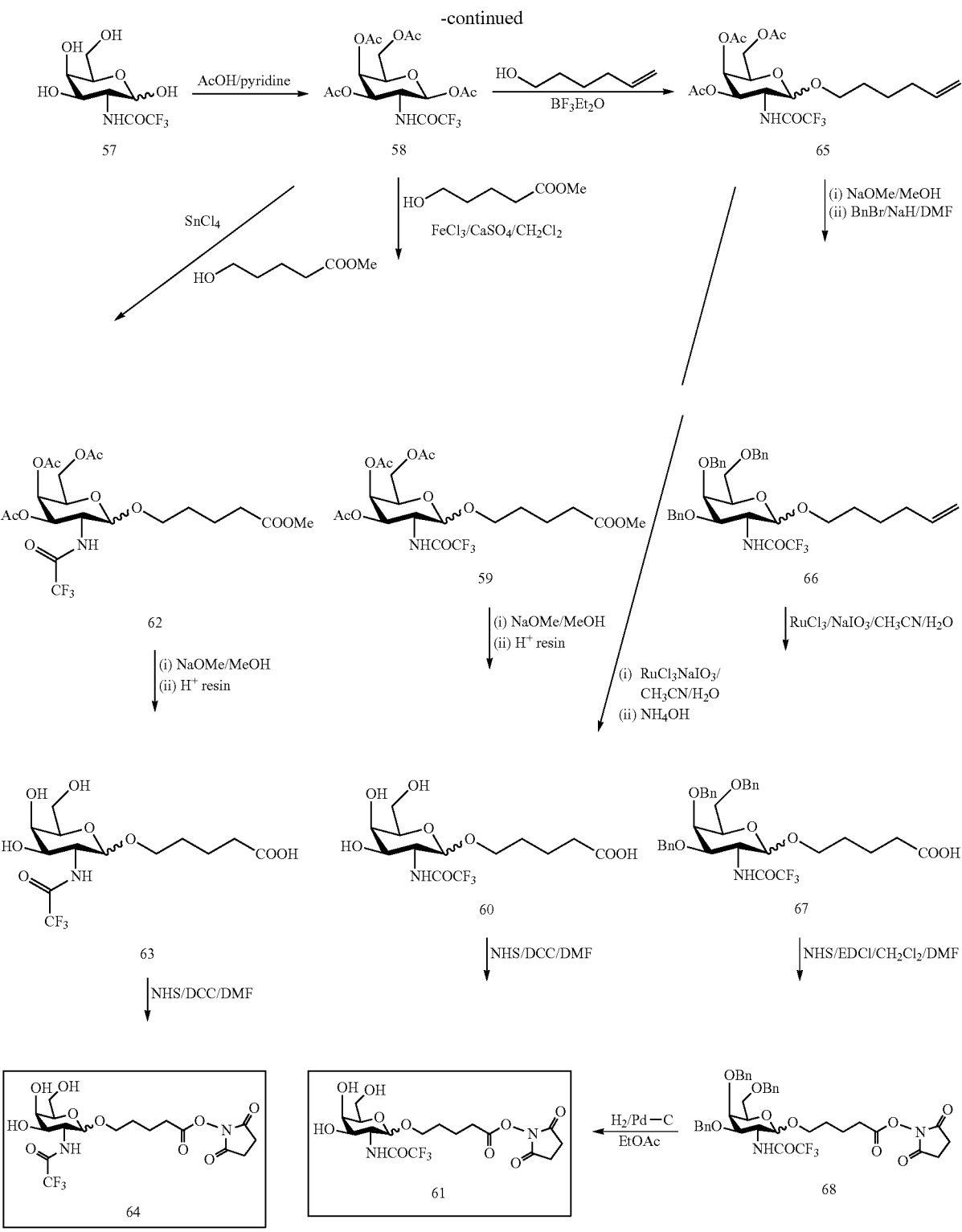

Compound 58 is prepared in a manner similar to that reported in International Publication No. WO 96/39411. O-glycosylation followed by hydrolysis affords compounds 60 and 63. The NHS ester compounds 61 and 64 are prepared by a standard esterification with NHS. The acetyl groups of compound 65 are removed selectively and the resulting hydroxyl groups are protected by benzyl groups to afford compound 66. Oxidative cleavage of the terminal alkene affords compound 67. Esterification followed by hydrogenation affords compounds 61 and 4. O-glycosylation of compound 58 followed by oxidation and hydrolysis affords compound 60. Esterification of compound 60 affords compound 61.

Scheme 114
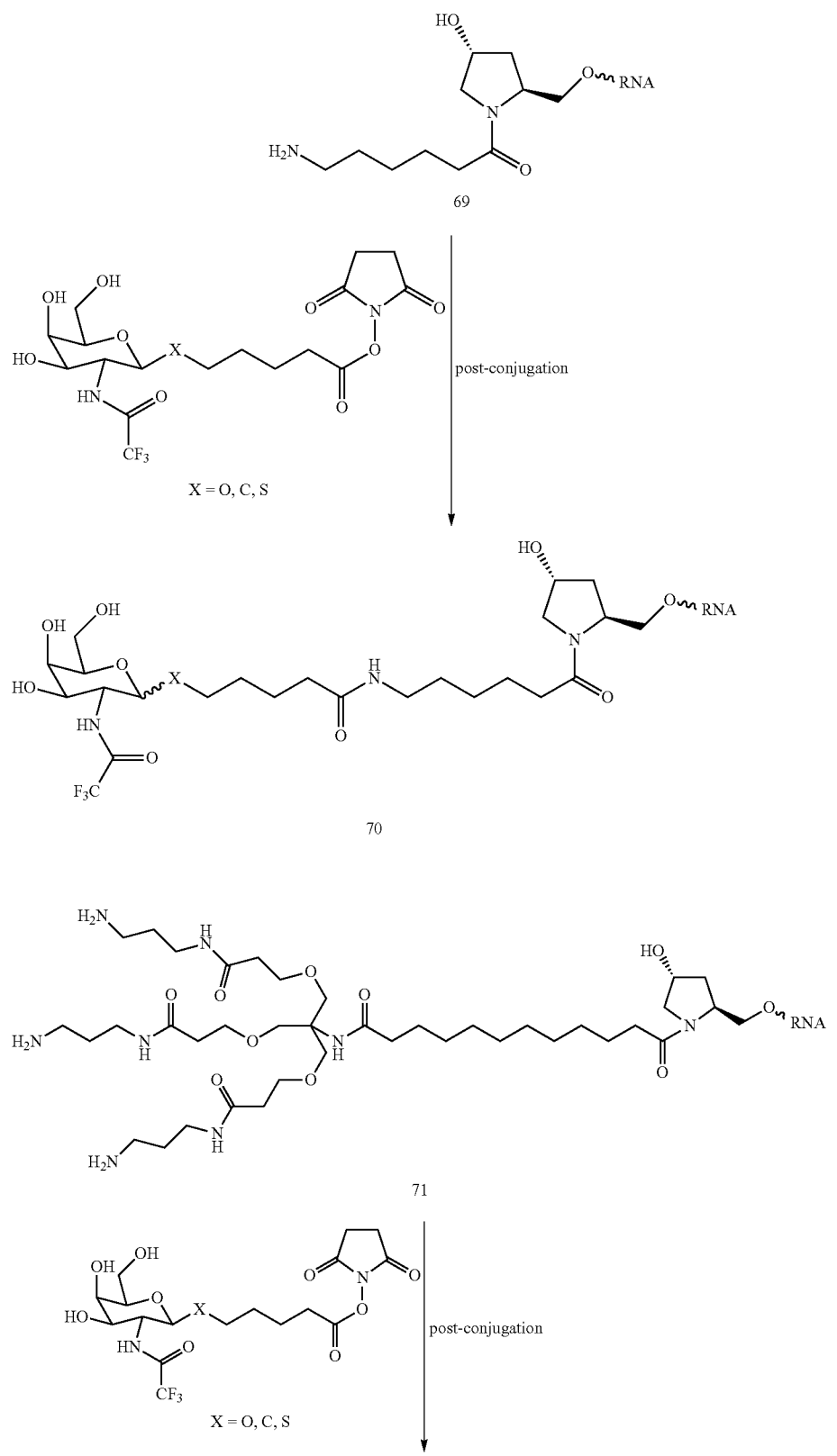

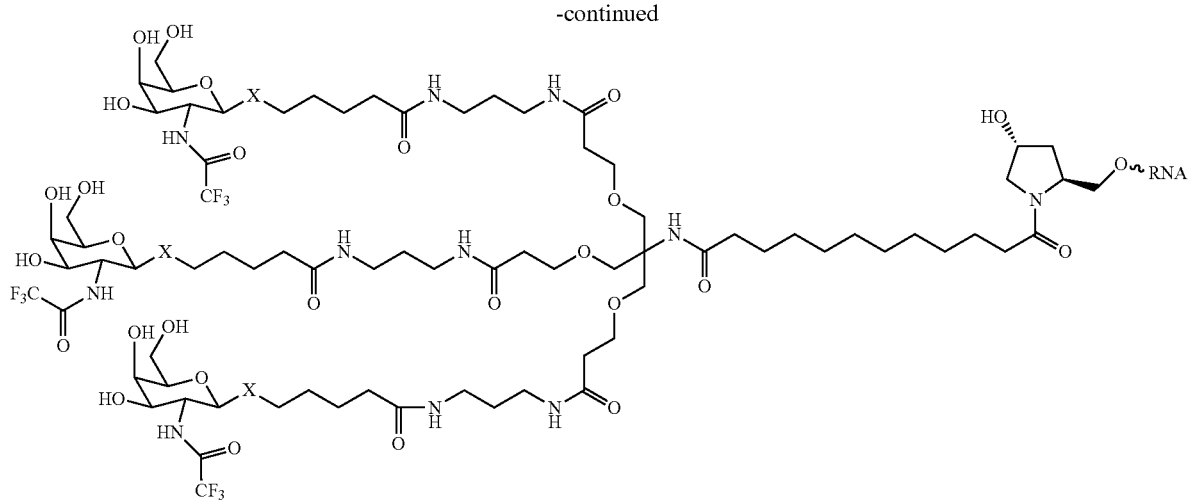

72

Trifluoromethyl acetamide (TFA) protected galactosamine (GalN-TFA) NHS esters are coupled with amine-containing oligonucleotides (compounds 69 and 71) to generate Gal-TFA containing oligonucleotides (compounds 70 and 72) in a post-synthetic approach.

Example 59

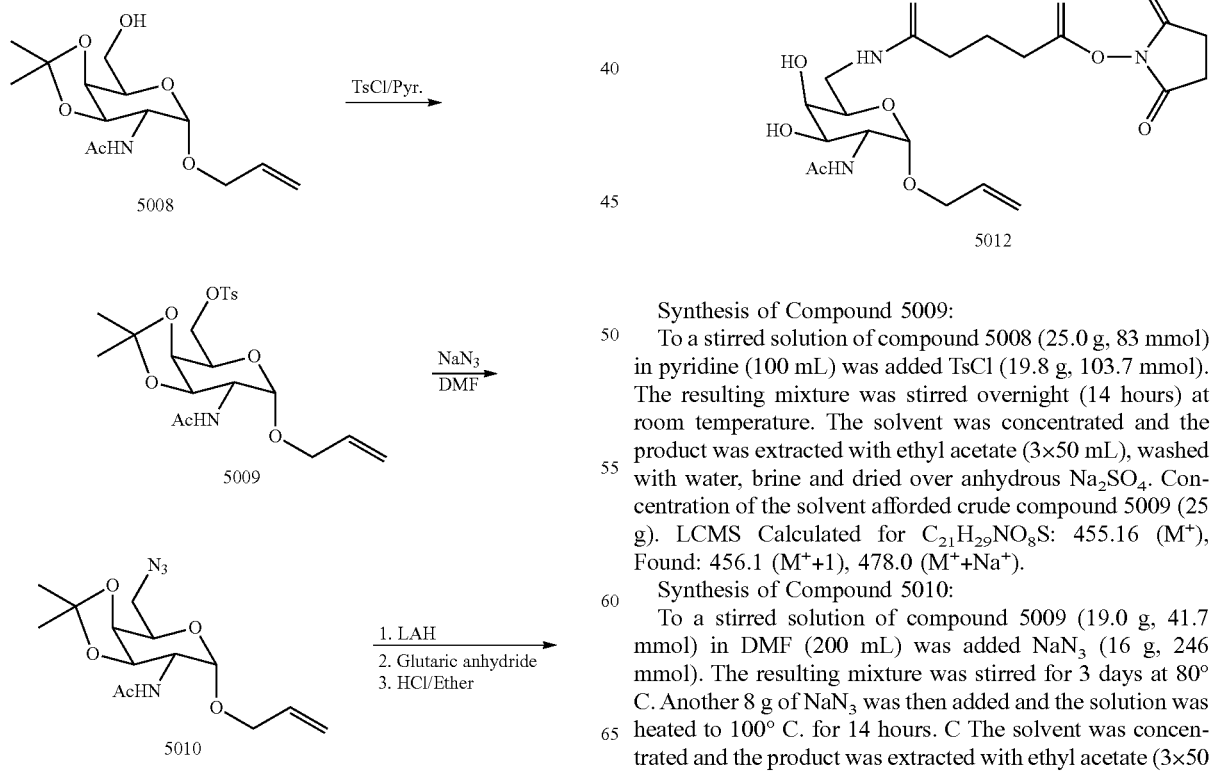

Synthesis of Compound 5009:

To a stirred solution of compound 5008 (25.0 g, 83 mmol) in pyridine (100 mL) was added TsCl (19.8 g, 103.7 mmol). The resulting mixture was stirred overnight (14 hours) at room temperature. The solvent was concentrated and the product was extracted with ethyl acetate (3×50 mL), washed with water, brine and dried over anhydrous $Na_2SO_4$. Concentration of the solvent afforded crude compound 5009 (25 g). LCMS Calculated for $C_{21}H_{29}NO_8S$: 455.16 ($M^+$), Found: 456.1 ($M^++1$), 478.0 ($M^++Na^+$).

Synthesis of Compound 5010:

To a stirred solution of compound 5009 (19.0 g, 41.7 mmol) in DMF (200 mL) was added $NaN_3$ (16 g, 246 mmol). The resulting mixture was stirred for 3 days at 80° C. Another 8 g of $NaN_3$ was then added and the solution was heated to 100° C. for 14 hours. C The solvent was concentrated and the product was extracted with ethyl acetate (3×50 mL), washed with water, brine and dried over anhydrous Na$_2$SO$_4$. Concentration of the solvent afforded crude compound 5010 which was purified by column chromatography (5 g, 37%). LCMS Calculated for C$_{14}$H$_{22}$N$_4$O$_5$: 326.35 (M$^+$), Found: 327.1 (M$^+$+1).

Synthesis of Compound 5011:

To a stirred solution of LAH (139 mg, 3.52 mmol) in THF (10 mL) was added drop wise a solution of compound 5010 (574 mg, 1.76 mmol) in THF (10 mL) at 0° C. The mixture was stirred overnight (14 hours) at room temperature. The reaction mixture was quenched with 1 mL of water followed by filtration over Celite and washing with ethyl acetate (25 mL). Concentration of the solvent afforded the crude product (0.5 g) which was dissolved in DCM (0 mL) and added to a stirred solution of glutaric anhydride (251 mg, 2.2 mmol). The reaction mixture was stirred for 14 hours at room temperature. Concentration of the solvent afforded the crude acid (285 mg) which was dissolved in 20 mL of 2N HCl in diethyl ether and stirred 3 hours. Concentration of the solvent afforded compound 5011 (200 mg). LCMS Calculated for C$_{16}$H$_{26}$N$_2$O$_8$: 374.39 (M$^+$), Found: 373.1 (M$^-$−1).

Synthesis of Compound 5012:

To a stirred solution of compound 5011 (200 mg, 0.53 mmol) and NHS (112 mg, 1.06 mmol) in DMF (10 mL) was added DCC (218 mg, 1.06 mmol). The mixture was stirred 14 hours at room temperature. 20 mL of ethyl acetate was then added Filtration of the solid afforded compound 5012 (150 mg, 60%). LCMS Calculated for C$_{20}$H$_{29}$N$_3$O$_{10}$: 471.46 (M$^+$), Found: 506 (M$^-$+Cl$^-$).

Example 60: Trivalent GalNAc-Conjugated Pseudouridine Building Blocks

Scheme 116

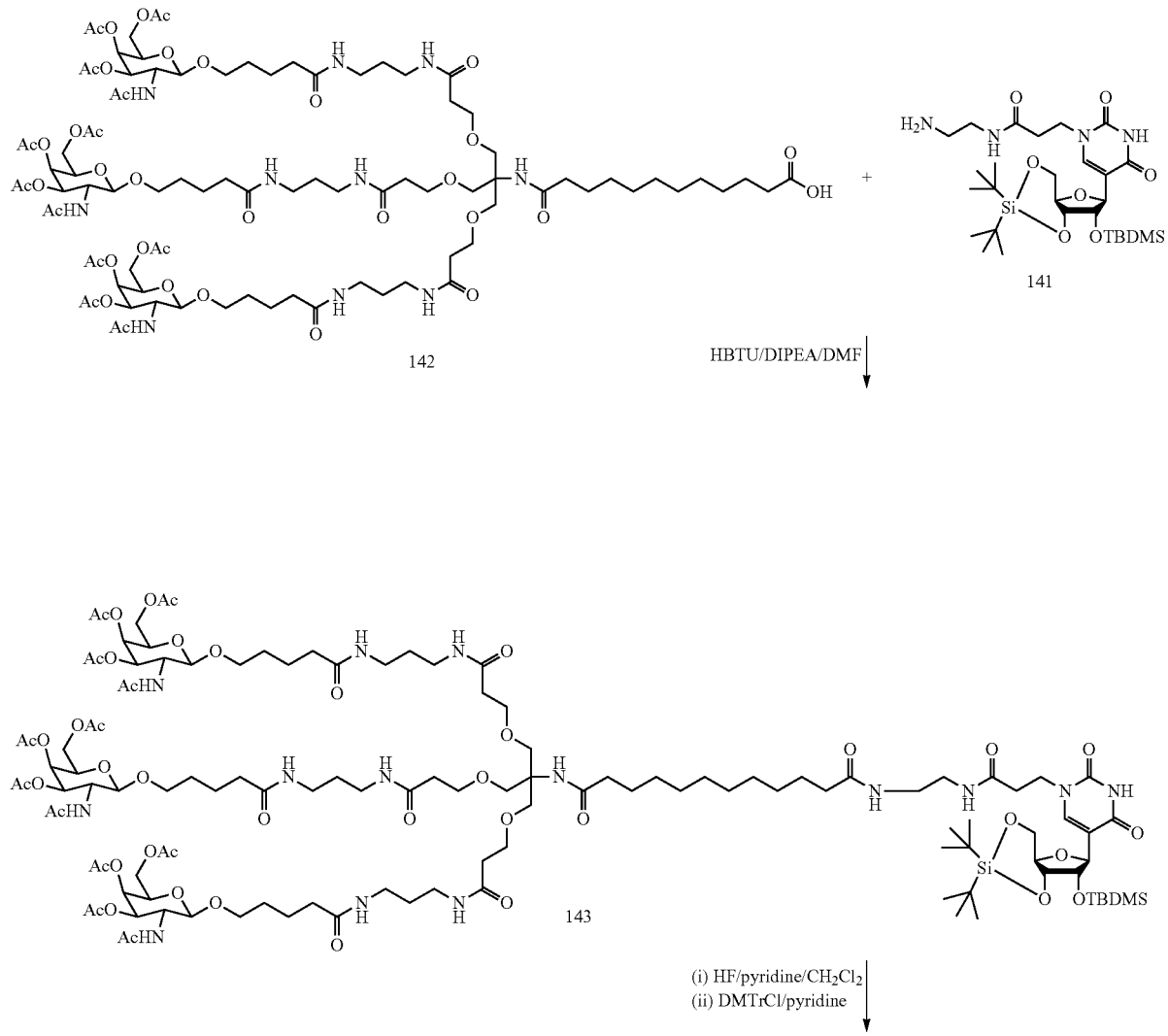

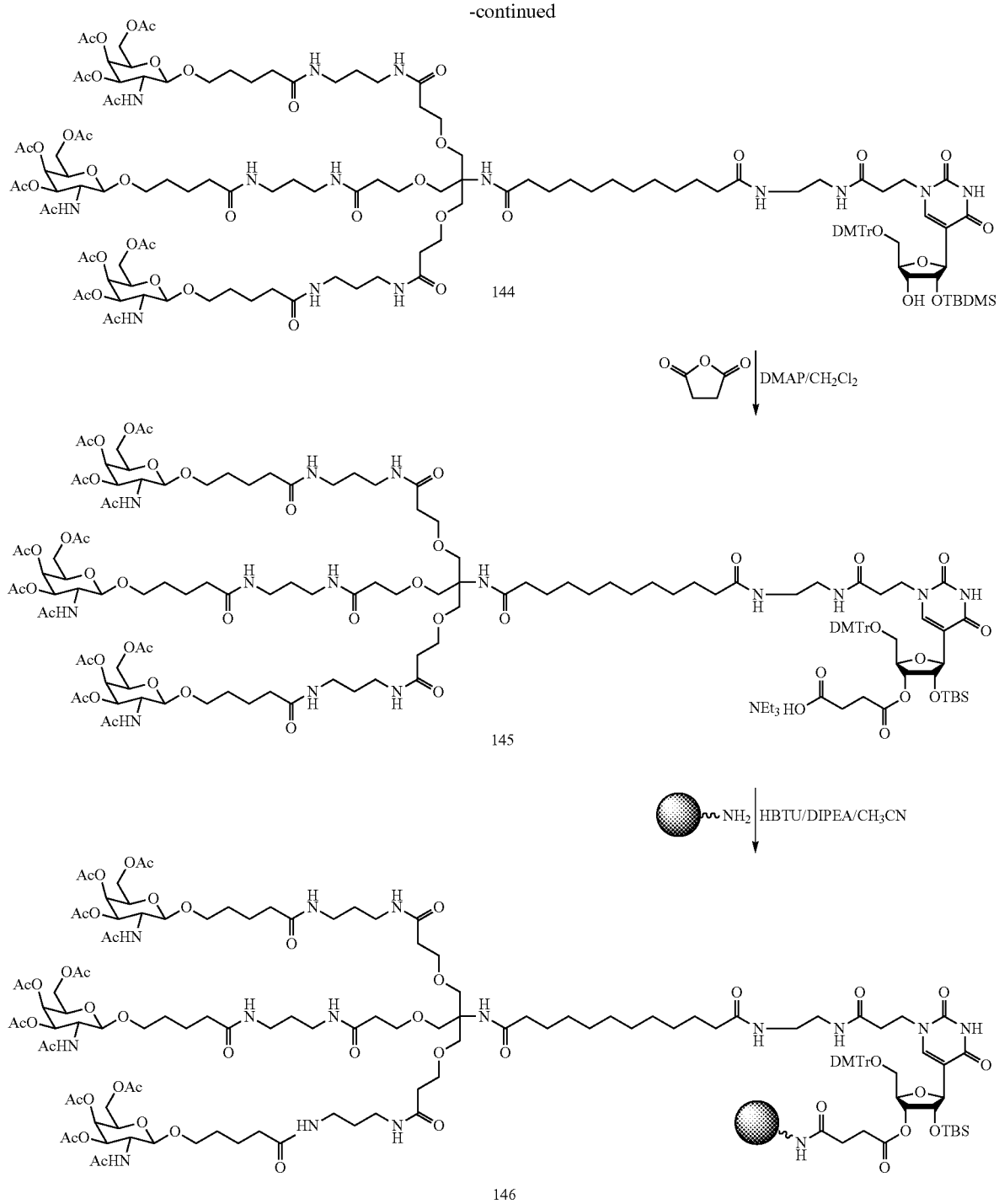

Synthesis of Compound 143:

To a solution of trivalent GalNAc acid compound 142 (1.80 g, 0.898 mmol) in DMF (12 mL), HBTU (341 mg, 0.898 mmol) and i-Pr$_2$NEt (0.568 mL, 3.26 mmol) were added. After 10 minutes, compound 141 (500 mg, 0.816 mmol) was added to the solution and the mixture was stirred overnight. After removing the DMF in vacuo, the residue was extracted with CH$_2$Cl$_2$ and saturated aqueous NaHCO$_3$. The organic layer was dried over anhydrous Na$_2$SO$_4$, filtered and concentrated. The crude product was purified by silica gel column chromatography (0-15% MeOH in CH$_2$Cl$_2$) to afford compound 143 (1.75 g, 0.673 mmol, 82%). $^1$H NMR (400 MHz, DMSO-d$_6$) δ 11.35 (s, 1H), 7.96 (s, 1H), 7.84-7.81 (m, 6H), 7.76-7.72 (m, 4H), 7.50 (d, J=0.9 Hz, 1H), 6.98 (s, 1H), 5.21 (d, J=3.4 Hz, 3H), 4.96 (dd, J=11.2, 3.4 Hz, 3H), 4.53 (s, 1H), 4.48 (d, J=8.5 Hz, 3H), 4.35-4.33 (m, 1H), 4.17 (d, J=4.5 Hz, 1H), 4.05-3.83 (m, 17H), 3.73-3.64 (m, 3H), 3.57-3.52 (m, 12H), 3.43-3.38 (m, 3H), 3.06-3.00 (m, 16H), 2.44-2.39 (m, 2H), 2.27 (t, J=6.4 Hz, 6H), 2.10 (s, 9H), 2.04 (t, J=7.3 Hz, 9H), 1.99 (s, 9H), 1.89 (s, 9H), 1.77 (s, 9H), 1.52-1.42 (m, 22H), 1.21 (s, 13H), 1.01 (s, 9H), 0.98 (s, 9H), 0.89 (s, 9H), 0.12 (s, 3H), 0.079 (s, 3H).

Synthesis of Compound 144:

Hydrogen fluoride-pyridine (~70% HF, 0.173 mL, 6.66 mmol) was diluted in pyridine (2 mL) with cooling at 0° C. The resulting solution was added to a solution of compound 143 in CH$_2$Cl$_2$ (20 mL) at 0° C. and the mixture was stirred at 0° C. for 2 hours. The reaction solution was diluted in CH$_2$Cl$_2$ and washed with saturated aqueous NaHCO$_3$ then dried over anhydrous Na$_2$SO$_4$. After evaporation of the volatiles, the crude product was dried in vacuo to afford its diol as a white foam. To a solution of this material in pyridine (15 mL), DMTrCl (691 mg, 2.04 mmol) was added. The reaction mixture was stirred at room temperature for 14 hours and then evaporated. The residue was extracted with CH$_2$Cl$_2$ and saturated aqueous NaHCO$_3$ then dried over anhydrous Na$_2$SO$_4$. The crude product was purified by silica gel column chromatography (0-10% MeOH in CH$_2$Cl$_2$) to afford compound 144 (3.31 g, 1.20 mmol, 65%).

Synthesis of Compound 145:

To a solution of compound 144 (3.25 g, 1.18 mmol) in CH$_2$Cl$_2$ (20 mL) were added DMAP (432 mg, 3.54 mmol) and succinic anhydride (236 mg, 2.36 mmol). The reaction mixture was stirred overnight at room temperature. After concentration, the crude was purified by silica gel column chromatography (8% MeOH/8% Et$_3$N in CH$_2$Cl$_2$) to afford compound 145 (3.03 g, 1.78 mmol, 87%). $^1$H NMR (400 MHz, DMSO-d$_6$) δ 12.22 (brs, 1H), 11.41 (s, 1H), 7.94 (brs, 1H), 7.85-7.81 (m, 6H), 7.75-7.72 (m, 4H), 7.66 (s, 1H), 7.41-7.38 (m, 2H), 7.32-7.19 (m, 9H), 6.98 (s, 1H), 6.89-6.87 (m, 4H), 5.21 (d, J=3.4 Hz, 3H), 5.07 (t, J=5.1 Hz, 1H), 4.96 (dd, J=11.2, 3.4 Hz, 3H), 4.55 (t, J=5.2 Hz, 1H), 4.56-4.44 (m, 4H), 4.05-3.97 (m, 10H), 3.91-3.83 (m, 3H), 3.73 (s, 6H), 3.71-3.64 (m, 4H), 3.56-3.52 (m, 14H), 3.43-3.38 (m, 3H), 3.23-3.14 (m, 2H), 3.06-3.00 (m, 16H), 2.46-2.38 (m, 4H), 2.27 (t, J=6.4 Hz, 6H), 2.10 (s, 9H), 2.06-2.01 (m, 9H), 1.99 (s, 9H), 1.89 (s, 9H), 1.77 (s, 9H), 1.52-1.43 (m, 22H), 1.21 (s, 13H), 0.95 (t, J=7.2 Hz, 1H), 0.80 (s, 9H), −0.013 (s, 3H), −0.046 (s, 3H).

Synthesis of Compound 146:

To a solution of compound 145 (103 mg, 0.0347 mmol) in CH$_3$CN (5 mL) were added HBTU (26 mg, 0.0694 mmol), iPr2NEt (0.026 mL, 0.149 mmol) and CPG-NH$_2$ (Prime Synthesis CPG-500, NH$_2$ loading considered as 80 µmol/g) (450 mg, 0.036 mmol). The mixture was shaken for 24 hours, then filtered, washed with CH$_2$Cl$_2$, and dried in vacuo. The residual amino groups were capped by shaking for 1 hour with pyridine (7.5 mL), acetic anhydride (2.5 mL) and triethylamine (0.5 mL). Filtering, washing with CH$_2$Cl$_2$ (100 mL), then 50% MeOH/CH$_2$Cl$_2$ (100 mL), and drying in vacuo afforded compound 146. Loading: 49 µmol/g.

Example 61: Primary Hepatocyte Binding for Triantennary and 1+1+1 Ligand Designs siRNA-Ligand conjugates were prepared. The siRNA in each conjugate was the same and targeted to TTR. The following ligands were attached to the 3' end of the sense strand of each siRNA. The structure of the ligands on the conjugates was the same as on conjugate 43527, except for the replacement of the sugar groups as indicated below.

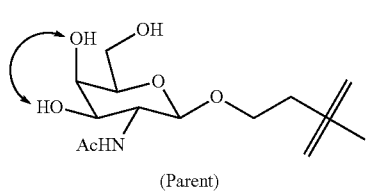

(Parent) AD-43527

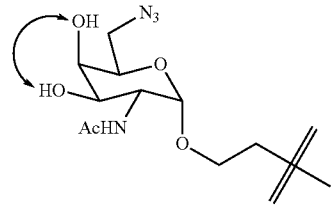

AD-61696

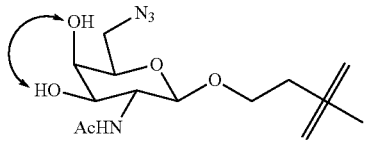

AD-61695

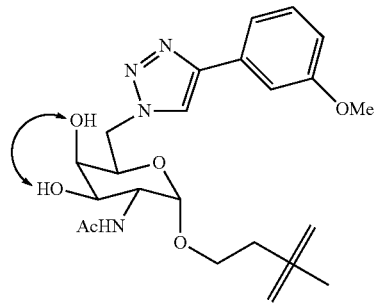

AD-61693/AD-61698

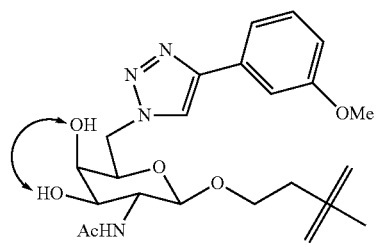

AD-61694/AD-61697

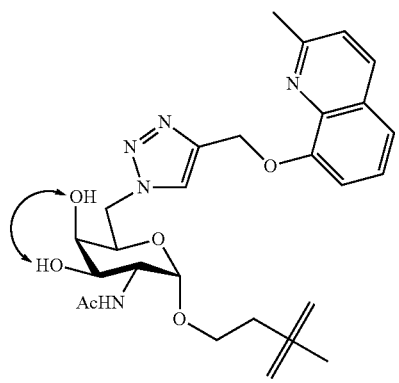

AD-61692

Figure 13:
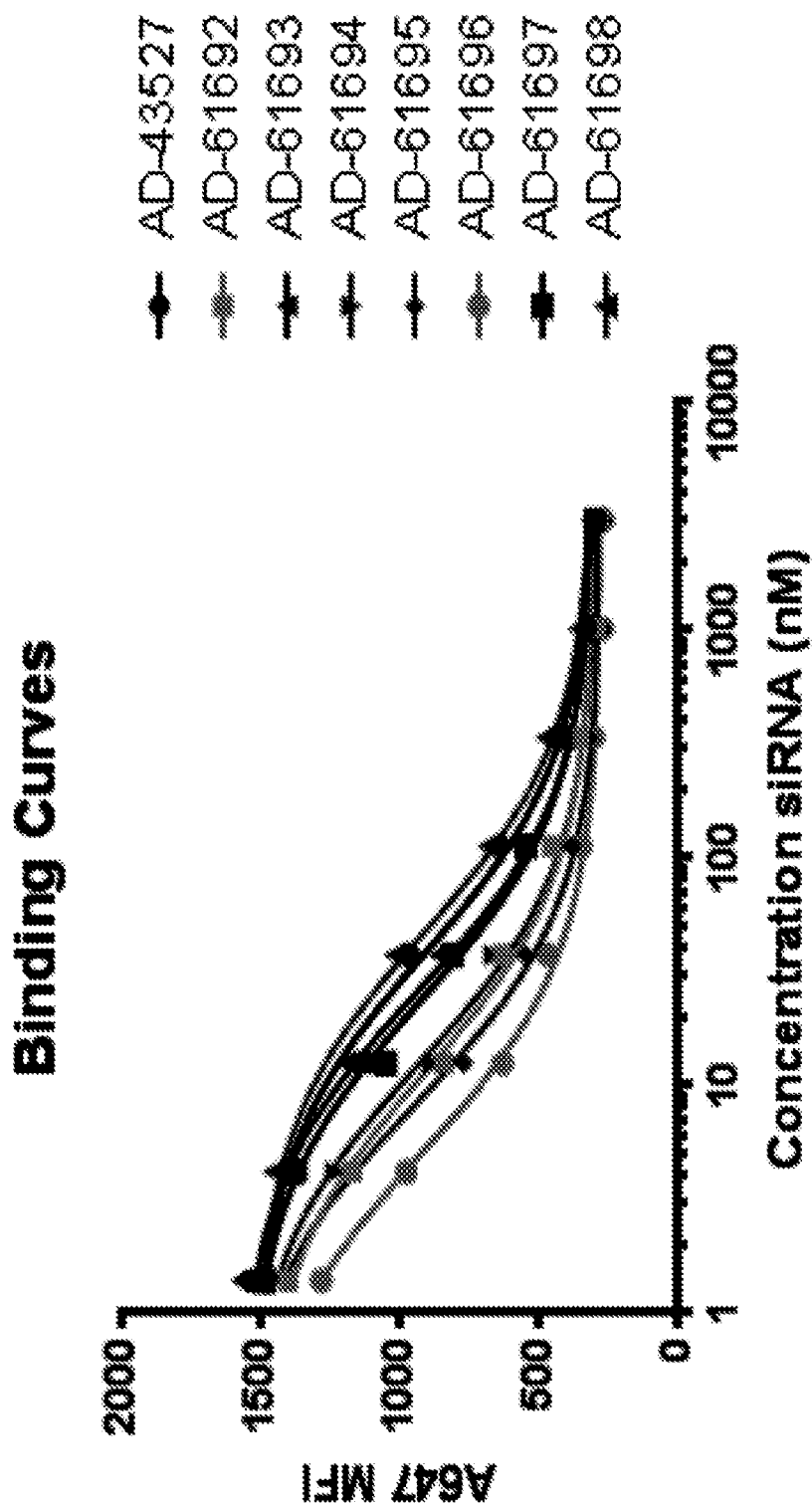
FIG. 13 is a graph showing the median fluorescence intensity (MFI) at various concentrations for the TTR siRNA conjugates 61696, 61695, 61692, 61694, 61697, 61693, 43527 and 61698 in Example 61.

FIG. 13 shows the primary hepatocyte binding affinities for siRNA-ligand conjugates 61696, 61695, 61692, 61694, 61697, 61693, 43527 and 61698, the structures of which are shown below. Binding affinity Ki values are presented in the table below.

| Conjugate | Ligand | $K_i$ (nM) | Std. Error |
|---|---|---|---|
| 61696 | Tri-α-C6-Azido | 2.2 | 0.2 |
| 61695 | Tri-β-C6-Azido | 3.5 | 0.4 |
| 61692 | Tri-α-C6-Bicyclo | 4.8 | 0.8 |
| 61694 | Tri-β-C6-Anisole | 5.2 | 0.8 |
| 61697 | 1 + 1 + 1-β-C6-Anisole | 9.8 | 1.4 |
| 61693 | Tri-α-C6-Anisole | 10.8 | 1.7 |
| 43527 | Triantennary-Parent | 15.9 | 3.4 |
| 61698 | 1 + 1 + 1-α-C6-Anisole | 19.8 | 2.9 |

Example 62: SiRNA GalNAC Conjugates with High Affinity Ligands siRNA-Ligand conjugates were prepared. The siRNA in each conjugate was the same and targeted to TTR. The following ligands were attached to the 3' end of the sense strand of each siRNA. The structure of the ligands on the conjugates was the same as on conjugate 57727, except for the replacement of the sugar groups as indicated below. The structures of L224, L223, L221, L96 and L227 are provided below.

| Conjugate | Ligand | Ligand type |
|---|---|---|
| 57727 | L96 | GalNAc |
| 63189 | L223 | β-Azido |
| 63190 | L224 | α-Azido |
| 63191 | L221 | β-Anisole |

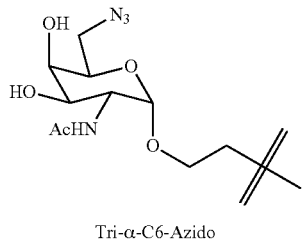

Tri-α-C6-Azido (L224)

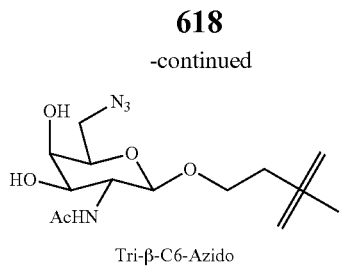

Tri-β-C6-Azido (L223)

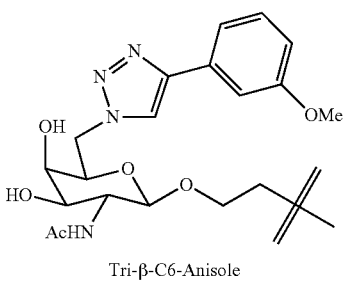

Tri-β-C6-Anisole (L221)

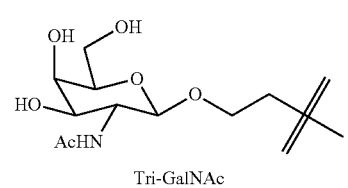

Tri-GalNAc (L96)

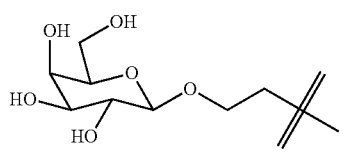

Tri-Galactose (L227)

Figure 3B:
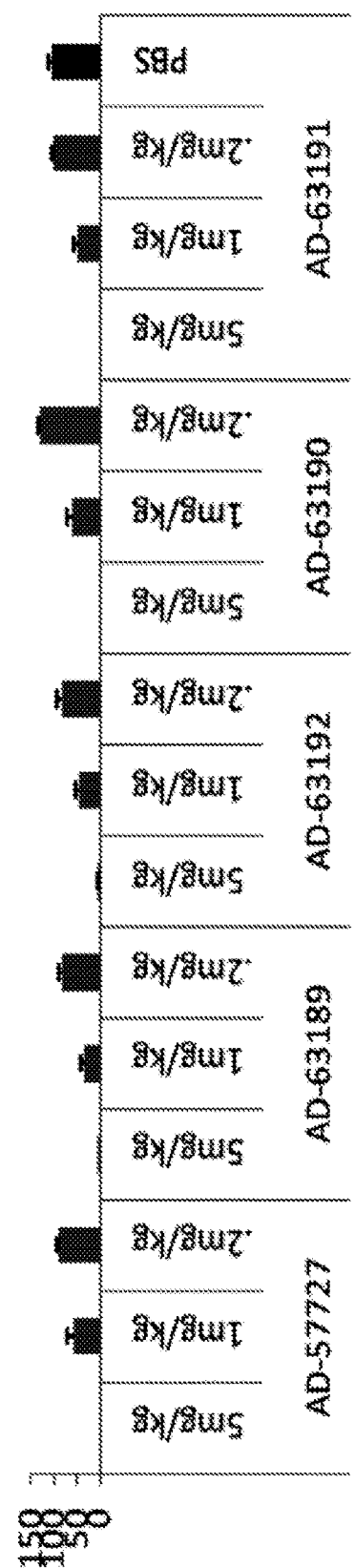
Figure 4:
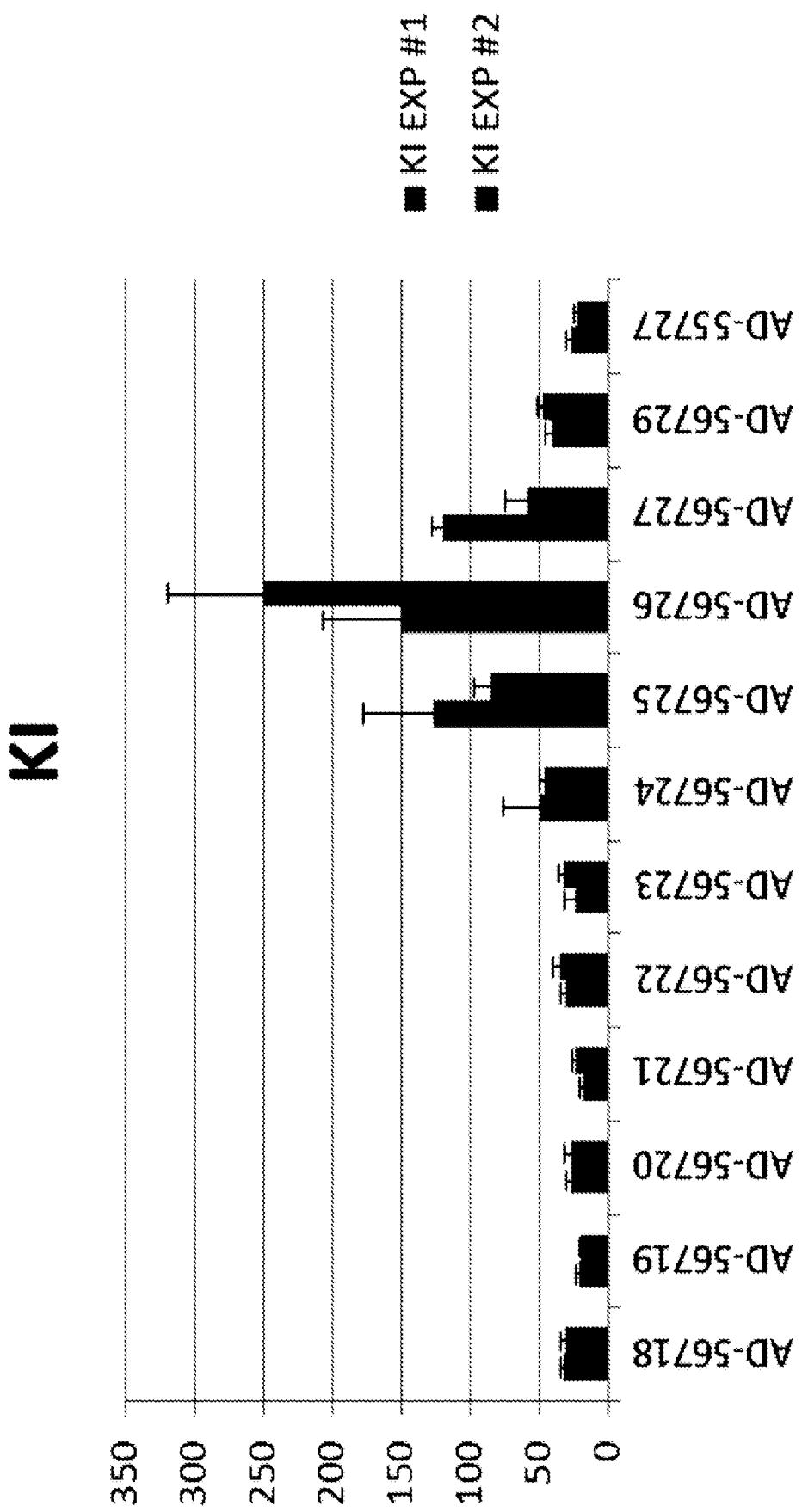
FIG. 4 is a bar graph of the binding affinities (Ki) of the TTR siRNA conjugates 56718-56727, 56729 and 55727 in Example 42.
Figure 5:
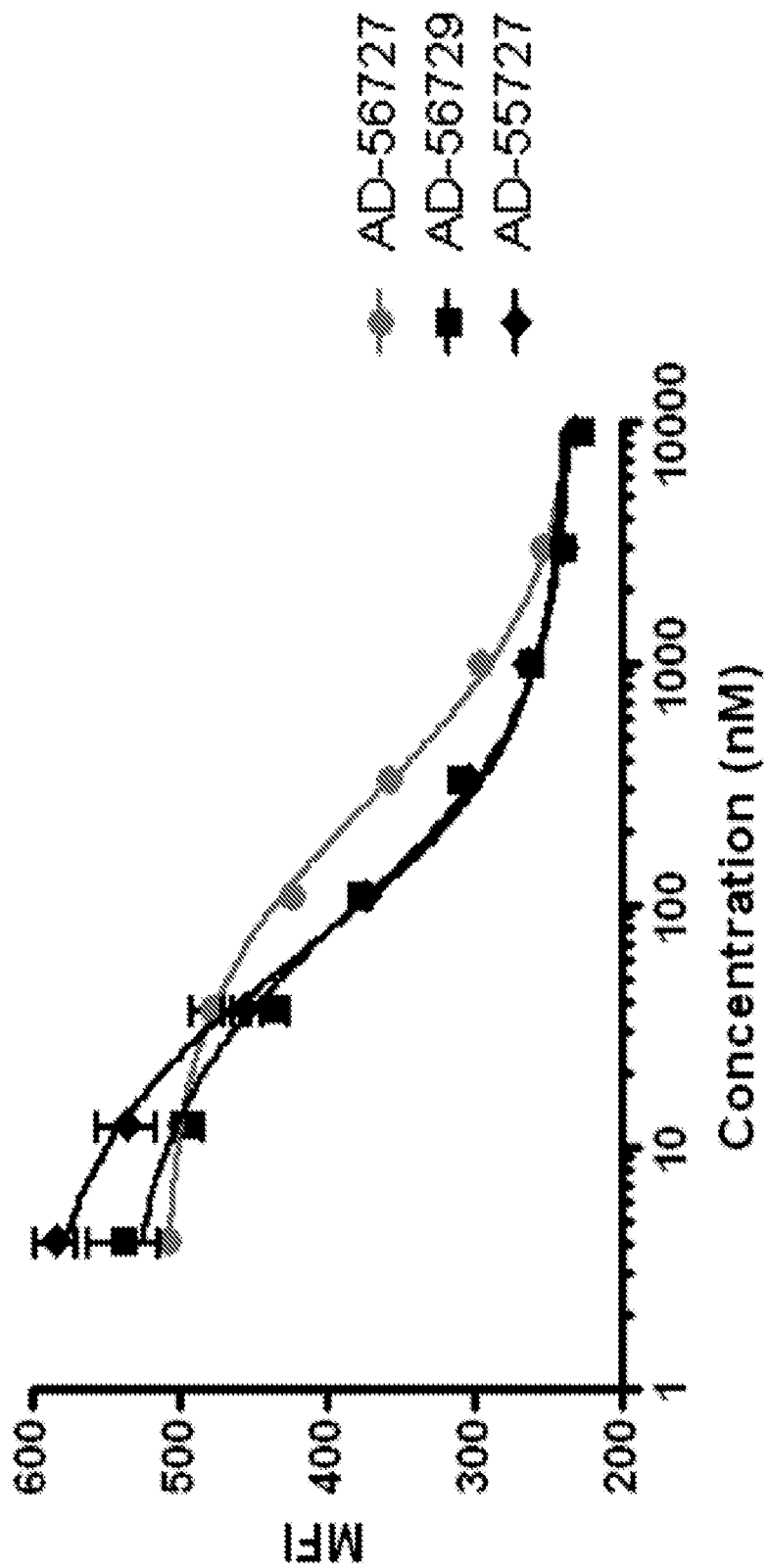
FIG. 5 is a graph (binding affinity curve) showing the median fluorescence intensity (MFI) at various concentrations for the TTR siRNA conjugates 56727, 56729 and 55727 in Example 42.
Figure 6:
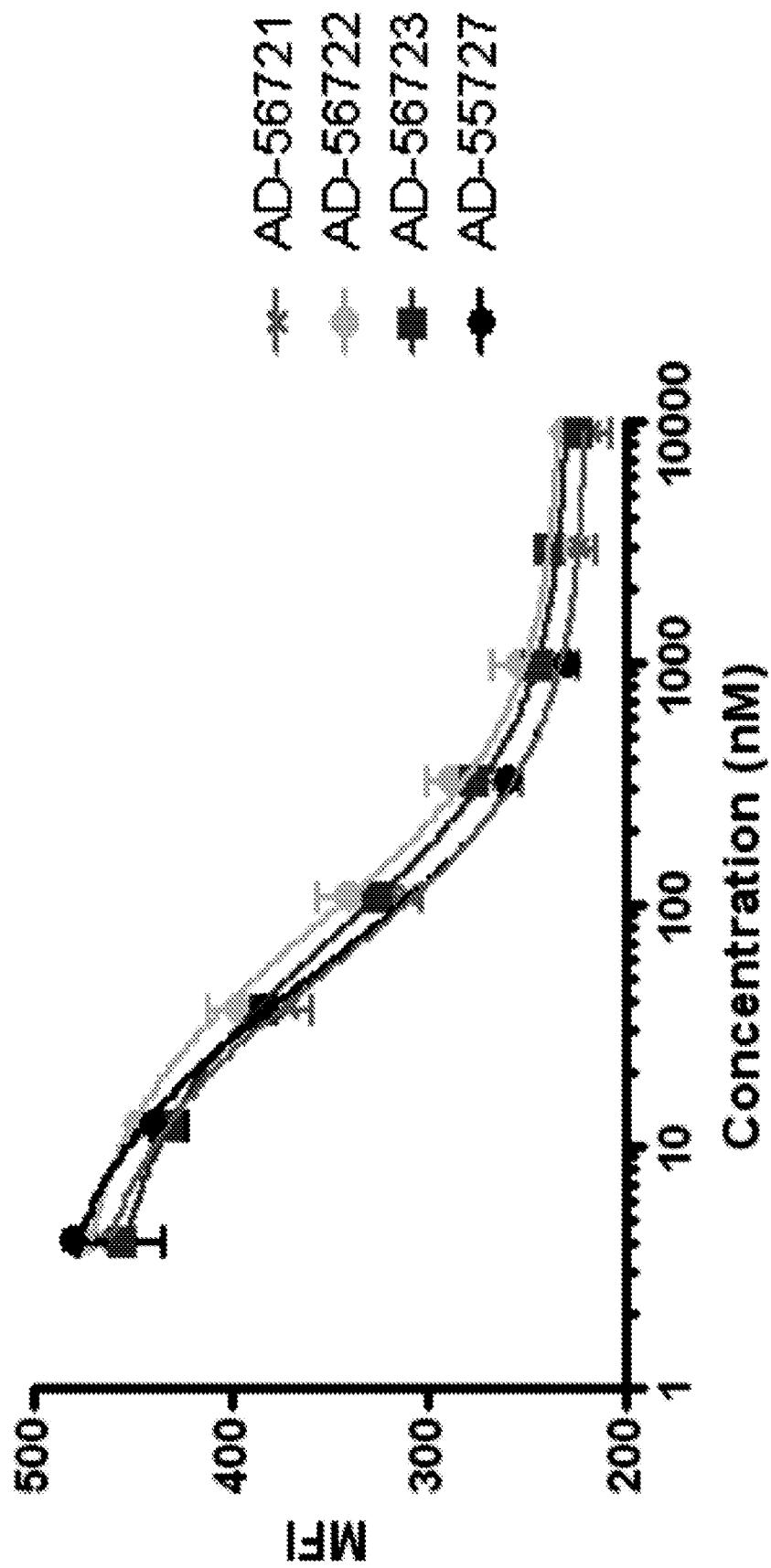
FIG. 6 is a graph showing the median fluorescence intensity (MFI) at various concentrations for the TTR siRNA conjugates 56721, 56722, 56723 and 55727 in Example 42.
Figure 7:
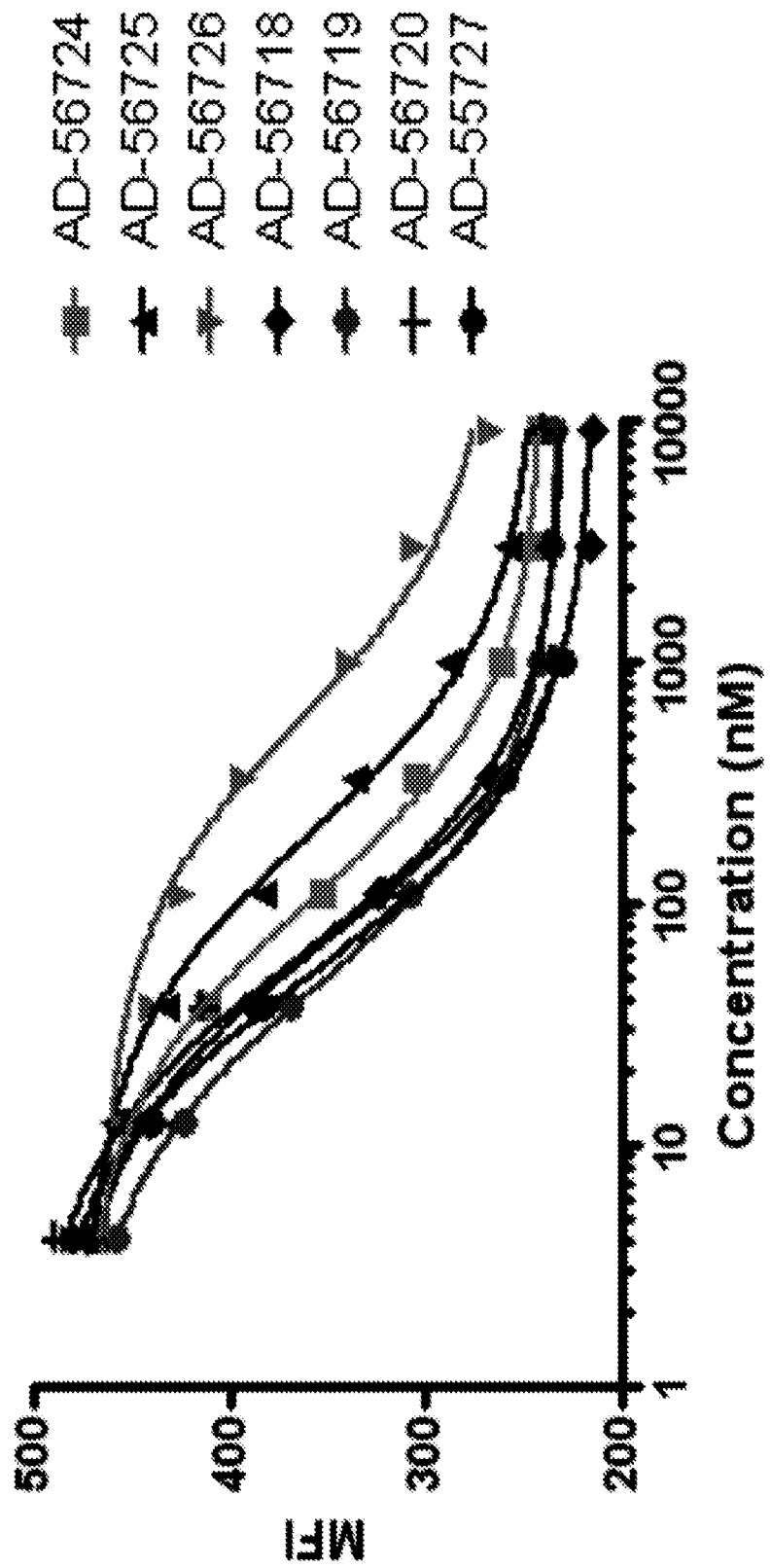
FIG. 7 is a graph showing the median fluorescence intensity (MFI) at various concentrations for the TTR siRNA conjugates 56724, 56725, 56726, 56718, 56719, 56720 and 55727 in Example 42.

FIGS. 3A and 3B show the circulating serum mTTR SiRNA levels after 72 hours (FIG. 3A) and 144 hours (FIG. 3B) following a single subcutaneous dose of conjugates 57727, 63189, 63192, 63190 and 63191 to mice according to the protocol in Example 33.

Example 63: Compounds for T-2'-GalNAc Building Block

Structures

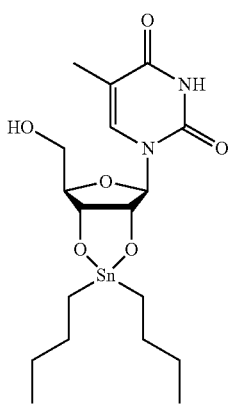

-continued
Structures
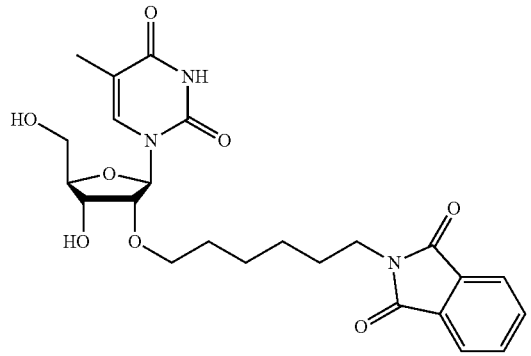
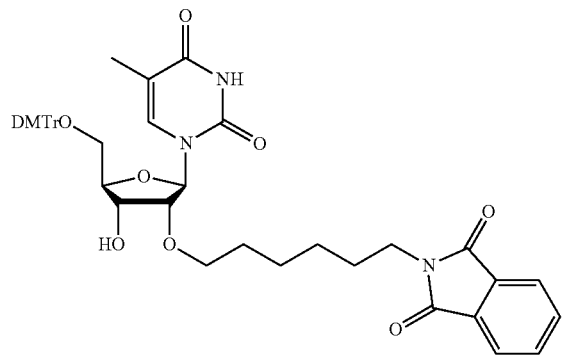
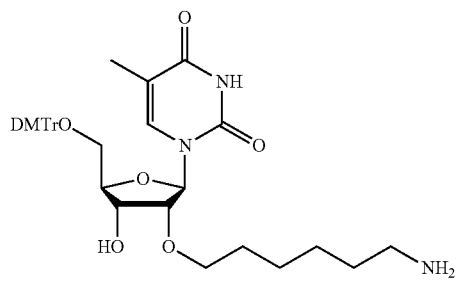
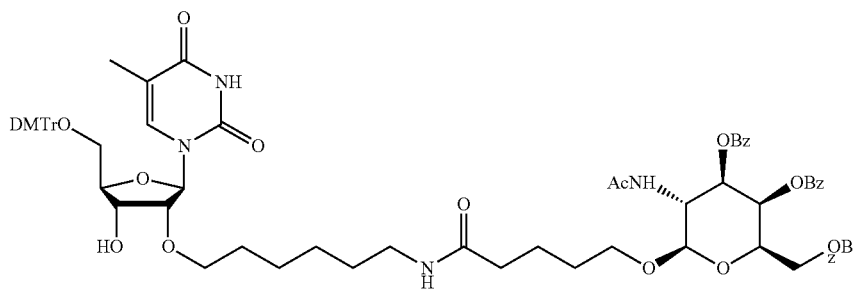

| Structures |
|---|
| 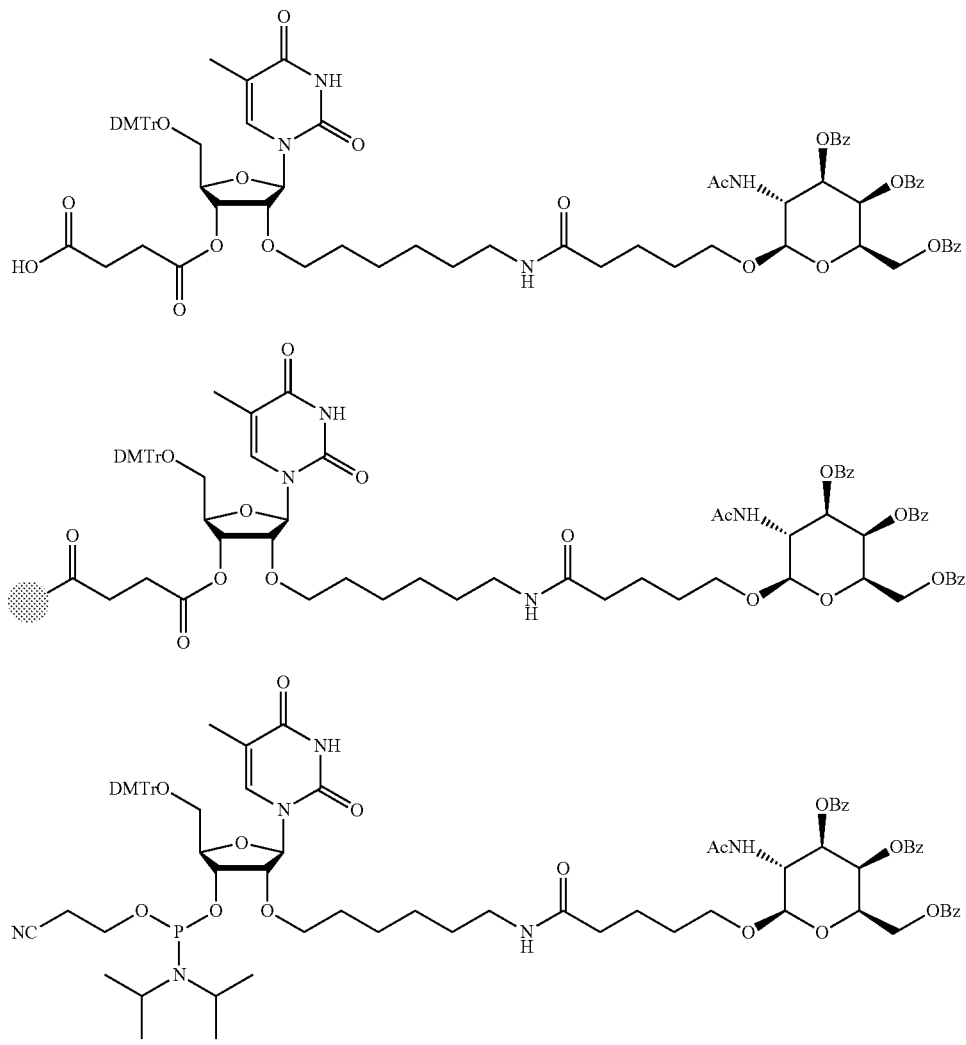 |
Example 64: Compounds for T-3'-GalNAc Building Block
| Structures |
|---|
| 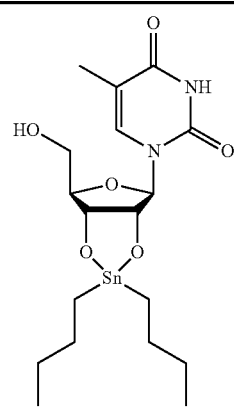 |

| Structures |
|---|
| 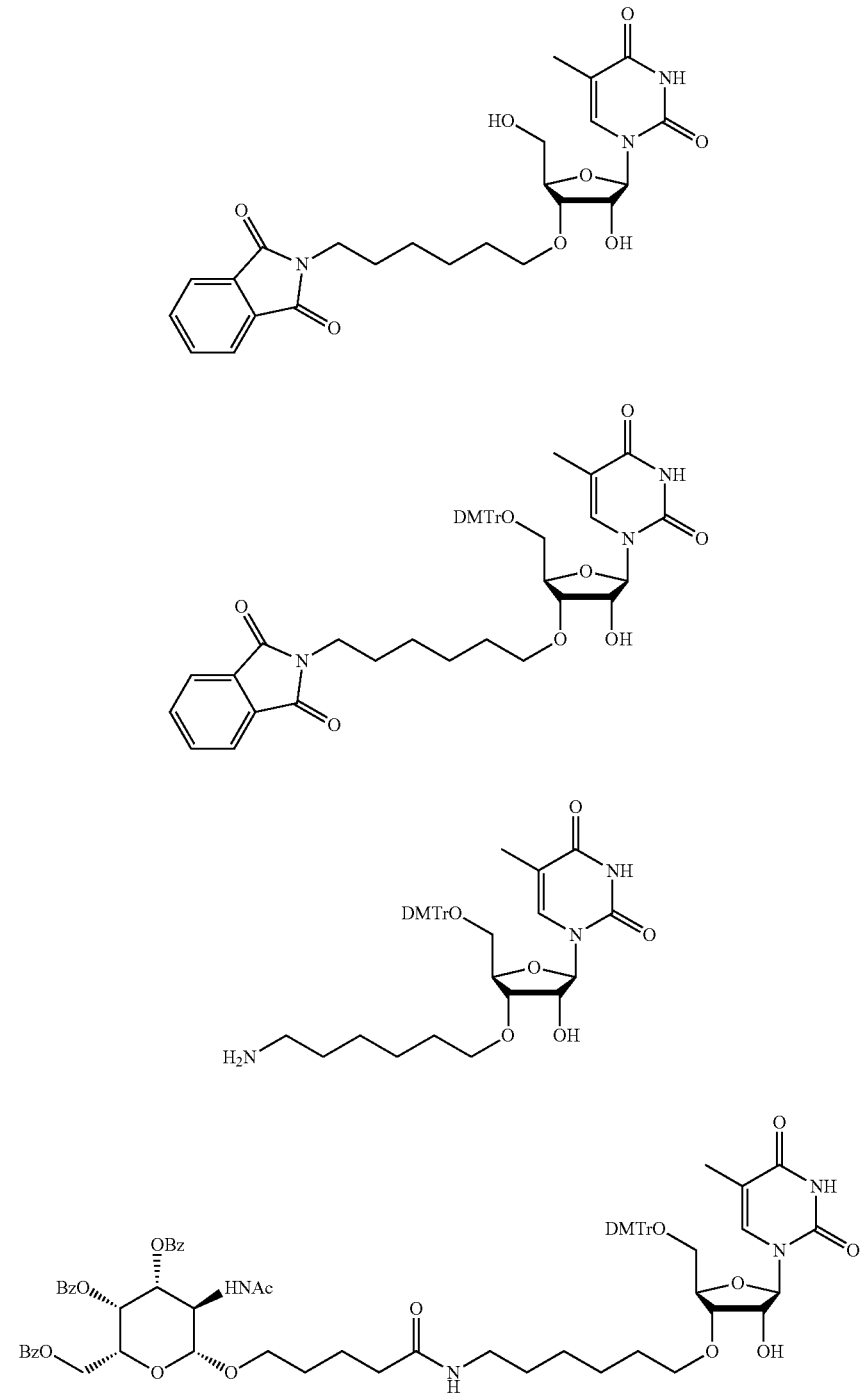 |

-continued
Structures
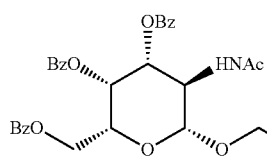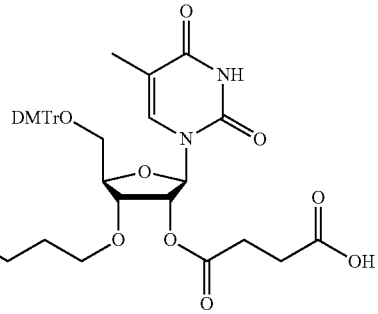
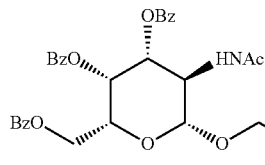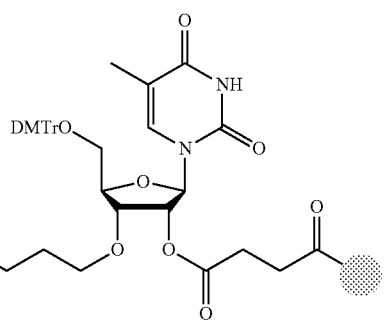
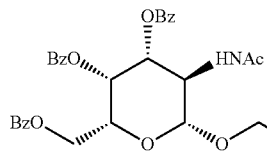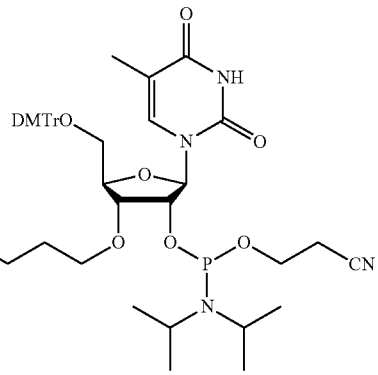
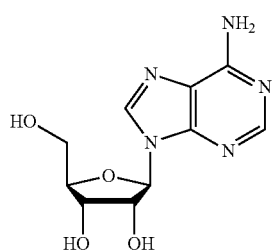

| Structures |
|---|
| 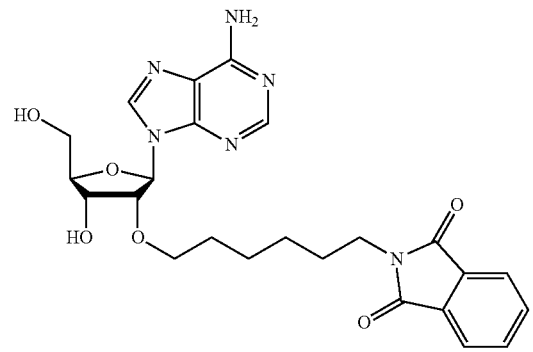 |
| 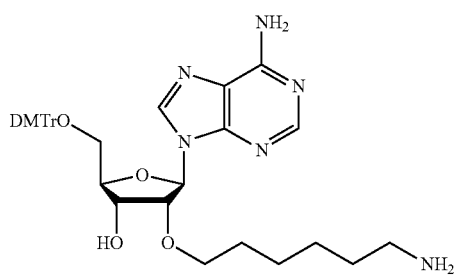 |
| 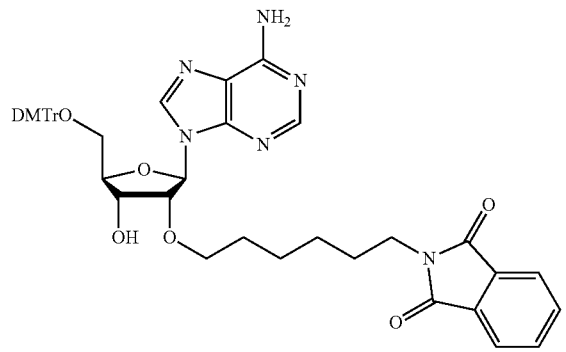 |
| 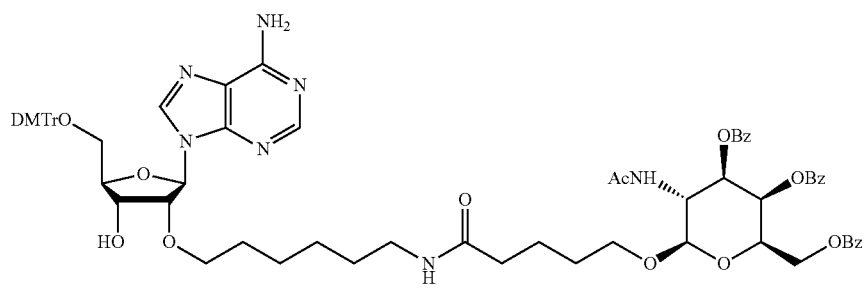 |
| 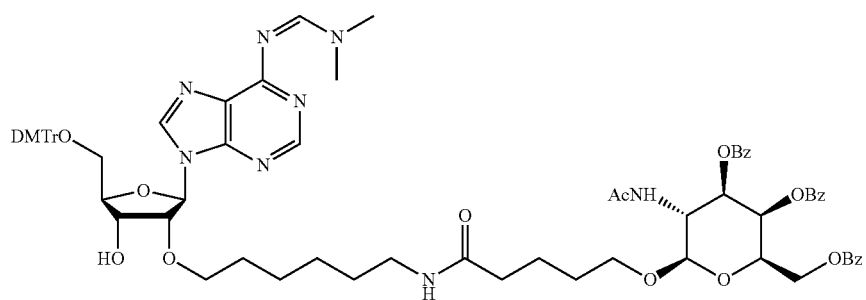 |

Structures
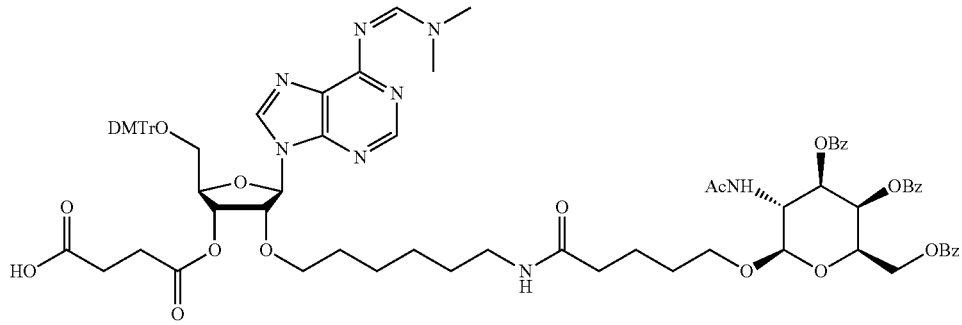
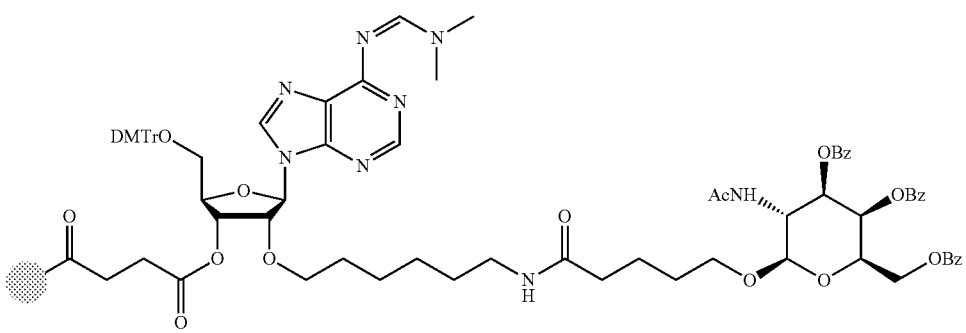
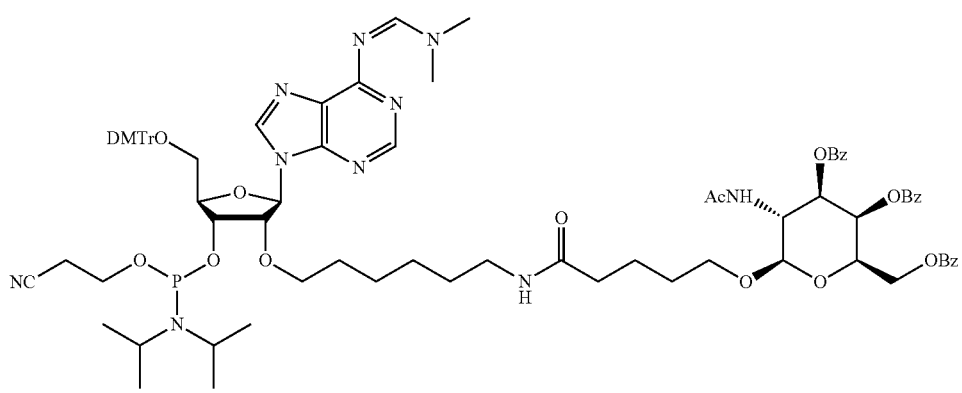
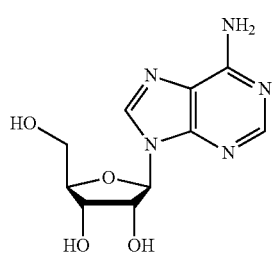

| Structures |
|---|
| 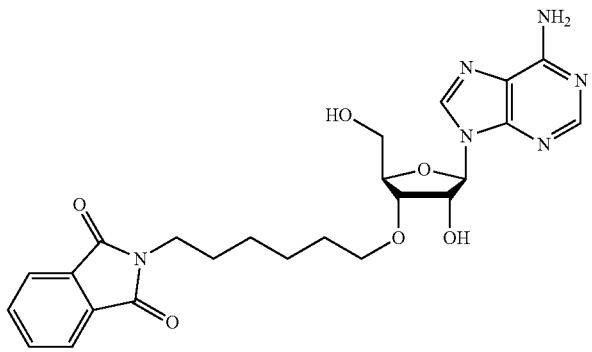 |
| 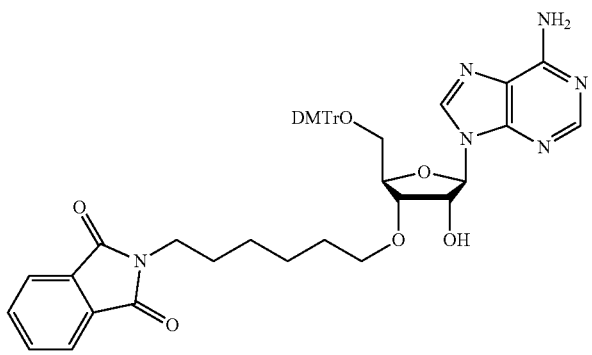 |
| 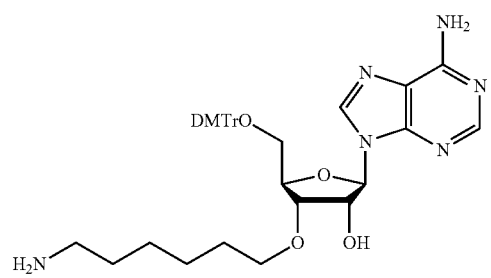 |
| 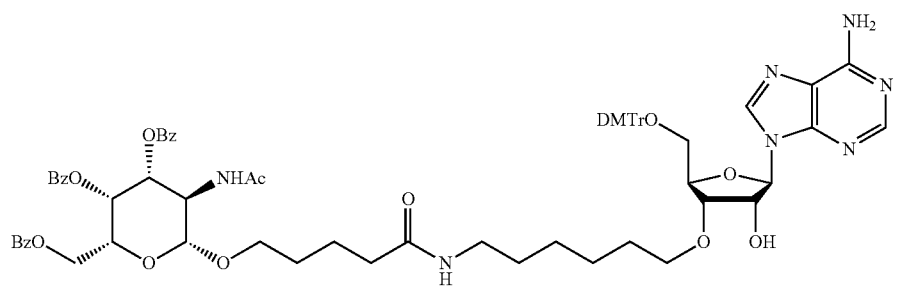 |
| 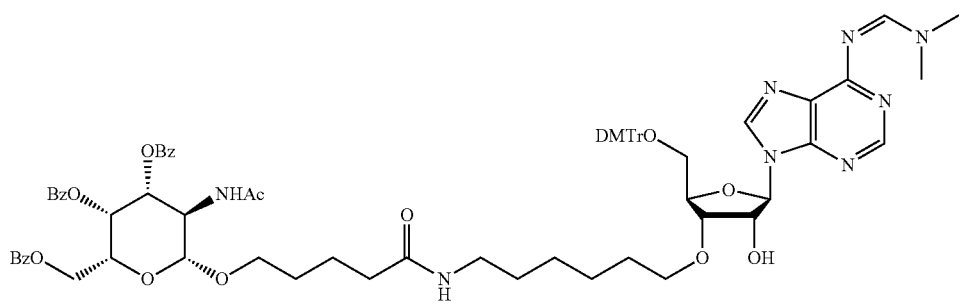 |

-continued
Structures
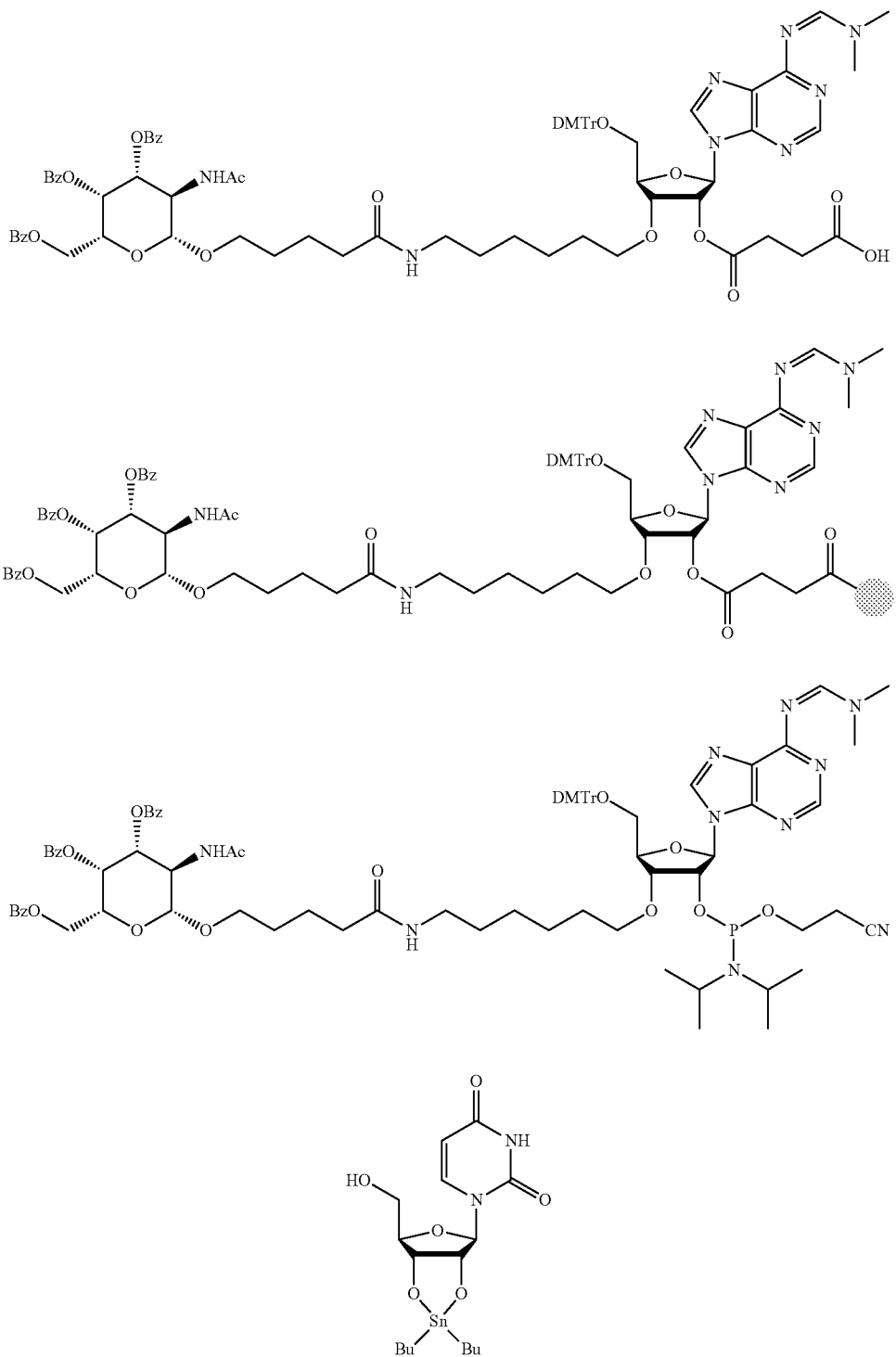

| Structures |
|---|
| 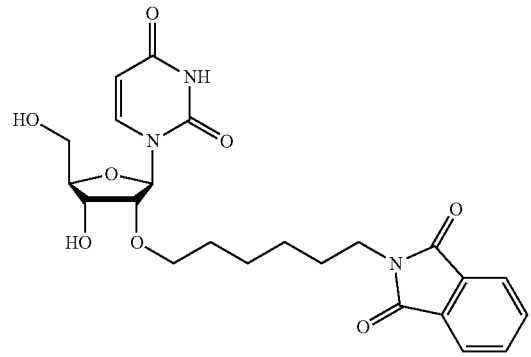 |
| 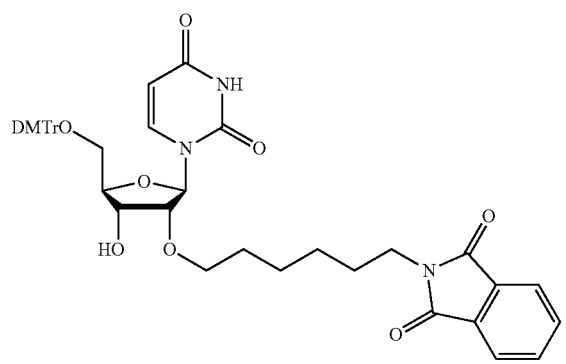 |
| 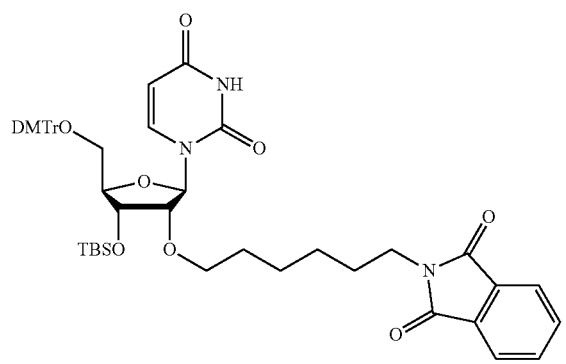 |
| 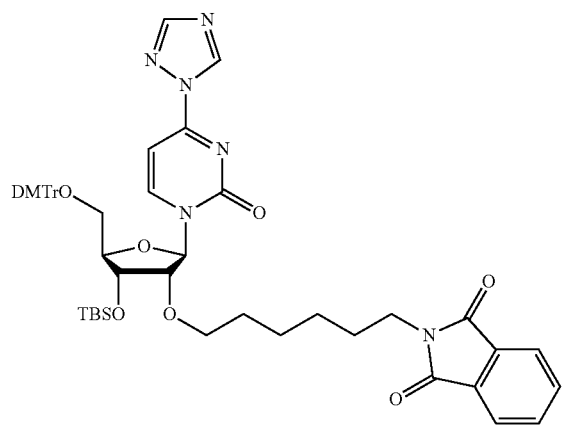 |

| Structures |
|---|
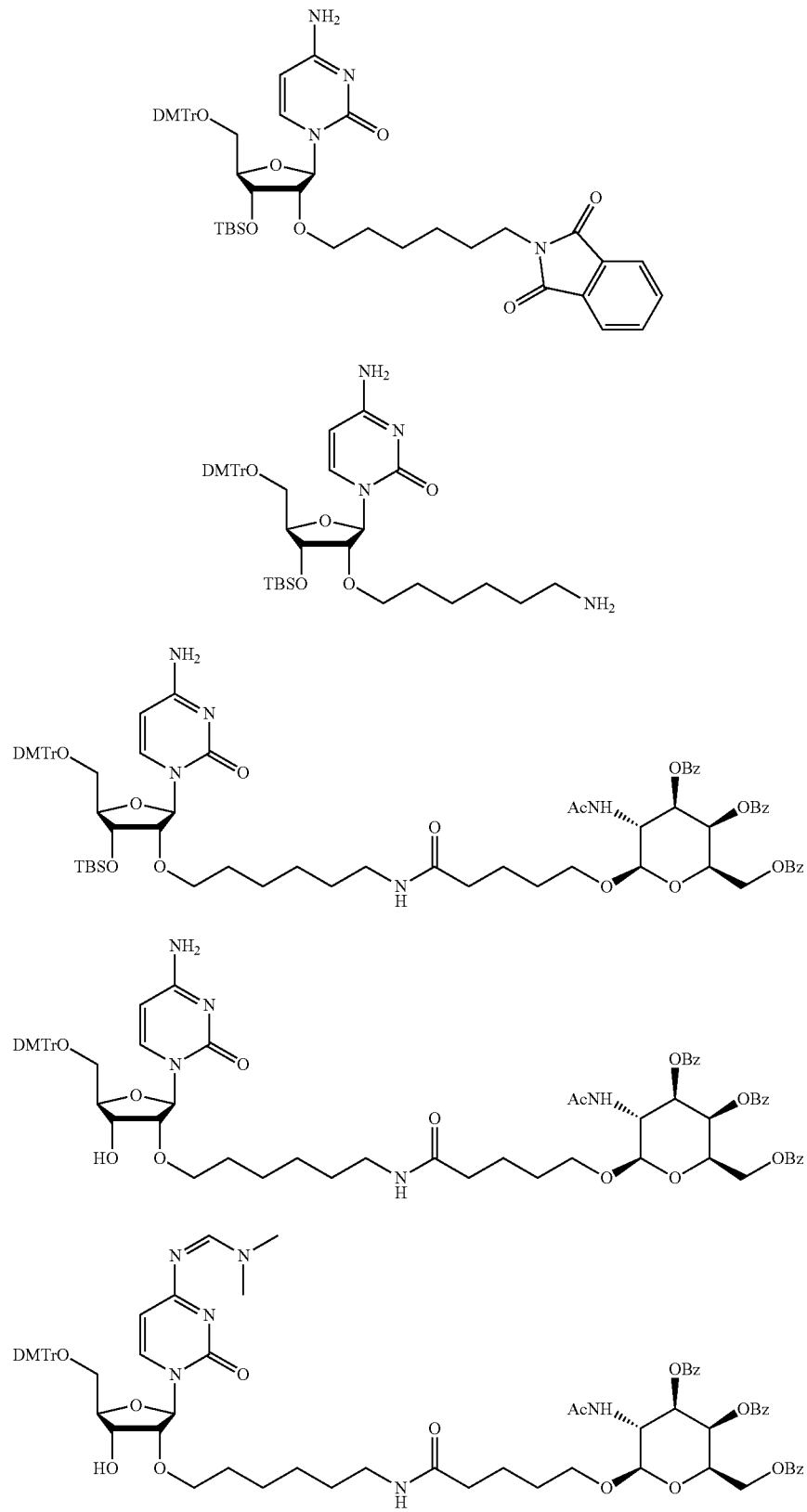

-continued
Structures
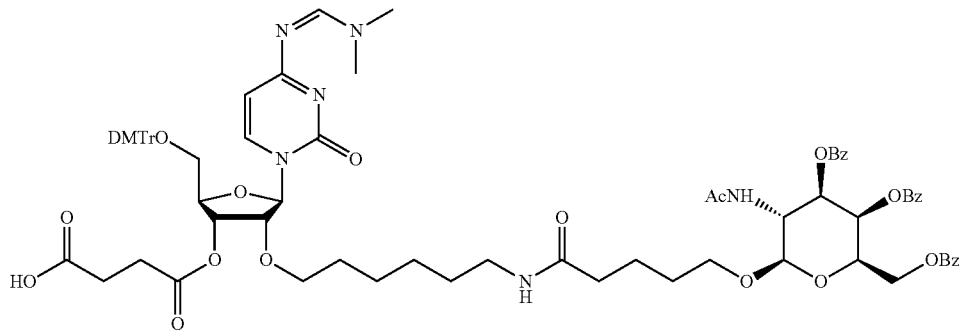
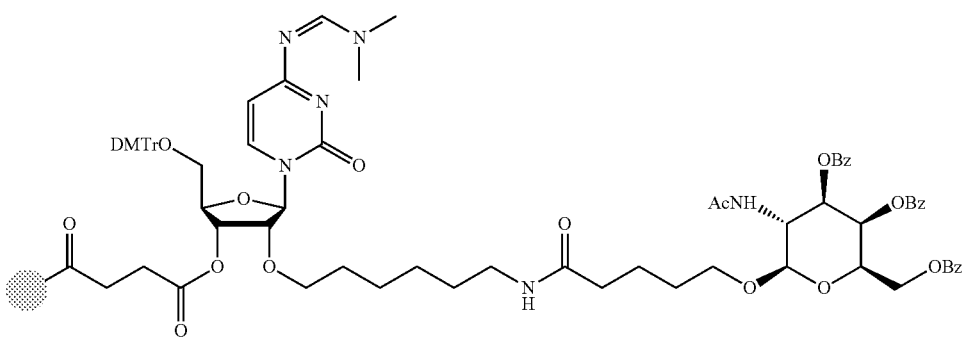
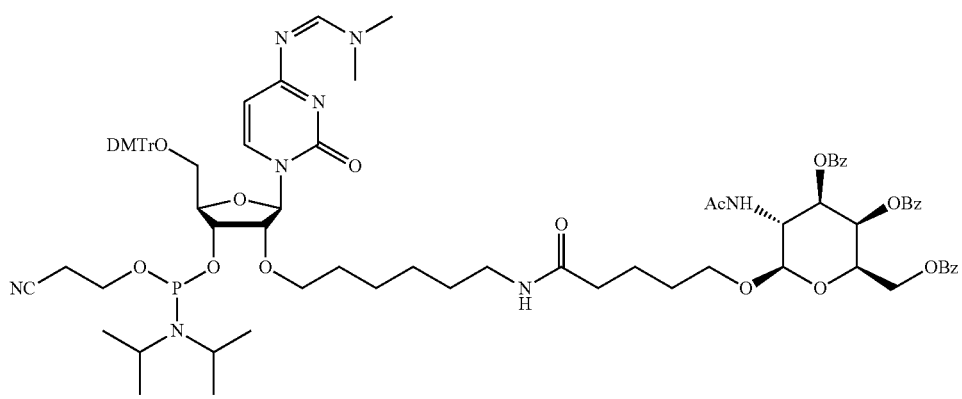
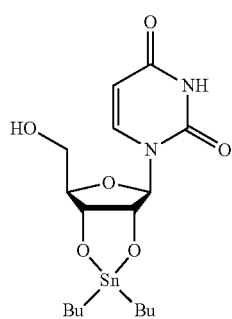

| Structures |
|---|
| 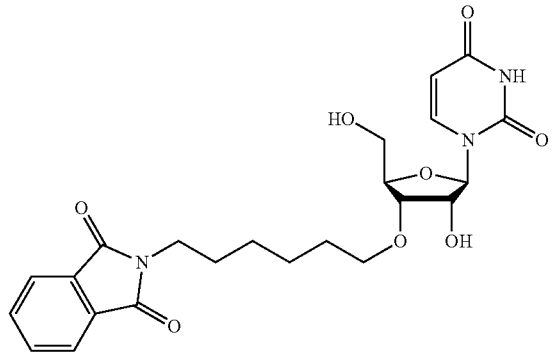 |
| 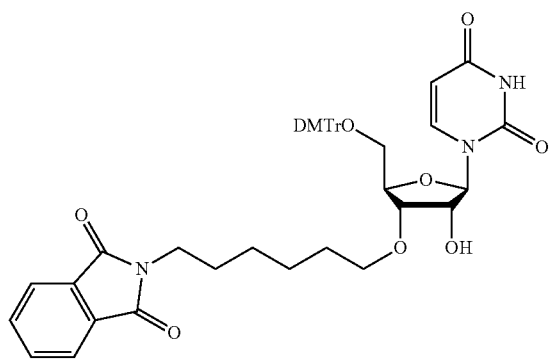 |
| 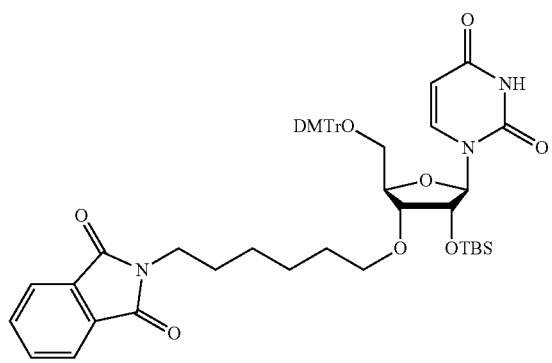 |
| 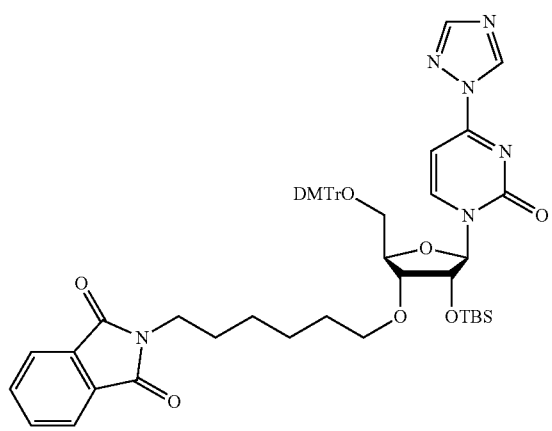 |

643 644
-continued
| Structures |
|---|
| 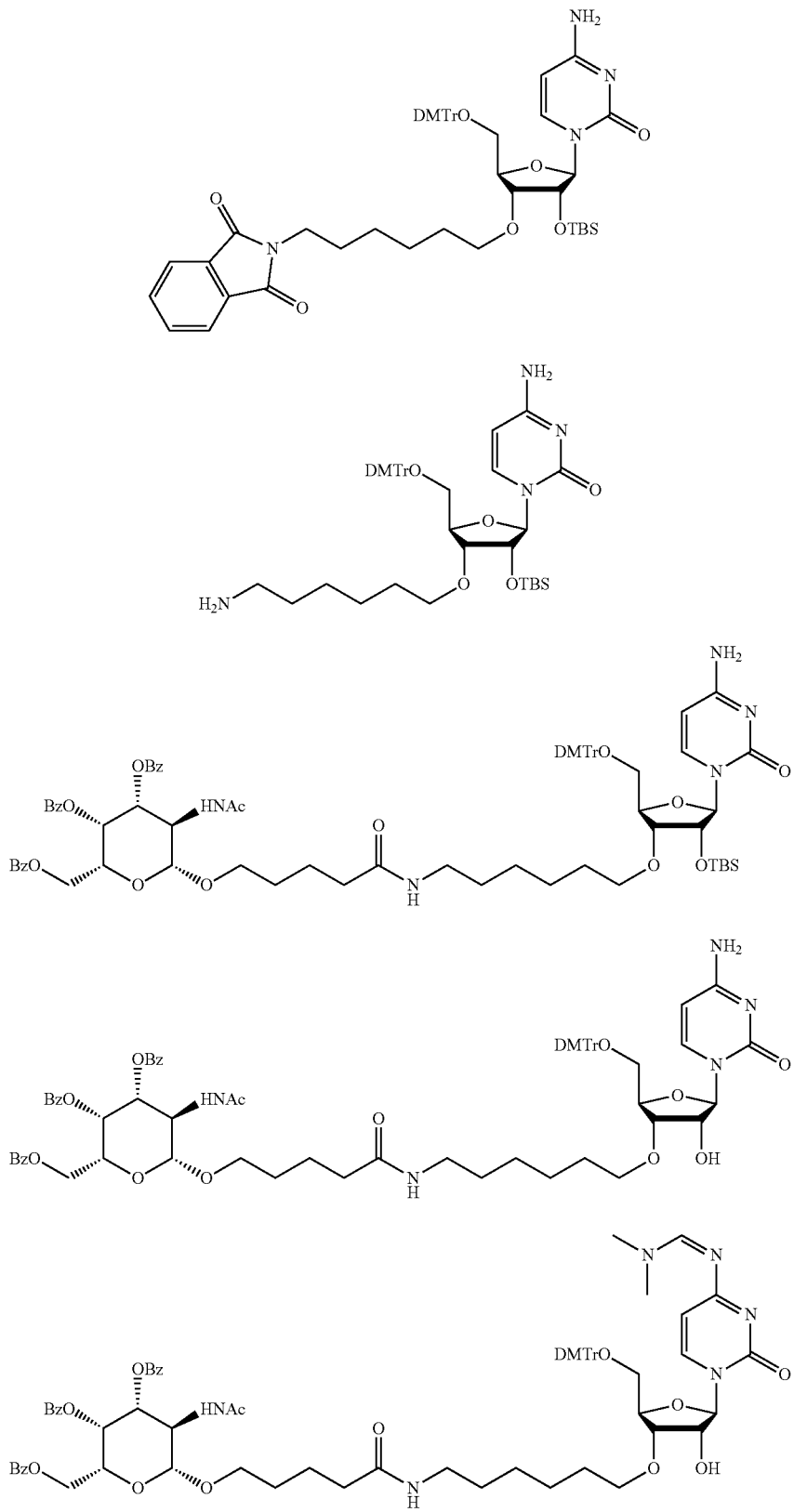 |

-continued
Structures
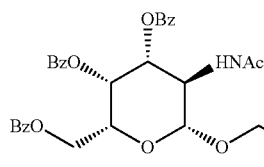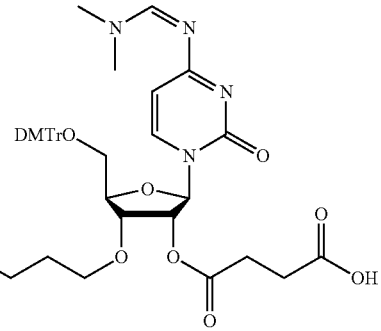
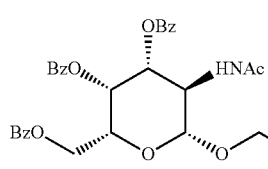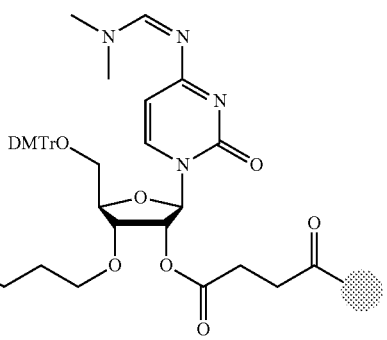
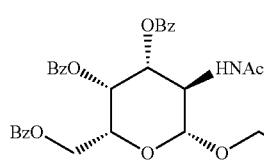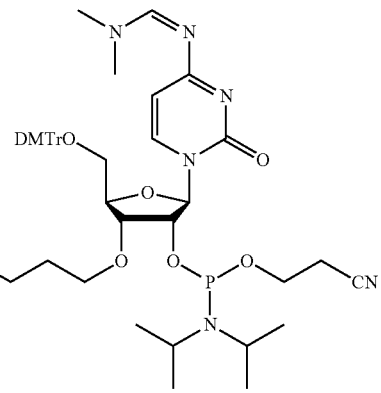
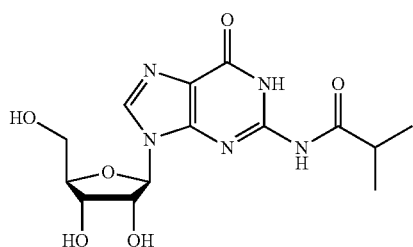

| Structures |
|---|
| 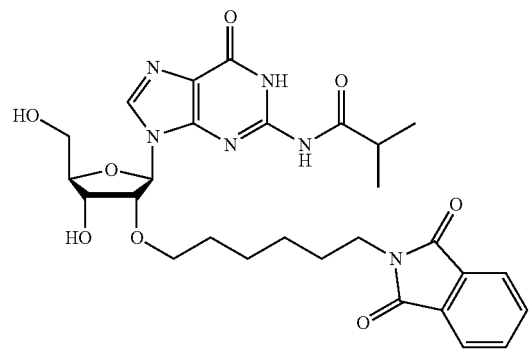 |
| 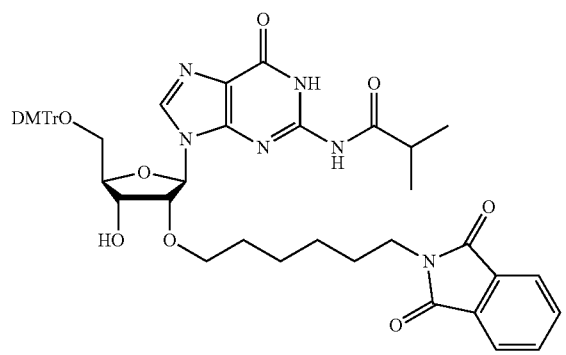 |
| 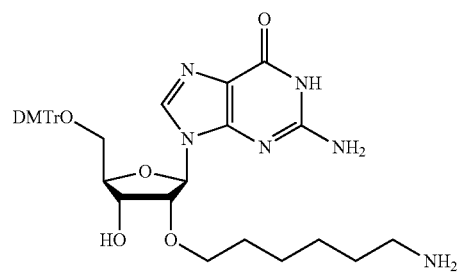 |
| 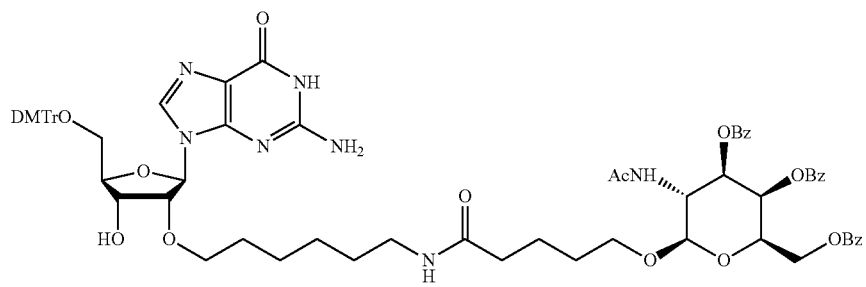 |
| 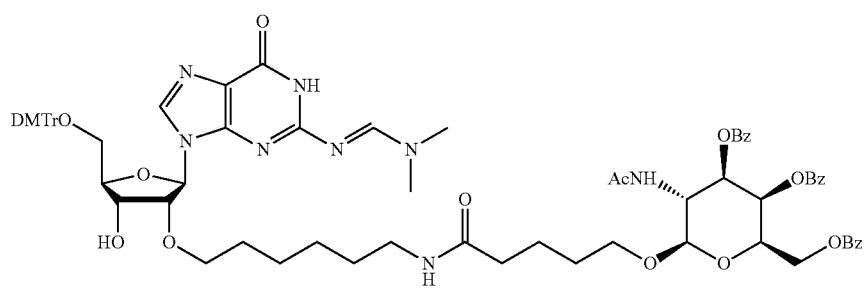 |

-continued
Structures
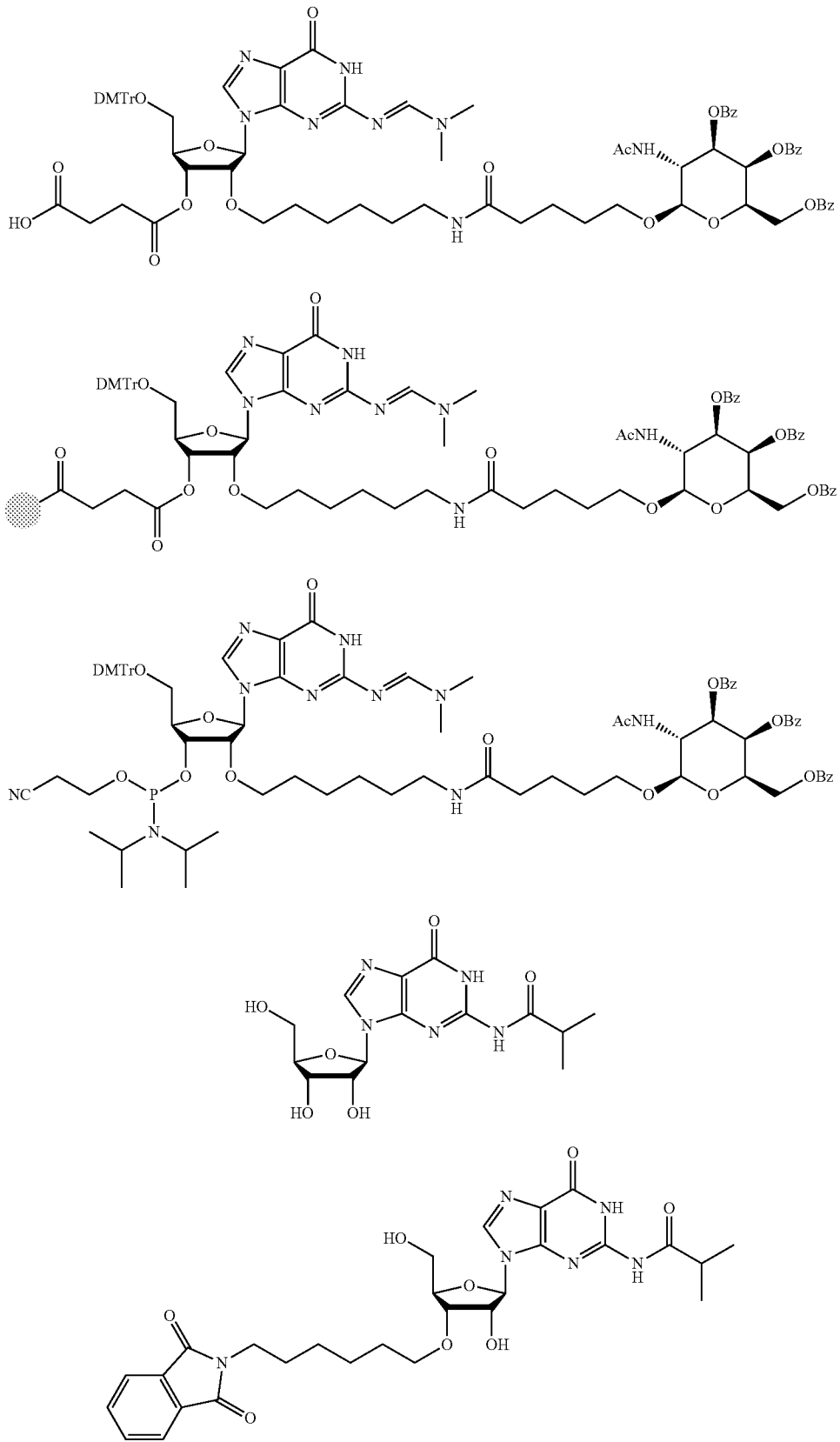

-continued
| Structures |
|---|
| 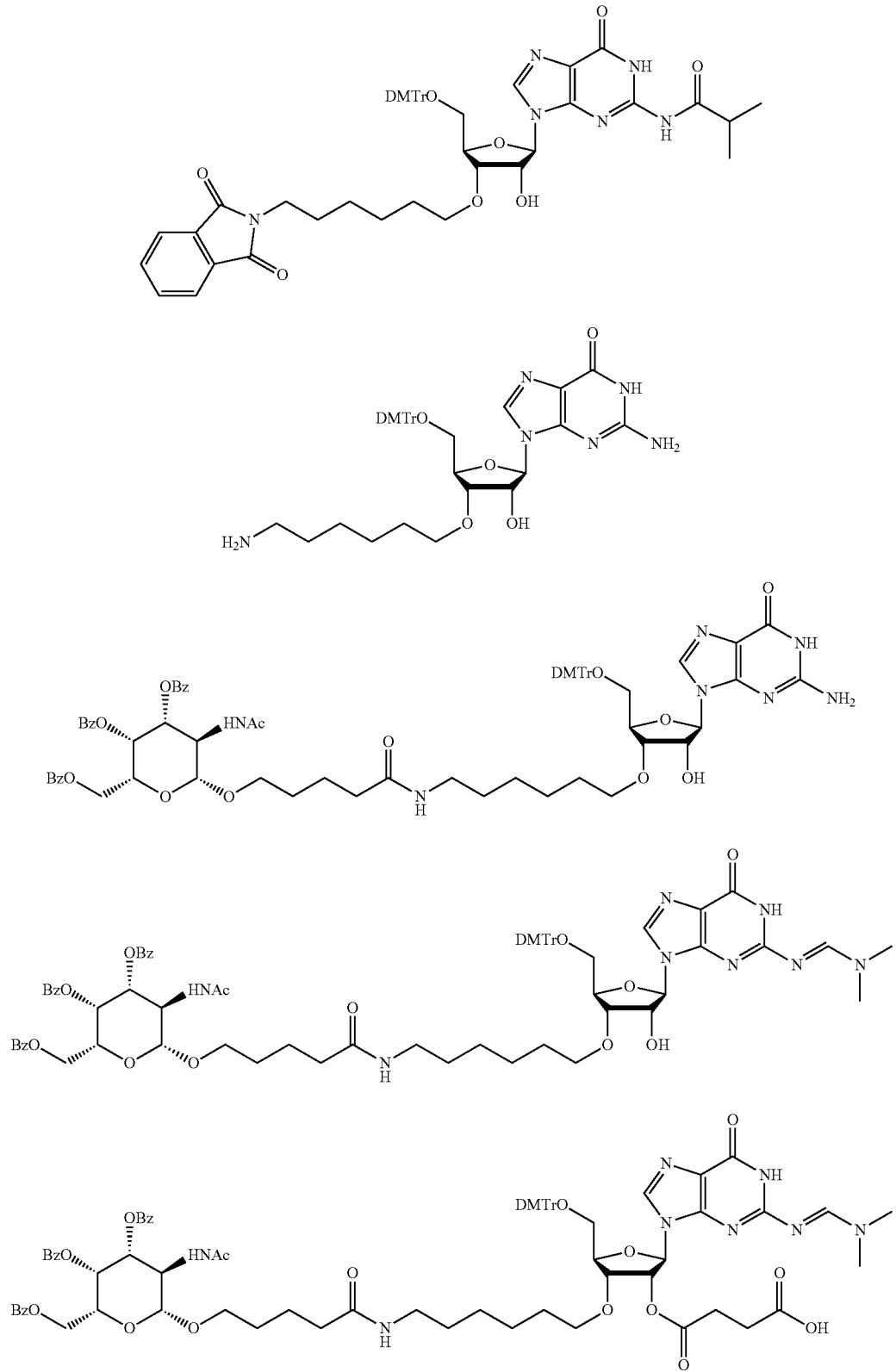 |

| Structures |
|---|
| 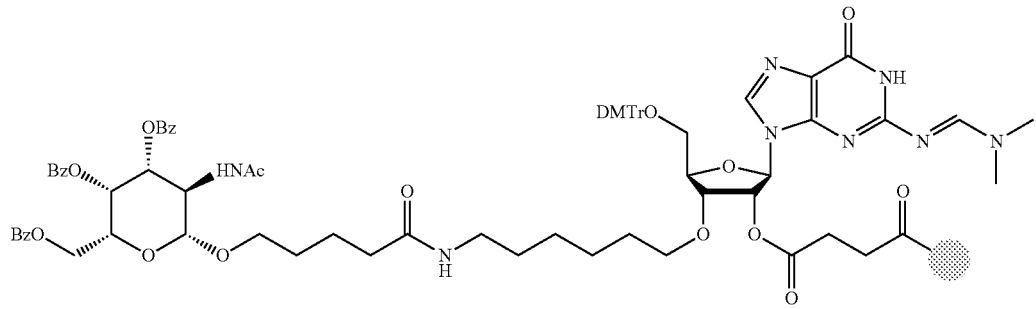 |
| 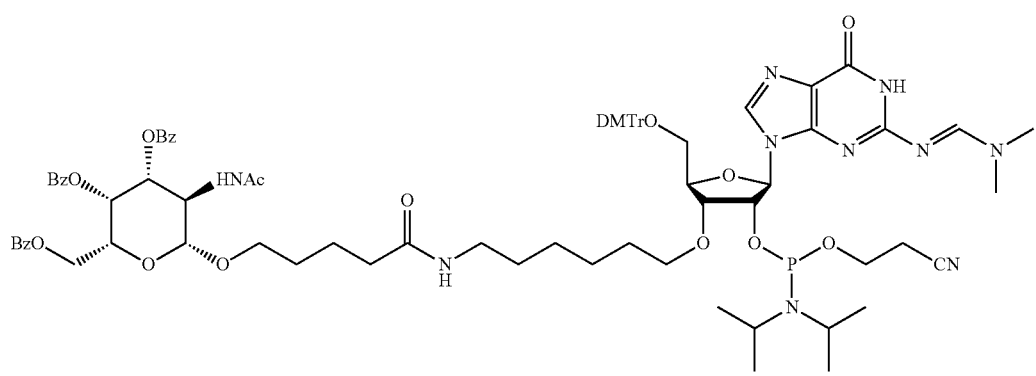 |
| 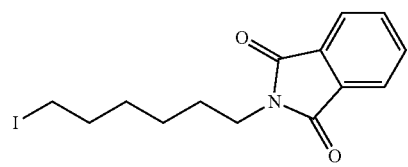 [SMILES: O=C1c2ccccc2C(=O)N1CCCCCCI] |
| 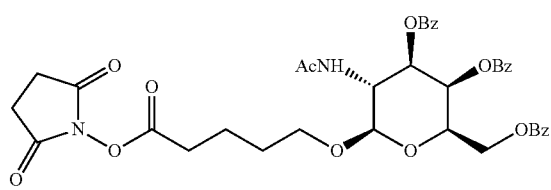 |
| 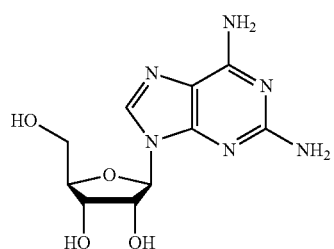 |

| Structures |
|---|
| 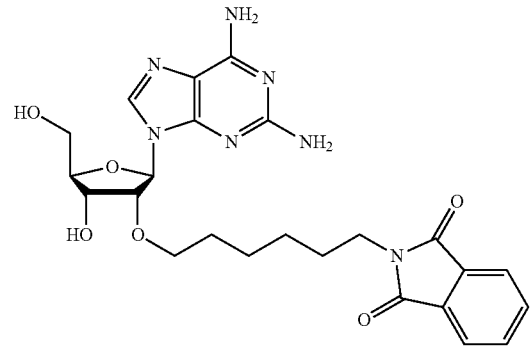 |
| 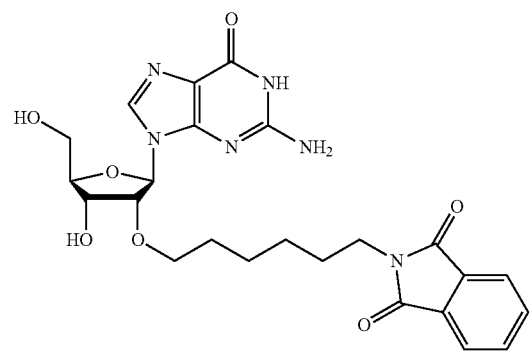 |
| 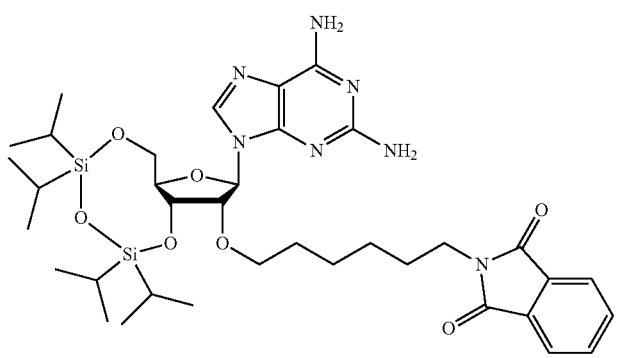 |
| 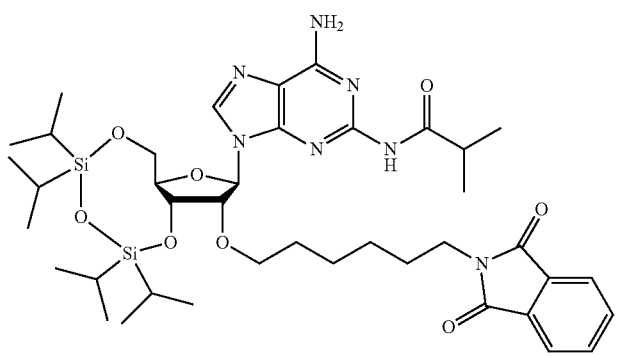 |

| Structures |
|---|
| 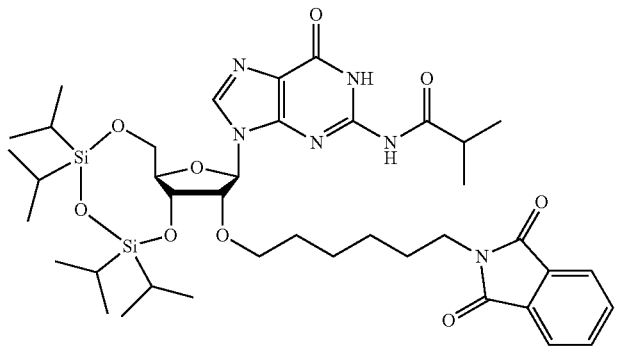 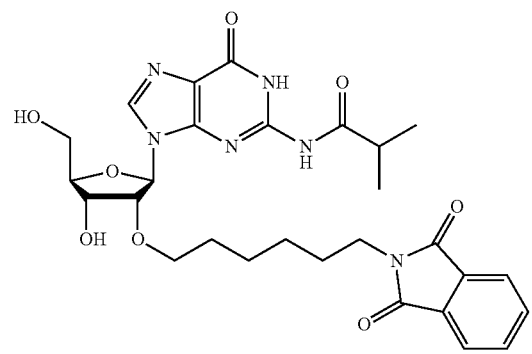 |
Example 65

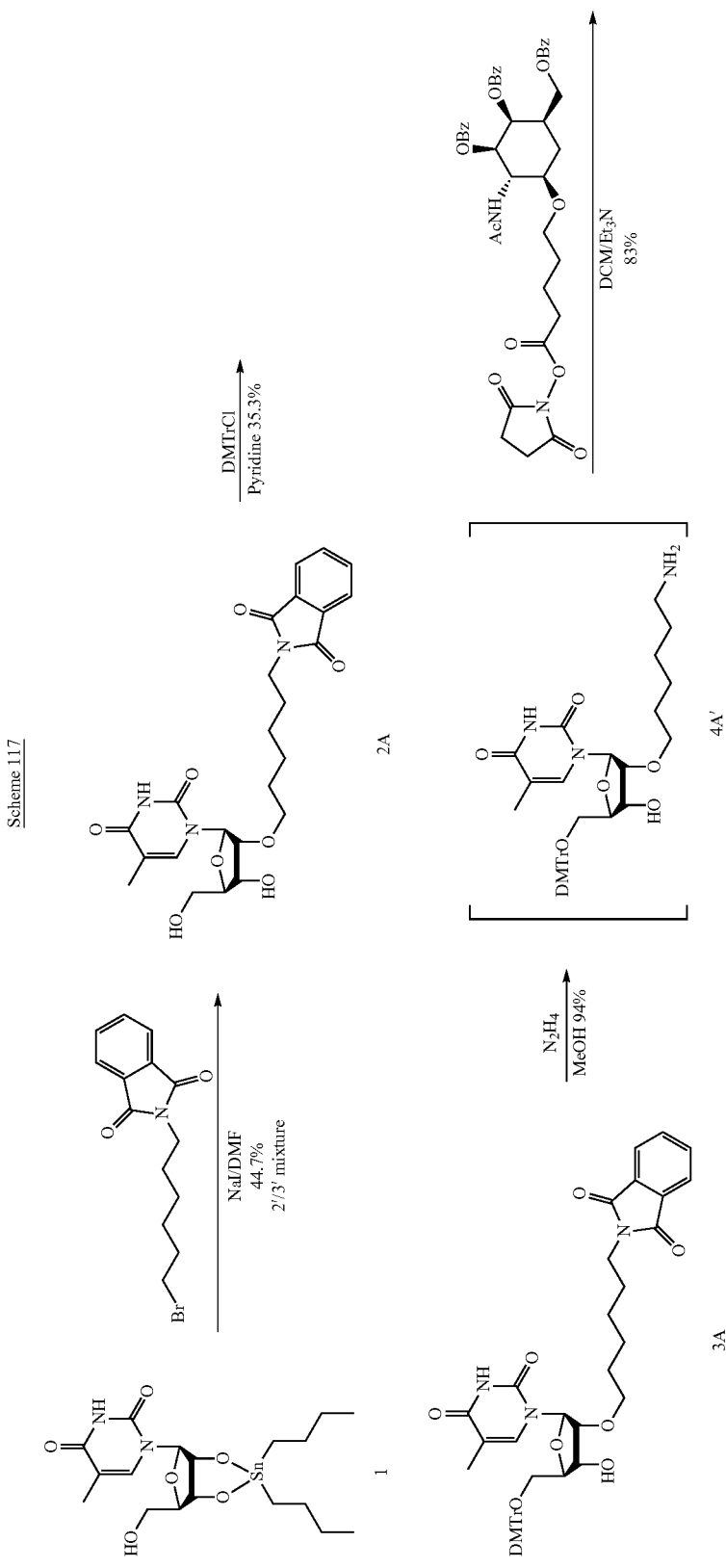

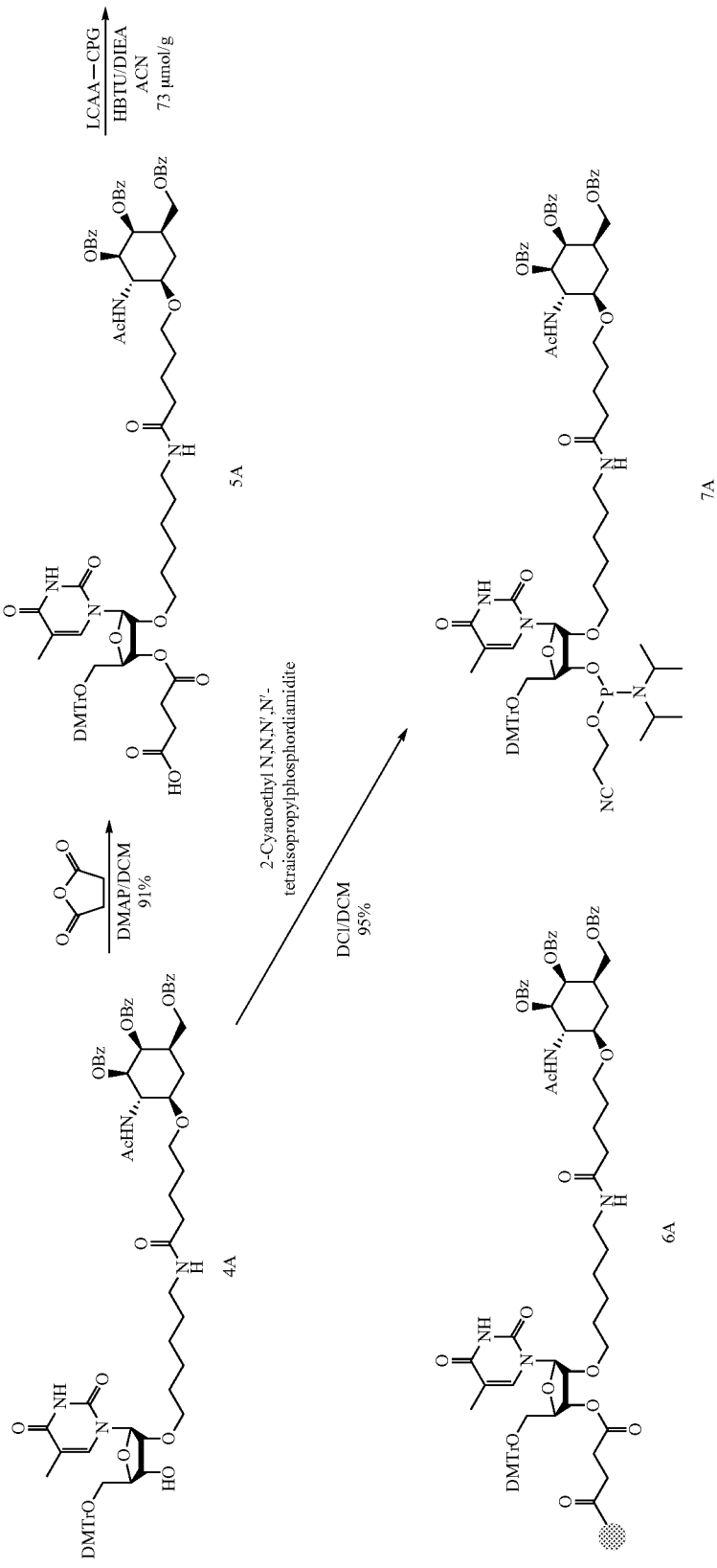

2'- and 3'-O-phthalimidohexyl-5-methyluridine (2A, 2B)

2',3'-O-dibutylstannylene-5-methyluridine (2.0 g, 4.1 mmol) was suspended in DMF (10 mL). 6-bromohexyl phthalimide (2.5 g, 8.2 mmol) and NaI (120 mg, 0.82 mmol) were added to the suspension. The reagents were microwaved for 3.5 hours at 100° C. resulting in a dark brown homogenous mixture. DMF was evaporated in vacuo and the residue adsorbed to silica gel. The silica gel was loaded into a cartridge for silica gel chromatography. The 2'- and 3'-isomers of the O-phthalimidohexyl-5-methyuridine eluted as an inseparable mixture to yield 890 mg of 2A and 2B (1.8 mmol, 45%).

$^1$H NMR (400 MHz, DMSO-$d_6$) δ 11.29 (s, 1H, $D_2O$ exchangeable), 7.88-7.80 (m, 4H), 7.78-7.76 (m, 1H), 7.73-7.70 (m, OH), 5.81 (d, J=5.3 Hz, 1H), 5.72 (d, J=5.6 Hz, 1H), 5.25 (d, J=6.2 Hz, 1H, $D_2O$ exchangeable), 5.12 (t, J=5.0 Hz, 1H, $D_2O$ exchangeable), 5.00 (d, J=5.9 Hz, 1H, $D_2O$ exchangeable), 4.14 (q, J=5.6 Hz, 1H), 4.07 (q, J=5.0 Hz, 1H), 3.90-3.79 (m, 2H), 3.74 (t, J=4.6 Hz, OH), 3.67-3.58 (m, 1H), 3.58-3.49 (m, 4H), 3.46-3.37 (m, 1H), 1.75 (d, J=3.7 Hz, 3H), 1.62-1.42 (m, 4H), 1.37-1.20 (m, 4H). $^{13}$C NMR (100 MHz, DMSO-$d_6$) δ 168.00, 167.97, 163.78, 163.73, 150.79, 150.57, 136.23, 136.07, 134.44, 134.40, 131.60, 131.56, 123.02, 109.38, 109.26, 87.73, 85.89, 85.07, 82.71, 80.82, 77.49, 72.43, 69.69, 69.51, 68.38, 60.86, 60.62, 29.23, 28.96, 27.93, 26.15, 26.07, 25.16, 24.96, 12.26. MS calculated for $C_{24}H_{29}N_3O_8$ 487.1955, found m/z 488.0 (M+1)$^+$, 510.2 (M+23)$^{Na+}$, 486.2 (M−1)$^-$, 522.2 (M+35)$^{Cl-}$. $R_f$=0.26 in 5% MeOH/DCM v/v

5'-O-Dimethoxytrityl-2'-O-phthalimidohexyl-5-methyluridine (3A)

The mixture of 2A and 2B (890 mg, 1.83 mmol) was co-evaporated with pyridine and then dissolved in pyridine (10 mL) under an argon atmosphere and cooled to 0° C. in an ice bath. To this mixture, DMTrCl (690 mg, 2.04 mmol) was added, and the reaction was stirred overnight while allowed to warm to room temperature. An additional 0.55 eq of DMTrCl was added and the reaction was stirred an additional 2 hours. The reaction was quenched with MeOH and evaporated in vacuo. The crude 2' and 3' isomers (3A and 3B) were dissolved in DCM and the organic layer washed twice with brine. The organic layer was dried with $Na_2SO_4$ and evaporated in vacuo. The compounds were purified via silica gel chromatography and concentrated in vacuo to yield 510 mg of 3A (0.65 mmol, 35%). The 2'-O-alkylated isomer was characterized by identification of the 3'-OH by $D_2O$ exchange followed by COSY.

$^1$H NMR (400 MHz, DMSO-$d_6$) δ 11.35 (s, 1H, $D_2O$ exchangeable), 7.88-7.77 (m, 4H), 7.48 (s, 1H), 7.38 (d, J=7.4 Hz, 2H), 7.33-7.19 (m, 7H), 6.89 (d, J=8.0 Hz, 4H), 5.82 (d, J=4.8 Hz, 1H), 5.10 (d, J=6.3 Hz, 1H, $D_2O$ exchangeable), 4.18 (q, J=5.5 Hz, 1H), 3.96 (q, J=4.8, 4.4 Hz, 2H), 3.72 (s, 6H), 3.62-3.46 (m, 4H), 3.27-3.14 (m, 2H), 1.59-1.45 (m, 4H), 1.38 (s, 3H), 1.34-1.20 (m, 4H). $^{13}$C NMR (100 MHz, DMSO-$d_6$) δ 167.91, 163.61, 158.19, 158.16, 150.41, 144.66, 135.45, 135.31, 135.11, 134.33, 131.58, 129.74, 127.93, 127.65, 126.84, 122.97, 113.27, 109.60, 86.46, 85.91, 83.09, 80.53, 69.63, 68.76, 63.19, 55.06, 37.31, 28.89, 27.91, 26.07, 24.95, 11.66. MS calculated for $C_{45}H_{47}N_3O_{10}$ 789.3261, found m/z 812.3 (M+23)$^{Na+}$, 788.3 (M−1)$^-$, 824.3 (M+35)$^{Cl-}$ $R_f$=0.35 in 60% EtOAc/Hexanes v/v

5'-O-Dimethoxytrityl-3'-O-phthalimidohexyl-5-methyluridine (3B)

The 3'-isomer (3B) was separated from the 2'-isomer (3A) during silica gel chromatography and concentrated in vacuo to yield 420 mg of 3B (29%, 0.53 mmol). The 3'-O-alkylated isomer was characterized in the same manner but with identification of the 2'-OH by $D_2O$ exchange.

$^1$H NMR (400 MHz, DMSO-$d_6$) δ 11.34 (s, 1H, $D_2O$ exchangeable), 7.87-7.79 (m, 4H), 7.49 (s, 1H), 7.36 (d, J=7.4 Hz, 2H), 7.29 (t, J=7.6 Hz, 2H), 7.26-7.19 (m, 5H), 6.94-6.81 (m, 4H), 5.71 (d, J=4.6 Hz, 1H), 5.36 (d, J=6.0 Hz, 1H, $D_2O$ exchangeable), 4.27 (q, J=5.2 Hz, 1H), 3.99-3.95 (m, 1H), 3.90 (t, J=5.3 Hz, 1H), 3.71 (s, 6H), 3.63-3.47 (m, 3H), 3.36 (t, J=6.8 Hz, 1H), 3.26-3.15 (m, 2H), 1.59-1.39 (m, 7H), 1.28-1.20 (m, 4H). $^{13}$C NMR (100 MHz, DMSO-$d_6$) δ 167.93, 163.69, 158.17, 158.15, 150.57, 144.63, 135.72, 135.30, 135.17, 134.35, 131.58, 129.71, 127.91, 127.63, 126.82, 122.97, 113.24, 109.37, 88.69, 85.91, 80.60, 77.27, 72.18, 69.67, 55.03, 39.50, 37.33, 29.09, 27.88, 26.08, 25.08, 11.74. MS calculated for $C_{45}H_{47}N_3O_{10}$ 789.3261, found m/z 812.0 (M+23)$^{Na+}$, 788.3 (M−1)$^-$, 824.3 (M+35)$^{Cl-}$ $R_f$=0.18 in 60% EtOAc/Hexanes v/v.

5'-O-Dimethoxytrityl-2'-O-aminohexyl-5-methyluridine (4A*)

To a solution of 3A (obtained from RI Chemicals, lot # H1010-04, 15.0 g, 18.99 mmol) in MeOH (190 mL) was added hydrazine (3.04 g, 94.52 mmol) and the heterogeneous mixture was heated to reflux for 3.5 hours. The mixture was cooled to room temperature and evaporated in vacuo to yield a white powder. The product was dissolved in DCM and washed with ammonium hydroxide. Brine was added to help remove the emulsion. The organic layer was dried with $MgSO_4$ and evaporated in vacuo to yield 11.80 g of crude product which was used without purification for the next step.

MS calculated for $C_{37}H_{45}N_3O_8$ 659.3207, found m/z 660.2 (M+1)$^+$, 682.1 (M+23)$^{Na+}$ 658.1 (M−1)$^-$, 694.1 (M+35)$^{Cl-}$. $R_f$=0.02 in 5% MeOH/DCM v/v. $^1$H NMR (400 MHz, DMSO-$d_6$) δ 7.48 (s, 1H), 7.38 (d, J=7.5 Hz, 2H), 7.30 (t, J=7.5 Hz, 2H), 7.24 (d, J=8.9 Hz, 5H), 6.89 (d, J=8.4 Hz, 4H), 5.84 (d, J=5.0 Hz, 1H), 5.74 (s, 1H), 4.19 (t, J=5.0 Hz, 1H), 3.97 (t, J=4.9 Hz, 2H), 3.72 (s, 6H), 3.63-3.45 (m, 3H), 3.27-3.15 (m, 3H), 1.48 (d, J=6.4 Hz, 2H), 1.38 (s, 3H), 1.34-1.18 (m, 6H).

5'-O-Dimethoxytrityl-2'-O-aminohexyl-C5-GalNAc (O-Bz)-5-methyluridine (4A)

To a solution of crude 4A* (6.00 g, 9.09 mmol) in DCM (250 mL) was added triethylamine (3.8 mL, 27.30 mmol) and the mixture was allowed to stir for 10 minutes. GalNAc-C5-NHS ester (7.31 g, 10.00 mmol) was added and the reaction mixture was stirred for 2 hours. The reaction mixture was washed with saturated bicarbonate and the organic layer was dried with $Na_2SO_4$ then evaporated in vacuo. The crude product was purified via silica gel chromatography to yield 9.56 g of 4A (7.49 mmol, 82%).

$^1$H NMR (400 MHz, DMSO-$d_6$) δ 11.37 (s, 1H, $D_2O$ exchangeable), 7.97 (d, J=9.3 Hz, 1H, $D_2O$ exchangeable), 7.91 (t, J=6.8 Hz, 4H), 7.73-7.45 (m, 11H), 7.41-7.19 (m, 11H), 6.88 (d, J=8.4 Hz, 4H), 5.84 (d, J=4.7 Hz, 1H), 5.74 (d, J=3.4 Hz, 1H), 5.36 (dd, J=11.1, 3.3 Hz, 1H), 5.12 (d, J=6.3 Hz, 1H, D$_2$O exchangeable), 4.73 (d, J=8.5 Hz, 1H), 4.45 (q, J=8.8, 7.6 Hz, 2H), 4.39-4.15 (m, 3H), 3.96 (t, J=4.7 Hz, 2H), 3.79 (dd, J=9.4, 3.8 Hz, 1H), 3.72 (s, 6H), 3.63-3.45 (m, 3H), 3.28-3.16 (m, 2H), 2.99 (q, J=6.5 Hz, 2H), 2.04 (s, 2H), 1.69 (s, 3H), 1.55-1.43 (m, 6H), 1.36 (d, J=17.6 Hz, 5H), 1.24 (s, 4H). $^{13}$C NMR (100 MHz, DMSO-d$_6$) δ 171.73, 169.40, 165.20, 165.16, 164.86, 163.62, 158.18, 158.15, 150.41, 144.64, 135.47, 135.31, 135.10, 133.77, 133.49, 129.73, 129.20, 129.16, 129.03, 129.00, 128.97, 128.70, 128.59, 127.91, 127.64, 126.82, 113.26, 109.59, 100.89, 86.47, 85.91, 83.09, 80.60, 71.85, 69.97, 69.74, 68.77, 67.92, 63.19, 62.03, 55.04, 49.74, 38.34, 35.03, 29.17, 29.04, 28.59, 26.25, 25.12, 22.69, 21.85, 11.66. MS calculated for C$_{71}$H$_{78}$N$_4$O$_{18}$ 1274.5311, found m/z 1298.3 (M+23)$^{Na+}$, 1309.4 (M+35)$^{Cl-}$. R$_f$=0.36 in 5% MeOH/DCM v/v.

5'-O-Dimethoxytrityl-2'-O-aminohexyl-C5-GalNAc (O-Bz)-3'-O-succinate-5-methyluridine (5A)

To a solution of 4A (2.00 g, 1.57 mmol) in DCM (50 mL) was added DMAP (574 mg, 4.70 mmol) and succinic anhydride (313 mg, 3.14 mmol). The reaction mixture was stirred over night at room temperature. The product was purified via silica gel chromatography (Φ=4.2 cm×15 cm, pretreated with 2% TEA in DCM). The product was eluted with 0-5% MeOH and 2-5% Et$_3$N in DCM v/v and co-evaporated with acetonitrile in vacuo to yield 2.11 g (1.43 mmol, 91%) of 6a as an Et$_3$N salt.

$^1$H NMR (400 MHz, DMSO-d$_6$) δ 11.44 (s, 1H), 8.05 (d, J=9.3 Hz, 1H), 7.91 (t, J=6.8 Hz, 4H), 7.74-7.45 (m, 11H), 7.40-7.27 (m, 6H), 7.23 (d, J=8.7 Hz, 5H), 6.89 (d, J=8.1 Hz, 4H), 5.84 (d, J=6.1 Hz, 1H), 5.74 (d, J=3.5 Hz, 1H), 5.36 (dd, J=11.1, 3.3 Hz, 1H), 5.27-5.22 (m, 1H), 4.74 (d, J=8.5 Hz, 1H), 4.48-4.40 (m, 2H), 4.38-4.22 (m, 3H), 4.13 (q, J=3.5 Hz, 1H), 3.78 (d, J=9.7 Hz, 1H), 3.72 (s, 6H), 3.54-3.28 (m, 5H), 3.25-3.19 (m, 1H), 2.97 (q, J=6.5 Hz, 2H), 2.57-2.51 (m, 2H), 2.44 (t, J=6.5 Hz, 2H), 2.04 (s, 2H), 1.69 (s, 3H), 1.57-1.27 (m, 11H), 1.18 (s, 4H). $^{13}$C NMR (100 MHz, DMSO-d$_6$) δ 173.40, 171.76, 171.63, 169.39, 165.20, 165.15, 164.86, 163.50, 158.22, 150.50, 144.48, 135.45, 135.12, 134.95, 133.76, 133.48, 129.70, 129.17, 129.03, 129.00, 128.97, 128.70, 128.58, 127.95, 127.61, 113.30, 110.16, 100.91, 86.13, 80.75, 78.22, 71.89, 70.67, 70.23, 69.97, 68.73, 67.91, 62.04, 55.04, 52.01, 49.73, 38.33, 34.98, 29.13, 28.92, 28.55, 26.19, 25.08, 22.68, 21.82, 11.69, 10.48. MS calculated for C$_{75}$H$_{81}$N$_4$O$_{21}^-$ 1374.5472, found m/z 1397.4 (M+23)$^{Na+}$, 1373.4 (M−1)$^-$, 1409.4 (M+35)$^{Cl-}$. R$_f$=0.41 in 5% MeOH/5% Et$_3$N/DCM v/v 5'-O-Dimethoxytrityl-2'-O-aminohexyl-C5-GalNAc (O-Bz)-3'-O-CPG-5-methyluridine (6A)

To a solution of 5A (2.01 g, 1.36 mmol) in acetonitrile (100 mL) was added HBTU (1.03 g, 2.72 mmol) and DIEA (528 mg, 4.08 mmol). The mixture was shaken for 5 minutes before the addition of CPG (16.00 g, 130 μmol/g, 540 A). The mixture was shaken for 24 hours. CPG was filtered and washed with DCM, 20% MeOH in DCM v/v, then ether. CPG was evaporated in vacuo and then treated with acetic anhydride (25 mL) in pyridine (75 mL) and Et$_3$N (1 mL) and shaken for 1 hour. CPG was filtered and washed with the same solvents as described above. The average loading was determined by trityl absorbance spectroscopy measurements of two samples and was calculated to be 73 μmol/g.

5'-O-Dimethoxytrityl-2'-O-aminohexyl-C5-GalNAc(O-Bz)-3'-O—(N,N-diisopropyl)-β-cyanoethylphosphoramidite-5-methyluridine (7A)

4A (2.90 g, 2.27 mmol) was co-evaporated with anhydrous acetonitrile twice then kept under a strict argon atmosphere. To a solution of 4A in anhydrous DCM (35 mL) at 0° C. was added 2-cyanoethyl-N,N,N',N'-tetraisopropyl-phosphordiamidite (1.37 g, 4.55 mmol) followed by DCI (268 mg, 2.27 mmol). The mixture was stirred at 0° C. for 20 minutes then at room temperature for 17 hours. The product was washed with saturated bicarbonate and extracted with DCM. The organic layer was dried with Na$_2$SO$_4$ to yield a pale yellow foam. Silica gel chromatography (Φ=4.2 cm×19 cm pretreated with 50% EtOAc and 1% TEA in hexane) was carried out. The column was washed with 80% EtOAc in hexane (8 CV) followed by 100% EtOAc (8 CV), then 3% MeOH in DCM (5 CV). Product 7A eluted with 100% EtOAc and again in 3% MeOH. Fractions containing 7A were combined and evaporated in vacuo to yield 3.20 g of 7A (2.17 mmol, 95%).

$^1$H NMR (400 MHz, DMSO-d$_6$) δ 11.39 (s, 1H), 7.98 (d, J=9.3 Hz, 1H), 7.91 (t, J=7.2 Hz, 4H), 7.72-7.45 (m, 11H), 7.38 (t, J=6.8 Hz, 4H), 7.33-7.20 (m, 7H), 6.88 (t, J=5.4 Hz, 4H), 5.82 (d, J=4.3 Hz, 1H), 5.75 (s, 1H), 5.35 (dd, J=11.1, 3.1 Hz, 1H), 4.73 (d, J=8.5 Hz, 1H), 4.48-4.31 (m, 4H), 4.15-4.04 (m, 2H), 3.71 (s, 8H), 3.58-3.45 (m, 5H), 3.28-3.20 (m, 2H), 3.03-2.93 (m, 2H), 2.76 (t, J=5.8 Hz, 1H), 2.57 (q, J=5.3 Hz, 1H), 2.04 (s, 2H), 1.69 (s, 3H), 1.49 (s, 6H), 1.42-1.29 (m, 5H), 1.27-1.15 (m, 5H), 1.14-1.03 (m, 10H), 0.94 (d, J=6.7 Hz, 3H). $^{13}$C NMR (125 MHz, DMSO-d$_6$) δ 171.60, 169.26, 165.07, 165.03, 164.73, 163.48, 158.10, 158.08, 158.07, 150.24, 150.22, 144.39, 144.34, 134.99, 134.97, 134.87, 134.80, 133.63, 133.37, 133.34, 129.65, 129.62, 129.60, 129.07, 129.05, 129.03, 128.90, 128.88, 128.87, 128.83, 128.56, 128.45, 127.75, 127.56, 127.50, 126.74, 118.72, 118.57, 113.10, 113.08, 109.63, 109.54, 100.76, 85.92, 85.90, 71.72, 69.84, 68.61, 67.78, 61.89, 54.91, 49.60, 45.53, 42.53, 42.42, 42.31, 38.23, 38.21, 34.88, 29.05, 29.02, 28.96, 28.45, 26.17, 25.08, 25.04, 24.18, 24.13, 24.09, 24.03, 22.55, 21.71, 19.71, 19.66, 19.62, 11.51, 11.49. $^{31}$P NMR (160 MHz, DMSO-d$_6$) δ 154.01, 153.65.

MS calculated for C$_{80}$H$_{95}$N$_6$O$_{19}$P 1474.6390, found m/z 1497.4 (M+23)$^{Na+}$, 1509.4 (M+35)$^{Cl-}$. R$_f$=0.39 in 100% EtOAc.

Example 66
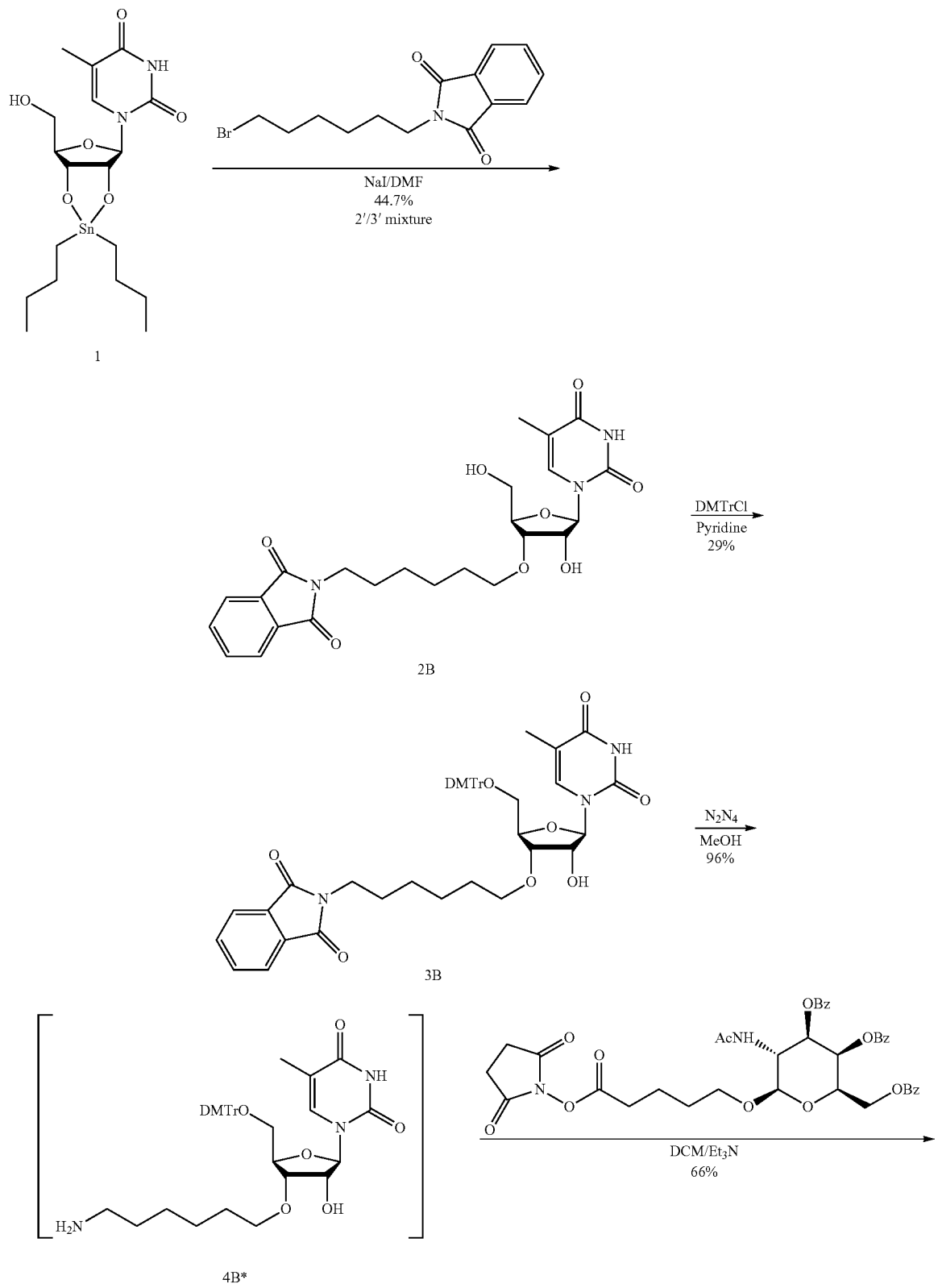

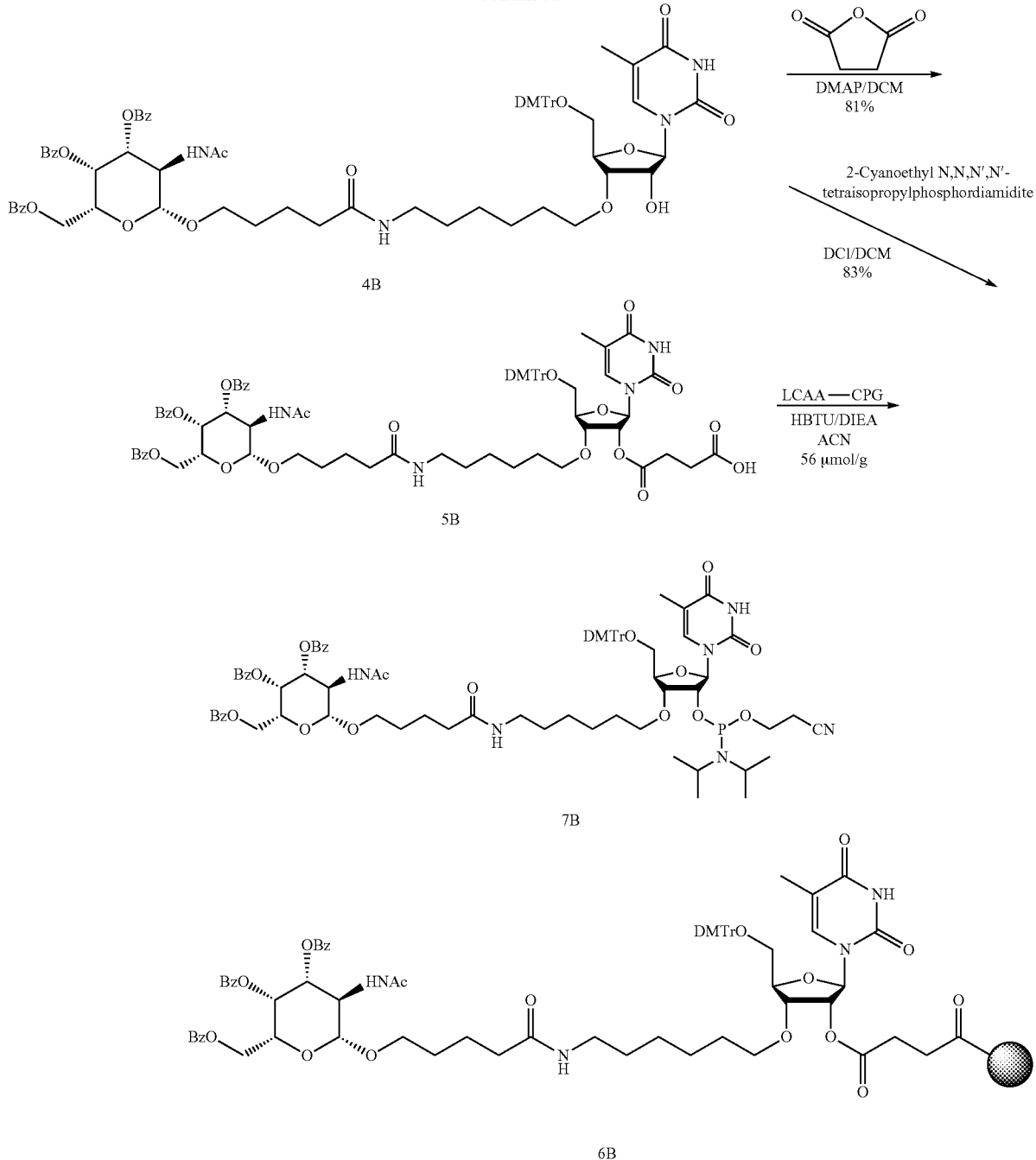

5'-O-Dimethoxytrityl-3'-O-aminohexyl-5-methyluridine (4B*)

To a solution of 3B (3.64 g, 4.61 mmol-1 g) in MeOH (46 ml) was added hydrazine (738 mg, 23.04 mmol) and the reaction mixture was refluxed for 5.5 hours. The workup procedure described for 4A* was used to isolate crude 4B*. Co-evaporation with acetonitrile yielded 2.93 g of crude 4B*.

MS calculated for $C_{37}H_{45}N_3O_8$ 659.3207, found m/z 660.2 (M+1)$^+$, 682.1 (M+23)$^{Na+}$, 658.1 (M−1)$^−$, 694.1 (M+35)$^{Cl−}$. $R_f$=0.02 in 5% MeOH/DCM v/v Crude 4B* NMR:

$^1$H NMR (400 MHz, DMSO-d$_6$) δ 7.50 (s, 1H), 7.43-7.16 (m, 9H), 6.88 (d, J=8.7 Hz, 4H), 5.73 (d, J=4.6 Hz, 1H), 4.29 (t, J=4.8 Hz, 1H), 4.02-3.89 (m, 3H), 3.46-3.15 (m, 5H), 2.24-2.16 (m, 1H), 2.05 (s, 1H), 1.58-1.10 (m, 13H). $^{13}$C NMR (125 MHz, DMSO-d$_6$) δ 163.73, 158.04, 158.02, 150.58, 144.49, 135.54, 135.18, 135.06, 129.56, 127.78, 127.50, 126.69, 113.11, 109.23, 88.49, 85.78, 80.47, 77.20, 72.02, 69.62, 62.85, 54.91, 54.90, 41.44, 33.12, 29.17, 26.11, 25.31, 11.62.

5'-O-Dimethoxytrityl-3'-O-aminohexyl-C5-GalNAc (O-Bz)-5-methyluridine (4B)

To a solution of 4B* (2.85 g, 4.32 mmol) in DCM (45 mL) treated with TEA (1.8 mL) was added GalNAc-NHS ester (3.47 g, 4.75 mmol). The reaction was stirred for 2 hours before an additional 0.2 eq of GalNAc-NHS ester was added. After 1 hour, the product was isolated in the same manner as described for 5A. Silica column purification yielded 3.62 g of 4B (2.84 mmol).

$^1$H NMR (400 MHz, DMSO-d$_6$) δ 11.35 (s, 1H), 8.00-7.89 (m, 5H), 7.73-7.45 (m, 11H), 7.40-7.35 (m, 4H), 7.33-7.20 (m, 7H), 6.88 (d, J=8.8 Hz, 4H), 5.74 (d, J=10.1 Hz, 2H), 5.42-5.33 (m, 2H), 4.73 (d, J=8.5 Hz, 1H), 4.48-4.41 (m, 2H), 4.38-4.23 (m, 3H), 3.99 (d, J=4.7 Hz, 1H), 3.91 (t, J=5.1 Hz, 1H), 3.82-3.76 (m, 1H), 3.72 (s, 6H), 3.62-3.47 (m, 2H), 3.41-3.36 (m, 1H), 3.27-3.17 (m, 2H), 2.99 (q, J=6.6 Hz, 2H), 2.04 (t, J=6.4 Hz, 2H), 1.69 (s, 3H), 1.55-1.28 (m, 11H), 1.28-1.15 (m, 4H). $^{13}$C NMR (75 MHz, DMSO-d$_6$) δ 171.72, 169.38, 165.19, 165.14, 164.85, 163.64, 162.25, 158.14, 150.55, 144.57, 135.68, 135.30, 135.16, 133.73, 133.45, 129.66, 129.18, 129.14, 129.00, 128.93, 128.66, 128.55, 127.88, 127.61, 126.80, 113.22, 109.36, 100.88, 88.57, 85.90, 80.63, 77.35, 72.16, 71.83, 69.97, 69.73, 68.73, 67.91, 62.97, 62.02, 55.01, 54.84, 49.75, 38.34, 35.73, 35.02, 30.73, 29.23, 29.11, 28.57, 26.25, 25.21, 22.66, 21.84, 11.68. MS calculated for $C_{71}H_{78}N_4O_{18}$ 1274.5311, found m/z 1297.4 (M+23)$^{Na+}$, 1309.4 (M+35)$^{Cl-}$. $R_f$=0.24 in 5% MeOH in DCM.

5'-O-Dimethoxytrityl-3'-O-aminohexyl-C5-GalNAc (O-Bz)-2'-O-succinate-5-methyluridine (5B)

To a solution of 4B (1.10 g, 0.86 mmol) in DCM (20 mL) and DMAP (315 mg, 2.58 mmol) was added succinic anhydride (172 mg, 1.73 mmol). The reaction mixture was stirred for 23 hours then purified using the procedure described for 5A and co-evaporated with acetonitrile in vacuo to yield 1.03 g of 5B (0.70 mmol, 81%).

$^1$H NMR (400 MHz, DMSO-d$_6$) δ 8.09 (d, J=9.3 Hz, 1H), 7.91 (t, J=6.9 Hz, 4H), 7.76 (t, J=5.4 Hz, 1H), 7.73-7.51 (m, 9H), 7.47 (t, J=7.7 Hz, 2H), 7.40-7.19 (m, 12H), 6.87 (d, J=8.7 Hz, 4H), 5.85 (d, J=3.9 Hz, 1H), 5.74 (d, J=3.2 Hz, 1H), 5.47-5.42 (m, 1H), 5.36 (dd, J=11.1, 3.2 Hz, 1H), 4.75 (d, J=8.5 Hz, 1H), 4.44 (q, J=9.1, 7.7 Hz, 2H), 4.38-4.20 (m, 4H), 4.01-3.94 (m, 2H), 3.80-3.76 (m, 2H), 3.71 (s, 6H), 3.40-3.16 (m, 10H), 3.07-2.94 (m, 3H), 2.56 (q, J=6.2, 5.7 Hz, 2H), 2.43 (d, J=4.1 Hz, 3H), 2.07-2.01 (m, 2H), 1.69 (s, 3H), 1.48 (d, J=15.0 Hz, 7H), 1.40-1.27 (m, 4H), 1.16 (s, 4H). $^{13}$C NMR (100 MHz, DMSO-d$_6$) δ 173.63, 173.45, 172.79, 171.92, 171.52, 169.54, 168.92, 165.29, 165.24, 164.94, 163.78, 158.23, 150.33, 144.57, 136.18, 135.27, 135.18, 133.84, 133.57, 129.77, 129.24, 129.09, 129.06, 129.04, 128.77, 128.65, 127.96, 127.70, 126.90, 113.29, 109.73, 100.97, 85.97, 80.75, 75.82, 73.31, 71.96, 70.48, 62.59, 62.40, 55.10, 55.07, 52.06, 51.40, 51.36, 45.45, 38.42, 35.04, 33.35, 29.20, 29.09, 28.95, 28.77, 22.70, 21.90, 11.81, 10.08, 7.26, 7.17. MS calculated for $C_{75}H_{81}N_4O_{21}{}^-$ 1374.5472, found m/z 1397.4 (M+23)$^{Na+}$, 1373.4 (M−1)$^-$. $R_f$=0.18 in 5% MeOH in DCM).

5'-O-Dimethoxytrityl-3'-O-aminohexyl-C5-GalNAc (O-Bz)-2'-O-CPG-5-methyluridine (6B)

To a solution of 5B (970 mg, 0.66 mmol) in acetonitrile (50 mL) was added HBTU (497 mg, 1.31 mmol) and DIEA (339 mg, 1.97 mmol). After 5 minutes of shaking, CPG (8.20 g, 130 μmol/g, 540 A) was added and shaking was continued for 21 hours. The CPG was removed by filtration, washed, capped, and loading determined as described for 6A to yield CPG with an average loading of 56 μmol/g.

5'-O-Dimethoxytrityl-3'-O-aminohexyl-C5-GalNAc (O-Bz)-2'-O-(cyanoethyl-N,N-diisopropyl)-phosphoramidite-5-methyluridine (7B)

4B (1.98 g, 1.55 mmol) was prepared in the same manner described in 7A and treated with the same reagents. The product 7B was loaded onto a column prepared in the same manner as described for 7A and eluted with 70% EtOAc in hexane (4 CV), 80% EtOAc in hexane (10 CV), 100% EtOAc (2 CV), then 3% MeOH in DCM (4 CV). The desired product eluted in 100% EtOAc and in 3% MeOH. Fractions containing the desired product were combined and evaporated in vacuo to yield 1.89 g (1.28 mmol, 83%) of 7B.

$^1$H NMR (400 MHz, DMSO-d$_6$) δ 11.38 (s, 1H), 8.00-7.88 (m, 5H), 7.72-7.45 (m, 11H), 7.41-7.34 (m, 4H), 7.33-7.20 (m, 7H), 6.91-6.85 (m, 4H), 5.88 (dd, J=9.3, 5.1 Hz, 1H), 5.75 (d, J=3.3 Hz, 1H), 5.36 (dd, J=11.1, 3.3 Hz, 1H), 4.73 (d, J=8.5 Hz, 1H), 4.62-4.50 (m, 1H), 4.45 (q, J=8.2, 7.2 Hz, 2H), 4.38-4.23 (m, 2H), 4.07-3.95 (m, 3H), 3.72 (s, 13H), 3.44-3.39 (m, 1H), 3.31-3.22 (m, 2H), 2.98 (s, 2H), 2.71-2.66 (m, 1H), 2.04 (s, 2H), 1.69 (s, 3H), 1.47 (d, J=28.1 Hz, 8H), 1.40-1.18 (m, 8H), 1.13-1.00 (m, 11H). $^{13}$C NMR (125 MHz, DMSO-d$_6$) δ 171.72, 171.70, 170.37, 170.29, 169.37, 165.18, 165.14, 164.85, 163.58, 163.50, 158.20, 158.18, 158.16, 158.14, 154.86, 150.48, 150.43, 144.53, 144.52, 144.50, 135.18, 135.14, 135.05, 134.98, 133.74, 133.48, 133.44, 129.69, 129.66, 129.63, 129.18, 129.16, 129.13, 129.01, 128.99, 128.98, 128.93, 128.67, 128.64, 128.56, 128.54, 128.52, 127.91, 127.88, 127.57, 118.81, 118.70, 113.25, 113.21, 109.72, 109.68, 100.87, 86.16, 86.15, 86.02, 71.83, 71.81, 69.95, 69.92, 68.72, 68.71, 67.89, 63.45, 59.71, 55.00, 54.98, 49.72, 42.79, 42.69, 42.64, 38.35, 38.33, 35.00, 30.12, 30.03, 29.26, 29.25, 29.14, 29.11, 29.09, 28.56, 28.54, 26.29, 25.27, 25.25, 24.34, 24.29, 24.24, 24.22, 24.08, 24.02, 22.66, 22.65, 21.84, 21.83, 21.36, 20.72, 20.67, 20.66, 19.80, 19.78, 19.74, 19.73, 19.67, 19.62, 18.82, 18.56, 16.57, 14.04, 13.65, 13.50, 11.69, 11.56, 11.56, 11.55, 11.53. $^{31}$P NMR (162 MHz, DMSO-d$_6$) δ 155.08, 154.60. MS calculated for $C_{80}H_{95}N_6O_{19}P$ 1474.6390, found m/z 1497.4 (M+23)$^{Na+}$, 1474.3 (M−1)$^-$, 1509.4 (M+35)$^{Cl-}$ $R_f$=0.43 in 100% EtOAc).

Example 67

Scheme 119
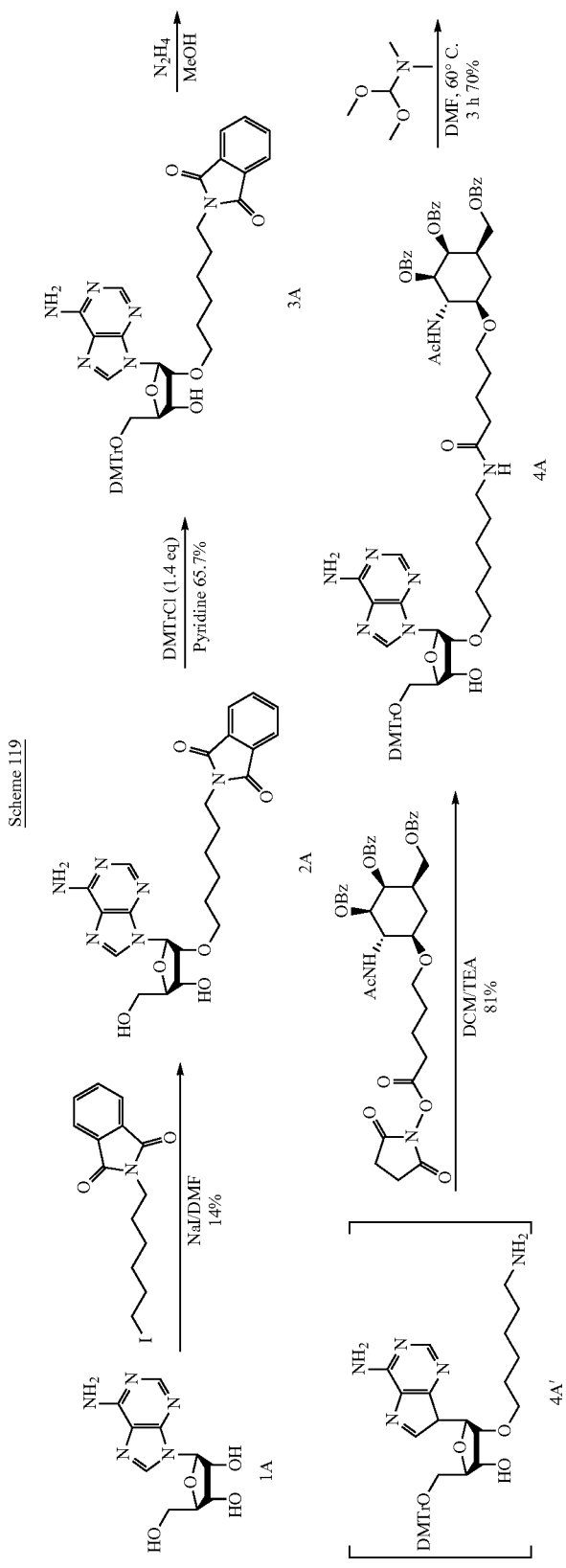

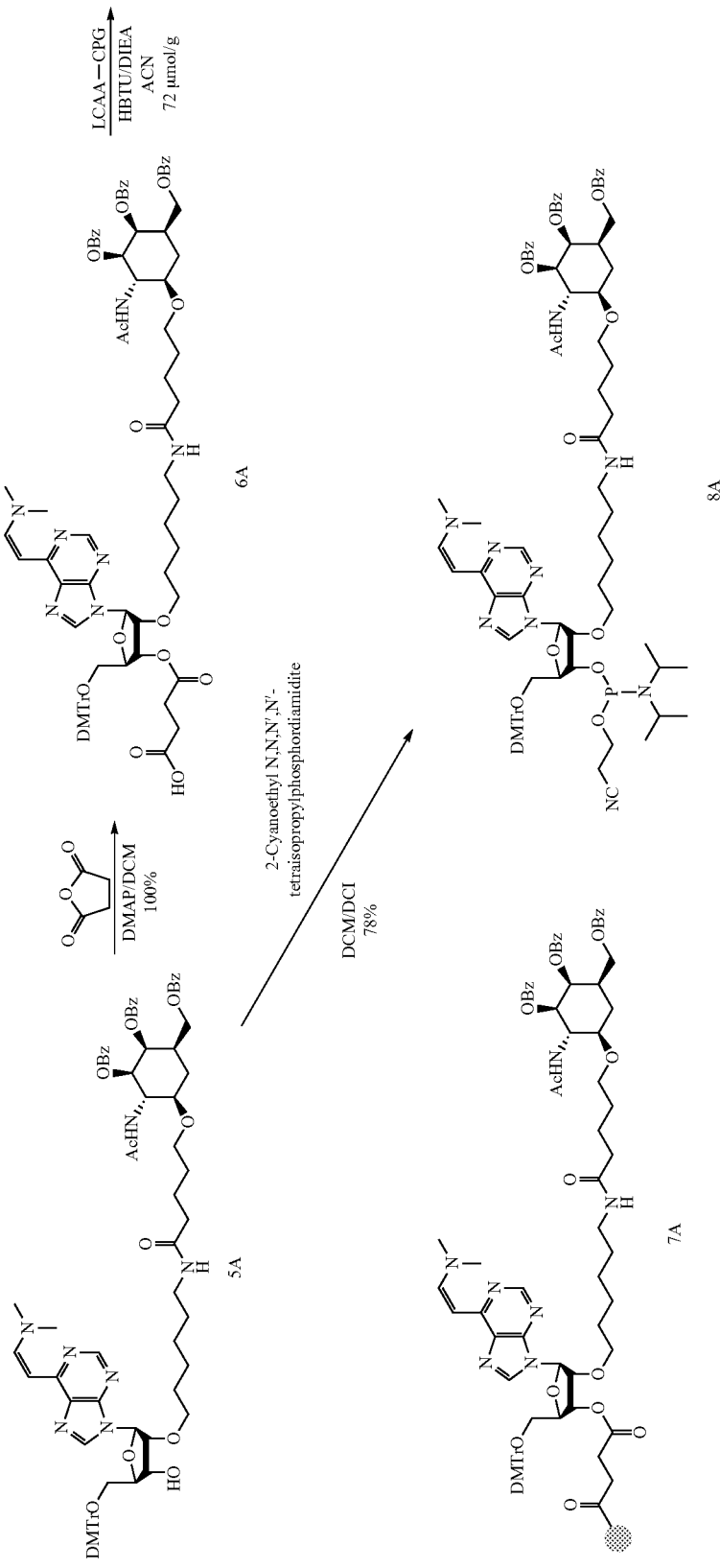

LRMS calculated for $C_{24}H_{28}N_6O_6$ 496.52, found m/z 497.2 $(M+1)^+$, 519.2 $(M+23)^{Na+}$, 486.2 $(M-1)^-$, 522.2 $(M+35)^{Cl-}$.

(2A/2B)—

Adenosine (20 g, 74.8 mmol) was treated with NaH (4.5 g, 112 mmol) in DMF (200 ml) at 0° C. for 20 minutes. N-(Iodohexyl)phthalimide (30.7 g, 86 mmol) was added to the solution and then heated to 80° C. for two days. DMF was evaporated in vacuo to yield a pale orange gum containing the 2'- and 3'-O-alkylated isomers. The crude mixture was adsorbed onto silica gel and purified (5% MeOH/DCM v/v) to yield 5.1 g (10.3 mmol, 14%) of 2A as well as a mixture of the regioisomers.

$^1$H NMR (400 MHz, DMSO-$d_6$) δ 8.36 (s, 1H), 8.12 (s, 1H), 7.95-7.68 (m, 4H), 7.32 (s, 2H, $D_2O$ exchangeable), 5.96 (d, J=6.2 Hz, 1H), 5.42 (t, J=7.1, 4.6 Hz, 1H, $D_2O$ exchangeable), 5.15 (d, J=5.1 Hz, 1H, $D_2O$ exchangeable), 4.44 (t, J=6.3, 4.7 Hz, 1H), 4.27 (q, J=4.9, 2.8 Hz, 1H), 3.96 (q, J=3.4 Hz, 1H), 3.66 (dt, J=12.2, 4.2 Hz, 1H), 3.60-3.42 (m, 4H), 3.30 (dd, J=9.5, 6.4 Hz, 1H), 1.41 (dt, J=33.8, 6.9 Hz, 4H), 1.25-1.04 (m, 4H). $^{13}$C NMR (100 MHz, DMSO-$d_6$) δ 167.89, 150.68, 148.24, 148.19, 134.35, 131.54, 128.38, 127.61, 125.44, 122.96, 118.74, 86.39, 86.03, 81.49, 69.66, 68.64, 28.85, 27.81, 25.93, 24.84. LRMS calculated for $C_{24}H_{28}N_6O_6$ 496.2070, found m/z 497.2 $(M+1)^+$, 519.2 $(M+23)^{Na+}$, 531.2 $(M+35)^{Cl-}$. $R_f$=0.28 in 5% MeOH/DCM v/v.

(3A)—

Compound 2A (7.4 g, 14.9 mmol) was coevaporated with pyridine then dissolved in pyridine (75 ml) under argon gas. Triethylamine (3.2 ml, 22.4 mmol) and 4-dimethylaminopyridine (45 mg, 0.37 mmol) were added and the reaction mixtured was stirred for 15 minutes. DMTrCl (5.6 g, 16.4 mmol) was then added and stirred overnight. An additional 1.5 g of DMTrCl was then added to drive the reaction to completion. The reaction mixture was quenched with MeOH (5 ml) and evaporated in vacuo. The crude product was washed with saturated NaHCO$_3$, extracted with EtOAc and dried with Na$_2$SO$_4$. The crude product was purified with a silica column (2.5% MeOH/DCM v/v) to yield 7.8 g (13 mmol, 66%) of pure 3A.

$^1$H NMR (400 MHz, DMSO-$d_6$) δ 8.26 (s, 1H), 8.09 (s, 1H), 7.88-7.77 (m, 4H), 7.42-7.33 (m, 2H), 7.33-7.16 (m, 9H), 6.88-6.78 (m, 4H), 6.01 (d, J=4.8 Hz, 1H), 5.17 (d, J=5.9 Hz, 1H), 4.56 (t, J=5.0 Hz, 1H), 4.38 (q, J=5.2 Hz, 1H), 4.06 (q, J=4.6 Hz, 1H), 3.72 (s, 6H), 3.62-3.37 (m, 4H), 3.34 (s, 2H), 3.23 (d, J=4.6 Hz, 2H), 1.60-1.37 (m, 4H), 1.31-1.11 (m, 4H). $^{13}$C NMR (100 MHz, DMSO-$d_6$) δ 167.90, 158.02, 156.08, 152.63, 149.21, 144.85, 139.58, 135.55, 135.45, 134.31, 131.57, 129.70, 127.75, 127.68, 126.62, 122.95, 119.20, 113.10, 85.97, 85.49, 83.48, 80.10, 69.76, 69.12, 63.53, 28.92, 27.85, 25.99, 24.91. LRMS calculated for $C_{45}H_{46}N_6O_8$ 798.3377, found m/z 799.2 $(M+1)^+$, 821.1 $(M+23)^{Na+}$, 833.1 $(M+35)^{Cl-}$ $R_f$=0.33 in 5% MeOH/DCM v/v.

(4A)—

Compound 3 (13 g, 16.2 mmol) was dissolved in MeOH (160 ml) and hydrazine (2.6 g, 81 mmol) was added to the solution. The reaction mixture was stirred at reflux for 3 hours. TLC analysis showed complete disappearance of 3A and the appearance of a more polar spot, presumably 4A*. The MeOH was evaporated in vacuo and the crude foam was washed with NH$_4$OH. The aqueous layer was extracted with DCM; saturated NaCl was needed to clear the emulsion. The organic layer was dried with MgSO$_4$ and evaporated in vacuo. 4A* was coevaporated with toluene before being dissolved in DCM (150 ml) and triethylamine (6.6 ml, 47.6 mmol). GalNAc(OBz)-C5-NHS ester (12.8 g, 17.4 mmol) was added to the mixture and the reaction proceeded for two hours at room temperature. An additional 1.7 g, 2.4 mmol of GalNAc(OBz)-C5-NHS ester was added to the reaction and allowed to stir for an additional two hours. The reaction mixture was evaporated in vacuo and the crude product was washed with NaHCO$_3$. The aqueous layer was extracted with DCM and dried with Na$_2$SO$_4$. Crude 4A was adsorbed to silica and purified (2.5-5% MeOH/DCM v/v) to yield 16.7 g (13.1 mmol, 81%) of 4A.

$^1$H NMR (400 MHz, DMSO-$d_6$) δ 8.26 (s, 1H), 8.09 (s, 1H), 8.02-7.85 (m, 5H), 7.76-7.45 (m, 10H), 7.44-7.17 (m, 13H), 6.83 (dd, J=8.8, 5.1 Hz, 4H), 6.01 (d, J=4.9 Hz, 1H), 5.78-5.74 (m, 1H), 5.37 (dd, J=11.1, 3.2 Hz, 1H), 5.18 (d, J=5.8 Hz, 1H), 4.74 (d, J=8.5 Hz, 1H), 4.57 (t, J=4.9 Hz, 1H), 4.46 (q, J=8.6, 7.4 Hz, 2H), 4.41-4.23 (m, 3H), 4.07 (q, J=4.5 Hz, 1H), 3.85-3.76 (m, 1H), 3.72 (s, 6H), 3.55 (ddd, J=24.2, 9.5, 5.1 Hz, 2H), 3.46-3.38 (m, 1H), 3.23 (d, J=4.4 Hz, 2H), 2.97 (q, J=6.5 Hz, 2H), 2.04 (s, 2H), 1.70 (s, 3H), 1.58-1.36 (m, 6H), 1.33-1.12 (m, 6H). $^{13}$C NMR (100 MHz, DMSO-$d_6$) δ 171.69, 169.38, 165.20, 165.15, 164.85, 158.00, 156.07, 152.62, 149.19, 144.82, 139.58, 135.53, 135.42, 133.77, 133.51, 133.47, 129.68, 129.19, 129.16, 129.02, 129.00, 128.97, 128.69, 128.59, 127.73, 127.65, 126.61, 119.18, 113.08, 100.88, 85.94, 85.47, 83.49, 80.08, 71.84, 69.96, 69.80, 69.10, 68.75, 67.91, 63.53, 62.02, 54.98, 54.89, 49.73, 35.01, 29.11, 29.03, 28.58, 26.17, 25.05, 22.69, 21.83. LRMS calculated for $C_{37}H_{44}N_6O_6$ 668.3322, found m/z 691.3 $(M+23)^{Na+}$, 703.2 $(M+35)^{Cl-}$ (4A*). LRMS calculated for $C_{71}H_{77}N_7O_{16}$ 1283.5427, found m/z 1306.3 $(M+23)^{Na+}$, 1282.3 $(M-1)^-$, 1318.3 $(M+35)^{Cl-}$ (4A). $R_f$=0.00 in 5% MeOH/DCM v/v (4A*). $R_f$=0.24 in 5% MeOH/DCM v/v (4A)

(5A)—

Compound 4A (16 g, 12.5 mmol) was dissolved in DMF (50 ml) and N,N-Dimethylformamide dimethyl acetal (7.4 g, 62.3 mmol) was added to the stirring solution. The reaction mixture was heated to 60° C. for 3 hours before removal of DMF in vacuo. Trace amounts of starting material were removed with a silica gel column (2.5% MeOH/DCM v/v) to yield 12.5 g (9.3 mmol, 75%) of 5A.

$^1$H NMR (400 MHz, DMSO-$d_6$) δ 8.88 (s, 1H), 8.35 (d, J=5.2 Hz, 2H), 7.98-7.88 (m, 5H), 7.59 (ddt, J=60.0, 30.9, 7.5 Hz, 11H), 7.37 (dd, J=16.2, 8.2 Hz, 4H), 7.21 (q, J=7.3 Hz, 8H), 6.81 (dd, J=8.8, 7.2 Hz, 4H), 6.05 (d, J=5.0 Hz, 1H), 5.74 (d, J=3.3 Hz, 1H), 5.35 (dd, J=11.1, 3.3 Hz, 1H), 5.18 (d, J=5.9 Hz, 1H), 4.72 (d, J=8.5 Hz, 1H), 4.58 (t, J=5.0 Hz, 1H), 4.44 (q, J=8.3, 7.3 Hz, 2H), 4.39-4.22 (m, 3H), 4.06 (q, J=4.6 Hz, 1H), 3.78 (dd, J=9.9, 4.5 Hz, 1H), 3.71 (s, 6H), 3.53 (dtd, J=19.4, 9.5, 5.1 Hz, 2H), 3.40 (dt, J=9.4, 6.4 Hz, 1H), 3.22 (d, J=4.5 Hz, 2H), 3.18 (s, 3H), 3.11 (s, 3H), 2.93 (q, J=6.5 Hz, 2H), 2.02 (s, 2H), 1.68 (s, 3H), 1.53-1.36 (m, 7H), 1.30-1.08 (m, 7H). $^{13}$C NMR (125 MHz, DMSO-$d_6$) δ 171.68, 169.38, 165.19, 165.15, 164.85, 159.23, 158.01, 157.98, 157.91, 151.93, 151.19, 144.80, 141.39, 135.49, 135.44, 133.76, 133.49, 133.46, 129.68, 129.63, 129.18, 129.17, 129.15, 129.02, 129.00, 128.99, 128.96, 128.68, 128.58, 127.73, 127.65, 126.61, 125.76, 118.03, 100.88, 85.97, 85.47, 83.59, 80.01, 71.84, 69.96, 69.79, 69.11, 68.74, 67.90, 63.54, 62.51, 62.02, 54.97, 54.95, 54.88, 51.97, 49.72, 45.62, 35.00, 34.52, 29.07, 29.00, 28.57, 26.14, 25.03, 22.68, 21.83, 7.15. LRMS calculated for $C_{74}H_{82}N_8O_{16}$ 1338.5849, found m/z 1339.4 (M), 1361.4 $(M+23)^{Na+}$, 1338.4 $(M-1)^-$, 1373.4 $(M+35)^{Cl-}$. $R_f$=0.29 in 5% MeOH/DCM v/v.

(6A)—

Compound 5A (2 g, 1.5 mmol) was dissolved in DCM (15 ml) and 4-Dimethylaminopyridine (550 mg, 4.5 mmol) was added to the stirring mixture. Succinic anhydride (300 mg, 3 mmol) was added and the solution was stirred at room temperature for 3 hours. DCM was evaporated in vacuo and the crude foam was loaded onto a 2% triethylamine in DCM v/v pretreated manual column (Φ=4.6×17). A gradient of 1-5% MeOH/2-5% triethylamine/DCM v/v was used to purify 6A. 6A came at 3% MeOH/3% triethylamine/DCM v/v in quantitative yield.

$^1$H NMR (500 MHz, DMSO-$d_6$) δ 8.89 (s, 1H), 8.42 (s, 1H), 8.30 (s, 1H), 8.09 (d, J=9.3 Hz, 1H), 7.91 (t, J=8.2 Hz, 4H), 7.75-7.65 (m, 4H), 7.65-7.53 (m, 4H), 7.47 (t, J=7.6 Hz, 2H), 7.37 (dd, J=13.9, 7.3 Hz, 4H), 7.21 (td, J=12.2, 10.6, 5.5 Hz, 7H), 6.82 (t, J=8.3 Hz, 4H), 6.04 (d, J=6.6 Hz, 1H), 5.74 (d, J=3.1 Hz, 1H), 5.45-5.41 (m, 1H), 5.36 (dd, J=11.1, 3.2 Hz, 1H), 5.08-5.02 (m, 1H), 4.75 (d, J=8.5 Hz, 1H), 4.48-4.39 (m, 3H), 4.38-4.19 (m, 5H), 3.78 (d, J=9.4 Hz, 2H), 3.70 (s, 6H), 3.50 (d, J=9.3 Hz, 2H), 3.40-3.26 (m, 6H), 3.18 (s, 3H), 3.11 (s, 3H), 2.59 (q, J=6.8, 6.3 Hz, 2H), 2.03 (s, 2H), 1.69 (s, 3H), 1.49 (s, 4H), 1.34-1.16 (m, 6H), 1.08-0.97 (m, 4H). $^{13}$C NMR (125 MHz, DMSO-$d_6$) δ 173.35, 171.73, 171.48, 169.39, 165.20, 165.14, 164.85, 159.33, 158.06, 158.03, 157.96, 151.94, 151.22, 144.68, 141.81, 135.31, 133.75, 133.48, 133.45, 129.69, 129.61, 129.17, 129.16, 129.14, 129.01, 128.98, 128.95, 128.68, 128.57, 127.75, 127.61, 126.66, 125.86, 113.11, 100.88, 85.82, 85.69, 81.39, 77.45, 71.89, 71.01, 70.19, 69.96, 68.70, 67.89, 63.28, 62.04, 54.98, 54.96, 52.01, 49.71, 34.95, 34.54, 29.00, 28.92, 28.85, 28.81, 28.53, 26.05, 24.95, 22.67, 21.80, 7.18. LRMS calculated for $C_{78}H_{86}N_8O_{19}$ 1438.6009, found m/z 1439.4 (M), 1463.4 $(M+23)^{Na+}$, 1437.4 (M-1)$^-$. $R_f$=0.23 in 5% MeOH/5% Et$_3$N/DCM v/v (7A)—

Compound 6A (2.2 g, 1.4 mmol) was dissolved in acetonitrile (110 ml) and HBTU (1.1 g, 2.9 mmol) and DIEA (550 mg, 4.3 mmol) were added. The mixture was shaken for 5 minutes then LCAA-CPG (18 g, 540 Å, 130 μmol/g) was added and shaken over night at room temperature. The CPG was filtered and washed with 300 ml each of DCM, 20% MeOH/DCM v/v, and diethyl ether then dried in vacuo. The CPG was shaken for 1 hour in acetic anhydride (25 ml), pyridine (75 ml), and triethylamine (1 ml) before being washed again by the same conditions as before. Compound 7A was dried in vacuo overnight and loading was measured with a spectrophotometer (72 μmol/g).

(8A)—

Compound 5A (1.0 g, 0.75 mmol) was coevaporated with ACN twice and put under a strict argon atmosphere. DCM (7.5 ml) was added to the flask and cooled to 0° C. before the addition of 2-Cyanoethyl N,N,N',N'-tetraisopropylphosphordiamidite (450 mg, 1.5 mmol). The mixture was stirred for 20 minutes then 4,5-Dicyanoimidazole (90 mg, 0.75 mmol) was added to the reaction. The reaction was slowly warmed to room temperature over night. The reaction was washed with saturated bicarbonate and the aqueous layer extracted with DCM. The organic layer was dried with Na$_2$SO$_4$, evaporated in vacuo to yield a pale yellow foam. The foam was loaded onto a pretreated manual column (Φ=4.6×17) prepared with 2% triethylamine/49% EtOAc/hexanes v/v. The impurities were eluted with 80% EtOAc/hexanes v/v (8 CV) followed by 100% EtOAc (8 CV). Then 8A was eluted with 2% MeOH/DCM v/v (5 CV), and 4% MeOH/DCM v/v (8 CV). 8A was evaporated in vacuo to yield 900 mg (0.58 mmol, 78%) of the amidite as a diastereomeric mixture.

$^1$H NMR (500 MHz, DMSO-$d_6$) δ 8.88 (d, J=1.9 Hz, 1H), 8.41 (s, 1H), 8.32 (d, J=9.1 Hz, 1H), 8.01 (d, J=9.3 Hz, 1H), 7.91 (t, J=8.4 Hz, 4H), 7.75-7.52 (m, 8H), 7.47 (t, J=7.7 Hz, 2H), 7.36 (dt, J=12.4, 7.4 Hz, 4H), 7.21 (t, J=8.6 Hz, 7H), 6.81 (q, J=7.7, 7.1 Hz, 4H), 6.06 (dd, J=8.8, 5.3 Hz, 1H), 5.75 (d, J=3.3 Hz, 1H), 5.37 (dd, J=11.1, 3.3 Hz, 1H), 4.84 (q, J=4.7 Hz, 1H), 4.74 (d, J=8.5 Hz, 1H), 4.63 (dd, J=10.1, 5.1 Hz, 1H), 4.49-4.41 (m, 2H), 4.38-4.15 (m, 3H), 3.80 (dd, J=17.4, 8.2 Hz, 3H), 3.70 (d, J=2.9 Hz, 7H), 3.67-3.19 (m, 14H), 3.17 (s, 3H), 3.11 (s, 3H), 2.77 (t, J=6.0 Hz, 1H), 2.60 (t, J=5.9 Hz, 1H), 2.03 (s, 2H), 1.90 (s, 1H), 1.69 (s, 3H), 1.49 (s, 4H), 1.43-1.34 (m, 2H), 1.23 (dt, J=14.6, 6.6 Hz, 3H), 1.01 (d, J=6.7 Hz, 3H). $^{13}$C NMR (100 MHz, DMSO-$d_6$) δ 172.00, 171.70, 169.39, 165.20, 165.16, 164.87, 159.29, 158.05, 158.03, 157.93, 151.89, 151.83, 151.13, 151.05, 144.73, 144.69, 141.97, 141.72, 135.42, 135.34, 133.75, 133.49, 133.45, 129.70, 129.66, 129.62, 129.20, 129.16, 129.02, 128.95, 128.80, 128.68, 128.57, 127.69, 127.62, 126.63, 125.93, 125.85, 118.86, 118.67, 113.05, 100.89, 86.40, 86.13, 85.62, 85.59, 82.88, 82.65, 78.92, 78.75, 71.84, 71.01, 70.54, 70.37, 70.06, 69.98, 69.88, 68.73, 67.91, 63.00, 62.83, 62.03, 58.83, 58.65, 58.22, 58.03, 54.96, 54.86, 49.74, 46.12, 45.65, 42.74, 42.62, 42.58, 42.46, 40.62, 38.30, 34.99, 34.52, 29.06, 28.97, 28.57, 26.18, 25.09, 25.06, 24.37, 24.29, 24.23, 24.16, 22.67, 21.83, 21.05, 19.89, 19.82, 19.78, 19.71, 19.07, 10.57. $^{31}$P NMR (160 MHz, DMSO-$d_6$) δ 154.09, 153.88. LRMS calculated for $C_{83}H_{99}N_{10}O_{17}P$ 1538.6927, found m/z 1539.3 (M), 1562.3 $(M+23)^{Na+}$, 1573.3 $(M+35)^{Cl-}$. $R_f$=0.35 in 5% MeOH/DCM v/v.

Example 68

Scheme 120

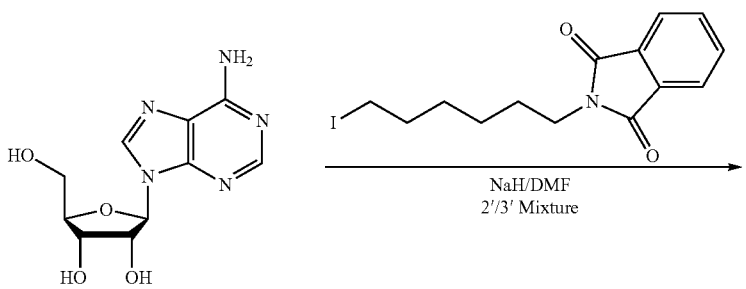

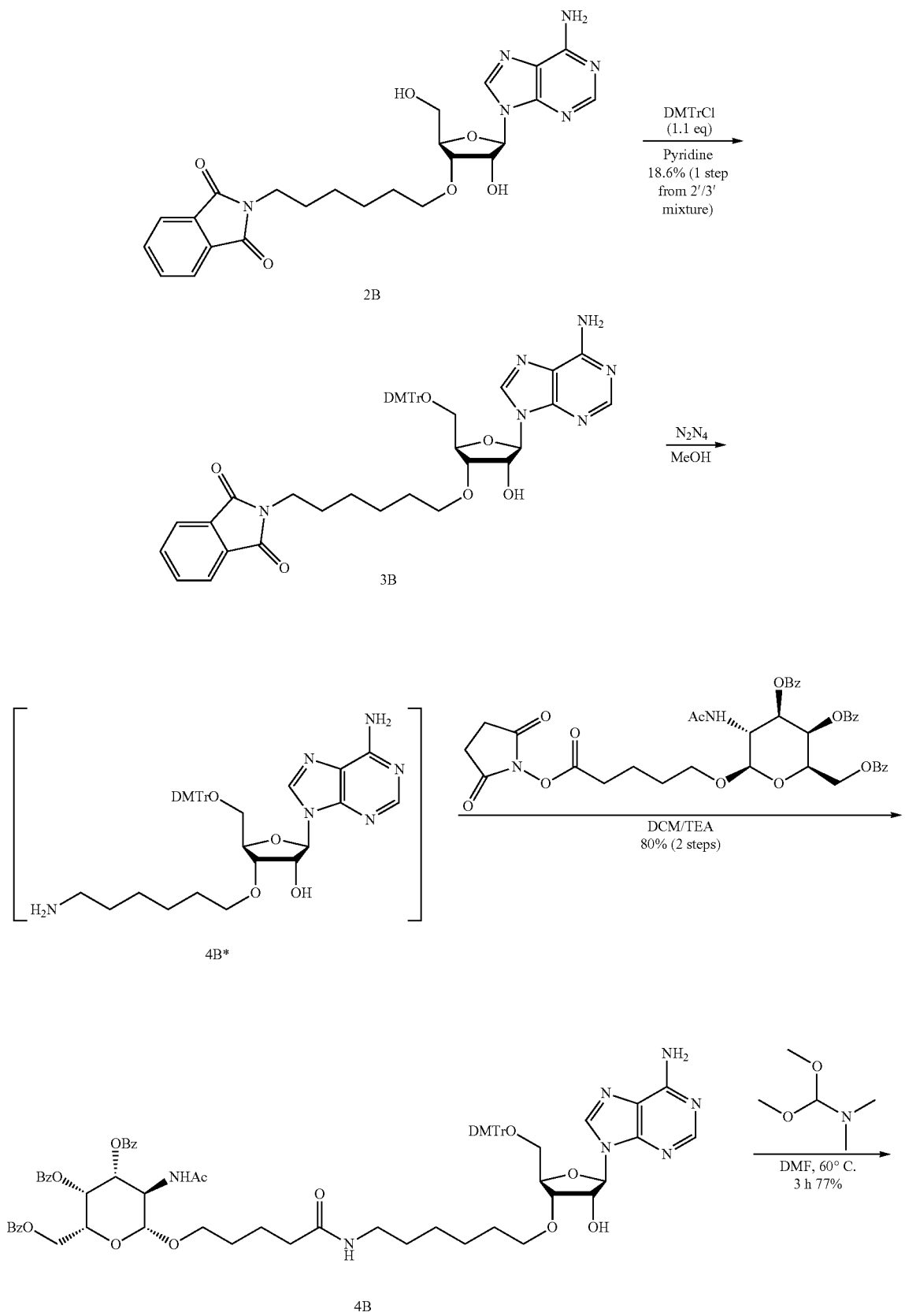

-continued
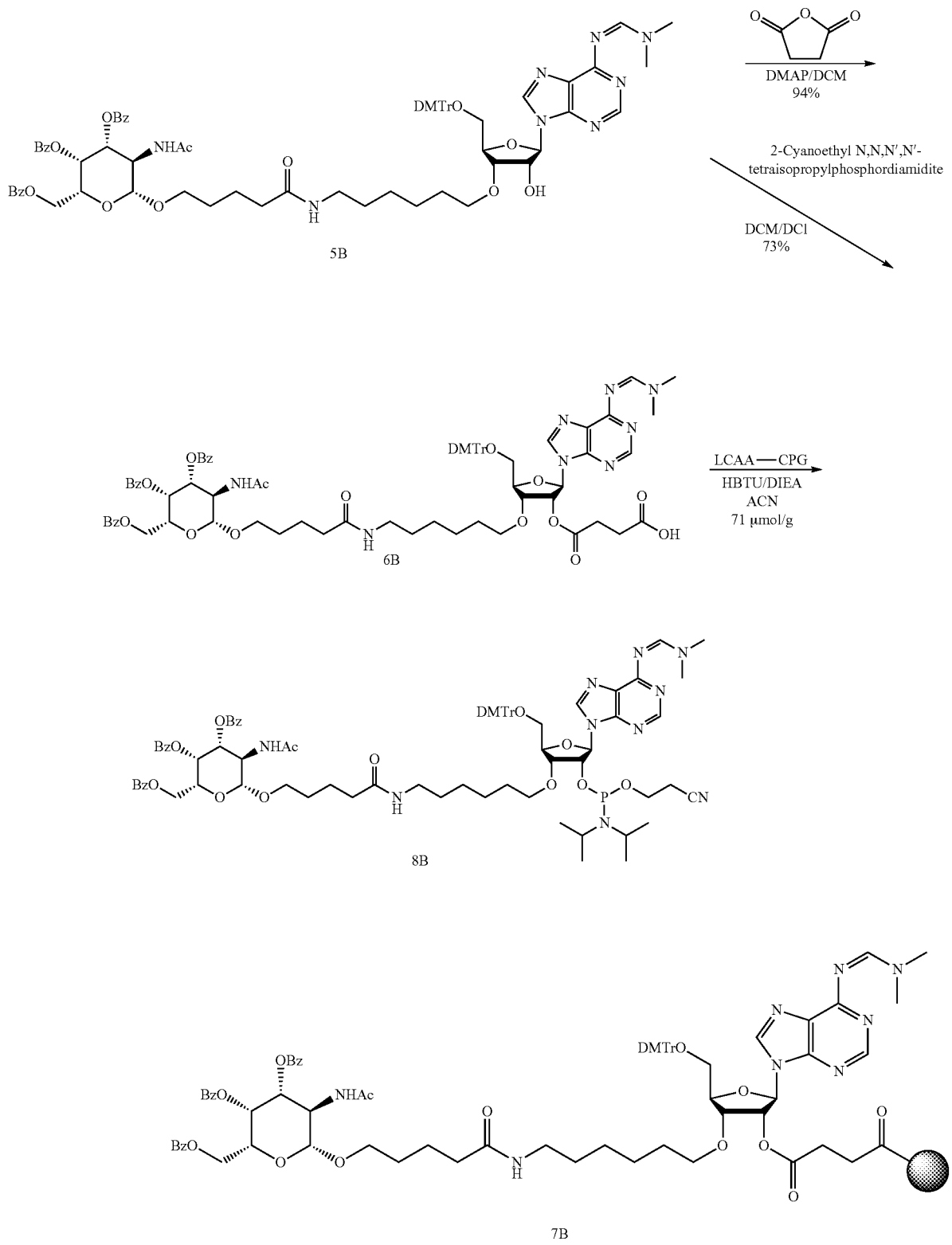

(3B)—

A mixture of 2A and 2B (12 g, 24.2 mmol) was purified again in the same manner previously described to remove as much of the 2'-O-alkylated isomer as possible. A mixture containing mostly 2B (2.8 g, 5.7 mmol) was tritylated in the same manner as compound 2A to yield 2.6 g of 3B (3.3 mmol, 58%).

$^1$H NMR (400 MHz, DMSO-d$_6$) δ 8.26 (s, 1H), 8.09 (s, 1H), 7.82 (d, J=7.5 Hz, 4H), 7.34-7.15 (m, 11H), 6.80 (d, J=6.8 Hz, 4H), 5.89 (d, J=4.1 Hz, 1H), 5.46 (d, J=5.8 Hz, 1H), 4.84 (d, J=4.6 Hz, 1H), 4.14 (t, J=4.7 Hz, 1H), 4.09-4.03 (m, 1H), 3.69 (s, 6H), 3.61-3.51 (m, 3H), 3.15 (dd, J=10.1, 4.3 Hz, 1H), 1.58-1.45 (m, 4H), 1.25 (d, J=8.0 Hz, 4H). $^{13}$C NMR (100 MHz, DMSO-d$_6$) δ 167.92, 158.01, 156.06, 152.59, 149.25, 144.78, 139.57, 135.47, 134.33, 131.58, 129.63, 127.73, 127.62, 126.61, 122.95, 119.16, 113.08, 88.22, 85.48, 80.83, 77.64, 71.70, 69.58, 63.09, 54.96, 52.00, 37.32, 29.05, 27.88, 26.07, 25.06, 7.15. LRMS calculated for C$_{45}$H$_{46}$N$_6$O$_8$ 798.3377, found m/z 799.2 (M+1)$^+$, 821.1 (M+23)$^{Na+}$. R$_f$=0.30 in 5% MeOH/DCM v/v (4B)—

Compound 3B was deprotected in a similar fashion as compound 3A to yield crude 4B*. Crude 4B* was then coupled to the GalNAc derivative as described previously in 3A* to yield 2.5 g of 4B (1.9 mmol, 80%).

$^1$H NMR (400 MHz, DMSO-d$_6$) δ 8.27 (s, 1H), 8.10 (s, 1H), 8.03-7.88 (m, 5H), 7.75-7.44 (m, 10H), 7.42-7.16 (m, 13H), 6.82 (dd, J=8.9, 2.4 Hz, 4H), 5.90 (d, J=4.4 Hz, 1H), 5.75 (d, J=3.2 Hz, 1H), 5.47 (d, J=6.0 Hz, 1H), 5.37 (dd, J=11.1, 3.2 Hz, 1H), 4.87 (q, J=5.0 Hz, 1H), 4.73 (d, J=8.5 Hz, 1H), 4.50-4.41 (m, 2H), 4.39-4.22 (m, 2H), 4.15 (t, J=5.0 Hz, 1H), 4.07 (q, J=4.4 Hz, 1H), 3.84-3.75 (m, 1H), 3.71 (s, 6H), 3.64-3.56 (m, 1H), 3.51 (d, J=9.7 Hz, 1H), 3.45-3.38 (m, 1H), 3.27 (dd, J=10.4, 3.6 Hz, 1H), 3.17 (dd, J=10.4, 4.7 Hz, 1H), 3.00 (q, J=6.5 Hz, 2H), 2.05 (s, 2H), 1.70 (s, 3H), 1.51 (s, 6H), 1.40-1.18 (m, 6H). $^{13}$C NMR (125 MHz, DMSO-d$_6$) δ 171.74, 169.41, 165.21, 165.16, 164.87, 158.01, 156.05, 152.58, 152.57, 149.25, 144.76, 139.58, 139.56, 135.48, 135.46, 133.78, 133.52, 133.48, 129.62, 129.19, 129.17, 129.04, 129.00, 128.99, 128.97, 128.70, 128.60, 127.75, 127.62, 126.63, 119.15, 113.09, 100.90, 88.16, 85.49, 80.86, 77.70, 71.85, 71.71, 69.96, 69.66, 68.77, 67.91, 63.11, 62.02, 54.97, 49.73, 35.03, 29.24, 29.17, 28.59, 26.30, 25.25, 22.70, 21.87. LRMS calculated for C$_{37}$H$_{44}$N$_6$O$_6$ 668.3322 found m/z 691.2 (M+1)$^+$, 703.2 (M+35)$^{Cl-}$ (4B*). LRMS calculated for C$_{71}$H$_{77}$N$_7$O$_{16}$ 1283.5427, found m/z 1306.2 (M+23)$^{Na+}$, 1282.2 (M−1)$^−$, 1318.2 (M+35)$^{Cl-}$. R$_f$=0.20 in 5% MeOH/DCM v/v (5B)—

Compound 4B (2.5 g, 1.9 mmol) was protected in the same way as compound 4A to yield 2.0 g of 5B (1.5 mmol, 77%).

$^1$H NMR (400 MHz, DMSO-d$_6$) δ 8.89 (s, 1H), 8.37 (d, J=5.5 Hz, 2H), 8.03-7.87 (m, 5H), 7.73-7.45 (m, 10H), 7.40-7.29 (m, 4H), 7.21 (dd, J=15.7, 8.2 Hz, 7H), 6.81 (dd, J=8.8, 4.4 Hz, 4H), 5.95 (d, J=4.5 Hz, 1H), 5.75 (d, J=3.2 Hz, 1H), 5.50 (d, J=5.9 Hz, 1H), 5.36 (dd, J=11.1, 3.2 Hz, 1H), 4.90 (q, J=5.1 Hz, 1H), 4.73 (d, J=8.5 Hz, 1H), 4.45 (q, J=8.1, 7.2 Hz, 2H), 4.39-4.23 (m, 2H), 4.15 (t, J=4.9 Hz, 1H), 4.08 (q, J=4.4 Hz, 1H), 3.84-3.75 (m, 1H), 3.70 (s, 6H), 3.65-3.56 (m, 1H), 3.54-3.47 (m, 1H), 3.17 (s, 4H), 3.11 (s, 3H), 3.00 (q, J=6.5 Hz, 2H), 2.05 (s, 2H), 1.70 (s, 3H), 1.57-1.43 (m, 6H), 1.40-1.19 (m, 6H). $^{13}$C NMR (100 MHz, DMSO-d$_6$) δ 171.77, 169.42, 165.21, 165.17, 164.88, 159.21, 158.02, 158.00, 157.92, 151.90, 151.27, 144.74, 141.47, 135.51, 135.46, 133.78, 133.52, 133.48, 129.63, 129.58, 129.19, 129.17, 129.04, 129.00, 128.97, 128.70, 128.60, 127.75, 127.63, 126.65, 125.76, 113.09, 100.90, 88.23, 85.49, 80.95, 77.75, 71.86, 71.65, 69.98, 69.69, 68.77, 67.92, 63.15, 62.04, 54.97, 49.75, 45.68, 40.64, 35.04, 34.54, 29.23, 29.16, 28.60, 26.30, 25.24, 22.70, 21.88, 11.35. LRMS calculated for C$_{74}$H$_{282}$N$_8$O$_{16}$ 1338.5849, found m/z 1341.3 (M+1)$^+$, 1361.3 (M+23)$^{Na+}$, 1337.4 (M−1)$^−$, 1373.4 (M+35)$^{Cl-}$. R$_f$=0.40 in 7% MeOH/DCM v/v (6B)—

Compound 5B (500 mg, 0.37 mmol) was treated with succinic anhydride in the same manner as compound 5A to yield 540 mg of 6B (0.35 mmol, 94%) $^1$H NMR (400 MHz, DMSO-d$_6$) δ 8.90 (s, 1H), 8.42 (d, J=9.1 Hz, 2H), 8.06 (d, J=9.3 Hz, 1H), 7.91 (t, J=6.9 Hz, 4H), 7.77-7.45 (m, 10H), 7.37 (t, J=7.7 Hz, 2H), 7.30-7.10 (m, 9H), 6.85-6.73 (m, 4H), 6.19 (d, J=3.0 Hz, 1H), 6.12-6.04 (m, 1H), 5.75 (d, J=2.2 Hz, 1H), 5.36 (dd, J=11.1, 3.1 Hz, 1H), 4.75 (d, J=8.5 Hz, 1H), 4.70-4.63 (m, 1H), 4.49-4.40 (m, 2H), 4.40-4.23 (m, 3H), 4.10-4.03 (m, 1H), 3.83-3.76 (m, 2H), 3.69 (s, 6H), 3.54-3.48 (m, 2H), 3.18 (s, 3H), 3.11 (s, 4H), 2.98 (q, J=6.4, 5.5 Hz, 3H), 2.80 (q, J=7.2 Hz, 4H), 2.57 (d, J=3.5 Hz, 2H), 2.05 (s, 2H), 1.69 (s, 3H), 1.50 (s, 4H), 1.41 (s, 2H), 1.33 (s, 2H), 1.26-1.14 (m, 7H). $^{13}$C NMR (125 MHz, DMSO-d$_6$) δ 174.17, 172.71, 172.37, 170.34, 166.14, 166.09, 165.80, 160.24, 158.93, 158.91, 158.88, 152.99, 151.83, 145.56, 142.79, 136.40, 136.26, 134.71, 134.45, 134.41, 130.51, 130.46, 130.10, 129.97, 129.95, 129.93, 129.90, 129.64, 129.53, 128.65, 128.52, 127.56, 126.65, 113.99, 101.84, 87.28, 86.31, 81.71, 76.73, 73.86, 72.82, 71.23, 70.90, 69.68, 68.84, 63.47, 62.97, 55.89, 52.92, 50.66, 46.35, 35.93, 35.49, 30.06, 29.74, 29.67, 29.50, 27.18, 26.12, 23.62, 22.78, 10.55, 8.11. LRMS calculated for C$_{78}$H$_{86}$N$_8$O$_{19}$ 1438.6009. R$_f$=0.38 in 5% MeOH/5% Et$_3$N/DCM v/v (7B)—

Compound 6B (510 mg, 0.33 mmol) was loaded on to LCAA-CPG in the same manner as 6A to yield 4.1 g of CPG (71 μmol/g).

(8B)—

Compound 5B (1.4 g, 1.07 mmol) was phosphitylated in the same manner as compound 5A to yield 1.2 g of the amidite 8B (0.78 mmol, 73%) as a diastereomeric mixture.

$^1$H NMR (400 MHz, DMSO-d$_6$) δ 8.88 (d, J=5.5 Hz, 1H), 8.41-8.30 (m, 2H), 7.98-7.89 (m, 5H), 7.72-7.45 (m, 11H), 7.41-7.29 (m, 4H), 7.29-7.14 (m, 8H), 6.84-6.78 (m, 4H), 6.09 (dd, J=28.1, 4.6 Hz, 1H), 5.74 (d, J=3.4 Hz, 1H), 5.35 (dd, J=11.1, 3.3 Hz, 1H), 5.27-5.14 (m, 1H), 4.72 (d, J=8.5 Hz, 1H), 4.44 (q, J=7.3, 6.8 Hz, 2H), 4.37-4.22 (m, 3H), 4.14-4.09 (m, 1H), 3.81-3.72 (m, 2H), 3.70 (s, 6H), 3.56-3.35 (m, 6H), 3.18 (s, 3H), 3.12-3.10 (m, 3H), 3.03-2.96 (m, 3H), 2.04 (s, 2H), 1.69 (s, 3H), 1.50 (s, 6H), 1.38-1.19 (m, 7H), 1.04 (q, J=7.0 Hz, 9H), 0.75 (d, J=6.7 Hz, 3H). $^{13}$C NMR (125 MHz, DMSO-d$_6$) δ 171.71, 169.36, 165.17, 165.13, 164.84, 159.18, 158.01, 157.86, 151.80, 151.13, 144.68, 144.64, 141.62, 135.41, 135.38, 133.73, 133.45, 133.42, 129.57, 129.14, 129.00, 128.92, 128.65, 128.55, 127.72, 127.58, 126.63, 125.82, 125.78, 118.75, 118.56, 113.06, 100.88, 87.48, 87.12, 85.55, 85.47, 81.28, 80.95, 77.36, 77.02, 73.45, 73.34, 72.81, 72.67, 71.83, 69.96, 69.74, 68.73, 67.90, 62.74, 62.57, 62.01, 58.73, 58.59, 58.15, 58.00, 54.94, 54.85, 49.74, 42.75, 42.66, 42.50, 42.40, 35.02, 34.52, 29.24, 29.14, 28.57, 26.31, 25.28, 24.26, 24.20, 24.14, 23.78, 23.73, 22.66, 21.85, 19.77, 19.72, 19.55, 19.49. $^{31}$P NMR (162 MHz, DMSO-d$_6$) δ 154.92, 154.69. LRMS calculated for C$_{83}$H$_{99}$N$_{10}$O$_{17}$P 1538.6927, found m/z 1539.3 (M+1)$^+$, 1562.3 (M+23)$^{Na+}$, 1573.3 (M+35)$^{Cl-}$. R$_f$=0.25 in 5% MeOH/DCM v/v Example 69
Scheme 121
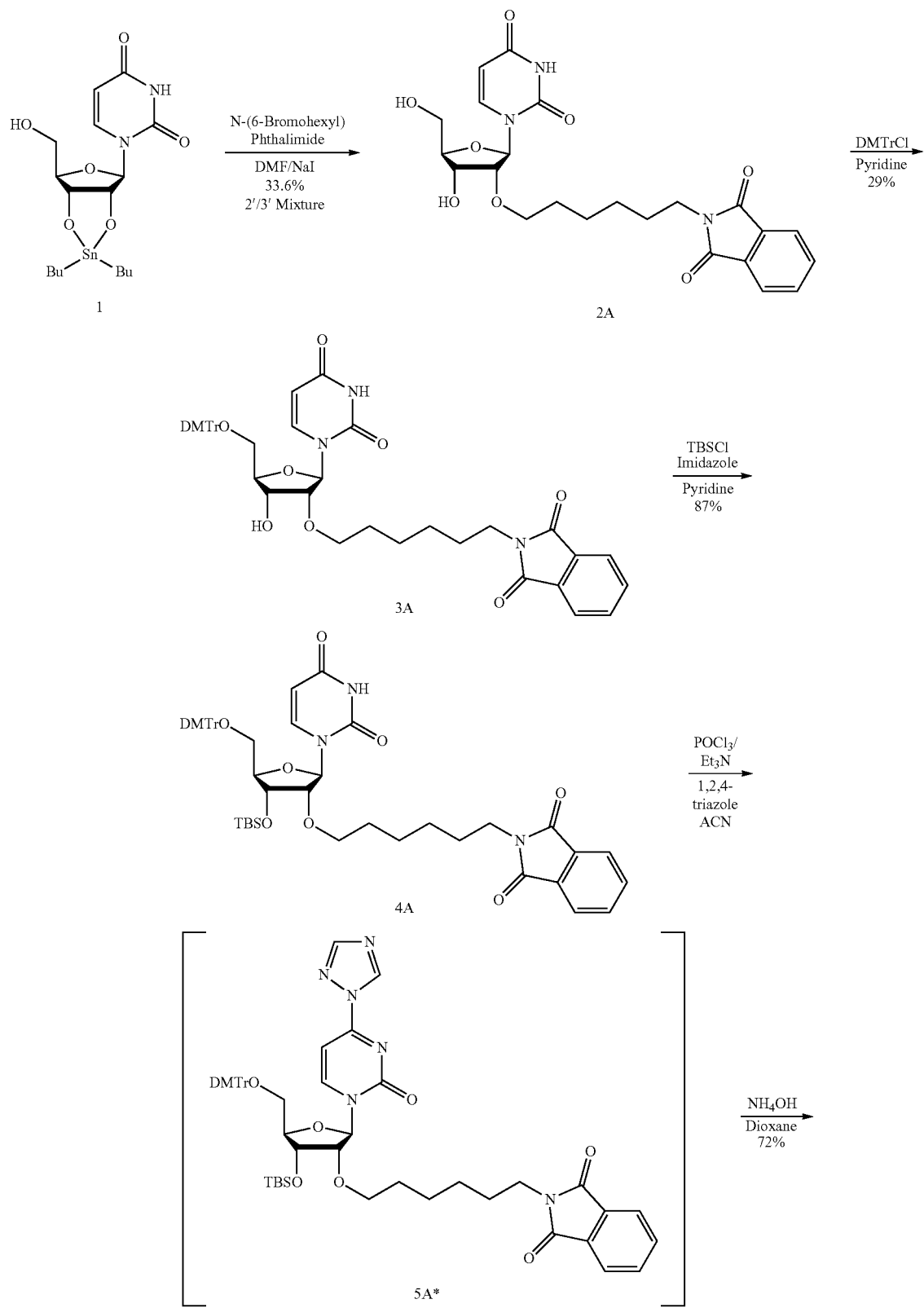

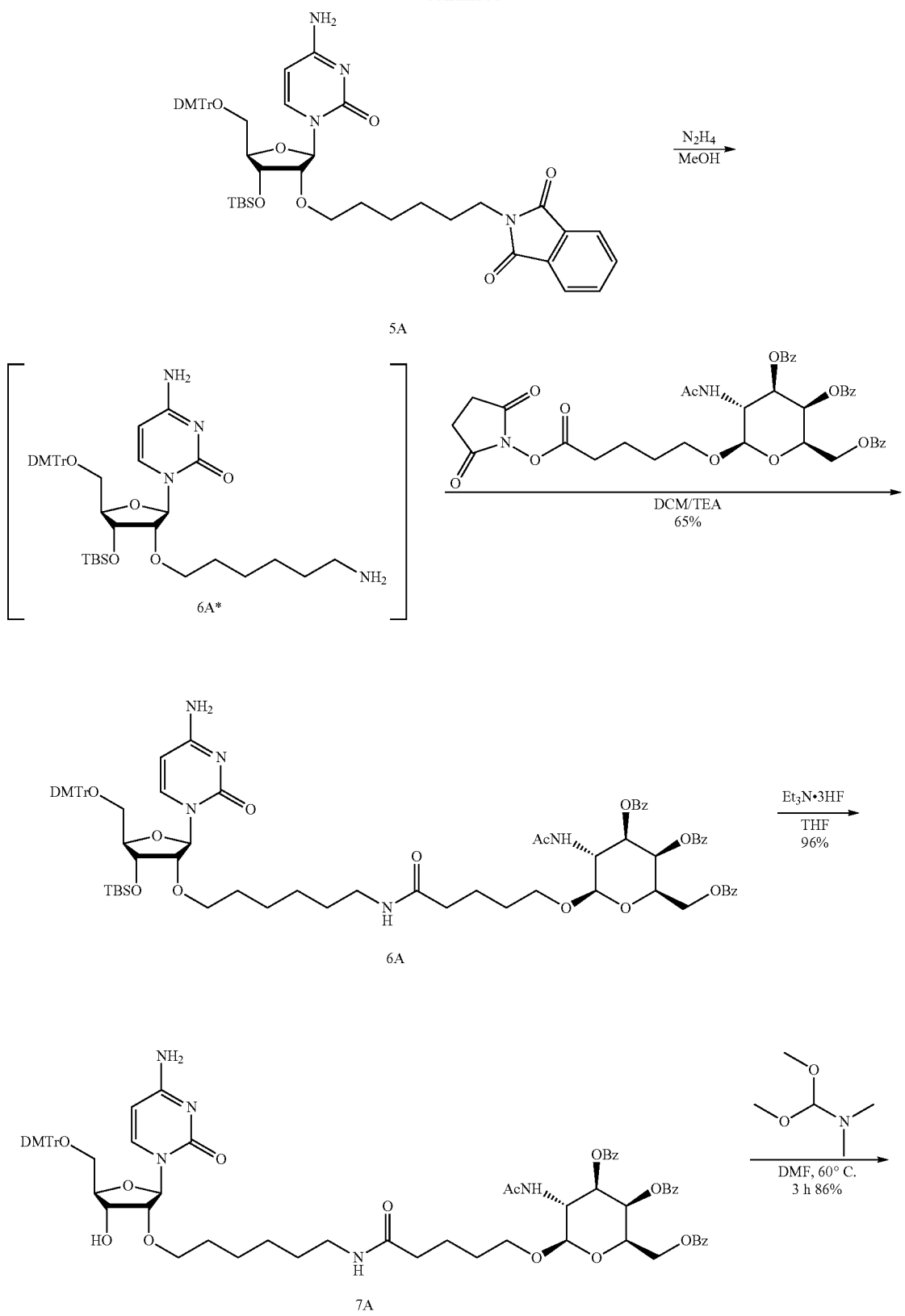

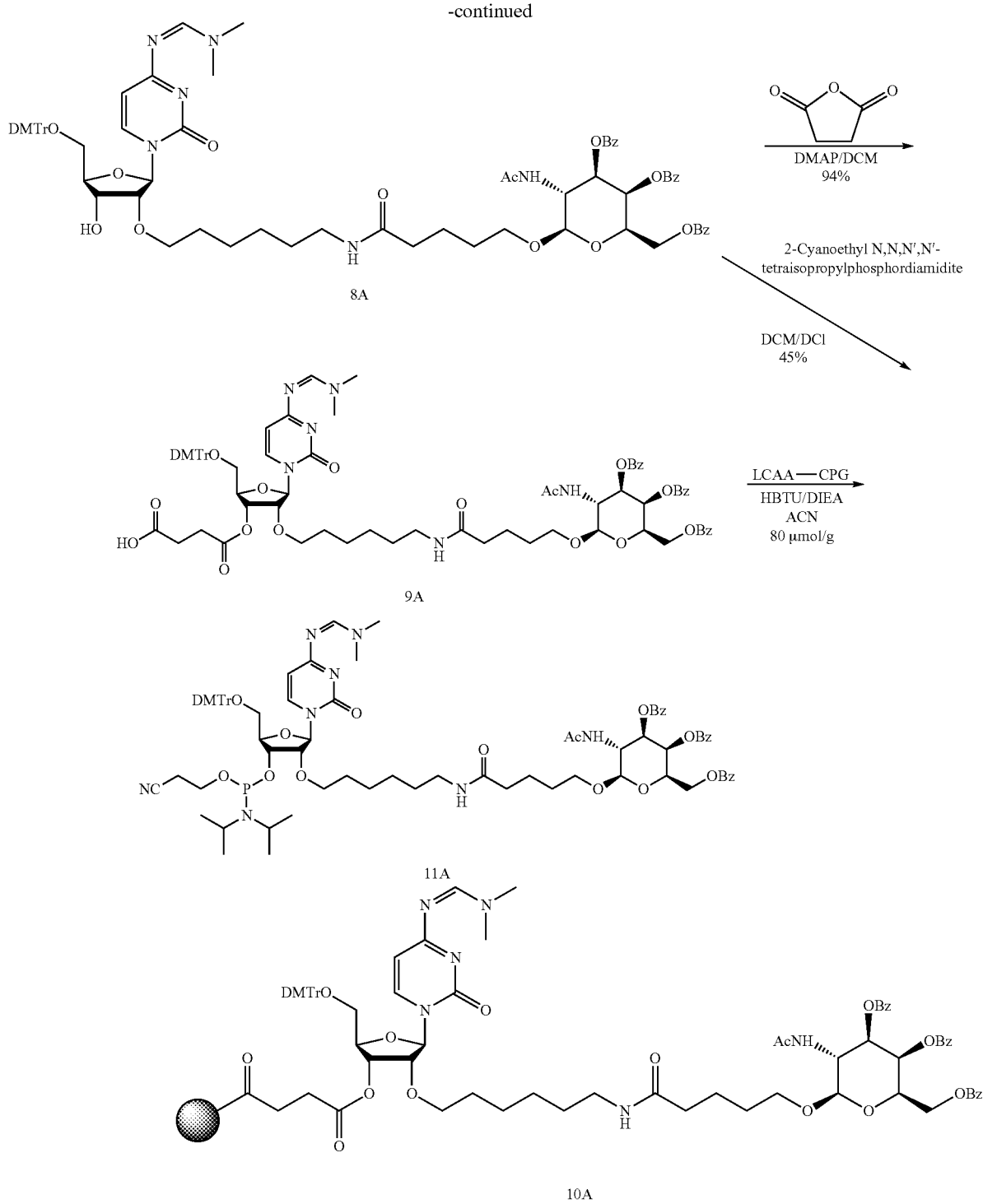

LRMS calculated for $C_{24}H_{28}N_6O_6$ 496.52, found m/z 497.2 $(M+1)^+$, 519.2 $(M+23)^{Na+}$, 486.2 $(M-1)^-$, 522.2 $(M+35)^{Cl-}$.

(2A/2B)—

Compound 1 (2.0 g, 4.2 mmol) was microwaved (100C, 200 W) in the presence of N-(6-Bromohexyl)Phthalimide (2.6 g, 8.4 mmol) in DMF (10 ml) for 6 hours. NaI (125 mg, 0.84 mmol) was used to speed up the reaction. DMF was evaporated in vacuo and the crude gum was adsorbed to silica and purified with a 40 g gold column. 2A, as well as the 3'-O-alkylated isomer 2B, eluted together with 5% MeOH in DCM v/v. 670 mg (1.4 mmol, 33%) of the regioisomeric mixture was collected in a roughly 1 to 1 ratio by 1H NMR. H NMR (500 MHz, DMSO-$d_6$) δ 11.31 (s, 2H), 7.93 (d, J=8.1 Hz, H), 7.88-7.81 (m, 7H), 5.82 (d, J=5.0 Hz, 1H), 5.73 (d, J=5.3 Hz, 1H), 5.63 (dd, J=8.1, 1.9 Hz, 2H), 5.30 (d, J=6.1 Hz, 1H), 5.12 (t, J=4.9 Hz, 2H), 5.03 (d, J=5.9 Hz, 1H), 4.15 (q, J=5.4 Hz, 1H), 4.07 (q, J=5.0 Hz, L H), 3.90 (d, J=3.9 Hz, 4H), 3.85 (t, found 3.75 (t, 5=4.6 Hz, 1H), 3.68-3.49 (m, 9H), 3.43 (dd, J=17.9, 9.5 Hz, 2H), 1.65-1.43 (m, 7H), 1.39-1.21 (m, 7H). $^{13}$C NMR (100 MHz, DMSO-$d_6$) δ 170.71, 170.69, 165.87, 165.82, 153.48, 153.27, 143.32, 143.14, 137.12, 134.36, 125.75, 104.53, 104.44, 90.81, 88.93, 87.82, 85.53, 83.85, 80.17, 75.40, 72.43, 72.33, 71.09, 63.50, 63.22, 57.68, 48.54, 40.13, 40.09, 31.95, 31.72, 30.68, 28.89, 28.81, 27.90, 27.71. LRMS calculated for $C_{23}H_{27}N_3O_8$ 473.1798, found m/z 474.1 $(M+1)^+$, 472.0 $(M-1)^-$, 508.0 $(M+35)^{Cl-}$. $R_f$=0.40 in 5% MeOH/DCM v/v (3A/3B)—

A mixture of compounds 2A and 2B (650 mg, 1.4 mmol) was initially coevaporated with pyridine to remove any trace water. Then the nucleoside mixture was cooled to 0° C. in pyridine (14 ml) before the addition of DMTrCl (510 mg, 1.5 mmol) and allowed to warm to room temperature over night. An additional 0.2 eq of DMTrCl was added and the reaction mixture stirred for 4 hours before another 0.2 eq of DMTrCl was added. The reaction was then stirred for 2 hours, quenched with MeOH and evaporated in vacuo. The crude mixture was washed with saturated NaHCO$_3$, extracted with DCM, and the organic layer dried with Na$_2$SO$_4$. The mixture was loaded onto a column (40 g gold) and eluted with 60-70% EtOAc/hexanes v/v to yield 310 mg (0.34 mmol, 29%) of 3A and 340 mg (0.44 mmol, 32%) of 3B.

3A)

$^1$H NMR (400 MHz, DMSO-$d_6$) δ 11.35 (s, 1H), 7.89-7.76 (m, 4H), 7.71 (d, J=8.1 Hz, 1H), 7.40-7.28 (m, 4H), 7.24 (dd, J=8.8, 2.1 Hz, 5H), 6.89 (d, J=8.6 Hz, 4H), 5.77 (d, J=3.6 Hz, 1H), 5.27 (d, J=8.1 Hz, 1H), 5.09 (d, J=6.7 Hz, 1H), 4.15 (q, J=6.1 Hz, 1H), 3.97-3.92 (m, 1H), 3.90-3.85 (m, 1H), 3.73 (s, 6H), 3.61-3.49 (m, 4H), 3.30-3.17 (m, 2H), 1.60-1.46 (m, 4H), 1.34-1.22 (m, 4H). $^{13}$C NMR (125 MHz, DMSO-$d_6$) δ 167.87, 162.92, 158.10, 158.09, 150.22, 144.60, 140.15, 135.31, 135.04, 134.28, 131.55, 129.73, 127.85, 127.66, 126.75, 122.92, 113.22, 113.20, 101.43, 101.40, 87.11, 87.09, 85.84, 82.56, 80.79, 69.71, 68.43, 62.58, 55.02, 55.00, 28.88, 27.86, 26.01, 24.92. LRMS calculated for $C_{44}H_{45}N_3O_{10}$ 775.3105, found m/z 798.0 $(M+23)^{Na+}$, 774.2 $(M-1)^-$, 810.1 $(M+35)^{Cl-}$ (3A). $R_f$=0.28 in 60% EtOAc/hexanes v/v (3A)

3B)

$^1$H NMR (400 MHz, DMSO-$d_6$) δ 11.34 (s, 1H), 7.88-7.71 (m, 5H), 7.38-7.18 (m, 9H), 6.87 (dd, J=8.8, 1.5 Hz, 4H), 5.68 (d, J=3.5 Hz, 1H), 5.40 (d, J=5.7 Hz, 1H), 5.29 (d, J=8.1 Hz, 1H), 4.22 (q, J=5.1 Hz, 1H), 3.97 (d, J=6.5 Hz, 1H), 3.92-3.86 (m, 1H), 3.71 (s, 6H), 3.54 (q, J=8.2, 7.2 Hz, 3H), 3.34 (t, J=6.7 Hz, 1H), 3.30-3.18 (m, 2H), 1.58-1.40 (m, 4H), 1.28-1.19 (m, 4H). $^{13}$C NMR (100 MHz, DMSO-$d_6$) δ 167.90, 163.02, 158.11, 150.41, 144.59, 140.45, 135.26, 135.09, 134.33, 131.57, 129.72, 127.87, 127.65, 126.78, 122.95, 113.21, 101.34, 89.41, 85.92, 80.35, 76.70, 72.01, 69.56, 63.47, 62.35, 55.01, 37.32, 30.15, 29.03, 27.87, 26.07, 25.07, 18.59. LRMS calculated for $C_{44}H_{45}N_3O_{10}$ 775.3105, found m/z 798.0 $(M+23)^{Na+}$, 774.2 $(M-1)^-$, 810.0 $(M+35)^{Cl-}$ (3B). $R_f$=0.16 in 60% EtOAc/hexanes v/v (3B).

(4A)—

Compound 3A (1.0 g, 1.3 mmol) was dissolved in pyridine (4.5 ml) and imidazole (260 mg, 3.9 mmol) was added. The mixture was stirred for 10 minutes at room temperature before the addition of TBSCl (290 mg, 1.9 mmol) and the reaction mixture was then stirred at room temperature over night. The reaction was quenched with MeOH and evaporated in vacuo. The crude product was washed with saturated NaHCO$_3$ and extracted with DCM. The organic layer was dried with Na$_2$SO$_4$ before silica gel purification. The product 4A eluted with 35-45% EtOAc/hexanes v/v to yield 1.0 g of product (1.1 mmol, 87%).

$^1$H NMR (400 MHz, DMSO-$d_6$) δ 11.35 (s, 1H), 7.89-7.76 (m, 5H), 7.39-7.27 (m, 4H), 7.27-7.18 (m, 5H), 6.93-6.83 (m, 4H), 5.74 (s, 1H), 5.27 (d, J=8.1 Hz, 1H), 4.28-4.21 (m, 1H), 3.89 (t, J=6.2 Hz, 2H), 3.72 (d, J=0.9 Hz, 6H), 3.62-3.49 (m, 3H), 3.46-3.35 (m, 2H), 3.17 (dd, J=10.9, 3.8 Hz, 1H), 1.60-1.42 (m, 4H), 1.26 (dd, J=15.9, 8.0 Hz, 4H), 0.71 (s, 9H), −0.06 (d, J=28.2 Hz, 6H). $^{13}$C NMR (125 MHz, dmso) δ 173.26, 168.44, 163.58, 155.55, 149.75, 145.74, 140.49, 140.30, 139.68, 136.94, 135.19, 135.15, 133.22, 133.12, 132.24, 128.32, 118.58, 118.56, 91.39, 87.57, 85.97, 75.01, 74.88, 60.43, 60.42, 42.70, 34.50, 33.29, 31.46, 30.82, 30.54, 22.96, 0.58, 0.00. LRMS calculated for $C_{50}H_{59}N_3O_{10}Si$ 889.3970, found m/z 912.2 $(M+23)^{Na+}$, 888.3 $(M-1)^-$, 925.2 $(M+35)^{Cl-}$. $R_f$=0.72 in 60% EtOAc/hexanes v/v (5A)—

1,2,4-triazole (9.1 g, 131 mmol) was added to acetonitrile (50 ml) and cooled to 0° C. POCl$_3$ (4.6 g, 30.2 mmol) was added to form a homogeneous solution. After 20 minutes at 0° C., Et$_3$N (13.2 g, 131 mmol) was added resulting in the formation of Et$_3$NHCl salt. In a separate flask, compound 4A (11.7 g, 13.1 mmol) was dissolved in acetonitrile (80 ml) and slowly added to the triazole containing flask and allowed to stir for 3 hours. Acetonitrile was removed in vacuo and the resulting crude foam was dissolved in EtOAc. The salt as filtered off and the organic layer was washed with saturated NaHCO$_3$ then dried with Na$_2$SO$_4$. EtOAc was removed in vacuo to yield 5A* as a light yellow foam.

LRMS calculated for $C_{52}H_{60}N_6O_9Si$ 940.4191, found m/z 963.0 $(M+23)^{Na+}$, 940.2 $(M-1)^-$, 975.1 $(M+35)^{Cl-}$. $R_f$=0.50 in 60% EtOAc/hexanes v/v.

5A* was then dissolved in dioxane (132 ml) and NH$_4$OH (33 ml, 28% w/v) was added. The reaction was allowed to stir over night at room temperature. Dioxane was evacuated in vacuo and the crude product was washed with water and extracted with DCM. Brine was used to clear any emulsions. The organic layer was dried with Na$_2$SO$_4$ and purified (eluted with 2.5% MeOH/DCM v/v) to yield 8.4 g of 5A (9.4 mmol, 72%). Crude LCMS suggested some phthalimide damage had occurred (LRMS calculated for $C_{50}H_{63}N_5O_9Si$ 906.15, found m/z 928.1 $(M+23)^{Na+}$, 904.2 $(M-1)^-$, 941.0 $(M+35)^{Cl-}$).

$^1$H NMR (400 MHz, DMSO-$d_6$) δ 7.91 (d, J=7.4 Hz, 1H), 7.87-7.74 (m, 4H), 7.40-7.15 (m, 11H), 6.92-6.83 (m, 4H), 5.80 (d, J=1.6 Hz, 1H), 5.50 (d, J=7.4 Hz, 1H), 4.24 (dd, J=7.6, 5.1 Hz, 1H), 3.91 (d, J=7.4 Hz, 1H), 3.72 (s, 8H), 3.53 (t, J=7.0 Hz, 2H), 3.45-3.40 (m, 2H), 3.12 (dd, J=10.9, 3.4 Hz, 1H), 1.62-1.41 (m, 4H), 1.36-1.20 (m, 5H), 0.69 (s, 9H), −0.05 (s, 3H), −0.13 (s, 3H). $^{13}$C NMR (125 MHz, DMSO-$d_6$) δ 167.90, 165.53, 158.21, 154.70, 144.37, 140.64, 135.15, 135.06, 134.32, 131.57, 129.78, 129.74, 127.84, 127.78, 126.88, 122.96, 113.21, 113.18, 85.93, 81.59, 81.38, 69.55, 55.07, 55.06, 37.37, 29.23, 27.95, 26.16, 25.43, 25.27, 17.59, −4.80, −5.38. LRMS calculated for $C_{50}H_{60}N_4O_9Si$ 888.4130, found m/z 889.0 $(M+1)^+$, 911.0 $(M+23)^{Na+}$, 888.1 $(M-1)^-$, 923.1 $(M+35)^{Cl-}$. $R_f$=0.34 in 5% MeOH/DCM v/v (6A)—

Compound 5A (8.4 g, 9.4 mmol) was refluxed in MeOH (90 ml) with hydrazine (1.5 g, 47.1 mmol) for 3 hours. MeOH was removed in vacuo and the crude compound washed with NH$_4$OH and the aqueous layer was extracted with DCM. The organic layer was dried with Na$_2$SO$_4$ and evaporated in vacuo to yield the crude product 6A* LRMS calculated for $C_{42}H_{58}N_4O_7Si$ 758.4075, found m/z 759.2 $(M+1)^+$, 757.2 $(M-1)^-$, 793.2 $(M+35)^{Cl-}$. $R_f$=0.11 in 15% MeOH/DCM v/v 6A* was dissolved in DCM (90 ml) with Et$_3$N (3.9 ml, 28.3 mmol) and stirred under argon briefly. GalNAc(OBz)-C5-NHS ester (7.6 g, 10.4 mmol) was then added and the reaction was allowed to proceed over night. An additional 0.2 eq of GalNAc(OBz)-C5-NHS ester was added to drive the reaction closer to completion but the TLC profile remained the same. The organic layer was washed with saturated NaHCO$_3$ and dried with Na$_2$SO$_4$. The crude product was purified with silica gel chromatography (eluted with 2.5% MeOH/DCM v/v) to yield 8.4 g of 6A (6.1 mmol, 65%)

$^1$H NMR (400 MHz, DMSO-d$_6$) δ 8.02-7.88 (m, 6H), 7.74-7.16 (m, 22H), 6.95-6.81 (m, 4H), 5.82 (s, 1H), 5.74 (d, J=2.6 Hz, 1H), 5.51 (d, J=7.4 Hz, 1H), 5.36 (dd, J=11.1, 3.3 Hz, 1H), 4.73 (d, J=8.5 Hz, 1H), 4.44 (q, J=8.6, 7.5 Hz, 2H), 4.39-4.21 (m, 3H), 3.92 (d, J=7.5 Hz, 1H), 3.78 (d, J=9.8 Hz, 1H), 3.72 (s, 8H), 3.46 (dd, J=30.5, 9.4 Hz, 3H), 3.17-2.93 (m, 4H), 2.04 (s, 2H), 1.69 (s, 3H), 1.49 (s, 6H), 1.40-1.20 (m, 6H), 0.71 (s, 9H), −0.07 (d, J=37.7 Hz, 6H). $^{13}$C NMR (125 MHz, DMSO-d$_6$) δ 171.53, 169.19, 165.27, 165.02, 164.97, 164.68, 158.01, 154.45, 144.18, 140.48, 134.95, 134.86, 133.58, 133.31, 133.28, 129.58, 129.55, 129.03, 129.00, 128.98, 128.85, 128.83, 128.78, 128.51, 128.40, 127.65, 127.59, 126.68, 113.02, 112.99, 100.71, 93.65, 93.62, 88.11, 88.09, 85.74, 81.43, 81.23, 71.68, 69.80, 69.46, 69.12, 68.55, 67.75, 61.86, 61.35, 54.87, 54.86, 49.57, 45.40, 34.83, 29.16, 28.99, 28.39, 26.13, 25.27, 25.22, 22.52, 22.51, 21.67, 17.43, 8.36, −4.95, −5.55. LRMS calculated for $C_{76}H_{91}N_5O_{17}Si$ 1373.6179, found m/z 1396.2 $(M+23)^{Na+}$, 1372.3 $(M-1)^-$, 1408.3 $(M+35)^{Cl-}$. $R_f$=0.29 in 5% MeOH/DCM v/v (7A)—

Compound 6A (500 mg, 0.36 mmol) was dissolved in THF (8 ml) and Et$_3$N*3HF was added to the reaction mixture. Silyl cleavage took 48 hours to complete. THF was evaporated in vacuo and the crude product was washed with water and extracted with DCM. The organic layer was dried with Na$_2$SO$_4$ and purified (elute with 5% MeOH/DCM v/v) to yield 440 mg of 7A (0.35 mmol, 96%).

$^1$H NMR (400 MHz, DMSO-d$_6$) δ 8.02-7.88 (m, 5H), 7.78 (d, J=7.5 Hz, 1H), 7.74-7.54 (m, 8H), 7.49 (t, J=7.7 Hz, 2H), 7.43-7.36 (m, 4H), 7.32 (t, J=7.6 Hz, 2H), 7.26 (dd, J=8.9, 2.3 Hz, 5H), 7.17 (d, J=20.1 Hz, 2H), 6.90 (d, J=8.7 Hz, 4H), 5.81 (d, J=2.4 Hz, 1H), 5.75 (d, J=4.1 Hz, 1H), 5.49 (d, J=7.4 Hz, 1H), 5.37 (dd, J=11.1, 3.3 Hz, 1H), 5.00 (d, J=7.0 Hz, 1H), 4.73 (d, J=8.5 Hz, 1H), 4.46 (d, J=7.6 Hz, 2H), 4.38-4.22 (m, 2H), 4.16 (q, J=7.1 Hz, 1H), 3.99-3.91 (m, 1H), 3.74 (s, 8H), 3.68-3.47 (m, 3H), 3.26 (d, J=2.8 Hz, 2H), 3.01 (q, J=6.6 Hz, 2H), 2.05 (s, 2H), 1.70 (s, 3H), 1.51 (s, 6H), 1.32 (dt, J=42.4, 8.9 Hz, 6H). $^{13}$C NMR (100 MHz, DMSO-d$_6$) δ 171.74, 169.40, 165.41, 165.19, 165.15, 164.85, 158.09, 154.72, 144.62, 140.55, 135.39, 135.16, 133.76, 133.48, 129.70, 129.18, 129.15, 129.02, 129.00, 128.98, 128.96, 128.69, 128.58, 127.86, 127.68, 126.77, 113.20, 100.87, 93.72, 87.86, 85.78, 81.73, 81.63, 71.85, 69.96, 69.73, 68.73, 68.25, 67.90, 62.25, 62.02, 55.01, 54.88, 49.73, 45.59, 35.01, 29.13, 28.56, 26.25, 25.17, 22.68, 21.84, 8.54. LRMS calculated for $C_{70}H_{77}N_5O_{17}$ 1259.5314, found m/z 1282.1 $(M+23)^{Na+}$, 1258.2 $(M-1)^-$, 1294.2 $(M+35)^{Cl-}$. $R_f$=0.33 in 7% MeOH/DCM v/v (8A)—

Compound 7A (6.4 g, 5.1 mmol) was dissolved in DMF (50 ml) and N,N-Dimethylformamide dimethyl acetal (3.0 g, 25.5 mmol) was added. The reaction mixture was stirred at 50° C. for 2 hours. The crude product was purified with a silica column (eluted with 2-4% MeOH/DCM v/v) to yield 5.8 g of 8A (4.4 mmol, 86%).

$^1$H NMR (400 MHz, DMSO-d$_6$) δ 8.60 (s, 1H), 8.06-7.88 (m, 6H), 7.75-7.45 (m, 10H), 7.42-7.21 (m, 11H), 6.90 (d, J=8.8 Hz, 4H), 5.84 (d, J=2.3 Hz, 1H), 5.75 (s, 1H), 5.61 (d, J=7.2 Hz, 1H), 5.36 (dd, J=11.1, 3.3 Hz, 1H), 5.06 (d, J=6.9 Hz, 1H), 4.73 (d, J=8.5 Hz, 1H), 4.45 (q, J=8.9, 7.6 Hz, 2H), 4.40-4.13 (m, 3H), 4.03-3.96 (m, 1H), 3.74 (s, 8H), 3.69-3.56 (m, 2H), 3.51 (d, J=9.8 Hz, 1H), 3.29-3.24 (m, 1H), 3.16 (s, 3H), 3.01 (d, J=9.8 Hz, 5H), 2.05 (s, 2H), 1.70 (s, 3H), 1.50 (d, J=5.5 Hz, 6H), 1.39-1.22 (m, 6H). $^{13}$C NMR (125 MHz, DMSO-d$_6$) δ 171.76, 171.07, 169.40, 165.22, 165.17, 164.87, 158.13, 157.87, 154.87, 144.65, 141.75, 135.43, 135.10, 133.77, 133.50, 133.48, 129.80, 129.76, 129.21, 129.17, 129.04, 129.02, 128.97, 128.70, 128.59, 127.89, 127.71, 126.79, 113.26, 113.24, 101.40, 100.90, 88.33, 85.85, 81.97, 81.72, 71.88, 70.00, 69.82, 68.75, 68.31, 67.94, 62.24, 62.05, 55.05, 52.03, 49.76, 45.47, 35.03, 34.78, 29.14, 29.11, 28.59, 26.25, 25.18, 22.70, 21.86, 8.54, 7.18. LRMS calculated for $C_{73}H_{82}N_5O_{17}$ 1314.5736, found m/z 1315.2 $(M+1)^+$, 1337.1 $(M+23)^{Na+}$, 1314.2 $(M-1)^-$, 1349.2 $(M+35)^{Cl-}$. $R_f$=0.41 in 7% MeOH/DCM v/v.

(9A)—

Compound 8A (1.0 g, 0.76 mmol) was dissolved in DCM (7.5 ml) and 4-(Dimethylamino)pyridine (280 mg, 2.3 mmol) was added. The reaction mixture was stirred for 20 minutes and then succinic anhydride (150 mg, 1.5 mmol) was added. The reaction mixture was stirred at room temperature for 3 hours. DCM was evaporated in vacuo and the crude foam was loaded onto a 2% triethylamine in DCM v/v pretreated manual column (Φ=4.6×20). A gradient of 1-5% MeOH/2-5% triethylamine/DCM v/v was used to purify 9A. 9A came between 3-4% MeOH/3-4% triethylamine/DCM v/v. 1.1 g of 9A (0.71 mmol, 94%) was collected.

$^1$H NMR (400 MHz, DMSO-d$_6$) δ 8.63 (s, 1H), 8.05 (d, J=9.3 Hz, 1H), 7.92 (q, J=6.3, 5.7 Hz, 5H), 7.75-7.47 (m, 10H), 7.41-7.21 (m, 11H), 6.90 (d, J=8.9 Hz, 4H), 5.90 (d, J=4.2 Hz, 1H), 5.74 (s, 1H), 5.38 (dd, J=11.1, 3.3 Hz, 1H), 5.17 (t, J=5.6 Hz, 1H), 4.76 (d, J=8.5 Hz, 1H), 4.46 (q, J=9.5, 7.9 Hz, 2H), 4.38-4.25 (m, 2H), 4.16 (q, J=5.2 Hz, 2H), 3.80 (d, J=9.7 Hz, 1H), 3.74 (s, 6H), 3.52 (dd, J=9.6, 6.1 Hz, 2H), 3.42-3.28 (m, 4H), 3.16 (s, 3H), 3.01 (d, J=16.5 Hz, 5H), 2.61-2.52 (m, 2H), 2.06 (s, 2H), 1.71 (s, 3H), 1.57-1.15 (m, 14H). $^{13}$C NMR (100 MHz, DMSO-d$_6$) δ 173.27, 171.74, 171.56, 171.23, 169.39, 165.20, 165.16, 164.87, 158.14, 158.05, 154.88, 144.54, 141.83, 135.19, 135.00, 133.77, 133.49, 129.70, 129.20, 129.17, 129.03, 129.01, 128.97, 128.70, 128.59, 127.93, 127.60, 126.81, 113.29, 101.96, 100.91, 88.17, 86.07, 80.16, 79.25, 71.88, 70.28, 70.13, 69.98, 68.73, 67.92, 62.25, 62.04, 55.03, 54.90, 51.99, 49.74, 45.46, 34.99, 34.82, 29.12, 28.95, 28.84, 28.71, 28.57, 26.19, 25.13, 22.69, 21.84, 10.00, 7.17. LRMS calculated for $C_{77}H_{86}N_6O_{20}$ 1414.5897, found m/z 1416.2 $(M+1)^+$, 1437.1 $(M+23)^{Na+}$, 1413.3 $(M-1)^-$. $R_f$=0.48 in 5% MeOH/5% Et$_3$N/DCM v/v (10A)—

Compound 9A (1.0 g, 0.66 mmol) was dissolved in acetonitrile (65 ml) and HBTU (500 mg, 1.3 mmol) and DIEA (250 mg, 1.9 mmol) were added. The mixture was shaken for 5 minutes then LCAA-CPG (8.2 g, 540A, 131 μmol/g) was added and shaken over night at room temperature. The CPG was filtered and washed with 200 ml each of DCM, 20% MeOH/DCM v/v, and diethyl ether then dried in vacuo. The CPG was shaken for 1 hour in acetic anhydride (25 ml), pyridine (75 ml), and triethylamine (1 ml) before being washed again by the same conditions as before. Compound 10A was dried in vacuo overnight and loading was measured with a spectrophotometer (84 μmol/g).

(11A)—

Compound 8A (4.0 g, 3.04 mmol) was coevaporated with acetonitrile twice then dissolved in anhydrous DCM (30 ml) under a strict argon atmosphere and cooled to 0° C. 2-Cyanoethyl N,N,N',N'-tetraisopropylphosphordiamidite (1.8 g, 6.08 mmol) was added and the reaction mixture was stirred for 20 minutes then 4,5-Dicyanoimidazole (360 mg, 3.04 mmol) was added to the reaction. The reaction was slowly warmed to room temperature and stirred over night. The reaction mixture was washed with saturated $NaHCO_3$ and the organic layer was dried over $Na_2SO_4$ before being evaporated in vacuo. The resultant foam was purified with a manual column (Φ=4.6×30) prepared with 2% triethylamine/49% EtOAc/hexanes v/v. The impurities were eluted with 50% EtOAc/hexanes v/v (1 CV), 80% EtOAc/hexanes v/v (7 CV) followed by 100% EtOAc (8 CV). Then 11A was eluted with 2% MeOH/DCM v/v (5 CV), and 4% MeOH/DCM v/v (7 CV). 11A was evaporated in vacuo to yield 2.1 mg (1.37 mmol, 45%) of the amidite as a diastereomeric mixture. 7.5% MeOH/DCM v/v eluted another DMTr containing compound that was characterized by mass as oxidized 11A (LCMS found m/z 1532.2 (M+1)$^+$, 1555.2 (M+23)$^{Na+}$).

$^1$H NMR (400 MHz, DMSO-$d_6$) δ 8.61 (s, 1H), 8.07-7.87 (m, 6H), 7.76-7.19 (m, 21H), 6.97-6.82 (m, 4H), 5.88 (dd, J=8.4, 2.6 Hz, 1H), 5.75 (d, J=3.1 Hz, 1H), 5.59 (dd, J=10.9, 7.2 Hz, 1H), 5.37 (dd, J=11.1, 3.3 Hz, 1H), 4.74 (d, J=8.5 Hz, 1H), 4.49-4.23 (m, 5H), 4.17-4.07 (m, 1H), 3.98-3.92 (m, 1H), 3.83-3.77 (m, 1H), 3.73 (d, J=2.5 Hz, 6H), 3.71-3.45 (m, 7H), 3.35 (d, J=22.0 Hz, 6H), 3.16 (s, 3H), 3.01 (d, J=5.1 Hz, 5H), 2.74 (t, J=5.9 Hz, 1H), 2.64-2.57 (m, 1H), 2.05 (s, 2H), 1.70 (s, 3H), 1.51 (s, 6H), 1.42-1.19 (m, 7H), 1.17-1.03 (m, 10H), 0.95 (d, J=6.7 Hz, 3H). $^{13}$C NMR (125 MHz, DMSO-$d_6$) δ 171.69, 171.08, 169.35, 165.17, 165.13, 164.84, 158.14, 157.85, 154.83, 154.81, 144.53, 144.45, 141.75, 141.54, 135.15, 134.91, 134.87, 133.71, 133.44, 133.41, 129.81, 129.75, 129.17, 129.13, 129.00, 128.91, 128.64, 128.53, 127.81, 127.70, 126.80, 118.75, 118.61, 113.16, 101.60, 101.51, 100.87, 88.81, 88.32, 85.99, 81.35, 80.96, 80.49, 71.83, 69.97, 69.80, 69.48, 69.38, 68.71, 67.90, 62.01, 61.87, 61.28, 58.40, 58.25, 58.17, 58.01, 54.99, 49.73, 45.61, 42.61, 42.56, 42.51, 42.45, 34.99, 34.73, 29.20, 29.14, 29.10, 28.56, 26.28, 25.27, 25.23, 24.30, 24.24, 24.17, 22.66, 21.83, 19.80, 19.75. $^{31}$P NMR (160 MHz, DMSO-$d_6$) δ 153.88, 153.40. LRMS calculated for $C_{82}H_{99}N_8O_{18}P$ 1514.6815, found m/z 1537.2 (M+23)$^{Na+}$, 1551.2 (M+35)$^{Cl}$. $R^f$=0.41 in 7% MeOH/DCM v/v.

Example 70

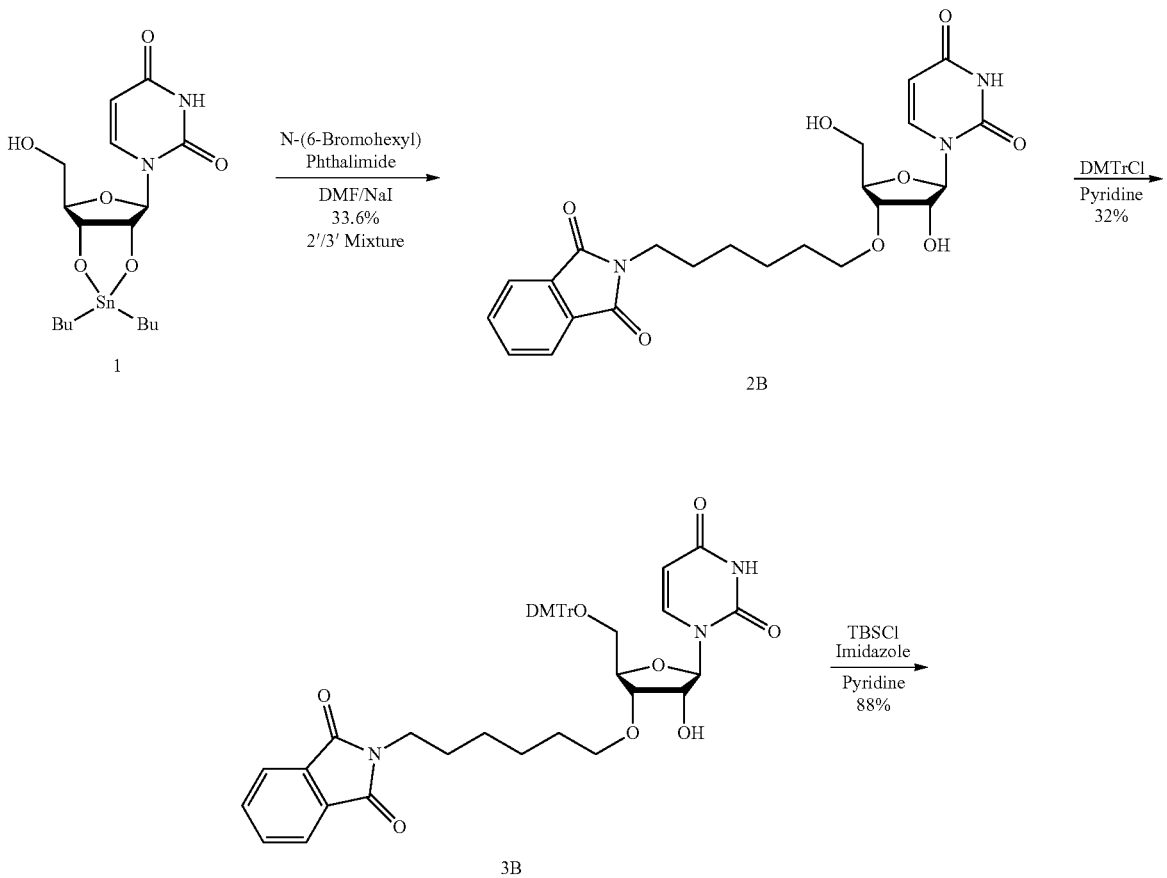

-continued
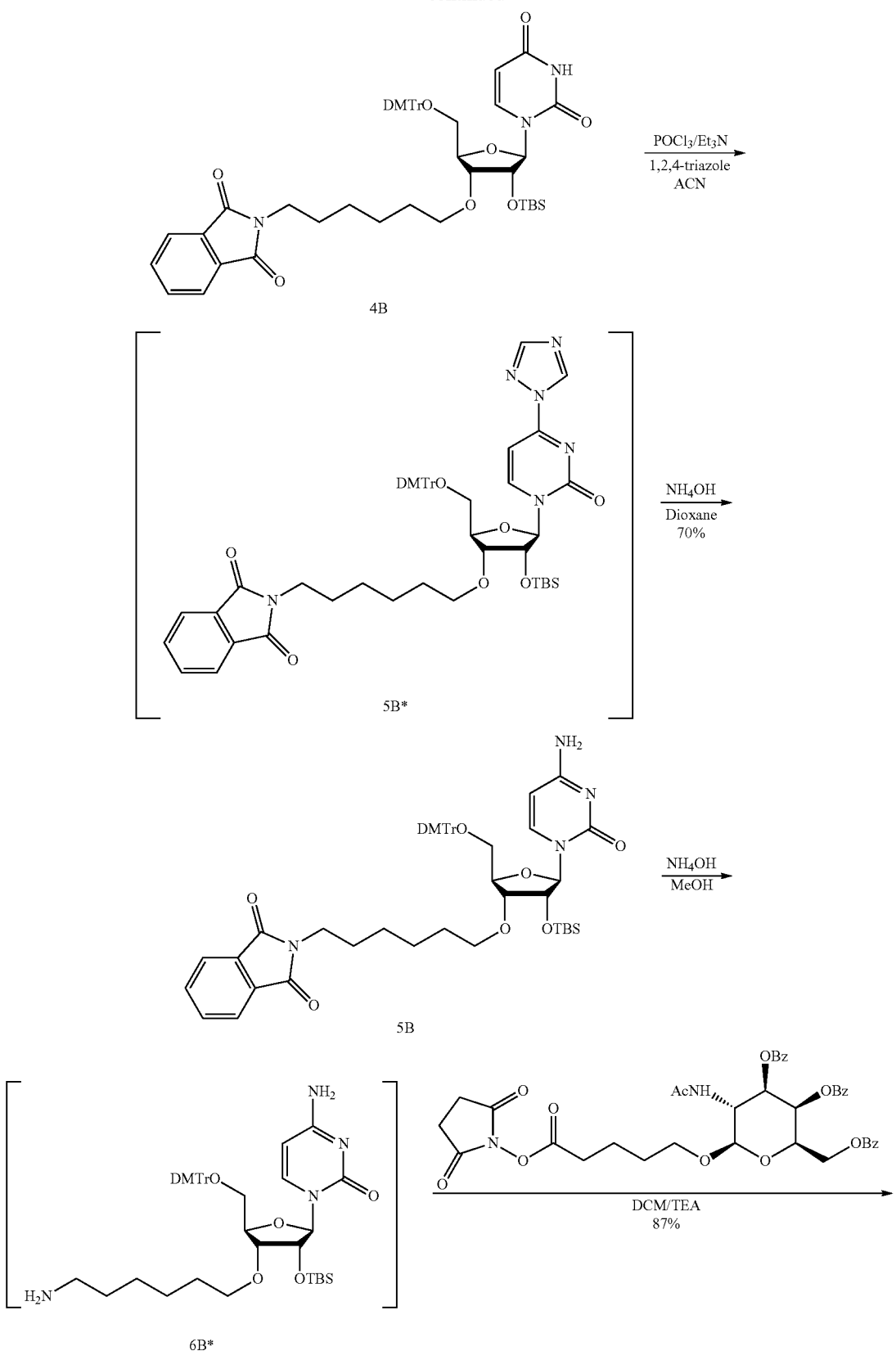

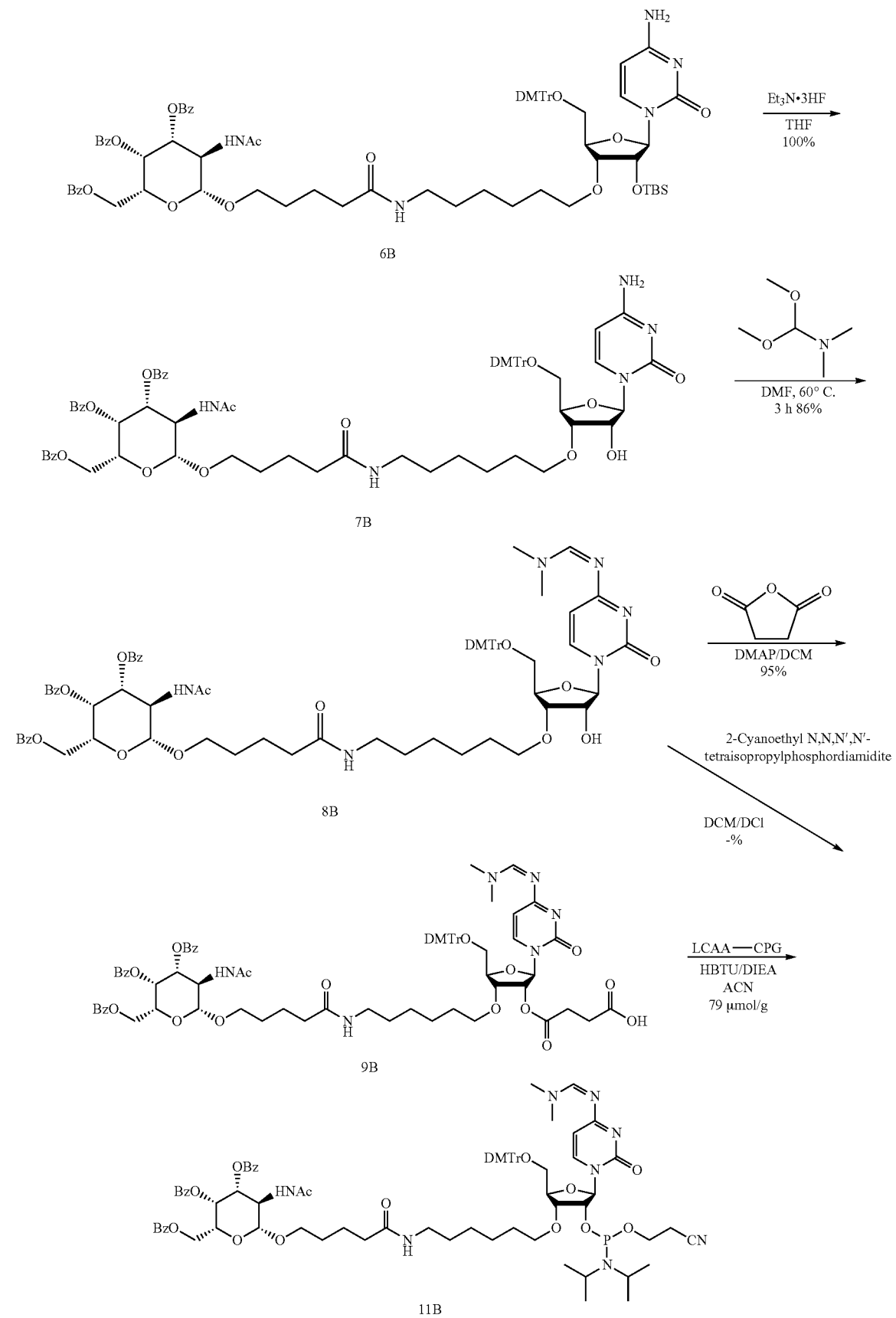

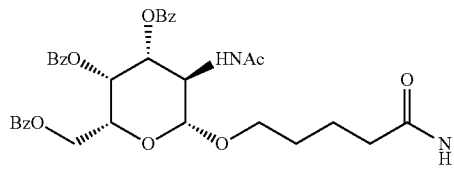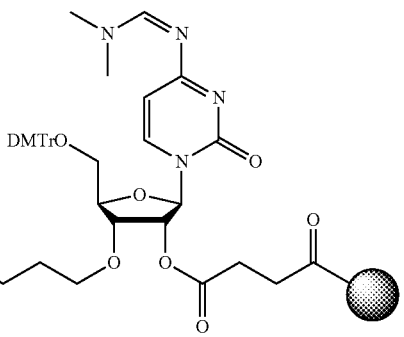

10B (4B)—

Compound 3B (4.95 g, 6.38 mmol) was protected with TBSCl (1.44 g, 9.57 mmol) in the same manner as compound 3A to yield 5.00 g of 4B (5.62 mmol, 88%).

$^1$H NMR (400 MHz, DMSO-$d_6$) δ 11.37 (s, 1H), 7.87-7.77 (m, 5H), 7.37-7.19 (m, 9H), 6.88 (dd, J=8.9, 1.8 Hz, 4H), 5.66 (d, J=3.7 Hz, 1H), 5.28 (d, J=8.1 Hz, 1H), 4.36 (t, J=4.1 Hz, 1H), 3.99 (t, J=2.9 Hz, 1H), 3.88-3.82 (m, 1H), 3.71 (s, 6H), 3.57-3.42 (m, 3H), 3.34 (d, J=10.7 Hz, 2H), 3.25 (dd, J=11.0, 3.5 Hz, 1H), 1.57-1.37 (m, 4H), 1.29-1.19 (m, 4H), 0.81 (s, 9H), 0.03 (d, J=4.4 Hz, 6H). $^{13}$C NMR (125 MHz, DMSO-$d_6$) δ 167.85, 162.93, 158.14, 150.33, 144.47, 139.87, 135.04, 134.89, 134.30, 131.53, 129.73, 127.85, 127.61, 126.81, 122.91, 113.20, 101.32, 88.72, 86.03, 80.60, 76.69, 73.71, 69.85, 62.08, 59.70, 54.99, 37.28, 29.07, 27.83, 26.04, 25.41, 25.09, 17.63, −5.07, −5.26. LRMS calculated for $C_{50}H_{59}N_3O_{10}Si$ 889.3970, found m/z 912.0 $(M+23)^{Na+}$, 888.2 $(M−1)^−$, 924.2 $(M+35)^{Cl−}$. $R_f$=0.71 in 60% EtOAc/Hexanes v/v (5B)—

Compound 4B (4.94 g, 5.55 mmol) was converted to 5B through the intermediate 5B* in the same manner as compound 4A. 3.45 g of 5B was obtained (3.88 mmol, 70%) for the two step reaction.

5B*)

LRMS calculated for $C_{52}H_{60}N_6O_9Si$ 940.4191, found m/z 964.4 $(M+23)^{Na+}$, 941.3 $(M−1)^−$, 976.3 $(M+35)^{Cl−}$. $R_f$=0.51 in 60% EtOAc/Hexanes v/v

5B)

$^1$H NMR (400 MHz, DMSO-$d_6$) δ 7.89-7.75 (m, 5H), 7.38-7.21 (m, 9H), 7.09 (s, 2H), 6.88 (d, J=7.9 Hz, 4H), 5.71 (d, J=14.2 Hz, 1H), 5.50 (d, J=7.2 Hz, 1H), 4.24 (s, 1H), 3.99 (d, J=6.1 Hz, 1H), 3.88-3.83 (m, 1H), 3.72 (s, 6H), 3.52 (t, J=6.8 Hz, 2H), 3.41 (dd, J=26.0, 9.6 Hz, 2H), 3.21 (d, J=11.1 Hz, 2H), 1.46 (d, J=55.9 Hz, 4H), 1.20 (s, 4H), 0.82 (s, 9H), 0.05 (d, J=18.7 Hz, 6H). $^{13}$C NMR (100 MHz, DMSO-$d_6$) δ 167.87, 165.54, 158.14, 154.95, 144.49, 140.38, 135.13, 135.06, 134.33, 131.56, 129.71, 127.86, 127.65, 126.82, 122.94, 113.19, 93.63, 89.79, 85.93, 79.86, 76.34, 74.03, 69.80, 61.80, 55.01, 54.90, 37.30, 29.10, 27.84, 26.07, 25.53, 25.10, 17.71, −4.77, −5.39. LRMS calculated for $C_{50}H_{60}N_4O_9Si$ 888.4130, found m/z 911.2 $(M+23)^{Na+}$, 888.3 $(M−1)^−$, 923.3 $(M+35)^{Cl−}$. $R_f$=0.46 in 7% MeOH/DCM v/v (6B)—

Compound 5B (3.45 g, 3.88 mmol) was treated with hydrazine in the same manner as 5A to yield intermediate 6B*.

6B*)

LRMS calculated for $C_{42}H_{58}N_4O_7Si$ 758.4075, found m/z 759.2 $(M+1)^+$, 781.2 $(M+23)^{Na+}$, 757.2 $(M−1)^−$, 793.2 $(M+35)^{Cl−}$. $R_f$=0.20 in 15% MeOH/DCM v/v Intermediate 6B* was then coupled to GalNAc(OBz)-C5-NHS ester in the same manner as 6A* to yield 4.64 g of 6B (3.38 mmol, 87%).

6B)

$^1$H NMR (500 MHz, DMSO-$d_6$) δ 7.99-7.86 (m, 6H), 7.73-7.53 (m, 9H), 7.48 (t, J=7.7 Hz, 2H), 7.41-7.34 (m, 4H), 7.31 (t, J=7.6 Hz, 2H), 7.24 (dd, J=8.8, 2.8 Hz, 6H), 6.89 (d, J=8.3 Hz, 4H), 5.75 (d, J=3.1 Hz, 1H), 5.70 (d, J=2.5 Hz, 1H), 5.51 (d, J=7.4 Hz, 1H), 5.37 (dd, J=11.1, 3.1 Hz, 1H), 4.74 (d, J=8.5 Hz, 1H), 4.45 (d, J=7.6 Hz, 2H), 4.38-4.24 (m, 3H), 4.01 (d, J=6.6 Hz, 1H), 3.90-3.85 (m, 1H), 3.79 (d, J=10.0 Hz, 1H), 3.73 (s, 6H), 3.55-3.42 (m, 2H), 3.38 (d, J=9.5 Hz, 1H), 3.30-3.18 (m, 2H), 2.98 (q, J=6.5 Hz, 2H), 2.04 (s, 2H), 1.69 (s, 3H), 1.51 (s, 4H), 1.44-1.28 (m, 4H), 1.23-1.14 (m, 4H), 0.83 (s, 9H), 0.10-0.02 (m, 6H). $^{13}$C NMR (125 MHz, DMSO-$d_6$) δ 172.22, 169.88, 166.00, 165.71, 165.67, 165.38, 158.68, 155.43, 145.00, 140.94, 135.71, 135.60, 134.27, 134.01, 133.97, 130.23, 129.73, 129.68, 129.55, 129.47, 129.20, 129.09, 128.39, 128.19, 127.36, 113.73, 101.42, 94.19, 90.20, 86.48, 80.46, 76.98, 74.58, 72.37, 70.51, 70.44, 69.26, 68.45, 67.51, 62.56, 62.43, 55.55, 55.54, 50.28, 38.87, 35.54, 29.83, 29.66, 29.11, 26.84, 26.05, 25.82, 25.63, 23.21, 22.39, 18.24, −4.26, −4.83. LRMS calculated for $C_{76}H_{91}N_5O_{17}Si$ 1373.6179, found m/z 1396.2 $(M+23)^{Na+}$, 1373.3 $(M−1)^−$, 1408.3 $(M+35)^{Cl−}$. $R_f$=0.48 in 7% MeOH/DCM v/v (7B)—

Compound 6B (4.60 g, 3.35 mmol) was desilylated with $Et_3N$*3HF (6.54 ml, 40.16 mmol) in THF (67 ml) in a similar manner as 6A to yield 7B quantitatively.

$^1$H NMR (500 MHz, DMSO-$d_6$) δ 8.00 (d, J=9.3 Hz, 1H), 7.91 (t, J=7.4 Hz, 4H), 7.82 (d, J=7.4 Hz, 1H), 7.70 (t, J=6.3 Hz, 4H), 7.63 (t, J=7.4 Hz, 1H), 7.56 (q, J=8.2 Hz, 3H), 7.48 (t, J=7.7 Hz, 2H), 7.41-7.34 (m, 4H), 7.31 (t, J=7.7 Hz, 2H), 7.24 (d, J=7.4 Hz, 6H), 7.10 (s, 1H), 6.88 (d, J=8.0 Hz, 4H), 5.76-5.73 (m, 2H), 5.52 (d, J=7.4 Hz, 1H), 5.39-5.31 (m, 2H), 4.74 (d, J=8.5 Hz, 1H), 4.45 (q, J=9.3, 7.9 Hz, 2H), 4.38-4.31 (m, 1H), 4.32-4.22 (m, 1H), 4.12 (q, J=5.0 Hz, 1H), 4.01-3.97 (m, 1H), 3.93-3.89 (m, 1H), 3.82-3.77 (m, 1H), 3.73 (s, 6H), 3.56-3.48 (m, 2H), 3.30 (d, J=9.4 Hz, 2H), 3.19 (dd, J=10.8, 3.5 Hz, 1H), 2.99 (q, J=6.6 Hz, 2H), 2.04 (t, J=6.6 Hz, 2H), 1.69 (s, 3H), 1.54-1.39 (m, 6H), 1.37-1.29 (m, 2H), 1.21 (d, J=7.1 Hz, 4H). $^{13}$C NMR (125 MHz,

DMSO-d$_6$) δ 171.68, 169.34, 165.53, 165.17, 165.12, 164.83, 158.08, 155.00, 144.52, 140.72, 135.34, 135.18, 133.72, 133.46, 133.43, 129.64, 129.61, 129.17, 129.13, 128.99, 128.92, 128.65, 128.54, 127.82, 127.64, 126.74, 113.17, 100.87, 93.63, 90.33, 85.81, 79.75, 76.44, 72.33, 71.83, 69.95, 69.49, 68.71, 67.89, 62.07, 62.01, 54.98, 49.71, 38.33, 34.98, 29.20, 29.11, 28.55, 26.26, 25.19, 22.66, 21.82. LRMS calculated for C$_{70}$H$_{77}$N$_5$O$_{17}$ 1259.5314, found m/z 1282.1 (M+23)$^{Na+}$, 1259.2 (M−1)$^−$, 1294.1 (M+35)$^{Cl−}$. R$_f$=0.24 in 7% MeOH/DCM v/v (8B)—

Compound 7B (4.21 g, 3.34 mmol) was protected at the N4 position with N,N-Dimethylformamide dimethyl acetal (1.99 g, 16.70 mmol) in the same manner as 7A to yield 3.79 g of compound 8A (2.88 mmol, 86%).

$^1$H NMR (500 MHz, DMSO-d$_6$) δ 8.62 (s, 1H), 8.02-7.88 (m, 6H), 7.74-7.52 (m, 8H), 7.48 (t, J=7.7 Hz, 2H), 7.41-7.21 (m, 11H), 6.93-6.85 (m, 4H), 5.75 (d, J=4.6 Hz, 3H), 5.62 (d, J=7.2 Hz, 1H), 5.43 (d, J=5.4 Hz, 1H), 5.37 (dd, J=11.1, 3.3 Hz, 1H), 4.73 (d, J=8.5 Hz, 1H), 4.49-4.41 (m, 2H), 4.37-4.24 (m, 2H), 4.20-4.15 (m, 1H), 4.07-4.02 (m, 1H), 3.97-3.93 (m, 1H), 3.82-3.76 (m, 1H), 3.73 (s, 6H), 3.58-3.48 (m, 2H), 3.31 (s, 2H), 3.26 (dd, J=10.8, 3.5 Hz, 1H), 3.15 (s, 3H), 3.05-2.95 (m, 5H), 2.09-2.00 (m, 2H), 1.70 (s, 3H), 1.55-1.40 (m, 6H), 1.38-1.29 (m, 2H), 1.22 (s, 4H). $^{13}$C NMR (126 MHz, DMSO-d$_6$) δ 171.68, 171.04, 169.35, 165.17, 165.12, 164.83, 158.09, 157.81, 154.99, 144.53, 141.90, 135.33, 135.06, 133.72, 133.46, 133.43, 129.71, 129.66, 129.17, 129.13, 128.99, 128.92, 128.65, 128.55, 127.83, 127.63, 126.76, 113.19, 101.28, 100.87, 90.81, 85.86, 79.97, 76.32, 72.35, 71.82, 69.95, 69.49, 68.72, 67.90, 62.00, 54.99, 54.85, 49.72, 45.67, 35.00, 34.72, 29.20, 29.11, 28.57, 26.25, 25.20, 22.66, 21.83. LRMS calculated for C$_{73}$H$_{82}$N$_6$O$_{17}$ 1314.5736, found m/z 1316.4 (M+1)$^+$, 1337.2 (M+23)$^{Na+}$, 1314.2 (M−1)$^−$, 1349.2 (M+35)$^{Cl−}$. R$_f$=0.32 in 7% MeOH/DCM v/v (9B)—

Compound 8B (500 mg, 0.380 mmol) was succinated under the same conditions as 9A to yield 550 mg of compound 9B (0.363 mmol, 95%).

$^1$H NMR (400 MHz, DMSO-d$_6$) δ 8.61 (s, 1H), 8.07 (d, J=9.2 Hz, 1H), 7.99-7.84 (m, 5H), 7.79-7.44 (m, 10H), 7.41-7.20 (m, 11H), 6.88 (d, J=8.5 Hz, 4H), 5.86 (d, J=2.0 Hz, 1H), 5.75 (d, J=3.4 Hz, 1H), 5.70 (d, J=7.2 Hz, 1H), 5.43-5.33 (m, 2H), 4.75 (d, J=8.5 Hz, 1H), 4.49-4.40 (m, 2H), 4.37-4.21 (m, 3H), 4.02-3.96 (m, 1H), 3.72 (s, 7H), 3.59-3.45 (m, 2H), 3.43-3.20 (m, 6H), 3.15 (s, 3H), 3.04-2.93 (m, 5H), 2.46-2.38 (m, 2H), 2.05 (s, 2H), 1.69 (s, 3H), 1.50 (s, 4H), 1.41-1.27 (m, 4H), 1.16 (s, 4H). $^{13}$C NMR (125 MHz, DMSO-d$_6$) δ 173.26, 171.72, 171.32, 171.10, 169.35, 165.17, 165.13, 164.83, 158.10, 157.92, 154.67, 144.47, 142.44, 135.23, 135.05, 133.72, 133.43, 129.69, 129.18, 129.13, 129.00, 128.92, 128.65, 128.54, 127.83, 127.65, 126.76, 113.18, 101.67, 100.89, 88.99, 85.87, 80.36, 75.39, 73.66, 71.87, 70.48, 69.95, 68.69, 67.90, 62.53, 62.02, 61.80, 54.98, 54.86, 51.98, 51.26, 49.72, 40.84, 38.32, 34.95, 34.77, 29.10, 29.06, 28.97, 28.88, 28.67, 28.53, 26.21, 25.16, 22.65, 21.80, 10.64, 7.14. LRMS calculated for C$_{77}$H$_{86}$N$_6$O$_{20}$ 1414.5897, found m/z 1438.9 (M+23)$^{Na+}$, 1413.2 (M−1)$^−$ (10B)—

Compound 9B (500 mg, 0.329 mmol) was loaded on to succinated in the same fashion as compound 10A to yield 4.11 g of 10B with a loading of 79 μmol/g.

Example 71

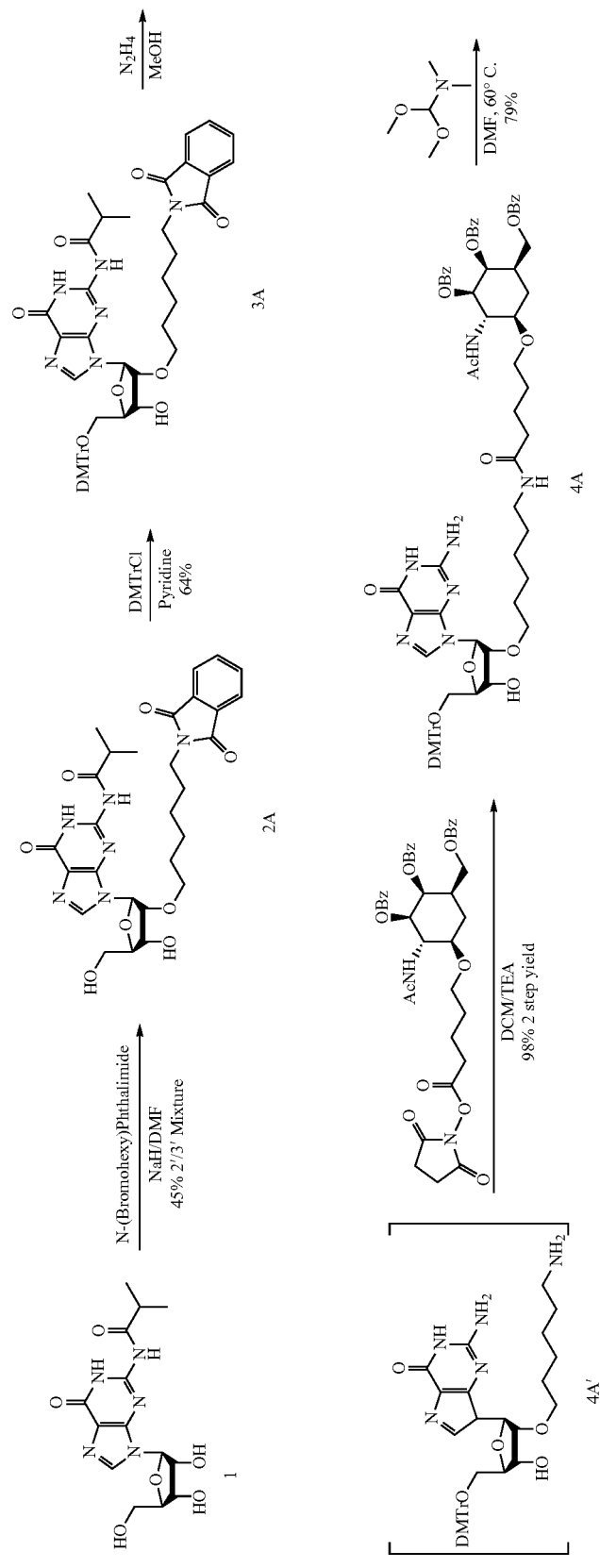

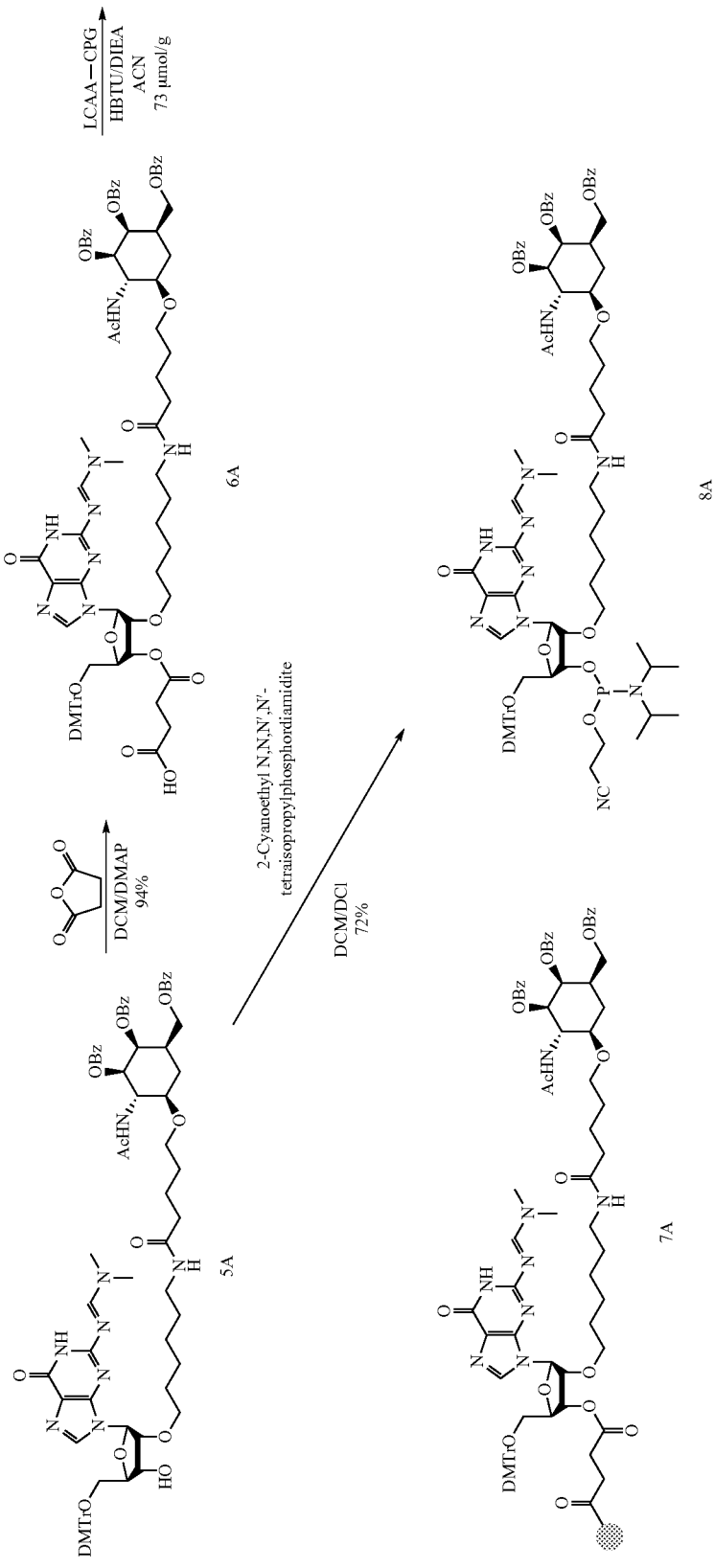

LRMS calculated for $C_{24}H_{28}N_6O_6$ 496.52, found m/z 497.2 $(M+1)^+$, 519.2 $(M+23)^{Na+}$, 486.2 $(M-1)^-$, 522.2 $(M+35)^{Cl-}$ (2A/2B)—

Compound 1 (40 g, 113.2 mmol) was dissolved in DMF (950 ml). NaH (60% in oil; 11.32 g, 283 mmol) was added and the reaction mixture was stirred till the evolution of gas ceased, about 3 hours. Then N-(BromohexylpPhthalimide (52.7 g, 169.8 mmol) was added and the reaction stirred for 3 hours at room temperature. The reaction mixture was heated to 50° C. and held for 72 hours. DMF was removed in vacuo and the resultant gum was adsorbed to silica for silica gel column purification. A mixture of 2A and 2B eluted between 4-6% MeOH/DCM v/v to yield 29.85 g of product (51.2 mmol, 45%).

$^1$H NMR (400 MHz, DMSO-$d_6$) δ 12.05 (d, J=9.9 Hz, 1H, $D_2O$ exchangeable), 11.65 (d, J=8.8 Hz, 1H, $D_2O$ exchangeable), 8.26 (d, J=9.5 Hz, 1H), 7.82 (p, J=4.3 Hz, 4H), 5.87 (d, J=6.5 Hz, 1H), 5.78 (d, J=6.0 Hz, 0H, $D_2O$ exchangeable), 5.39 (d, J=6.2 Hz, 0H, $D_2O$ exchangeable), 5.12 (d, J=4.6 Hz, 1H, $D_2O$ exchangeable), 5.04 (t, J=5.4 Hz, 1H, $D_2O$ exchangeable), 4.56-4.51 (m, OH), 4.33-4.27 (m, 1H), 4.24 (q, J=4.5 Hz, 1H), 3.94-3.87 (m, 1H), 3.64-3.42 (m, 6H), 2.74 (p, J=6.8 Hz, 1H), 1.43 (dt, J=27.1, 6.5 Hz, 4H), 1.23-1.12 (m, 4H), 1.09 (dd, J=6.6, 4.9 Hz, 6H). $^{13}$C NMR (125 MHz, DMSO-$d_6$) δ 180.03, 167.91, 167.89, 167.81, 154.72, 148.83, 148.19, 137.43, 137.41, 134.30, 131.55, 131.52, 122.92, 122.86, 119.99, 86.24, 84.46, 84.44, 81.41, 69.59, 68.89, 68.88, 61.25, 37.16, 34.70, 28.87, 27.84, 27.78, 25.90, 24.79, 18.82, 18.79, 18.75. LRMS calculated for $C_{28}H_{34}N_6O_8$ 582.2438, found m/z 583.2 $(M+1)^+$, 581.1 $(M-1)^-$, 617.1 $(M+35)^{Cl-}$. $R_f$=0.30 in 7% MeOH/DCM v/v (3A/3B)—

Compound 2A/2B (14.1 g, 24.2 mmol) was dissolved in anhydrous pyridine (240 ml) under a strict argon atmosphere and cooled to 0° C. Then DMTrCl (9.0 g, 26.6 mmol) was added and the reaction was warmed to room temperature and allowed to stir for 72 hours. The reaction was quenched with MeOH and pyridine removed in vacuo. The crude products were washed with saturated NaHCO$_3$ and extracted with DCM. The organic layer was dried over Na$_2$SO$_4$ and evaporated in vacuo. The products were purified with silica gel chromatography to yield 13.82 g (15.62 mmol, 65%) of 3A and 2.06 g (2.33 mmol, 10%) of 3B.

3A)

$^1$H NMR (400 MHz, DMSO-$d_6$) δ 12.06 (s, 1H), 11.59 (s, 1H), 8.12 (s, 1H), 7.81 (p, J=4.4 Hz, 4H), 7.33 (d, J=7.3 Hz, 2H), 7.27-7.16 (m, 7H), 6.82 (dd, J=8.7, 7.1 Hz, 4H), 5.92 (d, J=5.5 Hz, 1H), 5.14 (d, J=5.6 Hz, 1H), 4.39 (t, J=5.2 Hz, 1H), 4.27 (q, J=4.8 Hz, 1H), 4.03 (q, J=3.9 Hz, 1H), 3.71 (s, 6H), 3.57 (dd, J=11.2, 4.7 Hz, 1H), 3.51-3.38 (m, 3H), 3.27 (dd, J=10.4, 6.1 Hz, 1H), 3.15 (dd, J=10.3, 3.0 Hz, 1H), 2.74 (p, J=6.8 Hz, 1H), 1.47 (dt, J=21.2, 6.6 Hz, 4H), 1.28-1.15 (m, 4H), 1.10 (dd, J=6.6, 5.1 Hz, 6H). $^{13}$C NMR (125 MHz, DMSO-$d_6$) δ 180.04, 167.83, 158.02, 158.00, 154.74, 148.76, 148.16, 144.74, 137.44, 135.44, 135.35, 134.30, 131.52, 129.68, 129.65, 127.72, 127.65, 126.62, 122.92, 120.29, 113.06, 85.52, 85.02, 84.06, 80.59, 69.78, 69.12, 63.93, 63.45, 37.19, 34.72, 28.89, 27.79, 25.94, 24.83, 18.80, 18.78. LRMS calculated for $C_{49}H_{52}N_6O_{10}$ 884.3745, found m/z 885.2 $(M+1)^+$, 907.0 $(M+23)^{Na+}$, 883.2 $(M-1)^-$, 919.2 $(M+35)^{Cl-}$. $R_f$=0.52 in 100% EtOAc

3B)

$^1$H NMR (400 MHz, DMSO-$d_6$) δ 12.08 (s, 1H, $D_2O$ exchangeable), 11.67 (s, 1H, $D_2O$ exchangeable), 8.14 (s, 1H), 7.86-7.76 (m, 4H), 7.37-7.14 (m, 9H), 6.81 (dd, J=8.8, 4.0 Hz, 4H), 5.81 (d, J=4.7 Hz, 1H), 5.51 (d, J=5.7 Hz, 1H, $D_2O$ exchangeable), 4.67 (d, J=4.7 Hz, 1H), 4.05-3.91 (m, 2H), 3.70 (s, 6H), 3.55 (dt, J=14.2, 8.2 Hz, 3H), 3.39 (d, J=9.4 Hz, 1H), 3.26-3.14 (m, 2H), 2.76 (p, J=6.8 Hz, 1H), 1.50 (dt, J=35.7, 6.6 Hz, 4H), 1.32-1.19 (m, 4H), 1.11 (d, J=6.8 Hz, 6H). $^{13}$C NMR (126 MHz, $D_2O$) δ 180.10, 167.90, 158.02, 154.81, 148.81, 148.16, 144.70, 137.29, 135.39, 135.36, 134.33, 131.55, 129.64, 129.61, 127.74, 127.61, 126.64, 122.94, 120.28, 113.07, 87.17, 85.57, 81.14, 77.71, 72.22, 69.63, 63.31, 59.72, 54.94, 37.30, 34.73, 29.08, 27.86, 26.05, 25.03, 18.87, 18.78, 14.05. LRMS calculated for $C_{49}H_{52}N_6O_{10}$ 884.3745, found m/z 885.1 $(M+1)^+$, 883.0 $(M-1)^-$, 919.0 $(M+35)^{Cl-}$. $R_f$=0.32 in 100% EtOAc (4A)—

Compound 3A (5.0 g, 5.65 mmol) was treated with hydrazine (900 mg, 28 mmol) in refluxing MeOH (56 ml) for 3 hours. Both phthalimide and isobutyryl protecting groups were cleaved during the reaction. MeOH was removed in vacuo and the crude product was washed with NH$_4$OH. The aqueous layer was extracted with DCM and the organic layer was dried with Na$_2$SO$_4$. DCM was removed in vacuo to yield 4A* as a crude foam.

LRMS calculated for $C_{37}H_{44}N_6O_7$ 684.3271, found m/z 685.2 $(M+1)^+$, 683.1 $(M-1)^-$, 719.1 $(M+35)^{Cl-}$. $R_f$=0.00 in 7% MeOH/DCM v/v.

4A* was then dissolved in anhydrous DCM (56 ml) under a strict argon atmosphere and Et$_3$N (2.4 ml, 17 mmol) was added. GalNAc(OBz)-C5-NHS ester (4.5 g, 6.22 mmol) was then added and the reaction stirred at room temperature overnight. DCM was evaporated in vacuo and the crude foam was washed with saturated NaHCO$_3$ then the aqueous layer was extracted with DCM. The organic layer was dried with Na$_2$SO$_4$ and then removed in vacuo. The crude foam was purified with silica gel chromatography (eluted with 2.5-5% MeOH/DCM v/v) to yield 7.0 g (5.41 mmol, 96%) of 4A. Coevaporation with acetonitrile did not reduce the triethylamine peak seen in $^1$H NMR.

$^1$H NMR (400 MHz, DMSO-$d_6$) δ 10.73 (s, 1H), 9.90 (s, 1H), 8.02 (d, J=9.3 Hz, 1H), 7.91 (t, J=7.0 Hz, 4H), 7.79 (s, 1H), 7.74-7.52 (m, 8H), 7.48 (t, J=7.7 Hz, 2H), 7.37 (dd, J=13.9, 7.4 Hz, 4H), 7.30-7.16 (m, 7H), 6.84 (dd, J=8.9, 2.7 Hz, 4H), 6.53 (s, 2H), 5.81 (d, J=5.4 Hz, 1H), 5.75 (d, J=3.1 Hz, 1H), 5.36 (dd, J=11.1, 3.2 Hz, 1H), 5.13 (d, J=5.7 Hz, 1H), 4.74 (d, J=8.5 Hz, 1H), 4.49-4.40 (m, 2H), 4.39-4.19 (m, 4H), 3.99 (q, J=4.2 Hz, 1H), 3.78 (d, J=9.6 Hz, 1H), 3.71 (s, 6H), 3.61-3.46 (m, 2H), 3.46-3.37 (m, 1H), 3.24-3.12 (m, 2H), 2.97 (q, J=6.6 Hz, 2H), 2.04 (s, 2H), 1.69 (s, 3H), 1.56-1.37 (m, 6H), 1.36-1.25 (m, 2H). $^{13}$C NMR (125 MHz, DMSO-$d_6$) δ 171.72, 169.38, 165.19, 165.14, 164.84, 158.02, 156.66, 153.81, 151.30, 144.77, 135.47, 135.37, 134.89, 133.75, 133.47, 129.67, 129.18, 129.16, 129.14, 129.01, 128.98, 128.95, 128.68, 128.57, 127.77, 127.65, 126.64, 116.64, 113.12, 100.88, 85.53, 84.44, 83.53, 80.61, 71.86, 69.96, 69.78, 69.08, 68.73, 67.90, 63.84, 62.02, 54.98, 49.72, 45.42, 38.30, 34.99, 29.12, 29.06, 28.56, 26.17, 25.06, 22.68, 21.82, 8.47. LRMS calculated for $C_{71}H_{77}N_7O_{17}$ 1299.5376, found m/z 1301.1 $(M+1)^+$, 1322.1 $(M+23)^{Na+}$, 1298.2 $(M-1)^-$, 1336.2 $(M+35)^{Cl-}$. $R_f$=0.37 in 7% MeOH/DCM v/v.

(5A)—

Compound 4A (6.8 g, 5.23 mmol) was dissolved in DMF. N,N-Dimethylformamide dimethyl acetal (1.9 g, 15.7 mmol) was added to the reaction mixture and heated to 60° C. for 1.5 hours. DMF was removed in vacuo and the crude product adsorbed to silica. Purification was carried out with silica gel chromatography (eluted with 2.5-5% MeOH/DCM v/v) to yield 5.63 g of 5A (4.15 mmol, 79%).

¹H NMR (400 MHz, DMSO-d₆) δ 11.38 (s, 1H), 9.94 (s, 1H), 8.48 (s, 1H), 8.03 (d, J=9.3 Hz, 1H), 7.97-7.87 (m, 5H), 7.75-7.52 (m, 8H), 7.48 (t, J=7.7 Hz, 2H), 7.37 (dd, J=14.6, 7.4 Hz, 4H), 7.29-7.16 (m, 7H), 6.83 (dd, J=8.7, 4.6 Hz, 4H), 5.93 (d, J=4.9 Hz, 1H), 5.75 (d, J=3.1 Hz, 1H), 5.37 (dd, J=11.1, 3.2 Hz, 1H), 5.21 (d, J=5.7 Hz, 1H), 4.75 (d, J=8.5 Hz, 1H), 4.45 (q, J=8.3, 7.3 Hz, 2H), 4.39-4.23 (m, 4H), 4.02 (q, J=4.7 Hz, 1H), 3.78 (d, J=9.5 Hz, 1H), 3.71 (s, 6H), 3.52 (ddt, J=40.7, 16.1, 7.9 Hz, 4H), 3.25 (dd, J=10.3, 5.9 Hz, 1H), 3.15 (d, J=7.7 Hz, 1H), 3.07 (s, 3H), 3.01-2.92 (m, 5H), 2.04 (s, 2H), 1.70 (s, 3H), 1.55-1.38 (m, 6H), 1.35-1.24 (m, 2H). ¹³C NMR (125 MHz, DMSO-d₆) δ 171.74, 169.40, 165.20, 165.15, 164.85, 158.03, 158.01, 157.79, 157.58, 157.28, 149.86, 144.76, 136.33, 135.47, 135.38, 133.75, 133.48, 133.45, 129.66, 129.62, 129.15, 129.14, 129.01, 128.99, 128.94, 128.67, 128.56, 127.76, 127.63, 126.64, 119.78, 113.11, 100.88, 85.50, 85.06, 83.46, 80.78, 71.87, 69.97, 69.83, 69.04, 68.72, 67.91, 63.80, 62.03, 54.98, 49.73, 45.45, 45.43, 34.99, 34.63, 29.10, 29.06, 28.55, 26.16, 25.07, 22.67, 21.82, 8.48. LRMS calculated for $C_{74}H_{82}N_8O_{17}$ 1354.5798, found m/z 1356.1 (M+1)⁺, 1377.2 (M+23)$^{Na+}$, 1353.3 (M−1)⁻, 1389.2 (M+35)$^{Cl-}$. $R_f$=0.40 in 7% MeOH/DCM v/v (6A)—

Compound 5A (1.0 g, 0.74 mmol) was dissolved in DCM (7 ml) and 4-Dimethylaminopyridine (270 mg, 2.21 mmol) was added to the reaction mixture and stirred for 5 minutes. Then succinic anhydride (150 mg, 1.48 mmol) was added and the reaction mixture was stirred at room temperature over night. DCM was evaporated in vacuo and the crude foam was loaded onto a 2% triethylamine in DCM v/v pretreated manual column (Φ=4.6×17). A gradient of 1-5% MeOH/2-5% triethylamine/DCM v/v was used to purify 6A. 6A came at 4-5% MeOH/4-5% triethylamine/DCM v/v in quantitative yield.

¹H NMR (500 MHz, DMSO-d₆) δ 11.43 (s, 1H), 8.62 (s, 1H), 8.08-7.98 (m, 2H), 7.92 (t, J=8.0 Hz, 4H), 7.71 (dd, J=12.7, 7.3 Hz, 4H), 7.64 (t, J=7.4 Hz, 1H), 7.57 (q, J=7.7, 7.1 Hz, 3H), 7.50 (d, J=7.7 Hz, 2H), 7.39 (t, J=7.8 Hz, 2H), 7.30-7.14 (m, 9H), 6.81 (dd, J=8.8, 4.9 Hz, 4H), 5.94 (d, J=4.4 Hz, 1H), 5.76 (s, 1H), 5.63 (t, J=5.5 Hz, 1H), 5.38 (dd, J=11.1, 3.3 Hz, 1H), 4.90 (t, J=4.9 Hz, 1H), 4.76 (d, J=8.5 Hz, 1H), 4.46 (q, J=9.9, 8.2 Hz, 2H), 4.39-4.24 (m, 2H), 4.15 (q, J=4.9 Hz, 1H), 3.82-3.77 (m, 1H), 3.72 (s, 6H), 3.53-3.43 (m, 2H), 3.37 (q, J=7.2 Hz, 3H), 3.27 (dd, J=10.5, 5.2 Hz, 1H), 3.22-3.15 (m, 1H), 3.03 (s, 3H), 3.01-2.94 (m, 5H), 2.79 (q, J=7.0 Hz, 2H), 2.59 (q, J=6.4, 5.9 Hz, 2H), 2.05 (s, 2H), 1.70 (s, 3H), 1.56-1.46 (m, 4H), 1.38 (s, 2H), 1.33-1.26 (m, 2H), 1.15 (s, 4H). ¹³C NMR (125 MHz, DMSO-d₆) δ 173.21, 171.83, 171.69, 169.34, 165.16, 165.11, 164.81, 158.00, 157.99, 157.96, 157.55, 157.24, 149.59, 144.58, 137.75, 135.32, 135.29, 133.71, 133.43, 129.52, 129.41, 129.16, 129.13, 129.11, 128.98, 128.91, 128.64, 128.53, 127.71, 127.49, 126.58, 120.16, 113.06, 100.86, 86.36, 85.38, 80.12, 78.06, 71.84, 70.27, 69.94, 68.68, 67.89, 62.00, 54.94, 54.93, 54.84, 51.98, 49.70, 45.44, 34.94, 34.60, 29.05, 28.97, 28.68, 28.63, 28.52, 26.09, 25.03, 22.64, 21.78, 9.74, 7.13. LRMS calculated for $C_{78}H_{86}N_8O_{20}$ 1454.5958, found m/z 1455.2 (M+1)⁺, 1478.1 (M+23)$^{Na+}$, 1453.2 (M−1)⁻. $R_f$=0.32 in 7% MeOH/DCM v/v (7A)—

Compound 6A (1.0 g, 0.69 mmol) was dissolved in acetonitrile (70 ml) and HBTU (520 mg, 1.37 mmol) and DIEA (270 mg, 2.06 mmol) were added. The mixture was shaken for 5 minutes then LCAA-CPG (8.6 g, 510A, 131 µmol/g) was added and shaken over night at room temperature. The CPG was filtered and washed with 200 ml each of DCM, 20% MeOH/DCM v/v, and diethyl ether then dried in vacuo. The CPG was shaken for 1 hour in acetic anhydride (12.5 ml), pyridine (37.5 ml), and triethylamine (0.5 ml) before being washed again by the same conditions as before. Compound 7A was dried in vacuo overnight and loading was measured with a spectrophotometer (73 µmol/g).

(8A)—

Compound 5A (2.0 g, 1.48 mmol) was coevaporated with pyridine twice and put under a strict argon atmosphere. DCM (15 ml) was added to the flask and cooled to 0° C. before the addition of 2-Cyanoethyl N,N,N',N'-tetraisopropylphosphordiamidite (890 mg, 2.95 mmol). The mixture was stirred for 20 minutes then 4,5-Dicyanoimidazole (175 mg, 1.48 mmol) was added to the reaction. The reaction was slowly warmed to room temperature over night. The reaction was washed with saturated bicarbonate and the aqueous layer extracted with DCM. The organic layer was dried with Na₂SO₄, evaporated in vacuo to yield a pale yellow foam. The foam was loaded onto a pretreated manual column (Φ=4.6×19) prepared with 2% triethylamine/49% EtOAc/hexanes v/v. The impurities were eluted with 80% EtOAc/hexanes v/v (8 CV) followed by 100% EtOAc (8 CV). The EtOAc was then purged with 100% DCM (1 CV). 8A was eluted with 3% MeOH/DCM v/v (5 CV), and 6% MeOH/DCM v/v (5 CV). 8A was evaporated in vacuo to yield 1.65 g (1.06 mmol, 72%) of the amidite as a diastereomeric mixture.

¹H NMR (400 MHz, DMSO-d₆) δ 11.40 (s, 1H), 8.42 (s, 1H), 8.05-7.85 (m, 6H), 7.74-7.44 (m, 10H), 7.43-7.15 (m, 11H), 6.81 (q, J=8.8 Hz, 4H), 5.95 (t, J=3.7 Hz, 1H), 5.75 (d, J=3.2 Hz, 1H), 5.36 (dd, J=11.1, 3.2 Hz, 1H), 4.74 (d, J=8.5 Hz, 1H), 4.57-4.40 (m, 4H), 4.30 (dq, J=29.0, 9.1 Hz, 2H), 4.21-4.06 (m, 1H), 3.82-3.68 (m, 8H), 3.64-3.43 (m, 7H), 3.30-3.19 (m, 4H), 3.04 (d, J=2.6 Hz, 3H), 3.00 (s, 3H), 2.97-2.86 (m, 5H), 2.74 (t, J=5.6 Hz, 1H), 2.54 (t, J=5.9 Hz, 1H), 2.03 (s, 2H), 1.69 (s, 3H), 1.56-1.36 (m, 6H), 1.34-1.04 (m, 19H), 0.95 (d, J=6.7 Hz, 3H). ¹³C NMR (125 MHz, DMSO-d₆) δ 171.85, 169.52, 165.35, 165.30, 165.01, 158.23, 158.19, 157.72, 157.41, 157.39, 149.96, 149.93, 144.86, 144.83, 136.91, 136.66, 135.50, 135.49, 135.44, 135.40, 133.91, 133.64, 133.61, 129.84, 129.80, 129.77, 129.71, 129.34, 129.32, 129.30, 129.17, 129.15, 129.11, 128.84, 128.73, 127.91, 127.89, 127.79, 127.71, 126.83, 126.80, 120.20, 119.00, 118.79, 113.25, 101.04, 85.79, 85.75, 85.26, 82.88, 82.63, 80.07, 79.65, 72.01, 70.12, 68.88, 68.07, 63.50, 63.37, 62.18, 58.78, 58.65, 58.21, 58.06, 55.15, 55.14, 55.12, 49.88, 45.74, 35.15, 34.77, 29.30, 29.27, 29.24, 28.72, 26.39, 25.30, 25.28, 24.47, 24.44, 24.42, 24.38, 24.34, 24.28, 22.83, 21.98, 21.21, 19.96, 19.91, 19.88, 19.83, 18.96, 9.56. ³¹P NMR (160 MHz, DMSO-d₆) δ 154.02, 153.99. LRMS calculated for $C_{83}H_{99}N_{10}O_{18}P$ 1554.6876, found m/z 1555.3 (M+1)⁺, 1578.3 (M+23)$^{Na+}$, 1555.4 (M−1)⁻, 1590.2 (M+35)$^{Cl-}$. $R_f$=0.46 in 7% MeOH/DCM v/v.

Example 72

Scheme 124
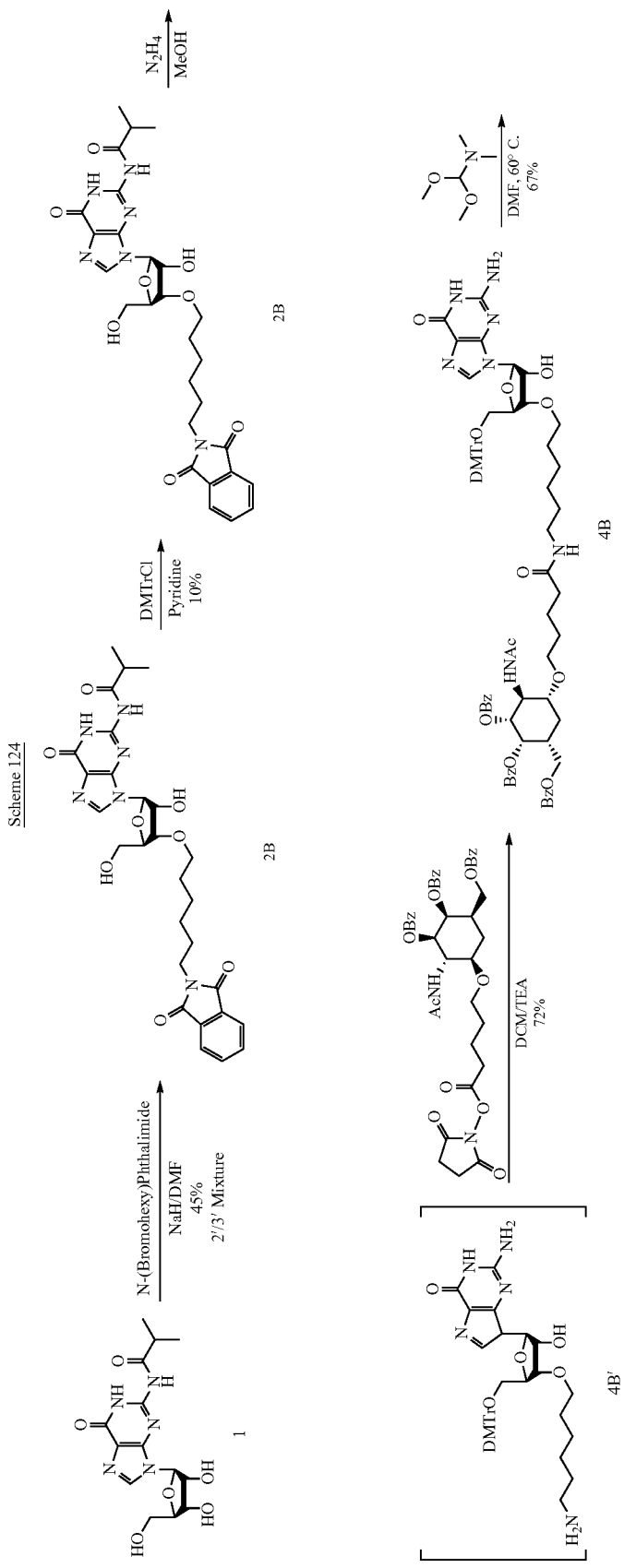

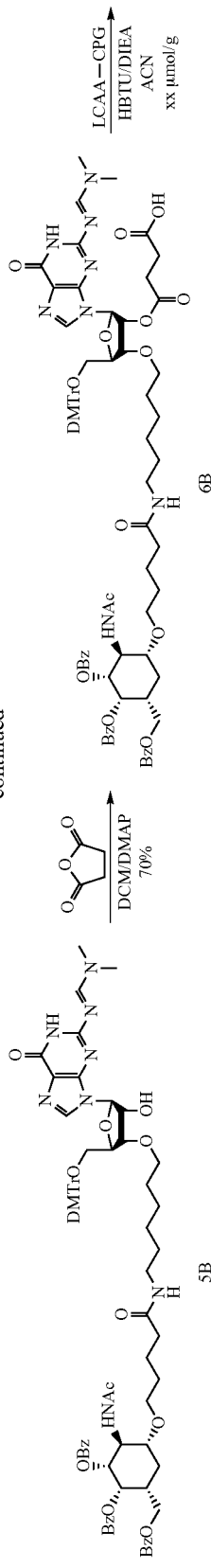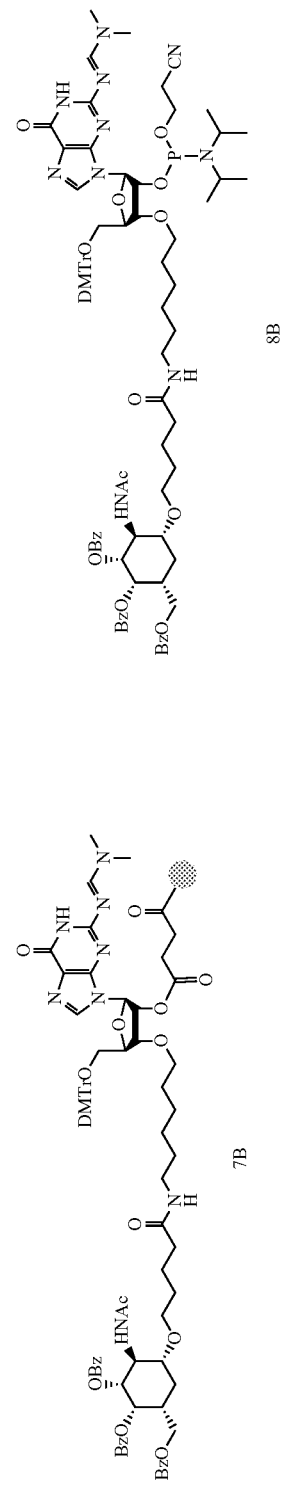

(4B)—

Compound 3B (4.2 g, 4.75 mmol) was deprotected using the same conditions as 3A to give compound 3B*. LRMS calculated for $C_{37}H_{44}N_6O_7$ 684.3271, found m/z 685.2 (M+1)⁺, 707.2 (M+23)^{Na+}, 683.3 (M−1)⁻, 719.3 (M+35)^{Cl−}. $R_f$=0.00 in 7% MeOH/DCM v/v Compound 3B* was then treated with GalNAc(OBz)-C5-NHS ester (3.8 g, 5.22 mmol) in the same manner as compound 3A*. 4.5 g of compound 4B was obtained (3.43 mmol, 72%).

LRMS calculated for $C_{71}H_{77}N_7O_{17}$ 1299.5376, found m/z 1300.1 (M+1)⁺, 1322.1 (M+23)^{Na+}, 1298.2 (M−1)⁻, 1334.2 (M+35)^{Cl−}. $R_f$=0.29 in 7% MeOH/DCM v/v. ¹H NMR (500 MHz, DMSO-$d_6$) δ 10.91 (s, 1H), 10.65 (s, 1H), 8.13 (d, J=9.3 Hz, 1H), 7.92 (t, J=6.5 Hz, 4H), 7.82 (d, J=7.5 Hz, 2H), 7.76-7.67 (m, 3H), 7.64 (t, J=7.4 Hz, 1H), 7.57 (q, J=8.0 Hz, 3H), 7.49 (t, J=7.7 Hz, 2H), 7.41-7.31 (m, 4H), 7.27 (t, J=7.6 Hz, 2H), 7.21 (d, J=8.5 Hz, 5H), 6.89-6.81 (m, 4H), 6.75 (s, 2H), 5.75 (d, J=3.2 Hz, 1H), 5.71 (d, J=4.7 Hz, 1H), 5.50 (d, J=6.0 Hz, 1H), 5.36 (s, 6H), 4.78 (d, J=8.5 Hz, 1H), 4.60 (q, J=4.9 Hz, 1H), 4.45 (q, J=10.0, 8.2 Hz, 2H), 4.38-4.24 (m, 2H), 4.03-3.95 (m, 2H), 3.79 (d, J=9.6 Hz, 1H), 3.72 (s, 6H), 3.62-3.47 (m, 2H), 3.18 (ddd, J=44.2, 10.5, 3.7 Hz, 2H), 3.01-2.95 (m, 2H), 2.06 (s, 2H), 1.70 (s, 3H), 1.56-1.41 (m, 6H), 1.35 (q, J=6.6, 6.1 Hz, 2H). ¹³C NMR (125 MHz, DMSO-$d_6$) δ 171.74, 169.35, 165.18, 165.12, 164.83, 158.00, 156.60, 153.94, 151.24, 144.70, 135.43, 134.92, 133.74, 133.45, 129.61, 129.17, 129.15, 129.13, 129.00, 128.98, 128.94, 128.68, 128.56, 127.75, 127.63, 126.63, 116.62, 113.10, 100.88, 86.80, 85.54, 80.71, 77.77, 72.13, 71.91, 69.96, 69.62, 68.69, 67.88, 63.34, 62.61, 62.04, 54.97, 54.90, 49.69, 34.95, 29.24, 29.12, 28.52, 26.27, 25.21, 22.67, 21.81, 8.43.

(5B)—

Compound 4B (4.3 g, 3.31 mmol) was protected in the same manner as compound 4A to yield 3.0 g of compound 5B (2.21 mmol, 67%)

¹H NMR (400 MHz, DMSO-$d_6$) δ 11.37 (s, 1H), 10.46 (s, 1H), 8.51 (s, 1H), 8.08 (d, J=9.3 Hz, 1H), 7.99-7.87 (m, 5H), 7.77 (t, J=5.5 Hz, 1H), 7.73-7.52 (m, 7H), 7.48 (t, J=7.7 Hz, 2H), 7.37 (t, J=7.8 Hz, 2H), 7.31 (d, J=7.3 Hz, 2H), 7.21 (dd, J=19.7, 8.2 Hz, 7H), 6.81 (dd, J=8.9, 2.4 Hz, 4H), 5.82 (d, J=4.1 Hz, 1H), 5.74 (d, J=3.3 Hz, 1H), 5.52 (d, J=5.8 Hz, 1H), 5.36 (dd, J=11.1, 3.3 Hz, 1H), 4.81-4.67 (m, 2H), 4.44 (q, J=8.7, 7.5 Hz, 2H), 4.38-4.23 (m, 2H), 4.10 (t, J=5.3 Hz, 1H), 3.99 (q, J=4.8 Hz, 1H), 3.78 (d, J=9.6 Hz, 1H), 3.71 (s, 6H), 3.64-3.56 (m, 1H), 3.50 (d, J=9.7 Hz, 1H), 3.24-3.12 (m, 2H), 3.03 (d, J=7.3 Hz, 10H), 2.05 (s, 2H), 1.69 (s, 3H), 1.55-1.29 (m, 8H). ¹³C NMR (125 MHz, DMSO-$d_6$) δ 171.73, 169.36, 165.19, 165.13, 164.84, 158.00, 157.99, 157.80, 157.57, 157.22, 149.83, 144.70, 136.79, 135.46, 135.43, 133.74, 133.47, 133.45, 129.58, 129.55, 129.17, 129.15, 129.14, 129.00, 128.98, 128.94, 128.68, 128.56, 127.73, 127.60, 126.63, 119.77, 113.08, 100.89, 87.65, 85.46, 80.73, 77.67, 72.05, 71.90, 69.96, 69.75, 68.71, 67.90, 63.22, 62.04, 54.99, 54.97, 49.71, 34.98, 34.63, 29.22, 29.13, 28.54, 26.26, 25.20, 22.67, 21.83, 8.38. LRMS calculated for $C_{74}H_{82}N_8O_{17}$ 1354.5798, found m/z 1355.3 (M+1)⁺, 1377.2 (M+23)^{Na+}, 1389.3 (M+35)^{Cl−}. $R_f$=0.37 in 7% MeOH/DCM v/v.

(6B)—

Compound 5B (150 mg, 0.11 mmol) was treated with succinic anhydride (22 mg, 0.22 mmol) in the same manner as compound 5A to yield 120 mg of compound 6B (0.082 mmol, 75%).

¹H NMR (500 MHz, DMSO-$d_6$) δ 11.47 (s, 1H), 8.51 (s, 1H), 8.09 (d, J=9.3 Hz, 1H), 7.99 (s, 1H), 7.92 (t, J=7.1 Hz, 4H), 7.76 (t, J=5.4 Hz, 1H), 7.74-7.67 (m, 3H), 7.63 (t, J=7.4 Hz, 1H), 7.57 (q, J=8.2 Hz, 3H), 7.49 (t, J=7.8 Hz, 2H), 7.38 (t, J=7.8 Hz, 2H), 7.29 (d, J=7.3 Hz, 2H), 7.27-7.14 (m, 7H), 6.81 (d, J=7.9 Hz, 4H), 6.03 (d, J=2.7 Hz, 1H), 6.00-5.97 (m, 1H), 5.76 (d, J=3.2 Hz, 1H), 5.37 (dd, J=11.1, 3.3 Hz, 1H), 4.76 (d, J=8.5 Hz, 1H), 4.55-4.49 (m, 1H), 4.45 (q, J=9.9, 8.2 Hz, 2H), 4.38-4.25 (m, 2H), 4.04-3.99 (m, 1H), 3.83-3.76 (m, 1H), 3.71 (s, 6H), 3.54-3.41 (m, 2H), 3.40-3.26 (m, 6H), 3.14 (dd, J=10.7, 4.1 Hz, 1H), 3.05 (s, 3H), 3.04-2.97 (m, 6H), 2.62-2.56 (m, 2H), 2.06 (s, 2H), 1.70 (s, 3H), 1.56-1.45 (m, 4H), 1.34 (dd, J=19.5, 13.0 Hz, 4H), 1.17 (s, 4H). ¹³C NMR (125 MHz, DMSO-$d_6$) δ 173.26, 172.01, 171.73, 171.46, 169.36, 168.68, 165.18, 165.13, 164.84, 158.00, 157.90, 157.54, 157.36, 149.37, 144.55, 137.17, 135.38, 135.31, 133.74, 133.48, 133.45, 129.54, 129.51, 129.18, 129.15, 129.14, 129.01, 128.99, 128.94, 128.68, 128.56, 127.73, 127.57, 126.63, 119.94, 113.06, 100.90, 86.10, 85.41, 80.53, 75.77, 72.98, 71.88, 70.43, 69.96, 68.70, 67.90, 62.55, 62.02, 54.96, 51.99, 49.71, 45.43, 34.97, 34.62, 33.24, 29.14, 29.10, 28.94, 28.84, 28.54, 26.20, 25.18, 22.66, 22.59, 21.82, 21.13, 14.72, 10.03, 7.16. LRMS calculated for $C_{78}H_{86}N_8O_{20}$ 1454.5958, found m/z 1455.3 (M+1)⁺, 1453.2 (M−1)⁻. $R_f$=0.43 in 5% MeOH/5% Et₃N/DCM v/v.

(7B)—

Compound 6B (80 mg, 0.051 mmol) was loaded on to LCAA-CPG in the same manner as 6A to yield 640 mg of CPG (69 µmol/g).

(8B)—

Compound 5B (200 mg, 0.148 mmol) was coevaporated with ACN and then with pyridine. 5B was then phosphitylated in a similar manner as 5A to yield 80 mg of 8B as a diastereomeric mixture (0.051 mmol, 34.7%).

¹H NMR (400 MHz, DMSO-$d_6$) δ 11.41 (s, 1H), 8.47 (d, J=11.9 Hz, 1H), 8.06-7.86 (m, 6H), 7.77-7.43 (m, 10H), 7.42-7.12 (m, 11H), 6.81 (dd, J=5.9, 2.7 Hz, 4H), 5.98 (dd, J=21.6, 3.6 Hz, 1H), 5.76 (d, J=3.2 Hz, 1H), 5.38 (dd, J=11.1, 3.2 Hz, 1H), 5.07-4.92 (m, 1H), 4.75 (d, J=8.5 Hz, 1H), 4.53-4.20 (m, 5H), 4.07-3.98 (m, 1H), 3.86-3.45 (m, 14H), 3.41-3.13 (m, 8H), 3.02 (dd, J=10.2, 3.3 Hz, 8H), 2.74 (dd, J=12.3, 6.3 Hz, 1H), 2.57 (t, J=5.9 Hz, 1H), 2.05 (s, 2H), 1.70 (s, 3H), 1.48 (d, J=27.8 Hz, 6H), 1.39-1.30 (m, 2H), 1.26-1.04 (m, 15H), 0.89 (d, J=6.7 Hz, 3H). ¹³C NMR (125 MHz, DMSO-$d_6$) δ 171.89, 169.54, 165.36, 165.31, 165.03, 158.21, 158.19, 157.82, 157.75, 157.71, 157.40, 149.88, 149.85, 144.82, 137.15, 137.02, 135.57, 135.52, 135.50, 133.92, 133.65, 133.61, 129.74, 129.35, 129.33, 129.32, 129.19, 129.17, 129.16, 129.11, 128.84, 128.73, 127.92, 127.76, 126.83, 120.14, 120.01, 118.98, 118.80, 113.25, 101.07, 85.74, 85.64, 72.02, 70.13, 68.92, 68.08, 62.19, 55.13, 55.11, 49.90, 46.32, 45.78, 42.96, 42.86, 35.19, 34.78, 29.47, 29.41, 29.33, 29.31, 28.75, 26.48, 25.44, 24.48, 24.43, 24.39, 24.37, 24.34, 24.05, 23.99, 22.84, 22.04. ³¹P NMR (162 MHz, DMSO) δ 151.33, 150.99. LRMS calculated for $C_{83}H_{99}N_{10}O_{18}P$ 1554.6876, found m/z 1555.3 (M+1)⁺, 1577.3 (M+23)^{Na+}, 1555.4 (M−1)⁻, 1591.2 (M+35)^{Cl−}. $R_f$=0.46 in 7% MeOH/DCM v/v.

Example 73
Scheme 125
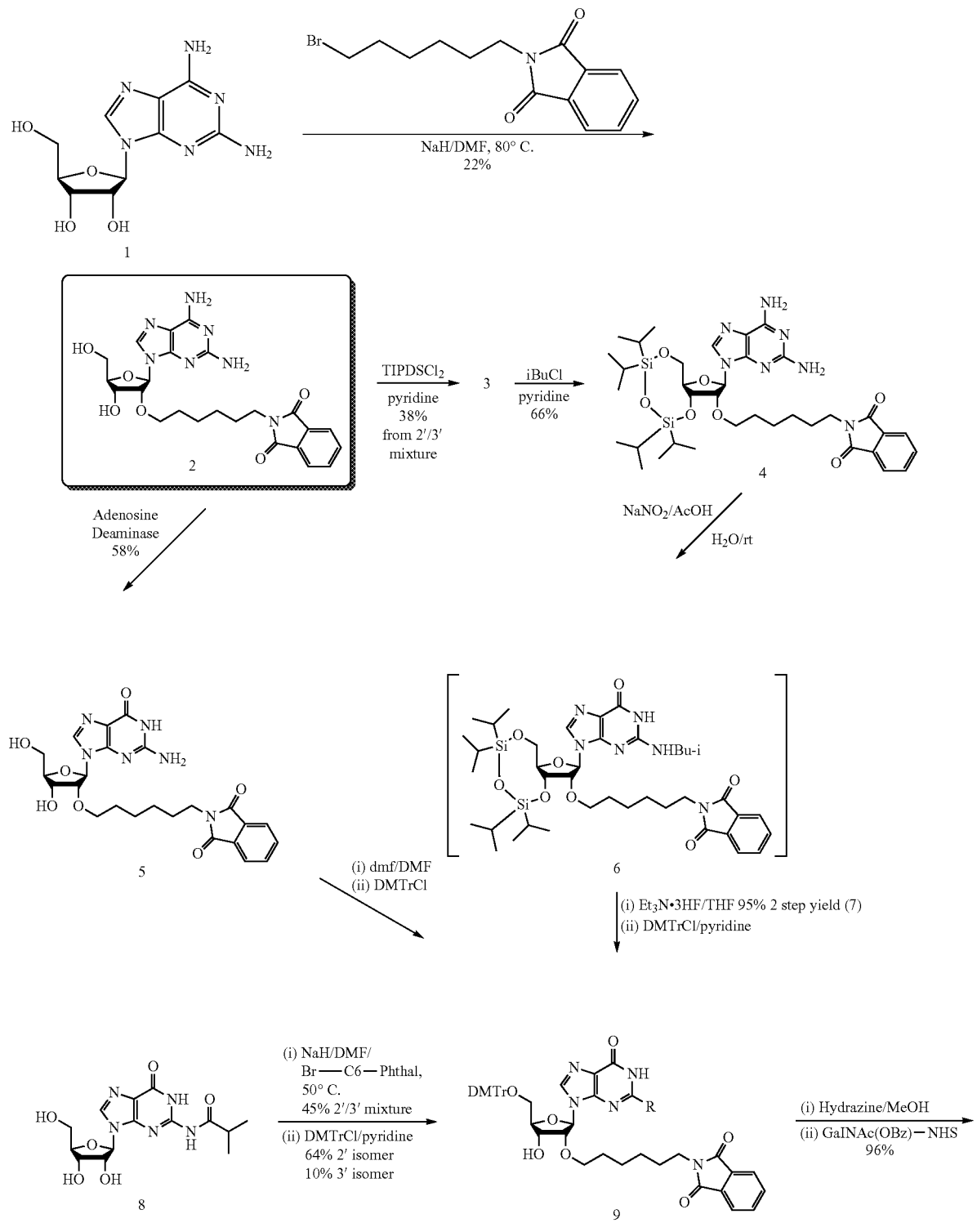

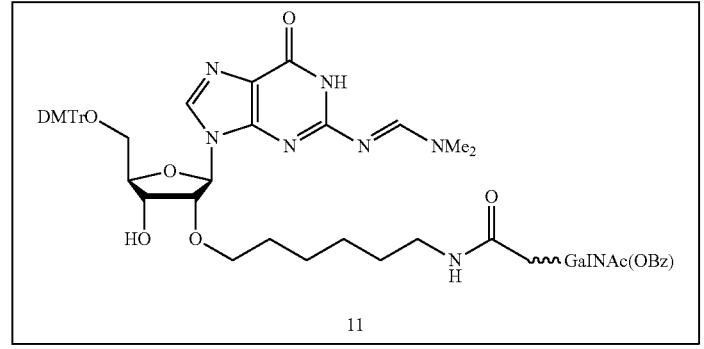

(2)—

Compound 1 (30.0 g, 106 mmol) was dissolved in DMF (300 ml) and cooled in an ice bath. NaH (3.86 g, 159 mmol) was added and the mixture stirred for 1 hour. N-(Bromohexyl)phthalimide (37.8 g, 122 mmol) was then added and the reaction heated to 70° C. over night. DMF was evaporated in vacuo to a brown gum. The brown gum was dissolved in a 1 to 1 mixture of DCM and MeOH for adsorption to silica gel. The solvent mixture was removed in vacuo and the crude product was purified to yield 8.10 g of 2 (15.83 mmol, 14.9%) as well as a mixture of 2 and its 3'-O-alkylated regioisomer (23.45 g, 45.84 mmol, 43.2%). The total yield of 2 and the regioisomer was 58%.

$^1$H NMR (400 MHz, DMSO-$d_6$) δ 7.95 (s, 1H), 7.89-7.77 (m, 4H), 6.78 (s, 2H, $D_2O$ exchangeable), 5.81 (d, J=6.7 Hz, 1H), 5.74 (s, 2H, $D_2O$ exchangeable), 5.51-5.43 (m, 1H, $D_2O$ exchangeable), 5.08 (d, J=4.9 Hz, 1H, $D_2O$ exchangeable), 4.37 (dd, J=6.6, 5.0 Hz, 1H), 4.27-4.21 (m, 1H), 3.92 (q, J=3.3 Hz, 1H), 3.67-3.59 (m, 1H), 3.52 (q, J=7.9, 7.0 Hz, 4H), 3.34-3.30 (m, 1H), 1.45 (dt, J=38.0, 6.6 Hz, 4H), 1.24-1.12 (m, 4H). $^{13}$C NMR (100 MHz, DMSO-$d_6$) δ 167.90, 160.03, 156.21, 151.36, 136.06, 134.31, 131.55, 122.95, 113.48, 86.18, 85.11, 80.52, 69.50, 69.12, 61.68, 54.88, 28.94, 27.84, 26.00, 24.86. LRMS calculated for $C_{24}H_{29}N_7O_6$ 511.5304, found m/z 512.2 (M+1)$^+$, 534.2 (M+23)$^{Na+}$, 546.2 (M+35)$^{Cl-}$. $R_f$=0.50 in 5% MeOH/DCM v/v.

(3)—

Compound 2 (100 mg, 0.195 mmol) was treated with 1,3-Dichloro-1,1,3,3-tetraisopropyldisiloxane (90 mg, 1.5 eq) in pyridine (1 ml). After 3 days at room temperature, the reaction was quenched with MeOH, washed with saturated bicarbonate, and extracted with DCM. The organic layer was dried with $Na_2SO_4$ and the crude product was purified with silica gel chromatography to yield 120 mg of 3 (0.159 mmol, 82%).

$^1$H NMR (500 MHz, DMSO-$d_6$) δ 7.83 (dtd, J=8.7, 6.2, 3.4 Hz, 4H), 7.73 (s, 1H), 6.76 (s, 2H), 5.73 (d, J=10.5 Hz, 3H), 4.52 (dd, J=8.6, 4.9 Hz, 1H), 4.18 (d, J=4.8 Hz, 1H), 4.03 (dd, J=12.9, 2.1 Hz, 1H), 3.96-3.85 (m, 2H), 3.78-3.70 (m, 1H), 3.66-3.58 (m, 1H), 3.53 (t, J=7.0 Hz, 2H), 1.53 (dp, J=20.7, 6.8 Hz, 4H), 1.30 (ddt, J=44.2, 14.5, 7.2 Hz, 4H), 1.07-0.95 (m, 28H). $^{13}$C NMR (125 MHz, DMSO-$d_6$) δ 167.89, 160.32, 156.12, 150.97, 134.39, 134.33, 131.55, 122.95, 113.27, 86.56, 80.81, 80.63, 70.46, 69.75, 60.23, 29.19, 27.95, 26.09, 25.25, 17.30, 17.18, 17.13, 17.08, 16.96, 16.85, 16.81, 16.74, 12.75, 12.37, 12.23, 12.07. LRMS calculated for $C_{36}H_{55}N_7O_7Si_2$ 754.0356, found m/z 754.3 (M+1)$^+$, 776.3 (M+23)$^{Na+}$, 753.3 (M−1)$^−$, 788.2 (M+35)$^{Cl-}$. $R_f$=0.31 in 5% MeOH/DCM v/v (4)—

Compound 3 (10 g, 13.26 mmol) was dissolved in pyridine (265 ml) and cooled in an EtOH ice bath. Isobutyryl chloride (1.55 g, 14.59 mmol) was added dropwise. The reaction mixture was stirred for 2 hours at −10° C. then 1 hour at room temperature. The reaction was quenched with MeOH and solvents were removed in vacuo. The crude product was washed with saturated bicarbonate and extracted with DCM. The organic layer was dried with $Na_2SO_4$ and purified with silica gel chromatography (eluted with EtoAc/Hexanes). Some N2 and N6 bis protection occurred. 7.21 g of pure 4 was obtained (8.75 mmol, 66%).

$^1$H NMR (400 MHz, DMSO-$d_6$) δ 9.73 (s, 1H), 8.02 (s, 1H), 7.83 (d, J=3.7 Hz, 4H), 7.19 (s, 2H), 5.83 (s, 1H), 4.65 (dd, J=8.3, 5.2 Hz, 1H), 4.32 (d, J=4.5 Hz, 1H), 4.15-4.07 (m, 1H), 3.97-3.85 (m, 2H), 3.81-3.72 (m, 1H), 3.68-3.59 (m, 1H), 3.53 (t, J=6.9 Hz, 2H), 2.91-2.80 (m, 1H), 1.62-1.45 (m, 4H), 1.41-1.21 (m, 4H), 1.20-1.07 (m, 3H), 1.06-0.83 (m, 31H). $^{13}$C NMR (101 MHz, DMSO-$d_6$) δ 174.75, 167.82, 156.01, 152.89, 149.44, 137.57, 134.27, 131.52, 122.89, 116.27, 87.34, 81.19, 80.98, 70.49, 70.30, 60.83, 37.31, 34.01, 29.19, 27.92, 26.08, 25.16, 19.24, 19.19, 17.28, 17.13, 16.97, 16.91, 16.88, 16.82, 12.53, 12.35, 12.12, 12.04. LRMS calculated for $C_{40}H_{61}N_7O_8Si_2$ 823.4120, found m/z 824.2 (M+1)$^+$, 846.2 (M+23)$^{Na+}$, 822.2 (M−1)$^−$, 858.2 (M+35)$^{Cl-}$. $R_f$=0.54 in 100% EtOAc.

(5)—

Compound 2 (500 mg, 0.977 mmol) was dissolved in DMSO (14 ml), PBS (0.1 M, 0.4 ml), and Tris (0.1 M, 12 ml). The pH was lowered to 7.33 with 0.1 M HCl before the addition of adenosine deaminase (250 units, S. thermophilus recombinant in E. coli, CAS: 9026-93-1, SKU: 52544). The formation of a white precipitate occurred shortly after the addition of the enzyme. The reaction proceeded for 3 days then was left an additional 2 days but no more deamination occurred. The addition of enzyme did not push the reaction forward. The pH of the reaction was monitored and adjusted to stay between 6.40 and 7.80. The white precipitate was centrifuged down and the supernatant was decanted. The precipitate was transferred to a flask with pyridine and evaporated in vacuo before being adsorbed to silica and purified with a manual column (Φ=4.6×13.5). DMSO was eluted with 100% EtOAc (2 CV), 4% MeOH in DCM v/v (1 CV) then 6% MeOH in DCM v/v (2 CV). The product 5 was then eluted with 8% MeOH in DCM v/v (2.8 CV), 9% MeOH in DCM v/v (1.2 CV), and finally 10% MeOH in DCM v/v (2.8 CV) to yield 290 mg of 5 (0.566 mmol, 58%).

$^1$H NMR (400 MHz, DMSO-$d_6$) δ 10.61 (s, 1H, $D_2O$ exchangeable), 7.95 (s, 1H), 7.88-7.78 (m, 4H), 6.44 (s, 2H, $D_2O$ exchangeable), 5.76 (d, J=6.1 Hz, 1H), 5.06 (s, 2H, D₂O exchangeable), 4.28-4.17 (m, 2H), 3.63-3.46 (m, 5H), 3.38-3.28 (m, 3H), 1.46 (dt, J=37.2, 6.7 Hz, 4H), 1.19 (d, J=5.6 Hz, 4H). ¹³C NMR (100 MHz, DMSO-d₆) δ 167.88, 156.61, 153.74, 151.18, 135.36, 134.32, 131.55, 122.95, 116.57, 85.85, 84.42, 81.07, 69.56, 68.88, 61.30, 37.26, 28.95, 27.83, 25.99, 24.86. LRMS calculated for $C_{24}H_{28}N_6O_7$ 512.2019, found m/z 513.1 (M+1)⁺, 511.0 (M−1)⁻, 547.0 (M+35)$^{Cl-}$. $R_f$=0.19 in 7% MeOH/DCM v/v.

(6)—

Compound 4 (6.20 g, 7.52 mmol) was dissolved in water (45 ml) and glacial acetic acid (105 ml). NaNO₂ (4.15 g, 60.19 mmol) was then added to the stirring mixture. After about 40 minutes, an additional 4.15 g of NaNO₂ was added and stirred for 2 days at room temperature. An additional 2.1 g of NaNO₂ was added and stirred for an additional 2 days. Starting material had been fully consumed according to TLC. Multiple spots were observed however corresponding to suspected silyl damage. The reaction was then diluted with water and extracted with DCM. The organic layer was washed with saturated bicarbonate then dried with Na₂SO₄. The product 6 was used as crude for the next desilylation step.

(7)—

Compound 6 (7.52 mmol) was desilylated in THF (150 ml) with Et₃N*3HF (14.6 g, 90.28 mmol) over night. THF was removed in vacuo and the crude product was adsorbed to silica then purified with silica gel chromatography (eluted with 5% MeOH/DCM v/v) to give a quantitative yield. NMR showed-95% purity with-5% relating to a diamino nucleoside.

¹H NMR (400 MHz, DMSO-d₆) δ 12.04 (s, 1H), 11.64 (s, 1H), 8.27 (s, 1H), 7.82 (p, J=4.4 Hz, 4H), 5.88 (d, J=6.6 Hz, 1H), 5.13 (d, J=4.7 Hz, 1H), 5.05 (t, J=5.4 Hz, 1H), 4.28 (ddd, J=23.5, 6.8, 4.7 Hz, 2H), 3.92 (q, J=4.0 Hz, 1H), 3.63-3.50 (m, 3H), 3.46 (t, J=7.2 Hz, 2H), 3.35 (d, J=6.5 Hz, 1H), 2.74 (p, J=6.9 Hz, 1H), 1.43 (dt, J=27.1, 6.5 Hz, 4H), 1.25-1.13 (m, 4H), 1.09 (dd, J=6.7, 4.8 Hz, 6H). LRMS calculated for $C_{28}H_{34}N_6O_8$ 582.2438, found m/z 582.2 (M+1)⁺, 581.1 (M−1)⁻, 616.0 (M+35)$^{Cl-}$. $R_f$=0.41 in 7% MeOH/DCM v/v.

Table of Chemical Groups

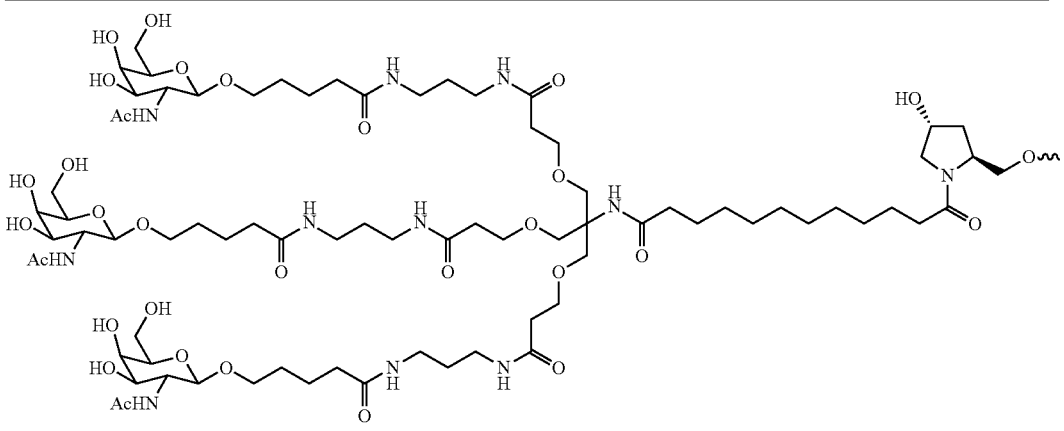

L96

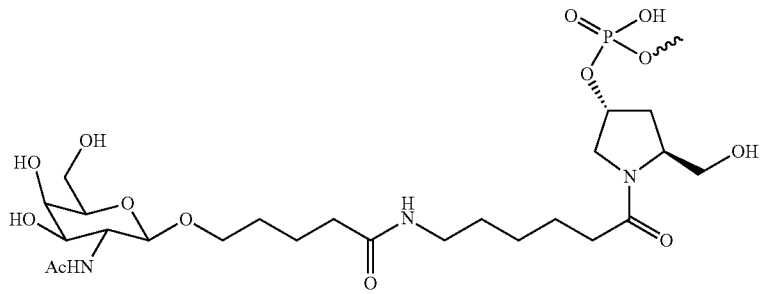

Q150

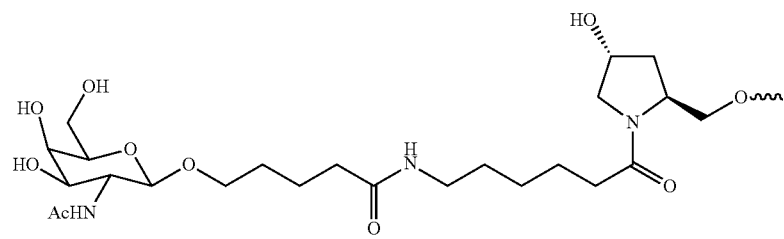

L193

Table of Chemical Groups
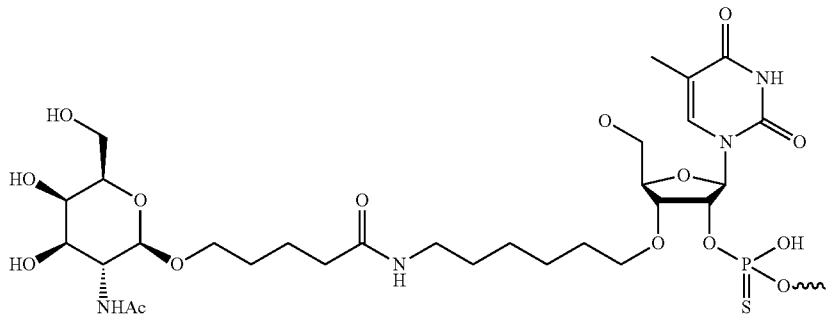
(T3gs)
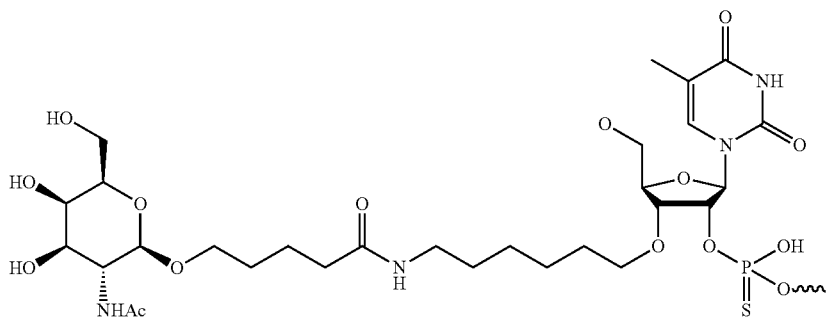
(T3g)
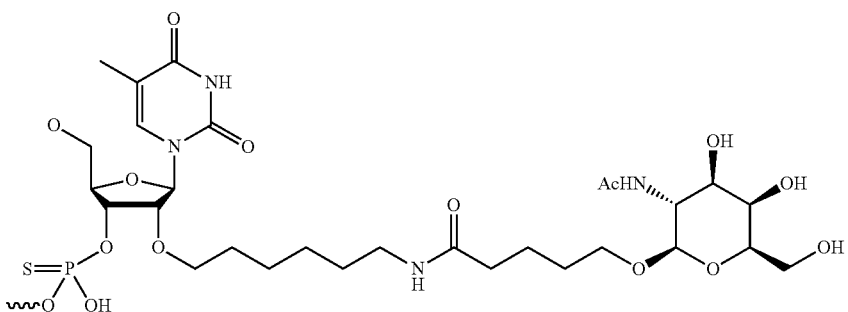
(Tgs)
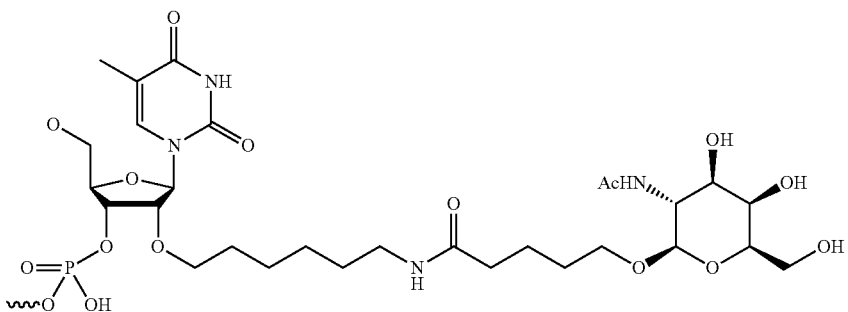
(Tg)

-continued
Table of Chemical Groups
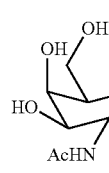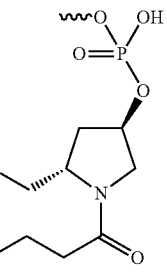
Q155
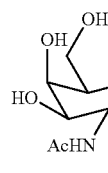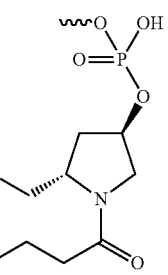
L199
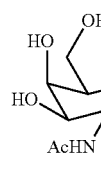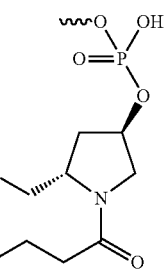
Q160
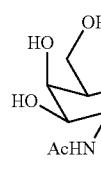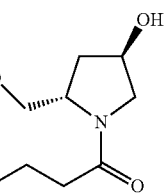
L204

US 10,808,246 B2
731 732
-continued
Table of Chemical Groups
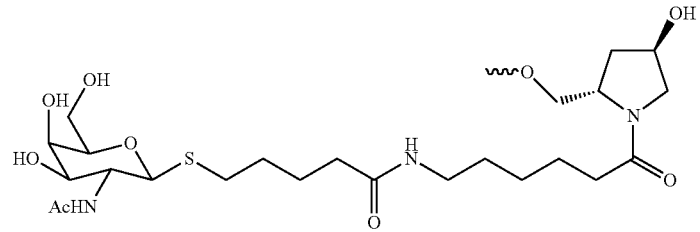
L200
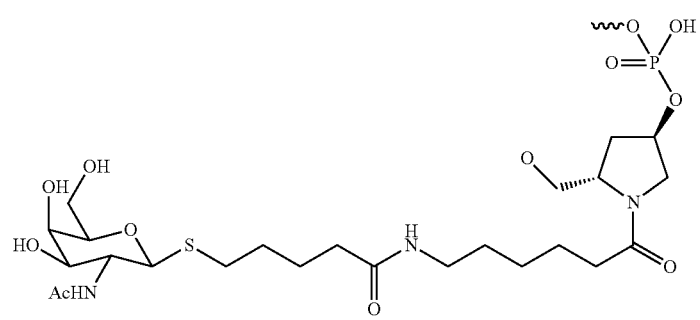
Q156
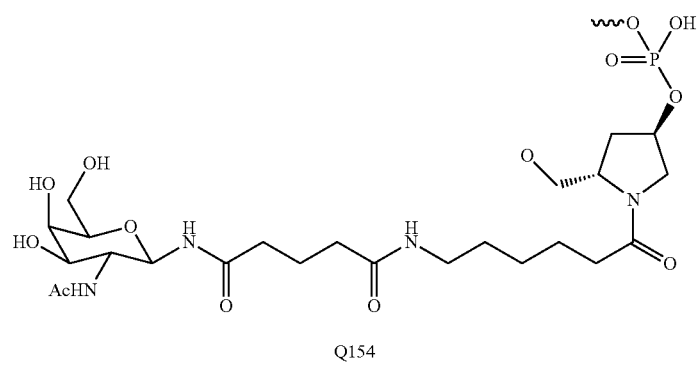
Q154
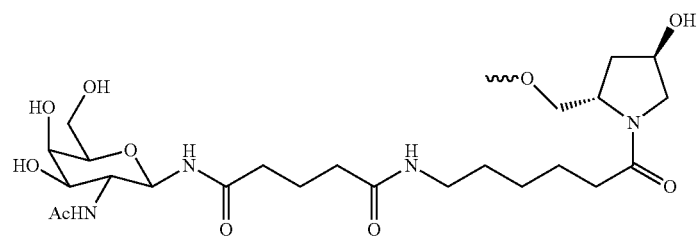
L198

-continued
Table of Chemical Groups
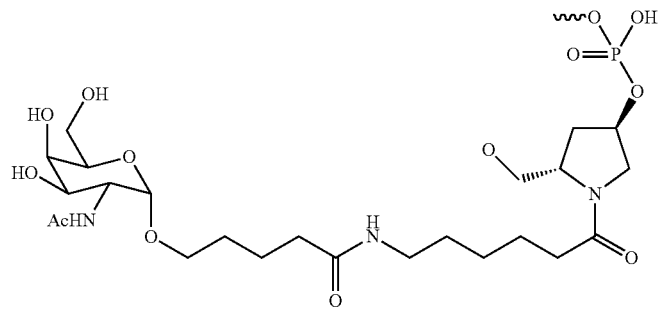
Q161
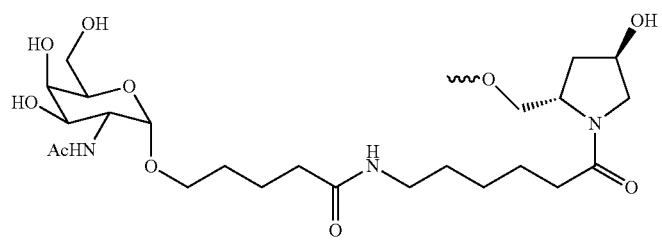
L207
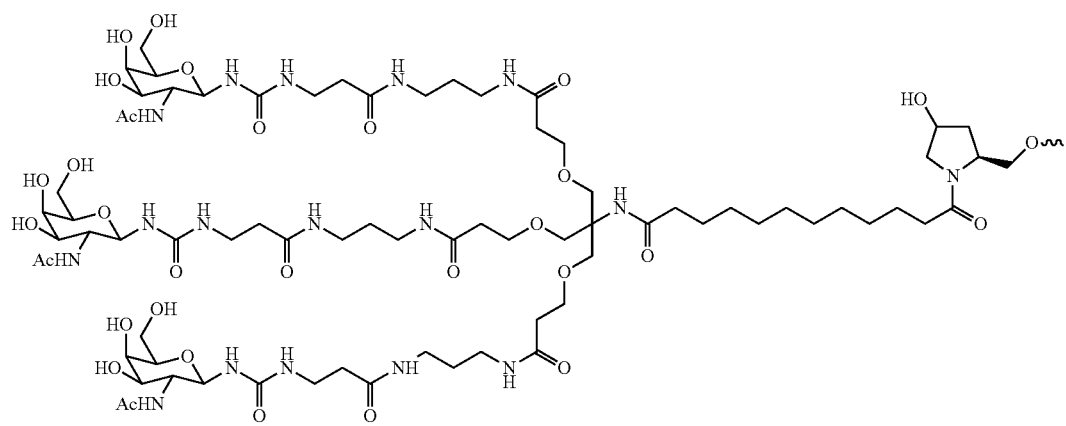
L206
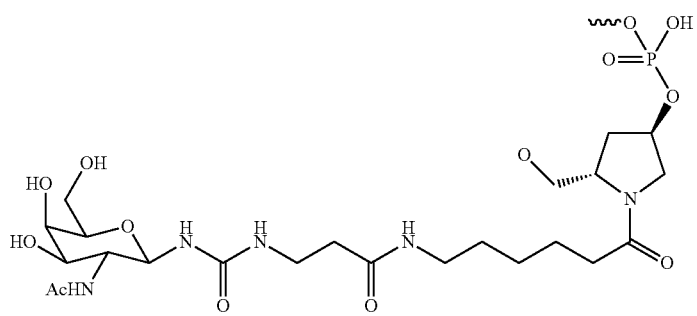
Q159

Table of Chemical Groups
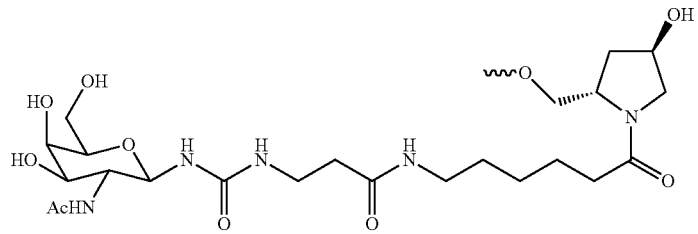
L203
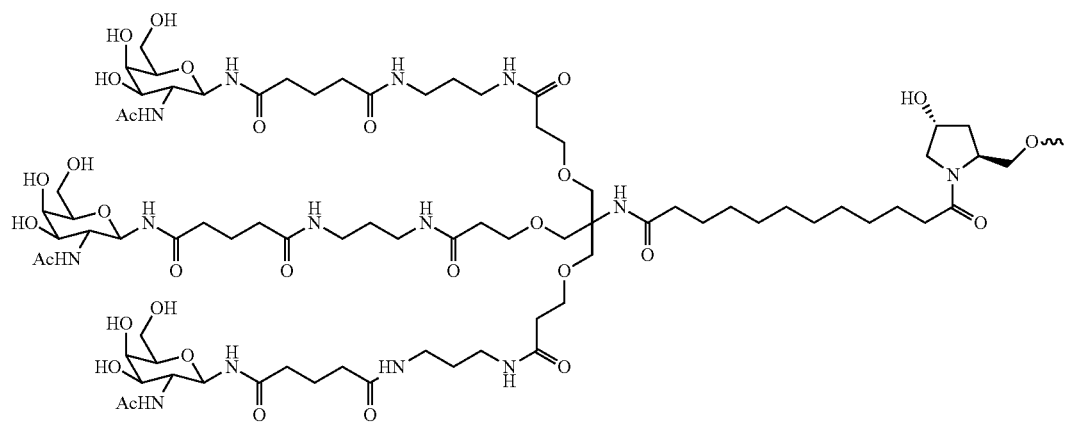
L197
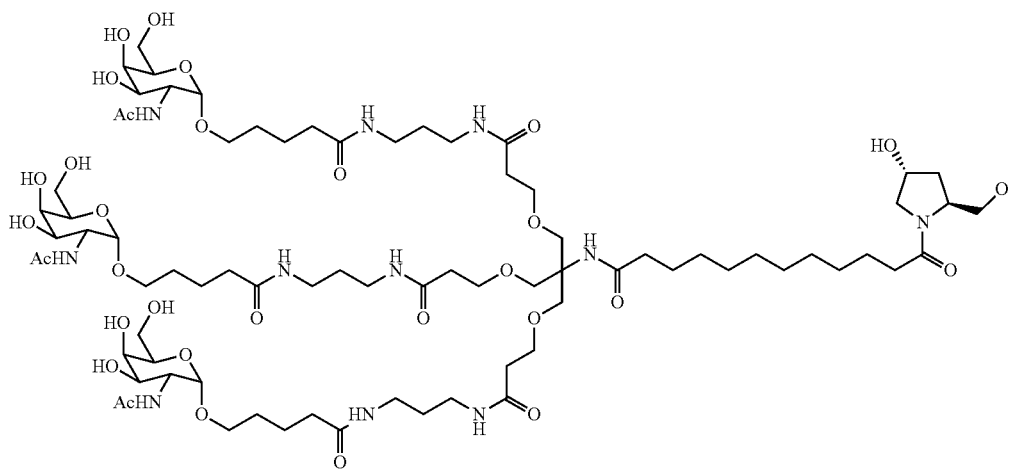 [SMILES: CC(=O)NC1C(OCCCCC(=O)NCCCNC(=O)CCOCC(COCCC(=O)NCCCNC(=O)CCCCOC2OC(CO)C(O)C(O)C2NC(C)=O)(COCCC(=O)NCCCNC(=O)CCCCOC2OC(CO)C(O)C(O)C2NC(C)=O)NC(=O)CCCCCCCCCCC(=O)N2C[C@H](O)C[C@H]2CO)OC(CO)C(O)C1O]
L208

-continued
Table of Chemical Groups
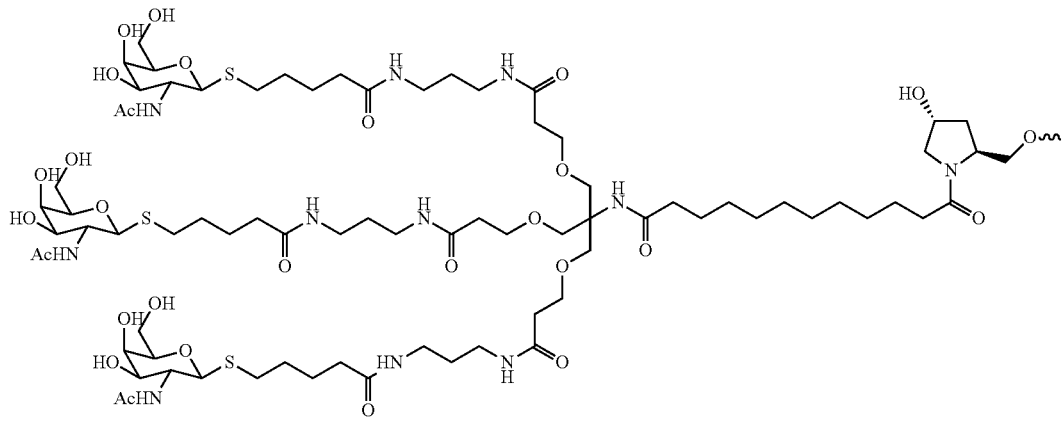
L202
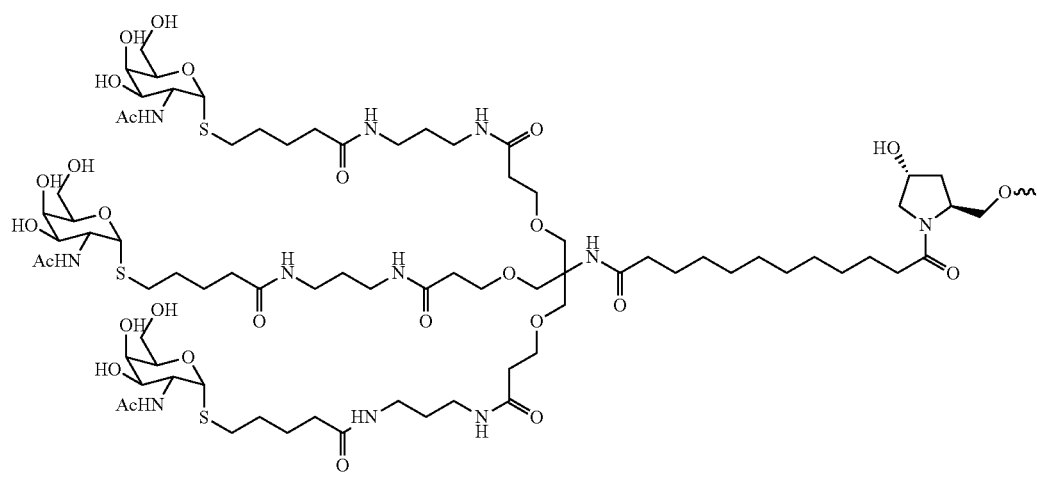
L201
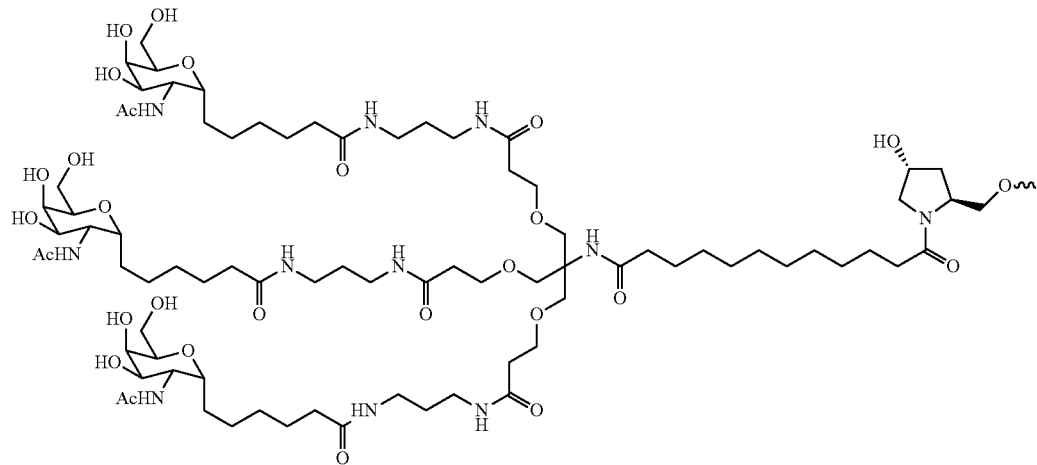
L205

| Table of Chemical Groups |
|---|
| 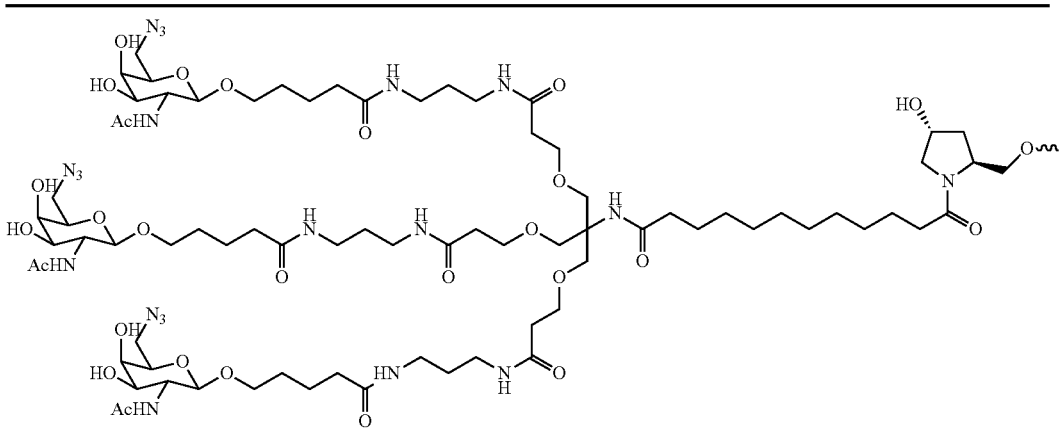<br>L223 |
| 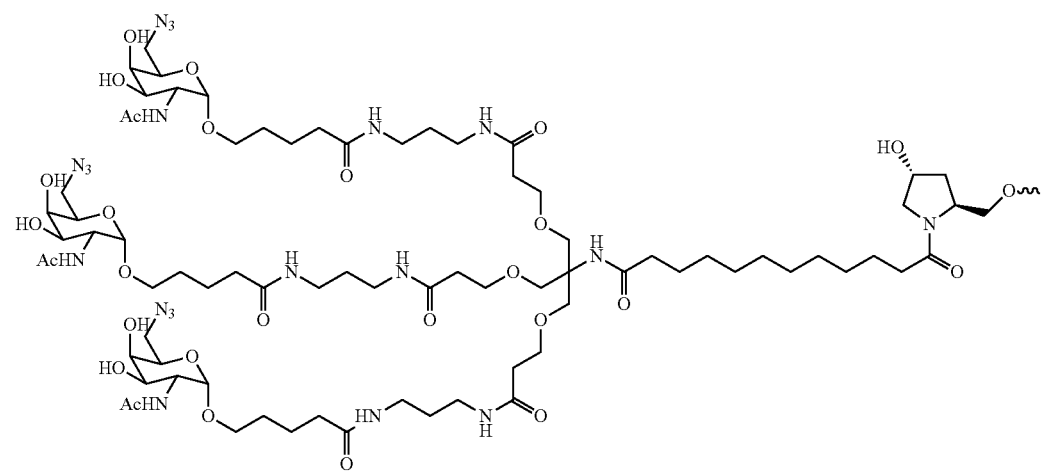<br>L224 |
| 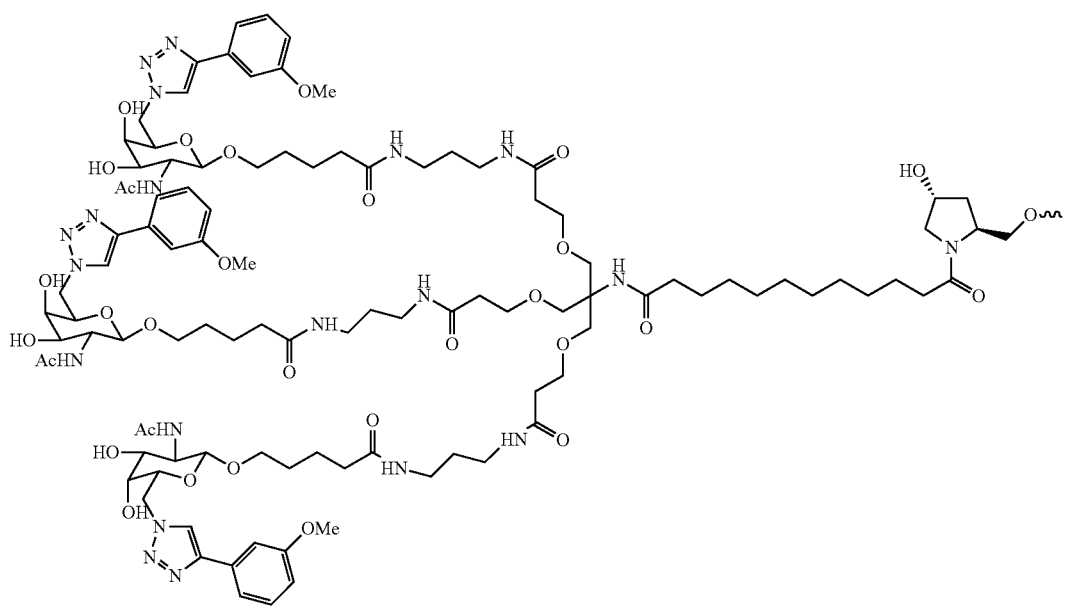<br>L221 |

Table of Chemical Groups
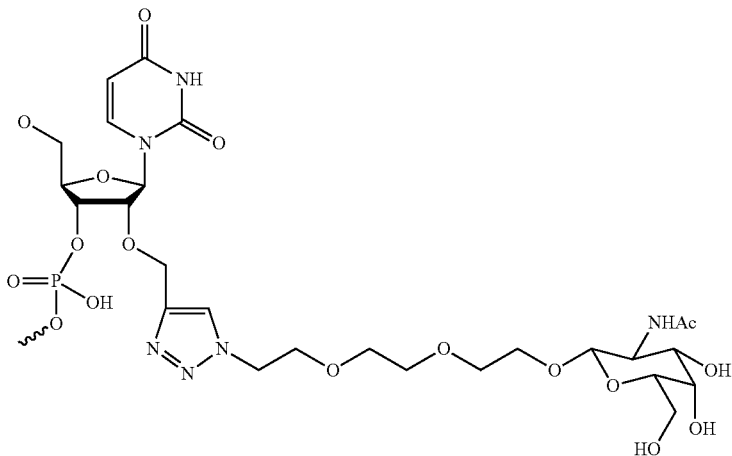
(Uyg)
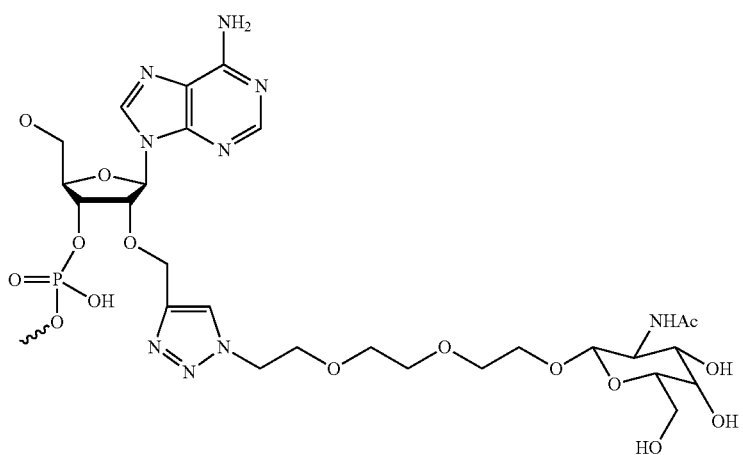
(Ayg)
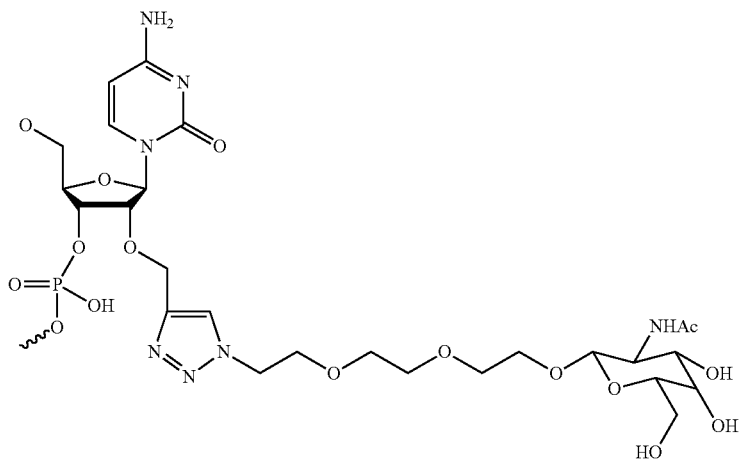
(Cyg)

Table of Chemical Groups
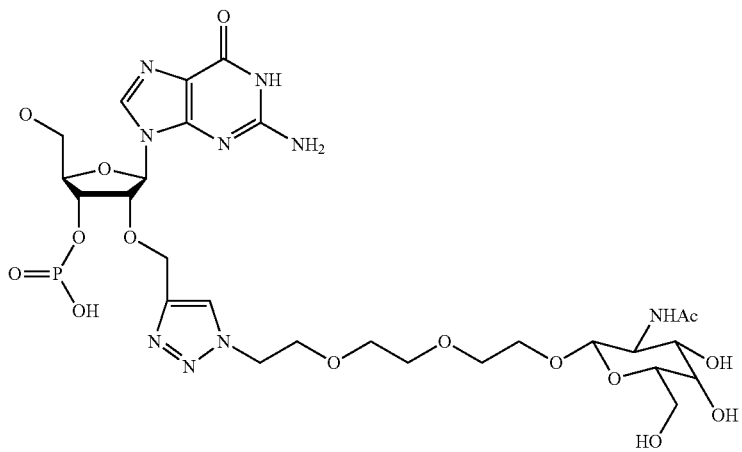
(Gyg)
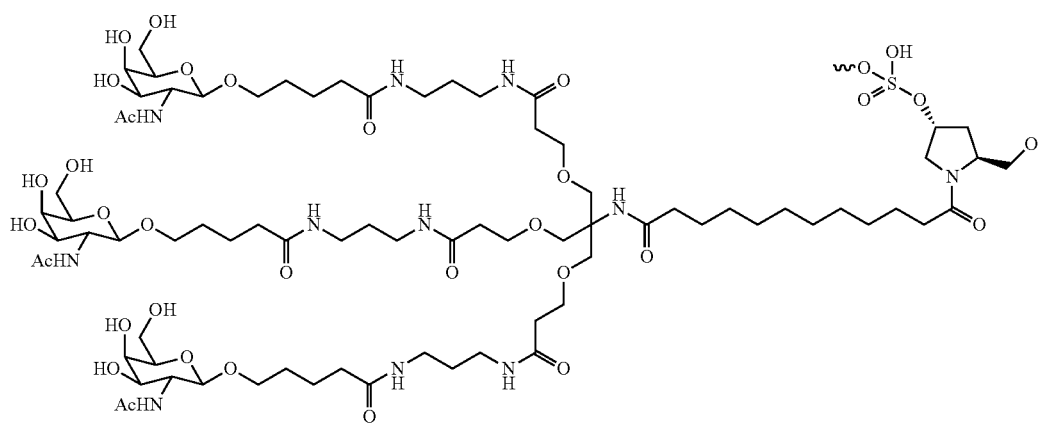
Q151
What is claimed is:
1. A conjugate of the formula:
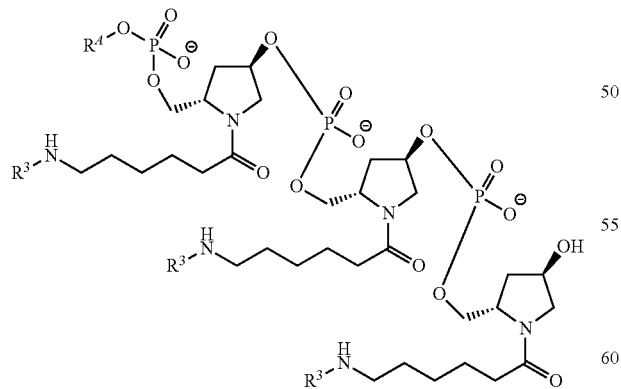
wherein
R$^A$ is a single stranded or double stranded oligonucleotide having (i) a 3' end attached to the oxygen atom shown and (ii) a length ranging from 6 to about 30; and
R$^3$ is selected from the following wherein the arrow → or squiggle indicates the site of conjugation:
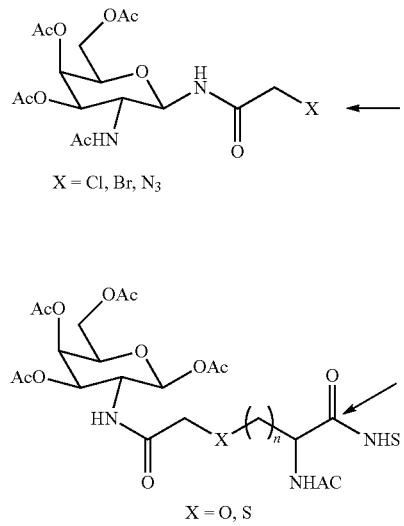
X = Cl, Br, N$_3$
X = O, S

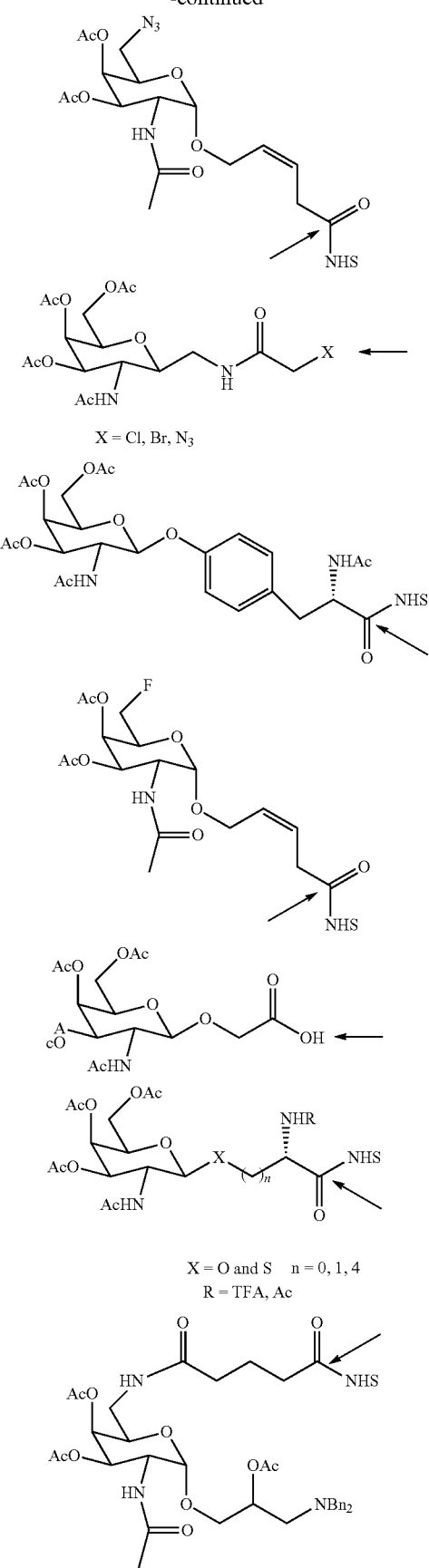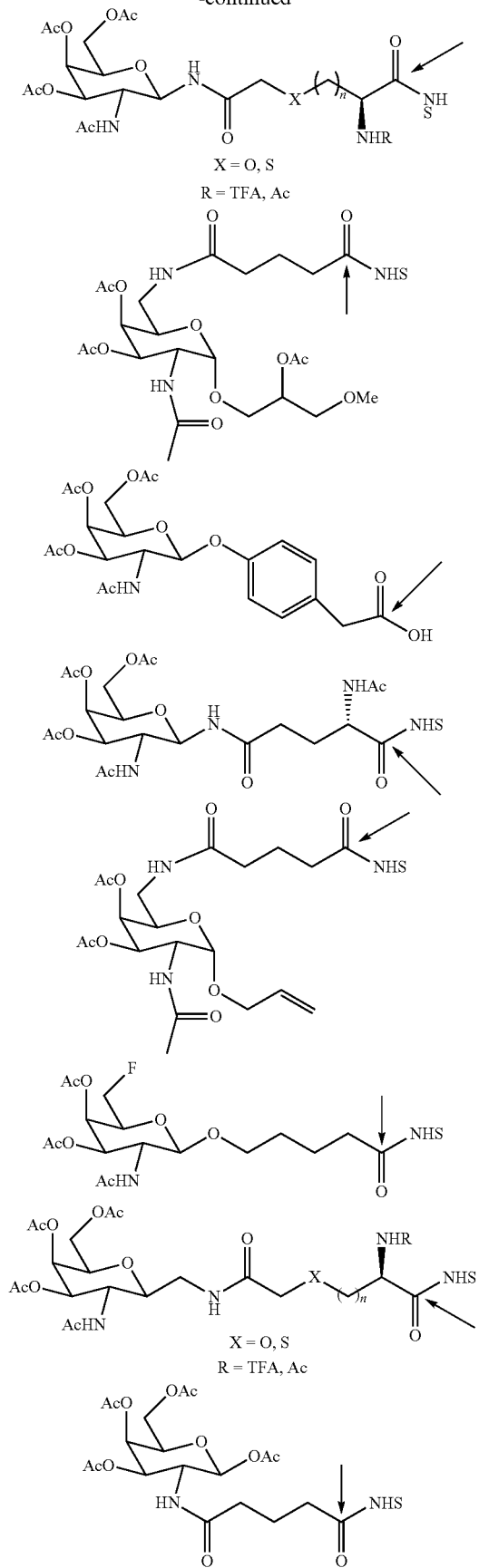

747
-continued
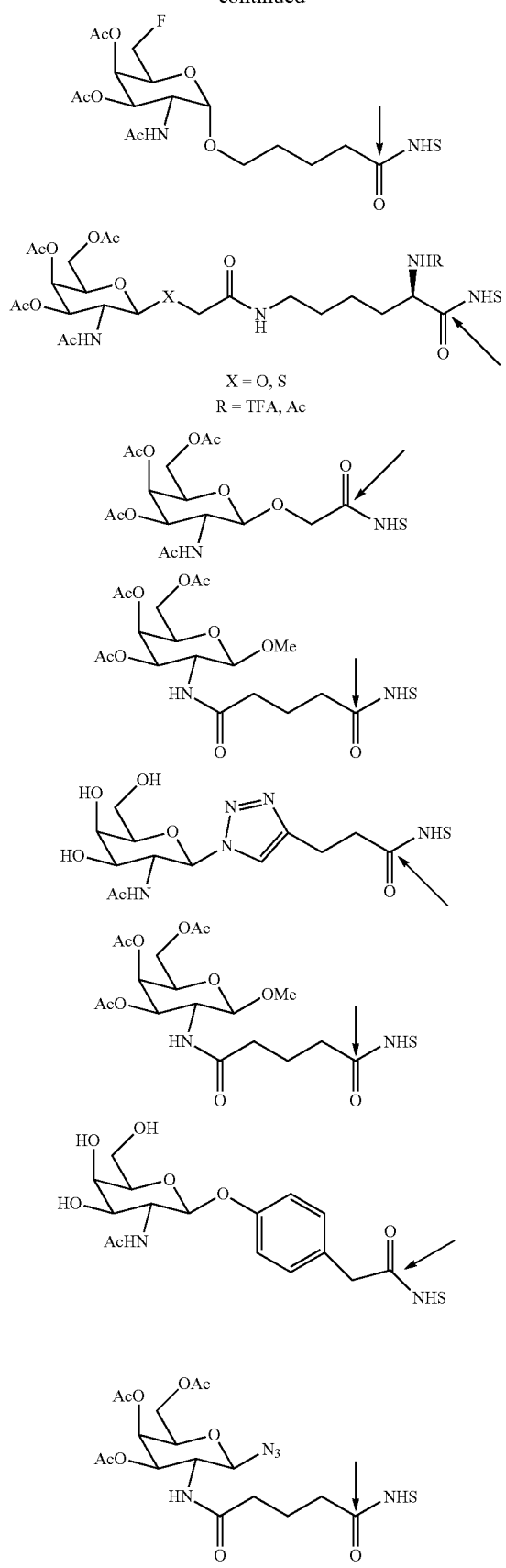
748
-continued
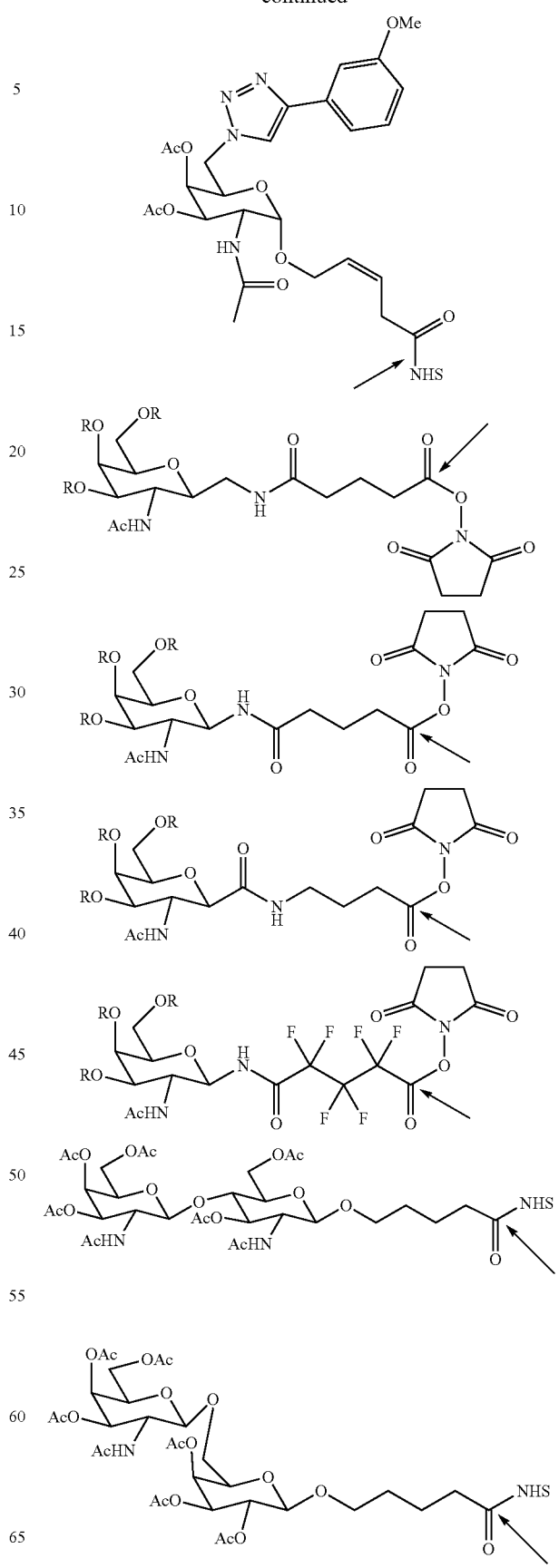

749
-continued
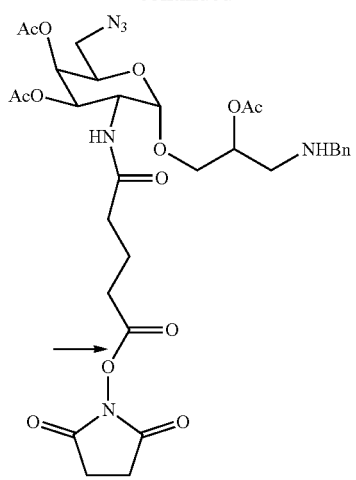
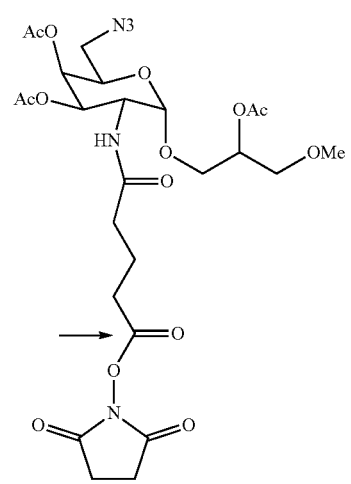
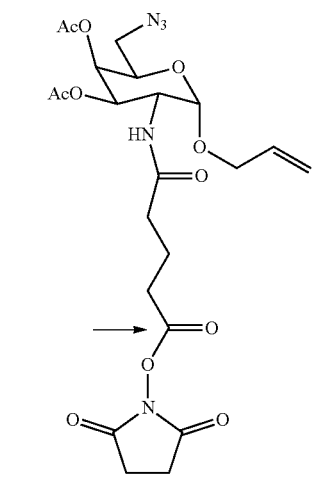
750
-continued
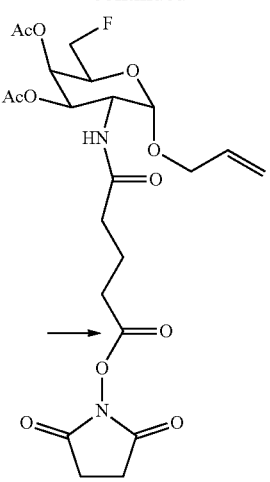
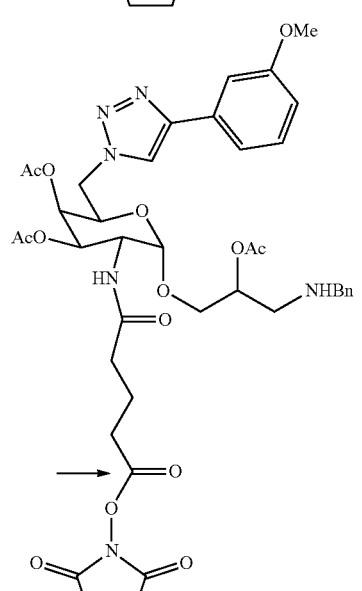
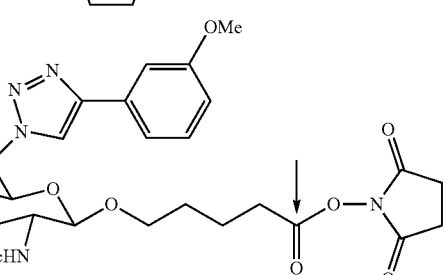
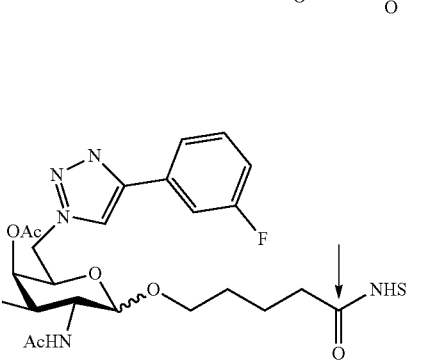

751
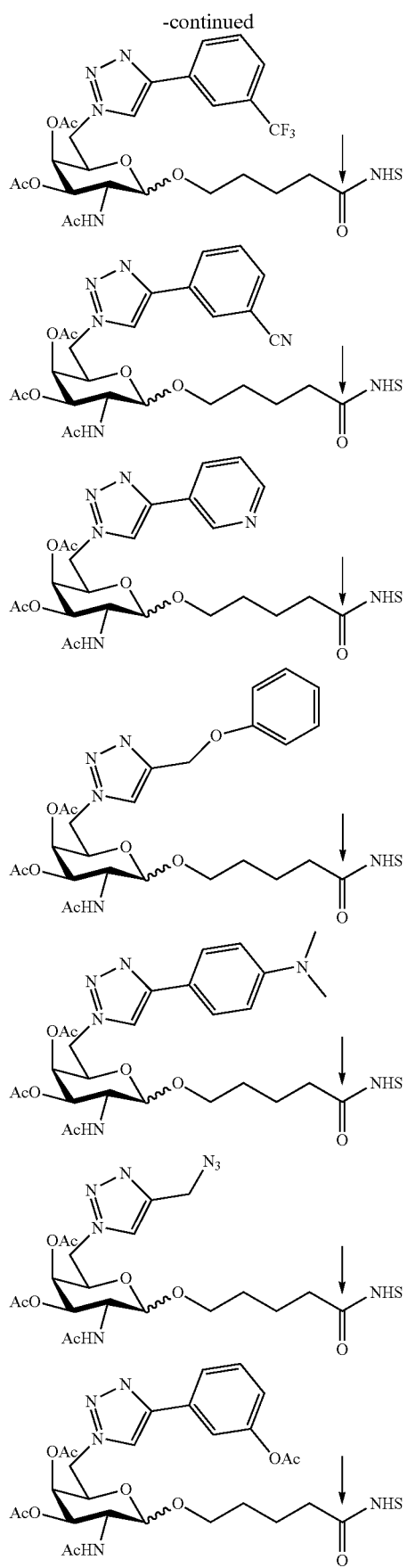
752
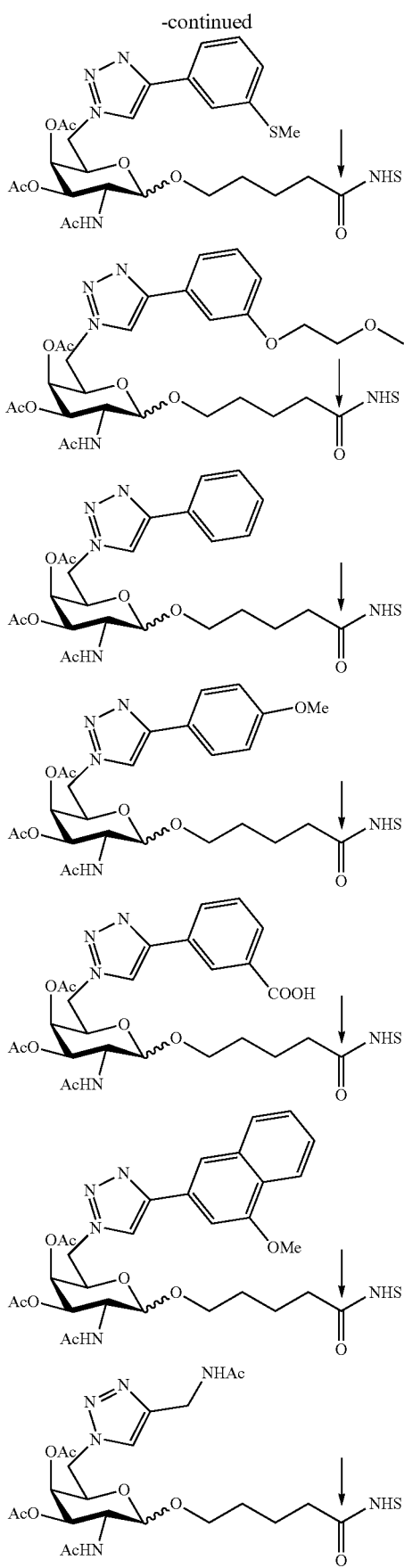

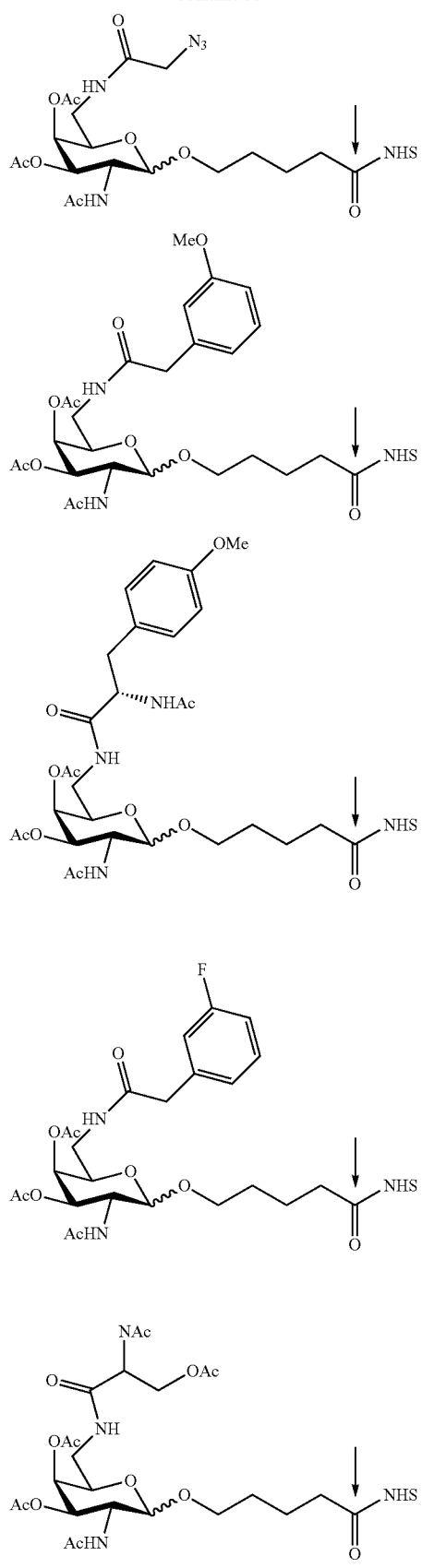
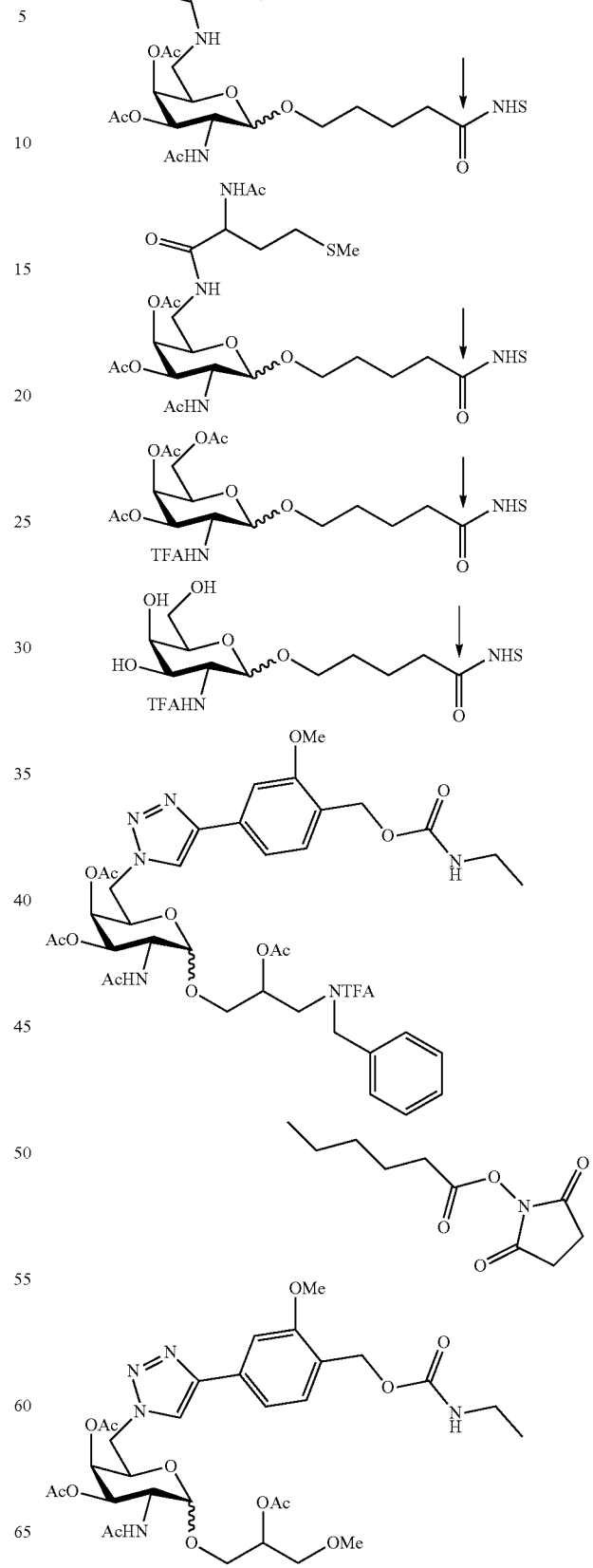

755
-continued
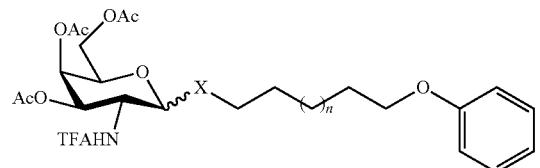
X = O, S, C, NHCO,
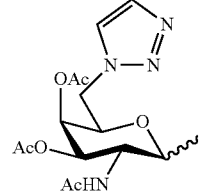
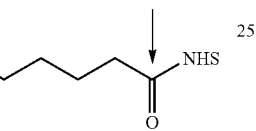
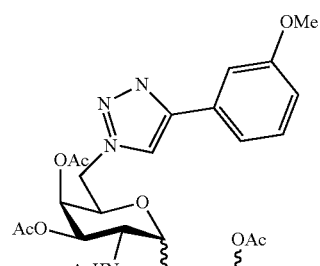
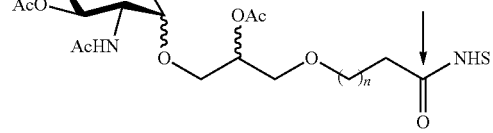
756
-continued
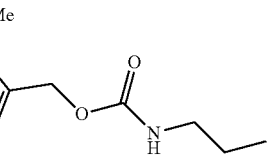
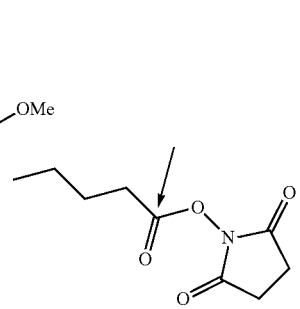
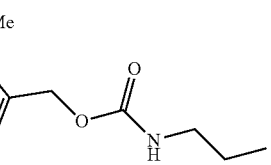
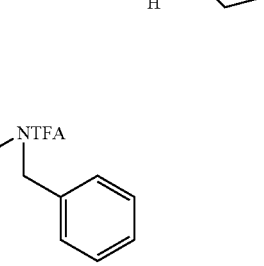
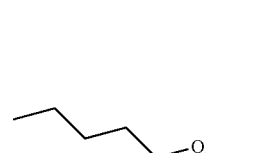
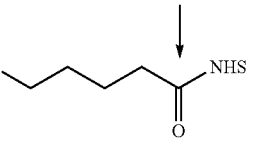
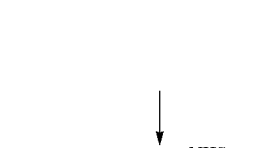
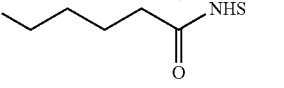

757
-continued
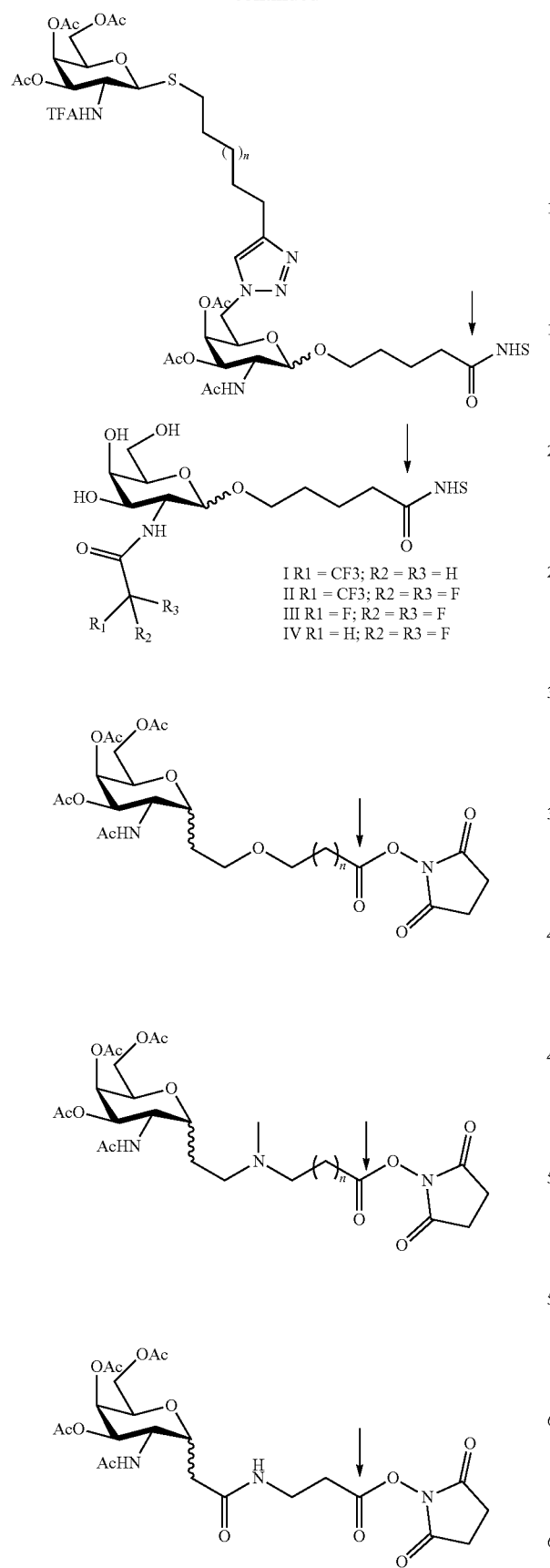
758
-continued
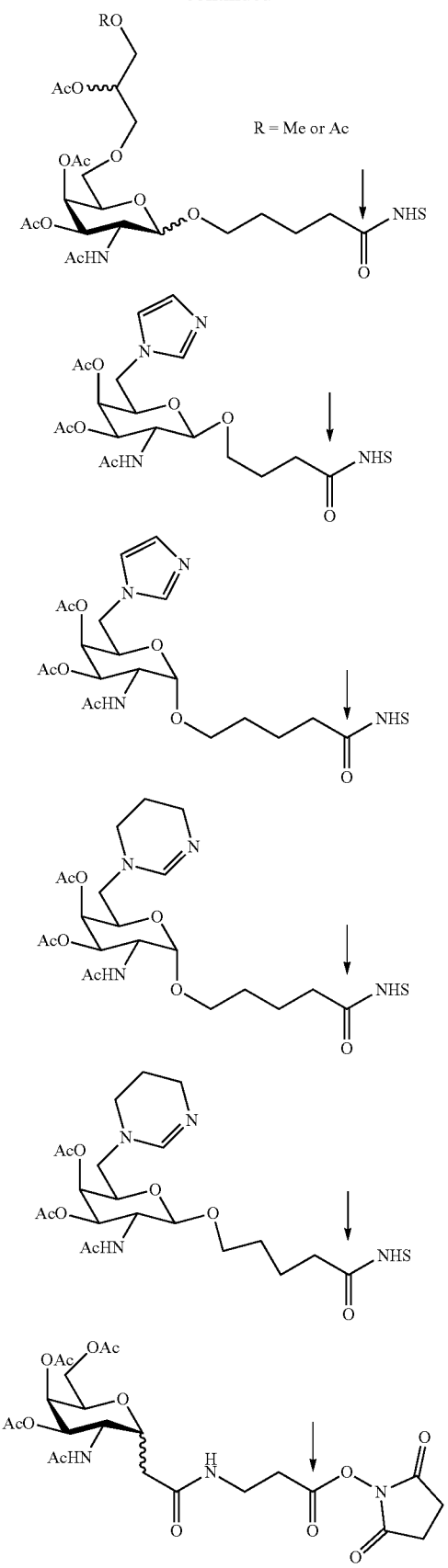

759
-continued
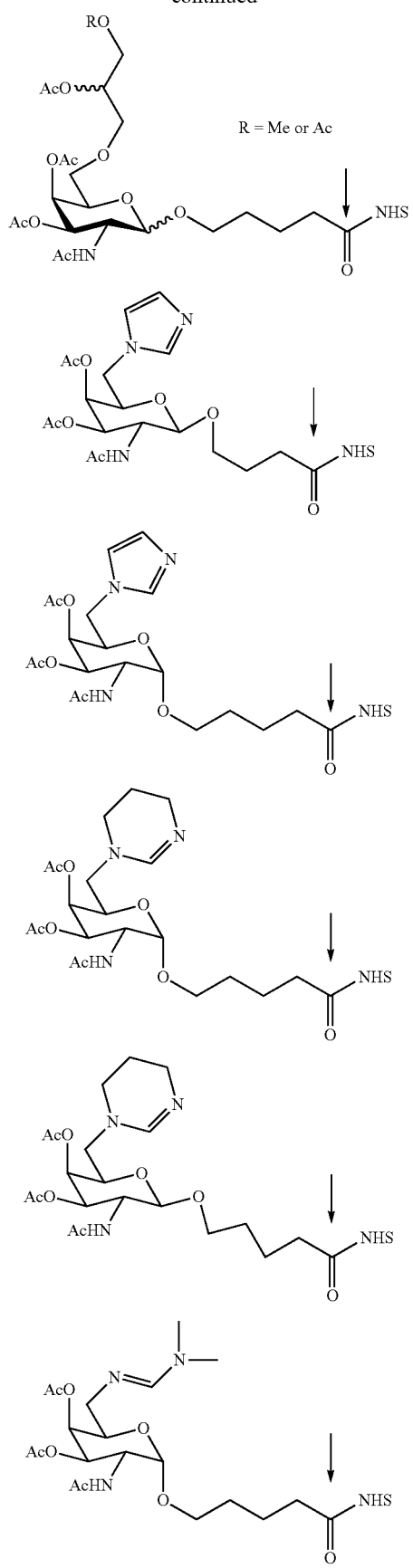
760
-continued
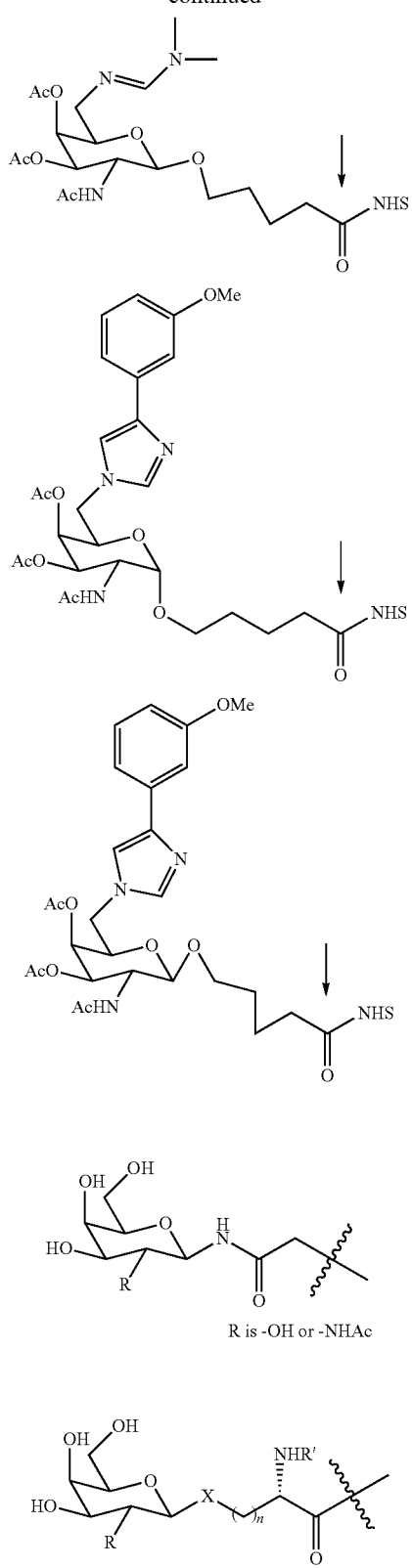
X = O and S   n = 0, 1, 4
R' = H, Ac
R is -OH or NHAc

761
-continued
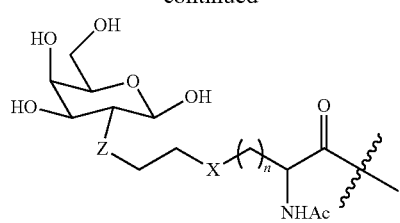
R = NH, NHAc or O
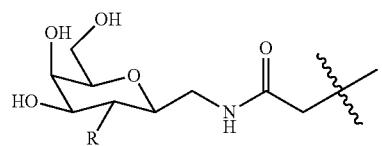
R is -OH or NHAc
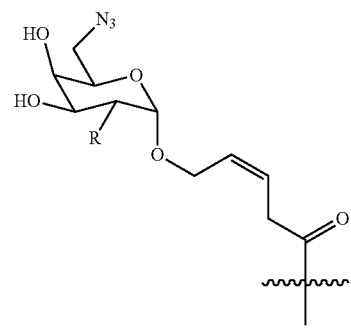
R is -OH or -NHAc
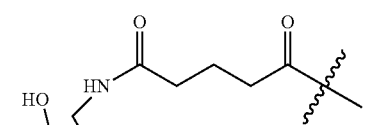
R is -OH or -NHAc
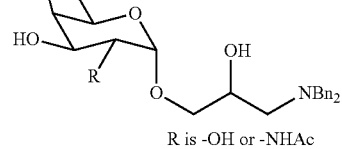
R is -OH or -NHAc
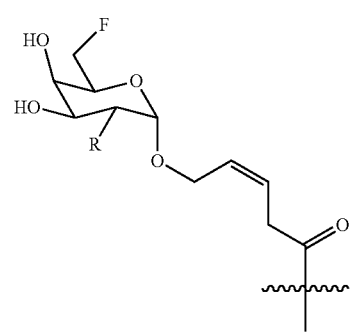
R is -OH or -NHAc
762
-continued
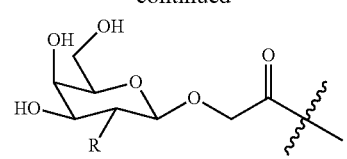
R is -OH or -NHAc
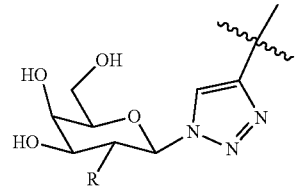
R is -OH or -NHAc
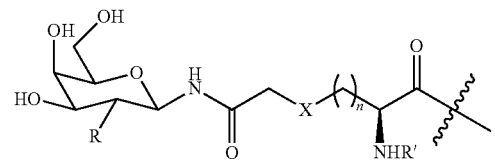
X = CH$_2$, O, S-S, NH
R = H or Ac
R' is H or Ac
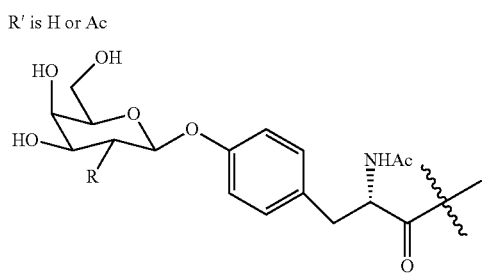
R is -OH or -NHAc
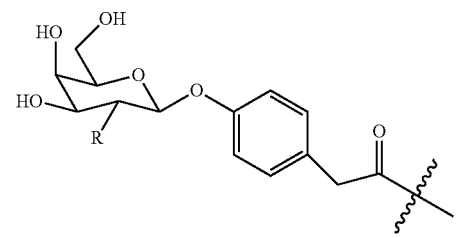
R is -OH or -NHAc
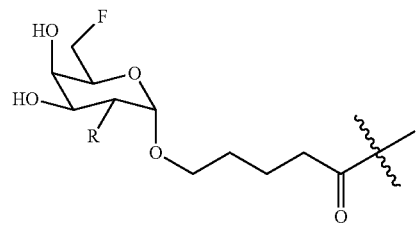
R is -OH or -NHAc
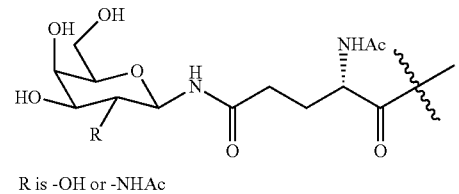
R is -OH or -NHAc 763
-continued
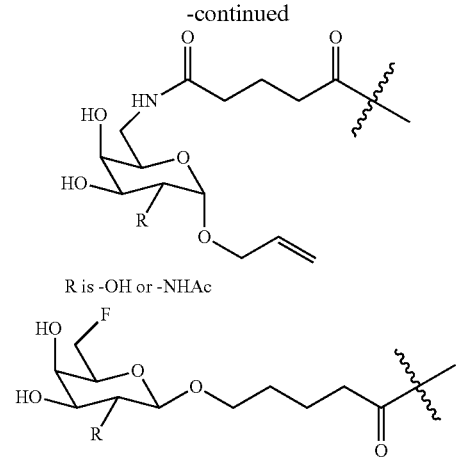
R is -OH or -NHAc
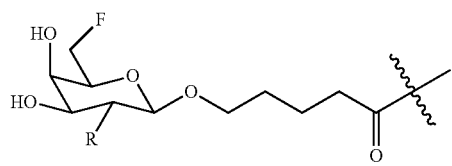
R is -OH or -NHAc
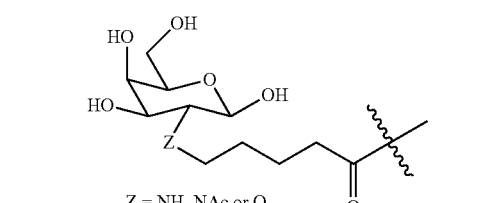
Z = NH, NAc or O
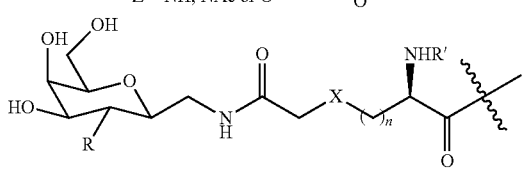
R' = H or Ac
R is -OH or -NHAc
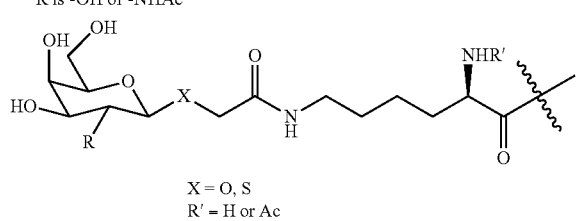
X = O, S
R' = H or Ac
R is -OH or -NHAc
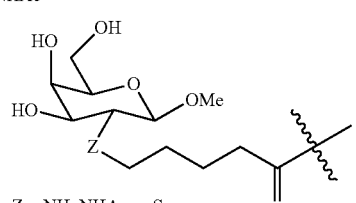
Z = NH, NHAc or S
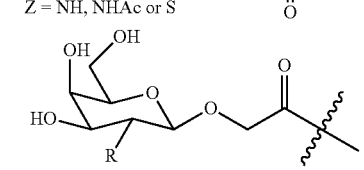
R is -OH or -NHAc
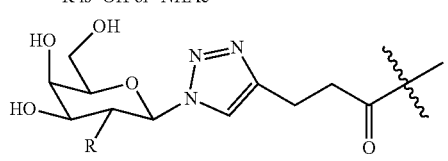
R is -OH or -NHAc
764
-continued
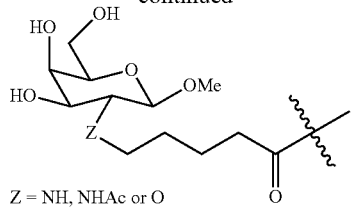
Z = NH, NHAc or O
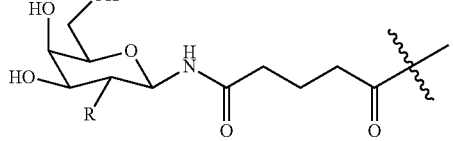
R is -OH or -NHAc
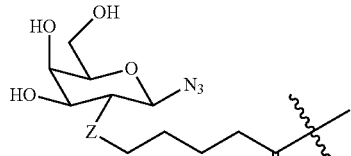
Z = NH, NAc or O
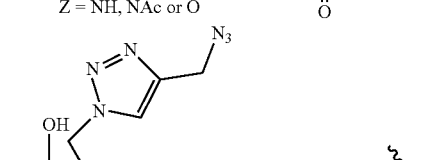
R is -OH or -NHAc
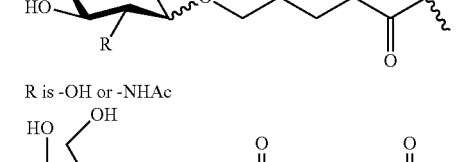
R is -OH or -NHAc
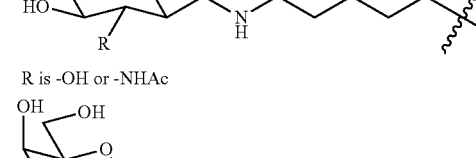
R' = OH or NHAc
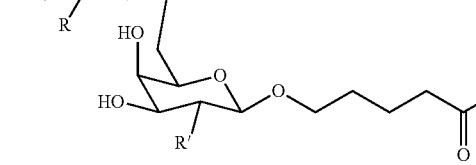
R' = OH or NHAc
R is -OH or -NHAc
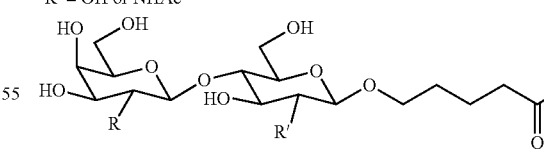
R is -OH or -NHAc

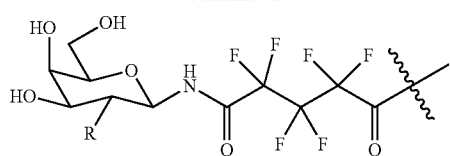
R is -OH or -NHAc
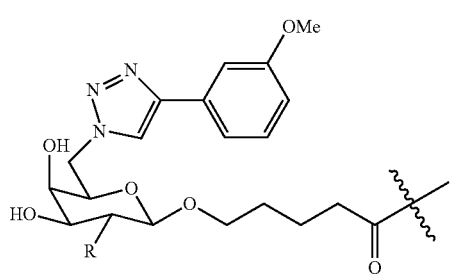
R is -OH or -NHAc
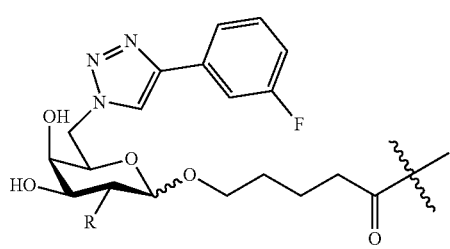
R is -OH or -NHAc
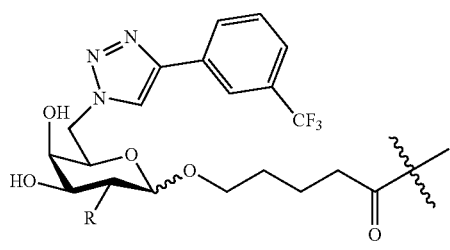
R is -OH or -NHAc
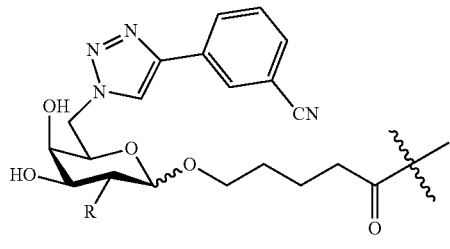
R is -OH or -NHAc
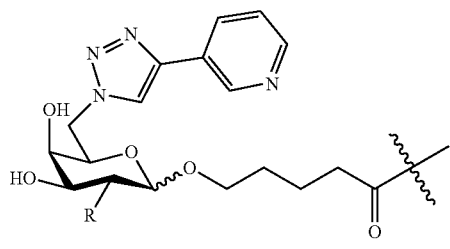
R is -OH or -NHAc
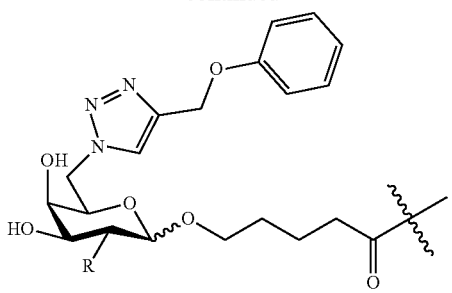
R is -OH or -NHAc
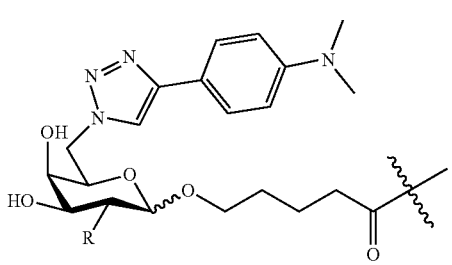
R is -OH or -NHAc
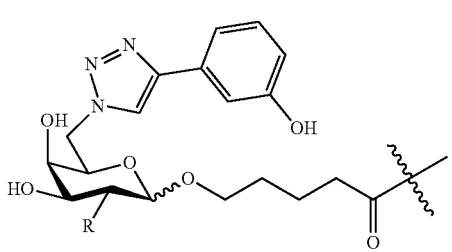
R is -OH or -NHAc
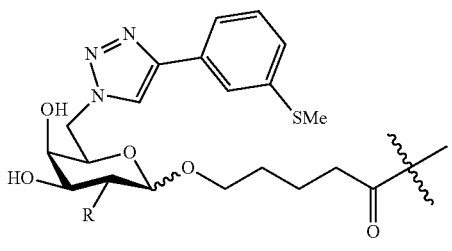
R is -OH or -NHAc
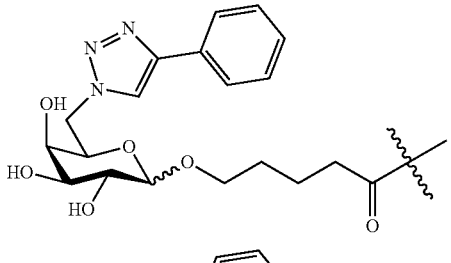
R is -OH or -NHAc
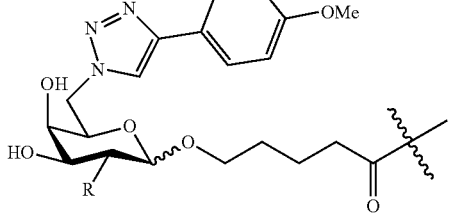
R is -OH or -NHAc -continued
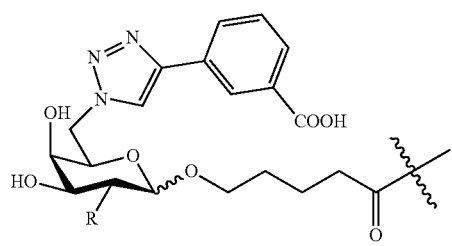
R is -OH or -NHAc
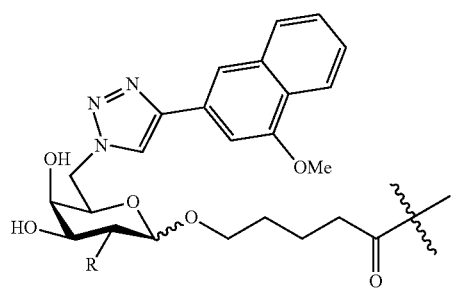
R is -OH or -NHAc
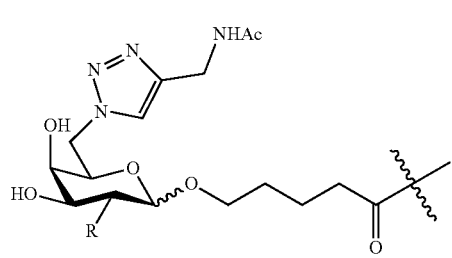
R is -OH or -NHAc
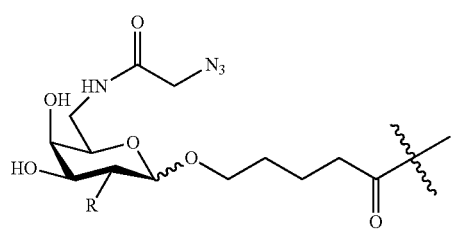
R is -OH or -NHAc
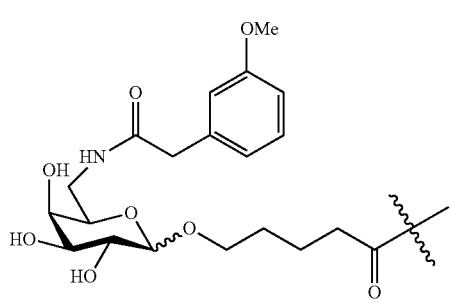
-continued
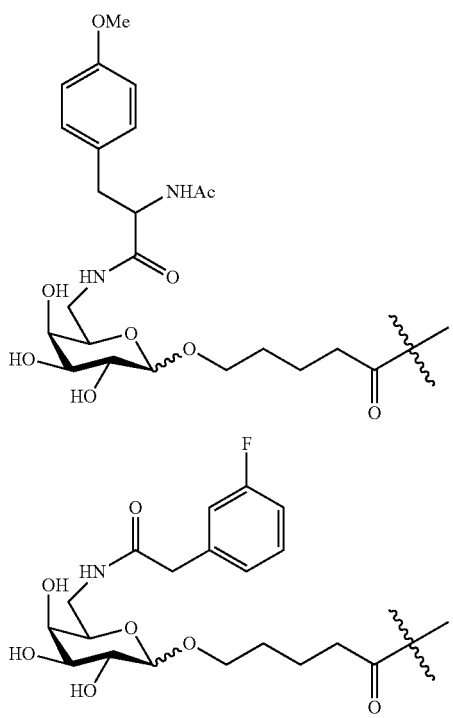
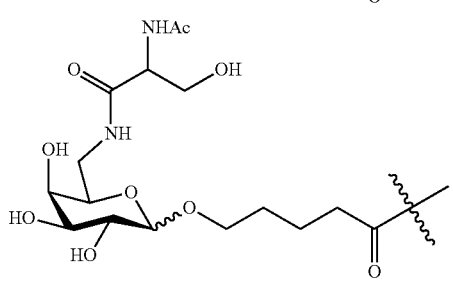
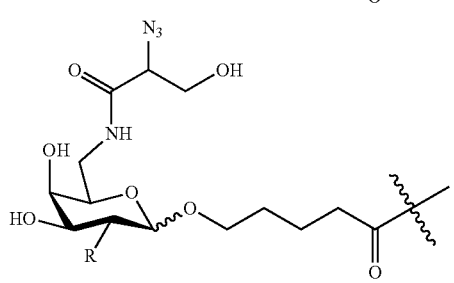
R is -OH or -NHAc
Example 55
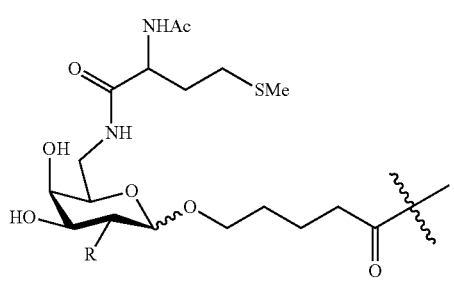
R is -OH or -NHAc

769
-continued
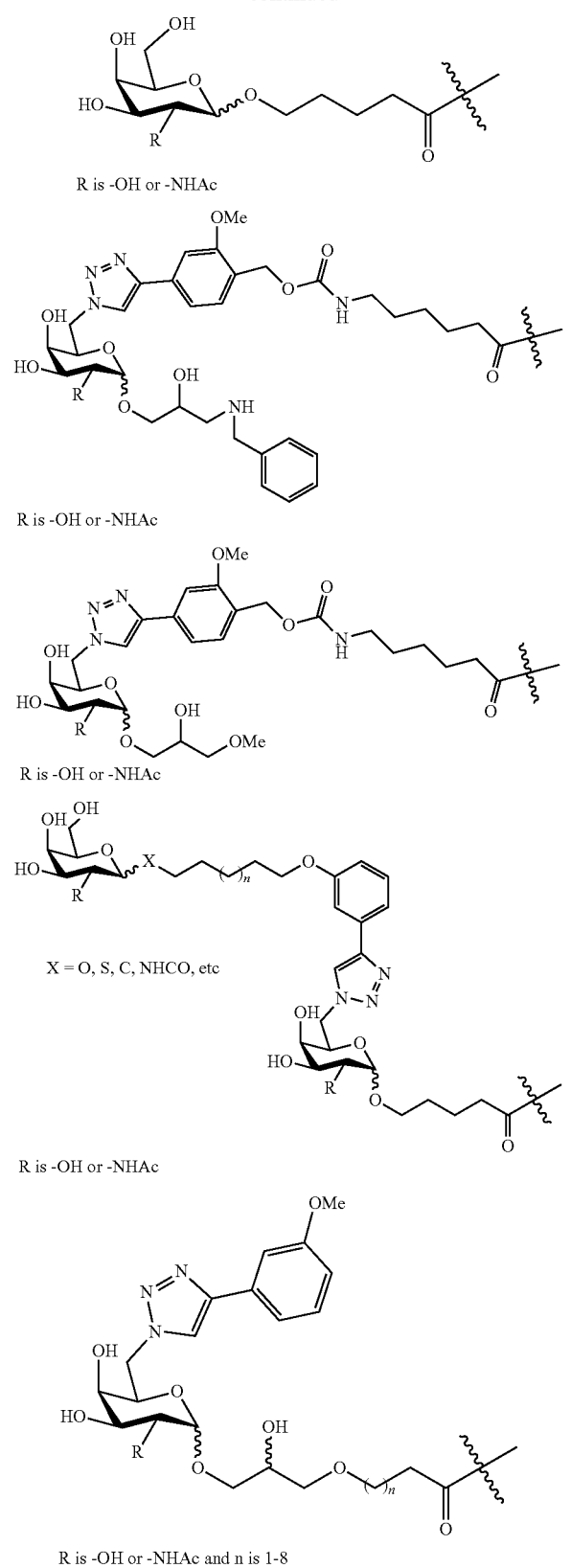
770
-continued
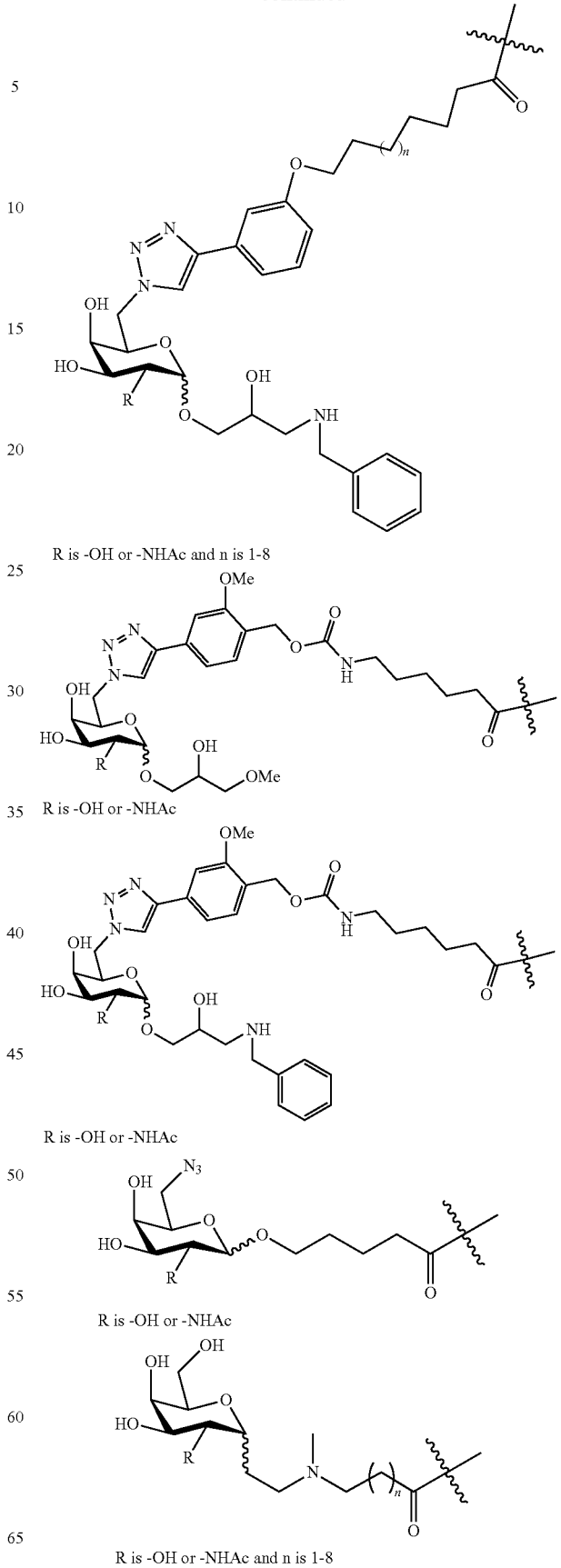

771
-continued
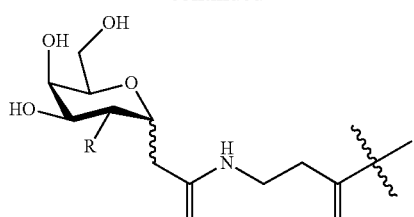
R is -OH or -NHAc
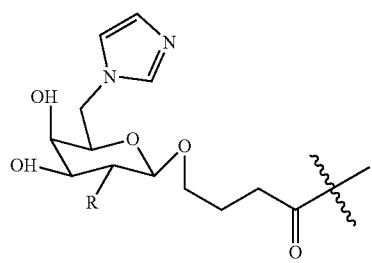
R is -OH or -NHAc
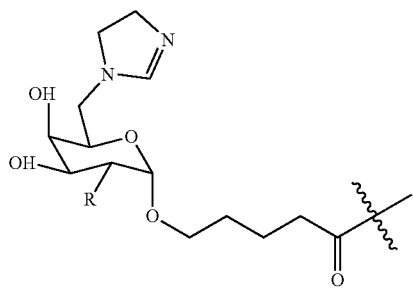
R is -OH or -NHAc
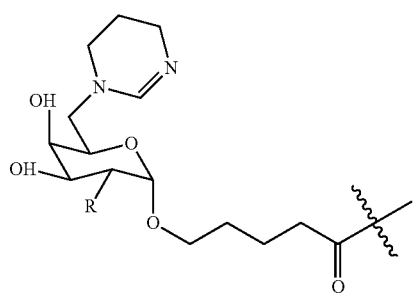
R is -OH or -NHAc
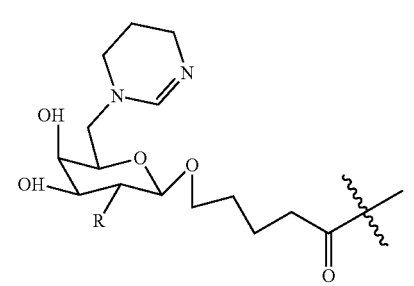
R is -OH or -NHAc
772
-continued
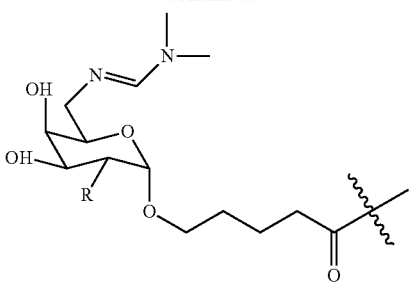
R is -OH or -NHAc
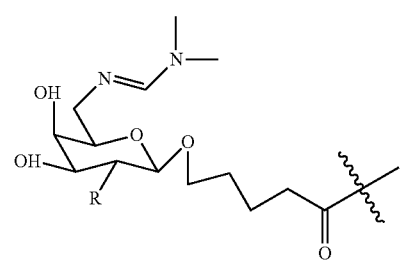
R is -OH or -NHAc
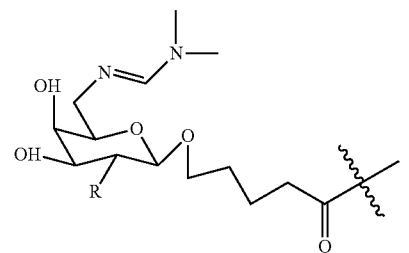
R is -OH or -NHAc
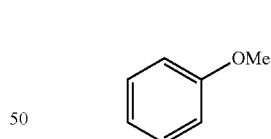
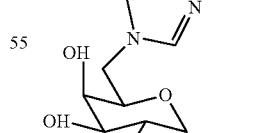
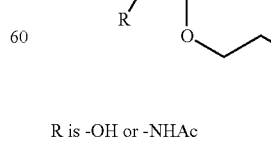
R is -OH or -NHAc -continued
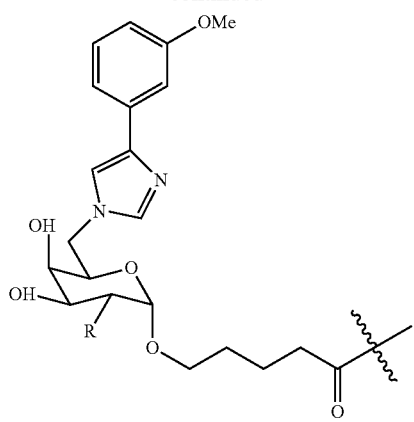
R is -OH or -NHAc
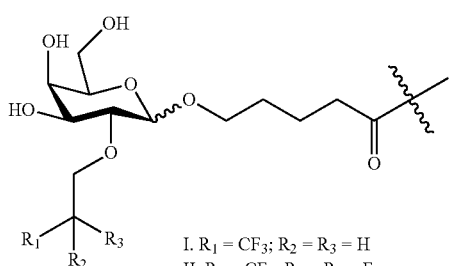
I. $R_1 = CF_3$; $R_2 = R_3 = H$
II. $R_1 = CF_3$; $R_2 = R_3 = F$
III. $R_1 = F$; $R_2 = R_3 = H$
IV. $R_1 = H$; $R_2 = R_3 = F$
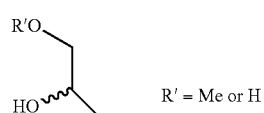
R' = Me or H
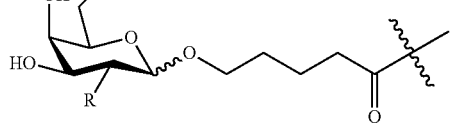
R is -OH or -NHAc
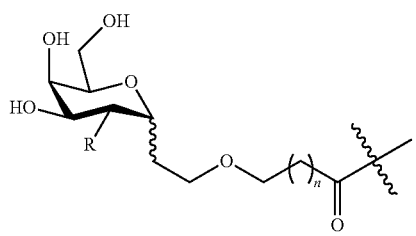
R is -OH or -NHAc and n is 1-8
-continued
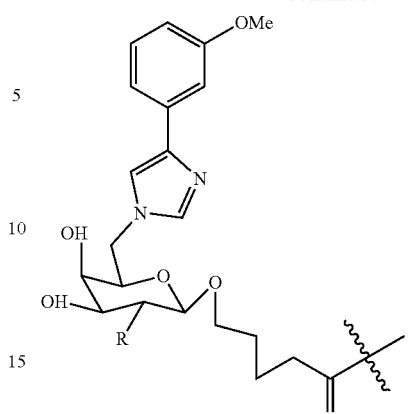
R is -OH or -NHAc
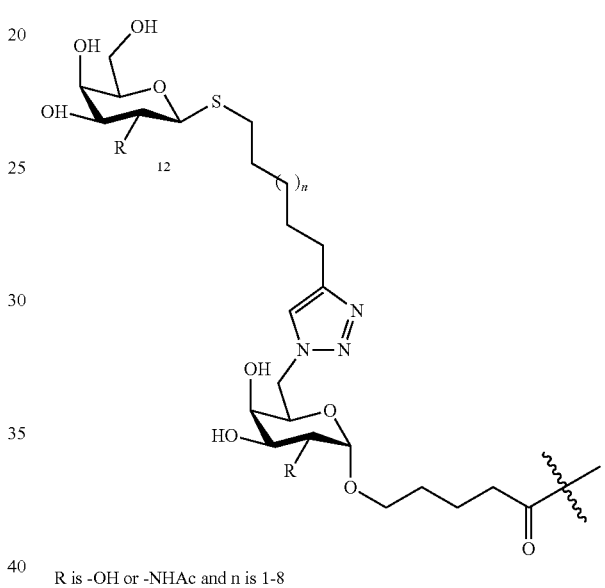
R is -OH or -NHAc and n is 1-8
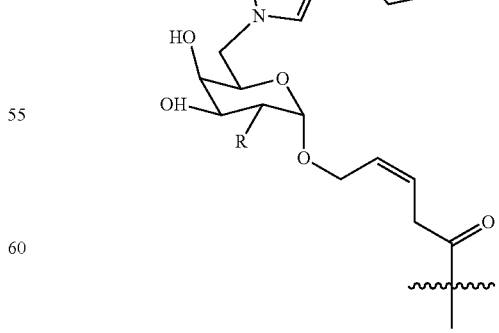
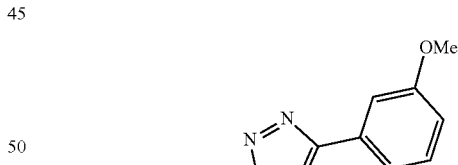
R is -OH or -NHAc 775
-continued
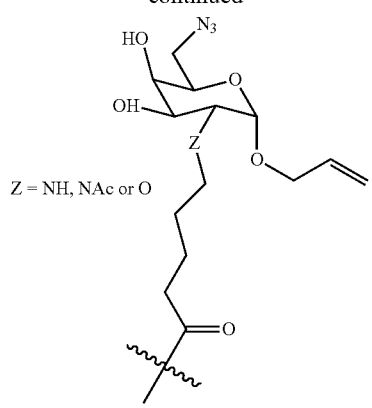
Z = NH, NAc or O
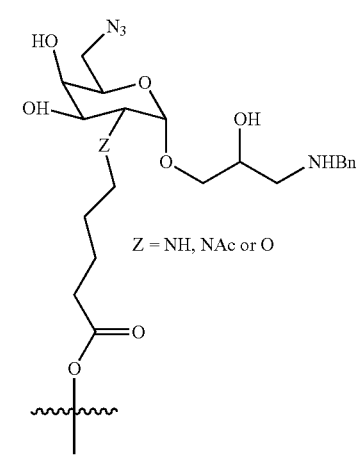
Z = NH, NAc or O
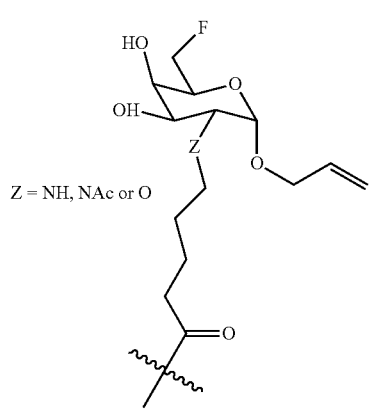
Z = NH, NAc or O
776
-continued
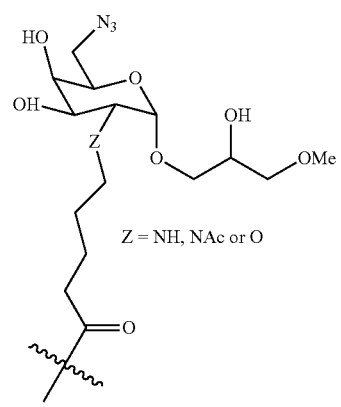
Z = NH, NAc or O
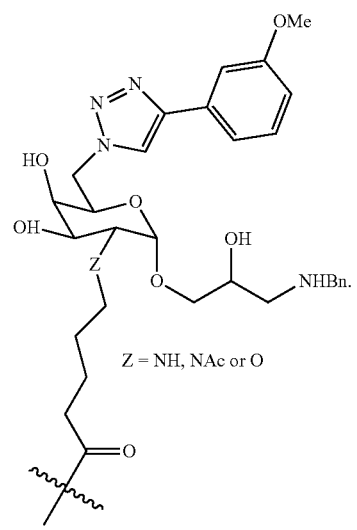
Z = NH, NAc or O
2. The conjugate of claim 1, wherein n is 1-4.
3. The conjugate of claim 1, wherein the conjugate has the formula:

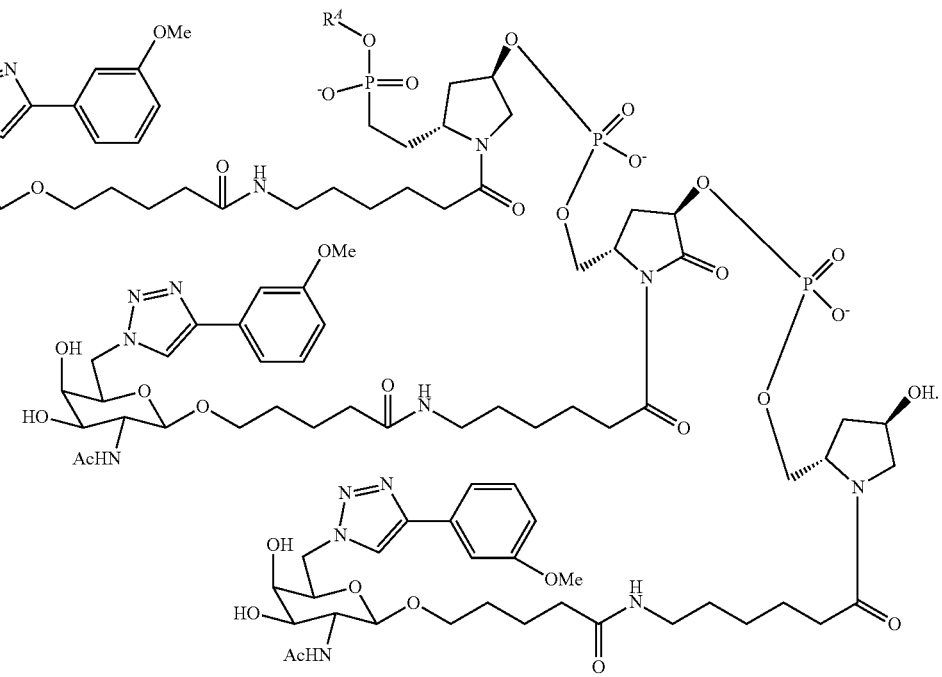

4. The conjugate of claim 1, wherein the oligonucleotide moiety in $R^A$ is double stranded and has a length ranging from 15 to about 30 nucleotide units.

5. The conjugate of claim 4, wherein the oligonucleotide moiety has a length ranging from 18 to about 23 nucleotide units.

6. A conjugate of the formula:

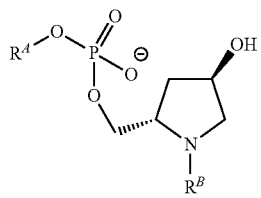

wherein $R^A$ is a single stranded or double stranded oligonucleotide having (i) a 3' end attached to the oxygen atom shown and (ii) a length ranging from 6 to about 30 nucleotide units;

$R^B$ is selected from Table 2 or Table 2A

TABLE 2
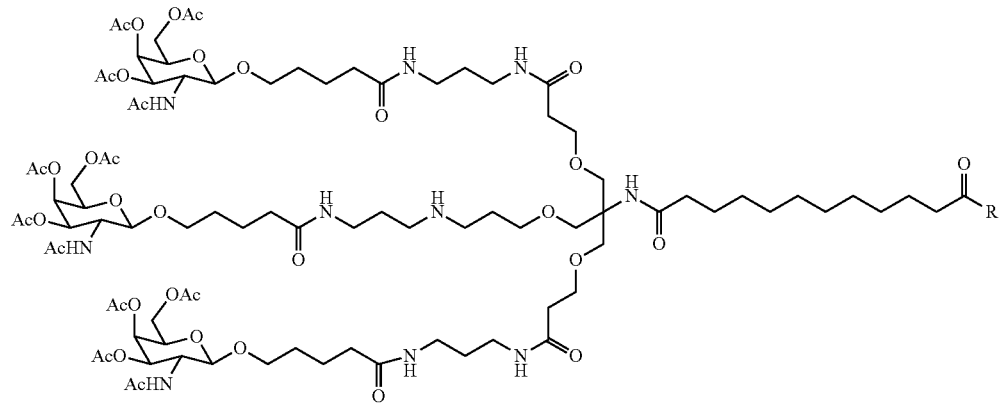
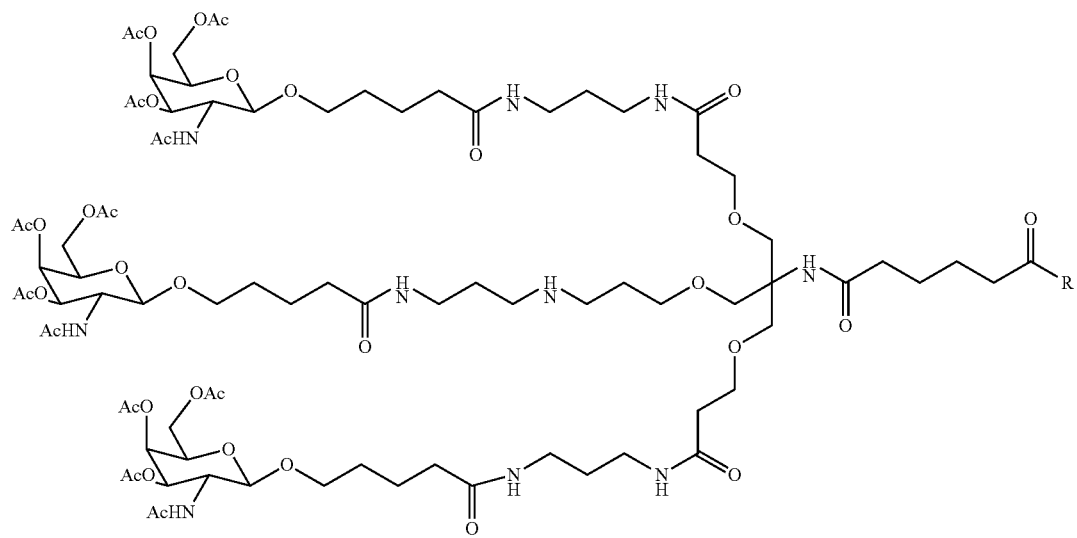
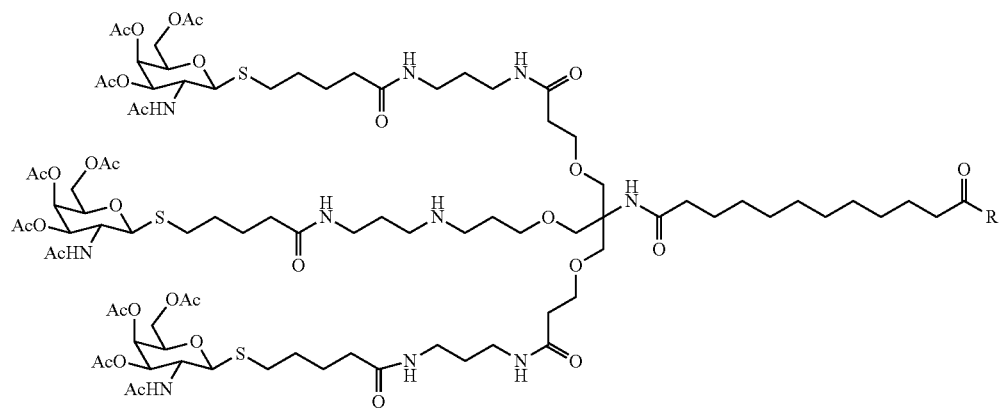

TABLE 2-continued
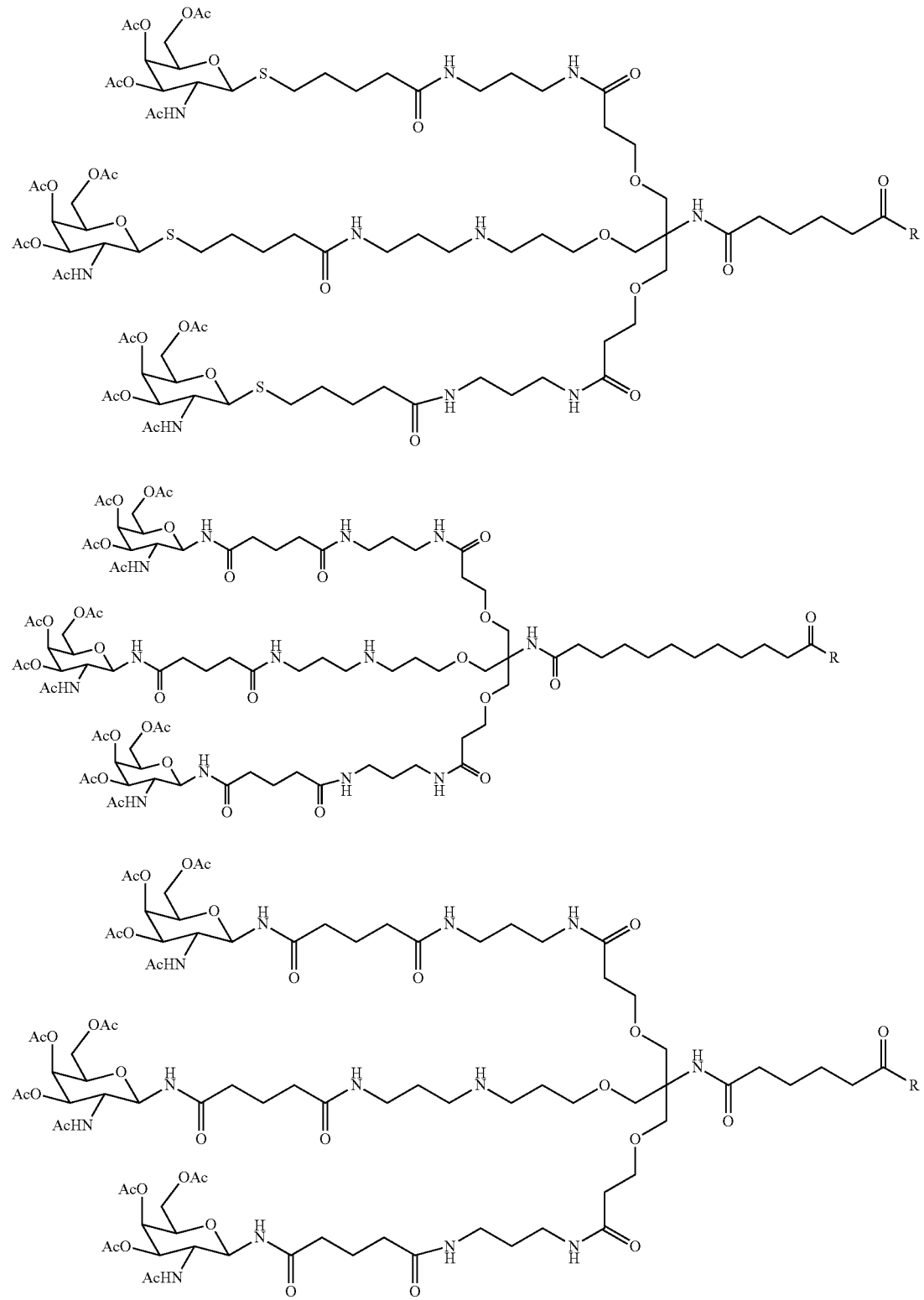

TABLE 2-continued
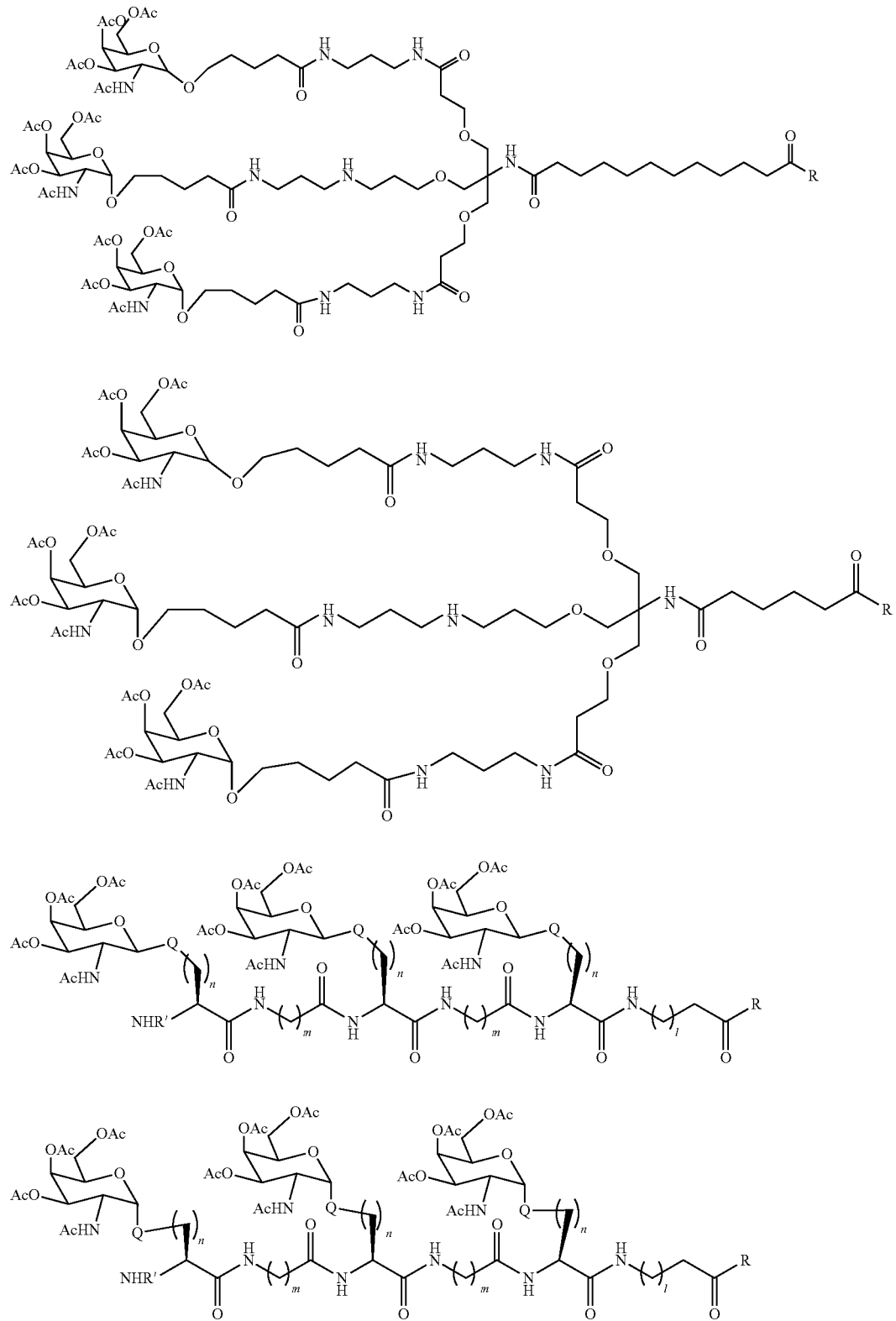

TABLE 2-continued
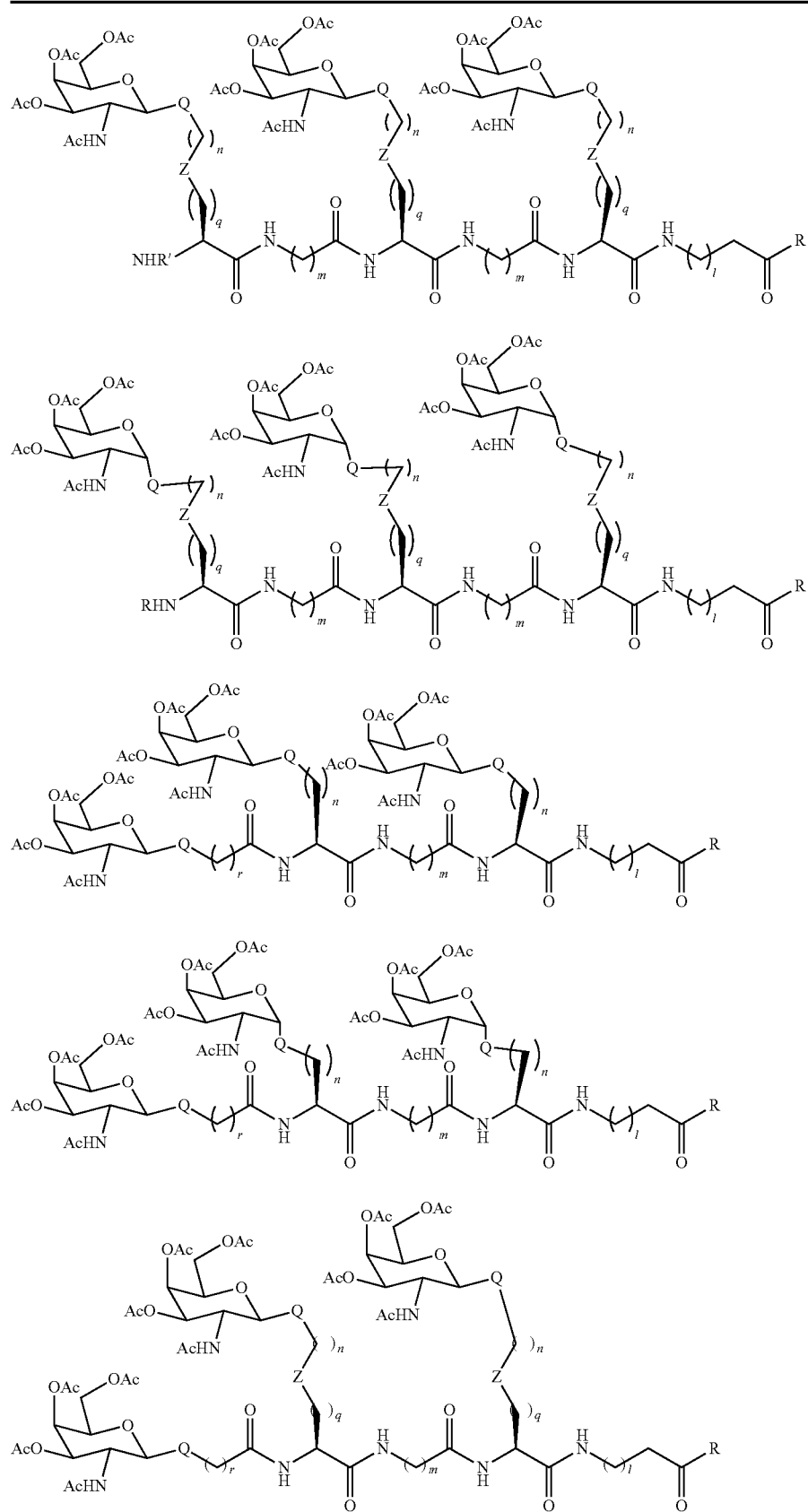

TABLE 2-continued
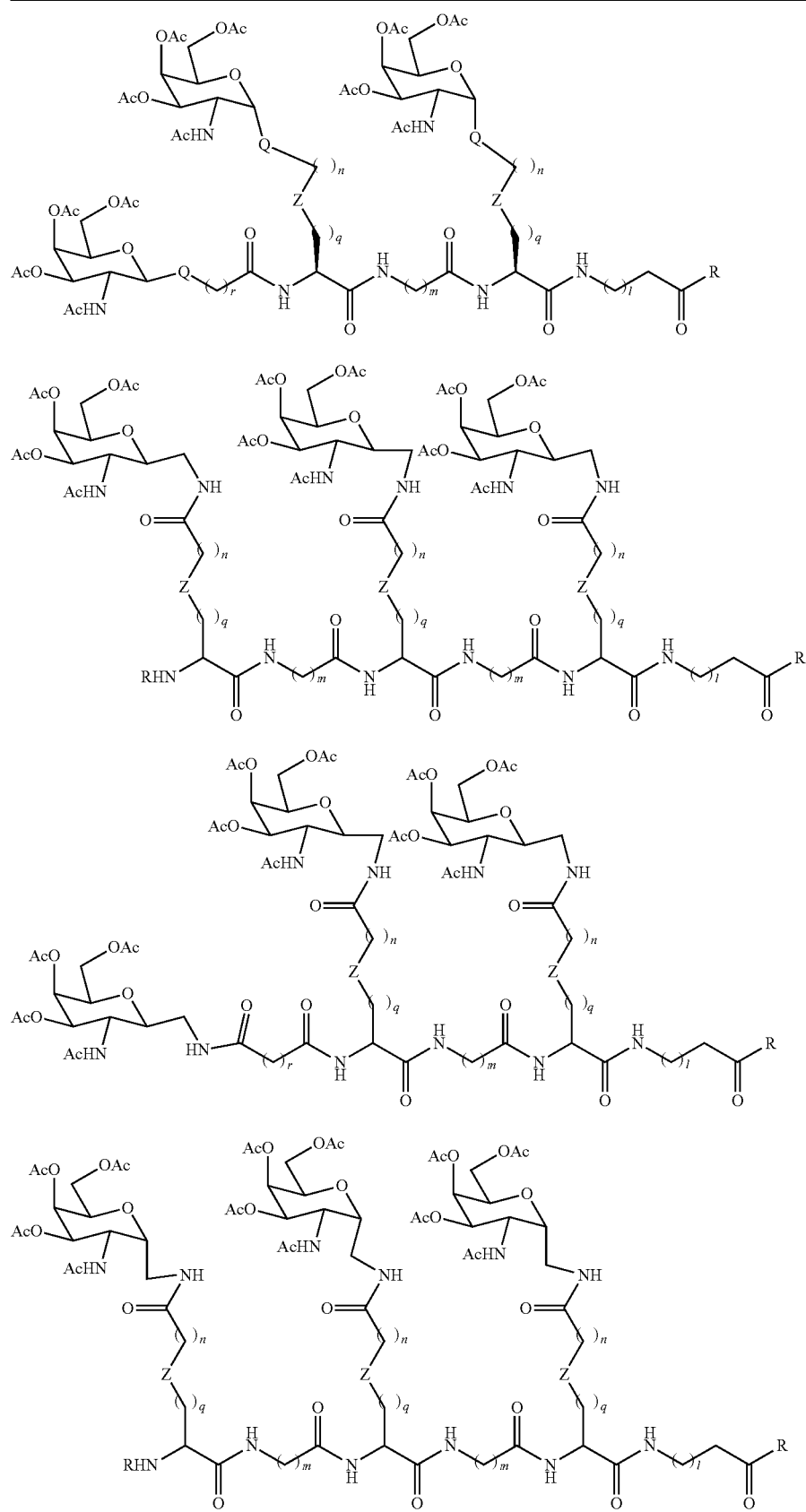

TABLE 2-continued
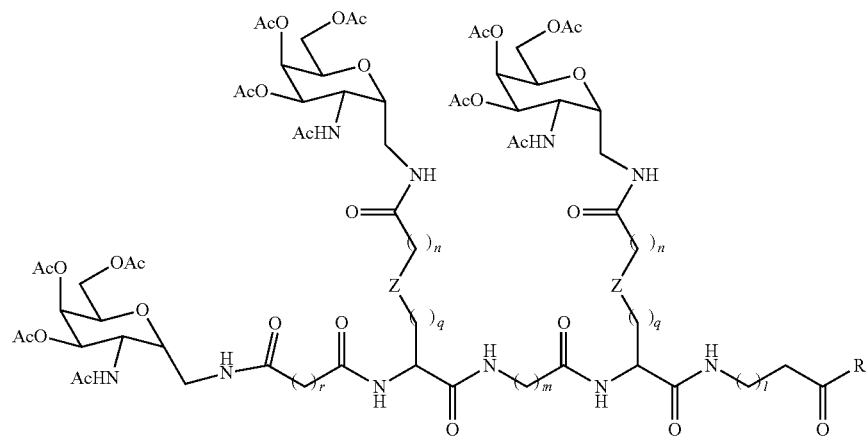
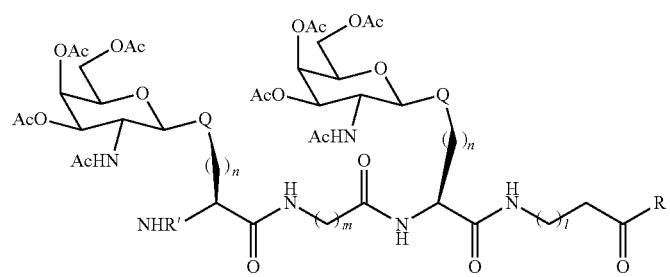
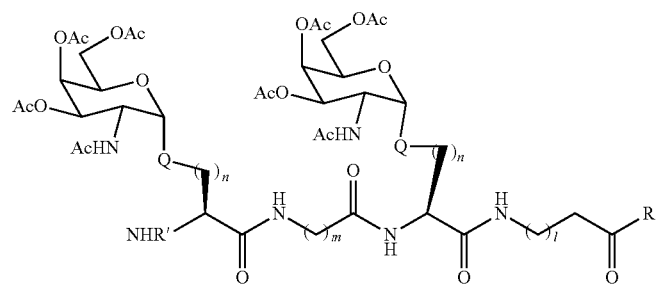
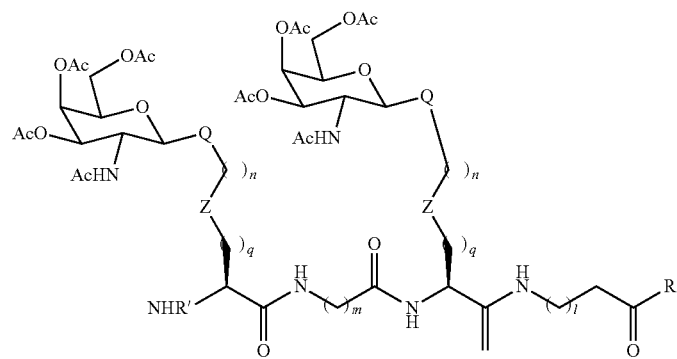

TABLE 2-continued
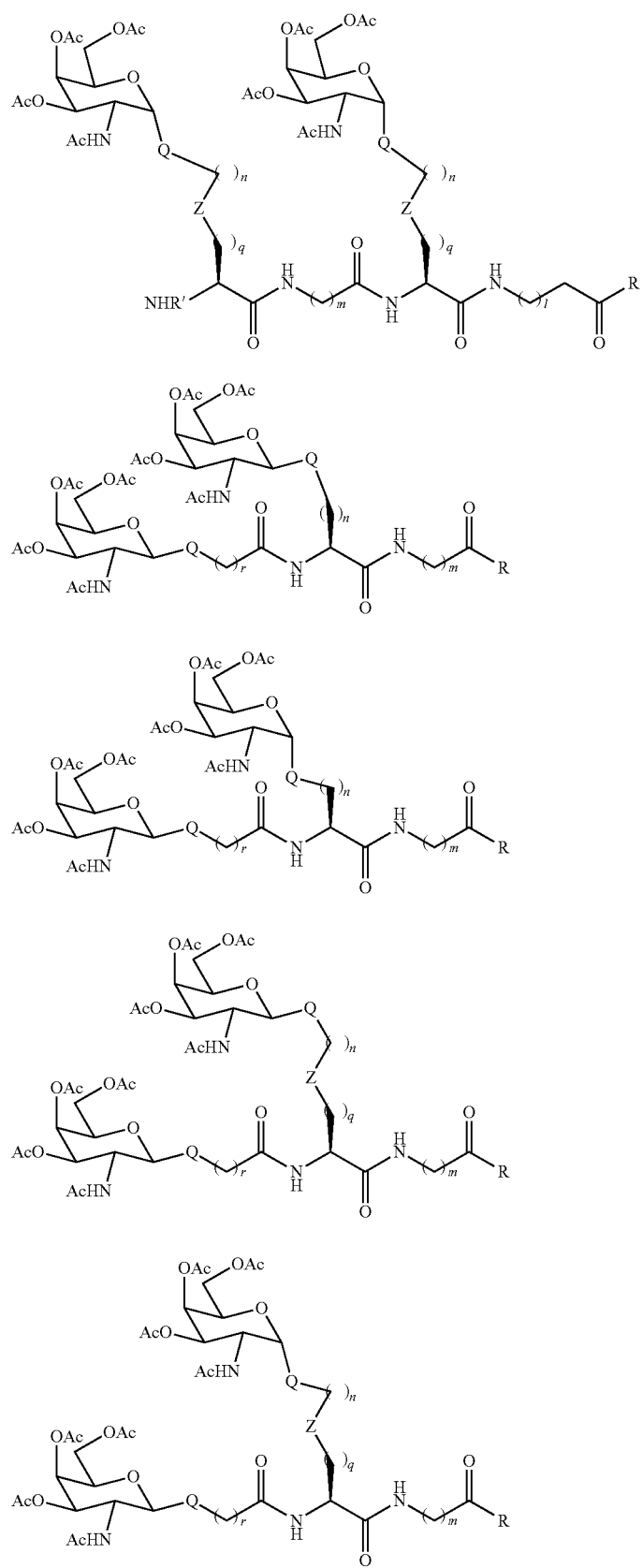

TABLE 2-continued
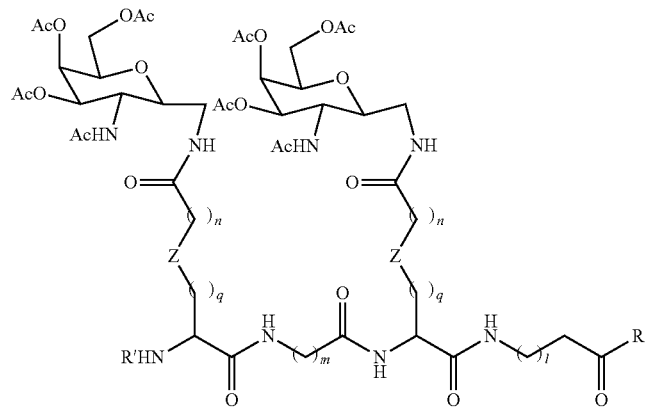
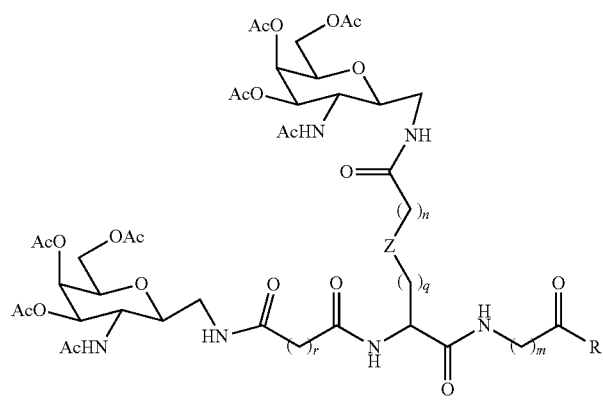
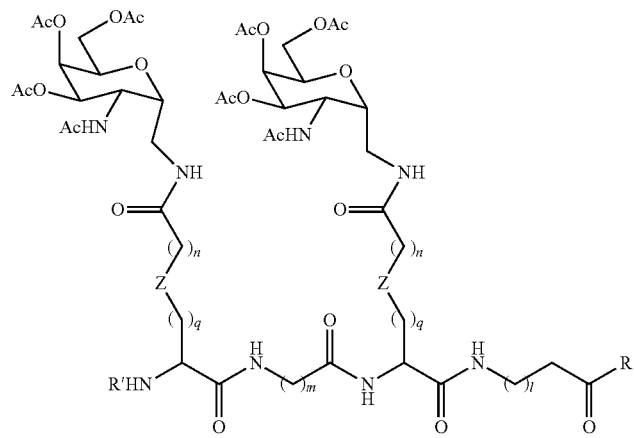

TABLE 2-continued
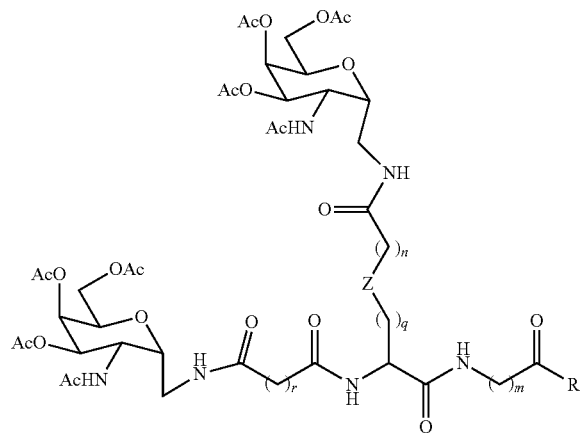
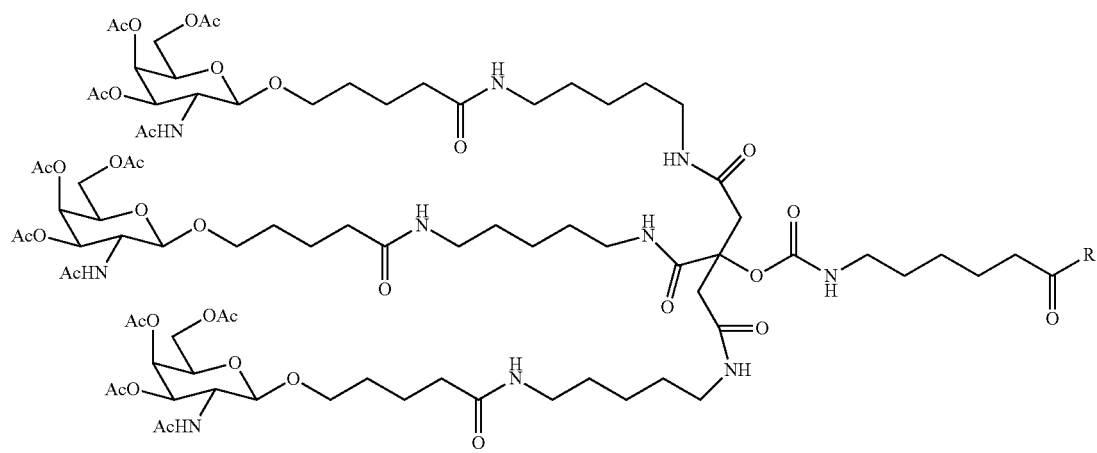
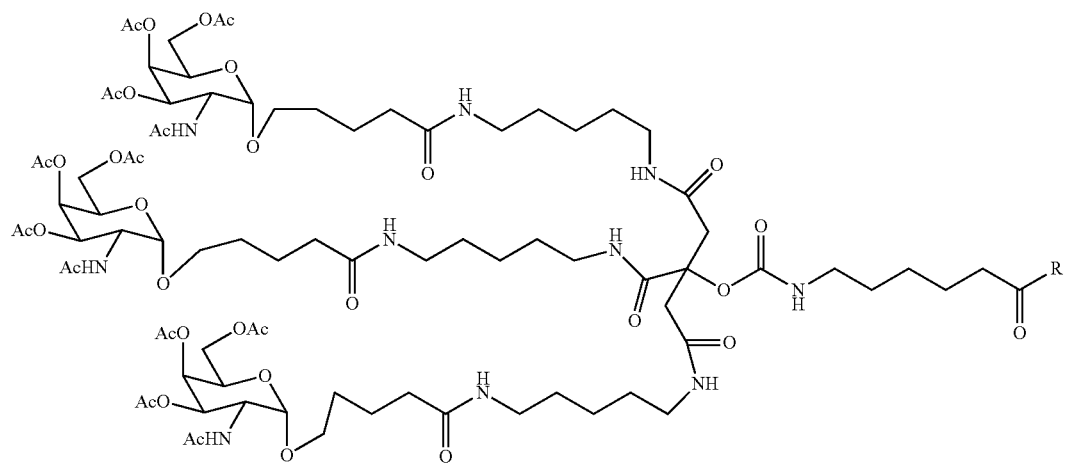

TABLE 2-continued
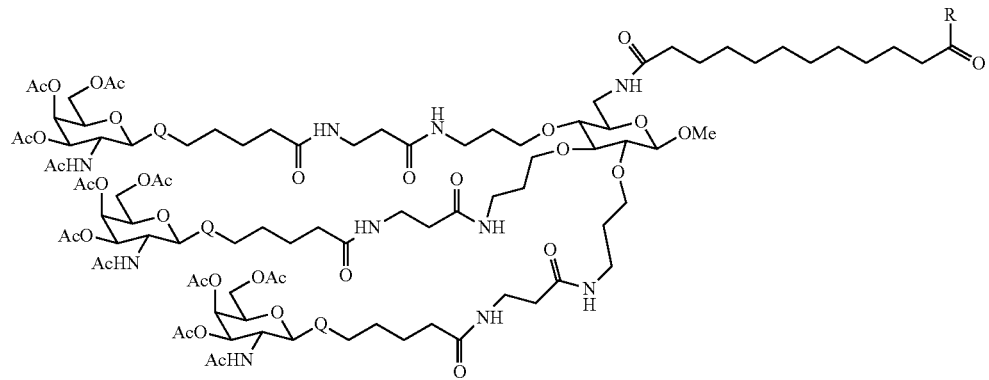
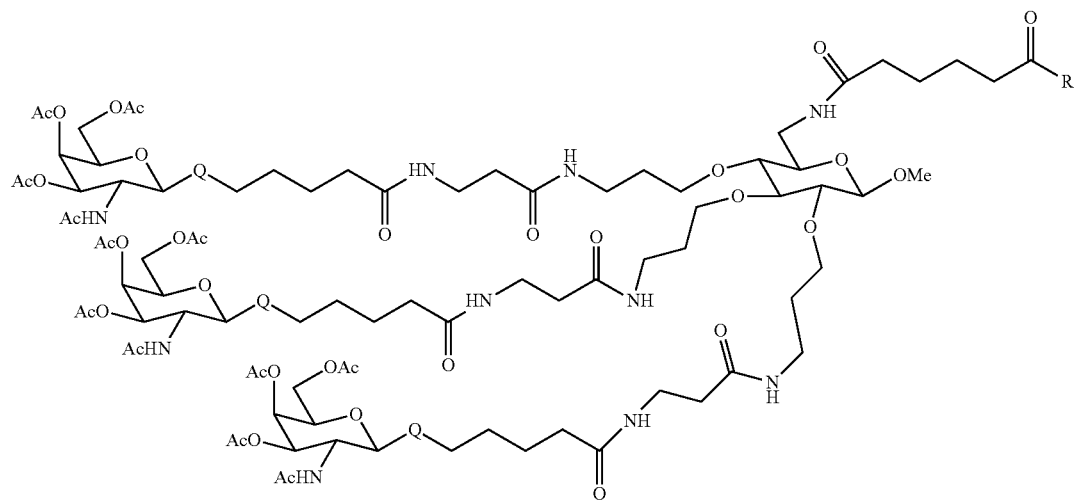
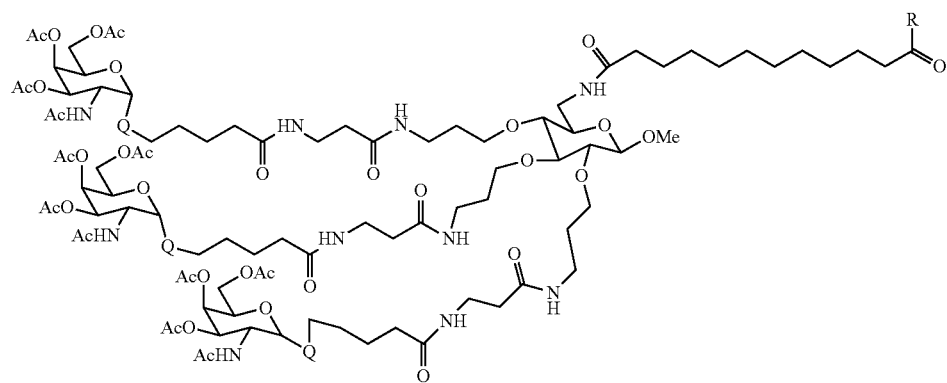

TABLE 2-continued
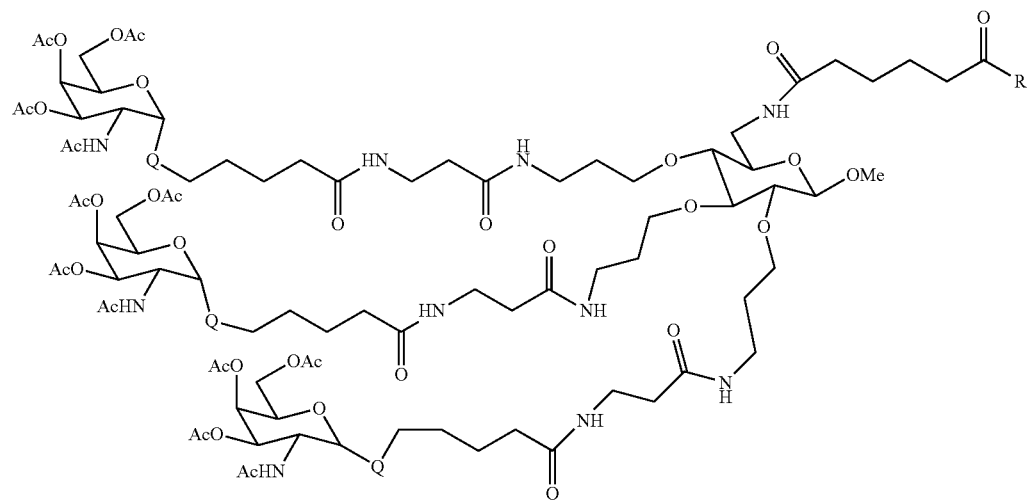
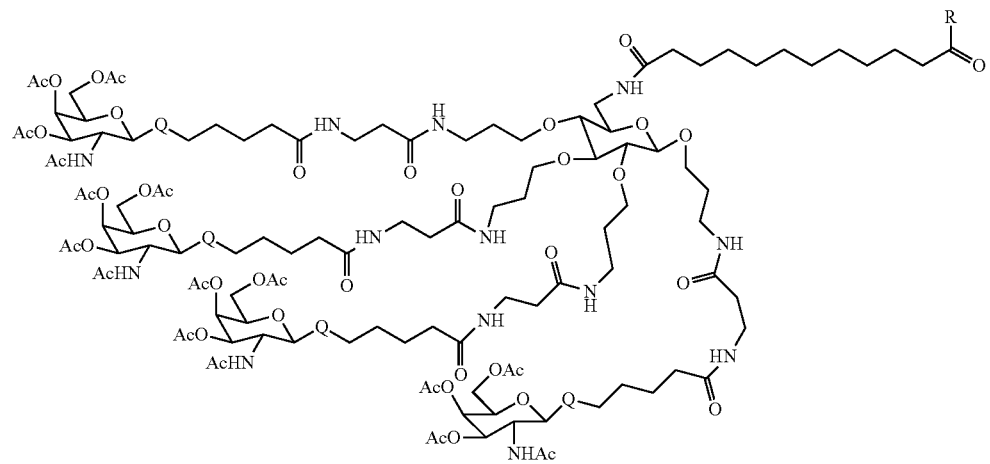
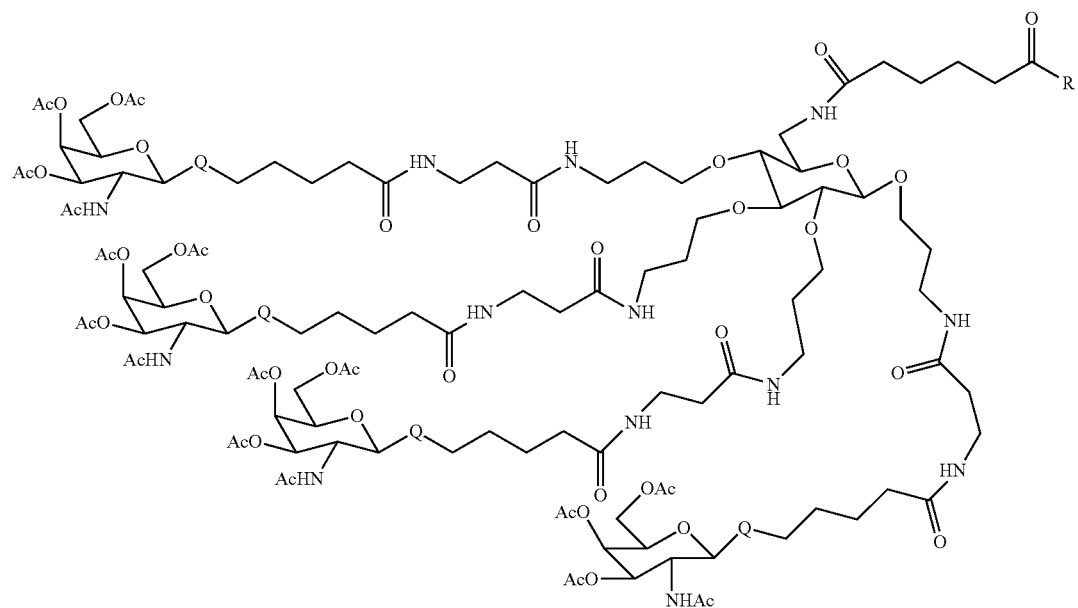

TABLE 2-continued
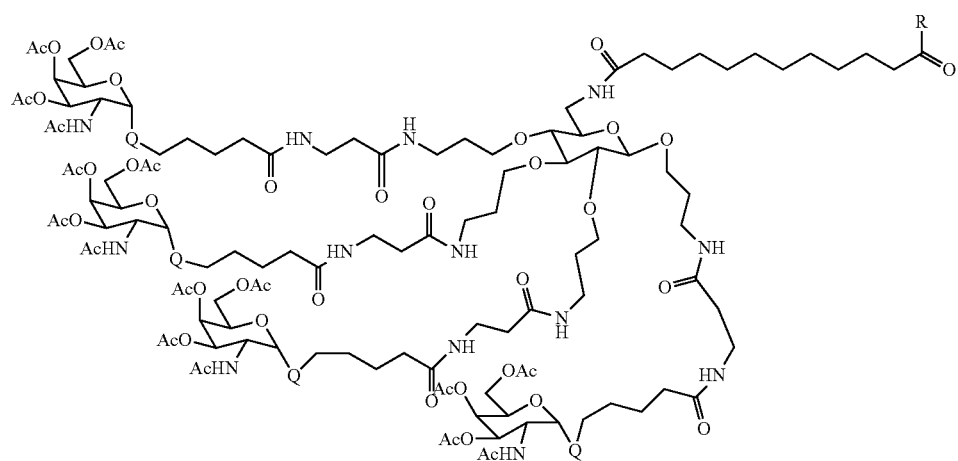
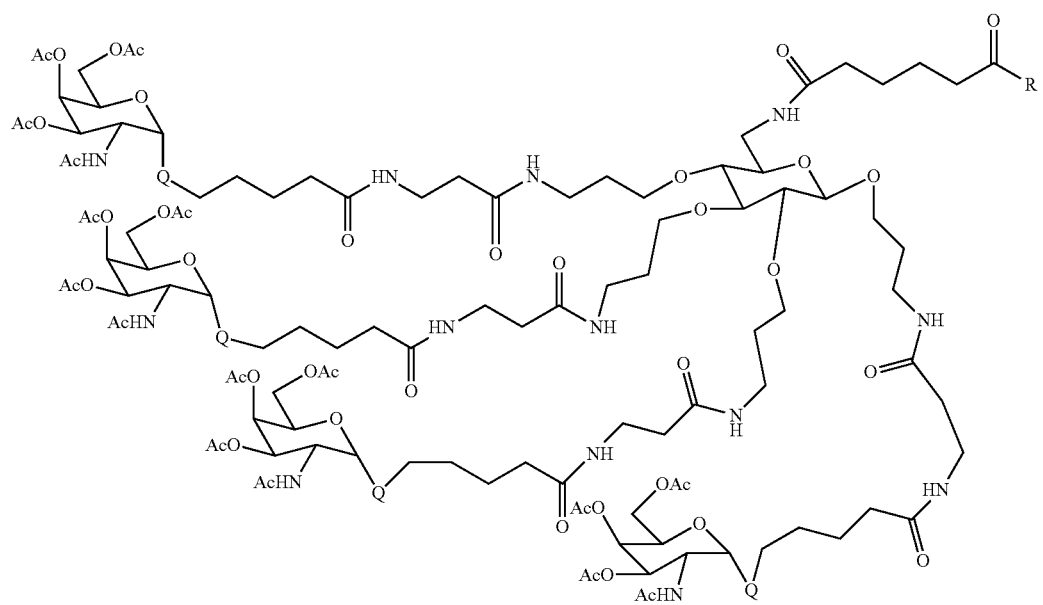
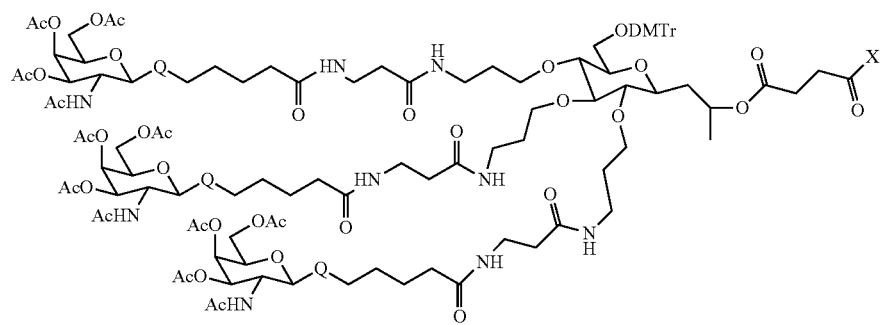

TABLE 2-continued
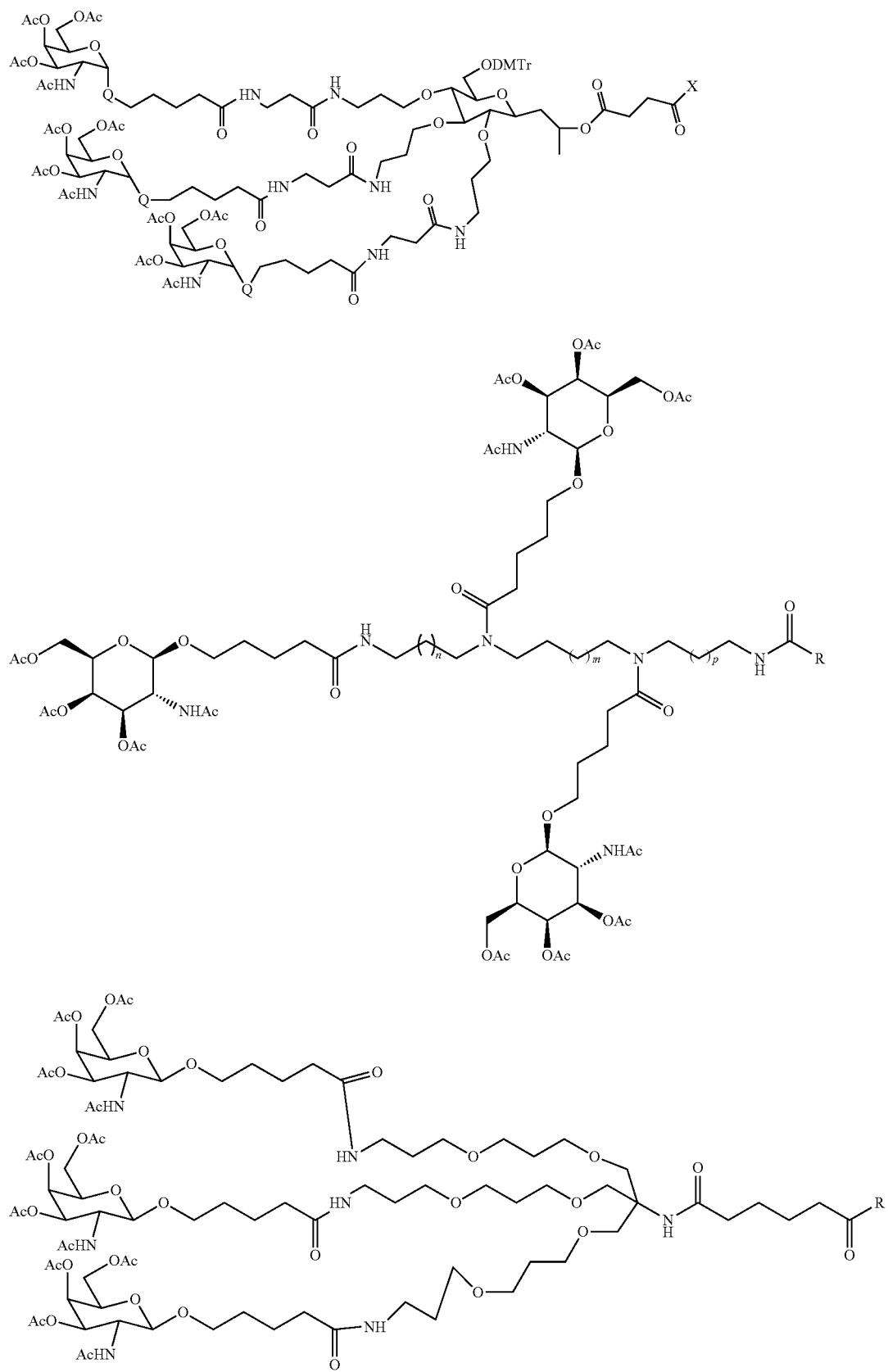

TABLE 2-continued
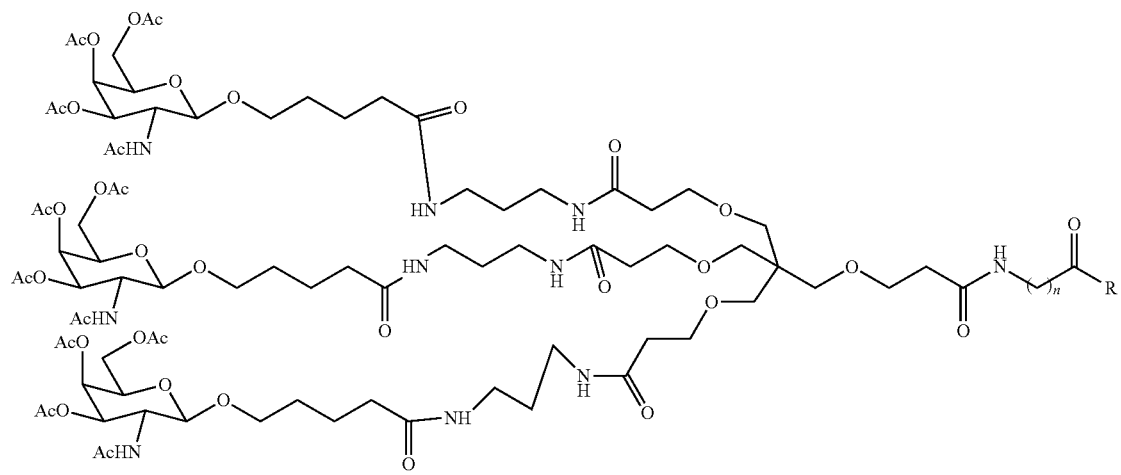
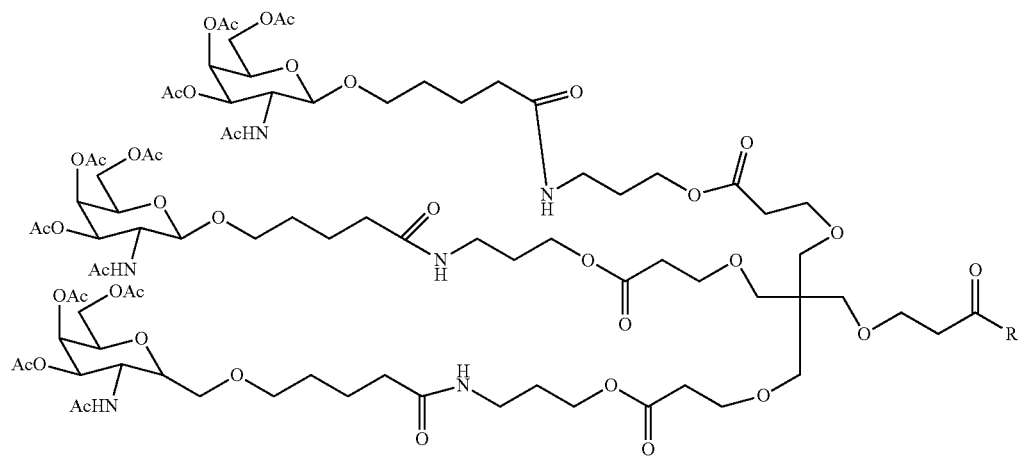
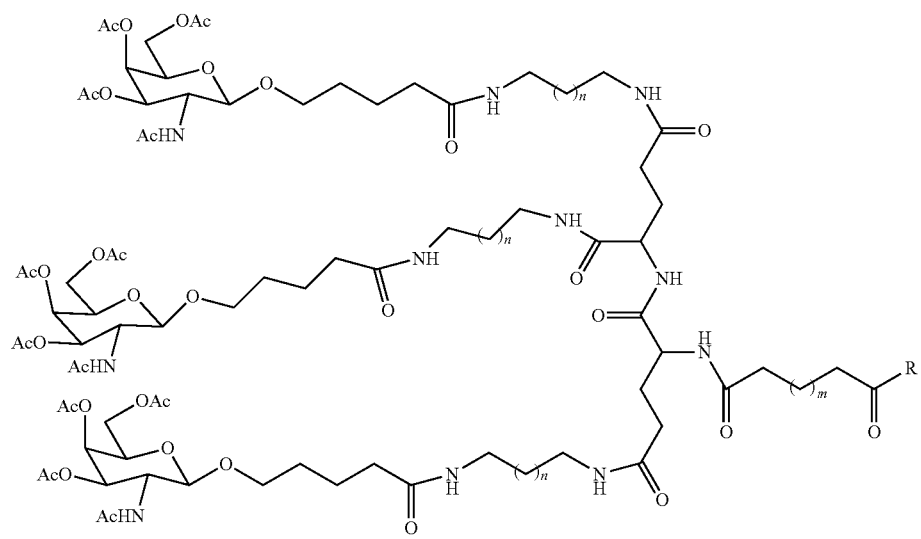

TABLE 2-continued
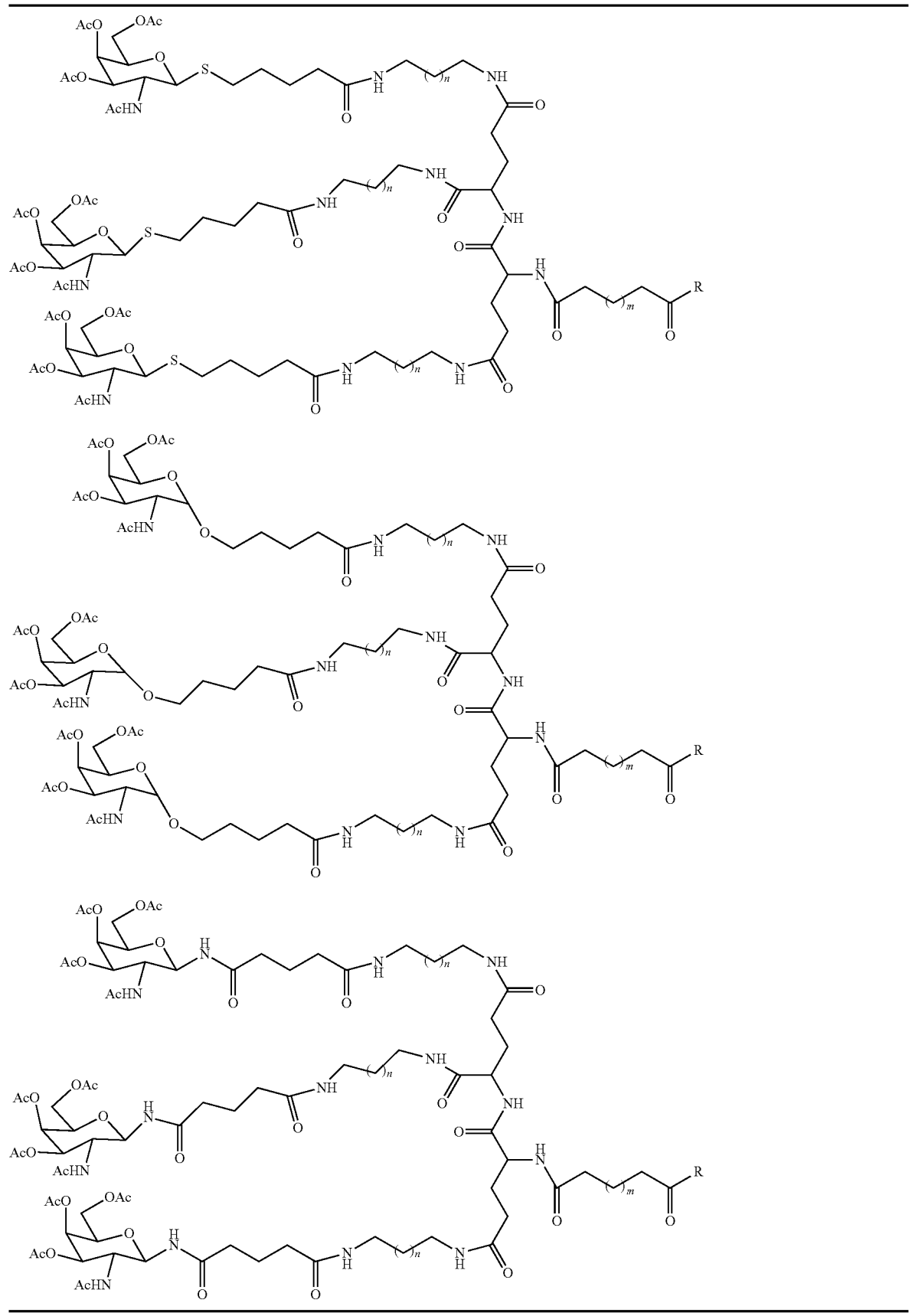

wherein in Table 2,
each occurrence of Q is independently O, S, or $CH_2$;
each occurrence of Z is independently —CONH—, —NHCO—, —OC(O)NH—, or —NHC(O)O—;
each of R, X and ~~~ represents the point of attachment to the rest of the conjugate;

each occurrence of R' is independently Ac, $COCF_3$ or any amine protecting group compatible with oligonucleotide (RNA/DNA) synthesis and deprotection conditions;
each of the variables l, m, n, p, q, and r independently ranges from about 0 to about 10; and

TABLE 2A

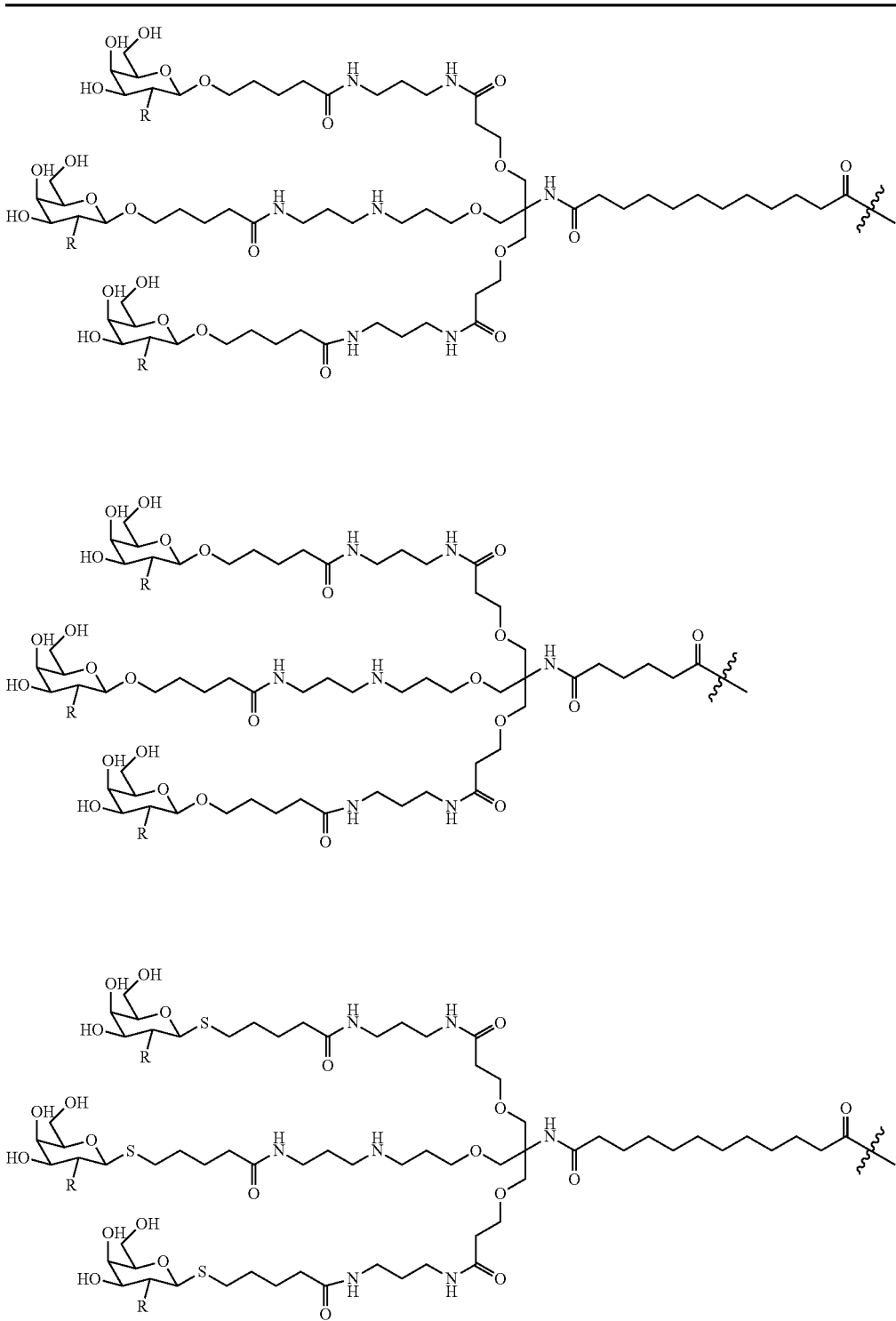

TABLE 2A-continued
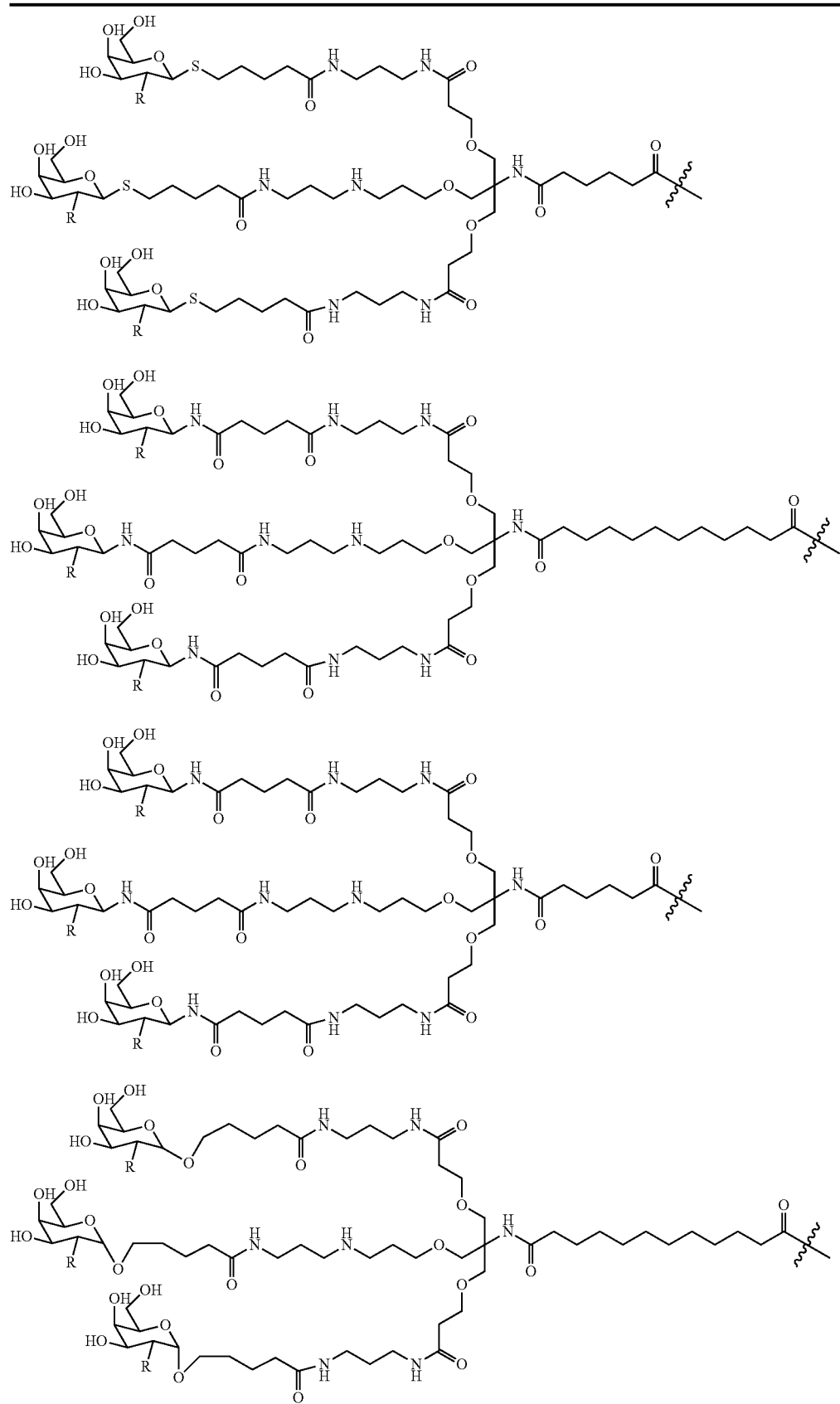

TABLE 2A-continued
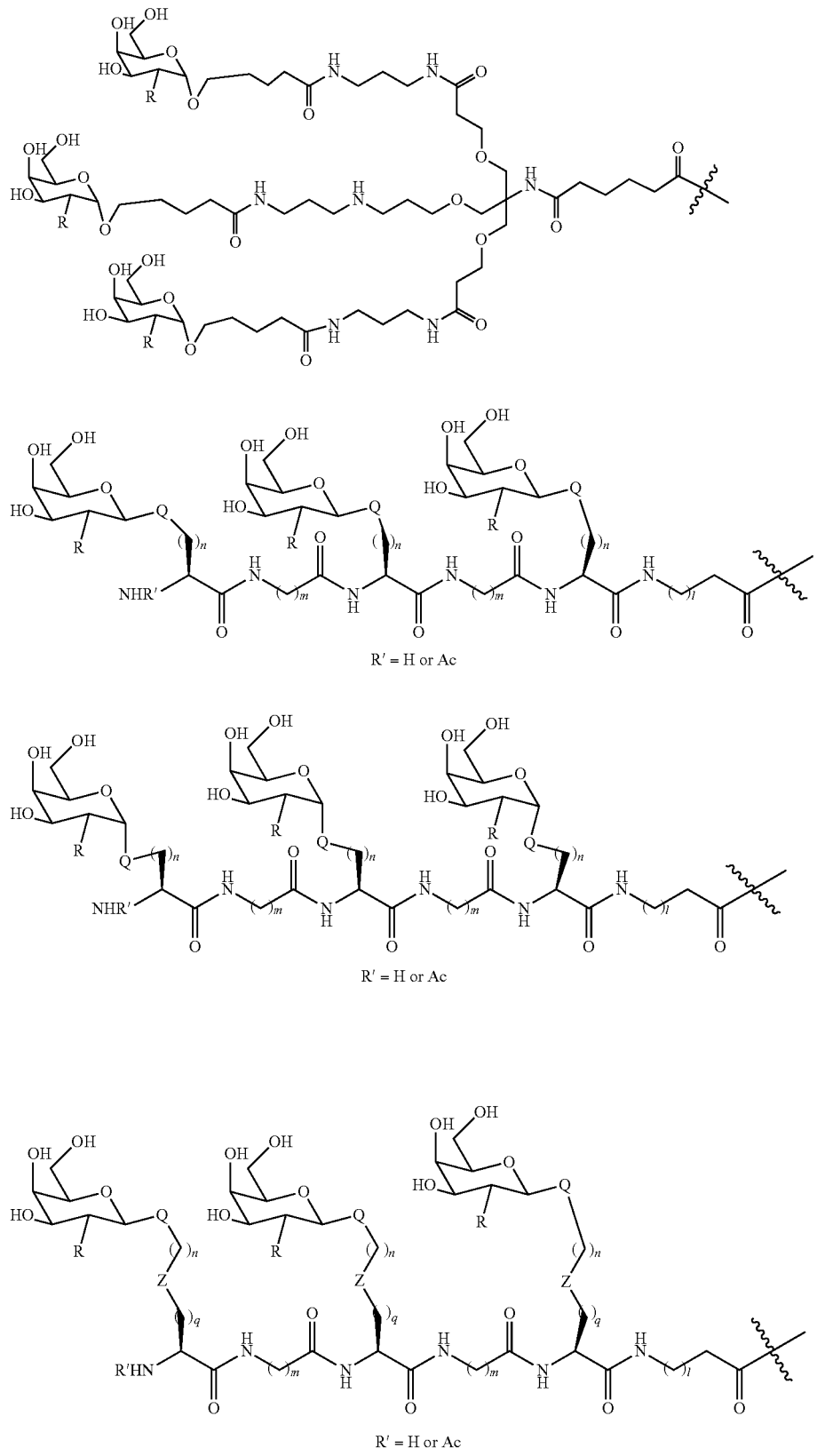
R' = H or Ac
R' = H or Ac
R' = H or Ac

TABLE 2A-continued
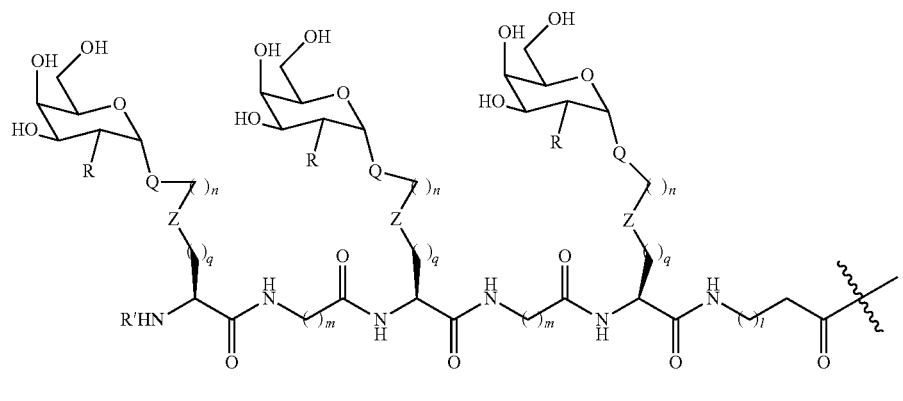
R' = H or Ac
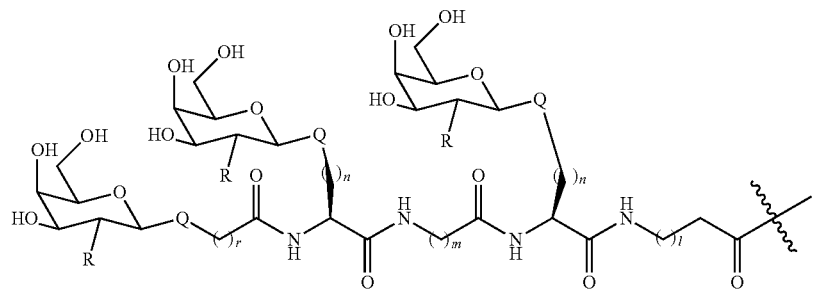
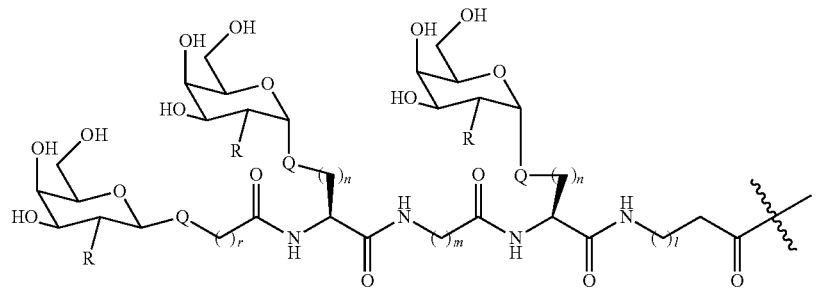
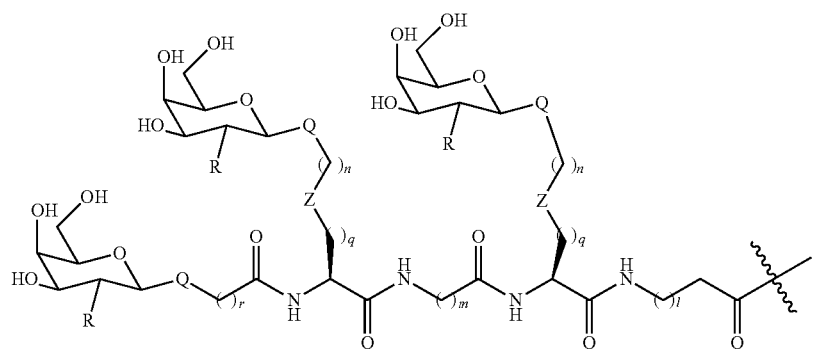

TABLE 2A-continued
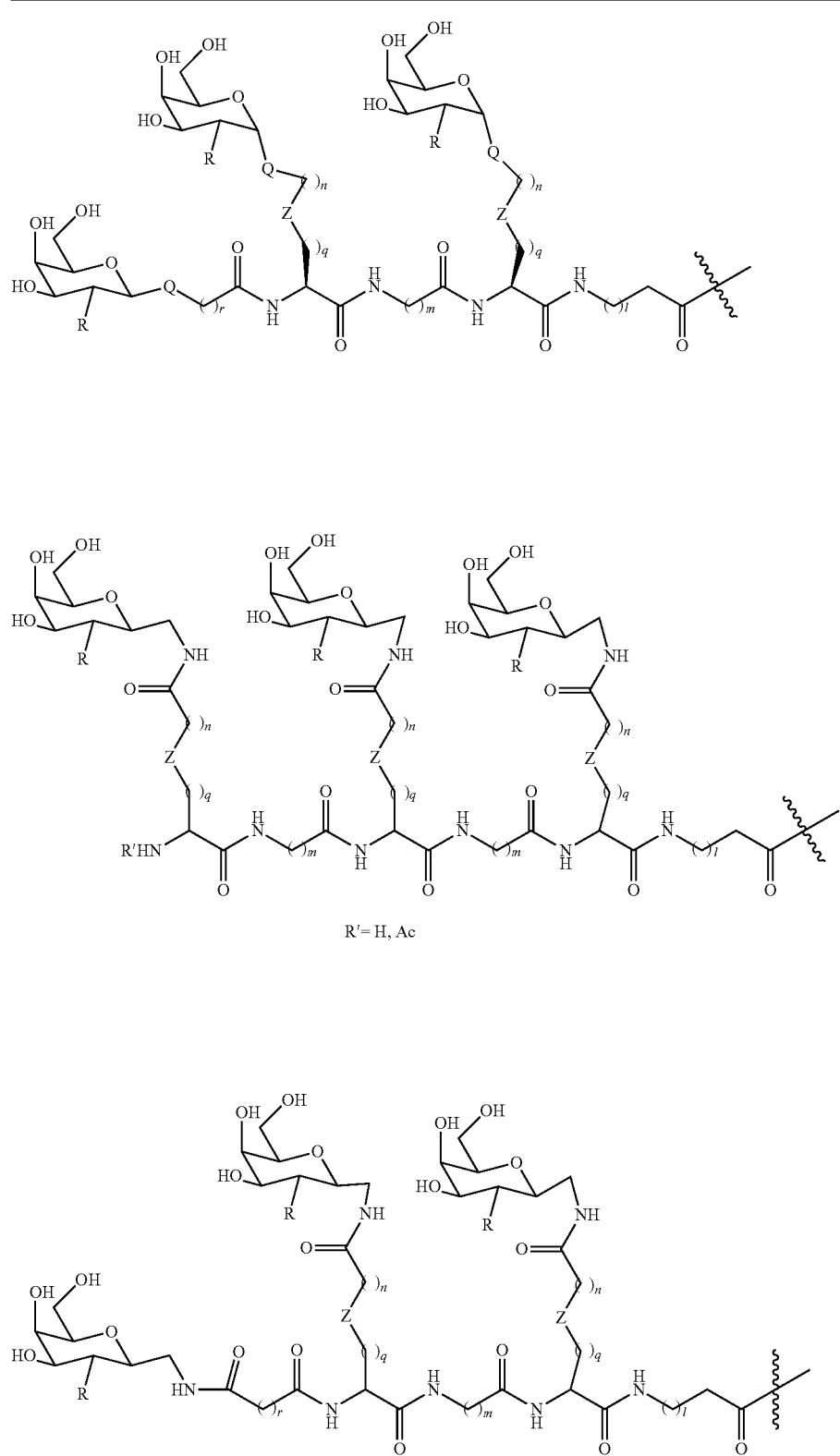

TABLE 2A-continued
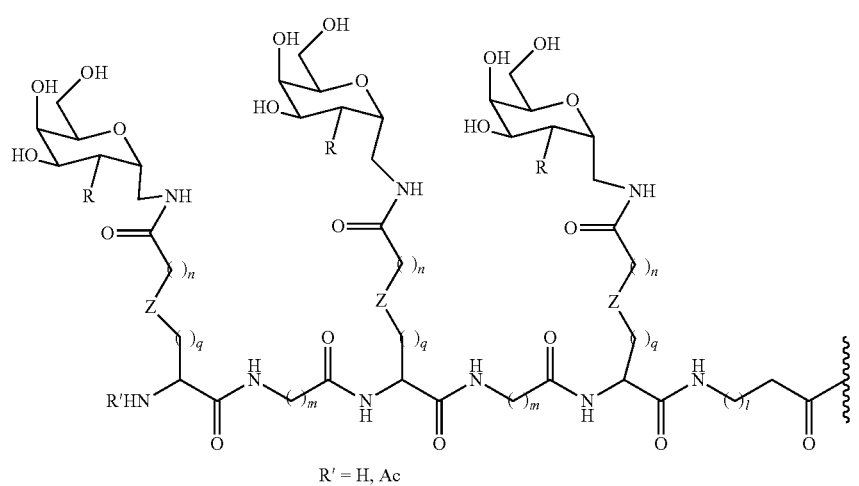
R' = H, Ac
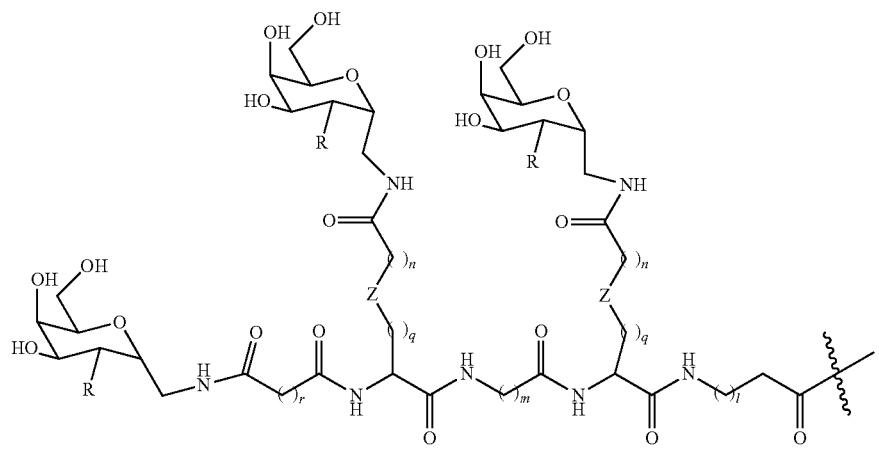
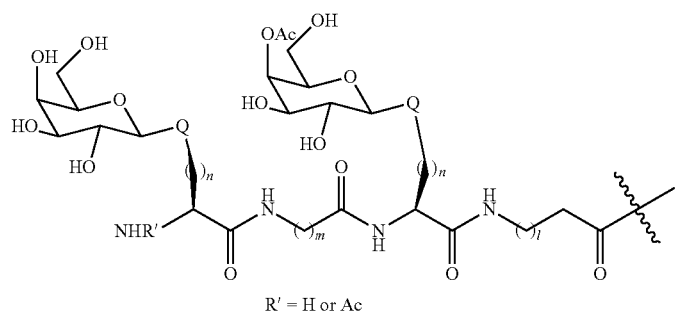
R' = H or Ac
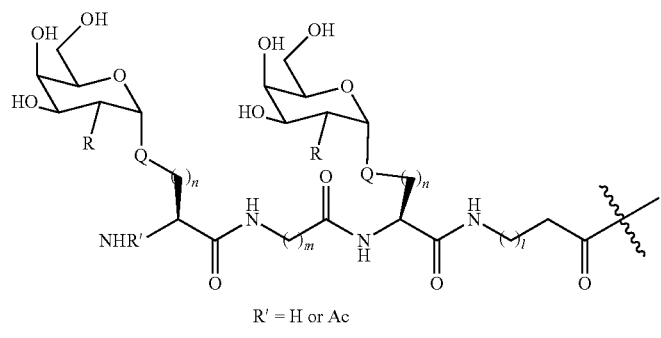
R' = H or Ac TABLE 2A-continued
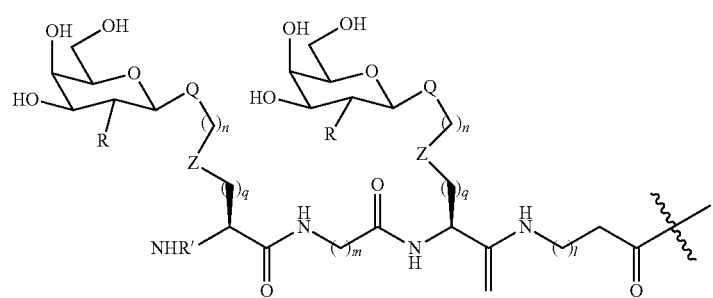
R' = H or Ac
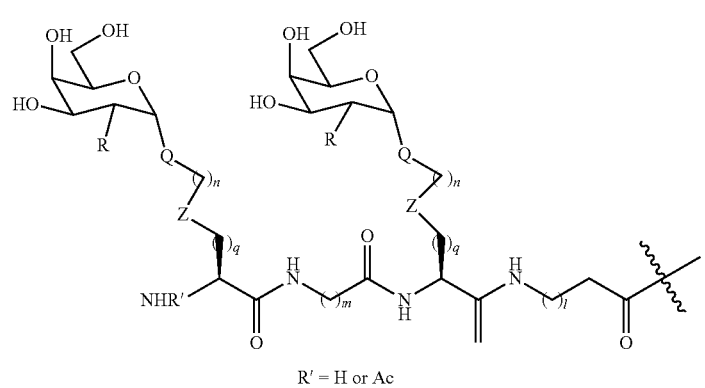
R' = H or Ac
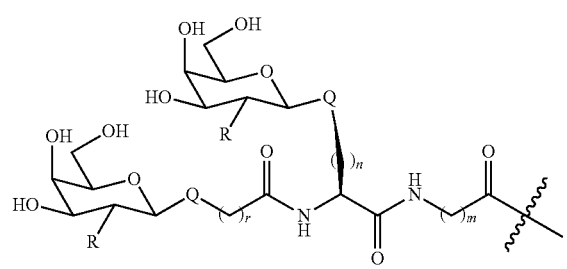
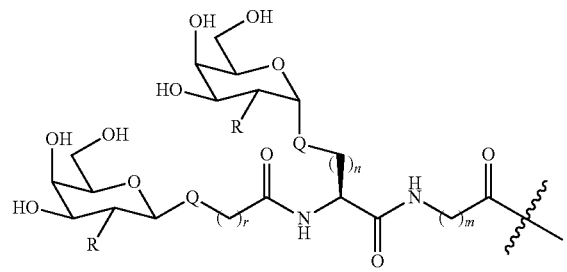
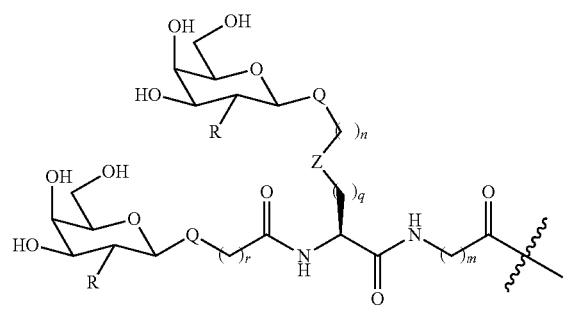

TABLE 2A-continued
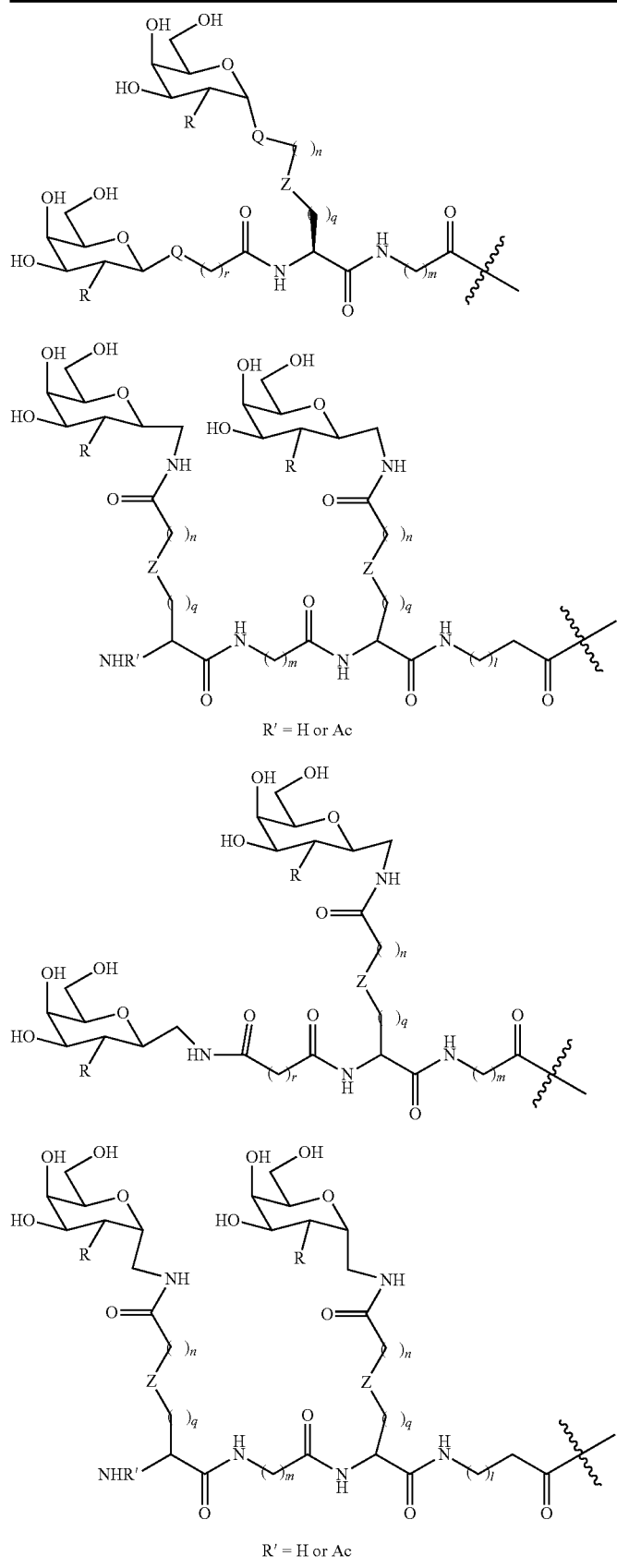

TABLE 2A-continued
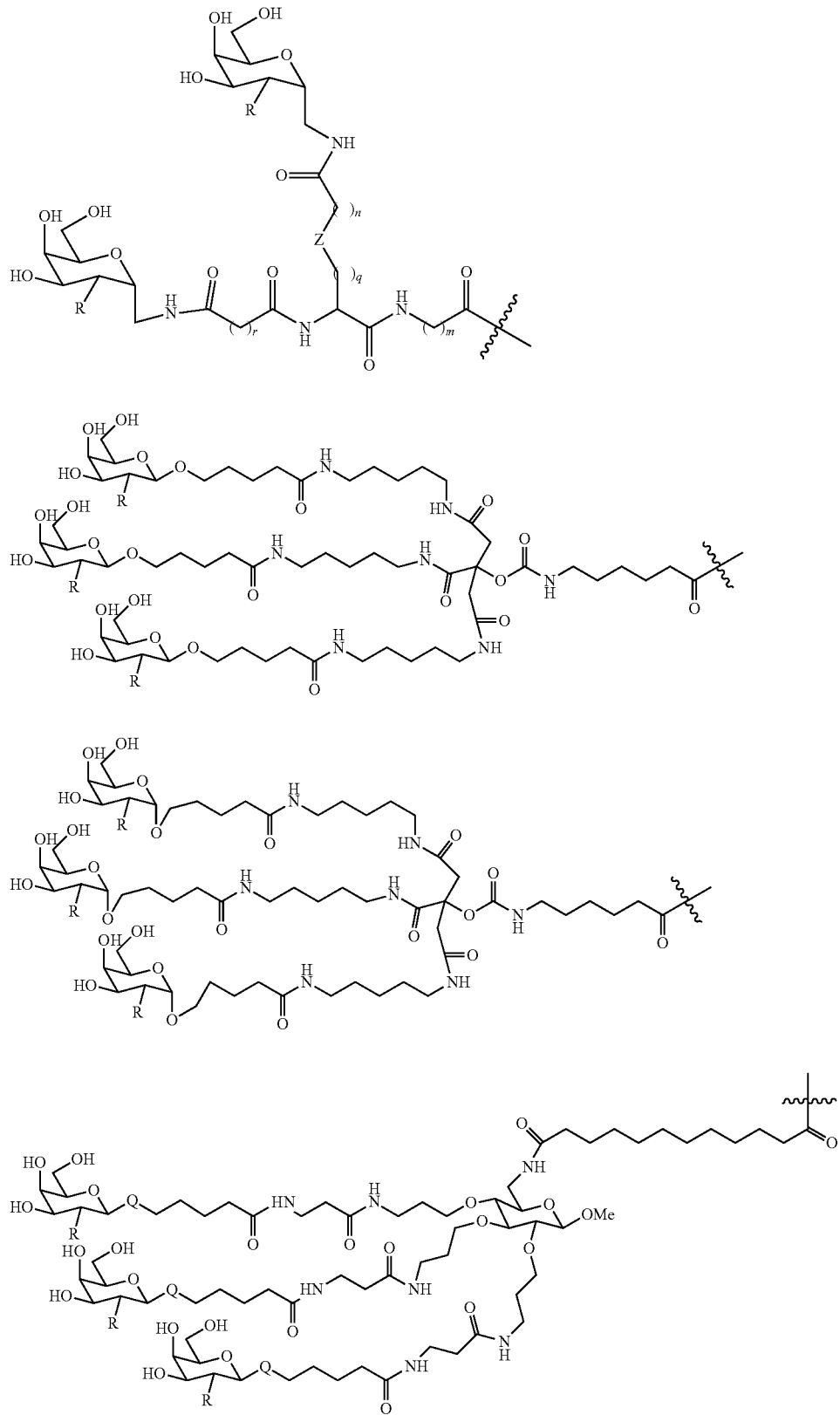

TABLE 2A-continued
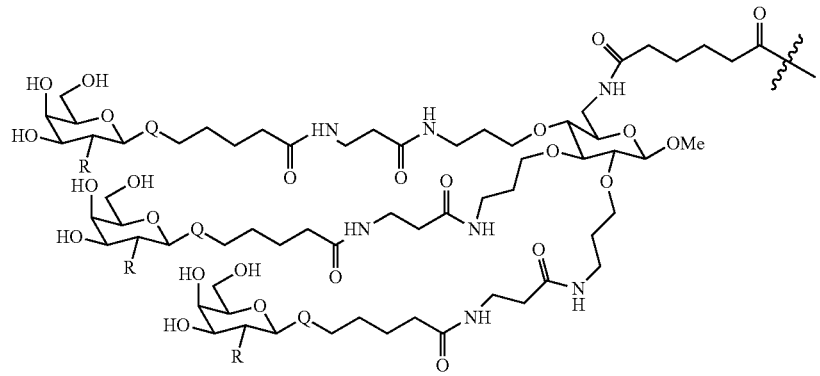
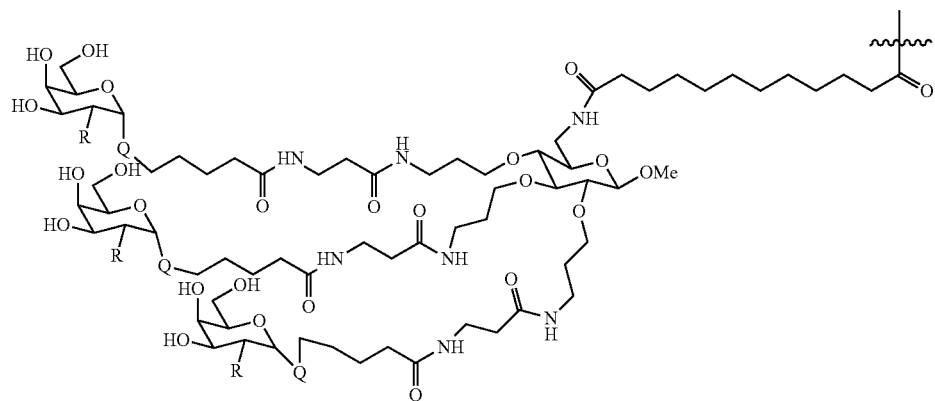
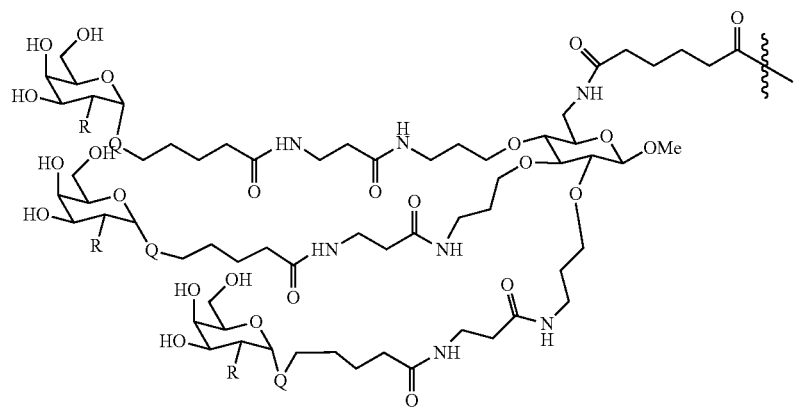

TABLE 2A-continued
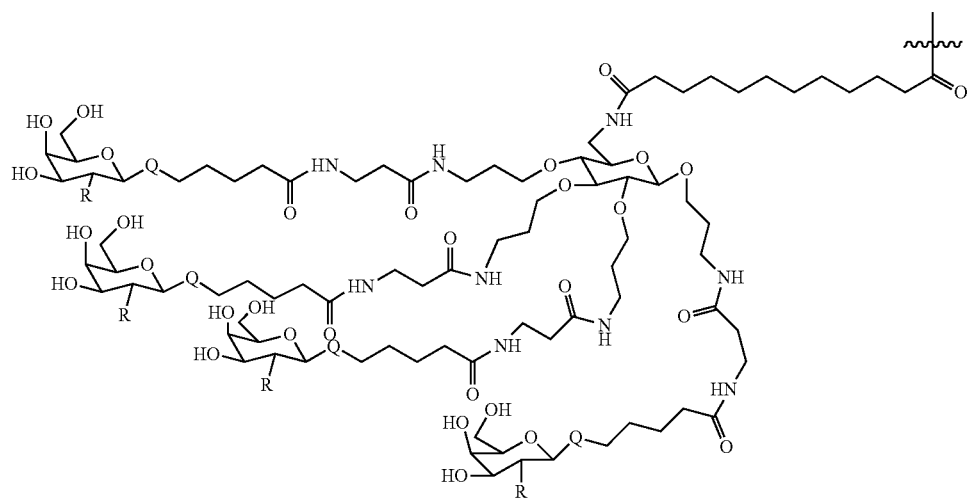
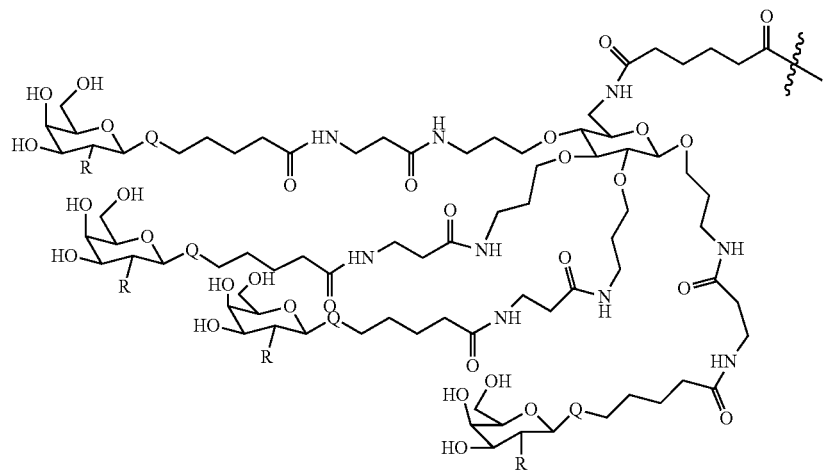
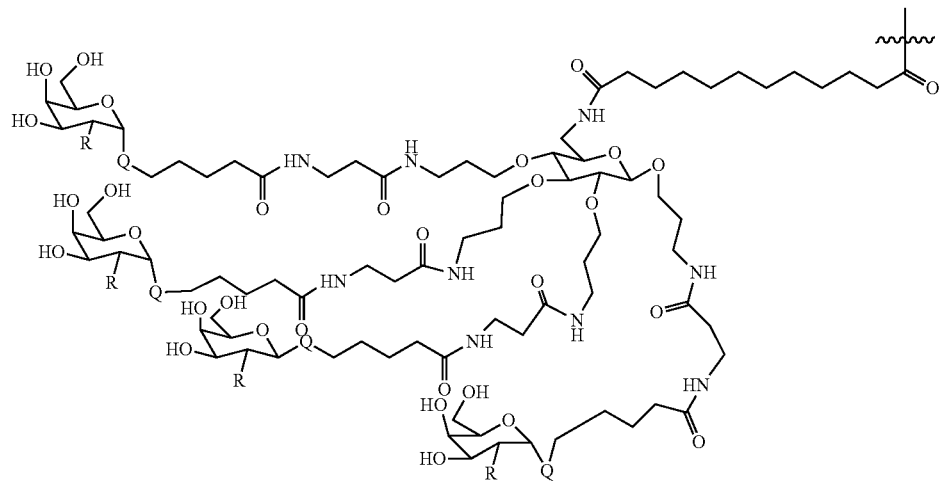

TABLE 2A-continued
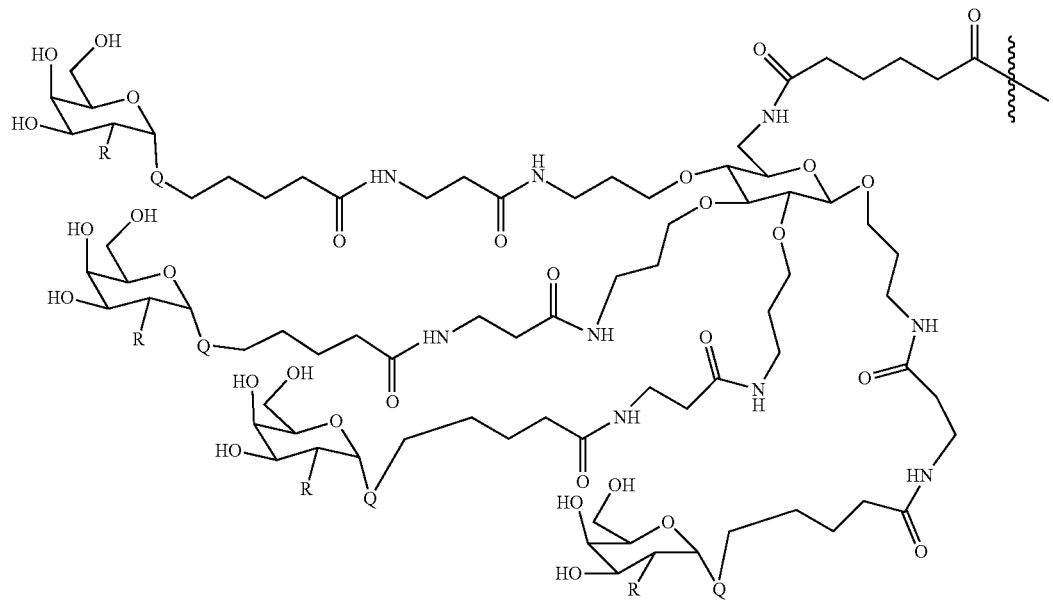
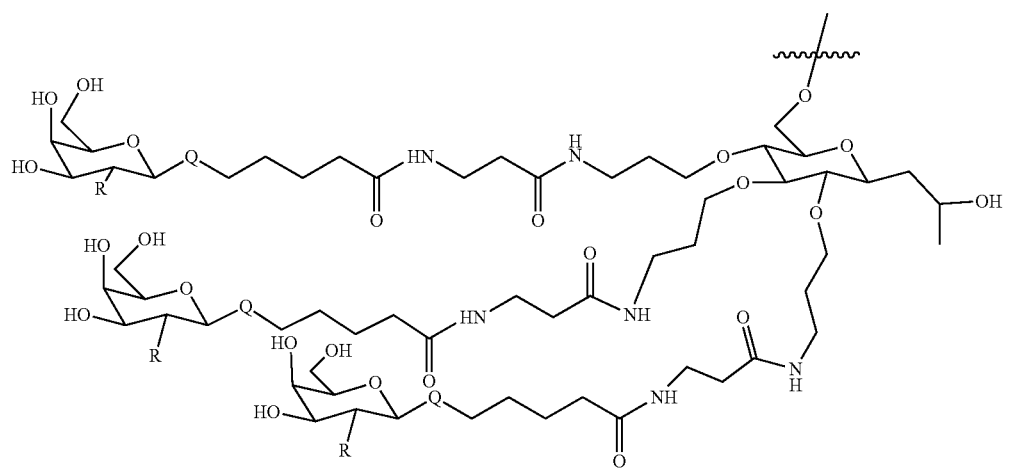
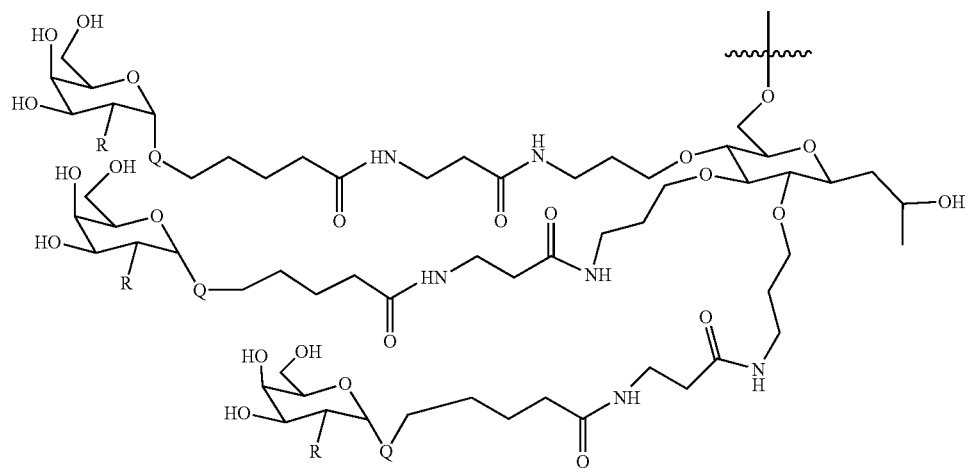

TABLE 2A-continued
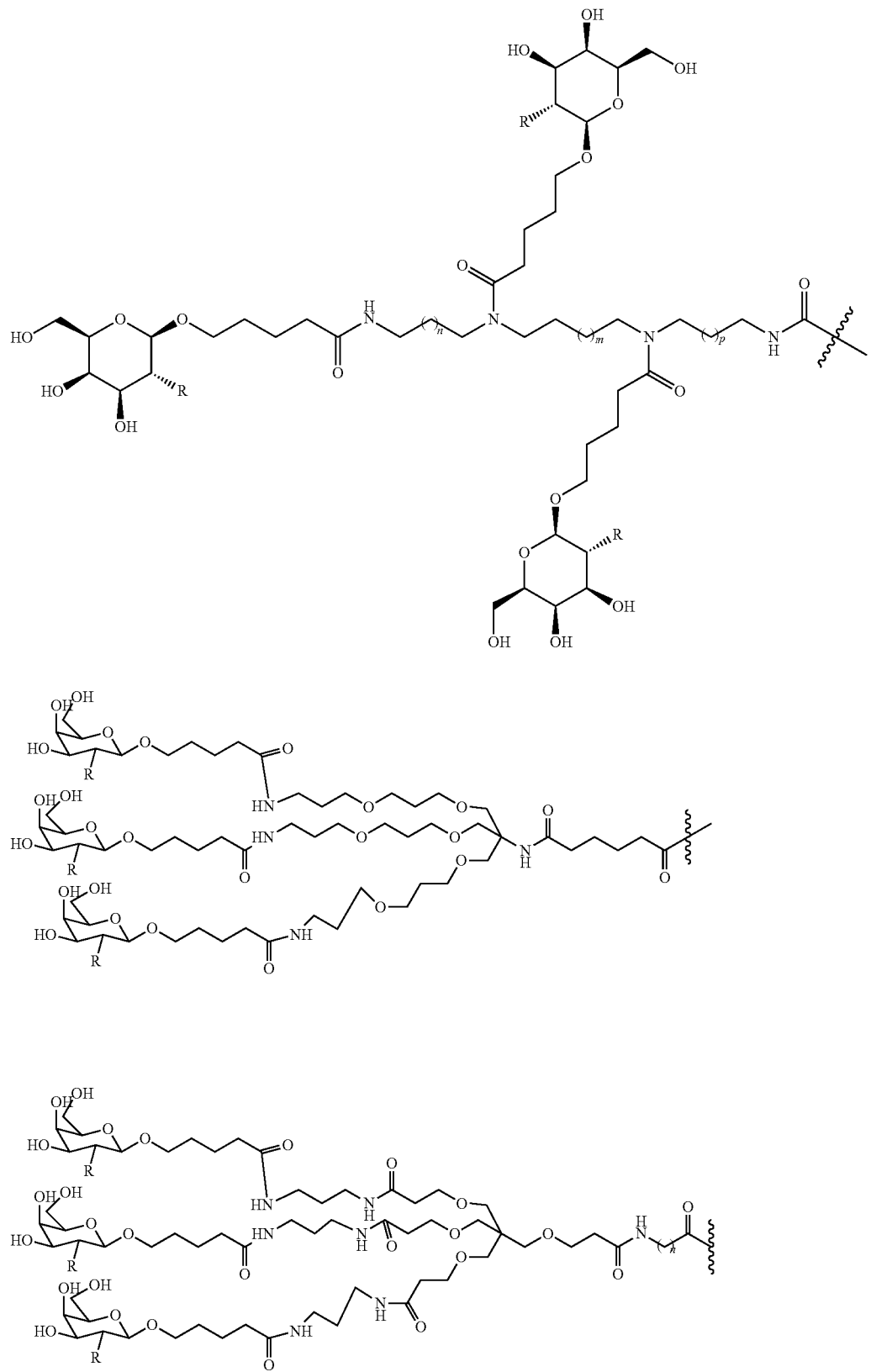

TABLE 2A-continued
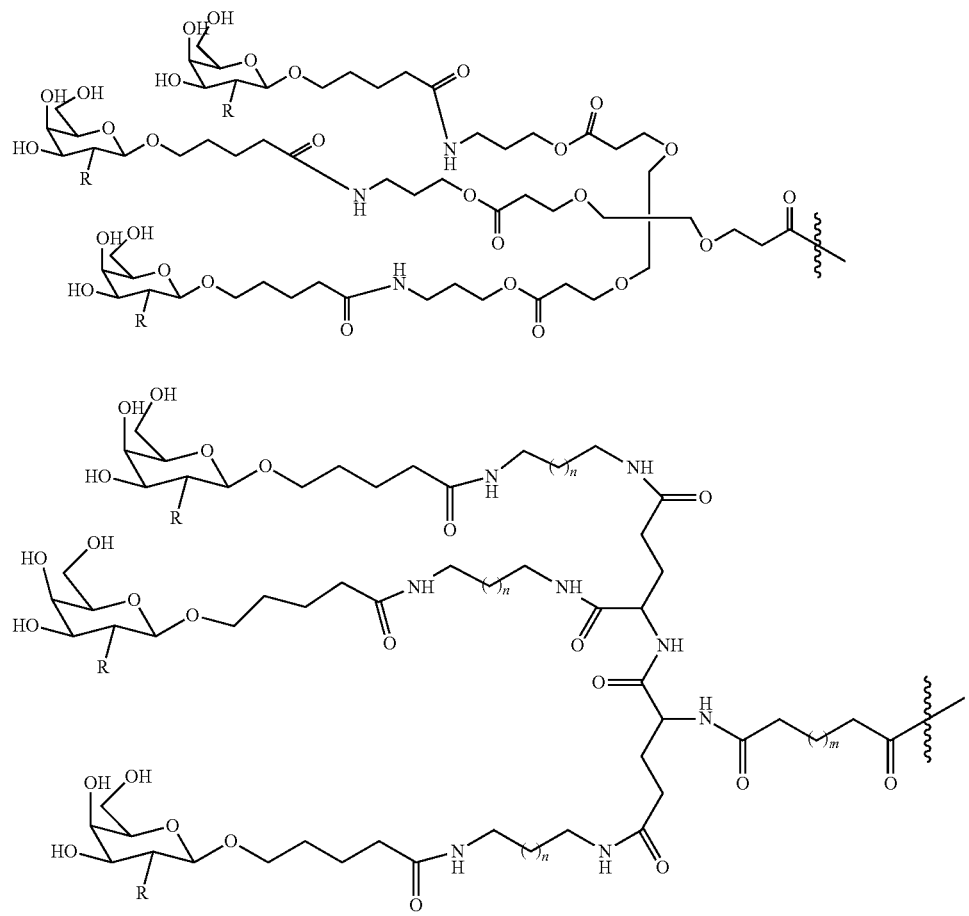
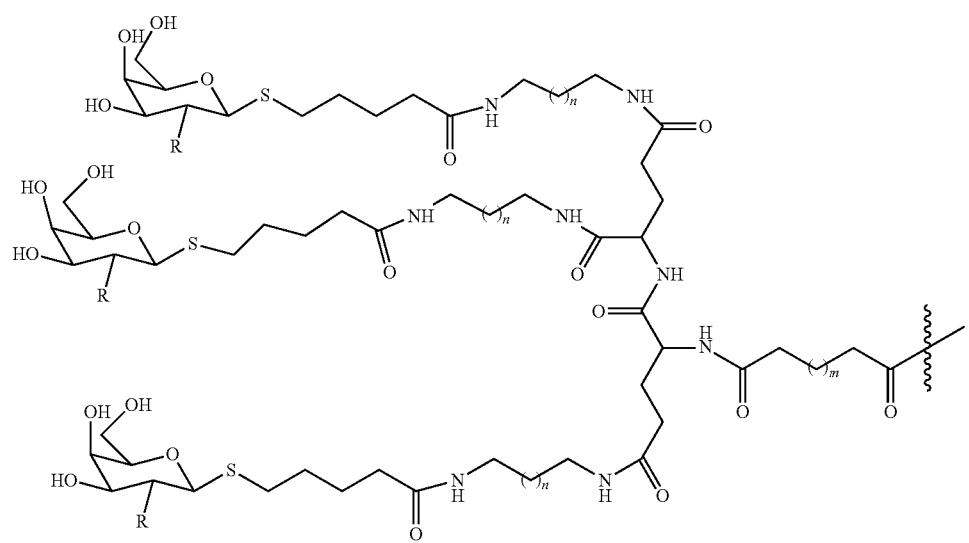

TABLE 2A-continued

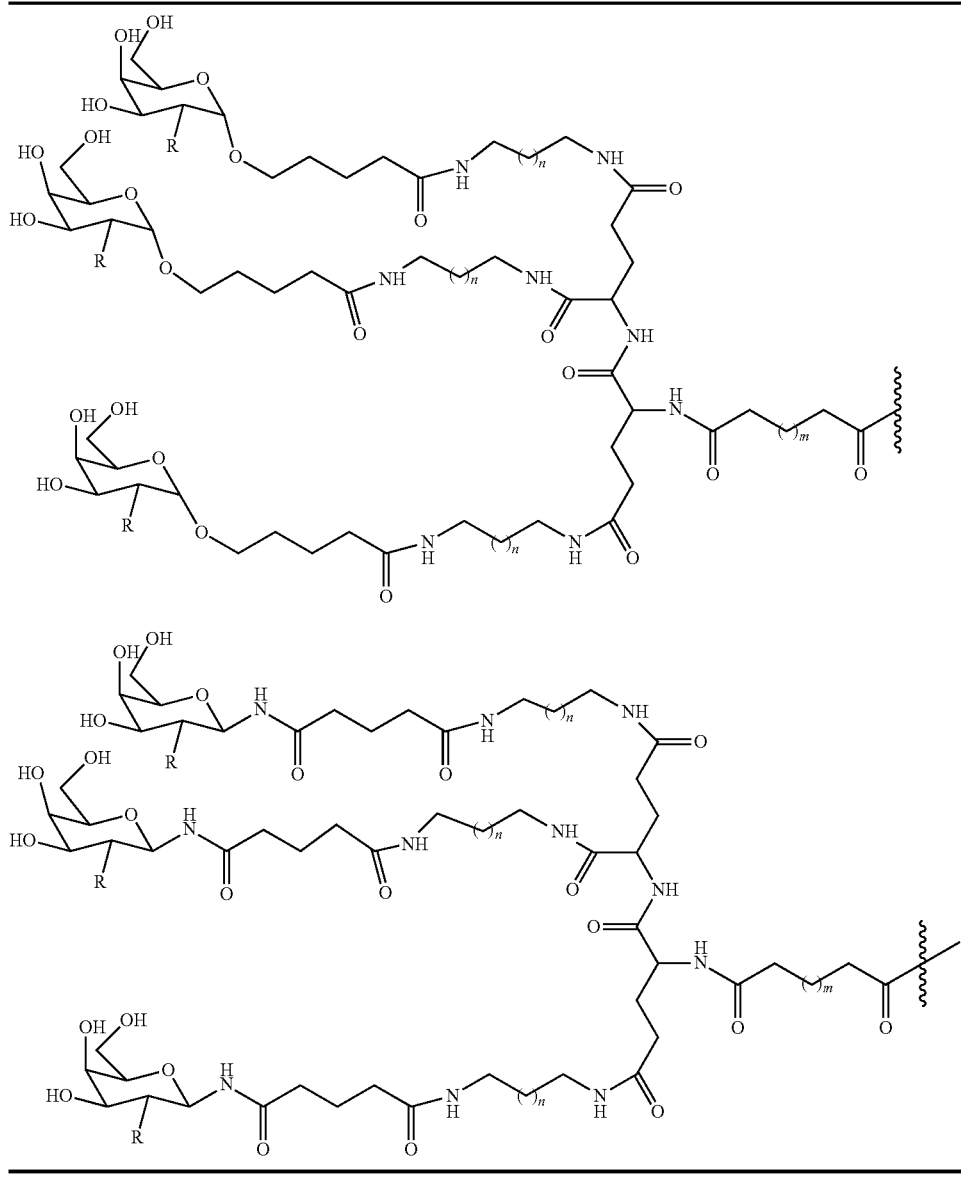

wherein in Table 2A,
each occurrence of Q is independently O, S, or $CH_2$;
each occurrence of Z is independently —CONH—, —NHCO—, —OC(O)NH—, or —NHC(O)O—;
⤳ represents the point of attachment to the rest of the conjugate;
each occurrence of R is independently OH or NHAc; and
each of the variables l, m, n, p, q, and r independently ranges from about 0 to about 10.

7. The conjugate of claim 6, wherein the oligonucleotide moiety in $R^A$ is double stranded and has a length ranging from 15 to about 30 nucleotide units.

8. The conjugate of claim 7, wherein the oligonucleotide moiety has a length ranging from 18 to about 23 nucleotide units.

9. The conjugate of claim 6, wherein the conjugate has the formula

839 840
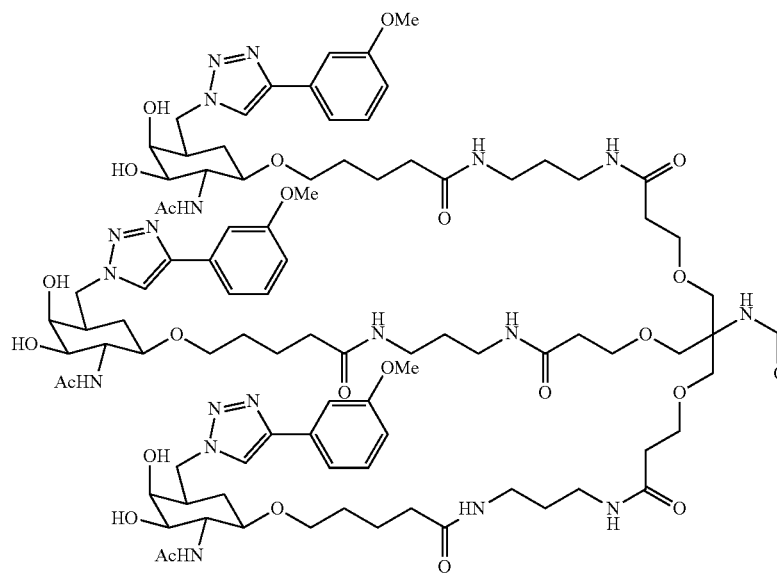
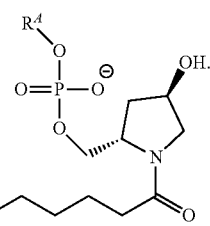
\* \* \* \* \*